US012552772B2

(12) United States Patent
Vanderhoydonck et al.

(10) Patent No.: US 12,552,772 B2
(45) Date of Patent: *Feb. 17, 2026

(54) 2-PYRAZOLE ANILINES AND RELATED ANALOGS FOR INHIBITING YAP/TAZ-TEAD

(71) Applicants: KATHOLIEKE UNIVERSITEIT LEUVEN, Leuven (BE); SpringWorks Therapeutics, Inc., Stamford, CT (US); VIB VZW, Ghent (BE)

(72) Inventors: Bart Vanderhoydonck, Diest (BE); Arnaud Marchand, Bierbeek (BE); Stephen L. Gwaltney, II, Stamford, CT (US); Stéphane Spieser, Munster (FR); Wim Smets, Rotselaar (BE); Aurélie Candi, Werchter (BE); Matthias Versele, Kessel-Lo (BE); Georg Halder, Herent (BE)

(73) Assignees: SPRINGWORKS THERAPEUTICS, INC., Stamford, CT (US); KATHOLIEKE UNIVERSITEIT LEUVEN, Leuven (BE); VIB VZW, Ghent (BE)

( * ) Notice: Subject to any disclaimer, the term of this patent is extended or adjusted under 35 U.S.C. 154(b) by 0 days.

This patent is subject to a terminal disclaimer.

(21) Appl. No.: 18/734,899

(22) Filed: Jun. 5, 2024

(65) Prior Publication Data

US 2025/0115574 A1 Apr. 10, 2025

Related U.S. Application Data

(63) Continuation of application No. 18/145,909, filed on Dec. 23, 2022, now Pat. No. 12,030,866.

(60) Provisional application No. 63/293,531, filed on Dec. 23, 2021.

(51) Int. Cl.

| | |
|---|---|
| *C07D 401/10* | (2006.01) |
| *C07D 213/16* | (2006.01) |
| *C07D 231/12* | (2006.01) |
| *C07D 255/02* | (2006.01) |
| *C07D 257/04* | (2006.01) |
| *C07D 401/04* | (2006.01) |
| *C07D 401/06* | (2006.01) |
| *C07D 401/14* | (2006.01) |
| *C07D 403/04* | (2006.01) |
| *C07D 403/10* | (2006.01) |
| *C07D 403/14* | (2006.01) |
| *C07D 405/04* | (2006.01) |
| *C07D 405/06* | (2006.01) |
| *C07D 405/14* | (2006.01) |
| *C07D 409/14* | (2006.01) |
| *C07D 413/04* | (2006.01) |
| *C07D 413/14* | (2006.01) |
| *C07D 417/04* | (2006.01) |
| *C07D 471/04* | (2006.01) |
| *C07D 471/08* | (2006.01) |

(52) U.S. Cl.

CPC ......... *C07D 401/10* (2013.01); *C07D 213/16* (2013.01); *C07D 231/12* (2013.01); *C07D 255/02* (2013.01); *C07D 257/04* (2013.01); *C07D 401/04* (2013.01); *C07D 401/06* (2013.01); *C07D 401/14* (2013.01); *C07D 403/04* (2013.01); *C07D 403/10* (2013.01); *C07D 403/14* (2013.01); *C07D 405/04* (2013.01); *C07D 405/06* (2013.01); *C07D 405/14* (2013.01); *C07D 409/14* (2013.01); *C07D 413/04* (2013.01); *C07D 413/14* (2013.01); *C07D 417/04* (2013.01); *C07D 471/04* (2013.01); *C07D 471/08* (2013.01); *C07B 2200/09* (2013.01)

(58) Field of Classification Search

CPC .................................................... C07D 401/10

See application file for complete search history.

(56) References Cited

U.S. PATENT DOCUMENTS

| | | | |
|---|---|---|---|
| 7,572,922 B2 | 8/2009 | Parmee et al. | |
| 7,989,475 B2 | 8/2011 | Parmee et al. | |
| 8,629,147 B2 | 1/2014 | Anikin et al. | |
| 10,414,739 B2 | 9/2019 | Barth et al. | |
| 12,030,866 B2 * | 7/2024 | Vanderhoydonck ......................... | C07D 255/02 |
| 2010/0190731 A1 | 7/2010 | Olgin et al. | |

(Continued)

FOREIGN PATENT DOCUMENTS

| | | |
|---|---|---|
| WO | 2013188138 A1 | 12/2013 |
| WO | 2014177524 A1 | 11/2014 |

(Continued)

OTHER PUBLICATIONS

"International Union of Pure and Applied Chemistry, 1957 Report of the Commission on the Nomenclature of Organic Chemistry," Definitive Rules for Nomenclature of Organic Chemistry, J. Am. Chem. Soc., 82:5545-5566, 1960, 30 pages.

(Continued)

*Primary Examiner* — Golam M Shameem
(74) *Attorney, Agent, or Firm* — Blank Rome LLP

(57) ABSTRACT

The present disclosure relates to novel compounds, to said compounds for use as a medicine, more in particular for the prevention or treatment of diseases mediated by activity of YAP/TAZ-TEAD transcription, yet more in particular for the prevention or treatment of cancer or fibrosis. The present disclosure also relates to a method for the prevention or treatment of said diseases comprising the use of the novel compounds.

12 Claims, No Drawings

(56) References Cited

U.S. PATENT DOCUMENTS

| | | | |
|---|---|---|---|
| 2011/0003814 A1 | 1/2011 | Wilson et al. | |
| 2019/0010136 A1 | 1/2019 | Danjo et al. | |

FOREIGN PATENT DOCUMENTS

| | | | |
|---|---|---|---|
| WO | 2015153683 | A1 | 10/2015 |
| WO | 2017053706 | A1 | 3/2017 |
| WO | 2017058716 | A1 | 4/2017 |
| WO | 2017064277 | A1 | 4/2017 |
| WO | 2018185266 | A1 | 10/2018 |
| WO | 2018204532 | A1 | 11/2018 |
| WO | 2018235926 | A1 | 12/2018 |
| WO | 2019040380 | A1 | 2/2019 |
| WO | 2019113236 | A1 | 6/2019 |
| WO | 2019222431 | A1 | 11/2019 |
| WO | 2019232216 | A1 | 12/2019 |
| WO | 2020051099 | A1 | 3/2020 |
| WO | 2020070181 | A1 | 4/2020 |
| WO | 2020081572 | A1 | 4/2020 |
| WO | 2020087063 | A1 | 4/2020 |
| WO | 2020097389 | A1 | 5/2020 |
| WO | 2021102204 | A1 | 5/2021 |

OTHER PUBLICATIONS

ISR and written opinion issued in PCT/US22/82323 on Jul. 14, 2023\.

PubChem-SID-279467773, Jan. 12, 2016 (Jan. 12, 2016), p. 2, figure.

Azzolin, Luca, et al., "YAP/TAZ Incorporation in the β-Catenin Destruction Complex Orchestrates the Wnt Response,", Cell, 2014, 158, 157-170.

Bueno, Raphael , et al., "Comprehensive Genomic Analysis of Malignant Pleural Mesothelioma Indentifiers Recurrent Mutations", Gene Fusions and Splicing Alterations, Nat Genet, 2016, 48, 407-416.

Diamantopoulou, Zoi , et al., "TIAM1 Antagonizes TAZ/YAP Both in the Destruction Complex in the Cytoplasm and in the Nucleus to Inhibit Invasion of Intestinal Epithelial Cells,", Cancer Cell, 2017, 31, 621-634.

Gokey, Jason J, et al., "Active Epithelial Hippo Signaling in Idiopathic Pulmonary Fibrosis", JCI Insight 3: e98738, 2018, 21 pages.

Gregorieff, Alex , et al., "Yap-dependent Reprogramming of Lgr5+ Stem Cells Drives Intestinal Regeneration and Cancer", Nature, 2015, 526, 715-718.

Johnson, Randy , et al., "The Two Faces of Hippo: Targeting the Hippo Pathway for Regenerative Medicine and Cancer Treatment,", Nat Rev Drug Discovery, 2014, 13, 63-79.

Lallemand, Dominique , et al., "NF2 Deficiency Promotes Tumorigenesis and Metastasis by Destabilizing Adherens Junctions", Genes & Development, 2003, 17, 1090-1100.

Liu-Chittenden, Yi Liu, et al., "Genetic and Pharmacological Disruption of the TEAD-YAP Complex Suppresses the Oncogenic Activity of YAP,", Genes & Development, 2012, 26, 1300-1305.

Machado, Mariana Verdelho, et al., "Accumulation of Duct Cells with Activated YAP Parallels Fibrosis Progression in Non-Alcoholic Fatty Liver Disease,", Journal of Hepatology, 2015, 63, 962-970.

Mannaerts, Inge , et al., "The Hippo Pathway Effector YAP Controls Mouse Hepatic Stellate Cell Activation,", Journal of Hepatology, 2015, 63, 679-688.

Piersma, Bram , et al., "YAP1 Is a Driver of Myofibroblast Differentiation in Normal and Diseased Fibroblasts,", The American Journal of Pathology, 2015, 185, 3326-3337.

Shirley, Matthew D, et al., "Sturge-Weber Syndrome and Port-Wine Stains Caused by Somatic Mutation in GNAQ,", The New England Journal of Medicine, 2013, 368, 1971-1979.

Striedinger, Katherine , et al., "The Neurofibromatosis 2 Tumor Suppressor Gene Product, Merlin, Regulates Human Meningioma Cell Growth by Singaling Through YAP1,", Neoplasia, 2008, 10, 1204-1210.

Szulzewsky, Frank , et al., "Comparison of Tumor-associated YAP1 Fusions Identifies a Recurrent Set of Functions Critical for Oncogenesis,", Genes & Development, 2020, 34: 1-14.

Wang, Guocan , et al., "Targeting YAP-Dependent MDSC Infiltration Impairs Tumor Progression,", Cancer Discovery, 2016, 6, 80-95.

Wenchao, Lu , et al., "Discovery and Biological Evaluation of Vinylsulfonamide Derivatives as Highly Potent, Covalent TEAD Autopalmitoylation Inhibitors", European Journal of Medicinal Chemistry, 2019, 184:111767, 15 pages.

Zhang, Wen-Qian , et al., "Targeting YAP in Malignant Pleural Mesothelioma", J. Cell. Mol. Med., 2017, 21:2663-2676.

Zhang, Nailing , et al., "The Merlin/NF2 Tumor Suppressor Functions Through the YAP Oncoprotein to Regulate Tissue Homeostasis in Mammals,", Developmental Cell, Cell 2010, 19, 27-38.

Office Action for European Patent Application No. 22912762.6 mailed Nov. 13, 2025, 4 Pages.

* cited by examiner

2-PYRAZOLE ANILINES AND RELATED ANALOGS FOR INHIBITING YAP/TAZ-TEAD

RELATED APPLICATIONS

This Application is a continuation of U.S. patent application Ser. No. 18/145,909, filed Dec. 23, 2022, which claims the benefit of U.S. Provisional Application No. 63/293,531, filed on Dec. 23, 2022. The entire contents of the above-referenced provisional patent application are incorporated herein by reference.

FIELD

The present disclosure relates to novel compounds. The present disclosure also relates to the compounds for use as a medicine, more in particular for the prevention or treatment of diseases mediated by activity of YAP/TAZ-TEAD transcription, such as for the prevention or treatment of cancer or fibrosis. Methods for the prevention or treatment of the diseases comprising the use of the novel compounds are also disclosed herein.

The present disclosure furthermore relates to pharmaceutical compositions or combination preparations of the novel compounds, as well as to the compositions or preparations for use as a medicine, for example for the prevention or treatment of diseases mediated by activity of YAP/TAZ-TEAD transcription such as the prevention or treatment of cancer or fibrosis. Processes for the preparation of the compounds are also disclosed herein.

BACKGROUND

Hippo signaling is critical to restrict organ size through inactivation of the YAP/TAZ-TEAD transcriptional complex. In several aggressive solid cancers, Hippo signaling is inactivated through loss-of-function mutations or deletions in the genes encoding the upstream regulators (e.g. NF2, MST1/2 or LATS1/2), unleashing constitutive YAP/TAZ-TEAD transcriptional activity leading to unbridled tumor growth and metastasis. Knock-out, knockdown or pharmacologic inactivation of YAP/TAZ-TEAD is sufficient to impair YAP/TAZ-dependent tumorigenesis. The YAP/TAZ-TEAD complex can be pharmacologically inactivated through targeted disruption of the YAP/TAZ-TEAD protein-protein interaction interface, or through an allosteric autopalmitoylation pocket in TEAD.

The main physiologic function of the Hippo pathway is to restrict tissue growth in adult tissue and modulate cell proliferation, differentiation and migration in developing organs. The core of the Hippo pathway consists of a kinase cascade, transcription coactivators and DNA-binding partners. In mammals, the Ste20-like kinases, MST1/2 (homologs of *Drosophila* Hippo) phosphorylate and activate Large Tumor Suppressor 1/2 (LATS1/2). NF2 is a scaffold for the core Hippo kinases, promoting LATS1/2 activation by tethering MST1/2 to LATS1/2 (Lallemand et al., 2003, Genes Dev 17, 1090-1100; Yin et al., 2013, Dev Cell 19, 27-38). The LATS kinases will in turn phosphorylate and inactivate two highly homologous transcriptional co-activators: Yes-associated Protein (YAP) and Transcriptional co-activator with PDZ-binding motif (TAZ) by cytoplasmic sequestration via 14-3-3 and by ubiquitin-mediated degradation induced by β-TRCP E3 ligase. When the Hippo pathway is inactive, YAP and TAZ translocate in the nucleus to bind to the TEAD transcription factor family to induce expression of a specific signature promoting matrix remodeling, cell proliferation, survival and migration. TEAD1-4 can also bind to VGLL4 in the nucleus and act as a transcriptional repressor. VGLL4 is not structurally related to YAP/TAZ, but competes with YAP/TAZ based on a partially overlapping binding site on TEAD (Johnson and Halder, 2014, Nat Rev Drug Discov 13, 63-79).

TEADs are evolutionarily conserved proteins required for cardiogenesis, myogenesis, and for the development of the neural crest, notochord, and trophoectoderm. In mammals, there are four genes encoding four homologous members of the TEAD family named TEAD1-4. Each TEAD gene has a distinct but not mutually exclusive expression pattern. All TEAD family members are controlled by YAP/TAZ.

In fruit flies, loss of function of Hippo or Warts kinases (MST1/2 or LATS1/2 in mammals), or overexpression of Yorkie (the *Drosophila* homolog of YAP and TAZ), results in a dramatic overgrowth of the cuticle, as a result of dysregulated cell proliferation and resistance to apoptosis, leading to increased organ size. In mice, YAP overexpression, loss of MST1/2 or LATS1/2 kinase activities, or loss of NF2 leads to TEAD target gene up-regulation and progenitor cell expansion, resulting in liver and cardiac overgrowth and ultimately cancer formation in the liver, the small intestine and in skin. In contrast, a serine to alanine mutation at position 94 in YAP, that is unable to bind to TEAD, is not oncogenic (Zhao et al., 2008, Genes Dev 22, 1962-1971). Likewise, a dominant-negative TEAD mutant that is unable to bind DNA, overcomes YAP-driven liver tumorigenesis. In addition, NF2 mutant liver carcinoma was greatly suppressed by heterozogous loss of Yap (Zhang et al., 2010, Dev Cell 19, 27-38). Finally, verteporfin, a small molecule that inhibits YAP-TEAD association significantly suppressed the oncogenic activity of YAP in these models (Liu-Chittenden et al., 2012, Genes Dev 26, 1300-1305).

Gene amplification of YAP1 (encoding for YAP) and WWTR1 (encoding for TAZ) as well as constitutive nuclear localization of YAP/TAZ have been reported in many human solid malignancies, including liver, lung, breast, skin, colon and ovarian cancer and YAP/TAZ promote the acquisition of several important cancer cell phenotypes, such as proliferation, resistance to apoptosis, invasion, and immune-suppression (e.g. by attracting myeloid derived suppressor cells (Wang et al., 2016, Cancer Discov 6, 80-95)).

In addition, gene fusions with YAP1 have been identified in several cancer types including ependymomas, vascular cancers, cervical carcinomas and porocarcinomas, which results in constitutive activation of YAP-TEAD, and are oncogenic in mice (Szulzewsky et al., 2020, Genes Dev 34: 1-14). In addition, several germline or somatic mutations in components of the Hippo pathway associated with various cancer types have been discovered in targeted and whole-genome sequencing studies. The best studied example is the NF2 locus, mutated with a high frequency in neurofibromatosis. Loss of NF2 and LATS2 are also frequently observed in schwannomas. Another tumor type that is commonly (in about 70% of all cases) associated with constitutive YAP-TEAD activation through genetic inactivation of NF2, LATS1/2, MST1/2 or SAV1, is malignant mesothelioma (Bueno et al., 2016, Nat Genet 48, 407-416.). Recent studies have shown that several mesothelioma cell lines with NF2 loss-of-function mutations exhibit a decrease in YAP phosphorylation and an increase in YAP-TEAD reporter activity. The YAP-TEAD transcription and viability of NF2 mutant mesothelioma cell lines (but not WT mesothelioma) are sensitive to YAP siRNA (an effect which can be rescued by overexpression of siRNA resistant YAP) and to treatment with verteporfin, a YAP antagonist (Zhang et al., 2017, J Cell Mol Med 21: 2663-2676).

Nuclear YAP has also emerged as a critical mediator of WNT dependent colorectal tumorigenesis. YAP-TEAD mediated transcription of genes involved in proliferation and stem cell renewal cooperate with WNT driven beta-catenin, and YAP is required for formation of adenomas following APC (adenomatous polyposis *coli*) inactivation (Azzolin et al., 2014 Cell 158, 157-170; Gregorieff et al., 2015 Nature 526, 715-718.). Recently, TIAM1, was identified as a suppressor of aggressive, metastatic colorectal cancer (CRC) by antagonizing YAP-TEAD transcription, again highlighting the role of YAP-TEAD in CRC (Diamantopoulou et al., 2017 Cancer Cell 31, 621-634).

In summary, YAP/TAZ activation has been shown to drive tumorigenesis and YAP/TAZ is hyperactivated in many different types of cancer in humans (often through loss-of-function mutations in upstream negative regulators). Genetic deletion or pharmacologic inhibition of YAP/TAZ has been shown to suppress tumor development and progression in different types of cancer. Therefore, it is believed that deregulation of the Hippo tumor suppressor pathway is a major event in the development of a wide range of cancer types and malignancies. Hence, pharmacological targeting of the Hippo cascade through inhibition of YAP, TAZ, TEAD, and/or the YAP/TAZ-TEAD protein-protein interaction would be a valuable approach for the treatment of cancers that harbor functional alterations of this pathway.

YAP/TAZ-TEAD activation has also been shown to play an important role in other diseases than cancer, namely such as in fibrosis and certain congenital disorders. A hallmark of fibrosis is the excessive deposition of extracellular matrix (ECM), including cross-linked collagen fibres, which results in the stiffening of tissues and eventually in dysfunctioning of affected organs. ECM stiffening promotes the nuclear activity of YAP/TAZ in cancer-associated fibroblasts, and fibroblasts of the liver, kidney, lung and skin (Mannaerts et al., 2015, J. Hepatol. 63, 679-688; Piersma et al., 2015, Am. J. Pathol. 185, 3326-3337). Nuclear YAP/TAZ promotes fibrotic cellular phenotypes, such as myofibroblast differentiation and increased matrix remodeling. Several genes that encode key secreted factors implicated in fibrosis are direct YAP/TAZ-TEAD targets. These genes include well-characterized pro-fibrotic factors, such as connective tissue growth factor (CTGF), plasminogen activator inhibitor 1 (PAI-1) and the lysyl oxidase (LOX) family of collagen cross-linking enzymes. Several lines of evidence support YAP/TAZ as contributors to fibrotic disease in vivo. These include reports of elevated YAP/TAZ levels and transcriptional activity in fibroblasts as well as in alveolar and respiratory epithelium of patients with idiopathic pulmonary fibrosis (Gokey et al., 2018 JCI Insight 3: e98738). Increased nuclear YAP has also been observed in patients with primary sclerosing cholangitis and primary biliary cirrhosis, which are chronic fibrotic disorders of liver injury. Expression of YAP or TAZ in the duct cells of the liver drives fibrosis progression that parallels fibrosis in nonalcoholic fatty liver disease (Machado et al., 2015, J. Hepatol 63, 962-970). Collectively, these studies suggest that targeting aberrant YAP/TAZ activity in fibrotic diseases may hold promise for therapy.

Neurofibromatosis type 2 is characterized by nervous system tumors including schwannomas, meningiomas, and ependymomas. Neurofibromatosis type 2 is an inheritable disorder caused by the inactivation of NF2 (Striedinger et al., 2008, Neoplasia 10, 1204-1210). Loss of NF2 leads to constitutive activation of YAP/TAZ-TEAD. The Sturge-Weber syndrome is a congenital eurocutaneous disorder characterized by a port-wine stain affecting the skin in the distribution of the ophthalmic branch of the trigeminal nerve, abnormal capillary venous vessels in the leptomeninges of the brain and choroid, glaucoma, seizures, stroke, and intellectual disability. The Sturge-Weber syndrome and port-wine stains are caused by a somatic activating mutation in GNAQ which leads to activation of YAP/TAZ-TEAD transcription (Shirley et al., 2013, NEJM, 368, 1971-1979). Therefore, several congenital disorders, characterized by constitutive YAP/TAZ-TEAD activation could be treated with inhibitors of YAP/TAZ-TEAD.

A few publications describe inhibitors of the YAP-TEAD transcriptional activation. Inventiva highlighted YAP-TEAD protein-protein interaction inhibitors in WO2020/070181, WO2018/185266, and WO2017/064277. The General Hospital Corporation, Boston described autopalmitoylation inhibitors in WO2017/053706. Vivace Therapeutics, Inc. disclosed non-fused tricyclic (WO2018/204532), benzosulfonyl (WO2019/040380), benzocarbonyl (WO2019/113236), oxadiazole (WO2019/222431), and bicyclic (WO2020/097389) compounds that modulate the interaction between YAP/TAZ and TEAD. The Regents of the University of California and Vivace Therapeutics, Inc. described tricyclic compounds that inhibit the Hippo-YAP signaling pathway in WO2013/188138 and WO2017/058716, respectively. Kyowa Hakko Kirin Co., Ltd. revealed alpha,beta-unsaturated amide compounds that display anti-cancer activity in WO2018/235926 and US2019/0010136. Genentech, Inc. disclosed carboxamide and sulfonamide derivatives useful as inhibitors of the YAP-TEAD protein-protein interaction in WO2019/232216 and WO2020/051099. Dana-Farber Cancer Institute, Inc. highlighted inhibitors of TEAD transcription factors in WO2020/081572. The Trustees of Indiana University described small-molecules that bind within the hydrophobic palmitate-binding pocket of TEADs in WO2020/087063. Wenchao Lu, et al. published vinylsulfonamides as covalent TEAD autopalmitoylation inhibitors (2019, European Journal of Medicinal Chemistry, 184, p. 111767). Korean Research Institute of Chemical Technology disclosed benzo[cd]indol-2(1H)-one derivatives that inhibit YAP-TEAD binding.

However, there is still a great need for novel, alternative or better therapeutics for the prevention or treatment of diseases mediated by the YAP/TAZ-TEAD activation, such as cancer and fibrosis among potentially other indications. Therapeutics with better potency, less side-effects, a higher activity, a lower toxicity or better pharmacokinetic or—dynamic properties or combinations thereof would be very welcome.

The present disclosure provides a class of novel compounds which can be used as inhibitors of the YAP/TAZ-TEAD activation mediated diseases.

SUMMARY OF THE DISCLOSURE

The present disclosure is based on the finding that at least one of the above-mentioned problems can be solved by the below described class of compounds.

The present disclosure provides new compounds which have been shown to possess inhibitory activity on the YAP/TAZ-TEAD transcription. The present disclosure furthermore demonstrates that these compounds efficiently inhibit the activity of YAP/TAZ-TEAD transcription. Therefore, these compounds constitute a useful class of new potent compounds that can be used in the treatment and/or prevention of Hippo mediated disorders in animals, mammals and humans, more specifically for the treatment and/or prevention of (i) cancer, more specifically lung cancer, breast cancer, head and neck cancer, oesophageal cancer, kidney cancer, bladder cancer, colon cancer, ovarian cancer, cervical cancer, endometrial cancer, liver cancer (including but not limited to cholangiocarcinoma), skin cancer, pancreatic cancer, gastric cancer, brain cancer and prostate cancer, mesotheliomas, and/or sarcomas (ii) fibrosis, and (iii) YAP/TAZ-TEAD activation related congenital disorders, among others.

In some aspects, the compounds described herein can be used in the treatment and/or prevention of Hippo mediated disorders in animals, mammals and humans, more specifically for the treatment and/or prevention of acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute T-cell leukemia, basal cell carcinoma, bile duct carcinoma, bronchogenic carcinoma, chondrosarcoma, chordoma, choriocarcinoma, chronic leukemia, chronic lymphocytic leukemia, chronic myelocytic (granulocytic) leukemia, chronic myelogenous leukemia, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, hemangioblastoma, hepatoma, hepatocellular cancer, hormone insensitive prostate cancer, leiomyosarcoma, leukemia, liposarcoma, lymphangioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, medullary carcinoma, medulloblastoma, melanoma, meningioma, mesothelioma, multiple myeloma, myelogenous leukemia, myeloma, myxosarcoma, neuroblastoma, NUT midline carcinoma (NMC), non-small cell lung cancer, oligodendroglioma, oral cancer, osteogenic sarcoma, papillary adenocarcinomas, papillary carcinoma, pinealoma, polycythemia vera, rectal cancer, renal cell carcinoma, retinoblastoma, rhabdomyosarcoma, sarcoma, sebaceous gland carcinoma, seminoma, small cell lung carcinoma, solid tumors (carcinomas and sarcomas), small cell lung cancer, stomach cancer, squamous cell carcinoma, synovioma, sweat gland carcinoma, thyroid cancer, Waldenstrom's macroglobulinemia, testicular tumors, uterine cancer and Wilms' tumor.

The present disclosure furthermore relates for the use of such compounds as medicines and to their use for the manufacture of medicaments, more in particular for treating and/or preventing YAP/TAZ-TEAD activation mediated diseases, in particular (i) cancer, more specifically lung cancer, breast cancer, head and neck cancer, oesophageal cancer, kidney cancer, bladder cancer, colon cancer, ovarian cancer, cervical cancer, endometrial cancer, liver cancer (including but not limited to cholangiocarcinoma), skin cancer, pancreatic cancer, gastric cancer, brain cancer and prostate cancer, mesotheliomas, and/or sarcomas and (ii) fibrosis in animals or mammals, more in particular in humans. The disclosure also relates to methods for the preparation of all such compounds and to pharmaceutical compositions comprising them in an effective amount.

In some embodiments, the disclosure relates to the compounds of the invention for use as a medicine, to the use of such compounds as medicines and to their use for the manufacture of medicaments, more in particular for treating and/or preventing YAP/TAZ-TEAD activation mediated diseases more specifically for the treatment and/or prevention of acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute T-cell leukemia, basal cell carcinoma, bile duct carcinoma, bronchogenic carcinoma, chondrosarcoma, chordoma, choriocarcinoma, chronic leukemia, chronic lymphocytic leukemia, chronic myelocytic (granulocytic) leukemia, chronic myelogenous leukemia, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, hemangioblastoma, hepatoma, hepatocellular cancer, hormone insensitive prostate cancer, leiomyosarcoma, leukemia, liposarcoma, lymphangioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, medullary carcinoma, medulloblastoma, melanoma, meningioma, mesothelioma, multiple myeloma, myelogenous leukemia, myeloma, myxosarcoma, neuroblastoma, NUT midline carcinoma (NMC), non-small cell lung cancer, oligodendroglioma, oral cancer, osteogenic sarcoma, papillary adenocarcinomas, papillary carcinoma, pinealoma, polycythemia vera, rectal cancer, renal cell carcinoma, retinoblastoma, rhabdomyosarcoma, sarcoma, sebaceous gland carcinoma, seminoma, small cell lung carcinoma, solid tumors (carcinomas and sarcomas), small cell lung cancer, stomach cancer, squamous cell carcinoma, synovioma, sweat gland carcinoma, thyroid cancer, Waldenstrom's macroglobulinemia, testicular tumors, uterine cancer and Wilms' tumor.

The present disclosure also relates to a method of treatment or prevention of TEAD activation mediated disorders in humans by the administration of one or more such compounds, optionally in combination with one or more other medicines, to a patient in need thereof. The present disclosure also relates to methods of preparing the compounds disclosed herein comprising the steps for synthesis of the compounds described herein.

DETAILED DESCRIPTION

Definitions

The term "YAP/TAZ-TEAD activation mediated diseases" refers to diseases in which hippo signaling is inactivated and whereby YAP/TAZ-TEAD activation is contributing, driving, sustaining, enabling or the like such disease. This might be through loss-of-function mutations or deletions in the genes encoding the upstream regulators of YAP/TAZ-TEAD (e.g. NF2, MST1/2,LATS1/2, FAT1 or SAV1), unleashing constitutive YAP-TEAD transcriptional activity leading to unbridled tumor growth and metastasis of some cancers. This might also be through YAP1 or WWTR1

(TAZ) gene amplifications, gene fusions or activating mutations, or YAP/TAZ overexpression or hyperactivity, among others. YAP/TAZ-TEAD activation mediated diseases therefore refers to cancer, but also includes fibrosis and certain congenital disorders. Cancers that are included in YAP/TAZ-TEAD mediated diseases are, without being limited thereto, lung cancer, breast cancer, head and neck cancer, oesophageal cancer, kidney cancer, bladder cancer, colon cancer, ovarian cancer, cervical cancer, endometrial cancer, liver cancer (including but not limited to cholangiocarcinoma), skin cancer, pancreatic cancer, gastric cancer, brain cancer and prostate cancer, mesotheliomas, and/or sarcomas. Also included are (i) squamous cell carcinomas of the lung, cervix, ovaries, head and neck, oesophagus, and/or skin, or (ii) cancers that originate from neuroectoderm-derived tissues, such as ependymomas, meningiomas, schwannomas, peripheral nerve-sheet tumors and/or neuroblastomas, or (iii) vascular cancers, such as epithelioid haemangioendotheliomas. Fibrotic diseases or fibrosis that is included in YAP/TAZ-TEAD mediated diseases are, without being limited thereto, liver fibrosis, lung fibrosis and heart fibrosis. Congenital disorders that are included in YAP/TAZ-TEAD mediated diseases are, without being limited thereto, Sturge-Weber syndrome and Neurofibromatosis type 2.

YAP/TAZ-TEAD mediated diseases also includes cancers that have developed resistance to prior treatments such has EGFR inhibitors, MEK inhibitors, AXL inhibitors, B-RAF inhibitors, RAS inhibitors and others.

The term "treat" or "treating" as used herein is intended to refer to administration of a compound or composition to a subject for the purpose of effecting a therapeutic benefit or prophylactic benefit through inhibition of the YAP/TAZ-TEAD transcription. Treating includes reversing, ameliorating, alleviating, inhibiting the progress of, lessening the severity of, or preventing a disease, disorder, or condition, or one or more symptoms of such disease, disorder or condition mediated through YAP/TAZ-TEAD transcription. By "therapeutic benefit" is meant eradication, amelioration, reversing, alleviating, inhibiting the progress of or lessening the severity of the underlying disorder being treated. Also, a therapeutic benefit is achieved with the eradication or amelioration of one or more of the physiological symptoms associated with the underlying disorder such that an improvement is observed in the patient, notwithstanding that the patient is afflicted with the underlying disorder in some embodiments. For prophylactic benefit, in some embodiments, the compositions are administered to a patient at risk of developing a particular disease, or to a patient reporting one or more of the physiological symptoms of a disease, even though a diagnosis of this disease has not been made.

The term "subject" as used herein, refers to an animal, for example a mammal, such as a human, a patient, who has been the object of treatment, observation or experiment or who is in need of such treatment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation or partial alleviation of the symptoms of the disease or disorder being treated.

The term "composition" as used herein is intended to encompass a product comprising the specified ingredients in the therapeutically effective amounts, as well as any product which results, directly or indirectly, from combinations of the specified ingredients in the specified amounts.

The term "antagonist" or "inhibitor" as used herein in reference to inhibitors of the YAP/TAZ-TEAD activation, refers to a compound capable of producing, depending on the circumstance, a functional antagonism of YAP/TAZ-TEAD activation.

It is to be noticed that the term "comprising", used in the claims, should not be interpreted as being restricted to the means listed thereafter; it does not exclude other elements or steps.

Reference throughout this specification to "one embodiment" or "an embodiment" means that a particular feature, structure or characteristic described in connection with the embodiment is included in at least one embodiment of the present disclosure..

Furthermore, the particular features, structures or characteristics may be combined in any suitable manner, as would be apparent to one of ordinary skill in the art from this disclosure, in one or more embodiments. Where an indefinite or definite article is used when referring to a singular noun e.g. "a" or "an", "the", this includes a plural of that noun unless something else is specifically stated.

Similarly it should be appreciated that in the description of exemplary embodiments of the disclosure, various features of the disclosure are sometimes grouped together in a single embodiment, figure, or description thereof for the purpose of streamlining the disclosure and aiding in the understanding of one or more of the various inventive aspects.

In each of the following definitions, the number of carbon atoms represents the maximum number of carbon atoms generally optimally present in the substituent or linker; it is understood that where otherwise indicated in the present application, the number of carbon atoms represents the optimal maximum number of carbon atoms for that particular substituent or linker.

The term "leaving group" or "LG" as used herein means a chemical group which is susceptible to be displaced by a nucleophile or cleaved off or hydrolyzed in basic or acidic conditions. In a particular embodiment, a leaving group is selected from a halogen atom (e.g., Cl, Br, I) or a sulfonate (e.g., mesylate, tosylate, triflate).

The term "protecting group" refers to a moiety of a compound that masks or alters the properties of a functional group or the properties of the compound as a whole. The chemical substructure of a protecting group varies widely. One function of a protecting group is to serve as intermediates in the synthesis of the parental drug substance. Chemical protecting groups and strategies for protection/deprotection are well known in the art. See: "Protective Groups in Organic Chemistry", Theodora W. Greene (John Wiley & Sons, Inc., New York, 1991. Protecting groups are often utilized to mask the reactivity of certain functional groups, to assist in the efficiency of desired chemical reactions, e.g. making and breaking chemical bonds in an ordered and planned fashion. Protection of functional groups of a compound alters other physical properties besides the reactivity of the protected functional group, such as the polarity, lipophilicity (hydrophobicity), and other properties which can be measured by common analytical tools. Chemically protected intermediates may themselves be biologically active or inactive.

Protected compounds may also exhibit altered, and in some cases, optimized properties in vitro and in vivo, such as passage through cellular membranes and resistance to enzymatic degradation or sequestration. In this role, protected compounds with intended therapeutic effects may be referred to as prodrugs. Another function of a protecting group is to convert the parental drug into a prodrug, whereby the parental drug is released upon conversion of the prodrug in vivo. Because active prodrugs may be absorbed more effectively than the parental drug, prodrugs may possess greater potency in vivo than the parental drug. Protecting groups are removed either in vitro, in the instance of chemical intermediates, or in vivo, in the case of prodrugs. With chemical intermediates, it is not particularly important that the resulting products after deprotection, e.g. alcohols, be physiologically acceptable, although in general it is more desirable if the products are pharmacologically innocuous.

The term "alkyl" or "$C_{1-18}$alkyl" as used herein means $C_1$-$C_{18}$ normal, secondary, or tertiary, linear, branched or straight hydrocarbon with no site of unsaturation. Examples are methyl, ethyl, 1-propyl (n-propyl), 2-propyl (iPr), 1-butyl, 2-methyl-1-propyl(i-Bu), 2-butyl (s-Bu), 2-dimethyl-2-propyl (t-Bu), 1-pentyl (n-pentyl), 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, and n-icosyl. In particular embodiments, the term alkyl refers to $C_{1-12}$alkyl ($C_{1-12}$ hydrocarbons), yet more in particular to $C_{1-9}$alkyl ($C_{1-9}$ hydrocarbons), yet more in particular to $C_{1-6}$alkyl ($C_{1-6}$ hydrocarbons) as further defined herein above.

The term "haloalkyl" as a group or part of a group, refers to an alkyl group having the meaning as defined above wherein one, two, or three hydrogen atoms are each replaced with a halogen as defined herein. Non-limiting examples of such haloalkyl groups include chloromethyl, 1-bromoethyl, fluoromethyl, difluoromethyl, trifluoromethyl, 1,1,1-trifluoroethyl and the like.

The term "alkoxy" or "alkyloxy", as a group or part of a group, refers to a group having the formula —$OR^b$ wherein $R^b$ is $C_{1-6}$alkyl as defined herein above. Non-limiting examples of suitable $C_{1-6}$alkoxy include methoxy, ethoxy, propoxy, isopropoxy, butoxy, isobutoxy, sec-butoxy, tert-butoxy, pentyloxy and hexyloxy.

The term "haloalkoxy", as a group or part of a group, refers to a group of formula —O—$R^c$, wherein $R^c$ is haloalkyl as defined herein. Non-limiting examples of suitable haloalkoxy include fluoromethoxy, difluoromethoxy, trifluoromethoxy, 2,2,2-trifluoroethoxy, 1,1,2,2-tetrafluoroethoxy, 2-fluoroethoxy, 2-chloroethoxy, 2,2-difluoroethoxy, 2,2,2-trichloroethoxy, trichloromethoxy, 2-bromoethoxy, pentafluoroethyl, 3,3,3-trichloropropoxy, 4,4,4-trichlorobutoxy.

The term "cycloalkyl" or "$C_{3-18}$ cycloalkyl" as used herein and unless otherwise stated means a saturated hydrocarbon monovalent group having from 3 to 18 carbon atoms consisting of or comprising a $C_{3-10}$ monocyclic or $C_{7-18}$ polycyclic saturated hydrocarbon, such as for instance cyclopropyl, cyclobutyl, cyclopentyl, cyclopropylethylene, methylcyclopropylene, cyclohexyl, cycloheptyl, cyclooctyl, cyclooctylmethylene, norbornyl, fenchyl, trimethyltricycloheptyl, decalinyl, adamantyl and the like. In particular embodiments, the term cycloalkyl refers to $C_{3-12}$cycloalkyl (saturated cyclic $C_{3-12}$hydrocarbons), yet more in particular to $C_{3-9}$cycloalkyl (saturated cyclic $C_{3-9}$hydrocarbons), still more in particular to $C_{3-6}$cycloalkyl (saturated cyclic $C_{3-6}$hydrocarbons) as further defined herein above. For the avoidance of doubt, fused systems of a cycloalkyl ring with a heterocyclic ring are considered as heterocycle irrespective of the ring that is bound to the core structure. Fused systems of a cycloalkyl ring with an aryl ring are considered as aryl irrespective of the ring that is bound to the core structure. Fused systems of a cycloalkyl ring with a heteroaryl ring are considered as heteroaryl irrespective of the ring that is bound to the core structure.

The term "alkenyl" or "$C_{2-18}$alkenyl" as used herein is $C_2$-$C_{18}$ normal, secondary or tertiary, linear, branched or straight hydrocarbon with at least one site (usually 1 to 3, preferably 1) of unsaturation, namely a carbon-carbon, sp2 double bond. Examples include, but are not limited to: ethylene or vinyl (—CH═$CH_2$), allyl (—$CH_2$CH═$CH_2$), and 5-hexenyl (—$CH_2CH_2CH_2CH_2$CH═$CH_2$). The double bond may be in the cis or trans configuration. In particular embodiments, the term alkenyl refers to $C_{2-12}$alkenyl ($C_{2-12}$hydrocarbons), yet more in particular to $C_{2-9}$ alkenyl ($C_{2-9}$ hydrocarbons), still more in particular to $C_{2-6}$ alkenyl ($C_{2-6}$hydrocarbons) as further defined herein above with at least one site (usually 1 to 3, preferably 1) of unsaturation, namely a carbon-carbon, sp2 double bond.

The term "alkenyloxy", as a group or part of a group, refers to a group having the formula —$OR^d$ wherein $R^d$ is alkenyl as defined herein above.

The term "cycloalkenyl" as used herein refers to a non-aromatic hydrocarbon group having from 5 to 18 carbon atoms with at least one site (usually 1 to 3, preferably 1) of unsaturation, namely a carbon-carbon, sp2 double bond and consisting of or comprising a $C_{5-10}$ monocyclic or $C_{7-18}$ polycyclic hydrocarbon. Examples include, but are not limited to: cyclopentenyl (—$C_5H_7$), cyclopentenylpropylene, methylcyclohexenylene and cyclohexenyl (—$C_6H_9$). The double bond may be in the cis or trans configuration. In particular embodiments, the term cycloalkenyl refers to $C_{5-12}$ cycloalkenyl (cyclic $C_{5-12}$ hydrocarbons), yet more in particular to $C_{5-9}$ cycloalkenyl (cyclic $C_{5-9}$ hydrocarbons), still more in particular to $C_{5-6}$ cycloalkenyl (cyclic $C_{5-6}$ hydrocarbons) as further defined herein above with at least one site of unsaturation, namely a carbon-carbon, sp2 double bond. For the avoidance of doubt, fused systems of a cycloalkenyl ring with a heterocyclic ring are considered as heterocycle irrespective of the ring that is bound to the core structure. Fused systems of a cycloalkenyl ring with an aryl ring are considered as aryl irrespective of the ring that is bound to the core structure. Fused systems of a cycloalkenyl ring with a heteroaryl ring are considered as heteroaryl irrespective of the ring that is bound to the core structure.

The term "alkynyl" or "$C_{2-18}$alkynyl" as used herein refers to $C_2$-$C_{18}$ normal, secondary, tertiary, linear, branched or straight hydrocarbon with at least one site (usually 1 to 3, preferably 1) of unsaturation, namely a carbon-carbon, sp triple bond. Examples include, but are not limited to: ethynyl (—C≡CH), 3-ethyl-cyclohept-1-ynylene, and 1-propynyl (propargyl, —$CH_2$C≡CH). In particular embodiments, the term alkynyl refers to $C_{2-12}$ alkynyl ($C_{2-12}$ hydrocarbons), yet more in particular to $C_{2-9}$ alkynyl ($C_{2-9}$ hydrocarbons) yet more in particular to $C_{2-6}$ alkynyl ($C_{2-6}$ hydrocarbons) as further defined herein above with at least one site (usually 1 to 3, preferably 1) of unsaturation, namely a carbon-carbon, sp triple bond.

The term "alkynyloxy", as a group or part of a group, refers to a group having the formula —$OR^e$ wherein $R^e$ is alkynyl as defined herein above.

The term "cycloalkynyl" as used herein refers to a non-aromatic hydrocarbon group having from 5 to 18 carbon atoms with at least one site (usually 1 to 3, preferably 1) of unsaturation, namely a carbon-carbon, sp triple bond and consisting of or comprising a $C_{5-10}$ monocyclic or $C_{7-18}$ polycyclic hydrocarbon. Examples include, but are not limited to: cyclohept-1-yne, 3-ethyl-cyclohept-1-ynylene, 4-cyclohept-1-yn-methylene and ethylene-cyclohept-1-yne. In particular embodiments, the term cycloalkynyl refers to $C_{5-10}$ cycloalkynyl (cyclic $C_{5-10}$ hydrocarbons), yet more in particular to $C_{5-9}$ cycloalkynyl (cyclic $C_{5-9}$ hydrocarbons), still more in particular to $C_{5-6}$ cycloalkynyl (cyclic $C_{5-6}$ hydrocarbons) as further defined herein above with at least one site (usually 1 to 3, preferably 1) of unsaturation, namely a carbon-carbon, sp triple bond. For the avoidance of doubt, fused systems of a cycloalkynyl ring with a heterocyclic ring are considered as heterocycle irrespective of the ring that is bound to the core structure. Fused systems of a cycloalkynyl ring with an aryl ring are considered as aryl irrespective of the ring that is bound to the core structure. Fused systems of a cycloalkynyl ring with a heteroaryl ring are considered as heteroaryl irrespective of the ring that is bound to the core structure.

The term "alkylene" as used herein each refer to a saturated, branched or straight chain hydrocarbon group of 1-18 carbon atoms (more in particular $C_{1-12}$, $C_{1-9}$ or $C_{1-6}$ carbon atoms), and having two monovalent group centers derived by the removal of two hydrogen atoms from the same or two different carbon atoms of a parent alkane. Typical alkylene include, but are not limited to: methylene ($—CH_2—$), 1,2-ethyl ($—CH_2CH_2—$), 1,3-propyl ($—CH_2CH_2CH_2—$), 1,4-butyl ($—CH_2CH_2CH_2CH_2—$), and the like.

The term "alkenylene" as used herein each refer to a branched or straight chain hydrocarbon of 2-18 carbon atoms (more in particular $C_{2-12}$, $C_{2-9}$ or $C_{2-6}$ carbon atoms) with at least one site (usually 1 to 3, preferably 1) of unsaturation, namely a carbon-carbon, sp2 double bond, and having two monovalent centers derived by the removal of two hydrogen atoms from the same or two different carbon atoms of a parent alkene.

The term "alkynylene" as used herein each refer to a branched or straight chain hydrocarbon of 2-18 carbon atoms (more in particular $C_{2-12}$, $C_{2-9}$ or $C_{2-6}$ carbon atoms) with at least one site (usually 1 to 3, preferably 1) of unsaturation, namely a carbon-carbon, sp triple bond, and having two monovalent centers derived by the removal of two hydrogen atoms from the same or two different carbon atoms of a parent alkyne.

The term "heteroalkyl" as used herein refers to an alkyl wherein one or more carbon atoms are replaced by one or more atoms selected from the group comprising oxygen, nitrogen or sulphur atom. The term heteroalkyl thus comprises $—O—R^b$, $—NR^o—R^b$, $—R^a—O—R^b$, and $—S—R^b$, wherein $R^a$ is alkylene, $R^b$ is alkyl, and $R^o$ is hydrogen or alky as defined herein. In particular embodiments, the term refers to $C_{1-12}$heteroalkyl, $C_{1-9}$heteroalkyl or $C_{1-6}$heteroalkyl. In some embodiments heteroalkyl is selected from the group comprising alkyloxy, alkyl-oxy-alkyl, (mono or di)alkylamino, (mono or di-)alkyl-amino-alkyl, alkylthio, and alkyl-thio-alkyl.

The term "heteroalkenyl" as used herein refers to an acyclic alkenyl wherein one or more carbon atoms are replaced by one or more atoms selected from oxygen, nitrogen or sulphur atom. The term heteroalkenyl thus comprises $—O—R^d$, $—NH—(R^d)$, $—N(R^d))_2$, $—N(R^b)(R^d)$, and $—S—R^d$ wherein $R^b$ is alkyl and $R^d$ is alkenyl as defined herein. In particular embodiments, the term refers to $C_{2-12}$heteroalkenyl, $C_{2-9}$heteroalkenyl or $C_{2-6}$heteroalkenyl. In some embodiments heteroalkenyl is selected from the group comprising alkenyloxy, alkenyl-oxy-alkenyl, (mono or di-)alkenylamino, (mono or di-)alkenyl-amino-alkenyl, alkenylthio, and alkenyl-thio-alkenyl.

The term "heteroalkynyl" as used herein refers to an acyclic alkynyl wherein one or more carbon atoms are replaced by an oxygen, nitrogen or sulphur atom. The term heteroalkynyl thus comprises but is not limited to $—O—R^d$, $—N(R^d)_2$, $NHR^d$, $—N(R^b)(R^e)$, $—N(R^d)(R^e)$, and $—S—R^d$ wherein $R^b$ is alkyl, $R^e$ is alkynyl and $R^d$ is alkenyl as defined herein. In particular embodiments, the term refers to $C_{2-12}$heteroalkynyl, $C_{2-9}$heteroalkynyl or $C_{2-6}$heteroalkynyl. In some embodiments the term heteroalkynyl is selected from the group comprising alkynyloxy, alkynyl-oxy-alkynyl, (mono or di-)alkynylamino, (mono or di-)alkynyl-amino-alkynyl, alkynylthio, alkynyl-thio-alkynyl, The term "heteroalkylene" as used herein refers to an alkylene wherein one or more carbon atoms are replaced by one or more oxygen, nitrogen or sulphur atoms.

The term "heteroalkenylene" as used herein refers to an alkenylene wherein one or more carbon atoms are replaced by one or more oxygen, nitrogen or sulphur atoms.

The term "heteroalkynylene" as used herein refers to an alkynylene wherein one or more carbon atoms are replaced by one or more oxygen, nitrogen or sulphur atom.

The term "aryl" as used herein means an aromatic hydrocarbon of 6-20 carbon atoms derived by the removal of hydrogen from a carbon atom of a parent aromatic ring system. Typical aryl groups include, but are not limited to 1 ring, or 2 or 3 rings fused together, derived from benzene, naphthalene, anthracene, biphenyl, and the like. In particular embodiments, the term aryl refers to a 6-14 carbon atoms membered aromatic cycle, yet more in particular refers to a 6-10 carbon atoms membered aromatic cycle.

Fused systems of an aryl ring with a cycloalkyl ring, or a cycloalkenyl ring, or a cycloalkynyl ring, are considered as aryl irrespective of the ring that is bound to the core structure. Fused systems of an aryl ring with a heterocycle are considered as heterocycle irrespective of the ring that is bound to the core structure. Thus, indoline, dihydrobenzofurane, dihydrobenzothiophene and the like are considered as heterocycle according to the disclosure. Fused systems of an aryl ring with a heteroaryl ring are considered as heteroaryl irrespective of the ring that is bound to the core structure.

The term "aryloxy", as a group or part of a group, refers to a group having the formula $—OR^g$ wherein $R^g$ is aryl as defined herein above.

The term "arylalkyl" or "arylalkyl-" as used herein refers to an alkyl in which one of the hydrogen atoms bonded to a carbon atom, typically a terminal or sp3 carbon atom, is replaced with an aryl. Typical arylalkyl groups include, but are not limited to, benzyl, 2-phenylethan-1-yl, 2-phenylethen-1-yl, naphthylmethyl, 2-naphthylethyl, and the like. The arylalkyl group comprises 6 to 20 carbon atoms, e.g. the alkyl moiety of the arylalkyl group is 1 to 6 carbon atoms and the aryl moiety is 6 to 14 carbon atoms.

The term "arylalkyloxy", as a group or part of a group, refers to a group having the formula $—O—R^a—R^g$ wherein $R^g$ is aryl, and $R^a$ is alkylene as defined herein above.

The term "arylalkenyl" or "arylalkenyl-" as used herein refers to an alkenyl in which one of the hydrogen atoms bonded to a carbon atom, is replaced with an aryl. The arylalkenyl group comprises 6 to 20 carbon atoms, e.g. the alkenyl moiety of the arylalkenyl group is 1 to 6 carbon atoms and the aryl moiety is 6 to 14 carbon atoms.

The term "arylalkynyl" or "arylalkynyl-" as used herein refers to an alkynyl in which one of the hydrogen atoms bonded to a carbon atom, is replaced with an aryl. The arylalkynyl group comprises 6 to 20 carbon atoms, e.g. the alkynyl moiety of the arylalkynyl group is 1 to 6 carbon atoms and the aryl moiety is 6 to 14 carbon atoms.

The term "arylheteroalkyl" or "arylheteroalkyl-" as used herein refers to a heteroalkyl in which one of the hydrogen atoms bonded to a carbon atom, typically a terminal or sp3 carbon atom, is replaced with an aryl. The arylheteroalkyl group comprises 6 to 20 carbon atoms, e.g. the heteroalkyl moiety of the arylheteroalkyl group is 1 to 6 carbon atoms and the aryl moiety is 6 to 14 carbon atoms. In some embodiments arylheteroalkyl is selected from the group comprising aryl-O-alkyl, arylalkyl-O-alkyl, aryl-NH-alkyl, aryl-N(alkyl)$_2$, arylalkyl-NH-alkyl, arylalkyl-N-(alkyl)$_2$, aryl-S-alkyl, and arylalkyl-S-alkyl.

The term "arylheteroalkenyl" or "arylheteroalkenyl-" as used herein refers to a heteroalkenyl in which one of the hydrogen atoms bonded to a carbon atom, is replaced with an aryl. The arylheteroalkenyl group comprises 6 to 20 carbon atoms, e.g. the heteroalkenyl moiety of the arylheteroalkenyl group is 1 to 6 carbon atoms and the aryl moiety is 6 to 14 carbon atoms. In some embodiments arylheteroalkenyl is selected from the group comprising aryl-O-alkenyl, arylalkenyl-O-alkenyl, aryl-NH-alkenyl, aryl-N(alkenyl)$_2$, arylalkenyl-NH-alkenyl, arylalkenyl-N-(alkenyl)$_2$, aryl-S-alkenyl, and arylalkenyl-S-alkenyl.

The term "arylheteroalkynyl" or "arylheteroalkynyl-" as used herein refers to a heteroalkynyl in which one of the hydrogen atoms bonded to a carbon atom, is replaced with an aryl. The arylheteroalkynyl group comprises 6 to 20 carbon atoms, e.g. the heteroalkynyl moiety of the arylheteroalkynyl group is 1 to 6 carbon atoms and the aryl moiety is 6 to 14 carbon atoms. In some embodiments arylheteroalkynyl is selected from the group comprising aryl-O-alkynyl, arylalkynyl-O-alkynyl, aryl-NH-alkynyl, aryl-N(alkynyl)$_2$, arylalkynyl-NH-alkynyl, arylalkynyl-N-(alkynyl)$_2$, aryl-S-alkynyl, and arylalkynyl-S-alkynyl.

The term "heterocycle" or "heterocyclyl" as used herein refer to non-aromatic, fully saturated or partially unsaturated ring system of 3 to 18 atoms including at least one N, O, S, or P (for example, 3 to 7 member monocyclic, 7 to 11 member bicyclic, or comprising a total of 3 to 10 ring atoms). Each ring of the heterocycle or heterocyclyl may have 1, 2, 3 or 4 heteroatoms selected from N, O and/or S, where the N and S heteroatoms may optionally be oxidized and the N heteroatoms may optionally be quaternized; and wherein at least one carbon atom of heterocyclyl can be oxidized to form at least one C═O. The heterocycle may be attached at any heteroatom or carbon atom of the ring or ring system, where valence allows. The rings of multi-ring heterocyclyls or heterocycles may be fused, bridged and/or joined through one or more spiro atoms. Fused systems of a heterocycle or heterocyclyl with an aryl ring are considered as heterocycle or heterocyclyl irrespective of the ring that is bound to the core structure. Fused systems of a heterocycle or heterocyclyl with a heteroaryl ring are considered as heteroaryl irrespective of the ring that is bound to the core structure.

Non limiting exemplary heterocycles or heterocyclic groups include piperidinyl, piperazinyl, homopiperazinyl, morpholinyl, tetrahydropyranyl, tetrahydrofuranyl, pyrrolidinyl, aziridinyl, oxiranyl, thiiranyl, azetidinyl, oxetanyl, thietanyl, 2-imidazolinyl, pyrazolidinyl imidazolidinyl, isoxazolinyl, oxazolidinyl, isoxazolidinyl, thiazolidinyl, isothiazolidinyl, succinimidyl, 3H-indolyl, indolinyl, isoindolinyl, chromanyl (also known as 3,4-dihydrobenzo[b]pyranyl), 2H-pyrrolyl, 1-pyrrolinyl, 2-pyrrolinyl, 3-pyrrolinyl, 4H-quinolizinyl, 2-oxopiperazinyl, 2-pyrazolinyl, 3-pyrazolinyl, tetrahydro-2H-pyranyl, 2H-pyranyl, 4H-pyranyl, 3,4-dihydro-2H-pyranyl, 3-dioxolanyl, 1,4-dioxanyl, 2,5-dioximidazolidinyl, 2-oxopiperidinyl, 2-oxopyrrolodinyl, indolinyl, tetrahydrothiophenyl, tetrahydroquinolinyl, tetrahydroisoquinolin-1-yl, tetrahydroisoquinolin-2-yl, tetrahydroisoquinolin-3-yl, tetrahydroisoquinolin-4-yl, thiomorpholin-4-yl, thiomorpholin-4-ylsulfoxide, thiomorpholin-4-ylsulfone, 1,3-dioxolanyl, 1,4-oxathianyl, 1,4-dithianyl, 1,3,5-trioxanyl, 1H-pyrrolizinyl, tetrahydro-1,1-dioxothiophenyl, N-formylpiperazinyl, and morpholin-4-yl. The term "aziridinyl" as used herein includes aziridin-1-yl and aziridin-2-yl. The term "oxyranyl" as used herein includes oxyranyl-2-yl. The term "thiiranyl" as used herein includes thiiran-2-yl. The term "azetidinyl" as used herein includes azetidin-1-yl, azetidin-2-yl and azetidin-3-yl. The term "oxetanyl" as used herein includes oxetan-2-yl and oxetan-3-yl. The term "thietanyl" as used herein includes thietan-2-yl and thietan-3-yl. The term "pyrrolidinyl" as used herein includes pyrrolidin-1-yl, pyrrolidin-2-yl and pyrrolidin-3-yl. The term "tetrahydrofuranyl" as used herein includes tetrahydrofuran-2-yl and tetrahydrofuran-3-yl. The term "tetrahydrothiophenyl" as used herein includes tetrahydrothiophen-2-yl and tetrahydrothiophen-3-yl. The term "succinimidyl" as used herein includes succinimid-1-yl and succininmid-3-yl. The term "dihydropyrrolyl" as used herein includes 2,3-dihydropyrrol-1-yl, 2,3-dihydro-1H-pyrrol-2-yl, 2,3-dihydro-1H-pyrrol-3-yl, 2,5-dihydropyrrol-1-yl, 2,5-dihydro-1H-pyrrol-3-yl and 2,5-dihydropyrrol-5-yl. The term "2H-pyrrolyl" as used herein includes 2H-pyrrol-2-yl, 2H-pyrrol-3-yl, 2H-pyrrol-4-yl and 2H-pyrrol-5-yl. The term "3H-pyrrolyl" as used herein includes 3H-pyrrol-2-yl, 3H-pyrrol-3-yl, 3H-pyrrol-4-yl and 3H-pyrrol-5-yl. The term "dihydrofuranyl" as used herein includes 2,3-dihydrofuran-2-yl, 2,3-dihydrofuran-3-yl, 2,3-dihydrofuran-4-yl, 2,3-dihydrofuran-5-yl, 2,5-dihydrofuran-2-yl, 2,5-dihydrofuran-3-yl, 2,5-dihydrofuran-4-yl and 2,5-dihydrofuran-5-yl. The term "dihydrothiophenyl" as used herein includes 2,3-dihydrothiophen-2-yl, 2,3-dihydrothiophen-3-yl, 2,3-dihydrothiophen-4-yl, 2,3-dihydrothiophen-5-yl, 2,5-dihydrothiophen-2-yl, 2,5-dihydrothiophen-3-yl, 2,5-dihydrothiophen-4-yl and 2,5-dihydrothiophen-5-yl. The term "imidazolidinyl" as used herein includes imidazolidin-1-yl, imidazolidin-2-yl and imidazolidin-4-yl. The term "pyrazolidinyl" as used herein includes pyrazolidin-1-yl, pyrazolidin-3-yl and pyrazolidin-4-yl. The term "imidazolinyl" as used herein includes imidazolin-1-yl, imidazolin-2-yl, imidazolin-4-yl and imidazolin-5-yl. The term "pyrazolinyl" as used herein includes 1-pyrazolin-3-yl, 1-pyrazolin-4-yl, 2-pyrazolin-1-yl, 2-pyrazolin-3-yl, 2-pyrazolin-4-yl, 2-pyrazolin-5-yl, 3-pyrazolin-1-yl, 3-pyrazolin-2-yl, 3-pyrazolin-3-yl, 3-pyrazolin-4-yl and 3-pyrazolin-5-yl. The term "dioxolanyl" also known as "1,3-dioxolanyl" as used herein includes dioxolan-2-yl, dioxolan-4-yl and dioxolan-5-yl. The term "dioxolyl" also known as "1,3-dioxolyl" as used herein includes dioxol-2-yl, dioxol-4-yl and dioxol-5-yl. The term "oxazolidinyl" as used herein includes oxazolidin-2-yl, oxazolidin-3-yl, oxazolidin-4-yl and oxazolidin-5-yl. The term "isoxazolidinyl" as used herein includes isoxazolidin-2-yl, isoxazolidin-3-yl, isoxazolidin-4-yl and isoxazolidin-5-yl. The term "oxazolinyl" as used herein includes 2-oxazolinyl-2-yl, 2-oxazolinyl-4-yl, 2-oxazolinyl-5-yl, 3-oxazolinyl-2-yl, 3-oxazolinyl-4-yl, 3-oxazolinyl-5-yl, 4-oxazolinyl-2-yl, 4-oxazolinyl-3-yl, 4-oxazolinyl-4-yl and 4-oxazolinyl-5-yl. The term "isoxazolinyl" as used herein includes 2-isoxazolinyl-3-yl, 2-isoxazolinyl-4-yl, 2-isoxazolinyl-5-yl, 3-isoxazolinyl-3-yl, 3-isoxazolinyl-4-yl, 3-isoxazolinyl-5-yl, 4-isoxazolinyl-2-yl, 4-isoxazolinyl-3-yl, 4-isoxazolinyl-4-yl and 4-isoxazolinyl-5-yl. The term "thiazolidinyl" as used herein includes thiazolidin-2-yl, thiazolidin-3-yl, thiazolidin-4-yl and thiazolidin-5-yl. The term "isothiazolidinyl" as used herein includes isothiazolidin-2-yl, isothiazolidin-3-yl, isothiazolidin-4-yl and isothiazolidin-5-yl. The term "thiazolinyl" as used herein includes 2-thiazolinyl-2-yl, 2-thiazolinyl-4-yl, 2-thiazolinyl-5-yl, 3-thiazolinyl-2-yl, 3-thiazolinyl-4-yl, 3-thiazolinyl-5-yl, 4-thiazolinyl-2-yl, 4-thiazolinyl-3-yl, 4-thiazolinyl-4-yl and 4-thiazolinyl-5-yl. The term "isothiazolinyl" as used herein includes 2-isothiazolinyl-3-yl, 2-isothiazolinyl-4-yl, 2-isothiazolinyl-5-yl, 3-isothiazolinyl-3-yl, 3-isothiazolinyl-4-yl, 3-isothiazolinyl-5-yl, 4-isothiazolinyl-2-yl, 4-isothiazolinyl-3-yl, 4-isothiazolinyl-4-yl and 4-isothiazolinyl-5-yl. The term "piperidyl" also known as "piperidinyl" as used herein includes piperid-1-yl, piperid-2-yl, piperid-3-yl and piperid-4-yl. The term "dihydropyridinyl" as used herein includes 1,2-dihydropyridin-1-yl, 1,2-dihydropyridin-2-yl, 1,2-dihydropyridin-3-yl, 1,2-dihydropyridin-4-yl, 1,2-dihydropyridin-5-yl, 1,2-dihydropyridin-6-yl, 1,4-dihydropyridin-1-yl, 1,4-dihydropyridin-2-yl, 1,4-dihydropyridin-3-yl, 1,4-dihydropyridin-4-yl, 2,3-dihydropyridin-2-yl, 2,3-dihydropyridin-3-yl, 2,3-dihydropyridin-4-yl, 2,3-dihydropyridin-5-yl, 2,3-dihydropyridin-6-yl, 2,5-dihydropyridin-2-yl, 2,5-dihydropyridin-3-yl, 2,5-dihydropyridin-4-yl, 2,5-dihydropyridin-5-yl, 2,5-dihydropyridin-6-yl, 3,4-dihydropyridin-2-yl, 3,4-dihydropyridin-3-yl, 3,4-dihydropyridin-4-yl, 3,4-dihydropyridin-5-yl and 3,4-dihydropyridin-6-yl. The term "tetrahydropyridinyl" as used herein includes 1,2,3,4-tetrahydropyridin-1-yl, 1,2,3,4-tetrahydropyridin-2-yl, 1,2,3,4-tetrahydropyridin-3-yl, 1,2,3,4-tetrahydropyridin-4-yl, 1,2,3,4-tetrahydropyridin-5-yl, 1,2,3,4-tetrahydropyridin-6-yl, 1,2,3,6-tetrahydropyridin-1-yl, 1,2,3,6-tetrahydropyridin-2-yl, 1,2,3,6-tetrahydropyridin-3-yl, 1,2,3,6-tetrahydropyridin-4-yl, 1,2,3,6-tetrahydropyridin-5-yl, 1,2,3,6-tetrahydropyridin-6-yl, 2,3,4,5-tetrahydropyridin-2-yl, 2,3,4,5-tetrahydropyridin-3-yl, 2,3,4,5-tetrahydropyridin-3-yl, 2,3,4,5-tetrahydropyridin-4-yl, 2,3,4,5-tetrahydropyridin-5-yl and 2,3,4,5-tetrahydropyridin-6-yl. The term "tetrahydropyranyl" also known as "oxanyl" or "tetrahydro-2H-pyranyl", as used herein includes tetrahydropyran-2-yl, tetrahydropyran-3-yl and tetrahydropyran-4-yl. The term "2H-pyranyl" as used herein includes 2H-pyran-2-yl, 2H-pyran-3-yl, 2H-pyran-4-yl, 2H-pyran-5-yl and 2H-pyran-6-yl. The term "4H-pyranyl" as used herein includes 4H-pyran-2-yl, 4H-pyran-3-yl and 4H-pyran-4-yl. The term "3,4-dihydro-2H-pyranyl" as used herein includes 3,4-dihydro-2H-pyran-2-yl, 3,4-dihydro-2H-pyran-3-yl, 3,4-dihydro-2H-pyran-4-yl, 3,4-dihydro-2H-pyran-5-yl and 3,4-dihydro-2H-pyran-6-yl. The term "3,6-dihydro-2H-pyranyl" as used herein includes 3,6-dihydro-2H-pyran-2-yl, 3,6-dihydro-2H-pyran-3-yl, 3,6-dihydro-2H-pyran-4-yl, 3,6-dihydro-2H-pyran-5-yl and 3,6-dihydro-2H-pyran-6-yl. The term "tetrahydrothiophenyl", as used herein includes tetrahydrothiophen-2-yl, tetrahydrothiophenyl-3-yl and tetrahydrothiophenyl-4-yl. The term "2H-thiopyranyl" as used herein includes 2H-thiopyran-2-yl, 2H-thiopyran-3-yl, 2H-thiopyran-4-yl, 2H-thiopyran-5-yl and 2H-thiopyran-6-yl. The term "4H-thiopyranyl" as used herein includes 4H-thiopyran-2-yl, 4H-thiopyran-3-yl and 4H-thiopyran-4-yl. The term "3,4-dihydro-2H-thiopyranyl" as used herein includes 3,4-dihydro-2H-thiopyran-2-yl, 3,4-dihydro-2H-thiopyran-3-yl, 3,4-dihydro-2H-thiopyran-4-yl, 3,4-dihydro-2H-thiopyran-5-yl and 3,4-dihydro-2H-thiopyran-6-yl. The term "3,6-dihydro-2H-thiopyranyl" as used herein includes 3,6-dihydro-2H-thiopyran-2-yl, 3,6-dihydro-2H-thiopyran-3-yl, 3,6-dihydro-2H-thiopyran-4-yl, 3,6-dihydro-2H-thiopyran-5-yl and 3,6-dihydro-2H-thiopyran-6-yl. The term "piperazinyl" also known as "piperazidinyl" as used herein includes piperazin-1-yl and piperazin-2-yl. The term "morpholinyl" as used herein includes morpholin-2-yl, morpholin-3-yl and morpholin-4-yl. The term "thiomorpholinyl" as used herein includes thiomorpholin-2-yl, thiomorpholin-3-yl and thiomorpholin-4-yl. The term "dioxanyl" as used herein includes 1,2-dioxan-3-yl, 1,2-dioxan-4-yl, 1,3-dioxan-2-yl, 1,3-dioxan-4-yl, 1,3-dioxan-5-yl and 1,4-dioxan-2-yl. The term "dithianyl" as used herein includes 1,2-dithian-3-yl, 1,2-dithian-4-yl, 1,3-dithian-2-yl, 1,3-dithian-4-yl, 1,3-dithian-5-yl and 1,4-dithian-2-yl. The term "oxathianyl" as used herein includes oxathian-2-yl and oxathian-3-yl. The term "trioxanyl" as used herein includes 1,2,3-trioxan-4-yl, 1,2,3-trioxan-5-yl, 1,2,4-trioxan-3-yl, 1,2,4-trioxan-5-yl, 1,2,4-trioxan-6-yl and 1,3,4-trioxan-2-yl. The term "azepanyl" as used herein includes azepan-1-yl, azepan-2-yl, azepan-3-yl and azepan-4-yl. The term "homopiperazinyl" as used herein includes homopiperazin-1-yl, homopiperazin-2-yl, homopiperazin-3-yl and homopiperazin-4-yl. The term "indolinyl" as used herein includes indolin-1-yl, indolin-2-yl, indolin-3-yl, indolin-4-yl, indolin-5-yl, indolin-6-yl, and indolin-7-yl. The term "quinolizinyl" as used herein includes quinolizidin-1-yl, quinolizidin-2-yl, quinolizidin-3-yl and quinolizidin-4-yl. The term "isoindolinyl" as used herein includes isoindolin-1-yl, isoindolin-2-yl, isoindolin-3-yl, isoindolin-4-yl, isoindolin-5-yl, isoindolin-6-yl, and isoindolin-7-yl. The term "3H-indolyl" as used herein includes 3H-indol-2-yl, 3H-indol-3-yl, 3H-indol-4-yl, 3H-indol-5-yl, 3H-indol-6-yl, and 3H-indol-7-yl. The term "quinolizinyl" as used herein includes quinolizidin-1-yl, quinolizidin-2-yl, quinolizidin-3-yl and quinolizidin-4-yl. The term "quinolizinyl" as used herein includes quinolizidin-1-yl, quinolizidin-2-yl, quinolizidin-3-yl and quinolizidin-4-yl. The term "tetrahydroquinolinyl" as used herein includes tetrahydroquinolin-1-yl, tetrahydroquinolin-2-yl, tetrahydroquinolin-3-yl, tetrahydroquinolin-4-yl, tetrahydroquinolin-5-yl, tetrahydroquinolin-6-yl, tetrahydroquinolin-7-yl and tetrahydroquinolin-8-yl. The term "tetrahydroisoquinolinyl" as used herein includes tetrahydroisoquinolin-1-yl, tetrahydroisoquinolin-2-yl, tetrahydroisoquinolin-3-yl, tetrahydroisoquinolin-4-yl, tetrahydroisoquinolin-5-yl, tetrahydroisoquinolin-6-yl, tetrahydroisoquinolin-7-yl and tetrahydroisoquinolin-8-yl. The term "chromanyl" as used herein includes chroman-2-yl, chroman-3-yl, chroman-4-yl, chroman-5-yl, chroman-6-yl, chroman-7-yl and chroman-8-yl. The term "1H-pyrrolizine" as used herein includes 1H-pyrrolizin-1-yl, 1H-pyrrolizin-2-yl, 1H-pyrrolizin-3-yl, 1H-pyrrolizin-5-yl, 1H-pyrrolizin-6-yl and 1H-pyrrolizin-7-yl. The term "3H-pyrrolizine" as used herein includes 3H-pyrrolizin-1-yl, 3H-pyrrolizin-2-yl, 3H-pyrrolizin-3-yl, 3H-pyrrolizin-5-yl, 3H-pyrrolizin-6-yl and 3H-pyrrolizin-7-yl.

The term "heteroaryl" refers to an aromatic ring system of 5 to 18 atoms including at least one N, O, S, or P, containing 1 or 2 rings which can be fused together or linked covalently, each ring typically containing 5 to 6 atoms; at least one of said rings is aromatic, where the N and S heteroatoms may optionally be oxidized and the N heteroatoms may optionally be quaternized, and wherein at least one carbon atom of said heteroaryl can be oxidized to form at least one C═O. Fused systems of a heteroaryl ring with a cycloalkyl ring, or a cycloalkenyl ring, or a cycloalkynyl ring, are considered as heteroaryl irrespective of the ring that is bound to the core structure. Fused systems of a heteroaryl ring with a heterocycle are considered as heteroaryl irrespective of the ring that is bound to the core structure. Fused systems of a hetero aryl ring with an aryl ring are considered as heteroaryl irrespective of the ring that is bound to the core structure.

Non-limiting examples of such heteroaryl, include: triazol-2-yl, pyridinyl, 1H-pyrazol-5-yl, pyrrolyl, furanyl, thiophenyl, pyrazolyl, imidazolyl, oxazolyl, isoxazolyl, thiazolyl, isothiazolyl, triazolyl, oxadiazolyl, thiadiazolyl, tetrazolyl, oxatriazolyl, thiatriazolyl, pyrimidyl, pyrazinyl, pyridazinyl, oxazinyl, dioxinyl, thiazinyl, triazinyl, imidazo[2,1-b][1,3]thiazolyl, thieno[3,2-b]furanyl, thieno[3,2-b]thiophenyl, thieno[2,3-d][1,3]thiazolyl, thieno[2,3-d]imidazolyl, tetrazolo[1,5-a]pyridinyl, indolyl, indolizinyl, isoindolyl, benzofuranyl, isobenzofuranyl, benzothiophenyl, isobenzothiophenyl, indazolyl, benzimidazolyl, 1,3-benzoxazolyl, 1,2-benzisoxazolyl, 2,1-benzisoxazolyl, 1,3-benzothiazolyl, 1,2-benzoisothiazolyl, 2,1-benzoisothiazolyl, benzotriazolyl, 1,2,3-benzoxadiazolyl, 2,1,3-benzoxadiazolyl, 1,2,3-benzothiadiazolyl, 2,1,3-benzothiadiazolyl, benzo[d]oxazol-2(3H)-one, 2,3-dihydro-benzofuranyl, thienopyridinyl, purinyl, imidazo[1,2-a]pyridinyl, 6-oxo-pyridazin-1(6H)-yl, 2-oxopyridin-1(2H)-yl, 6-oxo-pyridazin-1(6H)-yl, 2-oxopyridin-1(2H)-yl, 1,3-benzodioxolyl, quinolinyl, isoquinolinyl, cinnolinyl, quinazolinyl, quinoxalinyl; in some embodiments, said heteroaryl group is selected from the group comprising pyridyl, pyrazinyl, pyrimidinyl, pyrazolyl, pyrrolyl, isoxazolyl, thiophenyl, imidazolyl, indolyl, benzimidazolyl, s-triazinyl, oxazolyl, isothiazolyl, furyl, thienyl, triazolyl and thiazolyl; in some embodiments, said heteroaryl group is selected from the group comprising pyridyl, pyrazinyl, pyrimidinyl, indolyl and benzimidazolyl.

The term "pyrrolyl" (also called azolyl) as used herein includes pyrrol-1-yl, pyrrol-2-yl and pyrrol-3-yl. The term "furanyl" (also called "furyl") as used herein includes furan-2-yl and furan-3-yl (also called furan-2-yl and furan-3-yl). The term "thiophenyl" (also called "thienyl") as used herein includes thiophen-2-yl and thiophen-3-yl (also called thien-2-yl and thien-3-yl). The term "pyrazolyl" (also called 1H-pyrazolyl and 1,2-diazolyl) as used herein includes pyrazol-1-yl, pyrazol-3-yl or 1H-pyrazol-5-yl, pyrazol-4-yl and pyrazol-5-yl. The term "imidazolyl" as used herein includes imidazol-1-yl, imidazol-2-yl, imidazol-4-yl and imidazol-5-yl. The term "oxazolyl" (also called 1,3-oxazolyl) as used herein includes oxazol-2-yl, oxazol-4-yl and oxazol-5-yl. The term "isoxazolyl" (also called 1,2-oxazolyl), as used herein includes isoxazol-3-yl, isoxazol-4-yl, and isoxazol-5-yl. The term "thiazolyl" (also called 1,3-thiazolyl),as used herein includes thiazol-2-yl, thiazol-4-yl and thiazol-5-yl (also called 2-thiazolyl, 4-thiazolyl and 5-thiazolyl). The term "isothiazolyl" (also called 1,2-thiazolyl) as used herein includes isothiazol-3-yl, isothiazol-4-yl, and isothiazol-5-yl. The term "triazolyl" as used herein includes triazol-2-yl, 1H-triazolyl and 4H-1,2,4-triazolyl, "1H-triazolyl" includes 1H-1,2,3-triazol-1-yl, 1H-1,2,3-triazol-4-yl, 1H-1,2,3-triazol-5-yl, 1H-1,2,4-triazol-1-yl, 1H-1,2,4-triazol-3-yl and 1H-1,2,4-triazol-5-yl. "4H-1,2,4-triazolyl" includes 4H-1,2,4-triazol-4-yl, and 4H-1,2,4-triazol-3-yl. The term "oxadiazolyl" as used herein includes 1,2,3-oxadiazol-4-yl, 1,2,3-oxadiazol-5-yl, 1,2,4-oxadiazol-3-yl, 1,2,4-oxadiazol-5-yl, 1,2,5-oxadiazol-3-yl and 1,3,4-oxadiazol-2-yl. The term "thiadiazolyl" as used herein includes 1,2,3-thiadiazol-4-yl, 1,2,3-thiadiazol-5-yl, 1,2,4-thiadiazol-3-yl, 1,2,4-thiadiazol-5-yl, 1,2,5-thiadiazol-3-yl (also called furazan-3-yl) and 1,3,4-thiadiazol-2-yl. The term "tetrazolyl" as used herein includes 1H-tetrazol-1-yl, 1H-tetrazol-5-yl, 2H-tetrazol-2-yl, and 2H-tetrazol-5-yl. The term "oxatriazolyl" as used herein includes 1,2,3,4-oxatriazol-5-yl and 1,2,3,5-oxatriazol-4-yl. The term "thiatriazolyl" as used herein includes 1,2,3,4-thiatriazol-5-yl and 1,2,3,5-thiatriazol-4-yl. The term "pyridinyl" (also called "pyridyl") as used herein includes pyridin-2-yl, pyridin-3-yl and pyridin-4-yl (also called 2-pyridyl, 3-pyridyl and 4-pyridyl). The term "pyrimidyl" as used herein includes pyrimid-2-yl, pyrimid-4-yl, pyrimid-5-yl and pyrimid-6-yl. The term "pyrazinyl" as used herein includes pyrazin-2-yl and pyrazin-3-yl. The term "pyridazinyl as used herein includes pyridazin-3-yl and pyridazin-4-yl. The term "oxazinyl" (also called "1,4-oxazinyl") as used herein includes 1,4-oxazin-4-yl and 1,4-oxazin-5-yl. The term "dioxinyl" (also called "1,4-dioxinyl") as used herein includes 1,4-dioxin-2-yl and 1,4-dioxin-3-yl. The term "thiazinyl" (also called "1,4-thiazinyl") as used herein includes 1,4-thiazin-2-yl, 1,4-thiazin-3-yl, 1,4-thiazin-4-yl, 1,4-thiazin-5-yl and 1,4-thiazin-6-yl. The term "triazinyl" as used herein includes 1,3,5-triazin-2-yl, 1,2,4-triazin-3-yl, 1,2,4-triazin-5-yl, 1,2,4-triazin-6-yl, 1,2,3-triazin-4-yl and 1,2,3-triazin-5-yl. The term "imidazo[2,1-b][1,3]thiazolyl" as used herein includes imidazo[2,1-b][1,3]thiazol-2-yl, imidazo[2,1-b][1,3]thiazol-3-yl, imidazo[2,1-b][1,3]thiazol-5-yl and imidazo[2,1-b][1,3]thiazol-6-yl. The term "thieno[3,2-b]furanyl" as used herein includes thieno[3,2-b]furan-2-yl, thieno[3,2-b]furan-3-yl, thieno[3,2-b]furan-4-yl, and thieno[3,2-b]furan-5-yl. The term "thieno[3,2-b]thiophenyl" as used herein includes thieno[3,2-b]thien-2-yl, thieno[3,2-b]thien-3-yl, thieno[3,2-b]thien-5-yl and thieno[3,2-b]thien-6-yl. The term "thieno[2,3-d][1,3]thiazolyl" as used herein includes thieno[2,3-d][1,3]thiazol-2-yl, thieno[2,3-d][1,3]thiazol-5-yl and thieno[2,3-d][1,3]thiazol-6-yl. The term "thieno[2,3-d]imidazolyl" as used herein includes thieno[2,3-d]imidazol-2-yl, thieno[2,3-d]imidazol-4-yl and thieno[2,3-d]imidazol-5-yl. The term "tetrazolo[1,5-a]pyridinyl" as used herein includes tetrazolo[1,5-a]pyridine-5-yl, tetrazolo[1,5-a]pyridine-6-yl, tetrazolo[1,5-a]pyridine-7-yl, and tetrazolo[1,5-a]pyridine-8-yl. The term "indolyl" as used herein includes indol-1-yl, indol-2-yl, indol-3-yl,-indol-4-yl, indol-5-yl, indol-6-yl and indol-7-yl. The term "indolizinyl" as used herein includes indolizin-1-yl, indolizin-2-yl, indolizin-3-yl, indolizin-5-yl, indolizin-6-yl, indolizin-7-yl, and indolizin-8-yl. The term "isoindolyl" as used herein includes isoindol-1-yl, isoindol-2-yl, isoindol-3-yl, isoindol-4-yl, isoindol-5-yl, isoindol-6-yl and isoindol-7-yl. The term "benzofuranyl" (also called benzo[b]furanyl) as used herein includes benzofuran-2-yl, benzofuran-3-yl, benzofuran-4-yl, benzofuran-5-yl, benzofuran-6-yl and benzofuran-7-yl.

The term "isobenzofuranyl" (also called benzo[c]furanyl) as used herein includes isobenzofuran-1-yl, isobenzofuran-3-yl, isobenzofuran-4-yl, isobenzofuran-5-yl, isobenzofuran-6-yl and isobenzofuran-7-yl. The term "benzothiophenyl" (also called benzo[b]thienyl) as used herein includes 2-benzo[b]thiophenyl, 3-benzo[b]thiophenyl, 4-benzo[b]thiophenyl, 5-benzo[b]thiophenyl, 6-benzo[b]thiophenyl and -7-benzo[b]thiophenyl (also called benzothien-2-yl, benzothien-3-yl, benzothien-4-yl, benzothien-5-yl, benzothien-6-yl and benzothien-7-yl). The term "isobenzothiophenyl" (also called benzo[c]thienyl) as used herein includes isobenzothien-1-yl, isobenzothien-3-yl, isobenzothien-4-yl, isobenzothien-5-yl, isobenzothien-6-yl and isobenzothien-7-yl. The term "indazolyl" (also called 1H-indazolyl or 2-azaindolyl) as used herein includes 1H-indazol-1-yl, 1H-indazol-3-yl, 1H-indazol-4-yl, 1H-indazol-5-yl, 1H-indazol-6-yl, 1H-indazol-7-yl, 2H-indazol-2-yl, 2H-indazol-3-yl, 2H-indazol-4-yl, 2H-indazol-5-yl, 2H-indazol-6-yl, and 2H-indazol-7-yl. The term "benzimidazolyl" as used herein includes benzimidazol-1-yl, benzimidazol-2-yl, benzimidazol-4-yl, benzimidazol-5-yl, benzimidazol-6-yl and benzimidazol-7-yl. The term "1,3-benzoxazolyl" as used herein includes 1,3-benzoxazol-2-yl, 1,3-benzoxazol-4-yl, 1,3-benzoxazol-5-yl, 1,3-benzoxazol-6-yl and 1,3-benzoxazol-7-yl. The term "1,2-benzisoxazolyl" as used herein includes 1,2-benzisoxazol-3-yl, 1,2-benzisoxazol-4-yl, 1,2-benzisoxazol-5-yl, 1,2-benzisoxazol-6-yl and 1,2-benzisoxazol-7-yl. The term "2,1-benzisoxazolyl" as used herein includes 2,1-benzisoxazol-3-yl, 2,1-benzisoxazol-4-yl, 2,1-benzisoxazol-5-yl, 2,1-benzisoxazol-6-yl and 2,1-benzisoxazol-7-yl. The term "1,3-benzothiazolyl" as used herein includes 1,3-benzothiazol-2-yl, 1,3-benzothiazol-4-yl, 1,3-benzothiazol-5-yl, 1,3-benzothiazol-6-yl and 1,3-benzothiazol-7-yl. The term "1,2-benzoisothiazolyl" as used herein includes 1,2-benzisothiazol-3-yl, 1,2-benzisothiazol-4-yl, 1,2-benzisothiazol-5-yl, 1,2-benzisothiazol-6-yl and 1,2-benzisothiazol-7-yl. The term "2,1-benzoisothiazolyl" as used herein includes 2,1-benzisothiazol-3-yl, 2,1-benzisothiazol-4-yl, 2,1-benzisothiazol-5-yl, 2,1-benzisothiazol-6-yl and 2,1-benzisothiazol-7-yl. The term "benzotriazolyl" as used herein includes benzotriazol-1-yl, benzotriazol-4-yl, benzotriazol-5-yl, benzotriazol-6-yl and benzotriazol-7-yl. The term "1,2,3-benzoxadiazolyl" as used herein includes 1,2,3-benzoxadiazol-4-yl, 1,2,3-benzoxadiazol-5-yl, 1,2,3-benzoxadiazol-6-yl and 1,2,3-benzoxadiazol-7-yl. The term "2,1,3-benzoxadiazolyl" as used herein includes 2,1,3-benzoxadiazol-4-yl, 2,1,3-benzoxadiazol-5-yl, 2,1,3-benzoxadiazol-6-yl and 2,1,3-benzoxadiazol-7-yl. The term "1,2,3-benzothiadiazolyl" as used herein includes 1,2,3-benzothiadiazol-4-yl, 1,2,3-benzothiadiazol-5-yl, 1,2,3-benzothiadiazol-6-yl and 1,2,3-benzothiadiazol-7-yl. The term "2,1,3-benzothiadiazolyl" as used herein includes 2,1,3-benzothiadiazol-4-yl, 2,1,3-benzothiadiazol-5-yl, 2,1,3-benzothiadiazol-6-yl and 2,1,3-benzothiadiazol-7-yl. The term "thienopyridinyl" as used herein includes thieno[2,3-b]pyridinyl, thieno[2,3-c]pyridinyl, thieno[3,2-c]pyridinyl and thieno[3,2-b]pyridinyl. The term "purinyl" as used herein includes purin-2-yl, purin-6-yl, purin-7-yl and purin-8-yl. The term "imidazo[1,2-a]pyridinyl", as used herein includes imidazo[1,2-a]pyridin-2-yl, imidazo[1,2-a]pyridin-3-yl, imidazo[1,2-a]pyridin-4-yl, imidazo[1,2-a]pyridin-5-yl, imidazo[1,2-a]pyridin-6-yl and imidazo[1,2-a]pyridin-7-yl. The term "1,3-benzodioxolyl", as used herein includes 1,3-benzodioxol-4-yl, 1,3-benzodioxol-5-yl, 1,3-benzodioxol-6-yl, and 1,3-benzodioxol-7-yl. The term "quinolinyl" as used herein includes quinolin-2-yl, quinolin-3-yl, quinolin-4-yl, quinolin-5-yl, quinolin-6-yl, quinolin-7-yl and quinolin-8-yl. The term "isoquinolinyl" as used herein includes isoquinolin-1-yl, isoquinolin-3-yl, isoquinolin-4-yl, isoquinolin-5-yl, isoquinolin-6-yl, isoquinolin-7-yl and isoquinolin-8-yl. The term "cinnolinyl" as used herein includes cinnolin-3-yl, cinnolin-4-yl, cinnolin-5-yl, cinnolin-6-yl, cinnolin-7-yl and cinnolin-8-yl. The term "quinazolinyl" as used herein includes quinazolin-2-yl, quinazolin-4-yl, quinazolin-5-yl, quinazolin-6-yl, quinazolin-7-yl and quinazolin-8-yl. The term "quinoxalinyl" as used herein includes quinoxalin-2-yl, quinoxalin-5-yl, and quinoxalin-6-yl.

Heteroaryl and heterocycle or heterocyclyl as used herein includes by way of example and not limitation these groups described in Paquette, Leo A. "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; Katritzky, Alan R., Rees, C. W. and Scriven, E. "Comprehensive Heterocyclic Chemistry" (Pergamon Press, 1996); and J. Am. Chem. Soc. (1960) 82:5566.

The term "heterocyclyloxy" or "heterocycleoxy", as a group or part of a group, refers to a group having the formula —O—$R^i$ wherein $R^i$ is heterocyclyl as defined herein above.

The term "heterocyclylalkyloxy" or "heterocycleoxy", as a group or part of a group, refers to a group having the formula —O—$R^a$—$R^i$ wherein $R^i$ is heterocyclyl, and $R^a$ is alkyl as defined herein above.

The term "heteroaryloxy", as a group or part of a group, refers to a group having the formula —O—$R^k$ wherein $R^k$ is heteroaryl as defined herein above.

The term "heteroarylalkyloxy", as a group or part of a group, refers to a group having the formula —O—$R^a$—$R^i$ wherein $R^i$ is heteroaryl, and $R^a$ is alkyl as defined herein above.

The term "heterocyclyl-alkyl" or "heterocycle-alkyl" as a group or part of a group, refers to an alkyl in which one of the hydrogen atoms bonded to a carbon atom, typically a terminal or sp3 carbon atom, is replaced with a heterocyclyl. A non-limiting example of a heterocyclyl-alkyl or heterocycle-alkyl group is 2-piperidinyl-methylene. The heterocyclyl-alkyl or heterocycle-alkyl group can comprise 6 to 20 atoms, e.g. the alkyl moiety is 1 to 6 carbon atoms and the heterocyclyl moiety is 3 to 14 atoms.

The term "heterocyclyl-alkenyl" or "heterocycle-alkenyl" as a group or part of a group refers to an alkenyl in which one of the hydrogen atoms bonded to a carbon atom, is replaced with an heterocyclyl. The heterocyclyl-alkenyl or heterocycle-alkenyl group can comprise 6 to 20 atoms, e.g. the alkenyl moiety is 2 to 6 carbon atoms and the heterocyclyl moiety is 3 to 14 atoms.

The term "heterocyclyl-alkynyl" or "heterocycle-alkynyl" as a group or part of a group refers to an alkynyl in which one of the hydrogen atoms bonded to a carbon atom, is replaced with a heterocyclyl. The heterocyclyl-alkynyl or heterocycle-alkynyl group can comprise 6 to 20 atoms, e.g. the alkynyl moiety can comprise 2 to 6 carbon atoms and the heterocyclyl moiety can comprise 3 to 14 atoms.

The term "heterocyclyl-heteroalkyl" or "heterocycle-heteroalkyl" as a group or part of a group refers to a heteroalkyl in which one of the hydrogen atoms bonded to a carbon atom, typically a terminal or sp3 carbon atom, is replaced with a heterocyclyl. The heterocyclyl-heteroalkyl or heterocycle-heteroalkyl group can comprise 6 to 20 atoms, e.g. the heteroalkyl moiety can comprise 1 to 6 carbon atoms and the heterocyclyl moiety can comprise 3 to 14 atoms. In some embodiments heterocyclyl-heteroalkyl or heterocycle-heteroalkyl is selected from the group comprising heterocyclyl-O-alkyl, heterocyclylalkyl-O-alkyl, heterocyclyl-NH-alkyl, heterocyclyl-N(alkyl)$_2$, heterocyclylalkyl-NH-alkyl, heterocyclylalkyl-N-(alkyl)$_2$, heterocyclyl-S-alkyl, and heterocyclylalkyl-S-alkyl.

The term "heterocyclyl-heteroalkenyl" or "heterocycle-heteroalkenyl" as a group or part of a group refers to a heteroalkenyl in which one of the hydrogen atoms bonded to a carbon atom, is replaced with a heterocyclyl. The heterocyclyl-heteroalkenyl or heterocycle-heteroalkenyl group can comprise 6 to 20 atoms, e.g. the heteroalkenyl moiety can comprise 2 to 6 carbon atoms and the heterocyclyl moiety can comprise 3 to 14 atoms. In some embodiments heterocyclyl-heteroalkenyl or heterocycle-heteroalkenyl is selected from the group comprising heterocyclyl-O-alkenyl, heterocyclylalkyl-O-alkenyl, heterocyclyl-NH-alkenyl, heterocyclyl-N(alkenyl)$_2$, heterocyclylalkyl-NH-alkenyl, heterocyclylalkyl-N-(alkenyl)$_2$, heterocyclyl-S-alkenyl, and heterocyclylalkenyl-S-alkenyl.

The term "heterocyclyl-heteroalkynyl" or "heterocycle-heteroalkynyl" as a group or part of a group refers to a heteroalkynyl in which one of the hydrogen atoms bonded to a carbon atom, is replaced with a heterocyclyl. The heterocyclyl-heteroalkynyl or heterocycle-heteroalkynyl group can comprise 6 to 20 atoms, e.g. the heteroalkynyl moiety can comprise 2 to 6 carbon atoms and the heterocyclyl moiety can comprise 3 to 14 atoms. In some embodiments heterocyclyl-heteroalkynyl is selected from the group comprising heterocyclyl-O-alkynyl, heterocyclylalkynyl-O-alkynyl, heterocyclyl-NH-alkynyl, heterocyclyl-N(alkynyl)$_2$, heterocyclylalkynyl-NH-alkynyl, heterocyclylalkynyl-N-(alkynyl)$_2$, heterocyclyl-S-alkynyl, and heterocyclylalkynyl-S-alkynyl.

The term "heteroaryl-alkyl" as a group or part of a group refers to an alkyl in which one of the hydrogen atoms bonded to a carbon atom, typically a terminal or sp3 carbon atom, is replaced with a heteroaryl. An example of a heteroaryl-alkyl group is 2-pyridyl-methylene. The heteroaryl-alkyl group can comprise 6 to 20 atoms, e.g. the alkyl moiety of the heteroaryl-alkyl group can comprise 1 to 6 carbon atoms and the heteroaryl moiety can comprise 5 to 14 atoms.

The term "heteroaryl-alkenyl" as a group or part of a group refers to an alkenyl in which one of the hydrogen atoms bonded to a carbon atom, is replaced with an heteroaryl.

The heteroaryl-alkenyl group can comprise 6 to 20 atoms, e.g. the alkenyl moiety of the heteroaryl-alkenyl group can comprise 2 to 6 carbon atoms and the heteroaryl moiety can comprise 5 to 14 atoms.

The term "heteroaryl-alkynyl" as a group or part of a group as used herein refers to an alkynyl in which one of the hydrogen atoms bonded to a carbon atom, is replaced with a heteroaryl. The heteroaryl-alkynyl group comprises 6 to 20 atoms, e.g. the alkynyl moiety of the heteroaryl-alkynyl group is 2 to 6 carbon atoms and the heteroaryl moiety is 5 to 14 atoms.

The term "heteroaryl-heteroalkyl" as a group or part of a group as used herein refers to a heteroalkyl in which one of the hydrogen atoms bonded to a carbon atom, typically a terminal or sp3 carbon atom, is replaced with a heteroaryl. The heteroaryl-heteroalkyl group comprises 7 to 20 atoms, e.g. the heteroalkyl moiety of the heteroaryl-heteroalkyl group is 2 to 6 carbon atoms and the heteroaryl moiety is 5 to 14 atoms. In some embodiments heteroaryl-heteroalkyl is selected from the group comprising heteroaryl-O-alkyl, heteroarylalkyl-O-alkyl, heteroaryl-NH-alkyl, heteroaryl-N(alkyl)$_2$, heteroarylalkyl-NH-alkyl, heteroarylalkyl-N-(alkyl)$_2$, heteroaryl-S-alkyl, and heteroarylalkyl-S-alkyl.

The term "heteroaryl-heteroalkenyl" as a group or part of a group as used herein refers to a heteroalkenyl in which one of the hydrogen atoms bonded to a carbon atom, is replaced with an heteroaryl. The heteroaryl-heteroalkenyl group comprises 8 to 20 atoms, e.g. the heteroalkenyl moiety of the heteroaryl-heteroalkenyl group is 3 to 6 carbon atoms and the heteroaryl moiety is 5 to 14 atoms. In some embodiments heteroaryl-heteroalkenyl is selected from the group comprising heteroaryl-O-alkenyl, heteroarylalkenyl-O-alkenyl, heteroaryl-NH-alkenyl, heteroaryl-N(alkenyl)$_2$, heteroarylalkenyl-NH-alkenyl, heteroarylalkenyl-N-(alkenyl)$_2$, heteroaryl-S-alkenyl, and heteroarylalkenyl-S-alkenyl.

The term "heteroaryl-heteroalkynyl" as a group or part of a group as used herein refers to a heteroalkynyl in which one of the hydrogen atoms bonded to a carbon atom, is replaced with a heteroaryl. The heteroaryl-heteroalkynyl group comprises 8 to 20 atoms, e.g. the heteroalkynyl moiety of the heteroaryl-heteroalkynyl group is 2 to 6 carbon atoms and the heteroaryl moiety is 5 to 14 atoms. In some embodiments heteroaryl-heteroalkynyl is selected from the group comprising heteroaryl-O-alkynyl, heteroarylalkynyl-O-alkynyl, heteroaryl-NH-alkynyl, heteroaryl-N(alkynyl)$_2$, heteroarylalkynyl-NH-alkynyl, heteroarylalkynyl-N-(alkynyl)$_2$, heteroaryl-S-alkynyl, and heteroarylalkynyl-S-alkynyl.

By way of example, carbon bonded heteroaryl or heterocyclic rings (or heterocycles) can be bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heteroaryls and heterocyclyls include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl. By way of example, nitrogen bonded heterocyclic rings are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Still more typically, nitrogen bonded heteroaryls or heterocyclyls include 1-aziridyl, 1-azetedyl, 1-pyrrolyl, 1-imidazolyl, 1-pyrazolyl, and 1-piperidinyl.

As used herein and unless otherwise stated, the terms "alkoxy", "cyclo-alkoxy", "aryloxy", "arylalkyloxy", "heteroaryloxy" "heterocyclyloxy", "alkylthio", "cycloalkylthio", "arylthio", "arylalkylthio", "heteroarylthio" and "heterocyclylthio" refer to substituents wherein an alkyl group, respectively a cycloalkyl, aryl, arylalkyl heteroaryl, or heterocyclyl (each of them such as defined herein), are attached to an oxygen atom or a sulfur atom through a single bond, such as but not limited to methoxy, ethoxy, propoxy, butoxy, thioethyl, thiomethyl, phenyloxy, benzyloxy, mercaptobenzyl and the like. The same definitions will apply for alkenyl and alkynyl instead of alkyl.

The term "alkylthio", as a group or part of a group, refers to a group having the formula —S—$R^b$ wherein $R^b$ is alkyl as defined herein above. Non-limiting examples of alkylthio groups include methylthio (—$SCH_3$), ethylthio (—$SCH_2CH_3$), n-propylthio, isopropylthio, n-butylthio, isobutylthio, sec-butylthio, tert-butylthio and the like.

The term "alkenylthio", as a group or part of a group, refers to a group having the formula —S—$R^d$ wherein $R^d$ is alkenyl as defined herein above.

The term "alkynylthio", as a group or part of a group, refers to a group having the formula —S—$R^e$ wherein $R^e$ is alkynyl as defined herein above.

The term "arylthio", as a group or part of a group, refers to a group having the formula —S—$R^g$ wherein $R^g$ is aryl as defined herein above.

The term "arylalkylthio", as a group or part of a group, refers to a group having the formula —S—$R^a$—$R^g$ wherein $R^a$ is alkylene and $R^g$ is aryl as defined herein above.

The term "heterocyclylthio", as a group or part of a group, refers to a group having the formula —S—$R^i$ wherein $R^i$ is heterocyclyl as defined herein above.

The term "heteroarylthio", as a group or part of a group, refers to a group having the formula —S—$R^k$ wherein $R^k$ is heteroaryl as defined herein above.

The term "heterocyclylalkylthio", as a group or part of a group, refers to a group having the formula —S—$R^a$—$R^i$ wherein $R^a$ is alkylene and $R^i$ is heterocyclyl as defined herein above.

The term "heteroarylalkylthio", as a group or part of a group, refers to a group having the formula —S—$R^a$—$R^k$ wherein $R^a$ is alkylene and $R^k$ is heteroaryl as defined herein above.

The term "mono- or di-alkylamino", as a group or part of a group, refers to a group of formula —N($R^o$)($R^b$) wherein $R^o$ is hydrogen, or alkyl, $R^b$ is alkyl. Thus, alkylamino include mono-alkyl amino group (e.g. mono-alkylamino group such as methylamino and ethylamino), and di-alkylamino group (e.g. di-alkylamino group such as dimethylamino and diethylamino). Non-limiting examples of suitable mono- or di-alkylamino groups include n-propylamino, isopropylamino, n-butylamino, i-butylamino, sec-butylamino, t-butylamino, pentylamino, n-hexylamino, di-n-propylamino, di-i-propylamino, ethylmethylamino, methyl-n-propylamino, methyl-i-propylamino, n-butylmethylamino, i-butylmethylamino, t-butylmethylamino, ethyl-n-propylamino, ethyl-i-propylamino, n-butylethylamino, i-butylethylamino, t-butylethylamino, di-n-butylamino, di-i-butylamino, methylpentylamino, methylhexylamino, ethylpentylamino, ethylhexylamino, propylpentylamino, propylhexylamino, and the like.

The term "mono- or di-arylamino", as a group or part of a group, refers to a group of formula —N($R^q$)($R^r$) wherein $R^q$ and $R^r$ are each independently selected from hydrogen, aryl, or alkyl, wherein at least one of $R^q$ or $R^r$ is aryl.

The term "mono- or di-heteroarylamino", as a group or part of a group, refers to a group of formula —N($R^u$)($R^v$) wherein $R^u$ and $R^v$ are each independently selected from hydrogen, heteroaryl, or alkyl, wherein at least one of $R^u$ or $R^v$ is heteroaryl as defined herein.

The term "mono- or di-heterocyclylamino", as a group or part of a group, refers to a group of formula —N($R^w$)($R^x$) wherein $R^w$ and $R^x$ are each independently selected from hydrogen, heterocyclyl, or alkyl, wherein at least one of $R^w$ or $R^x$ is heterocyclyl as defined herein.

As used herein and unless otherwise stated, the term halogen means any atom selected from the group consisting of fluorine (F), chlorine (Cl), bromine (Br) and iodine (I).

The terminology regarding a chemical group "which optionally includes one or more heteroatoms, said heteroatoms being selected from the atoms consisting of O, S, and N" as used herein, refers to a group where one or more carbon atoms are replaced by an oxygen, nitrogen or sulphur atom and thus includes, depending on the group to which is referred, heteroalkyl, heteroalkenyl, heteroalkynyl, heteroalkyl, heteroalkenyl, heteroalkynyl, cycloheteroalkyl, cycloheteroalkenyl, cycloheteroalkynyl, heteroaryl, arylheteroalkyl, heteroarylalkyl, heteroarylheteroalkyl, arylheteroalkenyl, heteroarylalkenyl, heteroarylheteroalkenyl, heteroarylheteroalkenyl, arylheteroalkynyl, heteroarylalkynyl, heteroarylheteroalkynyl, among others. This term therefore comprises, depending on the group to which is referred, as an example alkoxy, alkenyloxy, alkynyloxy, alkyl-O-alkylene, alkenyl-O-alkylene, arylalkoxy, benzyloxy, heteroaryl-heteroalkyl, heterocyclyl-heteroalkyl, heteroaryl-alkoxy, heterocyclyl-alkoxy, among others. As an example, the terminology "alkyl which optionally includes one or more heteroatoms, said heteroatoms being selected from the atoms consisting of O, S, and N" therefore refers to heteroalkyl, meaning an alkyl which comprises one or more heteroatoms in the hydrocarbon chain, whereas the heteroatoms may be positioned at the beginning of the hydrocarbon chain, in the hydrocarbon chain or at the end of the hydrocarbon chain. Examples of heteroalkyl include methoxy, methylthio, ethoxy, propoxy, $CH_3$—O—$CH_2$—, $CH_3$—S—$CH_2$—, $CH_3$—$CH_2$—O—$CH_2$—, $CH_3$—NH—, $(CH_3)_2$—N—, $(CH_3)_2$—$CH_2$—NH—$CH_2$—$CH_2$—, among many other examples. As an example, the terminology "arylalkylene which optionally includes one or more heteroatoms in the alkylene chain, said heteroatoms being selected from the atoms consisting of O, S, and N" therefore refers to arylheteroalkylene, meaning an arylalkylene which comprises one or more heteroatoms in the hydrocarbon chain, whereas the heteroatoms may be positioned at the beginning of the hydrocarbon chain, in the hydrocarbon chain or at the end of the hydrocarbon chain. "Arylheteroalkylene" thus includes aryloxy, arylalkoxy, aryl-alkyl-NH— and the like and examples are phenyloxy, benzyloxy, aryl-$CH_2$—S—$CH_2$—, aryl-$CH_2$—O—$CH_2$—, aryl-NH—$CH_2$— among many other examples. The same counts for "heteroalkenylene", "heteroalkynylene", and other terms used herein when referred to "which optionally includes one or more heteroatoms, said heteroatoms being selected from the atoms consisting of O, S, and N".

The terminology regarding a chemical group "wherein optionally two or more hydrogen atoms on a carbon atom or heteroatom of said group can be taken together to form a ═O or ═S" as used herein, refers to a group where two or more hydrogen atoms on a carbon atom or heteroatom of said group are taken together to form ═O or ═S. As an example, the terminology refers to "an alkyl wherein optionally two or more hydrogen atoms on a carbon atom or heteroatom of said alkyl can be taken together to form a ═O or ═S", includes among other examples $CH_3$—C(O)—$CH_2$—, $CH_3$—C(O)—, $CH_3$—C(S)—$CH_2$—, $CH_3$—$S(O)_2$—$CH_2$— and $(CH_3)_2$—$CH_2$—C(O)—$CH_2$—$CH_2$—.

The combination for a group "which optionally includes one or more heteroatoms, said heteroatoms being selected from the atoms consisting of O, S, and N" and "wherein optionally two or more hydrogen atoms on a carbon atom or heteroatom of said group can be taken together to form a ═O or ═S" can combine the two aspects described herein above and includes, if the group referred to is alkyl, among other examples $CH_3$—C(O)O—, $CH_3$—C(O)O—$CH_2$—, $CH_3$—NH—C(O)—, $CH_3$—C(O)—NH—$CH_3$—NH—C(O)—$CH_2$—, $CH_3$—NH—C(S)—$CH_2$—, $CH_3$—NH—C(S)—NH—$CH_2$—, $CH_3$—NH—$S(O)_2$— and $CH_3$—NH—$S(O)_2$—NH—$CH_2$—.

The term "single bond" as used herein for a linking group i.e. in a way that a certain linking group is selected from a single bond, etc. in the formulas herein, refers to a molecule wherein the linking group is not present and therefore refers to compounds with a direct linkage via a single bond between the two moieties being linked by the linking group.

As used herein with respect to a substituting group, and unless otherwise stated, the terms "substituted" such as in "substituted alkyl", "substituted alkenyl", substituted alkynyl", "substituted aryl", "substituted heteroaryl", "substituted heterocyclyl", "substituted arylalkyl", "substituted heteroaryl-alkyl", "substituted heterocyclyl-alkyl" and the like refer to the chemical structures defined herein, and wherein the said alkyl, alkenyl, alkynyl, group and/or the said aryl, heteroaryl, or heterocyclyl may be optionally substituted with one or more substituents (preferable 1, 2, 3, 4, 5 or 6), meaning that one or more hydrogen atoms are each independently replaced with at least one substituent. Typical substituents include, but are not limited to and in a particular embodiment said substituents are being independently selected from the group consisting of halogen, amino, hydroxyl, sulfhydryl, alkyl, alkoxy, alkenyl, alkenyloxy, alkynyl, alkynyloxy, cycloalkyl, cycloalkenyl, cycloalkynyl, heteroalkyl, heteroalkenyl, heteroalkynyl, aryl, heteroaryl, heterocyclyl, arylalkyl, arylalkenyl, arylalkynyl, cycloalkyl-alkyl, cycloalkylalkenyl, cycloalkylalkynyl, heteroaryl-alkyl, heterocyclyl-alkyl, heteroaryl-alkenyl, heterocyclyl-alkenyl and heteroaryl-alkynyl, heterocyclyl-alkynyl, —X, —Z, —$O^-$, —OZ, =O, —SZ, —$S^-$, =S, —$NZ_2$, —$N^+Z_3$, =NZ, =N—OZ, —$CX_3$ (e.g. trifluoromethyl), —CN, —OCN, —SCN, —N=C=O, —N=C=S, —NO, —$NO_2$, =$N_2$, —$N_3$, —NZC(O)Z, —NZC(S)Z, —NZC(O)$O^-$, —NZC(O)OZ, —NZC(S)OZ, —NZC(O)NZZ, NZC(NZ)Z, NZC(NZ)NZZ, —C(O)NZZ, —C(NZ)Z, —$S(O)_2O^-$, —$S(O)_2OZ$, —$S(O)_2Z$, —$OS(O)_2OZ$, —$OS(O)_2Z$, —$OS(O)_2O^-$, —$S(O)_2NZZ$, —S(O)(NZ)Z, —S(O)Z, —OP(O)$(OZ)_2$, —P(O)$(OZ)_2$, —P(O)$(O^-)_2$, —P(O)(OZ)($O^-$), —P(O)$(OH)_2$, —C(O)Z, —C(O)X, —C(S)Z, —C(O)OZ, —C(O)$O^-$, —C(S)OZ, —C(O)SZ, —C(S)SZ, —C(O)NZZ, —C(S)NZZ, —C(NZ)NZZ, —OC(O)Z, —OC(S)Z, —OC(O)$O^-$, —OC(O)OZ, —OC(S)OZ, wherein each X is independently a halogen selected from F, Cl, Br, or I; and each Z is independently —H, alkyl, alkenyl, alkynyl, heteroalkyl, heteroalkenyl, heteroalkynyl, aryl, heteroaryl, heterocyclyl, cycloalkyl, protecting group or prodrug moiety, while two Z bonded to a nitrogen atom can be taken together with the nitrogen atom to which they are bonded to form a heteroaryl, or heterocyclyl. Alkyl(ene), alkenyl(ene), and alkynyl(ene) groups may also be similarly substituted.

Any substituent designation that is found in more than one site in a compound of this disclosure shall be independently selected.

Substituents optionally are designated with or without bonds. Regardless of bond indications, if a substituent is polyvalent (based on its position in the structure referred to), then any and all possible orientations of the substituent are intended.

As used herein and unless otherwise stated, the term "solvate" includes any combination which may be formed by a derivative of this disclosure with a suitable inorganic solvent (e.g. hydrates) or organic solvent, such as but not limited to alcohols, ketones, esters, ethers, nitriles and the like.

The term "heteroatom(s)" as used herein means an atom selected from nitrogen, which can be quaternized; oxygen; and sulfur, including sulfoxide and sulfone.

The term "hydroxy" as used herein means —OH.

The term "carbonyl" as used herein means carbon atom bonded to oxygen with a double bond, i.e., C=O.

The term "amino" as used herein means the —$NH_2$ group.

The present disclosure provides novel compounds which have been shown to possess YAP/TAZ-TEAD transcription inhibitory activity. The present disclosure furthermore demonstrates that these compounds efficiently inhibit TEAD activation and thereby inhibit YAP/TAZ-TEAD transcription activation. Therefore, these compounds constitute a useful class of new potent compounds that can be used in the treatment and/or prevention of YAP/TAZ-TEAD activation mediated diseases in subjects, more specifically for the treatment and/or prevention of cancer and fibrosis, among other diseases.

The present disclosure furthermore relates to the compounds for use as medicines and to their use for the manufacture of medicaments for treating and/or preventing cancer or fibrosis. The present disclosure relates to the compounds for use as medicines for treating and/or preventing YAP/TAZ-TEAD activation mediated diseases such as cancer or fibrosis in animals, mammals, more in particular in humans. The disclosure also relates to methods for the preparation of all such compounds and to pharmaceutical compositions comprising them in an effective amount. The present disclosure also relates to a method of treatment or prevention of cancer or fibrosis in humans by the administration of one or more such compounds, optionally in combination with one or more other medicines, to a patient in need thereof. The present disclosure also relates to the compounds for veterinary use and to their use as medicines for the prevention or treatment of diseases in a non-human mammal, such as cancer and fibrosis in non-human mammals.

In one embodiment, the disclosure provides a compound of Formula I:

I

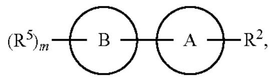

or a stereoisomer, tautomer, pharmaceutically acceptable salt, or solvate thereof, wherein:

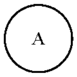

is selected from the group consisting of:

B-1

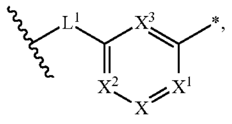

B-2

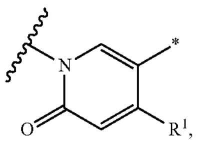

B-3

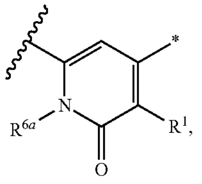

B-4

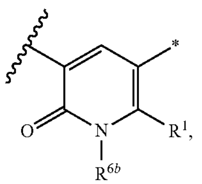

-continued

B-5

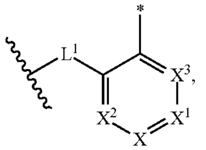

B-6

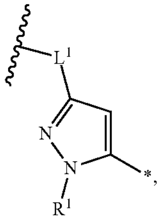

and

B-7

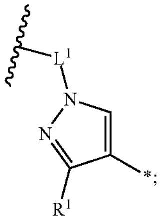

wherein the bond marked with an "*" is attached to $R^2$;

X is selected from the group consisting of —$CR^{10a}$═ and —N═; and $X^1$ is $CR^1$; or X is $CR^1$; and $X^1$ is selected from the group consisting of —$CR^{10b}$═ and —N═; or X is selected from the group consisting of —$CR^{10a}$═ and —N═; and $X^1$ is selected from the group consisting of —$CR^{10b}$═ and —N═;

$X^2$ is selected from the group consisting of —$CR^{10c}$═ and —N═;

$X^3$ is selected from the group consisting of —$CR^{10d}$═ and —N═;

$L^1$ is selected from the group consisting of —NH— and —$(CH_2)_p$—;

p is 0 or 1;

$R^1$ is selected from the group consisting of:

(i) hydrogen, (ii) -$L^2$-$NR^{4a}R^{4b}$, and (iii) unsubstituted or substituted 4- to 8-membered heterocycle, wherein one or more substituents are selected from the group consisting of:

(a) $C_1$-$C_6$ alkyl, (b) —C(═O)$Z^2$ (c) —C(═O)O$Z^2$, (d) —C(═O)N$Z^3Z^4$, (e) —S(═O)$_2Z^8$, (f) —S(═O)$_2$N$Z^3Z^4$, (g) cyano, (h) —O$Z^1$, and (i) halogen;

(iv) unsubstituted or substituted $C_6$-$C_{10}$ aryl, wherein one or more substituents are independently selected from the group consisting of —O$Z^1$, —C(═O)$Z^2$, halogen, $C_1$-$C_6$ alkyl, cyano, hydroxy, and $C_1$-$C_6$ haloalkyl;

(v)

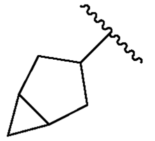

$L^2$ is selected from the group consisting —$(CH_2)_n$— and $C_3$-$C_6$ cycloalkylenyl n is 0 or 1;

$R^2$ is selected from the group consisting of:

$R^2$-1

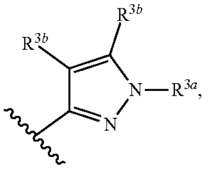

$R^2$-2

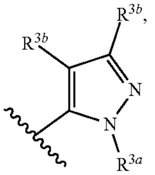

$R^2$-3

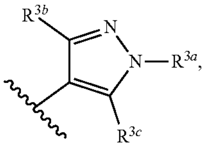

$R^2$-4

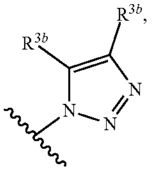

$R^2$-5

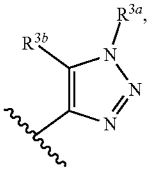

$R^2$-6

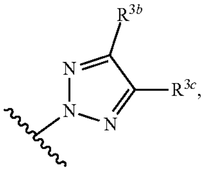

$R^2$-7

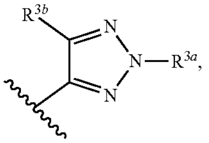

-continued
R²-8 → $R^2$-8
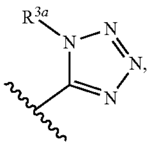
$R^2$-9
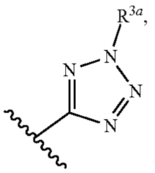
$R^2$-10
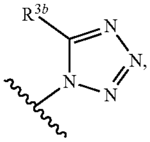
$R^2$-11
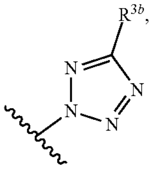
$R^2$-12
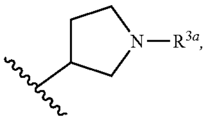
$R^2$-13
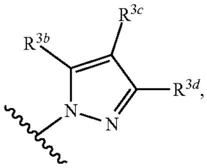
$R^2$-14
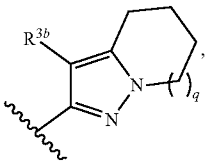
$R^2$-15
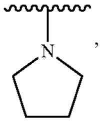
$R^2$-16
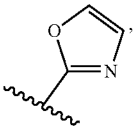
-continued
$R^2$-17
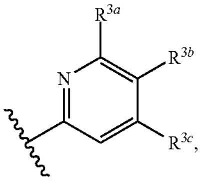
$R^2$-18
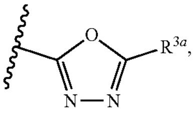
$R^2$-19
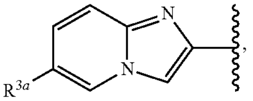
$R^2$-20
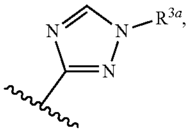
$R^2$-21
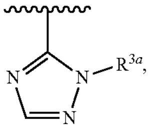
$R^2$-22
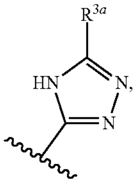
$R^2$-23
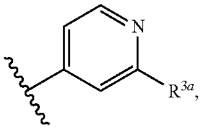
$R^2$-24
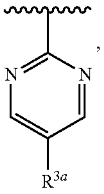
$R^2$-25
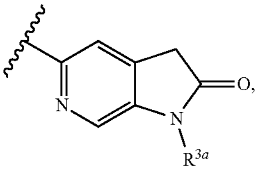
$R^2$-26
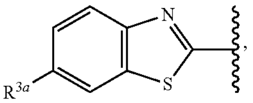

-continued $R^2$-27

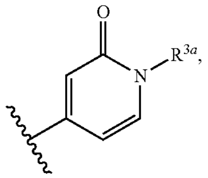

$R^2$-28

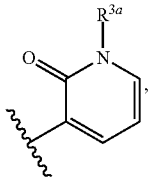

$R^2$-29

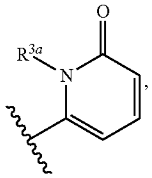

$R^2$-30

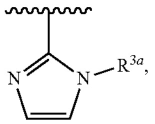

$R^2$-31

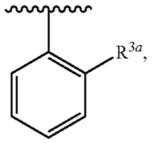

$R^2$-32

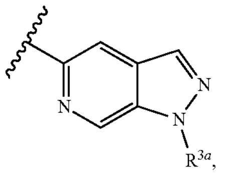

and $R^2$-33

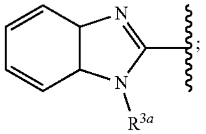

$R^{3a}$ is selected from the group consisting of:

(i) hydrogen, (ii) halogen, (iii) cyano, (iv) —$OZ^1$, (v) —C(═O)$NZ^3Z^4$, (vi) —$NZ^3Z^4$, (vii) unsubstituted or substituted $C_1$-$C_6$ alkyl, wherein one or more substituents are independently selected from the group consisting of:

(a) cyano, (b) —C(═O)$NZ^3Z^4$, (c) —$OZ^1$, (d) —$NZ^3Z^4$ (e) unsubstituted or substituted $C_6$-$C_{10}$ aryl, wherein one or more substituents are independently selected from the group consisting of:

(1) halogen, (2) cyano, (3) unsubstituted or substituted $C_1$-$C_6$ alkyl, wherein one or more substituents are independently selected from the group consisting of hydroxy, —$OZ^1$, and —$NZ^3Z^4$, (4) $C_1$-$C_6$ haloalkyl, (5) $C_3$-$C_6$ cycloalkyl, wherein one or more substituents are independently selected from the group consisting of $C_1$-$C_6$ alkyl, hydroxy, and —$NZ^3Z^4$, (6) —C(═O)$NZ^3Z^4$, (7) —$NZ^3Z^4$, (8) unsubstituted or substituted $C_2$-$C_6$ alkenyl, wherein one or more substituents are independently selected from the group consisting of halogen and unsubstituted or substituted $C_1$-$C_6$ alkyl, wherein one or more substituents are independently selected from the group consisting of —$NZ^3Z^4$ and 4- to 8-membered heterocycle, (9) unsubstituted or substituted $C_6$-$C_{10}$ aryl, wherein one or more substituents are independently selected from the group consisting of halo, —$OZ^1$, $C_1$-$C_6$ alkyl, cyano, hydroxy, and $C_1$-$C_6$ haloalkyl,

(10) unsubstituted or substituted 4- to 10-membered heterocycle, wherein one or more substituents are independently selected from the group consisting of $C_1$-$C_6$ alkyl, and $C_1$-$C_6$ haloalkyl,

(11) —$OZ^1$,

(12) —C(═O)OH,

(13) hydroxy,

(14) —$NZ^5C$(═O)$Z^2$,

(15) —$NZ^5S$(═O)$_2Z^2$, and

(16) —$NZ^5S$(═O)$_2NZ^3Z^4$, (f) unsubstituted or substituted $C_3$-$C_6$ cycloalkyl, wherein one or more substituents are independently selected from the group consisting of:

(1) $C_1$-$C_6$ alkyl, and (2) $C_1$-$C_6$ haloalkyl, (g) unsubstituted or substituted 5- to 10-membered heteroaryl, wherein one or more substituents are independently selected from the group consisting of:

(1) halogen, (2) cyano, (3) unsubstituted or substituted $C_1$-$C_6$ alkyl, wherein one or more substituents are independently selected from the group consisting of hydroxy, —$OZ^1$, and —$NZ^3Z^4$, (4) $C_1$-$C_6$ haloalkyl, (5) $C_3$-$C_6$ cycloalkyl, wherein one or more substituents are independently selected from the group consisting of $C_1$-$C_6$ alkyl, hydroxy, and —$NZ^3Z^4$, (6) —C(═O)$NZ^3Z^4$, (7) —$NZ^3Z^4$, (8) unsubstituted or substituted $C_2$-$C_6$ alkenyl, wherein one or more substituents are independently selected from the group consisting of halogen and unsubstituted or substituted $C_1$-$C_6$ alkyl, wherein one or more substituents are independently selected from the group consisting of —$NZ^3Z^4$, (9) unsubstituted or substituted $C_6$-$C_{10}$ aryl, wherein one or more substituents are independently selected from the group consisting of halo, —$OZ^1$, $C_1$-$C_6$ alkyl, cyano, hydroxy, and $C_1$-$C_6$ haloalkyl,

(10) unsubstituted or substituted 4- to 10-membered heterocycle, wherein one or more substituents are independently selected from the group consisting of $C_1$-$C_6$ alkyl, and $C_1$-$C_6$ haloalkyl,

(11) —$OZ^1$,

(12) —C(═O)OH,

(13) hydroxy, and

(14) —$NZ^5C(═O)Z^2$, (viii) $C_1$-$C_6$ haloalkyl, (ix) unsubstituted or substituted $C_3$-$C_6$ cycloalkyl, wherein one or more substituents are independently selected from the group consisting of halogen and $C_1$-$C_6$ alkyl;

(x) unsubstituted or substituted 4- to 10-membered heterocycle, wherein one or more substituents are independently selected from the group consisting of:

(a) $C_1$-$C_6$ alkyl, (b) —$C(═O)Z^2$, and (c) —$S(═O)_2Z^8$, (xi) unsubstituted or substituted 5- to 10-membered heteroaryl, wherein one or more substituents are independently selected from the group consisting of:

(a) halogen, (b) cyano, (c) unsubstituted or substituted $C_1$-$C_6$ alkyl, wherein one or more substituents are independently selected from the group consisting of hydroxy, —$OZ^1$, and —$NZ^3Z^4$, (d) $C_1$-$C_6$ haloalkyl, (e) unsubstituted or substituted $C_3$-$C_6$ cycloalkyl, wherein one or more substituents are independently selected from the group consisting of $C_1$-$C_6$ alkyl, hydroxy, and —$NZ^3Z^4$, (f) —$C(═O)NZ^3Z^4$, (g) —$NZ^3Z^4$, (h) unsubstituted or substituted $C_2$-$C_6$ alkenyl, wherein one or more substituents are independently selected from the group consisting of halogen and unsubstituted or substituted $C_1$-$C_6$ alkyl, wherein one or more substituents are independently selected from the group consisting of —$NZ^3Z^4$ and 4- to 8-membered heterocycle, (i) unsubstituted or substituted $C_6$-$C_{10}$ aryl, wherein one or more substituents are independently selected from the group consisting of halo, —$OZ^1$, $C_1$-$C_6$ alkyl, cyano, hydroxy, and $C_1$-$C_6$ haloalkyl, (j) unsubstituted or substituted 4- to 10-membered heterocycle, wherein one or more substituents are independently selected from the group consisting of $C_1$-$C_6$ alkyl, and $C_1$-$C_6$ haloalkyl, (k) —$OZ^1$, (l) —C(═O)OH, (m) hydroxy, and (n) —$NZ^5C(═O)Z^2$;

$R^{3b}$, $R^{3c}$, and $R^{3d}$ are independently selected from the group consisting of:

(i) hydrogen, (ii) halogen, (iii) cyano, (iv) —$C(═O)NZ^3Z^4$, (v) unsubstituted or substituted $C_1$-$C_6$ alkyl, wherein one or more substituents are independently selected from the group consisting of hydroxy, —$OZ^1$, and —$NZ^3Z^4$, (vi) $C_1$-$C_6$ haloalkyl, (vii) $C_3$-$C_6$ cycloalkyl, and (viii) $OZ^1$, q is 0, 1, or 2;

$R^{4a}$ is selected from the group consisting of:

(i) hydrogen, (ii) unsubstituted or substituted $C_1$-$C_6$ alkyl, wherein one or more substituents are independently selected from the group consisting of:

(a) halogen, (b) hydroxy, (c) cyano, (d) —$OZ^1$, (e) —$SZ^1$, (f) —$NZ^3Z^4$, (g) —$C(═O)Z^2$, (h) —C(═O)OH, (i) —$C(═O)OZ^2$, (j) —$C(═O)NZ^3Z^4$, (k) —$NZ^5C(═O)Z^2$, (l) —$NZ^5C(═O)OZ^2$, (m) —$NZ^5C(═O)NZ^3Z^4$, (n) —$S(═O)_2Z^8$, (o) —$S(═O)_2NZ^3Z^4$, (p) —$S(═O)(═NZ^6)Z^2$, (q) —$S(═Z^6)(═NZ^7)Z^2$, (r) —$S(═O)(═NZ^6)NZ^3Z^4$, (s) —$NZ^5S(═O)_2Z^2$, (t) —$NZ^5S(═O)_2NZ^3Z^4$, (u) —$NZ^5S(═O)(═NZ^6)Z^2$, (v) —$NZ^5S(═NZ^6)(═NZ^7)Z^2$, and (w) —$NZ^5S(═O)(═NZ^6)NZ^3Z^4$, (iii) unsubstituted or substituted 4- to 10-membered heterocycle, wherein one or more substituents are independently selected from the group consisting of:

(a) halogen, (b) hydroxy, (c) cyano, (d) —$OZ^1$, (e) —$SZ^1$, (f) —$NZ^3Z^4$, (g) —$C(═O)Z^2$ (h) C(═O)OH, (i) —$C(═O)OZ^2$, (j) —$C(═O)NZ^3Z^4$, (k) —$NZ^5C(═O)Z^2$, (l) —$NZ^5C(═O)OZ^2$, (m) —$NZ^5C(═O)NZ^3Z^4$, (n) —$S(═O)_2Z^8$, (o) —$S(═O)_2NZ^3Z^4$, (p) —$S(═O)(═NZ^6)Z^2$, (q) —$S(═Z^6)(═NZ^7)Z^2$, (r) —$S(═O)(═NZ^6)NZ^3Z^4$, (s) —$NZ^5S(═O)_2Z^2$, (t) —$NZ^5S(═O)_2NZ^3Z^4$, (u) —$NZ^5S(═O)(═NZ^6)Z^2$, (v) —$NZ^5S(═NZ^6)(═NZ^7)Z^2$, (w) —$NZ^5S(═O)(═NZ^6)NZ^3Z^4$, (x) $C_1$-$C_6$ alkyl, (y) $C_1$-$C_6$ haloalkyl, and (z) $C_3$-$C_6$ cycloalkyl, (iv) unsubstituted or substituted $C_2$-$C_6$ alkenyl, wherein one or more substituents are independently selected from the group consisting of —C(═O)OZ$^2$, halogen, and unsubstituted or substituted $C_1$-$C_6$ alkyl, wherein one or more substituents are independently selected from the group consisting of —NZ$^3$Z$^4$ and 4- to 8-membered heterocycle,
(v) —C(═O)Z$^2$
(vi) —C(═O)OZ$^2$,
(vii) —C(═O)NZ$^3$Z$^4$,
(viii) —S(═O)$_2$Z$^8$,
(ix) —S(═O)$_2$NZ$^3$Z$^4$,
(x) —S(═O)(═NZ$^6$)Z$^2$,
(xi) —S(═Z$^6$)(═NZ$^7$)Z$^2$, and
(xii) —S(═O)(═NZ$^6$)NZ$^3$Z$^4$, R$^{4b}$ is selected from the group consisting of:
(i) hydrogen, and
(ii) $C_1$-$C_6$ alkyl;

each Z$^1$ is independently selected from the group consisting of:
(i) hydrogen,
(ii) $C_1$-$C_6$ alkyl,
(iii) unsubstituted or substituted $C_2$-$C_6$ alkenyl, wherein one or more substituents are independently selected from the group consisting of halogen and unsubstituted or substituted $C_1$-$C_6$ alkyl, wherein one or more substituents are independently selected from the group consisting of —NZ$^3$Z$^4$ and 4- to 8-membered heterocycle,
(iv) $C_2$-$C_6$ alkynyl,
(v) $C_3$-$C_6$ cycloalkyl,
(vi) $C_3$-$C_6$ cycloalkenyl, and
(vii) $C_1$-$C_6$ haloalkyl;

each Z$^2$ is independently selected from the group consisting of:
(i) hydrogen,
(ii) $C_1$-$C_6$ alkyl,
(iii) unsubstituted or substituted $C_2$-$C_6$ alkenyl, wherein one or more substituents are independently selected from the group consisting of halogen and unsubstituted or substituted $C_1$-$C_6$ alkyl, wherein one or more substituents are independently selected from the group consisting of —NZ$^3$Z$^4$ and 4- to 8-membered heterocycle,
(iv) $C_2$-$C_6$ alkynyl,
(v) $C_3$-$C_6$ cycloalkyl,
(vi) $C_3$-$C_6$ cycloalkenyl, and
(vii) $C_1$-$C_6$ haloalkyl;

each Z$^3$ is independently selected from the group consisting of:
(i) hydrogen;
(ii) $C_1$-$C_6$ alkyl,
(iii) unsubstituted or substituted $C_2$-$C_6$ alkenyl, wherein one or more substituents are independently selected from the group consisting of halogen and unsubstituted or substituted $C_1$-$C_6$ alkyl, wherein one or more substituents are independently selected from the group consisting of —NZ$^3$Z$^4$ and 4- to 8-membered heterocycle,
(iv) $C_2$-$C_6$ alkynyl,
(v) $C_3$-$C_6$ cycloalkyl,
(vi) $C_3$-$C_6$ cycloalkenyl,
(vii) $C_1$-$C_6$ haloalkyl,
(viii) cyano, and
(ix) —C(═O)Z$^2$;

each Z$^4$, Z$^5$, Z$^6$ and Z$^7$ is independently selected from the group consisting of:
(i) hydrogen,
(ii) $C_1$-$C_6$ alkyl, and
(iii) $C_3$-$C_6$ cycloalkyl;

each Z$^8$ is independently selected from the group consisting of:
(i) hydrogen,
(ii) $C_1$-$C_6$ alkyl,
(iii) unsubstituted or substituted $C_2$-$C_6$ alkenyl, wherein one or more substituents are independently selected from the group consisting of halogen and unsubstituted or substituted $C_1$-$C_6$ alkyl, wherein one or more substituents are independently selected from the group consisting of —NZ$^3$Z$^4$ and 4- to 8-membered heterocycle,
(iv) halogen, and
(v) hydroxy;

R$^{3b}$ and R$^{3c}$ are independently selected from the group consisting of:
(i) hydrogen,
(ii) $C_1$-$C_6$ alkyl,
(iii) $C_1$-$C_6$ haloalkyl, and
(iv) $C_3$-$C_6$ cycloalkyl;

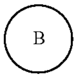

is selected from the group consisting of:
(i) $C_3$-$C_6$ cycloalkyl,
(ii) 4- to 10-membered heterocycle,
(iii) $C_6$-$C_{10}$ aryl, and
(iv) 5- to 10-membered heteroaryl;

each R$^5$ is independently selected from the group consisting of:
(i) halogen,
(ii) hydroxy,
(iii) cyano,
(iv) —OZ$^1$,
(v) —SZ$^1$,
(vi) —NZ$^3$Z$^4$,
(vii) —C(═O)Z$^2$
(viii) —C(═O)OH,
(ix) —C(═O)OZ$^2$,
(x) —C(═O)NZ$^3$Z$^4$,
(xi) —NZ$^5$C(═O)Z$^2$,
(xii) —NZ$^5$C(═O)OZ$^2$,
(xiii) —NZ$^5$C(═O)NZ$^3$Z$^4$,
(xiv) —S(═O)$_2$Z$^8$,
(xv) —S(═O)$_2$NZ$^3$Z$^4$,
(xvi) —S(═O)(═NZ$^6$)Z$^2$,
(xvii) —S(═Z$^6$)(═NZ$^7$)Z$^2$,
(xviii) —S(═O)(═NZ$^6$)NZ$^3$Z$^4$,
(xix) —NZ$^5$S(═O)$_2$Z$^2$,
(xx) —NZ$^5$S(═O)$_2$NZ$^3$Z$^4$,
(xxi) —NZ$^5$S(═O)(═NZ$^6$)Z$^2$,
(xxii) —NZ$^5$S(═NZ$^6$)(═NZ$^7$)Z$^2$,
(xxiii) —NZ$^5$S(═O)(═NZ$^6$)NZ$^3$Z$^4$,
(xxiv) unsubstituted or substituted $C_1$-$C_6$ alkyl, wherein one or more substituents are independently selected from the group consisting of hydroxy, —OZ$^1$, and —NZ$^3$Z$^4$,
(xxv) $C_1$-$C_6$ haloalkyl,
(xxvi) $C_3$-$C_6$ cycloalkyl, wherein one or more substituents are independently selected from the group consisting of $C_1$-$C_6$ alkyl, hydroxy, and —NZ$^3$Z$^4$, (xxvii) unsubstituted or substituted $C_2$-$C_6$ alkenyl, wherein one or more substituents are independently selected from the group consisting of halogen and unsubstituted or substituted $C_1$-$C_6$ alkyl, wherein one or more substituents are independently selected from the group consisting of —$NZ^3Z^4$ and 4- to 8-membered heterocycle, (xxviii) unsubstituted or substituted $C_6$-$C_{10}$ aryl, wherein one or more substituents are independently selected from the group consisting of halo, —$OZ^1$, $C_1$-$C_6$ alkyl, cyano, hydroxy, and $C_1$-$C_6$ haloalkyl, and (xxix) unsubstituted or substituted 4- to 10-membered heterocycle, wherein one or more substituents are independently selected from the group consisting of $C_1$-$C_6$ alkyl and $C_1$-$C_6$ haloalkyl, $R^{6a}$ is selected from the group consisting of:

(i) hydrogen, and (ii) $C_1$-$C_6$ alkyl;

$R^{6b}$ is selected from the group consisting of:

(i) hydrogen, and (ii) $C_1$-$C_6$ alkyl, m is 0, 1, 2, 3, or 4.

$R^{10a}$, $R^{10b}$, $R^{10c}$, and $R^{10d}$ are independently selected from the group consisting of:

(i) hydrogen, (ii) cyano, (iii) hydroxy (iv) —$OZ^1$, (v) —$SZ^1$, (vi) —$NZ^3Z^4$, (vii) $C_1$-$C_6$ alkyl, and (viii) $C_1$-$C_6$ haloalkyl;

In one embodiment, the disclosure provides a compound of Formula II:

II

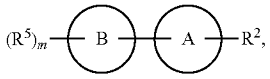

or a stereoisomer, tautomer, pharmaceutically acceptable salt, or solvate thereof, wherein:

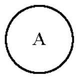

is selected from the group consisting of:

B-1

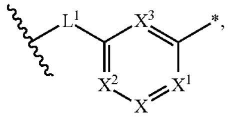

B-2

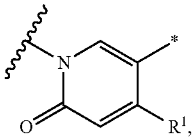

-continued

B-3

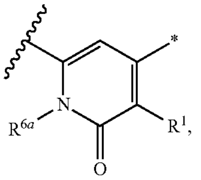

and

B-4

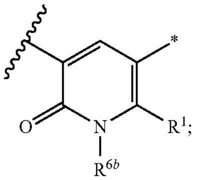

wherein the bond marked with an "*" is attached to $R^2$;

X is selected from the group consisting of —$CR^{10a}$═ and —N═; and $X^1$ is $CR^1$; or X is $CR^1$; and $X^1$ is selected from the group consisting of —$CR^{10b}$═ and —N═; or X is selected from the group consisting of —$CR^{10a}$═ and —N═; and $X^1$ is selected from the group consisting of —$CR^{10b}$═ and —N═;

$X^2$ is selected from the group consisting of —$CR^{10c}$═ and —N═;

$X^3$ is selected from the group consisting of —$CR^{10d}$═ and —N═;

$L^1$ is selected from the group consisting of —NH— and —$(CH_2)_p$—;

p is 0 or 1;

$R^1$ is selected from the group consisting of:

(i) hydrogen, (ii) -$L^2$-$NR^{4a}R^{4b}$, and (iii) unsubstituted or substituted 4- to 8-membered heterocycle, wherein one or more substituents are selected from the group consisting of:

(a) $C_1$-$C_6$ alkyl, (b) —C(═O)$Z^2$ (c) —C(═O)$OZ^2$, (d) —C(═O)$NZ^3Z^4$, (e) —S(═O)$_2Z^8$, and (f) —S(═O)$_2NZ^3Z^4$;

$L^2$ is selected from the group consisting —$(CH_2)_n$— and $C_3$-$C_6$ cycloalkylenyl n is 0 or 1;

$R^2$ is selected from the group consisting of:

$R^2$-1

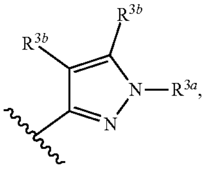

$R^2$-2

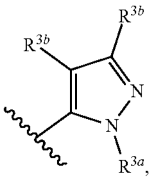

-continued $R^2$-3

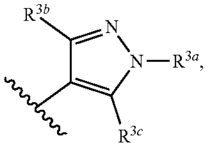

$R^2$-4

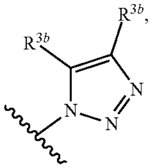

$R^2$-5

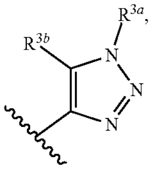

$R^2$-6

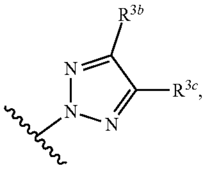

$R^2$-7

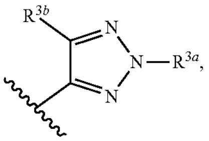

$R^2$-8

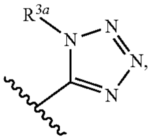

$R^2$-9

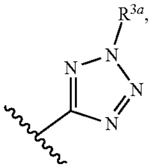

$R^2$-10

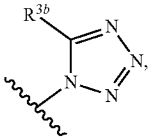

$R^2$-11

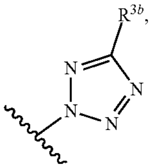

-continued $R^2$-12

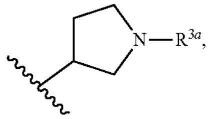

$R^2$-13

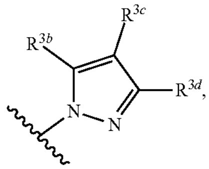

and $R^2$-14

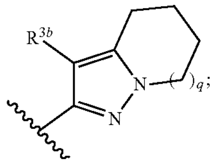

$R^{3a}$ is selected from the group consisting of:

(i) hydrogen, (ii) unsubstituted or substituted $C_1$-$C_6$ alkyl, wherein one or more substituents are independently selected from the group consisting of:

(a) hydroxy, (b) —$OZ^1$, (c) unsubstituted or substituted $C_6$-$C_{10}$ aryl, wherein one or more substituents are independently selected from the group consisting of:

(1) halogen, (2) cyano, (3) unsubstituted or substituted $C_1$-$C_6$ alkyl, wherein one or more substituents are independently selected from the group consisting of hydroxy, —$OZ^1$, and —$NZ^3Z^4$, (4) $C_1$-$C_6$ haloalkyl, (5) $C_3$-$C_6$ cycloalkyl, wherein one or more substituents are independently selected from the group consisting of $C_1$-$C_6$ alkyl, hydroxy, and —$NZ^3Z^4$, (6) —C(=O)$NZ^3Z^4$, (7) —$NZ^3Z^4$, (8) unsubstituted or substituted $C_2$-$C_6$ alkenyl, wherein one or more substituents are independently selected from the group consisting of halogen and unsubstituted or substituted $C_1$-$C_6$ alkyl, wherein one or more substituents are independently selected from the group consisting of —$NZ^3Z^4$ and 4- to 8-membered heterocycle, (9) unsubstituted or substituted $C_6$-$C_{10}$ aryl, wherein one or more substituents are independently selected from the group consisting of halo, —$OZ^1$, $C_1$-$C_6$ alkyl, cyano, hydroxy, and $C_1$-$C_6$ haloalkyl,

(10) unsubstituted or substituted 4- to 10-membered heterocycle, wherein one or more substituents are independently selected from the group consisting of $C_1$-$C_6$ alkyl, and $C_1$-$C_6$ haloalkyl,

(11) —$OZ^1$,

(12) —C(=O)OH,

(13) hydroxy,

(14) —$NZ^5C(=O)Z^2$,
(15) —$NZ^5S(=O)_2Z^2$, and
(16) —$NZ^5S(=O)_2NZ^3Z^4$,
(d) unsubstituted or substituted $C_3$-$C_6$ cycloalkyl, wherein one or more substituents are independently selected from the group consisting of:
(1) $C_1$-$C_6$ alkyl, and
(2) $C_1$-$C_6$ haloalkyl,
(e) unsubstituted or substituted 5- to 10-membered heteroaryl, wherein one or more substituents are independently selected from the group consisting of:
(1) halogen,
(2) cyano,
(3) unsubstituted or substituted $C_1$-$C_6$ alkyl, wherein one or more substituents are independently selected from the group consisting of hydroxy, —$OZ^1$, and —$NZ^3Z^4$,
(4) $C_1$-$C_6$ haloalkyl,
(5) $C_3$-$C_6$ cycloalkyl, wherein one or more substituents are independently selected from the group consisting of $C_1$-$C_6$ alkyl, hydroxy, and —$NZ^3Z^4$,
(6) —$C(=O)NZ^3Z^4$,
(7) —$NZ^3Z^4$,
(8) unsubstituted or substituted $C_2$-$C_6$ alkenyl, wherein one or more substituents are independently selected from the group consisting of halogen and unsubstituted or substituted $C_1$-$C_6$ alkyl, wherein one or more substituents are independently selected from the group consisting of —$NZ^3Z^4$,
(9) unsubstituted or substituted $C_6$-$C_{10}$ aryl, wherein one or more substituents are independently selected from the group consisting of halo, —$OZ^1$, $C_1$-$C_6$ alkyl, cyano, hydroxy, and $C_1$-$C_6$ haloalkyl,
(10) unsubstituted or substituted 4- to 10-membered heterocycle, wherein one or more substituents are independently selected from the group consisting of $C_1$-$C_6$ alkyl, and $C_1$-$C_6$ haloalkyl,
(11) —$OZ^1$,
(12) —$C(=O)OH$,
(13) hydroxy, and
(14) —$NZ^5C(=O)Z^2$,
(iii) $C_1$-$C_6$ haloalkyl
(iv) unsubstituted or substituted $C_3$-$C_6$ cycloalkyl, wherein one or more substituents are independently selected from the group consisting of halogen and $C_1$-$C_6$ alkyl;
(v) unsubstituted or substituted 4- to 10-membered heterocycle, wherein one or more substituents are independently selected from the group consisting of:
(a) $C_1$-$C_6$ alkyl,
(b) —$C(=O)Z^2$, and
(c) —$S(=O)_2Z^8$,
(vi) unsubstituted or substituted 5- to 10-membered heteroaryl, wherein one or more substituents are independently selected from the group consisting of:
(a) halogen,
(b) cyano,
(c) unsubstituted or substituted $C_1$-$C_6$ alkyl, wherein one or more substituents are independently selected from the group consisting of hydroxy, —$OZ^1$, and —$NZ^3Z^4$,
(d) $C_1$-$C_6$ haloalkyl,
(e) unsubstituted or substituted $C_3$-$C_6$ cycloalkyl, wherein one or more substituents are independently selected from the group consisting of $C_1$-$C_6$ alkyl, hydroxy, and —$NZ^3Z^4$,
(f) —$C(=O)NZ^3Z^4$,
(g) —$NZ^3Z^4$,
(h) unsubstituted or substituted $C_2$-$C_6$ alkenyl, wherein one or more substituents are independently selected from the group consisting of halogen and unsubstituted or substituted $C_1$-$C_6$ alkyl, wherein one or more substituents are independently selected from the group consisting of —$NZ^3Z^4$ and 4- to 8-membered heterocycle
(i) unsubstituted or substituted $C_6$-$C_{10}$ aryl, wherein one or more substituents are independently selected from the group consisting of halo, —$OZ^1$, $C_1$-$C_6$ alkyl, cyano, hydroxy, and $C_1$-$C_6$ haloalkyl,
(j) unsubstituted or substituted 4- to 10-membered heterocycle, wherein one or more substituents are independently selected from the group consisting of $C_1$-$C_6$ alkyl, and $C_1$-$C_6$ haloalkyl,
(k) —$OZ^1$,
(l) —$C(=O)OH$,
(m) hydroxy, and
(n) —$NZ^5C(=O)Z^2$;
$R^{3b}$, $R^{3c}$, and $R^{3d}$ are independently selected from the group consisting of:
(i) hydrogen,
(ii) $C_1$-$C_6$ alkyl,
(iii) $C_1$-$C_6$ haloalkyl, and
(iv) $C_3$-$C_6$ cycloalkyl;
q is 0, 1, or 2;
$R^{4a}$ is selected from the group consisting of:
(i) hydrogen,
(ii) unsubstituted or substituted $C_1$-$C_6$ alkyl, wherein one or more substituents are independently selected from the group consisting of:
(a) halogen,
(b) hydroxy,
(c) cyano,
(d) —$OZ^1$,
(e) —$SZ^1$,
(f) —$NZ^3Z^4$,
(g) —$C(=O)Z^2$
(h) $C(=O)OH$,
(i) —$C(=O)OZ^2$,
(j) —$C(=O)NZ^3Z^4$,
(k) —$NZ^5C(=O)Z^2$,
(l) —$NZ^5C(=O)OZ^2$,
(m) —$NZ^5C(=O)NZ^3Z^4$,
(n) —$S(=O)_2Z^8$,
(o) —$S(=O)_2NZ^3Z^4$,
(p) —$S(=O)(=NZ^6)Z^2$,
(q) —$S(=Z^6)(=NZ^7)Z^2$,
(r) —$S(=O)(=NZ^6)NZ^3Z^4$,
(s) —$NZ^5S(=O)_2Z^2$,
(t) —$NZ^5S(=O)_2NZ^3Z^4$,
(u) —$NZ^5S(=O)(=NZ^6)Z^2$,
(v) —$NZ^5S(=NZ^6)(=NZ^7)Z^2$, and
(w) —$NZ^5S(=O)(=NZ^6)NZ^3Z^4$,
(iii) unsubstituted or substituted 4- to 10-membered heterocycle, wherein one or more substituents are independently selected from the group consisting of:
(a) halogen,
(b) hydroxy,
(c) cyano,
(d) —$OZ^1$, (e) —$SZ^1$, (f) —$NZ^3Z^4$, (g) —C(═O)$Z^2$ (h) C(═O)OH, (i) —C(═O)$OZ^2$, (j) —C(═O)$NZ^3Z^4$, (k) —$NZ^5C$(═O)$Z^2$, (l) —$NZ^5C$(═O)$OZ^2$, (m) —$NZ^5C$(═O)$NZ^3Z^4$, (n) —S(═O)$_2Z^8$, (o) —S(═O)$_2NZ^3Z^4$, (p) —S(═O)(═$NZ^6$)$Z^2$, (q) —S(═$Z^6$)(═$NZ^7$)$Z^2$, (r) —S(═O)(═$NZ^6$)$NZ^3Z^4$, (s) —$NZ^5S$(═O)$_2Z^2$, (t) —$NZ^5S$(═O)$_2NZ^3Z^4$, (u) —$NZ^5S$(═O)(═$NZ^6$)$Z^2$, (v) —$NZ^5S$(═$NZ^6$)(═$NZ^7$)$Z^2$, (w) —$NZ^5S$(═O)(═$NZ^6$)$NZ^3Z^4$, (x) $C_1$-$C_6$ alkyl, (y) $C_1$-$C_6$ haloalkyl, and (z) $C_3$-$C_6$ cycloalkyl, (iv) —C(═O)$Z^2$ (v) —C(═O)$OZ^2$, (vi) —C(═O)$NZ^3Z^4$, (vii) —S(═O)$_2Z^8$, (viii) —S(═O)$_2NZ^3Z^4$, (ix) —S(═O)(═$NZ^6$)$Z^2$, (x) —S(═$Z^6$)(═$NZ^7$)$Z^2$, and (xi) —S(═O)(═$NZ^6$)$NZ^3Z^4$, $R^{4b}$ is selected from the group consisting of:

(i) hydrogen, and (ii) $C_1$-$C_6$ alkyl;

each $Z^1$ is independently selected from the group consisting of:

(i) hydrogen, (ii) $C_1$-$C_6$ alkyl, (iii) unsubstituted or substituted $C_2$-$C_6$ alkenyl, wherein one or more substituents are independently selected from the group consisting of halogen and unsubstituted or substituted $C_1$-$C_6$ alkyl, wherein one or more substituents are independently selected from the group consisting of —$NZ^3Z^4$ and 4- to 8-membered heterocycle, (iv) $C_2$-$C_6$ alkynyl, (v) $C_3$-$C_6$ cycloalkyl, (vi) $C_3$-$C_6$ cycloalkenyl, and (vii) $C_1$-$C_6$ haloalkyl;

each $Z^2$ is independently selected from the group consisting of:

(i) $C_1$-$C_6$ alkyl, (ii) unsubstituted or substituted $C_2$-$C_6$ alkenyl, wherein one or more substituents are independently selected from the group consisting of halogen and unsubstituted or substituted $C_1$-$C_6$ alkyl, wherein one or more substituents are independently selected from the group consisting of —$NZ^3Z^4$ and 4- to 8-membered heterocycle, (iii) $C_2$-$C_6$ alkynyl, (iv) $C_3$-$C_6$ cycloalkyl, (v) $C_3$-$C_6$ cycloalkenyl, and (vi) $C_1$-$C_6$ haloalkyl;

each $Z^3$ is independently selected from the group consisting of:

(i) hydrogen;

(ii) $C_1$-$C_6$ alkyl, (iii) unsubstituted or substituted $C_2$-$C_6$ alkenyl, wherein one or more substituents are independently selected from the group consisting of halogen and unsubstituted or substituted $C_1$-$C_6$ alkyl, wherein one or more substituents are independently selected from the group consisting of —$NZ^3Z^4$ and 4- to 8-membered heterocycle, (iv) $C_2$-$C_6$ alkynyl, (v) $C_3$-$C_6$ cycloalkyl, (vi) $C_3$-$C_6$ cycloalkenyl, and (vii) $C_1$-$C_6$ haloalkyl;

each $Z^4$, $Z^5$, $Z^6$ and $Z^7$ is independently selected from the group consisting of:

(i) hydrogen, (ii) $C_1$-$C_6$ alkyl, and (iii) $C_3$-$C_6$ cycloalkyl;

each $Z^8$ is independently selected from the group consisting of:

(i) hydrogen, (ii) $C_1$-$C_6$ alkyl, (iii) unsubstituted or substituted $C_2$-$C_6$ alkenyl, wherein one or more substituents are independently selected from the group consisting of halogen and unsubstituted or substituted $C_1$-$C_6$ alkyl, wherein one or more substituents are independently selected from the group consisting of —$NZ^3Z^4$ and 4- to 8-membered heterocycle, (iv) halogen, and (v) hydroxy;

$R^{3b}$ and $R^{3c}$ are independently selected from the group consisting of:

(i) hydrogen, (ii) $C_1$-$C_6$ alkyl, (iii) $C_1$-$C_6$ haloalkyl, and (iv) $C_3$-$C_6$ cycloalkyl;

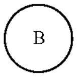

is selected from the group consisting of:

(i) $C_3$-$C_6$ cycloalkyl, (ii) 4- to 10-membered heterocycle, (iii) $C_6$-$C_{10}$ aryl, and (iv) 5- to 10-membered heteroaryl;

each $R^5$ is independently selected from the group consisting of:

(i) halogen, (ii) hydroxy, (iii) cyano, (iv) —$OZ^1$, (v) —$SZ^1$, (vi) —$NZ^3Z^4$, (vii) —C(═O)$Z^2$ (viii) C(═O)OH, (ix) —C(═O)$OZ^2$, (x) —C(═O)$NZ^3Z^4$, (xi) —$NZ^5C$(═O)$Z^2$, (xii) —$NZ^5C$(═O)$OZ^2$, (xiii) —$NZ^5C$(═O)$NZ^3Z^4$, (xiv) —S(═O)$_2Z^8$, (xv) —S(═O)$_2NZ^3Z^4$, (xvi) —S(═O)(═$NZ^6$)$Z^2$, (xvii) —S(═$Z^6$)(═$NZ^7$)$Z^2$, (xviii) —S(═O)(═$NZ^6$)$NZ^3Z^4$, (xix) $—NZ^5S(=O)_2Z^2$, (xx) $—NZ^5S(=O)_2NZ^3Z^4$, (xxi) $—NZ^5S(=O)(=NZ^6)Z^2$, (xxii) $—NZ^5S(=NZ^6)(=NZ^7)Z^2$, (xxiii) $—NZ^5S(=O)(=NZ^6)NZ^3Z^4$, (xxiv) unsubstituted or substituted $C_1$-$C_6$ alkyl, wherein one or more substituents are independently selected from the group consisting of hydroxy, $—OZ^1$, and $—NZ^3Z^4$, (xxv) $C_1$-$C_6$ haloalkyl, (xxvi) $C_3$-$C_6$ cycloalkyl, wherein one or more substituents are independently selected from the group consisting of $C_1$-$C_6$ alkyl, hydroxy, and $—NZ^3Z^4$, (xxvii) unsubstituted or substituted $C_2$-$C_6$ alkenyl, wherein one or more substituents are independently selected from the group consisting of halogen and unsubstituted or substituted $C_1$-$C_6$ alkyl, wherein one or more substituents are independently selected from the group consisting of $—NZ^3Z^4$ and 4- to 8-membered heterocycle, (xxviii) unsubstituted or substituted $C_6$-$C_{10}$ aryl, wherein one or more substituents are independently selected from the group consisting of halo, $—OZ^1$, $C_1$-$C_6$ alkyl, cyano, hydroxy, and $C_1$-$C_6$ haloalkyl, and (xxix) unsubstituted or substituted 4- to 10-membered heterocycle, wherein one or more substituents are independently selected from the group consisting of $C_1$-$C_6$ alkyl and $C_1$-$C_6$ haloalkyl, $R^{6a}$ is selected from the group consisting of:

(i) hydrogen, and (ii) $C_1$-$C_6$ alkyl;

$R^{6b}$ is selected from the group consisting of:

(i) hydrogen, and (ii) $C_1$-$C_6$ alkyl, m is 0, 1, 2, or 3.

$R^{10a}$, $R^{10b}$, $R^{10c}$, and $R^{10d}$ are independently selected from the group consisting of:

(i) hydrogen, (ii) cyano, (iii) hydroxy (iv) $—OZ^1$, (v) $—SZ^1$, (vi) $—NZ^3Z^4$, (vii) $C_1$-$C_6$ alkyl, and (viii) $C_1$-$C_6$ haloalkyl;

In another embodiment, the disclosure provides a compound of Formula III:

III

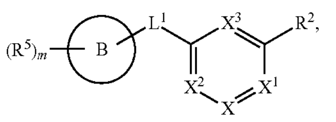

or a stereoisomer, tautomer, pharmaceutically acceptable salt, or solvate thereof, wherein $R^2$, $R^5$, X, $X^1$, $X^2$, $X^3$, $L^1$, m, and

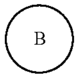

are as defined in connection with Formula I or II.

In another embodiment, the disclosure provides a compound of Formula IV:

IV

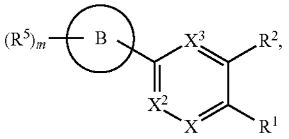

or a stereoisomer, tautomer, pharmaceutically acceptable salt, or solvate thereof, wherein $R^1$, $R^2$, $R^5$, X, $X^2$, $X^3$, m, and

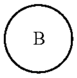

are as defined in connection with Formula I or II.

In another embodiment, the disclosure provides a compound of any one of Formula I-IV, or a stereoisomer, tautomer, pharmaceutically acceptable salt, or solvate thereof, wherein X, $X^2$, and $X^3$ are —CH═.

In another embodiment, the disclosure provides a compound of any one of Formula I-IV, or a stereoisomer, tautomer, pharmaceutically acceptable salt, or solvate thereof, wherein X is —N═; and $X^2$ and $X^3$ are —CH═.

In another embodiment, the disclosure provides a compound of any one of Formula I-IV, or a stereoisomer, tautomer, pharmaceutically acceptable salt, or solvate thereof, wherein X is —N═; and $X^2$ and $X^3$ are —CH═.

In another embodiment, the disclosure provides a compound of any one of Formula I-IV, or a stereoisomer, tautomer, pharmaceutically acceptable salt, or solvate thereof, wherein X and $X^3$ are —CH═; and $X^2$ is N═.

In another embodiment, the disclosure provides a compound of any one of Formula I-IV, or a stereoisomer, tautomer, pharmaceutically acceptable salt, or solvate thereof, wherein X and $X^2$ are —CH═; and $X^3$ is N═.

In another embodiment, the disclosure provides a compound of Formula V:

V

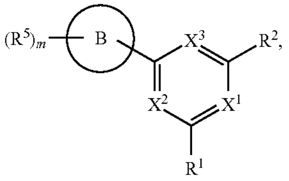

or a stereoisomer, tautomer, pharmaceutically acceptable salt, or solvate thereof, wherein $R^2$, $R^5$, $X^1$, $X^2$, $X^3$, m, and

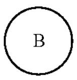

are as defined in connection with Formula I or II.

In another embodiment, the disclosure provides a compound of any one of Formula I, II, or V or a stereoisomer, tautomer, pharmaceutically acceptable salt, or solvate thereof, wherein $X^1$, $X^2$, and $X^3$ are —CH═.

In another embodiment, the disclosure provides a compound of any one of Formula I, II, or V, or a stereoisomer, tautomer, pharmaceutically acceptable salt, or solvate thereof, wherein $X^1$ is —N═; and $X^2$ and $X^3$ are —CH═.

In another embodiment, the disclosure provides a compound of any one of Formula I, II, or V, or a stereoisomer, tautomer, pharmaceutically acceptable salt, or solvate thereof, wherein $X^1$ and $X^3$ are —CH═; and $X^2$ is N═.

In another embodiment, the disclosure provides a compound of any one of Formula I, II, or V, or a stereoisomer, tautomer, pharmaceutically acceptable salt, or solvate thereof, wherein $X^1$ and $X^2$ are —CH═; and $X^3$ is N═.

In another embodiment the disclosure provides a compound of any one of Formula I, II, or V, or a stereoisomer, tautomer, pharmaceutically acceptable salt, or solvate thereof, wherein $R^1$ is $-L^2-NR^{4a}R^{4b}$.

In another embodiment the disclosure provides a compound of any one of Formula I, II, or V, or a stereoisomer, tautomer, pharmaceutically acceptable salt, or solvate thereof, wherein $L^2$ is $—(CH_2)_n—$.

In another embodiment, the disclosure provides a compound of any one of Formula I, II, or V, or a stereoisomer, tautomer, pharmaceutically acceptable salt, or solvate thereof, wherein $L^2$ is $—(CH_2)_n—$; and n is 0.

In another embodiment, the disclosure provides a compound of any one of Formula I, II, or V, or a stereoisomer, tautomer, pharmaceutically acceptable salt, or solvate thereof, wherein $L^2$ is $—(CH_2)_n—$; and n is 1.

In another embodiment, the disclosure provides a compound of any one of Formula I, II, or V, or a stereoisomer, tautomer, pharmaceutically acceptable salt, or solvate thereof, wherein $R^{4a}$ is selected from the group consisting of $—C(═O)Z^2$, $—C(═O)OZ^2$, $—C(═O)NZ^3Z^4$, $—S(═O)_2Z^8$, and $—S(═O)_2NZ^3Z^4$.

In another embodiment, the disclosure provides a compound of any one of Formula I, II, or V, or a stereoisomer, tautomer, pharmaceutically acceptable salt, or solvate thereof, wherein:

$Z^2$ is selected from the group consisting of $C_1$-$C_6$ alkyl and $C_2$-$C_6$ alkenyl;

$Z^3$ is selected from the group consisting of $C_1$-$C_6$ alkyl and $C_2$-$C_6$ alkenyl; and $Z^4$ is hydrogen.

In another embodiment, the disclosure provides a compound of any one of Formula I, II, or V, or a stereoisomer, tautomer, pharmaceutically acceptable salt, or solvate thereof, wherein $R^1$ is unsubstituted or substituted 4- to 8-membered heterocycle.

In another embodiment the disclosure provides a compound of any one of Formula I, II, or V, or a stereoisomer, tautomer, pharmaceutically acceptable salt, or solvate thereof, wherein $R^1$ is:

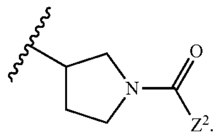

In another embodiment, the disclosure provides a compound of Formula VI:

VI

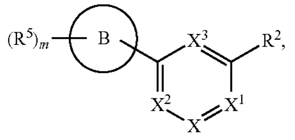

or a stereoisomer, tautomer, pharmaceutically acceptable salt, or solvate thereof, wherein:

X is selected from the group consisting of $—CR^{10a}═$ and —N═;

$X^1$ is selected from the group consisting of $—CR^{10b}═$ and —N═; and $R^2$, $R^5$, $X^2$, $X^3$, m, and

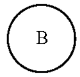

are as defined in connection with Formula I or II.

In another embodiment, the disclosure provides a compound of any one of Formula I, II, or VI, or a stereoisomer, tautomer, pharmaceutically acceptable salt, or solvate thereof, wherein X, $X^1$, $X^2$, and $X^3$ are —CH═.

In another embodiment, the disclosure provides a compound of Formula VII:

VII

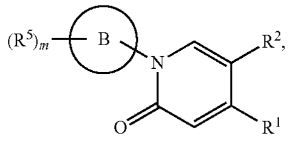

or a stereoisomer, tautomer, pharmaceutically acceptable salt, or solvate thereof, wherein $R^1$, $R^2$, $R^5$, m, and

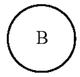

are as defined in connection with Formula I or II.

In another embodiment, the disclosure provides a compound of Formula VIII:

VIII

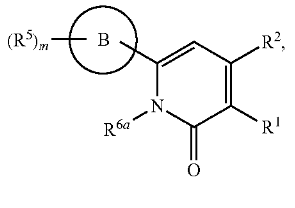

or a stereoisomer, tautomer, pharmaceutically acceptable salt, or solvate thereof, wherein $R^1$, $R^2$, $R^5$, $R^{6a}$, m, and

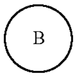

are as defined in connection with Formula I or II.

In another embodiment, the disclosure provides a compound of any one of Formula I, II, VII or VIII, or a stereoisomer, tautomer, pharmaceutically acceptable salt, or solvate thereof, wherein $R^{6a}$ is selected from the group consisting of hydrogen and $C_1$-$C_4$ alkyl.

In another embodiment, the disclosure provides a compound of Formula IX:

IX

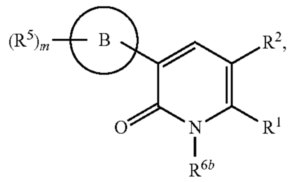

or a stereoisomer, tautomer, pharmaceutically acceptable salt, or solvate thereof, wherein $R^1$, $R^2$, $R^5$, $R^{6b}$, m, and

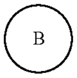

are as defined in connection with Formula I or II.

In another embodiment, the disclosure provides a compound of any one of Formula I, II, or IX, or a stereoisomer, tautomer, pharmaceutically acceptable salt, or solvate thereof, wherein $R^{6b}$ is selected from the group consisting of hydrogen and $C_1$-$C_4$ alkyl.

In another embodiment, the disclosure provides a compound of any one of Formulae I-IX, or a stereoisomer, tautomer, pharmaceutically acceptable salt, or solvate thereof, wherein $R^2$ is $R^2$-1.

In another embodiment, the disclosure provides a compound of Formulae I-IX, or a stereoisomer, tautomer, pharmaceutically acceptable salt, or solvate thereof, wherein

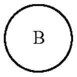

is $C_6$-$C_{10}$ aryl.

In another embodiment, the disclosure provides a compound of Formulae I-IX, wherein

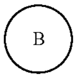

is phenyl, $R^5$ is halo; and m is 1 or 2.

In another embodiment, the disclosure provides a compound, or a stereoisomer, tautomer, pharmaceutically acceptable salt, or solvate thereof, selected from any one or more of the compounds of Table 1.

In another embodiment, the disclosure provides a compound selected from the group consisting of:

1-(3-(4-(1-(difluoromethyl)-1H-pyrazol-3-yl)-6-(4-fluorophenyl)pyridin-3-yl)pyrrolidin-1-yl)prop-2-en-1-one;

(S)-1-(3-(4-(1-(difluoromethyl)-1H-pyrazol-3-yl)-6-(4-fluorophenyl)pyridin-3-yl)pyrrolidin-1-yl)prop-2-en-1-one; and (R)-1-(3-(4-(1-(difluoromethyl)-1H-pyrazol-3-yl)-6-(4-fluorophenyl)pyridin-3-yl)pyrrolidin-1-yl)prop-2-en-1-one.

Preferred or particular statements (features) and embodiments of the compounds of this disclosure are set herein below. Each statement, aspect and embodiment of the disclosure so defined may be combined with any other statement, aspect and/or embodiment, unless clearly indicated to the contrary. In particular, any feature indicated as being preferred, particular or advantageous may be combined with any other features or statements indicated as being preferred, particular or advantageous. Hereto, the present disclosure is in particular captured by any one or any combination of one or more of the below numbered statements and embodiments, with any other statement, aspect and/or embodiment (which are not numbered).

Embodiment 1. A compound of Formula I:

I

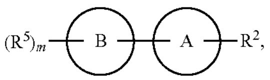

or a stereoisomer, tautomer, pharmaceutically acceptable salt, or solvate thereof, wherein:

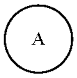

is selected from the group consisting of:

B-1

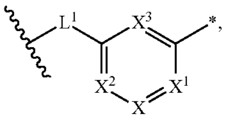

B-2

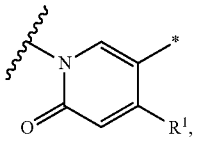

B-3

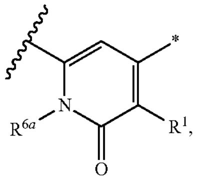

-continued

B-4

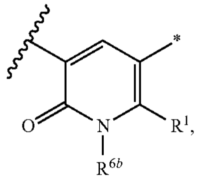

B-5

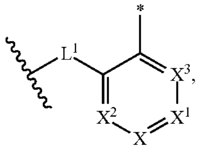

B-6

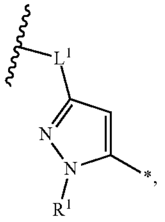

and

B-7

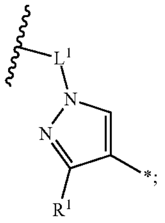

wherein the bond marked with an "*" is attached to $R^2$;

X is selected from the group consisting of —$CR^{10a}$═ and —N═; and $X^1$ is $CR^1$; or X is $CR^1$; and $X^1$ is selected from the group consisting of —$CR^{10b}$═ and —N═; or X is selected from the group consisting of —$CR^{10a}$═ and —N═; and $X^1$ is selected from the group consisting of —$CR^{10b}$═ and —N═;

$X^2$ is selected from the group consisting of —$CR^{10c}$═ and —N═;

$X^3$ is selected from the group consisting of —$CR^{10d}$═ and —N═;

$L^1$ is selected from the group consisting of —NH— and —$(CH_2)_p$—;

p is 0 or 1;

$R^1$ is selected from the group consisting of:

(i) hydrogen, (ii) -$L^2$-$NR^{4a}R^{4b}$, and (iii) unsubstituted or substituted 4- to 8-membered heterocycle, wherein one or more substituents are selected from the group consisting of:

(a) $C_1$-$C_6$ alkyl, (b) —C(═O)$Z^2$ (c) —C(═O)O$Z^2$, (d) —C(═O)N$Z^3Z^4$, (e) —S(═O)$_2Z^8$, (f) —S(═O)$_2$N$Z^3Z^4$, (g) cyano, (h) —O$Z^1$, and (i) halogen;

(iv) unsubstituted or substituted $C_6$-$C_{10}$ aryl, wherein one or more substituents are independently selected from the group consisting of —O$Z^1$, —C(═O)$Z^2$, halogen, $C_1$-$C_6$ alkyl, cyano, hydroxy, and $C_1$-$C_6$ haloalkyl;

(v)

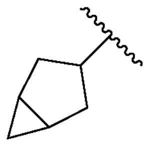

$L^2$ is selected from the group consisting —$(CH_2)_n$— and $C_3$-$C_6$ cycloalkylenyl n is 0 or 1;

$R^2$ is selected from the group consisting of:

$R^2$-1

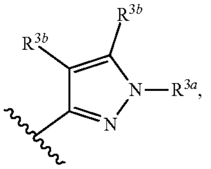

$R^2$-2

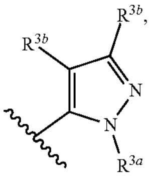

$R^2$-3

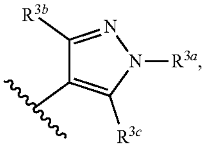

$R^2$-4

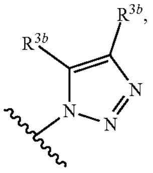

$R^2$-5

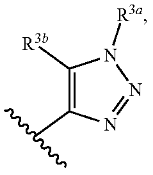

$R^2$-6

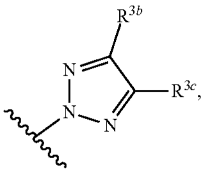

-continued
$R^2$-7
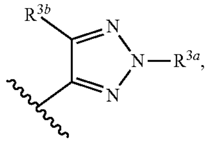
$R^2$-8
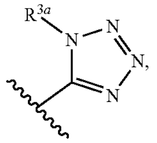
$R^2$-9
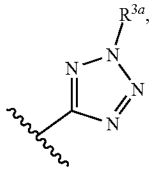
$R^2$-10
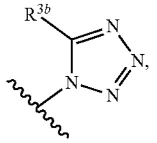
$R^2$-11
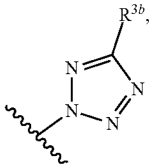
$R^2$-12
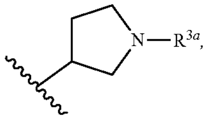
$R^2$-13
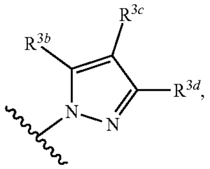
$R^2$-14
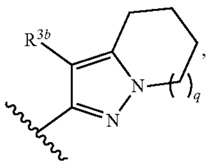
$R^2$-15
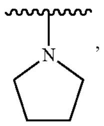
-continued
$R^2$-16
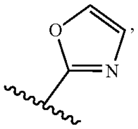
$R^2$-17
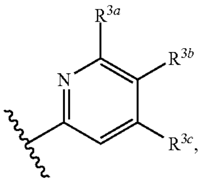
$R^2$-18
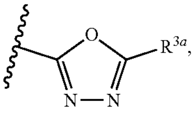
$R^2$-19
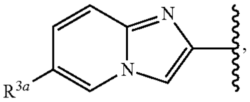
$R^2$-20
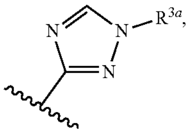
$R^2$-21
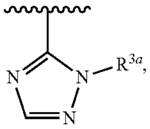
$R^2$-22
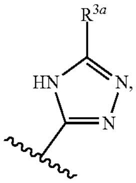
$R^2$-23
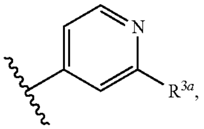
$R^2$-24
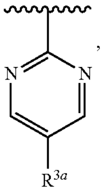
$R^2$-25
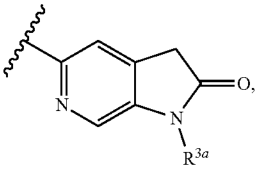

-continued $R^2$-26

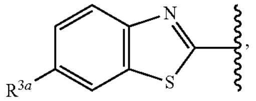

$R^2$-27

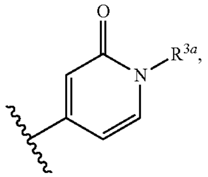

$R^2$-28

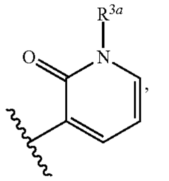

$R^2$-29

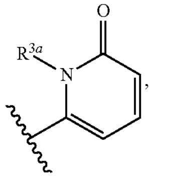

$R^2$-30

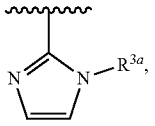

$R^2$-31

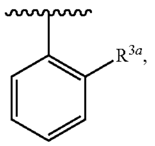

$R^2$-32

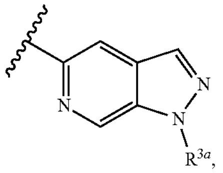

and $R^2$-33

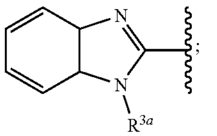

$R^{3a}$ is selected from the group consisting of:
(i) hydrogen,
(ii) halogen,
(iii) cyano,
(iv) —$OZ^1$,
(v) —C(═O)$NZ^3Z^4$,
(vi) —$NZ^3Z^4$,
(vii) unsubstituted or substituted $C_1$-$C_6$ alkyl, wherein one or more substituents are independently selected from the group consisting of:

(a) cyano,
(b) —C(═O)$NZ^3Z^4$,
(c) —$OZ^1$,
(d) —$NZ^3Z^4$
(e) unsubstituted or substituted $C_6$-$C_{10}$ aryl, wherein one or more substituents are independently selected from the group consisting of:
(1) halogen,
(2) cyano,
(3) unsubstituted or substituted $C_1$-$C_6$ alkyl, wherein one or more substituents are independently selected from the group consisting of hydroxy, —$OZ^1$, and —$NZ^3Z^4$,
(4) $C_1$-$C_6$ haloalkyl,
(5) $C_3$-$C_6$ cycloalkyl, wherein one or more substituents are independently selected from the group consisting of $C_1$-$C_6$ alkyl, hydroxy, and —$NZ^3Z^4$,
(6) —C(═O)$NZ^3Z^4$,
(7) —$NZ^3Z^4$,
(8) unsubstituted or substituted $C_2$-$C_6$ alkenyl, wherein one or more substituents are independently selected from the group consisting of halogen and unsubstituted or substituted $C_1$-$C_6$ alkyl, wherein one or more substituents are independently selected from the group consisting of —$NZ^3Z^4$ and 4- to 8-membered heterocycle,
(9) unsubstituted or substituted $C_6$-$C_{10}$ aryl, wherein one or more substituents are independently selected from the group consisting of halo, —$OZ^1$, $C_1$-$C_6$ alkyl, cyano, hydroxy, and $C_1$-$C_6$ haloalkyl,
(10) unsubstituted or substituted 4- to 10-membered heterocycle, wherein one or more substituents are independently selected from the group consisting of $C_1$-$C_6$ alkyl, and $C_1$-$C_6$ haloalkyl,
(11) —$OZ^1$,
(12) —C(═O)OH,
(13) hydroxy,
(14) —$NZ^5C$(═O)$Z^2$,
(15) —$NZ^5S$(═O)$_2Z^2$, and
(16) —$NZ^5S$(═O)$_2NZ^3Z^4$,
(f) unsubstituted or substituted $C_3$-$C_6$ cycloalkyl, wherein one or more substituents are independently selected from the group consisting of:
(1) $C_1$-$C_6$ alkyl, and
(2) $C_1$-$C_6$ haloalkyl,
(g) unsubstituted or substituted 5- to 10-membered heteroaryl, wherein one or more substituents are independently selected from the group consisting of:
(1) halogen,
(2) cyano,
(3) unsubstituted or substituted $C_1$-$C_6$ alkyl, wherein one or more substituents are independently selected from the group consisting of hydroxy, —$OZ^1$, and —$NZ^3Z^4$,
(4) $C_1$-$C_6$ haloalkyl,
(5) $C_3$-$C_6$ cycloalkyl, wherein one or more substituents are independently selected from the group consisting of $C_1$-$C_6$ alkyl, hydroxy, and —$NZ^3Z^4$,
(6) —C(═O)$NZ^3Z^4$,
(7) —$NZ^3Z^4$,
(8) unsubstituted or substituted $C_2$-$C_6$ alkenyl, wherein one or more substituents are independently selected from the group consisting of halogen and unsubstituted or substituted $C_1$-$C_6$ alkyl, wherein one or more substituents are independently selected from the group consisting of —$NZ^3Z^4$, (9) unsubstituted or substituted $C_6$-$C_{10}$ aryl, wherein one or more substituents are independently selected from the group consisting of halo, —$OZ^1$, $C_1$-$C_6$ alkyl, cyano, hydroxy, and $C_1$-$C_6$ haloalkyl,

(10) unsubstituted or substituted 4- to 10-membered heterocycle, wherein one or more substituents are independently selected from the group consisting of $C_1$-$C_6$ alkyl, and $C_1$-$C_6$ haloalkyl,

(11) —$OZ^1$,

(12) —C(═O)OH,

(13) hydroxy, and

(14) —$NZ^5C$(═O)$Z^2$, (viii) $C_1$-$C_6$ haloalkyl, (ix) unsubstituted or substituted $C_3$-$C_6$ cycloalkyl, wherein one or more substituents are independently selected from the group consisting of halogen and $C_1$-$C_6$ alkyl;

(x) unsubstituted or substituted 4- to 10-membered heterocycle, wherein one or more substituents are independently selected from the group consisting of:

(a) $C_1$-$C_6$ alkyl, (b) —C(═O)$Z^2$, and (c) —S(═O)$_2Z^8$, (xi) unsubstituted or substituted 5- to 10-membered heteroaryl, wherein one or more substituents are independently selected from the group consisting of:

(a) halogen, (b) cyano, (c) unsubstituted or substituted $C_1$-$C_6$ alkyl, wherein one or more substituents are independently selected from the group consisting of hydroxy, —$OZ^1$, and —$NZ^3Z^4$, (d) $C_1$-$C_6$ haloalkyl, (e) unsubstituted or substituted $C_3$-$C_6$ cycloalkyl, wherein one or more substituents are independently selected from the group consisting of $C_1$-$C_6$ alkyl, hydroxy, and —$NZ^3Z^4$, (f) —C(═O)$NZ^3Z^4$, (g) —$NZ^3Z^4$, (h) unsubstituted or substituted $C_2$-$C_6$ alkenyl, wherein one or more substituents are independently selected from the group consisting of halogen and unsubstituted or substituted $C_1$-$C_6$ alkyl, wherein one or more substituents are independently selected from the group consisting of —$NZ^3Z^4$ and 4- to 8-membered heterocycle, (i) unsubstituted or substituted $C_6$-$C_{10}$ aryl, wherein one or more substituents are independently selected from the group consisting of halo, —$OZ^1$, $C_1$-$C_6$ alkyl, cyano, hydroxy, and $C_1$-$C_6$ haloalkyl, (j) unsubstituted or substituted 4- to 10-membered heterocycle, wherein one or more substituents are independently selected from the group consisting of $C_1$-$C_6$ alkyl, and $C_1$-$C_6$ haloalkyl, (k) —$OZ^1$, (l) —C(═O)OH, (m) hydroxy, and (n) —$NZ^5C$(═O)$Z^2$;

$R^{3b}$, $R^{3c}$, and $R^{3d}$ are independently selected from the group consisting of:

(i) hydrogen, (ii) halogen, (iii) cyano, (iv) —C(═O)$NZ^3Z^4$, (v) unsubstituted or substituted $C_1$-$C_6$ alkyl, wherein one or more substituents are independently selected from the group consisting of hydroxy, —$OZ^1$, and —$NZ^3Z^4$, (vi) $C_1$-$C_6$ haloalkyl, (vii) $C_3$-$C_6$ cycloalkyl, and (viii) $OZ^1$, q is 0, 1, or 2;

$R^{4a}$ is selected from the group consisting of:

(i) hydrogen, (ii) unsubstituted or substituted $C_1$-$C_6$ alkyl, wherein one or more substituents are independently selected from the group consisting of:

(a) halogen, (b) hydroxy, (c) cyano, (d) —$OZ^1$, (e) —$SZ^1$, (f) —$NZ^3Z^4$, (g) —C(═O)$Z^2$, (h) —C(═O)OH, (i) —C(═O)$OZ^2$, (j) —C(═O)$NZ^3Z^4$, (k) —$NZ^5C$(═O)$Z^2$, (l) —$NZ^5C$(═O)$OZ^2$, (m) —$NZ^5C$(═O)$NZ^3Z^4$, (n) —S(═O)$_2Z^8$, (o) —S(═O)$_2NZ^3Z^4$, (p) —S(═O)(═$NZ^6$)$Z^2$, (q) —S(═$Z^6$)(═$NZ^7$)$Z^2$, (r) —S(═O)(═$NZ^6$)$NZ^3Z^4$, (s) —$NZ^5S$(═O)$_2Z^2$, (t) —$NZ^5S$(═O)$_2NZ^3Z^4$, (u) —$NZ^5S$(═O)(═$NZ^6$)$Z^2$, (v) —$NZ^5S$(═$NZ^6$)(═$NZ^7$)$Z^2$, and (w) —$NZ^5S$(═O)(═$NZ^6$)$NZ^3Z^4$, (iii) unsubstituted or substituted 4- to 10-membered heterocycle, wherein one or more substituents are independently selected from the group consisting of:

(a) halogen, (b) hydroxy, (c) cyano, (d) —$OZ^1$, (e) —$SZ^1$, (f) —$NZ^3Z^4$, (g) —C(═O)$Z^2$ (h) C(═O)OH, (i) —C(═O)$OZ^2$, (j) —C(═O)$NZ^3Z^4$, (k) —$NZ^5C$(═O)$Z^2$, (l) —$NZ^5C$(═O)$OZ^2$, (m) —$NZ^5C$(═O)$NZ^3Z^4$, (n) —S(═O)$_2Z^8$, (o) —S(═O)$_2NZ^3Z^4$, (p) —S(═O)(═$NZ^6$)$Z^2$, (q) —S(═$Z^6$)(═$NZ^7$)$Z^2$, (r) —S(═O)(═$NZ^6$)$NZ^3Z^4$, (s) —$NZ^5S$(═O)$_2Z^2$, (t) —$NZ^5S$(═O)$_2NZ^3Z^4$, (u) —$NZ^5S$(═O)(═$NZ^6$)$Z^2$, (v) —$NZ^5S$(═$NZ^6$)(═$NZ^7$)$Z^2$, (w) —$NZ^5S$(═O)(═$NZ^6$)$NZ^3Z^4$, (x) $C_1$-$C_6$ alkyl, (y) $C_1$-$C_6$ haloalkyl, and
(z) $C_3$-$C_6$ cycloalkyl,
(iv) unsubstituted or substituted $C_2$-$C_6$ alkenyl, wherein one or more substituents are independently selected from the group consisting of —C(═O)$OZ^2$, halogen, and unsubstituted or substituted $C_1$-$C_6$ alkyl, wherein one or more substituents are independently selected from the group consisting of —$NZ^3Z^4$ and 4- to 8-membered heterocycle,
(v) —C(═O)$Z^2$
(vi) —C(═O)$OZ^2$,
(vii) —C(═O)$NZ^3Z^4$,
(viii) —S(═O)$_2Z^8$,
(ix) —S(═O)$_2NZ^3Z^4$,
(x) —S(═O)(═$NZ^6$)$Z^2$,
(xi) —S(═$Z^6$)(═$NZ^7$)$Z^2$, and
(xii) —S(═O)(═$NZ^6$)$NZ^3Z^4$, $R^{4b}$ is selected from the group consisting of:
(i) hydrogen, and
(ii) $C_1$-$C_6$ alkyl;

each $Z^1$ is independently selected from the group consisting of:
(i) hydrogen,
(ii) $C_1$-$C_6$ alkyl,
(iii) unsubstituted or substituted $C_2$-$C_6$ alkenyl, wherein one or more substituents are independently selected from the group consisting of halogen and unsubstituted or substituted $C_1$-$C_6$ alkyl, wherein one or more substituents are independently selected from the group consisting of —$NZ^3Z^4$ and 4- to 8-membered heterocycle,
(iv) $C_2$-$C_6$ alkynyl,
(v) $C_3$-$C_6$ cycloalkyl,
(vi) $C_3$-$C_6$ cycloalkenyl, and
(vii) $C_1$-$C_6$ haloalkyl;

each $Z^2$ is independently selected from the group consisting of:
(i) hydrogen,
(ii) $C_1$-$C_6$ alkyl,
(iii) unsubstituted or substituted $C_2$-$C_6$ alkenyl, wherein one or more substituents are independently selected from the group consisting of halogen and unsubstituted or substituted $C_1$-$C_6$ alkyl, wherein one or more substituents are independently selected from the group consisting of —$NZ^3Z^4$ and 4- to 8-membered heterocycle,
(iv) $C_2$-$C_6$ alkynyl,
(v) $C_3$-$C_6$ cycloalkyl,
(vi) $C_3$-$C_6$ cycloalkenyl, and
(vii) $C_1$-$C_6$ haloalkyl;

each $Z^3$ is independently selected from the group consisting of:
(i) hydrogen;
(ii) $C_1$-$C_6$ alkyl,
(iii) unsubstituted or substituted $C_2$-$C_6$ alkenyl, wherein one or more substituents are independently selected from the group consisting of halogen and unsubstituted or substituted $C_1$-$C_6$ alkyl, wherein one or more substituents are independently selected from the group consisting of —$NZ^3Z^4$ and 4- to 8-membered heterocycle,
(iv) $C_2$-$C_6$ alkynyl,
(v) $C_3$-$C_6$ cycloalkyl,
(vi) $C_3$-$C_6$ cycloalkenyl,
(vii) $C_1$-$C_6$ haloalkyl,
(viii) cyano, and
(ix) —C(═O)$Z^2$;

each $Z^4$, $Z^5$, $Z^6$ and $Z^7$ is independently selected from the group consisting of:
(i) hydrogen,
(ii) $C_1$-$C_6$ alkyl, and
(iii) $C_3$-$C_6$ cycloalkyl;

each $Z^8$ is independently selected from the group consisting of:
(i) hydrogen,
(ii) $C_1$-$C_6$ alkyl,
(iii) unsubstituted or substituted $C_2$-$C_6$ alkenyl, wherein one or more substituents are independently selected from the group consisting of halogen and unsubstituted or substituted $C_1$-$C_6$ alkyl, wherein one or more substituents are independently selected from the group consisting of —$NZ^3Z^4$ and 4- to 8-membered heterocycle,
(iv) halogen, and
(v) hydroxy;

$R^{3b}$ and $R^{3c}$ are independently selected from the group consisting of:
(i) hydrogen,
(ii) $C_1$-$C_6$ alkyl,
(iii) $C_1$-$C_6$ haloalkyl, and
(iv) $C_3$-$C_6$ cycloalkyl;

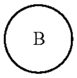

is selected from the group consisting of:
(i) $C_3$-$C_6$ cycloalkyl,
(ii) 4- to 10-membered heterocycle,
(iii) $C_6$-$C_{10}$ aryl, and
(iv) 5- to 10-membered heteroaryl;

each $R^5$ is independently selected from the group consisting of:
(i) halogen,
(ii) hydroxy,
(iii) cyano,
(iv) —$OZ^1$,
(v) —$SZ^1$,
(vi) —$NZ^3Z^4$,
(vii) —C(═O)$Z^2$
(viii) —C(═O)OH,
(ix) —C(═O)$OZ^2$,
(x) —C(═O)$NZ^3Z^4$,
(xi) —$NZ^5$C(═O)$Z^2$,
(xii) —$NZ^5$C(═O)$OZ^2$,
(xiii) —$NZ^5$C(═O)$NZ^3Z^4$,
(xiv) —S(═O)$_2Z^8$,
(xv) —S(═O)$_2NZ^3Z^4$,
(xvi) —S(═O)(═$NZ^6$)$Z^2$,
(xvii) —S(═$Z^6$)(═$NZ^7$)$Z^2$,
(xviii) —S(═O)(═$NZ^6$)$NZ^3Z^4$,
(xix) —$NZ^5$S(═O)$_2Z^2$,
(xx) —$NZ^5$S(═O)$_2NZ^3Z^4$,
(xxi) —$NZ^5$S(═O)(═$NZ^6$)$Z^2$,
(xxii) —$NZ^5$S(═$NZ^6$)(═$NZ^7$)$Z^2$,
(xxiii) —$NZ^5$S(═O)(═$NZ^6$)$NZ^3Z^4$,
(xxiv) unsubstituted or substituted $C_1$-$C_6$ alkyl, wherein one or more substituents are independently selected from the group consisting of hydroxy, —$OZ^1$, and —$NZ^3Z^4$,
(xxv) $C_1$-$C_6$ haloalkyl, (xxvi) $C_3$-$C_6$ cycloalkyl, wherein one or more substituents are independently selected from the group consisting of $C_1$-$C_6$ alkyl, hydroxy, and —$NZ^3Z^4$, (xxvii) unsubstituted or substituted $C_2$-$C_6$ alkenyl, wherein one or more substituents are independently selected from the group consisting of halogen and unsubstituted or substituted $C_1$-$C_6$ alkyl, wherein one or more substituents are independently selected from the group consisting of —$NZ^3Z^4$ and 4- to 8-membered heterocycle, (xxviii) unsubstituted or substituted $C_6$-$C_{10}$ aryl, wherein one or more substituents are independently selected from the group consisting of halo, —$OZ^1$, $C_1$-$C_6$ alkyl, cyano, hydroxy, and $C_1$-$C_6$ haloalkyl, and (xxix) unsubstituted or substituted 4- to 10-membered heterocycle, wherein one or more substituents are independently selected from the group consisting of $C_1$-$C_6$ alkyl and $C_1$-$C_6$ haloalkyl, $R^{6a}$ is selected from the group consisting of:

(i) hydrogen, and (ii) $C_1$-$C_6$ alkyl;

$R^{6b}$ is selected from the group consisting of:

(i) hydrogen, and (ii) $C_1$-$C_6$ alkyl, m is 0, 1, 2, 3, or 4.

$R^{10a}$, $R^{10b}$, $R^{10c}$, and $R^{10d}$ are independently selected from the group consisting of:

(i) hydrogen, (ii) cyano, (iii) hydroxy (iv) —$OZ^1$, (v) —$SZ^1$, (vi) —$NZ^3Z^4$, (vii) $C_1$-$C_6$ alkyl, and (viii) $C_1$-$C_6$ haloalkyl;

Embodiment 2. A compound of Formula II:

II

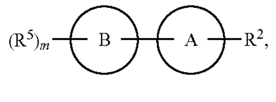

or a stereoisomer, tautomer, pharmaceutically acceptable salt, or solvate thereof, wherein:

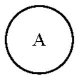

is selected from the group consisting of:

B-1

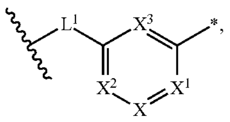

B-2

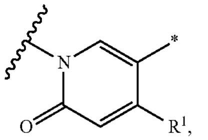

-continued

B-3

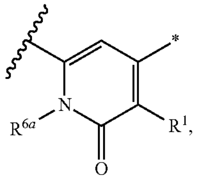

and

B-4

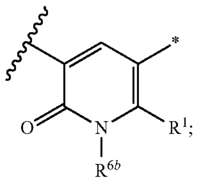

wherein the bond marked with an "*" is attached to $R^2$;

X is selected from the group consisting of —$CR^{10a}$= and —N=; and $X^1$ is $CR^1$; or X is $CR^1$; and $X^1$ is selected from the group consisting of —$CR^{10b}$= and —N=; or X is selected from the group consisting of —$CR^{10a}$= and —N=; and $X^1$ is selected from the group consisting of —$CR^{10b}$= and —N=;

$X^2$ is selected from the group consisting of —$CR^{10c}$= and —N=;

$X^3$ is selected from the group consisting of —$CR^{10d}$= and —N=;

$L^1$ is selected from the group consisting of —NH— and —$(CH_2)_p$—;

p is 0 or 1;

$R^1$ is selected from the group consisting of:

(i) hydrogen, (ii) -$L^2$-$NR^{4a}R^{4b}$, and (iii) unsubstituted or substituted 4- to 8-membered heterocycle, wherein one or more substituents are selected from the group consisting of:

(a) $C_1$-$C_6$ alkyl, (b) —C(=O)$Z^2$ (c) —C(=O)O$Z^2$, (d) —C(=O)$NZ^3Z^4$, (e) —$S(=O)_2Z^8$, and (f) —$S(=O)_2NZ^3Z^4$;

$L^2$ is selected from the group consisting —$(CH_2)_n$— and $C_3$-$C_6$ cycloalkylenyl n is 0 or 1;

$R^2$ is selected from the group consisting of:

$R^2$-1

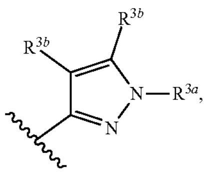

$R^2$-2

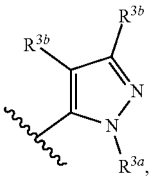

-continued $R^2$-3

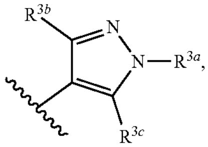

$R^2$-4

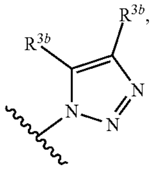

$R^2$-5

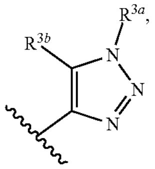

$R^2$-6

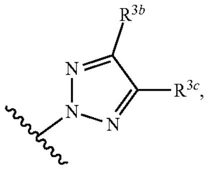

$R^2$-7

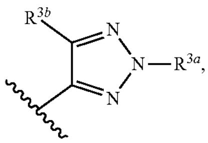

$R^2$-8

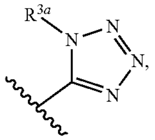

$R^2$-9

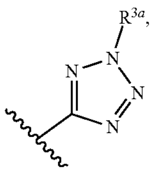

$R^2$-10

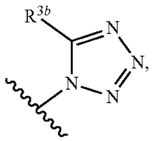

$R^2$-11

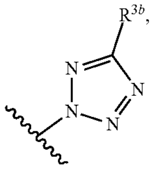

-continued $R^2$-12

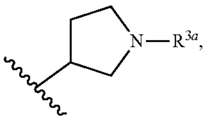

$R^2$-13

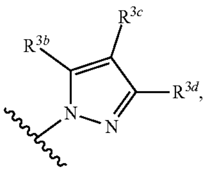

and $R^2$-14

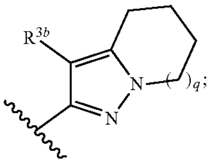

$R^{3a}$ is selected from the group consisting of:

(i) hydrogen, (ii) unsubstituted or substituted $C_1$-$C_6$ alkyl, wherein one or more substituents are independently selected from the group consisting of:

(a) hydroxy, (b) —$OZ^1$, (c) unsubstituted or substituted $C_6$-$C_{10}$ aryl, wherein one or more substituents are independently selected from the group consisting of:

(1) halogen, (2) cyano, (3) unsubstituted or substituted $C_1$-$C_6$ alkyl, wherein one or more substituents are independently selected from the group consisting of hydroxy, —$OZ^1$, and —$NZ^3Z^4$, (4) $C_1$-$C_6$ haloalkyl, (5) $C_3$-$C_6$ cycloalkyl, wherein one or more substituents are independently selected from the group consisting of $C_1$-$C_6$ alkyl, hydroxy, and —$NZ^3Z^4$, (6) —C(=O)$NZ^3Z^4$, (7) —$NZ^3Z^4$, (8) unsubstituted or substituted $C_2$-$C_6$ alkenyl, wherein one or more substituents are independently selected from the group consisting of halogen and unsubstituted or substituted $C_1$-$C_6$ alkyl, wherein one or more substituents are independently selected from the group consisting of —$NZ^3Z^4$ and 4- to 8-membered heterocycle, (9) unsubstituted or substituted $C_6$-$C_{10}$ aryl, wherein one or more substituents are independently selected from the group consisting of halo, —$OZ^1$, $C_1$-$C_6$ alkyl, cyano, hydroxy, and $C_1$-$C_6$ haloalkyl,

(10) unsubstituted or substituted 4- to 10-membered heterocycle, wherein one or more substituents are independently selected from the group consisting of $C_1$-$C_6$ alkyl, and $C_1$-$C_6$ haloalkyl,

(11) —$OZ^1$,

(12) —C(=O)OH,

(13) hydroxy,

(14) —$NZ^5C(=O)Z^2$,
(15) —$NZ^5S(=O)_2Z^2$, and
(16) —$NZ^5S(=O)_2NZ^3Z^4$,
(d) unsubstituted or substituted $C_3$-$C_6$ cycloalkyl, wherein one or more substituents are independently selected from the group consisting of:
(1) $C_1$-$C_6$ alkyl, and
(2) $C_1$-$C_6$ haloalkyl,
(e) unsubstituted or substituted 5- to 10-membered heteroaryl, wherein one or more substituents are independently selected from the group consisting of:
(1) halogen,
(2) cyano,
(3) unsubstituted or substituted $C_1$-$C_6$ alkyl, wherein one or more substituents are independently selected from the group consisting of hydroxy, —$OZ^1$, and —$NZ^3Z^4$,
(4) $C_1$-$C_6$ haloalkyl,
(5) $C_3$-$C_6$ cycloalkyl, wherein one or more substituents are independently selected from the group consisting of $C_1$-$C_6$ alkyl, hydroxy, and —$NZ^3Z^4$,
(6) —$C(=O)NZ^3Z^4$,
(7) —$NZ^3Z^4$,
(8) unsubstituted or substituted $C_2$-$C_6$ alkenyl, wherein one or more substituents are independently selected from the group consisting of halogen and unsubstituted or substituted $C_1$-$C_6$ alkyl, wherein one or more substituents are independently selected from the group consisting of —$NZ^3Z^4$,
(9) unsubstituted or substituted $C_6$-$C_{10}$ aryl, wherein one or more substituents are independently selected from the group consisting of halo, —$OZ^1$, $C_1$-$C_6$ alkyl, cyano, hydroxy, and $C_1$-$C_6$ haloalkyl,
(10) unsubstituted or substituted 4- to 10-membered heterocycle, wherein one or more substituents are independently selected from the group consisting of $C_1$-$C_6$ alkyl, and $C_1$-$C_6$ haloalkyl,
(11) —$OZ^1$,
(12) —$C(=O)OH$,
(13) hydroxy, and
(14) —$NZ^5C(=O)Z^2$,
(iii) $C_1$-$C_6$ haloalkyl
(iv) unsubstituted or substituted $C_3$-$C_6$ cycloalkyl, wherein one or more substituents are independently selected from the group consisting of halogen and $C_1$-$C_6$ alkyl;
(v) unsubstituted or substituted 4- to 10-membered heterocycle, wherein one or more substituents are independently selected from the group consisting of:
(a) $C_1$-$C_6$ alkyl,
(b) —$C(=O)Z^2$, and
(c) —$S(=O)_2Z^8$,
(vi) unsubstituted or substituted 5- to 10-membered heteroaryl, wherein one or more substituents are independently selected from the group consisting of:
(a) halogen,
(b) cyano,
(c) unsubstituted or substituted $C_1$-$C_6$ alkyl, wherein one or more substituents are independently selected from the group consisting of hydroxy, —$OZ^1$, and —$NZ^3Z^4$,
(d) $C_1$-$C_6$ haloalkyl,
(e) unsubstituted or substituted $C_3$-$C_6$ cycloalkyl, wherein one or more substituents are independently selected from the group consisting of $C_1$-$C_6$ alkyl, hydroxy, and —$NZ^3Z^4$,
(f) —$C(=O)NZ^3Z^4$,
(g) —$NZ^3Z^4$,
(h) unsubstituted or substituted $C_2$-$C_6$ alkenyl, wherein one or more substituents are independently selected from the group consisting of halogen and unsubstituted or substituted $C_1$-$C_6$ alkyl, wherein one or more substituents are independently selected from the group consisting of —$NZ^3Z^4$ and 4- to 8-membered heterocycle
(i) unsubstituted or substituted $C_6$-$C_{10}$ aryl, wherein one or more substituents are independently selected from the group consisting of halo, —$OZ^1$, $C_1$-$C_6$ alkyl, cyano, hydroxy, and $C_1$-$C_6$ haloalkyl,
(j) unsubstituted or substituted 4- to 10-membered heterocycle, wherein one or more substituents are independently selected from the group consisting of $C_1$-$C_6$ alkyl, and $C_1$-$C_6$ haloalkyl,
(k) —$OZ^1$,
(l) —$C(=O)OH$,
(m) hydroxy, and
(n) —$NZ^5C(=O)Z^2$;
$R^{3b}$, $R^{3c}$, and $R^{3d}$ are independently selected from the group consisting of:
(i) hydrogen,
(ii) $C_1$-$C_6$ alkyl,
(iii) $C_1$-$C_6$ haloalkyl, and
(iv) $C_3$-$C_6$ cycloalkyl;
q is 0, 1, or 2;
$R^{4a}$ is selected from the group consisting of:
(i) hydrogen,
(ii) unsubstituted or substituted $C_1$-$C_6$ alkyl, wherein one or more substituents are independently selected from the group consisting of:
(a) halogen,
(b) hydroxy,
(c) cyano,
(d) —$OZ^1$,
(e) —$SZ^1$,
(f) —$NZ^3Z^4$,
(g) —$C(=O)Z^2$
(h) $C(=O)OH$,
(i) —$C(=O)OZ^2$,
(j) —$C(=O)NZ^3Z^4$,
(k) —$NZ^5C(=O)Z^2$,
(l) —$NZ^5C(=O)OZ^2$,
(m) —$NZ^5C(=O)NZ^3Z^4$,
(n) —$S(=O)_2Z^8$,
(o) —$S(=O)_2NZ^3Z^4$,
(p) —$S(=O)(=NZ^6)Z^2$,
(q) —$S(=Z^6)(=NZ^7)Z^2$,
(r) —$S(=O)(=NZ^6)NZ^3Z^4$,
(s) —$NZ^5S(=O)_2Z^2$,
(t) —$NZ^5S(=O)_2NZ^3Z^4$,
(u) —$NZ^5S(=O)(=NZ^6)Z^2$,
(v) —$NZ^5S(=NZ^6)(=NZ^7)Z^2$, and
(w) —$NZ^5S(=O)(=NZ^6)NZ^3Z^4$,
(iii) unsubstituted or substituted 4- to 10-membered heterocycle, wherein one or more substituents are independently selected from the group consisting of:
(a) halogen,
(b) hydroxy,
(c) cyano,
(d) —$OZ^1$, (e) —$SZ^1$,
(f) —$NZ^3Z^4$,
(g) —C(═O)$Z^2$
(h) C(═O)OH,
(i) —C(═O)$OZ^2$,
(j) —C(═O)$NZ^3Z^4$,
(k) —$NZ^5$C(═O)$Z^2$,
(l) —$NZ^5$C(═O)$OZ^2$,
(m) —$NZ^5$C(═O)$NZ^3Z^4$,
(n) —S(═O)$_2Z^8$,
(o) —S(═O)$_2NZ^3Z^4$,
(p) —S(═O)(═$NZ^6$)$Z^2$,
(q) —S(═$Z^6$)(═$NZ^7$)$Z^2$,
(r) —S(═O)(═$NZ^6$)$NZ^3Z^4$,
(s) —$NZ^5$S(═O)$_2Z^2$,
(t) —$NZ^5$S(═O)$_2NZ^3Z^4$,
(u) —$NZ^5$S(═O)(═$NZ^6$)$Z^2$,
(v) —$NZ^5$S(═$NZ^6$)(═$NZ^7$)$Z^2$,
(w) —$NZ^5$S(═O)(═$NZ^6$)$NZ^3Z^4$,
(x) $C_1$-$C_6$ alkyl,
(y) $C_1$-$C_6$ haloalkyl, and
(z) $C_3$-$C_6$ cycloalkyl, (iv) —C(═O)$Z^2$
(v) —C(═O)$OZ^2$,
(vi) —C(═O)$NZ^3Z^4$,
(vii) —S(═O)$_2Z^8$,
(viii) —S(═O)$_2NZ^3Z^4$,
(ix) —S(═O)(═$NZ^6$)$Z^2$,
(xi) —S(═$Z^6$)(═$NZ^7$)$Z^2$, and
(x) —S(═O)(═$NZ^6$)$NZ^3Z^4$, $R^{4b}$ is selected from the group consisting of:
(i) hydrogen, and
(ii) $C_1$-$C_6$ alkyl;

each $Z^1$ is independently selected from the group consisting of:
(i) hydrogen,
(ii) $C_1$-$C_6$ alkyl,
(iii) unsubstituted or substituted $C_2$-$C_6$ alkenyl, wherein one or more substituents are independently selected from the group consisting of halogen and unsubstituted or substituted $C_1$-$C_6$ alkyl, wherein one or more substituents are independently selected from the group consisting of —$NZ^3Z^4$ and 4- to 8-membered heterocycle,
(iv) $C_2$-$C_6$ alkynyl,
(v) $C_3$-$C_6$ cycloalkyl,
(vi) $C_3$-$C_6$ cycloalkenyl, and
(vii) $C_1$-$C_6$ haloalkyl;

each $Z^2$ is independently selected from the group consisting of:
(i) $C_1$-$C_6$ alkyl,
(ii) unsubstituted or substituted $C_2$-$C_6$ alkenyl, wherein one or more substituents are independently selected from the group consisting of halogen and unsubstituted or substituted $C_1$-$C_6$ alkyl, wherein one or more substituents are independently selected from the group consisting of —$NZ^3Z^4$ and 4- to 8-membered heterocycle,
(iii) $C_2$-$C_6$ alkynyl,
(iv) $C_3$-$C_6$ cycloalkyl,
(v) $C_3$-$C_6$ cycloalkenyl, and
(vi) $C_1$-$C_6$ haloalkyl;

each $Z^3$ is independently selected from the group consisting of:
(i) hydrogen;
(ii) $C_1$-$C_6$ alkyl,
(iii) unsubstituted or substituted $C_2$-$C_6$ alkenyl, wherein one or more substituents are independently selected from the group consisting of halogen and unsubstituted or substituted $C_1$-$C_6$ alkyl, wherein one or more substituents are independently selected from the group consisting of —$NZ^3Z^4$ and 4- to 8-membered heterocycle,
(iv) $C_2$-$C_6$ alkynyl,
(v) $C_3$-$C_6$ cycloalkyl,
(vi) $C_3$-$C_6$ cycloalkenyl, and
(vii) $C_1$-$C_6$ haloalkyl;

each $Z^4$, $Z^5$, $Z^6$ and $Z^7$ is independently selected from the group consisting of:
(i) hydrogen,
(ii) $C_1$-$C_6$ alkyl, and
(iii) $C_3$-$C_6$ cycloalkyl;

each $Z^8$ is independently selected from the group consisting of:
(i) hydrogen,
(ii) $C_1$-$C_6$ alkyl,
(iii) unsubstituted or substituted $C_2$-$C_6$ alkenyl, wherein one or more substituents are independently selected from the group consisting of halogen and unsubstituted or substituted $C_1$-$C_6$ alkyl, wherein one or more substituents are independently selected from the group consisting of —$NZ^3Z^4$ and 4- to 8-membered heterocycle,
(iv) halogen, and
(v) hydroxy;

$R^{3b}$ and $R^{3c}$ are independently selected from the group consisting of:
(i) hydrogen,
(ii) $C_1$-$C_6$ alkyl,
(ii) $C_1$-$C_6$ haloalkyl, and
(iii) $C_3$-$C_6$ cycloalkyl;

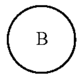

is selected from the group consisting of:
(i) $C_3$-$C_6$ cycloalkyl,
(ii) 4- to 10-membered heterocycle,
(iii) $C_6$-$C_{10}$ aryl, and
(iv) 5- to 10-membered heteroaryl;

each $R^5$ is independently selected from the group consisting of:
(i) halogen,
(ii) hydroxy,
(iii) cyano,
(iv) —$OZ^1$,
(v) —$SZ^1$,
(vi) —$NZ^3Z^4$,
(vii) —C(═O)$Z^2$
(viii) C(═O)OH,
(ix) —C(═O)$OZ^2$,
(x) —C(═O)$NZ^3Z^4$,
(xi) —$NZ^5$C(═O)$Z^2$,
(xii) —$NZ^5$C(═O)$OZ^2$,
(xiii) —$NZ^5$C(═O)$NZ^3Z^4$,
(xiv) —S(═O)$_2Z^8$,
(xv) —S(═O)$_2NZ^3Z^4$,
(xvi) —S(═O)(═$NZ^6$)$Z^2$,
(xvii) —S(═$Z^6$)(═$NZ^7$)$Z^2$,
(xviii) —S(═O)(═$NZ^6$)$NZ^3Z^4$, (xix) $—NZ^5S(═O)_2Z^2$, (xx) $—NZ^5S(═O)_2NZ^3Z^4$, (xxi) $—NZ^5S(═O)(═NZ^6)Z^2$, (xxii) $—NZ^5S(═NZ^6)(═NZ^7)Z^2$, (xxiii) $—NZ^5S(═O)(═NZ^6)NZ^3Z^4$, (xxiv) unsubstituted or substituted $C_1$-$C_6$ alkyl, wherein one or more substituents are independently selected from the group consisting of hydroxy, $—OZ^1$, and $—NZ^3Z^4$, (xxv) $C_1$-$C_6$ haloalkyl, (xxvi) $C_3$-$C_6$ cycloalkyl, wherein one or more substituents are independently selected from the group consisting of $C_1$-$C_6$ alkyl, hydroxy, and $—NZ^3Z^4$, (xxvii) unsubstituted or substituted $C_2$-$C_6$ alkenyl, wherein one or more substituents are independently selected from the group consisting of halogen and unsubstituted or substituted $C_1$-$C_6$ alkyl, wherein one or more substituents are independently selected from the group consisting of $—NZ^3Z^4$ and 4- to 8-membered heterocycle, (xxviii) unsubstituted or substituted $C_6$-$C_{10}$ aryl, wherein one or more substituents are independently selected from the group consisting of halo, $—OZ^1$, $C_1$-$C_6$ alkyl, cyano, hydroxy, and $C_1$-$C_6$ haloalkyl, and (xxix) unsubstituted or substituted 4- to 10-membered heterocycle, wherein one or more substituents are independently selected from the group consisting of $C_1$-$C_6$ alkyl and $C_1$-$C_6$ haloalkyl, $R^{6a}$ is selected from the group consisting of:

(i) hydrogen, and (ii) $C_1$-$C_6$ alkyl;

$R^{6b}$ is selected from the group consisting of:

(i) hydrogen, and (ii) $C_1$-$C_6$ alkyl, m is 0, 1, 2, or 3.

$R^{10a}$, $R^{10b}$, $R^{10c}$, and $R^{10d}$ are independently selected from the group consisting of:

(i) hydrogen, (ii) cyano, (iii) hydroxy (iv) $—OZ^1$, (v) $—SZ^1$, (vi) $—NZ^3Z^4$, (vii) $C_1$-$C_6$ alkyl, and (viii) $C_1$-$C_6$ haloalkyl;

Embodiment 3. The compound of Embodiment 1 or 2 of Formula III:

III

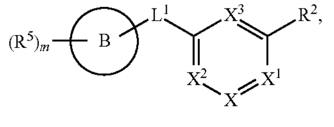

or a stereoisomer, tautomer, pharmaceutically acceptable salt, or solvate thereof.

Embodiment 4. The compound of Embodiment 1 or 2 of Formula IV:

IV

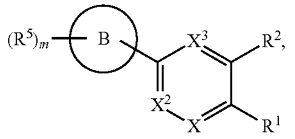

or a stereoisomer, tautomer, pharmaceutically acceptable salt, or solvate thereof.

Embodiment 5. The compound of Embodiment 1, 2, or 4, or a stereoisomer, tautomer, pharmaceutically acceptable salt, or solvate thereof, wherein X, $X^2$, and $X^3$ are —CH═.

Embodiment 6. The compound of Embodiment 1, 2, or 4, or a stereoisomer, tautomer, pharmaceutically acceptable salt, or solvate thereof, wherein X is —N═; and $X^2$ and $X^3$ are —CH═.

Embodiment 7. The compound of Embodiment I, 2, or 4, or a stereoisomer, tautomer, pharmaceutically acceptable salt, or solvate thereof, wherein X and $X^3$ are —CH═; and $X^2$ is N═.

Embodiment 8. The compound of Embodiment 1, 2, or 4, or a stereoisomer, tautomer, pharmaceutically acceptable salt, or solvate thereof, wherein X and $X^2$ are —CH═; and $X^3$ is N═.

Embodiment 9. The compound of Embodiment 1 or 2 of Formula V:

V

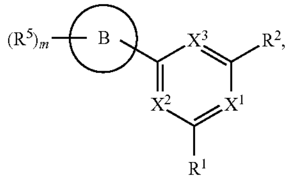

or a stereoisomer, tautomer, pharmaceutically acceptable salt, or solvate thereof.

Embodiment 10. The compound of Embodiment 1, 2, or 9 or a stereoisomer, tautomer, pharmaceutically acceptable salt, or solvate thereof, wherein $X^1$, $X^2$, and $X^3$ are —CH═.

Embodiment 11. The compound of Embodiment 1, 2, or 9, or a stereoisomer, tautomer, pharmaceutically acceptable salt, or solvate thereof, wherein $X^1$ is —N═; and $X^2$ and $X^3$ are —CH═.

Embodiment 12. The compound of Embodiment 1, 2, or 9, or a stereoisomer, tautomer, pharmaceutically acceptable salt, or solvate thereof, wherein $X^1$ and $X^3$ are —CH═; and $X^2$ is N═.

Embodiment 13. The compound of Embodiment 1, 2, or 9, or a stereoisomer, tautomer, pharmaceutically acceptable salt, or solvate thereof, wherein $X^1$ and $X^2$ are —CH═; and $X^3$ is N═.

Embodiment 14. The compound of any one of Embodiments 1-13, or a stereoisomer, tautomer, pharmaceutically acceptable salt, or solvate thereof, wherein $R^1$ is $-L^2-NR^{4a}R^{4b}$, Embodiment 15. The compound of any one of Embodiment 14, or a stereoisomer, tautomer, pharmaceutically acceptable salt, or solvate thereof, wherein $L^2$ is $—(CH_2)_n—$.

Embodiment 16. The compound of Embodiment 15, or a stereoisomer, tautomer, pharmaceutically acceptable salt, or solvate thereof, wherein n is 0.

Embodiment 17. The compound of Embodiment 15, or a stereoisomer, tautomer, pharmaceutically acceptable salt, or solvate thereof, wherein n is 1.

Embodiment 18. The compound of any one of Embodiments 1-17, or a stereoisomer, tautomer, pharmaceutically acceptable salt, or solvate thereof, wherein $R^{4a}$ is selected from the group consisting of —C(═O)$Z^2$, —C(═O)O$Z^2$, —C(═O)N$Z^3Z^4$, —S(═O)$_2Z^8$, and —S(═O)$_2$N$Z^3Z^4$.

Embodiment 19. The compound of any one of Embodiments 1-18, or a stereoisomer, tautomer, pharmaceutically acceptable salt, or solvate thereof, wherein:

$Z^2$ is selected from the group consisting of $C_1$-$C_6$ alkyl and $C_2$-$C_6$ alkenyl;

$Z^3$ is selected from the group consisting of $C_1$-$C_6$ alkyl and $C_2$-$C_6$ alkenyl; and $Z^4$ is hydrogen.

Embodiment 20. The compound of any one of Embodiments 1-19, or a stereoisomer, tautomer, pharmaceutically acceptable salt, or solvate thereof, wherein $R^1$ is unsubstituted or substituted 4- to 8-membered heterocycle.

Embodiment 21. The compound of Embodiment 20, or a stereoisomer, tautomer, pharmaceutically acceptable salt, or solvate thereof, wherein $R^1$ is:

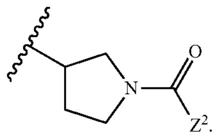

Embodiment 22. The compound of Embodiment 1 or 2 of Formula VI:

VI

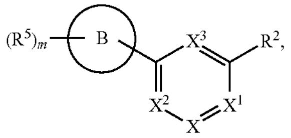

or a stereoisomer, tautomer, pharmaceutically acceptable salt, or solvate thereof, wherein:

X is selected from the group consisting of —$CR^{10a}$═ and —N═; and $X^1$ is selected from the group consisting of —$CR^{10b}$═ and —N═.

Embodiment 23. The compound of Embodiment 1, 2, or 22, or a stereoisomer, tautomer, pharmaceutically acceptable salt, or solvate thereof, wherein X, $X^1$, $X^2$, and $X^3$ are —CH═.

Embodiment 24. The compound of Embodiment 1 or 2 of Formula VII:

VII

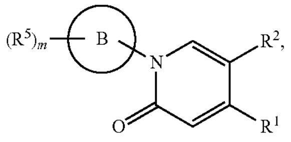

or a stereoisomer, tautomer, pharmaceutically acceptable salt, or solvate thereof.

Embodiment 25. The compound of Embodiment 1 or 2 of Formula VII:

VII

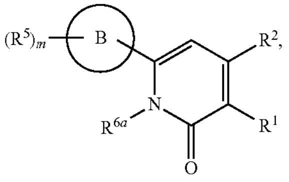

or a stereoisomer, tautomer, pharmaceutically acceptable salt, or solvate thereof.

Embodiment 26. The compound of Embodiment 1, 2, or 25, or a stereoisomer, tautomer, pharmaceutically acceptable salt, or solvate thereof, wherein $R^{6a}$ is selected from the group consisting of hydrogen and $C_1$-$C_4$ alkyl.

Embodiment 27. The compound of Embodiment 1 or 2 of Formula VII:

VII

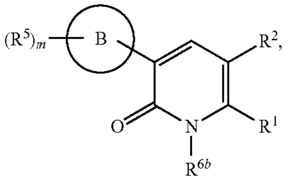

or a stereoisomer, tautomer, pharmaceutically acceptable salt, or solvate thereof.

Embodiment 28. The compound of Embodiment 1, 2, or 27, or a stereoisomer, tautomer, pharmaceutically acceptable salt, or solvate thereof, wherein $R^{6b}$ is selected from the group consisting of hydrogen and $C_1$-$C_4$ alkyl.

Embodiment 29. The compound of any one of Embodiments 1-28, or a stereoisomer, tautomer, pharmaceutically acceptable salt, or solvate thereof, wherein $R^2$ is $R^2$-1.

Embodiment 30. The compound of any one of Embodiments 1-29, or a stereoisomer, tautomer, pharmaceutically acceptable salt, or solvate thereof, wherein

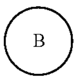

is $C_6$-$C_{10}$ aryl.

Embodiment 31. The compound any one of Embodiments 1-30, wherein

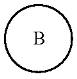

is phenyl, $R^5$ is halo; and m is 1 or 2.

Embodiment 32. A compound, or a stereoisomer, tautomer, pharmaceutically acceptable salt, or solvate thereof, selected from any one or more of the compounds of Table 1.

Embodiment 33. The compound of Embodiment 1 or 2, or a tautomer, pharmaceutically acceptable salt, or solvate thereof, selected from the group consisting of:

1-(3-(4-(1-(difluoromethyl)-1H-pyrazol-3-yl)-6-(4-fluorophenyl)pyridin-3-yl)pyrrolidin-1-yl)prop-2-en-1-one;

(S)-1-(3-(4-(1-(difluoromethyl)-1H-pyrazol-3-yl)-6-(4-fluorophenyl)pyridin-3-yl)pyrrolidin-1-yl)prop-2-en-1-one; and (R)-1-(3-(4-(1-(difluoromethyl)-1H-pyrazol-3-yl)-6-(4-fluorophenyl)pyridin-3-yl)pyrrolidin-1-yl)prop-2-en-1-one.

Embodiment 34. A pharmaceutical composition comprising the compound of any one of Embodiments 1-33, or a stereoisomer, tautomer, pharmaceutically acceptable salt, or solvate thereof, and a pharmaceutically acceptable carrier.

Embodiment 35. The compound of any one of Embodiments 1-33, or the pharmaceutical composition of Embodiment 34, for use as a medicine.

Embodiment 36. The compound of any one of Embodiments 1-33, or the pharmaceutical composition of Embodiment 34, for use in the prevention or treatment of a YAP/TAZ-TEAD activation mediated disorder in an animal, mammal or human.

Embodiment 37. The compound of any one of Embodiments 1-33, or the pharmaceutical composition of Embodiment 34, for use in the prevention or treatment of a YAP/TAZ-TEAD activation mediated disorder that is selected from the group comprising cancer, fibrosis and YAP/TAZ-TEAD activation mediated congenital disorders.

Embodiment 38. The compound of any one of Embodiments 1-33, or the pharmaceutical composition of Embodiment 34, for use in the prevention or treatment of a YAP/TAZ-TEAD activation mediated disorder that is selected from lung cancer, breast cancer, head and neck cancer, oesophageal cancer, kidney cancer, bladder cancer, colon cancer, ovarian cancer, cervical cancer, endometrial cancer, liver cancer (including but not limited to cholangiocarcinoma), skin cancer, pancreatic cancer, gastric cancer, brain cancer and prostate cancer, mesotheliomas, and/or sarcomas.

Embodiment 39. The compound of any one of Embodiments 1-33, or the pharmaceutical composition of Embodiment 34, for use in the prevention or treatment of a YAP/TAZ-TEAD activation mediated disorder selected from acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute T-cell leukemia, basal cell carcinoma, bile duct carcinoma, bronchogenic carcinoma, chondrosarcoma, chordoma, choriocarcinoma, chronic leukemia, chronic lymphocytic leukemia, chronic myelocytic (granulocytic) leukemia, chronic myelogenous leukemia, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, hemangioblastoma, hepatoma, hepatocellular cancer, hormone insensitive prostate cancer, leiomyosarcoma, leukemia, liposarcoma, lymphangioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, medullary carcinoma, medulloblastoma, melanoma, meningioma, mesothelioma, multiple myeloma, myelogenous leukemia, myeloma, myxosarcoma, neuroblastoma, NUT midline carcinoma (NMC), non-small cell lung cancer, oligodendroglioma, oral cancer, osteogenic sarcoma, papillary adenocarcinomas, papillary carcinoma, pinealoma, polycythemia vera, rectal cancer, renal cell carcinoma, retinoblastoma, rhabdomyosarcoma, sarcoma, sebaceous gland carcinoma, seminoma, small cell lung carcinoma, solid tumors (carcinomas and sarcomas), small cell lung cancer, stomach cancer, squamous cell carcinoma, synovioma, sweat gland carcinoma, thyroid cancer, Waldenstrom's macroglobulinemia, testicular tumors, uterine cancer and Wilms' tumor.

Embodiment 40. A method for the prevention or treatment of a YAP/TAZ-TEAD activation mediated disorders in an animal, mammal or human comprising administering to said animal, mammal or human in need for such prevention or treatment an effective dose of the compounds of any one of Embodiments 1-33.

Embodiment 41. A method of treatment or prevention of YAP/TAZ-TEAD activation mediated disorder according to Embodiment 40 to a patient in need thereof in combination with one or more other medicines selected from the group consisting of EGFR inhibitors, MEK inhibitors, AXL inhibitors, B-RAF inhibitors, and RAS inhibitors.

More generally, the disclosure relates to the compounds of the formulae described herein and embodiments, statements and aspects thereof being useful as agents having biological activity or as diagnostic agents. Any of the uses mentioned with respect to the present disclosure may be restricted to a non-medical use, a non-therapeutic use, a non-diagnostic use, or exclusively an in vitro use, or a use related to cells remote from an animal.

Compounds of the present disclosure are small molecule YAP/TAZ-TEAD inhibitors. Small molecule YAP/TAZ-TEAD inhibitors are useful, e.g., for the treatment of cancer, including with no limitations, lung cancer, breast cancer, head and neck cancer, oesophageal cancer, kidney cancer, bladder cancer, colon cancer, ovarian cancer, cervical cancer, endometrial cancer, liver cancer (including but not limited to cholangiocarcinoma), skin cancer, pancreatic cancer, gastric cancer, brain cancer and prostate cancer, mesotheliomas, and/or sarcomas. In other embodiments, small molecule YAP/TAZ-TEAD inhibitors are useful for the treatment of cancers characterized by squamous cell carcinomas of the lung, cervix, ovaries, head and neck, oesophagus, and/or skin. In other embodiments, small molecule YAP/TAZ-TEAD inhibitors are useful for the treatment of cancers that originate from neuroectoderm-derived tissues, such as ependymomas, meningiomas, schwannomas, peripheral nerve-sheet tumors and/or neuroblastomas. In other embodiments, small molecule YAP/TAZ-TEAD inhibitors are useful for the treatment of vascular cancers, such as epithelioid haemangioendotheliomas, or for the treatment of supratentorial ependymomas or porocarcinomas. In some embodiments, the solid tumors have gain-of-function gene amplifications, gene fusions or activating mutations in the YAP1 or WWTR1 (TAZ) genes.

In some embodiments the solid tumors have loss-of-function mutations or deletions in the NF2, LATS1/2, BAP1, FAT1, SAV1, and/or MST1/2 genes. In some embodiments solid tumors have gain-of-function mutations in the GNAQ and/or GNA11 genes, e.g. in uveal melanoma. In some embodiments, solid cancer are characterized by constitutive nuclear presence of YAP and/or TAZ. In some embodiments, solid cancers are characterized by the overexpression of YAP/TAZ-TEAD signature genes, including but not limited to CTGF, CYR61, AMOTL2, and/or ANKRD1.

Small molecule YAP/TAZ-TEAD inhibitors may also be useful to treat cancers that have developed resistance to prior treatments. This may include, for instance, the treatment of cancers that have developed resistance to chemotherapy, or to targeted therapy. In some embodiments, this may include the treatment of cancers that have developed resistance to inhibitors of receptor tyrosine kinases, such as EGFR (afatinib, erlotinib hydrochloride, osimertinib, gefitinib, dacomitinib, neratinib, canertinib, cetuximab) or AXL (crizotinib, cabozantinib, gilteritinib, sitravatinib, bemcentinib, dubermatinib), to components of the RAS-MAPK signaling cascade, including inhibitors of RAS itself (such as AMG510, MRTX849, BI1701963, ARS1620), inhibitors of B-RAF (sorafinib tosylate, dabrafenib, vemurafenib, regorafenib), or MEK1/2 (trametinib, selumetinib, cobimetinib, mirdametinib).

Small molecule YAP/TAZ-TEAD inhibitors may also be useful when combined, upon simultaneous administration, or subsequent administration, with other agents used for the treatment of cancer. This may include, for instance, the co-treatment with inhibitors or monoclonal antibodies targeting receptor tyrosine kinases such as EGFR (afatinib, erlotinib hydrochloride, osimertinib, gefitinib, dacomitinib, neratinib, canertinib, cetuximab) or AXL (crizotinib, cabozantinib, gilteritinib, sitravatinib, bemcentinib, dubermatinib), to components of the RAS-MAPK signaling cascade, including inhibitors of RAS itself (such as AMG510, MRTX849, BI1701963, ARS1620), inhibitors of B-RAF (sorafinib tosylate, dabrafenib, vemurafenib, regorafenib), or MEK1/2 (trametinib, selumetinib, cobimetinib, mirdametinib).

Small molecule YAP/TAZ-TEAD inhibitors may also be useful to treat a metastasized cancer. In some instances, the metastasized cancer is selected from metastasized uveal melanoma, mesothelioma, esophageal cancer, liver cancer, breast cancer, hepatocellular carcinoma, lung adenocarcinoma, glioma, colon cancer, colorectal cancer, gastric cancer, medulloblastoma, ovarian cancer, esophageal squamous cell carcinoma, sarcoma, Ewing sarcoma, head and neck cancer, prostate cancer, and meningioma.

In some embodiments, the cancer treated could be malignant pleural mesothelioma or lung cancer.

In some embodiments, the compounds of the disclosure can be used for the treatment of acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute T-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, hemangioblastoma, hepatoma, hepatocellular cancer, hormone insensitive prostate cancer, leiomyosarcoma, leukemia, liposarcoma, lung cancer, lymphangioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, medullary carcinoma, medulloblastoma, melanoma, meningioma, mesothelioma, multiple myeloma, myelogenous leukemia, myeloma, myxosarcoma, neuroblastoma, NUT midline carcinoma (NMC), non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenstrom's macroglobulinemia, testicular tumors, uterine cancer and Wilms' tumor.

Malignant Pleural Mesothelioma

Small molecule YAP/TAZ-TEAD inhibitors may also be useful to treat malignant pleural mesothelioma, as a single agent, or in combination with inhibitors such as pemetrexed disodium, raltitrexed, carboplatin, oxaliplatin, gemcitabine, doxorubicin, or monoclonal antibodies such as bevacizumab. Combinations with checkpoint inhibitors such as pembrolizumab, atezolizumab, and/or nivolumab. Combinations with cell therapy, for instance, chimeric antigen receptor (CAR) T therapy or CAR NK therapy, which may, for instance, use mesothelin (MSLN) as an antigen. Combinations with monoclonal antibodies that, for instance, recognize mesothelin as an antigen, for instance BMS-986148, BAY 94-9343, amatuximab, and/or LMB-100.

Lung Cancer

Small molecule YAP/TAZ-TEAD inhibitors may also be useful to treat lung cancer, as a single agent, or in combination with inhibitors such as afatinib, bevacizumab, cabozantinib, ceritinib, crizotinib, erlotinib hydrochloride, osimertinib, ramucirumab, gefitinib, alectinib, trastuzumab, cetuximab, ipilimumab, trametinib, dabrafenib, vemurafenib, dacomitinib, tivantinib, and/or onartuzumab. Combinations with checkpoint inhibitors such as pembrolizumab, atezolizumab, and/or nivolumab. Combinations with cisplatin, carboplatin, paclitaxel, paclitaxel protein bound, docetaxel, gemcitabine, vinorelbine, etoposide, nintedanib, vinblastine, pemetrexed, afatinib, bevacizumab, cabozantinib, ceritinib, crizotinib, erlotinib hydrochloride, osimertinib, ramucirumab, gefitinib, necitumumab, alectinib, trastuzumab, cetuximab, ipilimumab, trametinib, dabrafenib, vemurafenib, dacomitinib, tivantinib, onartuzumab, pembrolizumab, atezolizumab, and/or nivolumab In some embodiments, small molecule YAP/TAZ-TEAD inhibitors are useful, e.g., for the treatment of congenital disorders. In some embodiments, the congenital disease is mediated by activation of transcriptional coactivator with PDZ binding motif/Yes-associated protein transcription coactivator (TAZ/YAP). In some embodiments, the congenital disease is characterized by a mutant Ga-protein. In some embodiments, the mutant Ga-protein is selected from G12, G13, Gq, G11, Gi, Go, and Gs. In some embodiments, the congenital disease is characterized by loss-of-function mutations or deletions in the NF2 gene. Exemplary congenital diseases include, but are not limited to, Sturge-Weber Syndrome, Port-Wine stain, and Neurofibromatosis. In some embodiments the congenital disease is Neurofibromatosis, including but not limited to Neurofibromatosis type 2.

In some embodiments, small molecule YAP/TAZ-TEAD inhibitors are useful, e.g., for the treatment of fibrotic disorders, such as fibrosis of the liver, the lung, the kidney, the heart or the skin. In some embodiments, fibrosis can be treated in the context of non-alcoholic fatty liver disease, primary sclerosing cholangitis, primary biliary cirrhosis, idiopathic pulmonary fibrosis, chronic kidney disease, and/or myocardial infarction injury.

The compounds of the disclosure can inhibit YAP/TAZ-TEAD transcription activation. The compounds have been shown to inhibit YAP/TAZ-TEAD transcription activity in cellular models and in an animal model. The compounds have also been shown to have an inhibitory effect on cancer cell lines that are dependent on YAP/TAZ-TEAD transcription activity and on the growth of cancer in a xenograft cancer model.

The compounds of the disclosure can optionally be bound covalently to an insoluble matrix and used for affinity chromatography (separations, depending on the nature of the groups of the compounds, for example compounds with pendant aryl are useful in hydrophobic affinity separations).

When using one or more derivatives of the formulae as defined herein:

- the active ingredients of the compound(s) may be administered to the animal or mammal (including a human) to be treated by any means well known in the art, i.e. orally, intranasally, subcutaneously, intramuscularly, intradermally, intravenously, intra-arterially, parenterally or by catheterization.
- the therapeutically effective amount of the preparation of the compound(s), especially for the treatment of diseases mediated by activity of YAP/TAZ-TEAD transcription in humans and other mammals (such as cancer, fibrosis and certain congenital disorders), preferably is a YAP/TAZ-TEAD transcription inhibiting amount of the compounds of the formulae, statements, aspects and embodiments as defined herein and corresponds to an amount which ensures a plasma level that is able to inhibit the YAP/TAZ-TEAD activation and is between 1 μg/ml and 100 mg/ml.

Suitable dosages of the compounds or compositions of the disclosure should be used to treat or prevent the targeted diseases in a subject. Depending upon the pathologic condition to be treated and the patient's condition, the said effective amount may be divided into several sub-units per day or may be administered at more than one day intervals.

According to a particular embodiment of the disclosure, the compounds of the disclosure may be employed in combination with other therapeutic agents for the treatment or prophylaxis of diseases mediated by activity of YAP/TAZ-TEAD transcription in humans and other mammals (such as cancer, fibrosis and certain congenital disorders). The disclosure therefore relates to the use of a composition comprising:

(a) one or more compounds of the formulae and aspects, statements and embodiments herein, and (b) one or more further therapeutic or preventive agents that are used for the prevention or treatment of cancer or fibrosis as biologically active agents in the form of a combined preparation for simultaneous, separate or sequential use.

The compound or composition can be administered concurrently with, prior to, or subsequent to the one or more additional therapeutic agents, which are different from the compound described herein and may be useful as, e.g., combination therapies.

Examples of such further therapeutic agents for use in combinations include agents that are inhibitors of:

- EGFR (such as afatinib, erlotinib hydrochloride, osimertinib, gefitinib, dacomitinib, neratinib, canertinib, cetuximab),
- AXL (such as crizotinib, cabozantinib, gilteritinib, sitravatinib, bemcentinib, dubermatinib),
- components of the RAS-MAPK signaling cascade, including inhibitors of RAS itself (such as AMG510, MRTX849, BI1701963, ARS1620),
- B-RAF (such as sorafinib tosylate, dabrafenib, vemurafenib, regorafenib), or
- MEK1/2 (trametinib, selumetinib, cobimetinib, mirdametinib).

The pharmaceutical composition or combined preparation according to this disclosure may contain the compounds of the present disclosure over a broad content range depending on the contemplated use and the expected effect of the preparation. Generally, the content of the derivatives of the present disclosure of the combined preparation is within the range of 0.1 to 99.9% by weight, preferably from 1 to 99% by weight, more preferably from 5 to 95% by weight.

Those of skill in the art will also recognize that the compounds of the disclosure may exist in many different protonation states, depending on, among other things, the pH of their environment. While the structural formulae provided herein depict the compounds in only one of several possible protonation states, it will be understood that these structures are illustrative only, and that the disclosure is not limited to any particular protonation state—any and all protonated forms of the compounds are intended to fall within the scope of the disclosure.

The term "pharmaceutically acceptable salts" as used herein means the therapeutically active non-toxic salt forms which the compounds of formulae herein are able to form. Therefore, the compounds of this disclosure optionally comprise salts of the compounds herein, especially pharmaceutically acceptable non-toxic salts containing, for example, $Na^+$, $Li^+$, $K^+$, $Ca^{2+}$ and $Mg^{2+}$. Such salts may include those derived by combination of appropriate cations such as alkali and alkaline earth metal ions or ammonium and quaternary amino ions with an acid anion moiety, typically a carboxylic acid. The compounds of the disclosure may bear multiple positive or negative charges. The net charge of the compounds of the disclosure may be either positive or negative. Any associated counter ions are typically dictated by the synthesis and/or isolation methods by which the compounds are obtained. Typical counter ions include, but are not limited to ammonium, sodium, potassium, lithium, halides, acetate, trifluoroacetate, etc., and mixtures thereof. It will be understood that the identity of any associated counter ion is not a critical feature of the disclosure, and that the disclosure encompasses the compounds in association with any type of counter ion. Moreover, as the compounds can exist in a variety of different forms, the disclosure is intended to encompass not only forms of the compounds that are in association with counter ions (e.g., dry salts), but also forms that are not in association with counter ions (e.g., aqueous or organic solutions). Metal salts typically are prepared by reacting the metal hydroxide with a compound of this disclosure. Examples of metal salts which are prepared in this way are salts containing $Li^+$, $Na^+$, and $K^+$. A less soluble metal salt can be precipitated from the solution of a more soluble salt by addition of the suitable metal compound. In addition, salts may be formed from acid addition of certain organic and inorganic acids to basic centers, typically amines, or to acidic groups. Examples of such appropriate acids include, for instance, inorganic acids such as hydrohalogen acids, e.g. hydrochloric or hydrobromic acid, sulfuric acid, nitric acid, phosphoric acid and the like; or organic acids such as, for example, acetic, propanoic, hydroxyacetic, 2-hydroxypropanoic, 2-oxopropanoic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclohexanesulfamic, salicylic (i.e. 2-hydroxybenzoic), p-aminosalicylic and the like. Furthermore, this term also includes the solvates which the compounds of formulae herein as well as their salts are able to form, such as for example hydrates, alcoholates and the like. Finally, it is to be understood that the compositions herein comprise compounds of the disclosure in their unionized, as well as zwitterionic form, and combinations with stoichiometric amounts of water as in hydrates.

Also included within the scope of this disclosure are the salts of the parental compounds with one or more amino acids, especially the naturally-occurring amino acids found as protein components. The amino acid typically is one bearing a side chain with a basic or acidic group, e.g., lysine, arginine or glutamic acid, or a neutral group such as glycine, serine, threonine, alanine, isoleucine, or leucine.

The compounds of the disclosure also include physiologically acceptable salts thereof. Examples of physiologically acceptable salts of the compounds of the disclosure include salts derived from an appropriate base, such as an alkali metal (for example, sodium), an alkaline earth (for example, magnesium), ammonium and $NX_4^+$ (wherein X is $C_1$-$C_4$ alkyl). Physiologically acceptable salts of an hydrogen atom or an amino group include salts of organic carboxylic acids such as acetic, benzoic, lactic, fumaric, tartaric, maleic, malonic, malic, isethionic, lactobionic and succinic acids; organic sulfonic acids, such as methanesulfonic, ethanesulfonic, benzenesulfonic and p-toluenesulfonic acids; and inorganic acids, such as hydrochloric, sulfuric, phosphoric and sulfamic acids. Physiologically acceptable salts of a compound containing a hydroxy group include the anion of said compound in combination with a suitable cation such as $Na^+$ and $NX_4^+$ (wherein X typically is independently selected from H or a $C_1$-$C_4$ alkyl group). However, salts of acids or bases which are not physiologically acceptable may also find use, for example, in the preparation or purification of a physiologically acceptable compound. All salts, whether or not derived form a physiologically acceptable acid or base, are within the scope of the present disclosure.

As used herein and unless otherwise stated, the term “enantiomer” means each individual optically active form of a compound of the disclosure, having an optical purity or enantiomeric excess (as determined by methods standard in the art) of at least 80% (e.g. at least 90% of one enantiomer and at most 10% of the other enantiomer), preferably at least 90% and more preferably at least 98%.

The term “isomers” as used herein means all possible isomeric forms, including tautomeric and stereochemical forms, which the compounds of formulae herein may possess, but not including position isomers. Typically, the structures shown herein exemplify only one tautomeric or resonance form of the compounds, but the corresponding alternative configurations are contemplated as well. Unless otherwise stated, the chemical designation of compounds denotes the mixture of all possible stereochemically isomeric forms, said mixtures containing all diastereomers and enantiomers (since the compounds of formulae herein may have at least one chiral center) of the basic molecular structure, as well as the stereochemically pure or enriched compounds. More particularly, stereogenic centers may have either the R- or S-configuration, and multiple bonds may have either cis- or trans-configuration.

Pure isomeric forms of the said compounds are defined as isomers substantially free of other enantiomeric or diastereomeric forms of the same basic molecular structure. In particular, the term “stereoisomerically pure” or “chirally pure” relates to compounds having a stereoisomeric excess of at least about 80% (e.g. at least 90% of one isomer and at most 10% of the other possible isomers), preferably at least 90%, more preferably at least 94% and most preferably at least 97%. The terms “enantiomerically pure” and “diastereomerically pure” should be understood in a similar way, having regard to the enantiomeric excess, respectively the diastereomeric excess, of the mixture in question.

Separation of stereoisomers is accomplished by standard methods known to those in the art. One enantiomer of a compound of the disclosure can be separated substantially free of its opposing enantiomer by a method such as formation of diastereomers using optically active resolving agents (“Stereochemistry of Carbon Compounds,” (1962) by E. L. Eliel, McGraw Hill; Lochmuller, C. H., (1975) J. Chromatogr., 113:(3) 283-302). Separation of isomers in a mixture can be accomplished by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure enantiomers, or (3) enantiomers can be separated directly under chiral conditions. Under method (1), diastereomeric salts can be formed by reaction of enantiomerically pure chiral bases such as brucine, quinine, ephedrine, strychnine, a-methyl-b-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts. Alternatively, by method (2), the substrate to be resolved may be reacted with one enantiomer of a chiral compound to form a diastereomeric pair (Eliel, E. and Wilen, S. (1994) Stereochemistry of Organic Compounds, John Wiley & Sons, Inc., p. 322). Diastereomeric compounds can be formed by reacting asymmetric compounds with enantiomerically pure chiral derivatizing reagents, such as menthyl derivatives, followed by separation of the diastereomers and hydrolysis to yield the free, enantiomerically enriched compound. A method of determining optical purity involves making chiral esters, such as a menthyl ester or Mosher ester, a-methoxy-a-(trifluoromethyl)phenyl acetate (Jacob III. (1982) J. Org. Chem. 47:4165), of the racemic mixture, and analyzing the NMR spectrum for the presence of the two atropisomeric diastereomers. Stable diastereomers can be separated and isolated by normal- and reverse-phase chromatography following methods for separation of atropisomeric naphthyl-isoquinolines (Hoye, T., WO 96/15111).Under method (3), a racemic mixture of two asymmetric enantiomers is separated by chromatography using a chiral stationary phase. Suitable chiral stationary phases are, for example, polysaccharides, in particular cellulose or amylose derivatives. Commercially available polysaccharide based chiral stationary phases are ChiralCel™ CA, OA, OB5, OC5, OD, OF, OG, OJ and OK, and Chiralpak™ AD, AS, OP(+) and OT(+). Appropriate eluents or mobile phases for use in combination with said polysaccharide chiral stationary phases are hexane and the like, modified with an alcohol such as ethanol, isopropanol and the like. ("Chiral Liquid Chromatography" (1989) W. J. Lough, Ed. Chapman and Hall, New York; Okamoto, (1990) "Optical resolution of dihydropyridine enantiomers by High-performance liquid chromatography using phenylcarbamates of polysaccharides as a chiral stationary phase", J. of Chromatogr. 513:375-378).

The terms cis and trans are used herein in accordance with Chemical Abstracts nomenclature and include reference to the position of the substituents on a ring moiety. The absolute stereochemical configuration of the compounds of the formulae described herein may easily be determined by those skilled in the art while using well-known methods such as, for example, X-ray diffraction.

The present disclosure also includes isotopically labelled compounds, which are identical to those recited in the formulas recited herein, but for the fact that one or more atoms are replaced by an atom having an atomic mass or mass number different from the atomic mass or mass number usually found in nature. Examples of isotopes that may be incorporated into compounds of the present disclosure include isotopes of hydrogen, carbon, nitrogen, oxygen, phosphorous, sulfur, fluorine and chlorine, such as $^{2}H$, $^{3}H$, $^{13}C$, $^{11}C$, $^{14}C$, $^{15}N$, $^{18}G$, $^{17}G$, $^{31}P$, $^{32}P$, $^{35}S$, $^{18}F$, and $^{36}Cl$, respectively. Compounds of the present disclosure and pharmaceutically acceptable salts of said compounds or which contain the aforementioned isotopes and/or other isotopes of other atoms are within the scope of this disclosure. Certain isotopically labeled compounds of the present disclosure, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, may afford certain therapeutic advantages resulting from greater metabolic stability, for example increased in vivo half-life or reduced dosage requirements and, hence, may be preferred in some circumstances. Isotopically labelled compounds of the formulas of this disclosure may generally be prepared by carrying out the procedures disclosed in the examples and preparations described herein, by substituting a readily available isotopically labelled reagent for a non-isotopically labelled reagent.

Also encompassed within the disclosure are modifications of the compounds of formula (I) or other formulas, embodiments, aspects or parts thereof or metabolites thereof using PROTAC technology (Schapira M. et al, *Nat. Rev. Drug Discov.* 2019, 18(12), 949-963). Specifically, the PROTAC technology designs a bifunctional small molecule, one end of which is a compound of the general formula (I) or other formulas, embodiments, aspects or parts thereof or metabolites thereof, and the other end of which is connected with a ligand of E3 ubiquitin ligase through a connecting chain, to form a target-induced protein degradation complex. Because this degradation has a catalytic effect, a lower dosage can achieve efficient degradation. The compound of the general formula (I) or other formulas, embodiments, aspects or parts thereof or metabolites thereof can be connected via a linker arm (e.g. long-chain ethylene glycol with the length of 2-10, long-chain propylene glycol with the length of 2-10 and long-chain fatty alkane with the length of 2-10) to a ligand of E3 ubiquitin ligase such as e.g. thalidomide analogs.

The compounds of the disclosure may be formulated with conventional carriers and excipients, which will be selected in accord with ordinary practice. Tablets will contain excipients, glidants, fillers, binders and the like. Aqueous formulations are prepared in sterile form, and when intended for delivery by other than oral administration generally will be isotonic. Formulations optionally contain excipients such as those set forth in the "Handbook of Pharmaceutical Excipients" (1986) and include ascorbic acid and other antioxidants, chelating agents such as EDTA, carbohydrates such as dextrin, hydroxyalkylcellulose, hydroxyalkylmethylcellulose, stearic acid and the like.

Subsequently, the term "pharmaceutically acceptable carrier" as used herein means any material or substance with which the active ingredient is formulated in order to facilitate its application or dissemination to the locus to be treated, for instance by dissolving, dispersing or diffusing the said composition, and/or to facilitate its storage, transport or handling without impairing its effectiveness. The pharmaceutically acceptable carrier may be a solid or a liquid or a gas which has been compressed to form a liquid, e.g. the compositions of this disclosure can suitably be used as concentrates, emulsions, solutions, granulates, dusts, sprays, aerosols, suspensions, ointments, creams, tablets, pellets or powders.

Suitable pharmaceutical carriers for use in the said pharmaceutical compositions and their formulation are well known to those skilled in the art, and there is no particular restriction to their selection within the present disclosure. They may also include additives such as wetting agents, dispersing agents, stickers, adhesives, emulsifying agents, solvents, coatings, antibacterial and antifungal agents (for example phenol, sorbic acid, chlorobutanol), isotonic agents (such as sugars or sodium chloride) and the like, provided the same are consistent with pharmaceutical practice, e.g. carriers and additives which do not create permanent damage to mammals. The pharmaceutical compositions of the present disclosure may be prepared in any known manner, for instance by homogeneously mixing, coating and/or grinding the active ingredients, in a one-step or multi-steps procedure, with the selected carrier material and, where appropriate, the other additives such as surface-active agents. may also be prepared by micronisation, for instance in view to obtain them in the form of microspheres usually having a diameter of about 1 to 10 gm, namely for the manufacture of microcapsules for controlled or sustained release of the active ingredients.

Suitable surface-active agents, also known as emulgent or emulsifier, to be used in the pharmaceutical compositions of the present disclosure are non-ionic, cationic and/or anionic materials having good emulsifying, dispersing and/or wetting properties. Suitable anionic surfactants include both water-soluble soaps and water-soluble synthetic surface-active agents. Suitable soaps are alkaline or alkaline-earth metal salts, unsubstituted or substituted ammonium salts of higher fatty acids ($C_{10}$-$C_{22}$), e.g. the sodium or potassium salts of oleic or stearic acid, or of natural fatty acid mixtures obtainable from coconut oil or tallow oil. Synthetic surfactants include sodium or calcium salts of polyacrylic acids; fatty sulphonates and sulphates; sulphonated benzimidazole derivatives and alkylarylsulphonates. Fatty sulphonates or sulphates are usually in the form of alkaline or alkaline-earth metal salts, unsubstituted ammonium salts or ammonium salts substituted with an alkyl or acyl group having from 8 to 22 carbon atoms, e.g. the sodium or calcium salt of lignosulphonic acid or dodecylsulphonic acid or a mixture of fatty alcohol sulphates obtained from natural fatty acids, alkaline or alkaline-earth metal salts of sulphuric or sulphonic acid esters (such as sodium lauryl sulphate) and sulphonic acids of fatty alcohol/ethylene oxide adducts. Suitable sulphonated benzimidazole derivatives preferably contain 8 to 22 carbon atoms. Examples of alkylarylsulphonates are the sodium, calcium or alcoholamine salts of dodecylbenzene sulphonic acid or dibutyl-naphthalenesulphonic acid or a naphthalene-sulphonic acid/formaldehyde condensation product. Also suitable are the corresponding phosphates, e.g. salts of phosphoric acid ester and an adduct of p-nonylphenol with ethylene and/or propylene oxide, or phospholipids. Suitable phospholipids for this purpose are the natural (originating from animal or plant cells) or synthetic phospholipids of the cephalin or lecithin type such as e.g. phosphatidylethanolamine, phosphatidylserine, phosphatidylglycerine, lysolecithin, cardiolipin, dioctanylphosphatidyl-choline, dipalmitoylphoshatidyl-choline and their mixtures.

Suitable non-ionic surfactants include polyethoxylated and polypropoxylated derivatives of alkylphenols, fatty alcohols, fatty acids, aliphatic amines or amides containing at least 12 carbon atoms in the molecule, alkylarenesulphonates and dialkylsulphosuccinates, such as polyglycol ether derivatives of aliphatic and cycloaliphatic alcohols, saturated and unsaturated fatty acids and alkylphenols, said derivatives preferably containing 3 to 10 glycol ether groups and 8 to 20 carbon atoms in the (aliphatic) hydrocarbon moiety and 6 to 18 carbon atoms in the alkyl moiety of the alkylphenol. Further suitable non-ionic surfactants are water-soluble adducts of polyethylene oxide with poylypropylene glycol, ethylenediaminopolypropylene glycol containing 1 to 10 carbon atoms in the alkyl chain, which adducts contain 20 to 250 ethyleneglycol ether groups and/or 10 to 100 propyleneglycol ether groups. Such compounds usually contain from 1 to 5 ethyleneglycol units per propyleneglycol unit. Representative examples of non-ionic surfactants are nonylphenol-polyethoxyethanol, castor oil polyglycolic ethers, polypropylene/polyethylene oxide adducts, tributylphenoxypolyethoxyethanol, polyethyleneglycol and octylphenoxypolyethoxyethanol. Fatty acid esters of polyethylene sorbitan (such as polyoxyethylene sorbitan trioleate), glycerol, sorbitan, sucrose and pentaerythritol are also suitable non-ionic surfactants.

Suitable cationic surfactants include quaternary ammonium salts, particularly halides, having 4 hydrocarbon groups optionally substituted with halo, phenyl, substituted phenyl or hydroxy; for instance quaternary ammonium salts containing as N-substituent at least one $C_{8-22}$alkyl (e.g. cetyl, lauryl, palmityl, myristyl, oleyl and the like) and, as further substituents, unsubstituted or halogenated lower alkyl, benzyl and/or hydroxy-lower alkyl.

A more detailed description of surface-active agents suitable for this purpose may be found for instance in "McCutcheon's Detergents and Emulsifiers Annual" (MC Publishing Crop., Ridgewood, New Jersey, 1981), "Tensid-Taschenbucw', 2 d ed. (Hanser Verlag, Vienna, 1981) and "Encyclopaedia of Surfactants, (Chemical Publishing Co., New York, 1981).

Compounds of the disclosure and their pharmaceutically acceptable salts (hereafter collectively referred to as the active ingredients) may be administered by any route appropriate to the condition to be treated, suitable routes including oral, rectal, nasal, topical (including ocular, buccal and sublingual), vaginal and parenteral (including subcutaneous, intramuscular, intravenous, intradermal, intrathecal and epidural). The preferred route of administration may vary with for example the condition of the recipient.

While it is possible for the active ingredients to be administered alone it is preferable to present them as pharmaceutical formulations. The formulations, both for veterinary and for human use, of the present disclosure comprise at least one active ingredient, as above described, together with one or more pharmaceutically acceptable carriers therefore and optionally other therapeutic ingredients. The carrier (s) optimally are "acceptable" in the sense of being compatible with the other ingredients of the formulation and not deleterious to the recipient thereof. The formulations include those suitable for oral, rectal, nasal, topical (including buccal and sublingual), vaginal or parenteral (including subcutaneous, intramuscular, intravenous, intradermal, intrathecal and epidural) administration. The formulations may conveniently be presented in unit dosage form and may be prepared by any of the methods well known in the art of pharmacy. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present disclosure suitable for oral administration may be presented as discrete units such as capsules, cachets or tablets each containing a predetermined amount of the active ingredient; as a powder or granules; as solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein. For infections of the eye or other external tissues e.g. mouth and skin, the formulations are optionally applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base. If desired, the aqueous phase of the cream base may include, for example, at least 30% w/w of a polyhydric alcohol, e.g. an alcohol having two or more hydroxyl groups such as propylene glycol, butane 1,3-diol, mannitol, sorbitol, glycerol and polyethylene glycol (including PEG400) and mixtures thereof. The topical formulations may desirably include a compound which enhances absorption or penetration of the active ingredient through the skin or other affected areas. Examples of such dermal penetration enhancers include dimethylsulfoxide and related analogs.

The oily phase of the emulsions of this disclosure may be constituted from known ingredients in a known manner. While the phase may comprise merely an emulsifier (otherwise known as an emulgent), it desirably comprises a mixture of at least one emulsifier with a fat or an oil or with both a fat and an oil. Optionally, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

The choice of suitable oils or fats for the formulation is based on achieving the desired cosmetic properties, since the solubility of the active compound in most oils likely to be used in pharmaceutical emulsion formulations is very low. Thus the cream should optionally be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredient is dissolved or suspended in a suitable carrier, especially an aqueous solvent for the active ingredient. The active ingredient is optionally present in such formulations in a concentration of 0.5 to 20%, advantageously 0.5 to 10% particularly about 1.5% w/w. Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate. Formulations suitable for nasal administration wherein the carrier is a solid include a coarse powder having a particle size for example in the range 20 to 500 microns (including particle sizes in a range between 20 and 500 microns in increments of 5 microns such as 30 microns, 35 microns, etc), which is administered in the manner in which snuff is taken, e.g. by rapid inhalation through the nasal passage from a container of the powder held close up to the nose. Suitable formulations wherein the carrier is a liquid, for administration as for example a nasal spray or as nasal drops, include aqueous or oily solutions of the active ingredient. Formulations suitable for aerosol administration may be prepared according to conventional methods and may be delivered with other therapeutic agents.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit daily sub-dose, as herein above recited, or an appropriate fraction thereof, of an active ingredient.

It should be understood that in addition to the ingredients particularly mentioned above the formulations of this disclosure may include other agents conventional in the art having regard to the type of formulation in question, for example those suitable for oral administration may include flavoring agents.

Compounds of the disclosure can be used to provide controlled release pharmaceutical formulations containing as active ingredient one or more compounds of the disclosure ("controlled release formulations") in which the release of the active ingredient can be controlled and regulated to allow less frequency dosing or to improve the pharmacokinetic or toxicity profile of a given disclosed compound. Controlled release formulations adapted for oral administration in which discrete units comprising one or more compounds of the disclosure can be prepared according to conventional methods.

Additional ingredients may be included in order to control the duration of action of the active ingredient in the composition. Control release compositions may thus be achieved by selecting appropriate polymer carriers such as for example polyesters, polyamino acids, polyvinyl pyrrolidone, ethylene-vinyl acetate copolymers, methylcellulose, carboxymethylcellulose, protamine sulfate and the like. The rate of drug release and duration of action may also be controlled by incorporating the active ingredient into particles, e.g. microcapsules, of a polymeric substance such as hydrogels, polylactic acid, hydroxymethylcellulose, polymethyl methacrylate and the other above-described polymers. Such methods include colloid drug delivery systems like liposomes, microspheres, microemulsions, nanoparticles, nanocapsules and so on. Depending on the route of administration, the pharmaceutical composition may require protective coatings. Pharmaceutical forms suitable for injectionable use include sterile aqueous solutions or dispersions and sterile powders for the extemporaneous preparation thereof. Typical carriers for this purpose therefore include biocompatible aqueous buffers, ethanol, glycerol, propylene glycol, polyethylene glycol and the like and mixtures thereof.

In view of the fact that, when several active ingredients are used in combination, they do not necessarily bring out their joint therapeutic effect directly at the same time in the mammal to be treated, the corresponding composition may also be in the form of a medical kit or package containing the two ingredients in separate but adjacent repositories or compartments. In the latter context, each active ingredient may therefore be formulated in a way suitable for an administration route different from that of the other ingredient, e.g. one of them may be in the form of an oral or parenteral formulation whereas the other is in the form of an ampoule for intravenous injection or an aerosol.

Another embodiment of this disclosure relates to various precursor or "pro-drug" forms of the compounds of the present disclosure. It may be desirable to formulate the compounds of the present disclosure in the form of a chemical species which itself is not significantly biologically-active, but which when delivered to the animal, mammal or human will undergo a chemical reaction catalyzed by the normal function of the body of the fish, inter alia, enzymes present in the stomach or in blood serum, said chemical reaction having the effect of releasing a compound as defined herein. The term "pro-drug" thus relates to these species which are converted in vivo into the active pharmaceutical ingredient.

The pro-drugs of the compounds of the present disclosure can have any form suitable to the formulator, for example, esters are non-limiting common pro-drug forms. In the present case, however, the pro-drug may necessarily exist in a form wherein a covalent bond is cleaved by the action of an enzyme present at the target locus. For example, a C—C covalent bond may be selectively cleaved by one or more enzymes at said target locus and, therefore, a pro-drug in a form other than an easily hydrolysable precursor, inter alia an ester, an amide, and the like, may be used. The counterpart of the active pharmaceutical ingredient in the pro-drug can have different structures such as an amino acid or peptide structure, alkyl chains, sugar moieties and others as known in the art.

For the purpose of the present disclosure the term "therapeutically suitable pro-drug" is defined herein as "a compound modified in such a way as to be transformed in vivo to the therapeutically active form, whether by way of a single or by multiple biological transformations, when in contact with the tissues of the animal, mammal or human to which the pro-drug has been administered, and without undue toxicity, irritation, or allergic response, and achieving the intended therapeutic outcome".

More specifically the term "prodrug", as used herein, relates to an inactive or significantly less active derivative of a compound such as represented by the structural formulae herein described, which undergoes spontaneous or enzymatic transformation within the body in order to release the pharmacologically active form of the compound. For a comprehensive review, reference is made to Rautio J. et al. ("Prodrugs: design and clinical applications" Nature Reviews Drug Discovery, 2008, doi: 10.1038/nrd2468).

The compounds of the disclosure can be prepared while using a series of chemical reactions well known to those skilled in the art, altogether making up the process for preparing said compounds and exemplified further. The processes described further are only meant as examples and by no means are meant to limit the scope of the present disclosure.

EXAMPLES

General Syntheses

Representative compounds of the present disclosure can be synthesized in accordance with the general synthetic methods described below and illustrated in the schemes that follow. Since the schemes are an illustration, the disclosure should not be construed as being limited by the specific chemical reaction and specific conditions described in the schemes and examples. The various starting material used in the schemes are commercially available or may be prepared by methods well within the skill of persons versed in the art. The variables are as defined herein an within the skill of persons versed in the art.

The compounds of the disclosure can be prepared while using a series of chemical reactions well known to those skilled in the art, altogether making up the process for preparing said compounds and exemplified further. The processes described further are only meant as examples and by no means are meant to limit the scope of the present disclosure.

The present invention relates methods for the preparation of the compounds, comprising the steps of:

- Reacting consecutively dihalo-nitro(hetero)arenes or dihalo(hetero)arene nitriles with appropriate coupling agents to obtain azolyl-(hetero)aryl-nitro(hetero)arenes or azolyl-(hetero)aryl-(hetero)arene nitriles, respectively,
- Azole alkylation of the previously obtained azolyl-(hetero)aryl-nitro(hetero)arenes or azolyl-(hetero)aryl-(hetero)arene nitriles to obtain N-functionalized azolyl-(hetero)aryl-nitro(hetero)arenes or azolyl-(hetero)aryl-(hetero)arene nitriles, respectively;
- Reduction of the previously obtained azolyl-(hetero)aryl-nitro(hetero)arenes or azolyl-(hetero)aryl-(hetero)arene nitriles, followed by derivatization of the obtained amine or aniline moiety, respectively, to obtain the desired compounds of the invention.

The compounds of the present invention may be prepared according to the general procedure outlined in Scheme 1.

Scheme 1: all $R^{3a}$, $R^{4a}$, $R^{4b}$, $L^1$, and B are as described for the compounds of the present invention and its embodiments and formulae.

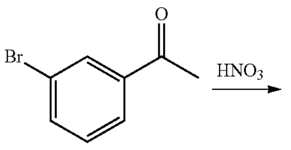

1

-continued

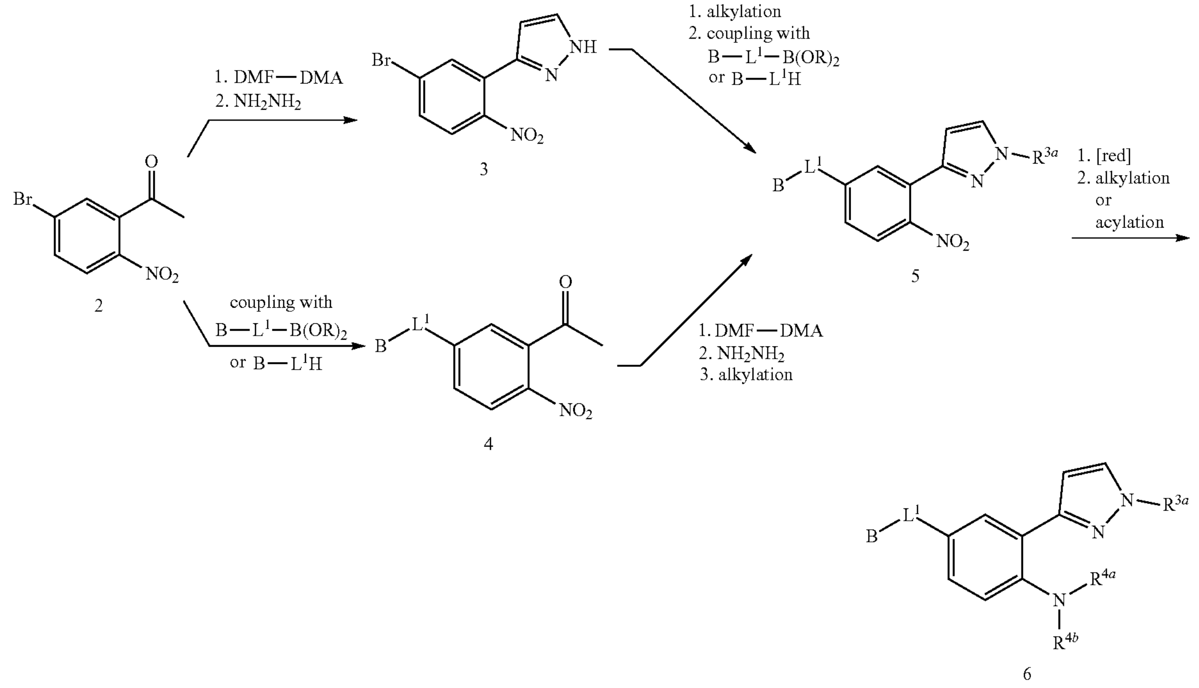

1-(5-bromo-2-nitrophenyl)ethan-1-one 2, commercially available or synthesized from 1-(2-nitrophenyl)ethan-1-one 1 by procedures known to the skilled in the art, may be reacted with N,N-dimethylformamide dimethyl acetal in a suitable solvent (e.g. toluene, 1,4-dioxane and the like) at a temperature raising from 100° C. to 120° C., followed by hydrazine in a suitable solvent (e.g. EtOH, 1,4-dioxane and the like) at a temperature raising from 80° C. to 120° C., to provide intermediate of general formula 3. Intermediates of general formula 5 may be obtained from intermediate 3 by pyrazole N-alkylation employing procedures known to the skilled in the art, followed by a coupling reaction applying appropriate coupling agents selected from, but not limited to, halo(hetero)aryls, (hetero) anilines, boronic acids, and boronic esters, in combination with corresponding Pd or Cu catalysts. Alternatively, intermediates of general formula 4 may be obtained by reacting intermediate 2 with appropriate coupling agents selected from, but not limited to, halo (hetero)aryls, (hetero) anilines, boronic acids, and boronic esters, in combination with corresponding Pd or Cu catalysts. Next, intermediates of general formula 4 may be reacted with N,N-dimethylformamide dimethyl acetal in a suitable solvent (e.g. toluene, 1,4-dioxane and the like) at a temperature raising from 100° C. to 120° C., followed by hydrazine in a suitable solvent (e.g. EtOH, 1,4-dioxane and the like) at a temperature raising from 80° C. to 120° C. Finally, pyrazole N-alkylation employing procedures known to the skilled in the art, may afford intermediates of general formula 5. Intermediates of general formula 6 may be obtained from intermediate 5 by reduction of the nitro moiety of intermediates of general formula 5 in a suitable solvent (e.g. EtOH and the like) at a temperature raising from 80° C. to 100° C., followed by reaction with alkyl halides or electron poor, polarized double bonds in the presence of a base (e.g. $K_2CO_3$, TEA, DIPEA and the like) in a suitable solvent (e.g. AcOH, ACN, MeOH and the like). More information can be found in Journal of Medicinal Chemistry 1999, 2831. Also, the reduction of the nitro moiety of intermediates of general formula 5 may be followed by coupling with carboxylic acid derivatives under standard peptide coupling conditions in the presence of a coupling agent (e.g. $T_3P$, HATU, EDC·HCl and the like) and a base (e.g. TEA, DIPEA and the like) in a polar aprotic solvent (e.g. $CH_2Cl_2$, DMF and the like), or by reaction with acyl chlorides in presence of a base (e.g. $NaHCO_3$, TEA, DIPEA and the like) in a suitable solvent (e.g. THF, 1,4-dioxane and the like). Additionally, the reduction of the nitro moiety of intermediates of general formula 5 may be followed by reaction with ketone or aldehyde derivatives in the presence of a reducing agent (e.g. $NaCNBH_3$, Pic-$BH_3$ and the like) in a suitable solvent (e.g. MeOH, AcOH and the like).

The compounds of the present invention may be prepared according to the general procedure outlined in Scheme 2.

Scheme 2: all $R^{3a}$, $R^{4a}$, $R^{4b}$, $L^1$, and B are as described for the compounds of the present invention and its embodiments and formulae.

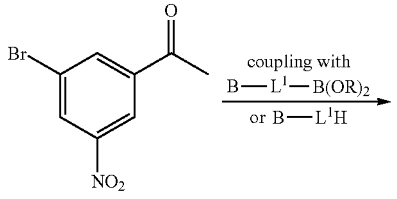

7

-continued

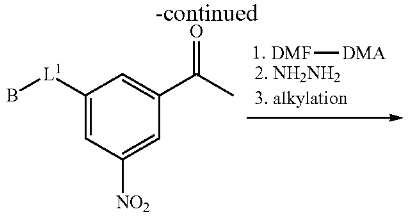

8

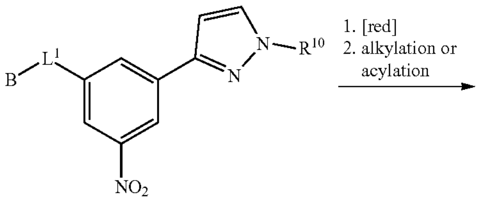

9

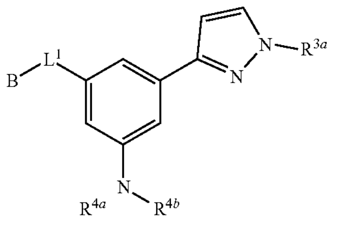

10

1-(3-bromo-5-nitrophenyl)ethan-1-one 7, commercially available or synthesized from 3-bromobenzaldehyde by procedures known to the skilled in the art, may be reacted with appropriate coupling agents selected from, but not limited to, halo(hetero)aryls, (hetero) anilines, boronic acids, and boronic esters, in combination with corresponding Pd or Cu catalysts to afford compounds of general formula 8. Intermediates of general formula 8 may be reacted with N,N-dimethylformamide dimethyl acetal in a suitable solvent (e.g. toluene, 1,4-dioxane and the like) at a temperature raising from 100° C. to 120° C., followed by hydrazine in a suitable solvent (e.g. EtOH, 1,4-dioxane and the like) at a temperature raising from 80° C. to 120° C. Finally, pyrazole N-alkylation employing procedures known to the skilled in the art, may afford intermediates of general formula 9. Intermediates of general formula 10 may be obtained from intermediate 9 by reduction of the nitro moiety of intermediates of general formula 9 in a suitable solvent (e.g. EtOH and the like) at a temperature raising from 80° C. to 100° C., followed by reaction with alkyl halides or electron poor, polarized double bonds in the presence of a base (e.g. $K_2CO_3$, TEA, DIPEA and the like) in a suitable solvent (e.g. AcOH, ACN, MeOH and the like). More information can be found in Journal of Medicinal Chemistry 1999, 2831. Also, the reduction of the nitro moiety of intermediates of general formula 9 may be followed by coupling with carboxylic acid derivatives under standard peptide coupling conditions in the presence of a coupling agent (e.g. $T_3P$, HATU, EDC·HCl and the like) and a base (e.g. TEA, DIPEA and the like) in a polar aprotic solvent (e.g. $CH_2Cl_2$, DMF and the like), or by reaction with acyl chlorides in presence of a base (e.g. $NaHCO_3$, TEA, DIPEA and the like) in a suitable solvent (e.g. THF, 1,4-dioxane and the like). Additionally, the reduction of the nitro moiety of intermediates of general formula 9 may be followed by reaction with ketone or aldehyde derivatives in the presence of a reducing agent (e.g. $NaCNBH_3$, Pic-$BH_3$ and the like) in a suitable solvent (e.g. MeOH, AcOH and the like).

In another embodiment, compounds of the present invention may also be synthesized according to the general procedure outlined in Scheme 3.

Scheme 3: all $R^{3a}$, $R^{4a}$, $R^{4b}$, $L^1$, and B are as described for the compounds of the present invention and its embodiments and formulae.

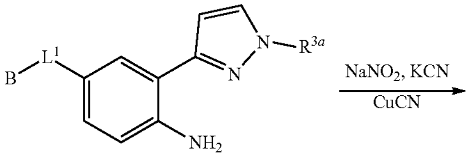

6 ($R^{4a}$, $R^{4b}$ = H)

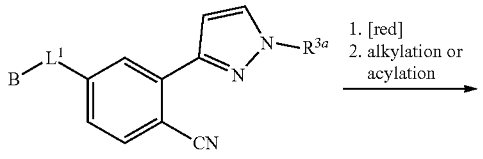

11

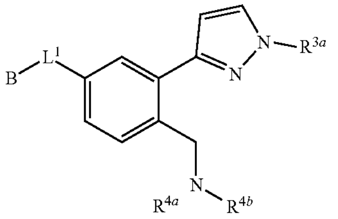

12

Intermediates of general formula 6 may be reacted with sodium nitrite in water at 0° C., followed by a mixture of potassium cyanide and copper(I) cyanide at a temperature raising from 0° C. to 50° C., to provide intermediate of general formula 11. More information can be found in *Journal of the American Chemical Society* 2000, 8376. Intermediates of general formula 12 may be obtained from intermediate 11 by reduction of the nitrile moiety employing procedures known to the skilled in the art, followed by reaction with alkyl halides or electron poor, polarized double bonds in the presence of a base (e.g. $K_2CO_3$, TEA, DIPEA and the like) in a suitable solvent (e.g. AcOH, ACN, MeOH and the like). Also, the reduction of the nitrile moiety of intermediates of general formula 11 may be followed by coupling with carboxylic acid derivatives under standard peptide coupling conditions in the presence of a coupling agent (e.g. $T_3P$, HATU, EDC·HCl and the like) and a base (e.g. TEA, DIPEA and the like) in a polar aprotic solvent (e.g. $CH_2Cl_2$, DMF and the like), or by reaction with acyl chlorides in presence of a base (e.g. $NaHCO_3$, TEA, DIPEA and the like) in a suitable solvent (e.g. THF, 1,4-dioxane and the like).

Alternatively, compounds of the present invention may also be synthesized according to the general procedure outlined in Scheme 4.

Scheme 4: all $R^{3a}$, $R^{3b}$, $R^{4a}$, X, $X^2$, $X^3$, $L^1$, and B are as described for the compounds of the present invention and its embodiments and formulae.

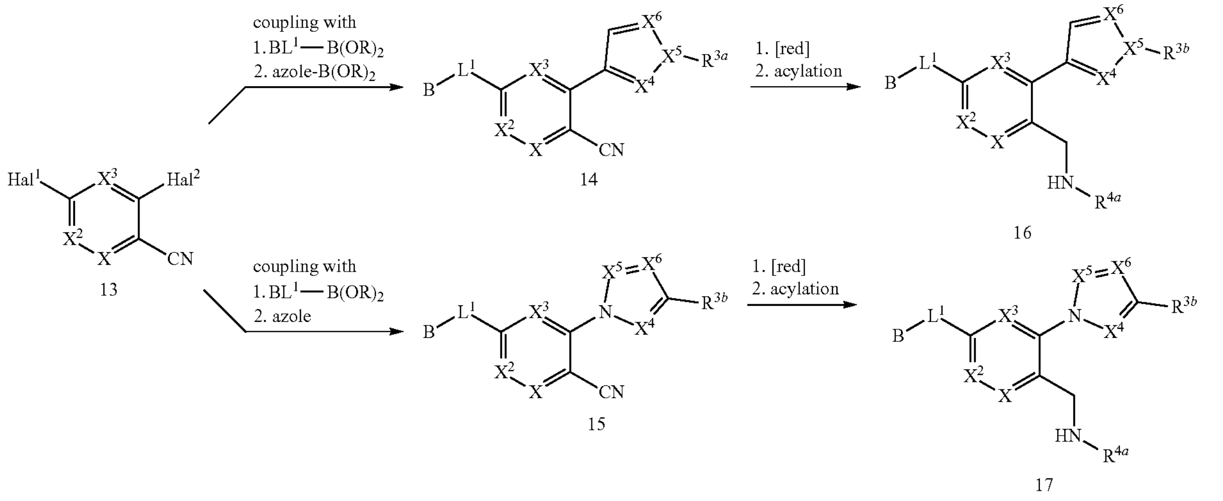

13 14 15 16 17

$Hal^1$, $Hal^2$ = Cl, Br; $X^4$, $X^5$, $X^6$ = CH, N.

Commercially available, halogenated (hetero)aryl nitrile 13 may be reacted with appropriate coupling agents selected from, but not limited to, halo(hetero)aryls, (hetero) anilines, boronic acids, and boronic esters, in combination with corresponding Pd or Cu catalysts, followed by coupling with azole boronic acids and esters, in combination with corresponding Pd catalysts, to afford compounds of general formula 14. More information can be found in *Journal of Medicinal Chemistry* 2011, 1914. Intermediates of general formula 15 may be obtained by reacting halogenated (hetero)aryl nitrile 13 with appropriate coupling agents selected from, but not limited to, halo(hetero)aryls, (hetero) anilines, boronic acids, and boronic esters, in combination with corresponding Pd or Cu catalysts, followed by a nucleophilic addition-elimination reaction (substituting $Z^2$) with azoles, employing procedures known to the skilled in the art. More information can be found in WO2013/048214 and WO2018/209030. Compounds of general formula 16 and 17 may be obtained from intermediates 14 and 15, respectively, via procedures as described in Scheme 3.

Compounds of the present invention may also be synthesized according to the general procedure outlined in Scheme 5.

Scheme 5: all $R^{3a}$, $R^{4a}$, $X^1$, $X^2$, $X^3$, $L^1$, and B as described for the compounds of the present invention and its embodiments and formulae.

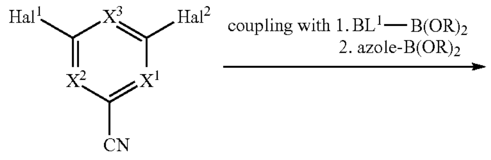

18

-continued

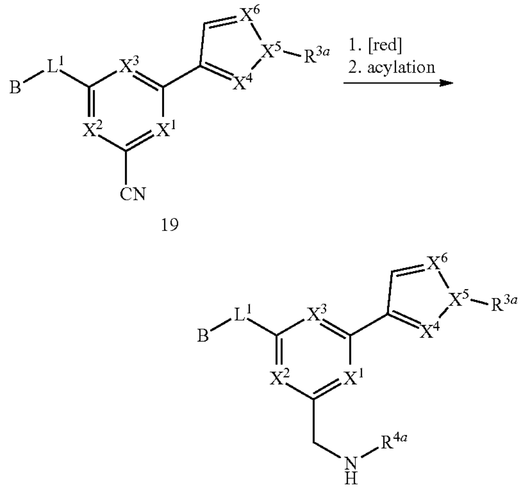

19

20

$Hal^1$, $Hal^2$ = Cl, Br; $X^4$, $X^5$, $X^6$ = CH, N.

Commercially available, halogenated (hetero)aryl nitrile 18 may be reacted with appropriate coupling agents selected from, but not limited to, halo(hetero)aryls, (hetero) anilines, boronic acids, and boronic esters, in combination with corresponding Pd or Cu catalysts, followed by coupling with azole boronic acids and esters, in combination with corresponding Pd catalysts, to afford compounds of general formula 19. More information can be found in *Journal of Medicinal Chemistry* 2011, 1914. Compounds of general formula 20 may be obtained from intermediate 19 via procedures as described in Scheme 3.

Compounds of the present invention may also be synthesized according to the general procedure outlined in Scheme 6.

Scheme 6: all $R^{3a}$, $R^{4a}$, $L^1$, and B are as described for the compounds of the present invention and its embodiments and formulae.

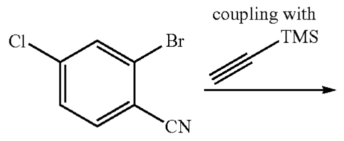

21

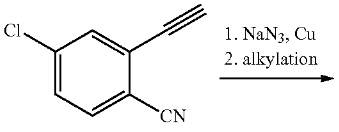

22

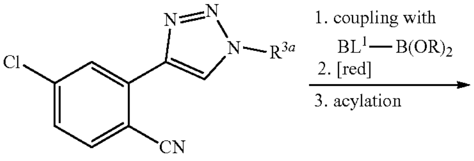

23

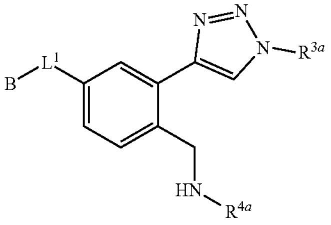

24

2-bromo-4-chlorobenzonitrile 21 may be reacted with ethynyltrimethylsilane in combination with corresponding Pd or Cu catalysts to afford compound 22. More information can be found in Chemical Communications 2012, 6052. Intermediates of general formula 23 may be obtained by reacting compound 2 with sodium azide (more information can be found in Organometallics 2018, 4224), followed by triazole N-alkylation employing procedures known to the skilled in the art. Compounds of general formula 24 may be obtained by reacting intermediate 23 with appropriate coupling agents selected from, but not limited to, halo(hetero)aryls, (hetero) anilines, boronic acids, and boronic esters, in combination with corresponding Pd or Cu catalysts to afford, followed by reduction and acylation reactions following procedures as described in Scheme 3.

In another embodiment, compounds of the present invention may also be synthesized according to the general procedure outlined in Scheme 7.

Scheme 7: all $R^{3a}$, $R^{4a}$, $L^1$, and B are as described for the compounds of the present invention and its embodiments and formulae.

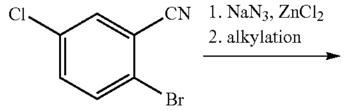

25

-continued

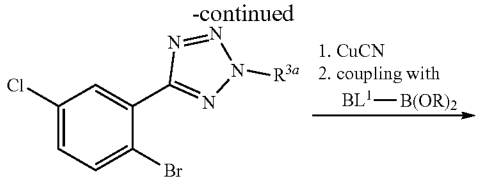

26

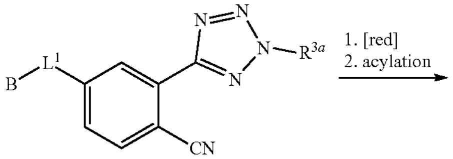

27

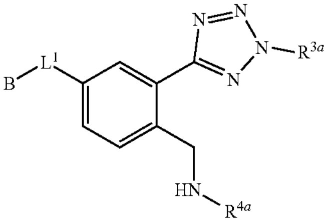

28

2-bromo-5-chlorobenzonitrile 25 may be reacted with sodium azide in a suitable solvent (e.g. DMF and the like) at a temperature raising from 100° C. to 120° C., followed by tetrazole N-alkylation, employing procedures known to the skilled in the art to afford intermediates of general formula 26. Intermediates of general formula 27 may be obtained by reaction with copper(I) cyanide, followed by a coupling reaction applying appropriate coupling agents selected from, but not limited to, halo(hetero)aryls, (hetero) anilines, boronic acids, and boronic esters, in combination with corresponding Pd or Cu catalysts. Compounds of general formula 28 may be obtained from intermediates 27 via procedures as described in Scheme 3.

Compounds of the present invention may also be synthesized according to the general procedure outlined in Scheme 8.

Scheme 8: all $R^{3a}$, $R^{3b}$, $R^{4a}$, X, $X^2$, $X^3$, $L^1$, and B are as described for the compounds of the present invention and its embodiments and formulae.

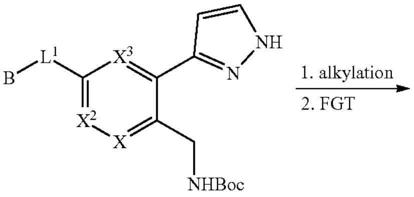

29

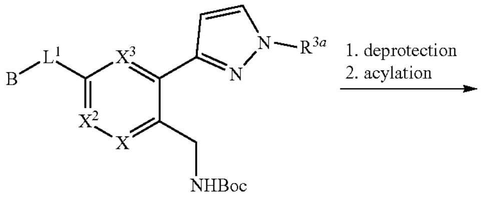

30

-continued

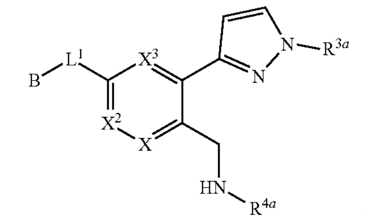

31

$X^4$, $X^5$, $X^6$ = CH or N.

Intermediates of general formula 29, synthesized according to Scheme 4, may be reacted with appropriate reagents such as alkyl halides and alkyl sulfonates in the presence of a base (e.g. TEA, DIPEA, $K_2CO_3$ and the like) and a suitable solvent (e.g. ACN, MeOH, DCM, DMF and the like) to provide intermediates of general formula 30. In some instances, intermediates of general formula 30 are produced by functional group transformations (e.g. hydrolysis, amidation, deprotection and the like) subsequent to an initial alkylation. Deprotection of intermediates of general formula 30 by treatment with acids such as TFA or HCl in suitable solvents (e.g., DCM or 1,4-dioxane) followed by acylation reactions according to procedures described in Scheme 3 provides compounds of general formula 31.

Alternatively, compounds of the present invention may also be synthesized according to the general procedure outlined in Scheme 9.

Scheme 9: all $R^{3a}$, $R^{3b}$, $R^{4a}$, X, $X^2$, $X^3$, $L^1$, and B are as described for the compounds of the present invention and its embodiments and formulae.

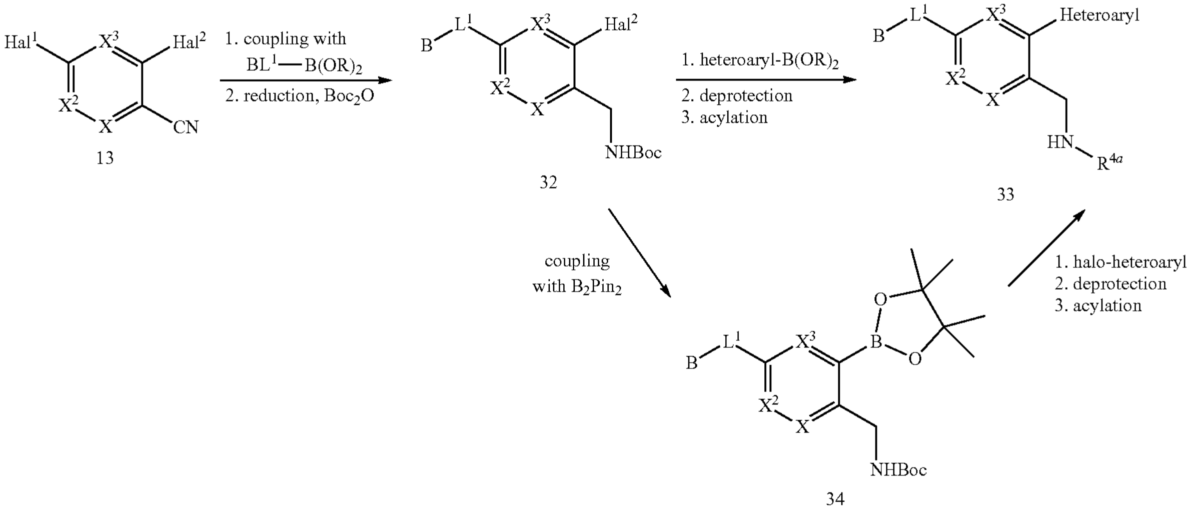

$Hal^1$, $Hal^2$ = Cl or Br; $X^4$, $X^5$, $X^6$ = CH or N.

Intermediates of general formula 13 may be coupled with appropriate reagents selected from, but not limited to, halo (hetero)aryls, (hetero) anilines, boronic acids, and boronic esters, in combination with corresponding Pd or Cu catalysts followed by reduction and protection to provide intermediates of general formula 32. Intermediates of general formula 32 may be coupled with boronic acids and boronic esters followed by deprotection and acylation, according to methods described in Scheme 8, to provide compounds of general formula 33. Alternatively, intermediates of general formula 32 may be converted to intermediates of general formula 34 by coupling with $B_2Pin_2$. Intermediates of general formula 34 may be reacted with appropriate reagents such as halo (hetero)aryls in combination with corresponding Pd or Cu catalysts followed by deprotection and acylation to provide compounds of general formula 33.

Compounds of the present invention may also be synthesized according to the general procedure outlined in Scheme 10.

Scheme 10: all $R^{3a}$, $R^{3b}$, $R^{4a}$, X, $X^2$, $X^3$, $L^1$, and B are as described for the compounds of the present invention and its embodiments and formulae.

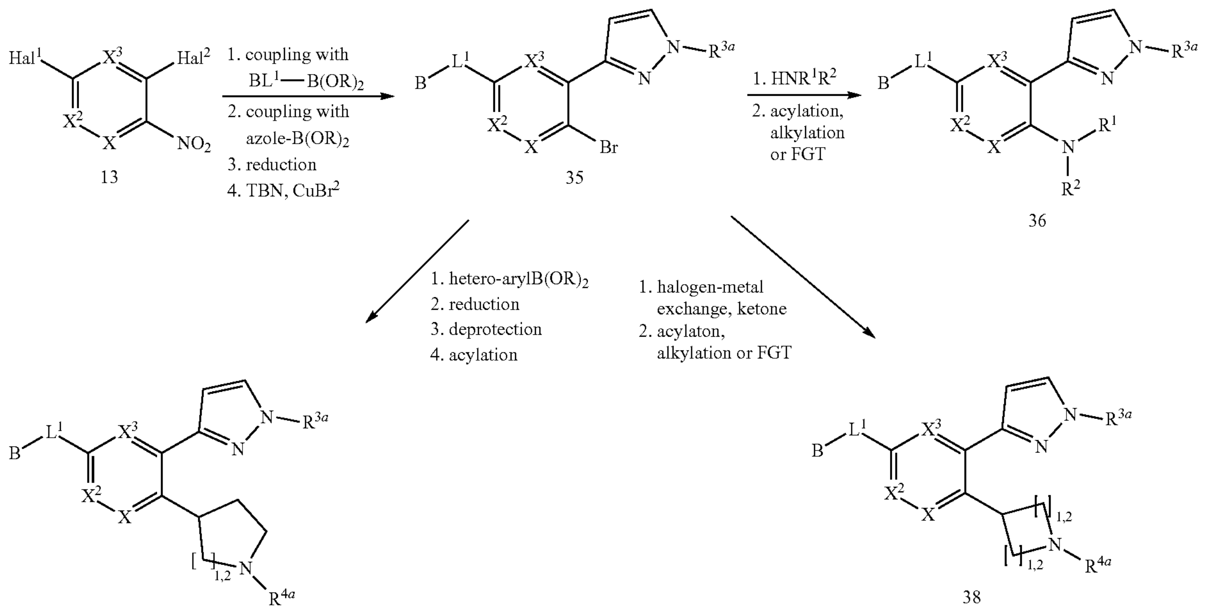

$Hal^1$, $Hal^2$ = Cl, Br, or I; $X^4$, $X^5$, $X^6$ = CH or N. FGT = functional group transformatin.

Intermediates of general formula 13 may be coupled with appropriate reagents selected from, but not limited to, halo (hetero)aryls, (hetero) anilines, boronic acids, and boronic esters, in combination with corresponding Pd or Cu catalysts followed by coupling with azole boronic acids or esters, reduction and diazotization to provide intermediates of general formula 35. Intermediates of general formula 35 may be coupled with amines in the presence of bases, Pd or Cu catalysts followed by acylation, alkylation or functional group transformations to provide compounds of general formula 36. Alternatively, intermediates of general formula 35 may be subjected to halogen metal exchange using alkyl lithium, alkyl Grignard or similar reagents and reacted with cyclic ketones followed by acylation, alkylation or functional group transformations to provide compounds of general formula 38. Or, intermediates of general formula 35 may be reacted with suitable coupling agents such as (hetero)aryl boronic acids and boronic esters in the presence of Pd catalysts followed by reduction, deprotection and acylation to provide compounds of general formula 37.

Alternatively, compounds of the present invention may also be synthesized according to the general procedure outlined in Scheme 11.

Scheme 11: all $R^{3a}$, $R^{3b}$, $R^{4a}$, X, $X^2$, $X^3$, $L^1$, and B are as described for the compounds of the present invention and its embodiments and formulae.

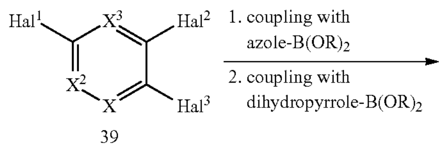

-continued

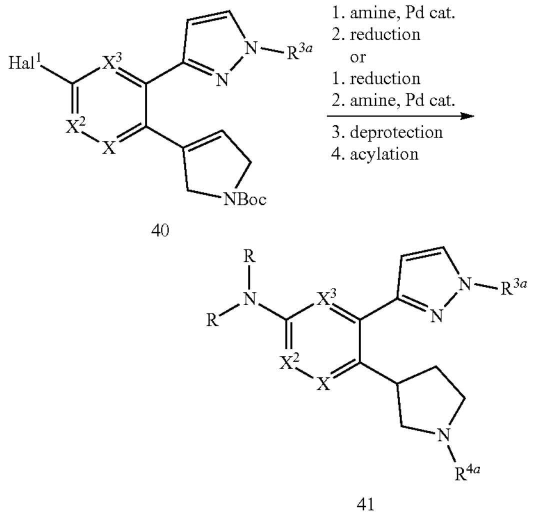

$Hal^1$, $Hal^2$ = Cl, Br, or I; $X^4$, $X^5$, $X^6$ = CH or N.
FGT = functional group transformation.

Commercially available starting materials of general formula 39 may be coupled with azole boronic acids or boronic esters in the presence of Pd catalysts, followed by coupling with dihydropyrrole boronic acids or boronic esters in the presence of Pd catalysts to provide intermediates of general formula 40. Intermediates of general formula 40 may be transformed to compounds of general formula 41 by way of a four-step sequence that includes displacement of the aryl halide with a nucleophile such as an amine or alcohol in the presence of a Pd catalyst, olefin reduction under conditions such as hydrogen gas with a suitable catalyst (e.g., Pd/C, $PtO_2$ or the like), deprotection under acidic conditions (e.g., TFA in DCM or HCl in dioxane) and acylation as described in Scheme 3.

In yet another approach, compounds of the invention may be synthesized according to the general procedure of Scheme 12.

Scheme 12: all $R^{3a}$, $R^{3b}$, $R^{4a}$, X, $X^2$, $X^3$, $L^1$, and B are as described for the compounds of the present invention and its embodiments and formulae.

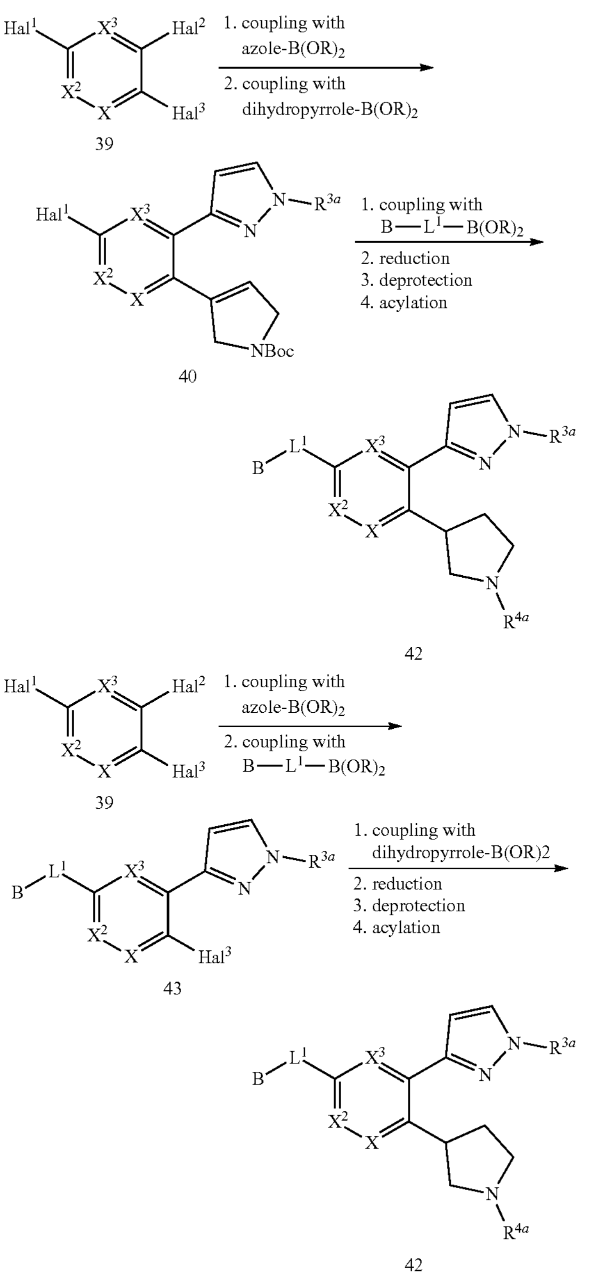

39, 40, 42, 39, 43, 42

$Hal^1$, $Hal^2$ = Cl, Br, or I; $X^4$, $X^5$, $X^6$ = CH or N.
FGT = functional group transformation.

Intermediates of general formula 40 or 43 may be synthesized from commercially available starting materials of general formula 39 by reaction with boronic acids and boronic esters in the presence of a Pd catalyst. Intermediates of general formula 40 and 43 may be further coupled with appropriate boronic acids and boronic esters in the presence of a Pd catalyst and then subjected to reduction, deprotection and acylation as described in Scheme 11 to provide compounds of general formula 42.

The general schemes depicted above should be considered as non-limiting examples. It will be understood that compounds of the invention may be obtained through other methods which are known to people skilled in the art.

Abbreviations used in the instant specification, particularly in the schemes and examples, are as follows: AIBN—Azobisisobutyronitrile, aq—Aqueous solution, ACN—acetonitrile, $Ac_2O$—Acetic anhydride, AcOH—Acetic acid, $BBr_3$—Boron tribromide, $BF_3 \cdot OEt_2$—Boron trifluoride diethyl etherate, BINAP—(2,2'-bis(diphenylphosphino)-1,1'-binaphthyl), Boc—tert-butyloxycarbonyl, $Boc_2O$—Di-tert-butyl dicarbonate, $BO_3H_3$—Boric acid, $Bu_3SnN_3$—Tributyltin azide, $CDCl_3$—Deuterated chloroform, Conc—Concentrated, $CBr_4$—Carbon tetrabromide, $CCl_4$—Carbon tetrachloride, mCPBA—meta-Chloroperoxybenzoic acid, $CuBr_2$—Copper(II) bromide, CuCN—Copper cyanide, CuI—Copper iodide, $Cu(OAc)_2$—Copper(II)acetate, $CuSO_4 \cdot 5H_2O$—Copper(II)sulfate pentahydrate, $Cs_2CO_3$—Caesium carbonate, d—day, DCM—Dichloromethane, DCE—1,2-Dichloroethane, DIPEA—Diisopropyl ethyl amine, DMF—N,N-Dimethylformamide, DMF-DMA—N,N-Dimethylformamide dimethyl acetal, DMSO—Dimethyl sulfoxide, DMSO-$d_6$—Deuterated dimethyl sulfoxide, DPPA—Diphenyl phosphoryl azide, EDA—Ethyl diazoacetate, EDC—1-(3-Dimethylaminopropyl)-3-ethylcarbodiimide, EtOH—Ethanol, EtOAc—Ethyl acetate, $Et_2O$—Diethyl ether, Eq.—Equivalent, FA—Formic acid, h—Hour, HATU—O-(7-Azabenzotriazol-1-yl)-N,N,N',N'-tetramethyluronium hexafluorophosphate, HCl—Hydrogen chloride, $HNO_3$—Nitric acid, $H_2O_2$—Hydrogen peroxide, $HO(CH_2O)_nH$—paraformaldehyde, HOAt—1-Hydroxy-7-azabenzotriazole, HPLC—High performance liquid chromatography, $H_2SO_4$—Sulfuric acid, IPA—2-propanol, $K_2CO_3$—Potassium carbonate, KCN—Potassium cyanide, KOH—Potassium hydroxide, $K_3PO_4$—Potassium phosphate, LAH—Lithiumaluminiumhydride, $LiOH \cdot H_2O$—Lithium hydroxide monohydrate, LG—Leaving group, MeOH—methanol, min—Minute, $MnO_2$—Manganese(IV) oxide, NaOtBu—Sodium tert-butoxide, $NaBH_4$—Sodium borohydride, $NaCNBH_3$—Sodium cyanoborohydride, NaH—Sodium hydride, $NaHCO_3$—Sodium bicarbonate, $Na_2CO_3$—Sodium carbonate, $NaNO_2$—Sodium nitrite, $Na_2SO_4$—Sodium sulfate, NBS—N-Bromosuccinimide, $NH_2NH_2 \cdot H_2O$—hydrazine monohydrate, $NH_2CO_2NH_4$—Ammonium carbamate, $NH_4OAc$—Ammonium acetate, $(NH_4)HCO_3$—Ammonium bicarbonate, $NH_4Cl$—Ammonium chloride, $NOBF_4$—Nitrosyl tetrafluoroborate, Pd(amphos)$Cl_2$—Bis(di-tert-butyl(4-dimethylaminophenyl)phosphine)dichloropalladium(II), $PBr_3$—Phosphorus tribromide, $Pd(PPh_3)_2Cl_2$—Bis(triphenylphosphine)palladium(II)dichloride, $Pd(PPh_3)_4$—Tetrakis(triphenylphosphine)palladium, $Pd_2(dba)_3$—Tris(dibenzylideneacetone)dipalladium, Pd(dppf)$Cl_2$—(1,1'-Bis(diphenylphosphino)ferrocene)palladium(II) dichloride, Pd(dppf)$Cl_2 \cdot$DCM—(1,1'-Bis(diphenylphosphino)ferrocene)dichloropalladium(II), complex with DCM, $Pd(OAc)_2$—Palladium(II) acetate, $PPh_3$—Triphenylphosphine, Pet ether—Petroleum ether, PFA—Paraformaldehyde, Pic-$BH_3$—2-Picoline-borane complex, $PhI(OAc)_2$—(Diacetoxyiodo)benzene, Raney Ni—Raney nickel, RF—Retention factor, RT—Room temperature, sat—Saturated, SCX—Strong cation exchange, TBAF—Tetra-n-butylammonium fluoride, TBN—tert-Butyl nitrite, $TiCl_4$—Titanium(IV)chloride, TEA—Triethylamine, THF—Tetrahydrofurane, THP—Tetrahydropyranyl, TFA—Trifluoroacetic acid, TFAA—Trifluoroacetic anhydride, $Ti(OiPr)_4$—Titanium(IV)isopropoxide, TLC—Thin layer chromatography, TMS—Trimethylsilyl, $TMSN_3$—Trimethylsilyl azide, $T_3P$—Propanephosphonic acid anhydride, Xanthphos—4,5-Bis(diphenylphosphino)-9,9-dimethylxanthene, XPhos—2-Dicyclohexylphosphino-2',4',6'-triisopropylbiphenyl, XPhos—Pd-G2—Chloro(2-dicyclohexylphosphino-2',4',6'-triisopropyl-1,1'-biphenyl)[2-(2'-amino-1,1'-biphenyl)]palladium(II), $Zn(CN)_2$—Zinc cyanide, $ZnEt_2$—Diethylzinc.

TABLE 1

Structures of example compounds of the disclosure and their respective codes

| Cpd. No. | Structure | Name |
|---|---|---|
| 001 | 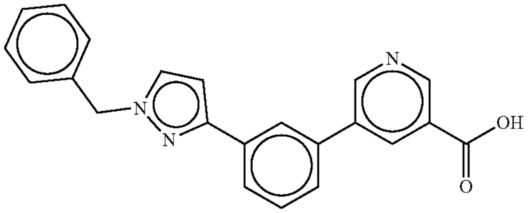 | 5-(3-(1-benzyl-1H-pyrazol-3-yl)phenyl)nicotinic acid |
| 002 | 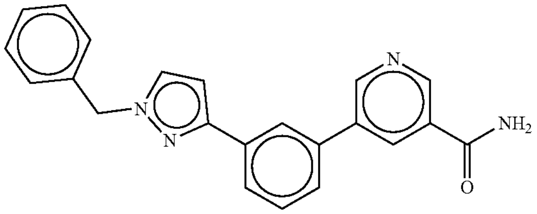 | 5-(3-(1-(benzyl-1H-pyrazol-3-yl)phenyl)nicotinamide |
| 003 | 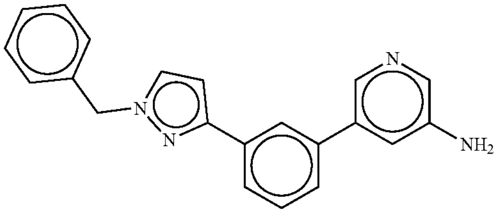 | 5-(3-(1-benzyl-1H-pyrazol-3-yl)phenyl)pyridin-3-amine |
| 004 | 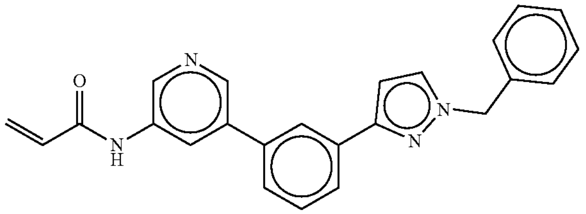 | N-(5-(3-(1-benzyl-1H-pyrazol-3-yl)phenyl)pyridin-3-yl)acrylamide |
| 005 | 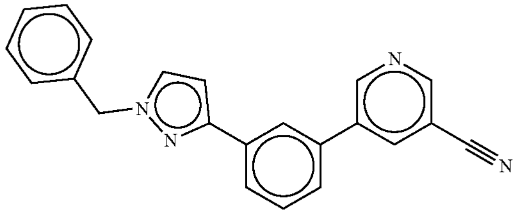 | 5-(3-(1-benzyl-1H-pyrazol-3-yl)phenyl)nicotinonitrile |
| 006 | 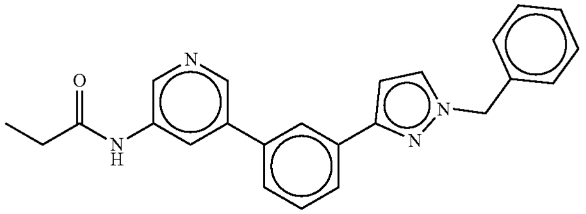 | N-(5-(3-(1-benzyl-1H-pyrazol-3-yl)phenyl)pyridin-3-yl)propionamide |

TABLE 1-continued

| Cpd. No. | Structure | Name |
|---|---|---|
| | Structures of example compounds of the disclosure and their respective codes | |
| 007 | 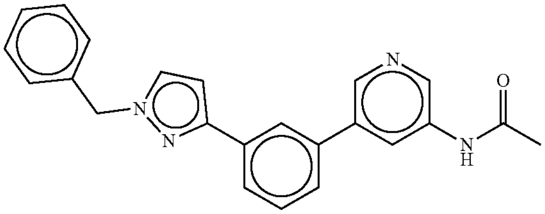 | N-(5-(3-(1-benzyl-1H-pyrazol-3-yl)phenyl)pyridin-3-yl)acetamide |
| 008 | 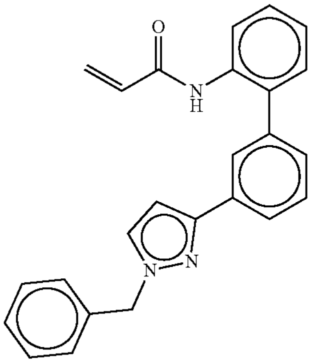 | N-(3'-(1-benzyl-1H-pyrazol-3-yl)-[1,1'-biphenyl]-2-yl)acrylamide |
| 009 | 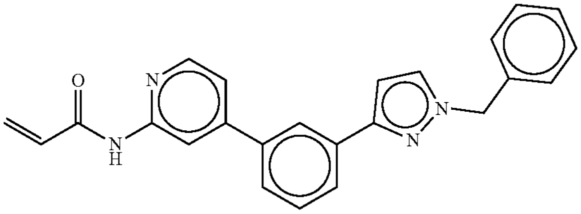 | N-(4-(3-(1-benzyl-1H-pyrazol-3-yl)phenyl)pyridin-2-yl)acrylamide |
| 010 | 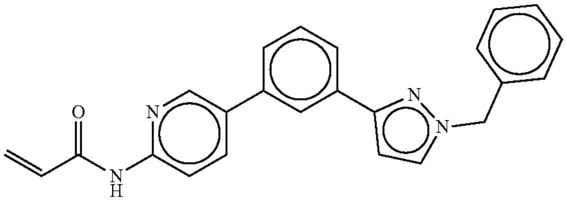 | N-(5-(3-(1-benzyl-1H-pyrazol-3-yl)phenyl)pyridin-2-yl)acrylamide |
| 011 | 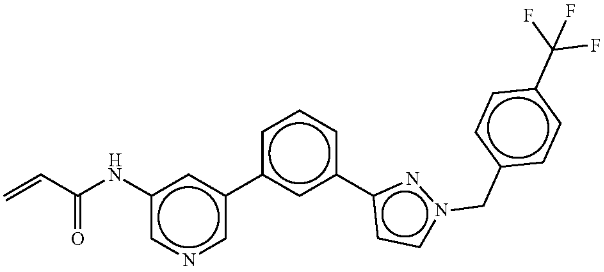 | N-(5-(3-(1-(4-(trifluoromethyl)benzyl)-1H-pyrazol-3-yl)phenyl)pyridin-3-yl)acrylamide |
| 012 | 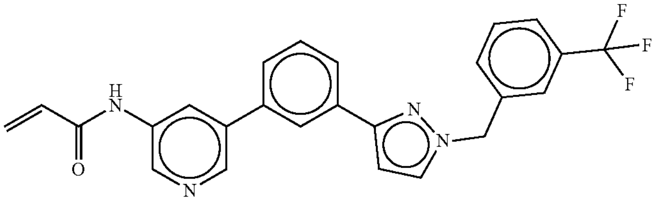 | N-(5-(3-(1-(3-(trifluoromethyl)benzyl)-1H-pyrazol-3-yl)phenyl)pyridin-3-yl)acrylamide |

TABLE 1-continued

| Cpd. No. | Structure | Name |
|---|---|---|
| | Structures of example compounds of the disclosure and their respective codes | |
| 013 | 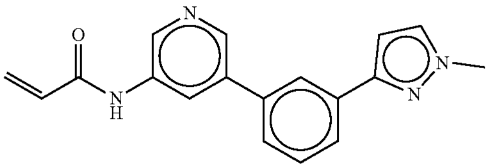 | N-(5-(3-(1-methyl-1H-pyrazol-3-yl)phenyl)pyridin-3-yl)acrylamide |
| 014 | 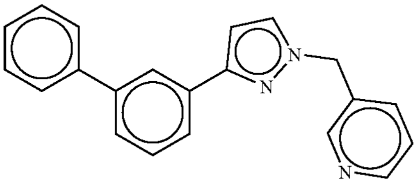 | 3-((3-([1,1'-biphenyl]-3-yl)-1H-pyrazol-1-yl)methyl)pyridine |
| 015 | 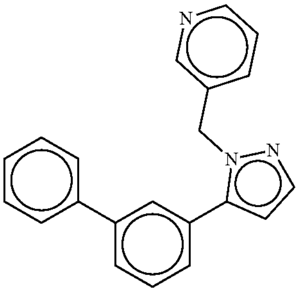 | 3-((5-([1,1'-biphenyl]-3-yl)-1H-pyrazol-1-yl)methyl)pyridine |
| 016 | 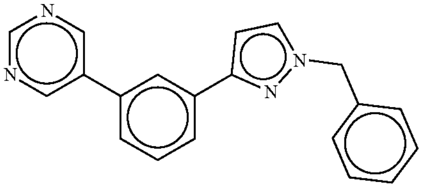 | 5-(3-(1-benzyl-1H-pyrazol-3-yl)phenyl)pyrimidine |
| 017 | 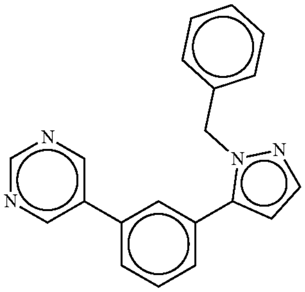 | 5-(3-(1-benzyl-1H-pyrazol-5-yl)phenyl)pyrimidine |
| 018 | 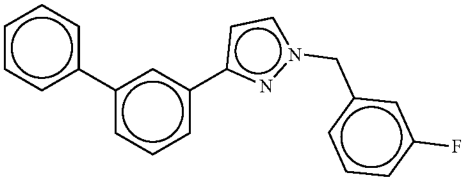 | 3-([1,1'-biphenyl]-3-yl)-1-(3-fluorobenzyl)-1H-pyrazole |
| 019 | 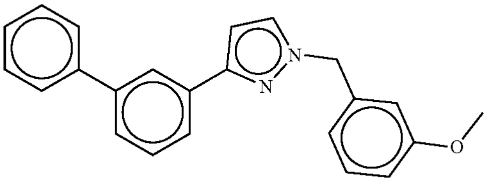 | 3-([1,1'-biphenyl]-3-yl)-1-(3-methoxybenzyl)-1H-pyrazole |

TABLE 1-continued

| Structures of example compounds of the disclosure and their respective codes | | |
|---|---|---|
| Cpd. No. | Structure | Name |
| 020 | 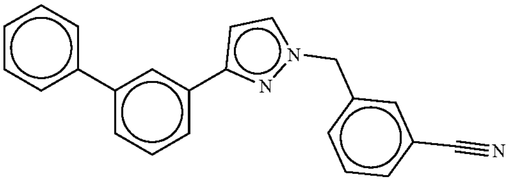 | 3-((3-([1,1'-biphenyl]-3-yl)-1H-pyrazol-1-yl)methyl)benzonitrile |
| 021 | 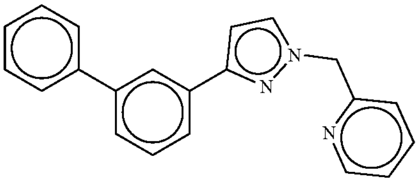 | 2-((3-([1,1'-biphenyl]-3-yl)-1H-pyrazol-1-yl)methyl)pyridine |
| 022 | 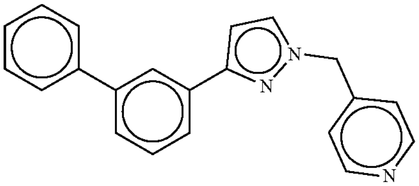 | 4-((3-([1,1'-biphenyl]-3-yl)-1H-pyrazol-1-yl)methyl)pyridine |
| 023 | 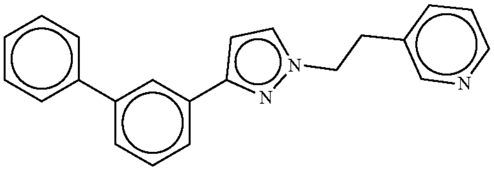 | 3-(2-(3-([1,1'-biphenyl]-3-yl)-1H-pyrazol-1-ethyl)pyridine |
| 024 | 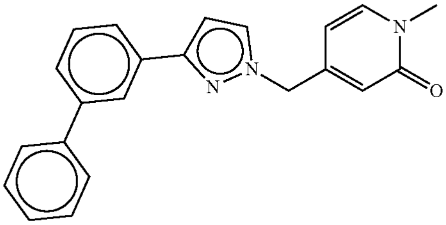 | 4-((3-([1,1'-biphenyl]-3-yl)-1H-pyrazol-1-yl)methyl)-1-methylpyridin-2(1H)-one |
| 025 | 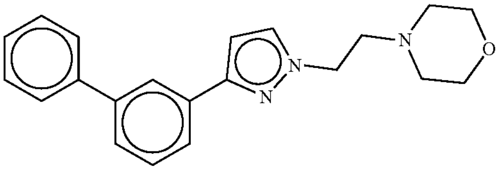 | 4-(2-(3-([1,1'-biphenyl]-3-yl)-1H-pyrazol-1-yl)ethyl)morpholine |
| 026 | 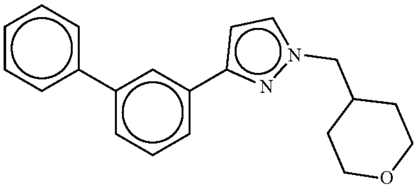 | 3-([1,1'-biphenyl]-3-yl)-1-((tetrahydro-2H-pyran-4-yl)methyl)-1H-pyrazole |

TABLE 1-continued

| Structures of example compounds of the disclosure and their respective codes | | |
|---|---|---|
| Cpd. No. | Structure | Name |
| 027 | 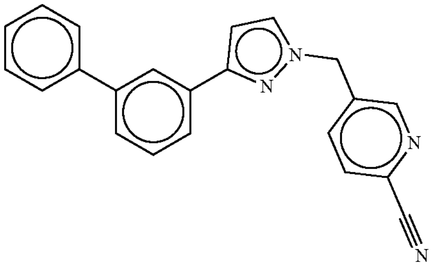 | 5-((3-([1,1'-biphenyl]-3-yl)-1H-pyrazol-1-yl)methyl)picolinonitrile |
| 028 | 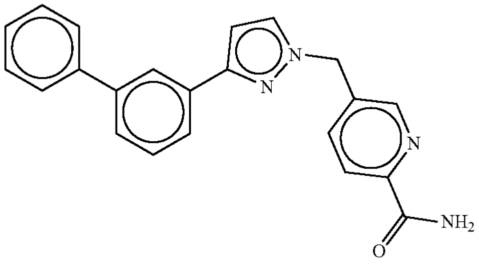 | 5-((3-([1,1'-biphenyl]-3-yl)-1H-pyrazol-1-yl)methyl)picolinamide |
| 029 | 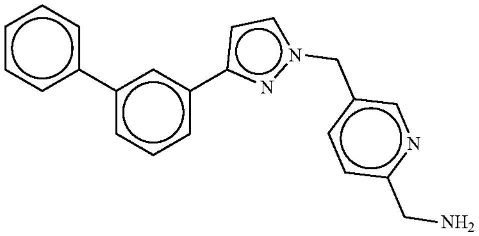 | (5-((3-([1,1'-biphenyl]-3-yl)-1H-pyrazol-1-yl)methyl)pyridin-2-yl)methanamine |
| 030 | 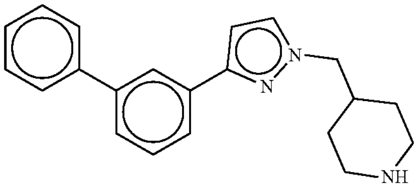 | 4-((3-([1,1'-biphenyl]-3-yl)-1H-pyrazol-1-yl)methyl)piperidine |
| 031 | 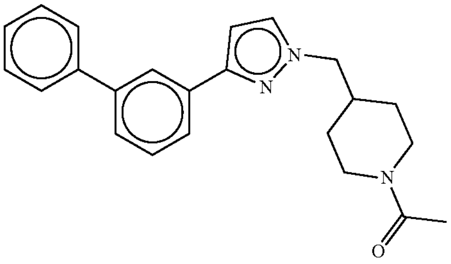 | 1-(4-((3-([1,1'-biphenyl]-3-yl)-1H-pyrazol-1-yl)methyl)piperidin-1-yl)ethan-1-one |
| 032 | 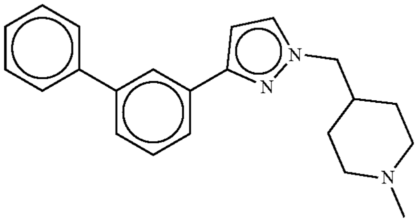 | 4-((3-([1,1'-biphenyl]-3-yl)-1H-pyrazol-1-yl)methyl)-1-methylpiperidine |

TABLE 1-continued

| Cpd. No. | Structure | Name |
|---|---|---|
| 033 | 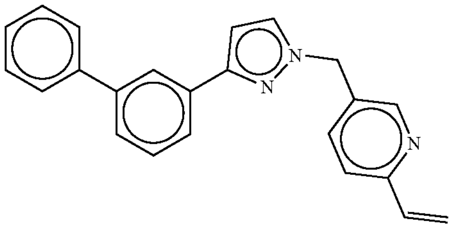 | 5-((3-([1,1'-biphenyl]-3-yl)-1H-pyrazol-1-yl)methyl)-2-vinylpyridine |
| 034 | 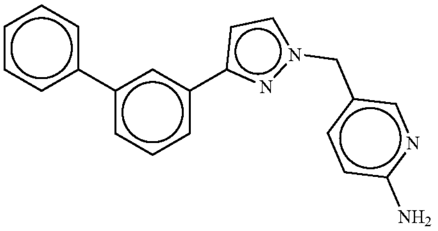 | 5-((3-([1,1'-biphenyl]-3-yl)-1H-pyrazol-1-yl)methyl)pyridin-2-amine |
| 035 | 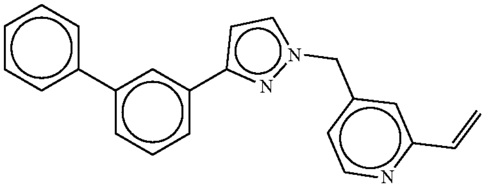 | 4-((3-([1,1'-biphenyl]-3-yl)-1H-pyrazol-1-yl)methyl)-2-vinylpyridine |
| 036 | 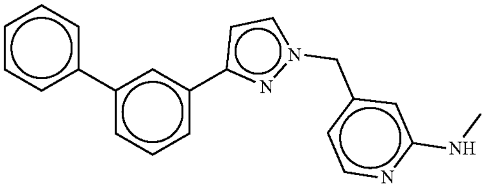 | 4-((3-([1,1'-biphenyl]-3-yl)-1H-pyrazol-1-yl)methyl)-N-methylpyridin-2-amine |
| 037 | 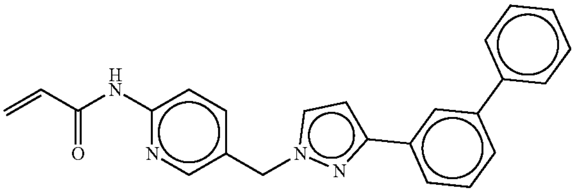 | N-(5-((3-([1,1'-biphenyl]-3-yl)-1H-pyrazol-1-yl)methyl)pyridin-2-yl)acrylamide |
| 038 | 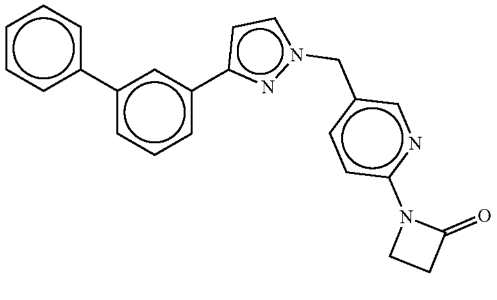 | 1-(5-((3-([1,1'-biphenyl]-3-yl)-1H-pyrazol-1-yl)methyl)pyridin-2-yl)azetidin-2-one |

Structures of example compounds of the disclosure and their respective codes

TABLE 1-continued

Structures of example compounds of the disclosure and their respective codes

| Cpd. No. | Structure | Name |
| --- | --- | --- |
| 039 | 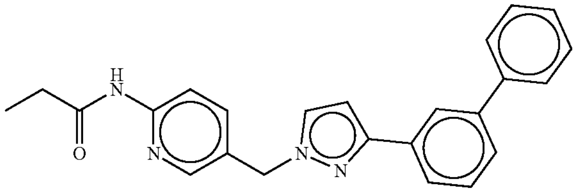 | N-(5-((3-([1,1'-biphenyl]-3-yl)-1H-pyrazol-1-yl)methyl)pyridin-2-yl)propionamide |
| 040 | 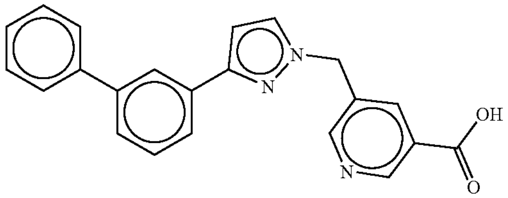 | 5-((3-([1,1'-biphenyl]-3-yl)-1H-pyrazol-1-yl)methyl)nicotinic acid |
| 041 | 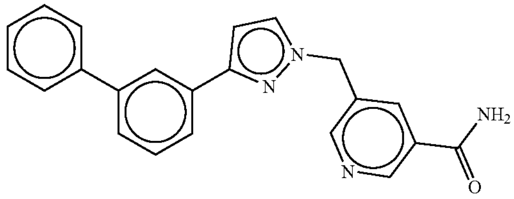 | 5-((3-([1,1'-biphenyl]-3-yl)-1H-pyrazol-1-yl)methyl)nicotinamide |
| 042 | 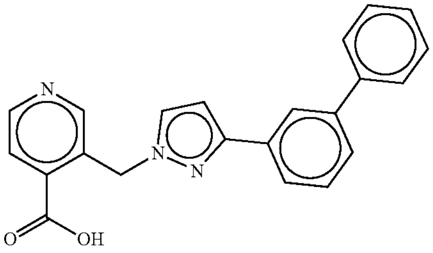 | 3-((3-([1,1'-biphenyl]-3-yl)-1H-pyrazol-1-yl)methyl)isonicotinic acid |
| 043 | 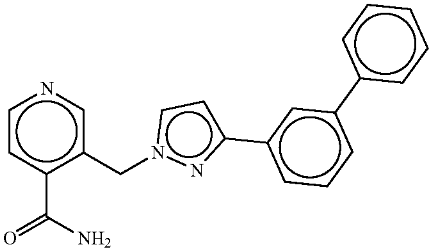 | 3-((3-([1,1'-biphenyl]-3-yl)-1H-pyrazol-1-yl)methyl)isonicotinamide |
| 044 | 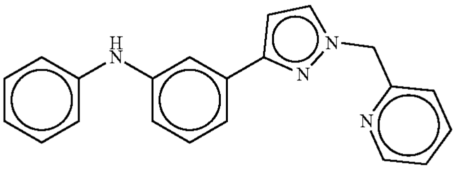 | N-phenyl-3-(1-(pyridin-2-ylmethyl)-1H-pyrazol-3-yl)aniline |
| 045 | 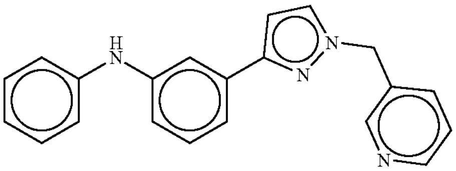 | N-phenyl-3-(1-(pyridin-3-ylmethyl)-1H-pyrazol-3-yl)aniline |

TABLE 1-continued

| Structures of example compounds of the disclosure and their respective codes | | |
|---|---|---|
| Cpd. No. | Structure | Name |
| 046 | 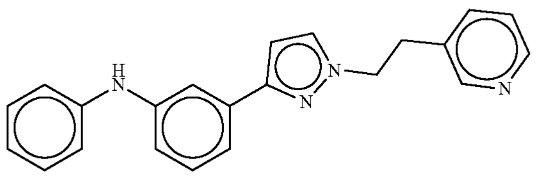 | N-phenyl-3-(1-(2-(pyridin-3-yl)ethyl)-1H-pyrazol-3-yl)aniline |
| 047 | 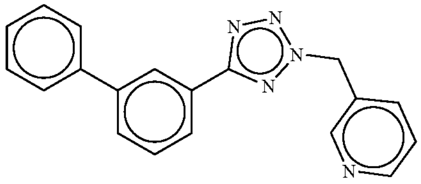 | 3-((5-([1,1'-biphenyl]-3-yl)-2H-tetrazol-2-yl)methyl)pyridine |
| 048 | 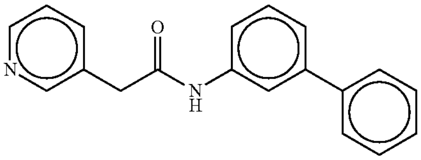 | N-([1,1'-biphenyl]-3-yl)-2-(pyridin-3-yl)acetamide |
| 049 | 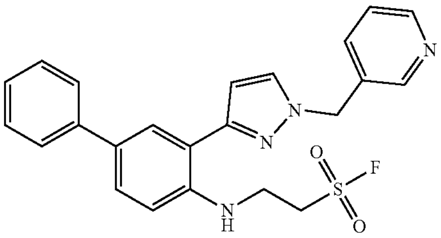 [SMILES: O=S(=O)(F)CCNc1ccc(-c2ccccc2)cc1-c1ccn(Cc2cccnc2)n1] | 2-((3-(1-(pyridin-3-ylmethyl)-1H-pyrazol-3-yl)-[1,1'-biphenyl]-4-yl)amino)ethane-1-sulfonyl fluoride |
| 050 | 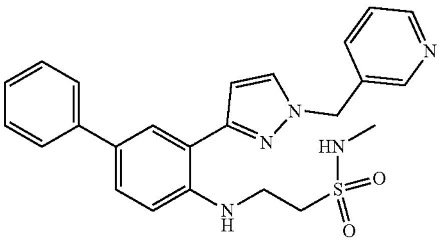 [SMILES: CNS(=O)(=O)CCNc1ccc(-c2ccccc2)cc1-c1ccn(Cc2cccnc2)n1] | N-methyl-2-((3-(1-(pyridin-3-ylmethyl)-1H-pyrazol-3-yl)-[1,1'-biphenyl]-4-yl)amino)ethane-1-sulfonamide |
| 051 | 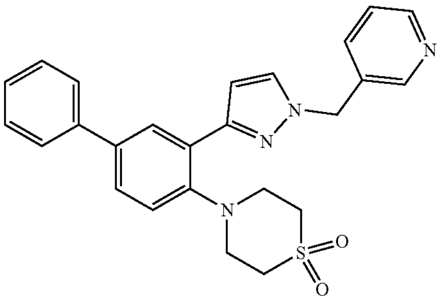 [SMILES: O=S1(=O)CCN(c2ccc(-c3ccccc3)cc2-c2ccn(Cc3cccnc3)n2)CC1] | 4-(3-(1-(pyridin-3-ylmethyl)-1H-pyrazol-3-yl)-[1,1'-biphenyl]-4-yl)thiomorpholine 1,1-dioxide |

TABLE 1-continued

Structures of example compounds of the disclosure and their respective codes

| Cpd. No. | Structure | Name |
|---|---|---|
| 052 | 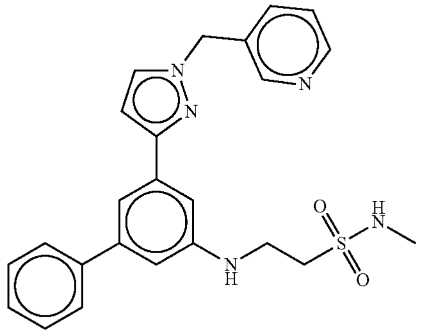 | N-methyl-2-((5-(1-(pyridin-3-ylmethyl)-1H-pyrazol-3-yl)-[1,1'-biphenyl]-3-yl)amino)ethane-1-sulfonamide |
| 053 | 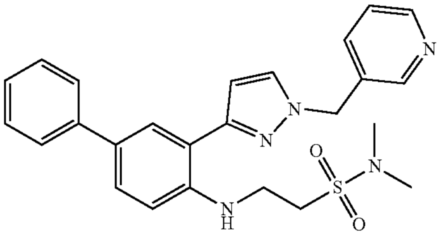 [SMILES: CN(C)S(=O)(=O)CCNc1ccc(-c2ccccc2)cc1-c1ccn(Cc2cccnc2)n1] | N,N-dimethyl-2-((3-(1-(pyridin-3-ylmethyl)-1H-pyrazol-3-yl)-[1,1'-biphenyl]-4-yl)amino)ethane-1-sulfonamide |
| 054 | 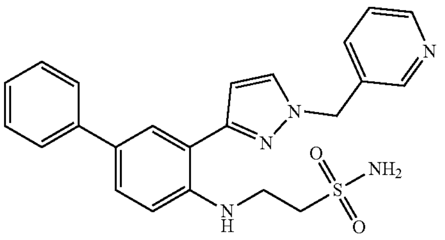 [SMILES: NS(=O)(=O)CCNc1ccc(-c2ccccc2)cc1-c1ccn(Cc2cccnc2)n1] | 2-((3-(1-(pyridin-3-ylmethyl)-1H-pyrazol-3-yl)-[1,1'-biphenyl]-4-yl)amino)ethane-1-sulfonamide |
| 055 | 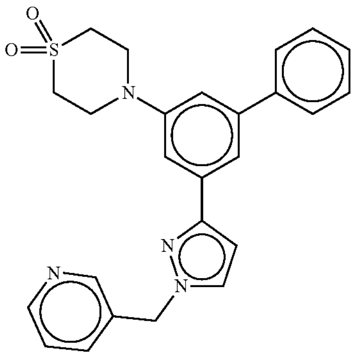 | 4-(5-(1-(pyridin-3-ylmethyl)-1H-pyrazol-3-yl)-[1,1'-biphenyl]-3-yl)thiomorpholine 1,1-dioxide |
| 056 | 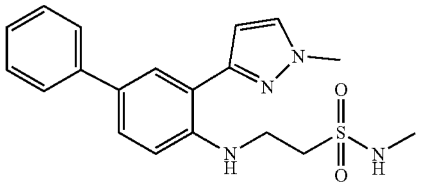 [SMILES: CNS(=O)(=O)CCNc1ccc(-c2ccccc2)cc1-c1ccn(C)n1] | N-methyl-2-((3-(1-methyl-1H-pyrazol-3-yl)-[1,1'-biphenyl]-4-yl)amino)ethane-1-sulfonamide |

TABLE 1-continued

| Structures of example compounds of the disclosure and their respective codes | | |
|---|---|---|
| Cpd. No. | Structure | Name |
| 057 | 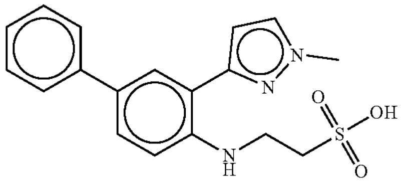 | 2-((3-(1-methyl-1H-pyrazol-3-yl)-[1,1'-biphenyl]-4-yl)amino)ethane-1-sulfonic acid |
| 058 | 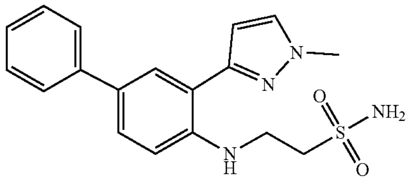 [SMILES: Cn1ccc(-c2cc(-c3ccccc3)ccc2NCCS(N)(=O)=O)n1] | 2-((3-(1-methyl-1H-pyrazol-3-yl)-[1,1'-biphenyl]-4-yl)amino)ethane-1-sulfonamide |
| 059 | 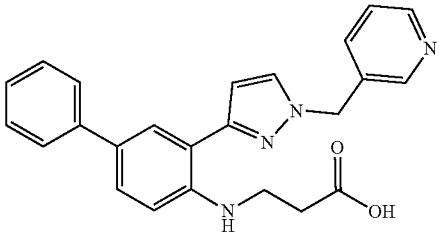 [SMILES: O=C(O)CCNc1ccc(-c2ccccc2)cc1-c1ccn(Cc2cccnc2)n1] | 3-((3-(1-(pyridin-3-ylmethyl)-1H-pyrazol-3-yl)-[1,1'-biphenyl]-4-yl)amino)propanoic acid |
| 060 | 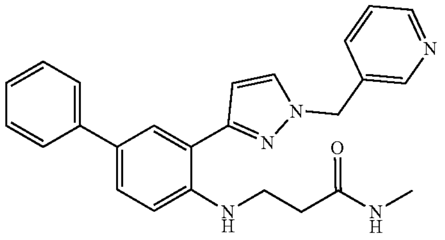 [SMILES: CNC(=O)CCNc1ccc(-c2ccccc2)cc1-c1ccn(Cc2cccnc2)n1] | N-methyl-3-((3-(1-(pyridin-3-ylmethyl)-1H-pyrazol-3-yl)-[1,1'-biphenyl]-4-yl)amino)propanamide |
| 061 | 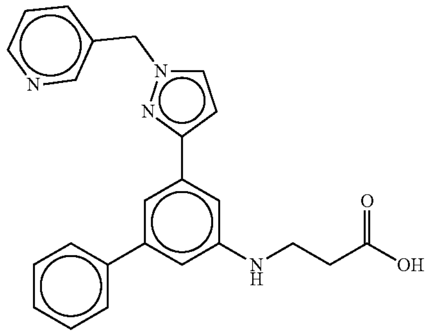 | 3-((5-(1-(pyridin-3-ylmethyl)-1H-pyrazol-3-yl)-[1,1'-biphenyl]-3-yl)amino)propanoic acid |
| 062 | 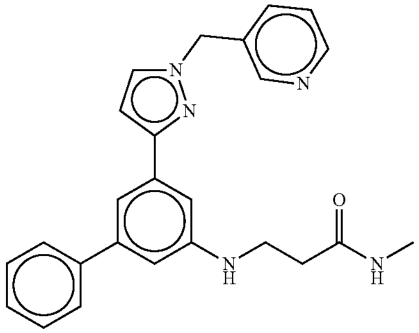 | N-methyl-3-((5-(1-(pyridin-3-ylmethyl)-1H-pyrazol-3-yl)-[1,1'-biphenyl]-3-yl)amino)propanamide |

TABLE 1-continued

Structures of example compounds of the disclosure and their respective codes

| Cpd. No. | Structure | Name |
|---|---|---|
| 063 | 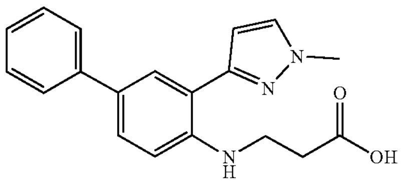 [SMILES: Cn1ccc(-c2cc(-c3ccccc3)ccc2NCCC(=O)O)n1] | 3-((3-(1-methyl-1H-pyrazol-3-yl)-[1,1'-biphenyl]-4-yl)amino)propanoic acid |
| 064 | 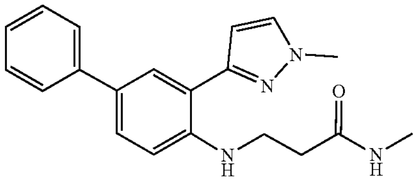 [SMILES: CNC(=O)CCNc1ccc(-c2ccccc2)cc1-c1ccn(C)n1] | N-methyl-3-((3-(1-methyl-1H-pyrazol-3-yl)-[1,1'-biphenyl]-4-yl)amino)propanamide |
| 065 | 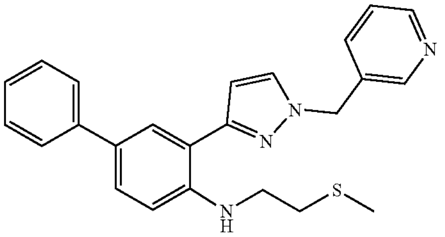 [SMILES: CSCCNc1ccc(-c2ccccc2)cc1-c1ccn(Cc2cccnc2)n1] | N-(2-(methylthio)ethyl)-3-(1-(pyridin-3-ylmethyl)-1H-pyrazol-3-yl)-[1,1'-biphenyl]-4-amine |
| 066 | 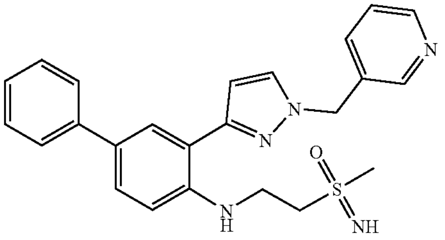 [SMILES: CS(=N)(=O)CCNc1ccc(-c2ccccc2)cc1-c1ccn(Cc2cccnc2)n1] | imino(methyl(2-((3-(1-(pyridin-3-ylmethyl)-1H-pyrazol-3-yl)-[1,1'-biphenyl]-4-yl)amino)ethyl)-l6-sulfanone |
| 067 | 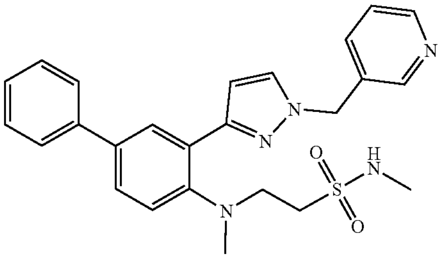 [SMILES: CNS(=O)(=O)CCN(C)c1ccc(-c2ccccc2)cc1-c1ccn(Cc2cccnc2)n1] | N-methyl-2-(methyl(3-(1-(pyridin-3-ylmethyl)-1H-pyrazol-3-yl)-[1,1'-biphenyl]-4-yl)amino)ethane-1-sulfonamide |
| 068 | 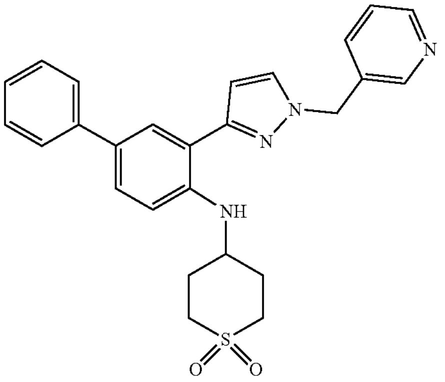 [SMILES: O=S1(=O)CCC(Nc2ccc(-c3ccccc3)cc2-c2ccn(Cc3cccnc3)n2)CC1] | 4-((3-(1-(pyridin-3-ylmethyl)-1H-pyrazol-3-yl)-[1,1'-biphenyl]-4-yl)amino)tetrahydro-2H-thiopyran 1,1-dioxide |

TABLE 1-continued

| Structures of example compounds of the disclosure and their respective codes | | |
|---|---|---|
| Cpd. No. | Structure | Name |
| 069 | 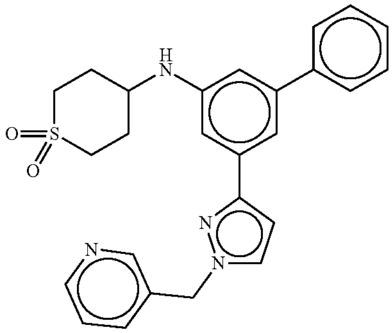 | 4-((5-(1-(pyridin-3-ylmethyl)-1H-pyrazol-3-yl)-[1,1'-biphenyl]-3-yl)amino)tetrahydro-2H-thiopyran 1,1-dioxide |
| 070 | 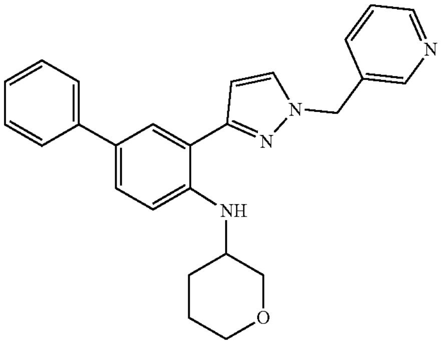 [SMILES: c1ccc(-c2ccc(NC3CCCOC3)c(-c3ccn(Cc4cccnc4)n3)c2)cc1] | N-(3-(1-(pyridin-3-ylmethyl)-1H-pyrazol-3-yl)-[1,1'-biphenyl]-4-yl)tetrahydro-2H-pyran-3-amine |
| 071 | 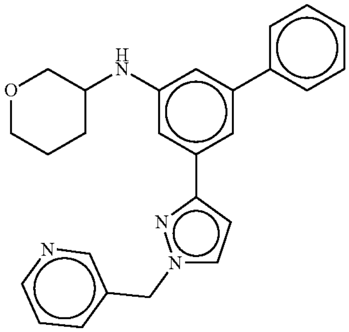 | N-(5-(1-(pyridin-3-ylmethyl)-1H-pyrazol-3-yl)-[1,1'-biphenyl]-3-yl)tetrahydro-2H-pyran-3-amine |
| 072 | 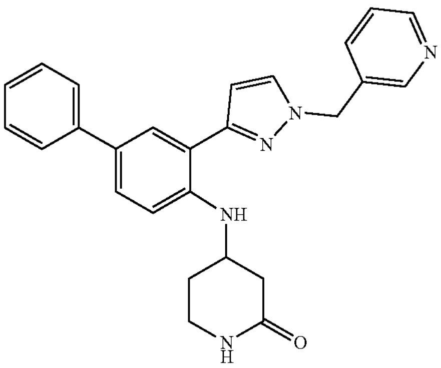 [SMILES: O=C1CC(Nc2ccc(-c3ccccc3)cc2-c2ccn(Cc3cccnc3)n2)CCN1] | 4-((3-(1-(pyridin-3-ylmethyl)-1H-pyrazol-3-yl)-[1,1'-biphenyl]-4-yl)amino)piperidin-2-one |

TABLE 1-continued

| Structures of example compounds of the disclosure and their respective codes | | |
|---|---|---|
| Cpd. No. | Structure | Name |
| 073 | 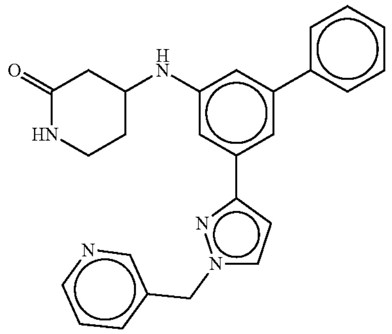 | 4-((5-(1-(pyridin-3-ylmethyl)-1H-pyrazol-3-yl)-[1,1'-biphenyl]-3-yl)amino)piperidin-2-one |
| 074 | 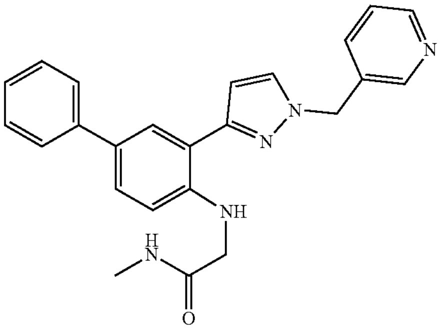 [SMILES: CNC(=O)CNc1ccc(-c2ccccc2)cc1-c1ccn(Cc2cccnc2)n1] | N-methyl-2-((3-(1-(pyridin-3-ylmethyl)-1H-pyrazol-3-yl)-[1,1'-biphenyl]-4-yl)amino)acetamide |
| 075 | 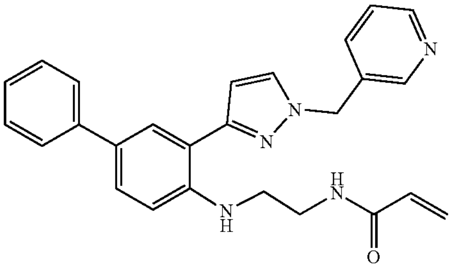 [SMILES: C=CC(=O)NCCNc1ccc(-c2ccccc2)cc1-c1ccn(Cc2cccnc2)n1] | N-(2-((3-(1-(pyridin-3-ylmethyl)-1H-pyrazol-3-yl)-[1,1'-biphenyl]-4-yl)amino)ethyl)acrylamide |
| 076 | 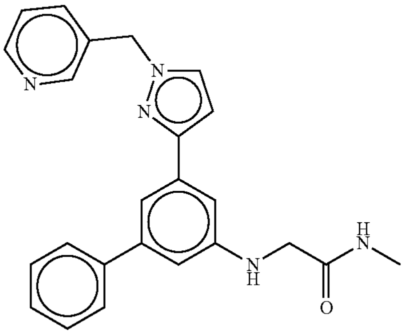 | N-methyl-2-((5-(1-(pyridin-3-ylmethyl)-1H-pyrazol-3-yl)-[1,1'-biphenyl]-3-yl)amino)acetamide |

TABLE 1-continued

Structures of example compounds of the disclosure and their respective codes

| Cpd. No. | Structure | Name |
| --- | --- | --- |
| 077 | 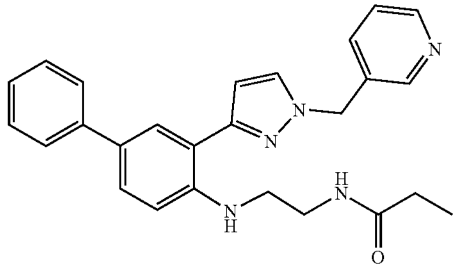 [SMILES: CCC(=O)NCCNc1ccc(-c2ccccc2)cc1-c1ccn(Cc2cccnc2)n1] | N-(2-((3-(1-(pyridin-3-ylmethyl)-1H-pyrazol-3-yl)-[1,1'-biphenyl]-4-yl)amino)propanionamide |
| 078 | 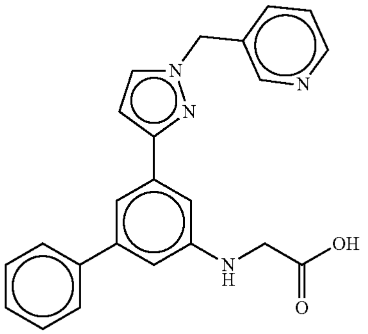 | (5-(1-(pyridin-3-ylmethyl)-1H-pyrazol-3-yl)-[1,1'-biphenyl]-3-yl)glycine |
| 079 | 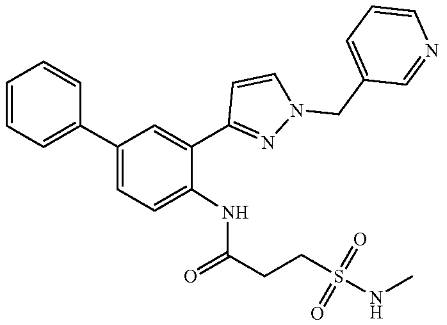 [SMILES: CNS(=O)(=O)CCC(=O)Nc1ccc(-c2ccccc2)cc1-c1ccn(Cc2cccnc2)n1] | 3-(N-methylsulfamoyl)-N-(3-(1-(pyridin-3-ylmethyl)-1H-pyrazol-3-yl)-[1,1'-biphenyl]-4-yl)propanamide |
| 080 | 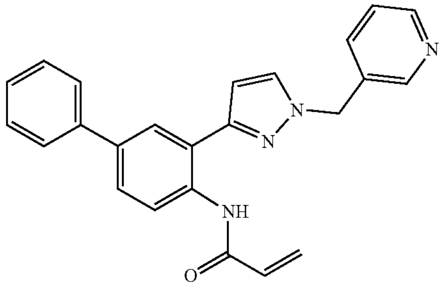 [SMILES: C=CC(=O)Nc1ccc(-c2ccccc2)cc1-c1ccn(Cc2cccnc2)n1] | N-(3-(1-(pyridin-3-ylmethy)-1H-pyrazol-3-yl)-[1,1'-biphenyl]-4-yl)acrylamide |
| 081 | 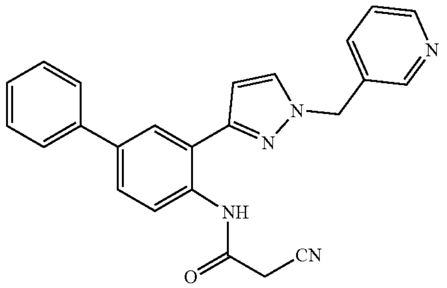 [SMILES: N#CCC(=O)Nc1ccc(-c2ccccc2)cc1-c1ccn(Cc2cccnc2)n1] | 2-cyano-N-(3-(1-(pyridin-3-ylmethyl)-1H-pyrazol-3-yl)-[1,1'-biphenyl]-4-yl)acetamide |

TABLE 1-continued

| Structures of example compounds of the disclosure and their respective codes | | |
|---|---|---|
| Cpd. No. | Structure | Name |
| 082 | 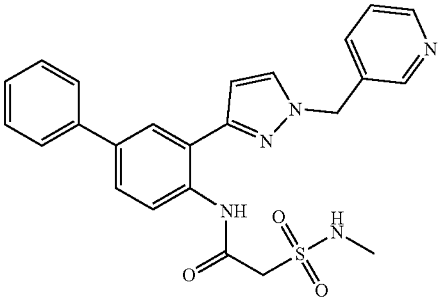 [SMILES: CNS(=O)(=O)CC(=O)Nc1ccc(-c2ccccc2)cc1-c1ccn(Cc2cccnc2)n1] | 2-(N-methylsulfamoyl)-N-(3-(1-(pyridin-3-ylmethyl)-1H-pyrazol-3-yl)-[1,1'-biphenyl]-4-yl)acetamide |
| 083 | 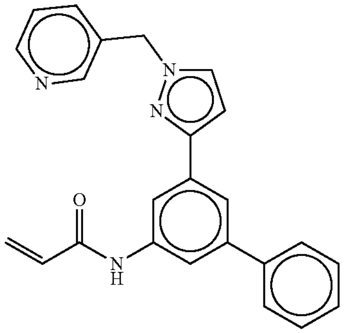 | N-(5-(1-(pyridin-3-ylmethyl)-1H-pyrazol-3-yl)-[1,1'-biphenyl]-3-yl)acrylamide |
| 084 | 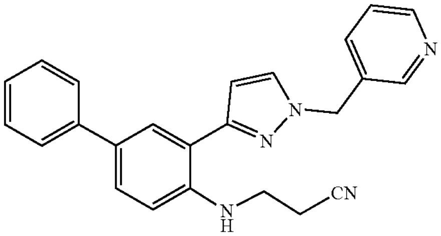 [SMILES: N#CCCNc1ccc(-c2ccccc2)cc1-c1ccn(Cc2cccnc2)n1] | 3-((3-(1-(pyridin-3-ylmethyl)-1H-pyrazol-3-yl)-[1,1'-biphenyl]-4-yl)amino)propanenitrile |
| 085 | 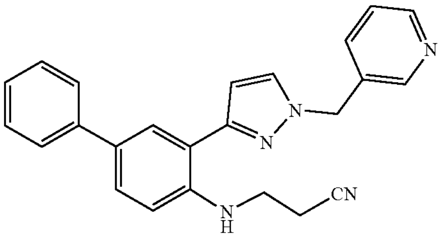 [SMILES: N#CCCNc1ccc(-c2ccccc2)cc1-c1ccn(Cc2cccnc2)n1] | 2-((3-(1-(pyridin-3-ylmethyl)-1H-pyrazol-3-yl)-[1,1'-biphenyl]-4-yl)amino)acetonitrile |
| 086 | 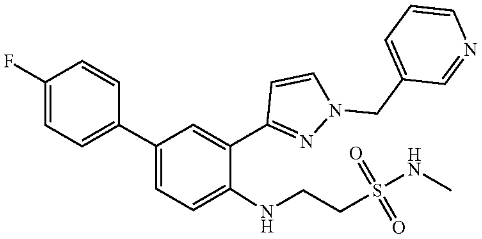 [SMILES: CNS(=O)(=O)CCNc1ccc(-c2ccc(F)cc2)cc1-c1ccn(Cc2cccnc2)n1] | 2-((4'-fluoro-3-(1-(pyridin-3-ylmethyl)-1H-pyrazol-3-yl)-[1,1'-biphenyl]-4-yl)amino)-N-methylethane-1-sulfonamide |

TABLE 1-continued

Structures of example compounds of the disclosure and their respective codes

| Cpd. No. | Structure | Name |
|---|---|---|
| 087 | 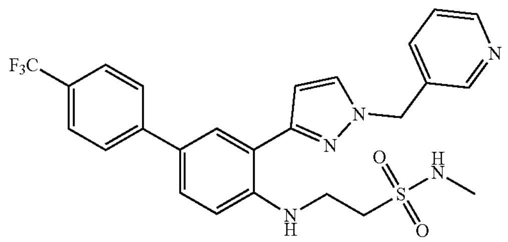 | N-methyl-2-((3-(1-(pyridin-3-ylmethyl)-1H-pyrazol-3-yl)-4'-(trifluoromethyl)-[1,1'-biphenyl]-4-yl)amino)ethane-1-sulfonamide |
| 088 | 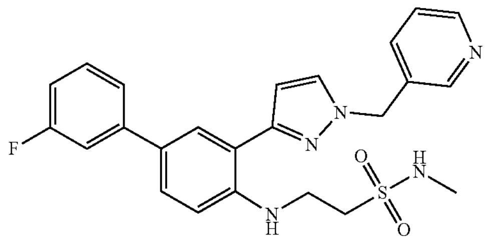 [SMILES: CNS(=O)(=O)CCNc1ccc(-c2cccc(F)c2)cc1-c1ccn(Cc2cccnc2)n1] | 2-((3'-fluoro-3-(1-pyridin-3-ylmethyl)-1H-pyrazol-3-yl)-[1,1'-biphenyl]-4-yl)amino)-N-methylethane-1-sulfonamide |
| 089 | 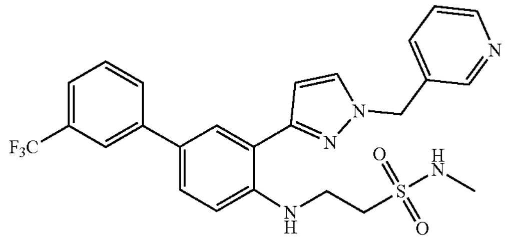 [SMILES: CNS(=O)(=O)CCNc1ccc(-c2cccc(C(F)(F)F)c2)cc1-c1ccn(Cc2cccnc2)n1] | N-methyl-2-((3-(1-pyridin-3-ylmethyl)-1H-pyrazol-3-yl)-3'-(trifluoromethyl)-[1,1'-biphenyl]-4-yl)amino)-ethane-1-sulfonamide |
| 090 | 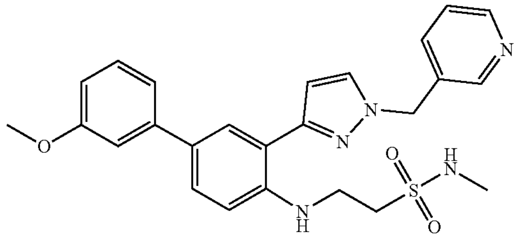 [SMILES: CNS(=O)(=O)CCNc1ccc(-c2cccc(OC)c2)cc1-c1ccn(Cc2cccnc2)n1] | 2-((3'-methoxy-3-(1-(pyridin-3-ylmethyl)-1H-pyrazol-3-yl)-[1,1'-biphenyl]-4-yl)amino)-N-methylethane-1-sulfonamide |
| 091 | 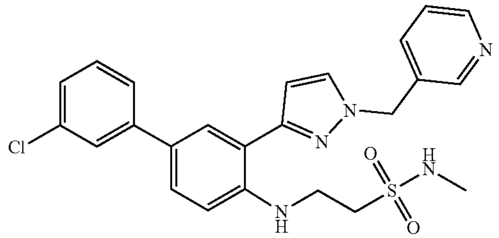 [SMILES: CNS(=O)(=O)CCNc1ccc(-c2cccc(Cl)c2)cc1-c1ccn(Cc2cccnc2)n1] | 2-((3'-chloro-3-(1-(pyridin-3-ylmethyl)-1H-pyrazol-3-yl)-[1,1'-biphenyl]-4-yl)amino)-N-methylethane-1-sulfonamide |
| 092 | 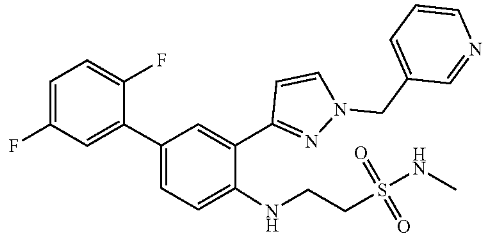 [SMILES: CNS(=O)(=O)CCNc1ccc(-c2cc(F)ccc2F)cc1-c1ccn(Cc2cccnc2)n1] | 2-((2',5'-difluoro-3-(1-(pyridin-3-ylmethyl)-1H-pyrazol-3-yl)-[1,1'-biphenyl]-4-yl)amino)-N-methylethane-1-sulfonamide |

TABLE 1-continued

| Cpd. No. | Structure | Name |
|---|---|---|
| Structures of example compounds of the disclosure and their respective codes | | |
| 093 | 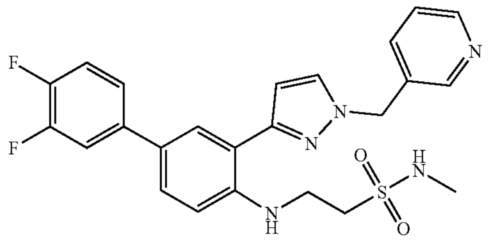 [SMILES: CNS(=O)(=O)CCNc1ccc(-c2ccc(F)c(F)c2)cc1-c1ccn(Cc2cccnc2)n1] | 2-((3',4'-difluoro-3-(1-(pyridin-3-ylmethyl)-1H-pyrazol-3-yl)-[1,1'-biphenyl]-4-yl)amino)-N-methylethane-1-sulfonamide |
| 094 | 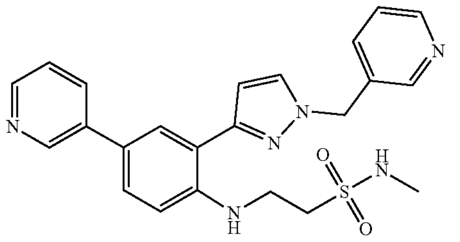 [SMILES: CNS(=O)(=O)CCNc1ccc(-c2cccnc2)cc1-c1ccn(Cc2cccnc2)n1] | N-methyl-2-((4-(pyridin-3-yl)-2-(1-(pyridin-3-ylmethyl)-1H-pyrazol-3-yl)phenyl)amino)ethane-1-sulfonamide |
| 095 | 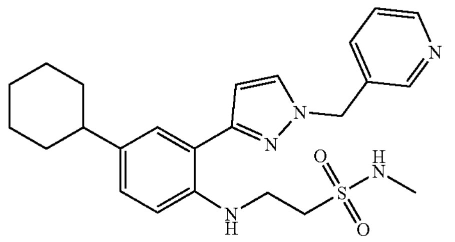 [SMILES: CNS(=O)(=O)CCNc1ccc(C2CCCCC2)cc1-c1ccn(Cc2cccnc2)n1] | 2-((4-cyclohexyl-2-(1-(pyridin-3-ylmethyl)-1H-pyrazol-3-yl)phenyl)amino)-N-methylethane-1-sulfonamide |
| 096 | 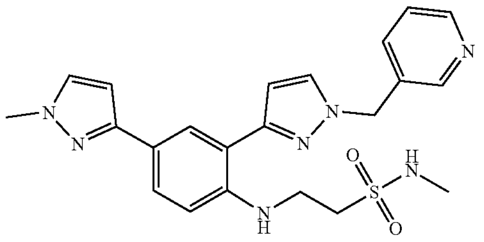 [SMILES: CNS(=O)(=O)CCNc1ccc(-c2ccn(C)n2)cc1-c1ccn(Cc2cccnc2)n1] | N-methyl-2-((4-(1-methyl-1H-pyrazol-3-yl)-2-(1-(pyridin-3-ylmethyl)-1H-pyrazol-3-yl)phenyl)amino)ethane-1-sulfonamide |
| 097 | 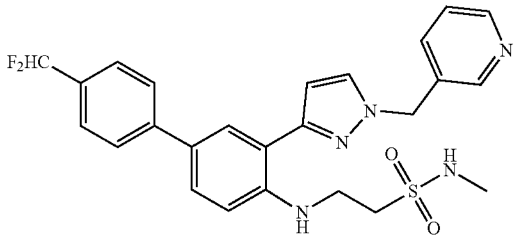 [SMILES: CNS(=O)(=O)CCNc1ccc(-c2ccc(OC(F)(F)F)cc2)cc1-c1ccn(Cc2cccnc2)n1] | 2-((4'-(difluoromethyl)-3-(1-(pyridin-3-ylmethyl)-1H-pyrazol-3-yl)-[1,1'-biphenyl]-4-yl)amino)-N-methylethane-1-sulfonamide |
| 098 | 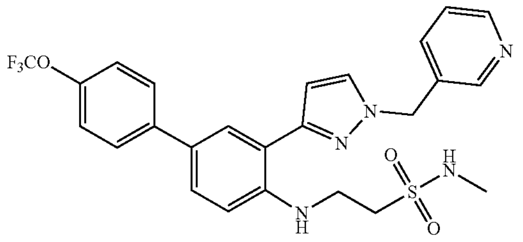 | N-methyl-2-((3-(1-(pyridin-3-ylmethyl)-1H-pyrazol-3-yl)-4'-(trifluoromethoxy)-[1,1'-biphenyl]-4-yl)amino)ethane-1-sulfonamide |

TABLE 1-continued

| Structures of example compounds of the disclosure and their respective codes | | |
|---|---|---|
| Cpd. No. | Structure | Name |
| 099 | 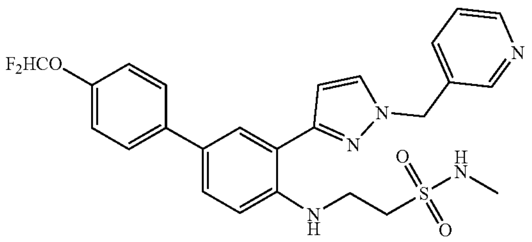 [SMILES: CNS(=O)(=O)CCNc1ccc(-c2ccc(OC(F)F)cc2)cc1-c1ccn(Cc2cccnc2)n1] | 2-((4'-(difluoromethoxy)-3-(1-(pyridin-3-ylmethyl)-1H-pyrazol-3-yl)-[1,1'-biphenyl]-4-yl)amino)-N-methylethane-1-sulfonamide |
| 100 | 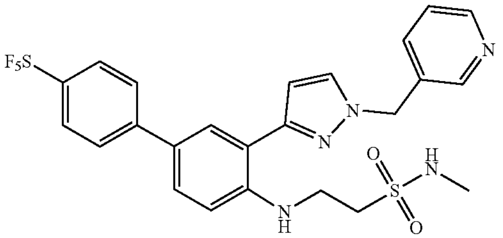 | 2-((4'-(2,2-difluoro-2-methyl-2l6-trifluoran-2-yl)-3-(1-(pyridin-3-ylmethyl)-1H-pyrazol-3-yl)-[1,1'-biphenyl]-4-yl)amino)-N-methylethane-1-sulfonamide |
| 101 | 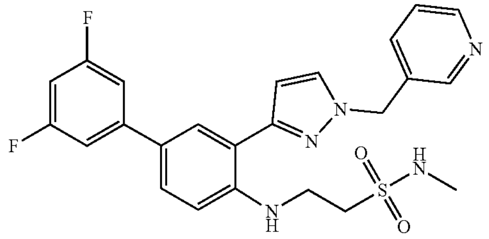 [SMILES: CNS(=O)(=O)CCNc1ccc(-c2cc(F)cc(F)c2)cc1-c1ccn(Cc2cccnc2)n1] | 2-((3',5'-difluoro-3-(1-(pyridin-3-ylmethyl)-1H-pyrazol-3-yl)-[1,1'-biphenyl]-4-yl)amino)-N-methylethane-1-sulfonamide |
| 102 | 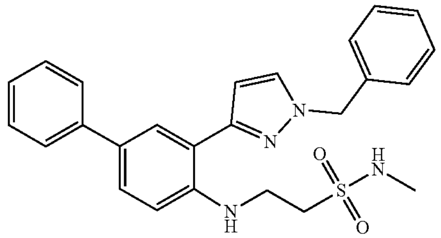 [SMILES: CNS(=O)(=O)CCNc1ccc(-c2ccccc2)cc1-c1ccn(Cc2ccccc2)n1] | 2-((3-(1-benzyl-1H-pyrazol-3-yl)-[1,1'-biphenyl]-4-yl)amino)-N-methylethane-1-sulfonamide |
| 103 | 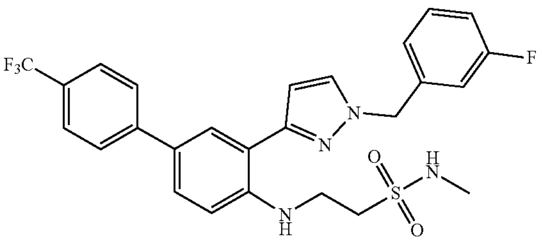 [SMILES: CNS(=O)(=O)CCNc1ccc(-c2ccc(C(F)(F)F)cc2)cc1-c1ccn(Cc2cccc(F)c2)n1] | 2-((3-(1-(3-fluorobenzyl)-1H-pyrazol-3-yl)-4'-(trifluoromethyl)-[1,1'-biphenyl]-4-yl)amino)-N-methylethane-1-sulfonamide |
| 104 | 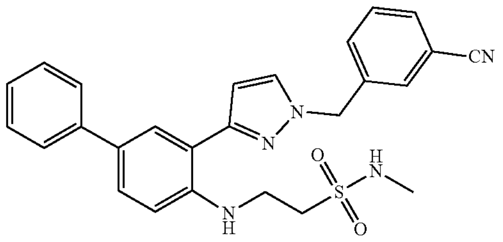 [SMILES: CNS(=O)(=O)CCNc1ccc(-c2ccccc2)cc1-c1ccn(Cc2cccc(C#N)c2)n1] | 2-((3-(1-(3-cyanobenzyl)-1H-pyrazol-3-yl)-[1,1'-biphenyl]-4-yl)amino)-N-methylethane-1-sulfonamide |

TABLE 1-continued

| Structures of example compounds of the disclosure and their respective codes | | |
|---|---|---|
| Cpd. No. | Structure | Name |
| 105 | 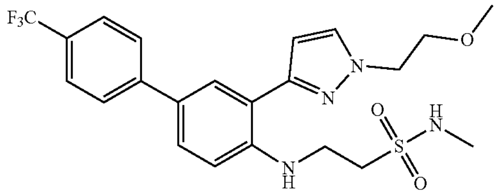 [SMILES: CNS(=O)(=O)CCNc1ccc(-c2ccc(C(F)(F)F)cc2)cc1-c1ccn(CCOC)n1] | 2-((3-(1-(2-methoxyethyl)-1H-pyrazol-3-yl)-4'-(trifluoromethyl)-[1,1'-biphenyl]-4-yl)amino)-N-methylethane-1-sulfonamide |
| 106 | 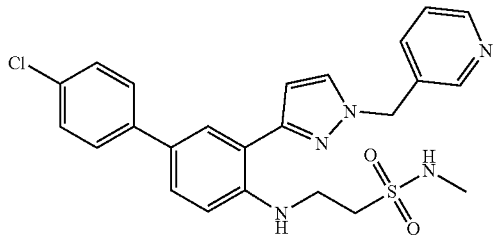 [SMILES: CNS(=O)(=O)CCNc1ccc(-c2ccc(Cl)cc2)cc1-c1ccn(Cc2cccnc2)n1] | 2-((4'-chloro-3-(1-(pyridin-3-ylmethyl)-1H-pyrazol-3-yl)-[1,1'-biphenyl]-4-yl)amino)-N-methylethane-1-sulfonamide |
| 107 | 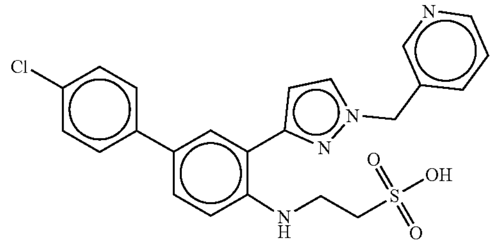 | 2-((4'-chloro-3-(1-(pyridin-3-ylmethyl)-1H-pyrazol-3-yl)-[1,1'-biphenyl]-4-yl)amino)ethane-1-sulfonic acid |
| 108 | 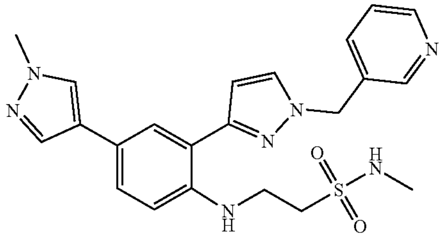 [SMILES: CNS(=O)(=O)CCNc1ccc(-c2cnn(C)c2)cc1-c1ccn(Cc2cccnc2)n1] | N-methyl-2-((4-(1-methyl-1H-pyrazol-4-yl)-2-(1-(pyridin-3-ylmethyl)-1H-pyrazol-3-yl)phenyl)amino)ethane-1-sulfonamide |
| 109 | 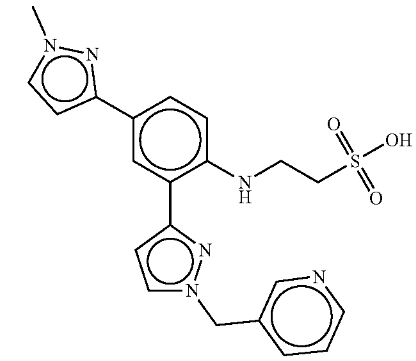 | 2-((4-(1-methyl-1H-pyrazol-3-yl)-2-(1-(pyridin-3-ylmethyl)-1H-pyrazol-3-yl)phenyl)amino)ethane-1-sulfonic acid |

TABLE 1-continued

Structures of example compound of the disclosure and their respective codes

| Cpd. No. | Structure | Name |
| --- | --- | --- |
| 110 | 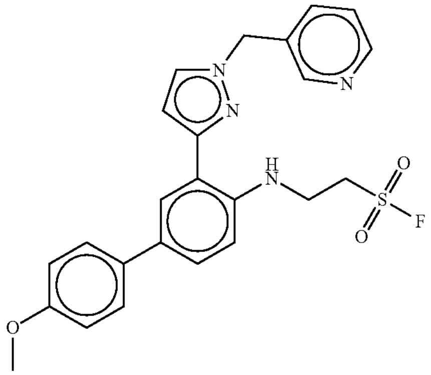 | 2-((4'-methoxy-3-(1-(pyridin-3-ylmethyl)-1H-pyrazol-3-yl)-[1,1'-biphenyl]-4-yl)amino)ethane-1-sulfonyl fluoride |
| 111 | 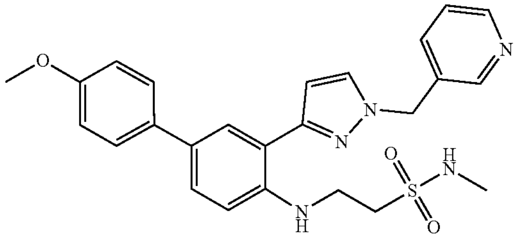 [SMILES: CNS(=O)(=O)CCNc1ccc(-c2ccc(OC)cc2)cc1-c1ccn(Cc2cccnc2)n1] | 2-((4'-methoxy-3-(1-(pyridin-3-ylmethyl)-1H-pyrazol-3-yl)-[1,1'-biphenyl]-4-yl)amino)-N-methylethane-1-sulfonamide |
| 112 | 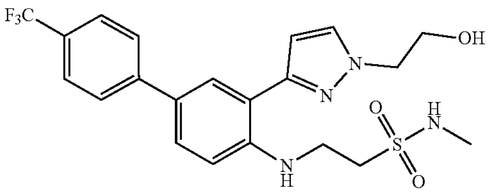 [SMILES: CNS(=O)(=O)CCNc1ccc(-c2ccc(C(F)(F)F)cc2)cc1-c1ccn(CCO)n1] | 2-((3-(1-(2-hydroxyethyl)-1H-pyrazol-3-yl)-4'-(trifluoromethyl)-[1,1'-biphenyl]-4-yl)amino)-N-methylethane-1-sulfonamide |
| 113 | 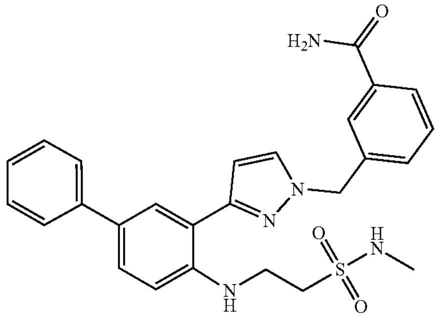 [SMILES: CNS(=O)(=O)CCNc1ccc(-c2ccccc2)cc1-c1ccn(Cc2cccc(C(N)=O)c2)n1] | 3-((3-(4-((2-(N-methylsulfamoyl)ethyl)amino)-[1,1'-biphenyl]-3-yl)-1H-pyrazol-1-yl)methyl)benzamide |
| 114 | 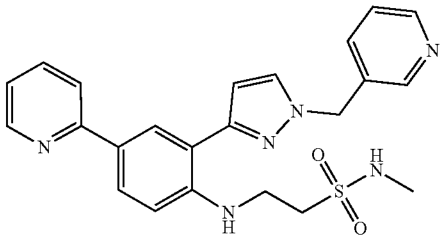 [SMILES: CNS(=O)(=O)CCNc1ccc(-c2ccccn2)cc1-c1ccn(Cc2cccnc2)n1] | N-methyl-2-((4-(pyridin-2-yl)-2-(1-(pyridin-3-ylmethyl)-1H-pyrazol-3-yl)phenyl)amino)ethane-1-sulfonamide |

TABLE 1-continued

Structures of example compounds of the disclosure and their respective codes

| Cpd. No. | Structure | Name |
| --- | --- | --- |
| 115 | 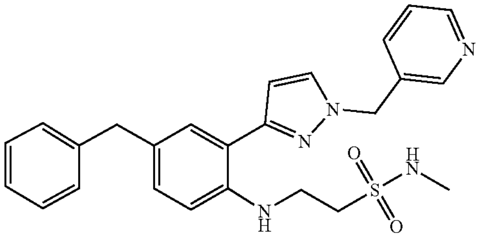 [SMILES: CNS(=O)(=O)CCNc1ccc(Cc2ccccc2)cc1-c1ccn(Cc2cccnc2)n1] | 2-((4-benzyl-2-(1-pyridin-3-ylmethyl)-1H-pyrazol-3-yl)phenyl)amino)-N-methylethane-1-sulfonamide |
| 116 | 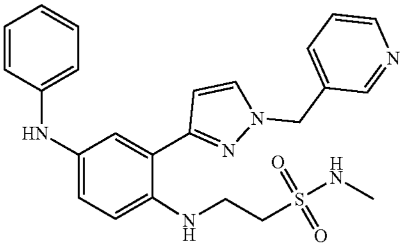 [SMILES: CNS(=O)(=O)CCNc1ccc(Nc2ccccc2)cc1-c1ccn(Cc2cccnc2)n1] | N-methyl-2-((4-(phenylamino)-2-(1-(pyridin-3-ylmethyl)-1H-pyrazol-3-yl)phenyl)amino)ethane-1-sulfonamide |
| 117 | 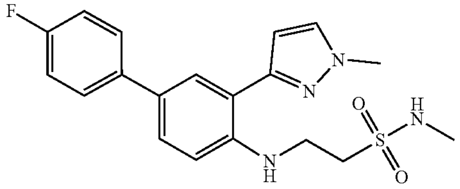 [SMILES: CNS(=O)(=O)CCNc1ccc(-c2ccc(F)cc2)cc1-c1ccn(C)n1] | 2-((4'-fluoro-3-(1-methyl-1H-pyrazol-3-yl)-[1,1'-biphenyl]-4-yl)amino)-N-methylethane-1-sulfonamide |
| 118 | 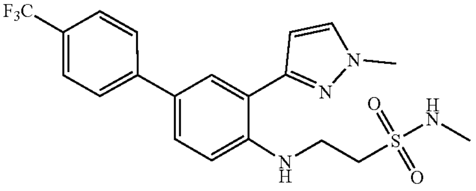 [SMILES: CNS(=O)(=O)CCNc1ccc(-c2ccc(C(F)(F)F)cc2)cc1-c1ccn(C)n1] | N-methyl-2-((3-(1-methyl-1H-pyrazol-3-yl)-4'-(trifluoromethyl)-[1,1'-biphenyl]-4-yl)amino)ethane-1-sulfonamide |
| 119 | 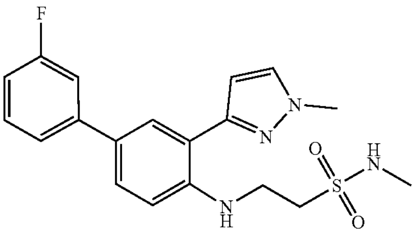 [SMILES: CNS(=O)(=O)CCNc1ccc(-c2cccc(F)c2)cc1-c1ccn(C)n1] | 2-((3'-fluoro-3-(1-methyl-1H-pyrazol-3-yl)-[1,1'-biphenyl]-4-yl)amino)-N-methylethane-1-sulfonamide |
| 120 | 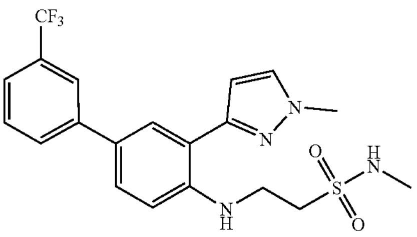 | N-methyl-2-((3-(1-methyl-1H-pyrazol-3-yl)-3'-(trifluoromethyl)-[1,1'-biphenyl-4-yl)amino)ethane-1-sulfonamide |

TABLE 1-continued

Structures of example compounds of the disclosure and their respective codes

| Cpd. No. | Structure | Name |
|---|---|---|
| 121 | 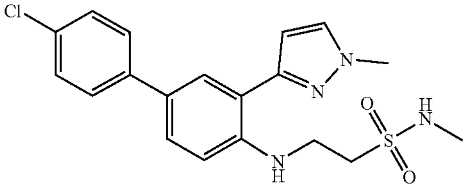 [SMILES: CNS(=O)(=O)CCNc1ccc(-c2ccc(Cl)cc2)cc1-c1ccn(C)n1] | 2-((4'-chloro-3-(1-methyl-1H-pyrazol-3-yl)-[1,1'-biphenyl]-4-yl)amino)-N-methylethane-1-sulfonamide |
| 122 | 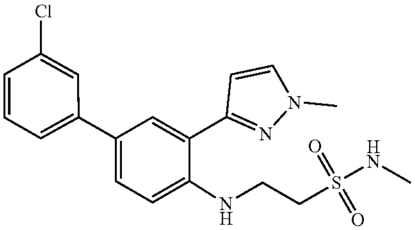 [SMILES: CNS(=O)(=O)CCNc1ccc(-c2cccc(Cl)c2)cc1-c1ccn(C)n1] | 2-((3'-chloro-3-(1-methyl-1H-pyrazol-3-yl)-[1,1'-biphenyl]-4-yl)amino)-N-methylethane-1-sulfonamide |
| 123 | 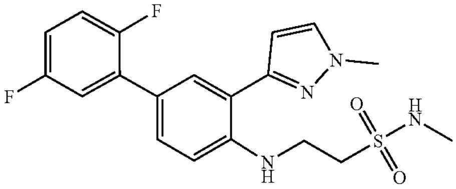 [SMILES: CNS(=O)(=O)CCNc1ccc(-c2cc(F)ccc2F)cc1-c1ccn(C)n1] | 2-((2',5'-difluoro-3-(1-methyl-1H-pyrazol-3-yl)-[1,1'-biphenyl]-4-yl)amino)-N-methylethane-1-sulfonamide |
| 124 | 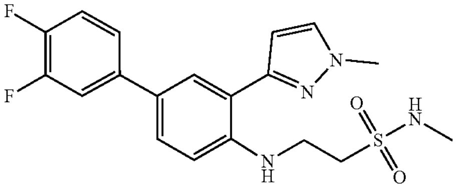 [SMILES: CNS(=O)(=O)CCNc1ccc(-c2ccc(F)c(F)c2)cc1-c1ccn(C)n1] | 2-((3',4'-difluoro-3-(1-methyl-1H-pyrazol-3-yl)-[1,1'-biphenyl-4-yl)amino)-N-methylethane-1-sulfonamide |
| 125 | 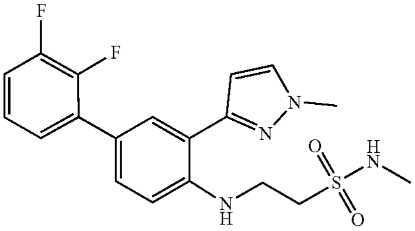 [SMILES: CNS(=O)(=O)CCNc1ccc(-c2cccc(F)c2F)cc1-c1ccn(C)n1] | 2-((2',3'-difluoro-3-(1-methyl-1H-pyrazol-3-yl)-[1,1'-biphenyl]-4-yl)amino)-N-methylethane-1-sulfonamide |
| 126 | 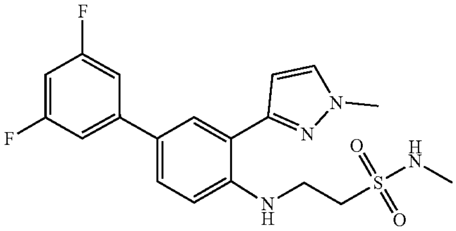 [SMILES: CNS(=O)(=O)CCNc1ccc(-c2cc(F)cc(F)c2)cc1-c1ccn(C)n1] | 2-((3',5'-difluoro-3-(1-methyl-1H-pyrazol-3-yl)-[1,1'-biphenyl]-4-yl)amino)-N-methylethane-1-sulfonamide |

TABLE 1-continued

Structures of example compound of the disclosure and their respective codes

| Cpd. No. | Structure | Name |
|---|---|---|
| 127 | 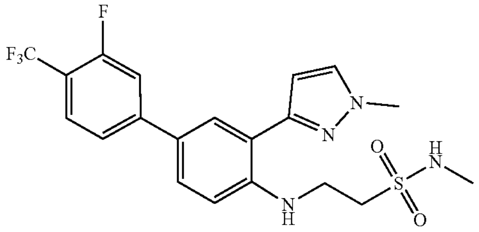 [SMILES: CNS(=O)(=O)CCNc1ccc(-c2ccc(C(F)(F)F)c(F)c2)cc1-c1ccn(C)n1] | 2-((3'-fluoro-3-(1-methyl-1H-pyrazol-3-yl)-4'-(trifluoromethyl)-[1,1'-biphenyl]-4-yl)amino)-N-methylethane-1-sulfonamide |
| 128 | 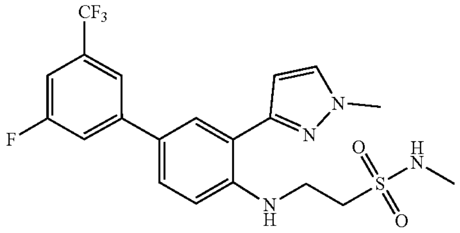 [SMILES: CNS(=O)(=O)CCNc1ccc(-c2cc(F)cc(C(F)(F)F)c2)cc1-c1ccn(C)n1] | 2-((3'-fluoro-3-(1-methyl-1H-pyrazol-3-yl)-5'-(trifluoromethyl)-[1,1'-biphenyl]-4-yl)amino)-N-methylethane-1-sulfonamide |
| 129 | 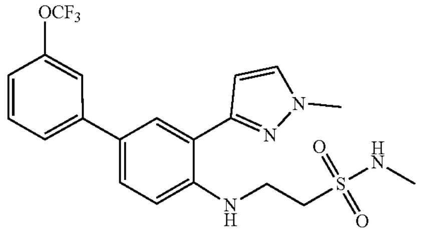 [SMILES: CNS(=O)(=O)CCNc1ccc(-c2cccc(OC(F)(F)F)c2)cc1-c1ccn(C)n1] | N-methyl-2-((3-(1-methyl-1H-pyrazol-3-yl)-3'-(trifluoromethoxy)-[1,1'-biphenyl]-4-yl)amino)ethane-1-sulfonamide |
| 130 | 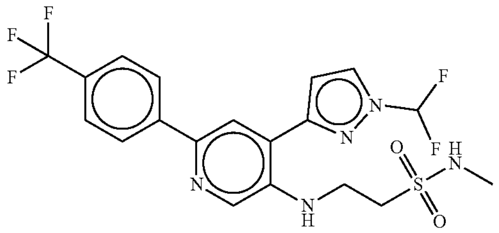 | 2-((4-(1-(difluoromethyl)-1H-pyrazol-3-yl)-6-(4-(trifluoromethyl)phenyl)pyridin-3-yl)amino)-N-methylethane-1-sulfonamide |
| 131 | 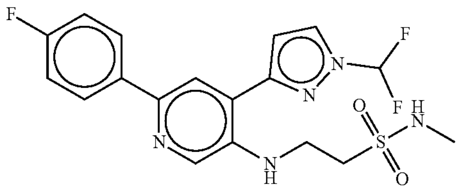 | 2-((4-(1-(difluoromethyl)-1H-pyrazol-3-yl)-6-(4-fluorophenyl)pyridin-3-yl)amino)-N-methylethane-1-sulfonamide |
| 132 | 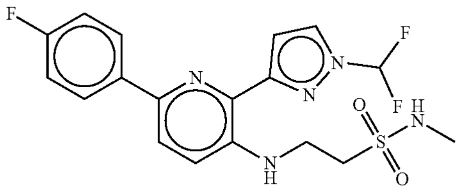 | 2-((2-(1-(difluoromethyl)-1H-pyrazol-3-yl)-6-(4-fluorophenyl)pyridin-3-yl)amino)-N-methylethane-1-sulfonamide |

TABLE 1-continued

| Cpd. No. | Structure | Name |
|---|---|---|
| | Structures of example compounds of the disclosure and their respective codes | |
| 133 | 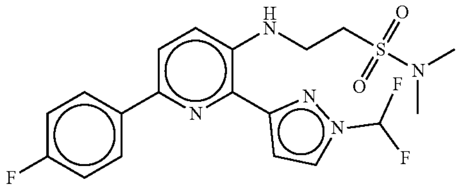 | 2-((2-(1-(difluoromethyl)-1H-pyrazol-3-yl)-6-(4-fluorophenyl)pyridin-3-yl)amino)-N,N-dimethylethane-1-sulfonamide |
| 134 | 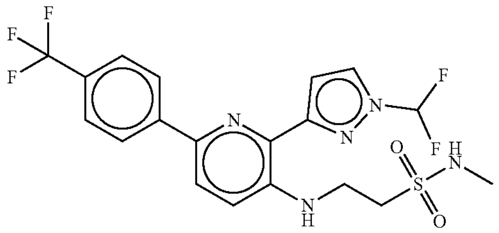 | 2-((2-(1-(difluoromethyl)-1H-pyrazol-3-yl)-6-(4-(trifluoromethyl)phenyl)pyridin-3-yl)amino)-N-methylethane-1-sulfonamide |
| 135 | 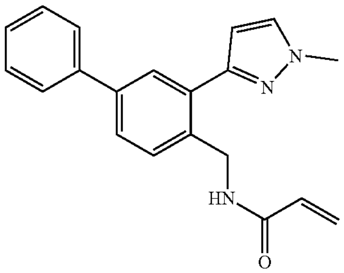 [SMILES: C=CC(=O)NCc1ccc(-c2ccccc2)cc1-c1ccn(C)n1] | N-((3-(1-methyl-1H-pyrazol-3-yl)-[1,1'-biphenyl]-4-yl)methyl)acrylamide |
| 136 | 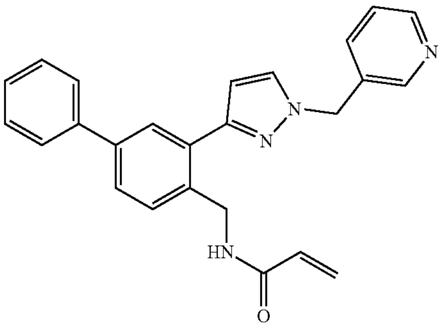 [SMILES: C=CC(=O)NCc1ccc(-c2ccccc2)cc1-c1ccn(Cc2cccnc2)n1] | N-((3-(1-(pyridin-3-ylmethyl)-1H-pyrazol-3-yl)-[1,1'-biphenyl]-4-yl)methyl)acrylamide |
| 137 | 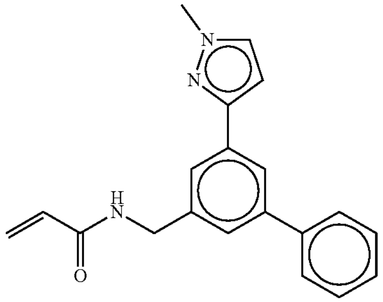 | N-((5-(1-methyl-1H-pyrazol-3-yl)-[1,1'-biphenyl]-3-yl)methyl)acrylamide |

TABLE 1-continued

Structures of example compounds of the disclosure and their respective codes

| Cpd. No. | Structure | Name |
|---|---|---|
| 138 | 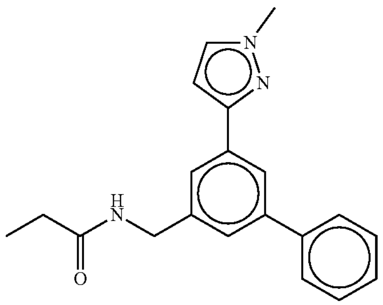 | N-((5-(1-methyl-1H-pyrazol-3-yl)-[1,1'-biphenyl]-3-yl)methyl)propionamide |
| 139 | 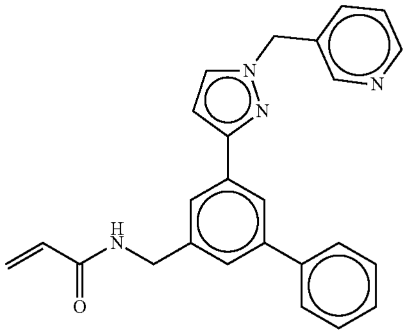 | N-((5-(1-(pyridin-3-ylmethyl)-1H-pyrazol-3-yl)-[1,1'-biphenyl]-3-yl)methyl)acrylamide |
| 140 | 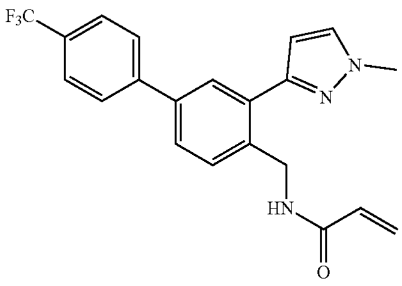 [SMILES: C=CC(=O)NCc1ccc(-c2ccc(C(F)(F)F)cc2)cc1-c1ccn(C)n1] | N-((3-(1-methyl-1H-pyrazol-3-yl)-4'-(trifluoromethyl)-[1,1'-biphenyl]-4-yl)methyl)acrylamide |
| 141 | 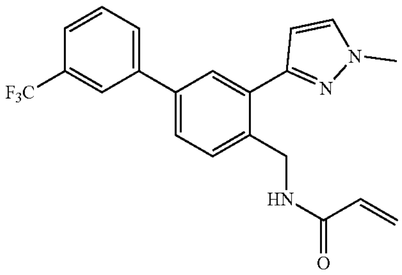 [SMILES: C=CC(=O)NCc1ccc(-c2cccc(C(F)(F)F)c2)cc1-c1ccn(C)n1] | N-((3-(1-methyl-1H-pyrazol-3-yl)-3'-(trifluoromethyl)-[1,1'-biphenyl]-4-yl)methyl)acrylamide |
| 142 | 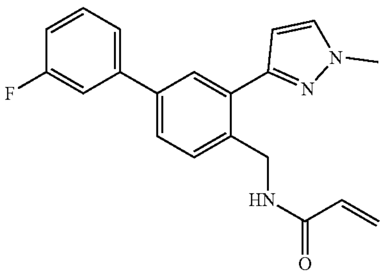 [SMILES: C=CC(=O)NCc1ccc(-c2cccc(F)c2)cc1-c1ccn(C)n1] | N-((3'-fluoro-3-(1-methyl-1H-pyrazol-3-yl)-[1,1'-biphenyl]-4-yl)methyl)acrylamide |

TABLE 1-continued

| Structures of example compounds of the disclosure and their respective codes | | |
|---|---|---|
| Cpd. No. | Structure | Name |
| 143 | 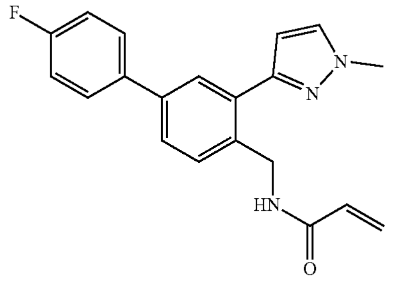 [SMILES: C=CC(=O)NCc1ccc(-c2ccc(F)cc2)cc1-c1ccn(C)n1] | N-((4'-fluoro-3-(1-methyl-1H-pyrazol-3-yl)-[1,1'-biphenyl]-4-yl)methyl)acrylamide |
| 144 | 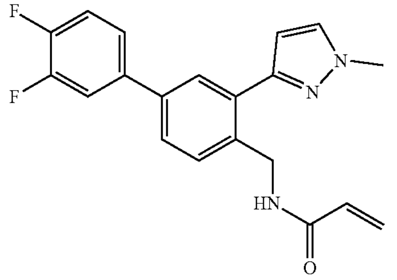 [SMILES: C=CC(=O)NCc1ccc(-c2ccc(F)c(F)c2)cc1-c1ccn(C)n1] | N-((3',4'-difluoro-3-(1-methyl-1H-pyrazol-3-yl)-[1,1'-biphenyl]-4-yl)methyl)acrylamide |
| 145 | 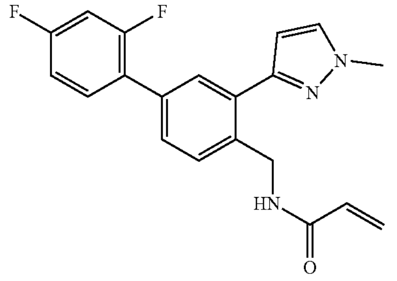 [SMILES: C=CC(=O)NCc1ccc(-c2ccc(F)cc2F)cc1-c1ccn(C)n1] | N-((2',4'-difluoro-3-(1-methyl-1H-pyrazol-3-yl)-[1,1'-biphenyl]-4-yl)methyl)acrylamide |
| 146 | 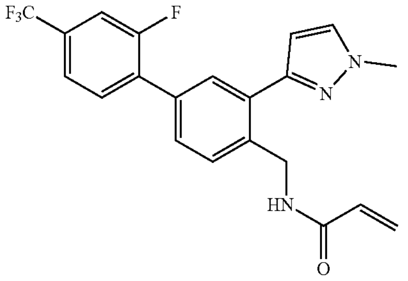 [SMILES: C=CC(=O)NCc1ccc(-c2ccc(C(F)(F)F)cc2F)cc1-c1ccn(C)n1] | N-((2'-fluoro-3-(1-methyl-1H-pyrazol-3-yl)-4'-(trifluoromethyl)-[1,1'-biphenyl]-4-yl)methyl)acrylamide |
| 147 | 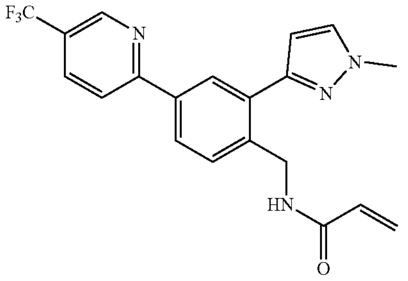 | N-(2-(1-methyl-1H-pyrazol-3-yl)-4-(5-(trifluoromethyl)pyridin-2-yl)benzyl)acrylamide |

TABLE 1-continued

Structures of example compounds of the disclosure and their respective codes

| Cpd. No. | Structure | Name |
|---|---|---|
| 148 | 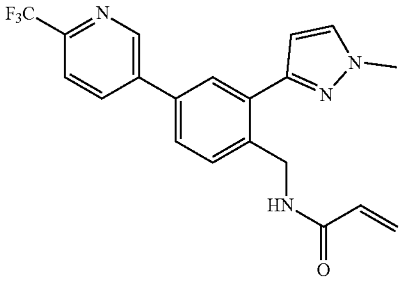 | N-(2-(1-methyl-1H-pyrazol-3-yl)-4-(6-(trifluoromethyl)pyridin-3-yl)benzyl)acrylamide |
| 149 | 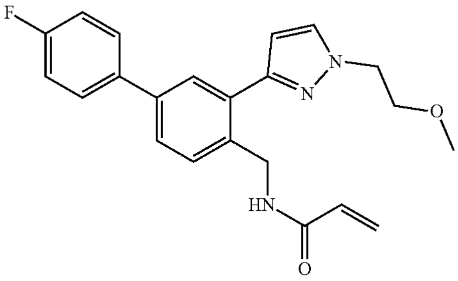 [SMILES: C=CC(=O)NCc1ccc(-c2ccc(F)cc2)cc1-c1ccn(CCOC)n1] | N-((4'-fluoro-3-(1-(2-methoxyethyl)-1H-pyrazol-3-yl)-[1,1'-biphenyl]-4-yl)methyl)acrylamide |
| 150 | 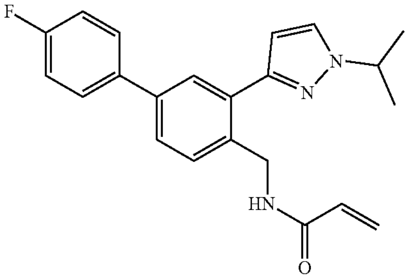 [SMILES: C=CC(=O)NCc1ccc(-c2ccc(F)cc2)cc1-c1ccn(C(C)C)n1] | N-((4'-fluoro-3-(1-isopropyl-1H-pyrazol-3-yl)-[1,1'-biphenyl]-4-yl)methyl)acrylamide |
| 151 | 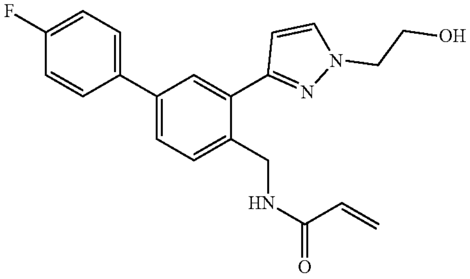 [SMILES: C=CC(=O)NCc1ccc(-c2ccc(F)cc2)cc1-c1ccn(CCO)n1] | N-((5-(4-fluorophenyl)-3-(1-(2-hydroxyethyl)-1H-pyrazol-3-yl)pyridin-2-yl)methyl)acrylamide |
| 152 | 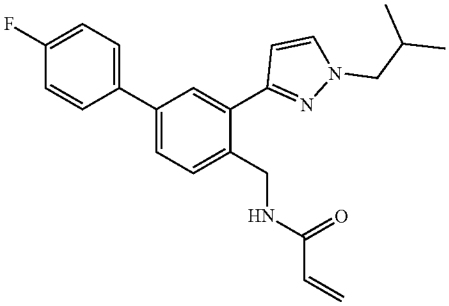 [SMILES: C=CC(=O)NCc1ccc(-c2ccc(F)cc2)cc1-c1ccn(CC(C)C)n1] | N-((4'-fluoro-3-(1-isobutyl-1H-pyrazol-3-yl)-[1,1'-biphenyl]-4-yl)methyl)acrylamide |

TABLE 1-continued

Structures of example compounds of the disclosure and their respective codes

| Cpd. No. | Structure | Name |
|---|---|---|
| 153 | 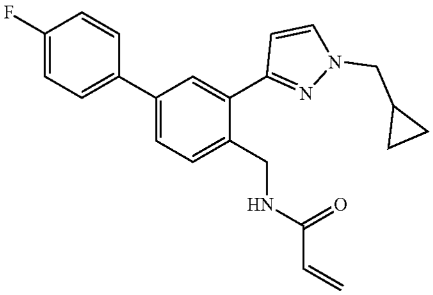 [SMILES: C=CC(=O)NCc1ccc(-c2ccc(F)cc2)cc1-c1ccn(CC2CC2)n1] | N-((3-(1-(cyclopropylmethyl)-1H-pyrazol-3-yl)-4'-fluoro-[1,1'-biphenyl]-4-yl)methyl)acrylamide |
| 154 | 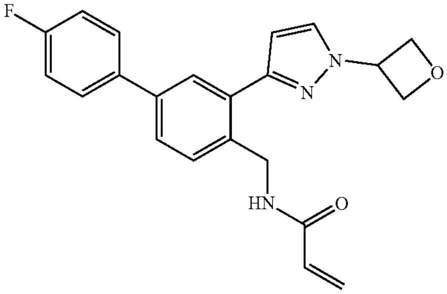 [SMILES: C=CC(=O)NCc1ccc(-c2ccc(F)cc2)cc1-c1ccn(C2COC2)n1] | N-((4'-fluoro-3-(1-(oxetan-3-yl)-1H-pyrazol-3-yl)-[1,1'-biphenyl]-4-yl)methyl)acrylamide |
| 155 | 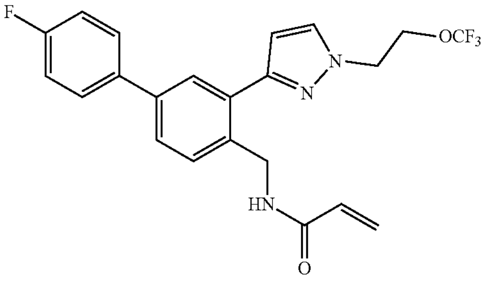 [SMILES: C=CC(=O)NCc1ccc(-c2ccc(F)cc2)cc1-c1ccn(CCOC(F)(F)F)n1] | N-((4'-fluoro-3-(1-(2-(trifluoromethoxy)ethyl)-1H-pyrazol-3-yl)-[1,1'-biphenyl]-4-yl)methyl)acrylamide |
| 156 | 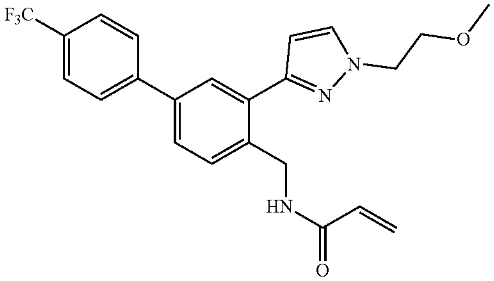 [SMILES: C=CC(=O)NCc1ccc(-c2ccc(C(F)(F)F)cc2)cc1-c1ccn(CCOC)n1] | N-((3-(1-(2-methoxyethyl)-1H-pyrazol-3-yl)-4'-(trifluoromethyl)-[1,1'-biphenyl]-4-yl)methyl)acrylamide |
| 157 | 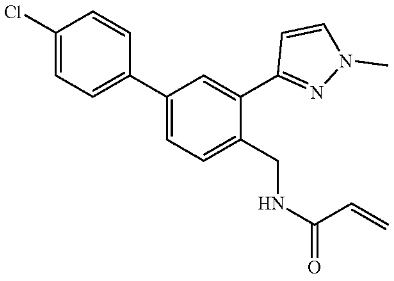 [SMILES: C=CC(=O)NCc1ccc(-c2ccc(Cl)cc2)cc1-c1ccn(C)n1] | N-((4'-chloro-3-(1-methyl-1H-pyrazol-3-yl)-[1,1'-biphenyl]-4-yl)methyl)acrylamide |

TABLE 1-continued

Structures of example compounds of the disclosure and their respective codes

| Cpd. No. | Structure | Name |
|---|---|---|
| 158 | 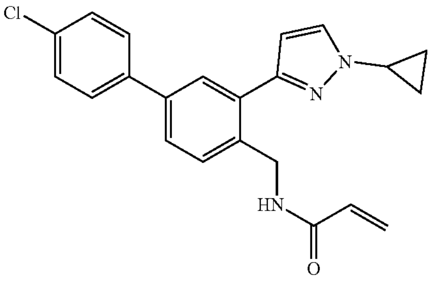 [SMILES: C=CC(=O)NCc1ccc(-c2ccc(Cl)cc2)cc1-c1ccn(C2CC2)n1] | N-((4'-chloro-3-(1-cyclopropyl-1H-pyrazol-3-yl)-[1,1'-biphenyl]-4-yl)methyl)acrylamide |
| 159 | 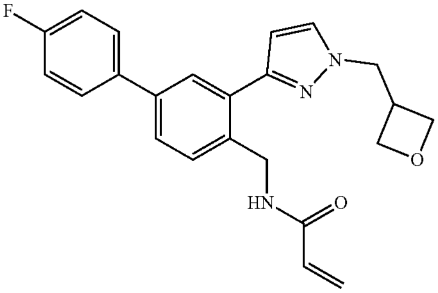 [SMILES: C=CC(=O)NCc1ccc(-c2ccc(F)cc2)cc1-c1ccn(CC2COC2)n1] | N-((4'-fluoro-3-(1-(oxetan-3-ylmethyl)-1H-pyrazol-3-yl)-[1,1'-biphenyl]-4-yl)methyl)acrylamide |
| 160 | 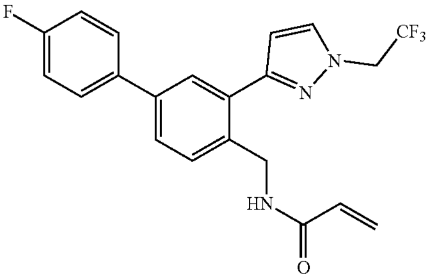 [SMILES: C=CC(=O)NCc1ccc(-c2ccc(F)cc2)cc1-c1ccn(CC(F)(F)F)n1] | N-((4'-fluoro-3-(1-(2,2,2-trifluoroethyl)-1H-pyrazol-3-yl)-[1,1'-biphenyl]-4-yl)methyl)acrylamide |
| 161 | 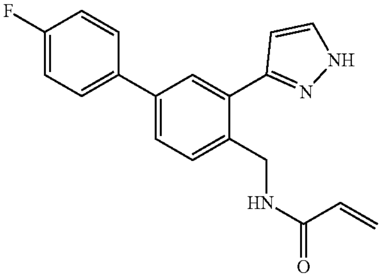 [SMILES: C=CC(=O)NCc1ccc(-c2ccc(F)cc2)cc1-c1cc[nH]n1] | N-((4'-fluoro-3-(1H-pyrazol-3-yl)-[1,1'-biphenyl]-4-yl)methyl)acrylamide |
| 162 | 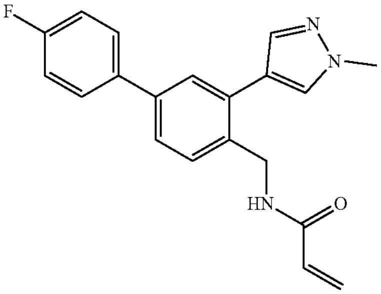 [SMILES: C=CC(=O)NCc1ccc(-c2ccc(F)cc2)cc1-c1cnn(C)c1] | N-((4'-fluoro-3-(1-methyl-1H-pyrazol-4-yl)-[1,1'-biphenyl]-4-yl)methyl)acrylamide |

TABLE 1-continued

| Structures of example compounds of the disclosure and their respective codes | | |
|---|---|---|
| Cpd. No. | Structure | Name |
| 163 | 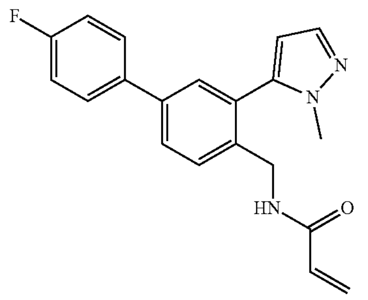 [SMILES: C=CC(=O)NCc1ccc(-c2ccc(F)cc2)cc1-c1ccnn1C] | N-((4'-fluoro-3-(1-methyl-1H-pyrazol-5-yl)-[1,1'-biphenyl]-4-yl)methyl)acrylamide |
| 164 | 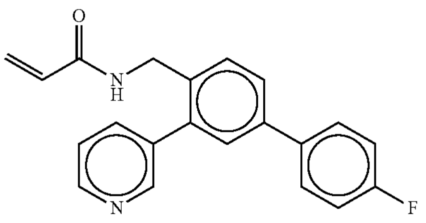 | N-((4'-fluoro-3-(pyridin-3-yl)-[1,1'-biphenyl]-4-yl)methyl)acrylamide |
| 165 | 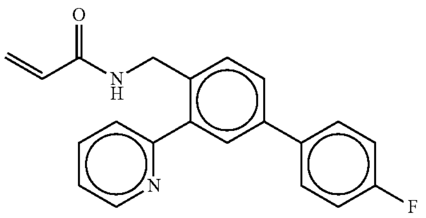 | N-((4'-fluoro-3-(pyridin-2-yl)-[1,1'-biphenyl]-4-yl)methyl)acrylamide |
| 166 | 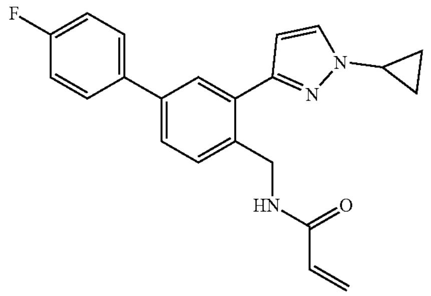 [SMILES: C=CC(=O)NCc1ccc(-c2ccc(F)cc2)cc1-c1ccn(C2CC2)n1] | N-((3-(1-cyclopropyl-1H-pyrazol-3-yl)-4'-fluoro-[1,1'-biphenyl]-4-yl)methyl)acrylamide |
| 167 | 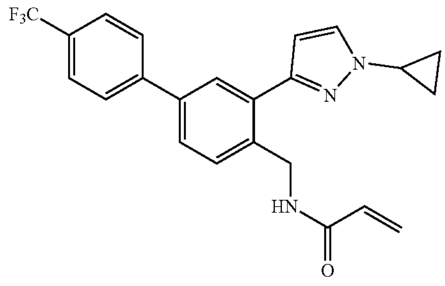 [SMILES: C=CC(=O)NCc1ccc(-c2ccc(C(F)(F)F)cc2)cc1-c1ccn(C2CC2)n1] | N-((3-(1-cyclopropyl-1H-pyrazol-3-yl)-4'-(trifluoromethyl)-[1,1'-biphenyl]-4-yl)methyl)acrylamide |

TABLE 1-continued

| Cpd. No. | Structure | Name |
| --- | --- | --- |
| 168 | 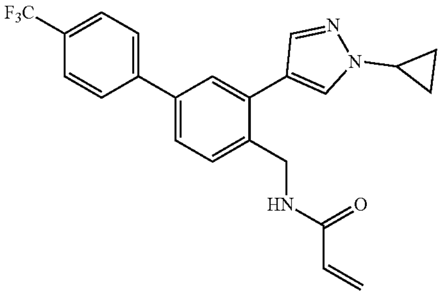 [SMILES: C=CC(=O)NCc1ccc(-c2ccc(C(F)(F)F)cc2)cc1-c1cnn(C2CC2)c1] | N-((3-(1-cyclopropyl-1H-pyrazol-4-yl)-4'-(trifluoromethyl)-[1,1'-biphenyl]-4-yl)methyl)acrylamide |
| 169 | 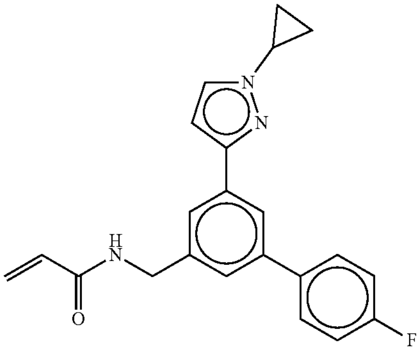 | N-((5-(1-cyclopropyl-1H-pyrazol-3-yl)-4'-fluoro[1,1'-biphenyl]-3-yl)methyl)acrylamide |
| 170 | 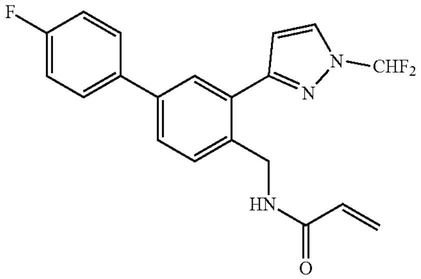 [SMILES: C=CC(=O)NCc1ccc(-c2ccc(F)cc2)cc1-c1ccn(C(F)F)n1] | N-((3-(1-(difluoromethyl)-1H-pyrazol-3-yl)-4'-fluoro-[1,1'-biphenyl]-4-yl)methyl)acrylamide |
| 171 | 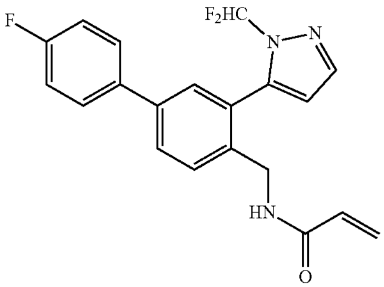 [SMILES: C=CC(=O)NCc1ccc(-c2ccc(F)cc2)cc1-c1ccnn1C(F)F] | N-((3-(1-(difluoromethyl)-1H-pyrazol-5-yl)-4'-fluoro-[1,1'-biphenyl]-4-yl)methyl0)acrylamide |
| 172 | 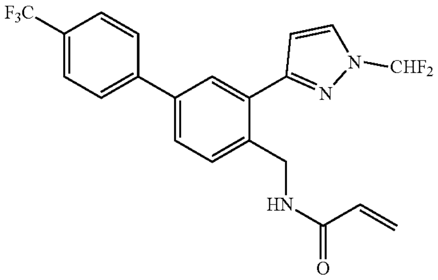 [SMILES: C=CC(=O)NCc1ccc(-c2ccc(C(F)(F)F)cc2)cc1-c1ccn(C(F)F)n1] | N-((3-(1-(difluoromethyl)-1H-pyrazol-3-yl)-4'-(trifluoromethyl)-[1,1'-biphenyl]-4-yl)methyl)acrylamide |

Structures of example compounds of the disclosure and their respective codes

TABLE 1-continued

| Structures of example compounds of the disclosure and their respective codes | | |
|---|---|---|
| Cpd. No. | Structure | Name |
| 173 | 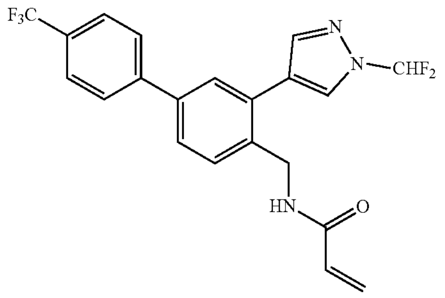 [SMILES: C=CC(=O)NCc1ccc(-c2ccc(C(F)(F)F)cc2)cc1-c1cnn(C(F)F)c1] | N-((3-(1-(difluoromethyl)-1H-pyrazol-4-yl)-4'-(trifluoromethyl)-[1,1'-biphenyl]-4-yl)methyl)acrylamide |
| 174 | 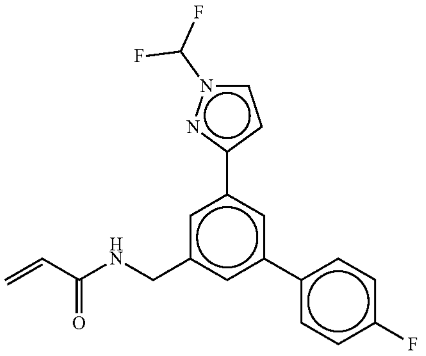 | N-((5-(1-(difluoromethyl)-1H-pyrazol-3-yl)-4'-fluoro-[1,1'-biphenyl]-3-yl)methyl)acrylamide |
| 175 | 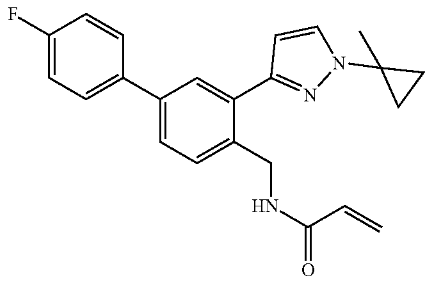 [SMILES: C=CC(=O)NCc1ccc(-c2ccc(F)cc2)cc1-c1ccn(C2(C)CC2)n1] | N-((4'-fluoro-3-(1-(1-methylcyclopropyl)-1H-pyrazol-3-yl)-[1,1'-biphenyl]-4-yl)methyl)acrylamide |
| 176 | 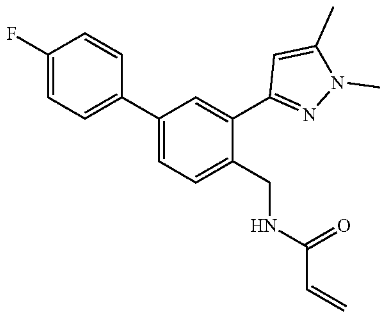 [SMILES: C=CC(=O)NCc1ccc(-c2ccc(F)cc2)cc1-c1cc(C)n(C)n1] | N-((3-(1,5-dimethyl-1H-pyrazol-3-yl)-4'-fluoro-[1,1'-biphenyl]-4-yl)methyl)acrylamide |

TABLE 1-continued

Structures of example compounds of the disclosure and their respective codes

| Cpd. No. | Structure | Name |
|---|---|---|
| 177 | 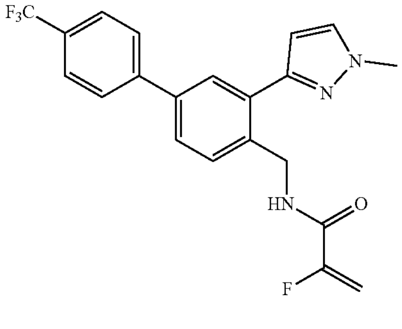 [SMILES: C=C(F)C(=O)NCc1ccc(-c2ccc(C(F)(F)F)cc2)cc1-c1ccn(C)n1] | 2-fluoro-N-((3-(1-methyl-1H-pyrazol-3-yl)-4'-(trifluoromethyl)-[1,1'-biphenyl]-4-yl)methyl)acrylamide |
| 178 | 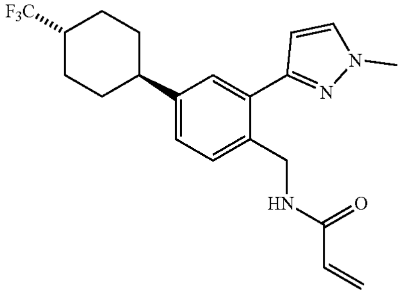 [SMILES: C=CC(=O)NCc1ccc([C@H]2CC[C@H](C(F)(F)F)CC2)cc1-c1ccn(C)n1] | trans-N-(2-(1-methyl-1H-pyrazol-3-yl)-4-(4-(trifluoromethyl)cyclohexyl)benzyl) acrylamide |
| 179 | 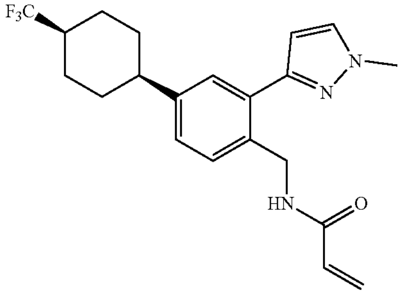 [SMILES: C=CC(=O)NCc1ccc([C@H]2CC[C@@H](C(F)(F)F)CC2)cc1-c1ccn(C)n1] | cis-N-(2-(1-methyl-1H-pyrazol-3-yl)-4-(4-(trifluoromethyl)cyclohexyl)benzyl) acrylamide |
| 180 | 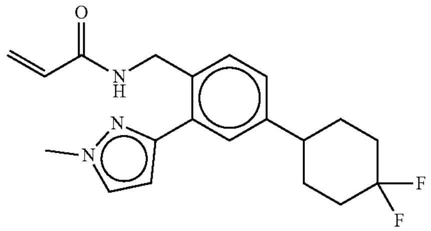 | N-(4-(4,4-difluorocyclohexyl)-2-(1-methyl-1H-pyrazol-3-yl)benzyl)acrylamide |
| 181 | 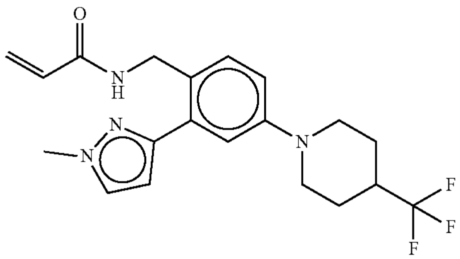 | N-(2-(1-methyl-1H-pyrazol-3-yl)-4-(4-(trifluoromethyl)piperidin-1-yl)benzyl)acrylamide |

TABLE 1-continued

| Cpd. No. | Structure | Name |
|---|---|---|
| 182 | 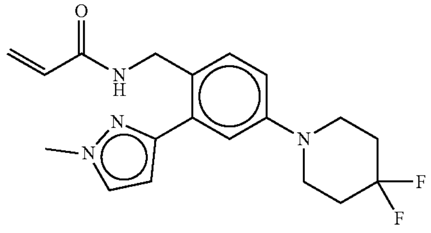 | N-(4-(4,4-difluoropiperidin-1-yl)-2-(1-methyl-1H-pyrazol-3-yl)benzyl)acrylamide |
| 183 | 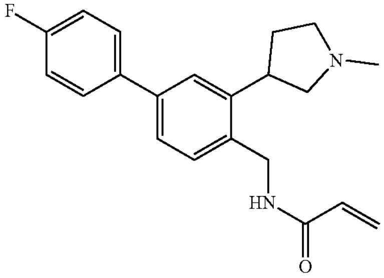 [SMILES: C=CC(=O)NCc1ccc(-c2ccc(F)cc2)cc1C1CCN(C)C1] | N-((4'-fluoro-3-(1-methylpyrrolidin-3-yl)-[1,1'-biphenyl]-4-yl)methyl)acrylamide |
| 184 | 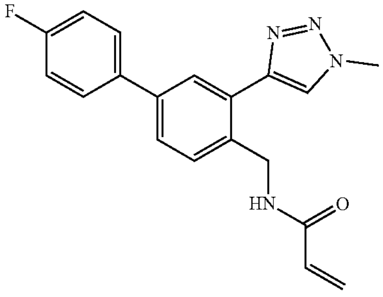 [SMILES: C=CC(=O)NCc1ccc(-c2ccc(F)cc2)cc1-c1cn(C)nn1] | N-((4'-fluoro-3-(1-methyl-1H-1,2,3-triazol-4-yl)-[1,1'-biphenyl]-4-yl)methyl)acrylamide |
| 185 | 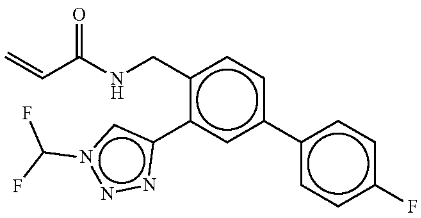 | N-((3-(1-(difluoromethyl)-1H-1,2,3-triazol-4-yl)-4'-fluoro-[1,1'-biphenyl]-4-yl)methyl)acrylamide |
| 186 | 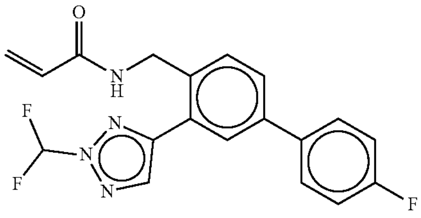 | N-((3-(2-(difluoromethyl)-2H-1,2,3-triazol-4-yl)-4'-fluoro-[1,1'-biphenyl]-4-yl)methyl)acrylamide |
| 187 | 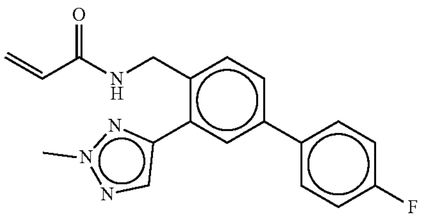 | N-((4'-fluoro-3-(2-methyl-2H-1,2,3-triazol-4-yl)-[1,1'-biphenyl]-4-yl)methyl)acrylamide |

Structures of example compounds of the disclosure and their respective codes

TABLE 1-continued

Structures of example compounds of the disclosure and their respective codes

| Cpd. No. | Structure | Name |
| --- | --- | --- |
| 188 | 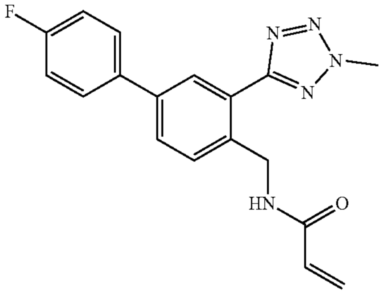 [SMILES: C=CC(=O)NCc1ccc(-c2ccc(F)cc2)cc1-c1nnn(C)n1] | N-((4'-fluoro-3-(2-methyl-2H-tetrazol-5-yl)[1,1'-biphenyl]-4-yl)methyl)acrylamide |
| 189 | 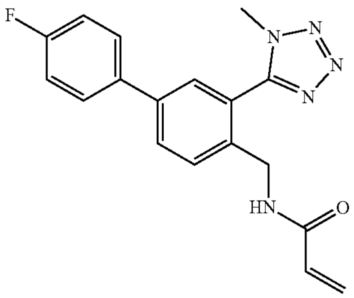 [SMILES: C=CC(=O)NCc1ccc(-c2ccc(F)cc2)cc1-c1nnnn1C] | N-((4'-fluoro-3-(1-methyl-1H-tetrazol-5-yl)-[1,1'-biphenyl]-4-yl)methyl)acrylamide |
| 190 | 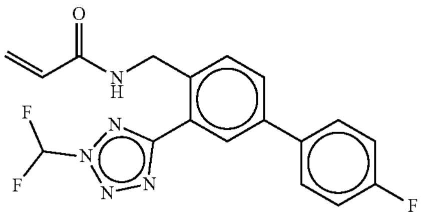 | N-((3-(2-(difluoromethyl)-2H-tetrazol-5-yl)-4'-fluoro-[1,1'-biphenyl]-4-yl)methyl)acrylamide |
| 191 | 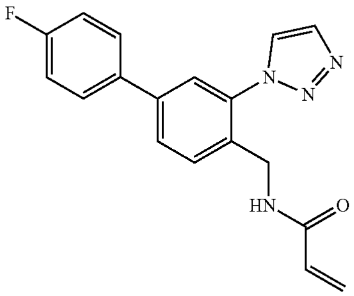 [SMILES: C=CC(=O)NCc1ccc(-c2ccc(F)cc2)cc1-n1ccnn1] | N-((4'-fluoro-3-(1H-1,2,3-triazol-1-yl)-[1,1'-biphenyl]-4-yl)methyl)acrylamide |
| 192 | 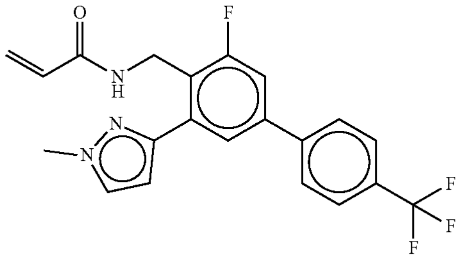 | N-((3-fluoro-5-(1-methyl-1H-pyrazol-3-yl)-4'-(trifluoromethyl)-[1,1'-biphenyl]-4-yl)methyl)acrylamide |

TABLE 1-continued

| Cpd. No. | Structure | Name |
|---|---|---|
| Structures of example compounds of the disclosure and their respective codes | | |
| 193 | 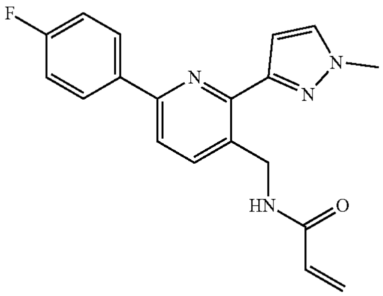 [SMILES: C=CC(=O)NCc1ccc(-c2ccc(F)cc2)nc1-c1ccn(C)n1] | N-((6-(4-fluorophenyl)-2-(1-methyl-1H-pyrazol-3-yl)pyridin-3-yl)methyl)acrylamide |
| 194 | 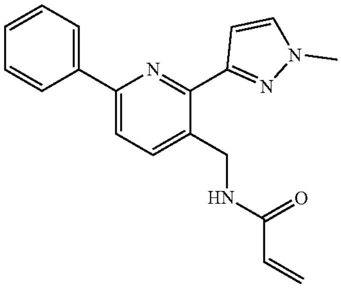 [SMILES: C=CC(=O)NCc1ccc(-c2ccccc2)nc1-c1ccn(C)n1] | N-((2-(1-methyl-1H-pyrazol-3-yl)-6-phenylpyridin-3-yl)methyl)acrylamide |
| 195 | 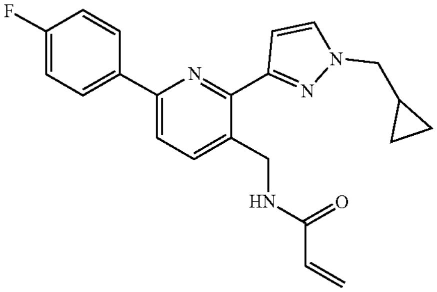 [SMILES: C=CC(=O)NCc1ccc(-c2ccc(F)cc2)nc1-c1ccn(CC2CC2)n1] | N-((2-(1-(cyclopropylmethyl)-1H-pyrazol-3-yl)-6-(4-fluorophenyl)pyridin-3-yl)methyl)acrylamide |
| 196 | 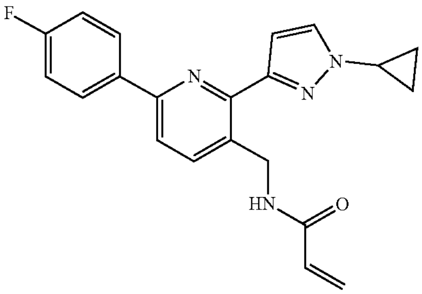 [SMILES: C=CC(=O)NCc1ccc(-c2ccc(F)cc2)nc1-c1ccn(C2CC2)n1] | N-((2-(1-cyclopropyl-1H-pyrazol-3-yl)-6-(4-fluorophenyl)pyridin-3-yl)methyl)acrylamide |
| 197 | 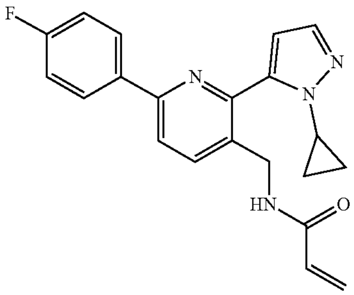 [SMILES: C=CC(=O)NCc1ccc(-c2ccc(F)cc2)nc1-c1ccnn1C1CC1] | N-((2-(1-cyclopropyl-1H-pyrazol-5-yl)-6-(4-fluorophenyl)pyridin-3-yl)methyl)acrylamide |

TABLE 1-continued

Structures of example compounds of the disclosure and their respective codes

| Cpd. No. | Structure | Name |
|---|---|---|
| 198 | 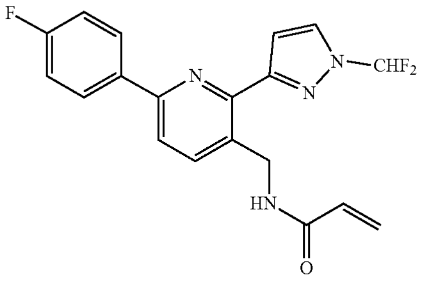 [SMILES: C=CC(=O)NCc1ccc(-c2ccc(F)cc2)nc1-c1ccn(C(F)F)n1] | N-((2-(1-(difluoromethyl)-1H-pyrazol-3-yl)-6-(4-fluorophenyl)pyridin-3-yl)methyl)acrylamide |
| 199 | 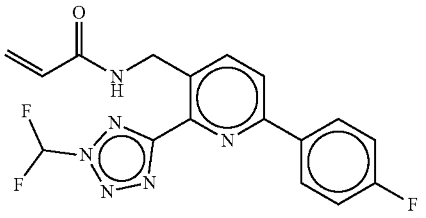 | N-((2-(2-(difluoromethyl)-2H-tetrazol-5-yl)-6-(4-fluorophenyl)pyridin-3-yl)methyl)acrylamide |
| 200 | 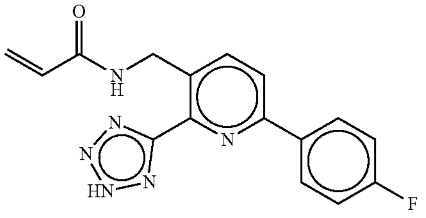 | N-((6-(4-fluorophenyl)-2-(2H-tetrazol-5-yl)pyridin-3-yl)methyl)acrylamide |
| 201 | 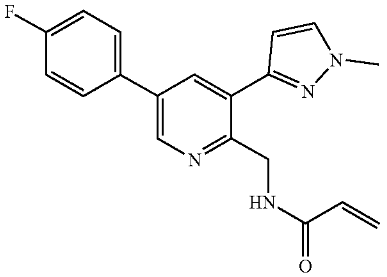 [SMILES: C=CC(=O)NCc1ncc(-c2ccc(F)cc2)cc1-c1ccn(C)n1] | N-((5-(4-fluorophenyl)-3-(1-methyl-1H-pyrazol-3-yl)pyridin-2-yl)methyl)acrylamide |
| 202 | 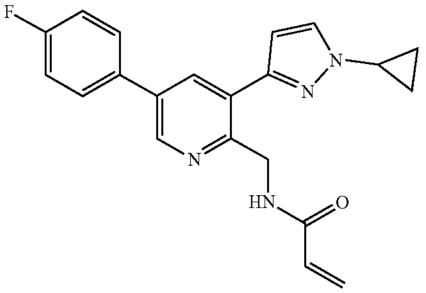 [SMILES: C=CC(=O)NCc1ncc(-c2ccc(F)cc2)cc1-c1ccn(C2CC2)n1] | N-((3-(1-cyclopropyl-1H-pyrazol-3-yl)-5-(4-fluorophenyl)pyridin-2-yl)mehtyl)acrylamide |

TABLE 1-continued

| Structures of example compounds of the disclosure and their respective codes | | |
|---|---|---|
| Cpd. No. | Structure | Name |
| 203 | 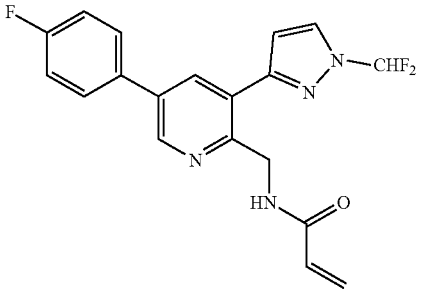 [SMILES: C=CC(=O)NCc1ncc(-c2ccc(F)cc2)cc1-c1ccn(C(F)F)n1] | N-((3-(1-(difluoromethyl)-1H-pyrazol-3-yl)-5-(4-fluorophenyl)pyridin-2-yl)methyl)acrylamide |
| 204 | 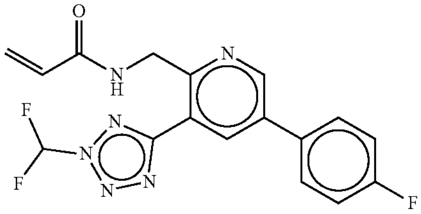 | N-((3-(2-(difluoromethyl)-2H-tetrazol-5-yl)-5-(4-fluorophenyl)pyridin-2-yl)methyl)acrylamide |
| 205 | 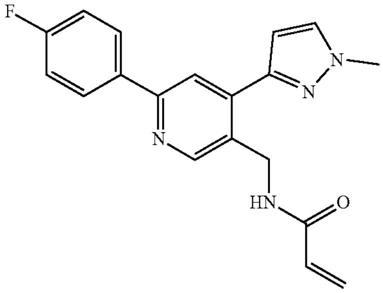 [SMILES: C=CC(=O)NCc1cnc(-c2ccc(F)cc2)cc1-c1ccn(C)n1] | N-((6-(4-fluorophenyl)-4-(1-methyl-1H-pyrazol-3-yl)pyridin-3-yl)methyl)acrylamide |
| 206 | 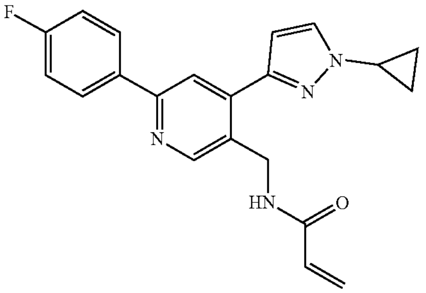 [SMILES: C=CC(=O)NCc1cnc(-c2ccc(F)cc2)cc1-c1ccn(C2CC2)n1] | N-((4-(1-cyclopropyl-1H-pyrazol-3-yl)-6-(4-fluorophenyl)pyridin-3-yl)methyl)acrylamide |
| 207 | 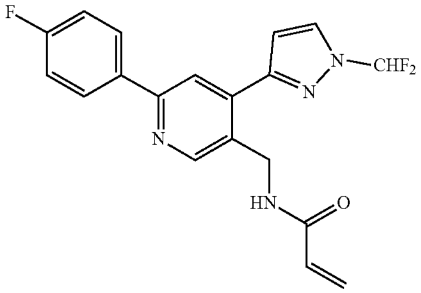 [SMILES: C=CC(=O)NCc1cnc(-c2ccc(F)cc2)cc1-c1ccn(C(F)F)n1] | N-((4-(1-(difluoromethyl)-1H-pyrazol-3-yl)-6-(4-fluorophenyl)pyridin-3-yl)methyl)acrylamide |

TABLE 1-continued

| Cpd. No. | Structure | Name |
|---|---|---|
| | Structures of example compounds of the disclosure and their respective codes | |
| 208 | 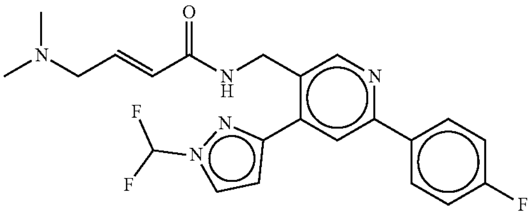 | (E)-N-((4-(1-(difluoromethyl)-1H-pyrazol-3-yl)-6-(4-fluorophenyl)pyridin-3-yl)methyl)-4-(dimethylamino)but-2-enamide |
| 209 | 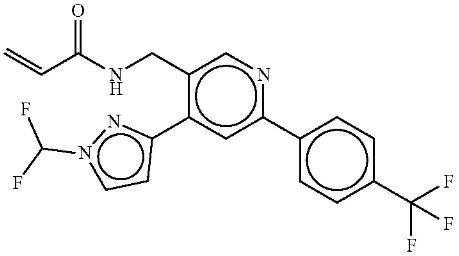 | N-((4-(1-(difluoromethyl)-1H-pyrazol-3-yl)-6-(4-(trifluoromethyl)phenyl)pyridin-3-yl)methyl)acrylamide |
| 210 | 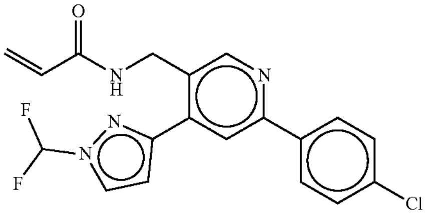 | N-((6-(4-chlorophenyl)-4-(1-(difluoromethyl)-1H-pyrazol-3-yl)pyridin-3-yl)methyl)acrylamide |
| 211 | 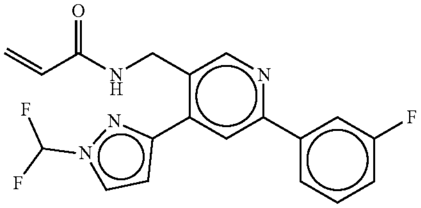 | N-((4-(1-(difluoromethyl)-1H-pyrazol-3-yl)-6-(3-fluorophenyl)pyridin-3-yl)methyl)acrylamide |
| 212 | 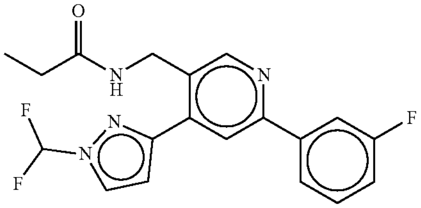 | N-((4-(1-(difluoromethyl)-1H-pyrazol-3-yl)-6-(3-fluorophenyl)pyridin-3-yl)methyl)propionamide |
| 213 | 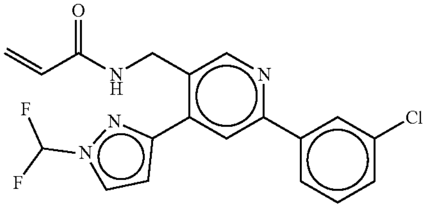 | N-((6-(3-chlorophenyl)-4-(1-(difluoromethyl)-1H-pyrazol-3-yl)pyridin-3-yl)methyl)acrylamide |

TABLE 1-continued

Structures of example compounds of the disclosure and their respective codes

| Cpd. No. | Structure | Name |
| --- | --- | --- |
| 214 | 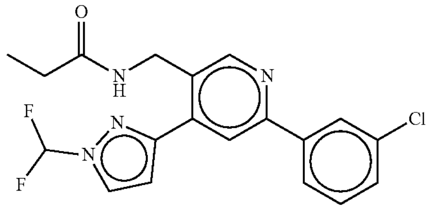 | N-((6-(3-chlorophenyl)-4-(1-(difluoromethyl)-1H-pyrazol-3-yl)pyridin-3-yl)methyl)propionamide |
| 215 | 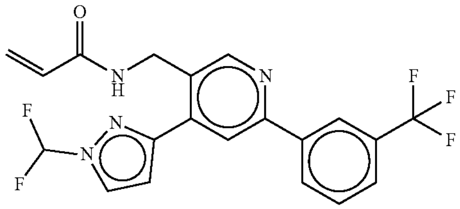 | N-((4-(1-(difluoromethyl)-1H-pyrazol-3-yl)-6-(3-(trifluoromethyl)phenyl)pyridin-3-yl)methyl)acrylamide |
| 216 | 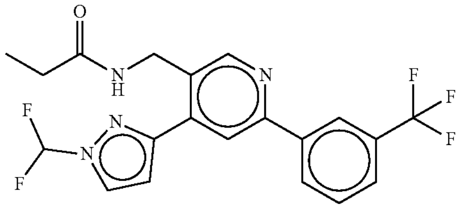 | N-((4-(1-(difluoromethyl)-1H-pyrazol-3-yl)-6-(3-(trifluoromethyl)phenyl)pyridin-3-yl)methyl)propionamide |
| 217 | 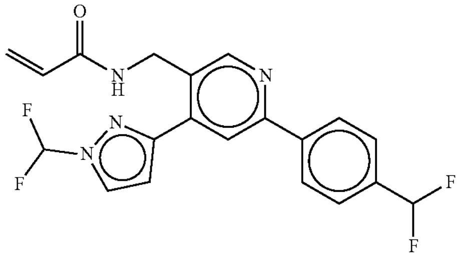 | N-((4-(1-(difluoromethyl)-1H-pyrazol-3-yl)-6-(4-(difluoromethyl)phenyl)pyridin-3-yl)methyl)acrylamide |
| 218 | 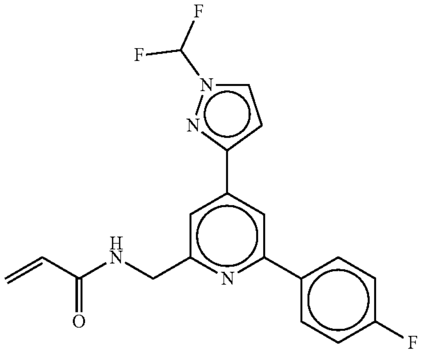 | N-((4-(1-(difluoromethyl)-1H-pyrazol-3-yl)-6-(4-fluorophenyl)pyridin-2-yl)methyl)acrylamide |
| 219 | 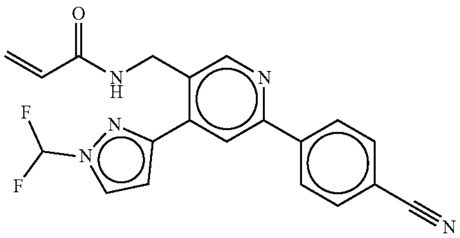 | N-((6-(4-cyanophenyl)-4-(1-(difluoromethyl)-1H-pyrazol-3-yl)pyridin-3-yl)methyl)acrylamide |

TABLE 1-continued

| Cpd. No. | Structure | Name |
|---|---|---|
| | Structures of example compounds of the disclosure and their respective codes | |
| 220 | 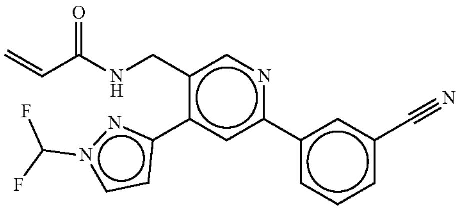 | N-((6-(3-cyanophenyl)-4-(1-(difluoromethyl)-1H-pyrazol-3-yl)pyridin-3-yl)methyl)acrylamide |
| 221 | 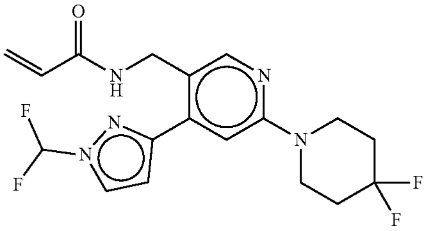 | N-((4-(1-(difluoromethyl)-1H-pyrazol-3-yl)-6-(4,4-difluoropiperidin-1-yl)pyridin-3-yl)methyl)acrylamide |
| 222 | 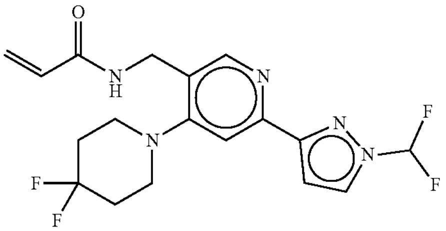 | N-((6-(1-(difluoromethyl)-1H-pyrazol-3-yl)-4-(4,4-difluoropiperidin-1-yl)pyridin-3-yl)methyl)acrylamide |
| 223 | 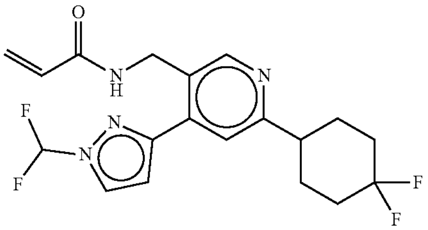 | N-((6-(4,4-difluorocyclohexyl)-4-(1-(difluoromethyl)-1H-pyrazol-3-yl)pyridin-3-yl)methyl)acrylamide |
| 224 | 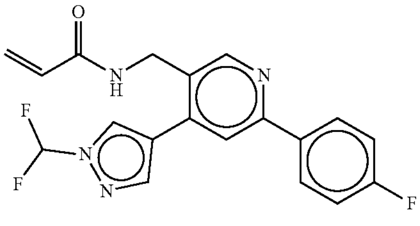 | N-((4-(1-(difluoromethyl)-1H-pyrazol-4-yl)-6-(4-fluorophenyl)pyridin-3-yl)methyl)acrylamide |
| 225 | 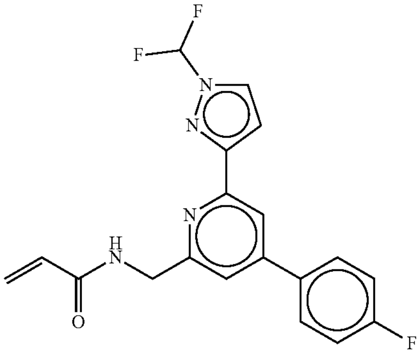 | N-((6-(1-(difluoromethyl)-1H-pyrazol-3-yl)-4-(4-fluorophenyl)pyridin-2-yl)methyl)acrylamide |

TABLE 1-continued

| Cpd. No. | Structure | Name |
|---|---|---|
| 226 | 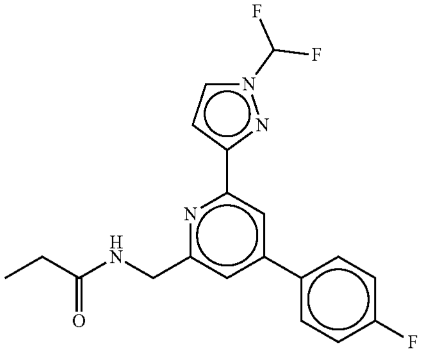 | N-((6-(1-(difluoromethyl)-1H-pyrazol-3-yl)-4-(4-fluorophenyl)pyridin-2-yl)methyl)propionamide |
| 227 | 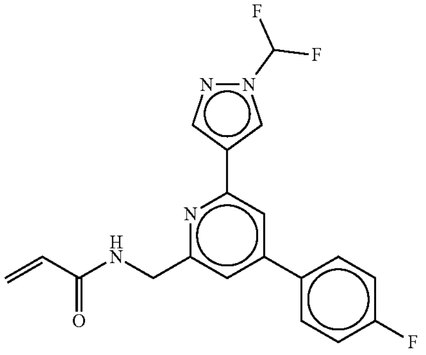 | N-((6-(1-(difluoromethyl)-1H-pyrazol-4-yl)-4-(4-fluorophenyl)pyridin-2-yl)methyl)acrylamide |
| 228 | 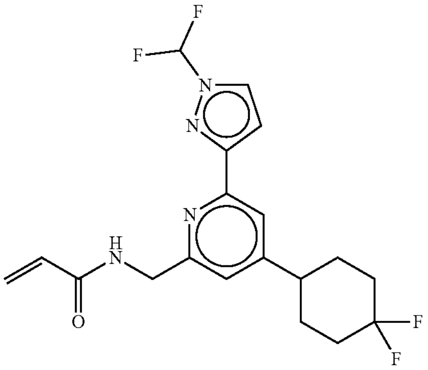 | N-((4-(4,4-difluorocyclohexyl)-6-(1-(difluoromethyl)-1H-pyrazol-3-yl)pyridin-2-yl)methyl)acrylamide |
| 229 | 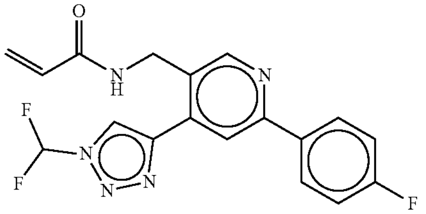 | N-((4-(1-(difluoromethyl)-1H-1,2,3-triazol-4-yl)-6-(4-fluorophenyl)pyridin-3-yl)methyl)acrylamide |
| 230 | 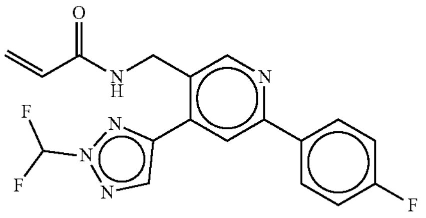 | N-((4-(2-(difluoromethyl)-2H-1,2,3-triazol-4-yl)-6-(4-fluorophenyl)pyridin-3-yl)methyl)acrylamide |

Structures of example compounds of the disclosure and their respective codes

TABLE 1-continued

| Structures of example compound of the disclosure and their respective codes | | |
|---|---|---|
| Cpd. No. | Structure | Name |
| 231 | 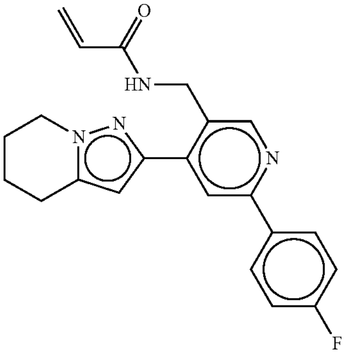 | N-((6-(4-fluorophenyl)-4-(4,5,6,7-tetrahydropyrazolo[1,5-a]pyridin-2-yl)pyridin-3-yl)methyl)acrylamide |
| 232 | 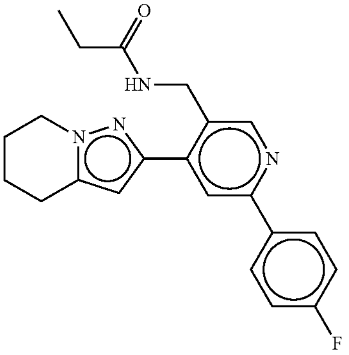 | N-((6-(4-fluorophenyl)-4-(4,5,6,7-tetrahydropyrazolo[1,5-a]pyridin-2-yl)pyridin-3-yl)methyl)propionamide |
| 233 | 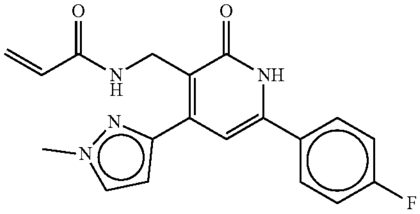 | N-((6-(4-fluorophenyl)-4-(1-methyl-1H-pyrazol-3-yl)-2-oxo-1,2-dihydropyridin-3-yl)methyl)acrylamide |
| 234 | 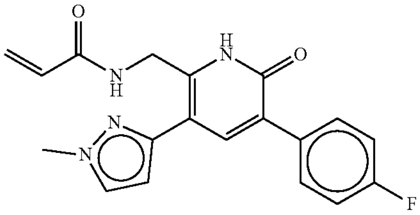 | N-((5-(4-fluorophenyl)-3-(1-methyl-1H-pyrazol-3-yl)-6-oxo-1,6-dihydropyridin-2-yl)methyl)acrylamide |
| 235 | 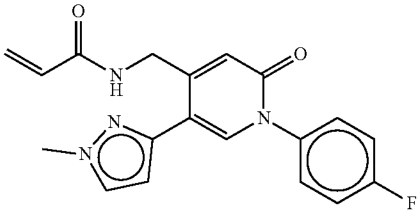 | N-((1-(4-fluorophenyl)-5-(1-methyl-1H-pyrazol-3-yl)-2-oxo-1,2-dihydropyridin-4-yl)methyl)acrylamide |

TABLE 1-continued

| Structures of example compounds of the disclosure and their respective codes | | |
|---|---|---|
| Cpd. No. | Structure | Name |
| 236 | 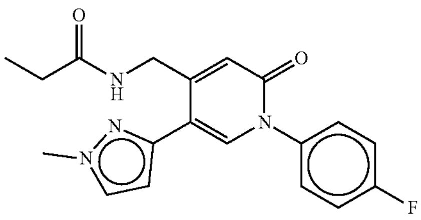 | N-((1-(4-fluorophenyl)-5-(1-methyl-1H-pyrazol-3-yl)-2-oxo-1,2-dihydropyridin-4-yl)methyl)propionamide |
| 237 | 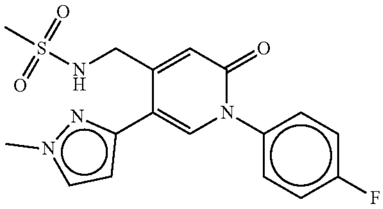 | N-((1-(4-fluorophenyl)-5-(1-methyl-1H-pyrazol-3-yl)-2-oxo-1,2-dihydropyridin-4-yl)methyl)methanesulfonamide |
| 238 | 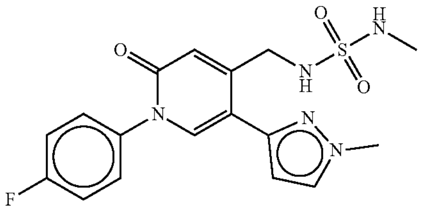 | N-methyl, N'-((1-(4-fluorophenyl)-5-(1-methyl-1H-pyrazol-3-yl)-2-oxo-1,2-dihydropyridin-4-yl)methyl)sulfamide |
| 239 | 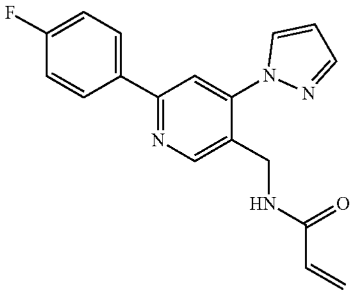 [SMILES: C=CC(=O)NCc1cnc(-c2ccc(F)cc2)cc1-n1cccn1] | N-((6-(4-fluorophenyl)-4-(1H-pyrazol-1-yl)pyridin-3-yl)methyl)acrylamide |
| 240 | 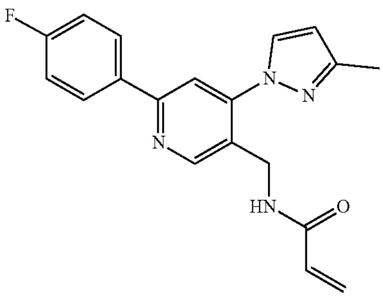 [SMILES: C=CC(=O)NCc1cnc(-c2ccc(F)cc2)cc1-n1ccc(C)n1] | N-((6-(4-fluorophenyl)-4-(3-methyl-1H-pyrazol-1-yl)pyridin-3-yl)methyl)acrylamide |
| 241 | 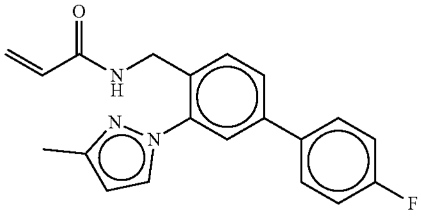 | N-((4'-fluoro-3-(3-methyl-1H-pyrazol-1-yl)-[1,1'-biphenyl]-4-yl)methyl)acrylamide |

TABLE 1-continued

| Cpd. No. | Structure | Name |
|---|---|---|
| | Structures of example compounds of the disclosure and their respective codes | |
| 242 | 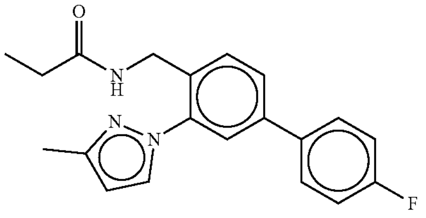 | N-((4'-fluoro-3-(3-methyl-1H-pyrazol-1-yl)-[1,1'-biphenyl]-4-yl)methyl)propionamide |
| 243 | 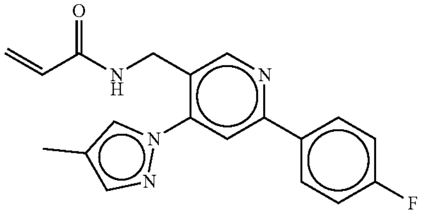 | N-((6-(4-fluorophenyl)-4-(4-methyl-1H-pyrazol-1-yl)pyridin-3-yl)methyl)acrylamide |
| 244 | 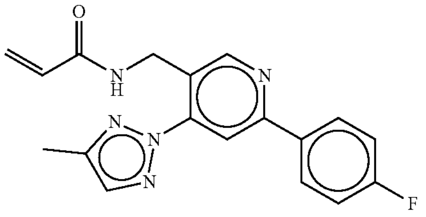 | N-((6-(4-fluorophenyl)-4-(4-methyl-2H-1,2,3-triazol-2-yl)pyridin-3-yl)methyl)acrylamide |
| 245 | 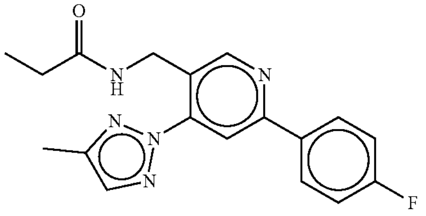 | N-((6-(4-fluorophenyl)-4-(4-methyl-2H-1,2,3-triazol-2-yl)pyridin-3-yl)methyl)propionamide |
| 246 | 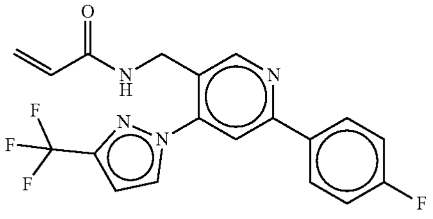 | N-((6-(4-fluorophenyl)-4-(3-(trifluoromethyl)-1H-pyrazol-1-yl)pyridin-3-yl)methyl)acrylamide |
| 247 | 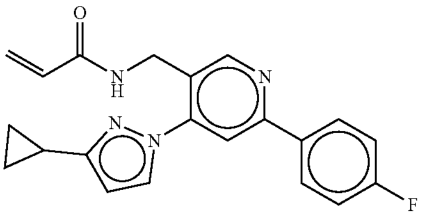 | N-((4-(3-cyclopropyl-1H-pyrazol-1-yl)-6-(4-fluorophenyl)pyridin-3-yl)methyl)acrylamide |

TABLE 1-continued

| Cpd. No. | Structure | Name |
| --- | --- | --- |
| | Structures of example compounds of the disclosure and their respective codes | |
| 248 | 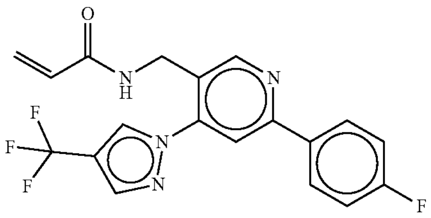 | N-((6-(4-fluorophenyl)-4-(4-(trifluoromethyl)-1H-pyrazol-1-yl)pyridin-3-yl)methyl)acrylamide |
| 249 | 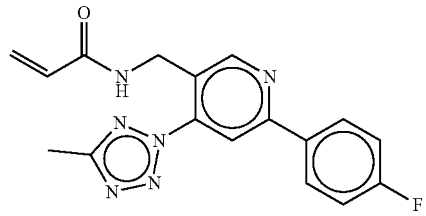 | N-((6-(4-fluorophenyl)-4-(5-methyl-2H-tetrazol-2-yl)pyridin-3-yl)methyl)acrylamide |
| 250 | 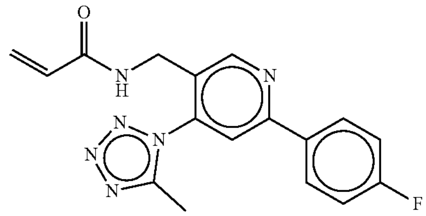 | N-((6-(4-fluorophenyl)-4-(5-methyl-1H-tetrazol-1-yl)pyridin-3-yl)methyl)acrylamide |
| 251 | 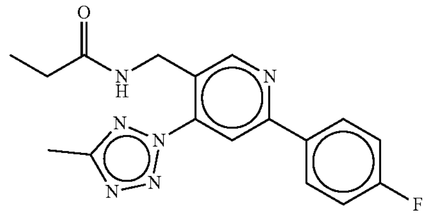 | N-((6-(4-fluorophenyl)-4-(5-methyl-2H-tetrazol-2-yl)pyridin-3-yl)methyl)propionamide |
| 252 | 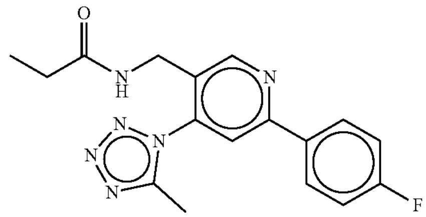 | N-((6-(4-fluorophenyl)-4-(5-methyl-1H-tetrazol-1-yl)pyridin-3-yl)methyl)propionamide |
| 253 | 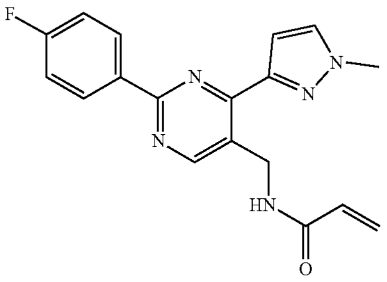 [SMILES: C=CC(=O)NCc1cnc(-c2ccc(F)cc2)nc1-c1ccn(C)n1] | N-((2-(4-fluorophenyl)-4-(1-methyl-1H-pyrazol-3-yl)pyrimidin-5-yl)methyl)acrylamide |

TABLE 1-continued

| Cpd. No. | Structure | Name |
|---|---|---|
| 254 | 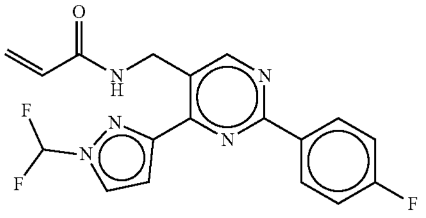 | N-((4-(1-(difluoromethyl)-1H-pyrazol-3-yl)-2-(4-fluorophenyl)pyrimidin-5-yl)methyl)acrylamide |
| 255 | 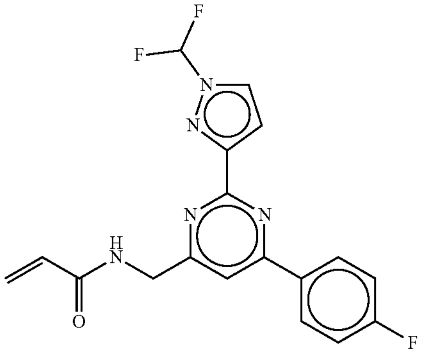 | N-((2-(1-(difluoromethyl)-1H-pyrazol-3-yl)-6-(4-fluorophenyl)pyrimidin-4-yl)methyl)acrylamide |
| 256 | 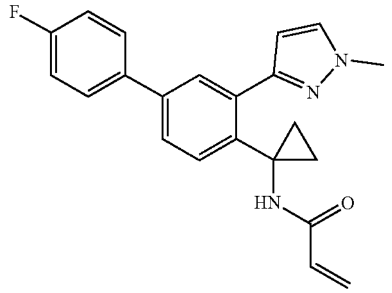 [SMILES: C=CC(=O)NC1(c2ccc(-c3ccc(F)cc3)cc2-c2ccn(C)n2)CC1] | N-(1-(4'-fluoro-3-(1-methyl-1H-pyrazol-3-yl)-[1,1'-biphenyl]-4-yl)cyclopropyl)acrylamide |
| 257 | 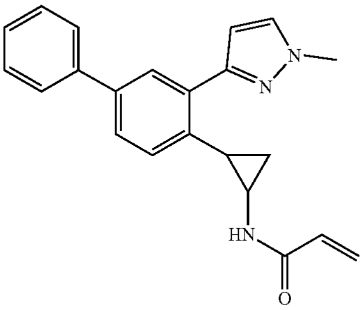 [SMILES: C=CC(=O)NC1CC1c1ccc(-c2ccccc2)cc1-c1ccn(C)n1] | N-(2-(4'-fluoro-3-(1-methyl-1H-pyrazol-3-yl)-[1,1'-biphenyl]-4-yl)cyclopropyl)acylamide |
| 258 | 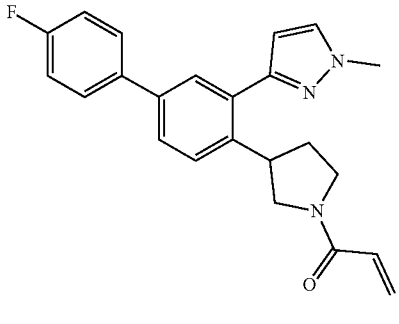 [SMILES: C=CC(=O)N1CCC(c2ccc(-c3ccc(F)cc3)cc2-c2ccn(C)n2)C1] | 1-(3-(4'-fluoro-3-(1-methyl-1H-pyrazol-3-yl)-[1,1'-biphenyl]-4-yl)pyrrolidin-1-yl)prop-2-en-1-one |

Structures of example compounds of the disclosure and their respective codes

TABLE 1-continued

| Cpd. No. | Structure | Name |
|---|---|---|
| 259 | 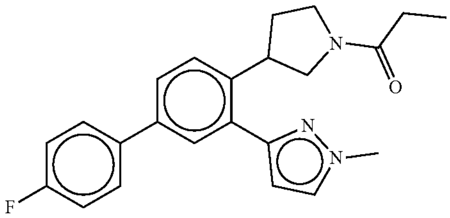 | 1-(3-(4'-fluoro-3-(1-methyl-1H-pyrazol-3-yl)-[1,1'-biphenyl]-4-yl)pyrrolidin-1-yl)propan-1-one |
| 260 | 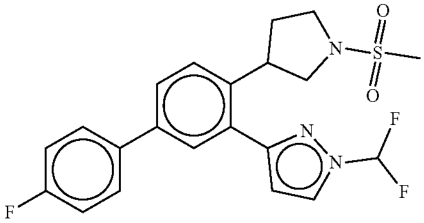 | 1-(difluoromethyl)-3-(4'-fluoro-4-(1-(methylsulfonyl)pyrrolidin-3-yl)-[1,1'-biphenyl]-3-yl)-1H-pyrazole |
| 261 | 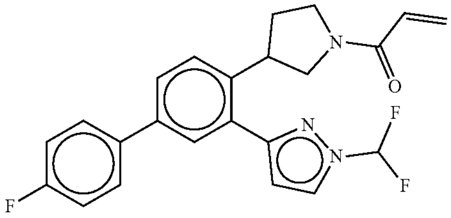 | 1-(3-(3-(1-(difluoromethyl)-1H-pyrazol-3-yl)-4'-fluoro-[1,1'-biphenyl]-4-yl)pyrrolidin-1-yl)prop-2-en-1-one |
| 261-En1 | 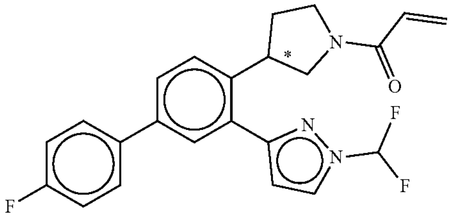 | 1-(3-(3-(1-(difluoromethyl)-1H-pyrazol-3-yl)-4'-fluoro-[1,1'-biphenyl]-4-yl)pyrrolidin-1-yl)prop-2-en-1-one |
| 261-En2 | 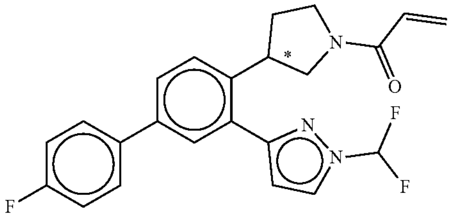 | 1-(3-(3-(1-(difluoromethyl)-1H-pyrazol-3-yl)-4'-fluoro-[1,1'-biphenyl]-4-yl)pyrrolidin-1-yl)prop-2-en-1-one |
| 262 | 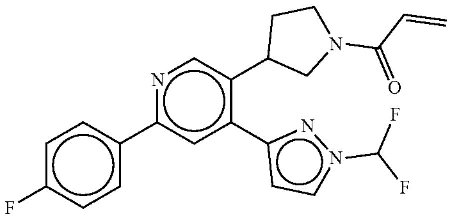 | 1-(3-(4-(1-(difluoromethyl)-1H-pyrazol-3-yl)-6-(4-fluorophenyl)pyridin-3-yl)pyrrolidin-1-yl)prop-2-en-1-one |

Structures of example compounds of the disclosure and their respective codes

TABLE 1-continued

| Structures of example compounds of the disclosure and their respective codes | | |
|---|---|---|
| Cpd. No. | Structure | Name |
| 262-En1 | 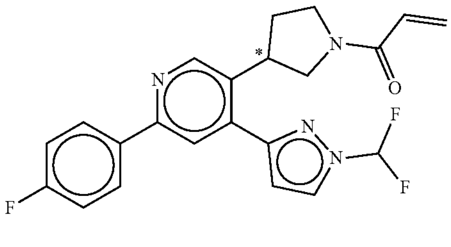 | 1-(3-(4-(1-(difluoromethyl)-1H-pyrazol-3-yl)-6-(4-fluorophenyl)pyridin-3-yl)pyrrolidin-1-yl)prop-2-en-1-one |
| 262-En2 | 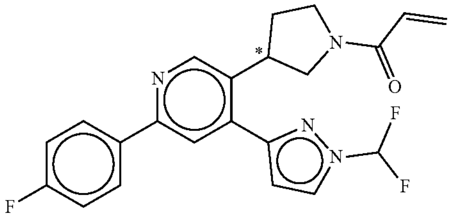 | 1-(3-(4-(1-(difluoromethyl)-1H-pyrazol-3-yl)-6-(4-fluorophenyl)pyridin-3-yl)pyrrolidin-1-yl)prop-2-en-1-one |
| 263 | 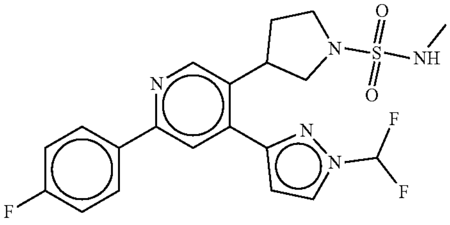 | 3-(4-(1-(difluoromethyl)-1H-pyrazol-3-yl)-6-(4-fluorophenyl)pyridin-3-yl)-N-methylpyrrolidine-1-sulfonamide |
| 264 | 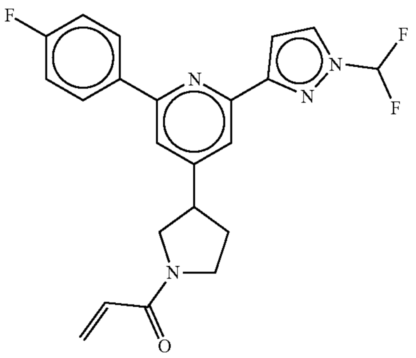 | 1-(3-(2-(1-(difluoromethyl)-1H-pyrazol-3-yl)-6-(4-fluorophenyl)pyridin-4-yl)pyrrolidin-1-yl)prop-2-en-1-one |
| 265 | 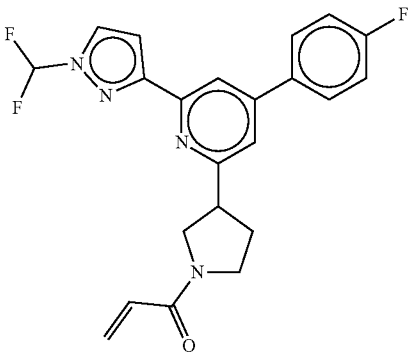 | 1-(3-(6-(1-(difluoromethyl)-1H-pyrazol-3-yl)-4-(4-fluorophenyl)pyridin-2-yl)pyrrolidin-1-yl)prop-2-en-1-one |

TABLE 1-continued

| Structures of example compounds of the disclosure and their respective codes | | |
|---|---|---|
| Cpd. No. | Structure | Name |
| 266 | 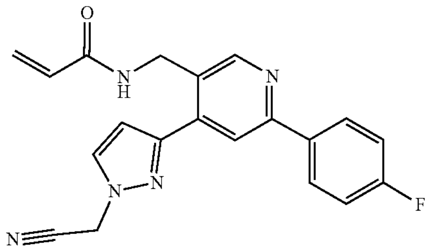 [SMILES: C=CC(=O)NCc1cnc(-c2ccc(F)cc2)cc1-c1ccn(CC#N)n1] | N-((4-(1-(cyanomethyl)-1H-pyrazol-3-yl)-6-(4-fluorophenyl)pyridin-3-yl)methyl)acrylamide |
| 267 | 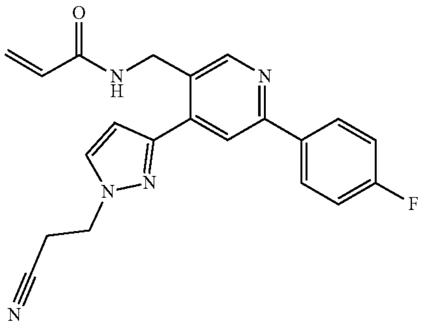 [SMILES: C=CC(=O)NCc1cnc(-c2ccc(F)cc2)cc1-c1ccn(CCC#N)n1] | N-((4-(1-(2-cyanoethyl)-1H-pyrazol-3-yl)-6-(4-fluorophenyl)pyridin-3-yl)methyl)acrylamide |
| 268 | 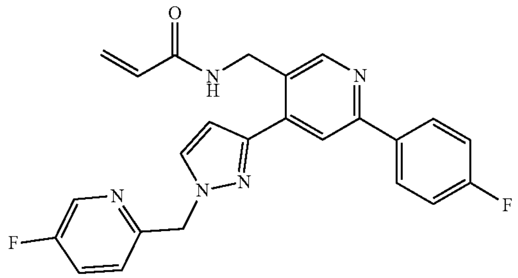 [SMILES: C=CC(=O)NCc1cnc(-c2ccc(F)cc2)cc1-c1ccn(Cc2ccc(F)cn2)n1] | N-((6-(4-fluorophenyl)-4-(1-((5-fluoropyridin-2-yl)methyl)-1H-pyrazol-3-yl)pyridin-3-yl)methyl)acrylamide |
| 269 | 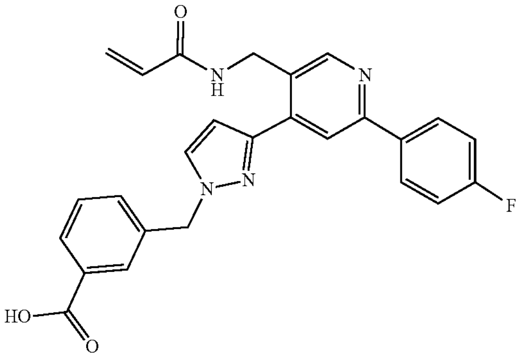 [SMILES: C=CC(=O)NCc1cnc(-c2ccc(F)cc2)cc1-c1ccn(Cc2cccc(C(=O)O)c2)n1] | 3-[[3-[2-(4-fluorophenyl)-5-[(prop-2-enoylamino)methyl]-4-pyridyl]pyrazol-1-yl]methyl]benzoic acid |

TABLE 1-continued

| Structures of example compounds of the disclosure and their respective codes | | |
|---|---|---|
| Cpd. No. | Structure | Name |
| 270 | 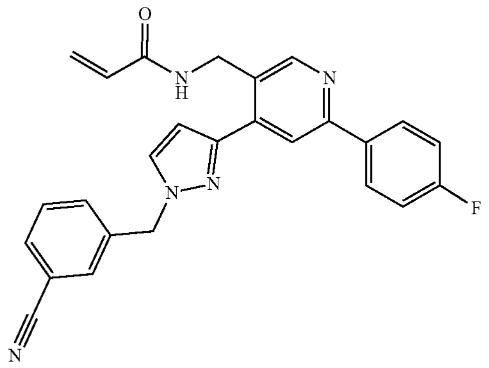 [SMILES: C=CC(=O)NCc1cnc(-c2ccc(F)cc2)cc1-c1ccn(Cc2cccc(C#N)c2)n1] | N-((4-(1-(3-cyanobenzyl)-1H-pyrazol-3-yl)-6-(4-fluorophenyl)pyridin-3-yl)methyl)acrylamide |
| 271 | 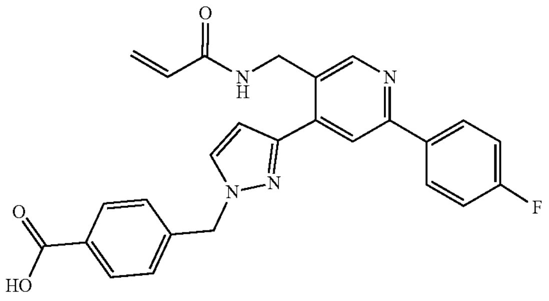 [SMILES: C=CC(=O)NCc1cnc(-c2ccc(F)cc2)cc1-c1ccn(Cc2ccc(C(=O)O)cc2)n1] | 4-[[3-[2-(4-fluorophenyl)-5-[(prop-2-enoylamino)methyl]-4-pyridyl]pyrazol-1-yl]methyl]benzoic acid |
| 272 | 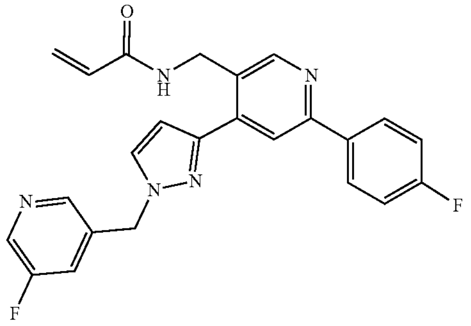 [SMILES: C=CC(=O)NCc1cnc(-c2ccc(F)cc2)cc1-c1ccn(Cc2cncc(F)c2)n1] | N-((6-(4-fluorophenyl)-4-(1-((5-fluoropyridin-3-yl)methyl)-1H-pyrazol-3-yl)pyridin-3-yl)methyl)acrylamide |
| 273 | 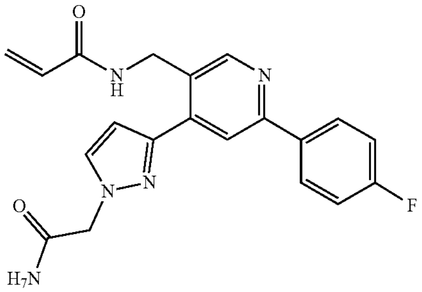 | N-((4-(1-(2-amino-2-oxoethyl)-1H-pyrazol-3-yl)-6-(4-fluorophenyl)pyridin-3-yl)methyl)acrylamide |

TABLE 1-continued

| Cpd. No. | Structure | Name |
| --- | --- | --- |
| Structures of example compounds of the disclosure and their respective codes | | |
| 274 | 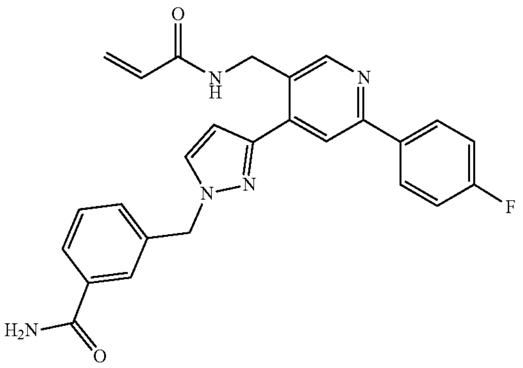 [SMILES: C=CC(=O)NCc1cnc(-c2ccc(F)cc2)cc1-c1ccn(Cc2cccc(C(N)=O)c2)n1] | 3-[[3-[2-(4-fluorophenyl)-5-[(prop-2-enoylamino)methyl]-4-pyridyl]pyrazol-1-yl]methyl]benzamide |
| 275 | 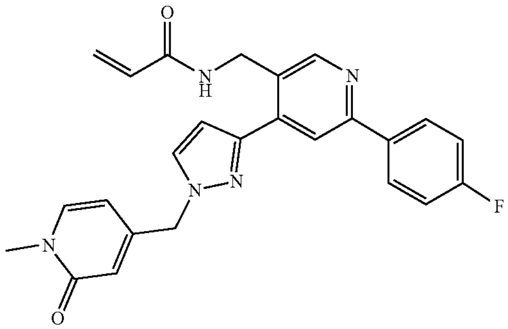 [SMILES: C=CC(=O)NCc1cnc(-c2ccc(F)cc2)cc1-c1ccn(Cc2ccn(C)c(=O)c2)n1] | N-((6-(4-fluorophenyl)-4-(1-((1-methyl-2-oxo-1,2-dihydropyridin-4-yl)methyl)-1H-pyrazol-3-yl)pyridin-3-yl)methyl)acrylamide |
| 276 | 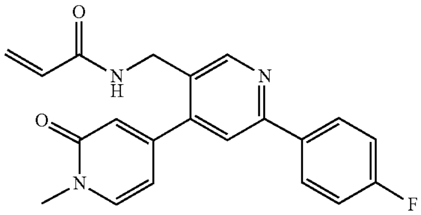 [SMILES: C=CC(=O)NCc1cnc(-c2ccc(F)cc2)cc1-c1ccn(C)c(=O)c1] | N-((6-(4-fluorophenyl)-1'-methyl-2'-oxo-1',2'-dihydro-[4,4'-bipyridin]-3-yl)methyl)acrylamide |
| 277 | 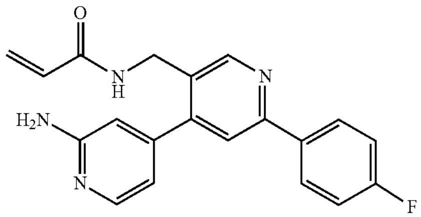 [SMILES: C=CC(=O)NCc1cnc(-c2ccc(F)cc2)cc1-c1ccnc(N)c1] | N-((2'-amino-6-(4-fluorophenyl)-[4,4'-bipyridin]-3-yl)methyl)acrylamide |
| 278 | 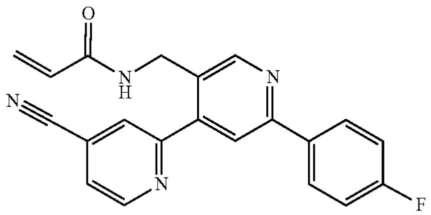 [SMILES: C=CC(=O)NCc1cnc(-c2ccc(F)cc2)cc1-c1cc(C#N)ccn1] | N-((4-cyano-6'-(4-fluorophenyl)-[2,4'-bipyridin]-3'-yl)methyl)acrylamide |

TABLE 1-continued

| Cpd. No. | Structure | Name |
|---|---|---|
| 279 | 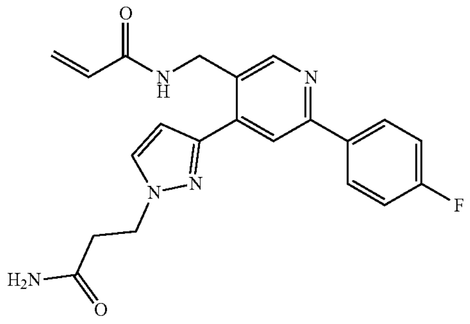 [SMILES: C=CC(=O)NCc1cnc(-c2ccc(F)cc2)cc1-c1ccn(CCC(N)=O)n1] | N-((4-(1-(3-amino-3-oxopropyl)-1H-pyrazol-3-yl)-6-(4-fluorophenyl)pyridin-3-yl)methyl)acrylamide |
| 280 | 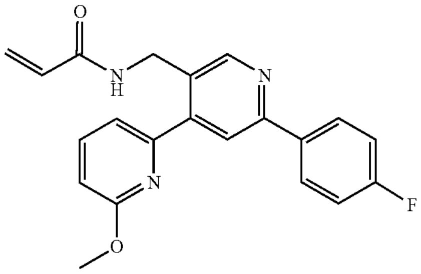 [SMILES: C=CC(=O)NCc1cnc(-c2ccc(F)cc2)cc1-c1cccc(OC)n1] | N-((6'-(4-fluorophenyl)-6-methoxy-[2,4'-bipyridin]-3'-yl)methyl)acrylamide |
| 281 | 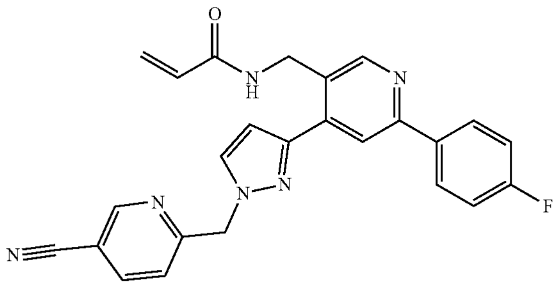 [SMILES: C=CC(=O)NCc1cnc(-c2ccc(F)cc2)cc1-c1ccn(Cc2ccc(C#N)cn2)n1] | N-((4-(1-((5-cyanopyridin-2-yl)methyl)-1H-pyrazol-3-yl)-6-(4-fluorophenyl)pyridin-3-yl)methyl)acrylamide |
| 282 | 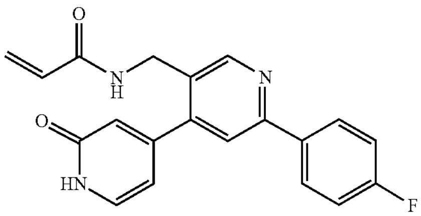 [SMILES: C=CC(=O)NCc1cnc(-c2ccc(F)cc2)cc1-c1cc[nH]c(=O)c1] | N-((6-(4-fluorophenyl)-2'-oxo-1',2'-dihydro-[4,4'-bipyridin]-3-yl)methyl)acrylamide |
| 283 | 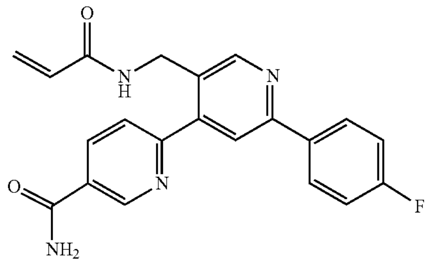 [SMILES: C=CC(=O)NCc1cnc(-c2ccc(F)cc2)cc1-c1ccc(C(N)=O)cn1] | 5'-(acrylamidomethyl)-2'-(4-fluorophenyl)-[2,4'-bipyridine]-5-carboxamide |

Structures of example compounds of the disclosure and their respective codes TABLE 1-continued

| Cpd. No. | Structure | Name |
|---|---|---|
| | Structures of example compounds of the disclosure and their respective codes | |
| 284 | 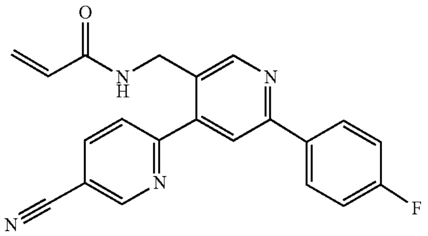 [SMILES: C=CC(=O)NCc1cnc(-c2ccc(F)cc2)cc1-c1ccc(C#N)cn1] | N-((5-cyano-6'-(4-fluorophenyl)-[2,4'-bipyridin]-3'-yl)methyl)acrylamide |
| 285 | 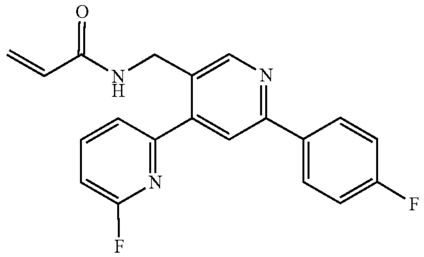 [SMILES: C=CC(=O)NCc1cnc(-c2ccc(F)cc2)cc1-c1cccc(F)n1] | N-((6-fluoro-6'-(4-fluorophenyl)-[2,4'-bipyridin]-3'-yl)methyl)acrylamide |
| 286 | 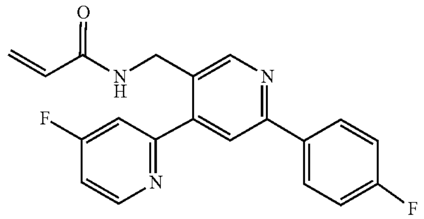 [SMILES: C=CC(=O)NCc1cnc(-c2ccc(F)cc2)cc1-c1cc(F)ccn1] | N-((4-fluoro-6'-(4-fluorophenyl)-[2,4'-bipyridin]-3'-yl)methyl)acrylamide |
| 287 | 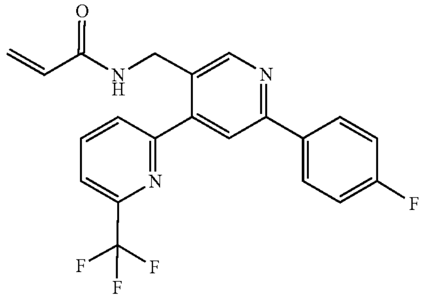 [SMILES: C=CC(=O)NCc1cnc(-c2ccc(F)cc2)cc1-c1cccc(C(F)(F)F)n1] | N-((6'-(4-fluorophenyl)-6-(trifluoromethyl)-[2',4'-bipyridin]-3'-yl)methyl)acrylamide |
| 288 | 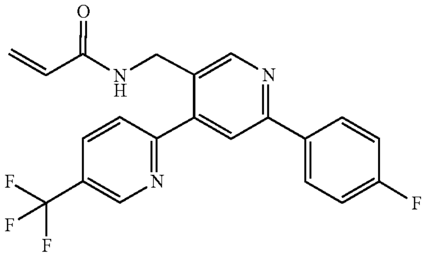 [SMILES: C=CC(=O)NCc1cnc(-c2ccc(F)cc2)cc1-c1ccc(C(F)(F)F)cn1] | N-((6'-(4-fluorophenyl)-5-(trifluoromethyl)-[2,4'-bipyridin]-3'-yl)methyl)acrylamide |
| 289 | 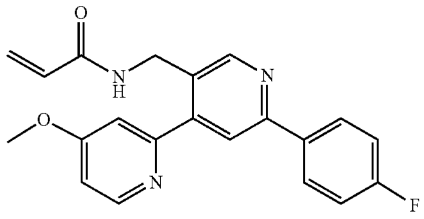 [SMILES: C=CC(=O)NCc1cnc(-c2ccc(F)cc2)cc1-c1cc(OC)ccn1] | N-((6'-(4-fluoropheenyl)-4-methoxy-[2,4'-bipyridin]-3'-yl)methyl)acrylamide |

TABLE 1-continued

Structures of example compounds of the disclosure and their respective codes

| Cpd. No. | Structure | Name |
|---|---|---|
| 290 | 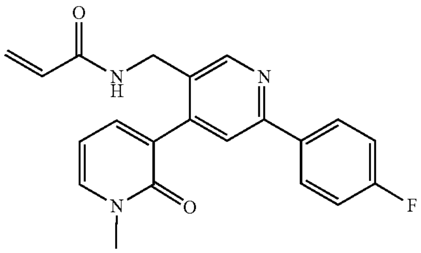 [SMILES: C=CC(=O)NCc1cnc(-c2ccc(F)cc2)cc1-c1cccn(C)c1=O] | N-((6'-(4-fluorophenyl)-1-methyl-2-oxo-1,2-dihydro-[3,4'-bipyridin]-3'-yl)methyl)acrylamide |
| 291 | 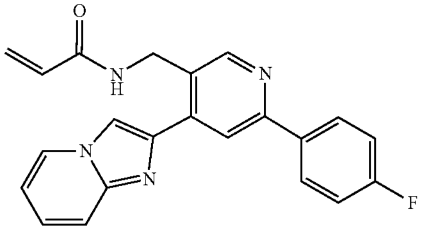 [SMILES: C=CC(=O)NCc1cnc(-c2ccc(F)cc2)cc1-c1cn2ccccc2n1] | N-((6-(4-fluorophenyl)-4-(imidazo[1,2-a]pyridin-2-yl)pyridin-3-yl)methyl)acrylamide |
| 292 | 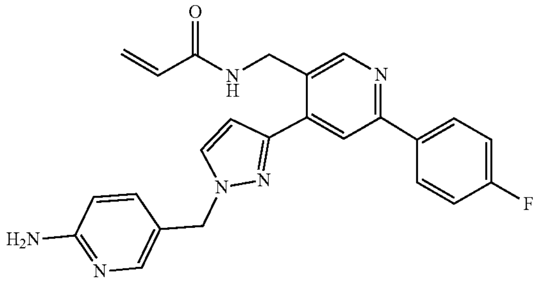 [SMILES: C=CC(=O)NCc1cnc(-c2ccc(F)cc2)cc1-c1ccn(Cc2ccc(N)nc2)n1] | N-((4-(1-((6-aminopyridin-3-yl)methyl)-1H-pyrazol-3-yl)-6-(4-fluorophenyl)pyridin-3-yl)methyl)acrylamide |
| 293 | 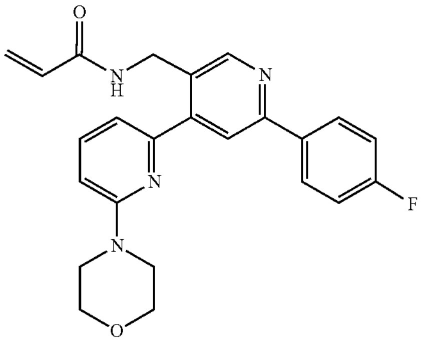 [SMILES: C=CC(=O)NCc1cnc(-c2ccc(F)cc2)cc1-c1cccc(N2CCOCC2)n1] | N-((6'-(4-fluorophenyl)-6-morpholino-[2,4'-bipyridin]-3'-yl)methyl)acrylamide |
| 294 | 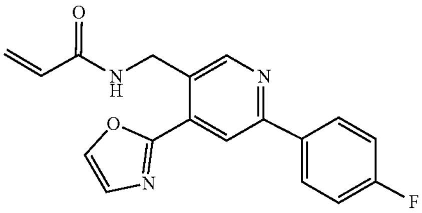 [SMILES: C=CC(=O)NCc1cnc(-c2ccc(F)cc2)cc1-c1ncco1] | N-((6-(4-fluorophenyl)-4-(oxazol-2-yl)pyridin-3-yl)methyl)acrylamide |

TABLE 1-continued

| Structures of example compounds of the disclosure and their respective codes | | |
|---|---|---|
| Cpd. No. | Structure | Name |
| 295 | 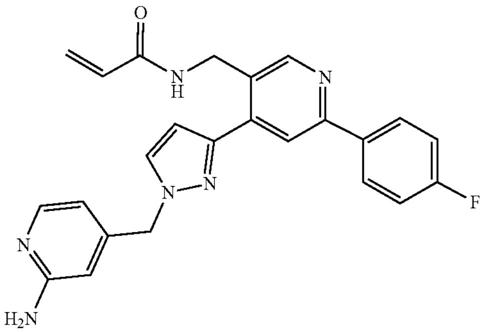 [SMILES: C=CC(=O)NCc1cnc(-c2ccc(F)cc2)cc1-c1ccn(Cc2ccnc(N)c2)n1] | N-((4-(1-((2-aminopyridin-4-yl)methyl)-1H-pyrazol-3-yl)-6-(4-fluorophenyl)pyridin-3-yl)methyl)acrylamide |
| 296 | 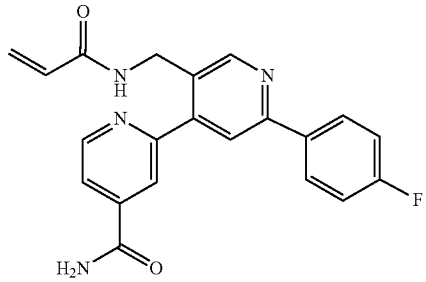 [SMILES: C=CC(=O)NCc1cnc(-c2ccc(F)cc2)cc1-c1cc(C(N)=O)ccn1] | 5'-(acrylamidomethyl)-2'-(4-fluorophenyl)-[2,4'-bipyridine]-4-carboxamide |
| 297 | 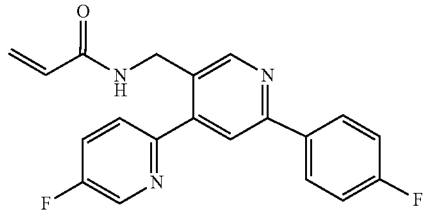 [SMILES: C=CC(=O)NCc1cnc(-c2ccc(F)cc2)cc1-c1ccc(F)cn1] | N-((5-fluoro-6'-(4-fluorophenyl)-[2,4'-bipyridin]-3'-yl)methyl)acrylamide |
| 298 | 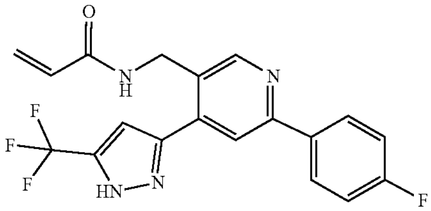 [SMILES: C=CC(=O)NCc1cnc(-c2ccc(F)cc2)cc1-c1cc(C(F)(F)F)[nH]n1] | N-((6-(4-fluorophenyl)-4-(5-(trifluoromethyl)-1H-pyrazol-3-yl)pyridin-3-yl)methyl)acrylamide |
| 299 | 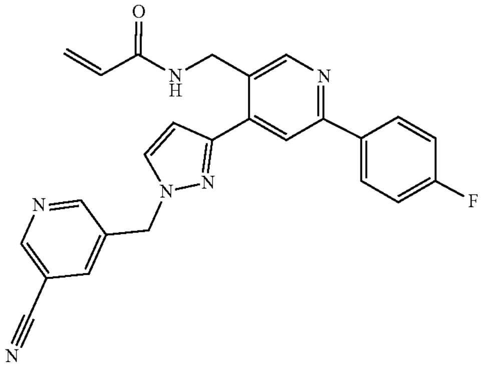 [SMILES: C=CC(=O)NCc1cnc(-c2ccc(F)cc2)cc1-c1ccn(Cc2cncc(C#N)c2)n1] | N-((4-(1-((5-cyanopyridin-3-yl)methyl)-1H-pyrazol-3-yl)-6-(4-fluorophenyl)pyridin-3-yl)methyl)acrylamide |

TABLE 1-continued

Structures of example compounds of the disclosure and their respective codes

| Cpd. No. | Structure | Name |
|---|---|---|
| 300 | 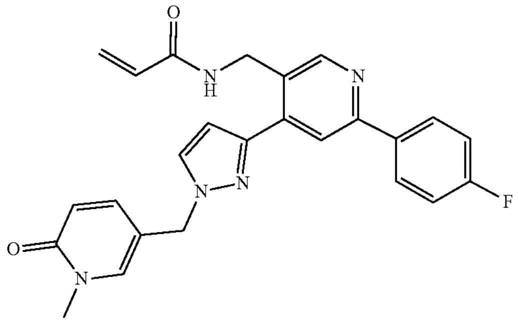 [SMILES: C=CC(=O)NCc1cnc(-c2ccc(F)cc2)cc1-c1ccn(Cc2ccc(=O)n(C)c2)n1] | N-((6-(4-fluorophenyl)-4-(1-((1-methyl-6-oxo-1,6-dihydropyridin-3-yl)methyl)-1H-pyrazol-3-yl)pyridin-3-yl)methyl)acrylamide |
| 301 | 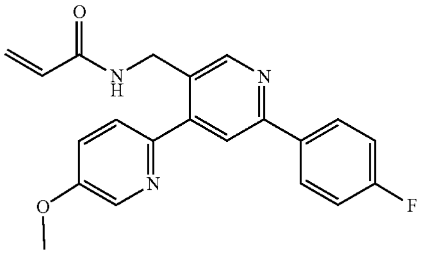 [SMILES: C=CC(=O)NCc1cnc(-c2ccc(F)cc2)cc1-c1ccc(OC)cn1] | N-((6'-(4-fluorophenyl)-5-methoxy-[2,4'-bipyridin]-3'-yl)methyl)acrylamide |
| 302 | 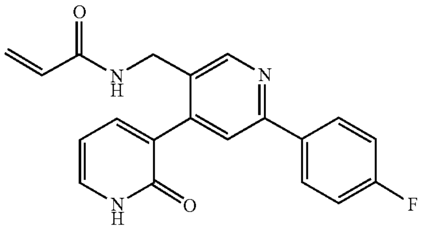 [SMILES: C=CC(=O)NCc1cnc(-c2ccc(F)cc2)cc1-c1ccc[nH]c1=O] | N-((6'-(4-fluorophenyl)-2-oxo-1,2-dihydro-[3,4'-bipyridin]-3'-yl)methyl)acrylamide |
| 303 | 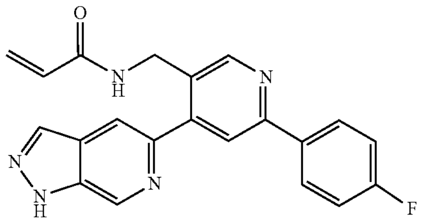 [SMILES: C=CC(=O)NCc1cnc(-c2ccc(F)cc2)cc1-c1cc2cn[nH]c2cn1] | N-((6-(4-fluorophenyl)-4-(1H-pyrazolo[3,4-c]pyridin-5-yl)pyridin-3-yl)methyl)acrylamide |
| 304 | 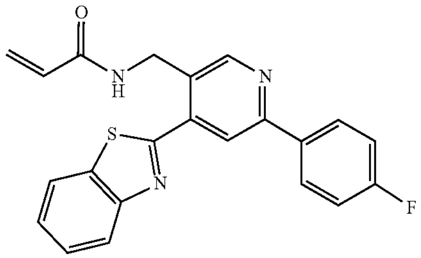 [SMILES: C=CC(=O)NCc1cnc(-c2ccc(F)cc2)cc1-c1nc2ccccc2s1] | N-((4-(benzo[d]thiazol-2-yl)-6-(4-fluorophenyl)pyridin-3-yl)methyl)acrylamide |

TABLE 1-continued

| Cpd. No. | Structure | Name |
| --- | --- | --- |
| Structures of example compounds of the disclosure and their respective codes | | |
| 305 | 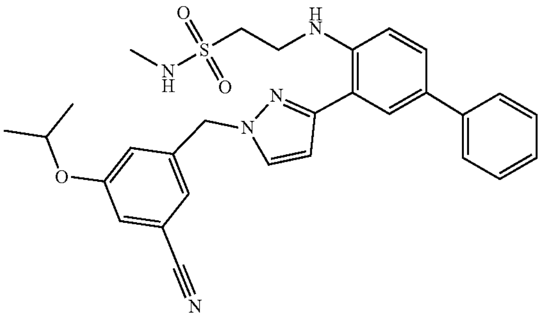 [SMILES: CNS(=O)(=O)CCNc1ccc(-c2ccccc2)cc1-c1ccn(Cc2cc(C#N)cc(OC(C)C)c2)n1] | 2-((3-(1-(3-cyano-5-isopropoxybenzyl)-1H-pyrazol-3-yl)-[1,1'-biphenyl]-4-yl)amino)-N-methylethane-1-sulfonamide |
| 306 | 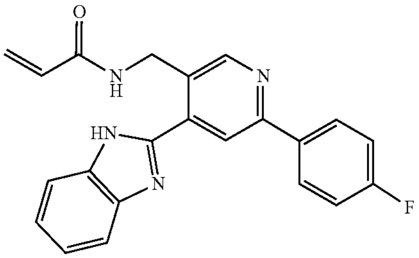 [SMILES: C=CC(=O)NCc1cnc(-c2ccc(F)cc2)cc1-c1nc2ccccc2[nH]1] | N-((4-(1H-benzo[d]imidazol-2-yl)-6-(4-fluorophenyl)pyridin-3-yl)methyl)acrylamide |
| 307 | 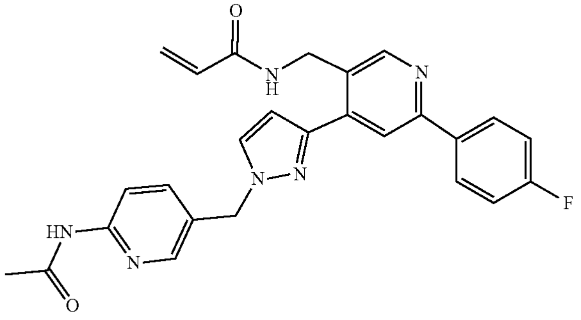 [SMILES: C=CC(=O)NCc1cnc(-c2ccc(F)cc2)cc1-c1ccn(Cc2ccc(NC(C)=O)nc2)n1] | N-((4-(1-((6-acetamidopyridin-3-yl)methyl)-1H-pyrazol-3-yl)-6-(4-fluorophenyl)pyridin-3-yl)methyl)acrylamide |
| 308 | 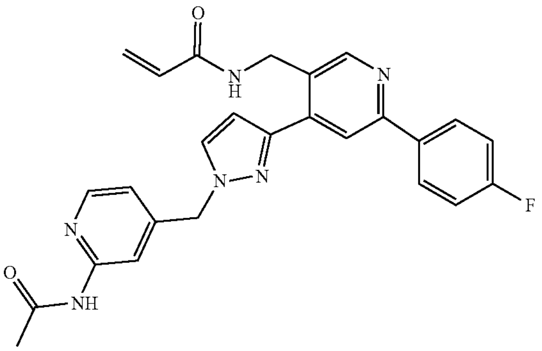 [SMILES: C=CC(=O)NCc1cnc(-c2ccc(F)cc2)cc1-c1ccn(Cc2ccnc(NC(C)=O)c2)n1] | N-((4-(1-((2-acetamidopyridin-4-yl)methyl)-1H-pyrazol-3-yl)-6-(4-fluorophenyl)pyridin-3-yl)methyl)acrylamide |

TABLE 1-continued

Structures of example compounds of the disclosure and their respective codes

| Cpd. No. | Structure | Name |
| --- | --- | --- |
| 309 | 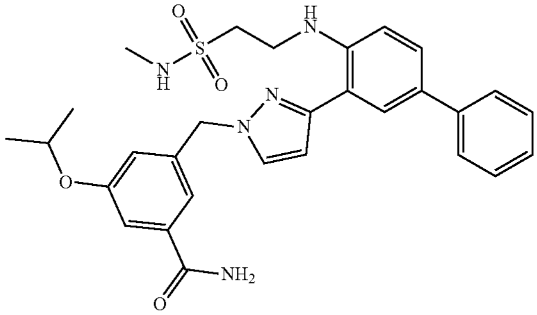 [SMILES: CNS(=O)(=O)CCNc1ccc(-c2ccccc2)cc1-c1ccn(Cc2cc(OC(C)C)cc(C(N)=O)c2)n1] | 3-isopropoxy-5-((3-(4-((2-(N-methylsulfamoyl)ethyl)amino)-[1,1'-biphenyl]-3-yl)-1H-pyrazol-1-yl)methyl)acrylamide |
| 310 | 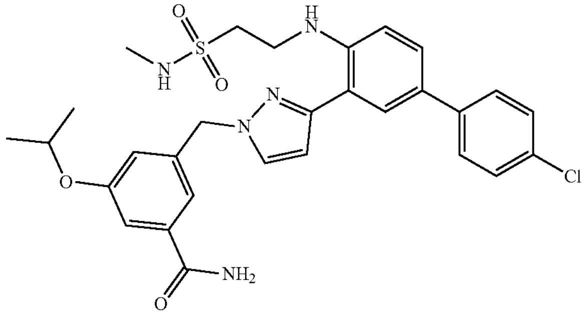 [SMILES: CNS(=O)(=O)CCNc1ccc(-c2ccc(Cl)cc2)cc1-c1ccn(Cc2cc(OC(C)C)cc(C(N)=O)c2)n1] | 3-((3-(4'-chloro-4-((2-(N-methylsulfamoyl)ethyl)amino)-[1,1'-biphenyl]-3-yl)-1H-pyrazol-1-yl)methyl)-5-isopropoxybenzamide |
| 311 | 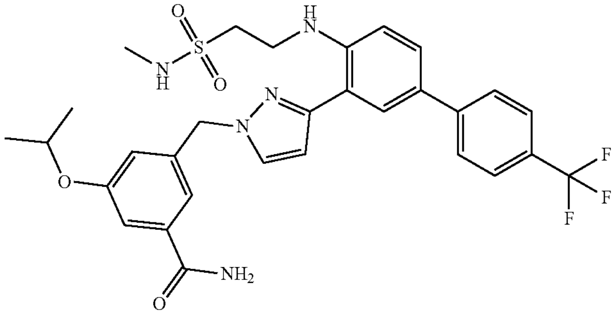 [SMILES: CNS(=O)(=O)CCNc1ccc(-c2ccc(C(F)(F)F)cc2)cc1-c1ccn(Cc2cc(OC(C)C)cc(C(N)=O)c2)n1] | 3-isopropoxy-5-((3-(4-((2-(N-methylsulfamoyl)ethyl)amino)-4'-(trifluoromethyl)-[1,1'-biphenyl]-3-yl)-1H-pyrazol-1-yl)methyl)benzamide |
| 312 | 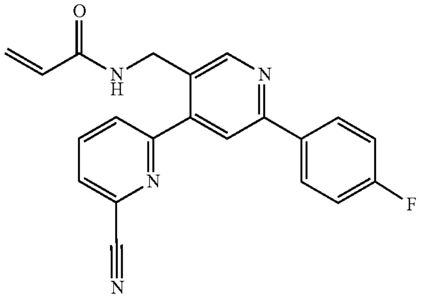 [SMILES: C=CC(=O)NCc1cnc(-c2ccc(F)cc2)cc1-c1cccc(C#N)n1] | N-((6-cyano-6'-(4-fluorophenyl)-[2,4'-bipyridin]-3'-yl)methyl)acrylamide |
| 313 | 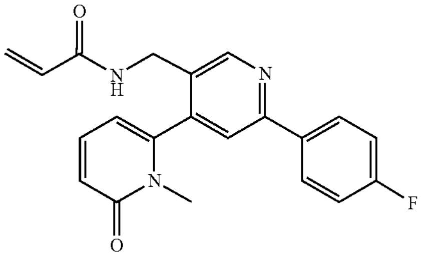 [SMILES: C=CC(=O)NCc1cnc(-c2ccc(F)cc2)cc1-c1cccc(=O)n1C] | N-((6'-(4-fluorophenyl)-1-methyl-6-oxo-1,6-dihydro-[2,4'-bipyridin]-3'-yl)methyl)acrylamide |

TABLE 1-continued

| Structures of example compounds of the disclosure and their respective codes | | |
|---|---|---|
| Cpd. No. | Structure | Name |
| 314 | 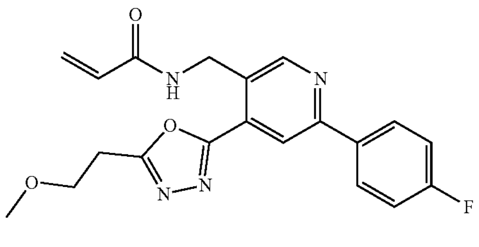 [SMILES: C=CC(=O)NCc1cnc(-c2ccc(F)cc2)cc1-c1nnc(CCOC)o1] | N-((6-(4-fluorophenyl)-4-(5-(2-methoxyethyl)-1,3,4-oxadiazol-2-yl)pyridin-3-yl)methyl)acrylamide |
| 315 | 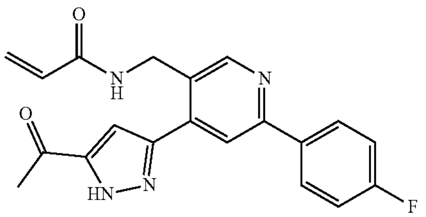 [SMILES: C=CC(=O)NCc1cnc(-c2ccc(F)cc2)cc1-c1cc(C(C)=O)[nH]n1] | 3-(5-(acrylamidomethyl)-2-(4-fluorophenyl)pyridin-4-yl)-1H-pyrazole-5-carboxamide |
| 316 | 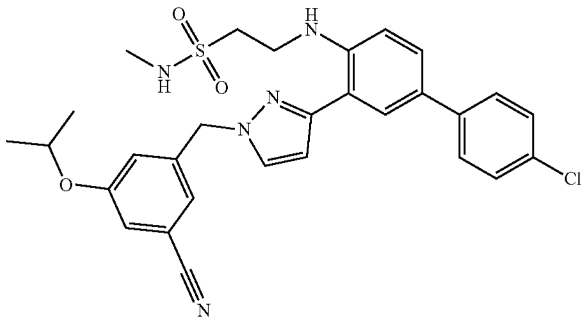 [SMILES: CNS(=O)(=O)CCNc1ccc(-c2ccc(Cl)cc2)cc1-c1ccn(Cc2cc(C#N)cc(OC(C)C)c2)n1] | 2-((4'-chloro-3-(1-(3-cyano-5-isopropoxybenzyl)-1H-pyrazol-3-yl)-[1,1'-biphenyl]-4-yl)amino)-N-methylethane-1-sulfonamide |
| 317 | 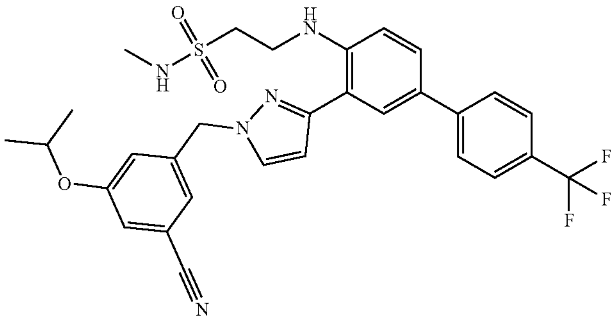 [SMILES: CNS(=O)(=O)CCNc1ccc(-c2ccc(C(F)(F)F)cc2)cc1-c1ccn(Cc2cc(C#N)cc(OC(C)C)c2)n1] | 2-((3-(1-(3-cyano-5-isopropoxybenzyl)-1H-pyrazol-3-yl)-4'-(trifluoromethyl)-[1,1'-biphenyl]-4-yl)amino)-N-methylethane-1-sulfonamide |
| 318 | 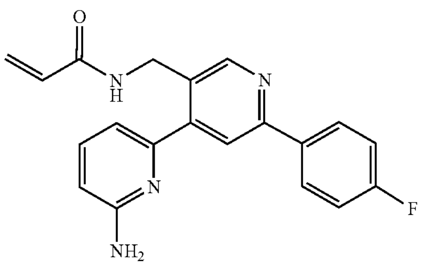 [SMILES: C=CC(=O)NCc1cnc(-c2ccc(F)cc2)cc1-c1cccc(N)n1] | N-((6-amino-6'-(4-fluorophenyl)-[2,4'-bipyridin]-3'-yl)methyl)acrylamide |

TABLE 1-continued

| Structures of example compounds of the disclosure and their respective codes | | |
|---|---|---|
| Cpd. No. | Structure | Name |
| 319 | 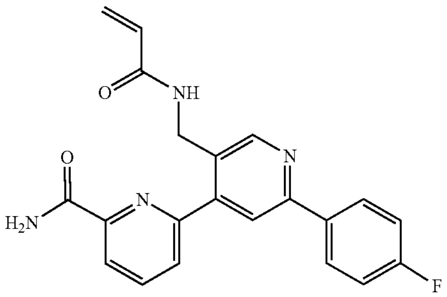 [SMILES: C=CC(=O)NCc1cnc(-c2ccc(F)cc2)cc1-c1cccc(C(N)=O)n1] | 5'-(acrylamidomethyl)-2'-(4-fluorophenyl)-[2,4'-bipyridin]-6-carboxamide |
| 320 | 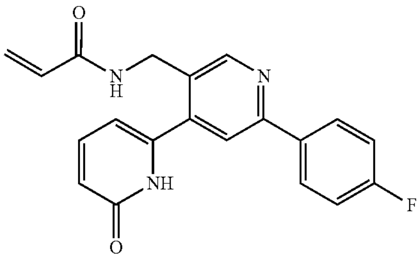 [SMILES: C=CC(=O)NCc1cnc(-c2ccc(F)cc2)cc1-c1cccc(=O)[nH]1] | N-((6'-(4-fluorophenyl)-6-oxo-1,6-dihydro-[2,4'-bipyridin]-3'-yl)methyl)acrylamide |
| 321 | 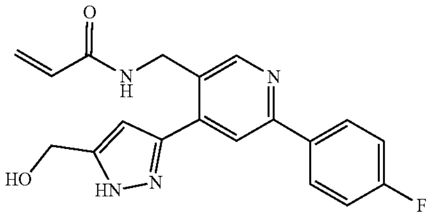 [SMILES: C=CC(=O)NCc1cnc(-c2ccc(F)cc2)cc1-c1cc(CO)[nH]n1] | N-((6-(4-fluorophenyl)-4-(5-(hydroxymethyl)-1H-pyrazol-3-yl)pyridin-3-yl)methyl)acrylamide |
| 322 | 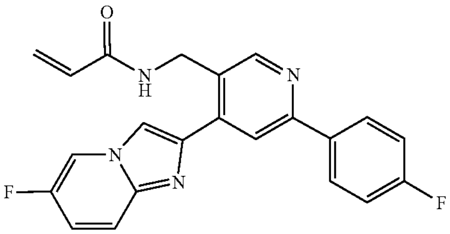 [SMILES: C=CC(=O)NCc1cnc(-c2ccc(F)cc2)cc1-c1cn2cc(F)ccc2n1] | N-((4-(6-fluoroimidazo[1,2-a]pyridin-2-yl)-6-(4-fluorophenyl)pyridin-3-yl)methyl)acrylamide |
| 323 | 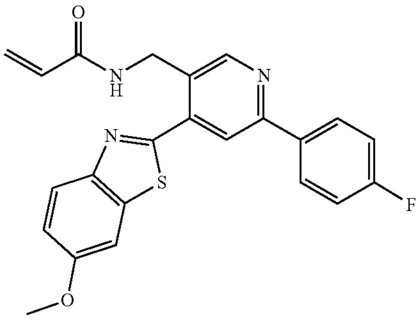 [SMILES: C=CC(=O)NCc1cnc(-c2ccc(F)cc2)cc1-c1nc2ccc(OC)cc2s1] | N-((6-(4-fluorophenyl)-4-(6-methoxybenzo[d]thiazol-2-yl)pyridin-3-yl)methyl)acrylamide |

TABLE 1-continued

Structures of example compounds of the disclosure and their respective codes

| Cpd. No. | Structure | Name |
|---|---|---|
| 324 | 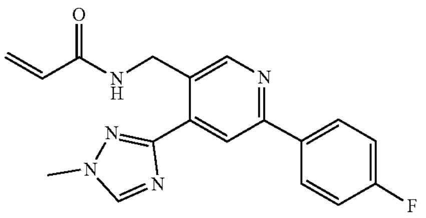 [SMILES: C=CC(=O)NCc1cnc(-c2ccc(F)cc2)cc1-c1ncn(C)n1] | N-((6-(4-fluorophenyl)-4-(1-methyl-1H-1,2,4-triazol-3-yl)pyridin-3-yl)methyl)acrylamide |
| 325 | 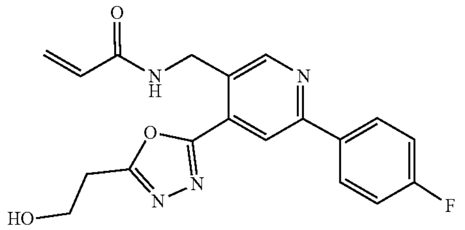 [SMILES: C=CC(=O)NCc1cnc(-c2ccc(F)cc2)cc1-c1nnc(CCO)o1] | N-((6-(4-fluorophenyl)-4-(5-(2-hydroxyethyl)-1,3,4-oxadiazol-2-yl)pyridin-3-yl)methyl)acrylamide |
| 326 | 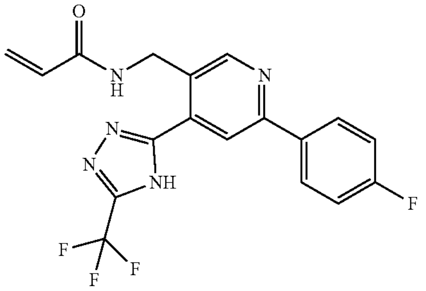 [SMILES: C=CC(=O)NCc1cnc(-c2ccc(F)cc2)cc1-c1nnc(C(F)(F)F)[nH]1] | N-((6-(4-fluorophenyl)-4-(5-(trifluoromethyl)-4H-1,2,4-triazol-3-yl)pyridin-3-yl)methyl)acrylamide |
| 327 | 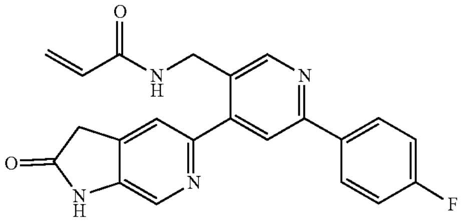 [SMILES: C=CC(=O)NCc1cnc(-c2ccc(F)cc2)cc1-c1cc2c(cn1)NC(=O)C2] | N-((6-(4-fluorophenyl)-4-(2-oxo-2,3-dihydro-1H-pyrrolo[2,3-c]pyridin-5-yl)pyridin-3-yl)methyl)acrylamide |
| 328 | 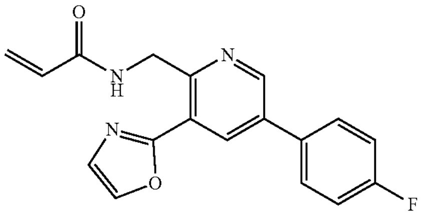 [SMILES: C=CC(=O)NCc1ncc(-c2ccc(F)cc2)cc1-c1ncco1] | N-((5-(4-fluorophenyl)-3-(oxazol-2-yl)pyridin-2-yl)methyl)acrylamide |
| 329 | 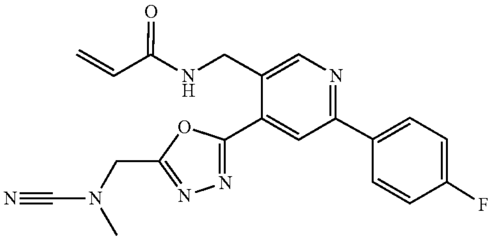 [SMILES: C=CC(=O)NCc1cnc(-c2ccc(F)cc2)cc1-c1nnc(CN(C)C#N)o1] | N-((6-(4-fluorophenyl)-4-(5-((N-methylcyanamido)methyl)-1,3,4-oxadiazol-2-yl)pyridin-3-yl)methyl)acrylamide |

TABLE 1-continued

Structures of example compounds of the disclosure and their respective codes

| Cpd. No. | Structure | Name |
|---|---|---|
| 330 | 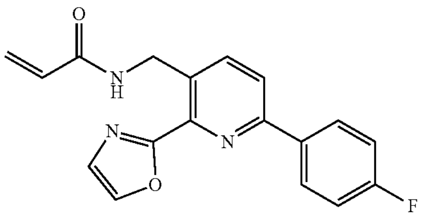 [SMILES: C=CC(=O)NCc1ccc(-c2ccc(F)cc2)nc1-c1ncco1] | N-((6-(4-fluorophenyl)-2-(oxazol-2-yl)pyridin-3-yl)methyl)acrylamide |
| 331 | 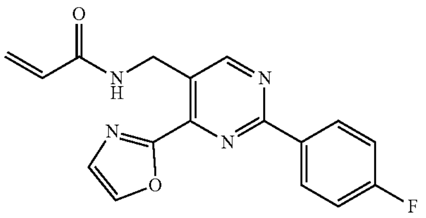 [SMILES: C=CC(=O)NCc1cnc(-c2ccc(F)cc2)nc1-c1ncco1] | N-((2-(4-fluorophenyl)-4-(oxazol-2-yl)pyrimidin-5-yl)methyl)acrylamide |
| 332 | 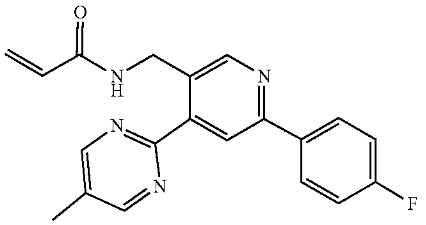 [SMILES: C=CC(=O)NCc1cnc(-c2ccc(F)cc2)cc1-c1ncc(C)cn1] | N-((6-(4-fluorophenyl)-4-(5-methylpyrimidin-2-yl)pyridin-3-yl)methyl)acrylamide |
| 333 | 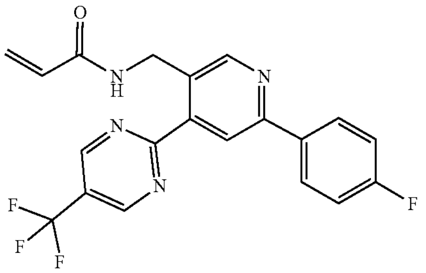 [SMILES: C=CC(=O)NCc1cnc(-c2ccc(F)cc2)cc1-c1ncc(C(F)(F)F)cn1] | N-((6-(4-fluorophenyl)-4-(5-(trifluoromethyl)pyrimidin-2-yl)pyridin-3-yl) yl)methyl)acrylamide |
| 334 | 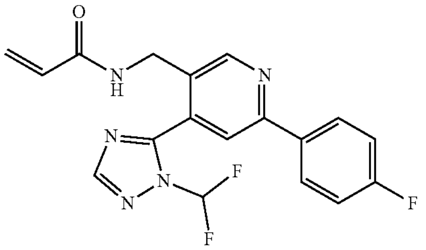 [SMILES: C=CC(=O)NCc1cnc(-c2ccc(F)cc2)cc1-c1ncnn1C(F)F] | N-((4-(1-(difluoromethyl)-1H-1,2,4-triazol-5-yl)-6-(4-fluorophenyl)pyridin-3-yl)methyl)acrylamide |
| 335 | 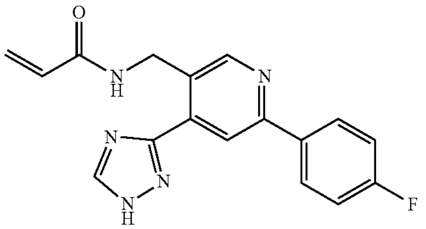 [SMILES: C=CC(=O)NCc1cnc(-c2ccc(F)cc2)cc1-c1nc[nH]n1] | N-((6-(4-fluorophenyl)-4-(1H-1,2,4-triazol-3-yl)pyridin-3-yl)methyl)acrylamide |

TABLE 1-continued

| Structures of example compounds of the disclosure and their respective codes | | |
|---|---|---|
| Cpd. No. | Structure | Name |
| 336 | 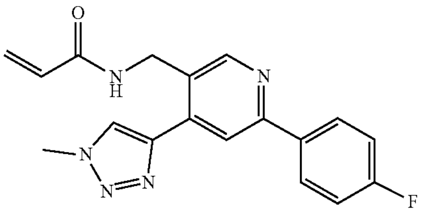 [SMILES: C=CC(=O)NCc1cnc(-c2ccc(F)cc2)cc1-c1cn(C)nn1] | N-((6-(4-fluorophenyl)-4-(1-methyl-1H-1,2,3-triazol-4-yl)pyridin-3-yl)methyl)acrylamide |
| 337 | 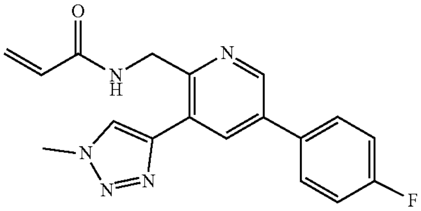 [SMILES: C=CC(=O)NCc1ncc(-c2ccc(F)cc2)cc1-c1cn(C)nn1] | N-((5-(4-fluorophenyl)-3-(1-methyl-1H-1,2,3-triazol-4-yl)pyridin-2-yl)methyl)acrylamide |
| 338 | 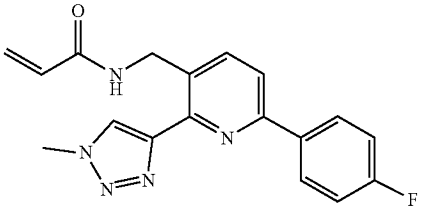 [SMILES: C=CC(=O)NCc1ccc(-c2ccc(F)cc2)nc1-c1cn(C)nn1] | N-((6-(4-fluorophenyl)-2-(1-methyl-1H-1,2,3-triazol-4-yl)pyridin-3-yl)methyl)acrylamide |
| 339 | 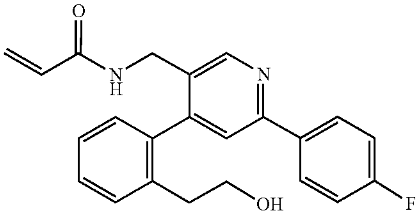 [SMILES: C=CC(=O)NCc1cnc(-c2ccc(F)cc2)cc1-c1ccccc1CCO] | N-((6-(4-fluorophenyl)-4-(2-(2-hydroxyethyl)phenyl)pyridin-3-yl)methyl)acrylamide |
| 340 | 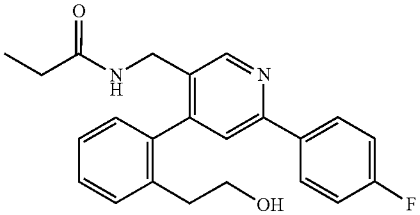 [SMILES: CCC(=O)NCc1cnc(-c2ccc(F)cc2)cc1-c1ccccc1CCO] | N-((6-(4-fluorophenyl)-4-(2-(2-hydroxyethyl)phenyl)pyridin-3-yl)methyl)propanionamide |
| 341 | 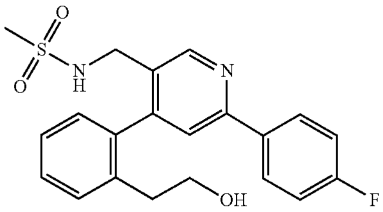 [SMILES: CS(=O)(=O)NCc1cnc(-c2ccc(F)cc2)cc1-c1ccccc1CCO] | N-((6-(4-fluorophenyl)-4-(2-(2-hydroxyethyl)phenyl)pyridin-3-yl)methyl)methanesulfonamide |

TABLE 1-continued

| Structures of example compounds of the disclosure and their respective codes | | |
|---|---|---|
| Cpd. No. | Structure | Name |
| 342 | 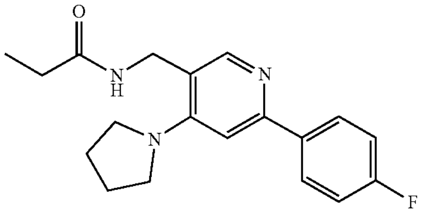 [SMILES: CCC(=O)NCc1cnc(-c2ccc(F)cc2)cc1N1CCCC1] | N-((6-(4-fluorophenyl)-4-(pyrrolidin-1-yl)pyridin-3-yl)methyl)propionamide |
| 343 | 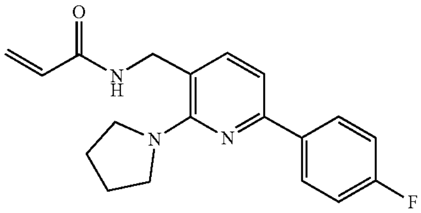 [SMILES: C=CC(=O)NCc1ccc(-c2ccc(F)cc2)nc1N1CCCC1] | N-((6-(4-fluorophenyl)-2-(pyrrolidin-1-yl)pyridin-3-yl)methyl)acrylamide |
| 344 | 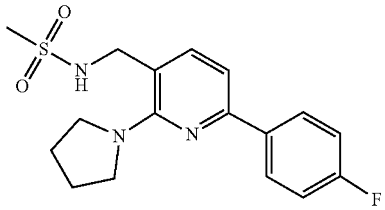 [SMILES: CS(=O)(=O)NCc1ccc(-c2ccc(F)cc2)nc1N1CCCC1] | N-((6-(4-fluorophenyl)-2-(pyrrolidin-1-yl)pyridin-3-yl)methyl)methanesulfonamide |
| 345 | 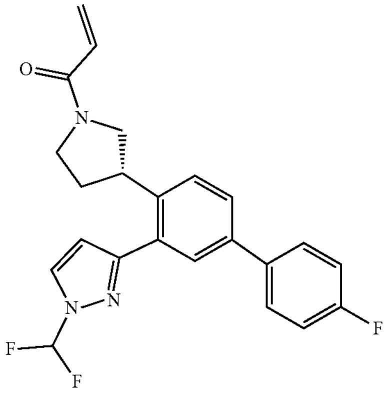 [SMILES: C=CC(=O)N1CC[C@@H](c2ccc(-c3ccc(F)cc3)cc2-c2ccn(C(F)F)n2)C1] | 1-[(3S)-3-[2-[1-(difluoromethyl)pyrazol-3-yl]-4-(4-fluorophenyl)phenyl]pyrrolidin-1-yl]prop-2-en-1-one |
| 346 | 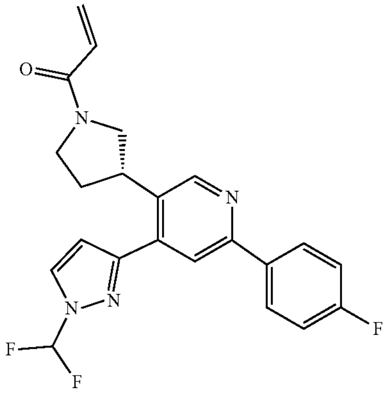 [SMILES: C=CC(=O)N1CC[C@@H](c2cnc(-c3ccc(F)cc3)cc2-c2ccn(C(F)F)n2)C1] | 1-[(3S)-3-[4-[1-(difluoromethyl)pyrazol-3-yl]-6-(4-fluorophenyl)-3-pyridyl]pyrrolidin-1-yl]prop-2-en-1-one |

TABLE 1-continued

Structures of example compounds of the disclosure and their respective codes

| Cpd. No. | Structure | Name |
|---|---|---|
| 347 | 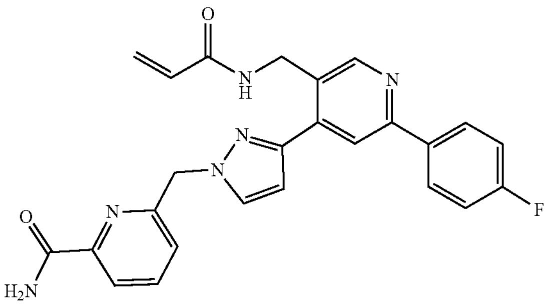 [SMILES: C=CC(=O)NCc1cnc(-c2ccc(F)cc2)cc1-c1ccn(Cc2cccc(C(N)=O)n2)n1] | 6-((3-(5-(acrylamidomethyl)-2-(4-fluorophenyl)pyridin-4-yl)-1H-pyrazol-1-yl)methyl)picolinamide |
| 348 | 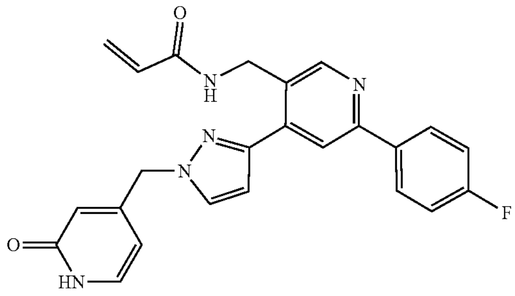 [SMILES: C=CC(=O)NCc1cnc(-c2ccc(F)cc2)cc1-c1ccn(Cc2cc[nH]c(=O)c2)n1] | N-((6-(4-fluorophenyl)-4-(1-((2-oxo-1,2-dihydropyridin-4-yl)methyl)-1H-pyrazol-3-yl)pyridin-3-yl)methyl)acrylamide |
| 349 | 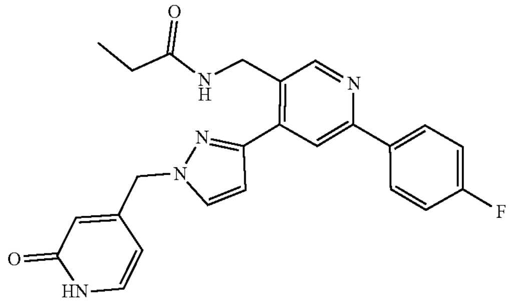 [SMILES: CCC(=O)NCc1cnc(-c2ccc(F)cc2)cc1-c1ccn(Cc2cc[nH]c(=O)c2)n1] | N-((6-(4-fluorophenyl)-4-(1-((2-oxo-1,2-dihydropyridin-4-yl)methyl)-1H-pyrazol-3-yl)pyridin-3-yl)methyl)propionamide |
| 350 | 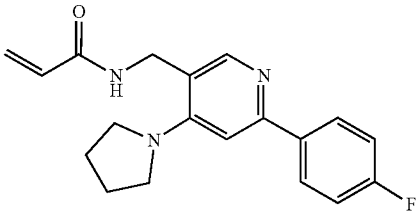 [SMILES: C=CC(=O)NCc1cnc(-c2ccc(F)cc2)cc1N1CCCC1] | N-((6-(4-fluorophenyl)-4-(pyrrolidin-1-yl)pyridin-3-yl)methyl)acrylamide |
| 351 | 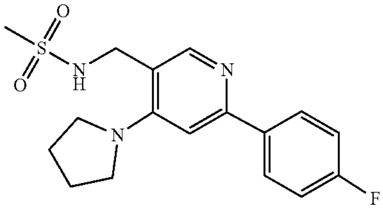 [SMILES: CS(=O)(=O)NCc1cnc(-c2ccc(F)cc2)cc1N1CCCC1] | N-((6-(4-fluorophenyl)-4-(pyrrolidin-1-yl)pyridin-3-yl)methyl)methanesulfonamide |

TABLE 1-continued

| Cpd. No. | Structure | Name |
|---|---|---|
| | Structures of example compounds of the disclosure and their respective codes | |
| 352 | 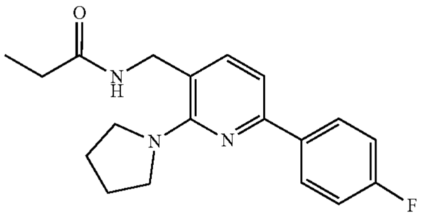 [SMILES: CCC(=O)NCc1ccc(-c2ccc(F)cc2)nc1N1CCCC1] | N-((6-(4-fluorophenyl)-2-(pyrrolidin-1-yl)pyridin-3-yl)methyl)propionamide |
| 353 | 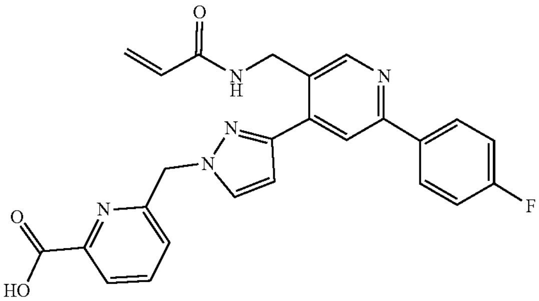 [SMILES: C=CC(=O)NCc1cnc(-c2ccc(F)cc2)cc1-c1ccn(Cc2cccc(C(=O)O)n2)n1] | 6-((3-(5-(acrylamidomethyl)-2-(4-fluorophenyl)pyridin-4-yl)-1H-pyrazol-1-yl)methyl)picolinic acid |
| 354 | 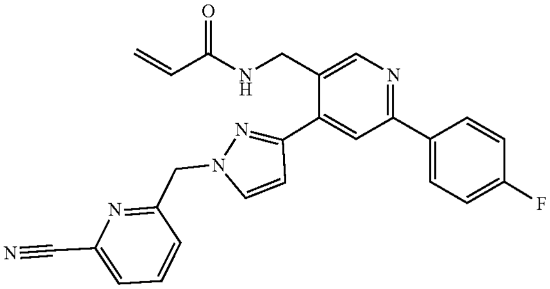 [SMILES: C=CC(=O)NCc1cnc(-c2ccc(F)cc2)cc1-c1ccn(Cc2cccc(C#N)n2)n1] | N-((4-(1-((6-cyanopyridin-2-yl)methyl)-1H-pyrazol-3-yl)-6-(4-fluorophenyl)pyridin-3-yl)methyl)acrylamide |
| 355 | 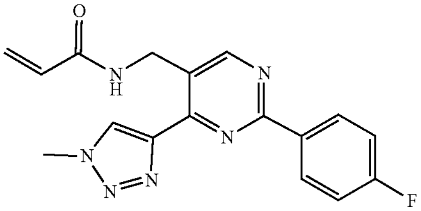 [SMILES: C=CC(=O)NCc1cnc(-c2ccc(F)cc2)nc1-c1cn(C)nn1] | N-((2-(4-fluorophenyl)-4-(1-methyl-1H-1,2,3-triazol-4-yl)pyrimidin-5-yl)methyl)acrylamide |
| 356 | 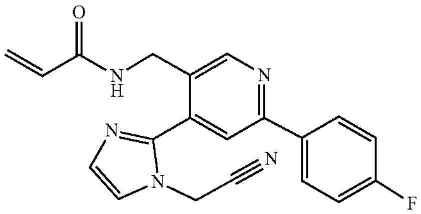 [SMILES: C=CC(=O)NCc1cnc(-c2ccc(F)cc2)cc1-c1nccn1CC#N] | N-((4-(1-(cyanomethyl)-1H-imidazol-2-yl)-6-(4-fluorophenyl)pyridin-3-yl)methyl)acrylamide |

TABLE 1-continued

Structures of example compounds of the disclosure and their respective codes

| Cpd. No. | Structure | Name |
| --- | --- | --- |
| 357 | 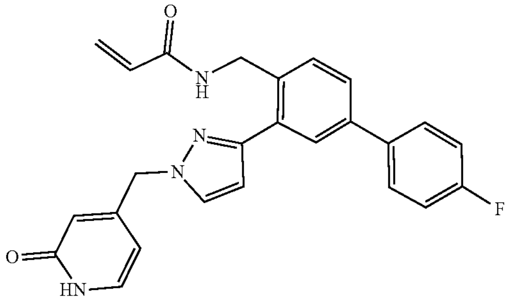 [SMILES: C=CC(=O)NCc1ccc(-c2ccc(F)cc2)cc1-c1ccn(Cc2cc[nH]c(=O)c2)n1] | N-((4'-fluoro-3-(1-((2-oxo-1,2-dihydropyridin-4-yl)methyl)-1H-pyrazol-3-yl)-[1,1'-biphenyl]-4-yl)methyl)acrylamide |
| 358 | 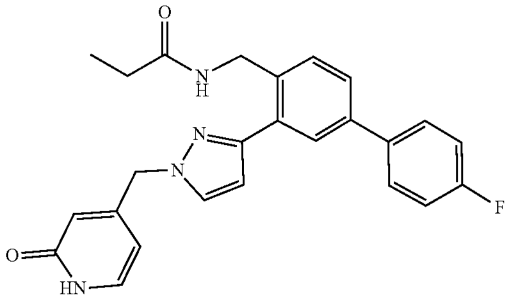 [SMILES: CCC(=O)NCc1ccc(-c2ccc(F)cc2)cc1-c1ccn(Cc2cc[nH]c(=O)c2)n1] | N-((4'-fluoro-3-(1-((2-oxo-1,2-dihydropyridin-4-yl)methyl)-1H-pyrazol-3-yl)-[1,1'-biphenyl]-4-yl)methyl)propionamide |
| 359 | 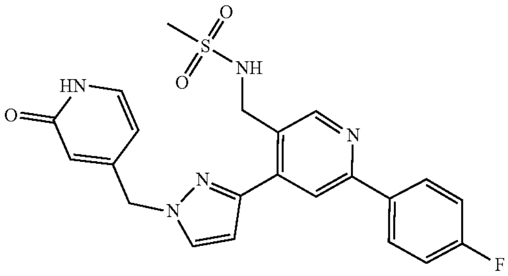 [SMILES: CS(=O)(=O)NCc1cnc(-c2ccc(F)cc2)cc1-c1ccn(Cc2cc[nH]c(=O)c2)n1] | N-((6-(4-fluorophenyl)-4-(1-((2-oxo-1,2-dihydropyridin-4-yl)methyl)-1H-pyrazol-3-yl)pyridin-3-yl)methyl)methanesulfonamide |
| 360 | 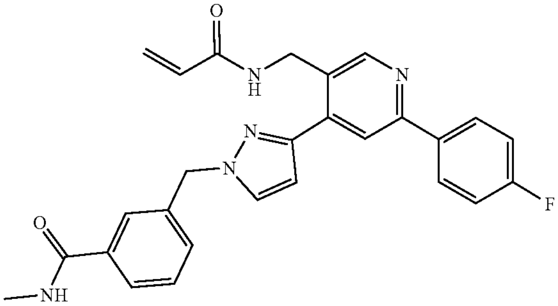 [SMILES: C=CC(=O)NCc1cnc(-c2ccc(F)cc2)cc1-c1ccn(Cc2cccc(C(=O)NC)c2)n1] | 3-((3-(5-(acrylamidomethyl)-2-(4-fluorophenyl)pyridin-4-yl)-1H-pyrazol-1-yl)methyl)-N-methylbenzamide |
| 361 | 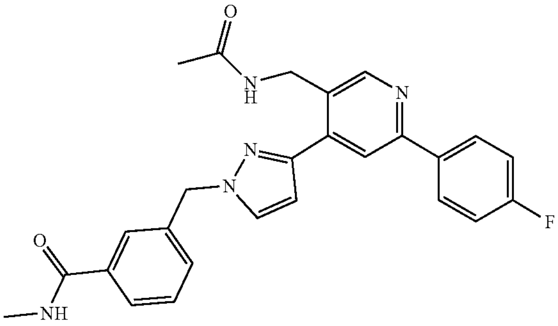 [SMILES: CNC(=O)c1cccc(Cn2ccc(-c3cc(-c4ccc(F)cc4)ncc3CNC(C)=O)n2)c1] | 3-((3-(5-(acetamidomethyl)-2-(4-fluorophenyl)pyridin-4-yl)-1H-pyrazol-1-yl)methyl)-N-methylbenzamide |

TABLE 1-continued

| Cpd. No. | Structure | Name |
|---|---|---|
| 362 | 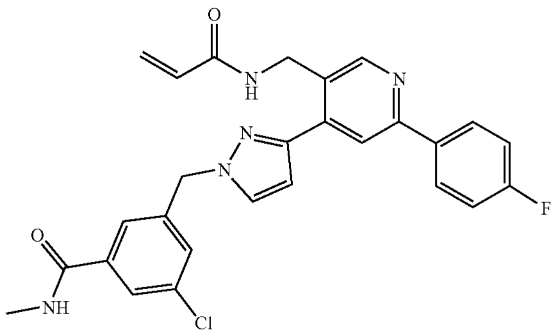 [SMILES: C=CC(=O)NCc1cnc(-c2ccc(F)cc2)cc1-c1ccn(Cc2cc(Cl)cc(C(=O)NC)c2)n1] | 3-((3-(5-(acrylamidomethyl)-2-(4-fluorophenyl)pyridin-4-yl)-1H-pyrazol-1-yl)methyl)-5-chloro-N-methylbenzamide |
| 363 | 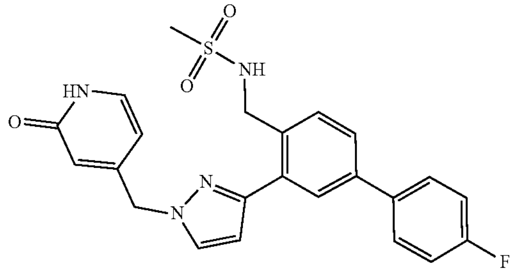 [SMILES: CS(=O)(=O)NCc1ccc(-c2ccc(F)cc2)cc1-c1ccn(Cc2cc[nH]c(=O)c2)n1] | N-((4'-fluoro-3-(1-((2-oxo-1,2-dihydropyridin-4-yl)methyl)-1H-pyrazol-3-yl)-[1,1'-biphenyl]-4-yl)methyl)methanesulfonamide |
| 364 | 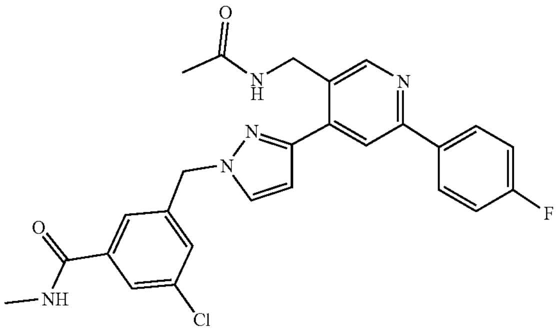 [SMILES: CNC(=O)c1cc(Cl)cc(Cn2ccc(-c3cc(-c4ccc(F)cc4)ncc3CNC(C)=O)n2)c1] | 3-((3-(5-(acetamidomethyl)-2-(4-fluorophenyl)pyridin-4-yl)-1H-pyrazol-1-yl)methyl)-5-chloro-N-methylbenzamide |
| 365 | 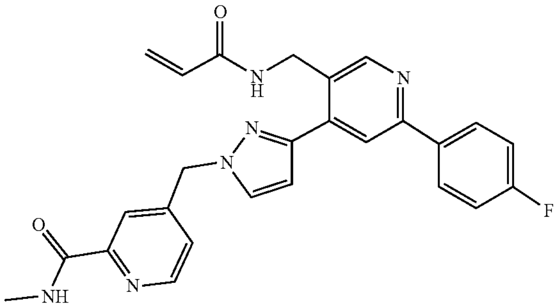 [SMILES: C=CC(=O)NCc1cnc(-c2ccc(F)cc2)cc1-c1ccn(Cc2ccnc(C(=O)NC)c2)n1] | 4-((3-(5-(acrylamidomethyl)-2-(4-fluorophenyl)pyridin-4-yl)-1H-pyrazol-1-yl)methyl)-N-methylpicolinamide |
| 366 | 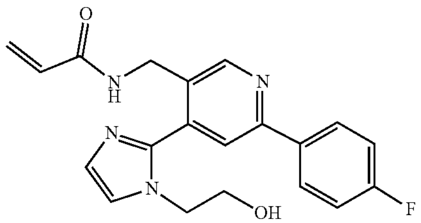 [SMILES: C=CC(=O)NCc1cnc(-c2ccc(F)cc2)cc1-c1nccn1CCO] | N-((6-(4-fluorophenyl)-4-(1-(2-hydroxyethyl)-1H-imidazol-2-yl)pyridin-3-yl)methyl)acrylamide |

Structures of example compounds of the disclosure and their respective codes

TABLE 1-continued

| Structures of example compounds of the disclosure and their respective codes | | |
|---|---|---|
| Cpd. No. | Structure | Name |
| 367 | 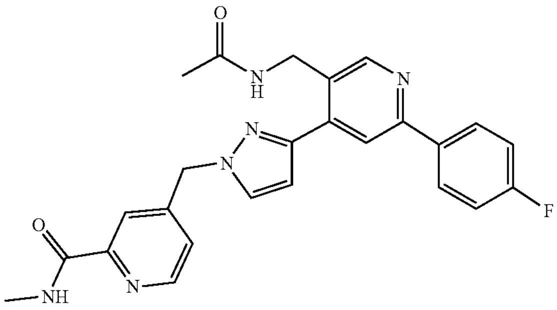 [SMILES: CNC(=O)c1cc(Cn2ccc(-c3cc(-c4ccc(F)cc4)ncc3CNC(C)=O)n2)ccn1] | 4-((3-(5-(acetamidomethyl)-2-(4-fluorophenyl)pyridin-4-yl)-1H-pyrazol-1-yl)methyl)-N-methylpicolinamide |
| 368 | 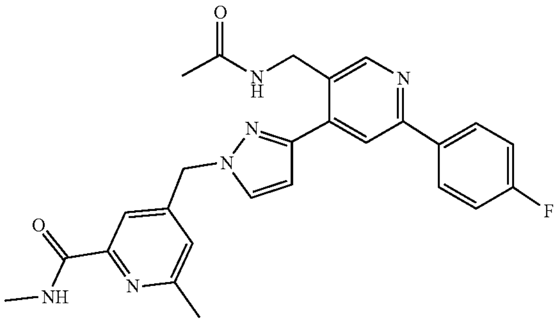 [SMILES: CNC(=O)c1cc(Cn2ccc(-c3cc(-c4ccc(F)cc4)ncc3CNC(C)=O)n2)cc(C)n1] | 4-((3-(5-(acrylamidomethyl)-2-(4-fluorophenyl)pyridin-4-yl)-1H-pyrazol-1-yl)methyl)-N,6-dimethylpicolinamide |
| 369 | 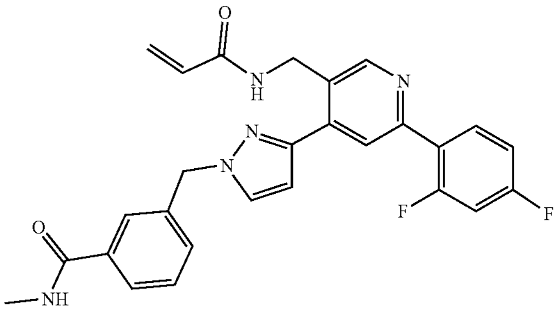 [SMILES: C=CC(=O)NCc1cnc(-c2ccc(F)cc2F)cc1-c1ccn(Cc2cccc(C(=O)NC)c2)n1] | 3-((3-(5-(acrylamidomethyl)-2-(2,4-difluorophenyl)pyridin-4-yl)-1H-pyrazol-1-yl)methyl)-N-methylbenzamide |
| 370 | 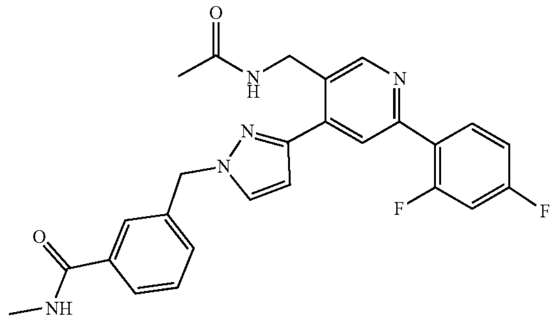 [SMILES: CNC(=O)c1cccc(Cn2ccc(-c3cc(-c4ccc(F)cc4F)ncc3CNC(C)=O)n2)c1] | 3-((3-(5-(acetamidomethyl)-2-(2,4-difluorophenyl)pyridin-4-yl)-1H-pyrazol-1-yl)methyl)-N-methylbenzamide |

TABLE 1-continued

| Cpd. No. | Structure | Name |
|---|---|---|
| | Structures of example compounds of the disclosure and their respective codes | |
| 371 | 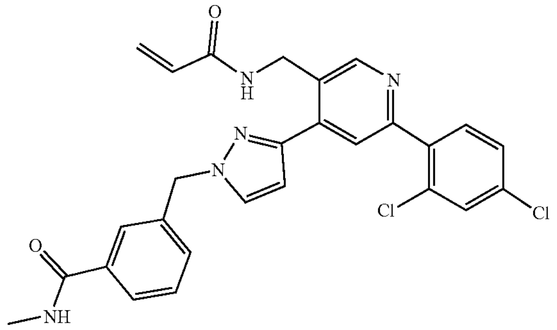 [SMILES: C=CC(=O)NCc1cnc(-c2ccc(Cl)cc2Cl)cc1-c1ccn(Cc2cccc(C(=O)NC)c2)n1] | 3-((3-(5-(acrylamidomethyl)-2-(2,4-dichlorophenyl)pyridin-4-yl)-1H-pyrazol-1-yl)methyl)-N-methylbenzamide |
| 372 | 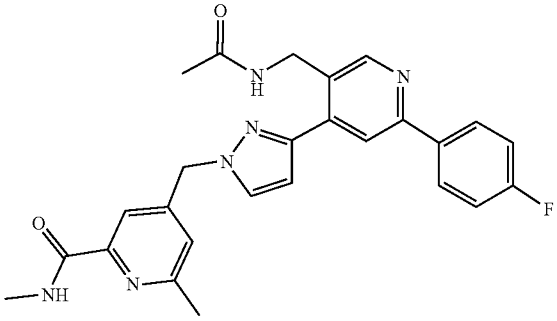 [SMILES: CNC(=O)c1cc(Cn2ccc(-c3cc(-c4ccc(F)cc4)ncc3CNC(C)=O)n2)cc(C)n1] | 4-((3-(5-(acetamidomethyl)-2-(4-fluorophenyl)pyridin-4-yl)-1H-pyrazol-1-yl)methyl)-N,6-dimethylpicolinamide |
| 373 | 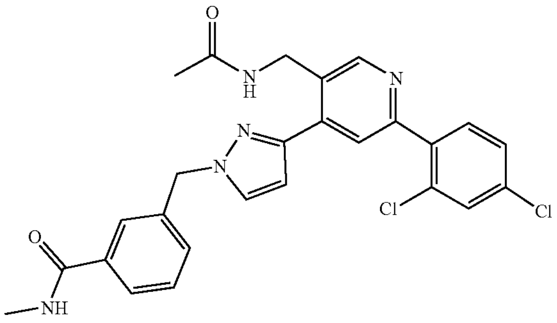 [SMILES: CNC(=O)c1cccc(Cn2ccc(-c3cc(-c4ccc(Cl)cc4Cl)ncc3CNC(C)=O)n2)c1] | 3-((3-(5-(acetamidomethyl)-2-(2,4-dichlorophenyl)pyridin-4-yl)-1H-pyrazol-1-yl)methyl)-N-methylbenzamide |
| 374 | 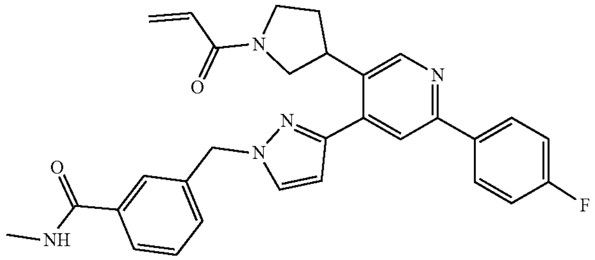 [SMILES: C=CC(=O)N1CCC(c2cnc(-c3ccc(F)cc3)cc2-c2ccn(Cc3cccc(C(=O)NC)c3)n2)C1] | 3-((3-(5-(1-acryloylpyrrolidin-3-yl)-2-(4-fluorophenyl)pyridin-4-yl)-1H-pyrazol-1-yl)methyl)-N-methylbenzamide |
| 375 | 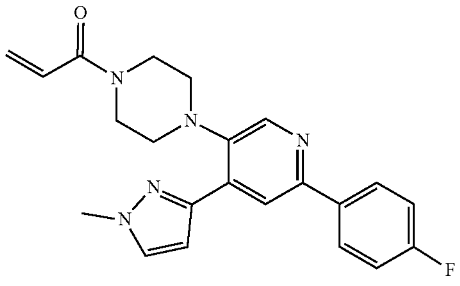 [SMILES: C=CC(=O)N1CCN(c2cnc(-c3ccc(F)cc3)cc2-c2ccn(C)n2)CC1] | 1-(4-(6-(4-fluorophenyl)-4-(1-methyl-1H-pyrazol-3-yl)pyridin-3-yl)piperazin-1-yl)prop-2-en-1-one |

TABLE 1-continued

| Structures of example compounds of the disclosure and their respective codes | | |
|---|---|---|
| Cpd. No. | Structure | Name |
| 376 | 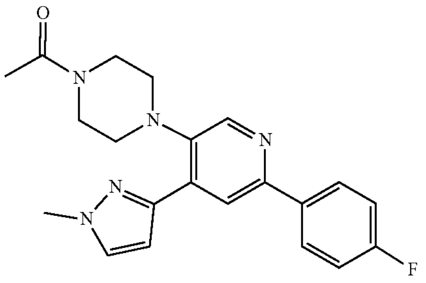 [SMILES: CC(=O)N1CCN(c2cnc(-c3ccc(F)cc3)cc2-c2ccn(C)n2)CC1] | 1-(4-(6-(4-fluorophenyl)-4-(1-methyl-1H-pyrazol-3-yl)pyridin-3-yl)piperazin-1-yl)ethan-1-one |
| 377 | 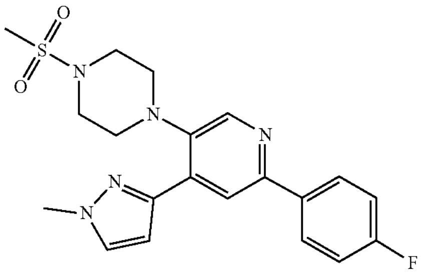 [SMILES: Cn1ccc(-c2cc(-c3ccc(F)cc3)ncc2N2CCN(S(C)(=O)=O)CC2)n1] | 1-(6-(4-fluorophenyl)-4-(1-methyl-1H-pyrazol-3-yl)pyridin-3-yl)-4-(methylsulfonyl)piperazine |
| 378 | 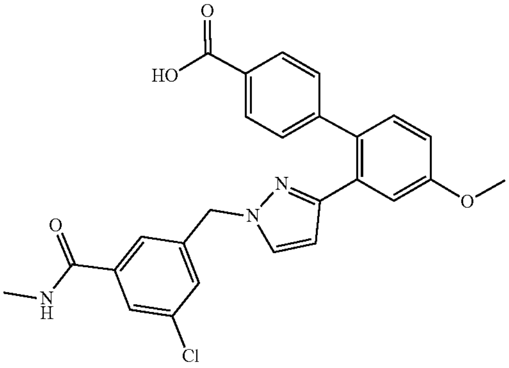 | 2'-(1-(3-chloro-5-(methylcarbamoyl)benzyl)-1H-pyrazol-3-yl)-4'-methoxy-[1,1'-biphenyl]-4-carboxylic acid |
| 379 | 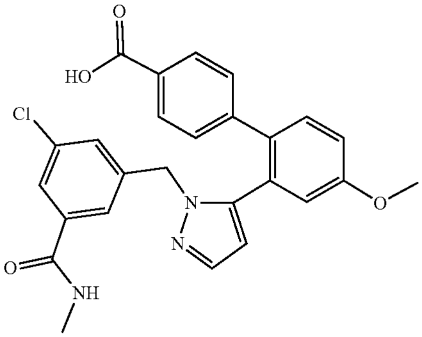 [SMILES: CNC(=O)c1cc(Cl)cc(Cn2nccc2-c2cc(OC)ccc2-c2ccc(C(=O)O)cc2)c1] | 2'-(1-(3-chloro-5-(methylcarbamoyl)benzyl)-1H-pyrazol-5-yl)-4'-methoxy-[1,1'-biphenyl]-4-carboxylic acid |

TABLE 1-continued

| Cpd. No. | Structure | Name |
|---|---|---|
| | Structures of example compounds of the disclosure and their respective codes | |
| 380 | 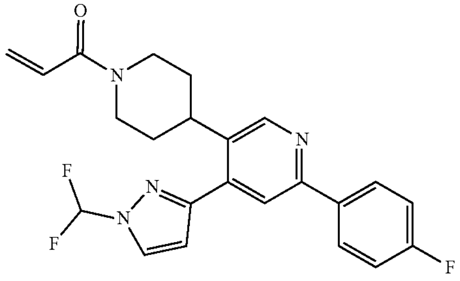 [SMILES: C=CC(=O)N1CCC(c2cnc(-c3ccc(F)cc3)cc2-c2ccn(C(F)F)n2)CC1] | 1-(4-(4-(1-(difluoromethyl)-1H-pyrazol-3-yl)-6-(4-fluorophenyl)pyridin-3-yl)piperidin-1-yl)prop-2-en-1-one |
| 381 | 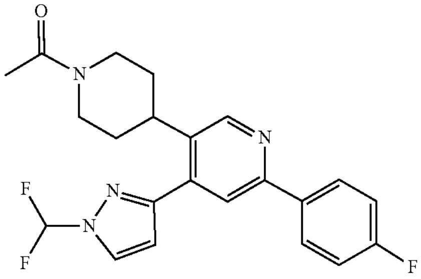 [SMILES: CC(=O)N1CCC(c2cnc(-c3ccc(F)cc3)cc2-c2ccn(C(F)F)n2)CC1] | 1-(4-(4-(1-(difluoromethyl)-1H-pyrazol-3-yl)-6-(4-fluorophenyl)pyridin-3-yl)piperidin-1-yl)ethan-1-one |
| 382 | 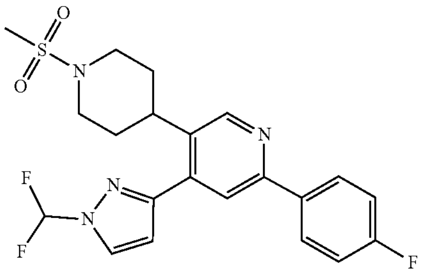 [SMILES: CS(=O)(=O)N1CCC(c2cnc(-c3ccc(F)cc3)cc2-c2ccn(C(F)F)n2)CC1] | 4-(1-(difluoromethyl)-1H-pyrazol-3-yl)-2-(4-fluorophenyl)-5-(1-(methylsulfonyl)piperidin-4-yl)pyridine |
| 383 | 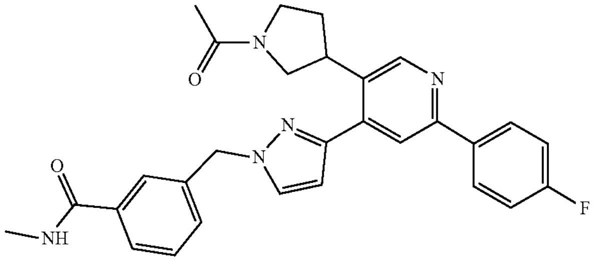 [SMILES: CNC(=O)c1cccc(Cn2ccc(-c3cc(-c4ccc(F)cc4)ncc3C3CCN(C(C)=O)C3)n2)c1] | 3-((3-(5-(1-acetylpyrrolidin-3-yl)-2-(4-fluorophenyl)pyridin-4-yl)-1H-pyrazol-1-yl)methyl)-N-methylbenzamide |
| 384 | 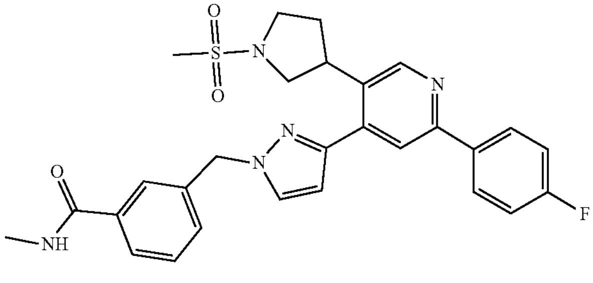 [SMILES: CNC(=O)c1cccc(Cn2ccc(-c3cc(-c4ccc(F)cc4)ncc3C3CCN(S(C)(=O)=O)C3)n2)c1] | 3-((3-(2-(4-fluorophenyl)-5-(1-(methylsulfonyl)pyrrolidin-3-yl)pyridin-4-yl)-1H-pyrazol-1-yl)methyl)-N-methylbenzamide |

TABLE 1-continued

| Cpd. No. | Structure | Name |
|---|---|---|
| 385 | 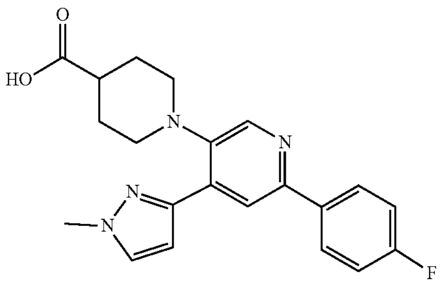 [SMILES: Cn1ccc(-c2cc(-c3ccc(F)cc3)ncc2N2CCC(C(=O)O)CC2)n1] | 1-(6-(4-fluorophenyl)-4-(1-methyl-1H-pyrazol-3-yl)pyridin-3-yl)piperidine-4-carboxylic acid |
| 386 | 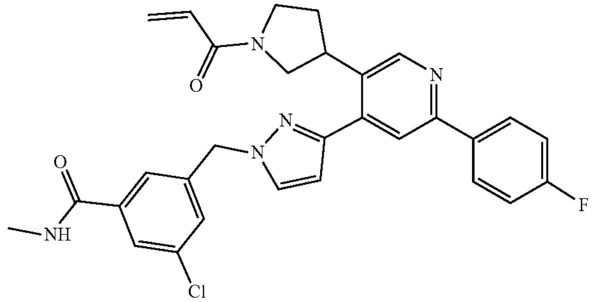 [SMILES: C=CC(=O)N1CCC(c2cnc(-c3ccc(F)cc3)cc2-c2ccn(Cc3cc(Cl)cc(C(=O)NC)c3)n2)C1] | 3-((3-(5-(1-acryloylpyrrolidin-3-yl)-2-(4-fluorophenyl)pyridin-4-yl)-1H-pyrazol-1-yl)methyl)-5-chloro-N-methylbenzamide |
| 387 | 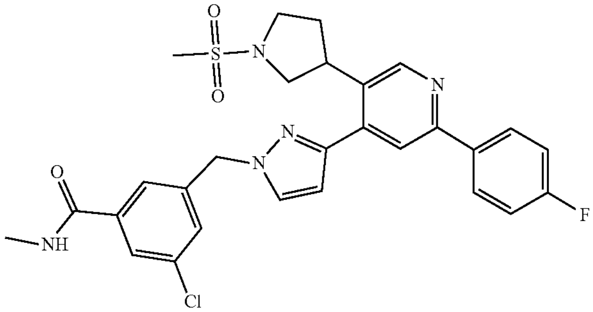 [SMILES: CNC(=O)c1cc(Cl)cc(Cn2ccc(-c3cc(-c4ccc(F)cc4)ncc3C3CCN(S(C)(=O)=O)C3)n2)c1] | 3-chloro-5-((3-(2-(4-fluorophenyl)-5-(1-(methylsulfonyl)pyrrolidin-3-yl)pyridin-4-yl)-1H-pyrazol-1-yl)methyl)-N-methylbenzamide |
| 388 | 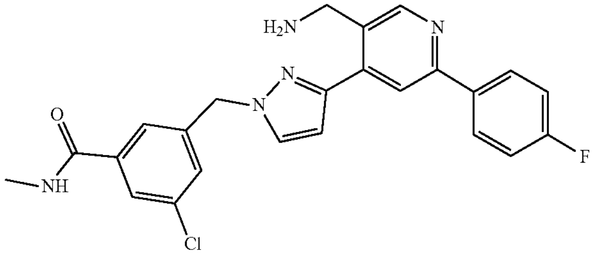 [SMILES: CNC(=O)c1cc(Cl)cc(Cn2ccc(-c3cc(-c4ccc(F)cc4)ncc3CN)n2)c1] | 3-((3-(5-(aminomethyl)-2-(4-fluorophenyl)pyridin-4-yl)-1H-pyrazol-1-yl)methyl)-5-chloro-N-methylbenzamide |
| 389 | 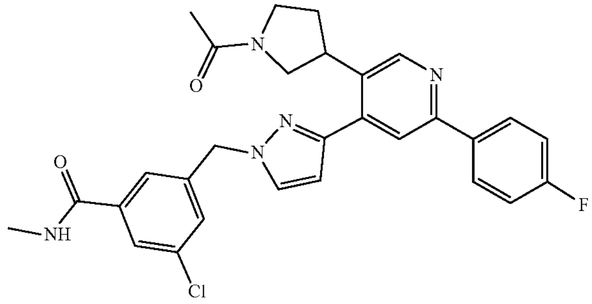 [SMILES: CNC(=O)c1cc(Cl)cc(Cn2ccc(-c3cc(-c4ccc(F)cc4)ncc3C3CCN(C(C)=O)C3)n2)c1] | 3-((3-(5-(1-acetylpyrrolidin-3-yl)-2-(4-fluorophenyl)pyridin-4-yl)-1H-pyrazol-1-yl)methyl)-5-chloro-N-methylbenzamide |

Structures of example compounds of the disclosure and their respective codes

TABLE 1-continued

| Structures of example compounds of the disclosure and their respective codes | | |
|---|---|---|
| Cpd. No. | Structure | Name |
| 390 | 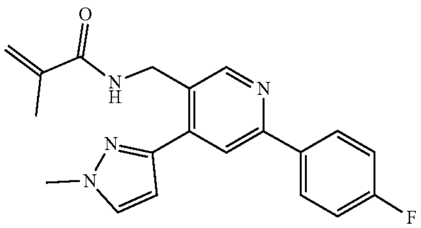 [SMILES: C=C(C)C(=O)NCc1cnc(-c2ccc(F)cc2)cc1-c1ccn(C)n1] | N-((6-(4-fluorophenyl)-4-(1-methyl-1H-pyrazol-3-yl)pyridin-3-yl)methylacrylamide |
| 391 | 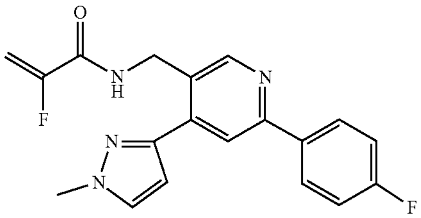 [SMILES: C=C(F)C(=O)NCc1cnc(-c2ccc(F)cc2)cc1-c1ccn(C)n1] | 2-fluoro-N-((6-(4-fluorophenyl)-4-(1-methyl-1H-pyrazol-3-yl)pyridin-3-yl)methyl)methacrylamide |
| 392 | 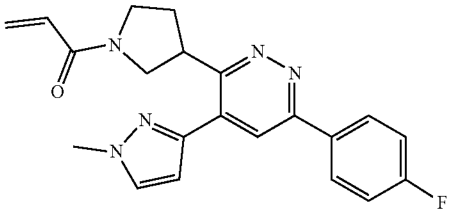 [SMILES: C=CC(=O)N1CCC(c2nnc(-c3ccc(F)cc3)cc2-c2ccn(C)n2)C1] | 1-(3-(6-(4-fluorophenyl)-4-(1-methyl-1H-pyrazol-3-yl)pyridazin-3-yl)pyrrolidin-1-yl)prop-2-en-1-one |
| 393 | 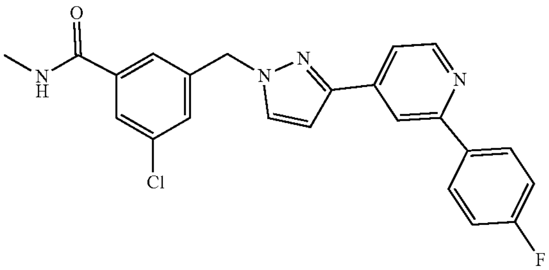 [SMILES: CNC(=O)c1cc(Cl)cc(Cn2ccc(-c3ccnc(-c4ccc(F)cc4)c3)n2)c1] | 3-chloro-5-((3-(2-(4-fluorophenyl)pyridin-4-yl)-1H-pyrazol-1-yl)methyl)-N-methylbenzamide |
| 394 | 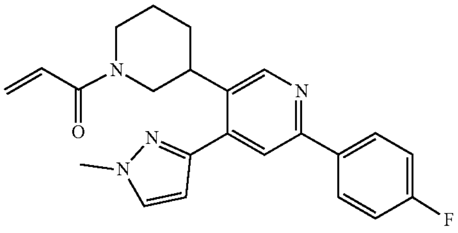 [SMILES: C=CC(=O)N1CCCC(c2cnc(-c3ccc(F)cc3)cc2-c2ccn(C)n2)C1] | 1-(3-(6-(4-fluorophenyl)-4-(1-methyl-1H-pyrazol-3-yl)pyridin-3-yl)piperidin-1-yl)prop-2-en-1-one |
| 395 | 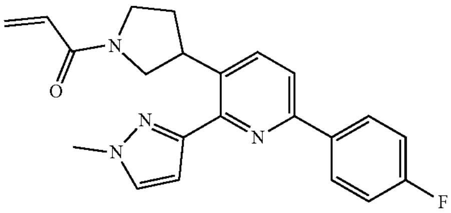 [SMILES: C=CC(=O)N1CCC(c2ccc(-c3ccc(F)cc3)nc2-c2ccn(C)n2)C1] | 1-(3-(6-(4-fluorophenyl)-2-(1-methyl-1H-pyrazol-3-yl)pyridin-3-yl)pyrrolidin-1-yl)prop-2-en-1-one |

TABLE 1-continued

| Structures of example compounds of the disclosure and their respective codes | | |
|---|---|---|
| Cpd. No. | Structure | Name |
| 396 | 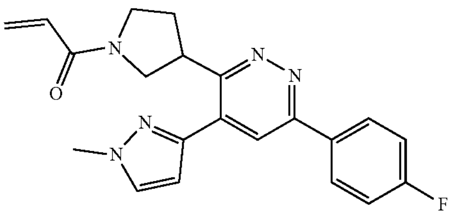 [SMILES: C=CC(=O)N1CCC(c2nnc(-c3ccc(F)cc3)cc2-c2ccn(C)n2)C1] | 1-(3-(6-(4-fluorophenyl)-4-(1-methyl-1H-pyrazol-3-yl)pyridazin-3-yl)pyrrolidin-1-yl)prop-2-en-1-one |
| 396-En1 | 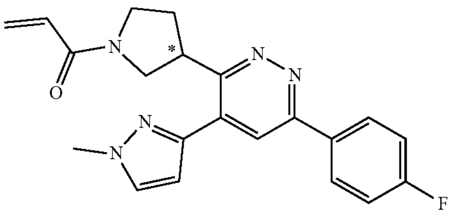 [SMILES: C=CC(=O)N1CCC(c2nnc(-c3ccc(F)cc3)cc2-c2ccn(C)n2)C1] | 1-(3-(6-(4-fluorophenyl)-4-(1-methyl-1H-pyrazol-3-yl)pyridazin-3-yl)pyrrolidin-1-yl)prop-2-en-1-one |
| 396-En2 | 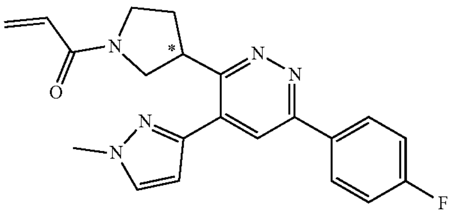 [SMILES: C=CC(=O)N1CCC(c2nnc(-c3ccc(F)cc3)cc2-c2ccn(C)n2)C1] | 1-(3-(6-(4-fluorophenyl)-4-(1-methyl-1H-pyrazol-3-yl)pyridazin-3-yl)pyrrolidin-1-yl)prop-2-en-1-one |
| 397 | 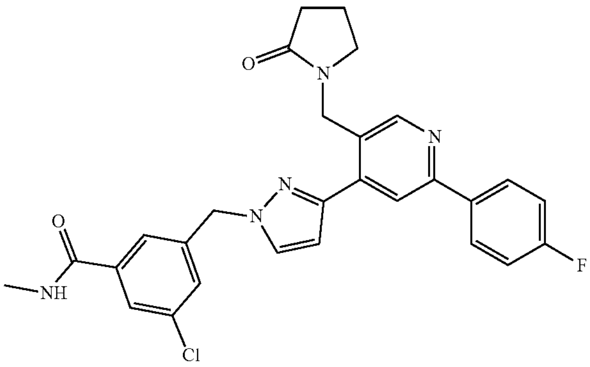 [SMILES: CNC(=O)c1cc(Cl)cc(Cn2ccc(-c3cc(-c4ccc(F)cc4)ncc3CN3CCCC3=O)n2)c1] | 3-chloro-5-((3-(2-(4-fluorophenyl)-5-((2-oxopyrrolidin-1-yl)methyl)pyridin-4-yl)-1H-pyrazol-1-yl)methyl-N-methylbenzamide |
| 398 | 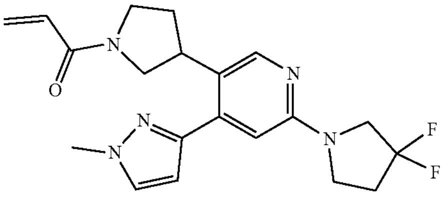 [SMILES: C=CC(=O)N1CCC(c2cnc(N3CCC(F)(F)C3)cc2-c2ccn(C)n2)C1] | 1-(3-(6-(3,3-difluoropyrrolidin-1-yl)-4-(1-methyl-1H-pyrazol-3-yl)pyridin-3-yl)pyrrolidin-1-yl)prop-2-en-1-one |
| 399 | 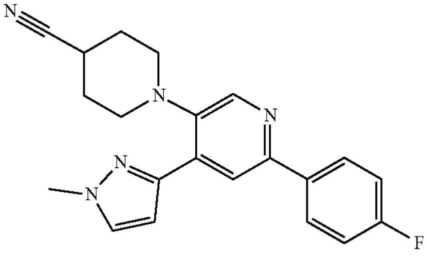 [SMILES: Cn1ccc(-c2cc(-c3ccc(F)cc3)ncc2N2CCC(C#N)CC2)n1] | 1-(6-(4-fluorophenyl)-4-(1-methyl-1H-pyrazol-3-yl)pyridin-3-yl)piperidine-4-carbonitrile |

TABLE 1-continued

| Cpd. No. | Structure | Name |
|---|---|---|
| Structures of example compounds of the disclosure and their respective codes | | |
| 400 | 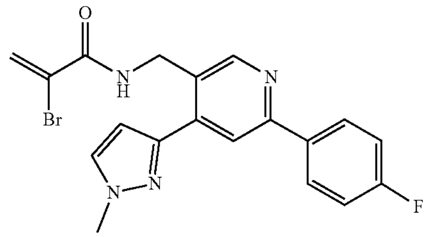 [SMILES: C=C(Br)C(=O)NCc1cnc(-c2ccc(F)cc2)cc1-c1ccn(C)n1] | 2-bromo-N-((6-(4-fluorophenyl)-4-(1-methyl-1H-pyrazol-3-yl)pyridin-yl)methyl)acrylamide |
| 401 | 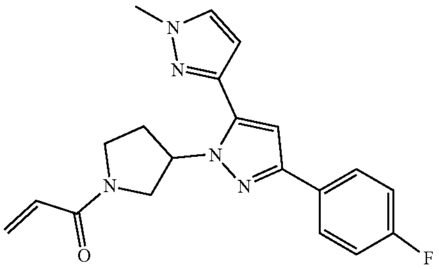 [SMILES: C=CC(=O)N1CCC(n2nc(-c3ccc(F)cc3)cc2-c2ccn(C)n2)C1] | 1-(3-(5'-(4-fluorophenyl)-1-methyl-1H,2'H-[3,3'-bipyrazol]-2'-yl)pyrrolidin-1-yl)prop-2-en-1-one |
| 401-En1 | 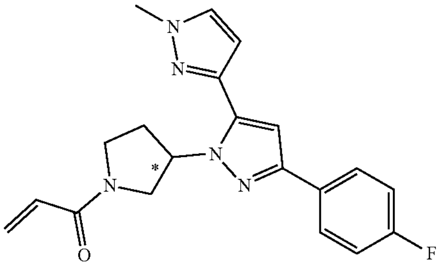 [SMILES: C=CC(=O)N1CCC(n2nc(-c3ccc(F)cc3)cc2-c2ccn(C)n2)C1] | (R)- or (S)-1-(3-(5'-(4-fluorophenyl)-1-methyl-1H,2'H-[3,3'-bipyrazol]-2'-yl)pyrrolidin-yl)prop-2-en-1-one |
| 401-En2 | 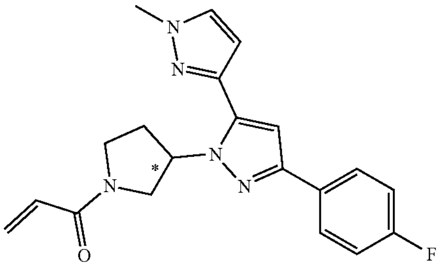 [SMILES: C=CC(=O)N1CCC(n2nc(-c3ccc(F)cc3)cc2-c2ccn(C)n2)C1] | (R)- or (S)-1-(3-(5'-(4-fluorophenyl)-1-methyl-1H,2'H-[3,3'-bipyrazol]-2'-yl)pyrrolidin-1-yl)prop-2-en-1-one |
| 402 | 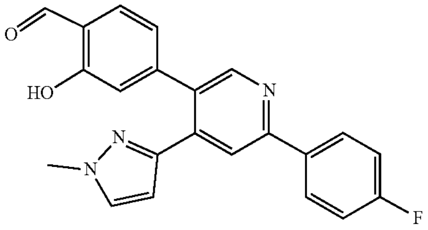 [SMILES: Cn1ccc(-c2cc(-c3ccc(F)cc3)ncc2-c2ccc(C=O)c(O)c2)n1] | 4-(6-(4-fluorophenyl)-4-(1-methyl-1H-pyrazol-3-yl)pyridin-3-yl)-2-hydroxybenzaldehyde |

TABLE 1-continued

Structures of example compounds of the disclosure and their respective codes

| Cpd. No. | Structure | Name |
| --- | --- | --- |
| 403 | 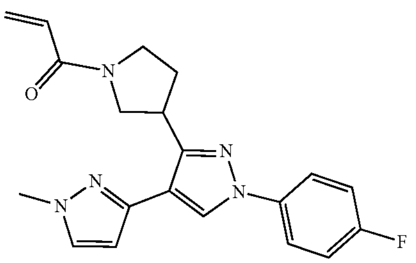 [SMILES: C=CC(=O)N1CCC(c2nn(-c3ccc(F)cc3)cc2-c2ccn(C)n2)C1] | 1-(3-(1'-(4-fluorophenyl)-1-methyl-1H,1'H-[3,4'-bipyrazol]-3'-yl)pyrrolidin-1-yl)prop-2-en-1-one |
| 404 | 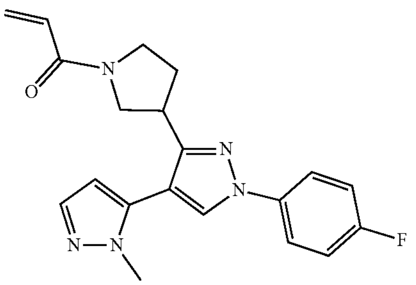 [SMILES: C=CC(=O)N1CCC(c2nn(-c3ccc(F)cc3)cc2-c2ccnn2C)C1] | 1-(3-(1'-(4-fluorophenyl)-2-methyl-1'H,2H-[3,4'-bipyrazol]-3'-yl)pyrrolidin-1-yl)prop-2-en-1-one |
| 405 | 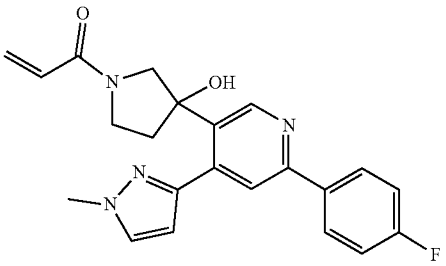 [SMILES: C=CC(=O)N1CCC(O)(c2cnc(-c3ccc(F)cc3)cc2-c2ccn(C)n2)C1] | 1-(3-(6-(4-fluorophenyl)-4-(1-methyl-1H-pyrazol-3-yl)pyridin-3-yl)-3-hydroxypyrrolidin-1-yl)prop-2-en-1-one |
| 406 | 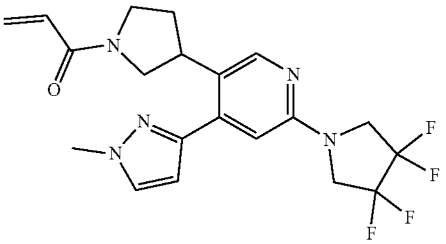 [SMILES: C=CC(=O)N1CCC(c2cnc(N3CC(F)(F)C(F)(F)C3)cc2-c2ccn(C)n2)C1] | 1-(3-(4-(1-methyl-1H-pyrazol-3-yl)-6-(3,3,4,4-tetrafluoropyrrolidin-1-yl)pyridin-3-yl)pyrrolidin-1-yl)prop-2-en-1-one |
| 407 | 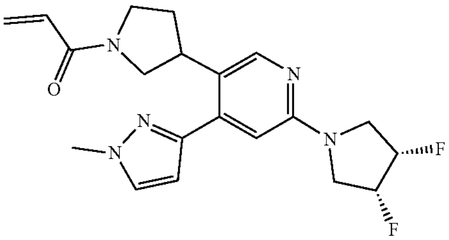 [SMILES: C=CC(=O)N1CCC(c2cnc(N3C[C@@H](F)[C@@H](F)C3)cc2-c2ccn(C)n2)C1] | 1-(3-(6-((cis)-3,4-difluoropyrrolidin-1-yl)-4-(1-methyl-1H-pyrazol-3-yl)pyridin-3-yl)pyrrolidin-1-yl)prop-2-en-1-one |

TABLE 1-continued

| Structures of example compounds of the disclosure and their respective codes | | |
|---|---|---|
| Cpd. No. | Structure | Name |
| 408 | 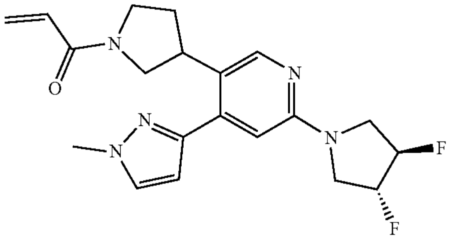 [SMILES: C=CC(=O)N1CCC(c2cnc(N3C[C@@H](F)[C@H](F)C3)cc2-c2ccn(C)n2)C1] | 1-(3-(6-((trans)-3,4-difluoropyrrolidin-1-yl)-4-(1-methyl-1H-pyrazol-3-yl)pyridin-3-yl)pyrrolidin-1-yl)prop-2-en-1-one |
| 409 | 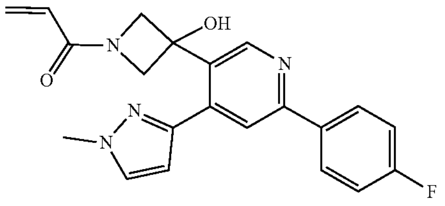 [SMILES: C=CC(=O)N1CC(O)(c2cnc(-c3ccc(F)cc3)cc2-c2ccn(C)n2)C1] | 1-(3-(6-(4-fluorophenyl)-4-(1-methyl-1H-pyrazol-3-yl)pyridin-3-yl)-3-hydroxyazetidin-1-yl)prop-2-en-1-one |
| 410 | 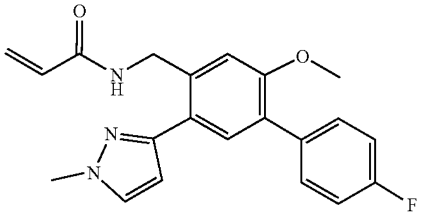 [SMILES: C=CC(=O)NCc1cc(OC)c(-c2ccc(F)cc2)cc1-c1ccn(C)n1] | N-((4'-fluoro-2-methoxy-5-(1-methyl-1H-pyrazol-3-yl)-[1,1'-biphenyl]-4-yl)methyl)acrylamide |
| 411 | 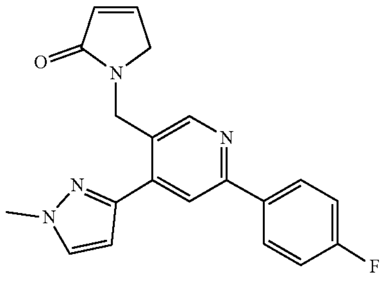 [SMILES: Cn1ccc(-c2cc(-c3ccc(F)cc3)ncc2CN2CC=CC2=O)n1] | 1-((6-(4-fluorophenyl)-4-(1-methyl-1H-pyrazol-3-yl)pyridin-3-yl)methyl)-1,5-dihydro-2H-pyrrol-2-one |
| 412 | 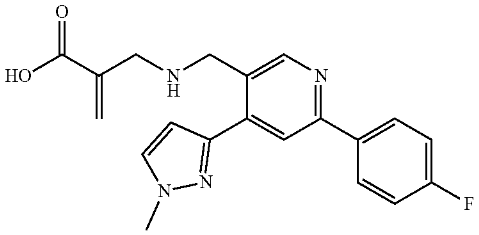 [SMILES: C=C(CNCc1cnc(-c2ccc(F)cc2)cc1-c1ccn(C)n1)C(=O)O] | 2-((((6-(4-fluorophenyl)-4-(1-methyl-1H-pyrazol-3-yl)pyridin-3-yl)methyl)amino)methyl)acrylic acid |
| 413 | 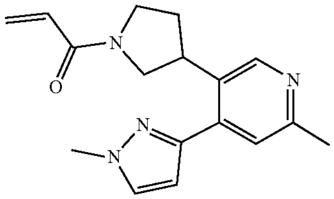 [SMILES: C=CC(=O)N1CCC(c2cnc(C)cc2-c2ccn(C)n2)C1] | 1-(3-(6-methyl-4-(1-methyl-1H-pyrazol-3-yl)pyridin-3-yl)pyrrolidin-1-yl)prop-2-en-1-one |

TABLE 1-continued

| Cpd. No. | Structure | Name |
|---|---|---|
| | Structures of example compounds of the disclosure and their respective codes | |
| 414 | 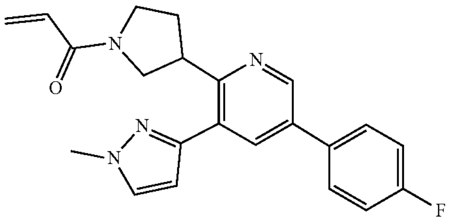 [SMILES: C=CC(=O)N1CCC(c2ncc(-c3ccc(F)cc3)cc2-c2ccn(C)n2)C1] | 1-(3-(5-(4-fluorophenyl)-3-(1-methyl-1H-pyrazol-3-yl)pyridin-2-yl)pyrrolidin-1-yl)prop-2-en-1-one |
| 415 | 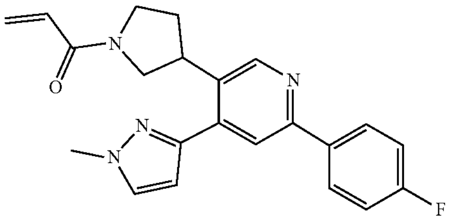 [SMILES: C=CC(=O)N1CCC(c2cnc(-c3ccc(F)cc3)cc2-c2ccn(C)n2)C1] | 1-(3-(6-(4-fluorophenyl)-4-(1-methyl-1H-pyrazol-3-yl)pyridin-3-yl)pyrrolidin-1-yl)prop-2-en-1-one |
| 416 | 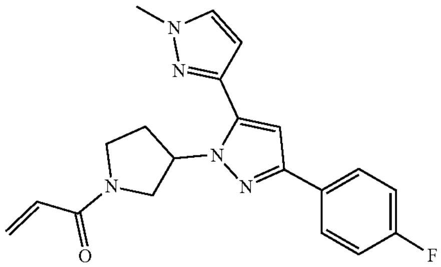 [SMILES: C=CC(=O)N1CCC(n2nc(-c3ccc(F)cc3)cc2-c2ccn(C)n2)C1] | 1-(3-(5'-(4-fluorophenyl)-1-methyl-1H,2'H-[3,3'-bipyrazol]-2'-yl)pyrrolidin-1-yl)prop-2-en-1-one |
| 417 | 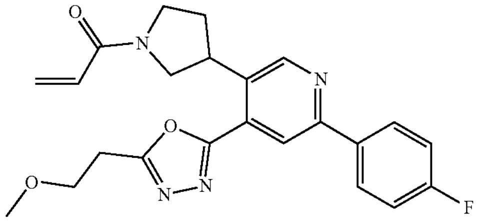 [SMILES: C=CC(=O)N1CCC(c2cnc(-c3ccc(F)cc3)cc2-c2nnc(CCOC)o2)C1] | 1-(3-(6-(4-fluorophenyl)-4-(5-(2-methoxyethyl)-1,3,4-oxadiazol-2-yl)pyridin-3-yl)pyrrolidin-1-yl)prop-2-en-1-one |
| 418 | 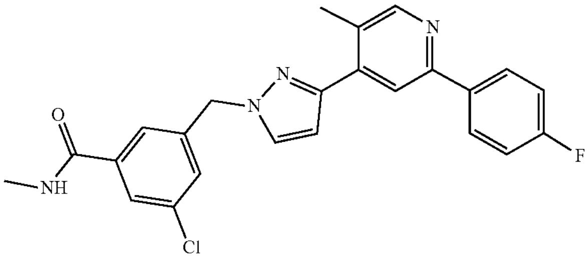 [SMILES: CNC(=O)c1cc(Cl)cc(Cn2ccc(-c3cc(-c4ccc(F)cc4)ncc3C)n2)c1] | 3-chloro-5-((3-(2-(4-fluorophenyl)-5-methylpyridin-4-yl)-1H-pyrazol-1-yl)methyl)-N-methylbenzamide |

TABLE 1-continued

| Structures of example compounds of the disclosure and their respective codes | | |
|---|---|---|
| Cpd. No. | Structure | Name |
| 419 | 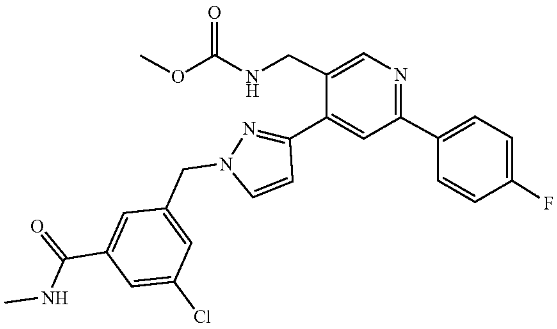 [SMILES: CNC(=O)c1cc(Cl)cc(Cn2ccc(-c3cc(-c4ccc(F)cc4)ncc3CNC(=O)OC)n2)c1] | methyl ((4-(1-(3-chloro-5-(methylcarbamoyl)benzyl)-1H-pyrazol-3-yl)-6-(4-fluorophenyl)pyridin-3-yl)methyl)carbamate |
| 420 | 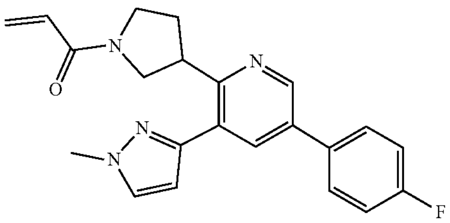 [SMILES: C=CC(=O)N1CCC(c2ncc(-c3ccc(F)cc3)cc2-c2ccn(C)n2)C1] | 1-(3-(5-(4-fluorophenyl)-3-(1-methyl-1H-pyrazol-3-yl)pyridin-2-yl)pyrrolidin-1-yl)prop-2-en-1-one |
| 420-En1 | 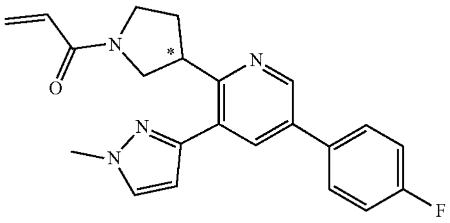 [SMILES: C=CC(=O)N1CCC(c2ncc(-c3ccc(F)cc3)cc2-c2ccn(C)n2)C1] | (R)- or (S)-1-(3-(5-(4-fluorophenyl)-3-(1-methyl-1H-pyrazol-3-yl)pyridin-2-yl)pyrrolidin-1-yl)prop-2-en-1-one |
| 420-En2 | 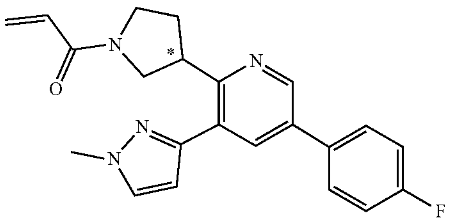 [SMILES: C=CC(=O)N1CCC(c2ncc(-c3ccc(F)cc3)cc2-c2ccn(C)n2)C1] | (R)- or (S)-1-(3-(5-(4-fluorophenyl)-3-(1-methyl-1H-pyrazol-3-yl)pyridin-2-yl)pyrrolidin-1-yl)prop-2-en-1-one |
| 421 | 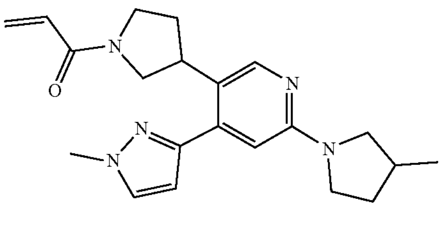 [SMILES: C=CC(=O)N1CCC(c2cnc(N3CCC(C)C3)cc2-c2ccn(C)n2)C1] | 1-(3-(4-(1-methyl-1H-pyrazol-3-yl)-6-(3-methylpyrrolidin-1-yl)pyridin-3-yl)pyrrolidin-1-yl)prop-2-en-1-one |
| 422 | 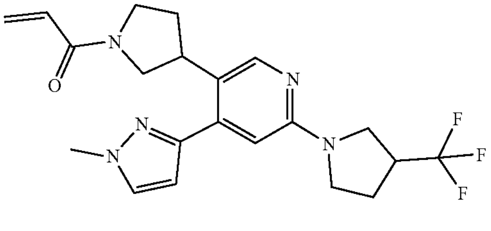 [SMILES: C=CC(=O)N1CCC(c2cnc(N3CCC(C(F)(F)F)C3)cc2-c2ccn(C)n2)C1] | 1-(3-(4-(1-methyl-1H-pyrazol-3-yl)-6-(3-(trifluoromethyl)pyrrolidin-1-yl)pyridin-3-yl)pyrrolidin-1-yl)prop-2-en-1-one |

TABLE 1-continued

| Cpd. No. | Structure | Name |
|---|---|---|
| 423 | 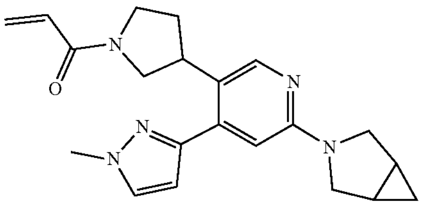 [SMILES: C=CC(=O)N1CCC(c2cnc(N3CC4CC4C3)cc2-c2ccn(C)n2)C1] | 1-(3-(6-(3-azabicyclo[3.1.0]hexan-3-yl)-4-(1-methyl-1H-pyrazol-3-yl)pyridin-3-yl)pyrrolidin-1-yl)prop-2-en-1-one |
| 424 | 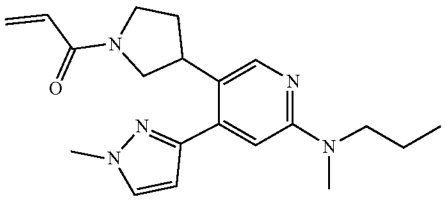 [SMILES: C=CC(=O)N1CCC(c2cnc(N(C)CCC)cc2-c2ccn(C)n2)C1] | 1-(3-(6-(methyl(propyl)amino)-4-(1-methyl-1H-pyrazol-3-yl)pyridin-3-yl)pyrrolidin-1-yl)prop-2-en-1-one |
| 425 | 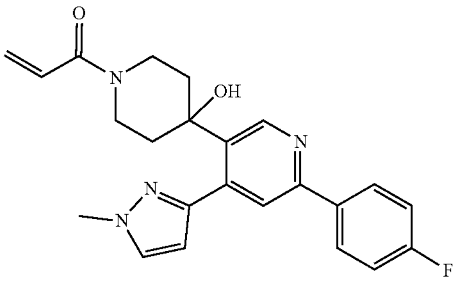 [SMILES: C=CC(=O)N1CCC(O)(c2cnc(-c3ccc(F)cc3)cc2-c2ccn(C)n2)CC1] | 1-(4-(6-(4-fluorophenyl)-4-(1-methyl-1H-pyrazol-3-yl)pyridin-3-yl)-4-hydroxypiperidin-1-yl)prop-2-en-1-one |
| 426 | 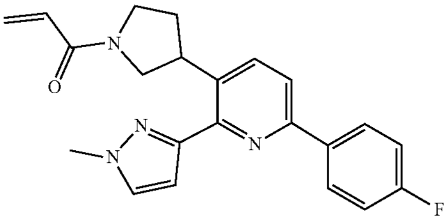 [SMILES: C=CC(=O)N1CCC(c2ccc(-c3ccc(F)cc3)nc2-c2ccn(C)n2)C1] | 1-(3-(6-(4-fluorophenyl)-2-(1-methyl-1H-pyrazol-3-yl)pyridin-3-yl)pyrrolidin-1-yl)prop-2-en-1-one |
| 426-En1 | 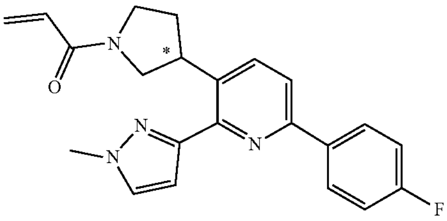 [SMILES: C=CC(=O)N1CCC(c2ccc(-c3ccc(F)cc3)nc2-c2ccn(C)n2)C1] | (R)- or (S)-1-(3-(6-(4-fluorophenyl)-2-(1-methyl-1H-pyrazol-3-yl)pyridin-3-yl)pyrrolidin-1-yl)prop-2-en-1-one |
| 426-En2 | 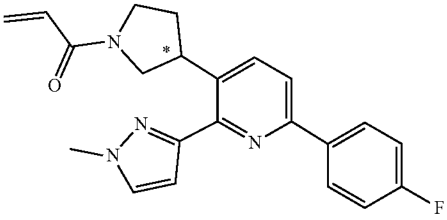 [SMILES: C=CC(=O)N1CCC(c2ccc(-c3ccc(F)cc3)nc2-c2ccn(C)n2)C1] | (R)- or (S)-1-(3-(6-(4-fluorophenyl)-2-(1-methyl-1H-pyrazol-3-yl)pyridin-3-yl)pyrrolidin-1-yl)prop-2-en-1-one |

Structures of example compounds of the disclosure and their respective codes

TABLE 1-continued

Structures of example compounds of the disclosure and their respective codes

| Cpd. No. | Structure | Name |
|---|---|---|
| 427 | 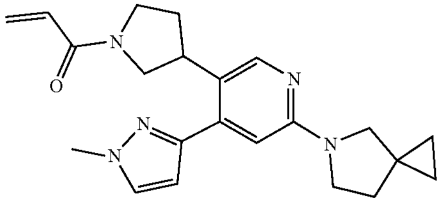 [SMILES: C=CC(=O)N1CCC(c2cnc(N3CCC4(CC4)C3)cc2-c2ccn(C)n2)C1] | 1-(3-(4-(1-methyl-1H-pyrazol-3-yl)-6-(5-azaspiro[2.4]heptan-5-yl)pyridin-3-yl)pyrrolidin-1-yl)prop-2-en-1-one |
| 428 | 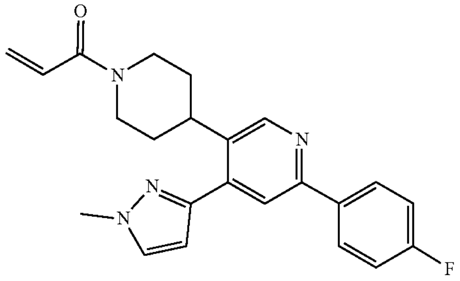 [SMILES: C=CC(=O)N1CCC(c2cnc(-c3ccc(F)cc3)cc2-c2ccn(C)n2)CC1] | 1-(4-(6-(4-fluorophenyl)-4-(1-methyl-1H-pyrazol-3-yl)pyridin-3-yl)piperidin-1-yl)prop-2-en-1-one |
| 429 | 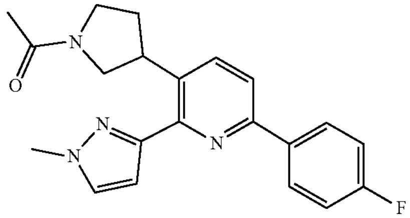 [SMILES: CC(=O)N1CCC(c2ccc(-c3ccc(F)cc3)nc2-c2ccn(C)n2)C1] | 1-(3-(6-(4-fluorophenyl)-2-(1-methyl-1H-pyrazol-3-yl)pyridin-3-yl)pyrrolidin-1-yl)ethan-1-one |
| 430 | 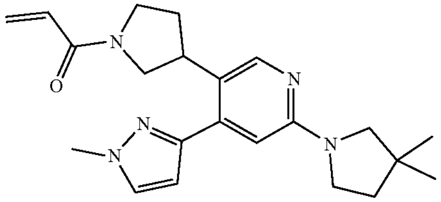 [SMILES: C=CC(=O)N1CCC(c2cnc(N3CCC(C)(C)C3)cc2-c2ccn(C)n2)C1] | 1-(3-(6-(3,3-dimethylpyrrolidin-1-yl)-4-(1-methyl-1H-pyrazol-3-yl)pyridin-3-yl)pyrrolidin-1-yl) prop-2-en-1-one |
| 431 | 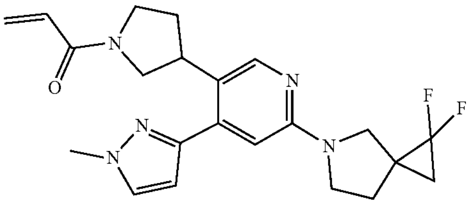 [SMILES: C=CC(=O)N1CCC(c2cnc(N3CCC4(C3)CC4(F)F)cc2-c2ccn(C)n2)C1] | 1-(3-(6-(1,1-difluoro-5-azaspiro[2.4]heptan-5-yl)-4-(1-methyl-1H-pyrazol-3-yl)pyridin-3-yl)pyrrolidin-1-yl)prop-2-en-1-one |
| 432 | 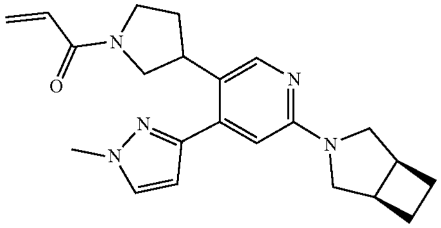 [SMILES: C=CC(=O)N1CCC(c2cnc(N3C[C@H]4CC[C@H]4C3)cc2-c2ccn(C)n2)C1] | 1-(3-(6-((cis)-3-azabicyclo[3.2.0]heptan-3-yl)-4-(1-methyl-1H-pyrazol-3-yl)pyridin-3-yl)pyrrolidin-1-yl)prop-2-en-1-one |

TABLE 1-continued

Structures of example compounds of the disclosure and their respective codes

| Cpd. No. | Structure | Name |
|---|---|---|
| 433 | 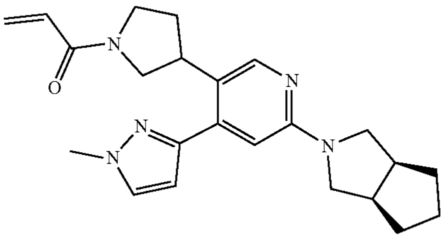 [SMILES: C=CC(=O)N1CCC(c2cnc(N3C[C@H]4CCC[C@H]4C3)cc2-c2ccn(C)n2)C1] | 1-(3-(6-((cis)-hexahydrocyclopenta[c]pyrrol-2(1H)-yl)-4-(1-methyl-1H-pyrazol-3-yl)pyridin-3-yl)pyrrolidin-1-yl)prop-2-en-1-one |
| 434 | 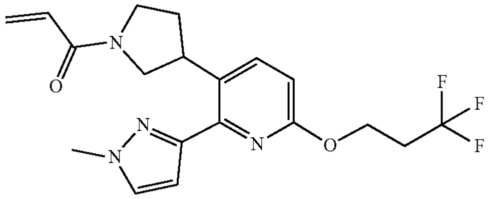 [SMILES: C=CC(=O)N1CCC(c2ccc(OCCC(F)(F)F)nc2-c2ccn(C)n2)C1] | 1-(3-(2-(1-methyl-1H-pyrazol-3-yl)-6-(3,3,3-trifluoropropoxy)pyridin-3-yl)pyrrolidin-1-yl)prop-2-en-1-one |
| 435 | 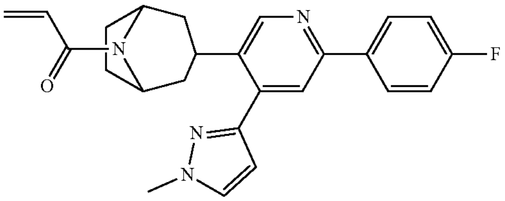 [SMILES: C=CC(=O)N1C2CCC1CC(c1cnc(-c3ccc(F)cc3)cc1-c1ccn(C)n1)C2] | 1-(3-(6-(4-fluorophenyl)-4-(1-methyl-1H-pyrazol-3-yl)pyridin-3-yl)-8-azabicyclo[3.2.1]octan-8-yl)prop-2-en-1-one |
| 436 | 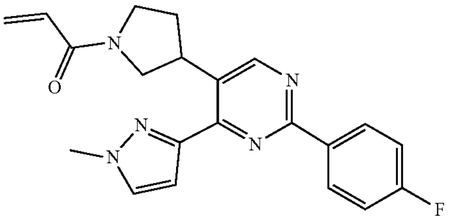 [SMILES: C=CC(=O)N1CCC(c2cnc(-c3ccc(F)cc3)nc2-c2ccn(C)n2)C1] | 1-(3-(2-(4-fluorophenyl)-4-(1-methyl-1H-pyrazol-3-yl)pyrimidin-5-yl)pyrrolidin-1-yl)prop-2-en-1-one |
| 437 | 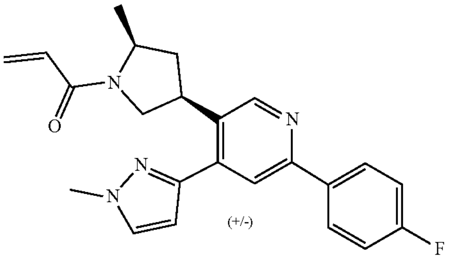 [SMILES: C=CC(=O)N1C[C@H](c2cnc(-c3ccc(F)cc3)cc2-c2ccn(C)n2)C[C@@H]1C] | 1-((cis)-4-(6-(4-fluorophenyl)-4-(1-methyl-1H-pyrazol-3-yl)pyridin-3-yl)-2-methylpyrrolidin-1-yl)prop-2-en-1-one |
| 438 | 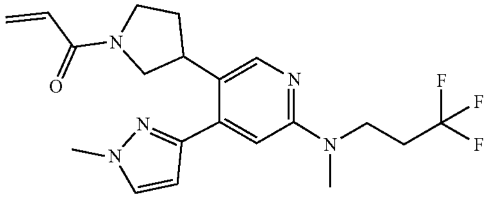 [SMILES: C=CC(=O)N1CCC(c2cnc(N(C)CCC(F)(F)F)cc2-c2ccn(C)n2)C1] | 1-(3-(6-(methyl(3,3,3-trifluoropropyl)amino)-4-(1-methyl-1H-pyrazol-3-yl)pyridin-3-yl)pyrrolidin-1-yl)prop-2-en-1-one |

TABLE 1-continued

| Cpd. No. | Structure | Name |
|---|---|---|
| 439 | 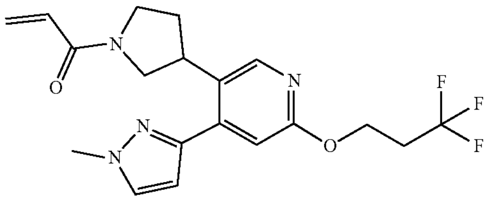 [SMILES: C=CC(=O)N1CCC(c2cnc(OCCC(F)(F)F)cc2-c2ccn(C)n2)C1] | 1-(3-(4-(1-methyl-1H-pyrazol-3-yl)-6-(3,3,3-trifluoropropoxy)pyridin-3-yl)pyrrolidin-1-yl)prop-2-en-1-one |
| 439-En1 | 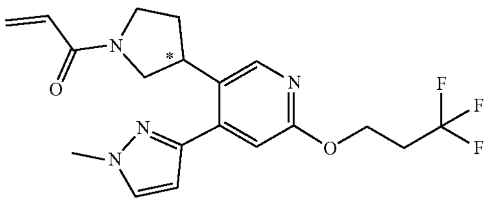 [SMILES: C=CC(=O)N1CCC(c2cnc(OCCC(F)(F)F)cc2-c2ccn(C)n2)C1] | (R)- or (S)-1-(3-(4-(1-methyl-1H-pyrazol-3-yl)-6-(3,3,3-trifluoropropoxy)pyridin-3-yl)pyrrolidin-1-yl)prop-2-en-1-one |
| 439-En2 | 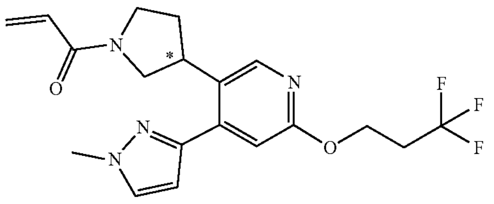 [SMILES: C=CC(=O)N1CCC(c2cnc(OCCC(F)(F)F)cc2-c2ccn(C)n2)C1] | (R)- or (S)-1-(3-(4-(1-methyl-1H-pyrazol-3-yl)-6-(3,3,3-trifluoropropoxy)pyridin-3-yl)pyrrolidin-1-yl)prop-2-en-1-one |
| 440 | 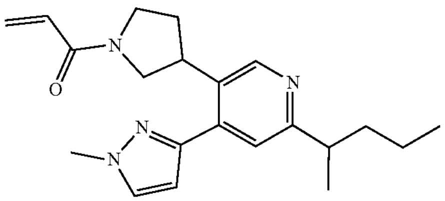 [SMILES: C=CC(=O)N1CCC(c2cnc(C(C)CCC)cc2-c2ccn(C)n2)C1] | 1-(3-(4-(1-methyl-1H-pyrazol-3-yl)-6-(pentan-2-yl)pyridin-3-yl)pyrrolidin-1-yl)prop-2-en-1-one |
| 441 | 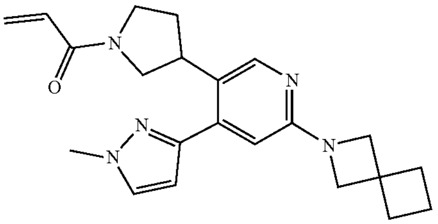 [SMILES: C=CC(=O)N1CCC(c2cnc(N3CC4(CCC4)C3)cc2-c2ccn(C)n2)C1] | 1-(3-(4-(1-methyl-1H-pyrazol-3-yl)-6-(2-azaspiro[3.3]heptan-2-yl)pyridin-3-yl)pyrrolidin-1-yl) prop-2-en-1-one |
| 442 | 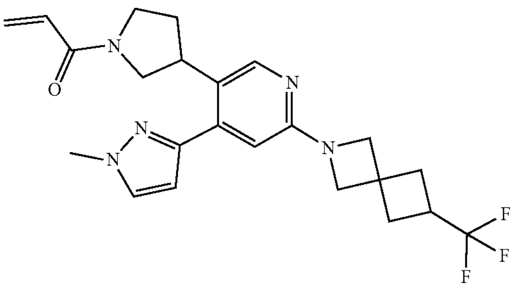 [SMILES: C=CC(=O)N1CCC(c2cnc(N3CC4(CC(C(F)(F)F)C4)C3)cc2-c2ccn(C)n2)C1] | 1-(3-(4-(1-methyl-1H-pyrazol-3-yl)-6-(6-(trifluoromethyl)-2-azaspiro[3.3]heptan-2-yl)pyridin-3-yl)pyrrolidin-1-yl)prop-2-en-1-one |

Structures of example compounds of the disclosure and their respective codes

TABLE 1-continued

| Structures of example compounds of the disclosure and their respective codes | | |
|---|---|---|
| Cpd. No. | Structure | Name |
| 443 | 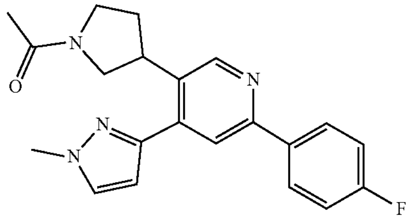 [SMILES: CC(=O)N1CCC(c2cnc(-c3ccc(F)cc3)cc2-c2ccn(C)n2)C1] | 1-(3-(6-(4-fluorophenyl)-4-(1-methyl-1H-pyrazol-3-yl)pyridin-3-yl)pyrrolidin-1-yl)ethan-1-one |
| 444 | 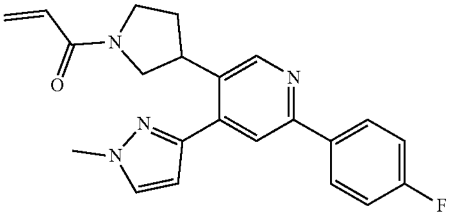 [SMILES: C=CC(=O)N1CCC(c2cnc(-c3ccc(F)cc3)cc2-c2ccn(C)n2)C1] | 1-(3-(6-(4-fluorophenyl)-4-(1-methyl-1H-pyrazol-3-yl)pyridin-3-yl)pyrrolidin-1-yl)prop-2-en-1-one |
| 444-En1 | 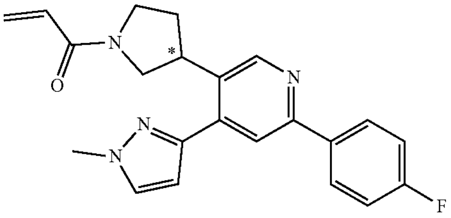 [SMILES: C=CC(=O)N1CCC(c2cnc(-c3ccc(F)cc3)cc2-c2ccn(C)n2)C1] | (R)- or (S)-1-(3-(6-(4-fluorophenyl)-4-(1-methyl-1H-pyrazol-3-yl)pyridin-3-yl)pyrrolidin-1-yl)prop-2-en-1-one |
| 444-En2 | 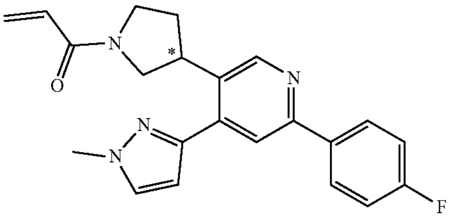 [SMILES: C=CC(=O)N1CCC(c2cnc(-c3ccc(F)cc3)cc2-c2ccn(C)n2)C1] | (R)- or (S)-1-(3-(6-(4-fluorophenyl)-4-(1-methyl-1H-pyrazol-3-yl)pyridin-3-yl)pyrrolidin-1-yl)prop-2-en-1-one |
| 445 | 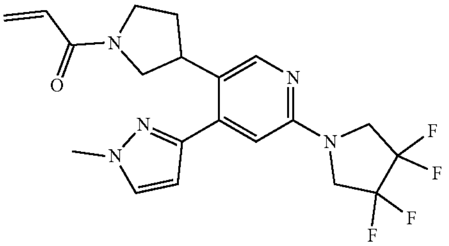 [SMILES: C=CC(=O)N1CCC(c2cnc(N3CC(F)(F)C(F)(F)C3)cc2-c2ccn(C)n2)C1] | 1-(3-(4-(1-methyl-1H-pyrazol-3-yl)-6-(3,3,4,4-tetrahydrofluoropyrrolidin-1-yl)pyridin-3-yl)pyrrolidin-1-yl)prop-2-en-1-one |
| 445-En1 | 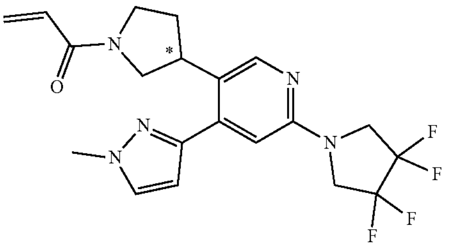 [SMILES: C=CC(=O)N1CCC(c2cnc(N3CC(F)(F)C(F)(F)C3)cc2-c2ccn(C)n2)C1] | (R)- or (S)-1-(3-(4-(1-methyl-1H-pyrazol-3-yl)-6-(3,3,4,4-tetrahydropyrrolidin-1-yl)pyridin-3-yl)pyrrolidin-1-yl)prop-2-en-1-one |

TABLE 1-continued

| Structures of example compounds of the disclosure and their respective codes | | |
|---|---|---|
| Cpd. No. | Structure | Name |
| 445-En2 | 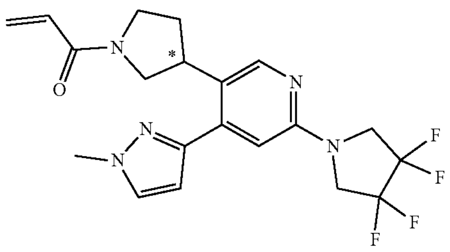 [SMILES: C=CC(=O)N1CCC(c2cnc(N3CC(F)(F)C(F)(F)C3)cc2-c2ccn(C)n2)C1] | (R)- or (S)-1-(3-(4-(1-methyl-1H-pyrazol-3-yl)-6-(3,3,4,4-tetrafluoropyrrolidin-1-yl)pyridin-3-yl)pyrrolidin-1-yl)prop-2-en-1-one |
| 446 | 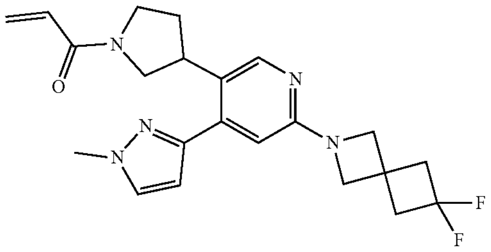 [SMILES: C=CC(=O)N1CCC(c2cnc(N3CC4(C3)CC(F)(F)C4)cc2-c2ccn(C)n2)C1] | 1-(3-(6-(6,6-difluoro-2-azaspiro[3.3]heptan-2-yl)-(4-(1-methyl-1H-pyrazol-3-yl)pyridin-3-yl)pyrrolidin-1-yl)prop-2-en-1-one |
| 447 | 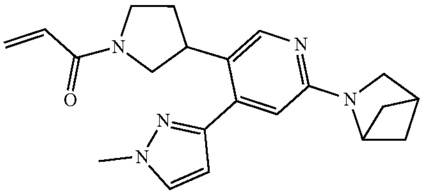 [SMILES: C=CC(=O)N1CCC(c2cnc(N3CC4CC3C4)cc2-c2ccn(C)n2)C1] | 1-(3-(6-(2-azabicyclo[2.1.1]hexan-2-yl)-4-(1-methyl-1H-pyrazol-3-yl)pyridin-3-yl)pyrrolidin-1-yl)prop-2-en-1-one |
| 448 | 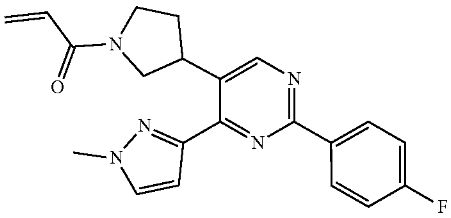 [SMILES: C=CC(=O)N1CCC(c2cnc(-c3ccc(F)cc3)nc2-c2ccn(C)n2)C1] | 1-(3-(2-(4-fluorophenyl)-4-(1-methyl-1H-pyrazol-3-yl)pyrimidin-5-yl)pyrrolidin-1-yl)prop-2-en-1-one |
| 448-En1 | 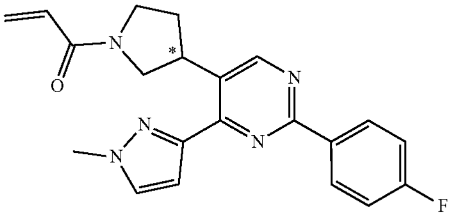 [SMILES: C=CC(=O)N1CCC(c2cnc(-c3ccc(F)cc3)nc2-c2ccn(C)n2)C1] | (R)- or (S)-1-(3-(2-(4-fluorophenyl)-4-(1-methyl-1H-pyrazol-3-yl)pyrimidin-5-yl)pyrrolidin-1-yl)prop-2-en-1-one |
| 448-En2 | 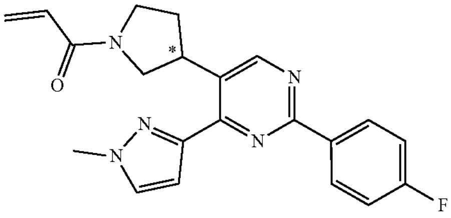 [SMILES: C=CC(=O)N1CCC(c2cnc(-c3ccc(F)cc3)nc2-c2ccn(C)n2)C1] | (R)- or (S)-1-(3-(2-(4-fluorophenyl)-4-(1-methyl-1H-pyrazol-3-yl)pyrimidin-5-yl)pyrrolidin-1-yl)prop-2-en-1-one |

TABLE 1-continued

| Structures of example compounds of the disclosure and their respective codes | | |
|---|---|---|
| Cpd. No. | Structure | Name |
| 449 | 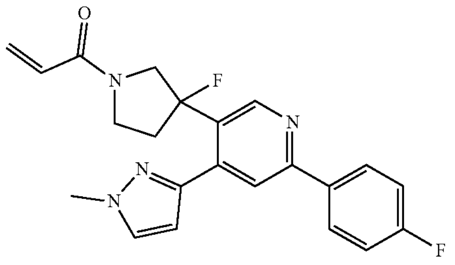 [SMILES: C=CC(=O)N1CCC(F)(c2cnc(-c3ccc(F)cc3)cc2-c2ccn(C)n2)C1] | 1-(3-fluoro-3-(6-(4-fluorophenyl)-4-(1-methyl-1H-pyrazol-3-yl)pyridin-3-yl)pyrrolidin-1-yl)prop-2-en-1-one |
| 450 | 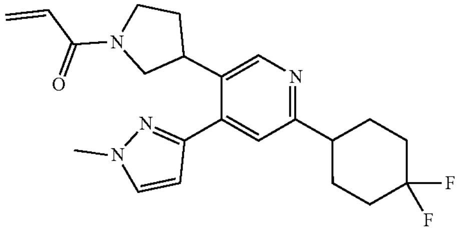 [SMILES: C=CC(=O)N1CCC(c2cnc(C3CCC(F)(F)CC3)cc2-c2ccn(C)n2)C1] | 1-(3-(6-(4,4-difluorocyclohexyl)-4-(1-methyl-1H-pyrazol-3-yl)pyridin-3-yl)pyrrolidin-1-yl)prop-2-en-1-one |
| 451 | 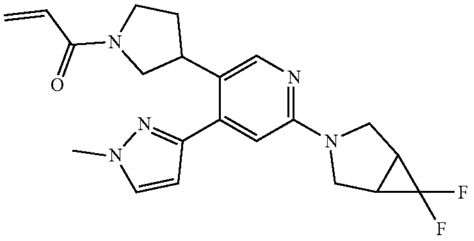 [SMILES: C=CC(=O)N1CCC(c2cnc(N3CC4C(C3)C4(F)F)cc2-c2ccn(C)n2)C1] | 1-(3-(6-(6,6-difluoro-3-azabicyclo[3.1.0]hexan-3-yl)-4-(1-methyl-1H-pyrazol-3-yl)pyridin-3-yl)pyrrolidin-1-yl)prop-2-en-1-one |
| 452 | 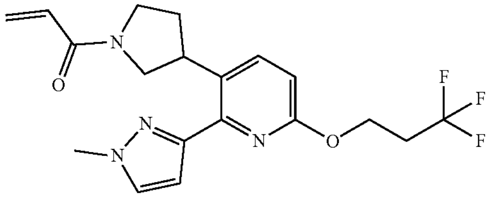 [SMILES: C=CC(=O)N1CCC(c2ccc(OCCC(F)(F)F)nc2-c2ccn(C)n2)C1] | 1-(3-(2-(1-methyl-1H-pyrazol-3-yl)-6-(3,3,3-trifluoropropoxy)pyridin-3-yl)pyrrolidin-1-yl)prop-2-en-1-one |
| 452-En1 | 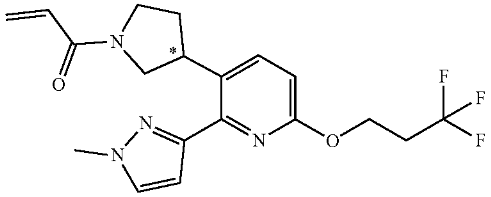 [SMILES: C=CC(=O)N1CCC(c2ccc(OCCC(F)(F)F)nc2-c2ccn(C)n2)C1] | (R)- or (S)-1-(3-(2-(1-methyl-1H-pyrazol-3-yl)-6-(3,3,3-trifluoropropoxy)pyridin-3-yl)pyrrolidin-1-yl)prop-2-en-1-one |
| 452-En2 | 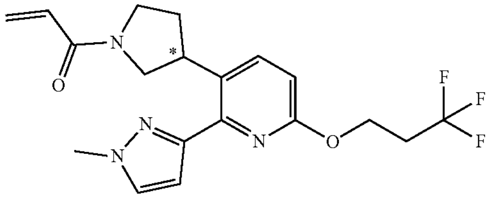 [SMILES: C=CC(=O)N1CCC(c2ccc(OCCC(F)(F)F)nc2-c2ccn(C)n2)C1] | (R)- or (S)-1-(3-(2-(1-methyl-1H-pyrazol-3-yl)-6-(3,3,3-trifluoropropoxy)pyridin-3-yl)pyrrolidin-1-yl)prop-2-en-1-one |

TABLE 1-continued

Structures of example compounds of the disclosure and their respective codes

| Cpd. No. | Structure | Name |
| --- | --- | --- |
| 453 | 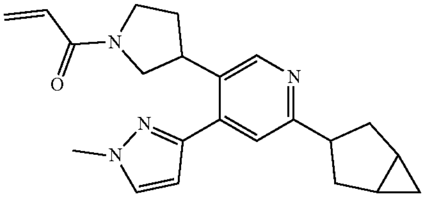 [SMILES: C=CC(=O)N1CCC(c2cnc(C3CC4CC4C3)cc2-c2ccn(C)n2)C1] | 1-(3-(6-(bicyclo[3.1.0]hexan-3-yl)-4-(1-methyl-1H-pyrazol-3-yl)pyridin-3-yl)pyrrolidin-1-yl)prop-2-en-1-one |
| 454 | 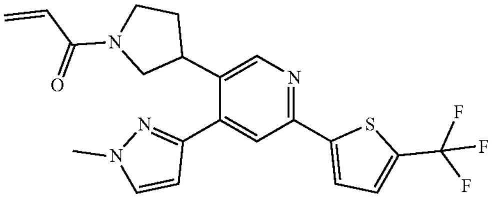 [SMILES: C=CC(=O)N1CCC(c2cnc(-c3ccc(C(F)(F)F)s3)cc2-c2ccn(C)n2)C1] | 1-(3-(4-(1-methyl-1H-pyrazol-3-yl)-6-(5-(trifluoromethyl)thiophen-2-yl)pyridin-3-yl)pyrrolidin-1-yl)prop-2-en-1-one |
| 455 | 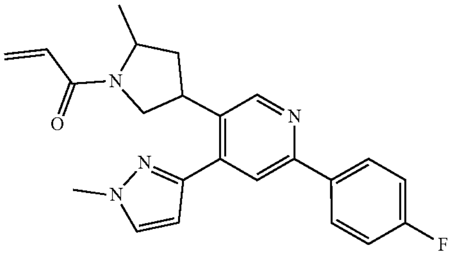 [SMILES: C=CC(=O)N1CC(c2cnc(-c3ccc(F)cc3)cc2-c2ccn(C)n2)CC1C] | 1-(-4-(6-(4-fluorophenyl)-4-(1-methyl-1H-pyrazol-3-yl)pyridin-3-yl)-2-methylpyrrolidin-1-yl)pyrrolidin-1-yl)prop-2-en-1-one |
| 455-En1 | 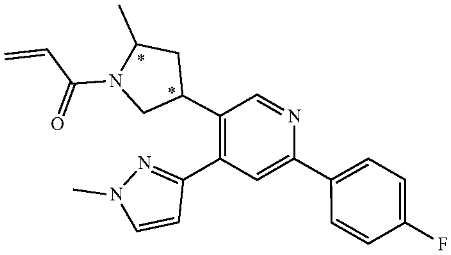 [SMILES: C=CC(=O)N1CC(c2cnc(-c3ccc(F)cc3)cc2-c2ccn(C)n2)CC1C] | (R)- or (S)-1-(-4-(6-(4-fluorophenyl)-4-(1-methyl-1H-pyrazol-3-yl)pyridin-3-yl)-2-methylpyrrolidin-1-yl)prop-2-en-1-one |
| 455-En2 | 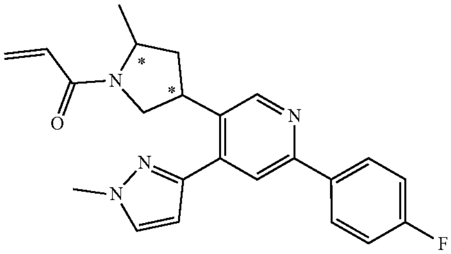 [SMILES: C=CC(=O)N1CC(c2cnc(-c3ccc(F)cc3)cc2-c2ccn(C)n2)CC1C] | (R)- or (S)-1-(4-(6-(4-fluorophenyl)-4-(1-methyl-1H-pyrazol-3-yl)pyridin-3-yl)-2-methylpyrrolidin-1-yl)prop-2-ne-1-one |
| 456 | 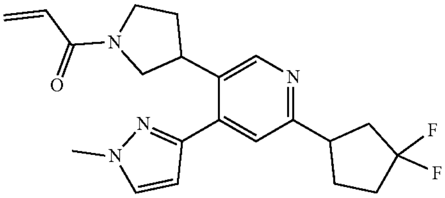 [SMILES: C=CC(=O)N1CCC(c2cnc(C3CCC(F)(F)C3)cc2-c2ccn(C)n2)C1] | 1-(3-(6-(3,3-difluorocyclopentyl)-4-(1-methyl-1H-pyrazol-3-yl)pyridin-3-yl)pyrrolidin-1-yl)pyrrolidin-1-yl)prop-2-en-1-one |

TABLE 1-continued

Structures of example compounds of the disclosure and their respective codes

| Cpd. No. | Structure | Name |
|---|---|---|
| 457 | 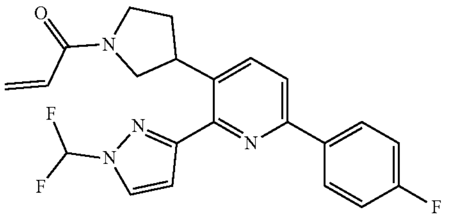 [SMILES: C=CC(=O)N1CCC(c2ccc(-c3ccc(F)cc3)nc2-c2ccn(C(F)F)n2)C1] | 1-(3-(2-(1-(difluoromethyl)-1H-pyrazol-3-yl)-6-(4-fluorophenyl)pyridin-3-yl)pyrrolidin-1-yl)prop-2-en-1-one |
| 458 | 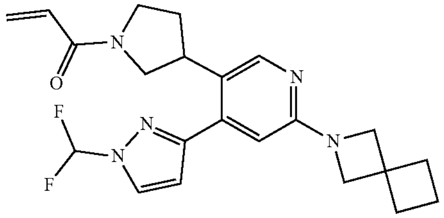 [SMILES: C=CC(=O)N1CCC(c2cnc(N3CC4(CCC4)C3)cc2-c2ccn(C(F)F)n2)C1] | 1-(3-(4-(1-methyl-1H-pyrazol-3-yl)-6-(2-azaspiro[3.3]heptan-2-yl)pyridn-3-yl)pyrrolidin-1-yl)prop-2-en-1-one |
| 458-En1 | 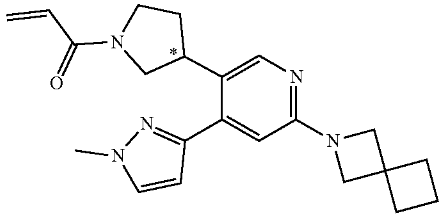 [SMILES: C=CC(=O)N1CCC(c2cnc(N3CC4(CCC4)C3)cc2-c2ccn(C)n2)C1] | (R)- or (S)-1-(3-(4-(1-methyl-1H-pyrazol-3-yl)-6-(2-azaspiro[3.3]heptan-2-yl)pyridin-3-yl)pyrrolidin-1-yl)prop-2-en-1-one |
| 458-En2 | 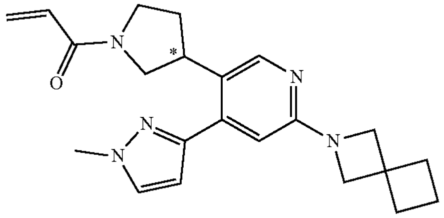 [SMILES: C=CC(=O)N1CCC(c2cnc(N3CC4(CCC4)C3)cc2-c2ccn(C)n2)C1] | (R)- or (S)-1-(3-(4-(1-methyl-1H-pyrazol-3-yl)-6-(2-azaspiro[3.3]heptan-2-yl)pyridin-3-yl)pyrrolidin-1-yl)prop-2-en-1-one |
| 459 | 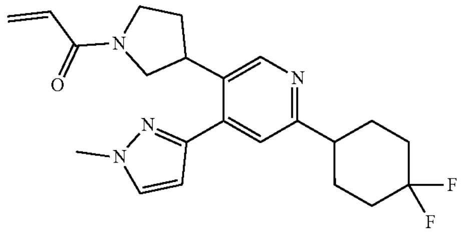 [SMILES: C=CC(=O)N1CCC(c2cnc(C3CCC(F)(F)CC3)cc2-c2ccn(C)n2)C1] | 1-(3-(6-(4,4-difluorocyclohexyl)-4-(1-methyl-1H-pyrazol-3-yl)pyridin-3-yl)pyrrolidin-1-yl)prop-2-en-1-one |
| 459-En1 | 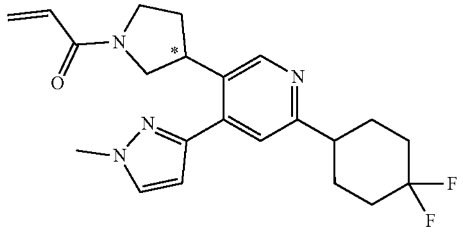 [SMILES: C=CC(=O)N1CCC(c2cnc(C3CCC(F)(F)CC3)cc2-c2ccn(C)n2)C1] | (R)- or (S)-1-(3-(6-(4,4-difluorocyclohexyl)-4-(1-methyl-1H-pyrazol-3-yl)pyridin-3-yl)pyrrolidin-1-yl)prop-2-en-1-one |

TABLE 1-continued

Structures of example compounds of the disclosure and their respective codes

| Cpd. No. | Structure | Name |
|---|---|---|
| 459-En2 | 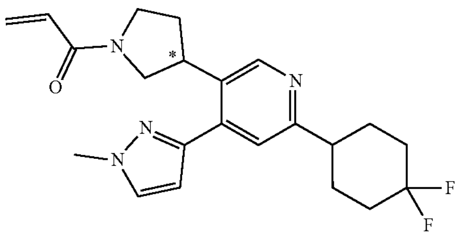 [SMILES: C=CC(=O)N1CCC(c2cnc(C3CCC(F)(F)CC3)cc2-c2ccn(C)n2)C1] | (R)- or (S)-1-(3-(6-(4,4-difluorocyclohexyl)-4-(1-methyl-1H-pyrazol-3-yl)pyridin-3-yl)pyrrolidin-1-yl)prop-2-en-1-one |
| 460 | 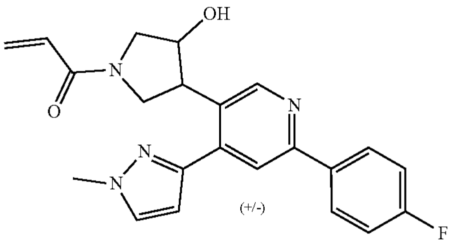 [SMILES: C=CC(=O)N1CC(O)C(c2cnc(-c3ccc(F)cc3)cc2-c2ccn(C)n2)C1] | 1-((trans)-3-(6-(4-fluorophenyl)-4-(1-methyl-1H-pyrazol-3-yl)pyridin-3-yl)-4-hydroxypyrrolidin-1-yl)prop-2-en-1-one |
| 461 | 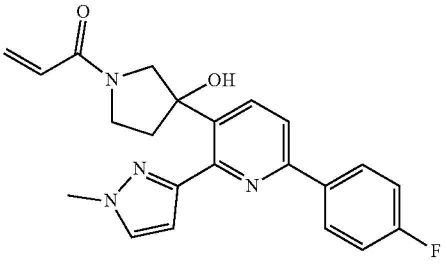 [SMILES: C=CC(=O)N1CCC(O)(c2ccc(-c3ccc(F)cc3)nc2-c2ccn(C)n2)C1] | 1-(3-(6-(4-fluorophenyl)-2-(1-methyl-1H-pyrazol-3-yl)pyridin-3-yl)-3-hydroxypyrrolidin-1-yl)prop-2-en-1-one |
| 462 | 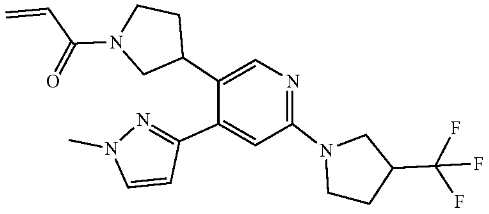 [SMILES: C=CC(=O)N1CCC(c2cnc(N3CCC(C(F)(F)F)C3)cc2-c2ccn(C)n2)C1] | 1-(3-(4-(1-methyl-1H-pyrazol-3-yl)-6-(3-(trifluoromethyl)pyrrolidin-1-yl)pyridin-3-yl)pyrrolidin-1-yl)prop-2-en-1-one |
| 462-En1 | 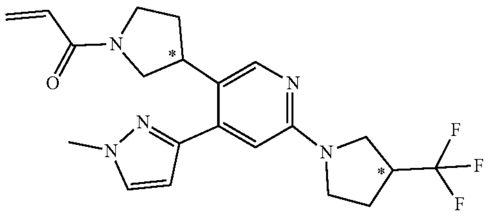 | (R,R)-, (R,S)-, (S,R)-, or (S,S)-1-(3-(4-(1-methyl-1H-pyrazol-3-yl)-6-(3-(trifluoromethyl)pyrrolidin-1-yl)pyridin-3-yl)pyrrolidin-1-yl)prop-2-en-1-one |
| 462-En2 | 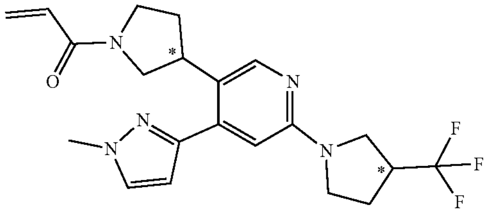 [SMILES: C=CC(=O)N1CCC(c2cnc(N3CCC(C(F)(F)F)C3)cc2-c2ccn(C)n2)C1] | (R,R)-, (R,S)-, (S,R)-, or (S,S)-1-(3-(4-(1-methyl-1H-pyrazol-3-yl)-6-(3-(trifluoromethyl)pyrrolidin-1-yl)pyridin-3-yl)pyrrolidin-1-yl)prop-2-en-1-one |

TABLE 1-continued

Structures of example compounds of the disclosure and their respective codes

| Cpd. No. | Structure | Name |
|---|---|---|
| 462-En3 | 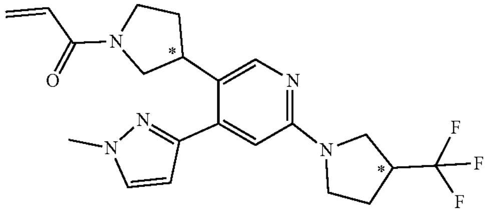 [SMILES: C=CC(=O)N1CCC(c2cnc(N3CCC(C(F)(F)F)C3)cc2-c2ccn(C)n2)C1] | (R,R)-, (R,S)-, (S,R)-, or (S,S)-1-(3-(4-(1-methyl-1H-pyrazol-3-yl)-6-(3-(trifluoromethyl)pyrrolidin-1-yl)pyridin-3-yl)pyrrolidin-1-yl)prop-2-en-1-one |
| 462-En4 | 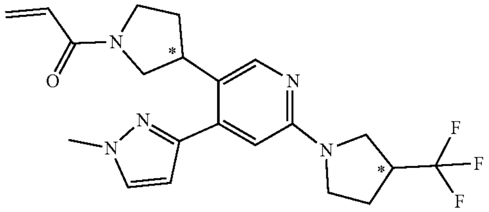 [SMILES: C=CC(=O)N1CCC(c2cnc(N3CCC(C(F)(F)F)C3)cc2-c2ccn(C)n2)C1] | (R,R)-, (R,S)-, (S,R)-, or (S,S)-1-(3-(4-(1-methyl-1H-pyrazol-3-yl)-6-(3-(trifluoromethyl)pyrrolidin-1-yl)pyridin-3-yl)pyrrolidin-1-yl)prop-2-en-1-one |
| 463 | 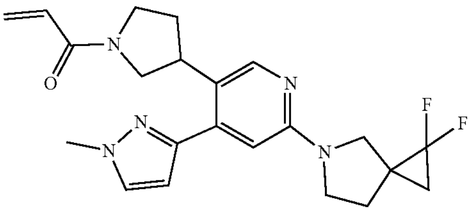 [SMILES: C=CC(=O)N1CCC(c2cnc(N3CCC4(C3)CC4(F)F)cc2-c2ccn(C)n2)C1] | 1-(3-(6-(1,1-difluoro-5-azaspiro[2.4]heptan-5-yl)-4-(1-methyl-1H-pyrazol-3-yl)pyridin-3-yl)pyrrolidin-1-yl)prop-2-en-1-one |
| 463-En1 | 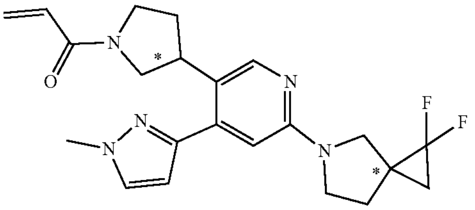 [SMILES: C=CC(=O)N1CCC(c2cnc(N3CCC4(C3)CC4(F)F)cc2-c2ccn(C)n2)C1] | (R,R)-, (R,S)-, (S,R)-, or (S,S)-1-(3-(6-(1,1-difluoro-5-azaspiro[2.4]heptan-5-yl)-4-(1-methyl-1H-pyrazol-3-y)pyridin-3-yl)pyrrolidin-1-yl)prop-2-en-1-one |
| 463-En2 | 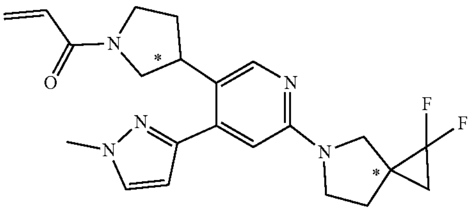 [SMILES: C=CC(=O)N1CCC(c2cnc(N3CCC4(C3)CC4(F)F)cc2-c2ccn(C)n2)C1] | (R,R)-, (R,S)-, (S,R)-, or (S,S)-1-(3-(6-(1,1-difluoro-5-azaspiro[2.4]heptan-5-yl)-4-(1-methyl-1H-pyrazol-3-y)pyridin-3-yl)pyrrolidin-1-yl)prop-2-en-1-one |
| 463-En3 | 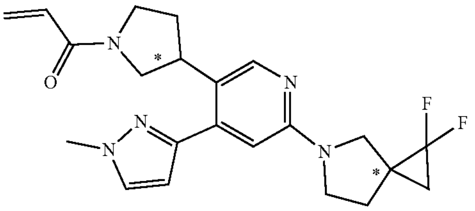 [SMILES: C=CC(=O)N1CCC(c2cnc(N3CCC4(C3)CC4(F)F)cc2-c2ccn(C)n2)C1] | (R,R)-, (R,S)-, (S,R)-, or (S,S)-1-(3-(6-(1,1-difluoro-5-azaspiro[2.4]heptan-5-yl)-4-(1-methyl-1H-pyrazol-3-y)pyridin-3-yl)pyrrolidin-1-yl)prop-2-en-1-one |
| 463-En4 | 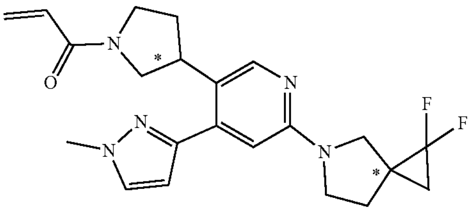 [SMILES: C=CC(=O)N1CCC(c2cnc(N3CCC4(C3)CC4(F)F)cc2-c2ccn(C)n2)C1] | (R,R)-, (R,S)-, (S,R)-, or (S,S)-1-(3-(6-(1,1-difluoro-5-azaspiro[2.4]heptan-5-yl)-4-(1-methyl-1H-pyrazol-3-y)pyridin-3-yl)pyrrolidin-1-yl)prop-2-en-1-one |

TABLE 1-continued

| Cpd. No. | Structure | Name |
|---|---|---|
| Structures of example compounds of the disclosure and their respective codes | | |
| 464 | 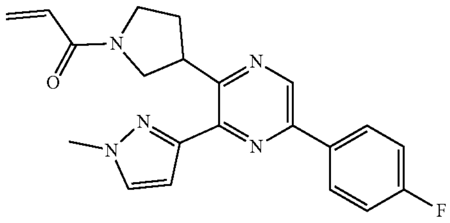 [SMILES: C=CC(=O)N1CCC(c2ncc(-c3ccc(F)cc3)nc2-c2ccn(C)n2)C1] | 1-(3-(5-(4-fluorophenyl)-3-(1-methyl-1H-pyrazol-3-yl)pyrazin-2-yl)pyrrolidin-1-yl)prop-2-en-1-one |
| 465 | 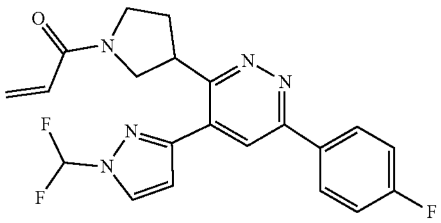 [SMILES: C=CC(=O)N1CCC(c2nnc(-c3ccc(F)cc3)cc2-c2ccn(C(F)F)n2)C1] | 1-(3-(4-(1-(difluoromethyl)-1H-pyrazol-3-yl)-6-(4-fluorophenyl)pyridazin-3-yl)pyrrolidin-1-yl)prop-2-en-1-one |
| 466 | 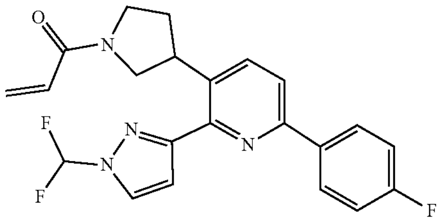 [SMILES: C=CC(=O)N1CCC(c2ccc(-c3ccc(F)cc3)nc2-c2ccn(C(F)F)n2)C1] | 1-(3-(2-(1-(difluoromethyl)-1H-pyrazol-3-yl)-6-(4-fluorophenyl)pyridin-3-yl)pyrrolidin-1-yl)prop-2-en-1-one |
| 466-En1 | 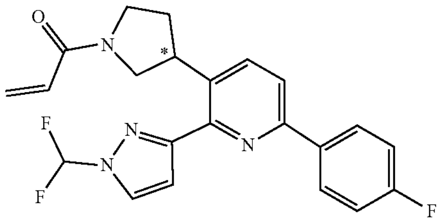 [SMILES: C=CC(=O)N1CCC(c2ccc(-c3ccc(F)cc3)nc2-c2ccn(C(F)F)n2)C1] | (R)- or (S)-1-(3-(2-(1-(difluoromethyl)-1H-pyrazol-3-yl)-6-(4-fluorophenyl)pyridin-3-yl)pyrrolidin-1-yl)prop-2-en-1-one |
| 466-En2 | 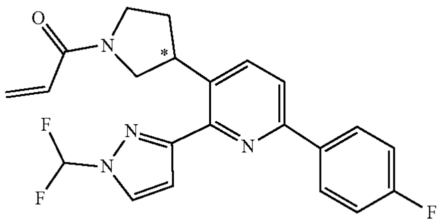 [SMILES: C=CC(=O)N1CCC(c2ccc(-c3ccc(F)cc3)nc2-c2ccn(C(F)F)n2)C1] | (R)- or (S)-1-(3-(2-(1-(difluoromethyl)-1H-pyrazol-3-yl)-6-(4-fluorophenyl)pyridin-3-yl)pyrrolidin-1-yl)prop-2-en-1-one |
| 467 | 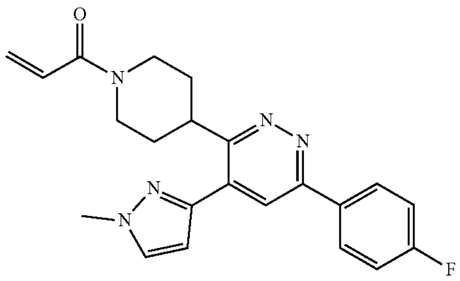 [SMILES: C=CC(=O)N1CCC(c2nnc(-c3ccc(F)cc3)cc2-c2ccn(C)n2)CC1] | 1-(4-(6-(4-fluorophenyl)-4-(1-methyl-1H-pyrazol-3-yl)pyridazin-3-yl)piperidin-1-yl)prop-2-en-1-one |

TABLE 1-continued

Structures of example compounds of the disclosure and their respective codes

| Cpd. No. | Structure | Name |
|---|---|---|
| 468 | 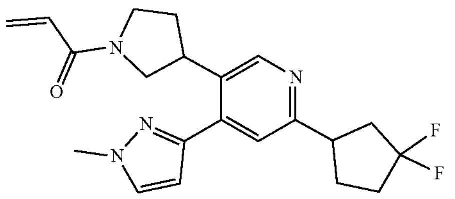 [SMILES: C=CC(=O)N1CCC(c2cnc(C3CCC(F)(F)C3)cc2-c2ccn(C)n2)C1] | 1-(3-(6-(3,3-difluorocyclopentyl)-4-(1-methyl-1H-pyrazol-3-yl)pyridin-3-yl)pyrrolidin-1-yl)prop-2-en-1-one |
| 468-En1 | 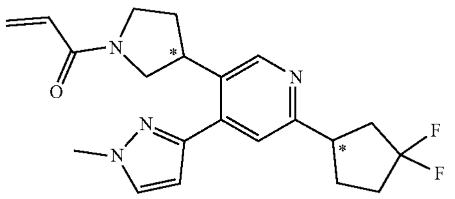 [SMILES: C=CC(=O)N1CCC(c2cnc(C3CCC(F)(F)C3)cc2-c2ccn(C)n2)C1] | (R,R)-, (R,S)-, (S,R)-, or (S,S)-1-(3-(6-(3,3-difluorocyclopentyl)-4-(1-methyl-1H-pyrazol-3-yl)pyridin-3-yl)pyrrolidin-1-yl)prop-2-en-1-one |
| 468-En2 | 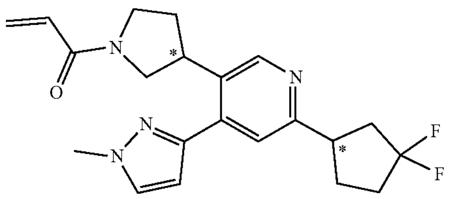 [SMILES: C=CC(=O)N1CCC(c2cnc(C3CCC(F)(F)C3)cc2-c2ccn(C)n2)C1] | (R,R)-, (R,S)-, (S,R)-, or (S,S)-1-(3-(6-(3,3-difluorocyclopentyl)-4-(1-methyl-1H-pyrazol-3-yl)pyridin-3-yl)pyrrolidin-1-yl)prop-2-en-1-one |
| 468-En3 | 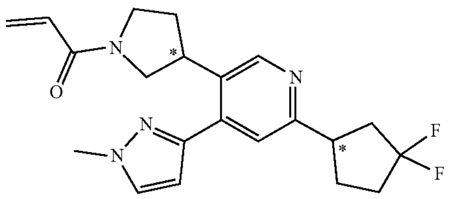 [SMILES: C=CC(=O)N1CCC(c2cnc(C3CCC(F)(F)C3)cc2-c2ccn(C)n2)C1] | (R,R)-, (R,S)-, (S,R)-, or (S,S)-1-(3-(6-(3,3-difluorocyclopentyl)-4-(1-methyl-1H-pyrazol-3-yl)pyridin-3-yl)pyrrolidin-1-yl)prop-2-en-1-one |
| 468-En4 | 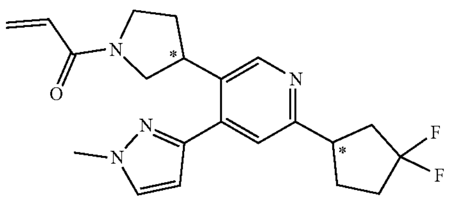 [SMILES: C=CC(=O)N1CCC(c2cnc(C3CCC(F)(F)C3)cc2-c2ccn(C)n2)C1] | (R,R)-, (R,S)-, (S,R)-, or (S,S)-1-(3-(6-(3,3-difluorocyclopentyl)-4-(1-methyl-1H-pyrazol-3-yl)pyridin-3-yl)pyrrolidin-1-yl)prop-2-en-1-one |
| 469 | 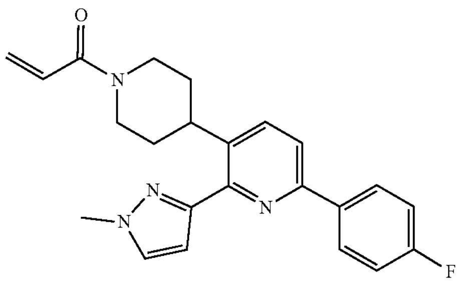 [SMILES: C=CC(=O)N1CCC(c2ccc(-c3ccc(F)cc3)nc2-c2ccn(C)n2)CC1] | 1-(4-(6-(4-fluorophenyl)-2-(1-methyl-1H-pyrazol-3-yl)pyridin-3-yl)piperidin-1-yl)prop-2-en-1-one |
| 470 | 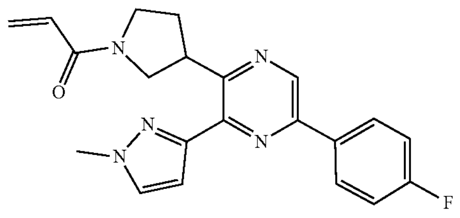 [SMILES: C=CC(=O)N1CCC(c2ncc(-c3ccc(F)cc3)nc2-c2ccn(C)n2)C1] | 1-(3-(5-(4-fluorophenyl)-3-(1-methyl-1H-pyrazol-3-yl)pyrazin-2-yl)pyrrolidin-1-yl)prop-2-en-1-one |

TABLE 1-continued

Structures of example compounds of the disclosure and their respective codes

| Cpd. No. | Structure | Name |
| --- | --- | --- |
| 470-En1 | 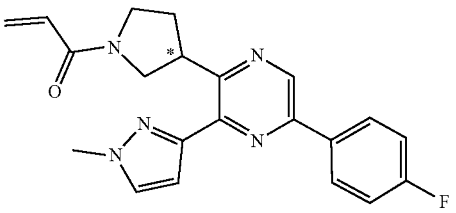 [SMILES: C=CC(=O)N1CCC(c2ncc(-c3ccc(F)cc3)nc2-c2ccn(C)n2)C1] | (R)- or (S)-1-(3-(5-(4-fluorophenyl)-3-(1-methyl-1H-pyrazol-3-yl)pyrazin-2-yl)pyrrolidin-1-yl)prop-2-en-1-one |
| 470-En2 | 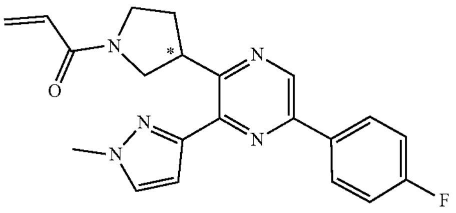 [SMILES: C=CC(=O)N1CCC(c2ncc(-c3ccc(F)cc3)nc2-c2ccn(C)n2)C1] | (R) or (S)-1-(3-(5-(4-fluorophenyl)-3-(1-methyl-1H-pyrazol-3-yl)pyrazin-2-yl)pyrrolidin-1-yl)prop-2-en-1-one |
| 471 | 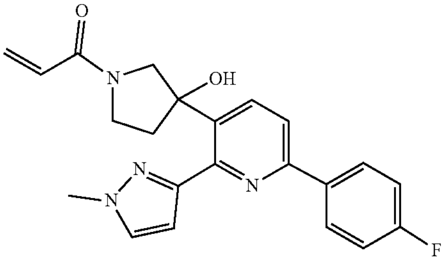 [SMILES: C=CC(=O)N1CCC(O)(c2ccc(-c3ccc(F)cc3)nc2-c2ccn(C)n2)C1] | 1-(3-(6-(4-fluorophenyl)-2-(1-methyl-1H-pyrazol-3-yl)pyridin-3-yl)-3-hydroxypyrrolidin-1-yl)prop-2-en-1-one |
| 471-En1 | 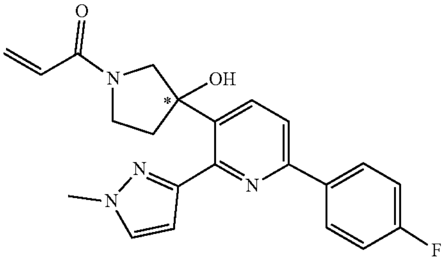 [SMILES: C=CC(=O)N1CCC(O)(c2ccc(-c3ccc(F)cc3)nc2-c2ccn(C)n2)C1] | (R)- or (S)-1-(3-(6-(4-fluorophenyl)-2-(1-methyl-1H-pyrazol-3-yl)pyridin-3-yl)-3-hydroxypyrrolidin-1-yl)prop-2-en-1-one |
| 471-En2 | 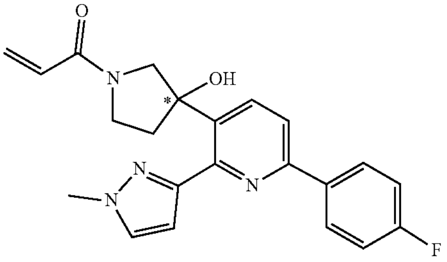 [SMILES: C=CC(=O)N1CCC(O)(c2ccc(-c3ccc(F)cc3)nc2-c2ccn(C)n2)C1] | (R)- or (S)-1-(3-(6-(4-fluorophenyl)-2-(1-methyl-1H-pyrazol-3-yl)pyridin-3-yl)-3-hydroxypyrrolidin-1-yl)prop-2-en-1-one |
| 472 | 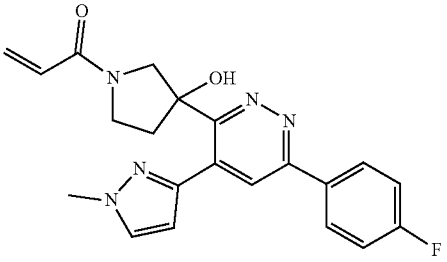 [SMILES: C=CC(=O)N1CCC(O)(c2nnc(-c3ccc(F)cc3)cc2-c2ccn(C)n2)C1] | 1-(3-(6-(4-fluorophenyl)-4-(1-methyl-1H-pyrazol-3-yl)pyridazin-3-yl)-3-hydroxypyrrolidin-1-yl)prop-2-en-1-one |

TABLE 1-continued

| Structures of example compounds of the disclosure and their respective codes | | |
|---|---|---|
| Cpd. No. | Structure | Name |
| 473 | 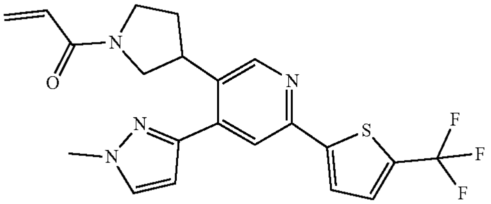 [SMILES: C=CC(=O)N1CCC(c2cnc(-c3ccc(C(F)(F)F)s3)cc2-c2ccn(C)n2)C1] | 1-(3-(4-(1-methyl-1H-pyrazol-3-yl)-6-(5-(trifluoromethyl)thiophen-2-yl)pyridin-3-yl)pyrrolidin-1-yl)prop-2-en-1-one |
| 473-En1 | 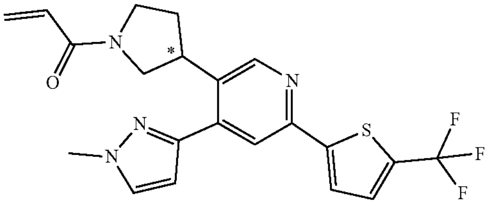 [SMILES: C=CC(=O)N1CCC(c2cnc(-c3ccc(C(F)(F)F)s3)cc2-c2ccn(C)n2)C1] | (R)- or (S)-1-(3-(4-(1-methyl-1H-pyrazol-3-yl)-6-(5-(trifluoromethyl)thiophen-2-yl)pyridin-3-yl)pyrrolidin-1-yl)prop-2-en-1-one |
| 473-En2 | 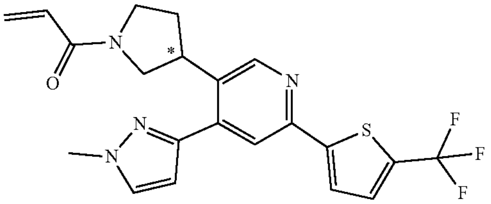 [SMILES: C=CC(=O)N1CCC(c2cnc(-c3ccc(C(F)(F)F)s3)cc2-c2ccn(C)n2)C1] | (R)- or (S)-1-(3-(4-(1-methyl-1H-pyrazol-3-yl)-6-(5-(trifluoromethyl)thiophen-2-yl)pyridin-3-yl)pyrrolidin-1-yl)prop-2-en-1-one |
| 474 | 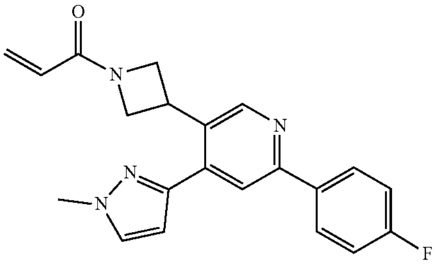 [SMILES: C=CC(=O)N1CC(c2cnc(-c3ccc(F)cc3)cc2-c2ccn(C)n2)C1] | 1-(3-(6-(4-fluorophenyl)-4-(1-methyl-1H-pyrazol-3-yl)pyridin-3-yl)azetidin-1-yl)prop-2-en-1-one |
| 475 | 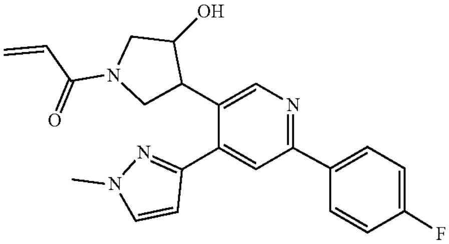 [SMILES: C=CC(=O)N1CC(O)C(c2cnc(-c3ccc(F)cc3)cc2-c2ccn(C)n2)C1] | 1-(3-(6-(4-fluorophenyl)-4-(1-methyl-1H-pyrazol-3-yl)pyridin-3-yl)-4-hydroxypyrrolidin-1-yl)prop-2-en-1-one |
| 475-En1 | 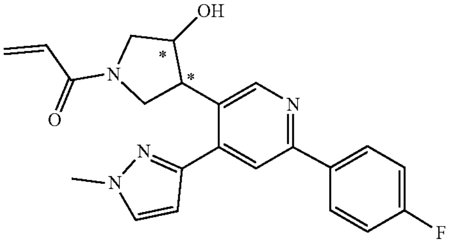 [SMILES: C=CC(=O)N1CC(O)C(c2cnc(-c3ccc(F)cc3)cc2-c2ccn(C)n2)C1] | (3R,4S)- or (3S,4R)1-(3-(6-(4-fluorophenyl)-4-(1-methyl-1H-pyrazol-3-yl)pyridin-3-yl)-4-hydroxypyrrolidin-1-yl)prop-2-en-1-one |

TABLE 1-continued

| Cpd. No. | Structure | Name |
|---|---|---|
| 475-En2 | 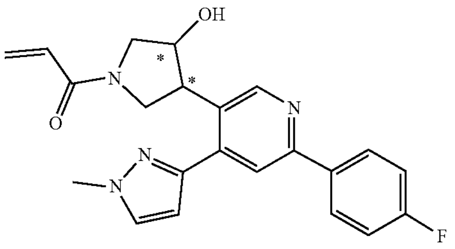 [SMILES: C=CC(=O)N1CC(O)C(c2cnc(-c3ccc(F)cc3)cc2-c2ccn(C)n2)C1] | (3R,4S)- or (3S,4R)1-(3-(6-(4-fluorophenyl)-4-(1-methyl-1H-pyrazol-3-yl)pyridin-3-yl)-4-hydroxypyrrolidin-1-yl)prop-2-en-1-one |
| 476 | 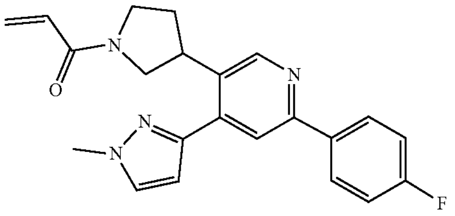 [SMILES: C=CC(=O)N1CCC(c2cnc(-c3ccc(F)cc3)cc2-c2ccn(C)n2)C1] | 1-(3-(6'-(4-fluorophenyl)-5-methoxy-[2,4'-bipyridin]-3'-yl)pyrrolidin-1-yl)prop-2-en-1-one |
| 477 | 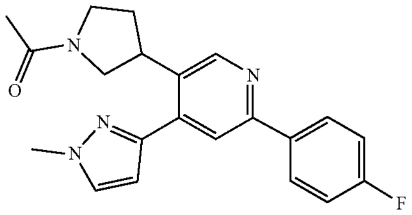 [SMILES: CC(=O)N1CCC(c2cnc(-c3ccc(F)cc3)cc2-c2ccn(C)n2)C1] | 1-(3-(6'-(4-fluorophenyl)-5-methoxy-[2,4'-bipyridin]-3'-yl)pyrrolidin-1-yl)ethan-1-one |
| 478 | 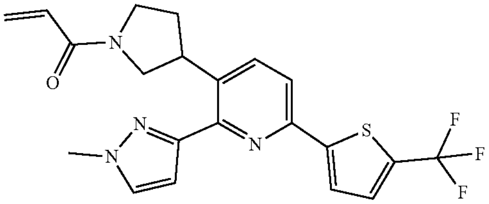 [SMILES: C=CC(=O)N1CCC(c2ccc(-c3ccc(C(F)(F)F)s3)nc2-c2ccn(C)n2)C1] | 1-(3-(2-(1-methyl-1H-pyrazol-3-yl)-6-(5-(trifluoromethyl)thiophen-2-yl)pyridin-3-yl)pyrrolidin-1-yl)prop-2-en-1-one |
| 479 | 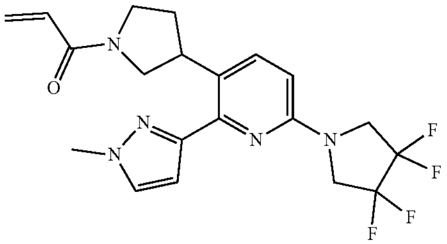 [SMILES: C=CC(=O)N1CCC(c2ccc(N3CC(F)(F)C(F)(F)C3)nc2-c2ccn(C)n2)C1] | 1-(3-(2-(1-methyl-1H-pyrazol-3-yl)-6-(3,3,4,4-tetrafluoropyrrolidin-1-yl)pyridin-3-yl)pyrrolidin-1-yl)prop-2-en-1-one |
| 480 | 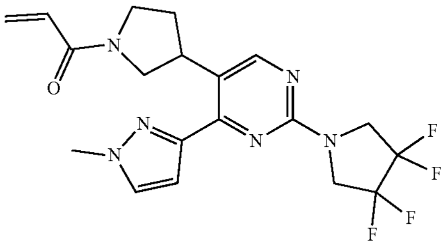 [SMILES: C=CC(=O)N1CCC(c2cnc(N3CC(F)(F)C(F)(F)C3)nc2-c2ccn(C)n2)C1] | 1-(3-(4-(1-methyl-1H-pyrazol-3-yl)-2-(3,3,4,4-tetrafluoropyrrolidin-1-yl)pyrimidin-5-yl)pyrrolidin-1-yl)prop-2-en-1-one |

TABLE 1-continued

| Structures of example compounds of the disclosure and their respective codes | | |
|---|---|---|
| Cpd. No. | Structure | Name |
| 481 | 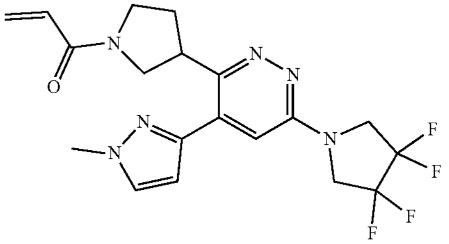 [SMILES: C=CC(=O)N1CCC(c2nnc(N3CC(F)(F)C(F)(F)C3)cc2-c2ccn(C)n2)C1] | 1-(3-(4-(1-methyl-1H-pyrazol-3-yl)-6-(3,3,4,4-tetrafluoropyrrolidin-1-yl)pyridazin-3-yl)pyrrolidin-1-yl)prop-2-en-1-one |
| 482 | 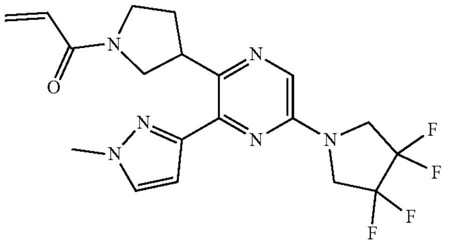 [SMILES: C=CC(=O)N1CCC(c2ncc(N3CC(F)(F)C(F)(F)C3)nc2-c2ccn(C)n2)C1] | 1-(3-(3-(1-methyl-1H-pyrazol-3-yl)-5-(3,3,4,4-tetrafluoropyrrolidin-1-yl)pyrazin-2-yl)pyrrolidin-1-yl)prop-2-en-1-one |

Compounds having an asymmetric carbon atom marked with an "*" were isolated as a single (R)- or (S)-enantiomer, but the absolute stereochemistry of these compounds has not been determined These examples are provided for the purpose of illustrating the present disclosure and by no means should be interpreted to limit the scope of the present disclosure.

Part A: Experimental Chemistry Procedures

All starting materials which are not explicitly described were either commercially available (the details of suppliers such as for example Acros, Avocado, Aldrich, Fluka, FluoroChem, MatrixScientific, Maybridge, Merck, Sigma, etc. can be found in the SciFinder® Database for example) or the synthesis thereof has already been described precisely in the specialist literature (experimental guidelines can be found in the Reaxys® Database or the SciFinder® Database respectively, for example) or can be prepared using the conventional methods known to the person skilled in the art.

The reactions were, if necessary, carried out under an inert atmosphere (mostly argon and $N_2$). The number of equivalents of reagents and the amounts of solvents employed as well as the reaction temperatures and times can vary slightly between different reactions carried out by analogous methods. The work-up and purification methods were adapted according to the characteristic properties of each compound and can vary slightly for analogous methods. The yields of the compounds prepared are not optimized.

The indication "equivalents" ("eq." or "eq" or "equiv.") means molar equivalents, "RT" or "rt" means room temperature T (23±7° C.), "M" are indications of concentration in mol/l, "sol." means solution, "conc." means concentrated. The mixing ratios of solvents are usually stated in the volume/volume ratio.

To perform reactions under microwave radiation a CEM Microwave (Discover SP) was employed (Heating rate: 2-6° C./sec; Temperature: 30-300° C. volume-independent infrared (IR) and 80-300° C. Fiber optic (FO) temperature measurement; Pressure: 0-435 psi, ActiVent™ technology; Power: 0-300 W; Magnetron frequency: 2450 MHz; Reaction agitation: electromagnetic stirring; Air Cooling: ≥25 psi (20 L/min flow); System control: Synergy™ software).

Key analytical characterization was carried out by means of $^{1}$H-NMR spectroscopy and/or mass spectrometry (MS, m/z for $[M+H]^+$ and/or $[M-H]^-$) for all the exemplary compounds and selected intermediate products. In certain cases, where e.g. regioisomers and/or diastereomers could be/were formed during the reaction, additional analytics, such as, e.g. $^{13}$C NMR and NOE (nuclear overhauser effect) NMR experiments were in some cases performed.

Analytical instruments employed were e.g. for NMR analysis a BRUKER AVANCE 400 MHz (Software Topspin) or a VARIAN MR 400 MHz (VNMRJ Sofware) machine was employed. For LC/MS analysis e.g. an Acquity UPLC H-Class, Mass: Acquity SQD2 Detector (ESI), an Acquity UPLC, Mass: Quatro premier XE Detector (ESI), an Acquity UPLC, Mass: Waters Xevo TQ-S Detector (ESI/ESCI), or an Alliance Waters 2695, Mass: Quattromicro™ (ESCI) multimode ionization was employed. Analytical HPLCs were measured e.g. on Alliance Waters 2695). Analytical SFC were performed e.g. on a PIC solution (Software: SFC PIC Lab Online), a WATERS-X5 (Software MASSLYNX), or a WATERS-UPC2 (Empower).

Preparative HPLC were performed e.g. on a Waters 2545 (Software Empower), a Gilson (Software Trilution), or a Shimadzu (Software LC Solution). Preparative SFC were performed e.g. on a Waters Thar SFC-80 (Software Chromscope), Waters Thar SFC-150 (Software Chromscope), Waters Thar SFC-200 (Software Chromscope), or a PIC SFC-175 (Software SFC PIC Lab Online).

Structures of example compounds that contain stereocentres are drawn and named with absolute stereochemistry, if known. In case of unknown absolute stereochemistry the compounds can be either racemic, a mixture of diatereomers, a pure diastereomer of unknown stereochemistry, or a pure enantiomer of unknown stereochemistry. Dia1 and Dia2 means that diastereoisomers were separated but the stereochemistry is unknown. En1 and En2 means that both enantiomers were separated but the absolute configuration is unknown. No suffix given after the compound code means that a compound containing stereocentres was obtained as a racemic mixture or a mixture of diatereomers, respectively, unless the chemical name of the compound specifies the exact stereochemistry.

The LC/MS analysis mentioned in the experimental part were also performed on a Alliance Waters 2695 HPLC (equipped with a PDA detector) connected to a mass spectrometer mass spectrometer Waters Quattromicro (ESCI, multimode ionization). (Method L in the table below).

Conditions used for the HPLC analysis in the experimental part. The LC/MS analysis mentioned in the experimental part were performed on a Alliance Waters 2695 HPLC (equipped with a PDA detector) connected to a mass spectrometer Waters Quattromicro (ESCI, multimode ionization). The separations were performed with a Acquity BEH C18 (1.7 μm, 2.1×50 mm) column, a Acquity BEH C18 (1.7 μm, 2.1×100 mm) column, or a X-Bridge C18 (3.5 μm, 4.6×75 mm) column thermostated to 30-35° C. and the PDA acquisition wavelength was set in the range of 210-400 nm (Acquisition Software: MassLynx) (Method L in the table below). Elutions were carried out with the methods described in the following tables. For Methods L1, L6, and L7 Solvent A: FA LC-MS grade 0.1% in milliQ water. Solvent B: FA LC-MS grade 0.1% in ACN LC-MS grade. For Methods L2 and L3 Solvent A: FA LC-MS grade 0.05% in milliQ water. Solvent B: FA LC-MS grade 0.05% in ACN LC-MS grade. For Methods L4 and L8 Solvent A: TFA LC-MS grade 0.05% in milliQ water. Solvent B: TFA LC-MS grade 0.05% in ACN LC-MS grade. For Method L5, Solvent A: 5 mM $(NH_4)HCO_3$ in milliQ water. Solvent B: ACN LC-MS grade.

| HPLC Method | System | Time (min) | Solvents A (%) | Solvents B (%) | Flow (mL/min) | Column |
|---|---|---|---|---|---|---|
| L1 | Alliance | 0 | 97 | 3 | 0.6 | Acquity BEH |
| | Waters | 0.4 | 97 | 3 | 0.6 | C18 (1.7 μm, |
| | 2695 | 3.2 | 2 | 98 | 0.6 | 2.1 × 50 mm) |
| | HPLC | 3.8 | 2 | 98 | 0.6 | (0.1% FA in |
| | | 4.2 | 97 | 3 | 0.6 | solvents A and |
| | | 4.5 | 97 | 3 | 0.6 | B) |
| L2 | Alliance | 0 | 97 | 3 | 0.6 | Acquity BEH |
| | Waters | 0.4 | 97 | 3 | 0.6 | C18 (1.7 μm, |
| | 2695 | 3.2 | 2 | 98 | 0.6 | 2.1 × 50 mm) |
| | HPLC | 3.8 | 2 | 98 | 0.6 | (0.05% FA in |
| | | 4.2 | 97 | 3 | 0.6 | solvents A and |
| | | 4.5 | 97 | 3 | 0.6 | B) |
| L3 | Alliance | 0 | 97 | 3 | 0.6 | Acquity BEH |
| | Waters | 0.4 | 97 | 3 | 0.6 | C18 (1.7 μm, |
| | 2695 | 7.5 | 2 | 98 | 0.6 | 2.1 × 50 mm) |
| | HPLC | 9.5 | 2 | 98 | 0.6 | (0.05% FA in |
| | | 9.6 | 97 | 3 | 0.6 | solvents A and |
| | | 10 | 97 | 3 | 0.6 | B) |
| L4 | Alliance | 0 | 97 | 3 | 0.6 | Acquity BEH |
| | Waters | 0.4 | 97 | 3 | 0.6 | C18 (1.7 μm, |
| | 2695 | 2.5 | 2 | 98 | 0.6 | 2.1 × 100 mm) |
| | HPLC | 3.4 | 2 | 98 | 0.6 | (0.05% TFA in |
| | | 3.5 | 97 | 3 | 0.6 | solvents A and |
| | | 4 | 97 | 3 | 0.6 | B) |
| L5 | Alliance | 0 | 95 | 5 | 1.3 | X-Bridge C18 |
| | Waters | 0.5 | 95 | 5 | 1.3 | (3.5 μm, |
| | 2695 | 1.0 | 85 | 15 | 1.3 | 4.6 × 75 mm) |
| | HPLC | 4.0 | 2 | 98 | 1.3 | (5 mM |
| | | 7.0 | 2 | 98 | 1.3 | $(NH_4)HCO_3$ in |
| | | 7.5 | 95 | 5 | 1.3 | solvent A) |
| | | 8.0 | 95 | 5 | 1.3 | |
| L6 | Alliance | 0 | 97 | 3 | 0.6 | Acquity BEH |
| | Waters | 0.4 | 97 | 3 | 0.6 | C18 (1.7 μm, |
| | 2695 | 2.5 | 2 | 98 | 0.6 | 2.1 × 50 mm) |

-continued

| HPLC Method | System | Time (min) | Solvents A (%) | Solvents B (%) | Flow (mL/min) | Column |
|---|---|---|---|---|---|---|
| | HPLC | 3.4 | 2 | 98 | 0.6 | (0.1% FA in |
| | | 3.5 | 97 | 3 | 0.6 | solvents A and |
| | | 4.0 | 97 | 3 | 0.6 | B) |
| L7 | Alliance | 0 | 97 | 3 | 0.55 | Acquity BEH |
| | Waters | 8.5 | 0 | 100 | 0.55 | C18 (1.7 μm, |
| | 2695 | 9.0 | 0 | 100 | 0.55 | 2.1 × 100 mm) |
| | HPLC | 9.5 | 97 | 3 | 0.55 | (0.1% FA in |
| | | 10.0 | 97 | 3 | 0.55 | solvents A and |
| | | | | | | B) |
| L8 | Alliance | 0 | 97 | 3 | 0.45 | Acquity BEH |
| | Waters | 0.4 | 97 | 3 | 0.45 | C18 (1.7 μm, |
| | 2695 | 3.5 | 2 | 98 | 0.45 | 2.1 × 100 mm) |
| | HPLC | 4.5 | 2 | 98 | 0.45 | (0.05% FA in |
| | | 5.0 | 3 | 97 | 0.45 | solvents A and |
| | | 5.5 | 3 | 97 | 0.45 | B) |

Conditions used for the UPLC analysis in the experimental part. The UPLC analysis mentioned in the experimental part were performed on a Acquity UPLC H-Class (equipped with a PDA detector) connected to a mass spectrometer Acquity TQ Detector (ESI/ESCI). The separations were performed with a Acquity UPLC BEH C18 (1.7 μm, 2.1×50 mm) column thermostated to 40° C. and the PDA acquisition wavelength was set in the range of 190-420 nm (Method U in the table below). Elutions were carried out with the methods described in the following tables. For Methods U1 and U2 Solvent A: 10 mM $(NH_4)OAc$ in milliQ water containing 5% ACN (UPLC grade, Biosolve). Solvent B: ACN (UPLC grade, Biosolve). For Method U3, U5, U8, U9, U10, Solvent A: FA LC-MS grade 0.05% in milliQ water. Solvent B: 0.05% FA LC-MS grade in ACN. Column temp=35° C. For Method U4, U11 Solvent A: TFA LC-MS grade 0.05% in milliQ water. Solvent B: ACN LC-MS grade. Column temp=35° C. For Method U6 Solvent A: TFA LC-MS grade 0.05% in milliQ water. Solvent B: ACN LC-MS grade. Column temp=50° C. For Method U7 Solvent A: TFA LC-MS grade 0.05% in milliQ water. Solvent B: ACN LC-MS grade. Column temp=35° C. For Method U12 Solvent A: $NH_4CO_3$ 10 mM in milliQ water. Solvent B: ACN LC-MS grade. Column temp=ambient.

| UPLC Method | System | Time (min) | Solvents A (%) | Solvents B (%) | Flow (mL/min) | Column |
|---|---|---|---|---|---|---|
| U1 | Acquity | 0 | 84 | 16 | 0.5 | Acquity UPLC |
| | UPLC | 3.4 | 42 | 58 | 0.5 | BEH C18 |
| | H-Class | 4.0 | 10 | 90 | 0.5 | |
| | | 5.0 | 10 | 90 | 0.5 | |
| U2 | Acquity | 0 | 52 | 48 | 0.5 | Acquity UPLC |
| | UPLC | | | | | |
| | H-Class | | | | | |
| U3 | Waters | 3.5 | 10 | 90 | 0.5 | BEH C18 |
| | Acquity | 5.0 | 10 | 90 | 0.5 | Acquity BEH |
| | UPLC | 0.0 | 97 | 3 | 0.6 | C18 (0.05% |
| | | 0.4 | 97 | 3 | 0.6 | TFA in solvents |
| | | 2.0 | 2 | 98 | 0.6 | A and B) |
| | | 3.4 | 2 | 98 | 0.6 | |
| | | 3.5 | 97 | 3 | 0.6 | |
| | | 4.0 | 97 | 3 | 0.6 | |
| U4 | Waters | 0.0 | 97 | 3 | 0.45 | Acquity BEH |
| | Acquity | 0.4 | 97 | 3 | 0.45 | C18 (0.05% |
| | UPLC | 3.5 | 2 | 2 | 0.45 | TFA in solvents |
| | | 4.5 | 2 | 2 | 0.45 | A and B) |
| | | 5.0 | 97 | 3 | 0.45 | |
| | | 5.5 | 97 | 3 | 0.45 | |

-continued

| UPLC Method | System | Time (min) | Solvents A (%) | Solvents B (%) | Flow (mL/min) | Column |
|---|---|---|---|---|---|---|
| U5 | Waters Acquity UPLC | 0.0 | 97 | 3 | 0.6 | Acquity BEH C18 (0.05% FA in solvents A and B) |
| | | 0.4 | 97 | 3 | 0.6 | |
| | | 2.0 | 2 | 98 | 0.6 | |
| | | 3.4 | 2 | 98 | 0.6 | |
| | | 3.5 | 97 | 3 | 0.6 | |
| | | 4.0 | 97 | 3 | 0.6 | |
| U6 | Waters Acquity UPLC | 0.0 | 97 | 3 | 0.55 | Acquity BEH C18 (0.05% TFA in solvents A and B) |
| | | 8.5 | 0 | 100 | 0.55 | |
| | | 9.0 | 0 | 100 | 0.55 | |
| | | 9.5 | 97 | 3 | 0.55 | |
| | | 10 | 97 | 3 | 0.55 | |
| U7 | Waters Acquity UPLC | 0.0 | 97 | 3 | 0.6 | Acquity BEH C18 (0.05% TFA in solvents A and B) |
| | | 0.4 | 97 | 3 | 0.6 | |
| | | 7.5 | 2 | 98 | 0.6 | |
| | | 9.5 | 2 | 98 | 0.6 | |
| | | 9.6 | 97 | 3 | 0.6 | |
| | | 10.0 | 97 | 3 | 0.6 | |
| U8 | Waters Acquity UPLC | 0.0 | 97 | 3 | 0.6 | Acquity BEH C18 (0.05% FA in solvents A and B) |
| | | 0.4 | 97 | 3 | 0.6 | |
| | | 2.5 | 2 | 98 | 0.6 | |
| | | 3.4 | 2 | 98 | 0.6 | |
| | | 3.5 | 97 | 3 | 0.6 | |
| | | 4.0 | 97 | 3 | 0.6 | |
| U9 | Waters Acquity UPLC | 0.0 | 97 | 3 | 0.6 | Acquity BEH C18 (0.05% FA in solvents A and B) |
| | | 0.4 | 97 | 3 | 0.6 | |
| | | 2.5 | 2 | 98 | 0.6 | |
| | | 3.5 | 2 | 98 | 0.6 | |
| | | 3.6 | 97 | 3 | 0.6 | |
| | | 4.0 | 97 | 3 | 0.6 | |
| U10 | Waters Acquity UPLC | 0.0 | 97 | 3 | 0.6 | Acquity BEH C18 (0.05% FA in solvents A and B) |
| | | 2.5 | 97 | 3 | 0.6 | |
| | | 7.5 | 2 | 98 | 0.6 | |
| | | 9.5 | 2 | 98 | 0.6 | |
| | | 9.6 | 97 | 3 | 0.6 | |
| | | 10.0 | 97 | 3 | 0.6 | |
| U11 | Waters Acquity UPLC | 0.0 | 97 | 3 | 0.6 | Acquity BEH C18 (0.05% TFA in solvents A and B) |
| | | 0.4 | 97 | 3 | 0.6 | |
| | | 2.5 | 2 | 98 | 0.6 | |
| | | 3.5 | 2 | 98 | 0.6 | |
| | | 3.6 | 97 | 3 | 0.6 | |
| | | 4.0 | 97 | 3 | 0.6 | |
| U12 | Waters Acquity UPLC | 0.0 | 95 | 5 | 1.0 | X-Select CSH C18 (10 mM $NH_4CO_3$ in solvents A and B) |
| | | 1.0 | 95 | 5 | 1.0 | |
| | | 3.0 | 85 | 15 | 1.0 | |
| | | 7.0 | 45 | 55 | 1.0 | |
| | | 11.0 | 2 | 98 | 1.0 | |
| | | 16.0 | 2 | 98 | 1.0 | |
| | | 16.1 | 95 | 5 | 1.0 | |
| | | 20.0 | 95 | 5 | 1.0 | |

Conditions used for the FC analysis in the experimental part. The F analysis mentioned in the experimental part were performed on a WATERS Acquity UPC2 QDa (Empower-3 Sofware) equipped with a Acquity PDA and an Acquity QDa Detector. The separations were performed with a Chiralpak IF-3 (3 µm, 4.6×150 mm) or Chiralpak IG-3 (3 µm, 4.6×150 mm) column, $CO_2$ as the mobile phase and MeOH as the co-solvent. The column was thermostated at 30° C. Elutions were carried out with the methods described in the following table.

| SCF Method | Column and conditions |
|---|---|
| S1 | Column: Chiralpak IF-3 (3 µm, 4.6 x 150 mm); % $CO_2$: 65; co-solvent: 35 (MeOH); Flow: 3 g/min; ABPR: 1500 psi; Temperature: 30° C. |
| S2 | Column: Chiralpak IG-3 (3 µm, 4.6 x 150 mm); % $CO_2$: 60; co-solvent: 40 (MeOH); Flow: 3 g/min; ABPR: 1500 psi; Temperature: 30° C. |
| S3 | Column: Chiralpak IF (5 µm, 4.6 x 250 mm); Mobile phase: 100% n-hexane:EtOH (60:40); Flow rate = 1 mL/min; Temperature: ambient. |
| S4 | Column: Chiralpak IF (5 µm, 4.6 x 250 mm); Mobile phase: 100% ACN; Flow rate = 1 mL/min; Temperature: ambient. |
| S5 | Column: Chiralcel OJ-H (5 µm, 4.6 x 250 mm); % $CO_2$: 70; % co-solvent: 30 (ACN); Flow rate = 3 g/min; ABPR = 1500 psi Temperature: 30° C. |
| S6 | Column: Chiralpak IG-3 (3 µm, 4.6 x 150 mm); % $CO_2$: 80; % co-solvent: 20 (0.5% isopropylamine in isopropanol); Flow rate = 3 g/min; ABPR = 1500 psi Temperature: 30° C. |
| S7 | Column: Chiralcel OD-3 (3 µm, 4.6 x 150 mm); % $CO_2$: 75; % co-solvent: 25 (MeOH); Flow rate = 3 g/min; ABPR = 1500 psi Temperature: 30° C. |
| S8 | Column: Chiralpak AY-H (5 µm, 4.6 x 150 mm); % $CO_2$: 70; % co-solvent: 30 (isopropanol); Flow rate = 3 g/min; ABPR = 1500 psi Temperature: 30° C. |
| S9 | Column: Chiralpak AD-H (5 µm, 4.6 x 250 mm); % $CO_2$: 80; % co-solvent: 20 (MeOH); Flow rate = 3 g/min; ABPR = 1500 psi Temperature: 30° C. |
| S10 | Column: Chiralcel OJ-H (5 µm, 4.6 x 250 mm); % $CO_2$: 90; % co-solvent: 10 (MeOH); Flow rate = 3 g/min; ABPR = 1500 psi Temperature: 30° C. |
| S11 | Column: Chiralpak IF (5 µm, 4.6 x 250 mm); Mobile phase: % $CO_2$: 80; % co-solvent: 20 (MeOH); Flow rate = 3 g/min; ABPR = 1500 psi Temperature: 30° C. |
| S12 | Column: Chiralpak IG (5 µm, 4.6 x 250 mm); Mobile phase: 100% MeOH; Flow rate = 1 mL/min; Temperature: ambient. |
| S13 | Column: Chiralcel OD-3 (3 µm, 4.6 x 150 mm); % $CO_2$: 70; % co-solvent: 30 (0.5% isopropylamine in isopropanol); Flow rate = 3 g/min; ABPR = 1500 psi Temperature: 30° C. |
| S14 | Column: Chiralpak IF (5 µm, 4.6 x 250 mm); Mobile phase: 100% MeOH; Flow rate = 0.7 mL/min; Temperature: ambient. |
| S15 | Column: Chiralpak IF (3 µm, 4.6 x 150 mm); Mobile phase: % $CO_2$: 60; % co-solvent: 40 (MeOH); Flow rate = 3 g/min; ABPR = 1500 psi Temperature: 30° C. |
| S16 | Column: Chiralpak AD-H (5 µm, 4.6 x 150 mm); % $CO_2$: 70; % co-solvent: 30 (MeOH); Flow rate = 3 g/min; ABPR = 1500 psi Temperature: 30° C. |
| S17 | Column: Chiralpak-IK (5 µm, 4.6 x 250 mm); % $CO_2$: 60; % co-solvent: 40 (MeOH); Flow rate = 3 g/min; ABPR = 1500 psi Temperature: 30° C. |

-continued

| SCF Method | Column and conditions |
|---|---|
| S18 | Column: Chiralcel OX-H (5 μm, 4.6 x 150 mm); % $CO_2$: 70; % co-solvent: 30 (MeOH); Flow rate = 3 g/min; ABPR = 1500 psi Temperature: 30° C. |
| S19 | Column: Chiralcel OJ-H (5 μm, 4.6 x 150 mm); % $CO_2$: 85; % co-solvent: 15 (MeOH); Flow rate = 3 g/min; ABPR = 1500 psi Temperature: 30° C. |
| S20 | Column: Chiralpak IF (5 μm, 4.6 x 250 mm); Mobile phase: % $CO_2$: 60; % co-solvent: 40 (0.5% diethylamine in MeOH); Flow rate = 4 g/min; ABPR = 1500 psi Temperature: 30° C. |
| S21 | Column: Chiralpak AD-H (5 μm, 4.6 x 150 mm); % $CO_2$: 60; % co-solvent: 40 (0.5% diethylamine in MeOH); Flow rate = 3 g/min; ABPR = 1500 psi Temperature: 30° C. |
| S22 | Column: Chiralpak IE (3 μm, 4.6 x 150 mm); % $CO_2$: 60; % co-solvent: 40 (MeOH); Flow rate = 3 g/min; ABPR = 1500 psi Temperature: 30° C. |

Preparative HPLC purifications mentioned in this experimental part have been carried out with the following system: on a Waters 2545 (Empower software, 2996 PDA detector, 2707 autosampler), a Gilson (Software Trilution, 171 DAD detector, GX-271 autosampler), or a Shimadzu (Software LC Solution, CMB-20A detector, SIL-10AP autosampler). The separations were performed with a Luna C18 (5 μm, 21.2×250 mm; or 10 μm, 21.2×250 mm) column, a X-Bridge 018 (5 μm, 29×250 mm; 5 μm, 19×150 mm; or rpm, 19×150 mm) column, a X-Select 018 (5 μm, 19×150 mm; 5 μm, 19×250 mm; 5 μm, 25×150 mm; 10 μm, 25×150 mm; or 10 μm, 25×250 mm) column, a X-Select SH Phenyl-Hexyl (5 μm, 19×150 mm; or 5 μm, 19×250 mm) column, a Synergi Polar-RP (5 μm, 21.2×250 mm), a Kromasil (5 μm, 19×150 mm), or a YM-Triart 018 (10 μm, 19×250 mm) column. Elutions were carried out with columns and solvents described in the following table. Gradients systems for each individual compound were employed using the solvents mentioned in the table. Detection wavelengths were fixed at 210 and 254 nm.

| HPLC Method | Column and conditions |
|---|---|
| H1 | Luna C18 (5 μm, 21.2 x 250 mm) or Luna C18 (10 μm, 21.2 x 250 mm); Solvent A: 10 mM $(NH_4)HCO_3$ in water; Solvent B: ACN; Flow: 15 mL/min. |
| H2 | X-Bridge C18 (5 μm, 19 x 150 mm), X-Bridge C18 (5 μm, 19 x 250 mm), or X-Bridge C18 (10 μm, 19 x 150 mm); Solvent A: 10 mM $(NH_4)HCO_3$ in water; Solvent B: ACN; Flow: 15 mL/min. |
| H3 | X-Select C18 (5 μm, 19 x 150 mm), X-Select C18 (5 μm, 19 x 250 mm), X-Select C18 (10 μm, 25 x 150 mm), or X-Select C18 (10 μm, 25 x 250 mm); Solvent A: 10 mM $(NH_4)HCO_3$ in water; Solvent B: ACN; Flow: 15 mL/min. |
| H4 | X-Select C18 (5 μm, 19 x 250 mm); Solvent A: 10 mM $(NH_4)HCO_3$ in water; Solvent B: ACN/MeOH (1:1); Flow: 13 mL/min. |
| H5 | X-Select CSH Phenyl-Hexyl (5 μm, 19 x 150 mm), X-Select CSH Phenyl-Hexyl (5 μm, 19 x 250 mm) or X-Select CSH Phenyl-Hexyl (10 μm, 21.2 x 250 mm); Solvent A: 10 mM $(NH_4)HCO_3$ in water; Solvent B: ACN; Flow: 15 mL/min. |
| H6 | X-Select C18 (5 μm, 20 x 250 mm) or X-Select C18 (10 μm, 25 x 150 mm); Solvent A: 10 mM $NH_4OAc$ in water; Solvent B: ACN; Flow: 20 mL/min. |
| H7 | X-Select CSH Phenyl-Hexyl (5 μm, 19 x 250 mm); Solvent A: 10 mM $NH_4OAc$ in water; Solvent B: ACN; Flow: 16 mL/min. |
| H8 | X-Select CSH Phenyl-Hexyl (5 μm, 19 x 250 mm); Solvent A: 0.1% FA in water; Solvent B: ACN; Flow: 14 mL/min. |
| H9 | X-Select C18 (5 μm, 25 x 150 mm), X-Select C18 (10 μm, 25 x 150 mm) or X-Select C18 (5 μm, 19 x 150 mm); Solvent A: 0.1% FA in water; Solvent B: ACN; Flow: 18 mL/min. |
| H10 | X-Bridge C18 (5 μm, 19 x 150 mm); Solvent A: 0.1% AcOH in water; Solvent B: ACN; Flow: 14 mL/min. |
| H11 | Synergi Polar-RP (5 μm, 21.2 x 250 mm); Solvent A: 0.1% FA in water; Solvent B: ACN; Flow: 17 mL/min. |
| H12 | Kromasil (5 μm, 19 x 150 mm); Solvent A: 10 mM $(NH_4)HCO_3$ in water; Solvent B: ACN; Flow: 15 mL/min. |
| H13 | Luna C18 (5 μm, 21.2 x 250 mm); Solvent A: 0.1% FA in water; Solvent B: ACN; Flow: 15 mL/min. |
| H14 | YMC-Triart C18 (10 μm, 19 x 250 mm); Solvent A: 10 mM $(NH_4)HCO_3$ in water; Solvent B: ACN; Flow: 20 mL/min. |
| H15 | YMC-Triart C18 (10 μm, 19 x 250 mm); Solvent A: 10 mM $(NH_4)HCO_3$ in water; Solvent B: ACN/MeOH (1:1); Flow: 22 mL/min. |
| H16 | X-Select CSH Phenyl-Hexyl (5 μm, 25 x 150 mm); Solvent A: 0.1% TFA in water; Solvent B: ACN; Flow: 15 mL/min. |
| H17 | Sunfire C18 (5 μm, 19 x 250 mm); Solvent A: 0.1% FA in water; Solvent B: ACN; Flow: 16 mL/min. |
| H18 | Princeton sphere C18 (5 μm, 21 x 250 mm); Solvent A: 0.1% FA in water; Solvent B: ACN; Flow: 17 mL/min. |

-continued

| HPLC Method | Column and conditions |
|---|---|
| H19 | HYDROSHPERE C18 (5 μm, 2 × 250 mm); Solvent A: 0.1% FA in water; Solvent B: ACN; Flow: 15 mL/min. |
| H20 | BEH C18 (1.7 μm, 2 × 100 mm); Solvent A: 0.05% FA in water; Solvent B: CAN; Flow: 0.55 mL/min. |

Preparative SFC purifications mentioned in this experimental part have been carried out with the following system: a Thar SCF-200 (Software Chromscope) equipped with a UV/PDA detector and a modifier stream injection mode. The separations were performed with a Chiralpak IC (5 μm, 30×250 mm), a Chiralpak IF (5 μm, 30×250 mm) or a Chiralpak IG (5 μm, 30×250 mm) column, 002 as the mobile phase and MeOH as the co-solvent. The column was thermostated at 30° C. Detection wavelengths were fixed at 214 nm. Elutions were carried out with the methods described in the following table.

| Prep SFC Method | Column and conditions |
|---|---|
| K1 | Chiralpak IC (5 μm, 30 × 250 mm); % $CO_2$: 85; % co-solvent: 15 (0.5% TFA in MeOH); Flow: 90 g/min; ABPR: 1450 psi; Temperature: 30° C. |
| K2 | Chiralpak IF (5 μm, 30 × 250 mm); % $CO_2$: 60; % co-solvent: 40 (MeOH); Flow: 70 g/min; ABPR: 1450 psi; Temperature: 30° C. |
| K3 | Chiralpak IG (5 μm, 30 × 250 mm); % $CO_2$: 55; % co-solvent: 45 (MeOH); Flow: 70 g/min; ABPR: 1450 psi; Temperature: 30° C. |
| K4 | Chiralpak IF (5 μm, 30 × 250 mm); Mobile phase: n-hexane:EtOH (60:40); Flow rate = 40 mL/min; Temperature = ambient. |
| K5 | Chiralcel OJ-H (5 μm, 30 × 250 mm); % $CO_2$: 70; % co-solvent: 30 (ACN); Flow: 60 g/min. ABPR = 1500 psi; Temperature: 30° C. |
| K6 | Chiralcel OD-H (5 μm, 30 × 250 mm); % $CO_2$: 75; % co-solvent: 25 (MeOH); Flow: 90 g/min. ABPR = 1500 psi; Temperature: 30° C. |
| K7 | Lux Amylose-2 (5 μm, 30 × 250 mm); % $CO_2$: 70; % co-solvent: 30 (isopropanol); Flow: 60 g/min. ABPR = 1500 psi; Temperature: 30° C. |
| K8 | Chiralpak AD-H (5 μm, 30 × 250 mm); Mobile phase: % $CO_2$: 85; % co-solvent: 15 (MeOH) Flow rate = 100 g/min; Temperature = 30° C. |
| K9 | Column: Chiralcel OJ-H (5 μm, 10 × 250 mm); % $CO_2$: 90; % co-solvent: 10 (MeOH); Flow rate = 15 g/min; ABPR = 1500 psi; Temperature: 30° C. |
| K10 | Column: Chiralpak-IK (5 μm, 30 × 250 mm); % $CO_2$: 60; % co-solvent: 40 (MeOH); Flow rate = 90 g/min; ABPR = 1500 psi; Temperature: 30° C. |
| K11 | Chiralpak OJ-H (5 μm, 30 × 250 mm); % $CO_2$: 85; % co-solvent: 15 (MeOH); Flow: 60 g/min. ABPR = 1500 psi; Temperature: ambient. |
| K12 | Chiral ART Amylose-C NEO (5 μm, 4.6 × 250 mm); % $CO_2$: 60; % co-solvent: 40 (MeOH); Flow: 3 g/min. ABPR = 1500 psi; Temperature: 30° C. |
| K13 | Chiralpak IE (5 μm, 10 × 250 mm); % $CO_2$: 60; % co-solvent: 40 (MeOH); Flow rate = 15 g/min; ABPR = 1500 psi Temperature: 30° C. |

Synthesis of 4-(bromomethyl)-1-methylpyridin-2(1H)-one (R1)

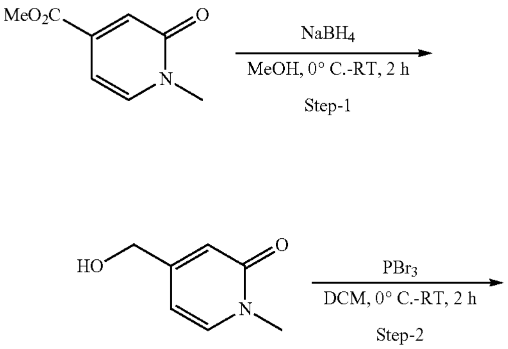

-continued

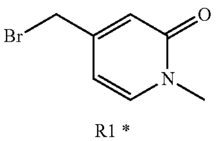

R1 *

Step 1: A solution of methyl 1-methyl-2-oxo-1,2-dihydropyridine-4-carboxylate (2.0 g, 12 mmol) in MeOH (30 mL) was cooled to 0° C. and treated with $NaBH_4$ (0.684 g, 18 mmol). The mixture was stirred at RT for 2 h and monitored by TLC. TLC mobile phase: 10% MeOH in DCM, RF: 0.2, TLC detection: UV. The reaction mixture was diluted with EtOAc (20 mL) and concentrated under reduced pressure to afford pale yellow gum (2.8 g) which was purified by normal phase flash column chromatography using neutral alumina and a gradient of 0-10% MeOH in DCM as an eluent to afford 4-(hydroxymethyl)-1-methylpyridin-2(1H)-one as an off-white solid (1.3 g, 75%, LC/MS 96%). (LC/MS; m/z 139.9 $[M+H]^+$).

Step 2: A solution of 4-(hydroxymethyl)-1-methylpyridin-2(1H)-one (300 mg, 2.16 mmol) in DCM (20 mL) was cooled to 0° C. and treated with $PBr_3$ (701 mg, 2.59 mmol). The mixture was stirred at RT for 2 h and monitored by TLC. TLC mobile phase: 100% EtOAc, RF: 0.3, TLC detection: UV. The reaction mixture was cooled to 0° C., quenched with sat aq $NaHCO_3$ (15 mL) and extracted with EtOAc (2×10 mL). The combined organic layer was dried over anhydrous $Na_2SO_4$ and concentrated under reduced pressure to afford 4-(bromomethyl)-1-methylpyridin-2(1H)-one (R1) as a brown gum (210 mg, 33%, LC/MS 69%). (LC/MS; m/z 202.0 $[M+H]^+$). The product was used as such without further purification.

Synthesis of 2-bromo-5-(bromomethyl)pyridine (R2)

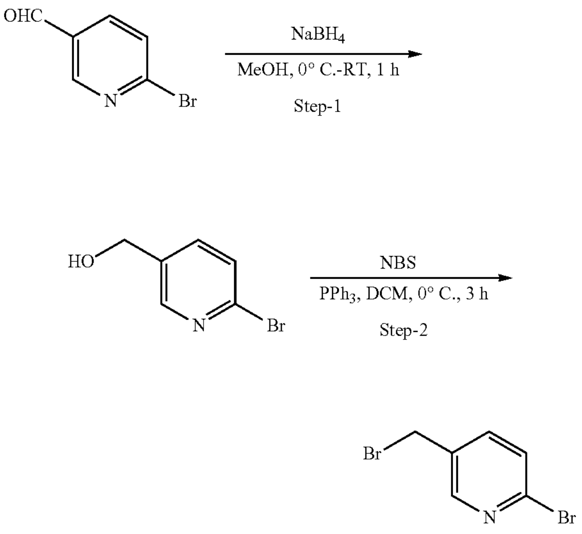

R2

Step 1: A solution of 6-bromonicotinaldehyde (500 mg, 2.68 mmol) in MeOH (5 mL) was cooled to 0° C. and treated with $NaBH_4$ (199 mg, 5.37 mmol). The mixture was stirred at RT for 1 h and monitored by TLC. TLC mobile phase: 20% EtOAc in pet ether, RF: 0.16, TLC detection: UV. The reaction mixture was poured into ice $H_2O$ (30 mL) and extracted with EtOAc (3×30 mL). The organic layer was dried over anhydrous $Na_2SO_4$ and concentrated under reduced pressure to afford (6-bromopyridin-3-yl)methanol as an off-white solid (470 mg, 93%, LC/MS 93%). (LC/MS; m/z 187.2 $[M+H]^+$).

Step 2: A solution of (6-bromopyridin-3-yl)methanol (370 mg, 1.96 mmol) and $PPh_3$ (619 mg, 2.36 mmol) in DCM (6 mL) was treated with NBS (420 mg, 2.36 mmol) at 0° C. The mixture was stirred at RT for 3 h and monitored by TLC. TLC mobile phase: 30% EtOAc in pet ether, RF: 0.4, TLC detection: UV. The reaction mixture was poured into ice $H_2O$ (40 mL) and extracted with DCM (3×40 mL). The organic layer was dried over anhydrous $Na_2SO_4$ and concentrated under reduced pressure to afford crude product (800 mg, LC/MS 78%) which was purified by normal phase flash column chromatography using silica gel (100-200 mesh) and a gradient of 0-10% EtOAc in pet ether as an eluent to afford 2-bromo-5-(bromomethyl)pyridine (R2) as an off-white solid (250 mg, 44%, LC/MS 87%). (LC/MS; m/z 350.0 $[M+H]^+$). $^1H$ NMR (400 MHz, DMSO-$d_6$) δ ppm: 8.38 (s, 1H), 7.58-7.61 (d, 1H), 7.47-7.49 (d, 1H), 4.42 (s, 2H). The product was used as such without further purification.

The following reagent was prepared in a manner similar (use of appropriate reagents and purification methods known to the person skilled in the art) to R2:

| Cpd. No. | Structure | $[M + H]^+$ (m/z) |
|---|---|---|
| R3 | 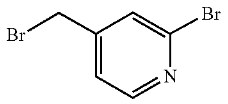 | 251.7 |

Synthesis of methyl 5-(bromomethyl)nicotinate (R4)

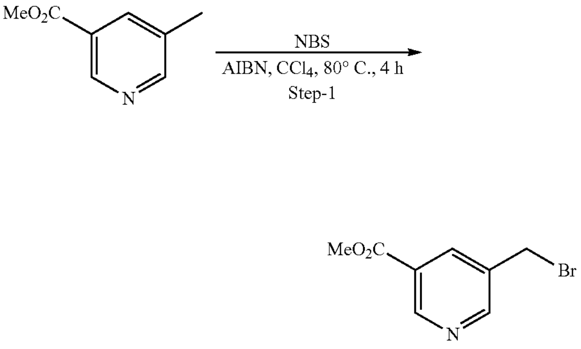

R4

Step 1: A solution of methyl 5-methylnicotinate (1.0 g, 6.6 mmol), NBS (1.40 g, 7.92 mmol) and AIBN (216 mg, 1.32 mmol) in $CCl_4$ (20 mL) was stirred at 80° C. for 4 h and monitored by TLC. TLC mobile phase: 10% EtOAc in pet ether, RF: 0.2, TLC detection: UV. The reaction mixture was cooled to RT, filtered through a celite pad, dried over anhydrous $Na_2SO_4$ and concentrated under reduced pressure to afford methyl 5-(bromomethyl)nicotinate (R4) as a pale yellow gum (1.2 g, 27%, LC/MS 35%). (LC/MS; m/z 230.0 $[M+H]^+$). The product is chemically labile and was used as such without further purification.

The following reagent was prepared in a manner similar (use of appropriate reagents and purification methods known to the person skilled in the art) to R4:

| Cpd. No. | Structure | $[M + H]^+$ (m/z) |
|---|---|---|
| R5 | 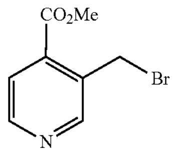 | 230.0 |

Synthesis of 1-benzyl-3-(3-bromophenyl)-1H-pyrazole (Int-1) and 3-([1,1'-biphenyl]-3-yl)-1H-pyrazole (Int-2)

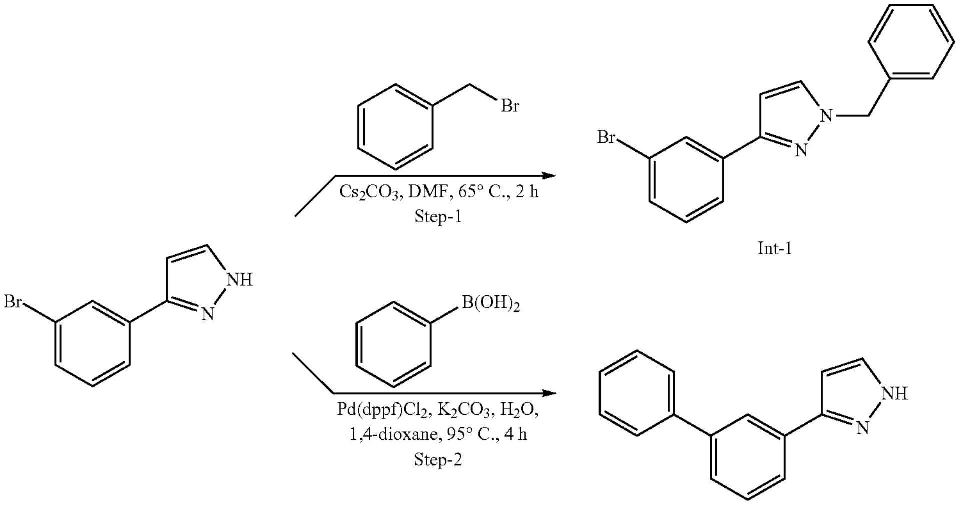

Step 1: A mixture of 5-(3-bromophenyl)-1H-pyrazole (600 mg, 2.64 mmol), $Cs_2CO_3$ (1.74 g, 5.27 mmol) and benzyl bromide (0.345 mL, 2.90 mmol) in DMF (20 mL) stirred at 65° C. for 2 h. The reaction mixture was poured into ice $H_2O$ and extracted with EtOAc (2×50 mL). The combined organic layer was washed with brine, dried over anhydrous $Na_2SO_4$ and concentrated under reduced pressure. The residue was purified by normal phase flash column chromatography using a 25 g column (silica) and a gradient of 0-20% EtOAc in pet ether as an eluent to afford 1-benzyl-3-(3-bromophenyl)-1H-pyrazole (Int-1) (623 mg, 74%). (LC/MS; m/z 313.2 $[M+H]^+$).

Step 2: Phenylboronic acid (164 mg, 1.34 mmol), 5-(3-bromophenyl)-1H-pyrazole (200 mg, 0.90 mmol), and $K_2CO_3$ (372 mg, 2.68 mmol) was dissolved in 1,4-dioxane (3 mL) and $H_2O$ (1.2 mL). The mixture was degassed with argon for 5 min and to the solution was added $Pd(dppf)Cl_2$ (66 mg, 0.09 mmol). The reaction mixture was stirred at 95° C. for 4 h. The reaction mixture was concentrated under reduced pressure and the resulting residue was purified by normal phase flash column chromatography using a 20 g column (silica) and a gradient of 0-40% EtOAc in pet ether as an eluent to afford 3-([1,1'-biphenyl]-3-yl)-1H-pyrazole (Int-2) (132 mg, 66%). (LC/MS; m/z 221.1 $[M+H]^+$).

The following intermediates were prepared in a manner similar (use of appropriate reagents and purification methods known to the person skilled in the art) to Int-1:

| Cpd. No. | Structure | $[M + H]^+$ (m/z) |
|---|---|---|
| Int-3 | 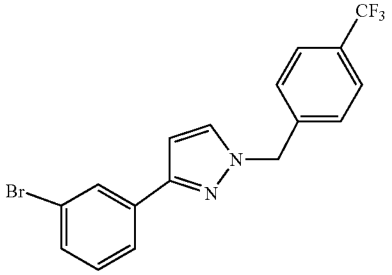 [SMILES: FC(F)(F)c1ccc(Cn2ccc(-c3cccc(Br)c3)n2)cc1] | 381.2 |
| Int-4 | 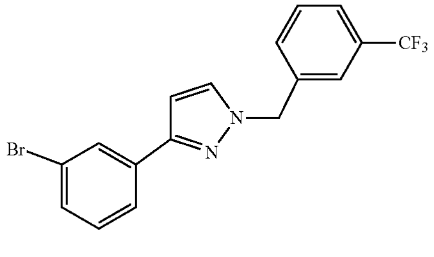 [SMILES: FC(F)(F)c1cccc(Cn2ccc(-c3cccc(Br)c3)n2)c1] | 381.2 |
| Int-5 | 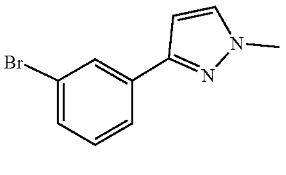 | 237.1 |

-continued

| Cpd. No. | Structure | [M + H]+ (m/z) |
|---|---|---|
| Int-6 | 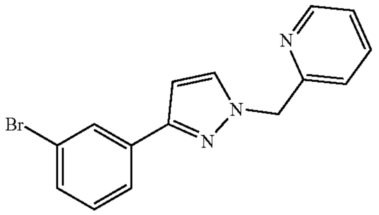 [SMILES: Brc1cccc(-c2ccn(Cc3ccccn3)n2)c1] | 313.9 |
| Int-7 | 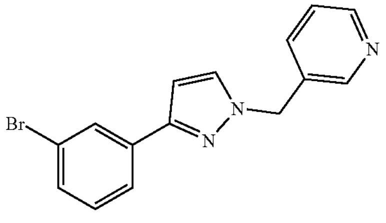 [SMILES: Brc1cccc(-c2ccn(Cc3cccnc3)n2)c1] | 314.1 |
| Int-8 | 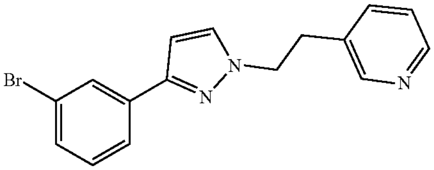 [SMILES: Brc1cccc(-c2ccn(CCc3cccnc3)n2)c1] | 327.9 |

The following intermediate was prepared in a manner similar (use of appropriate reagents and purification methods known to the person skilled in the art) to Int-2:

| Cpd. No. | Structure | [M + H]+ (m/z) |
|---|---|---|
| Int-9 | 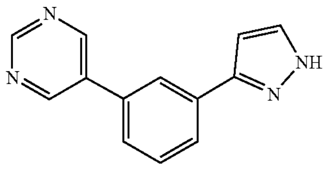 [SMILES: c1cc(-c2cncnc2)cc(-c2cc[nH]n2)c1] | 223.3 |

Examples 1-2: Synthesis of 5-(3-(1-benzyl-1H-pyrazol-3-yl)phenyl)nicotinic acid (Cpd. No. 001) and 5-(3-(1-benzyl-1H-pyrazol-3-yl)phenyl)nicotinamide (Cpd. No. 002)

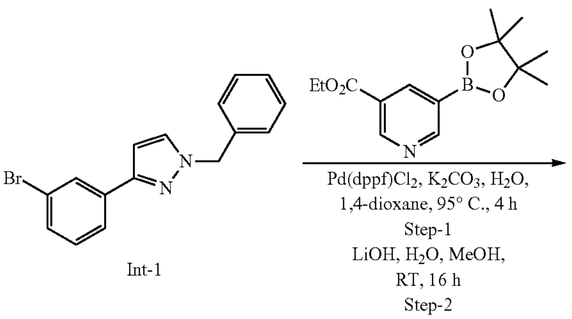

Int-1

-continued

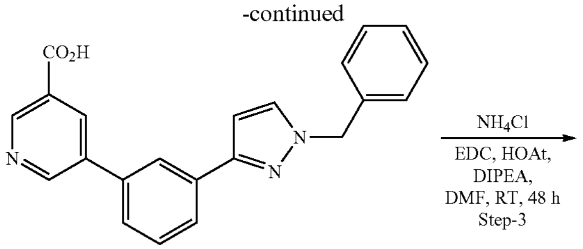

Cpd. No. 001

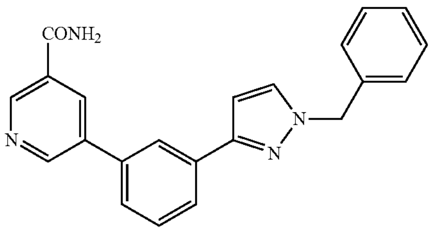

Cpd. No. 002

Step 1: A solution of Int-1 (100 mg, 0.32 mmol), $K_2CO_3$ (132 mg, 0.96 mmol) and ethyl 5-(4,4,5,5-tetramethyl-1,3,2-dioxaborolan-2-yl)pyridine-3-carboxylate (133 mg, 0.48 mmol) in 1,4-dioxane (1.1 mL) and $H_2O$ (0.4 mL) was degassed with argon for 5 min. To the solution was added Pd(dppf)$Cl_2$ (24 mg, 0.032 mmol) and the mixture was stirred at 95° C. for 2 h. The reaction mixture was diluted with $H_2O$ (5 mL) and DCM (10 mL), the organic layer was dried over anhydrous $Na_2SO_4$ and concentrated under reduced pressure. The residue was purified by normal phase flash column chromatography using a 12 g column (silica) and a gradient of 10-80% EtOAc in pet ether as an eluent to afford ethyl 5-(3-(1-benzyl-1H-pyrazol-3-yl)phenyl)nicotinate as an oil (81 mg, 66%). (LC/MS; m/z 384.3 $[M+H]^+$).

Step 2: To a mixture of ethyl 5-(3-(1-benzyl-1H-pyrazol-3-yl)phenyl)nicotinate (81 mg, 0.21 mmol) in MeOH (2 mL) was added aq LiOH (1.0 M, 0.845 mL) and the reaction mixture was stirred at RT for 16 h. The mixture was acidified using aq 1M HCl until a precipitate formed. The solids were filtered off, washed with $H_2O$ and dried under reduced pressure to afford 5-(3-(1-benzyl-1H-pyrazol-3-yl)phenyl) nicotinic acid (Cpd. No. 001) as a white solid (71 mg, 94%). (LC/MS; m/z 356.3 $[M+H]^+$).

Step 3: To a solution of $NH_4Cl$ (38 mg, 0.70 mmol), DIPEA (0.074 mL, 0.42 mmol), HOAt (19 mg, 0.14 mmol) and Cpd. No. 001 (50 mg, 0.14 mmol) in DMF (1 mL) was added EDC (0.038 mL, 0.21 mmol) and the mixture was stirred at RT for 48 h. The reaction mixture was diluted with EtOAc (10 mL), washed with a 10% citric acid solution, $H_2O$, aq 1M $Na_2CO_3$ and brine. The organic layer was dried over anhydrous $Na_2SO_4$ and concentrated under reduced pressure to afford 5-(3-(1-benzyl-1H-pyrazol-3-yl)phenyl) nicotinamide (Cpd. No. 002) as a white solid (37 mg, 74%). (LC/MS; m/z 355.1 $[M+H]^+$).

Examples 3-4: Synthesis of 5-(3-(1-benzyl-1H-pyrazol-3-yl)phenyl)pyridin-3-amine (Cpd. No. 003) and N-(5-(3-(1-benzyl-1H-pyrazol-3-yl)phenyl)pyridin-3-yl)acrylamide (Cpd. No. 004)

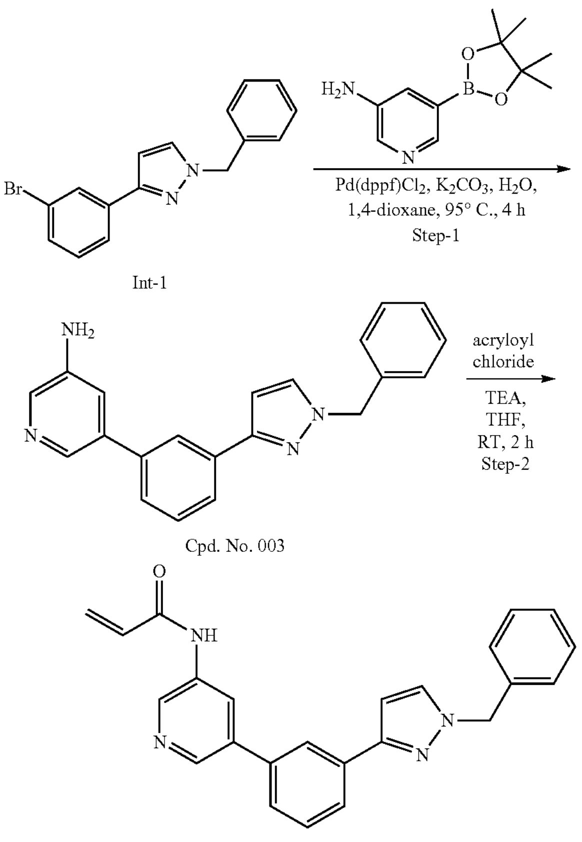

Int-1

Cpd. No. 003

Cpd. No. 004

Step 1: A solution of Int-1 (100 mg, 0.32 mmol), $K_2CO_3$ (132 mg, 0.96 mmol) and 5-(4,4,5,5-tetramethyl-1,3,2-dioxaborolan-2-yl)pyridin-3-amine (110 mg, 0.48 mmol) in 1,4-dioxane (1.1 mL) and $H_2O$ (0.4 mL) was degassed with argon for 5 min. To the mixture was added Pd(dppf)$Cl_2$ (24 mg, 0.032 mmol) and the mixture was stirred at 95° C. for 4 h. The reaction mixture was diluted with $H_2O$ (5 mL) and DCM (10 mL), the organic layer was dried over anhydrous $Na_2SO_4$ and concentrated under reduced pressure. The residue was purified by normal phase flash column chromatography using a 12 g column (silica) and a gradient of 20-100% EtOAc in pet ether as an eluent to afford 5-(3-(1-benzyl-1H-pyrazol-3-yl)phenyl)pyridin-3-amine (Cpd. No. 003) as a white solid (57 mg, 54%). (LC/MS; m/z 327.1 $[M+H]^+$).

Step 2: To a solution of Cpd. No. 003 (50 mg, 0.15 mmol) and TEA (0.043 mL, 0.31 mmol) in THF (1.5 mL) was added acryloyl chloride (0.014 mL, 0.17 mmol) and the mixture was stirred at RT 2 h. The reaction mixture was diluted with $H_2O$ (5 mL) and DCM (10 mL), the organic layer was dried over anhydrous $Na_2SO_4$ and concentrated under reduced pressure. The residue was purified by normal phase flash column chromatography using a 12 g column (silica) and a gradient of 1-10% MeOH in DCM as an eluent to afford N-(5-(3-(1-benzyl-1H-pyrazol-3-yl)phenyl)pyridin-3-yl)acrylamide (Cpd. No. 004) as an off-white solid (23 mg, 38%). (LC/MS; m/z 381.1 $[M+H]^+$).

Compound Cpd. No. 005 was prepared in a manner similar (use of appropriate reagents and purification methods known to the person skilled in the art) to cpd-Cpd. No. 003.

The following compounds were prepared in a manner similar (use of appropriate reagents and purification methods known to the person skilled in the art) to Cpd. No. 004: c Cpd. No. 006 (employing propionic anhydride and TEA in DCM at step 2), Cpd. No. 007 (employing acetyl chloride and TEA in DCM at step 2), Cpd. No. 008, Cpd. No. 009, Cpd. No. 010, Cpd. No. 011 (prepared from Int-3), Cpd. No. 012 (prepared from Int-4), and Cpd. No. 013 (prepared from Int-5).

Examples 5-6: Synthesis of 3-((3-([1,1'-biphenyl]-3-yl)-1H-pyrazol-1-yl)methyl)pyridine (Cpd. No. 014) and 3-((5-([1,1'-biphenyl]-3-yl)-1H-pyrazol-1-yl)methyl)pyridine (Cpd. No. 015)

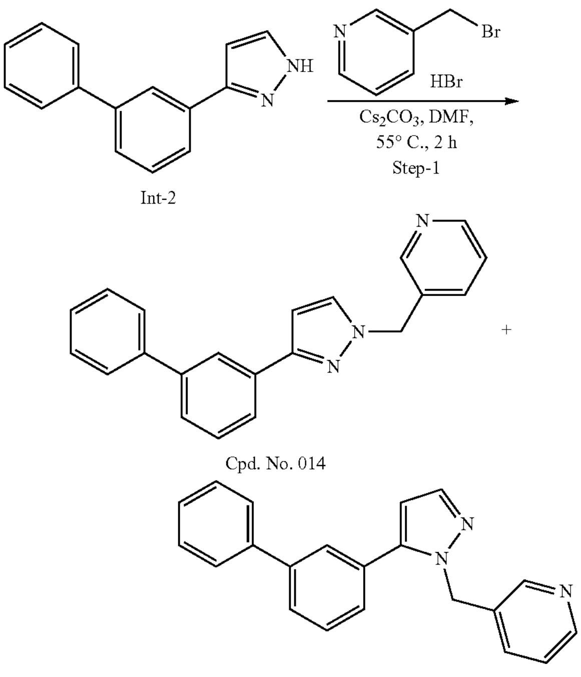

Int-2

Cpd. No. 014

+

Cpd. No. 015

Step 1: A solution of Int-2 (59 mg, 0.27 mmol), $Cs_2CO_3$ (264 mg, 0.80 mmol) and 3-(bromomethyl)pyridine hydrobromide (75 mg, 0.29 mmol) in DMF (1 mL) was stirred at 55° C. for 3 h. The reaction mixture was concentrated under reduced pressure and the resulting residue was purified by normal phase flash column chromatography using a 20 g column (silica) and a gradient of 0-20% EtOAc in pet ether as an eluent to afford 3-((3-([1,1'-biphenyl]-3-yl)-1H-pyrazol-1-yl)methyl)pyridine (Cpd. No. 014) (30 mg, 36%) and 3-((5-([1,1'-biphenyl]-3-yl)-1H-pyrazol-1-yl)methyl)pyridine (Cpd. No. 015) (1 mg, 1%). (LC/MS; m/z 312.4 $[M+H]^+$).

The following compounds were prepared in a manner similar (use of appropriate reagents and purification methods known to the person skilled in the art) to Cpd. No. 014 and Cpd. No. 015: Cpd. No. 016 (prepared from Int-9), Cpd. No. 017 (prepared from Int-9), Cpd. No. 018, Cpd. No. 019, Cpd. No. 020, Cpd. No. 021, Cpd. No. 022, Cpd. No. 023, Cpd. No. 024 (employing reagent R1), Cpd. No. 025, Cpd. No. 026, and Cpd. No. 027.

Examples 7-8: Synthesis of 5-((3-([1,1'-biphenyl]-3-yl)-1H-pyrazol-1-yl)methyl)picolinamide (Cpd. No. 028) and (5-((3-([1,1'-biphenyl]-3-yl)-1H-pyrazol-1-yl)methyl)pyridin-2-yl)methanamine (Cpd. No. 029)

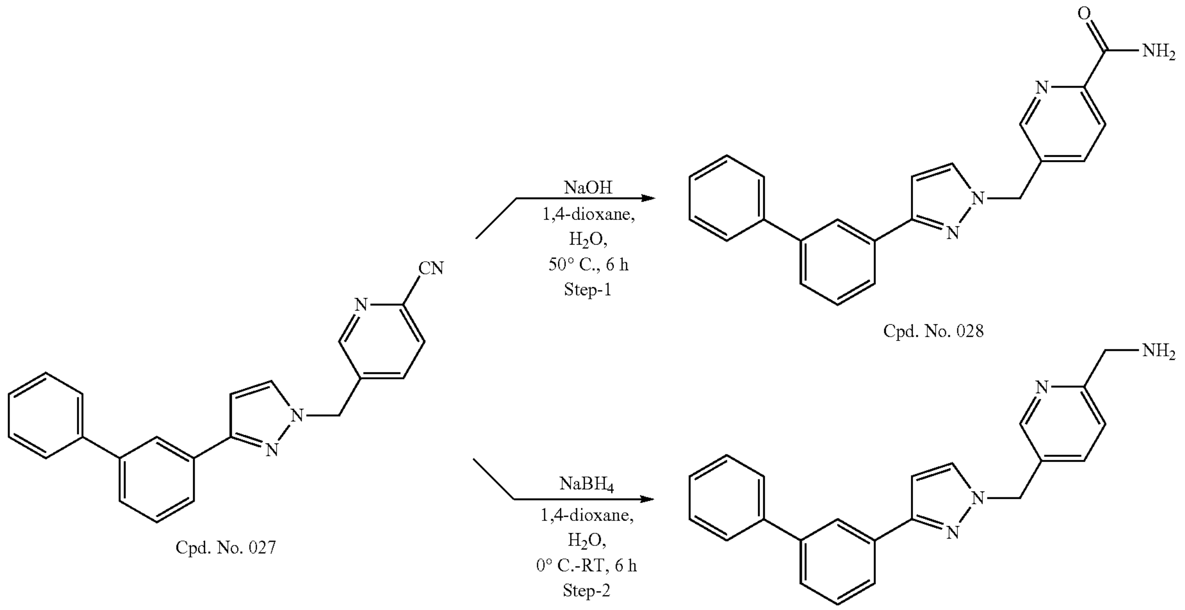

Cpd. No. 027

Cpd. No. 028

Cpd. No. 029

Step 1: A solution of Cpd. No. 027 (125 mg, 0.37 mmol, LC/MS 92%) and NaOH (14 mg, 0.03 mmol) in 1,4-dioxane (1 mL) and $H_2O$ (1 mL) was stirred at 50° C. for 6 h, and monitored by TLC. TLC mobile phase: 50% EtOAc in pet ether, RF: 0.19, TLC detection: UV. The reaction mixture was cooled to RT, diluted with EtOAc (10 mL) and $H_2O$ (10 mL). The organic layer was washed with $H_2O$ (10 mL), dried over anhydrous $Na_2SO_4$ and concentrated under reduced pressure to afford a pale yellow liquid (130 mg, LC/MS 69%). The crude product was purified by normal phase flash column chromatography using a 12 g column (silica) and a gradient of 0-40% EtOAc in pet ether as an eluent to afford a pale yellow liquid (70 mg, LC/MS 82%). The product was purified by preparative HPLC method H2. The collected fractions were lyophilised to afford 5-((3-([1,1'-biphenyl]-3-yl)-1H-pyrazol-1-yl)methyl)picolinamide (Cpd. No. 028) as a white solid (22 mg, 18%, LC/MS 99%). (LC/MS; m/z 355.2 $[M+H]^+$).

Step 2: A solution of Cpd. No. 027 (110 mg, 0.32 mmol, LC/MS 92%) in 1,4-dioxane (1 mL) and $H_2O$ (0.3 mL) was cooled to 0° C. and treated with $NaBH_4$ (31 mg, 0.81 mmol). The mixture was stirred at RT for 6 h and monitored by TLC. TLC mobile phase: 10% MeOH in DCM, RF: 0.10, TLC detection: UV. The reaction mixture was diluted with EtOAc (10 mL) and $H_2O$ (10 mL). The organic layer was washed with $H_2O$ (10 mL), dried over anhydrous $Na_2SO_4$ and concentrated under reduced pressure to afford a pale yellow solid (120 mg, LC/MS 57%). The crude product was purified by preparative HPLC method H3. The collected fractions were lyophilised to afford (5-((3-([1,1'-biphenyl]-3-yl)-1H-pyrazol-1-yl)methyl)pyridin-2-yl)methanamine (Cpd. No. 029) as a pale yellow solid (28 mg, 25%, LC/MS 95%). (LC/MS; m/z 341.3 $[M+H]^+$).

Examples 9-11: Synthesis of 4-((3-([1,1'-biphenyl]-3-yl)-1H-pyrazol-1-yl)methyl)piperidine (Cpd. No. 030), 1-(4-((3-([1,1'-biphenyl]-3-yl)-1H-pyrazol-1-yl)methyl)piperidin-1-yl)ethan-1-one (Cpd. No. 031), and 4-((3-([1,1'-biphenyl]-3-yl)-1H-pyrazol-1-yl)methyl)-1-methylpiperidine (Cpd. No. 032)

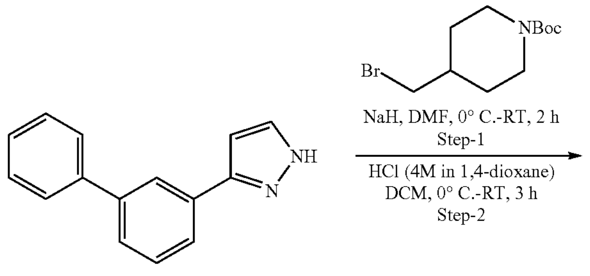

Int-2

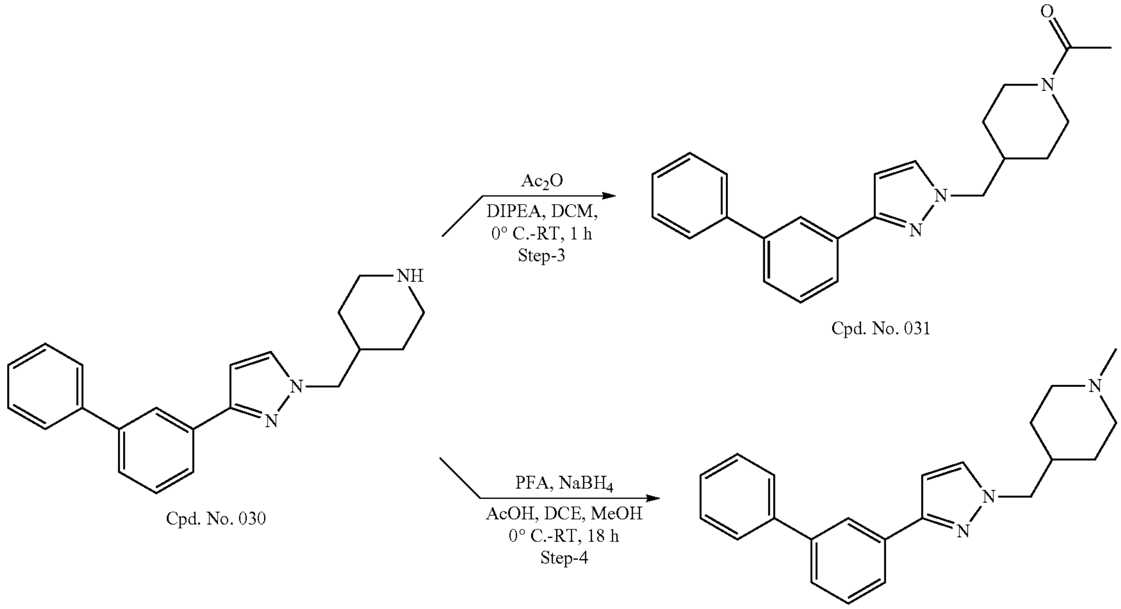

Cpd. No. 031

Cpd. No. 030

Cpd. No. 032

Step 1: A solution of Int-2 (100 mg, 0.454 mmol) in DMF (5 mL) was cooled to 0° C. and treated with NaH (27 mg, 1.135 mmol) and tert-butyl 4-(bromomethyl)piperidine-1-carboxylate (190 mg, 0.681 mmol). The mixture was stirred at RT for 2 h and monitored by TLC. TLC mobile phase: 50% EtOAc in pet ether, RF: 0.8, TLC detection: UV. The reaction mixture was quenched with ice $H_2O$ (10 mL) and extracted with EtOAc (2×20 mL). The combined organic layer was washed with $H_2O$ (2×30 mL), brine (30 mL), dried over anhydrous $Na_2SO_4$ and concentrated under reduced pressure to afford a pale yellow liquid (150 mg). The crude product was purified by normal phase flash column chromatography using a 12 g column (silica) and a gradient of 0-25% EtOAc in pet ether as an eluent to afford tert-butyl 4-((3-([1,1'-biphenyl]-3-yl)-1H-pyrazol-1-yl)methyl)piperidine-1-carboxylate as a pale yellow gum (100 mg, 52%, LC/MS 98%). (LC/MS; m/z 418.2 $[M+H]^+$).

Step 2: A solution of tert-butyl 4-((3-([1,1'-biphenyl]-3-yl)-1H-pyrazol-1-yl)methyl)piperidine-1-carboxylate (200 mg, 0.479 mmol) in DCM (5 mL) was cooled to 0° C. and treated with HCl (4M in 1,4-dioxane; 0.6 mL). The mixture was stirred at RT for 3 h and monitored by TLC. TLC mobile phase: 10% MeOH in DCM, RF: 0.2, TLC detection: UV. The reaction mixture was concentrated under reduced pressure to afford pale yellow gum (Cpd. No. 030.HCl; 200 mg). Cpd. No. 030.HCl (80 mg) was further purified by preparative HPLC method H3. The collected fractions were lyophilised to afford 4-((3-([1,1'-biphenyl]-3-yl)-1H-pyrazol-1-yl)methyl)piperidine (Cpd. No. 030) a pale yellow gum (30 mg, LC/MS 98%). (LC/MS; m/z 318.3 $[M+H]^+$).

Step 3: A solution of Cpd. No. 030.HCl (100 mg, 0.283 mmol) in DCM (5 mL) was cooled to 0° C. and treated with DIPEA (110 mg, 0.849 mmol) and a solution of $Ac_2O$ (43 mg, 0.424 mmol) in DCM (0.5 mL). The mixture was stirred at RT for 1 h and monitored by TLC. TLC mobile phase: 10% MeOH in DCM, RF: 0.3, TLC detection: UV. The reaction mixture was diluted with DCM (10 mL), washed with $H_2O$ (2×20 mL) and brine (30 mL). The organic layer was dried over anhydrous $Na_2SO_4$ and concentrated under reduced pressure to afford a pale yellow gum (87 mg) which was purified by preparative HPLC method $H_3$. The collected fractions were lyophilised to afford 1-(4-((3-([1,1'-biphenyl]-3-yl)-1H-pyrazol-1-yl)methyl)piperidin-1-yl)ethan-1-one (Cpd. No. 031) as a pale yellow gum (45 mg, 44%, LC/MS 99%). (LC/MS; m/z 360.3 $[M+H]^+$).

Step 4: A solution of Cpd. No. 030.HCl (150 mg, 0.424 mmol) in DCE (5 mL) was treated with PFA (43 mg, 1.413 mmol) and AcOH (0.01 mL) at 0° C. and the mixture was stirred at RT for 16 h. The reaction mixture was diluted with MeOH (5 mL), cooled to 0° C. and treated with $NaBH_4$ (45 mg, 1.189 mmol). The mixture was stirred at RT for 2 h and monitored by TLC. TLC mobile phase: 10% MeOH in DCM, RF: 0.2, TLC detection: UV. The reaction mixture was quenched with ice $H_2O$ (5 mL) and extracted with DCM (2×10 mL). The combined organic layer was washed with $H_2O$ (2×25 mL), brine (30 mL), dried over anhydrous $Na_2SO_4$ and concentrated under reduced pressure to afford a brown gum (120 mg). The crude product was purified by preparative HPLC method H3. The collected fractions were lyophilized to afford 4-((3-([1,1'-biphenyl]-3-yl)-1H-pyrazol-1-yl)methyl)-1-methylpiperidine (Cpd. No. 032) as a pale yellow gum (21 mg, 15%, LC/MS 99%). (LC/MS; m/z 332.3 $[M+H]^+$).

Examples 12-13: Synthesis of 5-((3-([1,1'-biphenyl]-3-yl)-1H-pyrazol-1-yl)methyl)-2-vinylpyridine (Cpd. No. 033) and 5-((3-([1,1'-biphenyl]-3-yl)-1H-pyrazol-1-yl)methyl)pyridin-2-amine (Cpd. No. 034)

Step 1: A solution of Int-2 (110 mg, 0.5 mmol) in DMF (4 mL) was cooled to 0° C. and treated with NaH (60% in mineral oil) (40 mg, 1.0 mmol) and 2-bromo-5-(bromomethyl)pyridine (R2) (251 mg, 1.0 mmol). The mixture was stirred at RT for 1 h and monitored by TLC. TLC mobile phase: 20% EtOAc in pet ether, RF: 0.1, TLC detection: UV. The reaction mixture was quenched with ice $H_2O$ (30 mL) and extracted with EtOAc (3×30 mL). The combined organic layer was dried over anhydrous $Na_2SO_4$ and concentrated under reduced pressure to afford crude product (285 mg, LC/MS 48%) which was purified by normal phase flash column chromatography using silica gel (100-200 mesh) and a gradient of 0-20% EtOAc in pet ether as an eluent to afford 5-((3-([1,1'-biphenyl]-3-yl)-1H-pyrazol-1-yl)methyl)-2-bromopyridine as a yellow liquid (152 mg, 57%, LC/MS 73%). (LC/MS; m/z 390.0 $[M+H]^+$).

Step 2: A solution of 5-((3-([1,1'-biphenyl]-3-yl)-1H-pyrazol-1-yl)methyl)-2-bromopyridine (100 mg, 0.25 mmol, LC/MS 73%), potassium vinyltrifluoroborate (103 mg, 0.77 mmol), $K_2CO_3$ (71 mg, 0.5 mmol) and $PPh_3$ (13 mg, 0.05 mmol) in DMF (5 mL) was degassed with argon for 15 min. The mixture was treated with $Pd(OAc)_2$ (17 mg, 0.02 mmol), stirred at 100° C. for 6 h and monitored by TLC. TLC mobile phase: 50% EtOAc in pet ether, RF: 0.4, TLC detection: UV. The reaction mixture was cooled to RT, poured into ice $H_2O$ (30 mL) and extracted with EtOAc (3×30 mL). The combined organic layer was dried over anhydrous $Na_2SO_4$ and concentrated under reduced pressure to afford crude product

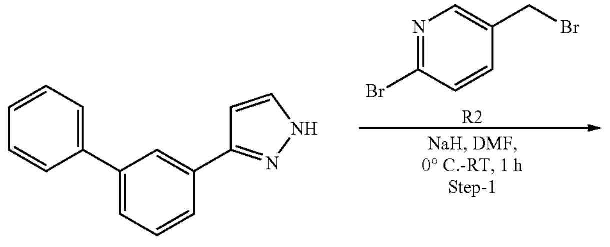

Int-2

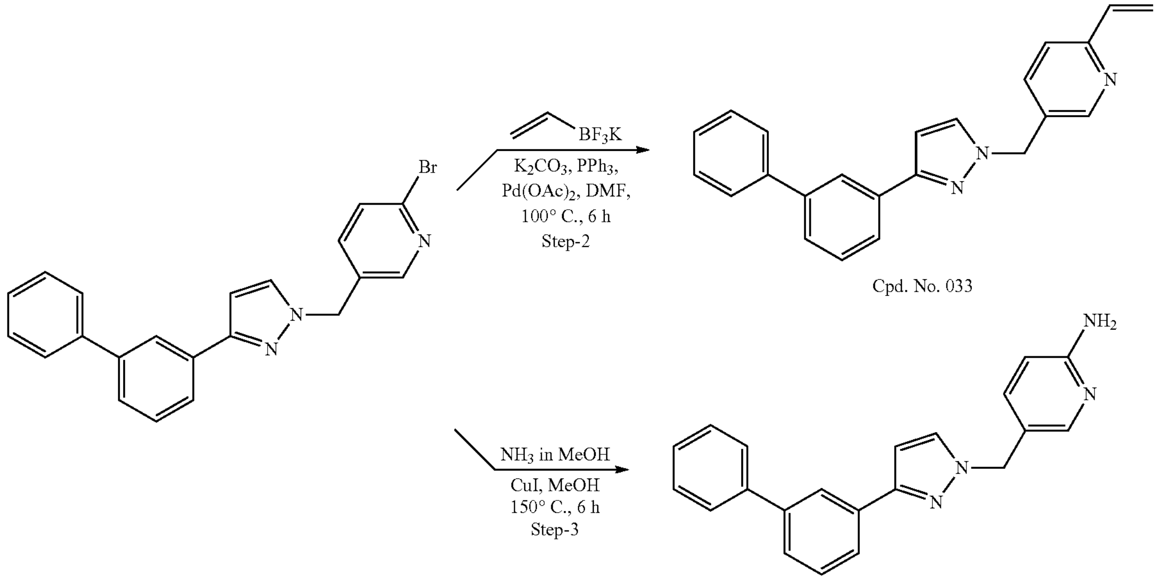

Cpd. No. 033

Cpd. No. 034

(90 mg, LC/MS 37%) which was purified by preparative HPLC method H1. The collected fractions were lyophilised to afford 5-((3-([1,1'-biphenyl]-3-yl)-1H-pyrazol-1-yl) methyl)-2-vinylpyridine (Cpd. No. 033) as a pale yellow gum (9 mg, 14%, LC/MS 99%). (LC/MS; m/z 338.3 $[M+H]^+$). H1

Step 3: A solution of 5-((3-([1,1'-biphenyl]-3-yl)-1H-pyrazol-1-yl)methyl)-2-bromopyridine (700 mg, 1.79 mmol) and CuI (68 mg, 0.35 mmol) in methanolic $NH_3$ (7M, 15 mL) was stirred at 150° C. for 6 h (sealed tube) and monitored by TLC. TLC mobile phase: 50% EtOAc in pet ether, RF: 0.1, TLC detection: UV. The reaction mixture was cooled to RT, diluted with $H_2O$ (40 mL) and extracted with EtOAc (3×40 mL). The combined organic layer was dried over anhydrous $Na_2SO_4$ and concentrated under reduced pressure to afford crude product (500 mg, LC/MS 51%) which was purified by normal phase flash column chromatography using silica gel (100-200 mesh) and a gradient of 70-80% EtOAc in pet ether as an eluent to afford 5-((3-([1,1'-biphenyl]-3-yl)-1H-pyrazol-1-yl)methyl)pyridin-2-amine (Cpd. No. 034) (200 mg, 29%, LC/MS 85%). Cpd. No. 034 (60 mg) was further purified by preparative HPLC method H3. The collected fractions were lyophilised to afford Cpd. No. 034 as an off-white solid (19 mg, LC/MS 99%). (LC/MS; m/z 327.2 $[M+H]^+$).

Compound Cpd. No. 035 (employing reagent R3) was prepared in a manner similar (use of appropriate reagents and purification methods known to the person skilled in the art) to Cpd. No. 033.

Compound Cpd. No. 036 (employing reagent R3 at step 1 and 33% $MeNH_2$ in EtOH at step 3) was prepared in a manner similar (use of appropriate reagents and purification methods known to the person skilled in the art) to Cpd. No. 034.

Examples 14-15: Synthesis of N-(5-((3-([1,1'-biphenyl]-3-yl)-1H-pyrazol-1-yl)methyl)pyridin-2-yl) acrylamide (Cpd. No. 037) and 1-(5-((3-([1,1'-biphenyl]-3-yl)-1H-pyrazol-1-yl)methyl)pyridin-2-yl) azetidin-2-one (Cpd. No. 038)

Step 1: A solution of Cpd. No. 034 (100 mg, 0.31 mmol) and TEA (0.053 mL, 0.38 mmol) in DCM (3 mL) was cooled to −70° C. and treated with acryloyl chloride (0.036 mL, 0.45 mmol). The mixture was stirred at −70° C. for 1 h and monitored by TLC. TLC mobile phase: 70% EtOAc in pet ether, RF: 0.06, TLC detection: UV. The reaction was quenched by ice $H_2O$ (15 mL) and extracted with EtOAc (2×15 mL). The combined organic layer was dried over anhydrous $Na_2SO_4$ and concentrated under reduced pressure to afford crude product (100 mg, LC/MS 68%) which was purified by preparative HPLC method H3. The collected fractions were lyophilised to afford N-(5-((3-([1,1'-biphenyl]-3-yl)-1H-pyrazol-1-yl)methyl)pyridin-2-yl)acrylamide (Cpd. No. 037) as an off-white solid (15 mg, 13%, LC/MS 99%). (LC/MS; m/z 381.3 $[M+H]^+$).

Step 2: A solution of Cpd. No. 034 (90 mg, 0.27 mmol) in THF (5 mL) was cooled to −20° C. and treated with acryloyl chloride (0.022 mL, 0.27 mmol). The reaction mixture was stirred at RT for 2 h and monitored by TLC. TLC mobile phase: 70% EtOAc in pet ether, RF: 0.06, TLC detection: UV. The reaction mixture was quenched with ice $H_2O$ (15 mL) and extracted with EtOAc (2×15 mL). The combined organic layer was dried over anhydrous $Na_2SO_4$ and concentrated under reduced pressure to afford crude product (85 mg, LC/MS 26%) which was purified by preparative HPLC method H1. The collected fractions were lyophilised to afford 1-(5-((3-([1,1'-biphenyl]-3-yl)-1H-pyrazol-1-yl) methyl)pyridin-2-yl)azetidin-2-one (Cpd. No. 038) as an off-white solid (15 mg, 14%, LC/MS 97%). (LC/MS; m/z 381.3 $[M+H]^+$).

Compound Cpd. No. 039 was prepared in a manner similar (use of appropriate reagents and purification methods known to the person skilled in the art) to Cpd. No. 037 (employing propionyl chloride at step 1).

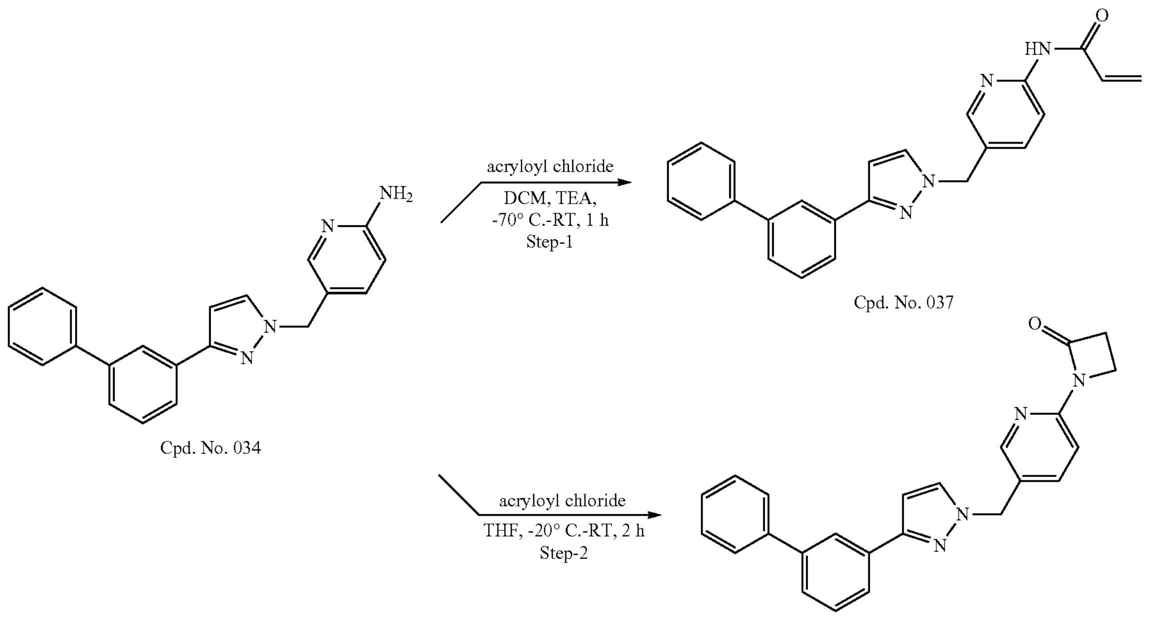

Cpd. No. 034

Cpd. No. 037

Cpd. No. 038

Examples 16-17: Synthesis of 5-((3-([1,1'-biphenyl]-3-yl)-1H-pyrazol-1-yl)methyl)nicotinic acid (Cpd. No. 040) and 5-((3-([1,1'-biphenyl]-3-yl)-1H-pyrazol-1-yl)methyl)nicotinamide (Cpd. No. 041)

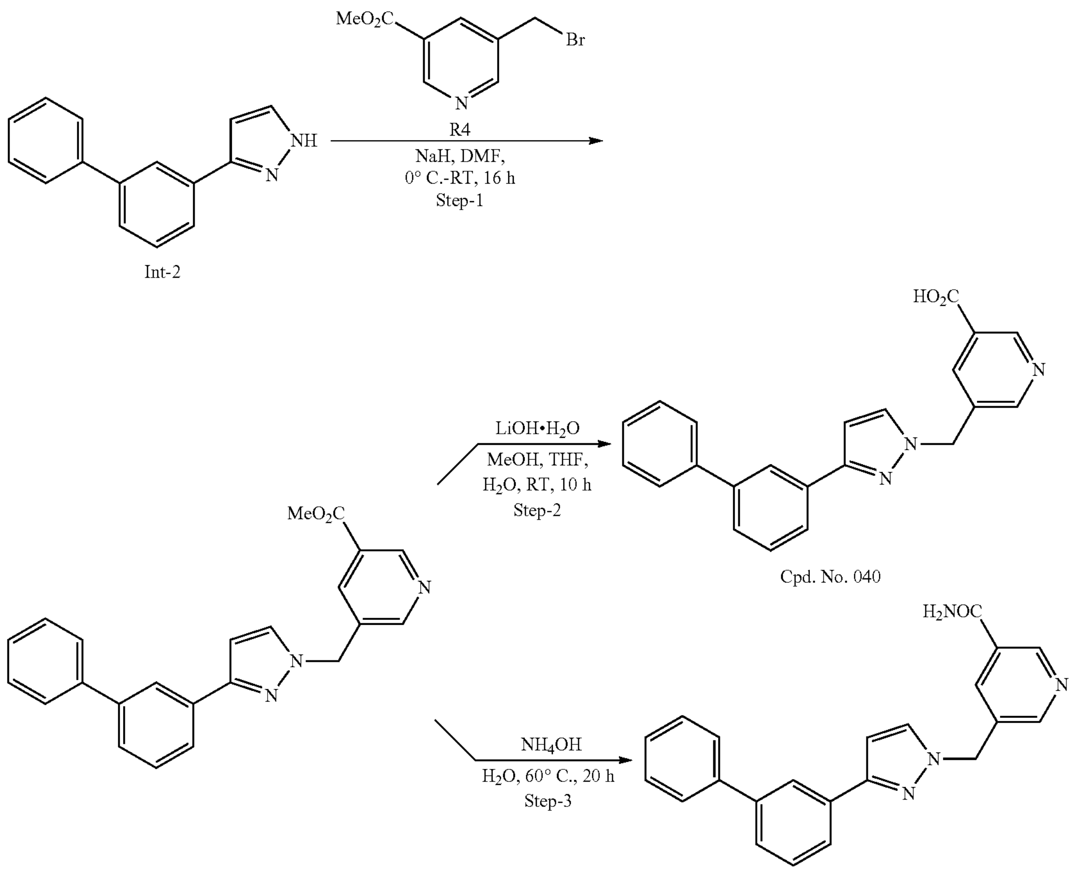

Cpd. No. 040

Cpd. No. 041

Step 1: This step was executed in a manner similar (use of appropriate reagents and purification methods known to the person skilled in the art) to step 1 towards Cpd. No. 033. From Int-2 (200 mg, 0.91 mmol) was obtained crude product (350 mg, LC/MS 36%) which was purified by normal phase flash column chromatography using silica gel (100-200 mesh) and a gradient of 0-10% EtOAc in pet ether as an eluent to afford methyl 5-((3-([1,1'-biphenyl]-3-yl)-1H-pyrazol-1-yl)methyl)nicotinate as a pale yellow gum (140 mg, 34%, LC/MS 83%). (LC/MS; m/z 370.2 $[M+H]^+$).

Step 2: A solution of methyl 5-((3-([1,1'-biphenyl]-3-yl)-1H-pyrazol-1-yl)methyl)nicotinate (100 mg, 0.27 mmol, LC/MS 83%) and $LiOH{\cdot}H_2O$ (45 mg, 1.08 mmol) in THF (1.5 mL), MeOH (1.5 mL) and $H_2O$ (1.5 mL) was stirred at RT for 10 h and monitored by TLC. TLC mobile phase: 10% MeOH in DCM, RF: 0.2, TLC detection: UV. The reaction mixture was concentrated under reduced pressure, acidified using aq 2M HCl (pH 5) and extracted with 10% MeOH in DCM (2×10 mL). The combined organic layer was washed with brine (8 mL), dried over anhydrous $Na_2SO_4$ and concentrated under reduced pressure to afford crude product (70 mg, LC/MS 84%) which was purified by preparative HPLC method H13. The collected fractions were lyophilised to afford 5-((3-([1,1'-biphenyl]-3-yl)-1H-pyrazol-1-yl)methyl) nicotinic acid (Cpd. No. 040) as an off-white solid (21 mg, 26%, LC/MS 99%). (LC/MS; m/z 356.2 $[M+H]^+$).

Step 3: A solution of methyl 5-((3-([1,1'-biphenyl]-3-yl)-1H-pyrazol-1-yl)methyl)nicotinate (135 mg, 0.36 mmol, LC/MS 83%) in aq $NH_3$ (25% in $H_2O$, 4 mL) was stirred at 60° C. for 20 h (sealed tube) and monitored by TLC. TLC mobile phase: 100% EtOAc, RF: 0.5, TLC detection: UV. The reaction mixture was extracted with EtOAc (10 mL), the organic layer was washed with brine (10 mL), dried over anhydrous $Na_2SO_4$ and concentrated under reduce pressure to afford crude product (60 mg, LC/MS 80%) which was purified by preparative HPLC method H3. The collected fractions were lyophilised to afford 5-((3-([1,1'-biphenyl]-3-yl)-1H-pyrazol-1-yl)methyl)nicotinamide (Cpd. No. 041) as an off-white solid (8 mg, 7%, LC/MS 99%). (LC/MS; m/z 355.3 $[M+H]^+$).

Compound Cpd. No. 042 was prepared in a manner similar (use of appropriate reagents and purification methods known to the person skilled in the art) to Cpd. No. 040 (employing reagent R5).

Compound Cpd. No. 043 was prepared in a manner similar (use of appropriate reagents and purification methods known to the person skilled in the art) to Cpd. No. 041 (employing reagent R5).

Example 18: Synthesis of N-phenyl-3-(1-(pyridin-2-ylmethyl)-1H-pyrazol-3-yl) aniline (Cpd. No. 044)

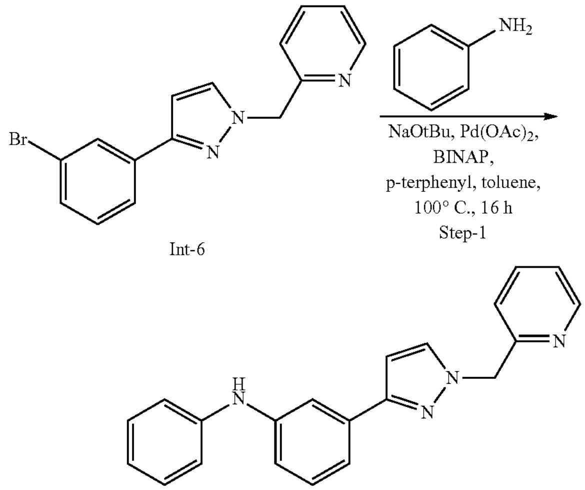

Int-6

Cpd. No. 044

Step 1: A solution of Int-6 (100 mg, 0.31 mmol, LC/MS 88%), aniline (74 mg, 0.79 mmol) and p-terphenyl (16.8 mg, 0.07 mmol) in toluene (5 mL) was treated with NaOtBu (42.8 mg, 0.44 mmol). The mixture was degassed with argon for 15 min and treated with BINAP (20 mg, 0.03 mmol) and $Pd(OAc)_2$ (11 mg, 0.01 mmol). The mixture was stirred at 100° C. for 16 h and monitored by TLC. TLC mobile phase: 50% EtOAc in pet ether, RF: 0.4, TLC detection: UV. The reaction mixture was cooled to RT, poured into ice $H_2O$ (30 mL) and filtered through a celite pad. The filtrate was extracted with EtOAc (2×20 mL) and the combined organic layer was dried over anhydrous $Na_2SO_4$ and concentrated under reduced pressure to afford crude product (140 mg, LC/MS 34%) which was purified by normal phase flash column chromatography using silica gel (100-200 mesh) and a gradient of 0-30% EtOAc in pet ether as an eluent to afford N-phenyl-3-(1-(pyridin-2-ylmethyl)-1H-pyrazol-3-yl) aniline (Cpd. No. 044) (90 mg, LC/MS 71%). The product was further purified by preparative HPLC method H16. The collected fractions were concentrated under reduced pressure and lyophilized to afford (23 mg, 19%, LC/MS 99%) Cpd. No. 044.TFA. The TFA salt was passed through a SCX cartridge to afford Cpd. No. 044 as a free base (10 mg, 11%). (LC/MS; m/z 327.3 $[M+H]^+$).

The following compounds were prepared in a manner similar (use of appropriate reagents and purification methods known to the person skilled in the art) to Cpd. No. 044: Cpd. No. 045 (prepared from Int-7) and Cpd. No. 046 (prepared from Int-8).

Example 19: Synthesis of 3-((5-([1,1'-biphenyl]-3-yl)-2H-tetrazol-2-yl)methyl)pyridine (Cpd. No. 047)

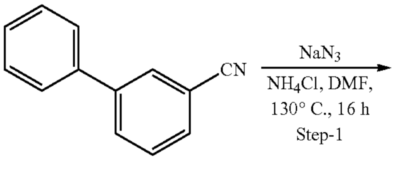

-continued

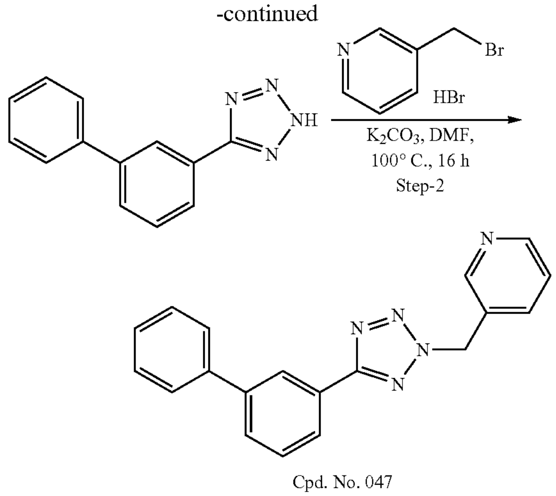

Cpd. No. 047

Step 1: A mixture of [1,1'-biphenyl]-3-carbonitrile (250 mg, 1.35 mmol), $NaN_3$ (267 mg, 4.06 mmol) and $NH_4Cl$ (219 mg, 4.06 mmol) in DMF (10 mL) was stirred at 130° C. for 16 h (sealed tube). The reaction mixture was diluted with $H_2O$ (10 mL) and acidified using aq 1 M HCl until a precipitate was formed. The solids were filtered off, washed with $H_2O$ (10 mL) and dried under reduced pressure to afford 5-([1,1'-biphenyl]-3-yl)-2H-tetrazole as a white solid (264 mg, 85%). (LC/MS; m/z 223.1 $[M+H]^+$).

Step 2: A mixture of 5-([1,1'-biphenyl]-3-yl)-2H-tetrazole (100 mg, 0.45 mmol), $K_2CO_3$ (187 mg, 1.35 mmol) and 3-(bromomethyl)pyridine hydrobromide (228 mg, 0.90 mmol) in DMF (4.5 mL) was stirred at 100° C. for 16 h (sealed tube). The reaction mixture was diluted with $H_2O$ (5 mL) and DCM (10 mL). The organic layer was dried over anhydrous $Na_2SO_4$ and concentrated under reduced pressure. The residue was purified by normal phase flash column chromatography using a 12 g column (silica) and a gradient of 10-80% EtOAc in pet ether as an eluent to afford 3-((5-([1,1'-biphenyl]-3-yl)-2H-tetrazol-2-yl)methyl)pyridine (Cpd. No. 047) as a white solid (43 mg, 30%). (LC/MS; m/z 314.1 $[M+H]^+$).

Example 20: Synthesis of N—([1,1'-biphenyl]-3-yl)-2-(pyridin-3-yl)acetamide (Cpd. No. 048)

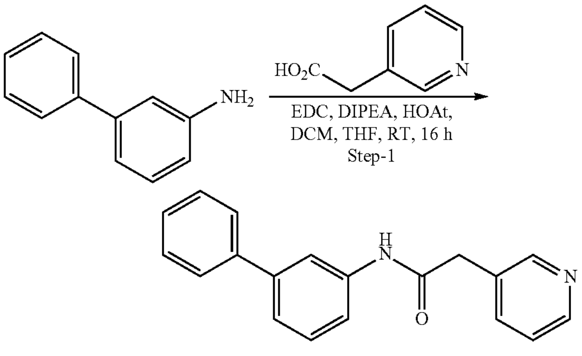

Cpd. No. 048

Step 1: To a solution of [1,1'-biphenyl]-3-amine (200 mg, 1.18 mmol), 2-(pyridin-3-yl)acetic acid (165 mg, 1.18 mmol), HOAt (199 mg, 1.42 mmol) and DIPEA (0.613 mL, 3.55 mmol) in DCM (5 mL) and THF (2.5 mL) was added EDC (0.317 mL, 1.77 mmol). The mixture was stirred at RT for 16 h. The reaction mixture was diluted with DCM (10 mL), washed with sat aq $NH_4Cl$ and brine, dried over anhydrous $Na_2SO_4$ and concentrated under reduced pressure. The residue was purified by normal phase flash column chromatography using a 12 g column (silica) and a gradient of 20-80% EtOAc in DCM as an eluent to afford N—([1, 1'-biphenyl]-3-yl)-2-(pyridin-3-yl)acetamide (Cpd. No. 048) as a white solid (205 mg, 60%). (LC/MS; m/z 289.3 $[M+H]^+$).

Synthesis of 1-(3-bromo-5-nitrophenyl)ethan-1-one (Int-10)

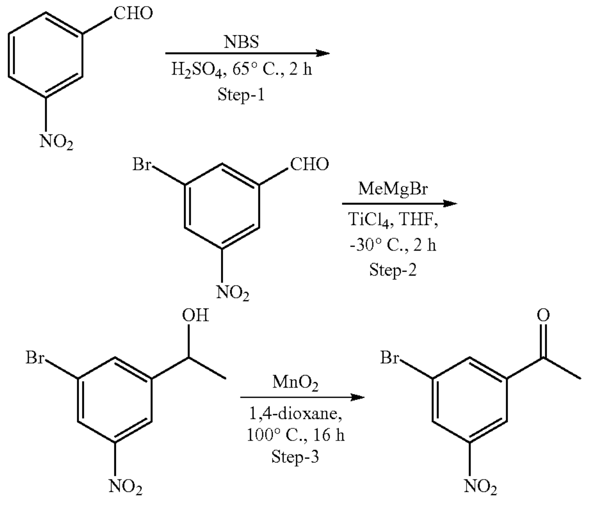

Int-10

Step 1: A solution of 3-nitrobenzaldehyde (100 g, 662 mmol) in conc $H_2SO_4$ (400 mL) was treated with NBS (141 g, 795 mmol) portionwise at RT. The reaction mixture was stirred at 65° C. for 2 h and monitored by TLC. TLC mobile phase: 20% EtOAc in pet ether, RF: 0.6, TLC detection: UV. The reaction mixture was poured into ice $H_2O$ and the obtained precipitate was collected by filtration (180 g). The crude product was purified by flash column chromatography using silica gel (100-200 mesh) and a gradient of 0-10% EtOAc in pet ether as an eluent to afford 3-bromo-5-nitrobenzaldehyde as an off-white solid (105 g, 69%). $^1H$ NMR (400 MHz, $CDCl_3$) δ ppm: 10.06 (s, 1H), 8.62-8.65 (m, 2H), 8.34-8.35 (m, 1H).

Step 2: To a solution of $TiCl_4$ (42.9 g, 227 mmol) and MeMgBr (131 mL, 262 mmol, 2M in THF) in THF (700 mL) was added dropwise at −30° C. a solution of 3-bromo-5-nitro-benzaldehyde (40 g, 175 mmol) in THF (100 mL). The reaction mixture was stirred at −30° C. for 2 h and monitored by TLC. TLC mobile phase: 20% EtOAc in pet ether, RF: 0.3, TLC detection: UV. The reaction mixture was quenched with ice $H_2O$ (300 mL) and extracted with DCM (700 mL). The organic layer was washed with brine (300 mL), dried over anhydrous $Na_2SO_4$ and concentrated under reduced pressure to afford crude product (45 g), which was purified by flash column chromatography using silica gel (100-200 mesh) and a gradient of 0-10% EtOAc in pet ether as an eluent to afford 1-(3-bromo-5-nitrophenyl)ethan-1-ol as an off-white solid (12 g, 28%). $^1H$ NMR (400 MHz, $CDCl_3$) 5 ppm: 8.27-8.28 (m, 1H), 8.17-8.19 (m, 1H), 7.87-7.88 (m, 1H), 4.99-5.01 (m, 1H), 1.53-1.56 (m, 1H).

Step 3: A solution of 1-(3-bromo-5-nitrophenyl)ethan-1-ol (12 g, 49.2 mmol) and $MnO_2$ (21.4 g, 246 mmol) in 1,4-dioxane (200 mL) was stirred at 100° C. for 16 h and monitored by TLC. TLC mobile phase: 20% EtOAc in pet ether, RF: 0.5, TLC detection: UV. The reaction mixture was filtered through a celite pad and the filtrate was concentrated under reduced pressure. The residue was diluted with $H_2O$ (150 mL) and extracted with EtOAc (300 mL). The organic layer was washed with brine (150 mL), dried over anhydrous $Na_2SO_4$ and concentrated under reduced pressure to afford crude product (14 g), which was purified by flash column chromatography using silica gel (100-200 mesh) and a gradient of 0-10% EtOAc in pet ether as an eluent to afford 1-(3-bromo-5-nitrophenyl)ethan-1-one (Int-10) as an off-white solid (10 g, 84%). $^1H$ NMR (400 MHz, $CDCl_3$) δ ppm: 8.69-8.70 (m, 1H), 8.56-8.57 (m, 1H), 8.39-8.40 (m, 1H), 2.68 (s, 3H).

Synthesis of 3-(4-nitro-[1,1'-biphenyl]-3-yl)-1H-pyrazole (Int-11) and 3-(5-bromo-2-nitrophenyl)-1H-pyrazole (Int-12)

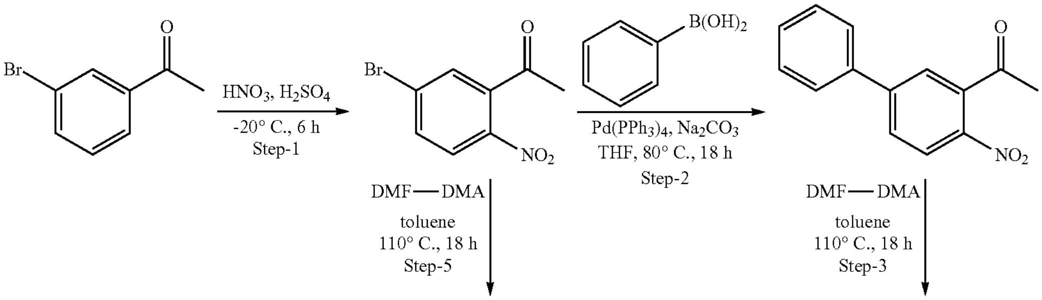

-continued

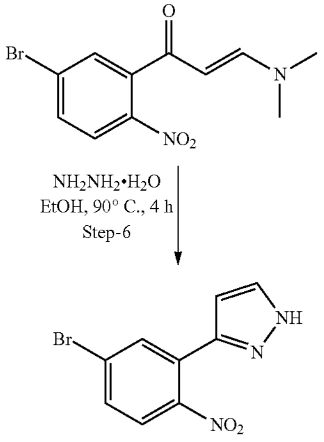

Int-12

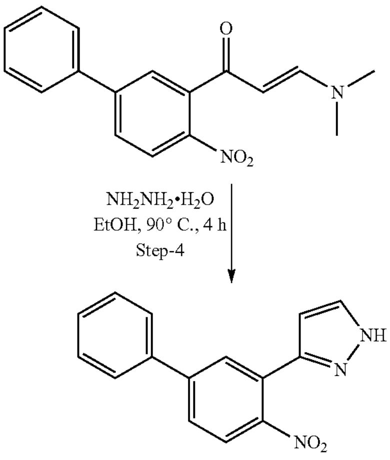

Int-11

Step 1: A mixture of $HNO_3$ (80 mL) and $H_2SO_4$ (12 mL) was treated with 1-(3-bromophenyl)ethan-1-one (20 g, 100 mmol) at −20° C. The mixture was stirred at −20° C. for 6 h and monitored by TLC. TLC mobile phase: 20% EtOAc in pet ether, RF: 0.51, TLC detection: UV. The reaction mixture was quenched with ice $H_2O$ (200 mL) and the mixture was stirred for 1 h. The precipitate obtained was collected on a Buchner funnel, washed with $H_2O$ (200 mL) and dried under reduced pressure to afford the crude product (17 g) which was purified by normal phase flash column chromatography using a 80 g column (silica) and a gradient of 0-10% EtOAc in pet ether as an eluent to afford afford 1-(5-bromo-2-nitrophenyl)ethan-1-one (11 g, 45%) as an off-white solid. (LC/MS; m/z 245.6 $[M+H]^+$).

Step 2: A mixture of 1-(5-bromo-2-nitrophenyl)ethan-1-one (11 g, 45.3 mmol), phenylboronic acid (6.63 g, 54.4 mmol) and 10% aq $Na_2CO_3$ (45 mL) in THF (110 mL) was degassed with argon for 10 min. To the solution was added $Pd(PPh_3)_4$ (1.05 g, 0.91 mmol) at RT and the reaction mixture was stirred at 80° C. for 18 h and monitored by TLC. TLC mobile phase: 10% EtOAc in pet ether, RF: 0.39, TLC detection: UV. The reaction mixture was filtered through a celite pad and washed with EtOAc (110 mL). The filtrate was diluted with $H_2O$ (110 mL) and the aqueous layer was extracted with EtOAc (110 mL). The combined organic layer was washed with brine (300 mL), dried over anhydrous $Na_2SO_4$ and concentrated under reduced pressure to afford crude product (15 g) which was purified by normal phase flash column chromatography using a 80 g column (silica) and a gradient of 0-10% EtOAc in pet ether as an eluent to afford 1-(4-nitro-[1,1'-biphenyl]-3-yl)ethan-1-one (10 g, 91%) as a brown solid. (LC/MS; m/z 242.1 $[M+H]^+$)

Step 3: A solution of 1-(4-nitro-[1,1'-biphenyl]-3-yl) ethan-1-one (10 g, 41.4 mmol) in toluene (110 mL) was treated with DMF-DMA (10 mL) at RT. The reaction mixture was stirred at 110° C. for 18 h and monitored by TLC. TLC mobile phase: 10% MeOH in DCM, RF: 0.31, TLC detection: UV. The reaction mixture was cooled and diluted with $H_2O$ (100 mL) and extracted with EtOAc (2×100 mL). The combined organic layer was dried over anhydrous $Na_2SO_4$ and concentrated under reduced pressure to afford crude product (13 g) which was purified by normal phase flash column chromatography using a 12 g column (silica) and a gradient of 0-10% EtOAc in pet ether as an eluent to afford (E)-3-(dimethylamino)-1-(4-nitro-[1,1'-biphenyl]-3-yl)prop-2-en-1-one (9 g, 73%) as a yellow solid. (LC/MS; m/z 297.2 $[M+H]^+$)

Step 4: A stirred solution of (E)-3-(dimethylamino)-1-(4-nitro-[1,1'-biphenyl]-3-yl)prop-2-en-1-one (9 g, 30.4 mmol) in EtOH (50 mL) was treated with $NH_2NH_2 \cdot H_2O$ (50-60% solution in $H_2O$) (3.1 g, 60.8 mmol) at RT and the mixture was stirred at 90° C. for 4 h and monitored by TLC. TLC mobile phase: 50% EtOAc in pet ether, RF: 0.58, TLC detection: UV. The reaction mixture was concentrated under reduced pressure and the residue was diluted with $H_2O$ (100 mL) and extracted with EtOAc (2×250 mL). The combined organic layer was dried over anhydrous $Na_2SO_4$ and concentrated under reduced pressure to afford 3-(4-nitro-[1,1'-biphenyl]-3-yl)-1H-pyrazole (Int-11) as a brown gum (8 g, 99%). (LC/MS; m/z 266.2 $[M+H]^+$)

Steps 5-6: These steps were executed in a manner similar (use of appropriate reagents and purification methods known to the person skilled in the art) to step 3 and 4 to Int-11. Starting material (55 g, 226.3 mmol) yielded 3-(5-bromo-2-nitrophenyl)-1H-pyrazole (Int-12) as a pale yellow solid (40.8 g, 67%). (LC/MS; m/z 267.9 $[M+H]^+$).

Intermediate Int-13 (prepared from Int-10) was prepared in a manner similar (use of appropriate reagents and purification methods known to the person skilled in the art) to Int-11:

| Cpd. No. | Structure | $[M + H]^+$ (m/z) |
|---|---|---|
| Int-13 | 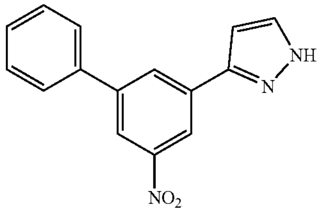 [SMILES: O=[N+]([O-])c1cc(-c2ccccc2)cc(-c2cc[nH]n2)c1] | 266.2 |

Synthesis of 3-(1-(pyridin-3-ylmethyl)-1H-pyrazol-3-yl)-[1,1'-biphenyl]-4-amine (Int-14)

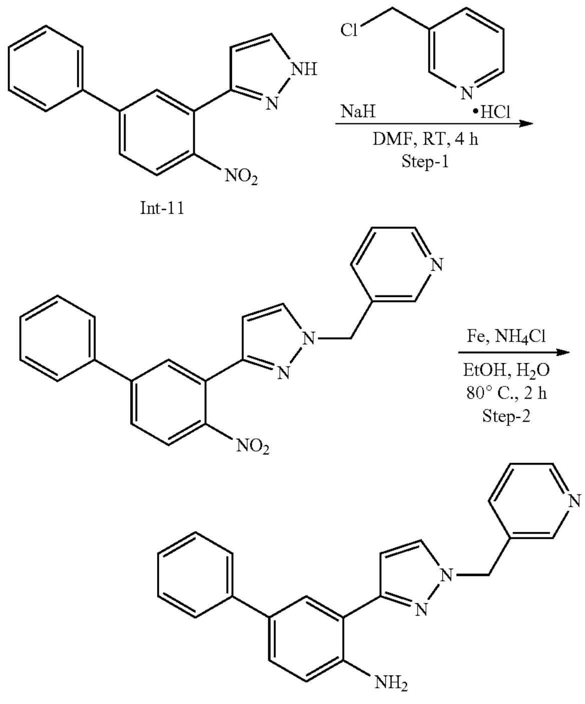

Int-14

Step 1: A solution of 3-(4-nitro-[1,1'-biphenyl]-3-yl)-1H-pyrazole (Int-11) (7 g, 26.4 mmol) in DMF (50 mL) was treated with NaH (60% in mineral oil) (4.44 g, 185 mmol), followed by 3-(chloromethyl)pyridine hydrochloride (5.17 g, 31.7 mmol) at 0° C. The resulting mixture was stirred at RT for 4 h and monitored by TLC. TLC mobile phase: 30% EtOAc in pet ether, RF: 0.41, TLC detection: UV. The reaction mixture was cooled to 0° C., quenched with ice $H_2O$ (50 mL) and extracted with EtOAc (2×50 mL). The combined organic layer was washed with brine (50 mL), dried over anhydrous $Na_2SO_4$ and concentrated under reduced pressure to afford crude product which was purified by normal phase flash column chromatography using a 48 g column (silica) and a gradient of 0-10% EtOAc in pet ether as an eluent to afford 3-((3-(4-nitro-[1,1'-biphenyl]-3-yl)-1H-pyrazol-1-yl)methyl)pyridine as a brown solid (5.2 g, 55%). (LC/MS; m/z 357.2 $[M+H]^+$).

Step 2: A solution of 3-((3-(4-nitro-[1,1'-biphenyl]-3-yl)-1H-pyrazol-1-yl)methyl)pyridine (5.2 g, 14.6 mmol) in EtOH (50 mL) and $H_2O$ (5 mL) was treated with Fe powder (3.8 g, 73 mmol) and $NH_4Cl$ (1.58 g, 29.2 mmol) at RT. The reaction mixture was stirred at 70° C. for 2 h and monitored by TLC. TLC mobile phase: 50% EtOAc in pet ether, RF: 0.41, TLC detection: UV. The reaction mixture was cooled and filtered through a celite pad and washed with EtOAc (50 mL). The filtrate was concentrated under reduced pressure to get brown colored residue that was diluted with $H_2O$ (50 mL) and extracted with EtOAc (50 mL). The combined organic layer was dried over anhydrous $Na_2SO_4$ and concentrated under reduced pressure to afford crude product. The crude was triturated with pentane (50 mL) to afford 3-(1-(pyridin-3-ylmethyl)-1H-pyrazol-3-yl)-[1,1'-biphenyl]-4-amine (Int-14) (3.5 g, 76%) as a brown solid. (LC/MS; m/z 327.3 $[M+H]^+$).

Intermediate Int-15 (prepared from Int-11), intermediate Int-16 (prepared from Int-13), and Int-17 (prepared from Int-13) were prepared in a manner similar (use of appropriate reagents and purification methods known to the person skilled in the art) to Int-14:

| Cpd. No. | Structure | $[M + H]^+$ (m/z) |
|---|---|---|
| Int-15 | 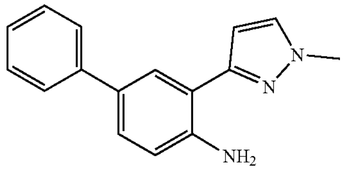 [SMILES: Cn1ccc(-c2cc(-c3ccccc3)ccc2N)n1] | 250.1 |
| Int-16 | 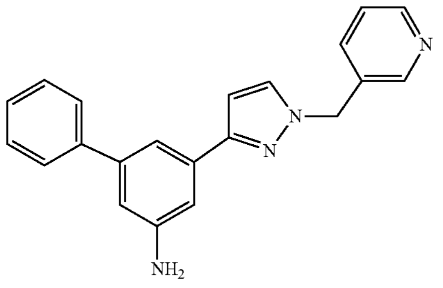 [SMILES: Nc1cc(-c2ccccc2)cc(-c2ccn(Cc3cccnc3)n2)c1] | 327.3 |
| Int-17 | 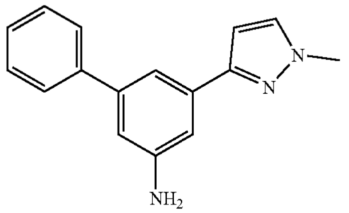 [SMILES: Cn1ccc(-c2cc(N)cc(-c3ccccc3)c2)n1] | 250.1 |

Synthesis of 3-((3-(5-bromo-2-nitrophenyl)-1H-pyrazol-1-yl)methyl)pyridine (Int-18)

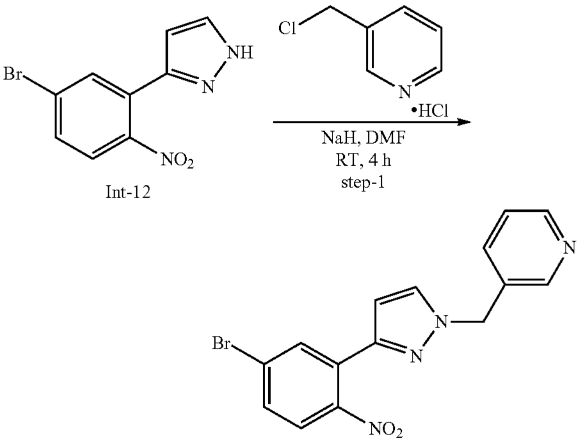

Int-18

Step 1: A solution of 3-(5-bromo-2-nitrophenyl)-1H-pyrazole (Int-12) (30 g, 112.4 mmol) in DMF (200 mL) was treated with NaH (60% in mineral oil) (9.4 g, 393 mmol), followed by 3-(chloromethyl)pyridine hydrochloride (21.9 g, 134.8 mmol) at 0° C. The resulting mixture was stirred at RT for 4 h and monitored by TLC. TLC mobile phase: 30% EtOAc in pet ether, RF: 0.28, TLC detection: UV. The reaction mixture was cooled to 0° C., quenched with ice $H_2O$ (200 mL) and extracted with EtOAc (2×500 mL). The combined organic layer was washed with brine (100 mL), dried over anhydrous $Na_2SO_4$ and concentrated under reduced pressure to afford crude product which was purified by normal phase flash column chromatography using silica gel (100-200 mesh) and a gradient of 0-25% EtOAc in pet ether as an eluent to afford 3-((3-(5-bromo-2-nitrophenyl)-1H-pyrazol-1-yl)methyl)pyridine (Int-18) as a brown gum (15 g, 58%). (LC/MS; m/z 358.8 [M+H]$^+$).

The following intermediates were prepared in a manner similar (use of appropriate reagents and purification methods known to the person skilled in the art) to Int-18:

| Cpd. No. | Structure | $[M + H]^+$ (m/z) |
|---|---|---|
| Int-19 | 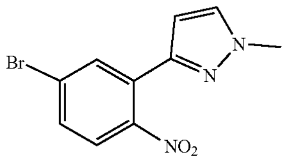 | 281.9 |
| Int-20 | 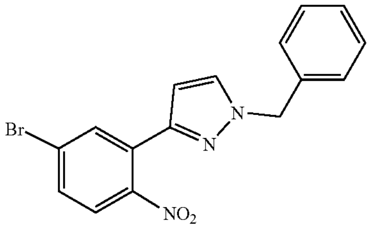 [SMILES: O=[N+]([O-])c1ccc(Br)cc1-c1ccn(Cc2ccccc2)n1] | 358.1 |
| Int-21 | 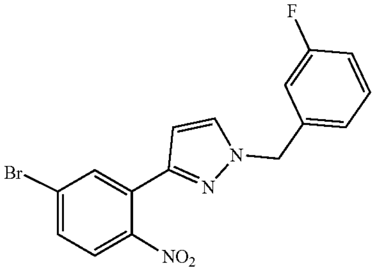 [SMILES: O=[N+]([O-])c1ccc(Br)cc1-c1ccn(Cc2cccc(F)c2)n1] | 376.1 |

-continued

| Cpd. No. | Structure | $[M + H]^+$ (m/z) |
|---|---|---|
| Int-22 | 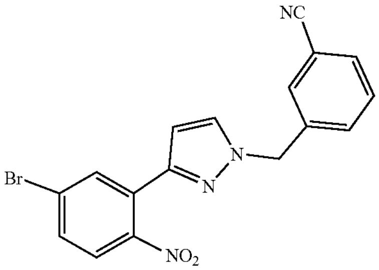 [SMILES: N#Cc1cccc(Cn2ccc(-c3cc(Br)ccc3[N+](=O)[O-])n2)c1] | 383.1 |
| Int-23 | 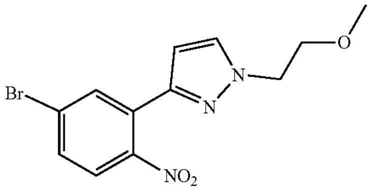 [SMILES: COCCn1ccc(-c2cc(Br)ccc2[N+](=O)[O-])n1] | 326.2 |
| Int-24 | 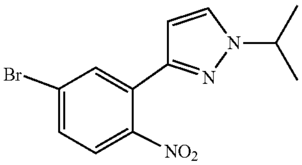 [SMILES: CC(C)n1ccc(-c2cc(Br)ccc2[N+](=O)[O-])n1] | 310.1 |

Examples 21-23: Synthesis of 2-((3-(1-(pyridin-3-ylmethyl)-1H-pyrazol-3-yl)-[1,1'-biphenyl]-4-yl)amino)ethane-1-sulfonyl fluoride (Cpd. No. 049), N-methyl-2-((3-(1-(pyridin-3-ylmethyl)-1H-pyrazol-3-yl)-[1,1'-biphenyl]-4-yl)amino)ethane-1-sulfonamide (Cpd. No. 050), and 4-(3-(1-(pyridin-3-ylmethyl)-1H-pyrazol-3-yl)-[1,1'-biphenyl]-4-yl)thiomorpholine 1,1-dioxide (Cpd. No. 051)

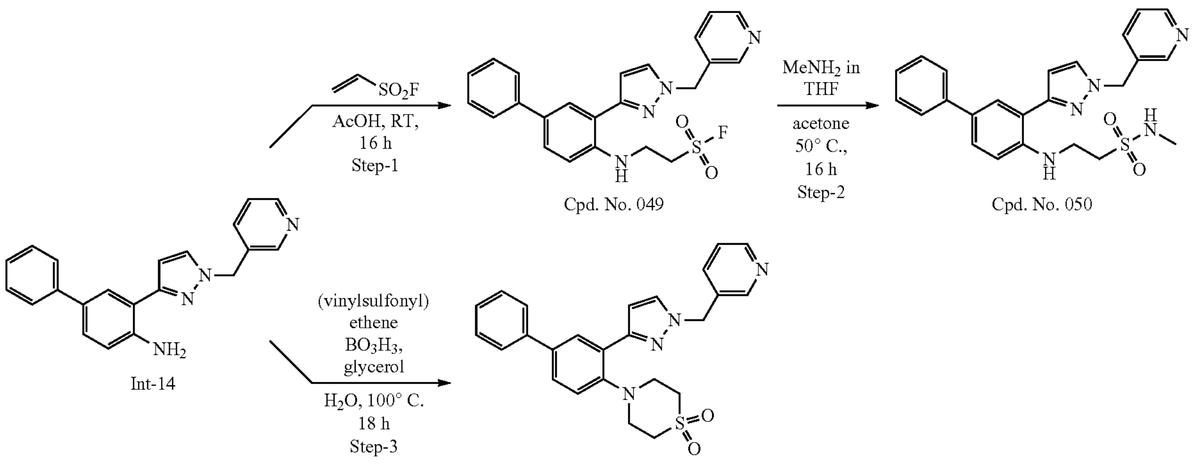

Cpd. No. 049

Cpd. No. 050

Int-14

Cpd. No. 051

Step 1: Ethenesulfonyl fluoride (40 mg, 368 mmol) was added to a stirred solution of 3-(1-(pyridin-3-ylmethyl)-1H-pyrazol-3-yl)-[1,1'-biphenyl]-4-amine (Int-14) (100 mg, 0.306 mmol) in AcOH (3 mL) at RT. The mixture was stirred at RT for 16 h and monitored by TLC. TLC mobile phase: 50% EtOAc in pet ether, RF: 0.50, TLC detection: UV. Reaction mixture was concentrated under reduced pressure yielding crude compound (100 mg) which was purified by normal phase flash column chromatography using a 12 g column (silica) and 0-25% EtOAc in pet ether as a gradient to afford a brown solid (130 mg). The compound was further purified by preparative HPLC method H10. The collected fractions were lyophilised to afford 2-((3-(1-(pyridin-3-ylmethyl)-1H-pyrazol-3-yl)-[1,1'-biphenyl]-4-yl)amino)ethane-1-sulfonyl fluoride (Cpd. No. 049) as an off-white solid (30 mg, 22%). (LC/MS; m/z 437.4 $[M+H]^+$).

Step 2: A solution of Cpd. No. 049 (130 mg, 0.297 mmol) in acetone (5 mL) was treated with methylamine in THF (2M) (4 mL) at RT and the mixture was stirred at 50° C. for 16 h (sealed tube) and monitored by TLC. TLC mobile phase: 5% MeOH in DCM, RF: 0.32, TLC detection: UV. The reaction mixture was concentrated under reduced pressure to afford crude product (200 mg) which was purified by preparative HPLC method H9. The collected fractions were lyophilised to afford N-methyl-2-((3-(1-(pyridin-3-ylmethyl)-1H-pyrazol-3-yl)-[1,1'-biphenyl]-4-yl)amino)ethane-1-sulfonamide (Cpd. No. 050) as a brown solid (52 mg, 39%). (LC/MS; m/z 448.4 $[M+H]^+$).

Step 3: (vinylsulfonyl)ethene (362 mg, 3.07 mmol) was added to a stirred solution of 3-(1-(pyridin-3-ylmethyl)-1H-pyrazol-3-yl)-[1,1'-biphenyl]-4-amine (Int-14) (100 mg, 0.306 mmol) and $BO_3H_3$ (9.5 mg, 0.153 mmol) in $H_2O$ (5 mL) and glycerol (10 mg) at RT. The mixture was stirred at 100° C. for 18 h (sealed tube) and monitored by TLC. TLC mobile phase: 50% EtOAc in pet ether, RF: 0.32, TLC detection: UV. The reaction mixture was cooled to RT and diluted with $H_2O$ (10 mL) and extracted with EtOAc (2×10 mL). The combined organic layer was washed with brine (20 mL), dried over anhydrous $Na_2SO_4$ and concentrated under reduced pressure to afford a brown residue (200 mg) which was purified by preparative HPLC method H2. The collected fractions were lyophilised to afford 4-(3-(1-(pyridin-3-ylmethyl)-1H-pyrazol-3-yl)-[1,1'-biphenyl]-4-yl)thiomorpholine-1,1-dioxide (Cpd. No. 051) as an off-white solid (10 mg, 7%). (LC/MS; m/z 445.3 $[M+H]^+$).

The following compounds were prepared in a manner similar (use of appropriate reagents and purification methods known to the person skilled in the art) to Cpd. No. 050: Cpd. No. 052 (prepared from Int-16), Cpd. No. 053, and Cpd. No. 054.

Compound Cpd. No. 055 (prepared from Int-16) was prepared in a manner similar (use of appropriate reagents and purification methods known to the person skilled in the art) to Cpd. No. 051.

Examples 24-25: Synthesis of N-methyl-2-((3-(1-methyl-1H-pyrazol-3-yl)-[1,1'-biphenyl]-4-yl)amino)ethane-1-sulfonamide (Cpd. No. 056) and 2-((3-(1-methyl-1H-pyrazol-3-yl)-[1,1'-biphenyl]-4-yl)amino)ethane-1-sulfonic acid (Cpd. No. 057)

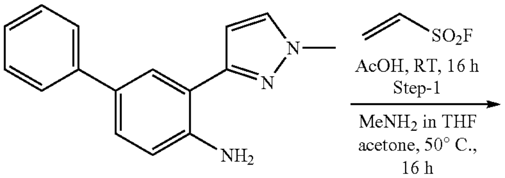

Int-15

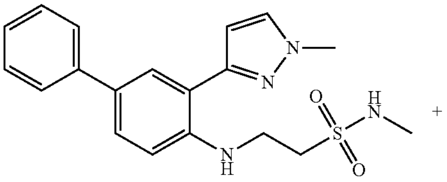

Cpd. No. 056

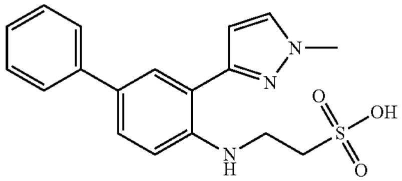

Cpd. No. 057

Steps 1-2: These steps were executed in a manner similar (use of appropriate reagents and purification methods known to the person skilled in the art) to step 1 and 2 towards Cpd. No. 050. From (370 mg, 1.48 mmol) was obtained crude product (320 mg, LC/MS 28%) which was purified by preparative HPLC method H2. The collected fractions were lyophilised to afford N-methyl-2-((3-(1-methyl-1H-pyrazol-3-yl)-[1,1'-biphenyl]-4-yl)amino)ethane-1-sulfonamide (Cpd. No. 056) as a white solid (35 mg, 6%, LC/MS 99%) (LC/MS; m/z 369.1 $[M-H]^-$) and 2-((3-(1-methyl-1H-pyrazol-3-yl)-[1,1'-biphenyl]-4-yl)amino)ethane-1-sulfonic acid (Cpd. No. 057) as a white solid (12 mg, 2%, LC/MS 95%). (LC/MS; m/z 258.2 $[M+H]^+$).

Compound Cpd. No. 058 was prepared in a manner similar (use of appropriate reagents and purification methods known to the person skilled in the art) to Cpd. No. 056.

Examples 26-27: Synthesis of 3-((3-(1-(pyridin-3-ylmethyl)-1H-pyrazol-3-yl)-[1,1'-biphenyl]-4-yl)amino)propanoic acid (Cpd. No. 059) and N-methyl-3-((3-(1-(pyridin-3-ylmethyl)-1H-pyrazol-3-yl)-[1,1'-biphenyl]-4-yl)amino)propanamide (Cpd. No. 060)

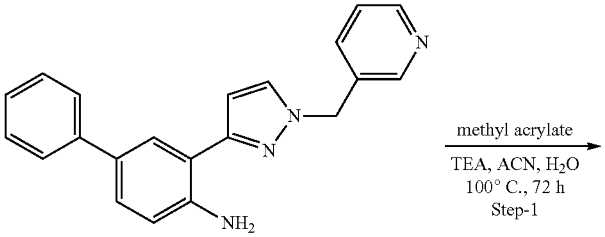

Int-14

-continued

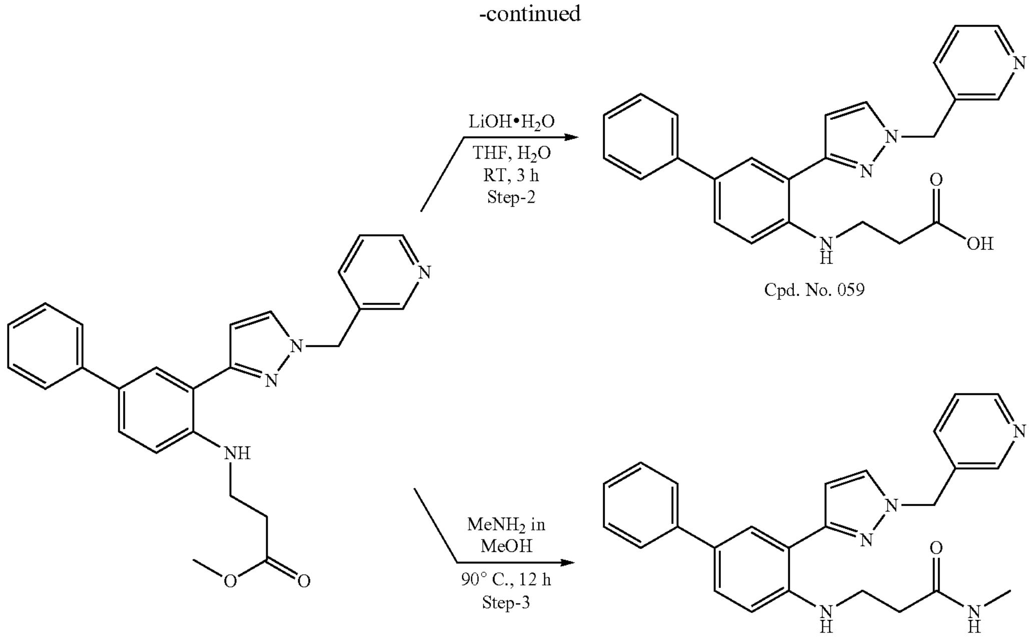

Cpd. No. 059

Cpd. No. 060

Step 1: A solution of 3-(1-(pyridin-3-ylmethyl)-1H-pyrazol-3-yl)-[1,1'-biphenyl]-4-amine (Int-14) (400 mg, 1.22 mmol) in ACN (10 mL) and $H_2O$ (2 mL) was treated with methyl acrylate (3.17 g, 36.81 mmol) and TEA (2.5 g, 24.54 mmol) at RT. The mixture was stirred at 100° C. for 72 h and monitored by TLC. TLC mobile phase: 5% MeOH in pet ether, RF: 0.49, TLC detection: UV. The reaction mixture was diluted with $H_2O$ (30 mL) and extracted with EtOAc (2×30 mL). The combined organic layer was washed with brine (20 mL), dried over anhydrous $Na_2SO_4$, and concentrated under reduced pressure to afford crude product (600 mg) which was purified by normal phase flash column chromatography using a 24 g column (silica) and a gradient of 0-50% EtOAc in pet ether as an eluent to afford methyl 3-((3-(1-(pyridin-3-ylmethyl)-1H-pyrazol-3-yl)-[1,1'-biphenyl]-4-yl)amino)propanoate (300 mg, 59%) as a brown gum. (LC/MS; m/z 413.3 $[M+H]^+$).

Step 2: A solution of methyl 3-((3-(1-(pyridin-3-ylmethyl)-1H-pyrazol-3-yl)-[1,1'-biphenyl]-4-yl)amino)propanoate (100 mg, 0.242 mmol) in THF (3 mL) and $H_2O$ (1 mL) was treated with $LiOH \cdot H_2O$ (50 mg, 1.213 mmol). The mixture was stirred at RT for 3 h and monitored by TLC. TLC mobile phase: 5% MeOH in DCM, RF: 0.01, TLC detection: UV. The reaction mixture was concentrated under reduced pressure and the residue diluted with $H_2O$ (10 mL) and neutralized using 2N HCl. The solution was extracted with DCM (2×10 mL) and the combined organic layer was washed with brine (20 mL), dried over anhydrous $Na_2SO_4$ and concentrated under reduced pressure to afford crude compound (55 mg) which was purified by preparative HPLC method H1. The collected fractions were lyophilised to afford 3-((3-(1-(pyridin-3-ylmethyl)-1H-pyrazol-3-yl)-[1,1'-biphenyl]-4-yl)amino)propanoic acid (Cpd. No. 059) as an off-white solid (14 mg, 14%). (LC/MS; m/z 399.3 $[M+H]^+$).

Step 3: A solution of methyl 3-((3-(1-(pyridin-3-ylmethyl)-1H-pyrazol-3-yl)-[1,1'-biphenyl]-4-yl)amino)propanoate (100 mg, 242 mmol) in MeOH was treated with methylamine in MeOH (2M) (4 mL). The mixture was stirred at 90° C. for 12 h (sealed tube) and monitored by TLC. TLC mobile phase: 5% MeOH in pet ether, RF: 0.5, TLC detection: UV. The reaction mixture was concentrated under reduced pressure to afford the crude compound (110 mg) which was purified by preparative HPLC method H1. The collected fractions were lyophilised to afford N-methyl-3-((3-(1-(pyridin-3-ylmethyl)-1H-pyrazol-3-yl)-[1,1'-biphenyl]-4-yl)amino)-propanamide (Cpd. No. 060) as an off-white solid (25 mg, 25%). (LC/MS; m/z 412.3 $[M+H]^+$).

Compounds Cpd. No. 061 and Cpd. No. 062 (both prepared from Int-16) were prepared in a manner similar (use of appropriate reagents and purification methods known to the person skilled in the art) to respectively Cpd. No. 059 and Cpd. No. 060.

Examples 28-29: Synthesis of 3-((3-(1-methyl-1H-pyrazol-3-yl)-[1,1'-biphenyl]-4-yl)amino)propanoic acid (Cpd. No. 063) and N-methyl-3-((3-(1-methyl-1H-pyrazol-3-yl)-[1,1'-biphenyl]-4-yl)amino)propanamide (Cpd. No. 064)

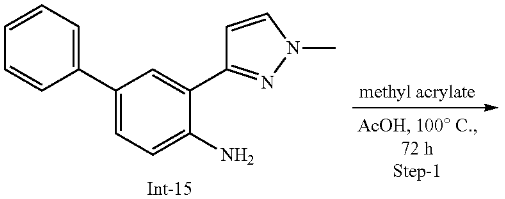

Int-15

-continued

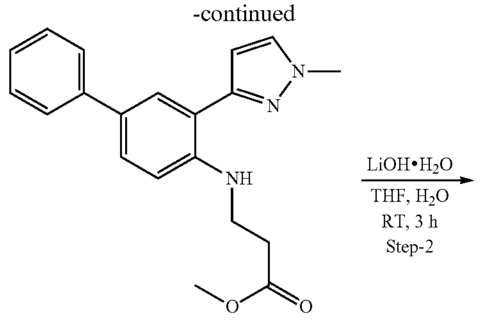

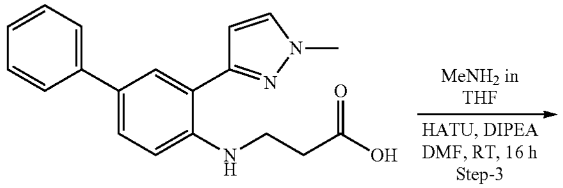

Cpd. No. 063

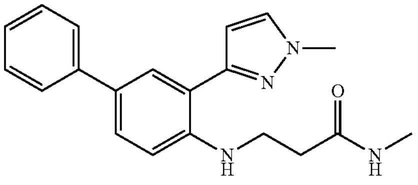

Cpd. No. 064

Steps 1-2: These steps were executed in a manner similar (use of appropriate reagents and purification methods known to the person skilled in the art) to Cpd. No. 059. Starting material Int-15 (300 mg, 1.2 mmol) yielded crude product (230 mg) which was purified by preparative HPLC method H5. The collected fractions were lyophilised to afford 3-((3-(1-methyl-1H-pyrazol-3-yl)-[1,1'-biphenyl]-4-yl)amino) propanoic acid (Cpd. No. 063) as an off-white solid (46 mg, 23%). (LC/MS; m/z 322.4 $[M+H]^+$).

Step 3: A solution of Cpd. No. 063 (130 mg, 0.4 mmol) and HATU (307 mg, 0.8 mmol) in DMF (10 mL) was treated with methylamine in THF (2M) (0.8 mL, 1.6 mmol) and DIPEA (130 mg, 1 mmol) at 0° C. The mixture was stirred at RT for 16 h and monitored by TLC. TLC mobile phase: 50% EtOAc in pet ether, RF: 0.5, TLC detection: UV. The reaction mixture was diluted with EtOAc (100 mL) and washed with brine (2×50 mL). The combined organic layer was dried over anhydrous $Na_2SO_4$ and concentrated under reduced pressure to afford the crude product (320 mg) which was purified by preparative HPLC method H3. The collected fractions were lyophilised to afford N-methyl-3-((3-(1-methyl-1H-pyrazol-3-yl)-[1,1'-biphenyl]-4-yl)amino)propanamide (Cpd. No. 064) as an off-white solid (110 mg, 95%). (LC/MS; m/z 335.4 $[M+H]^+$).

Examples 30-31: Synthesis of N-(2-(methylthio)ethyl)-3-(1-(pyridin-3-ylmethyl)-1H-pyrazol-3-yl)-[1,1'-biphenyl]-4-amine (Cpd. No. 065) and imino(methyl)(2-((3-(1-(pyridin-3-ylmethyl)-1H-pyrazol-3-yl)-[1,1'-biphenyl]-4-yl)amino)ethyl)-$\lambda^6$-sulfanone (Cpd. No. 066)

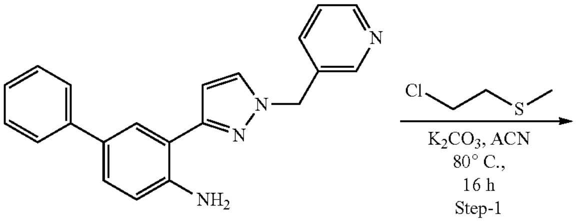

Int-14

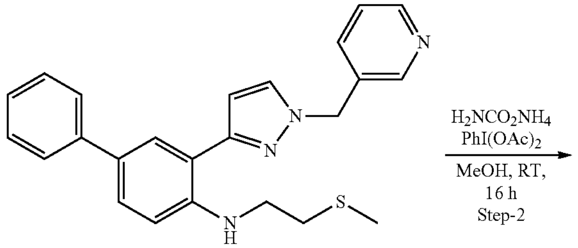

Cpd. No. 065

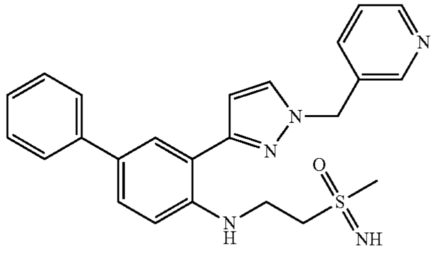

Cpd. No. 066

Step 1: To a solution of 3-(1-(pyridin-3-ylmethyl)-1H-pyrazol-3-yl)-[1,1'-biphenyl]-4-amine (Int-14) (1.0 g, 3.1 mmol) in ACN (10 mL) was added $K_2CO_3$ (1.06 g, 7.75 mmol) followed by (2-chloroethyl)(methyl)sulfane (857 mg, 7.75 mmol) at RT. The reaction mixture was stirred at 80° C. for 16 h (sealed tube) and monitored by TLC. TLC mobile phase: 70% EtOAc in pet ether, RF: 0.34, TLC detection: UV. The reaction mixture was diluted with EtOAc (30 mL) and $H_2O$ (20 mL). The organic layer was dried over anhydrous $Na_2SO_4$ and concentrated under reduced pressure to afford crude product (800 mg, LC/MS 22%) as a brown gum. The crude product was purified by normal phase flash column chromatography using a 24 g column (silica) and a gradient of 0-70% EtOAc in pet ether as an eluent to afford a brown gum (200 mg, LC/MS 16%). The compound was further purified by preparative HPLC method H1. The collected fractions were lyophilised to afford N-(2-(methylthio)ethyl)-3-(1-(pyridin-3-ylmethyl)-1H-pyrazol-3-yl)-[1,1'-biphenyl]-4-amine (Cpd. No. 065) as a pale yellow gum (38 mg, 13%). (LC/MS; m/z 401.3 $[M+H]^+$).

Step 2: A solution of Cpd. No. 065 (150 mg, 0.37 mmol) in MeOH (5 mL) was treated with ammonium carbamate (294 mg, 1.87 mmol) and $PhI(OAc)_2$ (181 mg, 0.56 mmol) at RT. The mixture was stirred at RT for 16 h and monitored by TLC. TLC mobile phase: 70% EtOAc in pet ether, RF: 0.47, TLC detection: UV. The reaction mixture was diluted with EtOAc (30 mL) and $H_2O$ (20 mL). The organic layer was dried over anhydrous $Na_2SO_4$ and concentrated under reduced pressure to afford a brown gum (150 mg, LC/MS 19%). The crude product was purified by preparative HPLC method H2. The collected fractions were lyophilised to afford imino(methyl)(2-((3-(1-(pyridin-3-ylmethyl)-1H-pyrazol-3-yl)-[1,1'-biphenyl]-4-yl)amino)ethyl)-$\lambda^6$-sulfanone (Cpd. No. 066) as an off-white solid (8.8 mg, 6%). (LC/MS; m/z 432.3 $[M+H]^+$).

Example 32: Synthesis of N-methyl-2-(methyl(3-(1-(pyridin-3-ylmethyl)-1H-pyrazol-3-yl)-[1,1'-biphenyl]-4-yl)amino)ethane-1-sulfonamide (Cpd. No. 067)

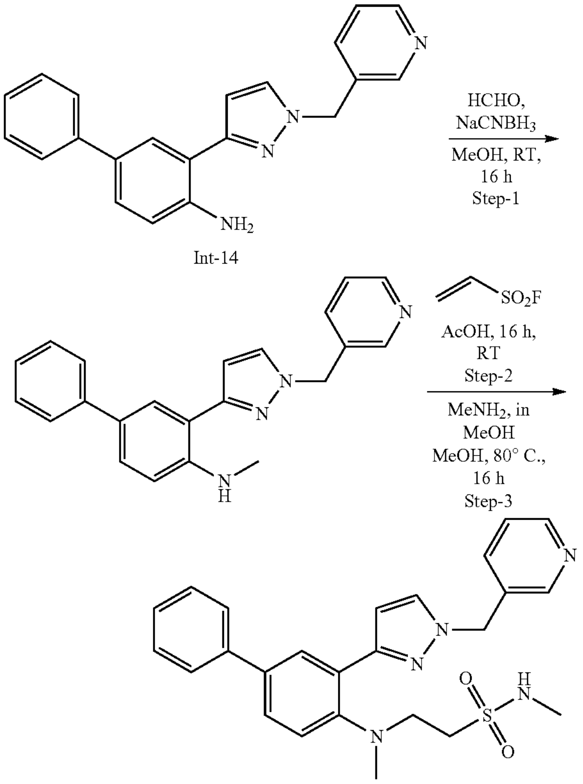

Int-14

Cpd. No. 067

Step 1: A mixture of 3-(1-(pyridin-3-ylmethyl)-1H-pyrazol-3-yl)-[1,1'-biphenyl]-4-amine (Int-14) (500 mg, 1.53 mmol) and paraformaldehyde (50.6 mg, 1.69 mmol) in MeOH (10 mL) was stirred at RT for 2 h. To the mixture was added $NaCNBH_3$ (190.2 mg, 3.07 mmol) at 0° C. The reaction mixture was stirred at RT for 14 h and monitored by TLC. TLC mobile phase: 70% EtOAc in pet ether, RF: 0.4, TLC detection: UV. The reaction mixture was concentrated under reduced pressure and the residue diluted with $H_2O$ (15 mL) and extracted with EtOAc (50 mL). The organic layer was dried over anhydrous $Na_2SO_4$ and concentrated under reduced pressure to afford a crude product (500 mg, LC/MS 58%) which was purified by normal phase flash column chromatography using a 12 g column (silica) and a gradient of 0-30% EtOAc in pet ether as an eluent to afford N-methyl-3-(1-(pyridin-3-ylmethyl)-1H-pyrazol-3-yl)-[1,1'-biphenyl]-4-amine (300 mg, 58%) as a pale yellow solid. (LC/MS; m/z 341.5 $[M+H]^+$).

Steps 2-3: These steps were executed in a manner similar (use of appropriate reagents and purification methods known to the person skilled in the art) to Cpd. No. 050. Starting material (250 mg, 0.73 mmol) yielded crude product (250 mg) which was purified by preparative HPLC method H3. The collected fractions were lyophilised to afford N-methyl-2-(methyl(3-(1-(pyridin-3-ylmethyl)-1H-pyrazol-3-yl)-[1,1'-biphenyl]-4-yl)amino)ethane-1-sulfonamide (Cpd. No. 067) as an off-white solid (10 mg, 3%). (LC/MS; m/z 462.4 $[M+H]^+$).

Example 33: Synthesis of 4-((3-(1-(pyridin-3-ylmethyl)-1H-pyrazol-3-yl)-[1,1'-biphenyl]-4-yl)amino)tetrahydro-2H-thiopyran-1,1-dioxide (Cpd. No. 068)

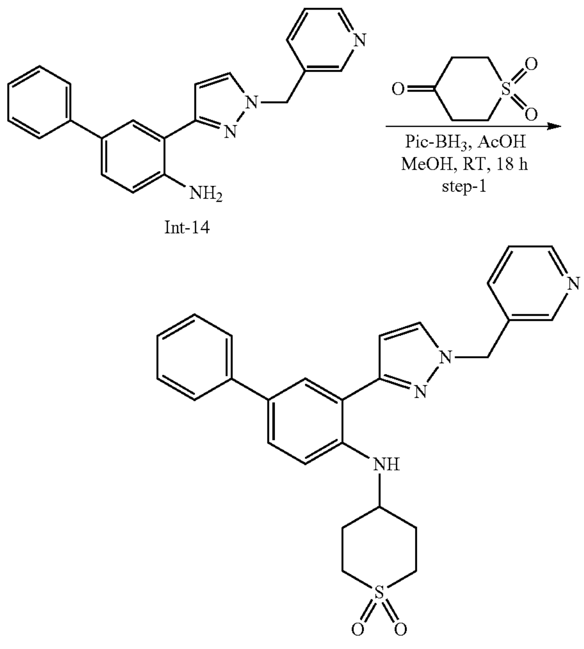

Int-14

Cpd. No. 068

Step 1: A mixture of 3-(1-(pyridin-3-ylmethyl)-1H-pyrazol-3-yl)-[1,1'-biphenyl]-4-amine (Int-14) (100 mg, 0.306 mmol), tetrahydro-4H-thiopyran-4-one-1,1-dioxide (55 mg, 0.368 mmol) and AcOH (92 mg, 1.53 mmol) in MeOH (5 mL) was stirred at RT for 2 h and was then treated with 2-picoline-borane complex (64 mg, 0.613 mmol). The reaction mixture was stirred at RT for 16 h and monitored by TLC. TLC mobile phase: 50% EtOAc in pet ether, RF: 0.35, TLC detection: UV. The reaction mixture was concentrated under reduced pressure and the residue was diluted with $H_2O$ (10 mL) and extracted with EtOAc (2×10 mL). The combined organic layer was dried over anhydrous $Na_2SO_4$ and concentrated under reduced pressure to afford a brown residue which was purified by preparative HPLC method H4. The collected fractions were lyophilised to afford 4-((3-(1-(pyridin-3-ylmethyl)-1H-pyrazol-3-yl)-[1,1'-biphenyl]-4-yl)amino)tetrahydro-2H-thiopyran-1,1-dioxide (Cpd. No. 068) as an off-white solid (35 mg, 28%). (LC/MS; m/z 459.3 $[M+H]^+$).

The following compounds were prepared in a manner similar (use of appropriate reagents and purification methods known to the person skilled in the art) to Cpd. No. 068: Cpd. No. 069 (prepared from Int-16), Cpd. No. 070, and Cpd. No. 071 (prepared from Int-16), Cpd. No. 072, and Cpd. No. 073 (prepared from Int-16).

Examples 34-35: Synthesis of N-methyl-2-((3-(1-(pyridin-3-ylmethyl)-1H-pyrazol-3-yl)-[1,1'-biphenyl]-4-yl)amino)acetamide (Cpd. No. 074) and N-(2-((3-(1-(pyridin-3-ylmethyl)-1H-pyrazol-3-yl)-[1,1'-biphenyl]-4-yl)amino)ethyl)acrylamide (Cpd. No. 075)

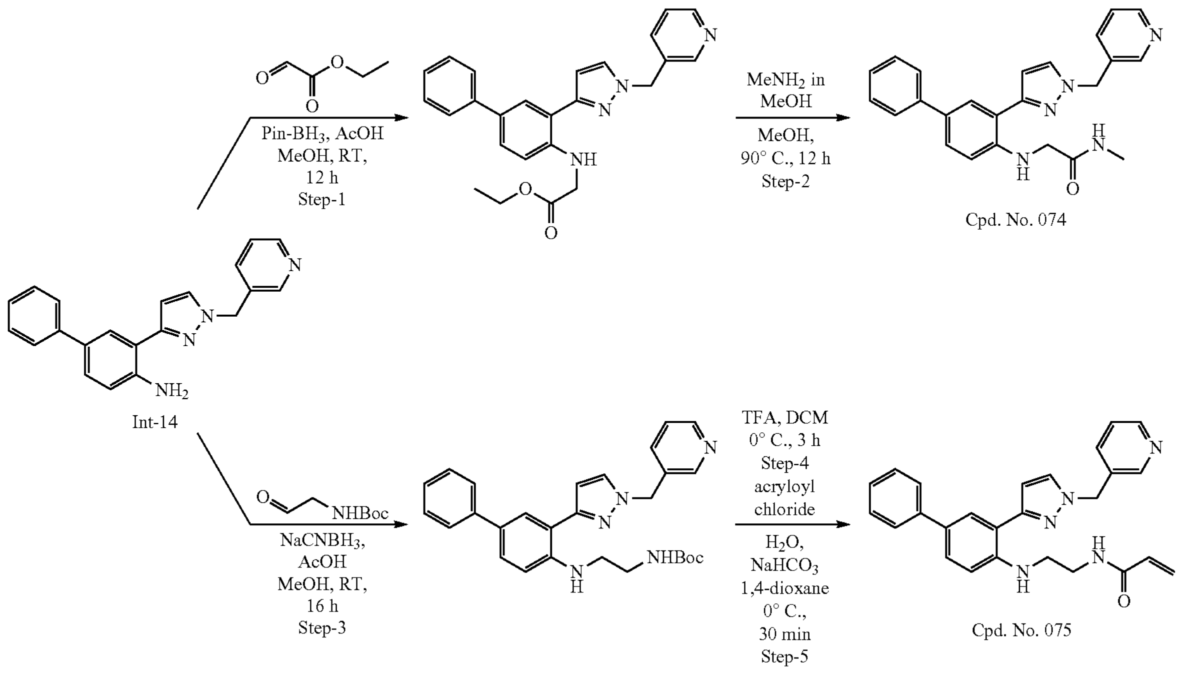

Step 1: This step was executed in a manner similar (use of appropriate reagents and purification methods known to the person skilled in the art) to Cpd. No. 068. Int-14 (400 mg, 1.23 mmol) yielded crude product (500 mg) which was purified by normal phase flash column chromatography using a 12 g column (silica) and a gradient of 0-50% EtOAc in pet ether as an eluent to afford ethyl (3-(1-(pyridin-3-ylmethyl)-1H-pyrazol-3-yl)-[1,1'-biphenyl]-4-yl)glycinate (260 mg, 51%). (LC/MS; m/z 413.3 $[M+H]^+$).

Step 2: This step was executed in a manner similar (use of appropriate reagents and purification methods known to the person skilled in the art) to Cpd. No. 050. Starting material (130 mg, 0.315 mmol) yielded crude product which was purified by preparative HPLC method H1. The collected fractions were lyophilised to afford N-methyl-2-((3-(1-(pyridin-3-ylmethyl)-1H-pyrazol-3-yl)-[1,1'-biphenyl]-4-yl) amino)acetamide (Cpd. No. 074) as an off-white solid (15 mg, 12%). (LC/MS; m/z 398.3 $[M+H]^+$).

Step 3: A solution of 3-(1-(pyridin-3-ylmethyl)-1H-pyrazol-3-yl)-[1,1'-biphenyl]-4-amine (Int-14) (500 mg, 1.53 mmol) and tert-butyl (2-oxoethyl)carbamate (292.6 mg, 1.84 mmol) in AcOH (276.1 mg, 4.60 mmol) and MeOH (10 mL) was stirred at RT for 2 h. $NaBH_3CN$ (193.2 mg, 3.17 mmol) was added and the reaction mixture stirred was stirred at RT for 14 h and monitored by TLC. TLC mobile phase: 70% EtOAc in pet ether, RF: 0.3, TLC detection: UV. The mixture was concentrated under reduced pressure and the residue was diluted with $H_2O$ (30 mL) and extracted with EtOAc (80 mL). The organic layer was washed with brine (30 mL), dried over anhydrous $Na_2SO_4$ and concentrated under reduced pressure to afford the crude product (650 mg, LC/MS 42%). (LC/MS; m/z 470.3 $[M+H]^+$). The product was used as such without further purification.

Step 4: A solution of tert-butyl (2-((3-(1-(pyridin-3-ylmethyl)-1H-pyrazol-3-yl)-[1,1'-biphenyl]-4-yl) amino)ethyl) carbamate (650 mg, 1.38 mmol) in DCM (10 mL) was treated with TFA (473.9 mg, 4.16 mmol) at 0° C. The reaction mixture was stirred for at 0° C. for 3 h and monitored by TLC. TLC mobile phase: 10% MeOH in DCM, RF: 0.1, TLC detection: UV. The reaction mixture was diluted with sat aq $NaHCO_3$ (10 mL) and extracted with DCM (80 mL). The organic layer was washed with brine (40 mL), dried over anhydrous $Na_2SO_4$ and concentrated under reduced pressure to afford the crude product (500 mg, LC/MS 45%) which was purified by normal phase flash column chromatography using a 12 g column (silica) and a gradient of 0-5% MeOH in DCM as an eluent to afford $N^1$-(3-(1-(pyridin-3-ylmethyl)-1H-pyrazol-3-yl)-[1,1'-biphenyl]-4-yl)ethane-1,2-diamine (400 mg, 86%) as a pale brown solid. (LC/MS; m/z 370.2 $[M+H]^+$).

Step 5: A solution of $N^1$-(3-(1-(pyridin-3-ylmethyl)-1H-pyrazol-3-yl)-[1,1'-biphenyl]-4-yl)ethane-1,2-diamine (200 mg, 0.54 mmol) in 1,4-dioxane (3 mL) was treated with $NaHCO_3$ (136.6 mg, 1.63 mmol), dissolved in $H_2O$ (0.5 mL), followed by acryloyl chloride (48.8 mg, 0.54 mmol), dissolved in 1,4-dioxane (2 mL), at 0° C. The mixture was stirred at 0° C. for 30 min and monitored by TLC. TLC mobile phase: 10% MeOH in DCM, RF: 0.3, TLC detection: UV. The mixture was diluted with $H_2O$ (10 mL) and extracted with DCM (30 mL). The organic layer was dried over anhydrous $Na_2SO_4$ and concentrated under reduced pressure to afford the crude product (230 mg, LC/MS 24%)

which was purified by preparative HPLC method H2. The collected fractions were lyophilised to afford N-(2-((3-(1-(pyridin-3-ylmethyl)-1H-pyrazol-3-yl)-[1,1'-biphenyl]-4-yl)amino)ethyl)-acrylamide (Cpd. No. 075) as an off-white solid (6 mg, 5%). (LC/MS; m/z 424.3 [M+H]$^+$).

Compound Cpd. No. 076 (prepared from Int-16) was prepared in a manner similar (use of appropriate reagents and purification methods known to the person skilled in the art) to Cpd. No. 074.

Compound Cpd. No. 077 was prepared in a manner similar (use of appropriate reagents and purification methods known to the person skilled in the art) to Cpd. No. 075.

Example 36: Synthesis of (5-(1-(pyridin-3-ylmethyl)-1H-pyrazol-3-yl)-[1,1'-biphenyl]-3-yl)glycine (Cpd. No. 078)

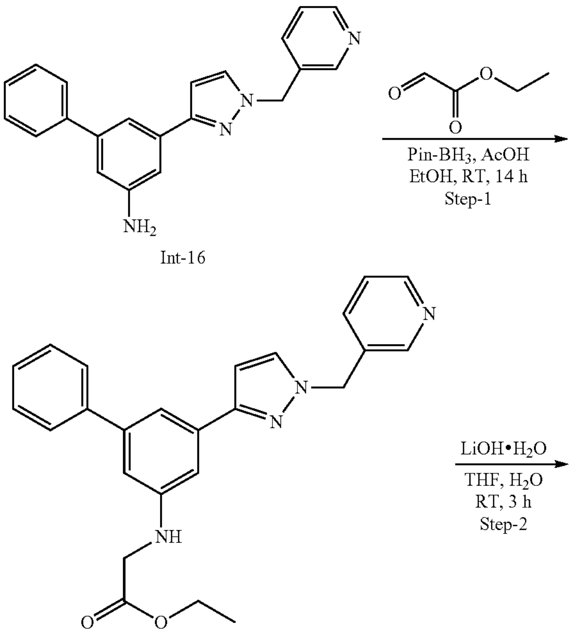

Int-16

-continued

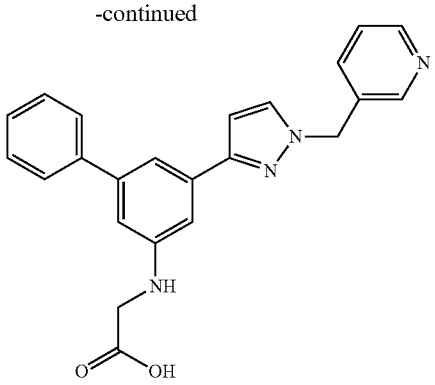

Cpd. No. 078

Step 1: This step was executed in a manner similar (use of appropriate reagents and purification methods known to the person skilled in the art) to Cpd. No. 068. Starting material (Int-16) (500 mg, 1.53 mmol) yielded crude product (400 mg, LC/MS 34%) which was purified by normal phase flash column chromatography using a 12 g column (silica) and a gradient of 0-50% EtOAc in pet ether as an eluent to afford ethyl (5-(1-(pyridin-3-ylmethyl)-1H-pyrazol-3-yl)-[1,1'-biphenyl]-3-yl)glycinate (200 mg, 25%, LC/MS 80%). (LC/MS; m/z 413.1 [M+H]$^+$).

Step 2: This step was executed in a manner similar (use of appropriate reagents and purification methods known to the person skilled in the art) to Cpd. No. 059. Starting material (200 mg, 0.48 mmol) yielded crude product (220 mg, LC/MS 34%) which was purified by preparative HPLC method H2. The collected fractions were lyophilised to afford 5-(1-(pyridin-3-ylmethyl)-1H-pyrazol-3-yl)-[1,1'-biphenyl]-3-yl)glycine (Cpd. No. 078) as a white solid (6 mg, 4%, LC/MS 99%). (LC/MS; m/z 385.3 [M+H]$^+$).

Examples 37-38: Synthesis of 3-(N-methylsulfamoyl)-N-(3-(1-(pyridin-3-ylmethyl)-1H-pyrazol-3-yl)-[1,1'-biphenyl]-4-yl)propanamide (Cpd. No. 079) and N-(3-(1-(pyridin-3-ylmethyl)-1H-pyrazol-3-yl)-[1,1'-biphenyl]-4-yl)acrylamide (Cpd. No. 080)

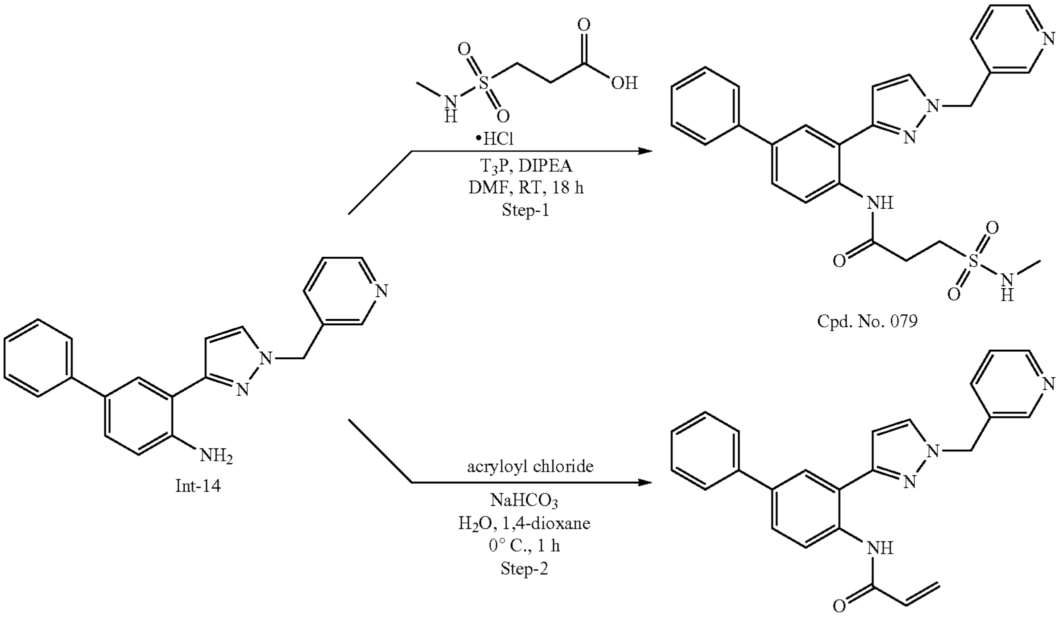

Cpd. No. 079

Int-14

Cpd. No. 080

Step 1: A solution of 3-(1-(pyridin-3-ylmethyl)-1H-pyrazol-3-yl)-[1,1'-biphenyl]-4-amine (Int-14) (200 mg, 0.613 mmol) in DMF (5 mL) was treated with 3-(N-methylsulfamoyl)propanoic acid hydrochloride (125 mg, 0.613 mmol), $T_3P$ (390 mg, 1.226 mmol) and DIPEA (237 mg, 1.839 mmol). The mixture mixture was stirred at RT for 18 h and monitored by TLC. TLC mobile phase: 5% MeOH in DCM, RF: 0.56, TLC detection: UV. The reaction mixture was diluted with ice $H_2O$ (20 mL) and EtOAc (50 mL). The organic layer was dried over anhydrous $Na_2SO_4$ and concentrated under reduced pressure to afford crude product (250 mg, LC/MS 50%) which was purified by preparative HPLC method H5. The collected fractions were lyophilised to afford 3-(N-methylsulfamoyl)-N-(3-(1-(pyridin-3-ylmethyl)-1H-pyrazol-3-yl)-[1,1'-biphenyl]-4-yl)propanamide (Cpd. No. 079) as an off-white solid (74 mg, 30%). (LC/MS, m/z 476.5 $[M+H]^+$).

Step 2: A mixture of 3-(1-(pyridin-3-ylmethyl)-1H-pyrazol-3-yl)-[1,1'-biphenyl]-4-amine (Int-14) (100 mg, 0.306 mmol) and NaHCO3 (77 mg, 0.920 mmol) in 1,4-dioxane (5 mL) and $H_2O$ (1 mL) was treated with acryloyl chloride (33.2 mg, 0.368 mmol) at 0° C. and stirred for 1 h. The reaction was monitored by TLC. TLC mobile phase: 50% EtOAc in pet ether, RF: 0.45, TLC detection: UV. The reaction mixture was diluted with $H_2O$ (10 mL) and extracted with EtOAc (2×10 mL). The combined organic layer was dried over anhydrous $Na_2SO_4$ and concentrated under reduced pressure to afford a brown residue which was purified by preparative HPLC method H6. The collected fractions were lyophilised to afford N-(3-(1-(pyridin-3-ylmethyl)-1H-pyrazol-3-yl)-[1,1'-biphenyl]-4-yl)acrylamide (Cpd. No. 080) as an off-white solid (50 mg, 43%). (LC/MS; m/z 381.3 $[M+H]^+$).

The following compounds were prepared in a manner similar (use of appropriate reagents and purification methods known to the person skilled in the art) to Cpd. No. 079: Cpd. No. 081 and Cpd. No. 082.

Compound Cpd. No. 083 (prepared from Int-16) was prepared in a manner similar (use of appropriate reagents and purification methods known to the person skilled in the art) to Cpd. No. 080.

Examples 39-40: Synthesis of 3-((3-(1-(pyridin-3-ylmethyl)-1H-pyrazol-3-yl)-[1,1'-biphenyl]-4-yl)amino)propanenitrile (Cpd. No. 084) and 2-((3-(1-(pyridin-3-ylmethyl)-1H-pyrazol-3-yl)-[1,1'-biphenyl]-4-yl)amino)acetonitrile (Cpd. No. 085)

Step 1: A solution of 3-(1-(pyridin-3-ylmethyl)-1H-pyrazol-3-yl)-[1,1'-biphenyl]-4-amine (Int-14) (170 mg, 0.52 mmol) in acrylonitrile (1.7 mL) and AcOH (0.05 mL) was stirred at 100° C. for 24 h (sealed tube) and monitored by TLC. TLC mobile phase: 70% EtOAc in pet ether, RF: 0.5, TLC detection: UV. The cooled reaction mixture was diluted with EtOAc (25 mL) and washed sequentially with sat aq $NaHCO_3$ (2×15 mL) and brine (30 mL). The combined organic layer was dried over anhydrous $Na_2SO_4$ and concentrated under reduced pressure to afford crude product (300 mg) which was purified by preparative HPLC method H2. The collected fractions were lyophilised to afford 3-((3-(1-(pyridin-3-ylmethyl)-1H-pyrazol-3-yl)-[1,1'-biphenyl]-4-yl)amino)-propanenitrile (Cpd. No. 084) as an off-white solid (25 mg, 13%). (LC/MS; m/z 380.3 $[M+H]^+$).

Step 2: A solution of 3-(1-(pyridin-3-ylmethyl)-1H-pyrazol-3-yl)-[1,1'-biphenyl]-4-amine (Int-14) (200 mg, 0.61 mmol) in ACN (10 mL) was treated with bromoacetonitrile (88 mg, 0.73 mmol) and $K_2CO_3$ (254 mg, 1.84 mmol). The reaction mixture was heated to 60° C. for 3 h (sealed tube) and monitored by TLC. TLC mobile phase: 5% MeOH in DCM, RF: 0.55, TLC detection: UV. The reaction mixture was diluted with $H_2O$ (20 mL) and EtOAc (50 mL). The organic layer was dried over anhydrous $Na_2SO_4$ and concentrated under reduced pressure to afford crude product (250 mg, LC/MS 27%) which was purified by normal phase flash column chromatography using silica gel (100-200 mesh) and a gradient of 0-2% MeOH in DCM as an eluent to afford crude product (130 mg, LC/MS 40%) which was further purified by preparative HPLC method H3. The collected fractions were lyophilised to afford 2-((3-(1-(pyridin-3-ylmethyl)-1H-pyrazol-3-yl)-[1,1'-biphenyl]-4-yl)amino)-acetonitrile (Cpd. No. 085) as an off-white solid (20 mg, 10%). (LC/MS; m/z 366.2 $[M+H]^+$).

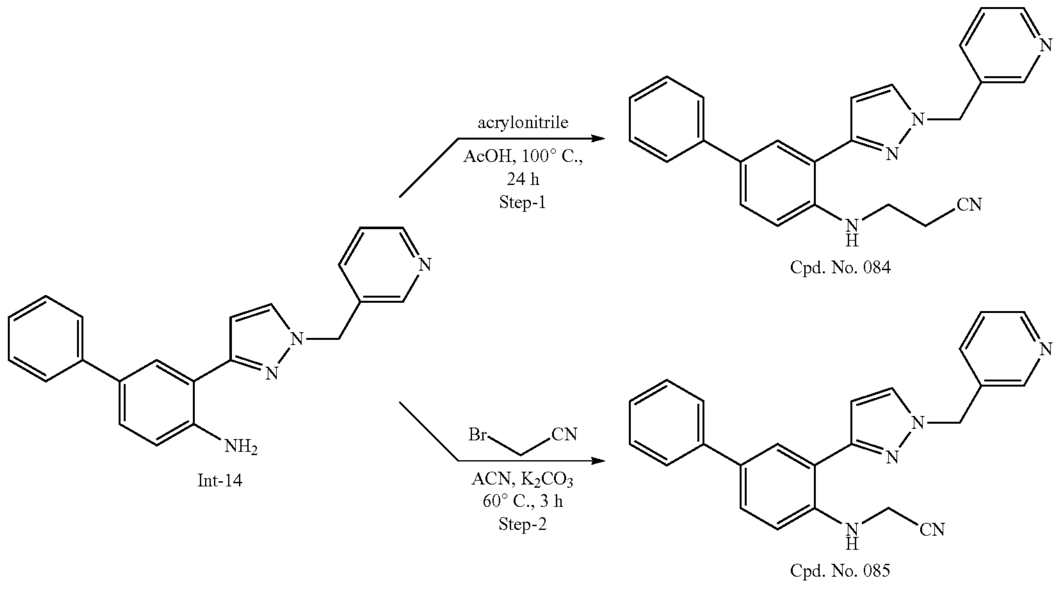

Example 41: Synthesis of 2-((4'-fluoro-3-(1-(pyridin-3-ylmethyl)-1H-pyrazol-3-yl)-[1,1'-biphenyl]-4-yl)amino)-N-methylethane-1-sulfonamide (Cpd. No. 086)

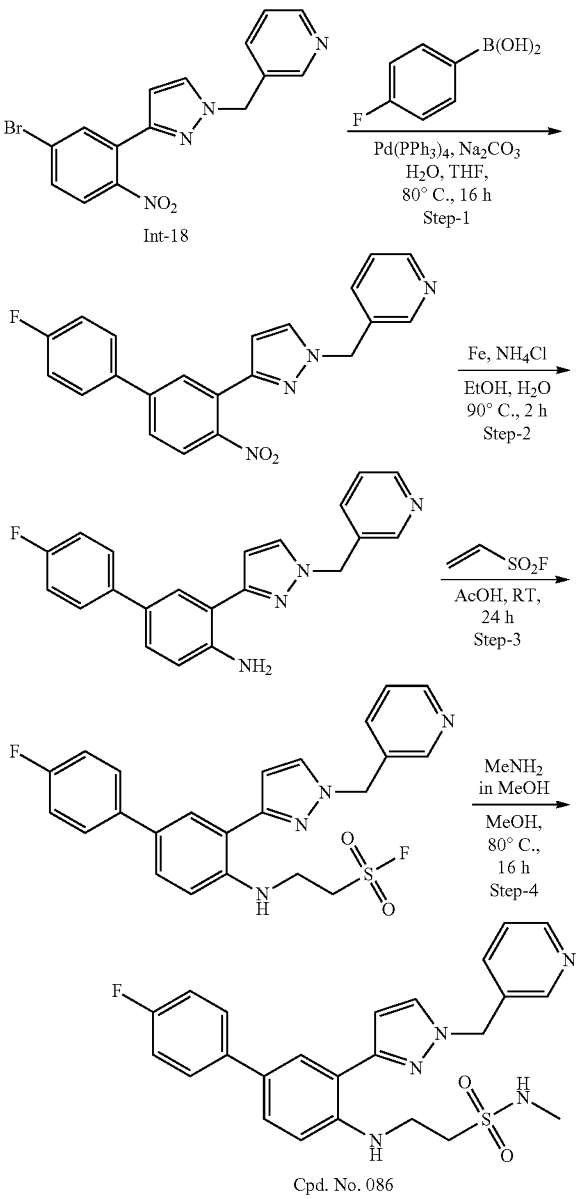

Int-18

Cpd. No. 086

Step 1: A solution of 3-((3-(5-bromo-2-nitrophenyl)-1H-pyrazol-1-yl)methyl)pyridine (Int-18) (1.0 g, 2.8 mmol) and (4-fluorophenyl)boronic acid (470 mg, 3.36 mmol) in 10% aq $Na_2CO_3$ solution (5 mL) and THF (15 mL) was degassed with argon for 5 min. To the solution was added $Pd(PPh_3)_4$ (64 mg, 56 μmol) and the reaction mixture was stirred at 80° C. for 16 h and monitored by TLC. TLC mobile phase: 5% MeOH in DCM, RF: 0.55, TLC detection: UV. The reaction mixture was cooled to RT and diluted with EtOAc (50 mL) and $H_2O$ (20 mL). The organic layer was dried over anhydrous $Na_2SO_4$ and concentrated under reduced pressure to afford crude product (1.2 g) which was purified by normal phase flash column chromatography using silica gel (100-200 mesh) and DCM as an eluent to afford 3-((3-(4'-fluoro-4-nitro-[1,1'-biphenyl]-3-yl)-1H-pyrazol-1-yl)methyl)pyridine as pale brown solid (850 mg, 77%). (LC/MS; m/z 375.2 $[M+H]^+$).

Step 2: A solution of 3-((3-(4'-fluoro-4-nitro-[1,1'-biphenyl]-3-yl)-1H-pyrazol-1-yl)methyl)pyridine (850 mg, 2.27 mmol) and $NH_4Cl$ (245 mg, 4.54 mmol) in EtOH (15 mL) and $H_2O$ (3 mL) was treated with Fe powder (590 mg, 11.36 mmol. The reaction mixture was stirred at 90° C. for 2 h and monitored by TLC. TLC mobile phase: 5% MeOH in DCM, RF: 0.44, TLC detection: UV. The reaction mixture was filtered through a celite pad and washed with EtOAc (30 mL). The filtrate was concentrated under reduced pressure and the residue was dissolved in EtOAc (50 mL) and $H_2O$ (15 mL). The organic layer was dried over anhydrous $Na_2SO_4$ and concentrated under reduced pressure to afford 4'-fluoro-3-(1-(pyridin-3-ylmethyl)-1H-pyrazol-3-yl)-[1,1'-biphenyl]-4-amine as pale yellow solid (700 mg). (LC/MS; m/z 345.1 $[M+H]^+$). The product was used as such without further purification.

Step 3: A solution of 4'-fluoro-3-(1-(pyridin-3-ylmethyl)-1H-pyrazol-3-yl)-[1,1'-biphenyl]-4-amine (600 mg, 1.74 mmol) in AcOH (5 mL) was treated with ethenesulfonyl fluoride (230 mg, 2.09 mmol). The reaction mixture was stirred at RT for 5 h and monitored by TLC. TLC mobile phase: 5% MeOH in DCM, RF: 0.71, TLC detection: UV. The reaction mixture was diluted with ice $H_2O$ (30 mL) and extracted with EtOAc (30 mL). The organic layer was dried over anhydrous $Na_2SO_4$ and concentrated under reduced pressure to afford 2-((4'-fluoro-3-(1-(pyridin-3-ylmethyl)-1H-pyrazol-3-yl)-[1,1'-biphenyl]-4-yl)amino)ethane-1-sulfonyl fluoride as a brown gum (700 mg). (LC/MS; m/z 455.7 $[M+H]^+$). The product was used as such without further purification.

Step 4: A solution of 2-((4'-fluoro-3-(1-(pyridin-3-ylmethyl)-1H-pyrazol-3-yl)-[1,1'-biphenyl]-4-yl)amino)ethane-1-sulfonyl fluoride (550 mg, 1.21 mmol) in MeOH (5 mL) was treated with methylamine (25% in MeOH) (2.5 mL). The mixture was heated at 80° C. for 16 h (sealed tube) and monitored by TLC. TLC mobile phase: 5% MeOH in DCM, RF: 0.36, TLC detection: UV. The reaction mixture was concentrated under reduced pressure and the crude product was purified by normal phase flash column chromatography using a 24 g column (silica) and a gradient of 0-2% MeOH in DCM as an eluent to afford the product which was further purified by preparative HPLC method H3. The collected fractions were lyophilised to afford 2-((4'-fluoro-3-(1-(pyridin-3-ylmethyl)-1H-pyrazol-3-yl)-[1,1'-biphenyl]-4-yl)amino)-N-methylethane-1-sulfonamide (Cpd. No. 086) as an off-white solid (70 mg, 20%). (LC/MS; m/z 466.3 $[M+H]^+$).

The following compounds were prepared in a manner similar (use of appropriate reagents and purification methods known to the person skilled in the art) to Cpd. No. 086: Cpd. No. 087, Cpd. No. 088, Cpd. No. 089, Cpd. No. 090, Cpd. No. 091, Cpd. No. 092, Cpd. No. 093, Cpd. No. 094, Cpd. No. 095, Cpd. No. 096, Cpd. No. 097, Cpd. No. 098, Cpd. No. 099, Cpd. No. 100, Cpd. No. 101.

The compounds Cpd. No. 102, Cpd. No. 103, Cpd. No. 104, and Cpd. No. 105 were prepared from respectively Int-20, Int-21, Int-22, and Int-23 in a manner similar (use of appropriate reagents and purification methods known to the person skilled in the art) to Cpd. No. 086.

Examples 42-43: synthesis of 2-((4'-chloro-3-(1-(pyridin-3-ylmethyl)-1H-pyrazol-3-yl)-[1,1'-biphenyl]-4-yl)amino)-N-methylethane-1-sulfonamide (Cpd. No. 106) and 2-((4'-chloro-3-(1-(pyridin-3-ylmethyl)-1H-pyrazol-3-yl)-[1,1'-biphenyl]-4-yl)amino)ethane-1-sulfonic acid (Cpd. No. 107)

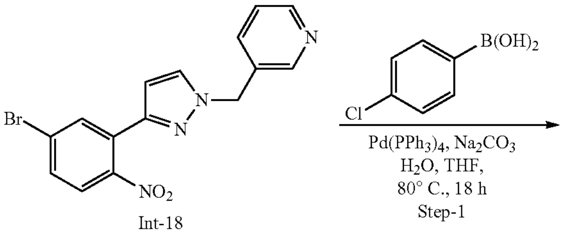

Int-18

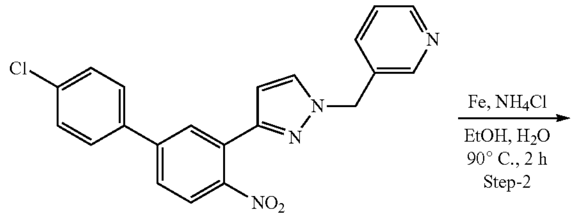

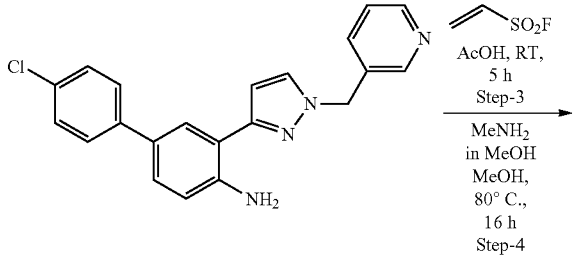

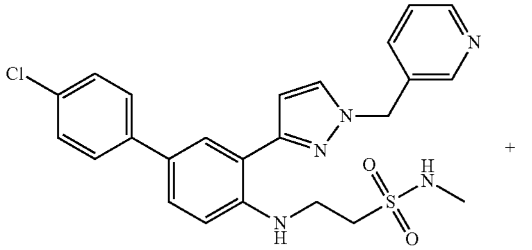

Cpd. No. 106

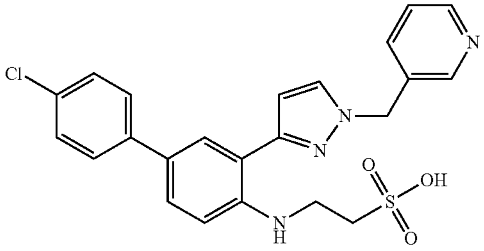

Cpd. No. 107

Steps 1-4: These steps were executed in a manner similar (use of appropriate reagents and purification methods known to the person skilled in the art) to Cpd. No. 086. From Int-18 (800 mg, 2.23 mmol) was obtained crude product (640 mg, LC/MS 36% & 45%) which was purified by normal phase flash column chromatography using silica gel (100-200 mesh) and a gradient of 0-8% MeOH in DCM as an eluent to afford 2-((4'-chloro-3-(1-(pyridin-3-ylmethyl)-1H-pyrazol-3-yl)-[1,1'-biphenyl]-4-yl)amino)-N-methylethane-1-sulfonamide (Cpd. No. 106) (300 mg, LC/MS 73%) and 2-((4'-chloro-3-(1-(pyridin-3-ylmethyl)-1H-pyrazol-3-yl)-[1,1'-biphenyl]-4-yl)amino)ethane-1-sulfonic acid (Cpd. No. 107) (150 mg, LC/MS 88%). Cpd. No. 106 was further purified by preparative HPLC method $H_1$. The collected fractions were lyophilised to afford an off-white solid (45 mg, 4%, LC/MS 99%). (LC/MS; m/z 482.2 $[M+H]^+$). Cpd. No. 107 was further purified by preparative HPLC method H3. The collected fractions were lyophilised to afford an off-white solid (60 mg, 6%, LC/MS 99%). (LC/MS; m/z 469.2 $[M+H]^+$).

The following compounds were prepared in a manner similar (use of appropriate reagents and purification methods known to the person skilled in the art) to Cpd. No. 106 and Cpd. No. 107: Cpd. No. 108 and Cpd. No. 109.

Examples 44-45: synthesis of 2-((4'-methoxy-3-(1-(pyridin-3-ylmethyl)-1H-pyrazol-3-yl)-[1,1'-biphenyl]-4-yl)amino)ethane-1-sulfonyl fluoride (Cpd. No. 110) and 2-((4'-methoxy-3-(1-(pyridin-3-ylmethyl)-1H-pyrazol-3-yl)-[1,1'-biphenyl]-4-yl)amino)-N-methylethane-1-sulfonamide (Cpd. No. 111)

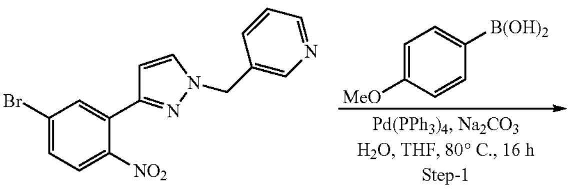

Int-18

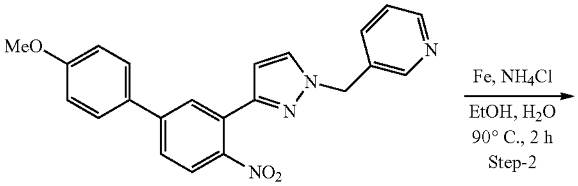

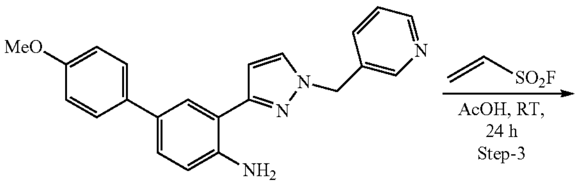

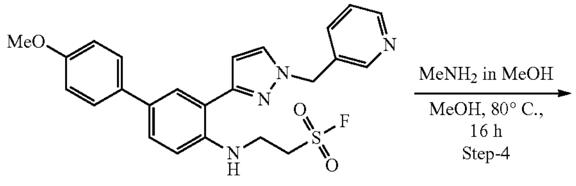

Cpd. No. 110

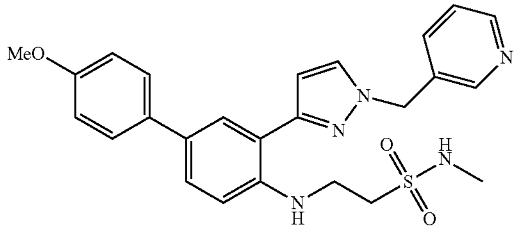

Cpd. No. 111

Steps 1-2: These steps were executed in a manner similar (use of appropriate reagents and purification methods known to the person skilled in the art) to step 1 and 2 towards Cpd. No. 086. From Int-18 (1.0 g, 2.8 mmol) was obtained 4'-methoxy-3-(1-(pyridin-3-ylmethyl)-1H-pyrazol-3-yl)-[1,1'-biphenyl]-4-amine as an off-white white solid (550 mg, 42%, LC/MS 75%). (LC/MS; m/z 357.1 $[M+H]^+$).

Step 3: This step was executed in a manner similar (use of appropriate reagents and purification methods known to the person skilled in the art) to step 3 towards Cpd. No. 86. From 4'-methoxy-3-(1-(pyridin-3-ylmethyl)-1H-pyrazol-3-yl)-[1,1'-biphenyl]-4-amine (450 mg, 1.26 mmol) was obtained crude product (550 mg, LC/MS 62%). The product was used as such without further purification. Crude product (150 mg, LC/MS 62%) was purified by normal phase flash column chromatography using silica gel (100-200 mesh) and a gradient of 0-2% MeOH in DCM as an eluent to afford crude 2-((4'-methoxy-3-(1-(pyridin-3-ylmethyl)-1H-pyrazol-3-yl)-[1,1'-biphenyl]-4-yl)amino)ethane-1-sulfonyl fluoride (Cpd. No. 110) (100 mg, LC/MS 86%). Cpd. No. 110 was further purified by preparative HPLC method H3. The collected fractions were lyophilised to afford a pale brown solid (45 mg, 29%, LC/MS 95%). (LC/MS; m/z 467.3 $[M+H]^+$).

Step 4: This step was executed in a manner similar (use of appropriate reagents and purification methods known to the person skilled in the art) to step 4 towards Cpd. No. 086. From Cpd. No. 110 (400 mg, 0.86 mol, LC/MS 62%) was obtained crude product (550 mg, LC/MS 37%) which was purified by preparative HPLC method H11. The collected fractions were lyophilised to afford 2-((4'-methoxy-3-(1-(pyridin-3-ylmethyl)-1H-pyrazol-3-yl)-[1,1'-biphenyl]-4-yl)amino)-N-methylethane-1-sulfonamide (Cpd. No. 111) as an off-white solid (8 mg, 3%, LC/MS 97%). (LC/MS; m/z 478.3 $[M+H]^+$).

Example 46: Synthesis of 2-((3-(1-(2-hydroxyethyl)-1H-pyrazol-3-yl)-4'-(trifluoromethyl)-[1,1'-biphenyl]-4-yl)amino)-N-methylethane-1-sulfonamide (Cpd. No. 112)

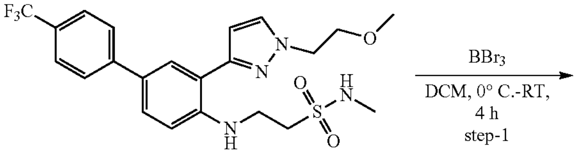

Cpd. No. 105

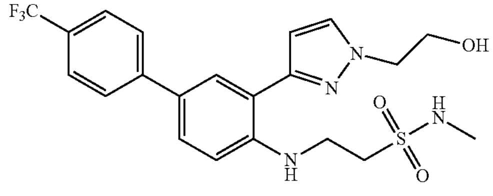

Cpd. No. 112

Step 1: A solution of Cpd. No. 105 (50 mg, 0.10 mmol) in DCM (3 mL) was treated with $BBr_3$ (1.0 M in DCM) (0.41 mL, 0.41 mmol) at 0° C. The mixture was stirred at RT for 4 h and monitored by TLC. TLC mobile phase: 70% EtOAc in pet ether, RF: 0.27, TLC detection: UV. The reaction mixture was quenched with ice $H_2O$ (20 mL) and extracted with DCM (30 mL). The organic layer was washed with brine (10 mL), dried over anhydrous $Na_2SO_4$ and concentrated under reduced pressure to afford the crude product (50 mg, LC/MS 91%) which was purified by preparative HPLC method H2. The collected fractions were lyophilised to afford 2-((3-(1-(2-hydroxyethyl)-1H-pyrazol-3-yl)-4'-(trifluoromethyl)-[1,1'-biphenyl]-4-yl)amino)-N-methylethane-1-sulfonamide (Cpd. No. 112) as an off-white solid (35 mg, 72%). (LC/MS; m/z 469.3 $[M+H]^+$).

Example 47: Synthesis of 3-((3-(4-((2-(N-methylsulfamoyl)ethyl)amino)-[1,1'-biphenyl]-3-yl)-1H-pyrazol-1-yl)methyl)benzamide (Cpd. No. 113)

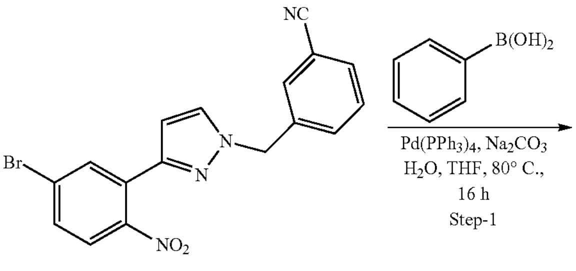

Int-22

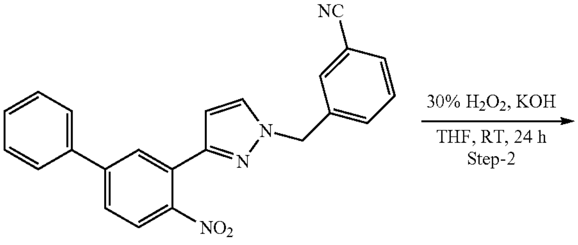

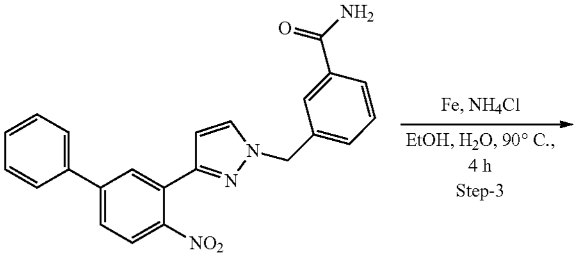

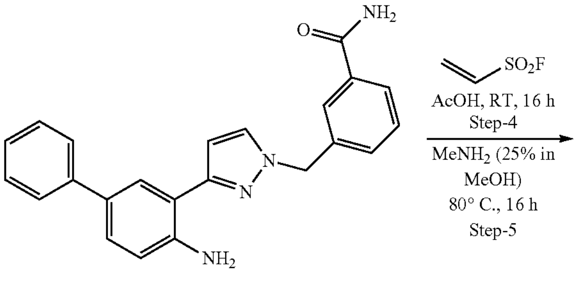

-continued

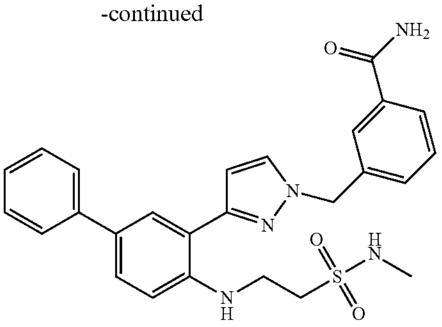

Cpd. No. 113

Step 1: This step was executed in a manner similar (use of appropriate reagents and purification methods known to the person skilled in the art) to step 1 towards Cpd. No. 086. Int-22 (600 mg, 1.57 mmol) yielded crude product (700 mg) which was purified by normal phase flash column chromatography using silica gel (100-200 mesh) and 0-15% EtOAc in pet ether as an eluent to afford 3-((3-(4-nitro-[1,1'-biphenyl]-3-yl)-1H-pyrazol-1-yl)methyl)benzonitrile as a pale yellow solid (400 mg, 88%). (LC/MS; m/z 381.2 $[M+H]^+$).

Step 2: A mixture of 3-((3-(4-nitro-[1,1'-biphenyl]-3-yl)-1H-pyrazol-1-yl)methyl)benzonitrile (500 mg, 1.31 mmol) and KOH (221 mg, 3.94 mmol) in THF (5 mL) was treated with 30% $H_2O_2$ (5 mL). The mixture was stirred at RT for 24 h and monitored by TLC. TLC mobile phase: 50% EtOAc in pet ether, RF: 0.26, TLC detection: UV. The reaction mixture was cooled to RT and diluted with EtOAc (10 mL) and $H_2O$ (5 mL). The organic layer was dried over anhydrous $Na_2SO_4$ and concentrated under reduced pressure to afford a brown gum (410 mg, LC/MS 77%). The crude product was purified by normal phase flash column chromatography using a 80 g column (silica) and a gradient of 0-65% EtOAc in pet ether as an eluent to afford 3-((3-(4-nitro-[1,1'-biphenyl]-3-yl)-1H-pyrazol-1-yl)methyl)benzamide as an off-white solid (200 mg, 52%). (LC/MS; m/z 399.2 $[M+H]^+$).

Steps 3-5: These steps were executed in a manner similar (use of appropriate reagents and purification methods known to the person skilled in the art) to step 2, 3 and 4 towards Cpd. No. 086. Starting material (200 mg, 0.50 mmol) yielded crude product (200 mg, LC/MS 27%) which was purified by preparative HPLC method H2. The collected fractions were lyophilised to afford 3-((3-(4-((2-(N-methylsulfamoyl)ethyl)amino)-[1,1'-biphenyl]-3-yl)-1H-pyrazol-1-yl)methyl)benzamide (Cpd. No. 113) as an off-white solid (25 mg, 13%). (LC/MS; m/z 490.3 $[M+H]^+$).

Example 48: Synthesis of N-methyl-2-((4-(pyridin-2-yl)-2-(1-(pyridin-3-ylmethyl)-1H-pyrazol-3-yl)phenyl)amino)ethane-1-sulfonamide (Cpd. No. 114)

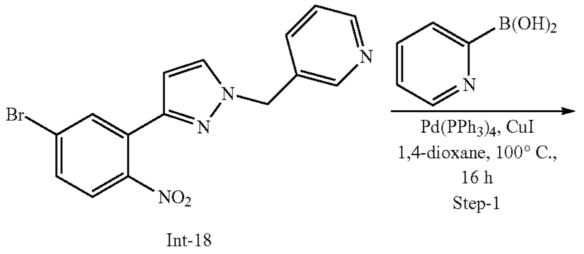

Int-18

-continued

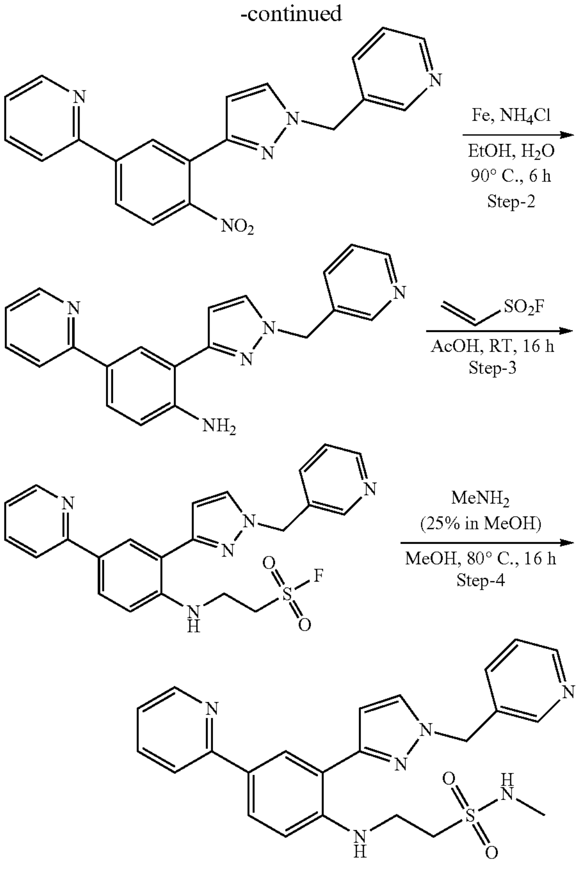

Cpd. No. 114

Step 1: A solution of 3-((3-(5-bromo-2-nitrophenyl)-1H-pyrazol-1-yl) methyl) pyridine (Int-18) (700 mg, 1.95 mmol), 2-(tributylstannyl)pyridine (793.6 mg, 2.15 mmol) and CuI (408.6 mg, 2.15 mmol) in 1,4-dioxane (10 mL) was degassed with argon for 20 min. To the solution was added $Pd(PPh_3)_4$ (225.8 mg, 0.19 mmol). The reaction mixture was stirred at 100° C. for 16 h (sealed tube) and monitored by TLC. TLC mobile phase: 70% EtOAc in pet ether, RF: 0.3, TLC detection: UV. The reaction mixture was cooled to RT and filtered through a celite pad and washed with EtOAc (60 mL). The filtrate was concentrated under reduced pressure to afford crude product (500 mg, LC/MS 34%) which was purified by normal phase flash column chromatography using a 12 g column (silica) and a gradient of 0-50% EtOAc in pet ether as an eluent to afford 2-(4-nitro-3-(1-(pyridin-3-ylmethyl)-1H-pyrazol-3-yl)phenyl)pyridine as a light brown solid (200 mg, 24%). (LC/MS; m/z 358.2 $[M+H]^+$).

Steps 2-4: These steps were executed in a manner similar (use of appropriate reagents and purification methods known to the person skilled in the art) to step 2, 3 and 4 towards Cpd. No. 086. Starting material (250 mg, 0.56 mmol) yielded crude product (200 mg, LC/MS 9%) which was purified by normal phase flash column chromatography using a 12 g column (silica) and a gradient of 0-2% MeOH in DCM as an eluent to afford product (90 mg, LC/MS 31%) which was further purified by preparative HPLC method H8. The collected fractions were lyophilised to afford N-methyl-2-((4-(pyridin-2-yl)-2-(1-(pyridin-3-ylmethyl)-1H-pyrazol-3-yl)phenyl)amino)ethane-1-sulfonamide (Cpd. No. 114) as an off-white solid (6 mg, 5%). (LC/MS; m/z 449.3 $[M+H]^+$).

Example 49: Synthesis of 2-((4-benzyl-2-(1-(pyridin-3-ylmethyl)-1H-pyrazol-3-yl)phenyl)amino)-N-methylethane-1-sulfonamide (Cpd. No. 115)

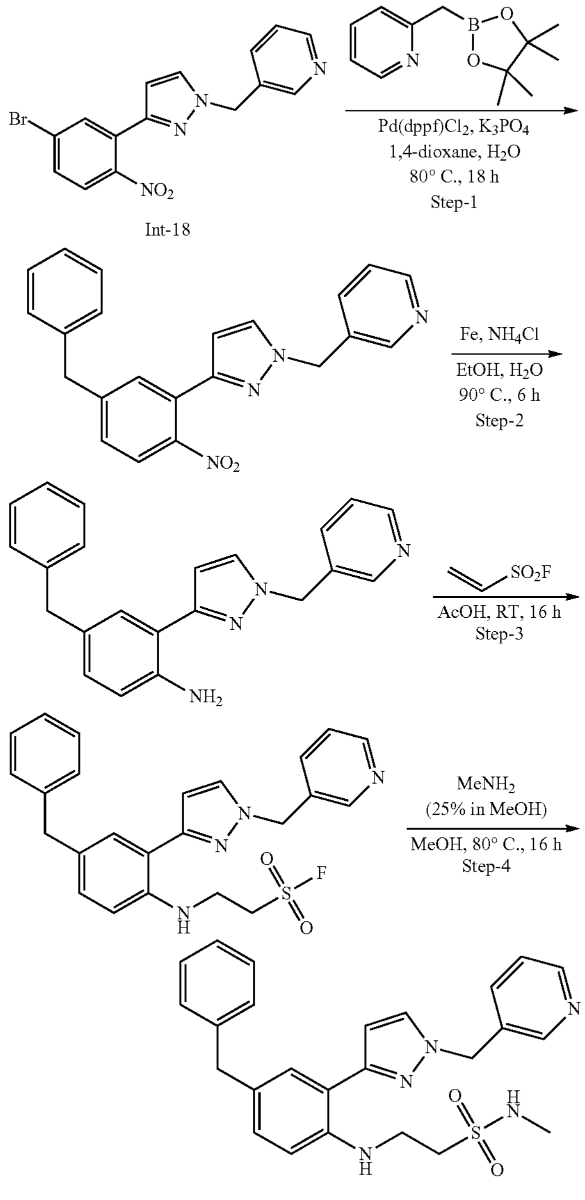

Cpd. No. 115

Step 1: A solution of 3-((3-(5-bromo-2-nitrophenyl)-1H-pyrazol-1-yl)methyl)pyridine (Int-18) (500 mg, 1.396 mmol), 2-benzyl-4,4,5,5-tetramethyl-1,3,2-dioxaborolane (365 mg, 1.675 mmol) and $K_3PO_4$ (740 mg, 3.491 mmol) in 1,4-dioxane (10 mL) and $H_2O$ (2 mL) was degassed with argon for 5 min. To the mixture was added $Pd(dppf)Cl_2$ (102 mg, 0.139 mmol). The reaction mixture was stirred at 80° C. for 18 h (sealed tube) and monitored by TLC. TLC mobile phase: 50% EtOAc in pet ether, RF: 0.37, TLC detection: UV. The reaction mixture was cooled to RT, diluted with $H_2O$ (20 mL) and extracted with EtOAc (2×20 mL). The combined organic layer was dried over anhydrous $Na_2SO_4$ and concentrated under reduced pressure to afford the crude compound (450 mg) which was purified by normal phase flash column chromatography using a 12 g column (silica) and a gradient of 0-70% EtOAc in pet ether as an eluent to afford 3-((3-(5-benzyl-2-nitrophenyl)-1H-pyrazol-1-yl)methyl)pyridine as a brown mass (310 mg, 62%). (LC/MS; m/z 371.3 $[M+H]^+$).

Steps 2-4: These steps were executed in a manner similar (use of appropriate reagents and purification methods known to the person skilled in the art) to step 2, 3 and 4 towards Cpd. No. 086. Starting material (310 mg, 0.837 mmol) yielded crude product (260 mg, LC/MS 30%) which was purified by normal phase flash column chromatography using a 12 g column (silica) and a gradient of 0-10% MeOH in DCM as an eluent to afford product (100 mg, LC/MS 50%) which was further purified by preparative HPLC method H2. The collected fractions were lyophilised to afford 2-((4-benzyl-2-(1-(pyridin-3-ylmethyl)-1H-pyrazol-3-yl)phenyl)amino)-N-methylethane-1-sulfonamide (Cpd. No. 115) as a white solid (30 mg, 13%). (LC/MS; m/z 462.3 $[M+H]^+$).

Example 50: Synthesis of N-methyl-2-((4-(phenylamino)-2-(1-(pyridin-3-ylmethyl)-1H-pyrazol-3-yl)phenyl)amino)ethane-1-sulfonamide (Cpd. No. 116)

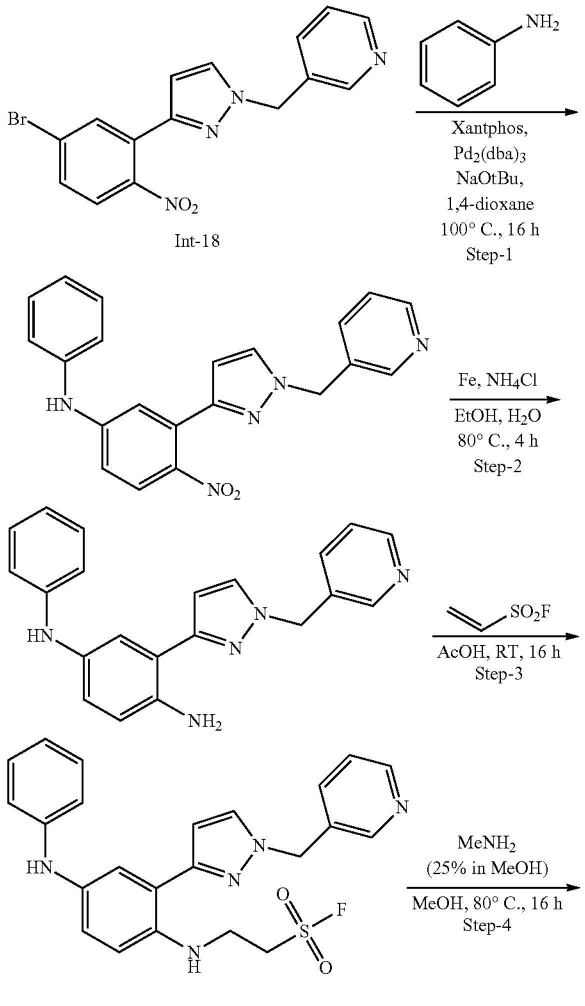

-continued

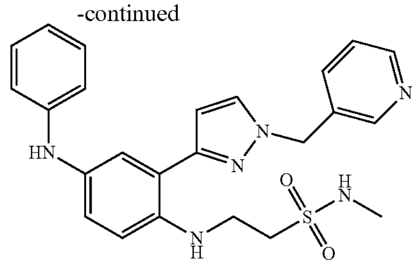

Cpd. No. 116

Step 1: A solution of 3-((3-(5-bromo-2-nitrophenyl)-1H-pyrazol-1-yl)methyl)pyridine (Int-18) (500 mg, 1.39 mmol), aniline (324 mg, 3.49 mmol) and NaOtBu (536 mg, 5.58 mmol) in 1,4-dioxane (25 mL) was degassed with argon for 5 min. To the solution was added $Pd_2(dba)_3$ (64 mg, 0.07 mmol) and XantPhos (40 mg, 0.07 mmol). The reaction mixture was stirred at 100° C. for 16 h and monitored by TLC. TLC mobile phase: 50% EtOAc in pet ether, RF: 0.4, TLC detection: UV. The reaction mixture was cooled to RT, diluted with $H_2O$ (25 mL) and extracted with EtOAc (3×20 mL). The combined organic layer was dried over anhydrous $Na_2SO_4$ and concentrated under reduced pressure to afford crude product (800 mg, LC/MS 84%) which was purified by normal phase flash column chromatography using a 40 g column (alumina) and a gradient of 0-70% EtOAc in pet ether as an eluent to afford 4-nitro-N-phenyl-3-(1-(pyridin-3-ylmethyl)-1H-pyrazol-3-yl) aniline as an off-white solid (430 mg, 83%). (LC/MS; m/z 372.2 $[M+H]^+$).

Steps 2-4: These steps were executed in a manner similar (use of appropriate reagents and purification methods known to the person skilled in the art) to step 2, 3 and 4 towards Cpd. No. 086. Starting material (430 mg, 1.16 mmol) yielded crude product which was purified by preparative HPLC method H2. The collected fractions were lyophilised to afford N-methyl-2-((4-(phenylamino)-2-(1-(pyridin-3-ylmethyl)-1H-pyrazol-3-yl)phenyl)amino)-ethane-1-sulfonamide (Cpd. No. 116) as a brown solid (43 mg, 14%). (LC/MS; m/z 463.1 $[M+H]^+$).

Example 51: Synthesis of 2-((4'-fluoro-3-(1-methyl-1H-pyrazol-3-yl)-[1,1'-biphenyl]-4-yl)amino)-N-methylethane-1-sulfonamide (Cpd. No. 117)

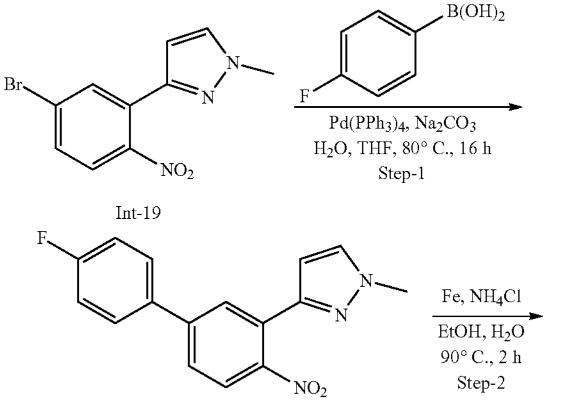

Int-19

-continued

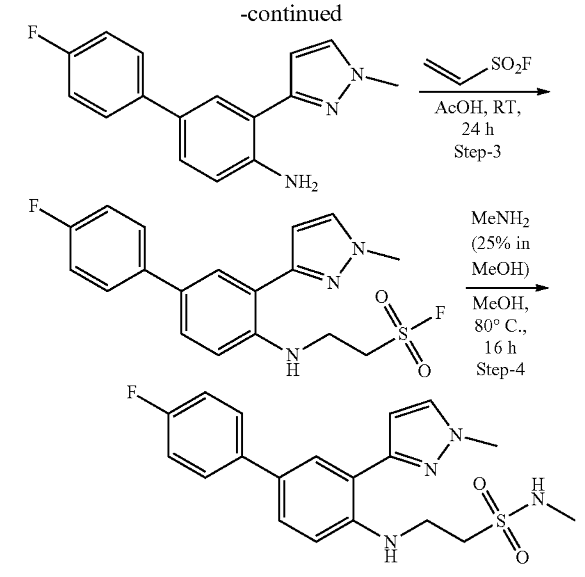

Cpd. No. 117

Steps 1-4: These steps were executed in a manner similar (use of appropriate reagents and purification methods known to the person skilled in the art) to Cpd. No. 086. Starting material (Int-19) (500 mg, 1.77 mmol) yielded crude product (500 mg, LC/MS 21%) which was purified by normal phase flash column chromatography using a 24 g column (silica) and a gradient of 0-20% EtOAc in pet ether as an eluent to afford a brown gum (60 mg, LC/MS 96%). The product was further purified by preparative HPLC method H3. The collected fractions were lyophilised to afford 2-((4'-fluoro-3-(1-methyl-1H-pyrazol-3-yl)-[1,1'-biphenyl]-4-yl)amino)-N-methylethane-1-sulfonamide (Cpd. No. 117) as an off-white solid (30 mg, 12%). (LC/MS; m/z 389.2 $[M+H]^+$).

The following compounds were prepared in a manner similar (use of appropriate reagents and purification methods known to the person skilled in the art) to Cpd. No. 117: Cpd. No. 118, Cpd. No. 119, Cpd. No. 120, Cpd. No. 121, Cpd. No. 122, Cpd. No. 123, Cpd. No. 124, Cpd. No. 125, Cpd. No. 126, Cpd. No. 127, Cpd. No. 128, Cpd. No. 129.

Example 52: Synthesis of 2-((4-(1-(difluoromethyl)-1H-pyrazol-3-yl)-6-(4-(trifluoromethyl)phenyl)pyridin-3-yl)amino)-N-methylethane-1-sulfonamide (Cpd. No. 130)

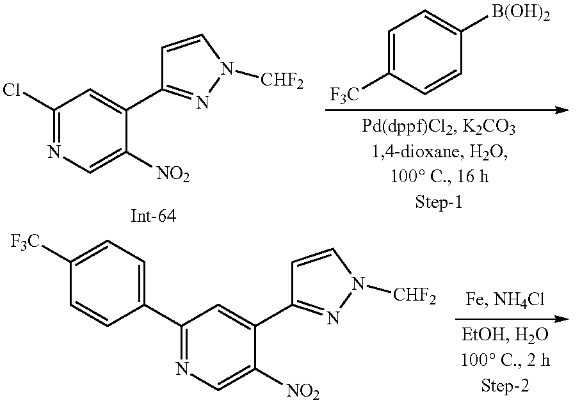

Int-64

-continued

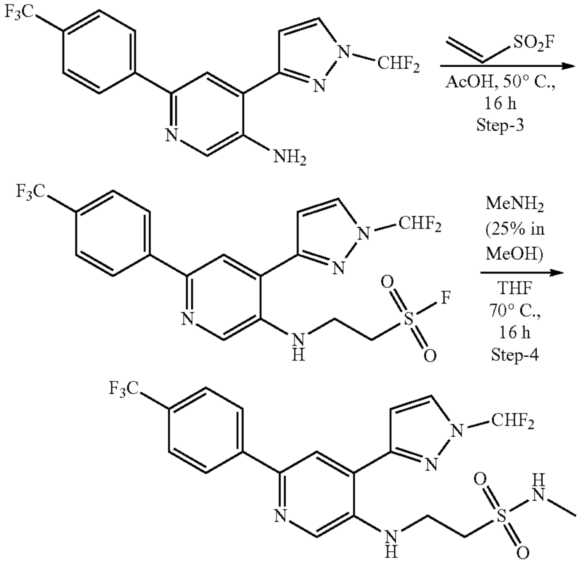

Cpd. No. 130

Step 1: A solution of Int-64 (650 mg, 2.37 mmol) in 1,4-dioxane (10 mL) was treated with (4-(trifluoromethyl) phenyl)boronic acid (541 mg, 2.84 mmol) and $K_2CO_3$ (655 mg, 4.74 mmol) in $H_2O$ (1 mL). The mixture was degassed with argon for 5 min and Pd(dppf)$Cl_2$ (87 mg, 0.11 mmol) was added. The reaction mixture was stirred at 100° C. for 16 h (sealed tube) and monitored by TLC. TLC mobile phase: 30% EtOAc in pet ether, RF: 0.3, TLC detection: UV. The reaction mixture was filtered through a celite pad and washed with EtOAc (150 mL), and the filtrate was washed with $H_2O$ (40 mL) and brine (60 mL). The combined organic layer was dried over anhydrous $Na_2SO_4$ and concentrated under reduced pressure to afford crude product (800 mg, LC/MS 73%) which was purified by normal phase flash column chromatography using a 12 g column (silica) and a gradient of 0-10% EtOAc in pet ether as an eluent to afford 4-(1-(difluoromethyl)-1H-pyrazol-3-yl)-5-nitro-2-(4-(trifluoromethyl)phenyl)pyridine as a white solid (650 mg, 71%). (LC/MS; m/z 385.2 $[M+H]^+$).

Steps 2-4: These steps were executed in a manner similar (use of appropriate reagents and purification methods known to the person skilled in the art) to step 2, 3 and 4 towards Cpd. No. 086. Starting material (650 mg, 1.69 mmol) yielded crude product (1.0 g, LC/MS 54%) which was purified by preparative HPLC method H1. The collected fractions were lyophilised to afford 2-((4-(1-(difluoromethyl)-1H-pyrazol-3-yl)-6-(4-(trifluoromethyl)phenyl)pyridin-3-yl)amino)-N-methylethane-1-sulfonamide (Cpd. No. 130) as an off-white solid (101 mg, 12%). (LC/MS; m/z 476.3 $[M+H]^+$).

Compound Cpd. No. 131 was prepared in a manner similar (use of appropriate reagents and purification methods known to the person skilled in the art) to Cpd. No. 130.

Example 53: Synthesis of 2-((2-(1-(difluoromethyl)-1H-pyrazol-3-yl)-6-(4-fluorophenyl)pyridin-3-yl) amino)-N-methylethane-1-sulfonamide (Cpd. No. 132)

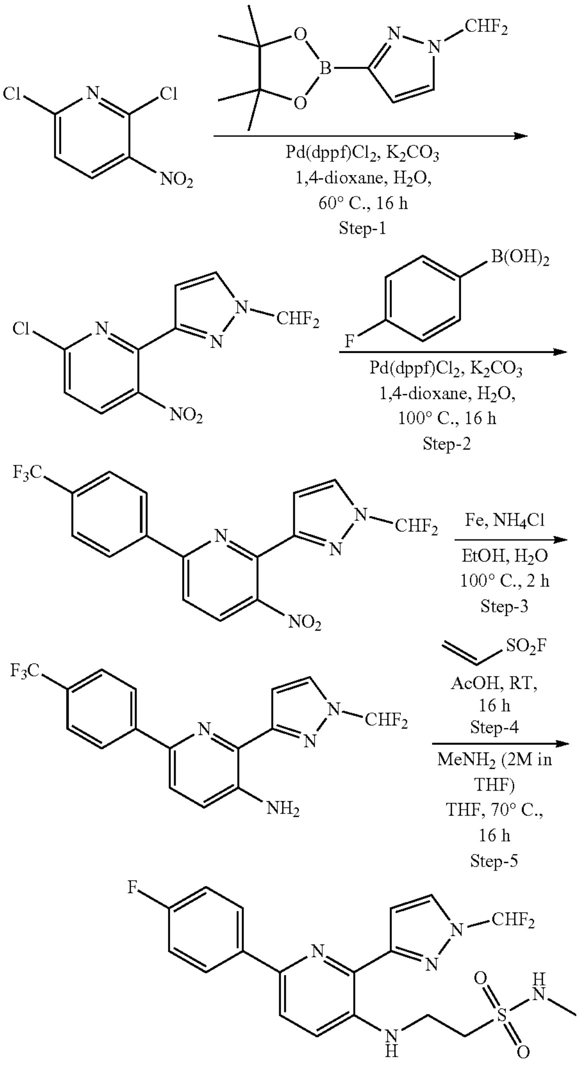

Cpd. No. 132

Step 1: A solution of 2,6-dichloro-3-nitropyridine (1.5 g, 7.77 mmol) in 1,4-dioxane (30 mL) and $H_2O$ (3 mL) was treated with 1-(difluoromethyl)-3-(4,4,5,5-tetramethyl-1,3,2-dioxaborolan-2-yl)-1H-pyrazole (2.08 g, 8.55 mmol) and $K_2CO_3$ (2.14 g, 15.54 mmol). The mixture was degassed with argon for 5 min and Pd(dppf)$Cl_2$ (114 mg, 0.15 mmol) was added. The reaction mixture was stirred at 60° C. for 16 h and monitored by TLC. TLC mobile phase: 20% EtOAc in pet ether, RF: 0.4, TLC detection: UV. The reaction mixture was filtered through a celite pad, washed with EtOAc (100 mL) and the filtrate was washed with brine (3×50 mL). The organic layer was dried over anhydrous $Na_2SO_4$ and concentrated under reduced pressure to afford crude product (2.0 g) which was purified by normal phase flash column chromatography using silica gel (100-200 mesh) and a gradient of 0-15% EtOAc in pet ether as an eluent to afford 6-chloro-2-(1-(difluoromethyl)-1H-pyrazol-3-yl)-3-nitropyridine as an off-white solid (1.3 g, 47%, LC/MS 78%). (LC/MS; m/z 275.1 [M+H]$^+$).

Step 2: A solution of 6-chloro-2-(1-(difluoromethyl)-1H-pyrazol-3-yl)-3-nitropyridine (650 mg, 2.37 mmol) in 1,4-dioxane (20 mL) was treated with (4-fluorophenyl)boronic acid (497 mg, 3.55 mmol) and $K_2CO_3$ (980 mg, 7.10 mmol) in $H_2O$ (3 mL). The mixture was degassed with argon for 5 min and Pd(dppf)$Cl_2$ (173 mg, 0.23 mmol) was added. The reaction mixture was stirred at 100° C. for 16 h (sealed tube) and monitored by TLC. TLC mobile phase: 20% EtOAc in pet ether, RF: 0.38, TLC detection: UV. The reaction mixture was filtered through a celite pad, washed with EtOAc (200 mL) and the filtrate was washed with brine (2×150 mL). The organic layer was dried over anhydrous $Na_2SO_4$ and concentrated under reduced pressure to yield crude product (780 mg) which was purified by normal phase flash column chromatography using silica gel (100-200 mesh) and a gradient of 0-15% EtOAc in pet ether as an eluent to afford 2-(1-(difluoromethyl)-1H-pyrazol-3-yl)-6-(4-fluorophenyl)-3-nitropyridine as an off-white solid (580 mg, 91%). (LC/MS; m/z 335.2 [M+H]$^+$).

Steps 3-5: These steps were executed in a manner similar (use of appropriate reagents and purification methods known to the person skilled in the art) to step 2, 3 and 4 towards Cpd. No. 086. Starting material (580 mg, 1.73 mmol) yielded crude product (540 mg, LC/MS 76%) which was purified by preparative HPLC method H14. The collected fractions were lyophilised to afford 2-((2-(1-(difluoromethyl)-1H-pyrazol-3-yl)-6-(4-fluorophenyl)pyridin-3-yl)amino)-N-methylethane-1-sulfonamide (Cpd. No. 132) as an off-white solid (318 mg, 43%). (LC/MS; m/z 426.1 [M+H]$^+$).

The following compounds were prepared in a manner similar (use of appropriate reagents and purification methods known to the person skilled in the art) to Cpd. No. 132: Cpd. No. 133 (employing 2M $Me_2NH$ in THF) and Cpd. No. 134.

Examples 54-55: Synthesis of N-((3-(1-methyl-1H-pyrazol-3-yl)-[1,1'-biphenyl]-4-yl)methyl)acrylamide (Cpd. No. 135) and N-((3-(1-(pyridin-3-ylmethyl)-1H-pyrazol-3-yl)-[1,1'-biphenyl]-4-yl)methyl)acrylamide (Cpd. No. 136)

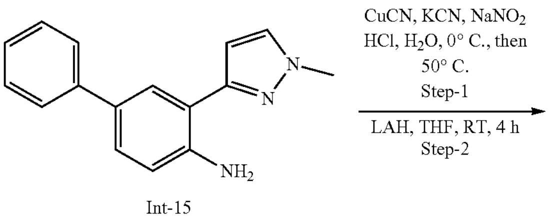

Int-15

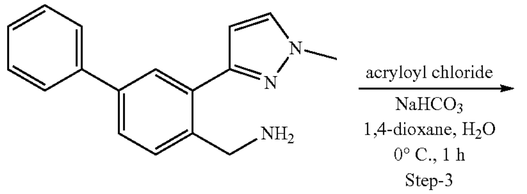

-continued

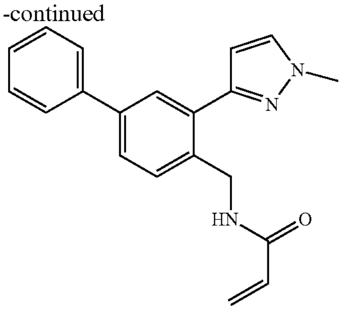

Cpd. No. 135

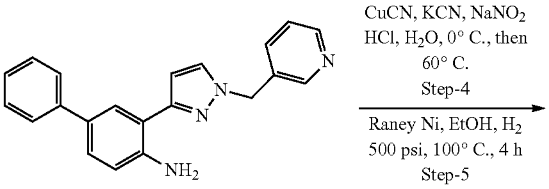

Int-14

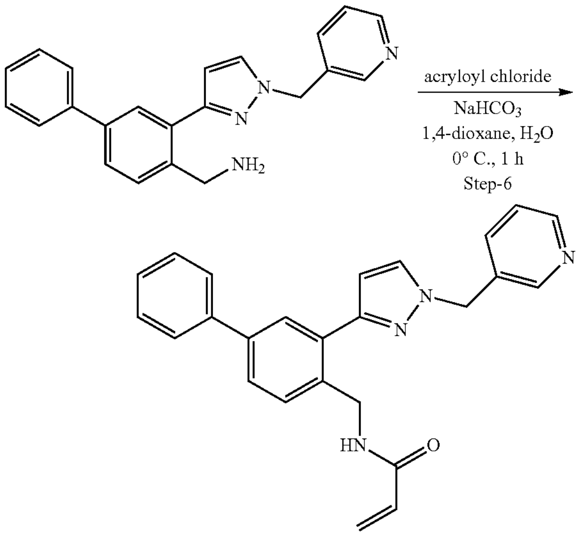

Cpd. No. 136

Step 1: A solution of 3-(1-methyl-1H-pyrazol-3-yl)-[1,1'-biphenyl]-4-amine (Int-15) (500 mg, 2.01 mmol) in conc. HCl (1.5 mL) and $H_2O$ (10 mL) was cooled to 0° C. To the solution was added dropwise a solution of $NaNO_2$ (180 mg, 2.61 mmol) in $H_2O$ (2.5 mL) and the mixture was stirred at 0° C. for 30 min. The reaction mixture was neutralized (pH 6) with a sat aq $Na_2CO_3$ (10 mL) solution. The neutralized solution was added dropwise to a reaction flask containing a solution of CuCN (271 mg, 3.01 mmol) and KCN (183 mg, 3.012 mmol) in $H_2O$ (25 mL) at RT. The reaction mixture was stirred at 60° C. for 1 h and monitored by TLC. TLC mobile phase: 20% EtOAc in pet ether, RF: 0.39, TLC detection: UV. The reaction mixture was cooled to RT and filtered through a celite pad. The filtrate was diluted with $H_2O$ (20 mL), extracted with EtOAc (2×20 mL) and the combined organic layer was dried over anhydrous $Na_2SO_4$ and concentrated under reduced pressure to afford crude product (345 mg). The crude product (345 mg) was mixed with a second crude batch (325 mg) and purified by normal phase flash column chromatography using a 48 g column (silica) and a gradient of 0-10% EtOAc in pet ether as an eluent to afford 3-(1-methyl-1H-pyrazol-3-yl)-[1,1'-biphenyl]-4-carbonitrile as a brown solid (180 mg, 17%). (LC/MS; m/z 260.2 [M+H]$^+$).

Step 2: A solution of 3-(1-methyl-1H-pyrazol-3-yl)-[1,1'-biphenyl]-4-carbonitrile (160 mg, 617 mmol) in THF (5 mL) was treated with LAH (2 M in THF) (0.62 mL) at 0°. The reaction was stirred at RT for 4 h and monitored by TLC. TLC mobile phase: 10% MeOH in DCM, RF: 0.12, TLC detection: UV. The reaction mixture was cooled to 0° C., quenched with $H_2O$ (5 mL) and stirred for 30 min at 0° C. The mixture was filtered through a celite pad and the filtrate was extracted with EtOAc (2×20 mL). The combined organic layer was dried over anhydrous $Na_2SO_4$ and concentrated under reduced pressure to afford (3-(1-methyl-1H-pyrazol-3-yl)-[1,1'-biphenyl]-4-yl)methanamine as a brown solid (130 mg). (LC/MS; m/z 264.2 [M+H]$^+$). The product was used as such without further purification.

Step 3: To a stirred solution of (3-(1-methyl-1H-pyrazol-3-yl)-[1,1'-biphenyl]-4-yl)methanamine (130 mg, 0.494 mmol) and $NaHCO_3$ (124 mg, 1.482 mmol) in 1,4-dioxane (5 mL) and $H_2O$ (1 mL) was added acryloyl chloride (54 mg, 0.593 mmol) at 0° C. The reaction mixture was stirred for 1 h at 0° C. and monitored by TLC. TLC mobile phase: 10% MeOH in DCM, RF: 0.47, TLC detection: UV. The reaction mixture was diluted with $H_2O$ (10 mL) and extracted with EtOAc (2×10 mL). The combined organic layer was dried over anhydrous $Na_2SO_4$ and concentrated under reduced pressure to afford crude product (130 mg) which was purified by preparative HPLC method H1. The collected fractions were lyophilised to afford N-((3-(1-methyl-1H-pyrazol-3-yl)-[1,1'-biphenyl]-4-yl)methyl)acrylamide (Cpd. No. 135) as a pale yellow gum (35 mg, 22%). (LC/MS; m/z 318.3 [M+H]$^+$).

Step 4: This step was executed in a manner similar (use of appropriate reagents and purification methods known to the person skilled in the art) step 1 towards Cpd. No. 135. Starting material (Int-14) (500 mg, 1.53 mmol) yielded crude product (570 mg, LC/MS 52%) which was purified by normal phase flash column chromatography using a 48 g column (silica) and a gradient of 0-3% MeOH in DCM as an eluent to afford 3-(1-(pyridin-3-ylmethyl)-1H-pyrazol-3-yl)-[1,1'-biphenyl]-4-carbonitrile as a sticky solid (407 mg, 79%). (LC/MS; m/z 337.1 [M+H]$^+$).

Step 5: A mixture of 3-(1-(pyridin-3-ylmethyl)-1H-pyrazol-3-yl)-[1,1'-biphenyl]-4-carbonitrile (570 mg, 1.69 mmol) and Raney Ni (100 mg) in EtOH (15 mL) was stirred at 100° C. for 4 h under $H_2$ (500 psi) in a steel bomb. The reaction was monitored by TLC. TLC mobile phase: 10% MeOH in DCM, RF: 0.2, TLC detection: UV. The reaction mixture was filtered through a celite pad and washed with EtOAc (50 mL). The filtrate was concentrated under reduced pressure to afford crude product (580 mg, LC/MS 19%) which was purified by normal phase flash column chromatography using a 12 g column (silica) and a gradient of 0-10% MeOH in DCM as an eluent to afford (3-(1-(pyridin-3-ylmethyl)-1H-pyrazol-3-yl)-[1,1'-biphenyl]-4-yl)methanamine as a light brown gum (65 mg, 19%). (LC/MS; m/z 341.3 [M+H]$^+$).

Step 6: This step was executed in a manner similar (use of appropriate reagents and purification methods known to the person skilled in the art) step 3 towards Cpd. No. 135. Starting material (100 mg, 0.29 mmol) yielded crude product (100 mg, LC/MS 41%) which was purified by preparative HPLC method H2. The collected fractions were lyophilised to afford N-((3-(1-(pyridin-3-ylmethyl)-1H-pyrazol-3-yl)-[1,1'-biphenyl]-4-yl)methyl)acrylamide (Cpd. No. 136) as a pale yellow solid (2 mg, 2%). (LC/MS; m/z 395.1 [M+H]$^+$).

The following compounds were prepared in a manner similar (use of appropriate reagents and purification methods known to the person skilled in the art) to Cpd. No. 135: Cpd. No. 137 and Cpd. No. 138 (both prepared from Int-16).

Compound Cpd. No. 139 (prepared from Int-16) was prepared in a manner similar (use of appropriate reagents and purification methods known to the person skilled in the art) to Cpd. No. 136.

Example 56: Synthesis of N-((3-(1-methyl-1H-pyrazol-3-yl)-4'-(trifluoromethyl)-[1,1'-biphenyl]-4-yl)methyl)acrylamide (Cpd. No. 140)

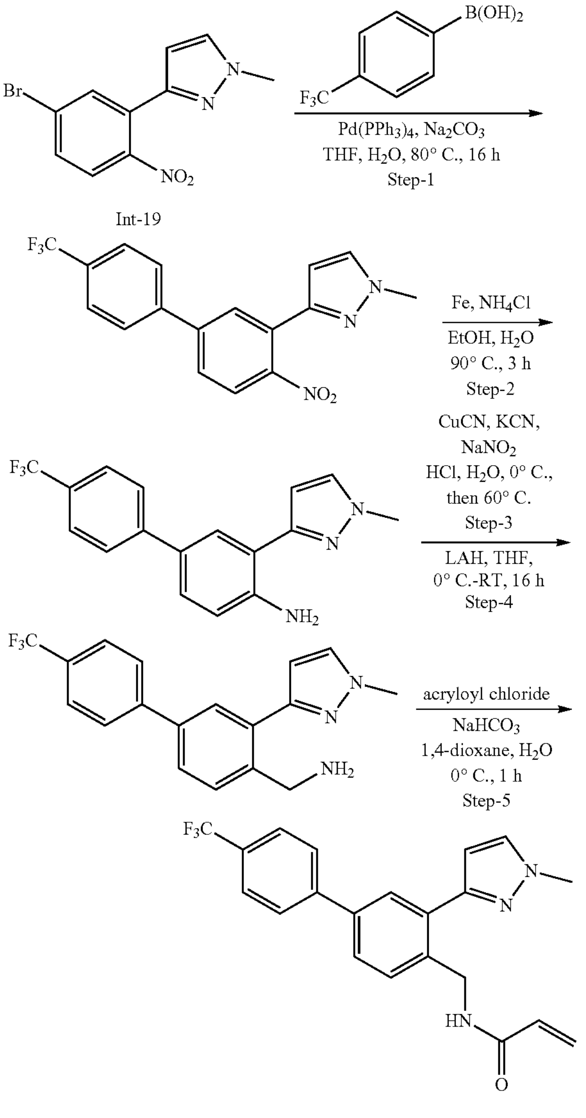

Cpd. No. 140

Step 1: This step was executed in a manner similar (use of appropriate reagents and purification methods known to the person skilled in the art) to step 1 towards Cpd. No. 086. Starting material (Int-19) (1.02 g, 5.4 mmol) yielded crude product which was purified by normal phase flash column chromatography using a 24 g column (silica) and a gradient of 0-40% EtOAc in pet ether as an eluent to afford 1-methyl-3-(4-nitro-4'-(trifluoromethyl)-[1,1'-biphenyl]-3-yl)-1H-pyrazole as an off-white solid (900 mg, 73%). (LC/MS; m/z 348.4 $[M+H]^+$).

Step 2: This step was executed in a manner similar (use of appropriate reagents and purification methods known to the person skilled in the art) to step 2 towards Cpd. No. 086. Starting material (800 mg, 2.3 mmol) yielded crude product 3-(1-methyl-1H-pyrazol-3-yl)-4'-(trifluoromethyl)-[1,1'-biphenyl]-4-amine as a brown solid (580 mg, 79%; LC/MS 98%). (LC/MS; m/z 318.1 $[M+H]^+$).

Steps 3-5: These steps were executed in a manner similar (use of appropriate reagents and purification methods known to the person skilled in the art) to Cpd. No. 135. Starting material (600 mg, 1.89 mmol) yielded crude product (300 mg, LC/MS 12%) which was purified by normal phase flash column chromatography using a 24 g column (silica) and a gradient of 0-1% MeOH in DCM as an eluent to afford product (90 mg, LC/MS 29%) which was further purified by preparative HPLC method H2. The collected fractions were lyophilised to afford N-((3-(1-methyl-1H-pyrazol-3-yl)-4'-(trifluoromethyl)-[1,1'-biphenyl]-4-yl)methyl)acrylamide (Cpd. No. 140) as an off-white solid (8.3 mg, 9%). (LC/MS; m/z 386.2 $[M+H]^+$).

The following compounds were prepared in a manner similar (use of appropriate reagents and purification methods known to the person skilled in the art) to Cpd. No. 140: Cpd. No. 141, Cpd. No. 142, Cpd. No. 143, Cpd. No. 144, Cpd. No. 145, Cpd. No. 146, Cpd. No. 147, Cpd. No. 148.

The following compounds were prepared in a manner similar (use of appropriate reagents and purification methods known to the person skilled in the art) to Cpd. No. 140: Cpd. No. 149 (prepared from Int-23) and Cpd. No. 150 (prepared from Int-24).

Example 57: Synthesis of N-((4'-fluoro-3-(1-(2-hydroxyethyl)-1H-pyrazol-3-yl)-[1,1'-biphenyl]-4-yl)methyl)acrylamide (Cpd. No. 151)

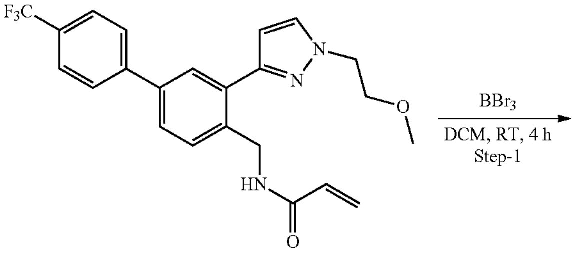

Cpd. No. 149

-continued

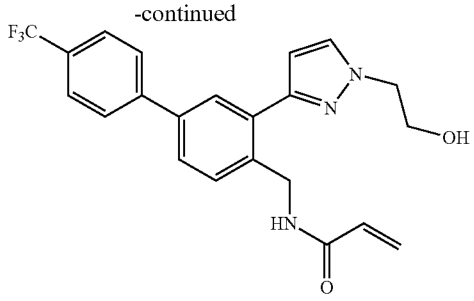

Cpd. No. 151

Step 1: A solution of Cpd. No. 149 (600 mg, 1.58 mmol, LC/MS 85%) in DCM (10.0 mL) was treated with $BBr_3$ (1 M in DCM) (6.49 mL, 6.49 mmol) at 0° C. The reaction mixture was stirred at RT for 4 h and monitored by TLC. TLC mobile phase: 50% EtOAc in pet ether, RF: 0.47, TLC detection: UV. The reaction mixture was poured into ice $H_2O$ (100 mL) and extracted with DCM (2×80 mL). The organic layer was washed with brine (50 mL), dried over anhydrous $Na_2SO_4$ and concentrated under reduced pressure to afford crude product (570 mg, LC/MS 56%) which was purified by preparative HPLC method $H_2$. The collected fractions were lyophilised to afford N-((4'-fluoro-3-(1-(2-hydroxyethyl)-1H-pyrazol-3-yl)-[1,1'-biphenyl]-4-yl)methyl)acrylamide (Cpd. No. 151) as an off-white solid (125 mg, 22%). (LC/MS; m/z 366.3 $[M+H]^+$).

Synthesis of 3-chloro-4'-fluoro-[1,1'-biphenyl]-4-carbonitrile (Int-25), 4'-fluoro-3-(1H-pyrazol-3-yl)-[1,1'-biphenyl]-4-carbonitrile (Int-26), 4'-fluoro-3-(1H-pyrazol-3-yl)-[1,1'-biphenyl]-4-carbonitrile hydrochloride (Int-26.HCl), and 4-chloro-2-(1-(tetrahydro-2H-pyran-2-yl)-1H-pyrazol-5-yl)benzonitrile (Int-27)

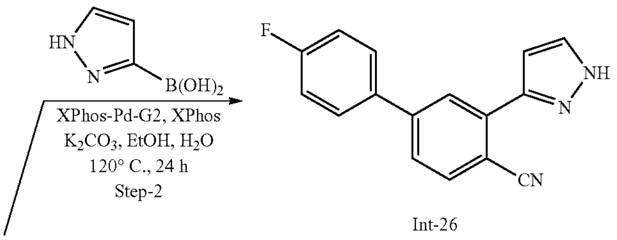

Int-26

-continued

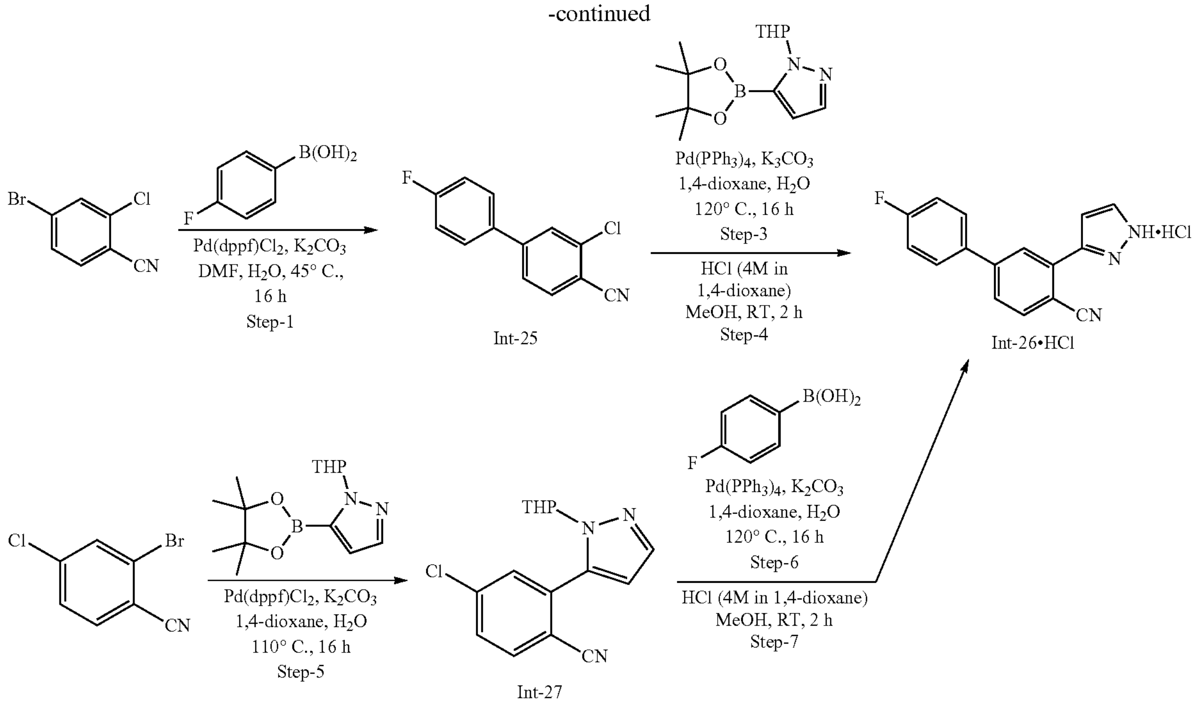

Step 1: A mixture of 4-bromo-2-chlorobenzonitrile (5.0 g, 23.3 mmol), (4-fluorophenyl)boronic acid (3.36 g, 23.3 mmol) and $K_2CO_3$ (3.85 g, 27.96 mmol) in DMF (50 mL) and $H_2O$ (5 mL) was degassed with argon for 10 min. To the mixture was added Pd(dppf)$Cl_2$·DCM (76 mg, 0.09 mmol). The reaction mixture was stirred at 45° C. for 16 h and monitored by TLC. TLC mobile phase: 10% EtOAc in pet ether, RF: 0.2, TLC detection: UV. The reaction mixture was filtered through a celite pad and washed with EtOAc (100 mL). The filtrate was diluted with $H_2O$ (50 mL) and the aqueous layer was extracted with EtOAc (200 mL). The combined organic layer was washed with brine (50 mL), dried over anhydrous $Na_2SO_4$ and concentrated under reduced pressure to afford the crude product (5.0 g) which was purified by normal phase flash column chromatography using a 80 g column (silica) and a gradient of 0-5% EtOAc in pet ether as an eluent to afford 3-chloro-4'-fluoro-[1,1'-biphenyl]-4-carbonitrile (Int-25) as pale brown solid (3.2 g, 60%). $^1$H NMR (400 MHz, $CDCl_3$) δ ppm: 7.72-7.74 (d, 1H), 7.68-7.69 (d, 1H), 7.52-7.57 (m, 3H), 7.16-7.26 (m, 2H).

Step 2: A degassed mixture of Int-25 (1 g, 4.3 mmol) in EtOH (10 mL) and $H_2O$ (2 mL) was treated with $K_2CO_3$ (2.96 mg, 21.5 mmol), XPhos (307 mg, 0.645 mmol), XPhos-Pd-G2 (507 mg, 0.645 mmol) and (1H-pyrazol-3-yl) boronic acid (1.44 mg, 12.9 mmol) at RT. The reaction mixture was heated at 120° C. for 24 h (sealed tube) and monitored by TLC. TLC mobile phase: 50% EtOAc in pet ether, RF: 0.5, TLC detection: UV. The cooled reaction mixture was filtered through a celite pad and washed with EtOAc (100 mL). The filtrate was concentrated under reduced pressure to afford crude product (2.0 g) which was purified by normal phase flash column chromatography using silica gel (100-200 mesh) and a gradient of 0-30% EtOAc in pet ether as an eluent to afford 4'-fluoro-3-(1H-pyrazol-3-yl)-[1,1'-biphenyl]-4-carbonitrile (Int-26) as an off-white solid (900 mg, 79%). (LC/MS; m/z 264.0 $[M+H]^+$).

Step 3: A mixture of Int-25) (1.0 g, 4.3 mmol), 1-(tetrahydro-2H-pyran-2-yl)-5-(4,4,5,5-tetramethyl-1,3,2-dioxaborolan-2-yl)-1H-pyrazole (1.4 g, 5.16 mmol) and $K_2CO_3$ (1.2 g, 8.6 mmol) in 1,4-dioxane (15 mL) and $H_2O$ (1.5 mL) was degassed with argon for 10 min. To the mixture was added $Pd(PPh_3)_4$ (0.1 g, 0.07 mmol). The reaction mixture was stirred at 120° C. for 16 h (sealed tube) and monitored by TLC. TLC mobile phase: 20% EtOAc in pet ether, RF: 0.3, TLC detection: UV. The reaction mixture was cooled and filtered through a celite pad and washed with EtOAc (40 mL). The filtrate was diluted with $H_2O$ (30 mL) and the aqueous layer was extracted with EtOAc (40 mL). The combined organic layer was washed with brine (40 mL), dried over anhydrous $Na_2SO_4$ and concentrated under reduced pressure to afford the crude product (1.4 g, LC/MS 43%) which was purified by normal phase flash column chromatography using a 12 g column (silica) and a gradient of 0-10% EtOAc in pet ether as an eluent to afford 4'-fluoro-3-(1-(tetrahydro-2H-pyran-2-yl)-1H-pyrazol-5-yl)-[1,1'-biphenyl]-4-carbonitrile as a light brown solid (900 mg, 60%). (LC/MS; m/z 348.3 $[M+H]^+$).

Step 4: A solution of 4'-fluoro-3-(1-(tetrahydro-2H-pyran-2-yl)-1H-pyrazol-5-yl)-[1,1'-biphenyl]-4-carbonitrile (950 mg, 2.74 mmol) in MeOH (10 mL) was treated with HCl (4M in 1,4-dioxane; 5 mL) at RT. The reaction mixture was stirred at the RT for 2 h and monitored by TLC. TLC mobile phase: 30% EtOAc in pet ether, RF: 0.2, TLC detection: UV. The reaction mixture was concentrated under reduced pressure to afford 4'-fluoro-3-(1H-pyrazol-3-yl)-[1,1'-biphenyl]-4-carbonitrile hydrochloride (Int-26.HCl) (600 mg, LC/MS 82%). (LC/MS; m/z 264.2 $[M+H]^+$). The product was used as such without further purification.

Step 5: This step was executed in a manner similar (use of appropriate reagents and purification methods known to the person skilled in the art) to step 3 to Int-26.HCl. Reacting 2-bromo-4-chlorobenzonitrile (20 g, 92.6 mmol) with 1-(tetrahydro-2H-pyran-2-yl)-5-(4,4,5,5-tetramethyl-1,3,2-dioxa-borolan-2-yl)-1H-pyrazole (25.74 g, 92.6 mmol) in the presence of Pd(dppf)$Cl_2$ (6.76 g, 9.26 mmol) yielded crude product (30 g, LC/MS 87%) which was purified by normal phase flash column chromatography using a 120 g column (silica) and a gradient of 0-15% EtOAc in pet ether as an eluent to afford 4-chloro-2-(1-(tetrahydro-2H-pyran-2-yl)-1H-pyrazol-5-yl)benzonitrile (Int-27) as a white solid (18 g, 68%). (LC/MS; m/z 288.1 $[M+H]^+$).

Steps 6-7: These steps were executed in a manner similar (use of appropriate reagents and purification methods known to the person skilled in the art) to step 3 and 4 to Int-26.HCl. From Int-27 (1.92 g, 6.7 mmol) was obtained 4'-fluoro-3-(1H-pyrazol-3-yl)-[1,1'-biphenyl]-4-carbonitrile hydrochloride (Int-26.HCl) (1.6 g, LC/MS 95%). (LC/MS; m/z 264.1 $[M+H]^+$). The product was used as such without further purification.

Intermediates Int-28 and Int-29 (both prepared from 3-bromo-5-chlorobenzonitrile) were prepared in a manner similar (use of appropriate reagents and purification methods known to the person skilled in the art) to respectively Int-25 and Int-26.HCl:

| Cpd. No. | Structure | $[M + H]^+$ (m/z) |
|---|---|---|
| Int-28 | 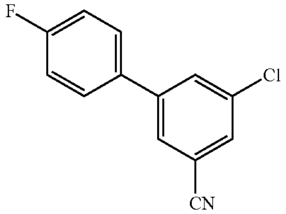 [SMILES: N#Cc1cc(Cl)cc(-c2ccc(F)cc2)c1] | 232.1 |
| Int-29 | 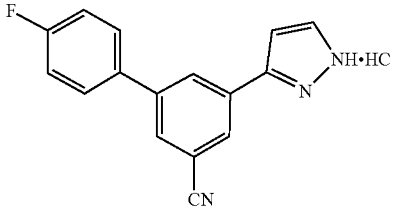 | 264.2 |

Synthesis of 3-(1H-pyrazol-3-yl)-4'-(trifluoromethyl)-[1,1'-biphenyl]-4-carbonitrile hydrochloride (Int-30)

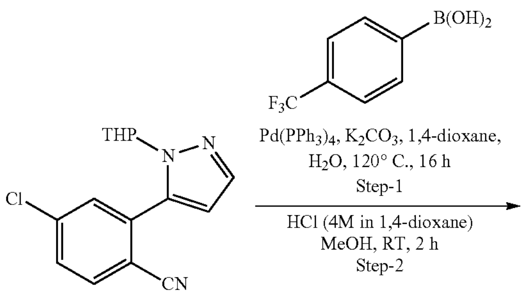

Int-27

-continued

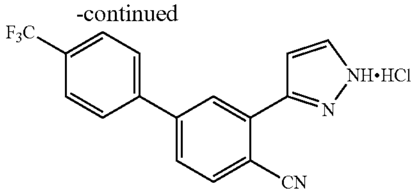

Int-30

Steps 1-2: These steps were executed in a manner similar (use of appropriate reagents and purification methods known to the person skilled in the art) to step 3 and 4 to Int-26.HCl. From Int-27 (3.0 g, 10.5 mmol) was obtained 3-(1H-pyrazol-3-yl)-4'-(trifluoromethyl)-[1,1'-biphenyl]-4-carbonitrile hydrochloride (Int-30) (1.8 g, LC/MS 95%). (LC/MS; m/z 314.1 $[M+H]^+$). The product was used as such without further purification.

Synthesis of 3-(1H-pyrazol-4-yl)-4'-(trifluoromethyl)-[1,1'-biphenyl]-4-carbonitrile (Int-31)

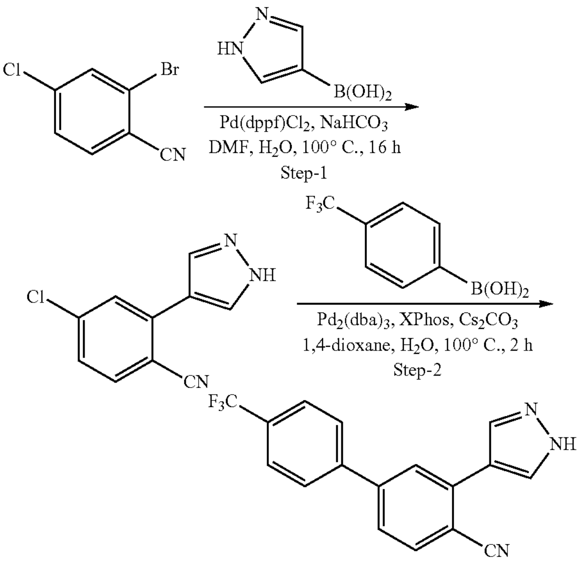

Int-31

Step 1: A solution of 2-bromo-4-chlorobenzonitrile (5.0 g, 23.1 mmol) in DMF (50 mL) and $H_2O$ (5 mL) was treated with (1H-pyrazol-4-yl)boronic acid (3.10 g, 27.7 mmol) and $NaHCO_3$ (4.85 g, 57.7 mmol). The mixture was degassed with argon for 20 min followed by addition of Pd(dppf) $Cl_2$·DCM (942 mg, 1.15 mmol). The reaction mixture was stirred at 100° C. for 16 h (sealed tube) and monitored by TLC. TLC mobile phase: 50% EtOAc in pet ether, RF: 0.36, TLC detection: UV. The reaction mixture was diluted with $H_2O$ (200 mL) and extracted with EtOAc (2×60 mL). The organic layer was washed with $H_2O$ (80 mL), dried over anhydrous $Na_2SO_4$ and concentrated under reduced pressure to afford crude product (5.0 g, LC/MS 58%) which was purified by normal phase flash column chromatography using a 80 g column (silica) and a gradient of 0-25% EtOAc in pet ether as an eluent to afford 4-chloro-2-(1H-pyrazol-4-yl)benzonitrile as a pale brown solid (2.5 g, 47%). (LC/MS; m/z 204.0 $[M+H]^+$).

Step 2: A solution of 4-chloro-2-(1H-pyrazol-4-yl)benzonitrile (2.4 g, 11.8 mmol) in 1,4-dioxane (12 mL) and $H_2O$ (6 mL) was treated with (4-(trifluoromethyl)phenyl)boronic acid (2.69 g, 14.16 mmol) and $Cs_2CO_3$ (7.74 g, 23.6 mmol). The mixture was degassed with argon for 20 min followed by addition of $Pd_2(dba)_3$ (540 mg, 0.59 mmol) and XPhos (562 mg, 1.18 mmol). The reaction mixture was stirred at 100° C. for 2 h under microwave radiation (sealed microwave vial) and monitored by TLC. TLC mobile phase: 50% EtOAc in pet ether, RF: 0.43, TLC detection: UV. The reaction mixture was diluted with $H_2O$ (100 mL) and extracted with EtOAc (2×50 mL). The organic layer was washed with $H_2O$ (50 mL), dried over anhydrous $Na_2SO_4$ and concentrated under reduced pressure to afford crude product (4.0 g, LC/MS 59%) which was purified by normal phase flash column chromatography using a 80 g column (silica) and a gradient of 0-60% EtOAc in pet ether as an eluent to afford 3-(1H-pyrazol-4-yl)-4'-(trifluoromethyl)-[1,1'-biphenyl]-4-carbonitrile (Int-31) as a pale yellow solid (1.2 g, 32%). (LC/MS; m/z 314.1 [M+H]$^+$).

Synthesis of 4-chloro-2-(1-methyl-1H-pyrazol-3-yl)benzonitrile (Int-32) and 4-chloro-2-(1-cyclopropyl-1H-pyrazol-3-yl)benzonitrile (Int-33)

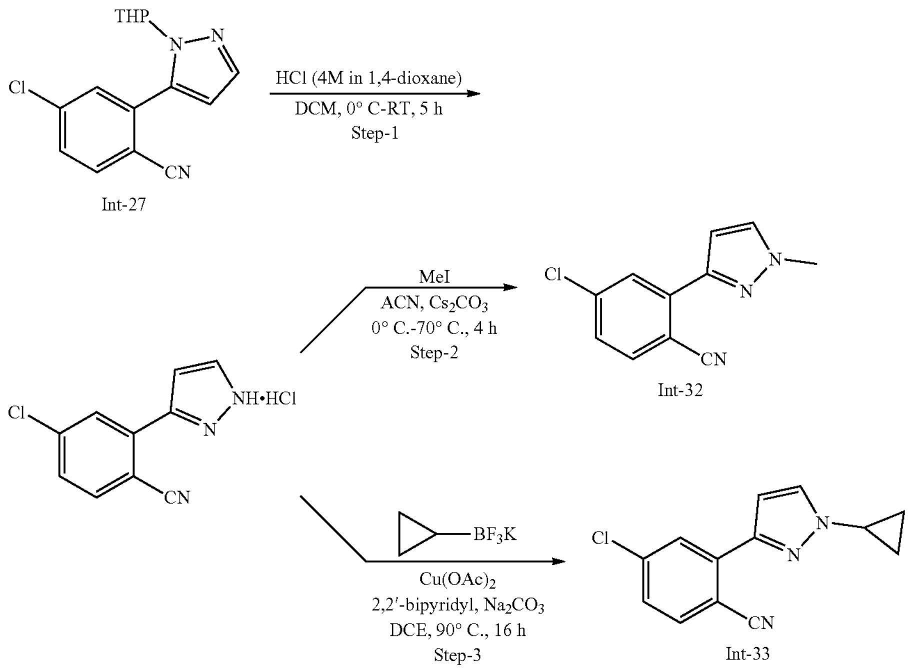

Int-27
Int-32
Int-33

Step 1: This step was executed in a manner similar (use of appropriate reagents and purification methods known to the person skilled in the art) to step 4 to Int-26.HCl. From Int-27 (9.0 g, 31.4 mmol) was obtained by filtration 4-chloro-2-(1H-pyrazol-3-yl)benzonitrile hydrochloride as an off-white solid (6.5 g, 86%). (LC/MS; m/z 204.1 [M+H]$^+$).

Step 2: A solution of 4-chloro-2-(1H-pyrazol-3-yl)benzonitrile hydrochloride (6.6 g, 27.6 mmol) in ACN (200 mL) was treated with $Cs_2CO_3$ (32.4 g, 99.4 mmol) and stirred for 30 min at 0° C. To the mixture was added MeI (9.0 g, 63.4 mmol). The reaction mixture was stirred at 70° C. for 4 h and monitored by TLC. TLC mobile phase: 20% EtOAc in pet ether, RF: 0.3 & 0.45, TLC detection: UV. The reaction was cooled to RT, diluted with $H_2O$ (100 mL) and extracted with EtOAc (300 mL). The organic layer was dried over anhydrous $Na_2SO_4$ and concentrated under reduced pressure to afford crude product (4.8 g, 27:73 mixture of N-Me regioisomers) which was purified by preparative SFC method K1 to afford 4-chloro-2-(1-methyl-1H-pyrazol-3-yl)benzonitrile (Int-32) as pale yellow solid (2.2 g, 37%). (LC/MS; m/z 218.1 [M+H]$^+$).

Step 3: This step was executed in a manner similar (use of appropriate reagents and purification methods known to the person skilled in the art) to Int-47. From 4-chloro-2-(1H-pyrazol-3-yl)benzonitrile hydrochloride (1.30 g, 5.4 mmol) was obtained 4-chloro-2-(1-cyclopropyl-1H-pyrazol-3-yl)benzonitrile (Int-33) as an off-white solid (550 mg, 42%). (LC/MS; m/z 244.0 [M+H]$^+$).

The following intermediates were prepared in a manner similar (use of appropriate reagents and purification methods known to the person skilled in the art) to Int-32:

| Cpd. No. | Structure | [M + H]$^+$ (m/z) |
|---|---|---|
| Int-34 | 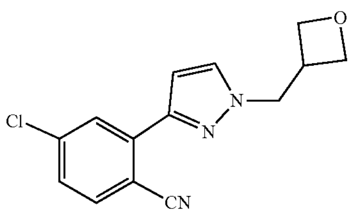 [SMILES: N#Cc1ccc(Cl)cc1-c1ccn(CC2COC2)n1] | 274.1 |

-continued

| Cpd. No. | Structure | [M + H]+ (m/z) |
|---|---|---|
| Int-35 | 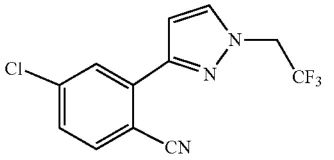 [SMILES: N#Cc1ccc(Cl)cc1-c1ccn(CC(F)(F)F)n1] | 286.1 |

Example 58: Synthesis of N-((4'-fluoro-3-(1-isobutyl-1H-pyrazol-3-yl)-[1,1'-biphenyl]-4-yl)methyacrylamide (Cpd. No. 152)

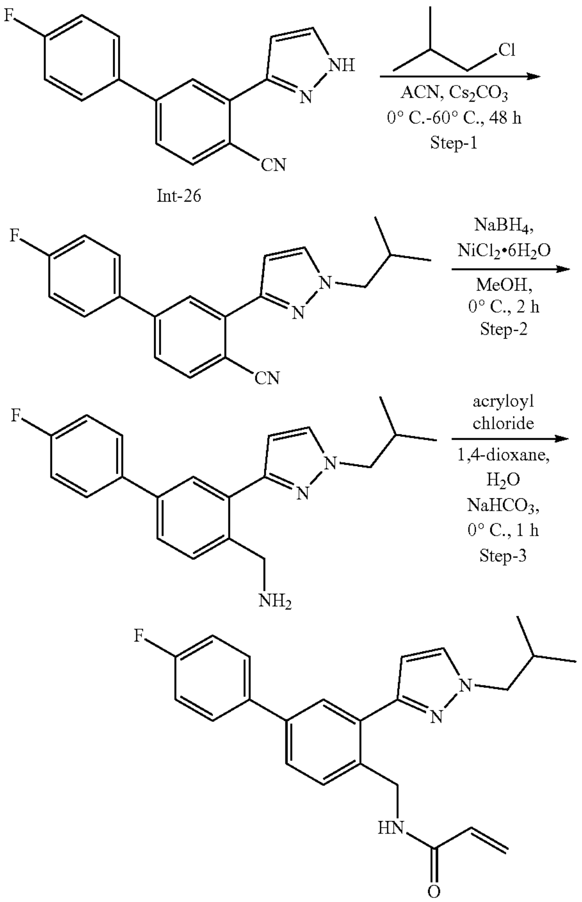

Int-26

Cpd. No. 152

Step 1: A solution of Int-26 (400 mg, 1.52 mmol) and $Cs_2CO_3$ (2.47 g, 7.60 mmol) in ACN (10 mL) was stirred for 30 min at 0° C. To the mixture was added 1-chloro-2-methylpropane (210 mg, 2.28 mmol). The reaction mixture was stirred at 60° C. for 48 h and monitored by TLC. TLC mobile phase: 30% EtOAc in pet ether, RF: 0.76, TLC detection: UV. The cooled reaction mixture was diluted with $H_2O$ (10 mL) and extracted with EtOAc (50 mL). The organic layer was dried over anhydrous $Na_2SO_4$ and concentrated under reduced pressure to afford 4'-fluoro-3-(1-isobutyl-1H-pyrazol-3-yl)-[1,1'-biphenyl]-4-carbonitrile (300 mg). (LC/MS; m/z 320.2 $[M+H]^+$). The product was used as such without further purification.

Step 2: A solution of 4'-fluoro-3-(1-isobutyl-1H-pyrazol-3-yl)-[1,1'-biphenyl]-4-carbonitrile (200 mg, 0.63 mmol) and $NiCl_2 \cdot 6H_2O$ (132 mg, 0.55 mmol) in MeOH (10 mL) was treated with $NaBH_4$ (250 mg, 6.6 mmol) at 0° C. The reaction mixture was stirred at 0° C. for 2 h and monitored by TLC. TLC mobile phase: 10% MeOH in DCM, RF: 0.36, TLC detection: UV. The reaction mixture was diluted with EtOAc (20 mL), filtered through a celite pad and washed with EtOAc (50 mL). The filtrate was concentrated under reduced pressure to afford (4'-fluoro-3-(1-isobutyl-1H-pyrazol-3-yl)-[1,1'-biphenyl]-4-yl)methanamine (300 mg, LC/MS 62%). (LC/MS; m/z 324.2 $[M+H]^+$). The product was used as such without further purification.

Step 3: A solution of (4'-fluoro-3-(1-isobutyl-1H-pyrazol-3-yl)-[1,1'-biphenyl]-4-yl)methanamine (300 mg, 0.93 mmol) and $NaHCO_3$ (234 mg, 2.78 mmol) in 1,4-dioxane (5 mL) and $H_2O$ (3 mL) was treated at 0° C. with acryloyl chloride (83 mg, 0.928 mmol) (dissolved in 1,4-dioxane (5 mL)). The reaction mixture was stirred at 0° C. for 1 h and monitored by TLC. TLC mobile phase: 10% MeOH in DCM, RF: 0.72, TLC detection: UV. The reaction mixture was diluted with EtOAc (30 mL) and $H_2O$ (10 mL). The organic layer was dried over anhydrous $Na_2SO_4$ and concentrated under reduced pressure to afford crude product (450 mg, LC/MS 45%) which was purified by preparative HPLC method H2. The collected fractions were lyophilised to afford N-((4'-fluoro-3-(1-isobutyl-1H-pyrazol-3-yl)-[1,1'-biphenyl]-4-yl)methyl)acrylamide (Cpd. No. 152) as a sticky gum (31 mg, 9%). (LC/MS; m/z 378.3 $[M+H]^+$).

The following compounds were prepared in a manner similar (use of appropriate reagents and purification methods known to the person skilled in the art) to Cpd. No. 152: Cpd. No. 153 (employing NaH in DMF), Cpd. No. 154, Cpd. No. 155, and Cpd. No. 156 (prepared from Int-30).

Example 59: Synthesis of N-((4'-chloro-3-(1-methyl-1H-pyrazol-3-yl)-[1,1'-biphenyl]-4-yl)methyl)acrylamide (Cpd. No. 157)

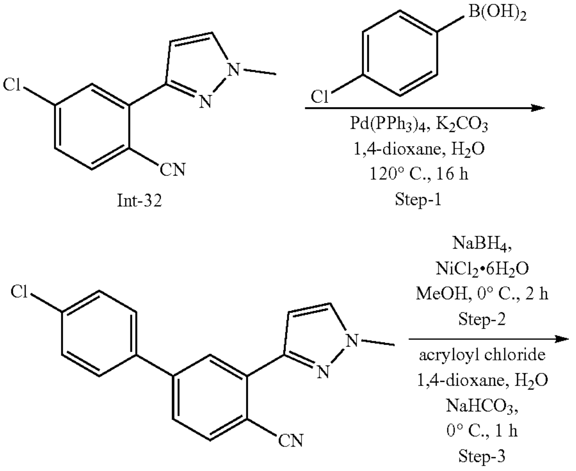

Int-32

-continued

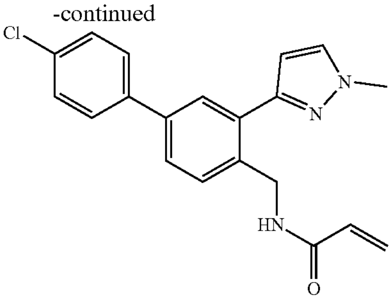

Cpd. No. 157

-continued

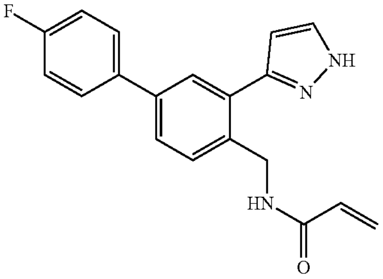

Cpd. No. 161

Step 1: This step was executed in a manner similar (use of appropriate reagents and purification methods known to the person skilled in the art) to step 6 to Int-26.HCl. Reacting Int-32 (600 mg, 2.76 mmol) with (4-chlorophenyl)boronic acid (516 mg, 3.31 mmol) afforded 4'-chloro-3-(1-methyl-1H-pyrazol-3-yl)-[1,1'-biphenyl]-4-carbonitrile as an off-white solid (450 mg, 56%). (LC/MS; m/z 294.0 [M+H]$^+$).

Steps 2-3: These steps were executed in a manner similar (use of appropriate reagents and purification methods known to the person skilled in the art) to step 2 and 3 towards Cpd. No. 152. From 4'-chloro-3-(1-methyl-1H-pyrazol-3-yl)-[1,1'-biphenyl]-4-carbonitrile (400 mg, 1.36 mmol) was obtained crude product (608 mg, LC/MS 43%) which was purified by preparative HPLC method H13. The collected fractions were lyophilised to afford N-((4'-chloro-3-(1-methyl-1H-pyrazol-3-yl)-[1,1'-biphenyl]-4-yl)methyl)acrylamide (Cpd. No. 157) as an off-white solid (121 mg, 25%). (LC/MS; m/z 352.2 [M+H]$^+$).

The following compounds were prepared in a manner similar (use of appropriate reagents and purification methods known to the person skilled in the art) to Cpd. No. 157: Cpd. No. 158 (prepared from Int-33), Cpd. No. 159 (prepared from Int-34 employing Pd(amphos)$Cl_2$ and $Na_2CO_3$ at step 1), and Cpd. No. 160 (prepared from Int-35).

Example 60: Synthesis of N-((4'-fluoro-3-(1H-pyrazol-3-yl)-[1,1'-biphenyl]-4-yl)methyl)acrylamide (Cpd. No. 161)

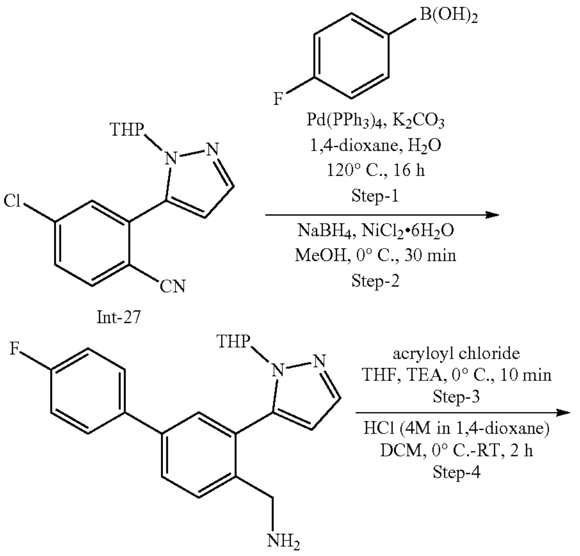

Step 1: This step was executed in a manner similar (use of appropriate reagents and purification methods known to the person skilled in the art) to step 6 to Int-26.HCl. From Int-27 (2.5 g, 8.7 mmol) was obtained 4'-fluoro-3-(1-(tetrahydro-2H-pyran-2-yl)-1H-pyrazol-5-yl)-[1,1'-biphenyl]-4-carbonitrile as an off-white solid (2.6 g, 86%). (LC/MS; m/z 348.2 [M+H]$^+$).

Steps 2-3: These steps were executed in a manner similar (use of appropriate reagents and purification methods known to the person skilled in the art) to step 2 and 3 towards Cpd. No. 152. From 4'-fluoro-3-(1-(tetrahydro-2H-pyran-2-yl)-1H-pyrazol-5-yl)-[1,1'-biphenyl]-4-carbonitrile (500 mg, 1.44 mmol) was obtained N-((4'-fluoro-3-(1-(tetrahydro-2H-pyran-2-yl)-1H-pyrazol-5-yl)-[1,1'-biphenyl]-4-yl)methyl)acrylamide as a light brown solid (470 mg, 80%). (LC/MS; m/z 406.3 [M+H]$^+$).

Step 4: This step was executed in a manner similar (use of appropriate reagents and purification methods known to the person skilled in the art) to step 4 to Int-26.HCl. From N-((4'-fluoro-3-(1-(tetrahydro-2H-pyran-2-yl)-1H-pyrazol-5-yl)-[1,1'-biphenyl]-4-yl)methyl)-acrylamide (450 mg, 1.11 mmol) was obtained crude product (400 mg, LC/MS 16%) which was purified by normal phase flash column chromatography using silica gel (100-200 mesh) and a gradient of 0-5% MeOH in DCM as an eluent to afford product which was further purified by preparative HPLC method H2. The collected fractions were lyophilised to afford to afford N-((4'-fluoro-3-(1H-pyrazol-3-yl)-[1,1'-biphenyl]-4-yl)methyl)acrylamide (Cpd. No. 161) as a white solid (6 mg, 2%). (LC/MS; m/z 322.2 [M+H]$^+$).

Example 61: Synthesis of N-((4'-fluoro-3-(1-methyl-1H-pyrazol-4-yl)-[1,1'-biphenyl]-4-yl)methyl)acrylamide (Cpd. No. 162)

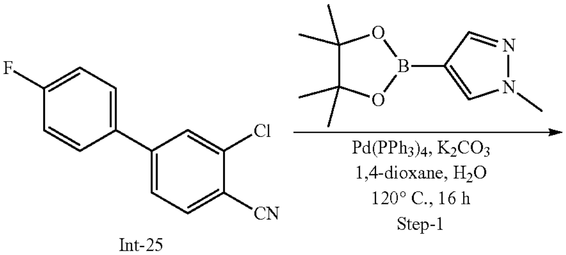

Int-25

-continued

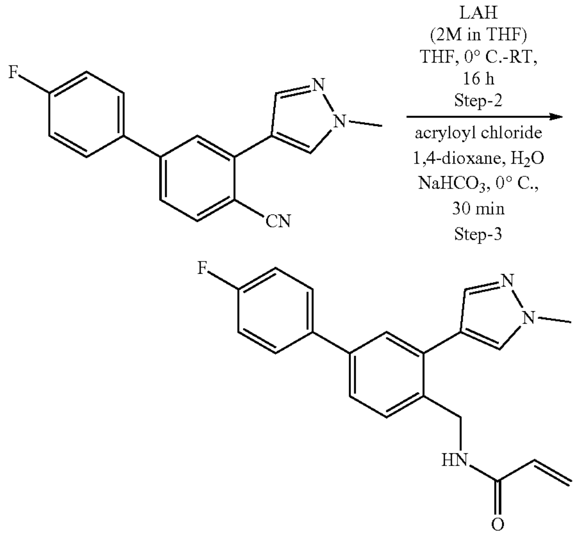

Cpd. No. 162

Step 1: This step was executed in a manner similar (use of appropriate reagents and purification methods known to the person skilled in the art) to step 3 to Int-26.HCl. Reacting Int-25 (750 mg, 3.25 mmol) with 1-methyl-4-(4,4,5,5-tetramethyl-1,3,2-dioxaborolan-2-yl)-1H-pyrazole (810 mg, 3.89 mmol) afforded 4'-fluoro-3-(1-methyl-1H-pyrazol-4-yl)-[1,1'-biphenyl]-4-carbonitrile as an off-white solid (600 mg, 67%). (LC/MS; m/z 278.1 $[M+H]^+$).

Steps 2-3: These steps were executed in a manner similar (use of appropriate reagents and purification methods known to the person skilled in the art) to step 2 and 3 towards Cpd. No. 152. From 4'-fluoro-3-(1-methyl-1H-pyrazol-4-yl)-[1,1'-biphenyl]-4-carbonitrile (600 mg, 2.17 mmol) was obtained crude product (700 mg, LC/MS 30%) which was purified by preparative HPLC method H3. The collected fractions were lyophilised to afford N-((4'-fluoro-3-(1-methyl-1H-pyrazol-4-yl)-[1,1'-biphenyl]-4-yl)methyl)acrylamide (Cpd. No. 162) as a white solid (89 mg, 12%). (LC/MS; m/z 336.2 $[M+H]^+$).

The following compounds were prepared in a manner similar (use of appropriate reagents and purification methods known to the person skilled in the art) to Cpd. No. 162: Cpd. No. 163 (employing $K_3PO_4$ in DMF and $H_2O$ in step 1) and Cpd. No. 164 (employing $NaBH_4$, $NiCl_2 \cdot 6H_2O$ in MeOH in step 2).

Example 62: Synthesis of N-((4'-fluoro-3-(pyridin-2-yl)-[1,1'-biphenyl]-4-yl)methyl)acrylamide (Cpd. No. 165)

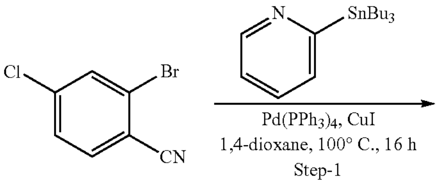

-continued

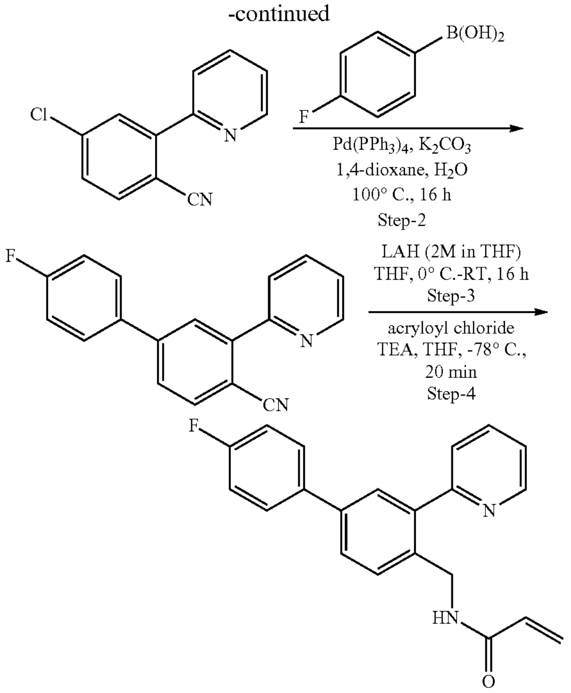

Cpd. No. 165

Step 1: A solution of 2-bromo-4-chlorobenzonitrile (3.0 g, 13.9 mmol), 2-(tributylstannyl)pyridine (5.64 g, 15.3 mmol), CuI (2.9 g, 15.3 mmol) in 1,4-dioxane (30 mL) was degassed with argon for 10 min. To the mixture was added $Pd(PPh_3)_4$ (1.6 g, 1.39 mmol). The reaction mixture was stirred at 100° C. for 16 h (sealed tube) and monitored by TLC. TLC mobile phase: 20% EtOAc in pet ether, RF: 0.62, TLC detection: UV. The reaction mixture was cooled, filtered through a celite pad and washed with EtOAc (100 mL). The filtrate was washed with $H_2O$ (2×100 mL), dried over anhydrous $Na_2SO_4$ and concentrated under reduced pressure to afford crude product (4 g, LC/MS 74%) which was purified by normal phase flash column chromatography using a 40 g column (silica) and a gradient of 0-6% EtOAc in pet ether as an eluent to afford 4-chloro-2-(pyridin-2-yl)benzonitrile (2.3 g, 77%) as a white solid. (LC/MS; m/z 215.1 $[M+H]^+$).

Step 2: This step was executed in a manner similar (use of appropriate reagents and purification methods known to the person skilled in the art) to step 6 to Int-26.HCl. From 4-chloro-2-(pyridin-2-yl)benzonitrile (1.7 g, 7.9 mmol) was obtained 4'-fluoro-3-(pyridin-2-yl)-[1,1'-biphenyl]-4-carbonitrile (1.1 g, 50%) as a white solid. (LC/MS; m/z 275.2 $[M+H]^+$).

Steps 3-4: These steps were executed in a manner similar (use of appropriate reagents and purification methods known to the person skilled in the art) to step 2 and 3 towards Cpd. No. 152. From 4'-fluoro-3-(pyridin-2-yl)-[1,1'-biphenyl]-4-carbonitrile (800 mg, 2.9 mmol) was obtained crude product (860 mg, LC/MS 51%) which was purified by preparative HPLC method H3. The collected fractions were lyophilised to afford N-((4'-fluoro-3-(pyridin-2-yl)-[1,1'-biphenyl]-4-yl)methyl)acrylamide (Cpd. No. 165) as an off-white solid (108 mg, 11%). (LC/MS; m/z 333.2 $[M+H]^+$).

Example 63: Synthesis of N-((3-(1-cyclopropyl-1H-pyrazol-3-yl)-4'-fluoro-[1,1'-biphenyl]-4-yl)methyl) acrylamide (Cpd. No. 166)

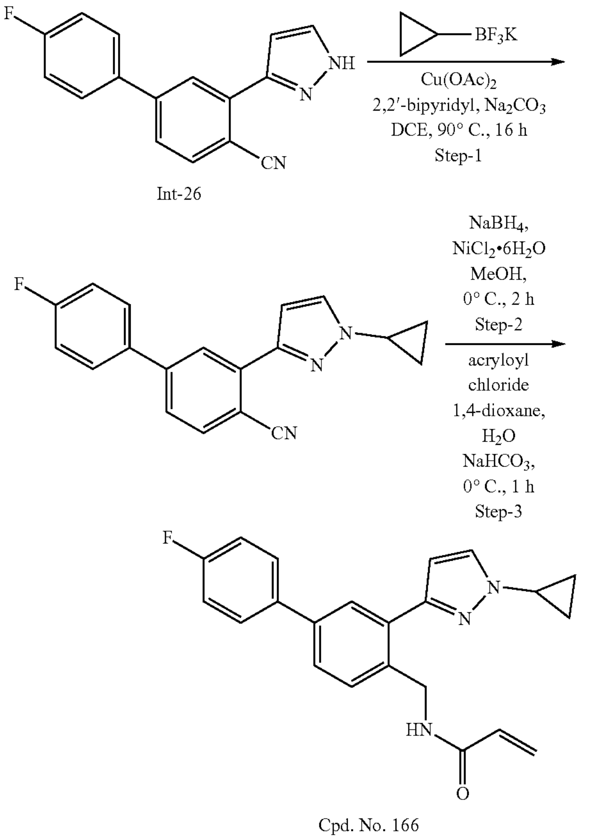

Step 1: This step was executed in a manner similar (use of appropriate reagents and purification methods known to the person skilled in the art) to Int-47. From Int-26 (130 mg, 0.49 mmol) was obtained 3-(1-cyclopropyl-1H-pyrazol-3-yl)-4'-fluoro-[1,1'-biphenyl]-4-carbonitrile as an off-white solid (120 mg, 80%). (LC/MS; m/z 304.0 $[M+H]^+$).

Steps 2-3: These steps were executed in a manner similar (use of appropriate reagents and purification methods known to the person skilled in the art) to step 2 and 3 towards Cpd. No. 152. From 3-(1-cyclopropyl-1H-pyrazol-3-yl)-4'-fluoro-[1,1'-biphenyl]-4-carbonitrile (100 mg, 0.33 mmol) was obtained crude product (130 mg, LC/MS 32%) which was purified by preparative HPLC method H5. The collected fractions were lyophilised to afford N-((3-(1-cyclopropyl-1H-pyrazol-3-yl)-4'-fluoro-[1,1'-biphenyl]-4-yl)methyl) acrylamide (Cpd. No. 166) as an off-white solid (28 mg, 23%). (LC/MS; m/z 362.4 $[M+H]^+$).

The following compounds were prepared in a manner similar (use of appropriate reagents and purification methods known to the person skilled in the art) to Cpd. No. 166: Cpd. No. 167 (prepared from Int-30), Cpd. No. 168 (prepared from Int-31), and Cpd. No. 169 (prepared from Int-29).

Examples 64-65: Synthesis of N-((3-(1-(difluoromethyl)-1H-pyrazol-3-yl)-4'-fluoro-[1,1'-biphenyl]-4-yl)methyl)acrylamide (Cpd. No. 170) and N-((3-(1-(difluoromethyl)-1H-pyrazol-5-yl)-4'-fluoro-[1,1'-biphenyl]-4-yl)methyl)acrylamide (Cpd. No. 171)

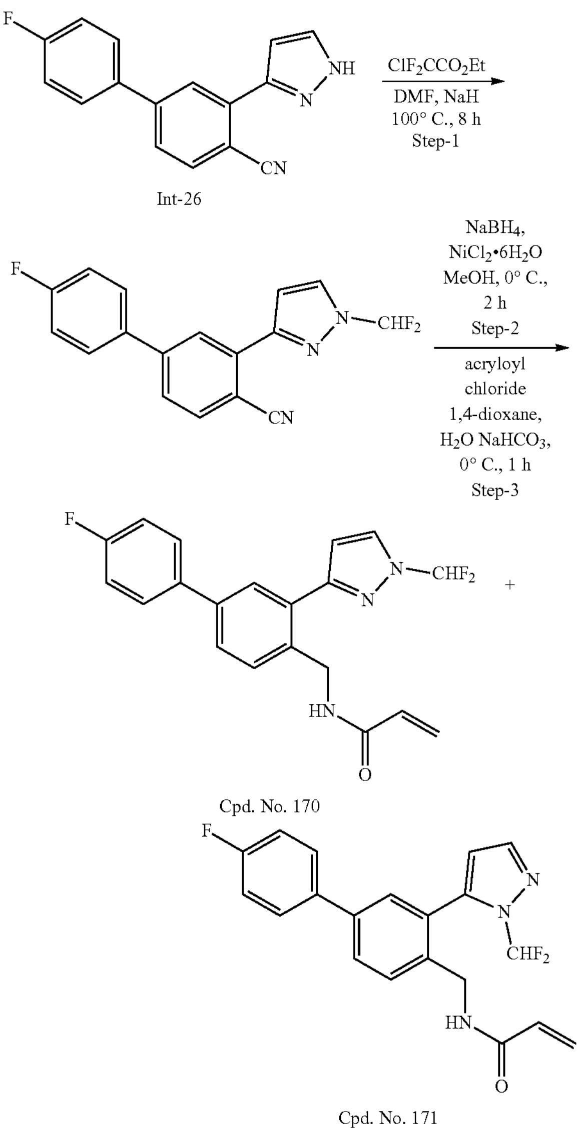

Step 1: This step was executed in a manner similar (use of appropriate reagents and purification methods known to the person skilled in the art) to Int-49. Treating Int-26 (1.5 g, 5.7 mmol) with NaH (60% in mineral oil) (0.55 g, 22.81 mmol) and ethyl 2-chloro-2,2-difluoroacetate (1.1 g, 6.84 mmol) afforded 3-(1-(difluoromethyl)-1H-pyrazol-3-yl)-4'-fluoro-[1,1'-biphenyl]-4-carbonitrile as an off-white solid (350 mg, LC/MS 25%) (mixture of N—$CHF_2$ regioisomers). (LC/MS; m/z 314.1 $[M+H]^+$). The product was used as such without further purification.

Steps 2-3: These steps were executed in a manner similar (use of appropriate reagents and purification methods known to the person skilled in the art) to step 2 and 3 towards Cpd. No. 152. From 3-(1-(difluoromethyl)-1H-pyrazol-3-yl)-4'-fluoro-[1,1'-biphenyl]-4-carbonitrile (300 mg, 0.96 mmol)

(mixture of regioisomers) was obtained crude product (400 mg, LC/MS 37%) which was purified by preparative HPLC method H2. The collected fractions were lyophilised to afford both regioisomers N-((3-(1-(difluoromethyl)-1H-pyrazol-3-yl)-4'-fluoro-[1,1'-biphenyl]-4-yl)methyl)acrylamide (Cpd. No. 170) (56 mg, 16%) and N-((3-(1-(difluoromethyl)-1H-pyrazol-5-yl)-4'-fluoro-[1,1'-biphenyl]-4-yl) methyl)acrylamide (Cpd. No. 171) (28 mg, 8%) as white solids. (LC/MS; m/z 372.2 $[M+H]^+$).

The following compounds were prepared in a manner similar (use of appropriate reagents and purification methods known to the person skilled in the art) to Cpd. No. 170: Cpd. No. 172 (prepared from Int-30) and Cpd. No. 173 (prepared from Int-31).

Example 66: Synthesis of N-((5-(1-(difluoromethyl)-1H-pyrazol-3-yl)-4'-fluoro-[1,1'-biphenyl]-3-yl)methyl)acrylamide (Cpd. No. 174)

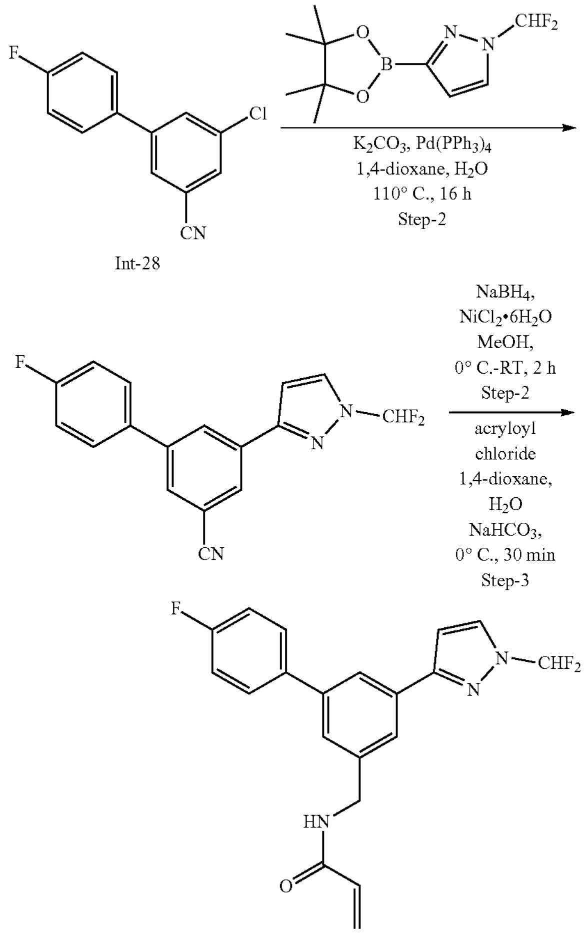

Int-28

Cpd. No. 174

Step 1: This step was executed in a manner similar (use of appropriate reagents and purification methods known to the person skilled in the art) to step 2 towards Cpd. No. 209. From Int-28 (600 mg, 2.59 mmol) was obtained crude product (700 mg, LC/MS 31%) which was purified by normal phase flash column chromatography using a 24 g column (silica) and a gradient of 0-18% EtOAc in pet ether as an eluent to afford 5-(1-(difluoromethyl)-1H-pyrazol-3-yl)-4'-fluoro-[1,1'-biphenyl]-3-carbonitrile (350 mg, 41%, LC/MS 96%). (LC/MS; m/z 314.2 $[M+H]^+$).

Steps 2-3: These steps were executed in a manner similar (use of appropriate reagents and purification methods known to the person skilled in the art) to step 2 and 3 towards Cpd. No. 152. From 5-(1-(difluoromethyl)-1H-pyrazol-3-yl)-4'-fluoro-[1,1'-biphenyl]-3-carbonitrile (330 mg, 1.05 mmol) was obtained crude product (410 mg, LC/MS 36%) which was purified by preparative HPLC method H3. The collected fractions were lyophilised to afford N-((5-(1-(difluoromethyl)-1H-pyrazol-3-yl)-4'-fluoro-[1,1'-biphenyl]-3-yl) methyl)acrylamide (Cpd. No. 174) as an off-white solid (27 mg, 7%, LC/MS 99%). (LC/MS; m/z 372.2 $[M+H]^+$).

Example 67: Synthesis of N-((4'-fluoro-3-(1-(1-methylcyclopropyl)-1H-pyrazol-3-yl)-[1,1'-biphenyl]-4-yl)methyl)acrylamide (Cpd. No. 175)

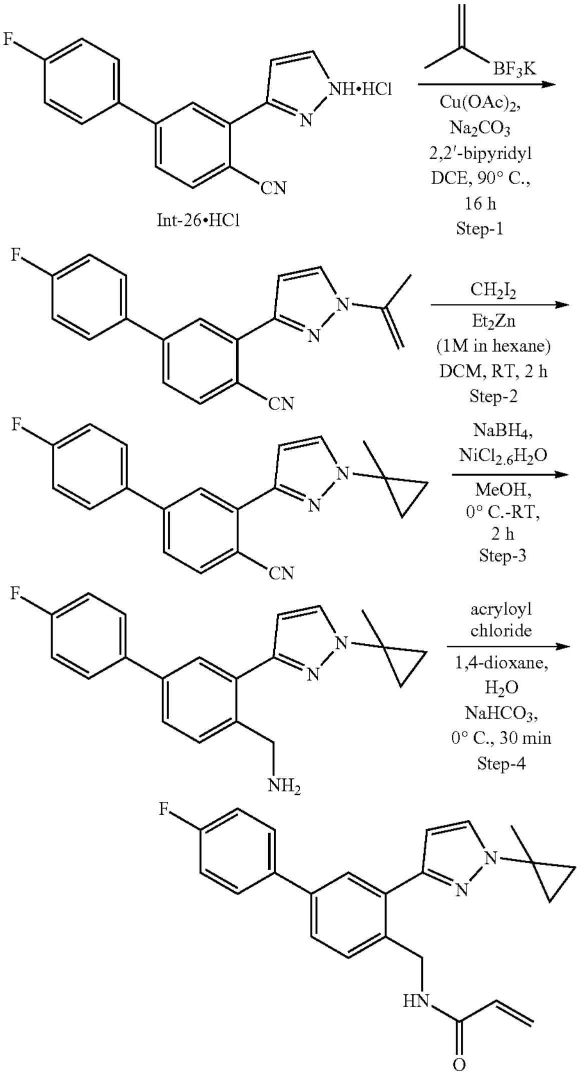

Int-26•HCl

Cpd. No. 175

Step 1: A solution of 4'-fluoro-3-(1H-pyrazol-3-yl)-[1,1'-biphenyl]-4-carbonitrile hydrochloride (Int-26.HCl) (1.40 g, 4.7 mmol) in DCE (20 mL) was treated with potassium trifluoro(prop-1-en-2-yl)borate (1.38 g, 9.4 mmol), $Cu(OAc)_2$ (850 mg, 4.7 mmol), 2,2'-bipyridyl (730 mg, 4.7 mmol) and $Na_2CO_3$ (2.0 g 18.8 mmol) at RT. The reaction mixture was stirred at 90° C. for 16 h and monitored by TLC. TLC mobile phase: 30% EtOAc in pet ether, RF: 0.3, TLC detection: UV. The cooled mixture was filtered through a celite pad and washed with EtOAc (80 mL). The filtrated was diluted with $H_2O$ (50 mL) and the aqueous layer was extracted with EtOAc (80 mL). The combined organic layer was dried over anhydrous $Na_2SO_4$ and concentrated under reduced pressure to afford crude product (1.8 g, LC/MS 46%) which was purified by normal phase flash column chromatography using a 24 g column (silica) and a gradient of 0-15% EtOAc in pet ether as an eluent to afford 4'-fluoro-3-(1-(prop-1-en-2-yl)-1H-pyrazol-3-yl)-[1,1'-biphenyl]-4-carbonitrile as an off-white solid (800 mg, 56%). (LC/MS; m/z 304.3 $[M+H]^+$).

Step 2: A solution of 4'-fluoro-3-(1-(prop-1-en-2-yl)-1H-pyrazol-3-yl)-[1,1'-biphenyl]-4-carbonitrile (300 mg, 0.99 mmol) in DCM (7 mL) was treated with diethylzinc (1M in hexanes) (4.95 mL, 4.95 mmol) at RT and stirred for 1 h. To the mixture was added diiodomethane (1.33 g, 4.95 mmol) dissolved in DCM (3 mL). The reaction mixture was stirred at RT for 1 h and monitored by TLC. TLC mobile phase: 30% EtOAc in pet ether, RF: 0.35, TLC detection: UV. The reaction mixture was diluted with EtOAc (30 mL), quenched with 1N HCl (10 mL) and $H_2O$ (20 mL) and the aqueous layer was extracted with EtOAc (40 mL). The organic layer was dried over anhydrous $Na_2SO_4$ and concentrated under reduced pressure to afford crude product (300 mg, LC/MS 37%) which was purified by normal phase flash column chromatography using a 12 g column (silica) and a gradient of 0-15% EtOAc in pet ether as an eluent to afford 4'-fluoro-3-(1-(1-methylcyclopropyl)-1H-pyrazol-3-yl)-[1,1'-biphenyl]-4-carbonitrile as an off-white solid (120 mg, 38%). (LC/MS; m/z 318.1 $[M+H]^+$).

Steps 3-4: These steps were executed in a manner similar (use of appropriate reagents and purification methods known to the person skilled in the art) to step 2 and 3 towards Cpd. No. 152. From 4'-fluoro-3-(1-(1-methylcyclopropyl)-1H-pyrazol-3-yl)-[1,1'-biphenyl]-4-carbonitrile (120 mg, 0.38 mmol) was obtained crude product (100 mg, LC/MS 31%) which was purified by preparative HPLC method H2. The collected fractions were lyophilised to afford N-((4'-fluoro-3-(1-(1-methylcyclopropyl)-1H-pyrazol-3-yl)-[1,1'-biphenyl]-4-yl)methyl)acrylamide (Cpd. No. 175) as an off-white solid (15 mg, 9%). (LC/MS; m/z 376.3 $[M+H]^+$).

Example 68: Synthesis of N-((3-(1,5-dimethyl-1H-pyrazol-3-yl)-4'-fluoro-[1,1'-biphenyl]-4-yl)methyl) acrylamide (Cpd. No. 176)

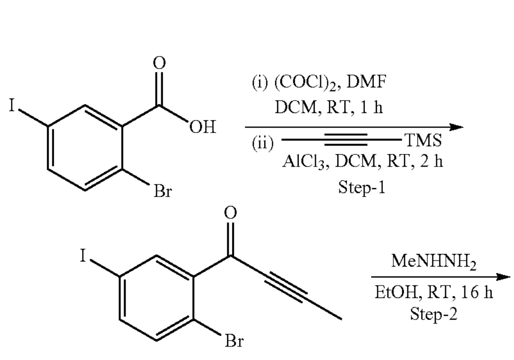

-continued

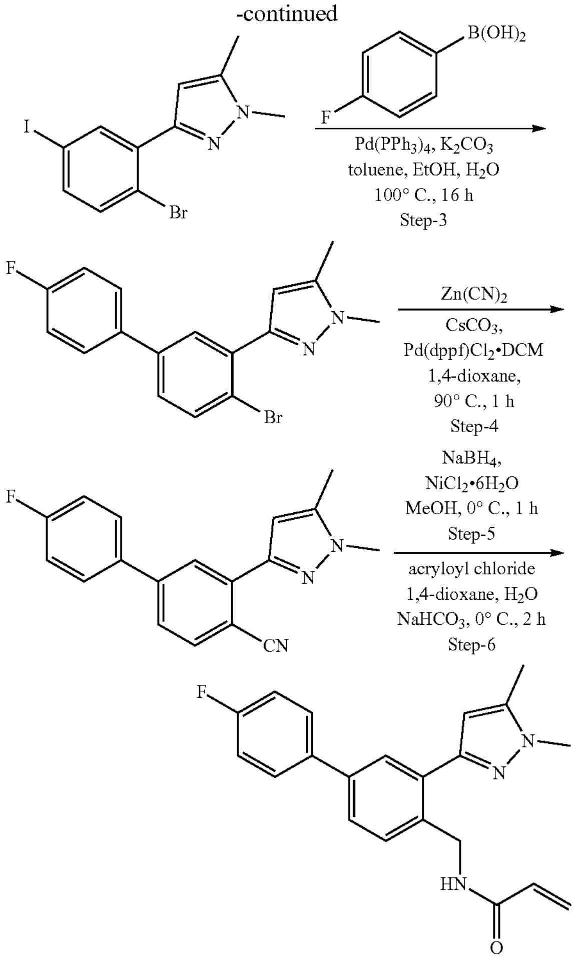

Cpd. No. 176

Step 1: A solution of 2-bromo-5-iodobenzoic acid (40 g, 122.4 mmol) in DCM (240 mL) was treated with oxalyl chloride (46.6 g, 367.2 mmol) and DMF (1.34 g, 18.4 mmol) at 0° C. The reaction mixture was stirred at RT for 1 h. The reaction was concentrated under reduced pressure and the residue was dissolved in DCM (840 mL). To the solution was added trimethyl(prop-1-yn-1-yl)silane (13.7 g, 122.2 mmol) and $AlCl_3$ (19.5 g, 146.6 mmol) at RT. The reaction mixture was stirred at RT for 2 h and monitored by TLC. TLC mobile phase: 10% EtOAc in pet ether, RF: 0.2, TLC detection: UV. The reaction was quenched with 1M HCl (850 mL). The organic layer was washed with brine (2×150 mL), dried over anhydrous $Na_2SO_4$ and concentrated under reduced pressure to afford crude product (20 g, LC/MS 45%) which was purified by normal phase flash column chromatography using silica gel (100-200 mesh) and a gradient of 0-5% EtOAc in pet ether as an eluent to afford 1-(2-bromo-5-iodophenyl)but-2-yn-1-one (15 g, LC/MS 59%) as a yellow solid. (LC/MS; m/z 348.9 $[M+H]^+$). The product was used as such without further purification.

Step 2: A solution of 1-(2-bromo-5-iodophenyl)but-2-yn-1-one (2 g, 5.7 mmol) in EtOH (40 mL) was treated with N-methyl hydrazine (85% in $H_2O$) (341 mg, 7.41 mmol) at RT. The reaction mixture was stirred at RT for 16 h and monitored by TLC. TLC mobile phase: 20% EtOAc in pet ether, RF: 0.3, TLC detection: UV. The mixture was diluted with $H_2O$ (100 mL) and extracted with EtOAc (2×100 mL).

The organic layer was dried over anhydrous $Na_2SO_4$ and concentrated under reduced pressure to afford crude product (1 g, LC/MS 47%) which was purified by normal phase flash column chromatography using a 24 g column (silica) and a gradient of 0-10% EtOAc in pet ether as an eluent to afford 3-(2-bromo-5-iodophenyl)-1,5-dimethyl-1H-pyrazole as an off-white solid (400 mg, 18%). (LC/MS; m/z 376.8 [M+H]$^+$).

Step 3: This step was executed in a manner similar (use of appropriate reagents and purification methods known to the person skilled in the art) to step 6 to Int-26.HCl. From 3-(2-bromo-5-iodophenyl)-1,5-dimethyl-1H-pyrazole (3.8 g, 10.1 mmol) was obtained 3-(4-bromo-4'-fluoro-[1,1'-biphenyl]-3-yl)-1,5-dimethyl-1H-pyrazole as a yellow solid (2.2 g, 63%). (LC/MS; m/z 345.1 [M+H]$^+$).

Step 4: A solution of 3-(4-bromo-4'-fluoro-[1,1'-biphenyl]-3-yl)-1,5-dimethyl-1H-pyrazole (1.3 g, 3.8 mmol) in 1,4-dioxane (10 mL) was treated with $Zn(CN)_2$ (1.11 g, 9.5 mmol), $Cs_2CO_3$ (2.47 g, 7.6 mmol) and Pd(dppf)$Cl_2$·DCM (310 mg, 0.38 mmol) at RT. The reaction mixture was stirred at 90° C. for 1 h under microwave radiation (sealed microwave vial) and monitored by TLC. TLC mobile phase: 20% EtOAc in pet ether, RF: 0.2, TLC detection: UV. The reaction mixture cooled, filtered through a celite pad and washed with EtOAc (150 mL). The filtrate was washed with brine (2×150 mL), dried over anhydrous $Na_2SO_4$ and concentrated under reduced pressure to afford crude product (1.2 g, LC/MS 68%) which was purified by normal phase flash column chromatography using silica gel (100-200 mesh) and a gradient of 0-14% EtOAc in pet ether to afford 3-(1,5-dimethyl-1H-pyrazol-3-yl)-4'-fluoro-[1,1'-biphenyl]-4-carbonitrile as a yellow solid (600 mg, LC/MS 51%). (LC/MS; m/z 292.2 [M+H]$^+$). The product was used as such without further purification.

Steps 5-6: These steps were executed in a manner similar (use of appropriate reagents and purification methods known to the person skilled in the art) to step 2 and 3 towards Cpd. No. 152. From 3-(1,5-dimethyl-1H-pyrazol-3-yl)-4'-fluoro-[1,1'-biphenyl]-4-carbonitrile (600 mg, 2.05 mmol) was obtained crude (800 mg, LC/MS 40%) which was purified by preparative HPLC method H1. The collected fractions were lyophilised to afford N-((3-(1,5-dimethyl-1H-pyrazol-3-yl)-4'-fluoro-[1,1'-biphenyl]-4-yl)methyl)acrylamide (Cpd. No. 176) as a white solid (155 mg, 22%). (LC/MS; m/z 350.3 [M+H]$^+$).

Example 69: Synthesis of 2-fluoro-N-((3-(1-methyl-1H-pyrazol-3-yl)-4'-(trifluoromethyl)-[1,1'-biphenyl]-4-yl)methyl)acrylamide (Cpd. No. 177)

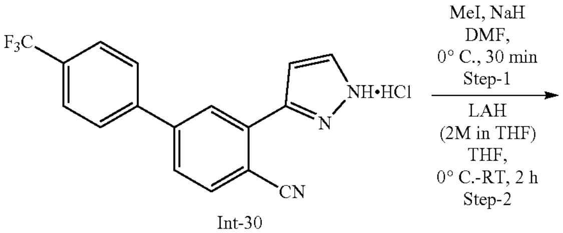

Int-30

-continued

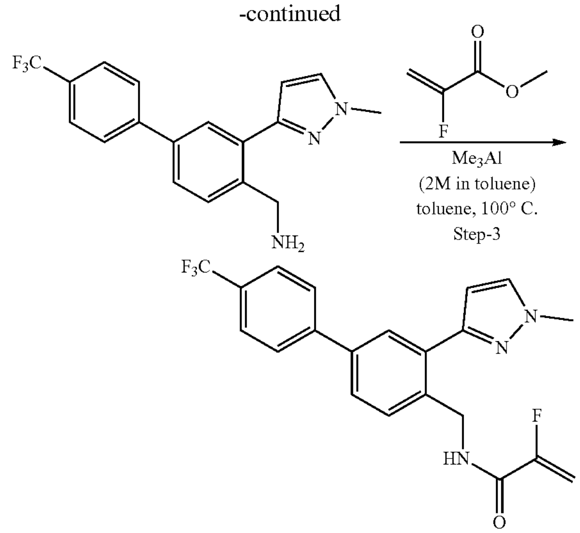

Cpd. No. 177

Step 1: A solution of Int-30 (700 mg, 2.00 mmol) in DMF (14 mL) was treated with NaH (60% in mineral oil) (192 mg, 8.02 mmol) and iodomethane (342 mg, 2.41 mmol) at 0° C. The reaction mixture was stirred at 0° C. for 30 min and monitored by TLC. TLC mobile phase: 30% EtOAc in pet ether, RF: 0.52, TLC detection: UV. The reaction was quenched with ice $H_2O$ (100 mL) and extracted with EtOAc (2×50 mL). The combined organic layer was washed with brine (50 mL), dried over anhydrous $Na_2SO_4$ and concentrated under reduced pressure to afford 3-(1-methyl-1H-pyrazol-3-yl)-4'-(trifluoromethyl)-[1,1'-biphenyl]-4-carbonitrile (89:11 mixture of N-Me regioisomers) as a brown gum (600 mg, 92%). (LC/MS; m/z 328.1 [M+H]$^+$).

Step 2: This step was executed in a manner similar (use of appropriate reagents and purification methods known to the person skilled in the art) to step 2 towards Cpd. No. 152. From 3-(1-methyl-1H-pyrazol-3-yl)-4'-(trifluoromethyl)-[1,1'-biphenyl]-4-carbonitrile (600 mg, 1.83 mmol) was obtained 3-(1-methyl-1H-pyrazol-3-yl)-4'-(trifluoromethyl)-[1,1'-biphenyl]-4-yl)methanamine (90:10 mixture of N-Me regioisomers) as a yellow gum (600 mg). (LC/MS; m/z 332.3 [M+H]$^+$). The product was used as such without further purification.

Step 3: A solution of (3-(1-methyl-1H-pyrazol-3-yl)-4'-(trifluoromethyl)-[1,1'-biphenyl]-4-yl)methanamine (300 mg, 0.906 mmol, LC/MS 86%) (mixture of N-Me regioisomers) in toluene (8 mL) was treated with methyl 2-fluoroacrylate (141 mg, 1.36 mmol) and $Me_3Al$ (2.0M in toluene) (1.13 mL, 2.26 mmol) at 0° C. The reaction mixture was stirred at 100° C. for 16 h (sealed tube) and monitored by TLC. TLC mobile phase: 10% MeOH in DCM, RF: 0.84, TLC detection: UV. The reaction was quenched with ice $H_2O$ (30 mL) and extracted with EtOAc (2×30 mL). The combined organic layer was washed with brine (30 mL), dried over anhydrous $Na_2SO_4$ and concentrated under reduced pressure to afford crude product (350 mg, LC/MS 59%) which was purified by preparative HPLC method H2. The collected fractions were lyophilised to afford 2-fluoro-N-((3-(1-methyl-1H-pyrazol-3-yl)-4'-(trifluoromethyl)-[1,1'-biphenyl]-4-yl)methyl)-acrylamide (Cpd. No. 177) as a white gum (55 mg, 15%). (LC/MS; m/z 404.3 [M+H]$^+$).

Examples 70-71: Synthesis of trans-N-(2-(1-methyl-1H-pyrazol-3-yl)-4-(4-(trifluoromethyl)cyclohexyl)benzyl)acrylamide (Cpd. No. 178) and cis-N-(2-(1-methyl-1H-pyrazol-3-yl)-4-(4-(trifluoromethyl)cyclohexyl)benzyl)acrylamide (Cpd. No. 179)

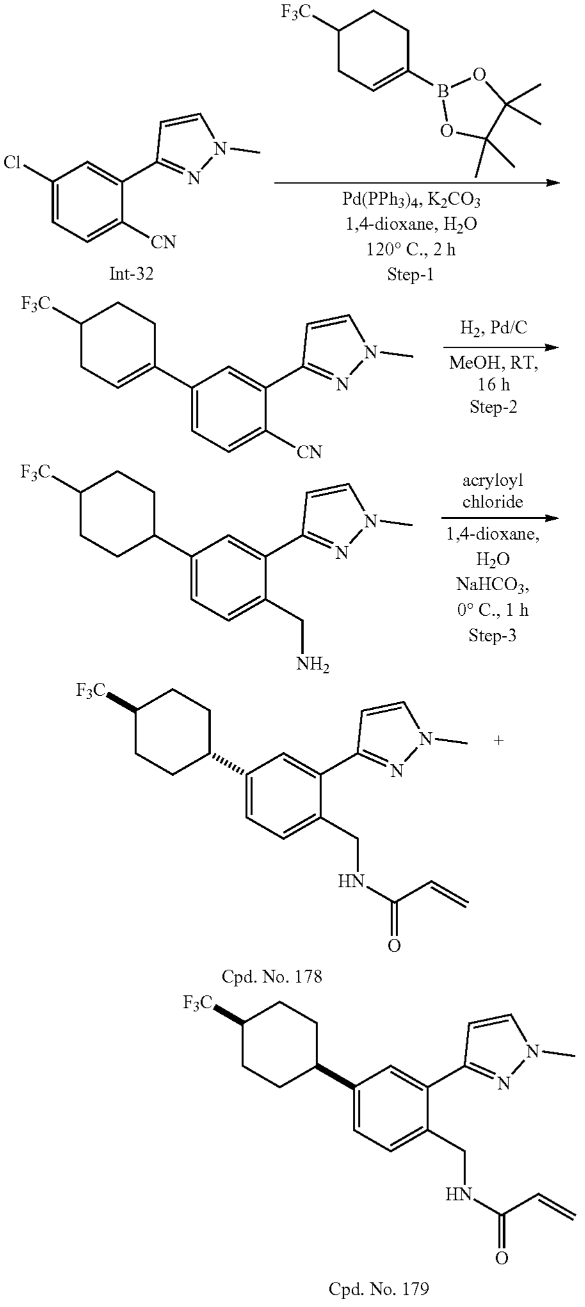

Int-32

Cpd. No. 178

Cpd. No. 179

Step 1: This step was executed in a manner similar (use of appropriate reagents and purification methods known to the person skilled in the art) to step 6 to Int-26.HCl. Reacting Int-32 (300 mg, 1.38 mmol) with 4,4,5,5-tetramethyl-2-(4-(trifluoromethyl)cyclohex-1-en-1-yl)-1,3,2-dioxaborolane (572 mg, 2.07 mmol) afforded 3-(1-methyl-1H-pyrazol-3-yl)-4'-(trifluoromethyl)-2',3',4',5'-tetrahydro-[1,1'-biphenyl]-4-carbonitrile as an off-white solid (100 mg, 22%). (LC/MS; m/z 332.2 $[M+H]^+$).

Step 2: To a solution of 3-(1-methyl-1H-pyrazol-3-yl)-4'-(trifluoromethyl)-2',3',4',5'-tetrahydro-[1,1'-biphenyl]-4-carbonitrile (100 mg, 0.302 mmol) in MeOH (5 mL) was added Pd/C (10 wt. %) (100 mg). The reaction mixture was stirred under hydrogen gas (balloon pressure) at RT for 16 h and monitored by TLC. TLC mobile phase: 10% MeOH in DCM, RF: 0.24, TLC detection: UV. The mixture was filtered through a celite pad and washed with MeOH (20 mL). The filtrate was concentrated under reduced pressure to afford (2-(1-methyl-1H-pyrazol-3-yl)-4-(4-(trifluoromethyl)cyclohexyl)phenyl)methanamine (cis:trans mixture) (80 mg). (LC/MS; m/z 338.4 $[M+H]^+$). The product was used as such without further purification.

Step 3: This step was executed in a manner similar (use of appropriate reagents and purification methods known to the person skilled in the art) to step 3 towards Cpd. No. 152. From 2-(1-methyl-1H-pyrazol-3-yl)-4-(4-(trifluoromethyl)cyclohexyl)phenyl)methanamine (cis:trans mixture) (80 mg, 0.237 mmol) was obtained crude product (100 mg, LC/MS 59%) which was purified by preparative HPLC method H2. The collected fractions were lyophilised to afford trans-N-(2-(1-methyl-1H-pyrazol-3-yl)-4-(4-(trifluoromethyl)cyclohexyl)benzyl)-acrylamide (Cpd. No. 178) as an off-white solid (6 mg, 6%) and cis-N-(2-(1-methyl-1H-pyrazol-3-yl)-4-(4-(trifluoromethyl)cyclohexyl)-benzyl)acrylamide (Cpd. No. 179) as an off-white solid (23 mg, 25%). (LC/MS; m/z 392.3 $[M+H]^+$).

Example 72: Synthesis of N-(4-(4,4-difluorocyclohexyl)-2-(1-methyl-1H-pyrazol-3-yl)benzyl)acrylamide (Cpd. No. 180)

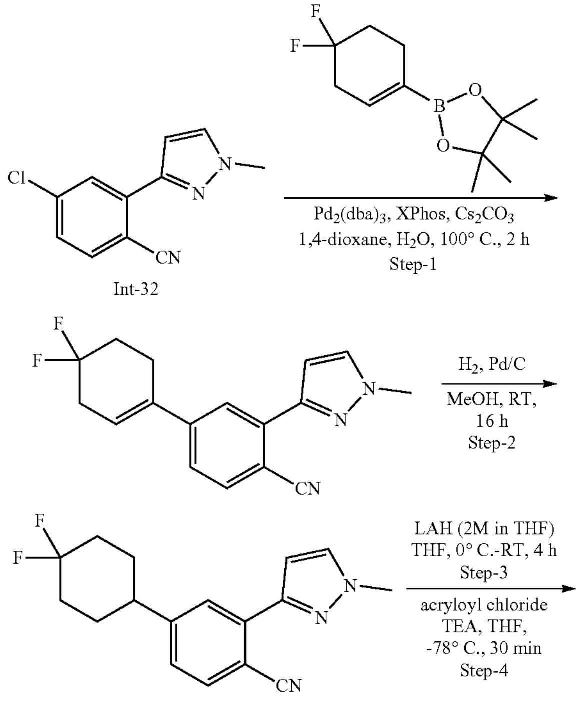

Int-32

-continued

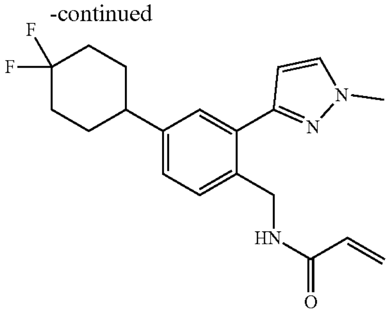

Cpd. No. 180

Step 1: A mixture of Int-32 (1.0 g, 4.6 mmol), 2-(4,4-difluorocyclohex-1-en-1-yl)-4,4,5,5-tetramethyl-1,3,2-dioxaborolane (1.1 g, 4.6 mmol) and $Cs_2CO_3$ (2.9 g, 9.2 mmol) in 1,4-dioxane (20 mL) and $H_2O$ (2 mL) was degassed with argon for 5 min. To the mixture was added XPhos (0.22 g, 0.46 mmol) and $Pd_2(dba)_3$ (0.21 g, 0.23 mmol). The reaction mixture was stirred at 100° C. for 2 h under microwave radiation (sealed microwave vial) and monitored by TLC. TLC mobile phase: 30% EtOAc in pet ether, RF: 0.3, TLC detection: UV. The mixture was cooled, filtered through a celite pad and washed with EtOAc (50 mL). The filtrated was diluted with $H_2O$ (40 mL) and the aqueous layer was extracted with EtOAc (60 mL). The combined organic layer was dried over anhydrous $Na_2SO_4$ and concentrated under reduced pressure to afford crude product (1.2 g, LC/MS 45%) which was purified by normal phase flash column chromatography using a 40 g column (silica) and a gradient of 0-20% EtOAc in pet ether as an eluent to afford 4',4'-difluoro-3-(1-methyl-1H-pyrazol-3-yl)-2',3',4',5'-tetrahydro-[1,1'-biphenyl]-4-carbonitrile as a brown gum (738 mg, 54%). (LC/MS; m/z 300.2 $[M+H]^+$).

Step 2: This step was executed in a manner similar (use of appropriate reagents and purification methods known to the person skilled in the art) to step 2 towards Cpd. No. 179. From 4',4'-difluoro-3-(1-methyl-1H-pyrazol-3-yl)-2',3',4',5'-tetrahydro-[1,1'-biphenyl]-4-carbonitrile (700 mg, 2.34 mmol) was obtained 4-(4,4-difluorocyclohexyl)-2-(1-methyl-1H-pyrazol-3-yl)benzonitrile (700 mg). (LC/MS; m/z 302.2 $[M+H]^+$). The product was used as such without further purification.

Steps 3-4: These steps were executed in a manner similar (use of appropriate reagents and purification methods known to the person skilled in the art) to step 2 and 3 towards Cpd. No. 152. From 4-(4,4-difluorocyclohexyl)-2-(1-methyl-1H-pyrazol-3-yl)benzonitrile (700 mg, 2.32 mmol) was obtained crude product (930 mg, LC/MS 43%) which was purified by preparative HPLC method H1. The collected fractions were lyophilised to afford N-(4-(4,4-difluorocyclohexyl)-2-(1-methyl-1H-pyrazol-3-yl)benzyl)acrylamide (Cpd. No. 180) as a colorless gum (185 mg, 22%). (LC/MS; m/z 360.3 $[M+H]^+$).

Example 73: Synthesis of N-(2-(1-methyl-1H-pyrazol-3-yl)-4-(4-(trifluoromethyl)piperidin-1-yl)benzyl)acrylamide (Cpd. No. 181)

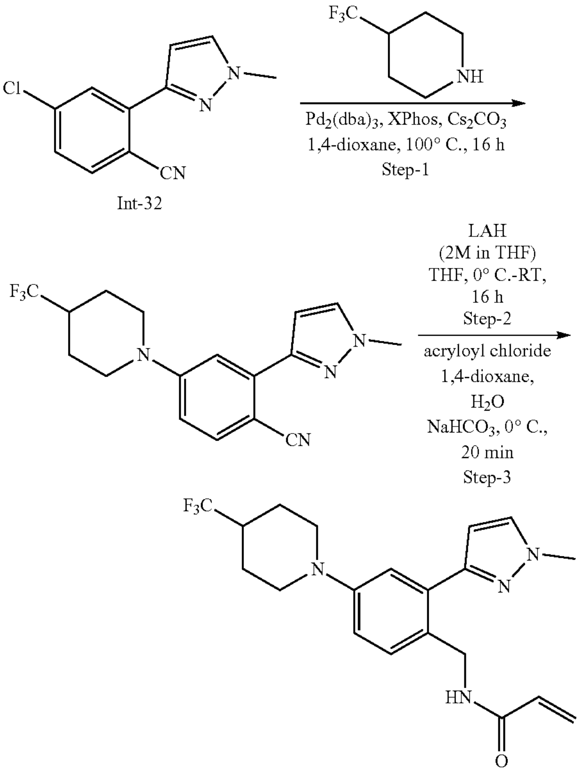

Cpd. No. 181

Step 1: This step was executed in a manner similar (use of appropriate reagents and purification methods known to the person skilled in the art) to step 1 towards Cpd. No. 180. Reacting Int-32 (800 mg, 3.67 mmol) with 4-(trifluoromethyl)piperidine (1.13 g, 7.37 mmol) afforded 2-(1-methyl-1H-pyrazol-3-yl)-4-(4-(trifluoromethyl)piperidin-1-yl)benzonitrile as a pale brown solid (706 mg, 57%). (LC/MS; m/z 335.2 $[M+H]^+$).

Steps 2-3: These steps were executed in a manner similar (use of appropriate reagents and purification methods known to the person skilled in the art) to step 2 and 3 towards Cpd. No. 152. From 2-(1-methyl-1H-pyrazol-3-yl)-4-(4-(trifluoromethyl)piperidin-1-yl)benzonitrile (650 mg, 1.95 mmol) was obtained crude product (700 mg, LC/MS 31%) which was purified by preparative HPLC method H1. The collected fractions were lyophilised to afford N-(2-(1-methyl-1H-pyrazol-3-yl)-4-(4-(trifluoromethyl)piperidin-1-yl)benzyl) acrylamide (Cpd. No. 181) as an off-white solid (54 mg, 7%). (LC/MS; m/z 393.3 $[M+H]^+$).

Compound Cpd. No. 182 was prepared in a manner similar (use of appropriate reagents and purification methods known to the person skilled in the art) to Cpd. No. 181.

Example 74: Synthesis of 4'-fluoro-3-(1-methylpyrrolidin-3-yl)-[1,1'-biphenyl]-4-carbonitrile (Cpd. No. 183)

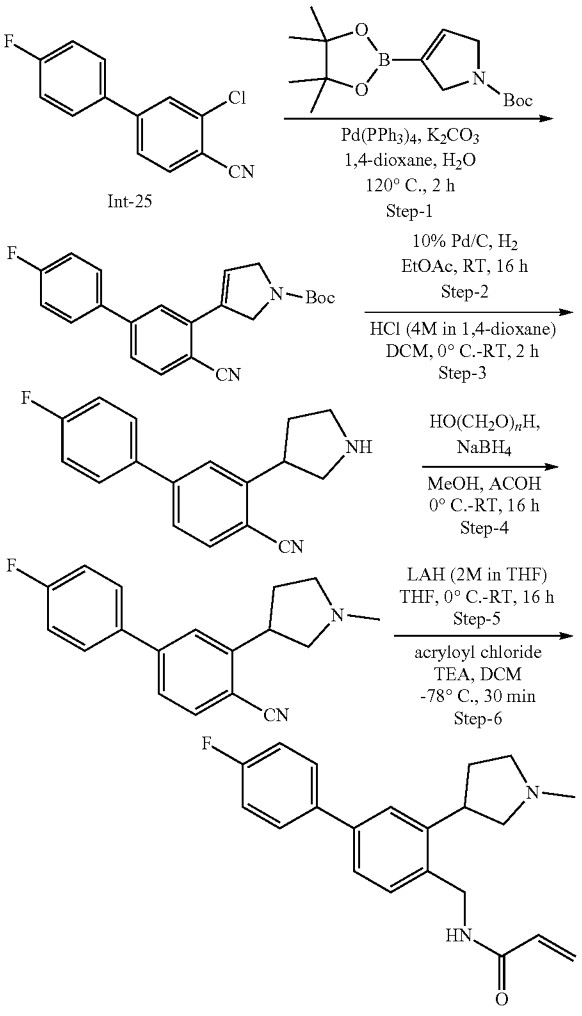

Cpd. No. 183

Steps 1-2: This step was executed in a manner similar (use of appropriate reagents and purification methods known to the person skilled in the art) to step 1 and 2 towards Cpd. No. 178 and Cpd. No. 179. Reacting Int-25 (1.50 g, 6.5 mmol) with tert-butyl 3-(4,4,5,5-tetramethyl-1,3,2-dioxaborolan-2-yl)-2,5-dihydro-1H-pyrrole-1-carboxylate (1.91 g, 6.5 mmol) afforded tert-butyl 3-(4-cyano-4'-fluoro-[1,1'-biphenyl]-3-yl)pyrrolidine-1-carboxylate (1.50 g, LC/MS 94%). (LC/MS; m/z 311.2 $[M-But+H]^+$). The product was used as such without further purification.

Step 3: This step was executed in a manner similar (use of appropriate reagents and purification methods known to the person skilled in the art) to step 4 to Int-26.HCl. From tert-butyl 3-(4-cyano-4'-fluoro-[1,1'-biphenyl]-3-yl)pyrrolidine-1-carboxylate (1.50 g, 4.1 mmol) was obtained 4'-fluoro-3-(pyrrolidin-3-yl)-[1,1'-biphenyl]-4-carbonitrile (900 mg, LC/MS 72%). (LC/MS; m/z 267.0 $[M+H]^+$). The product was used as such without further purification.

Step 4: A solution of 4'-fluoro-3-(pyrrolidin-3-yl)-[1,1'-biphenyl]-4-carbonitrile (800 mg, 3.01 mmol) in MeOH (16 mL) was treated with paraformaldehyde (451 mg, 15.03 mmol) and AcOH (361 mg, 6.01 mmol) and the reaction mixture was stirred at RT for 2 h. To the mixture was added $NaBH_4$ (341 mg, 9.02 mmol) at 0° C. The reaction mixture was stirred at RT for 16 h and monitored by TLC. TLC mobile phase: 10% MeOH in DCM, RF: 0.30, TLC detection: UV. The reaction mixture was concentrated under reduced pressure, the residue dissolved in DCM (40 mL) and basified with sat aq $NaHCO_3$ (20 mL). The organic layer was washed with brine (20 mL), dried over anhydrous $Na_2SO_4$ and concentrated under reduced pressure to afford crude product (800 mg, LC/MS 60%) which was purified by normal phase flash column chromatography using a 12 g column (silica) and a gradient of 0-8% MeOH in DCM as an eluent to afford 4'-fluoro-3-(1-methylpyrrolidin-3-yl)-[1,1'-biphenyl]-4-carbonitrile as a pale brown gum (350 mg, 41%). (LC/MS; m/z 281.5 $[M+H]^+$).

Steps 5-6: These steps were executed in a manner similar (use of appropriate reagents and purification methods known to the person skilled in the art) to step 2 and 3 towards Cpd. No. 152. From 4'-fluoro-3-(1-methylpyrrolidin-3-yl)-[1,1'-biphenyl]-4-carbonitrile (330 mg, 1.18 mmol) was obtained crude product (243 mg, LC/MS 35%) which was purified by preparative HPLC method H1. The collected fractions were lyophilised to afford N-((4'-fluoro-3-(1-methylpyrrolidin-3-yl)-[1,1'-biphenyl]-4-yl)methyl)acrylamide (Cpd. No. 183) as a white solid (25 mg, 6%). (LC/MS; m/z 339.3 $[M+H]^+$).

Example 75: Synthesis of N-((4'-fluoro-3-(1-methyl-1H-1,2,3-triazol-4-yl)-[1,1'-biphenyl]-4-yl)methyl)acrylamide (Cpd. No. 184)

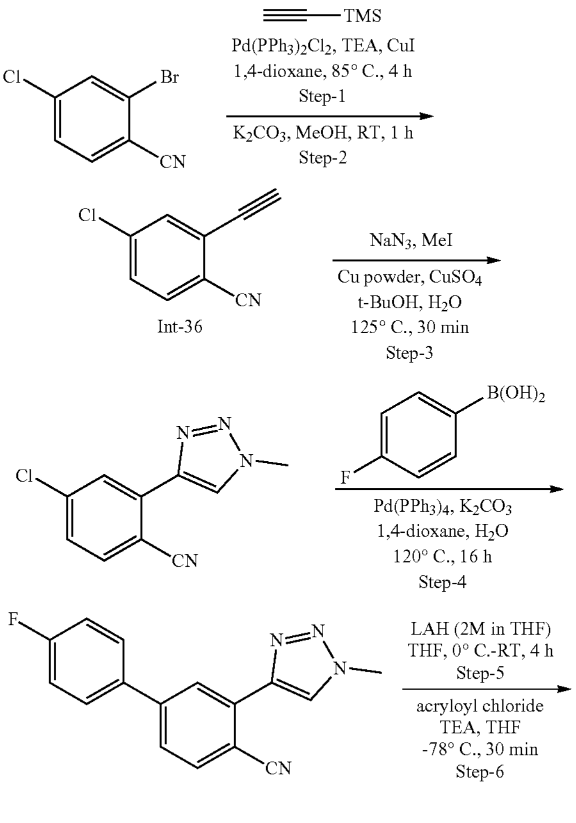

-continued

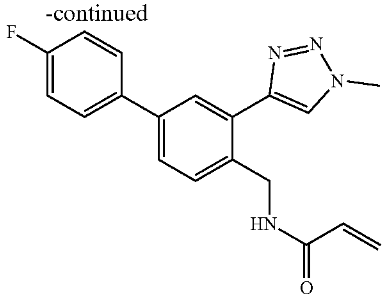

Cpd. No. 184

Step 1: A solution of 2-bromo-4-chlorobenzonitrile (6.54 g, 30.3 mmol) in 1,4-dioxane (50 mL) was treated with TEA (4.6 g, 45.5 mmol) and CuI (0.1 g, 0.61 mmol) and degassed with argon for 10 min. To the mixture was added $Pd(PPh_3)_2Cl_2$ (1.1 g, 1.51 mmol) and trimethylsilylacetylene (3.6 g, 36.4 mmol). The reaction mixture was stirred at 85° C. for 4 h (sealed tube) and monitored by TLC. TLC mobile phase: 20% EtOAc in pet ether, RF: 0.4, TLC detection: UV. The reaction mixture was cooled, filtered through a celite pad and EtOAc (150 mL). The filtrate was diluted with $H_2O$ (100 mL) and the aqueous layer was extracted with EtOAc (150 mL). The combined organic layer was dried over anhydrous $Na_2SO_4$ and concentrated under reduced pressure to afford crude product (5 g, LC/MS 84%) which was purified by normal phase flash column chromatography using a 40 g column (silica) and a gradient of 0-5% EtOAc in pet ether as an eluent to afford 4-chloro-2-((trimethylsilyl)ethynyl) benzonitrile as an off-white solid (3.5 g, 49%). $^1H$ NMR (400 MHz, $CDCl_3$) δ ppm: 7.55-7.57 (m, 2H), 7.36-7.39 (dd, 1H), 0.29 (s, 9H).

Step 2: A solution of 4-chloro-2-((trimethylsilyl)ethynyl) benzonitrile (3.0 g, 12.8 mmol) and $K_2CO_3$ (1.8 g, 12.9 mmol) in MeOH (30 mL) was stirred at RT for 1 h and monitored by TLC. TLC mobile phase: 20% EtOAc in pet ether, RF: 0.3, TLC detection: UV. The reaction mixture was concentrated under reduced pressure and the residue was diluted with $H_2O$ (100 mL) and extracted with EtOAc (200 mL). The organic layer was dried over anhydrous $Na_2SO_4$ and concentrated under reduced pressure to afford crude product (3.0 g, LC/MS 98%) which was purified by normal phase flash column chromatography using a 40 g column (silica) and a gradient of 0-8% EtOAc in pet ether as an eluent to afford 4-chloro-2-ethynylbenzonitrile (Int-36) as an off-white solid (2.0 g, 97%). (LC/MS; m/z 162.1 $[M+H]^+$).

Step 3: A solution of Int-36 (2.0 g, 12.4 mmol) in t-BuOH (10 mL) and $H_2O$ (10 mL) was treated with MeI (1.76 g, 12.4 mmol), $NaN_3$ (0.806 g, 12.4 mmol), Cu powder (0.55 g, 8.7 mmol) and $CuSO_4{\cdot}5H_2O$ (1M in $H_2O$) (1.68 mL) at RT. The reaction mixture was stirred under microwave radiation (sealed microwave vial) at 125° C. for 30 min and monitored by TLC. TLC mobile phase: 30% EtOAc in pet ether, RF: 0.3, TLC detection: UV. The reaction mixture was cooled, filtered through a celite pad and washed with EtOAc (80 mL). The filtrate was diluted with $H_2O$ (50 mL) and extracted with EtOAc (100 mL). The organic layer was dried over anhydrous $Na_2SO_4$ and concentrated under reduced pressure to afford crude product (3.0 g, LC/MS 43%) which was purified by normal phase flash column chromatography using a 12 g column (silica) and a gradient of 0-25% EtOAc in pet ether to afford 4-chloro-2-(1-methyl-1H-1,2,3-triazol-4-yl)benzonitrile as an off-white solid (1.0 g, 29%). (LC/MS; m/z 219.1 $[M+H]^+$).

Step 4: This step was executed in a manner similar (use of appropriate reagents and purification methods known to the person skilled in the art) to step 6 to Int-26.HCl. From 4-chloro-2-(1-methyl-1H-1,2,3-triazol-4-yl)benzonitrile (1.0 g, 4.6 mmol) was obtained 4'-fluoro-3-(1-methyl-1H-1,2,3-triazol-4-yl)-[1,1'-biphenyl]-4-carbonitrile as a light brown solid (700 mg, 55%). (LC/MS; m/z 279.2 $[M+H]^+$).

Steps 5-6: These steps were executed in a manner similar (use of appropriate reagents and purification methods known to the person skilled in the art) to step 2 and 3 towards Cpd. No. 152. From 4'-fluoro-3-(1-methyl-1H-1,2,3-triazol-4-yl)-[1,1'-biphenyl]-4-carbonitrile (650 mg, 2.34 mmol) was obtained crude product (360 mg, LC/MS 45%) which was purified by preparative HPLC method H1. The collected fractions were lyophilised to afford N-((4'-fluoro-3-(1-methyl-1H-1,2,3-triazol-4-yl)-[1,1'-biphenyl]-4-yl)methyl) acrylamide (Cpd. No. 184) as an off-white solid (91 mg, 11%). (LC/MS; m/z 337.2 $[M+H]^+$).

Synthesis of 4-chloro-2-(1-(difluoromethyl)-1H-1,2,3-triazol-4-yl)benzonitrile (Int-37) and 4-chloro-2-(2-(difluoromethyl)-2H-1,2,3-triazol-4-yl)benzonitrile (Int-38)

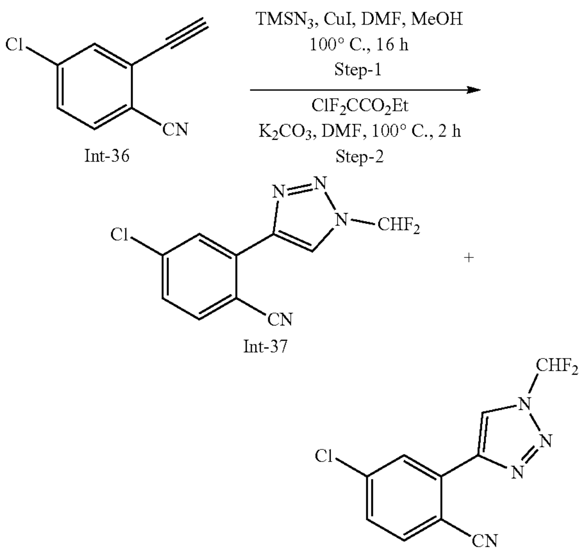

Int-38

Step 1: A solution of Int-36 (3.0 g, 18.45 mmol, LC/MS 91%) in MeOH (50 mL) and DMF (5 mL) was treated with $TMSN_3$ (2.55 g, 22.14 mmol) and CuI (0.07 g, 0.36 mmol) at RT. The mixture was stirred at 100° C. for 16 h (sealed tube) and monitored by TLC. TLC mobile phase: 30% EtOAc in pet ether, RF: 0.15, TLC detection: UV. The reaction mixture was filtered through a celite pad, washed with EtOAc (80 mL) and the filtrate was washed with brine (100 mL). The organic layer was dried over anhydrous $Na_2SO_4$ and concentrated under reduced pressure to afford a pale yellow gum (3.5 g). The crude product was purified by normal phase flash column chromatography using a 12 g column (silica) and a gradient of 0-10% EtOAc in pet ether to afford 4-chloro-2-(1H-1,2,3-triazol-4-yl)benzonitrile as an off-white solid (1.20 g, 27%, LC/MS 78%). (LC/MS; m/z 205.2 $[M+H]^+$).

Step 2: A solution of 4-chloro-2-(1H-1,2,3-triazol-4-yl) benzonitrile (1.0 g, 4.86 mmol) in DMF (25 mL) was treated with $K_2CO_3$ (4.03 g, 29.18 mmol) and ethyl 2-chloro-2,2-difluoroacetate (2.31 g, 14.59 mmol). The mixture was stirred at 100° C. for 2 h and monitored by TLC. TLC mobile phase: 5% EtOAc in pet ether, RF: 0.32 & 0.38, TLC detection: UV. The reaction mixture was diluted with $H_2O$ (30 mL) and extracted with EtOAc (2×50 mL). The organic layer was dried over anhydrous $Na_2SO_4$ and concentrated under reduced pressure to afford a pale yellow gum (1.35 g). The crude product was purified by normal phase flash column chromatography using a 12 g column (silica) and a gradient of 0-20% EtOAc in pet ether as an eluent to afford 4-chloro-2-(1-(difluoromethyl)-1H-1,2,3-triazol-4-yl)benzonitrile (Int-37) (550 mg, 40%, LC/MS 71%) and 4-chloro-2-(2-(difluoromethyl)-2H-1,2,3-triazol-4-yl)benzonitrile (Int-38) (250 mg, 16%, LC/MS 61%), both as an off-white solid. (LC/MS; m/z 255.1 $[M+H]^+$). Int-37: $^1H$ NMR (400 MHz, DMSO-$d_6$) δ ppm: 9.32 (s, 1H), 8.24-8.53 (t, 1H), 8.14-8.15 (d, 1H), 8.05-8.07 (d, 1H), 7.73-7.76 (dd, 1H). Int-38: $^1H$ NMR (400 MHz, DMSO-$d_6$) δ ppm: 8.78 (s, 1H), 8.15-8.42 (t, 2H), 8.07-8.09 (d, 1H), 7.79-7.81 (dd, 1H). The structure of regioisomers Int-37 and Int-38 was confirmed by 2D NMR.

Example 76: Synthesis of N-((3-(1-(difluoromethyl)-1H-1,2,3-triazol-4-yl)-4'-fluoro-[1,1'-biphenyl]-4-yl)methyl)acrylamide (Cpd. No. 185)

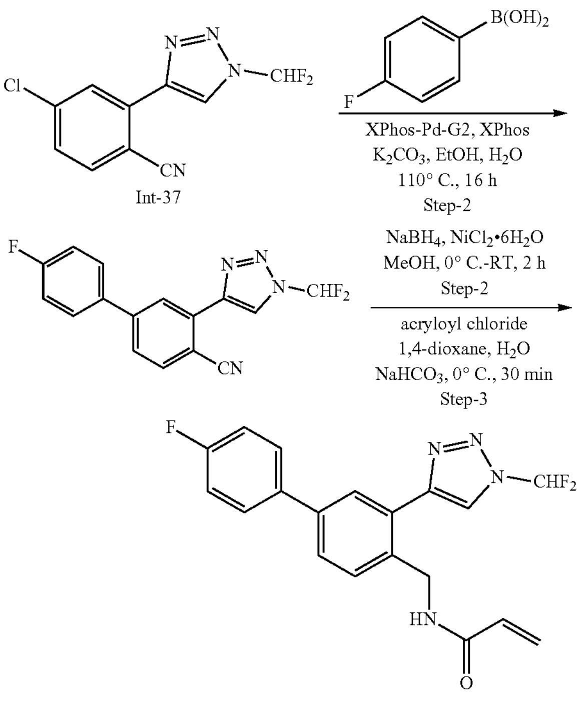

Cpd. No. 185

Step 1: A solution of Int-37 (600 mg, 2.35 mmol), $K_2CO_3$ (1.62 g, 11.78 mmol) and (4-fluorophenyl)boronic acid (395 mg, 2.82 mmol) in EtOH (20 ml) and $H_2O$ (2 mL) was degassed with argon for 5 min and treated with XPhos (168 mg, 0.35 mmol) and Xphos-Pd-G2 (278 mg, 0.35 mmol). The mixture was stirred at 110° C. for 16 h (sealed tube) and monitored by TLC. TLC mobile: 10% EtOAc in pet ether, RF: 0.17, TLC detection: UV. The reaction mixture was filtered through a celite pad, washed with EtOAc (150 mL) and the filtrate was washed with $H_2O$ (100 mL) and brine (150 mL). The organic layer was dried over anhydrous $Na_2SO_4$ and concentrated under reduced pressure to afford a black gum (650 mg). The crude product was purified by normal phase flash column chromatography using a 40 g column (silica) and a gradient of 0-5% EtOAc in pet ether as an eluent to afford 3-(1-(difluoromethyl)-1H-1,2,3-triazol-4-yl)-4'-fluoro-[1,1'-biphenyl]-4-carbonitrile as an off-white solid (450 mg, 65%, LC/MS 77%). (LC/MS; m/z 315.2 $[M+H]^+$).

Steps 2-3: These steps were executed in a manner similar (use of appropriate reagents and purification methods known to the person skilled in the art) to step 2 and 3 towards Cpd. No. 157. From 3-(1-(difluoromethyl)-1H-1,2,3-triazol-4-yl)-4'-fluoro-[1,1'-biphenyl]-4-carbonitrile (400 mg, 1.27 mmol, LC/MS 77%) was obtained crude product (458 mg, LC/MS 36%) which was purified by preparative HPLC method H1. The collected fractions were lyophilised to afford N-((3-(1-(difluoromethyl)-1H-1,2,3-triazol-4-yl)-4'-fluoro-[1,1'-biphenyl]-4-yl)methyl)acrylamide (Cpd. No. 185) as an off-white solid (141 mg, 38%). (LC/MS; m/z 373.3 $[M+H]^+$).

Compound Cpd. No. 186 (prepared from Int-38) was prepared in a manner similar (use of appropriate reagents and purification methods known to the person skilled in the art) to Cpd. No. 185.

Example 77: Synthesis of N-((4'-fluoro-3-(2-methyl-2H-1,2,3-triazol-4-yl)-[1,1'-biphenyl]-4-yl)methyl)acrylamide (Cpd. No. 187)

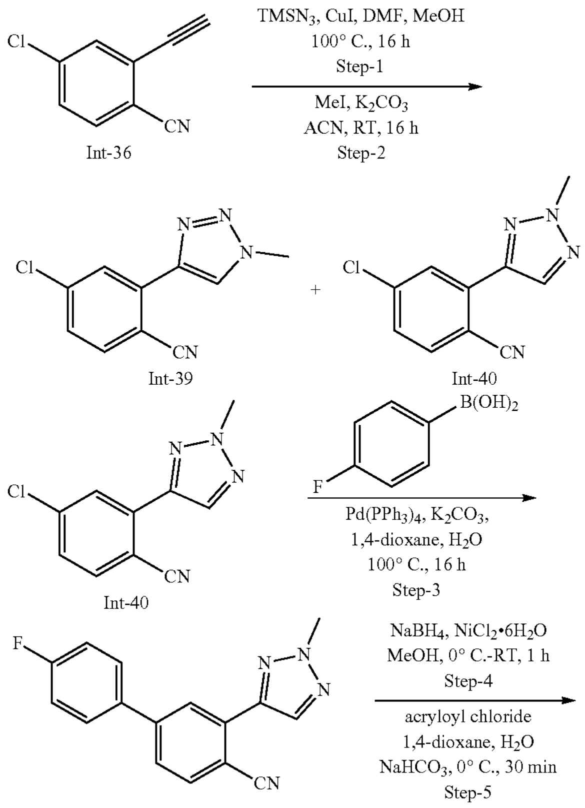

-continued

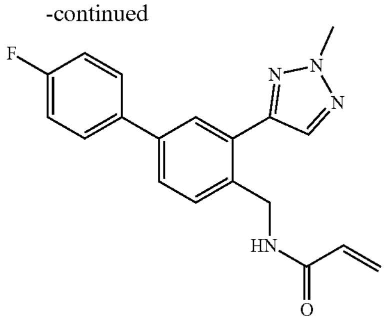

Cpd. No. 187

Step 1: A solution of Int-36 (3.0 g, 18.45 mmol, LC/MS 91%) in MeOH (50 mL) and DMF (5 mL) was treated with $TMSN_3$ (2.55 g, 22.14 mmol) and CuI (0.07 g, 0.36 mmol) at RT. The mixture was stirred at 100° C. for 16 h (sealed tube) and monitored by TLC. TLC mobile phase: 30% EtOAc in pet ether, RF: 0.15, TLC detection: UV. The reaction mixture was filtered through a celite pad, washed with EtOAc (80 mL) and the filtrate was washed with brine (100 mL). The organic layer was dried over anhydrous $Na_2SO_4$ and concentrated under reduced pressure to afford a pale yellow gum (3.5 g). The crude product was purified by normal phase flash column chromatography using a 12 g column (silica) and a gradient of 0-10% EtOAc in pet ether to afford 4-chloro-2-(1H-1,2,3-triazol-4-yl)benzonitrile as an off-white solid (1.20 g, 27%, LC/MS 78%). (LC/MS; m/z 205.2 $[M+H]^+$).

Step 2: A solution of 4-chloro-2-(1H-1,2,3-triazol-4-yl) benzonitrile (750 mg, 3.66 mmol, LC/MS 78%) in ACN (20 ml) was treated with $K_2CO_3$ (2.02 g, 14.66 mmol) and iodomethane (0.27 ml, 4.39 mmol). The mixture was stirred at RT for 16 h and monitored by TLC. TLC mobile phase: 30% EtOAc in pet ether, RF: 0.61 & 0.18, TLC detection: UV. The reaction mixture was diluted with $H_2O$ (100 ml) and extracted with EtOAc (2×300 mL). The combined organic layer was washed with brine (200 mL), dried over anhydrous $Na_2SO_4$ and concentrated under reduced pressure to afford a brown solid (850 mg, LC/MS 36% and 35%). The crude product was purified by normal phase flash column chromatography using a 80 g column (silica) and a gradient of 10-30% EtOAc in pet ether as an eluent to afford 4-chloro-2-(1-methyl-1H-1,2,3-triazol-4-yl)benzonitrile (Int-39) (330 mg, 47%, LC/MS 93%) and 4-chloro-2-(2-methyl-2H-1,2,3-triazol-4-yl)benzonitrile (Int-40) (300 mg, 49%, LC/MS 98%), both as a white solid. (LC/MS; m/z 219.1 $[M+H]^+$). Int-39: $^1$H NMR (400 MHz, DMSO-$d_6$) δ ppm: 8.71 (s, 1H), 8.09-8.10 (d, 1H), 7.98-8.00 (d, 1H), 7.63-7.66 (dd, 1H), 4.17 (s, 3H). Int-40: $^1$H NMR (400 MHz, $CDCl_3$) δ ppm: 8.26 (s, 1H), 8.00-8.01 (d, 1H), 7.67-7.69 (d, 1H), 7.40-7.43 (dd, 1H), 4.31 (s, 3H). The structure of regioisomers Int-39 and Int-40 was confirmed by NOESY and $^{15}$N-HMBC.

Steps 3-5: These steps were executed in a manner similar (use of appropriate reagents and purification methods known to the person skilled in the art) to step 1, 2 and 3 towards Cpd. No. 157. From Int-40 (290 mg, 1.32 mmol, LC/MS 98%) was obtained crude product (380 mg, LC/MS 55%) which was purified by preparative HPLC method H5. The collected fractions were lyophilised to afford N-((4'-fluoro-3-(2-methyl-2H-1,2,3-triazol-4-yl)-[1,1'-biphenyl]-4-yl) methyl)acrylamide (Cpd. No. 187) as a white solid (54 mg, 12%). (LC/MS; m/z 337.3 $[M+H]^+$).

Synthesis of 5-(2-bromo-5-chlorophenyl)-2H-tetrazole (Int-41), 5-(2-bromo-5-chlorophenyl)-2-methyl-2H-tetrazole (Int-42) and 5-(2-bromo-5-chlorophenyl)-1-methyl-1H-tetrazole (Int-43)

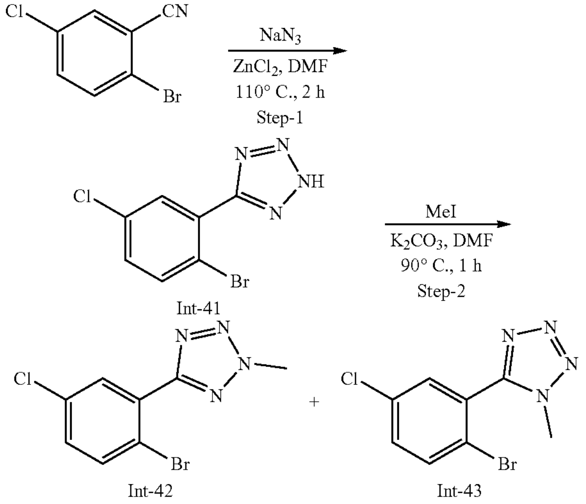

Step 1: A solution of 2-bromo-5-chlorobenzonitrile (6.0 g, 27.7 mmol) in DMF (60 mL) was treated with $ZnCl_2$ (4.1 g, 30.47 mmol) and $NaN_3$ (3.96 g, 60.94 mmol) at RT. The reaction mixture was stirred at 110° C. for 2 h and monitored by TLC. TLC mobile phase: 10% MeOH in DCM, RF: 0.1, TLC detection: UV. The reaction mixture was cooled, diluted with $H_2O$ (200 mL) and stirred for 30 min. The precipitated solid was collected by filtration, washed with $H_2O$ (50 mL) and dried under reduced pressure to afford 5-(2-bromo-5-chlorophenyl)-2H-tetrazole (Int-41) as an off-white solid (6.0 g, LC/MS 61%). (LC/MS; m/z 258.8 $[M+H]^+$). The product was used as such without further purification.

Step 2: This step was executed in a manner similar (use of appropriate reagents and purification methods known to the person skilled in the art) to step 5 towards Cpd. No. 192. From Int-41 was obtained crude product (4 g, LC/MS 97%; 73:27 mixture of N-Me regioisomers) which was purified by normal phase flash column chromatography using silica gel (100-200 mesh) and a gradient of 0-10% EtOAc in pet ether as an eluent to afford 5-(2-bromo-5-chlorophenyl)-2-methyl-2H-tetrazole (Int-42) (2.5 g, 39%) and 5-(2-bromo-5-chlorophenyl)-1-methyl-1H-tetrazole (Int-43) (1 g, 16%). (LC/MS; m/z 272.7 $[M+H]^+$).

Example 78: Synthesis of N-((4'-fluoro-3-(2-methyl-2H-tetrazol-5-yl)-[1,1'-biphenyl]-4-yl) methyl)acrylamide (Cpd. No. 188)

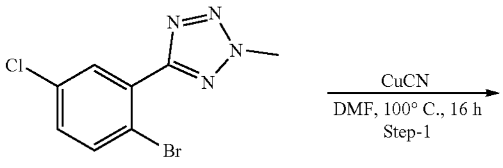

Int-42

-continued

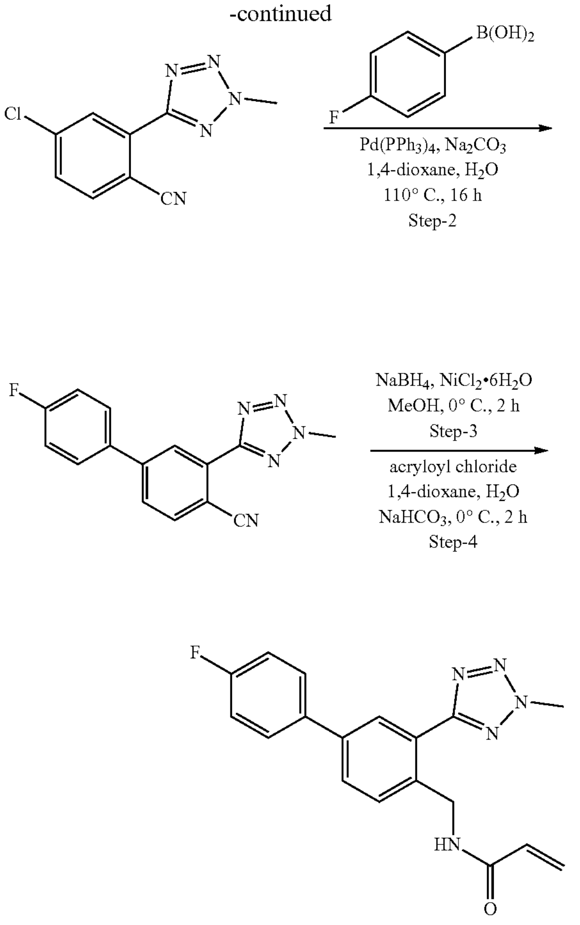

Cpd. No. 188

Step 1: A solution of Int-42 (2.5 g, 9.1 mmol) in DMF (20 mL) was treated with CuCN (6.25 g, 69.8 mmol) at RT. The reaction mixture was stirred at 100° C. for 16 h and monitored by TLC. TLC mobile phase: 20% EtOAc in pet ether, RF: 0.2, TLC detection: UV. The reaction mixture was cooled, diluted with $H_2O$ (100 mL) and extracted with EtOAc (2×200 mL). The organic layer was dried over anhydrous $Na_2SO_4$ and concentrated under reduced pressure to afford crude product (1.3 g) which was purified by normal phase flash column chromatography using silica gel (100-200 mesh) and a gradient of 0-15% EtOAc in pet ether as an eluent to afford 4-chloro-2-(2-methyl-2H-tetrazol-5-yl)benzonitrile as a yellow solid (350 mg, LC/MS 82%). (LC/MS; m/z 219.8 $[M+H]^+$).

Steps 2-4: These steps were executed in a manner similar (use of appropriate reagents and purification methods known to the person skilled in the art) to step 1, 2 and 3 towards Cpd. No. 157. From 4-chloro-2-(2-methyl-2H-tetrazol-5-yl) benzonitrile (330 mg, 1.5 mmol) was obtained crude product (300 mg, LC/MS 77%) which was purified by preparative HPLC method H2. The collected fractions were lyophilised to afford N-((4'-fluoro-3-(2-methyl-2H-tetrazol-5-yl)-[1,1'-biphenyl]-4-yl)methyl)acrylamide (Cpd. No. 188) as a white solid (94 mg, 18%). (LC/MS; m/z 338.2 $[M+H]^+$).

Compound Cpd. No. 189 (prepared from Int-43) was prepared in a manner similar (use of appropriate reagents and purification methods known to the person skilled in the art) to Cpd. No. 188.

Example 79: Synthesis of N-((3-(2-(difluoromethyl)-2H-tetrazol-5-yl)-4'-fluoro-[1,1'-biphenyl]-4-yl)methyl)acrylamide (Cpd. No. 190)

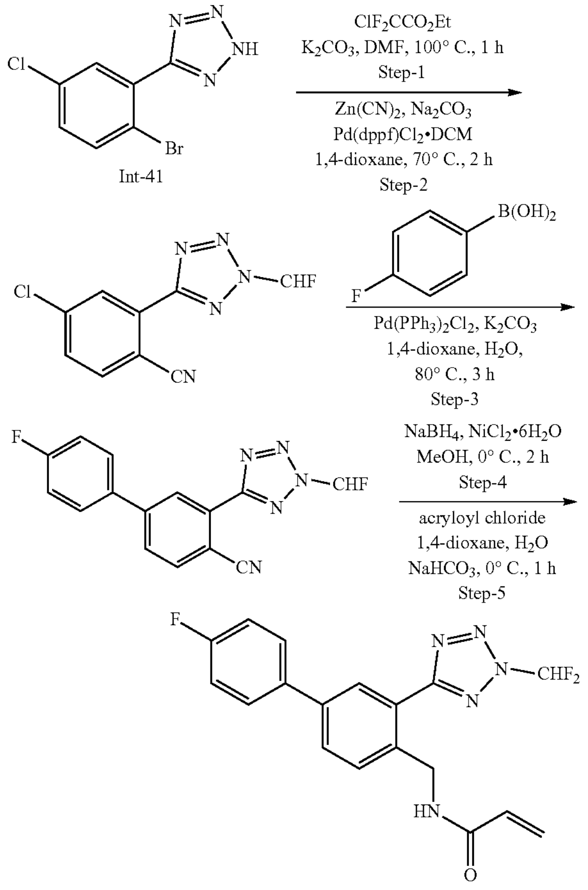

Cpd. No. 190

Step 1: This step was executed in a manner similar (use of appropriate reagents and purification methods known to the person skilled in the art) to step 3 towards Int-49. From Int-41 (5.0 g, 19.27 mmol) was obtained 5-(2-bromo-5-chlorophenyl)-2-(difluoromethyl)-2H-tetrazole as an off-white solid (1.3 g, 20%, LC/MS 89%). (LC/MS; m/z 308.9 $[M+H]^+$). $^1H$ NMR (400 MHz, DMSO-$d_6$) δ ppm: 8.56-8.85 (m, 1H), 7.98-7.99 (d, 1H), 7.92-7.94 (d, 1H), 7.64-7.67 (m, 1H).

Step 2: This step was executed in a manner similar (use of appropriate reagents and purification methods known to the person skilled in the art) to step 4 towards Cpd. No. 176. From 5-(2-bromo-5-chlorophenyl)-2-(difluoromethyl)-2H-tetrazole (3.0 g, 9.69 mmol, LC/MS 88%) was obtained 4-chloro-2-(2-(difluoromethyl)-2H-tetrazol-5-yl)benzonitrile as a pale yellow solid (900 mg, 33%, LC/MS 80%). (LC/MS; m/z 256.1 $[M+H]^+$).

Steps 3-5: These steps were executed in a manner similar (use of appropriate reagents and purification methods known to the person skilled in the art) to step 1, 2 and 3 towards Cpd. No. 157. From 4-chloro-2-(2-(difluoromethyl)-2H-tetrazol-5-yl)benzonitrile (380 mg, 1.5 mmol, LC/MS 80%) was obtained crude product (300 mg, LC/MS 50%) which was purified by preparative HPLC method H2. The collected fractions were lyophilised to afford N-((3-(2-(difluoromethyl)-2H-tetrazol-5-yl)-4'-fluoro-[1,1'-biphenyl]-4-yl) methyl)acrylamide (Cpd. No. 190) as an off-white solid (42 mg, 9%). (LC/MS; m/z 374.3 $[M+H]^+$).

Example 80: Synthesis of N-((4'-fluoro-3-(1H-1,2,3-triazol-1-yl)-[1,1'-biphenyl]-4-yl)methyl)acrylamide (Cpd. No. 191)

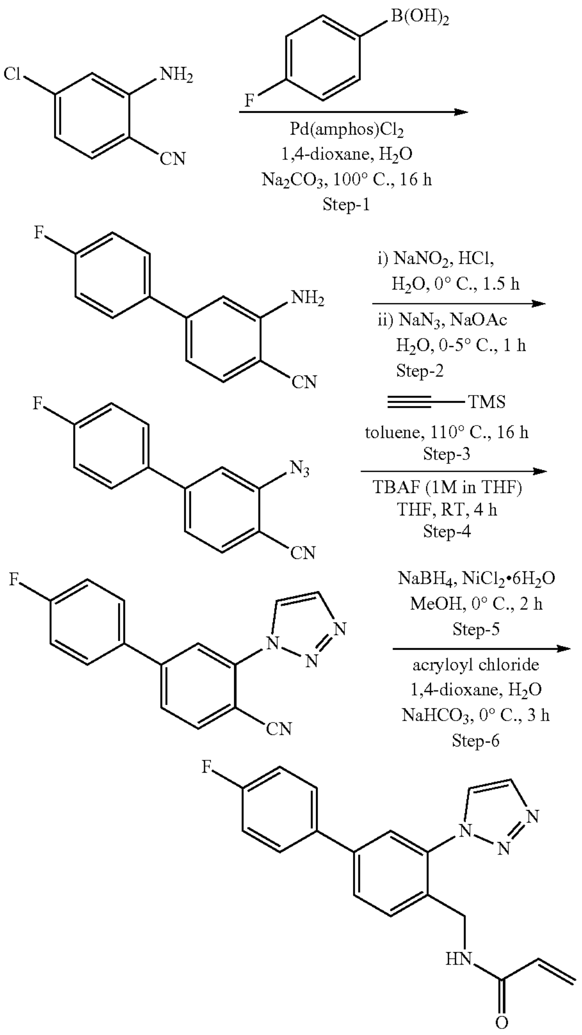

Cpd. No. 191

Step 1: This step was executed in a manner similar (use of appropriate reagents and purification methods known to the person skilled in the art) to step 6 to Int-26.HCl. From 2-amino-4-chlorobenzonitrile (2.0 g, 13.1 mmol) was obtained 3-amino-4'-fluoro-[1,1'-biphenyl]-4-carbonitrile as a yellow solid (1.8 g, 64%). (LC/MS; m/z 213.1 $[M+H]^+$).

Step 2: To a stirred suspension of 3-amino-4'-fluoro-[1,1'-biphenyl]-4-carbonitrile (1.70 g, 8.02 mmol) in conc HCl (8.5 mL) and $H_2O$ (8.5 mL) was added dropwise an aq $NaNO_2$ solution (828 mg, 12 mmol; in 8.5 mL $H_2O$) at 0° C. The reaction mixture was stirred at 0° C. for 1.5 h and treated with $NaN_3$ (780 mg, 12.0 mmol) and NaOAc (984 mg, 12.0 mmol), dissolved in $H_2O$ (42.5 mL). The reaction mixture was stirred for 1 h at 0° C. and monitored by TLC. TLC mobile phase: 20% EtOAc in pet ether, RF: 0.5, TLC detection: UV. The mixture was extracted with EtOAc (2×200 mL). The combined organic layer was washed with brine (2×125 mL), dried over anhydrous $Na_2SO_4$ and concentrated under reduced pressure to afford crude product (1.7 g) which was purified by normal phase flash column chromatography using silica gel (100-200 mesh) and a gradient of 0-10% EtOAc in pet ether as an eluent to afford 3-azido-4'-fluoro-[1,1'-biphenyl]-4-carbonitrile as a white solid (1.1 g, 57%). $^1H$ NMR (300 MHz, $CDCl_3$) b ppm: 7.68-7.65 (dd, 1H), 7.58-7.53 (m, 2H), 7.38-7.35 (dd, 2H), 7.22-7.16 (m, 2H).

Step 3: A solution of 3-azido-4'-fluoro-[1,1'-biphenyl]-4-carbonitrile (1.09 g, 4.60 mmol) and trimethylsilylacetylene (1.35 g, 13.80 mmol) in toluene (5.5 mL) was heated at 110° C. for 16 h (sealed tube) and monitored by TLC. TLC mobile phase: 20% EtOAc in pet ether, RF: 0.7, TLC detection: UV. The reaction mixture was concentrated under reduced pressure to afford the crude residue which was triturated with n-pentane (10.0 mL) to afford 4'-fluoro-3-(4-(trimethylsilyl)-1H-1,2,3-triazol-1-yl)-[1,1'-biphenyl]-4-carbonitrile as a yellow solid (1.2 g, 77%). (LC/MS; m/z 337.2 $[M+H]^+$).

Step 4: To a solution of 4'-fluoro-3-(4-(trimethylsilyl)-1H-1,2,3-triazol-1-yl)-[1,1'-biphenyl]-4-carbonitrile (1.20 g, 3.57 mmol) in THF (15.0 mL) was added dropwise TBAF (1M in THF) (3.96 mL, 3.96 mmol) at RT. the reaction mixture was stirred at RT for 4 h and monitored by TLC. TLC mobile phase: 30% EtOAc in pet ether, RF: 0.4, TLC detection: UV. The reaction mixture was concentrated under reduced pressured and the crude residue was triturated with n-pentane (15.0 mL) to afford 4'-fluoro-3-(1H-1,2,3-triazol-1-yl)-[1,1'-biphenyl]-4-carbonitrile as an off white solid (930 mg, 99%). (LC/MS; m/z 265.2 $[M+H]^+$).

Steps 5-6: These steps were executed in a manner similar (use of appropriate reagents and purification methods known to the person skilled in the art) to step 3 and 4 towards Cpd. No. 193. From 4'-fluoro-3-(1H-1,2,3-triazol-1-yl)-[1,1'-biphenyl]-4-carbonitrile (500 mg, 1.89 mmol) was obtained crude product (250 mg, LC/MS 53%) which was purified by preparative HPLC method H1. The collected fractions were lyophilised to afford N-((4'-fluoro-3-(1H-1,2,3-triazol-1-yl)-[1,1'-biphenyl]-4-yl)methyl)-acrylamide (Cpd. No. 191) as an off-white solid (50 mg, 8%). (LC/MS; m/z 323.2 $[M+H]^+$).

Example 81: Synthesis of N-((3-fluoro-5-(1-methyl-1H-pyrazol-3-yl)-4'-(trifluoromethyl)-[1,1'-biphenyl]-4-yl)methyl)acrylamide (Cpd. No. 192)

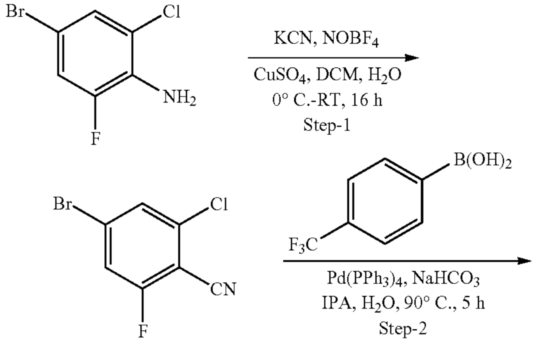

-continued

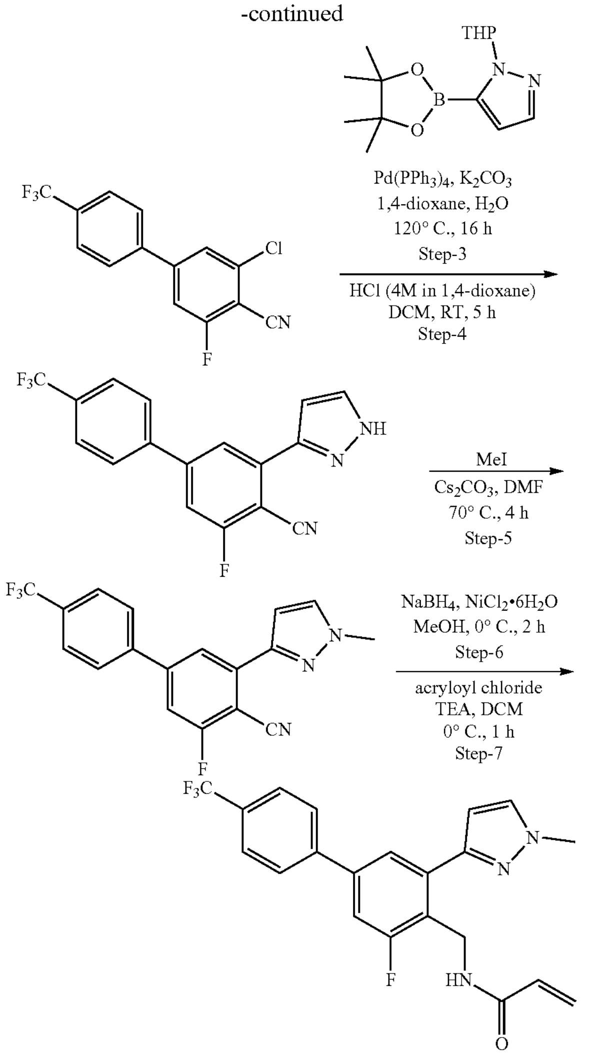

Cpd. No. 192

Step 1: A mixture of 4-bromo-2-chloro-6-fluoroaniline (10 g, 44.5 mmol) and $NOBF_4$ (5.76 g, 49.3 mmol) in DCM (100 mL) was stirred at 25° C. for 1 h. The mixture was cooled to 0° C. and treated with KCN (5.82 g, 89.6 mmol) and $CuSO_4 \cdot 5H_2O$ (22.4 g, 89.6 mmol), dissolved in $H_2O$ (50 mL). The reaction mixture was stirred for 16 h at RT and monitored by TLC. TLC mobile phase: 10% EtOAc in pet ether, RF: 0.72, TLC detection: UV. The reaction mixture was diluted with sat aq $Na_2CO_3$ (50 mL) and DCM (50 mL) and filtered through a celite pad. The organic layer was dried over anhydrous $Na_2SO_4$ and concentrated under vacuum to afford crude product (5.0 g) which was purified by normal phase flash column chromatography using a 24 g column (silica) and pet ether as an eluent to afford 4-bromo-2-chloro-6-fluorobenzonitrile as an orange solid (3.0 g, 29%). $^1H$ NMR: (400 MHz, $CDCl_3$) δ ppm: 7.53-7.54 (s, 1H), 7.26-7.37 (d, 1H).

Step 2: This step was executed in a manner similar (use of appropriate reagents and purification methods known to the person skilled in the art) to step 1 towards Cpd. No. 193. Reacting 4-bromo-2-chloro-6-fluorobenzonitrile (2.7 g, 11.5 mmol) with (4-(trifluoromethyl)phenyl)boronic acid (3.5 g, 18.6 mmol) afforded 3-chloro-5-fluoro-4'-(trifluoromethyl)-[1,1'-biphenyl]-4-carbonitrile as an off-white solid (1.7 g, 49%). (LC/MS; m/z 299.1 [M+H]$^+$).

Steps 3-4: These steps were executed in a manner similar (use of appropriate reagents and purification methods known to the person skilled in the art) to step 3 and 4 to Int-26.HCl. From 3-chloro-5-fluoro-4'-(trifluoromethyl)-[1,1'-biphenyl]-4-carbonitrile (2.0 g, 6.7 mmol) was obtained 3-fluoro-5-(1H-pyrazol-3-yl)-4'-(trifluoromethyl)-[1,1'-biphenyl]-4-carbonitrile as a brown gum (350 mg, 16%). (LC/MS; m/z 332.0 [M+H]$^+$).

Step 5: A solution of 3-fluoro-5-(1H-pyrazol-3-yl)-4'-(trifluoromethyl)-[1,1'-biphenyl]-4-carbonitrile (330 mg, 0.997 mmol) in ACN (20 mL) was treated with $Cs_2CO_3$ (1.17 g, 3.589 mmol) at 0° C. After 30 min of stirring at 0° C., MeI (184 mg, 1.29 mmol) was added. The reaction mixture was stirred at 70° C. for 4 h and monitored by TLC. TLC mobile phase: 30% EtOAc in pet ether, RF: 0.30, TLC detection: UV. The reaction mixture was cooled, diluted with $H_2O$ (10 mL) and extracted with EtOAc (50 mL). The organic layer was dried over anhydrous $Na_2SO_4$ and concentrated under reduced pressure to afford crude product (400 mg, LC/MS 39%; 79:21 mixture of N-Me regioisomers) which was purified by normal phase flash column chromatography using a 24 g column (silica) and a gradient of 0-15% EtOAc in pet ether as an eluent to afford 3-fluoro-5-(1-methyl-1H-pyrazol-3-yl)-4'-(trifluoromethyl)-[1,1'-biphenyl]-4-carbonitrile (75:24 mixture of N-Me regioisomers) as pale yellow solid (200 mg, 58%). (LC/MS; m/z 346.2 [M+H]$^+$).

Steps 6-7: These steps were executed in a manner similar (use of appropriate reagents and purification methods known to the person skilled in the art) to step 2 and 3 towards Cpd. No. 152. From 3-fluoro-5-(1-methyl-1H-pyrazol-3-yl)-4'-(trifluoromethyl)-[1,1'-biphenyl]-4-carbonitrile (180 mg, 0.521 mmol) was obtained crude product (300 mg, LC/MS 35%) which was purified by preparative HPLC method H1. The collected fractions were lyophilised to afford N-((3-fluoro-5-(1-methyl-1H-pyrazol-3-yl)-4'-(trifluoromethyl)-[1,1'-biphenyl]-4-yl)methyl)-acrylamide (Cpd. No. 192) as an off-white solid (15 mg, 7%). (LC/MS; m/z 404.2[M+H]$^+$).

Example 82: Synthesis of N-((6-(4-fluorophenyl)-2-(1-methyl-1H-pyrazol-3-yl)pyridin-3-yl)methyl) acrylamide (Cpd. No. 193)

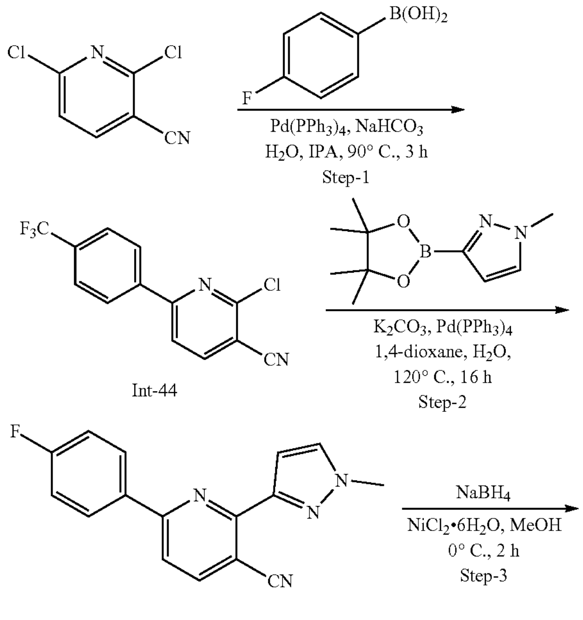

Int-44

-continued

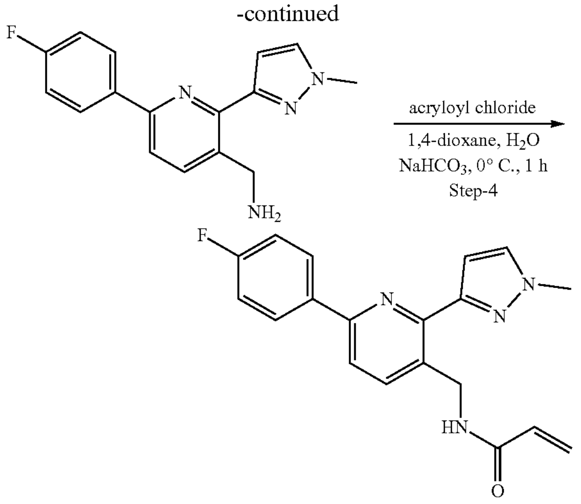

Cpd. No. 193

Step 1: A mixture of 2,6-dichloronicotinonitrile (1.5 g, 8.7 mmol), (4-fluorophenyl)boronic acid (1.94 g, 13.9 mmol) and $NaHCO_3$ (1 M, 33 mL) in IPA (100 mL) was degassed with argon for 10 min followed by addition of $Pd(PPh_3)_4$ (1.00 g, 0.87 mmol). The mixture was stirred at 90° C. for 3 h and monitored by TLC. TLC mobile phase: 10% EtOAc in pet ether, RF: 0.47, TLC detection: UV. The cooled reaction mixture was filtered through a celite pad and washed with EtOAc (100 mL). The filtrate was washed with $H_2O$ (30 mL) and the organic layer was dried over anhydrous $Na_2SO_4$ and concentrated under reduced pressure to afford the crude product (1.5 g). The crude product was purified by normal phase flash column chromatography using a 24 g column (silica) and a gradient of 0-6% EtOAc in pet ether as an eluent to afford 2-chloro-6-(4-fluorophenyl)nicotinonitrile (Int-44) as an off-white solid (1.1 g, 54%). (LC/MS; m/z 233.1 $[M+H]^+$).

Step 2: A mixture of Int-44 (1.1 g, 4.7 mmol), 1-methyl-3-(4,4,5,5-tetramethyl-1,3,2-dioxaborolan-2-yl)-1H-pyrazole (0.98 g, 4.7 mmol) and $K_2CO_3$ (1.3 g, 9.4 mmol) in 1,4-dioxane (10 mL) and $H_2O$ (1 mL) was degassed with argon for 10 min followed by addition of $Pd(PPh_3)_4$ (0.54 g, 0.47 mmol). The mixture was stirred at 120° C. for 16 h (sealed tube) and monitored by TLC. TLC mobile phase: 20% EtOAc in pet ether, RF: 0.45, TLC detection: UV. The cooled reaction mixture was filtered through a celite pad and washed with EtOAc (100 mL). The filtrate was washed with $H_2O$ (20 mL) and the organic layer was dried over anhydrous $Na_2SO_4$ and concentrated under reduced pressure to afford the crude product (1.2 g, LC/MS 34%). The crude product was purified by normal phase flash column chromatography using a 24 g column (silica) and a gradient of 0-10% EtOAc in pet ether as an eluent to afford 6-(4-fluorophenyl)-2-(1-methyl-1H-pyrazol-3-yl)nicotinonitrile (0.40 g, 31%). (LC/MS; m/z 279.2 $[M+H]^+$).

Step 3: A solution of 6-(4-fluorophenyl)-2-(1-methyl-1H-pyrazol-3-yl)nicotinonitrile (0.200 g, 0.71 mmol) in MeOH (10 mL) was treated with $NiCl_2 \cdot 6H_2O$ (0.10 g, 0.42 mmol) and $NaBH_4$ (0.188 g, 4.97 mmol) at 0° C. The mixture was stirred at 0° C. for 2 h and monitored by TLC. TLC mobile phase: 10% MeOH in DCM, RF: 0.1, TLC detection: UV. The reaction mixture was filtered through a celite pad and washed with EtOAc (50 mL). The filtrate was washed with brine (50 mL) and the organic layer was dried over anhydrous $Na_2SO_4$ and concentrated under reduced pressure to afford (6-(4-fluorophenyl)-2-(1-methyl-1H-pyrazol-3-yl)pyridin-3-yl)methanamine (0.180 g, 89%). (LC/MS; m/z 283.3 $[M+H]^+$). The product was used as such without further purification.

Step 4: To a solution of (6-(4-fluorophenyl)-2-(1-methyl-1H-pyrazol-3-yl)pyridin-3-yl)methanamine (0.170 g, 0.6 mmol) in 1,4-dioxane (10 mL) and $H_2O$ (2 mL) was added $NaHCO_3$ (0.152 g, 1.8 mmol). To the mixture was added acryloyl chloride (55 mg, 0.6 mmol) at 0° C. The reaction mixture was stirred at 0° C. for 1 h and monitored by TLC. TLC mobile phase: 5% MeOH in DCM, RF: 0.4, TLC detection: UV. The reaction mixture was diluted with DCM (50 mL) and washed with brine (50 mL). The organic layer was dried over anhydrous $Na_2SO_4$ and concentrated under reduced pressure to afford the crude product (200 mg, LC/MS 32%) which was purified by preparative HPLC method H1. The collected fractions were lyophilised to afford N-((6-(4-fluorophenyl)-2-(1-methyl-1H-pyrazol-3-yl)pyridin-3-yl)methyl)acrylamide (Cpd. No. 193) as a white solid (27 mg, 13%). (LC/MS; m/z 337.2 $[M+H]^+$).

Compound Cpd. No. 194 was prepared in a manner similar (use of appropriate reagents and purification methods known to the person skilled in the art) towards Cpd. No. 193.

Synthesis of 6-(4-fluorophenyl)-2-(1H-pyrazol-5-yl) nicotinonitrile hydrochloride (Int-45)

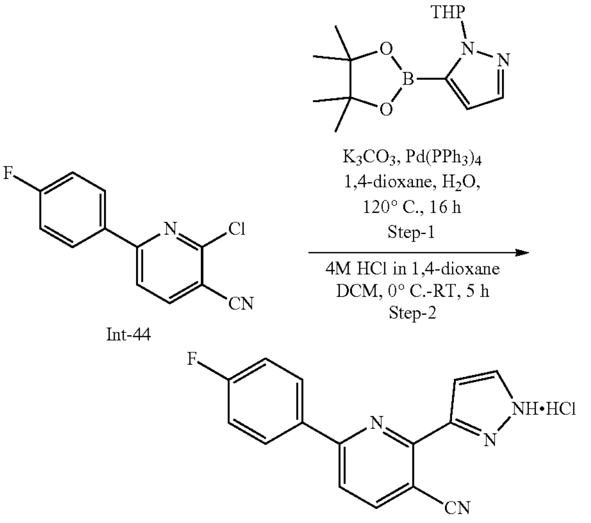

Int-44

Int-45

Step 1: This step was executed in a manner similar (use of appropriate reagents and purification methods known to the person skilled in the art) to step 2 towards Cpd. No. 193. Reacting Int-44 (6.7 g, 28.9 mmol) with 1-(tetrahydro-2H-pyran-2-yl)-5-(4,4,5,5-tetramethyl-1,3,2-dioxaborolan-2-yl)-1H-pyrazole (12.0 g, 43.3 mmol) yielded crude product (7.5 g, LC/MS 47%) which was purified by normal phase flash column chromatography using a 40 g column (silica) and a gradient of 0-12% EtOAc in pet ether as an eluent to afford 6-(4-fluorophenyl)-2-(1-(tetrahydro-2H-pyran-2-yl)-1H-pyrazol-5-yl)nicotinonitrile as a pale yellow solid (3.5 g, 35%). (LC/MS; m/z 349.3 $[M+H]^+$).

Step 2: A solution of 6-(4-fluorophenyl)-2-(1-(tetrahydro-2H-pyran-2-yl)-1H-pyrazol-5-yl)nicotinonitrile (3.5 g, 10.0 mmol) in DCM (10 mL) at 0° C. was treated with HCl (4M in 1,4-dioxane; 40 mL). The reaction mixture was stirred at RT for 5 h and monitored by TLC. TLC mobile phase: 30% EtOAc in pet ether, RF: 0.25, TLC detection: UV. The reaction mixture was diluted with DCM (10 mL) and the solid obtained was collected by filtration, washed with DCM (50 mL) and dried under vacuum to afford 6-(4-fluorophenyl)-2-(1H-pyrazol-3-yl)nicotinonitrile hydrochloride (Int-45) as an off-white solid (1.8 g, 60%). (LC/MS; m/z 265.1 $[M+H]^+$).

Synthesis of 2-(1-(cyclopropylmethyl)-1H-pyrazol-3-yl)-6-(4-fluorophenyl)nicotinonitrile (Int-46), 2-(1-cyclopropyl-1H-pyrazol-3-yl)-6-(4-fluorophenyl)nicotinonitrile (Int-47), 2-(1-cyclopropyl-1H-pyrazol-5-yl)-6-(4-fluorophenyl)nicotinonitrile (Int-48), and 2-(1-(difluoromethyl)-1H-pyrazol-3-yl)-6-(4-fluorophenyl)nicotinonitrile (Int-49)

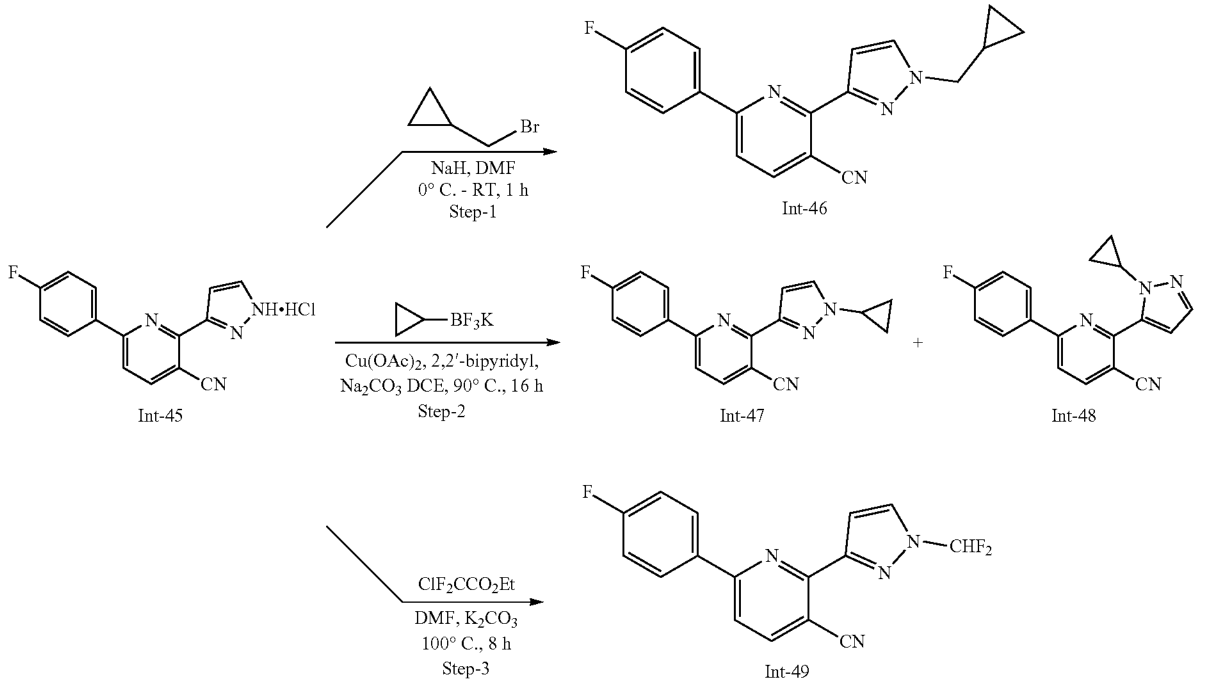

Step 1: A solution of Int-45 (0.5 g, 1.7 mmol) in DMF (6.0 mL) was cooled to 0° C., treated with NaH (60% in mineral oil) (120 mg, 5.0 mmol) and stirred for 10 min. (Bromomethyl)cyclopropane (337 mg, 2.49 mmol) was added and the reaction mixture was stirred at RT for 1 h. The reaction was monitored by TLC. TLC mobile phase: 30% EtOAc in pet ether, RF: 0.53, TLC detection: UV. The reaction mixture was poured into ice $H_2O$ (50 mL) and extracted with EtOAc (2×30 mL). The combined organic layer was washed with brine (20 mL), dried over anhydrous $Na_2SO_4$ and concentrated under reduced pressure to afford the crude product which was purified by normal phase flash column chromatography using a 24 g column (silica) and a gradient of 0-10% EtOAc in pet ether as an eluent to afford a 75:25 mixture of two regioisomers as a pale yellow gum (0.484 g, 91%). The major regioisomer was identified as 2-(1-(cyclopropylmethyl)-1H-pyrazol-3-yl)-6-(4-fluorophenyl)nicotinonitrile Int-46. (LC/MS; m/z 319.2 $[M+H]^+$). The product was used as such without further purification.

Step 2: A suspension of Int-45 (0.5 g, 1.7 mmol) and potassium cyclopropyltrifluoroborate (491 mg, 3.33 mmol) in DCE (5 mL) was treated with $Na_2CO_3$ (704 mg, 6.64 mmol), 2,2'-bipyridyl (259 mg, 1.66 mmol) and $Cu(OAc)_2$ (301 mg, 1.66 mmol). The reaction mixture was stirred at 90° C. for 16 h and monitored by TLC. TLC mobile phase: 20% EtOAc in pet ether, RF: 0.6, TLC detection: UV. The reaction mixture was cooled to RT, filtered through a celite pad and washed with EtOAc (40 mL). The filtrate was washed with brine (2×30 mL), dried over anhydrous $Na_2SO_4$ and concentrated under reduced pressure to afford the crude product which was purified by normal phase flash column chromatography using 12 g column (silica) and a gradient of 0-10% EtOAc in pet ether as an eluent to afford a 55:45 mixture of two regioisomers 2-(1-cyclopropyl-1H-pyrazol-3-yl)-6-(4-fluorophenyl)nicotinonitrile (Int-47) and 2-(1-cyclopropyl-1H-pyrazol-5-yl)-6-(4-fluorophenyl)nicotinonitrile (Int-48) as an off-white solid (420 mg, 83%). (LC/MS; m/z 305.2 $[M+H]^+$). The product was used as such without further purification.

Step 3: A solution of Int-45 (0.5 g, 1.7 mmol) in DMF (10 mL) at RT was treated with $K_2CO_3$ (2.74 g, 19.9 mmol) and ethyl 2-chloro-2,2-difluoroacetate (2.15 g, 13.6 mmol). The reaction mixture was stirred at 100° C. for 8 h and monitored by TLC. TLC mobile phase: 23% EtOAc in pet ether, RF: 0.3, TLC detection: UV. The reaction mixture was cooled to RT, filtered through a celite pad and washed with EtOAc (150 mL). The filtrate was washed with brine (100 mL), dried over anhydrous $Na_2SO_4$ and concentrated under reduced pressure to afford the crude product which was purified by normal phase flash column chromatography using a 40 g column (silica) and a gradient of 0-18% EtOAc in pet ether as an eluent to afford 2-(1-(difluoromethyl)-1H-pyrazol-3-yl)-6-(4-fluorophenyl)nicotinonitrile (Int-49) as a white solid (150 mg, 28%). (LC/MS; m/z 315.2 $[M+H]^+$).

Example 83: Synthesis of N-((2-(1-(cyclopropylmethyl)-1H-pyrazol-3-yl)-6-(4-fluorophenyl)pyridin-3-yl)methyl)acrylamide (Cpd. No. 195)

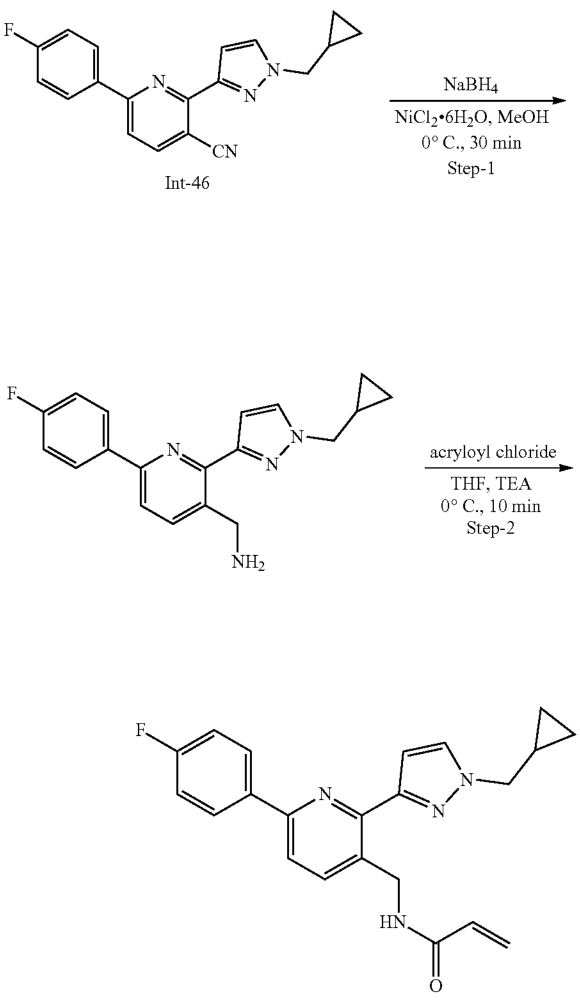

Int-46

Cpd. No. 195

Steps 1-2: These steps were executed in a manner similar (use of appropriate reagents and purification methods known to the person skilled in the art) to step 3 and 4 towards Cpd. No. 193. Int-46 (0.55 g, 1.7 mmol) (75:25 mixture of two regioisomers) yielded crude product which was purified by normal phase flash column chromatography using a 24 g column (silica) and a gradient of 0-34% EtOAc in pet ether as an eluent. The obtained product was further purified by preparative HPLC method H1. The collected fractions were lyophilised to afford N-((2-(1-(cyclopropylmethyl)-1H-pyrazol-3-yl)-6-(4-fluorophenyl)pyridin-3-yl)methyl)acrylamide (Cpd. No. 195) as an off-white solid (64 mg, 10%). (LC/MS; m/z 377.3 $[M+H]^+$).

The following compounds were prepared in a manner similar (use of appropriate reagents and purification methods known to the person skilled in the art) to Cpd. No. 195: Cpd. No. 196 and Cpd. No. 197 (prepared from a 55:45 mixture of regioisomers Int-47 and Int-48), and Cpd. No. 198 (prepared from Int-49).

Example 84: Synthesis of N-((2-(2-(difluoromethyl)-2H-tetrazol-5-yl)-6-(4-fluorophenyl)pyridin-3-yl)methyl)acrylamide (Cpd. No. 199)

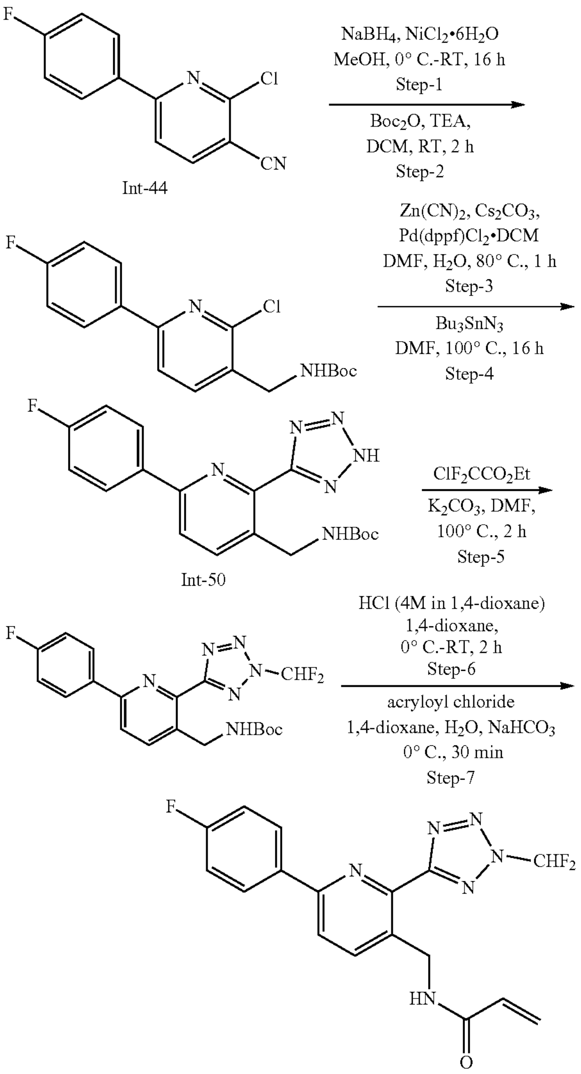

Int-44

Int-50

Cpd. No. 199

Step 1: This step was executed in a manner similar (use of appropriate reagents and purification methods known to the person skilled in the art) to step 3 towards Cpd. No. 193. From Int-44 (6.0 g, 25.9 mmol) was obtained (2-chloro-6-(4-fluorophenyl)pyridin-3-yl)methanamine as an off-white solid (6.0 g, LC/MS 49%). (LC/MS; m/z 237.1 $[M+H]^+$). The product was used as such without further purification.

Step 2: A solution of (2-chloro-6-(4-fluorophenyl)pyridin-3-yl)methanamine (6.0 g, 25.42 mmol) in DCM (150 mL) was treated with TEA (5.1 g, 5.84 mmol) and $Boc_2O$ (5.5 g, 25.42 mmol). The reaction mixture was stirred at RT for 2 h and monitored by TLC. TLC mobile phase: 20% EtOAc in pet ether, RF: 0.4, TLC detection: UV. The reaction mixture was diluted with $H_2O$ (200 mL) and extracted with DCM (200 mL). The combined organic layer was dried over anhydrous $Na_2SO_4$ and concentrated under reduced pressure to afford crude product (6.0 g, LC/MS 37%) which was purified by normal phase flash column chromatography using a 80 g column (silica) and a gradient of 0-5% EtOAc in pet ether as an eluent to afford tert-butyl ((2-chloro-6-(4-fluorophenyl)pyridin-3-yl)methyl)carbamate as a white solid (2.5 g, 47%, LC/MS 79%). (LC/MS; m/z 337.2 $[M+H]^+$).

Step 3: This step was executed in a manner similar (use of appropriate reagents and purification methods known to the person skilled in the art) to step 4 towards Cpd. No. 176. From tert-butyl ((2-chloro-6-(4-fluorophenyl)pyridin-3-yl) methyl)carbamate (2.5 g, 7.44 mmol) was obtained tert-butyl ((2-cyano-6-(4-fluorophenyl)pyridin-3-yl)methyl)carbamate as an off-white solid (370 mg, 18%, LC/MS 97%). (LC/MS; m/z 328.3 $[M+H]^+$).

Step 4: This step was executed in a manner similar (use of appropriate reagents and purification methods known to the person skilled in the art) to step 1 towards Cpd. No. 204. From tert-butyl ((2-cyano-6-(4-fluorophenyl)pyridin-3-yl) methyl)carbamate (900 mg, 2.75 mmol) was obtained tert-butyl ((6-(4-fluorophenyl)-2-(2H-tetrazol-5-yl)pyridin-3-yl) methyl)carbamate (Int-50) as a light brown gum (1.0 g, 83%, LC/MS 82%). (LC/MS; m/z 371.3 $[M+H]^+$).

Step 5: This step was executed in a manner similar (use of appropriate reagents and purification methods known to the person skilled in the art) to step 3 towards Int-49. From Int-50 (800 mg, 2.16 mmol) was obtained tert-butyl ((2-(2-(difluoromethyl)-2H-tetrazol-5-yl)-6-(4-fluorophenyl)pyridin-3-yl)methyl)carbamate as a pale yellow solid (420 mg, 55%, LC/MS 98%). (LC/MS; m/z 421.3 $[M+H]^+$). The structure was confirmed by NOESY and 2D NMR.

Step 6: A solution of tert-butyl ((2-(2-(difluoromethyl)-2H-tetrazol-5-yl)-6-(4-fluorophenyl) pyridin-3-yl)methyl) carbamate (300 mg, 0.74 mmol) in 1,4-dioxane (3 mL) was treated with HCl (4M in 1,4-dioxane; 3 mL) at 0° C. The reaction mixture was stirred at RT for 2 h and monitored by TLC. TLC mobile phase: 5% MeOH in DCM, RF: 0.2, TLC detection: UV. The reaction mixture was concentrated under reduced pressure to afford crude (2-(2-(difluoromethyl)-2H-tetrazol-5-yl)-6-(4-fluorophenyl)pyridin-3-yl)methanamine hydrochloride (300 mg, LC/MS 94%). (LC/MS; m/z 321.2 $[M+H]^+$). The product was used as such without further purification.

Step 7: This step was executed in a manner similar (use of appropriate reagents and purification methods known to the person skilled in the art) to step 4 towards Cpd. No. 193. (2-(2-(difluoromethyl)-2H-tetrazol-5-yl)-6-(4-fluorophenyl) pyridin-3-yl)methanamine hydrochloride (300 mg, 0.84 mmol) yielded crude product (300 mg, LC/MS 88%) which was purified by preparative HPLC method H5. The collected fractions were lyophilised to afford N-((2-(2-(difluoromethyl)-2H-tetrazol-5-yl)-6-(4-fluorophenyl)pyridin-3-yl) methyl)acrylamide (Cpd. No. 199) as an off-white solid (141 mg, 47%). (LC/MS; m/z 375.2 $[M+H]^+$).

Example 85: Synthesis of N-((6-(4-fluorophenyl)-2-(2H-tetrazol-5-yl)pyridin-3-yl)methyl)acrylamide (Cpd. No. 200)

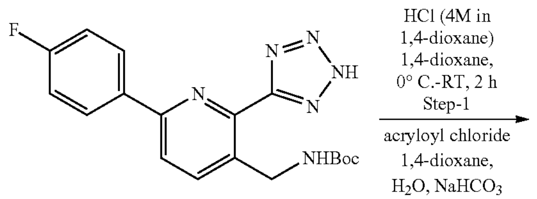

Int-50

-continued

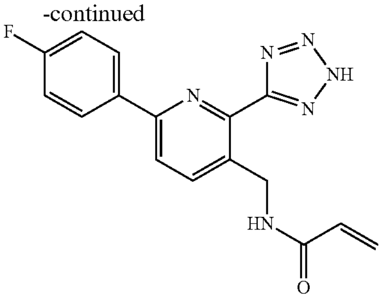

Cpd. No. 200

Step 1: A solution of Int-50 (150 mg, 0.40 mmol, LC/MS 83%) in 1,4-dioxane (3 mL) was treated with HCl (4M in 1,4-dioxane; 3 mL) at 0° C. The reaction mixture was stirred at RT for 2 h and was monitored by TLC. TLC mobile phase: 10% MeOH in DCM, RF: 0.1, TLC detection: UV. The reaction mixture was concentrated under reduced pressure to afford crude (6-(4-fluorophenyl)-2-(2H-tetrazol-5-yl)pyridin-3-yl)methanamine (150 mg, LC/MS 52%). (LC/MS; m/z 271.3 $[M+H]^+$). The product was used as such without further purification.

Step 2: This step was executed in a manner similar (use of appropriate reagents and purification methods known to the person skilled in the art) to step 4 towards Cpd. No. 193. (6-(4-fluorophenyl)-2-(2H-tetrazol-5-yl)pyridin-3-yl)methanamine (150 mg, 0.49 mmol, LC/MS 52%) yielded crude product (150 mg, LC/MS 39%) which was purified by preparative HPLC method H3. The collected fractions were lyophilised to afford N-((6-(4-fluorophenyl)-2-(2H-tetrazol-5-yl)pyridin-3-yl)methyl)acrylamide (Cpd. No. 200) as a white solid (11 mg, 12%). (LC/MS; m/z 325.2 $[M+H]^+$).

Example 86: Synthesis of N-((5-(4-fluorophenyl)-3-(1-methyl-1H-pyrazol-3-yl)pyridin-2-yl)methyl) acrylamide (Cpd. No. 201)

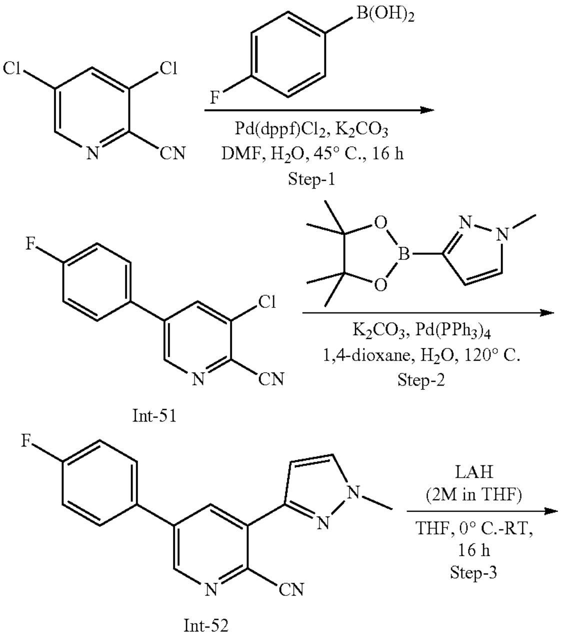

-continued

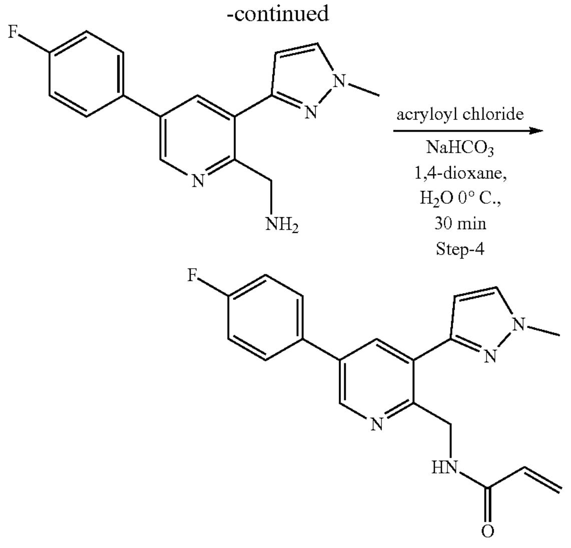

Cpd. No. 201

Steps 1-4: These steps were executed in a manner similar (use of appropriate reagents and purification methods known to the person skilled in the art) to Cpd. No. 193. 3,5-Dichloropicolinonitrile (2.0 g, 11.6 mmol) yielded crude product which was purified by preparative HPLC method H5. The collected fractions were lyophilised to afford N-((5-(4-fluorophenyl)-3-(1-methyl-1H-pyrazol-3-yl)pyridin-2-yl)methyl)acrylamide (Cpd. No. 201) as a white solid (2 mg, 0.5%). (LC/MS; m/z 337.2 [M+H]$^+$).

Synthesis of 5-(4-fluorophenyl)-3-(1H-pyrazol-3-yl) picolinonitrile hydrochloride (Int-53)

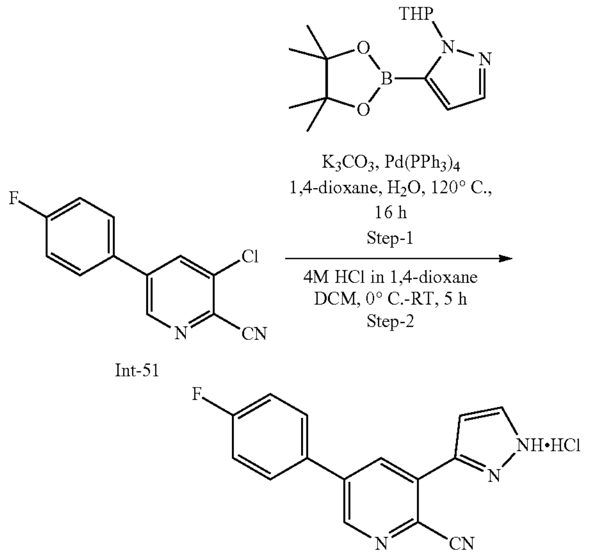

Int-51

Int-53

Steps 1-2: These steps were executed in a manner similar (use of appropriate reagents and purification methods known to the person skilled in the art) to Int-45. Int-51 (4.5 g, 19.4 mmol) yielded 5-(4-fluorophenyl)-3-(1H-pyrazol-5-yl)picolinonitrile hydrochloride (Int-53) as a white solid (2.9 g, 50%). (LC/MS; m/z 265.2 [M+H]$^+$).

Example 87: Synthesis of N-((3-(1-cyclopropyl-1H-pyrazol-3-yl)-5-(4-fluorophenyl)pyridin-2-yl) methyl)acrylamide (Cpd. No. 202)

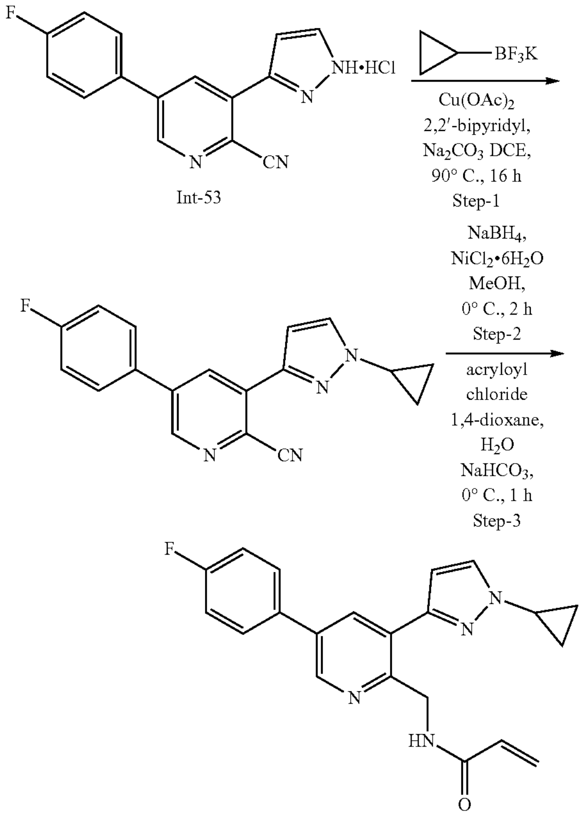

Int-53

Cpd. No. 202

Steps 1-3: These steps were executed in a manner similar (use of appropriate reagents and purification methods known to the person skilled in the art) to Cpd. No. 196. Int-53) (500 mg, 1.7 mmol) yielded crude product which was purified by preparative HPLC method H1. The collected fractions were lyophilised to afford N-((3-(1-cyclopropyl-1H-pyrazol-3-yl)-5-(4-fluorophenyl)pyridin-2-yl)methyl)-acrylamide (Cpd. No. 202) as an off-white solid (24 mg, 4%). (LC/MS; m/z 363.2 [M+H]$^+$).

Example 88: Synthesis of N-((3-(1-(difluoromethyl)-1H-pyrazol-3-yl)-5-(4-fluorophenyl)pyridin-2-yl)methyl)acrylamide (Cpd. No. 203)

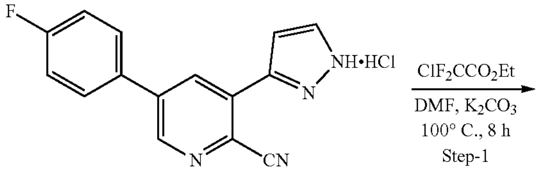

Int-53

-continued

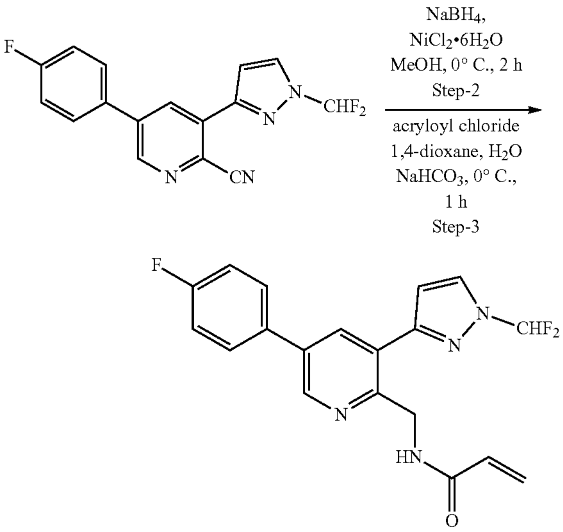

Cpd. No. 203

Steps 1-3: These steps were executed in a manner similar (use of appropriate reagents and purification methods known to the person skilled in the art) to Cpd. No. 198. Int-53 (600 mg, 2.0 mmol) yielded crude product which was purified by preparative HPLC method H3. The collected fractions were lyophilised to afford N-((3-(1-(difluoromethyl)-1H-pyrazol-3-yl)-5-(4-fluorophenyl)pyridin-2-yl)methyl)-acrylamide (Cpd. No. 203) as an off-white solid (32 mg, 4%). (LC/MS; m/z 373.3 $[M+H]^+$).

Example 89: Synthesis of N-((3-(2-(difluoromethyl)-2H-tetrazol-5-yl)-5-(4-fluorophenyl)pyridin-2-yl)methyl)acrylamide (Cpd. No. 204)

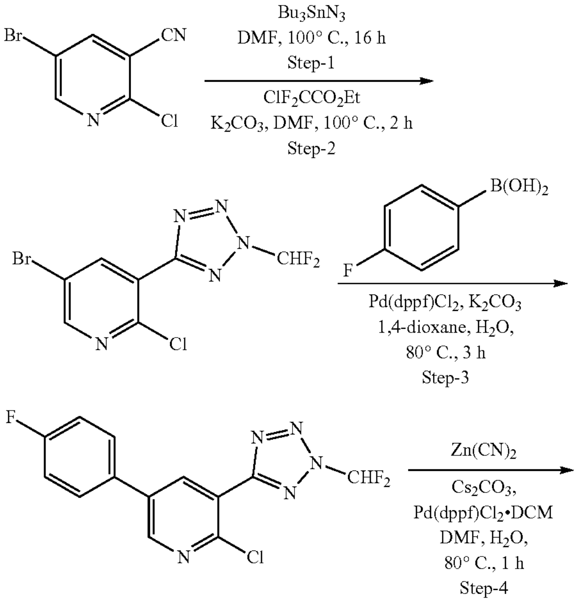

-continued

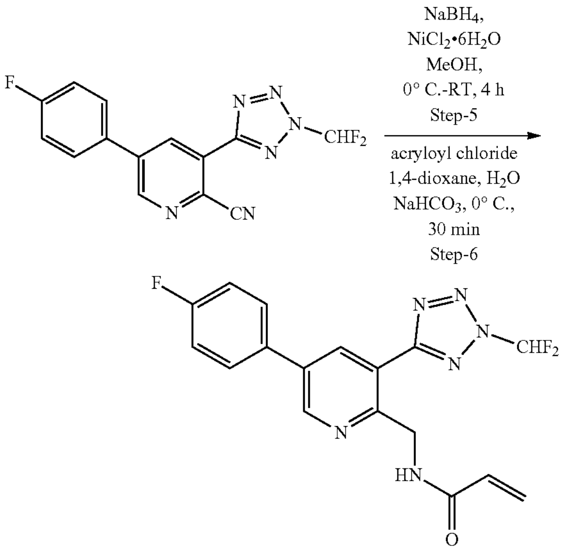

Cpd. No. 204

Step 1: A solution of 5-bromo-2-chloronicotinonitrile (5.0 g, 23.0 mmol) and $Bu_3SnN_3$ (15.26 g, 46.0 mmol) in DMF (50 mL) was stirred at 100° C. for 16 h (sealed tube) and monitored by TLC. TLC mobile phase: 10% MeOH in DCM, RF: 0.2, TLC detection: UV. The reaction mixture was diluted with ice $H_2O$ (150 mL) and extracted with EtOAc (250 mL). The organic layer was dried over anhydrous $Na_2SO_4$ and concentrated under reduced pressure to afford a black gum (7.0 g, LC/MS 57%). The crude product was purified by normal phase flash column chromatography using a 40 g column (silica) and a gradient of 0-8% MeOH in DCM as an eluent to afford 5-bromo-2-chloro-3-(2H-tetrazol-5-yl)pyridine as a light brown gum (5.0 g, 61%, LC/MS 73%). (LC/MS; m/z 259.8 $[M+H]^+$).

Step 2: This step was executed in a manner similar (use of appropriate reagents and purification methods known to the person skilled in the art) to step 3 towards Int-49. From 5-bromo-2-chloro-3-(2H-tetrazol-5-yl)pyridine (5.0 g, 19.40 mmol) was obtained 5-bromo-2-chloro-3-(2-(difluoromethyl)-2H-tetrazol-5-yl)pyridine as an off-white solid (1.8 g, 39%, LC/MS 95%). (LC/MS; m/z 310.0 $[M+H]^+$).

Step 3: This step was executed in a manner similar (use of appropriate reagents and purification methods known to the person skilled in the art) to step 1 towards Cpd. No. 157. From 5-bromo-2-chloro-3-(2-(difluoromethyl)-2H-tetrazol-5-yl)pyridine (1.8 g, 5.81 mmol) was obtained 2-chloro-3-(2-(difluoromethyl)-2H-tetrazol-5-yl)-5-(4-fluorophenyl) pyridine as a white solid (1.2 g, 41%, LC/MS 62%). (LC/MS; m/z 326.1 $[M+H]^+$).

Step 4: This step was executed in a manner similar (use of appropriate reagents and purification methods known to the person skilled in the art) to step 4 towards Cpd. No. 176. From 2-chloro-3-(2-(difluoromethyl)-2H-tetrazol-5-yl)-5-(4-fluorophenyl)pyridine (1.2 g, 3.69 mmol, LC/MS 62%) was obtained 3-(2-(difluoromethyl)-2H-tetrazol-5-yl)-5-(4-fluorophenyl)picolinonitrile as an off-white solid (320 mg, 40%, LC/MS 91%). (LC/MS; m/z 317.3 $[M+H]^+$).

Steps 5-6: These steps were executed in a manner similar (use of appropriate reagents and purification methods known to the person skilled in the art) to step 2 and 3 towards Cpd. No. 157. From 3-(2-(difluoromethyl)-2H-tetrazol-5-yl)-5-(4-fluorophenyl)picolinonitrile (300 mg, 0.95 mmol, LC/MS 91%) was obtained crude product (325 mg, LC/MS 23%) which was purified by preparative HPLC method H9. The collected fractions were lyophilised to afford N-((3-(2-(difluoromethyl)-2H-tetrazol-5-yl)-5-(4-fluorophenyl)pyridin-2-yl)methyl)acrylamide (Cpd. No. 204) as an off-white solid (19 mg, 6%). (LC/MS; m/z 375.2 [M+H]$^+$).

Example 90: Synthesis of N-((6-(4-fluorophenyl)-4-(1-methyl-1H-pyrazol-3-yl)pyridin-3-yl)methyl) acrylamide (Cpd. No. 205)

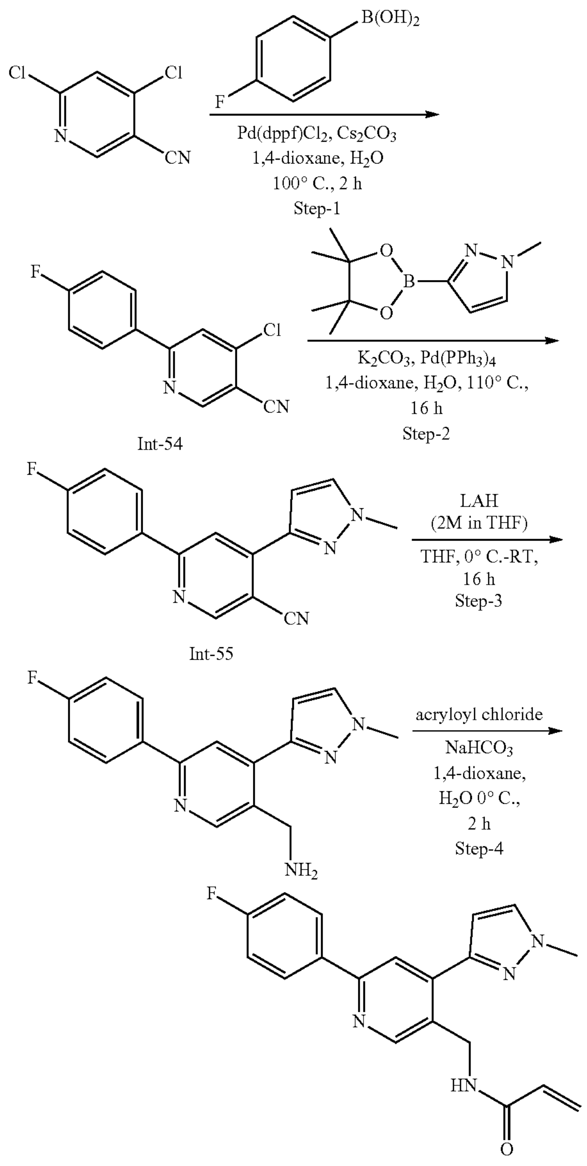

Cpd. No. 205

Steps 1-4: These steps were executed in a manner similar (use of appropriate reagents and purification methods known to the person skilled in the art) to Cpd. No. 193. 4,6-Dichloropicolinonitrile (1.0 g, 5.8 mmol) yielded crude product which was purified by preparative HPLC method H1. The collected fractions were lyophilised to afford N-((6-(4-fluorophenyl)-4-(1-methyl-1H-pyrazol-3-yl)pyridin-3-yl)methyl)acrylamide (Cpd. No. 205) as a white solid (31 mg, 2%). (LC/MS; m/z 337.2 [M+H]$^+$).

The following compounds were prepared in a manner similar (use of appropriate reagents and purification methods known to the person skilled in the art) to Cpd. No. 205: Cpd. No. 390 (using methacryloyl chloride and TEA in step 4), Cpd. No. 391 (using 2-fluoroacrylic acid, HATU and DIPEA in step 4), Cpd. No. 400 (using 2-bromoacrylic acid, HATU and DIPEA in step 4), Cpd. No. 411 (using 2,5-dimethoxy-2,5-dihydrofuran and HCl in step 4).

Synthesis of 6-(4-fluorophenyl)-4-(1H-pyrazol-3-yl) nicotinonitrile hydrochloride (Int-56)

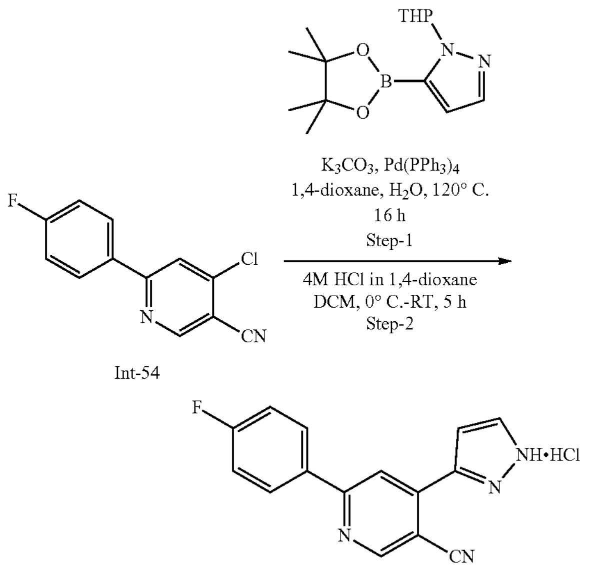

Int-56

Steps 1-2: These steps were executed in a manner similar (use of appropriate reagents and purification methods known to the person skilled in the art) to Int-45. Starting material Int-54 (2.5 g, 10.7 mmol) yielded 6-(4-fluorophenyl)-4-(1H-pyrazol-3-yl)nicotinonitrile hydrochloride (Int-56) as a white solid (1.6 g, 50%). (LC/MS; m/z 265.0 [M+H]$^+$).

Example 91: Synthesis of N-((4-(1-cyclopropyl-1H-pyrazol-3-yl)-6-(4-fluorophenyl)pyridin-3-yl) methyl)acrylamide (Cpd. No. 206)

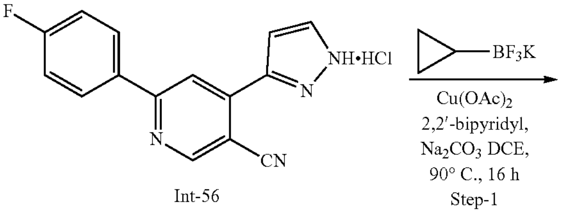

-continued

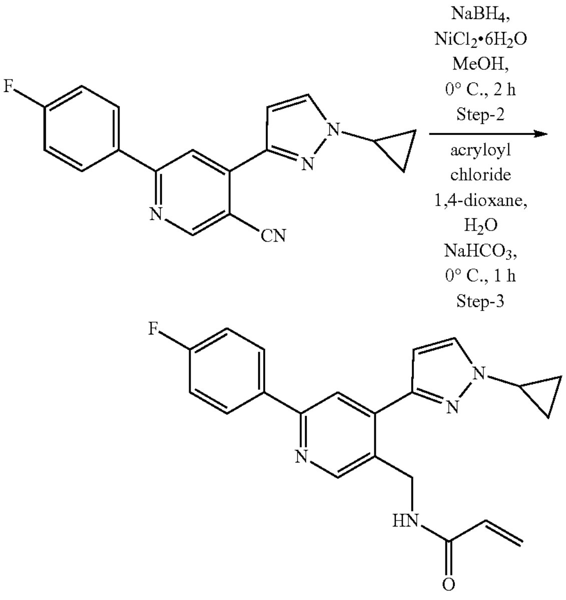

Cpd. No. 206

Steps 1-3: These steps were executed in a manner similar (use of appropriate reagents and purification methods known to the person skilled in the art) to Cpd. No. 196. Int-56 (600 mg, 2.0 mmol) yielded crude product which was purified by preparative HPLC method H2. The collected fractions were lyophilised to afford N-((4-(1-cyclopropyl-1H-pyrazol-3-yl)-6-(4-fluorophenyl)pyridin-3-yl)methyl)-acrylamide (Cpd. No. 206) as a white solid (17 mg, 2%). (LC/MS; m/z 363.2 $[M+H]^+$).

Example 92: Synthesis of N-((4-(1-(difluoromethyl)-1H-pyrazol-3-yl)-6-(4-fluorophenyl)pyridin-3-yl)methyl)acrylamide (Cpd. No. 207)

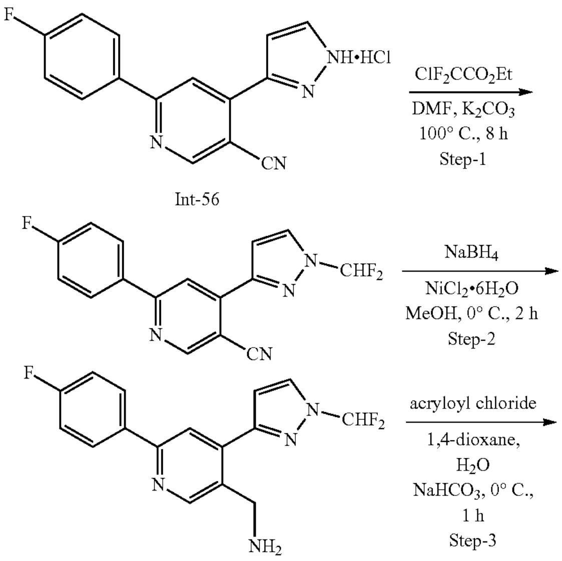

Int-56

Int-57

-continued

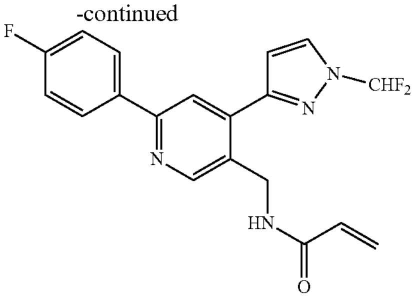

Cpd. No. 207

Steps 1-3: These steps were executed in a manner similar (use of appropriate reagents and purification methods known to the person skilled in the art) to Cpd. No. 198. Int-56 (600 mg, 2.0 mmol) yielded crude product which was purified by preparative HPLC method H2. The collected fractions were lyophilised to afford N-((4-(1-(difluoromethyl)-1H-pyrazol-3-yl)-6-(4-fluorophenyl)pyridin-3-yl)methyl)-acrylamide (Cpd. No. 207) as a white solid (118 mg, 16%). (LC/MS; m/z 373.2 $[M+H]^+$).

Example 93: Synthesis of (E)-N-((4-(1-(difluoromethyl)-1H-pyrazol-3-yl)-6-(4-fluorophenyl)pyridin-3-yl)methyl)-4-(dimethylamino)but-2-enamide (Cpd. No. 208)

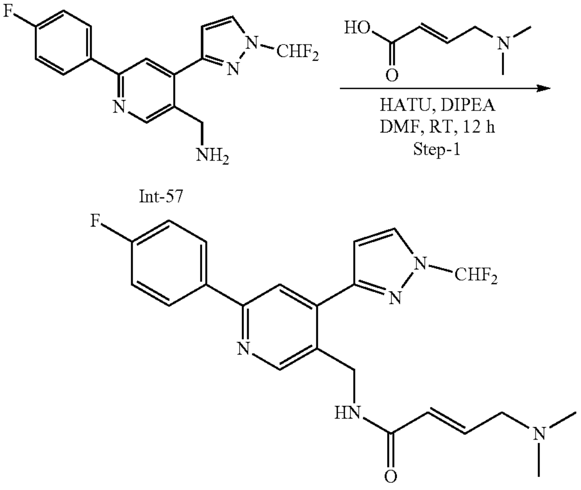

Int-57

Cpd. No. 208

Step 1: A solution of Int-57 (300 mg, 0.94 mmol, LC/MS 85%), DIPEA (487 mg, 3.77 mmol), (E)-4-(dimethylamino) but-2-enoic acid (146 mg, 1.13 mmol) and HATU (717 mg, 1.88 mmol) was stirred at RT for 12 h and monitored by TLC. TLC mobile phase: 10% MeOH in DCM, RF: 0.61, TLC detection: UV. The reaction mixture was extracted with EtOAc (2×80 mL), and the combined organic layer was washed with brine (2×25 mL), dried over anhydrous $Na_2SO_4$ and concentrated under reduced pressure to afford crude product (350 mg, LC/MS 79%) which was purified by preparative HPLC method H14. The collected fractions were lyophilised to afford (E)-N-((4-(1-(difluoromethyl)-1H-pyrazol-3-yl)-6-(4-fluorophenyl)pyridin-3-yl)methyl)-

4-(dimethylamino)but-2-enamide (Cpd. No. 208) as an off-white solid (155 mg, 45%). (LC/MS; m/z 430.3 $[M+H]^+$).

Example 94: Synthesis of N-((4-(1-(difluoromethyl)-1H-pyrazol-3-yl)-6-(4-(trifluoromethyl)phenyl)pyridin-3-yl)methyl)acrylamide (Cpd. No. 209)

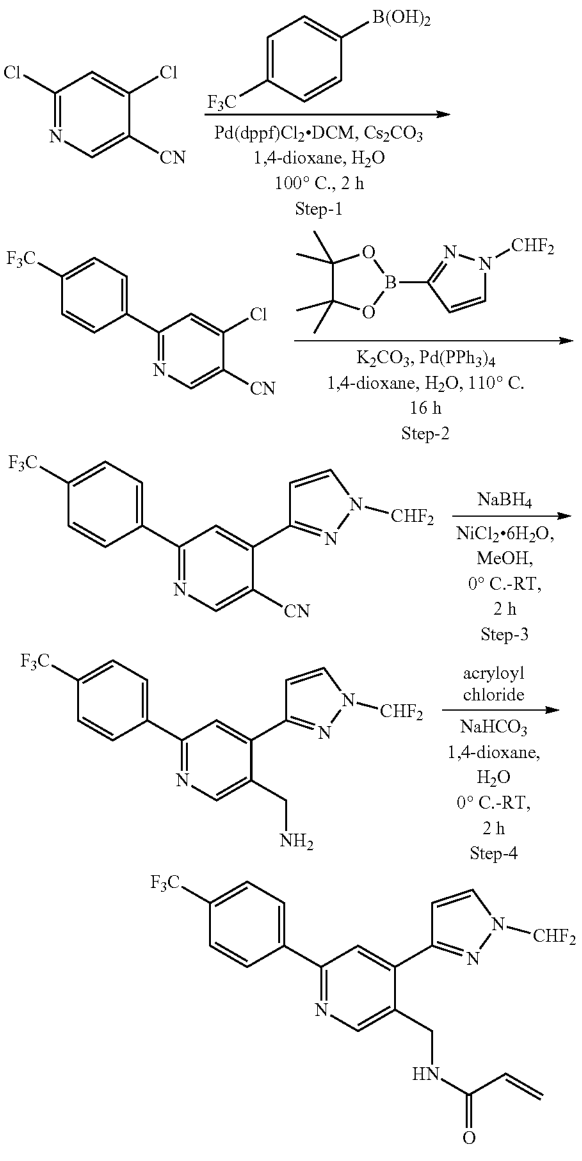

Cpd. No. 209

Step 1: This step was executed in a manner similar (use of appropriate reagents and purification methods known to the person skilled in the art) to step 1 towards Cpd. No. 193. 4,6-Dichloropicolinonitrile (500 mg, 2.89 mmol) yielded crude product (550 mg) which was purified by normal phase flash column chromatography using silica gel (100-200 mesh) and a gradient of 0-2% EtOAc in pet ether as an eluent to afford 4-chloro-6-(4-(trifluoromethyl)phenyl)nicotinonitrile as a white solid (250 mg, 28%, LC/MS 93%). (LC/MS; m/z 283.1 $[M+H]^+$) The structure was confirmed by 2D NMR and $^{13}C$ NMR.

Step 2: A degassed solution of 4-chloro-6-(4-(trifluoromethyl)phenyl)nicotinonitrile (250 mg, 0.88 mmol, LC/MS 93%) in 1,4-dioxane (4 mL) and $H_2O$ (0.5 mL) was treated with 1-(difluoromethyl)-3-(4,4,5,5-tetramethyl-1,3,2-dioxaborolan-2-yl)-1H-pyrazole (324 mg, 1.33 mmol), $K_2CO_3$ (245 mg, 1.77 mmol) and $Pd(PPh_3)_4$ (102 mg, 0.09 mmol). The reaction mixture was stirred at 110° C. for 16 h and monitored by TLC. TLC mobile phase: 10% EtOAc in pet ether, RF: 0.42, TLC detection: UV. The reaction mixture was filtered through a celite pad and washed with EtOAc (50 mL). The filtrate was washed with $H_2O$ (20 mL) and brine (20 mL). The EtOAc layer was dried over anhydrous $Na_2SO_4$ and the filtrate was concentrated under reduced pressure to afford crude product (280 mg). The crude product was purified by normal phase flash column chromatography using a 24 g column (silica) and a gradient of 0-10% EtOAc in pet ether as an eluent to afford 4-(1-(difluoromethyl)-1H-pyrazol-3-yl)-6-(4-(trifluoromethyl)phenyl)nicotinonitrile as a yellow solid (250 mg, 59%, LC/MS 71%). (LC/MS; m/z 365.2 $[M+H]^+$)

Steps 3-4: These steps were executed in a manner similar (use of appropriate reagents and purification methods known to the person skilled in the art) to step 3 and 4 towards Cpd. No. 193. 4-(1-(difluoromethyl)-1H-pyrazol-3-yl)-6-(4-(trifluoromethyl)phenyl)nicotinonitrile (250 mg, 0.68 mmol, LC/MS 71%) yielded crude product (300 mg, LC/MS 40%) which was purified by preparative HPLC method H3. The collected fractions were lyophilised to afford N-((4-(1-(difluoromethyl)-1H-pyrazol-3-yl)-6-(4-(trifluoromethyl)phenyl)pyridin-3-yl)methyl)acrylamide (Cpd. No. 209) as a white solid (40 mg, 19%). (LC/MS; m/z 423.2 $[M+H]^+$).

The following compounds were prepared in a manner similar (use of appropriate reagents and purification methods known to the person skilled in the art) to Cpd. No. 209: Cpd. No. 210, Cpd. No. 211, Cpd. No. 212, Cpd. No. 213, Cpd. No. 214, Cpd. No. 215, Cpd. No. 216, Cpd. No. 217, and Cpd. No. 218 (prepared from 4,6-dichloropicolinonitrile).

Example 95: Synthesis of N-((6-(4-cyanophenyl)-4-(1-(difluoromethyl)-1H-pyrazol-3-yl)pyridin-3-yl)methyl)acrylamide (Cpd. No. 219)

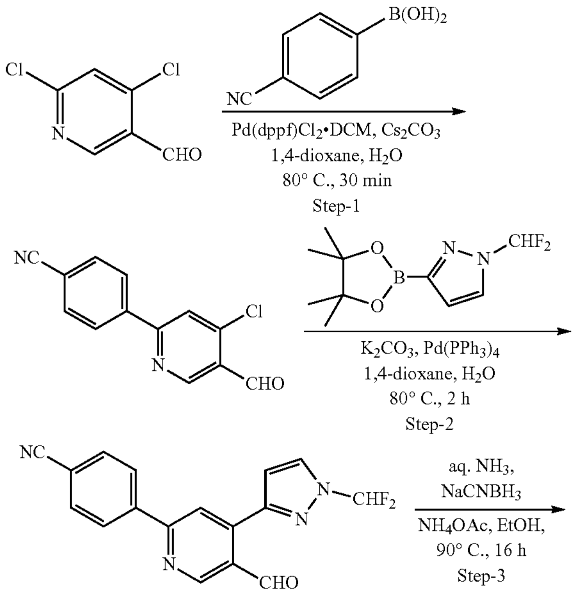

-continued

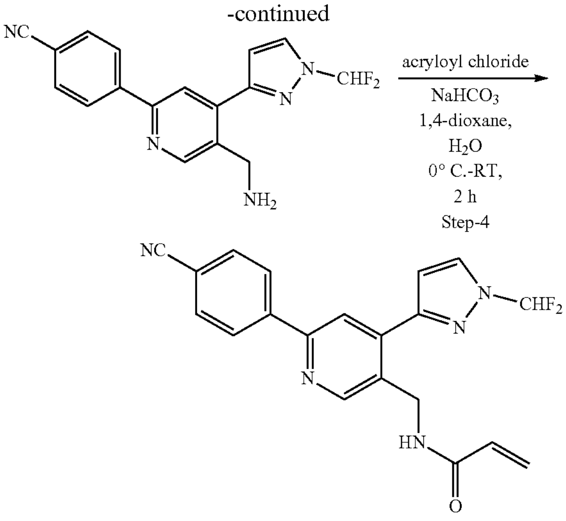

Cpd. No. 219

Steps 1-2: These steps were executed in a manner similar (use of appropriate reagents and purification methods known to the person skilled in the art) to step 1 and 2 towards Cpd. No. 209. From 4,6-dichloronicotinaldehyde (1.0 g, 5.68 mmol) was obtained 4-(4-(1-(difluoromethyl)-1H-pyrazol-3-yl)-5-formylpyridin-2-yl)benzonitrile as a yellow solid (350 mg, 19%). (LC/MS; m/z 325.2 $[M+H]^+$). The structure was confirmed by NOESY.

Step 3: At RT, a stirred solution of 4-(4-(1-(difluoromethyl)-1H-pyrazol-3-yl)-5-formylpyridin-2-yl)benzonitrile (200 mg, 0.62 mmoL) in sat $NH_4OAc$ in EtOH (20 mL) was treated with $NaCNBH_3$ (117 mg, 1.86 mmoL) followed by the addition of aq $NH_3$ (1.1 g, 30.87 mmol) (28% in $H_2O$). The reaction mixture was stirred at 90° C. for 16 h (sealed tube) and monitored by TLC. TLC mobile phase: 10% MeOH in DCM, RF: 0.05. TLC detection: UV. The reaction mixture was cooled to RT, diluted with $H_2O$ (50 mL) and extracted with EtOAc (3x25 mL). The combined organic layer was washed with brine (15 mL), dried over anhydrous $Na_2SO_4$ and concentrated under reduced pressure to afford crude product (210 mg, LC/MS 65%). The crude product was triturated with $Et_2O$ (3x1 mL) and dried under reduced pressure to afford 4-(5-(aminomethyl)-4-(1-(difluoromethyl)-1H-pyrazol-3-yl)pyridin-2-yl)benzonitrile (200 mg, 88%, LC/MS 88%) as an off-white solid. (LC/MS; m/z 326.2 $[M+H]^+$).

Step 4: This step was executed in a manner similar (use of appropriate reagents and purification methods known to the person skilled in the art) to step 4 towards Cpd. No. 193. 4-(5-(aminomethyl)-4-(1-(difluoromethyl)-1H-pyrazol-3-yl)pyridin-2-yl)benzonitrile (176 mg, 0.54 mmol, LC/MS 88%) yielded crude product (300 mg, LC/MS 27%) which was purified by preparative HPLC method H6. The collected fractions were lyophilised to afford N-((6-(4-cyanophenyl)-4-(1-(difluoromethyl)-1H-pyrazol-3-yl)pyridin-3-yl)methyl)acrylamide (Cpd. No. 219) as a white solid (35 mg, 17%). (LC/MS; m/z 380.1 $[M+H]^+$).

Compound Cpd. No. 220 was prepared in a manner similar (use of appropriate reagents and purification methods known to the person skilled in the art) to Cpd. No. 219.

Examples 96-97: Synthesis of N-((4-(1-(difluoromethyl)-1H-pyrazol-3-yl)-6-(4,4-difluoropiperidin-1-yl)pyridin-3-yl)methyl)acrylamide (Cpd. No. 221) and N-((6-(1-(difluoromethyl)-1H-pyrazol-3-yl)-4-(4,4-difluoropiperidin-1-yl)pyridin-3-yl)methyl) acrylamide (Cpd. No. 222)

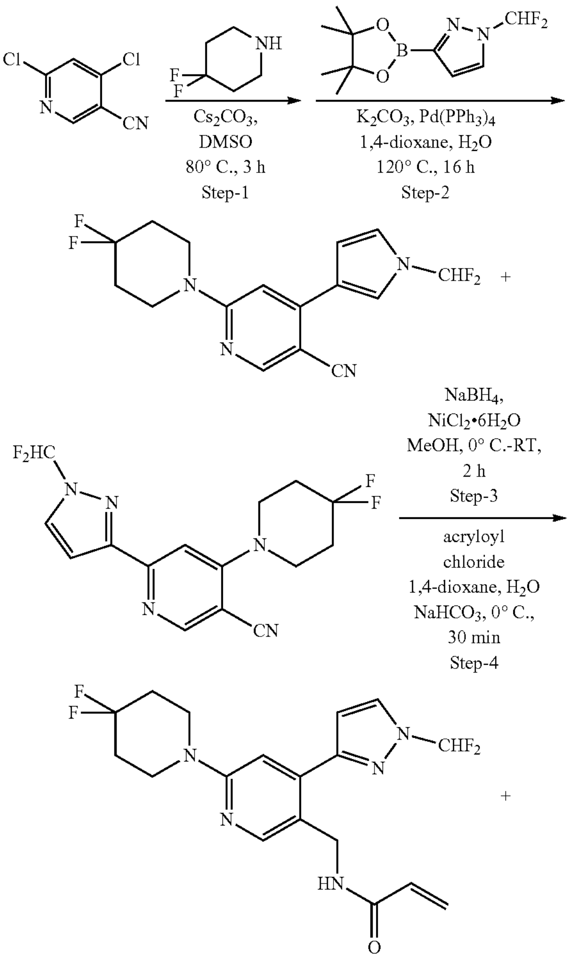

Cpd. No. 221

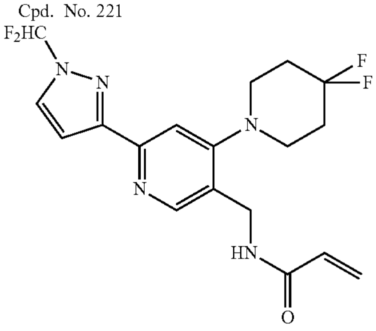

Cpd. No. 222

Step 1: A solution of 4,6-dichloronicotinonitrile (1.5 g, 8.67 mmol) in DMSO (25 mL) was treated with $Cs_2CO_3$ (5.63 g, 17.34 mmol) and 4,4-difluoropiperidine (1.05 g, 8.67 mmol) at 0° C. The reaction mixture was stirred at 80° C. for 4 h (sealed tube) and monitored by TLC. TLC mobile phase: 20% EtOAc in pet ether, RF: 0.16, TLC detection:

UV. The reaction mixture was cooled to RT and extracted with EtOAc (50 mL). The combined organic layer was dried over anhydrous $Na_2SO_4$ and concentrated under reduced pressure to afford crude product, which was purified by normal phase flash column chromatography using a 40 g column (silica) and a gradient of 0-5% EtOAc in pet ether as an eluent to afford a 36:64 mixture of 4-chloro-6-(4,4-difluoropiperidin-1-yl)nicotinonitrile and its regioisomer 6-chloro-4-(4,4-difluoropiperidin-1-yl)nicotinonitrile as an off-white solid (1.80 g, 80%, LC/MS 96%). (LC/MS; m/z 258.1 $[M+H]^+$). The 36:64 mixture of regioisomers was used as such in the next step.

Step 2: This step was executed in a manner similar (use of appropriate reagents and purification methods known to the person skilled in the art) to step 2 towards Cpd. No. 209. Starting material (1.5 g, 5.82 mmol, LC/MS 96%) yielded a mixture of 4-(1-(difluoromethyl)-1H-pyrazol-3-yl)-6-(4,4-difluoropiperidin-1-yl)nicotinonitrile and its regioisomer 6-(1-(difluoromethyl)-1H-pyrazol-3-yl)-4-(4,4-difluoropiperidin-1-yl)nicotinonitrile as a white solid (1.8 g, 69%, LC/MS 73%). (LC/MS; m/z 340.2 $[M+H]^+$). The 45:55 mixture of regioisomers was used as such in the next step.

Steps 3-4: These steps were executed in a manner similar (use of appropriate reagents and purification methods known to the person skilled in the art) to step 3 and 4 towards Cpd. No. 193. Starting material (0.85 g, 2.50 mmol, LC/MS 73%) yielded crude product which was purified by preparative HPLC method H5. The collected fractions were lyophilised to afford N-((4-(1-(difluoromethyl)-1H-pyrazol-3-yl)-6-(4,4-difluoropiperidin-1-yl)pyridin-3-yl)methyl)-acrylamide (Cpd. No. 221) (20 mg, 3%, LC/MS 99%) and N-((6-(1-(difluoromethyl)-1H-pyrazol-3-yl)-4-(4,4-difluoropiperidin-1-yl)pyridin-3-yl)methyl)acrylamide (Cpd. No. 222) (14 mg, 2%, LC/MS 96%), both as an off-white solid. (LC/MS; m/z 398.2 $[M+H]^+$).

Example 98: Synthesis of N-((6-(4,4-difluorocyclohexyl)-4-(1-(difluoromethyl)-1H-pyrazol-3-yl)pyridin-3-yl)methyl)acrylamide (Cpd. No. 223)

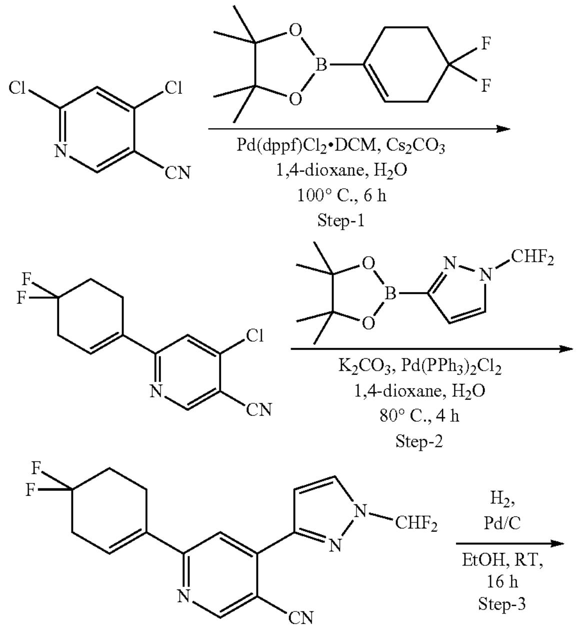

-continued

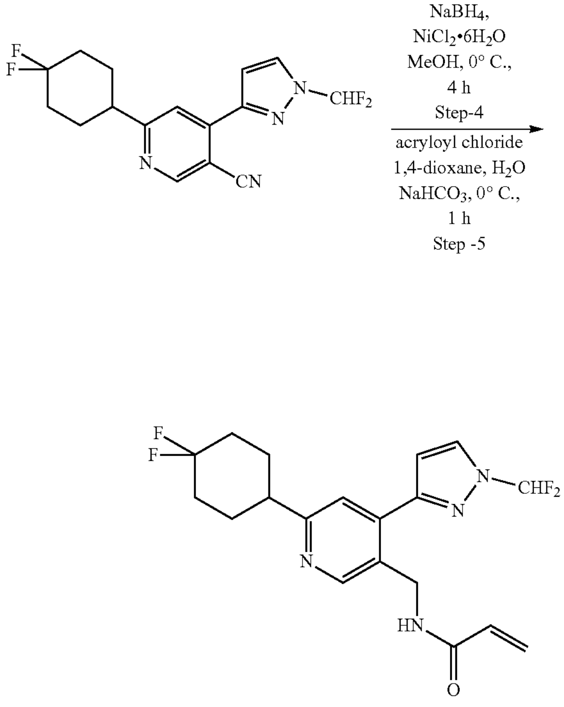

Cpd. No. 223

Steps 1-2: These steps were executed in a manner similar (use of appropriate reagents and purification methods known to the person skilled in the art) to step 1 and 2 towards Cpd. No. 209. From 4,6-dichloronicotinonitrile (1.0 g, 5.78 mmol) was obtained 6-(4,4-difluorocyclohex-1-en-1-yl)-4-(1-(difluoromethyl)-1H-pyrazol-3-yl)nicotinonitrile as a white solid (650 mg, 27%, LC/MS 82%). (LC/MS; m/z 337.2 $[M+H]^+$).

Step 3: A solution of 6-(4,4-difluorocyclohex-1-en-1-yl)-4-(1-(difluoromethyl)-1H-pyrazol-3-yl)nicotinonitrile (550 mg, 1.63 mmol, LC/MS 82%) and Pd/C (10 wt. %) (225 mg, 0.21 mmol) in EtOH (20 ml) was stirred at RT for 16 h and monitored by TLC. TLC mobile phase: 30% EtOAc in pet ether, RF: 0.45, TLC detection: UV. The reaction mixture was filtered through a celite pad, washed with EtOAc (50 mL) and the filtrate was concentrated under reduced pressure to afford yellow gum (550 mg, LC/MS 64%). (LC/MS; m/z 339.3 $[M+H]^+$). The product was used as such without further purification.

Steps 4-5: These steps were executed in a manner similar (use of appropriate reagents and purification methods known to the person skilled in the art) to step 3 and 4 towards Cpd. No. 193. Starting material (550 mg, 1.62 mmol, LC/MS 64%) yielded a yellow gum (450 mg, LC/MS 74%) which was purified by preparative HPLC method H3. The collected fractions were lyophilised to afford N-((6-(4,4-difluorocyclohexyl)-4-(1-(difluoromethyl)-1H-pyrazol-3-yl)pyridin-3-yl)methyl)acrylamide (Cpd. No. 223) as a white solid (77 mg, 18%). (LC/MS; m/z 397.3 $[M+H]^+$).

Example 99: Synthesis of N-((4-(1-(difluoromethyl)-1H-pyrazol-4-yl)-6-(4-fluorophenyl)pyridin-3-yl)methyl)acrylamide (Cpd. No. 224)

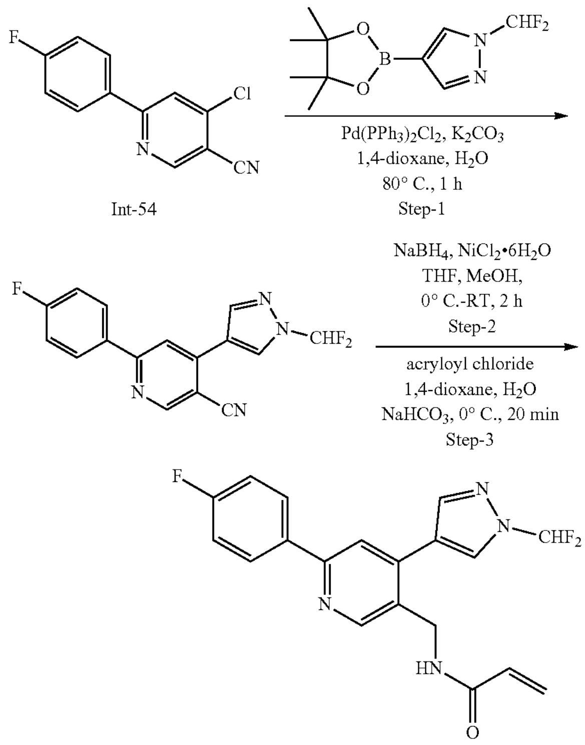

Int-54

Cpd. No. 224

Steps 1-3: These steps were executed in a manner similar (use of appropriate reagents and purification methods known to the person skilled in the art) to step 2, 3 and 4 towards Cpd. No. 209. Int-54 (450 mg, 1.39 mmol) yielded a pale brown solid (400 mg, LC/MS 71%) which was purified by preparative HPLC method H3. The collected fractions were lyophilised to afford N-((4-(1-(difluoromethyl)-1H-pyrazol-4-yl)-6-(4-fluorophenyl)pyridin-3-yl)methyl)acrylamide (Cpd. No. 224) as a white solid (165 mg, 32%). (LC/MS; m/z 373.3 [M+H]$^+$).

Example 100: Synthesis of N-((6-(1-(difluoromethyl)-1H-pyrazol-3-yl)-4-(4-fluorophenyl)pyridin-2-yl)methyl)acrylamide (Cpd. No. 225)

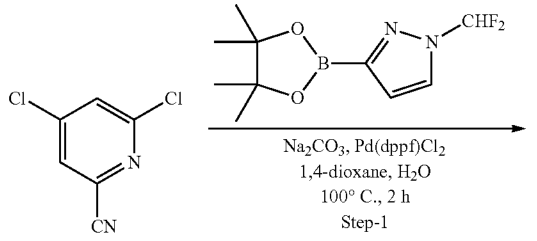

-continued

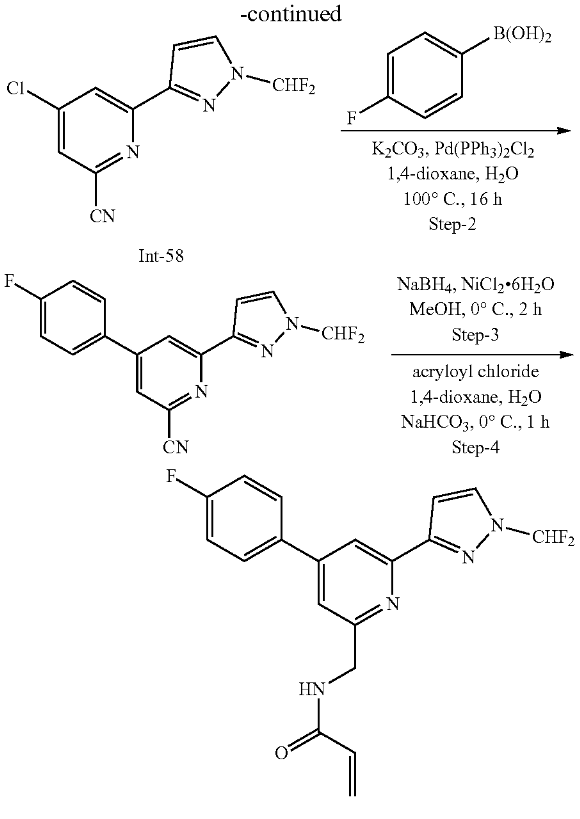

Int-58

Cpd. No. 225

Step 1: A solution of 4,6-dichloropicolinonitrile (500 mg, 2.89 mmol), $Na_2CO_3$ (612 mg, 5.78 mmol) and 1-(difluoromethyl)-3-(4,4,5,5-tetramethyl-1,3,2-dioxaborolan-2-yl)-1H-pyrazole (778 mg, 3.18 mmol) in 1,4-dioxane (10 mL) and $H_2O$ (2 mL) was degassed with argon for 10 min followed by the addition of Pd(dppf)$Cl_2$ (105 mg, 0.145 mmol). The reaction mixture was stirred at 100° C. for 2 h (sealed tube) and monitored by TLC. TLC mobile phase: 5% EtOAc in pet ether, RF: 0.39, TLC detection: UV. The reaction mixture was filtered through a celite pad and washed with EtOAc (150 mL). The filtrate was washed with $H_2O$ (75 mL) and brine (75 mL), dried over anhydrous $Na_2SO_4$ and concentrated under reduced pressure to afford a brown solid (600 mg, LC/MS 72%). The crude product was purified by normal phase flash column chromatography using silica gel (100-200 mesh) and a gradient of 0-3% EtOAc in pet ether as an eluent to afford 4-chloro-6-(1-(difluoromethyl)-1H-pyrazol-3-yl)picolinonitrile (Int-58) as an off-white solid (400 mg, 53%, LC/MS 98%). (LC/MS; m/z 255.1 [M+H]$^+$).

Step 2: A solution of Int-58 (400 mg, 1.57 mmol), $K_2CO_3$ (434 mg, 3.14 mmol) and (4-fluorophenyl)boronic acid (242 mg, 1.73 mmol) in 1,4-dioxane (4 mL) and $H_2O$ (0.5 mL) was degassed with argon for 10 min followed by the addition of $Pd(PPh_3)_2Cl_2$ (165 mg, 0.24 mmol). The reaction mixture was stirred at 100° C. for 16 h (sealed tube) and monitored by TLC. TLC mobile phase: 10% EtOAc in pet ether, RF: 0.41, TLC detection: UV. The reaction mixture was filtered through a celite pad and washed with EtOAc (100 mL). The filtrate was washed with $H_2O$ (20 mL), brine (20 mL), dried over anhydrous $Na_2SO_4$ and concentrated under reduced pressure to afford a black gum (450 mg). The crude product was purified by normal phase flash column chromatography using silica gel (100-200 mesh) and a gradient of 0-8% EtOAc in pet ether as an eluent to afford 6-(1-(difluoromethyl)-1H-pyrazol-3-yl)-4-(4-fluorophenyl)picolinonitrile as a white solid (400 mg, 81%, LC/MS 98%). (LC/MS; m/z 315.1 $[M+H]^+$).

Steps 3-4: These steps were executed in a manner similar (use of appropriate reagents and purification methods known to the person skilled in the art) to step 2 and 3 towards Cpd. No. 152. From 6-(1-(difluoromethyl)-1H-pyrazol-3-yl)-4-(4-fluorophenyl)picolinonitrile (200 mg, 0.63 mmol) was obtained crude product (135 mg, LC/MS 53%) which was purified by preparative HPLC method H1. The collected fractions were lyophilised to afford N-((6-(1-(difluoromethyl)-1H-pyrazol-3-yl)-4-(4-fluorophenyl)pyridin-2-yl)methyl)acrylamide (Cpd. No. 225) as a white solid (41 mg, 17%, LC/MS 99%). (LC/MS; m/z 373.3 $[M+H]^+$).

The following compounds were prepared in a manner similar (use of appropriate reagents and purification methods known to the person skilled in the art) to Cpd. No. 225: Cpd. No. 226 (employing propionyl chloride at step 4) and Cpd. No. 227 (employing 1-(difluoromethyl)-4-(4,4,5,5-tetramethyl-1,3,2-dioxaborolan-2-yl)-1H-pyrazole at step 1).

Example 101: Synthesis of N-((4-(4,4-difluorocyclohexyl)-6-(1-(difluoromethyl)-1H-pyrazol-3-yl)pyridin-2-yl)methyl)acrylamide (cpd-Cpd. No. 228)

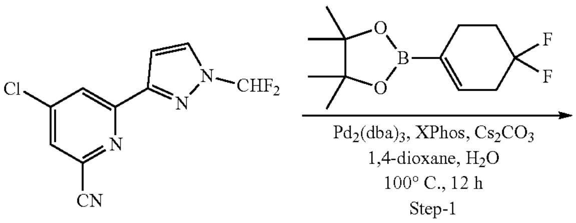

Int-58

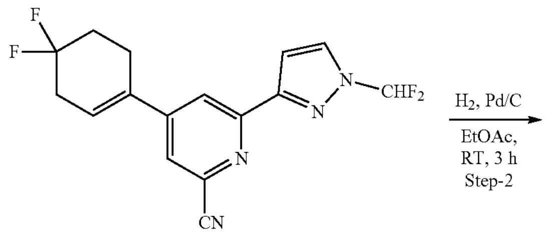

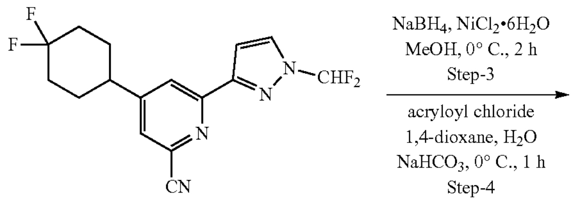

-continued

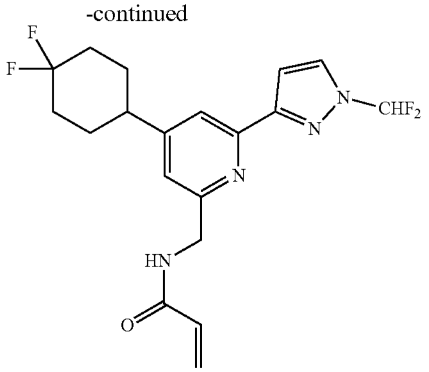

Cpd. No. 228

Step 1: A solution of Int-58 (1.3 g, 5.11 mmol), $Cs_2CO_3$ (3.32 g, 10.21 mmol) and 2-(4,4-difluorocyclohex-1-en-1-yl)-4,4,5,5-tetramethyl-1,3,2-dioxaborolane (1.24 g, 5.11 mmol) in 1,4-dioxane (10 mL) and $H_2O$ (3 mL) was degassed with argon for 10 min followed by the addition of Xphos (243 mg, 0.51 mmol) and $Pd_2(dba)_3$ (234 mg, 0.25 mmol). The reaction mixture was stirred at 100° C. for 12 h (sealed tube) and monitored by TLC. TLC mobile phase: 10% EtOAc in pet ether, RF: 0.39, TLC detection: UV. The reaction mixture was filtered through a celite pad and washed with EtOAc (150 mL). The filtrate was washed with $H_2O$ (80 mL), brine (80 mL), dried over anhydrous $Na_2SO_4$ and concentrated under reduced pressure to afford crude product (1.5 g, LC/MS 64%). The crude product was purified by normal phase flash column chromatography using a 40 g column (silica) and a gradient of 0-6% EtOAc in pet ether as an eluent to afford 4-(4,4-difluorocyclohex-1-en-1-yl)-6-(1-(difluoromethyl)-1H-pyrazol-3-yl)picolinonitrile as light brown solid (1.0 g, 53%, LC/MS 92%). (LC/MS; m/z 337.1 $[M+H]^+$).

Steps 2-4: These steps were executed in a manner similar (use of appropriate reagents and purification methods known to the person skilled in the art) to step 3, 4 and 5 towards Cpd. No. 223. From 4-(4,4-difluorocyclohex-1-en-1-yl)-6-(1-(difluoromethyl)-1H-pyrazol-3-yl)picolinonitrile (700 mg, 2.08 mmol) was obtained crude product (140 mg, LC/MS 40%) which was purified by preparative HPLC method H5. The collected fractions were lyophilised to afford N-((4-(4,4-difluorocyclohexyl)-6-(1-(difluoromethyl)-1H-pyrazol-3-yl)pyridin-2-yl)methyl)-acrylamide (Cpd. No. 228) as a white solid (20 mg, 2%, LC/MS 99%). (LC/MS; m/z 397.3 $[M+H]^+$).

Synthesis of 4-ethynyl-6-(4-fluorophenyl)nicotinonitrile (Int-59) and 4-(2-(difluoromethyl)-2H-1,2,3-triazol-4-yl)-6-(4-fluorophenyl)nicotinonitrile (Int-60)

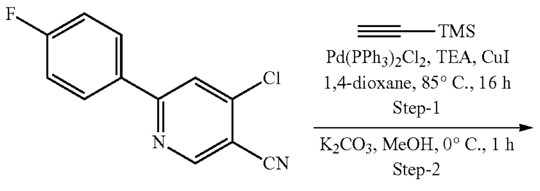

Int-54

-continued

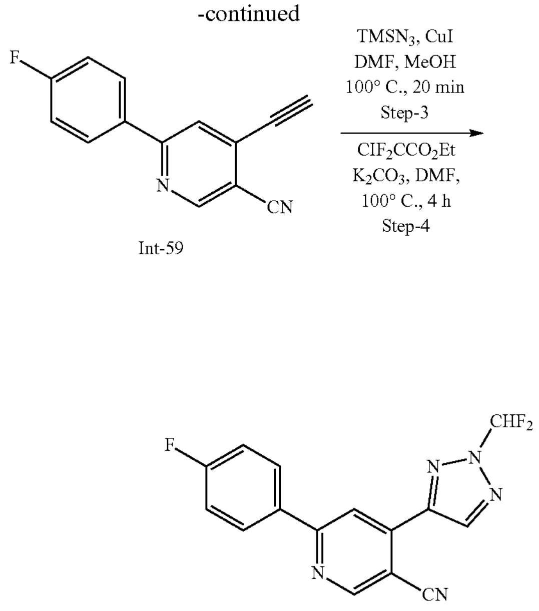

Int-59

Int-60

Steps 1-2: These steps were executed in a manner similar (use of appropriate reagents and purification methods known to the person skilled in the art) to step 1 and 2 towards Cpd. No. 184. From Int-54 (2.0 g, 8.60 mmol) was obtained 4-ethynyl-6-(4-fluorophenyl)nicotinonitrile (Int-59) as a pale yellow solid (820 mg, 41%, LC/MS 96%). (LC/MS; m/z 223.2 $[M+H]^+$).

Steps 3-4: These steps were executed in a manner similar (use of appropriate reagents and purification methods known to the person skilled in the art) to step 1 and 2 towards Int-37 and Int-38. Int-59 (820 mg, 3.69 mmol) yielded a crude product (650 mg, LC/MS 28% and 13%) which was purified by normal phase flash column chromatography using a 40 g column (silica) and a gradient of 0-15% EtOAc in pet ether as an eluent to afford 4-(2-(difluoromethyl)-2H-1,2,3-triazol-4-yl)-6-(4-fluorophenyl)nicotinonitrile (Int-60) as an off-white solid (180 mg, 18%, LC/MS 91%). (LC/MS; m/z 316.2 $[M+H]^+$). The structure was confirmed by NOESY and 2D NMR. $^1H$ NMR (400 MHz, DMSO-$d_6$) δ ppm: 9.23-9.24 (d, 1H), 9.04 (s, 1H), 8.60 (s, 1H), 8.19-8.60 (m, 3H), 7.37-7.46 (m, 2H).

Synthesis of ethyl 2-azido-2,2-difluoroacetate (R6)

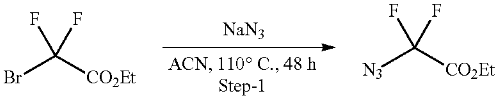

R6

Step 1: A solution of ethyl 2-bromo-2,2-difluoroacetate (1.0 g, 4.92 mmol) in ACN (15 mL) was treated with $NaN_3$ (640 mg, 9.85 mmol) at RT. The mixture was stirred at 110° C. for 48 h (sealed tube). The reaction mixture was cooled to 0° C., the obtained solids were filtered and washed with ACN (10 mL). The filtrate (25 ml), containing ethyl 2-azido-2,2-difluoroacetate (R6) was used as such without further workup and purification.

Synthesis of 4-(1-(difluoromethyl)-1H-1,2,3-triazol-4-yl)-6-(4-fluorophenyl)nicotinonitrile (Int-61)

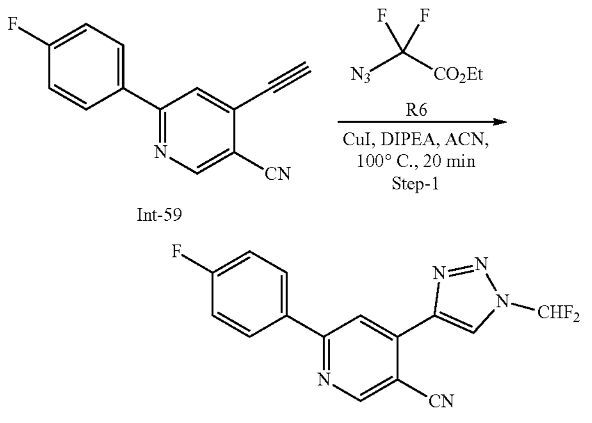

Int-59

Int-61

Step 1: A solution of Int-59 (550 mg, 2.47 mmol) in ACN (2 mL) was treated with ethyl 2-azido-2,2-difluoroacetate (R6) (22 mL), CuI (47 mg, 0.24 mmol) and DIPEA (319 mg, 2.47 mmol). The reaction mixture was stirred at 100° C. for 20 min under microwave radiation (sealed microwave vial) and monitored by TLC. TLC mobile phase: 10% EtOAc in pet ether, RF: 0.41, TLC detection: UV. The reaction mixture was diluted with $H_2O$ (50 mL) and extracted with EtOAc (2×30 mL). The organic layer was washed with brine (20 mL), dried over anhydrous $Na_2SO_4$ and concentrated under reduced pressure to afford a brown liquid (600 mg, LC/MS 57%). The crude product was purified by normal phase flash column chromatography using a 24 g column (silica) and a gradient of 0-15% EtOAc in pet ether as an eluent to afford 4-(1-(difluoromethyl)-1H-1,2,3-triazol-4-yl)-6-(4-fluorophenyl)nicotinonitrile (Int-61) as an off-white solid (300 mg, 35%, LC/MS 87%). (LC/MS; m/z 316.2 $[M+H]^+$). The structure was confirmed by NOE and HSQC. $^1H$ NMR (400 MHz, DMSO-$d_6$) δ ppm: 9.61 (s, 1H), 9.20 (s, 1H), 8.30-8.60 (m, 4H), 7.40-7.45 (m, 2H).

Example 102: Synthesis of N-((4-(1-(difluoromethyl)-1H-1,2,3-triazol-4-yl)-6-(4-fluorophenyl)pyridin-3-yl)methyl)acrylamide (Cpd. No. 229)

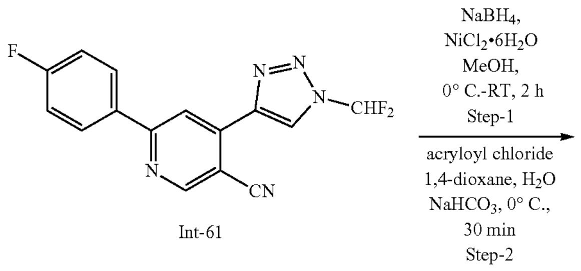

Int-61

-continued

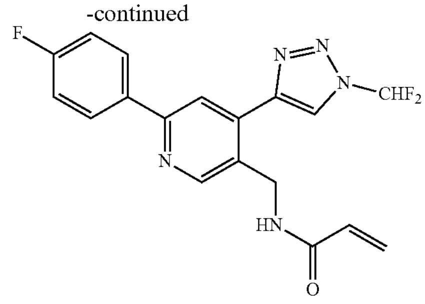

Cpd. No. 229

Steps 1-2: These steps were executed in a manner similar (use of appropriate reagents and purification methods known to the person skilled in the art) to step 2 and 3 towards Cpd. No. 157. From Int-61 (280 mg, 0.88 mmol, LC/MS 87%) was obtained crude product (300 mg, LC/MS 49%) which was purified by preparative HPLC method H3. The collected fractions were lyophilised to afford N-((4-(1-(difluoromethyl)-1H-1,2,3-triazol-4-yl)-6-(4-fluorophenyl)pyridin-3-yl)methyl)acrylamide (Cpd. No. 229) as a white solid (91 mg, 31%). (LC/MS; m/z 374.3 [M+H]$^+$).

Compound Cpd. No. 230 (prepared from Int-60) was prepared in a manner similar (use of appropriate reagents and purification methods known to the person skilled in the art) to Cpd. No. 229.

Synthesis of 4,5,6,7-tetrahydro-[1,2,3]oxadiazolo[3,4-a]pyridin-2-ium-3-olate (R7)

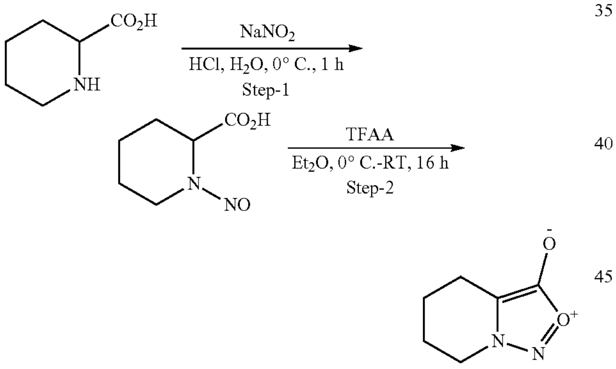

R7

Step 1: A solution of piperidine-2-carboxylic acid (40 g, 309.7 mmol) in $H_2O$ (144 mL) was cooled to 0° C. and treated with conc. HCl (37 mL) followed by a solution of $NaNO_2$ (22.1 g, 325.5 mmol) in $H_2O$ (47 mL). The reaction mixture was stirred at 0° C. for 1 h and monitored by TLC. TLC mobile phase: 10% MeOH in DCM, RF: 0.16, TLC detection: UV. The reaction mixture was diluted with $H_2O$ (50 mL) and extracted with DCM (2×30 mL). The organic layer was dried over anhydrous $Na_2SO_4$ and concentrated under reduced pressure to afford 1-nitrosopiperidine-2-carboxylic acid as a yellow liquid (20 g, 41%). (LC/MS; m/z 159.1 [M+H]$^+$).

Step 2: A solution of 1-nitrosopiperidine-2-carboxylic acid (20 g, 126.6 mmol) in $Et_2O$ (500 mL) was cooled to 0° C. and treated with TFAA (40 mL). The reaction mixture was stirred at RT for 16 h and monitored by TLC. TLC mobile phase: 10% MeOH in DCM, RF: 0.63, TLC detection: UV. The reaction mixture was concentrated under reduced pressure to afford a brown liquid (20 g). The crude product was purified by normal phase flash column chromatography using a 80 g column (silica) and a gradient of 0-10% MeOH in DCM as an eluent to afford 4,5,6,7-tetrahydro-[1,2,3]oxadiazolo[3,4-a]pyridin-2-ium-3-olate (R7) as a brown gum (6.0 g, 33%). $^1$H NMR (400 MHz, $CDCl_3$) δ ppm: 4.24-4.27 (t, 2H), 2.63-2.67 (t, 2H), 2.08-2.14 (m, 2H), 1.96-1.98 (m, 2H).

Example 103: Synthesis of N-((6-(4-fluorophenyl)-4-(4,5,6,7-tetrahydropyrazolo[1,5-a]pyridin-2-yl)pyridin-3-yl)methyl)acrylamide (Cpd. No. 231)

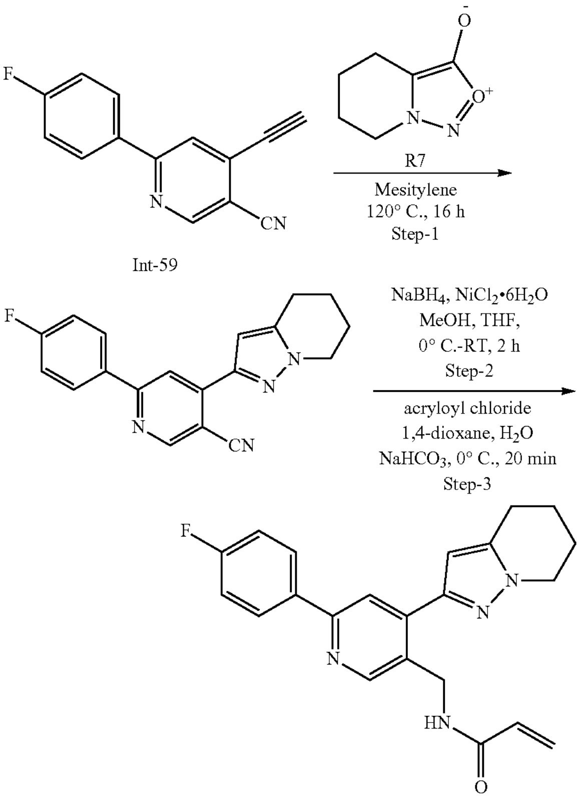

Cpd. No. 231

Step 1: A solution of Int-59 (700 mg, 3.15 mmol) in mesitylene (14 mL) was treated with 4,5,6,7-tetrahydro-[1,2,3]oxadiazolo[3,4-a]pyridin-2-ium-3-olate (R7) (883 mg, 6.30 mmol). The mixture was stirred at 120° C. for 16 h and monitored by TLC. TLC mobile phase: 50% EtOAc in pet ether, RF: 0.56, TLC detection: UV. The reaction mixture was diluted with $H_2O$ (50 mL) an extracted with EtOAc (2×30 mL). The combined organic layer was washed with brine (30 mL), dried over $Na_2SO_4$ and concentrated under reduced pressure to afford a brown liquid (1.5 g). The crude product was purified by normal phase flash column chromatography using a 40 g column (silica) and a gradient of 0-18% EtOAc in pet ether as an eluent to afford 6-(4-fluorophenyl)-4-(4,5,6,7-tetrahydropyrazolo[1,5-a]pyridin-2-yl)nicotinonitrile as a pale yellow solid (450 mg, 45%, LC/MS 97%). (LC/MS; m/z 319.2 [M+H]$^+$).

Steps 2-3: These steps were executed in a manner similar (use of appropriate reagents and purification methods known to the person skilled in the art) to step 3 and 4 towards Cpd. No. 193. 6-(4-fluorophenyl)-4-(4,5,6,7-tetrahydropyrazolo[1,5-a]pyridin-2-yl)nicotinonitrile (450 mg, 1.41 mmol) yielded crude product (580 mg, LC/MS 82%) which was purified by preparative HPLC method H3. The collected fractions were lyophillised to afford N-((6-(4-fluorophenyl)-4-(4,5,6,7-tetrahydropyrazolo[1,5-a]pyridin-2-yl)pyridin-3-yl)methyl)acrylamide (Cpd. No. 231) as a white solid (246 mg, 46%). (LC/MS; m/z 377.3 $[M+H]^+$).

Compound Cpd. No. 232 was prepared in a manner similar (use of appropriate reagents and purification methods known to the person skilled in the art) to Cpd. No. 231.

Example 104: Synthesis of N-((6-(4-fluorophenyl)-4-(1-methyl-1H-pyrazol-3-yl)-2-oxo-1,2-dihydropyridin-3-yl)methyl)acrylamide (Cpd. No. 233)

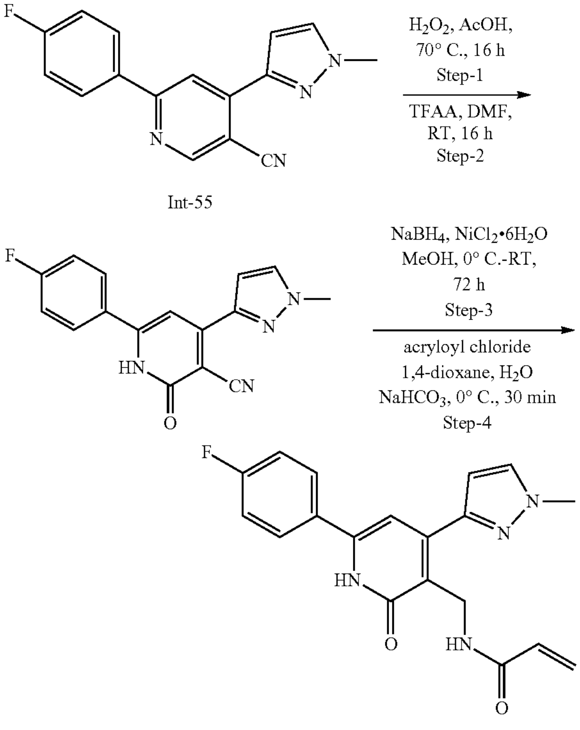

Int-55

Cpd. No. 230

Step 1: To a solution of Int-55 (3.0 g, 10.8 mmol, LC/MS 94%) in AcOH (10 mL) was added $H_2O_2$ (9.16 g, 269.5 mmol) (33% in $H_2O$) at RT. The reaction mixture was stirred at 70° C. for 16 h and monitored by TLC. TLC mobile phase: 30% EtOAc in pet ether, RF: 0.19, TLC detection: UV. The reaction mixture was cooled to RT and extracted with EtOAc (3×50 mL). The combined organic layer was washed with brine (15 mL), dried over anhydrous $Na_2SO_4$ and concentrated under reduced pressure to afford crude product (2.8 g, LC/MS 65%). The crude product was purified by normal phase flash column chromatography using silica gel (100-200 mesh) and a gradient of 0-20% EtOAc in pet ether as an eluent to afford 5-cyano-2-(4-fluorophenyl)-4-(1-methyl-1H-pyrazol-3-yl) pyridine 1-oxide as a yellow solid (1.0 g, 28%, LC/MS 85%). (LC/MS; m/z 295.2 $[M+H]^+$).

Step 2: To a solution of 5-cyano-2-(4-fluorophenyl)-4-(1-methyl-1H-pyrazol-3-yl) pyridine 1-oxide (1.0 g, 3.40 mmol, LC/MS 85%) in DMF (10 mL) was added dropwise TFAA (25 g, 119.04 mmol) at 0° C. The reaction mixture was stirred at RT for 16 hr and monitored by TLC. TLC mobile phase: 50% EtOAc in pet ether, RF: 0.35, TLC detection: UV. The reaction mixture was concentrated under reduced pressure and diluted with ice $H_2O$ (50 mL), then stirred for 10 min. The obtained precipitate was filtered and the collected solid product was dried under reduced pressure to afford 6-(4-fluorophenyl)-4-(1-methyl-1H-pyrazol-3-yl)-2-oxo-1,2-dihydropyridine-3-carbonitrile as a yellow solid (800 mg, 85%, LC/MS 91%). (LC/MS; m/z 295.2 $[M+H]^+$).

Steps 3-4: These steps were executed in a manner similar (use of appropriate reagents and purification methods known to the person skilled in the art) to step 3 and 4 towards Cpd. No. 193. Starting material (600 mg, 2.04 mmol, LC/MS 91%) yielded crude product (240 mg, LC/MS 46%) which was purified by preparative HPLC method H1. The collected fractions were lyophilised to afford N-((6-(4-fluorophenyl)-4-(1-methyl-1H-pyrazol-3-yl)-2-oxo-1,2-dihydropyridin-3-yl)methyl)acrylamide (Cpd. No. 233) as a white solid (22 mg, 3%). (LC/MS; m/z 353.3 $[M+H]^+$).

Example 105: Synthesis of N-((5-(4-fluorophenyl)-3-(1-methyl-1H-pyrazol-3-yl)-6-oxo-1,6-dihydropyridin-2-yl)methyl)acrylamide (Cpd. No. 234)

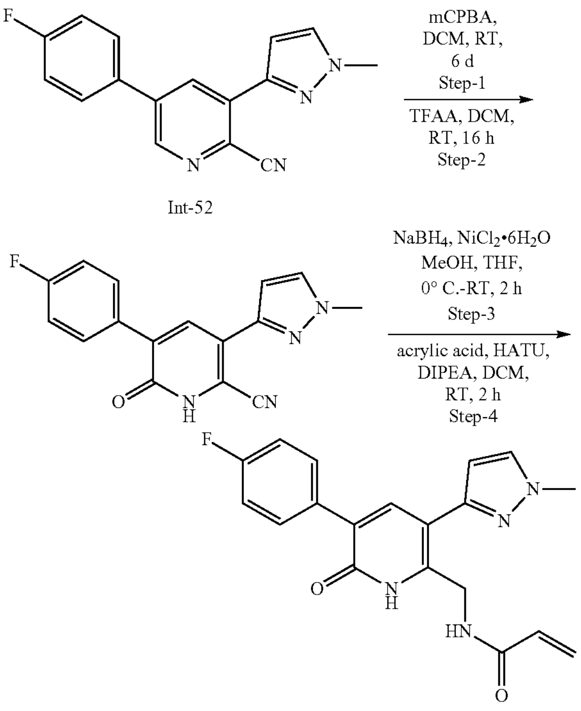

Int-52

Cpd. No. 234

Step 1: To a solution of Int-52 (325 mg, 1.17 mmol) in DCM (1 mL) was added mCPBA (220 mg, 1.28 mmol). The reaction mixture was stirred at RT for 6 d and monitored by LC/MS. An additional amount of mCPBA (110 mg, 0.64 mmol) was added after 3 d and after 4 d. The reaction mixture was diluted with DCM (10 mL) and washed with sat aq $NaHCO_3$ (10 mL). The aqueous layer was extracted with DCM (10 mL) and the organic layer was washed with brine, dried over anhydrous $Na_2SO_4$, filtered and concentrated under reduced pressure to afford crude 2-cyano-5-(4-fluorophenyl)-3-(1-methyl-1H-pyrazol-3-yl)pyridine 1-oxide (450 mg). (LC/MS; m/z 295 $[M+H]^+$). The product was used as such without further purification.

Step 2: To a solution 2-cyano-5-(4-fluorophenyl)-3-(1-methyl-1H-pyrazol-3-yl)pyridine 1-oxide (450 mg, 1.53 mmol) in DMF (14 mL) was added TFAA (7.0 mL, 49.59 mmol). The reaction mixture was stirred at RT for 16 h. The reaction mixture was poured into ice $H_2O$ (100 mL) and the suspension was extracted with EtOAc (2×100 mL). The organic layer was washed with brine, dried over anhydrous $Na_2SO_4$ and concentrated under reduced pressure. The residue was purified by normal phase flash column chromatography using a 40 g column (silica) and a gradient of 5-60% EtOAc in DCM as an eluent to afford crude 5-(4-fluorophenyl)-3-(1-methyl-1H-pyrazol-3-yl)-6-oxo-1,6-dihydropyridine-2-carbonitrile (427 mg, 95%). (LC/MS; m/z 295 $[M+H]^+$). The product was used as such without further purification.

Step 3: This step was executed in a manner similar (use of appropriate reagents and purification methods known to the person skilled in the art) to step 3 towards Cpd. No. 193. From 5-(4-fluorophenyl)-3-(1-methyl-1H-pyrazol-3-yl)-6-oxo-1,6-dihydropyridine-2-carbonitrile (150 mg, 0.51 mmol) was obtained crude 6-(aminomethyl)-3-(4-fluorophenyl)-5-(1-methyl-1H-pyrazol-3-yl)pyridin-2(1H)-one (71 mg, 47%). (LC/MS; m/z 299.1 $[M+H]^+$). The product was used as such without further purification.

Step 4: To 6-(aminomethyl)-3-(4-fluorophenyl)-5-(1-methyl-1H-pyrazol-3-yl)pyridin-2(1H)-one (63 mg, 0.21 mmol) and HATU (90 mg, 0.24 mmol) was added a solution of acrylic acid (14 μL, 0.21 mmol) in DCM (2 mL) followed by DIPEA (55 μL, 0.32 mmol). The reaction mixture was stirred at RT for 2 h and monitored by LC/MS. The reaction mixture was diluted with DCM (10 mL), washed with sat aq $NaHCO_3$ (5 mL), filtered over a phase separator and concentrated under reduced pressure. The residue was purified by normal phase flash column chromatography using silica gel (100-200 mesh) and a gradient of 1-70% MeOH in DCM as an eluent to afford N-((5-(4-fluorophenyl)-3-(1-methyl-1H-pyrazol-3-yl)-6-oxo-1,6-dihydropyridin-2-yl)methyl)acrylamide (Cpd. No. 234) as a white solid (2 mg, 7%). (LC/MS; m/z 353.3 $[M+H]^+$).

Example 106: Synthesis of N-((1-(4-fluorophenyl)-5-(1-methyl-1H-pyrazol-3-yl)-2-oxo-1,2-dihydropyridin-4-yl)methyl)acrylamide (Cpd. No. 235)

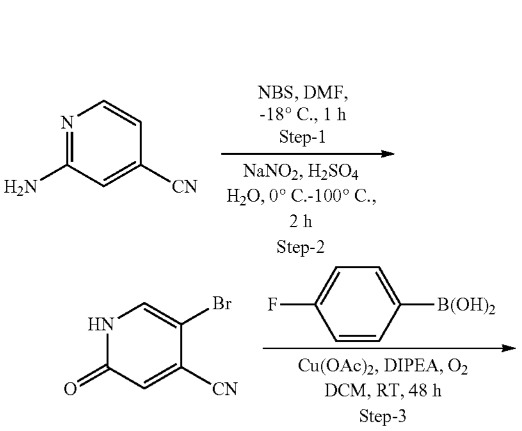

-continued

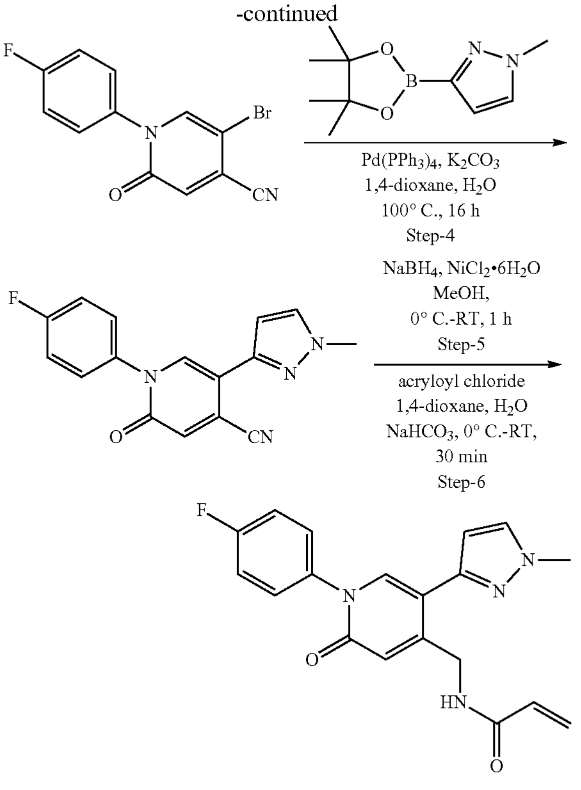

Cpd. No. 235

Step 1: To a solution of 2-amino-5-bromoisonicotinonitrile (10 g, 83.9 mmol) in DMF (20 mL) was added NBS (16.4 g, 92.3 mmol) portionwise at −18° C. The reaction mixture was stirred at RT for 1 h and monitored by TLC. TLC mobile phase: 20% EtOAc in pet ether, RF: 0.48, TLC detection: UV. The reaction mixture was quenched with $H_2O$ (500 mL), extracted with EtOAc (2×400 mL). The combined organic layer was washed with brine, dried over anhydrous $Na_2SO_4$ and concentrated under reduced pressure to afford crude product (11 g, LC/MS 86%) which was triturated with EtOAc (20 mL). The solid product was filtered, washed with $Et_2O$ (50 mL) and dried to afford 2-amino-5-bromoisonicotinonitrile as a pale yellow solid (9.0 g, 56%). (LC/MS; m/z 189.2 $[M+H]^+$).

Step 2: To a solution of 2-amino-5-bromoisonicotinonitrile (2 g, 10.10 mmol) in $H_2SO_4$ (7 mL) was added a solution of $NaNO_2$ (1.39 g, 20.20 mmol) in $H_2O$ (40 mL) dropwise at 0° C. The reaction mixture was stirred at 100° C. for 2 h and monitored by TLC. TLC mobile phase: 70% EtOAc in pet ether, RF: 0.70, TLC detection: UV. The reaction mixture was cooled to 0° C. and diluted with $H_2O$ (150 mL). The obtained solids were filtered, washed with $H_2O$ (30 mL) and dried to afford 5-bromo-2-oxo-1,2-dihydropyridine-4-carbonitrile as a pale yellow solid (1.5 g, 65%, LC/MS 90%). (LC/MS; m/z 199.1 $[M+H]^+$).

Step 3: A solution of 5-bromo-2-oxo-1,2-dihydropyridine-4-carbonitrile (1.5 g, 7.53 mmol) in DCM (30 mL) was treated with DIPEA (4.88 g, 37.68 mmol), (4-fluorophenyl) boronic acid (1.58 g, 11.30 mmol) and $Cu(OAc)_2$ (1.64 g, 9.04 mmol). The reaction mixture was stirred at RT for 24 h under an oxygen atmosphere and monitored by TLC. TLC mobile phase: 70% EtOAc in pet ether, RF: 0.70, TLC detection: UV. The reaction mixture was filtered through a celite pad, washed with EtOAc (200 mL) and the filtrate was washed with $H_2O$ (80 mL) and brine (80 mL). The organic layer was dried over anhydrous $Na_2SO_4$ and concentrated under reduced pressure to afford crude product (1.6 g, LC/MS 62%) which was purified by normal phase flash column chromatography using a 40 g column (silica) and a gradient of 0-50% EtOAc in pet ether to afford 1-(4-fluorophenyl)-5-(1-methyl-1H-pyrazol-3-yl)-2-oxo-1,2-dihydropyridine-4-carbonitrile as a grey solid (0.92 g, 46%). (LC/MS; m/z 293.1 $[M+H]^+$).

Steps 4-6: These steps were executed in a manner similar (use of appropriate reagents and purification methods known to the person skilled in the art) to step 2, 3 and 4 towards Cpd. No. 193. Starting material (1.0 g, 3.41 mmol, LC/MS 97%) yielded a brown gum (250 mg, LC/MS 51%) which was purified by preparative HPLC method H2. The collected fractions were lyophilised to afford N-((1-(4-fluorophenyl)-5-(1-methyl-1H-pyrazol-3-yl)-2-oxo-1,2-dihydropyridin-4-yl)methyl)acrylamide (Cpd. No. 235) as a white solid (18 mg, 1.5%). (LC/MS; m/z 353.3 $[M+H]^+$).

The following compounds were prepared in a manner similar (use of appropriate reagents and purification methods known to the person skilled in the art) to Cpd. No. 235: Cpd. No. 236, Cpd. No. 237 (employing methanesulfonyl chloride and TEA at step 6), Cpd. No. 238 (employing methylsulfamoyl chloride and TEA at step 6).

Example 107: Synthesis of N-((6-(4-fluorophenyl)-4-(1H-pyrazol-1-yl)pyridin-3-yl)methyl)acrylamide (cpd-Cpd. No. 239)

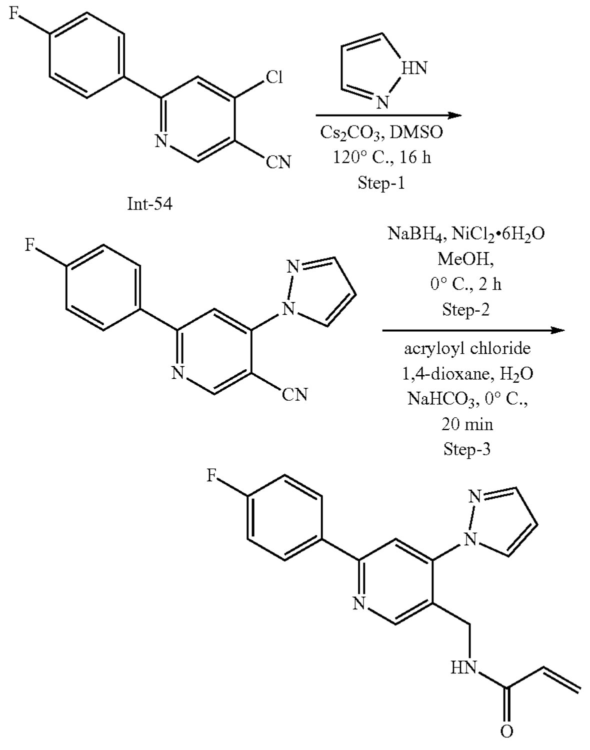

Int-54

Cpd. No. 239

Step 1: A solution of 4-chloro-6-(4-fluorophenyl)nicotinonitrile (Int-54) (1.0 g, 4.3 mmol) in DMSO (10 mL) was treated with $Cs_2CO_3$ (1.54 g, 4.73 mmol) and pyrazole (278 mg, 4.08 mmol) at RT. The reaction mixture was stirred at 120° C. for 16 h (sealed tube) and monitored by TLC. TLC mobile phase: 20% EtOAc in pet ether, RF: 0.61, TLC detection: UV. The reaction mixture was diluted with $H_2O$ (80 mL) and extracted with EtOAc (2×40 mL). The organic layer was washed with brine solution (40 mL), dried over anhydrous $Na_2SO_4$ and concentrated under reduced pressure to afford crude product (1.5 g, LC/MS 41%) which was purified by normal phase flash column chromatography using a 24 g column (silica) and a gradient of 0-18% EtOAc in pet ether as an eluent to afford 6-(4-fluorophenyl)-4-(1H-pyrazol-1-yl)nicotinonitrile as an off-white solid (500 mg, 44%). (LC/MS; m/z 265.1 $[M+H]^+$).

Steps 2-3: These steps were executed in a manner similar (use of appropriate reagents and purification methods known to the person skilled in the art) to step 3 and 4 towards Cpd. No. 193. From 6-(4-fluorophenyl)-4-(1H-pyrazol-1-yl)nicotinonitrile (460 mg, 1.74 mmol) was obtained crude product (480 mg, LC/MS 68%) which was purified by preparative HPLC method H1. The collected fractions were lyophilised to afford N-((6-(4-fluorophenyl)-4-(1H-pyrazol-1-yl)pyridin-3-yl)methyl)acrylamide (Cpd. No. 239) as a white solid (194 mg, 34%). (LC/MS; m/z 323.2 $[M+H]^+$).

The following compounds were prepared in a manner similar (use of appropriate reagents and purification methods known to the person skilled in the art) to Cpd. No. 239: Cpd. No. 240, Cpd. No. 241 (prepared from Int-25), Cpd. No. 242 (prepared from Int-25), Cpd. No. 243, Cpd. No. 244, Cpd. No. 245, Cpd. No. 246, Cpd. No. 247, Cpd. No. 248.

Example 108: Synthesis of N-((6-(4-fluorophenyl)-4-(5-methyl-2H-tetrazol-2-yl)pyridin-3-yl)methyl) acrylamide (Cpd. No. 249)

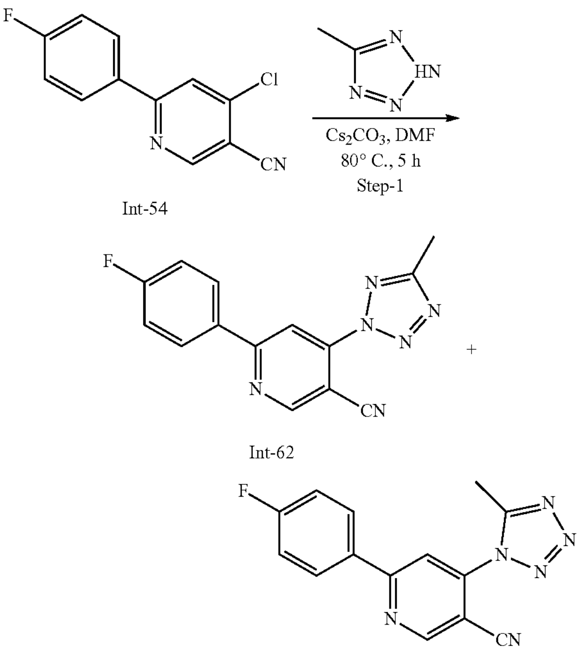

Int-54

Int-62

+

Int-63

-continued

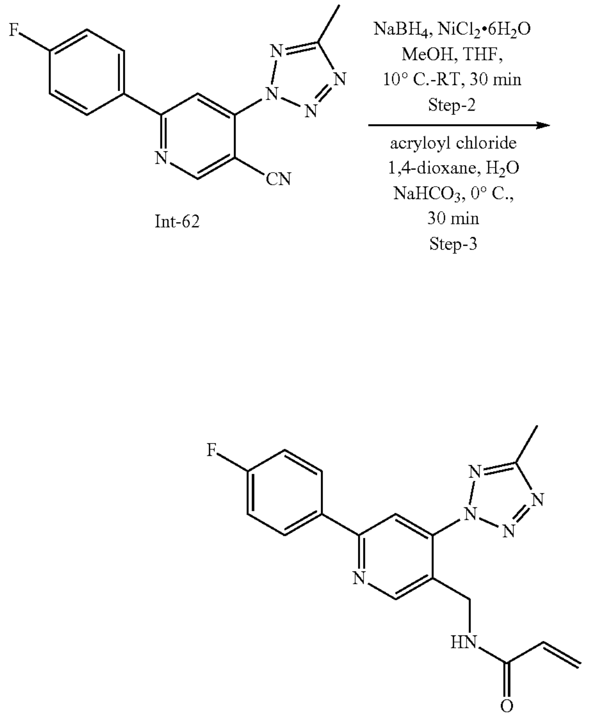

Int-62

Cpd. No. 249

Step 1: This step was executed in a manner similar (use of appropriate reagents and purification methods known to the person skilled in the art) to step 1 towards Cpd. No. 239. Reacting Int-54 (3 g, 12.9 mmol) with 5-methyl-2H-tetrazole (1.54 g, 19.3 mmol) yielded crude product (3.2 g, LC/MS 18% Int-62, 8% Int-63) which was purified by normal phase flash column chromatography using silica gel (100-200 mesh) and a gradient of 10-20% EtOAc in pet ether as an eluent to afford 6-(4-fluorophenyl)-4-(5-methyl-2H-tetrazol-2-yl)nicotinonitrile (Int-62) as a white solid (450 mg, 12%) and 6-(4-fluorophenyl)-4-(5-methyl-1H-tetrazol-1-yl)nicotinonitrile (Int-63) as a brown solid (150 mg, 4%). Int-62: $^1$H NMR (400 MHz, DMSO-$d_6$) δ ppm: 9.11 (s, 1H), 8.51 (s, 1H), 8.16-8.19 (m, 2H), 7.22-7.27 (m, 2H), 2.74 (s, 3H); (LC/MS; m/z 281.2 $[M+H]^+$). Int-63: $^1$H NMR (400 MHz, DMSO-$d_6$) δ ppm: 9.41 (s, 1H), 8.63 (s, 1H), 8.31-8.34 (m, 2H), 7.42-7.47 (t, 2H), 2.71 (s, 3H); (LC/MS; m/z 281.2 $[M+H]^+$). The structures of Int-62 and Int-63 were determined by NOESY and $^{15}$N HMBC.

Steps 2-3: These steps were executed in a manner similar (use of appropriate reagents and purification methods known to the person skilled in the art) to step 2 and 3 towards Cpd. No. 239. Int-62 (200 mg, 0.71 mmol) yielded crude product (220 mg) which was purified by preparative HPLC method H1. The collected fractions were lyophilised to afford N-((6-(4-fluorophenyl)-4-(5-methyl-2H-tetrazol-2-yl)pyridin-3-yl)methyl)acrylamide (Cpd. No. 249) as a white solid (30 mg, 12%). (LC/MS; m/z 339.2 $[M+H]^+$).

The following compounds were prepared in a manner similar (use of appropriate reagents and purification methods known to the person skilled in the art) to Cpd. No. 249: Cpd. No. 250 (prepared from Int-63), Cpd. No. 251 and Cpd. No. 252 (prepared from Int-63).

Example 109: Synthesis of N-((2-(4-fluorophenyl)-4-(1-methyl-1H-pyrazol-3-yl)pyrimidin-5-yl)methyl) acrylamide (Cpd. No. 253)

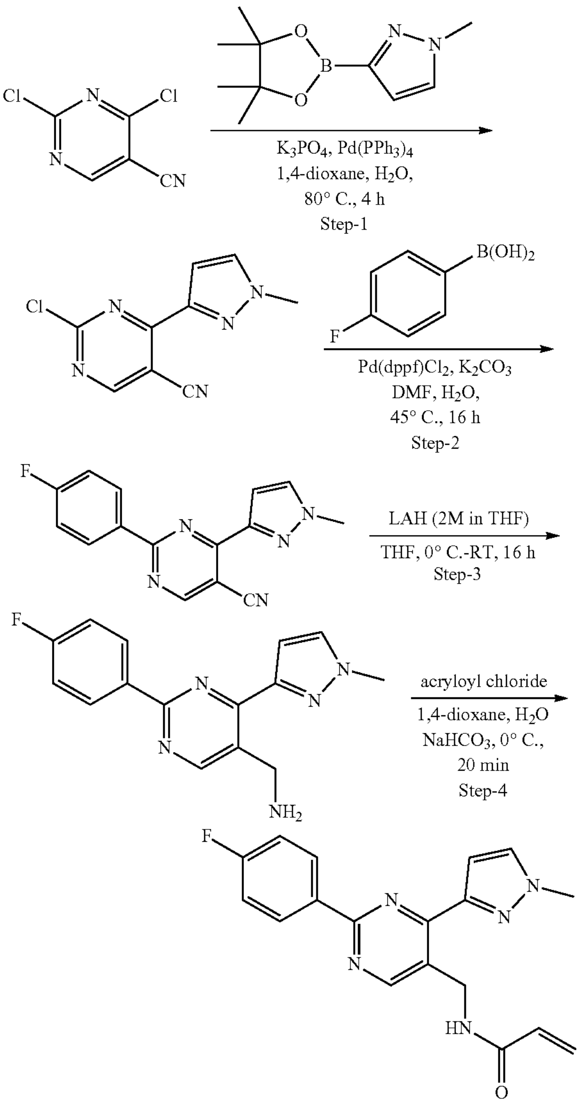

Cpd. No. 253

Step 1: A solution of 2,4-dichloropyrimidine-5-carbonitrile (2.0 g, 11.5 mmol), 1-methyl-3-(4,4,5,5-tetramethyl-1,3,2-dioxaborolan-2-yl)-1H-pyrazole (2.39 g, 11.5 mmol) and $K_3PO_4$ (4.88 g, 23 mmol) in 1,4-dioxane (60 mL) and $H_2O$ (6 mL) was degassed with argon for 20 min. To the mixture was added $Pd(PPh_3)_4$ (265 mg, 0.23 mmol). The reaction mixture was stirred at 80° C. for 4 h (sealed tube) and monitored by TLC. TLC mobile phase: 50% EtOAc in pet ether, RF: 0.67, TLC detection: UV. The reaction mixture was cooled to RT, diluted with $H_2O$ (100 mL) and extracted with EtOAc (2×50 mL). The combined organic layer was washed with brine (50 mL), dried over anhydrous $Na_2SO_4$ and concentrated under reduced pressure to afford crude product (1.5 g, LC/MS 35%) which was purified by normal phase flash column chromatography using a 40 g column (silica) and a gradient of 0-13% EtOAc in pet ether as an eluent to afford 2-chloro-4-(1-methyl-1H-pyrazol-3-yl)pyrimidine-5-carbonitrile as an off-white solid (244 mg, 10%). (LC/MS; m/z 220.1 [M+H]$^+$).

Step 2: A solution of 2-chloro-4-(1-methyl-1H-pyrazol-3-yl)pyrimidine-5-carbonitrile (400 mg, 1.83 mmol), (4-fluorophenyl)boronic acid (307 mg, 2.19 mmol) and $K_2CO_3$ (302 mg, 2.19 mmol) in DMF (8 mL) and $H_2O$ (2 mL) was degassed with argon for 20 min. To the mixture was added Pd(dppf)$Cl_2$·DCM (83 mg, 0.1 mmol). The reaction mixture was stirred at 45° C. for 16 h and monitored by TLC. TLC mobile phase: 50% EtOAc in pet ether, RF: 0.75, TLC detection: UV. The reaction mixture was cooled to RT, diluted with $H_2O$ (40 mL) and extracted with EtOAc (2×30 mL). The combined organic layer was washed with brine (20 mL), dried over anhydrous $Na_2SO_4$ and concentrated under reduced pressure to afford crude product (600 mg, LC/MS 33%) which was purified by normal phase flash column chromatography using a 12 g column (silica) and a gradient of 0-38% EtOAc in pet ether as an eluent to afford 2-(4-fluorophenyl)-4-(1-methyl-1H-pyrazol-3-yl)pyrimidine-5-carbonitrile (100 mg, 20%) as a white solid. (LC/MS; m/z 280.0 [M+H]$^+$).

Step 3: A solution of 2-(4-fluorophenyl)-4-(1-methyl-1H-pyrazol-3-yl)pyrimidine-5-carbonitrile (80 mg, 0.29 mmol) in THF (2 mL) at 0° C. was treated with LAH (2M in THF, 1.7 mL, 3.44 mmol). The reaction mixture was stirred at RT for 16 h and monitored by TLC. TLC mobile phase: 10% MeOH in DCM, RF: 0.10, TLC detection: UV. The reaction mixture was cooled to 0° C., quenched with wet $Na_2SO_4$, filtered through a celite pad and washed with EtOAc (30 mL). The filtrate was dried over anhydrous $Na_2SO_4$ and concentrated under reduced pressure to afford (2-(4-fluorophenyl)-4-(1-methyl-1H-pyrazol-3-yl)pyrimidin-5-yl)methanamine (80 mg, LC/MS 36%). (LC/MS; m/z 284.2 [M+H]$^+$). The product was used as such without further purification.

Step 4: A solution of (2-(4-fluorophenyl)-4-(1-methyl-1H-pyrazol-3-yl)pyrimidin-5-yl)methanamine (70 mg, 0.25 mmol) in 1,4-dioxane (2 mL) at 0° C. was treated with $NaHCO_3$ (62 mg, 0.74 mmol) in $H_2O$ (0.5 mL), and acryloyl chloride (22 mg, 0.25 mmol) dissolved in 1,4-dioxane (1 mL). The reaction mixture was stirred at 0° C. for 20 min and monitored by TLC. TLC mobile phase: 10% MeOH in DCM, RF: 0.3, TLC detection: UV. The reaction mixture was diluted with $H_2O$ (20 mL) and extracted with EtOAc (2×20 mL). The combined organic layer was washed with brine (20 mL), dried over anhydrous $Na_2SO_4$ and concentrated under reduced pressure to afford crude product (50 mg, LC/MS 17%) which was purified by preparative HPLC method H2. The collected fractions were lyophilised to afford N-((2-(4-fluorophenyl)-4-(1-methyl-1H-pyrazol-3-yl)pyrimidin-5-yl)methyl)acrylamide (Cpd. No. 253) as a white solid (3.5 mg, 4%). (LC/MS; m/z 338.2 [M+H]$^+$).

Compound Cpd. No. 254 (employing 1-(difluoromethyl)-3-(4,4,5,5-tetramethyl-1,3,2-dioxa-borolan-2-yl)-1H-pyrazole and Pd$(PPh_3)_2Cl_2$ in step 1) was prepared in a manner similar (use of appropriate reagents and purification methods known to the person skilled in the art) to Cpd. No. 253.

Example 110: Synthesis of N-((2-(1-(difluoromethyl)-1H-pyrazol-3-yl)-6-(4-fluorophenyl)pyrimidin-4-yl)methyl)acrylamide (Cpd. No. 255)

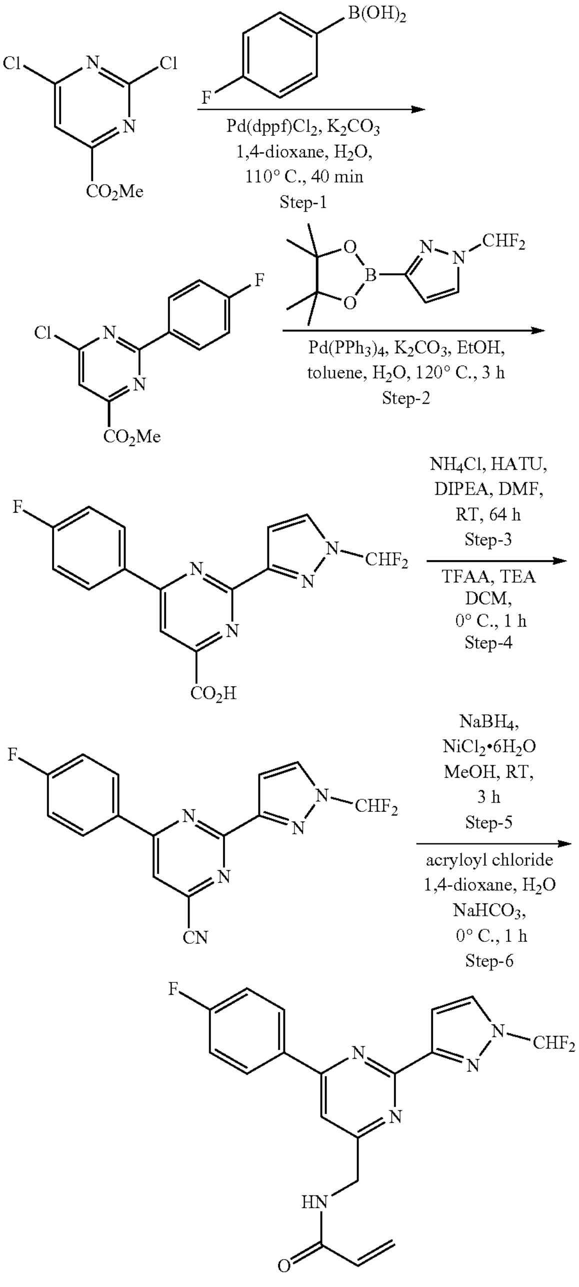

Cpd. No. 255

Step 1: This step was executed in a manner similar (use of appropriate reagents and purification methods known to the person skilled in the art) to step 1 towards Cpd. No. 193. From methyl 2,6-dichloropyrimidine-4-carboxylate (3.0 g, 14.5 mmol) was obtained crude product (3.5 g) which was purified by normal phase flash column chromatography using silica gel (100-200 mesh) and a gradient of 0-6% EtOAc in pet ether as an eluent to afford methyl 2-chloro-6-(4-fluorophenyl)pyrimidine-4-carboxylate (1.5 g, 38%, LC/MS 99%) as a white solid. (LC/MS; m/z 267.1 [M+H]$^+$).

Step 2: This step was executed in a manner similar (use of appropriate reagents and purification methods known to the person skilled in the art) to step 2 towards Cpd. No. 209. From (1.5 g, 5.63 mmol) was obtained crude product which was triturated with n-pentane (25 mL) to afford 2-(1-(difluoromethyl)-1H-pyrazol-3-yl)-6-(4-fluorophenyl)pyrimidine-4-carboxylic acid (1.0 g, 43%, LC/MS 79%) as a yellow solid. (LC/MS; m/z 335.2 $[M+H]^+$).

Step 3: A solution of 2-(1-(difluoromethyl)-1H-pyrazol-3-yl)-6-(4-fluorophenyl)pyrimidine-4-carboxylic acid (950 mg, 2.84 mmol), DIPEA (1.09 g, 8.52 mmol), HATU (1.62 g, 4.26 mmol) and $NH_4Cl$ (304 mg, 5.68 mmol) in DMF (10 ml) was stirred at RT for 64 h and monitored by TLC. TLC mobile phase: 70% EtOAc in pet ether, RF: 0.21, TLC detection: UV. The reaction mixture was triturated with ice $H_2O$ (100 ml) and the obtained solids were washed with n-pentane (20 ml). The solids were dried under reduced pressure to afford 2-(1-(difluoromethyl)-1H-pyrazol-3-yl)-6-(4-fluorophenyl)pyrimidine-4-carboxamide (850 mg, LC/MS 62%) as a brown solid. (LC/MS; m/z 334.1 $[M+H]^+$). The product was used as such without further purification.

Step 4: A solution of 2-(1-(difluoromethyl)-1H-pyrazol-3-yl)-6-(4-fluorophenyl)pyrimidine-4-carboxamide (500 mg, 1.50 mmol) in DCM (25 mL) was treated with TFAA (2.20 g, 10.51 mmol) and TEA (1.06 g, 10.51 mmol) at 0° C. The reaction mixture was stirred at 0° C. for 1 h and monitored by TLC. TLC mobile phase: 50% EtOAc in pet ether, RF: 0.5, TLC detection: UV. The reaction mixture was diluted with DCM (100 mL) and washed with brine (2×100 mL). The organic layer was dried over anhydrous $Na_2SO_4$ and concentrated under reduced pressure to afford a brown gum (300 mg). The crude product was purified by normal phase flash column chromatography using silica gel (100-200 mesh) and a gradient of 0-25% EtOAc in pet ether as an eluent to afford 2-(1-(difluoromethyl)-1H-pyrazol-3-yl)-6-(4-fluorophenyl)pyrimidine-4-carbonitrile (100 mg, 32%, LC/MS 95%) as a white solid. (LC/MS; m/z 316.2 $[M+H]^+$).

Steps 5-6: These steps were executed in a manner similar (use of appropriate reagents and purification methods known to the person skilled in the art) to step 2 and 3 towards Cpd. No. 239. From 2-(1-(difluoromethyl)-1H-pyrazol-3-yl)-6-(4-fluorophenyl)pyrimidine-4-carbonitrile (100 mg, 0.31 mmol) was obtained crude product (100 mg, LC/MS 36%) which was purified by preparative HPLC method H3. The collected fractions were lyophilised to afford N-((2-(1-(difluoromethyl)-1H-pyrazol-3-yl)-6-(4-fluorophenyl)pyrimidin-4-yl)methyl)acrylamide (Cpd. No. 255) as a white solid (16 mg, 14%, LC/MS 99%). (LC/MS; m/z 374.2 $[M+H]^+$).

Example 111: Synthesis of N-(1-(4'-fluoro-3-(1-methyl-1H-pyrazol-3-yl)-[1,1'-biphenyl]-4-yl)cyclopropyl)acrylamide (Cpd. No. 256)

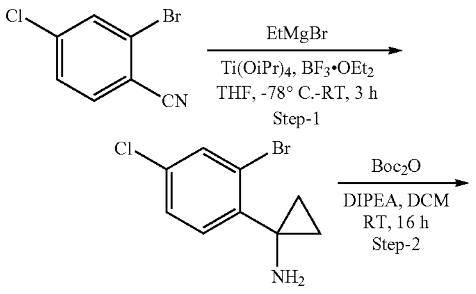

-continued

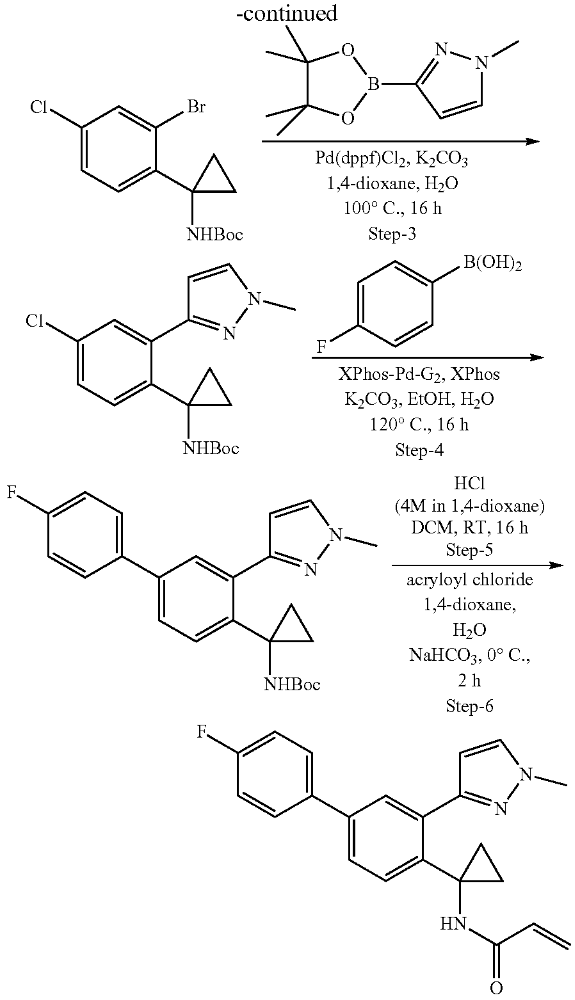

Cpd. No. 256

Step 1: To a cooled (−78° C.) solution of 2-bromo-4-chlorobenzonitrile (10 g, 46.2 mmol) in THF (250 mL) was added dropwise $Ti(OiPr)_4$ (14.4 g, 50.8 mmol) and the mixture was stirred for 5 minutes. To the mixture was added dropwise EtMgBr (3M in $Et_2O$) (46.2 mL, 138.6 mmol). The reaction mixture was stirred for 30 minutes at −78° C., then 1 hour at RT after which $BF_3{\cdot}OEt_2$ (13.1 g, 92.4 mmol) was added dropwise. The reaction was stirred for 2 hours and monitored by TLC. TLC mobile phase: 5% MeOH in DCM, RF: 0.5, TLC detection: UV. The reaction was quenched with 1 M HCl (pH 4) and the aqueous layer was washed with $Et_2O$ (2×200 mL). To the aqueous layer was added 1M NaOH (pH 10) and the layer was extracted with EtOAc (2×100 mL). The organic layer was dried over anhydrous $Na_2SO_4$ and concentrated under reduced pressure to afford crude product (20 g) which was purified by normal phase flash column chromatography using silica gel (100-200 mesh) and a gradient of 0-2% MeOH in DCM as an eluent to afford 1-(2-bromo-4-chlorophenyl)cyclopropan-1-amine as a pale yellow gum (5.0 g, LC/MS 56%). (LC/MS; m/z 246.1 $[M+H]^+$). The product was used as such without further purification.

Step 2: A solution of 1-(2-bromo-4-chlorophenyl)cyclopropan-1-amine (5.0 g, 20.4 mmol) in DCM (100 mL) was treated with DIPEA (5.51 g, 42.6 mmol) and $Boc_2O$ (7.53 g, 34.5 mmol) at RT. The reaction mixture was stirred at RT for 16 h and monitored by TLC. TLC mobile phase: 5% EtOAc in pet ether, RF: 0.5, TLC detection: UV. The reaction was diluted with $H_2O$ (500 mL), the aqueous layer was extracted with DCM (100 mL) and the organic layer was washed with brine (200 mL), dried over anhydrous $Na_2SO_4$ and concentrated under reduced pressure to afford crude product (7 g, LC/MS 54%) which was purified by normal phase flash column chromatography using a 80 g column (silica) and a gradient of 0-3% EtOAc in pet ether as an eluent to afford tert-butyl (1-(2-bromo-4-chlorophenyl)cyclopropyl)carbamate as a yellow solid (3.3 g, LC/MS 83%). (LC/MS; m/z 346.2 $[M+H]^+$). The product was used as such without further purification.

Step 3: This step was executed in a manner similar (use of appropriate reagents and purification methods known to the person skilled in the art) to step 5 to Int-27. From tert-butyl (1-(2-bromo-4-chlorophenyl)-cyclopropyl)carbamate (1.5 g, 4.3 mmol) was obtained tert-butyl (1-(4-chloro-2-(1-methyl-1H-pyrazol-3-yl)phenyl)cyclopropyl) carbamate as a yellow solid (450 mg, 30%). (LC/MS; m/z 348.1 $[M+H]^+$).

Step 4: This step was executed in a manner similar (use of appropriate reagents and purification methods known to the person skilled in the art) to step 2 to Int-26. From tert-butyl (1-(4-chloro-2-(1-methyl-1H-pyrazol-3-yl)phenyl)cyclopropyl)carbamate (450 mg, 1.29 mmol) was obtained tert-butyl (1-(4'-fluoro-3-(1-methyl-1H-pyrazol-3-yl)-[1,1'-biphenyl]-4-yl)cyclopropyl)carbamate as an off-white solid (420 mg, 80%). (LC/MS; m/z 408.2 $[M+H]^+$).

Steps 5: This step was executed in a manner similar (use of appropriate reagents and purification methods known to the person skilled in the art) to step 4 to Int-26.HCl. From tert-butyl (1-(4'-fluoro-3-(1-methyl-1H-pyrazol-3-yl)-[1,1'-biphenyl]-4-yl)cyclopropyl)carbamate (420 mg, 1.03 mmol) was obtained 1-(4'-fluoro-3-(1-methyl-1H-pyrazol-3-yl)-[1,1'-biphenyl]-4-yl)cyclopropan-1-amine hydrochloride as a white solid (318 mg, LC/MS 95%). (LC/MS; m/z 308.2 $[M+H]^+$).

Step 6: This step was executed in a manner similar (use of appropriate reagents and purification methods known to the person skilled in the art) to step 3 towards Cpd. No. 152. From 1-(4'-fluoro-3-(1-methyl-1H-pyrazol-3-yl)-[1,1'-biphenyl]-4-yl)cyclopropan-1-amine hydrochloride (300 mg, 0.87 mmol) was obtained crude product (390 mg, LC/MS 86%) which was purified by preparative HPLC method H5. The collected fractions were lyophilised to afford N-(1-(4'-fluoro-3-(1-methyl-1H-pyrazol-3-yl)-[1,1'-biphenyl]-4-yl) cyclopropyl)acrylamide (Cpd. No. 256) as a white solid (70 mg, 22%). (LC/MS; m/z 362.3 $[M+H]^+$).

Example 112: Synthesis of N-(2-(3-(1-methyl-1H-pyrazol-3-yl)-[1,1'-biphenyl]-4-yl)cyclopropyl)acrylamide (Cpd. No. 257)

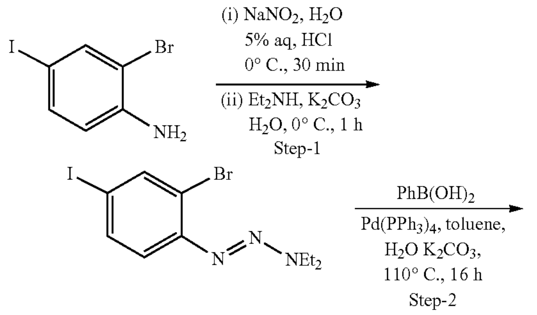

-continued

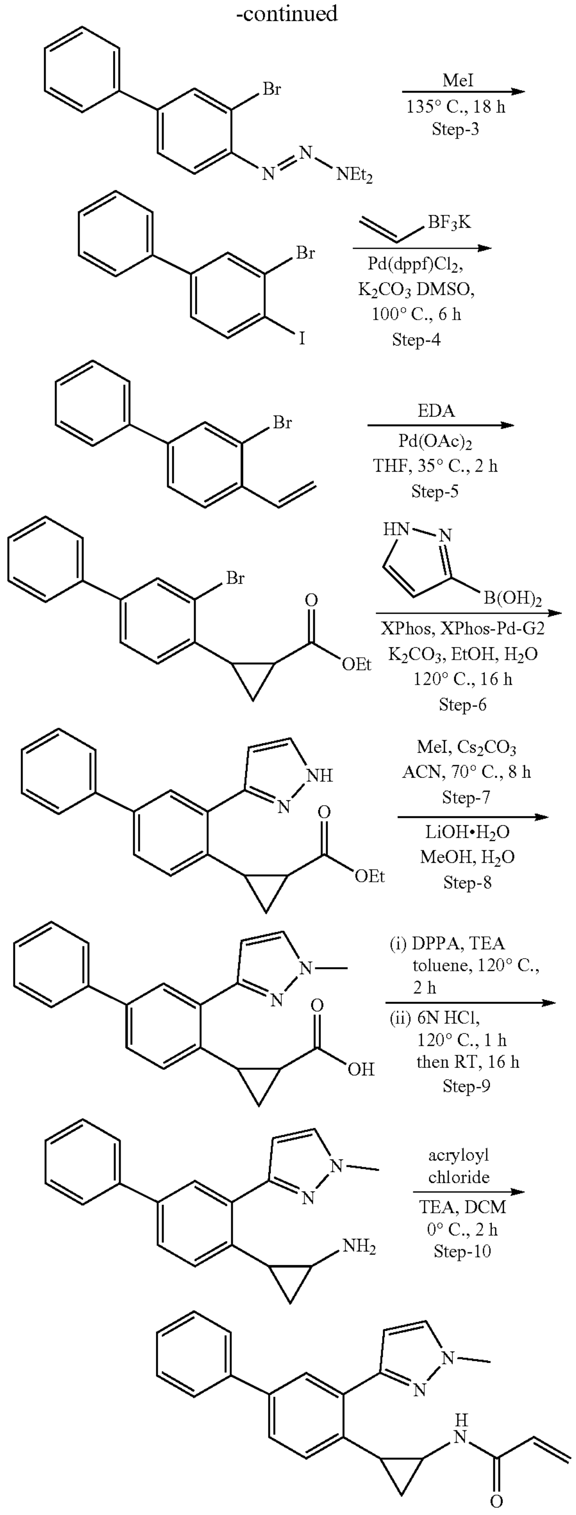

Cpd. No. 257

Step 1: $NaNO_2$ (19.6 g, 283 mmol) in $H_2O$ (169 mL) was added drop-wise to a stirred solution of 2-bromo-4-iodoaniline (65 g, 218 mmol) in 5% aq HCl (442 mL) at 0° C. and the reaction mixture stirred at 0° C. for 30 min. In a separate flask, a solution of $K_2CO_3$ (69 g, 502 mmol) in $H_2O$ (1.04 L) at 0° C. was treated with $Et_2NH$ (28.6 g, 393 mmol) and stirred at 0° C. for 30 min. This solution was added to the reaction mixture which was stirred at 0° C. for 1 h. The reaction was monitored by TLC. TLC mobile phase: pet ether, RF: 0.63, TLC detection: UV. The reaction mixture was basified using sat aq $NaHCO_3$, followed by extraction with EtOAc (3×500 mL). The combined organic layer was dried over anhydrous $Na_2SO_4$ and concentrated under reduced pressure to afford (E)-1-(2-bromo-4-iodophenyl)-3,3-diethyltriaz-1-ene as a brown liquid (50 g, 57%). (LC/MS; m/z 382.1 $[M+H]^+$).

Step 2: A solution of (E)-1-(2-bromo-4-iodophenyl)-3,3-diethyltriaz-1-ene (20 g, 52.5 mmol), phenyl boronic acid (9.6 g, 78.7 mmol) and aq $K_2CO_3$ (2.0 M, 133 mL) in toluene (266 mL) was degassed with argon for 15 min followed by addition of $Pd(PPh_3)_4$ (606 mg, 0.525 mmol). The mixture was stirred for 16 h at 110° C. and monitored by TLC. TLC mobile phase: pet ether, RF: 0.32, TLC detection: UV. The reaction mixture was cooled and diluted with $H_2O$ (200 mL) and extracted with EtOAc (2×500 mL). The combined organic layer was dried over anhydrous $Na_2SO_4$ and concentrated under reduced pressure to afford the crude product (26 g) which was purified by normal phase flash column chromatography using 120 g column (silica) and pet ether as an eluent to afford (E)-1-(3-bromo-[1,1'-biphenyl]-4-yl)-3,3-diethyltriaz-1-ene as a pale yellow liquid (10 g, 57%). (LC/MS; m/z 332.2 $[M+H]^+$).

Step 3: A mixture of (E)-1-(3-bromo-[1,1'-biphenyl]-4-yl)-3,3-diethyltriaz-1-ene (10 g, 30.1 mmol) and MeI (50 mL) was stirred at 130° C. for 18 h (sealed tube) and monitored by TLC. TLC mobile phase: pet ether, RF: 0.66, TLC detection: UV. The cooled reaction mixture was concentrated under reduced pressure to afford the crude product (11 g) which was purified by normal phase flash column chromatography using 80 g column (silica) and pet ether as an eluent to afford 3-bromo-4-iodo-1,1'-biphenyl as a yellow gum (9.5 g, 88%). (LC/MS; m/z 358.4 $[M+H]^+$).

Step 4: A degassed solution of 3-bromo-4-iodo-1,1'-biphenyl (6.0 g, 16.7 mmol), potassium vinyltrifluoroborate (6.71 g, 50.1 mmol) in DMSO (300 mL) was treated with $K_2CO_3$ (6.91 g, 50.1 mmol) and $Pd(dppf)Cl_2$ (610 mg, 0.83 mmol) at RT. The mixture stirred for 6 h at 100° C. and the reaction was monitored by TLC. TLC mobile phase: pet ether, RF: 0.9, TLC detection: UV. The reaction mixture was diluted with $H_2O$ (600 mL) and extracted with EtOAc (3×300 mL). The combined organic layer was washed with brine (2×300 mL), dried over anhydrous $Na_2SO_4$ and concentrated under reduced pressure to afford the crude product (6.5 g) which was purified by normal phase flash column chromatography using silica gel (100-200 mesh) and pet ether as an eluent to afford 3-bromo-4-vinyl-1,1'-biphenyl as a light yellow gum (3 g, 44%). (LC/MS; m/z 258.3 $[M+H]^+$).

Step 5: A degassed mixture of 3-bromo-4-vinyl-1,1'-biphenyl (2.5 g, 9.7 mmol) and $Pd(OAc)_2$ (60 mg, 1.49 mmol) in dry THF (125 mL) was treated at 35° C. with a solution of EDA (1.49 g, 13.09 mmol) in THF (125 mL) over 15 min. The mixture was stirred for 2 h at 35° C. and monitored by TLC. TLC mobile phase: 20% EtOAc in pet ether, RF: 0.3, TLC detection: UV. The cooled reaction mixture was diluted with EtOAc (300 mL) and washed with brine (2×150 mL). The combined organic layer was dried over anhydrous $Na_2SO_4$ and concentrated under reduced pressure to afford the crude product (3.2 g) which was purified by normal phase flash column chromatography using silica gel (100-200 mesh) and a gradient of 0-10% EtOAc in pet ether as an eluent to afford ethyl 2-(3-bromo-[1,1'-biphenyl]-4-yl)cyclopropane-1-carboxylate as a yellow gum (1.5 g). (LC/MS; m/z 344.1 $[M+H]^+$). The product, a mixture of two diastereoisomers, was used as such without further purification.

Step 6: A degassed mixture of ethyl 2-(3-bromo-[1,1'-biphenyl]-4-yl)cyclopropane-1-carboxylate (1.5 g, 4.4 mmol) in EtOH (15 mL) and $H_2O$ (3 mL) was treated with $K_2CO_3$ (3.03 g, 22 mmol), XPhos (314 mg, 0.66 mmol), XPhos-Pd-G2 (518 mg, 0.66 mmol) and (1H-pyrazol-3-yl) boronic acid (1.47 g, 13.2 mmol) at RT. The reaction mixture was heated at 120° C. for 16 h (sealed tube) and monitored by TLC. TLC mobile phase: 80% EtOAc in pet ether, RF: 0.6, TLC detection: UV. The cooled reaction mixture was filtered through a celite pad and washed with EtOAc (175 mL). The solvent was concentrated under reduced pressure to afford crude product (4.0 g) which was purified by normal phase flash column chromatography using silica gel (100-200 mesh) and a gradient of 0-50% EtOAc in pet ether as an eluent to afford ethyl 2-(3-(1H-pyrazol-3-yl)-[1,1'-biphenyl]-4-yl)cyclopropane-1-carboxylate as a yellow gum (500 mg, LC/MS 71%). (LC/MS; m/z 333.4 $[M+H]^+$). The product, a mixture of two diastereoisomers, was used as such without further purification.

Step 7: A solution of ethyl 2-(3-(1H-pyrazol-3-yl)-[1,1'-biphenyl]-4-yl)cyclopropane-1-carboxylate (400 mg, 1.2 mmol) in ACN (40 mL) was treated with $Cs_2CO_3$ (1.4 g, 4.32 mmol) at 0° C. and stirred for 30 min. To the mixture was added MeI (400 mg, 2.8 mmol). The reaction mixture was stirred for 8 h at 70° C. and monitored by TLC. TLC mobile phase: 80% EtOAc in pet ether, RF: 0.65, TLC detection: UV. The cooled reaction mixture was diluted with $H_2O$ (50 mL) and extracted with EtOAc (2×100 mL). The combined organic layer was dried over anhydrous $Na_2SO_4$ and concentrated under reduced pressure to afford ethyl 2-(3-(1-methyl-1H-pyrazol-3-yl)-[1,1'-biphenyl]-4-yl)cyclopropane-1-carboxylate as a yellow gum (400 mg, LC/MS 73%). (LC/MS; m/z 347.3 $[M+H]^+$). The product, a mixture of two diastereoisomers, was used as such without further purification.

Step 8: A solution of ethyl 2-(3-(1-methyl-1H-pyrazol-3-yl)-[1,1'-biphenyl]-4-yl)cyclopropane-1-carboxylate (400 mg, 1.2 mmol) in MeOH (40 mL) and $H_2O$ (10 mL) was treated with $LiOH \cdot H_2O$ (410 mg, 9.8 mmol) at RT. The reaction mixture was stirred for 8 h at RT and monitored by TLC. TLC mobile phase: 5% MeOH in DCM, RF: 0.2, TLC detection: UV. The reaction mixture was concentrated under reduced pressure and the residue diluted with $H_2O$ (10 mL), acidified using aq 1M HCl and extracted with EtOAc (2×150 mL). The combined organic layer was dried over anhydrous $Na_2SO_4$ and concentrated under reduced pressure to afford 2-(3-(1-methyl-1H-pyrazol-3-yl)-[1,1'-biphenyl]-4-yl)cyclopropane-1-carboxylic acid as a white solid (290 mg, LC/MS 82%). (LC/MS; m/z 319.1 $[M+H]^+$). The product, a mixture of two diastereoisomers, was used as such without further purification.

Step 9: A solution of 2-(3-(1-methyl-1H-pyrazol-3-yl)-[1,1'-biphenyl]-4-yl)cyclopropane-1-carboxylic acid (260 mg, 0.81 mmol), DPPA (222 mg, 0.81 mmol) and TEA (122 mg, 1.2 mmol) in toluene (10 mL) was stirred for 2 h at 120° C. To the mixture was added 6N HCl (10 mL) and the reaction mixture was stirred for an additional 1 h at 120° C. The mixture was cooled to RT and stirred for 16 h. The reaction was monitored by TLC. TLC mobile phase: 5% MeOH in DCM, RF: 0.1, TLC detection: UV. The reaction mixture was concentrated under reduced pressure and the residue was diluted with $H_2O$ (50 mL), basified with sat aq $NaHCO_3$ and extracted with EtOAc (2×75 mL). The combined organic layer was dried over anhydrous $Na_2SO_4$ and concentrated under reduced pressure to afford 2-(3-(1-methyl-1H-pyrazol-3-yl)-[1,1'-biphenyl]-4-yl)cyclopropan-1-amine as a black gum (100 mg, LC/MS 44%). (LC/MS; m/z 290.2 [M+H]$^+$). The product, a mixture of two diastereoisomers, was used as such without further purification.

Step 10: A solution of 2-(3-(1-methyl-1H-pyrazol-3-yl)-[1,1'-biphenyl]-4-yl)cyclopropan-1-amine (100 mg, 0.34 mmol) in DCM (20 mL) was treated with TEA (137 mg, 1.36 mmol) and acryloyl chloride (34 mg, 0.37 mmol) at 0° C. The reaction mixture was stirred for 2 h at 0° C. and monitored by TLC. TLC mobile phase: 5% MeOH in DCM, RF: 0.3, TLC detection: UV. The reaction mixture diluted with DCM (50 mL) and washed with brine (2x25 mL). The combined organic layer was dried over anhydrous $Na_2SO_4$ and concentrated under reduced pressure to afford crude product (130 mg, LC/MS 25%) which was purified by preparative HPLC method H1. The collected fractions were lyophilised to afford N-(2-(3-(1-methyl-1H-pyrazol-3-yl)-[1,1'-biphenyl]-4-yl)cyclopropyl)acrylamide (Cpd. No. 257) as a white solid (9 mg, 7%; a 57:43 mixture of two diastereoisomers). (LC/MS; m/z 344.2 [M+H]$^+$).

Example 113: Synthesis of 1-(3-(4'-fluoro-3-(1-methyl-1H-pyrazol-3-yl)-[1,1'-biphenyl]-4-yl)pyrrolidin-1-yl)prop-2-en-1-one (Cpd. No. 258)

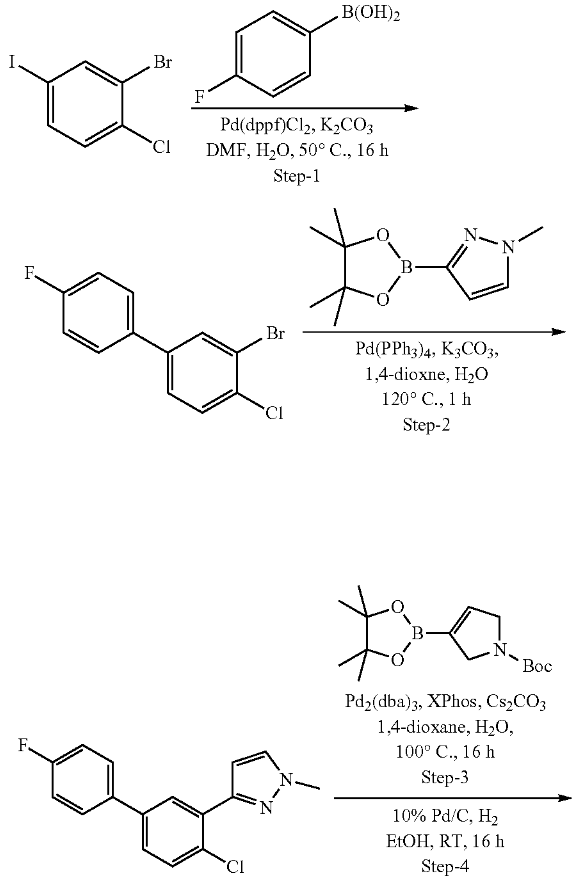

-continued

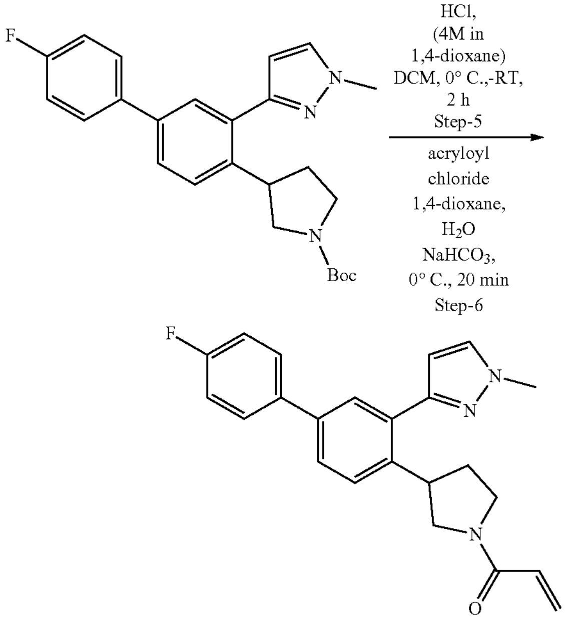

Cpd. No. 258

Step 1: This step was executed in a manner similar (use of appropriate reagents and purification methods known to the person skilled in the art) to step 1 to Int-25. From 2-bromo-1-chloro-4-iodobenzene (5.0 g, 15.8 mmol) was obtained 3-bromo-4-chloro-4'-fluoro-1,1'-biphenyl as a pale yellow solid (3.5 g, 78%). $^1$H NMR (400 MHz, $CDCl_3$) δ ppm: 7.78-7.79 (d, 1H), 7.46-7.51 (m, 3H), 7.38-7.41 (dd, 1H), 7.10-7.16 (m, 2H).

Step 2: This step was executed in a manner similar (use of appropriate reagents and purification methods known to the person skilled in the art) to step 2 to Int-26.HCl. Reacting 3-bromo-4-chloro-4'-fluoro-1,1'-biphenyl (2.5 g, 8.8 mmol) with 1-methyl-3-(4,4,5,5-tetramethyl-1,3,2-dioxaborolan-2-yl)-1H-pyrazole (2.19 g, 10.5 mmol) under microwave radiation (sealed microwave vial) afforded 3-(4-chloro-4'-fluoro-[1,1'-biphenyl]-3-yl)-1-methyl-1H-pyrazole as a pale yellow gum (1.2 g, 48%). (LC/MS; m/z 287.1 [M+H]$^+$).

Steps 3-4: These step were executed in a manner similar (use of appropriate reagents and purification methods known to the person skilled in the art) to step 1 and 2 towards Cpd. No. 183. From 3-(4-chloro-4'-fluoro-[1,1'-biphenyl]-3-yl)-1-methyl-1H-pyrazole (1.2 g, 4.2 mmol) was obtained tert-butyl 3-(4'-fluoro-3-(1-methyl-1H-pyrazol-3-yl)-[1,1'-biphenyl]-4-yl)pyrrolidine-1-carboxylate as a yellow gum (350 mg, LC/MS 85%). (LC/MS; m/z 422.4 [M+H]$^+$). The product was used as such without further purification.

Step 5: This step was executed in a manner similar (use of appropriate reagents and purification methods known to the person skilled in the art) to step 4 to Int-26.HCl. From tert-butyl 3-(4'-fluoro-3-(1-methyl-1H-pyrazol-3-yl)-[1,1'-biphenyl]-4-yl)pyrrolidine-1-carboxylate (350 mg, 0.83 mmol) was obtained 3-(4'-fluoro-4-(pyrrolidin-3-yl)-[1,1'-biphenyl]-3-yl)-1-methyl-1H-pyrazole hydrochloride as a pale yellow gum (300 mg, LC/MS 98%). (LC/MS; m/z 322.2 [M+H]$^+$). The product was used as such without further purification.

Step 6: This step was executed in a manner similar (use of appropriate reagents and purification methods known to the person skilled in the art) to step 3 towards Cpd. No. 152.

From 3-(4'-fluoro-4-(pyrrolidin-3-yl)-[1,1'-biphenyl]-3-yl)-1-methyl-1H-pyrazole hydrochloride (300 mg, 0.84 mmol) was obtained crude product (300 mg, LC/MS 89%) which was purified by preparative HPLC method H3. The collected fractions were lyophilised to afford 1-(3-(4'-fluoro-3-(1-methyl-1H-pyrazol-3-yl)-[1,1'-biphenyl]-4-yl)pyrrolidin-1-yl)prop-2-en-1-one (Cpd. No. 258) as a white gum (70 mg, 22%). (LC/MS; m/z 376.3 $[M+H]^+$).

The following compounds were prepared in a manner similar (use of appropriate reagents and purification methods known to the person skilled in the art) to Cpd. No. 258: Cpd. No. 259, Cpd. No. 260 (employing 1-(difluoromethyl)-3-(4,4,5,5-tetramethyl-1,3,2-dioxaborolan-2-yl)-1H-pyrazole and the conditions used for Cpd. No. 209 at step 2, and methanesulfonyl chloride at step 6) and Cpd. No. 261 (employing 1-(difluoromethyl)-3-(4,4,5,5-tetramethyl-1,3,2-dioxaborolan-2-yl)-1H-pyrazole and the conditions used for Cpd. No. 209 at step 2).

The enantiomers of Cpd. No. 261 were separated by chiral SFC: 280 mg of Cpd. No. 261 was further purified by preparative SFC method $K_2$ to afford Cpd. No. 261-En1 (62 mg, 22%) and Cpd. No. 261-En2 (55 mg, 20%), both as a white solid. (LC/MS; m/z 412.3 $[M+H]^+$). The chiral purity of both enantiomers was assessed by analytic SFC method S1: Cpd. No. 261-En1, 99.6% ee; Cpd. No. 261-En2, 97.9% ee.

Example 114: Synthesis of 1-(3-(4-(1-(difluoromethyl)-1H-pyrazol-3-yl)-6-(4-fluorophenyl)pyridin-3-yl)pyrrolidin-1-yl)prop-2-en-1-one (Cpd. No. 262)

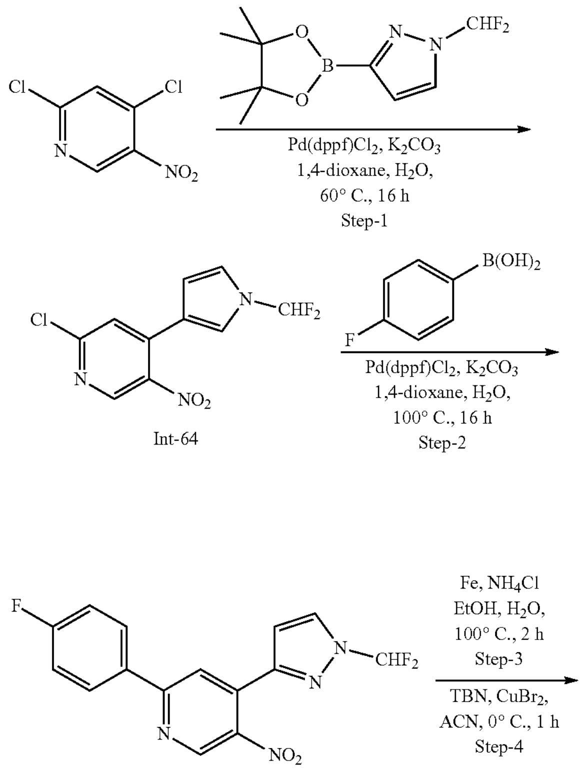

-continued

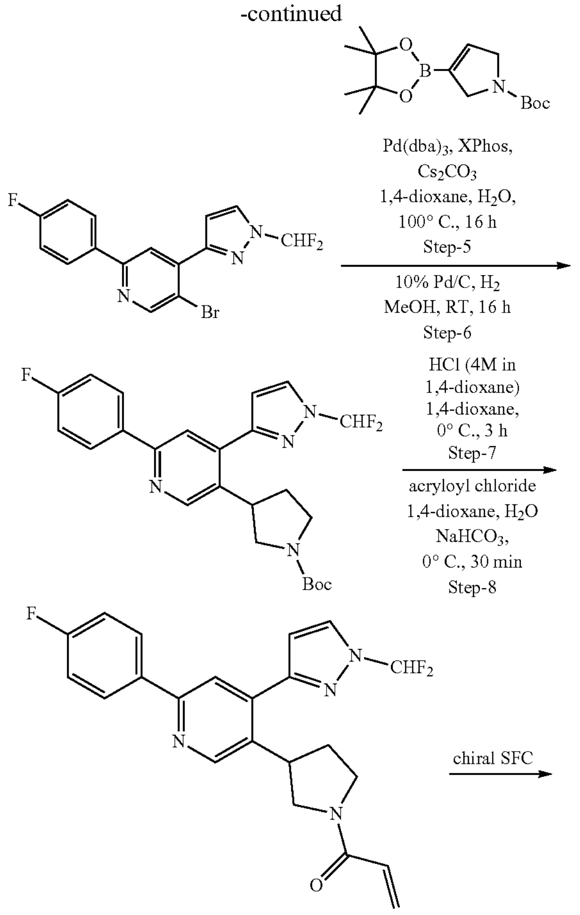

Cpd. No. 262

Cpd. No. 262-En1
Cpd. No. 262-En2

Step 1: This step was executed in a manner similar (use of appropriate reagents and purification methods known to the person skilled in the art) to step 2 towards Cpd. No. 209. 2,4-dichloro-5-nitropyridine (2.0 g, 10.4 mmol) yielded 2-chloro-4-(1-(difluoromethyl)-1H-pyrazol-3-yl)-5-nitropyridine (Int-64) as an off-white solid (2.0 g, 61%, LC/MS 86%). (LC/MS; m/z 275.1 $[M+H]^+$).

Step 2: This step was executed in a manner similar (use of appropriate reagents and purification methods known to the person skilled in the art) to step 1 towards Cpd. No. 209. 2-chloro-4-(1-(difluoromethyl)-1H-pyrazol-3-yl)-5-nitropyridine (1.3 g, 4.74 mmol, LC/MS 86%) yielded 4-(1-(difluoromethyl)-1H-pyrazol-3-yl)-2-(4-fluorophenyl)-5-nitropyridine as an off-white solid (1.3 g, 87%, LC/MS 92%). (LC/MS; m/z 335.2 $[M+H]^+$).

Step 3: A solution of 4-(1-(difluoromethyl)-1H-pyrazol-3-yl)-2-(4-fluorophenyl)-5-nitropyridine (1.3 g, 3.89 mmol, LC/MS 92%) in EtOH (20 mL) and $H_2O$ (2 mL) was treated with Fe powder (650 mg, 11.67 mmol) and $NH_4Cl$ (410 mg, 7.78 mmol) at RT. The reaction mixture was stirred at 100° C. for 2 h and monitored by TLC. TLC mobile phase: 30% EtOAc in pet ether, RF: 0.3, TLC detection: UV. The reaction mixture was filtered through a celite pad and washed with EtOAc (100 mL). The filtrate was concentrated under reduced pressure and the crude product was washed with n-pentane and dried to afford product 4-(1-(difluoromethyl)-1H-pyrazol-3-yl)-6-(4-fluorophenyl)pyridin-3-amine (1.3 g, LC/MS 90%). (LC/MS; m/z 305.2 [M+H]$^+$). The product was used as such without further purification.

Step 4: A solution of 4-(1-(difluoromethyl)-1H-pyrazol-3-yl)-6-(4-fluorophenyl)pyridin-3-amine (700 mg, 2.30 mmol, LC/MS 90%), TBN (1.4 mL) and $CuBr_2$ (257 mg, 1.15 mmol) in ACN (10 mL) was stirred at 0° C. for 1 h and monitored by TLC. TLC mobile phase: 20% EtOAc in pet ether, RF: 0.4, TLC detection: UV. The reaction mixture was diluted with $H_2O$ (80 mL) and extracted with EtOAc (120 mL). The organic layer was dried over anhydrous $Na_2SO_4$ and concentrated under reduced pressure to afford crude product (900 mg, LC/MS 34%). The crude product was purified by normal phase flash column chromatography using a 12 g column (silica) and a gradient of 0-5% EtOAc in pet ether as an eluent to afford 5-bromo-4-(1-(difluoromethyl)-1H-pyrazol-3-yl)-2-(4-fluorophenyl)pyridine (450 mg, 55%, LC/MS 93%) as an off-white solid. (LC/MS; m/z 368.1 [M+H]$^+$).

Steps 5-8: These steps were executed in a manner similar (use of appropriate reagents and purification methods known to the person skilled in the art) to step 3, 4, 5 and 6 towards Cpd. No. 258. 5-bromo-4-(1-(difluoromethyl)-1H-pyrazol-3-yl)-2-(4-fluorophenyl)pyridine (280 mg, 0.76 mmol, LC/MS 93%) yielded crude product (200 mg, LC/MS 85%) which was purified by preparative HPLC method H14. The collected fractions were lyophilised to afford 1-(3-(4-(1-(difluoromethyl)-1H-pyrazol-3-yl)-6-(4-fluorophenyl)pyridin-3-yl)pyrrolidin-1-yl)prop-2-en-1-one (Cpd. No. 262) as a white solid (75 mg, 25%). (LC/MS; m/z 413.3 [M+H]$^+$). Chiral SFC purification: 57 mg of Cpd. No. 262 was purified by preparative SFC method $K_3$ to afford Cpd. No. 262-En1 (18 mg, 31%) and Cpd. No. 262-En2 (10 mg, 17%), both as a white solid. (LC/MS; m/z 413.3 [M+H]$^+$). The chiral purity of both enantiomers was assessed by analytic SFC method S2: Cpd. No. 262-En1, 99.8% ee; Cpd. No. 262-En2, 99.8% ee.

The following compounds were prepared in a manner similar (use of appropriate reagents and purification methods known to the person skilled in the art) to Cpd. No. 262: Cpd. No. 263 (employing methylsulfamoyl chloride and TEA at step 8), Cpd. No. 380, Cpd. No. 381 (using acetyl chloride and TEA in step 8), Cpd. No. 382 (using MsCl and TEA in step 8), Cpd. No. 395 (using 2,6-dichloro-3-nitropyridine and 1-methyl-3-(4,4,5,5-tetramethyl-1,3,2-dioxaborolan-2-yl)-1H-pyrazole in step 1), Cpd. No. 402 (using 2-hydroxy-4-(4,4,5,5-tetramethyl-1,3,2-dioxaborolan-2-yl)benzaldehyde in step 5 and omitting steps 6-8), Cpd. No. 415, Cpd. No. 428, Cpd. No. 429 (using acetyl chloride and TEA in step 8), Cpd. No. 435, Cpd. No. 440 (using 1-methyl-3-(4,4,5,5-tetramethyl-1,3,2-dioxaborolan-2-yl)-1H-pyrazole in step 1 and 4,4,5,5-tetramethyl-2-(pent-2-en-2-yl)-1,3,2-dioxaborolane in step 2), Cpd. No. 443 (using acetyl chloride and TEA in Step 8), Cpd. No. 457 (using 2,6-dichloro-3-nitropyridine in step 1).

The following single enantiomers were isolated in a manner similar (use of appropriate purification methods known to the person skilled in the art) to Cpd. No. 262-En1 and Cpd. No. 262-En2: Cpd. No. 444-En1 (99.6% ee), Cpd. No. 444-En2 (98% ee), Cpd. No. 426-En1 (98.8% ee), Cpd. No. 426-En2 (93% ee), Cpd. No. 466-En1 (99.9% ee), Cpd. No. 466-En2 (99.6% ee).

Example 115: Synthesis of 1-(3-(2-(1-(difluoromethyl)-1H-pyrazol-3-yl)-6-(4-fluorophenyl)pyridin-4-yl)pyrrolidin-1-yl)prop-2-en-1-one (Cpd. No. 264)

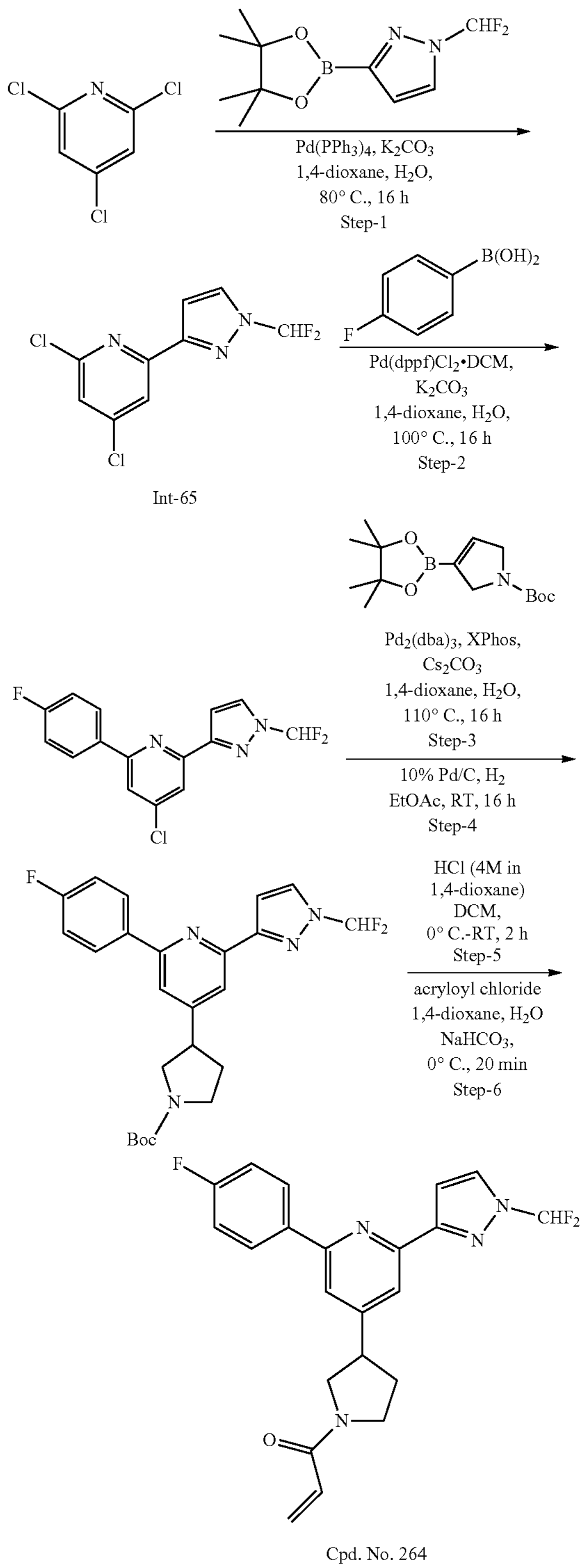

Cpd. No. 264

Steps 1: This step was executed in a manner similar (use of appropriate reagents and purification methods known to the person skilled in the art) to step 2 towards Cpd. No. 209. From 2,4,6-trichloropyridine (1.0 mg, 5.48 mmol) was obtained crude product (2.0 g) which was purified by normal phase flash column chromatography using a 24 g column (silica) and a gradient of 0-8% EtOAc in pet ether as an eluent to afford 2,4-dichloro-6-(1-(difluoromethyl)-1H-pyrazol-3-yl)pyridine (Int-65) as a pale yellow solid (800 mg, 51%, LC/MS 93%). (LC/MS; m/z 264.1 $[M+H]^+$).

Steps 2: This step was executed in a manner similar (use of appropriate reagents and purification methods known to the person skilled in the art) to step 1 towards Cpd. No. 209. From Int-65 (800 mg, 3.03 mmol) was obtained crude product (1.2 g) which was purified by normal phase flash column chromatography using a 40 g column (silica) and a gradient of 0-2% EtOAc in pet ether as an eluent to afford 4-chloro-2-(1-(difluoromethyl)-1H-pyrazol-3-yl)-6-(4-fluorophenyl)pyridine as a pale brown solid (700 mg, 45%, LC/MS 59%). (LC/MS; m/z 324.2 $[M+H]^+$).

Step 3: This step was executed in a manner similar (use of appropriate reagents and purification methods known to the person skilled in the art) to step 3 towards Cpd. No. 258. From 4-chloro-2-(1-(difluoromethyl)-1H-pyrazol-3-yl)-6-(4-fluorophenyl)pyridine (650 mg, 2.01 mmol) was obtained crude product (1.0 g, LC/MS 42%) which was purified by normal phase flash column chromatography using a 40 g column (silica) and a gradient of 0-18% EtOAc in pet ether as an eluent to afford tert-butyl 3-(2-(1-(difluoromethyl)-1H-pyrazol-3-yl)-6-(4-fluorophenyl)pyridin-4-yl)-2,5-dihydro-1H-pyrrole-1-carboxylate as a pale brown gum (600 mg, 85%, LC/MS 77%). (LC/MS; m/z 457.3 $[M+H]^+$).

Steps 4-6: These steps were executed in a manner similar (use of appropriate reagents and purification methods known to the person skilled in the art) to step 4, 5 and 6 towards Cpd. No. 258. From tert-butyl 3-(2-(1-(difluoromethyl)-1H-pyrazol-3-yl)-6-(4-fluorophenyl)pyridin-4-yl)-2,5-dihydro-1H-pyrrole-1-carboxylate (330 mg, 0.72 mmol) was obtained crude product (260 mg, LC/MS 63%) which was purified by preparative HPLC method H9. The collected fractions were lyophilised to afford 1-(3-(2-(1-(difluoromethyl)-1H-pyrazol-3-yl)-6-(4-fluorophenyl)pyridin-4-yl) pyrrolidin-1-yl)prop-2-en-1-one (Cpd. No. 264) as a white solid (40 mg, 17%, LC/MS 99%). (LC/MS; m/z 413.3 $[M+H]^+$).

Example 116: Synthesis of 1-(3-(6-(1-(difluoromethyl)-1H-pyrazol-3-yl)-4-(4-fluorophenyl)pyridin-2-yl)pyrrolidin-1-yl)prop-2-en-1-one (Cpd. No. 265)

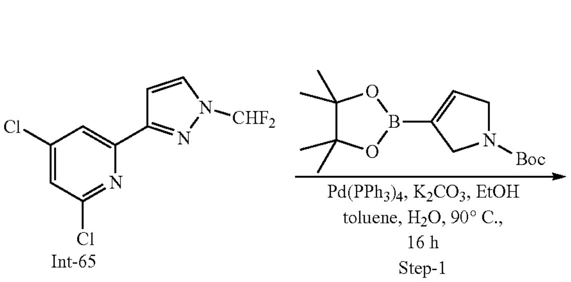

Int-65

-continued

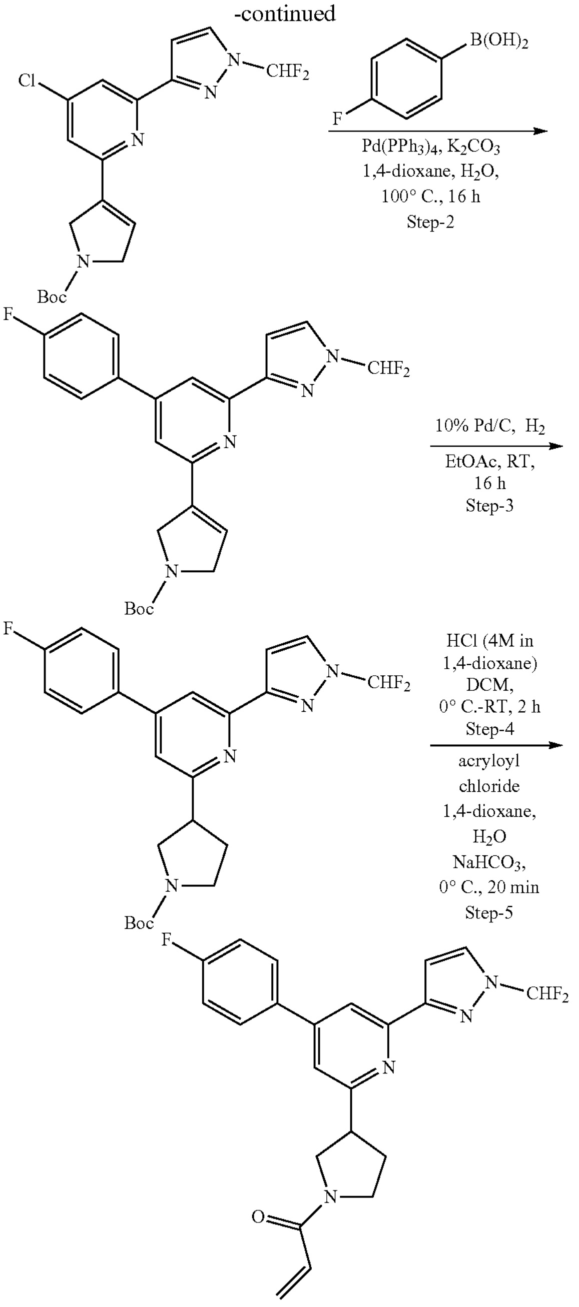

Cpd. No. 265

Step 1: This step was executed in a manner similar (use of appropriate reagents and purification methods known to the person skilled in the art) to step 1 towards Cpd. No. 183. From Int-65 (1.3 g, 4.92 mmol) was obtained crude product (1.0 g, LC/MS 26%) which was purified by normal phase flash column chromatography using a 80 g column (silica) and a gradient of 0-10% EtOAc in pet ether as an eluent to afford tert-butyl 3-(4-chloro-6-(1-(difluoromethyl)-1H-pyrazol-3-yl)pyridin-2-yl)-2,5-dihydro-1H-pyrrole-1-carboxylate as an off-white solid (500 mg, 24%, LC/MS 94%). (LC/MS; m/z 397.3 $[M+H]^+$).

Step 2: This step was executed in a manner similar (use of appropriate reagents and purification methods known to the person skilled in the art) to step 1 towards Cpd. No. 209. From tert-butyl 3-(4-chloro-6-(1-(difluoromethyl)-1H-pyrazol-3-yl)pyridin-2-yl)-2,5-dihydro-1H-pyrrole-1-carboxylate (500 mg, 1.26 mmol) was obtained crude product (800 mg, LC/MS 69%) which was purified by normal phase flash column chromatography using a 24 g column (silica) and a gradient of 0-10% EtOAc in pet ether as an eluent to afford tert-butyl 3-(6-(1-(difluoromethyl)-1H-pyrazol-3-yl)-4-(4-fluorophenyl)pyridin-2-yl)-2,5-dihydro-1H-pyrrole-1-carboxylate as a white solid (400 mg, 70%, LC/MS 95%). (LC/MS; m/z 457.3 [M+H]$^+$).

Steps 3-5: These steps were executed in a manner similar (use of appropriate reagents and purification methods known to the person skilled in the art) to step 4, 5 and 6 towards Cpd. No. 258. From tert-butyl 3-(6-(1-(difluoromethyl)-1H-pyrazol-3-yl)-4-(4-fluorophenyl)pyridin-2-yl)-2,5-dihydro-1H-pyrrole-1-carboxylate (400 mg, 0.88 mmol) was obtained crude product (290 mg, LC/MS 75%) which was purified by preparative HPLC method H3. The collected fractions were lyophilised to afford 1-(3-(6-(1-(difluoromethyl)-1H-pyrazol-3-yl)-4-(4-fluorophenyl)pyridin-2-yl)pyrrolidin-1-yl)prop-2-en-1-one (Cpd. No. 265) as an off-white solid (41 mg, 12%, LC/MS 98%). (LC/MS; m/z 413.3 [M+H]$^+$).

Synthesis of tert-butyl ((6-(4-fluorophenyl)-4-(1H-pyrazol-3-yl)pyridin-3-yl)methyl) carbamate (Int-66)

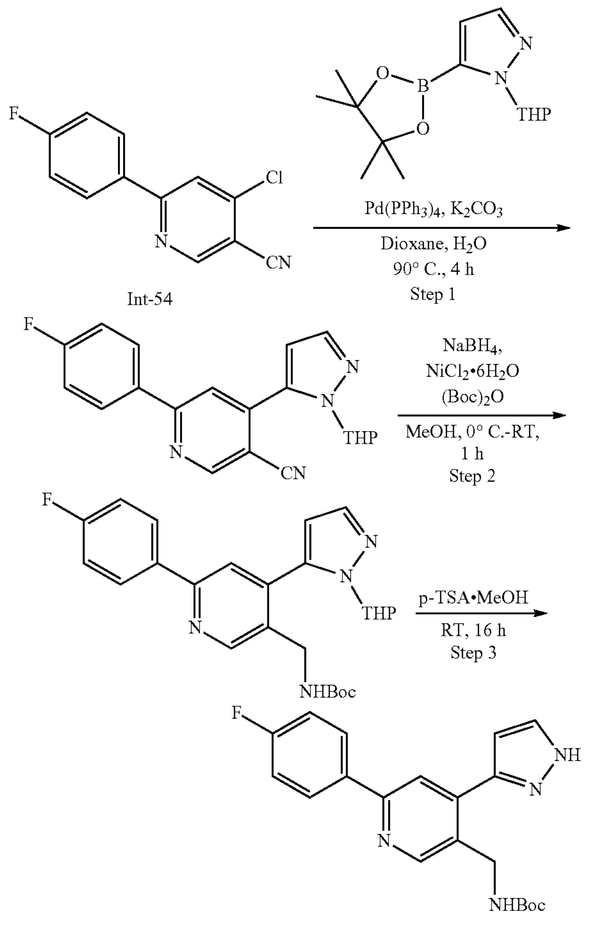

Int-54

Int-66

Step 1: A solution of Int-54 (5 g, 21.49 mmol) in 1,4-dioxane (93 mL) and water (6 mL) was treated with 1-methyl-3-(4,4,5,5-tetramethyl-1,3,2-dioxaborolan-2-yl)-1H-pyrazole (6.57 g, 23.64 mmol) and $K_2CO_3$ (5.93 g, 42.98 mmol) at room temperature. The reaction mixture was degassed by bubbling argon for 10 minutes, then $Pd(PPh_3)_4$ (2.48 g, 2.14 mmol) was added and the reaction mixture was stirred at 90° C. for 4 h. The reaction was monitored by TLC (mobile phase: 20% EtOAc in Pet ether. Rf: 0.2. detection: UV). The reaction mixture was cooled and filtered through a pad of Celite and washed with EtOAc (100 mL). The filtrate was concentrated under reduced pressure to afford a brown gum (8 g, LC/MS: 26%). The crude product was purified by normal phase column chromatography using a 48 g column (silica) eluted with 15% EtOAc in Pet ether to afford 6-(4-fluorophenyl)-4-(1-methyl-1H-pyrazol-3-yl) nicotinonitrile as an off-white solid (5 g, LC/MS: 99%). (LC/MS; m/z 349.4 [M+H]$^+$).

Step 2: A solution of 6-(4-fluorophenyl)-4-(1-(tetrahydro-2H-pyran-2-yl)-1H-pyrazol-5-yl)nicotinonitrile (5.0 g, 14.36 mmol) in MeOH (125 mL) was treated with $NiCl_2 \cdot 6H_2O$ (2.04 g, 8.62 mmol) and $(Boc)_2O$ (3.95 mL, 17.24 mmol) at room temperature. The mixture was cooled to 0° C. and $NaBH_4$ (3.72 g, 100.57 mmol) was added slowly, portion wise and the reaction mixture was allowed to stir at room temperature for 1 h. Progress of the reaction was monitored by TLC (mobile phase: 30% EtOAc in pet ether. Rf: 0.29. detection: UV). The reaction mixture was filtered through a pad of Celite and washed with EtOAc (300 mL). The filtrate was washed with brine (3×50 mL), dried over anhydrous $Na_2SO_4$ and concentrated under reduced pressure to afford a black gum (7 g, LC/MS: 86%). The crude product was purified by normal phase column chromatography using a 48 g column (silica) and eluted with 20% EtOAc in pet ether to afford tert-butyl-((6-(4-fluorophenyl)-4-(1-(tetrahydro-2H-pyran-2-yl)-1H-pyrazol-5-yl)pyridin-3-yl) methyl)carbamate as an off-white solid (3.5 g, LC/MS: 99%). (LC/MS; m/z 453.6 [M+H]$^+$).

Step 3: A solution of tert-butyl ((6-(4-fluorophenyl)-4-(1-(tetrahydro-2H-pyran-2-yl)-1H-pyrazol-5-yl)pyridin-3-yl) methyl) carbamate (3.5 g, 7.74 mmol) in methanol (20 mL) was treated with pTSA (736 mg, 3.87 mmol) at room temperature. The reaction mixture was stirred at room temperature for 16 h. The reaction was monitored by TLC (mobile phase: 40% EtOAc in pet ether. Rf: 0.32. detection: UV). The reaction mixture was concentrated under reduced pressure and the residue was diluted with water (250 mL) and extracted with EtOAc (2×150 mL). The combined organic layer was dried over anhydrous $Na_2SO_4$ and concentrated under reduced pressure. The residue was triturated with n-pentane (15 mL) and dried under high vacuum to afford tert-butyl ((6-(4-fluorophenyl)-4-(1H-pyrazol-3-yl) pyridin-3-yl)methyl) carbamate (Int-66) as an off-white solid (2.3 g, LC/MS: 99%). (LC/MS; m/z 369.4 [M+H]$^+$).

The following intermediates were prepared in a manner similar (use of appropriate reagents and purification methods known to the person skilled in the art) to Int-66:

| Intermediate | Structure | Comments |
|---|---|---|
| Int-74 | 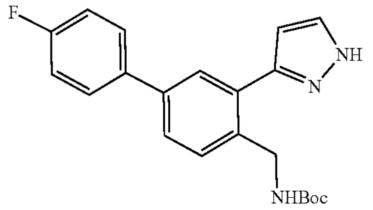 [SMILES: CC(C)(C)OC(=O)NCc1ccc(-c2ccc(F)cc2)cc1-c1cc[nH]n1] | Using Int-25 in Step 1 |
| Int-75 | 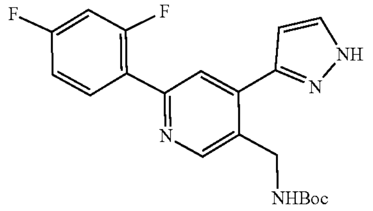 [SMILES: CC(C)(C)OC(=O)NCc1cnc(-c2ccc(F)cc2F)cc1-c1cc[nH]n1] | Using 4-chloro-6-(2,4-difluorophenyl)pyridine-3-carbonitrile in Step 1 |
| Int-76 | 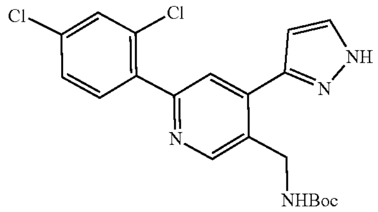 [SMILES: CC(C)(C)OC(=O)NCc1cnc(-c2ccc(Cl)cc2Cl)cc1-c1cc[nH]n1] | Using 4-chloro-6-(2,4-dichlorophenyl)pyridine-3-carbonitrile in Step 1 |

Synthesis of (6-acetamidopyridin-3-yl)methylmethanesulfonate (Int-A)

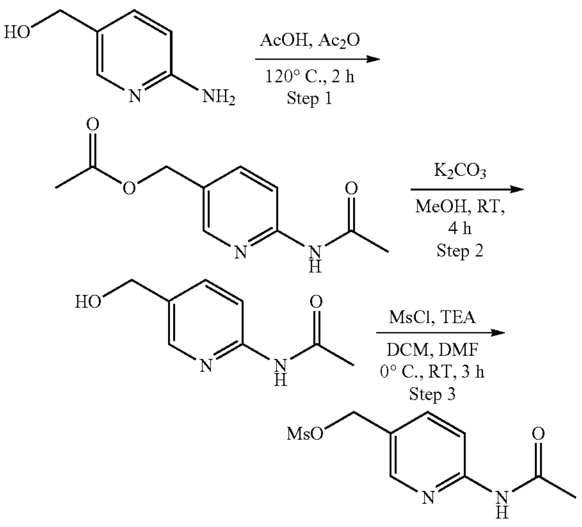

Int-A

Step 1: A solution of (6-aminopyridin-3-yl)methanol (1 g, 8.05 mmol) in AcOH (1.8 mL, 32.22 mmol) was treated with $Ac_2O$ (3.5 mL, 36.24 mmol) at room temperature. The reaction mixture was stirred at 120° C. for 2 h and progress of the reaction was monitored by TLC (mobile phase: 5% MeOH in DCM. Rf: 0.4. detection: UV). The reaction mixture was diluted with water (80 mL), basified (pH~9) by addition of $NH_4OH$, and extracted with EtOAc (2×200 mL). The combined organic layer was washed with brine solution (80 mL), dried over $Na_2SO_4$ and concentrated under reduced pressure to afford 6-acetamidopyridin-3-yl)methyl acetate as an off-white solid (1.25 g, LC/MS: 83%). (LC/MS; m/z 209.3 $[M+H]^+$).

Step 2: A solution of (6-acetamidopyridin-3-yl)methyl acetate (1.25 g, 6.00 mmol) in MeOH (25 mL) was treated with $K_2CO_3$ (2.48 g, 18.01 mmol) at room temperature. The reaction mixture was stirred at room temperature for 4 h and progress of the reaction was monitored by TLC (mobile phase: 50% EtOAc in pet ether. Rf: 0.3. detection: UV). The reaction mixture was concentrated under reduced pressure and the residue was diluted with EtOAc (200 mL) and washed with brine (400 mL), dried over $Na_2SO_4$ and concentrated under reduced pressure to afford N-(5-(hydroxymethyl)pyridin-2-yl)acetamide as a white solid (850 mg, LC/MS: 98%). (LC/MS; m/z 167.1 $[M+H]^+$).

Step 3: A solution of N-(5-(hydroxymethyl)pyridin-2-yl) acetamide (650 mg, 3.91 mmol) in DCM (26 mL) and DMF (5 mL) was treated with TEA (0.65 mL, 4.69 mmol) and MsCl (0.33 mL, 4.30 mmol) at 0° C. The reaction mixture was stirred at room temperature for 3 h and progress of the reaction was monitored by TLC (mobile phase: 10% MeOH in DCM. Rf: 0.5. detection: UV). The reaction mixture was concentrated under reduced pressure to afford (6-acetamidopyridin-3-yl)methylmethanesulfonate (Int-A) (1.2 g, LC/MS purity: 15%). (LC/MS; m/z 245.2 $[M+H]^+$).

The following intermediates were prepared in a manner similar (use of appropriate reagents and purification methods known to the person skilled in the art) to Int-A:

| Intermediate | Structure | Comments |
|---|---|---|
| Int-B | 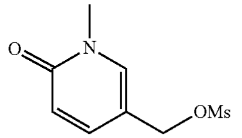 | Employing step 3 only, using 5-(hydroxymethyl)-1-methylpyridin-2(1H)-one |

Synthesis of 3-chloro-5-(methylcarbamoyl)benzyl methanesulfonate (Int-F)

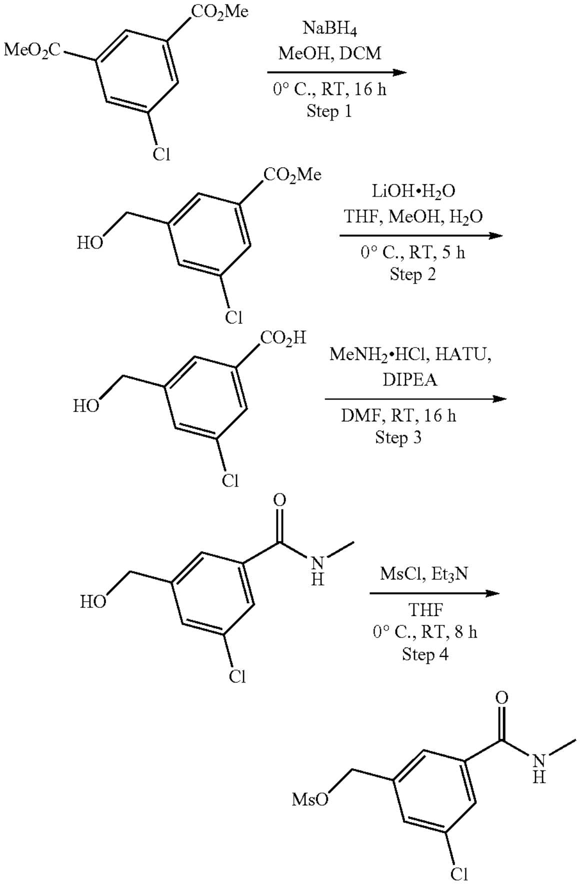

Int-F

Step 1: A solution of dimethyl 5-chloroisophthalate (2 g, 8.74 mmol) in MeOH (10 mL) and DCM (2 mL) was treated with $NaBH_4$ (330 mg, 8.74 mmol) at 0° C. The reaction mixture was stirred at room temperature for 16 h. Progress of the reaction monitored by TLC (mobile phase: 30% EtOAc in Pet ether. Rf: 0.30. detection: UV). The reaction mixture was concentrated under reduced pressure and the residue was diluted with EtOAc (200 mL). The organic layer was washed with 1 N HCl (50 mL), brine (50 mL), dried over sodium sulphate and concentrated under reduced pressure to afford a white solid (2.5 g, LC/MS: 39%). The crude product was purified by gravity column chromatography using silica gel and 15% EtOAc in pet-ether as eluent to afford methyl 3-chloro-5-(hydroxymethyl)benzoate as a white solid (1 g, LC/MS: 95%). (LC/MS; m/z 201.1 $[M+H]^+$).

Step 2: A solution of methyl 3-chloro-5-(hydroxymethyl) benzoate (1 g, 5.0 mmol) in THF (6 mL), MeOH (2 mL) and water (2 mL) was treated with $LiOH{\cdot}H_2O$ (1.26 g, 30.00 mmol) at 0° C. The reaction mixture was stirred at room temperature for 5 h and progress of the reaction was monitored by TLC. (mobile phase: 30% EtOAc in pet ether. Rf: 0.13. detection: UV). The reaction mixture was concentrated under reduced pressure and the residue was diluted with water (10 mL), pH was adjusted to 2 by addition of 1N HCl and the mixture was extracted with EtOAc (50 mL). The organic layer was dried over sodium sulphate and concentrated under reduced pressure to afford 3-chloro-5-(hydroxymethyl)benzoic acid as a white solid (900 mg, LC/MS: 96%). (LC/MS; m/z 201.1 $[M+H]^+$).

Step 3: A solution of 3-chloro-5-(hydroxymethyl)benzoic acid (900 mg, 4.48 mmol) in DMF (15 mL) was treated with HATU (3.15 g, 8.29 mmol), methylamine hydrochloride (3.02 mg, 44.86 mmol) and DIPEA (10.63 mL, 61.01 mmol) at 0° C. The reaction mixture was stirred at room temperature for 16 h and progress of the reaction was monitored by TLC (mobile phase: EtOAc, Rf: 0.3. detection: UV). The reaction mixture was diluted with water (100 mL) and extracted with EtOAc (200 mL). The organic layer was washed with brine (100 mL), dried over sodium sulphate and concentrated under reduced pressure to afford 3-chloro-5-(hydroxymethyl)-N-methylbenzamide as a white solid (700 mg, LC/MS: 84%). (LC/MS; m/z 200.2 $[M+H]^+$).

Step 4: A solution of 3-chloro-5-(hydroxymethyl)-N-methylbenzamide (600 mg, 3.00 mmol) in THF (20 mL) was treated with $Et_3N$ (1.25 mL, 9.01 mmol) and MsCl (0.27 mL, 3.60 mmol) at 0° C. The reaction mixture was stirred at room temperature for 8 h and progress of the reaction was monitored by TLC (mobile phase: 10% MeOH in DCM. Rf: 0.49. detection: UV). The reaction mixture was concentrated under reduced pressure and the residue was diluted with EtOAc (100 mL). The organic layer was washed with saturated $NaHCO_3$ (50 mL), brine (50 mL), dried over sodium sulphate and concentrated under reduced pressure to afford 3-chloro-5-(methylcarbamoyl)benzyl methanesulfonate (Int-F) as a yellow liquid (750 mg, LC/MS: 55%). (LC/MS; m/z 278.1 $[M+H]^+$).

Example 117: Synthesis of N-((4-(1-(cyanomethyl)-1H-pyrazol-3-yl)-6-(4-fluorophenyl)pyridin-3-yl)methyl)acrylamide (Cpd. No. 266)

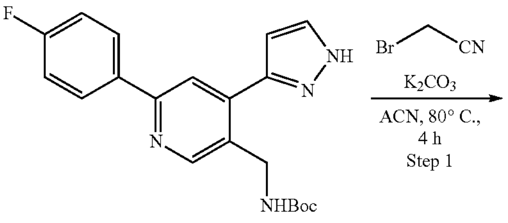

Int-66

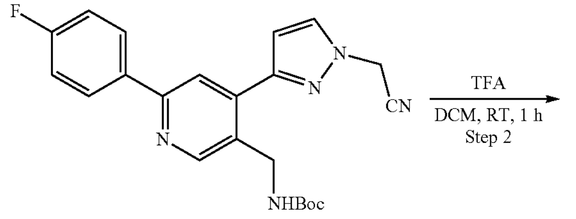

Int-67

-continued

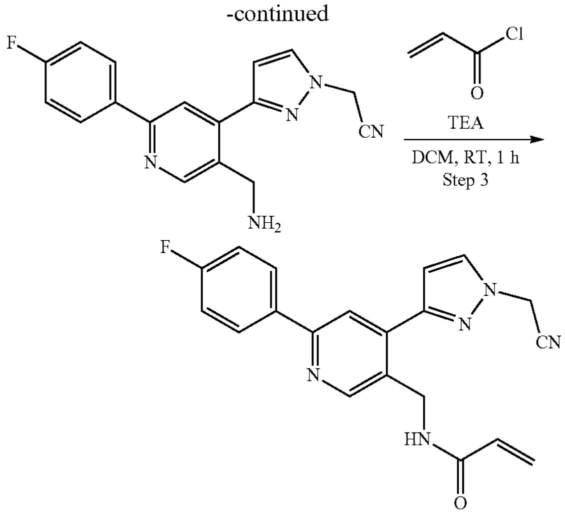

Cpd. No. 266

Step 1: A solution of Int-66 (500 mg, 1.35 mmol) in acetonitrile (10 mL) was treated with potassium carbonate (559 mg, 4.04 mmol) and 2-bromo acetonitrile (210 mg, 1.75 mmol) at room temperature. The reaction mixture was stirred at 80° C. for 4 h. Progress of the reaction was monitored by TLC (Mobile phase: 30% EtOAc in pet ether. Rf: 0.37. Detection: UV). The reaction mixture was cooled to room temperature, diluted with water (50 mL) and extracted with EtOAc (2×75 mL). The organic layer was washed with brine solution (75 mL), dried over anhydrous $Na_2SO_4$ and concentrated under reduced pressure to afford a yellow gum (550 mg, LC/MS: 84%). The crude product was purified by normal phase column chromatography using a 12 g column (silica) and an eluent of 30% EtOAc in pet ether to afford tert-butyl ((4-(1-(cyanomethyl)-1H-pyrazol-3-yl)-6-(4-fluorophenyl)pyridin-3-yl)methyl)carbamate (Int-67) as a yellow solid (250 mg, LC/MS: 84%). (LC/MS; m/z 408.4 $[M+H]^+$).

Step 2: A solution of tert-butyl ((4-(1-(cyanomethyl)-1H-pyrazol-3-yl)-6-(4-fluorophenyl)pyridin-3-yl)methyl)carbamate (240 mg, 0.58 mmol) in DCM (2 mL) was cooled to 0° C. and treated with TFA (0.45 ml, 5.89 mmol). The reaction mixture was stirred at room temperature for 1 h. Progress of the reaction was monitored by TLC (Mobile phase: 10% MeOH in DCM. Rf: 0.1. Detection: UV). The reaction mixture was concentrated under reduced pressure to afford 2-(3-(5-(aminomethyl)-2-(4-fluorophenyl)pyridin-4-yl)-1H-pyrazol-1-yl) acetonitrile as a yellow solid (200 mg, LC/MS: 80%). (LC/MS; m/z 308.4 $[M+H]^+$).

Step 3: A solution of 2-(3-(5-(aminomethyl)-2-(4-fluorophenyl)pyridin-4-yl)-1H-pyrazol-1-yl) acetonitrile 2 (200 mg, 0.65 mmol) in DCM (3 mL) was cooled to 0° C. and treated with TEA (263.1 mg, 2.60 mmol) and a solution of acryloyl chloride (58.96 mg, 0.65 mmol) in DCM (2 mL) under nitrogen atmosphere. The reaction mixture was stirred at 0° C. for 1 h. Progress of the reaction was monitored by TLC (Mobile phase: 10% MeOH in DCM. Rf: 0.5. Detection: UV). The reaction mixture was diluted with DCM (20 mL) and washed with brine (2×20 mL) and the organic layer was dried over anhydrous $Na_2SO_4$ and concentrated under reduced pressure to afford a yellow gum (150 mg, LC/MS: 79%). The crude product was purified by preparative HPLC method H2 to afford N-((4-(1-(cyanomethyl)-1H-pyrazol-3-yl)-6-(4-fluorophenyl)pyridin-3-yl)methyl)acrylamide (Cpd. No. 266) as a white solid (16.4 mg, LC/MS: 99%). (LC/MS; m/z 362.4 $[M+H]^+$).

The following compounds were prepared in a manner similar (use of appropriate reagents and purification methods known to the person skilled in the art) to Cpd. No. 266: Cpd. No. 267, Cpd. No. 268, Cpd. No. 269, Cpd. No. 270, Cpd. No. 271, Cpd. No. 272, Cpd. No. 275, Cpd. No. 281, Cpd. No. 292, Cpd. No. 295, Cpd. No. 299, Cpd. No. 300 (using Int-B in step 1), Cpd. No. 307 (using Int-A in step 1), Cpd. No. 308, Cpd. No. 348, Cpd. No. 349 (using priopionyl chloride in step 3), Cpd. No. 354, Cpd. No. 357 (using Int-74 in step 1), Cpd. No. 358 (using Int-74 in Step 1 and propionyl chloride in Step 3), Cpd. No. 359 (using MsCl in step 3), Cpd. No. 363 (using Int-74 in step 1 and MsCl in step 3), Cpd. No. 365, Cpd. No. 367 (using acetyl chloride in step 3), Cpd. No. 369 (using Int-75 in step 1), Cpd. No. 370 (using Int-75 in step 1 and acetyl chloride in step 3), Cpd. No. 371 (using Int-76 in step 1), Cpd. No. 373 (using Int-76 in step 1 and acetyl chloride in step 3), Cpd. No. 419 (using methyl chloroformate in step 3).

Example 118: Synthesis of N-((4-(1-(2-amino-2-oxoethyl)-1H-pyrazol-3-yl)-6-(4-fluorophenyl)pyridin-3-yl)methyl) acrylamide (Cpd. No. 273)

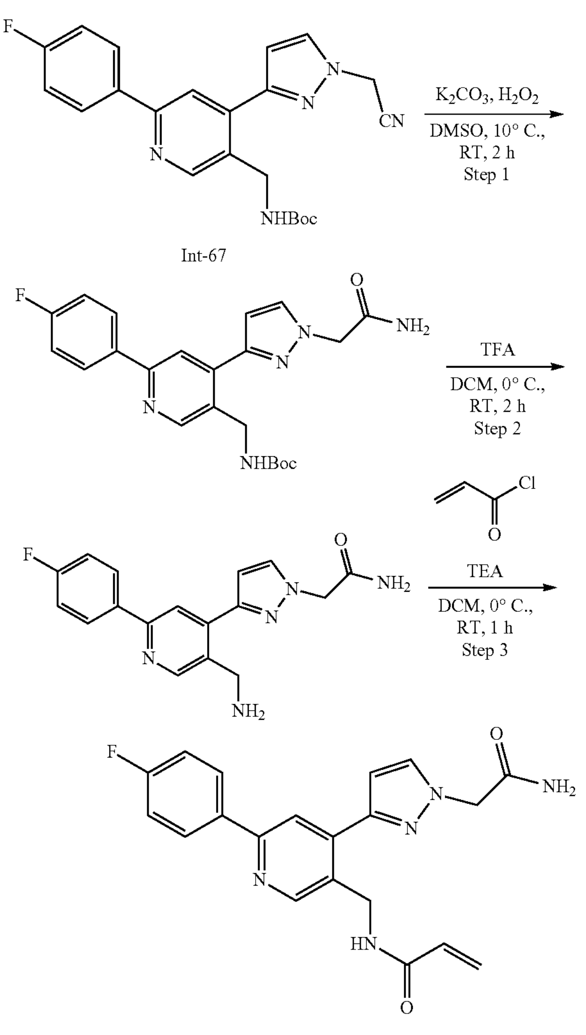

Cpd. No. 273

Step 1: A solution of Int-67 (600 mg, 1.47 mmol) in DMSO (5 mL) was treated with $K_2CO_3$ (75 mg, 0.54 mmol) and 30% hydrogen peroxide (0.3 mL) at 10° C. The reaction mixture was stirred at room temperature for 2 h. Progress of the reaction was monitored by TLC (mobile phase: 10% MeOH in DCM. Rf: 0.42. detection: UV). The reaction mixture was diluted with water (20 mL) and extracted with EtOAc (2×20 mL). The combined organic layer was washed with brine solution (25 mL), dried over $Na_2SO_4$ and concentrated under reduced pressure. The residue was triturated with diethyl ether (10 mL) and dried under high vacuum to afford tert-butyl((4-(1-(2-amino-2-oxoethyl)-1H-pyrazol-3-yl)-6-(4-fluorophenyl)pyridin-3yl)methyl)carbamate as a white solid (400 mg, LC/MS: 96%). (LC/MS; m/z 426.4 $[M+H]^+$).

Step 2: A solution of tert-butyl ((4-(1-(2-amino-2-oxoethyl)-1H-pyrazol-3-yl)-6-(4-fluorophenyl)pyridin-3-yl)methyl)carbamate (400 mg, 0.94 mmol) in DCM (5 mL) was treated with TFA (0.61 mL, 9.41 mmol) at 0° C. The reaction mixture was stirred at room temperature for 2 h and progress of the reaction was monitored by TLC (mobile phase: 10% MeOH in DCM. Rf: 0.1. detection: UV). The reaction mixture was concentrated under reduced pressure and the residue was diluted with EtOAc (100 mL) and washed with saturated $NaHCO_3$ (150 mL) and brine (2×150 mL). The organic layer was dried over $Na_2SO_4$ and concentrated under reduced pressure. The residue was triturated with diethyl ether (10 mL) and dried under high vacuum to afford 2-(3-(5-(aminomethyl)-2-(4-fluorophenyl)pyridin-4-yl)-1H-pyrazol-1yl)acetamide as a white solid (300 mg, LC/MS: 96%). (LC/MS; m/z 326.4 $[M+H]^+$).

Step 3: A solution of 2-(3-(5-(aminomethyl)-2-(4-fluorophenyl)pyridin-4-yl)-1H-pyrazol-1-yl)acetamide (300 mg, 0.92 mmol) in DCM (3 mL) was cooled to 0° C., treated with TEA (1.74 mL, 3.69 mmol) and a solution of acryloyl chloride (92 mg, 1.01 mmol) in DCM (2 mL) under nitrogen atmosphere. The reaction mixture was stirred at room temperature for 1 h. Progress of the reaction was monitored by TLC (mobile phase: 10% MeOH in DCM. Rf: 0.5. detection: UV). The reaction mixture was diluted with DCM (100 mL) and washed with brine (2×100 mL) and the organic layer was dried over $Na_2SO_4$ and concentrated under reduced pressure to afford a yellow gum (250 mg, LC/MS: 70%). The crude product was triturated with diethyl ether (10 mL) and dried under high vacuum to afford an off-white solid (200 mg, LC/MS 69%). The crude compound was purified by preparative HPLC method H2 and collected fractions were concentrated under reduced pressure to afford N-((4-(1-(2-amino-2-oxoethyl)-1H-pyrazol-3-yl)-6-(4-fluorophenyl)pyridin-3-yl)methyl) acrylamide (Cpd. No. 273) as a white solid (47 mg, LC/MS: 99%). (LC/MS; m/z 380.36 $[M+H]^+$).

The following compounds were prepared in a manner similar (use of appropriate reagents and purification methods known to the person skilled in the art) to Cpd. No. 273: Cpd. No. 274, Cpd. No. 279, Cpd. No. 319, Cpd. No. 347.

Synthesis of tert-butyl ((6-(4-fluorophenyl)-4-(4,4,5,5-tetramethyl-1,3,2-dioxaborolan-2-yl)pyridin-3-yl)methyl)carbamate (Int-69)

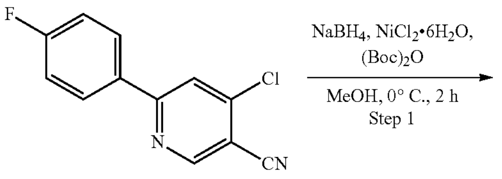

Int-54

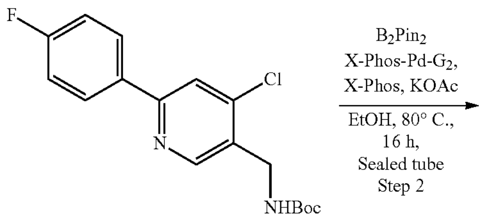

Int-68

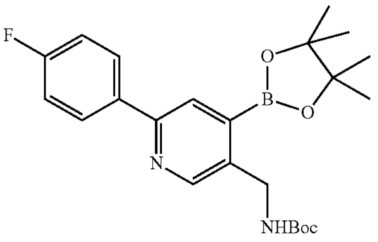

Int-69

Step 1: A solution of Int-54 (10 g, 42.98 mmol) in MeOH (150 mL) was cooled to 0° C., treated with $NiCl_2 \cdot 6H_2O$ (1.02 g, 4.29 mmol) and $(Boc)_2O$ (19.72 mL, 85.96 mmol) and then $NaBH_4$ (7.95 g, 214.9 mmol) was added portion wise. The reaction mixture was stirred at 0° C. for 2 h and monitored by TLC (mobile phase: 10% EtOAc in pet ether. Rf: 0.38. detection: UV). The reaction mixture was quenched with cold water (500 mL), concentrated under reduced pressure and the remaining mixture was extracted with EtOAc (2×200 mL). The combined organic layer was washed with brine (100 mL), dried over anhydrous $Na_2SO_4$ and concentrated under reduced pressure to afford a brown gum (13 g, LC/MS: 38%). The crude product was purified by normal phase column chromatography using silica gel and an eluent of 5% EtOAc in pet ether to afford tert-butyl ((4-chloro-6-(4-fluorophenyl)pyridin-3-yl)methyl)carbamate (Int-68) as an off-white solid (6.3 g, LC/MS: 42%). (LC/MS; m/z 337.3 $[M+H]^+$).

Step 2: In a glass screw-cap pressure vessel, a solution of tert-butyl ((4-chloro-6-(4-fluorophenyl)pyridin-3-yl)methyl)carbamate (3.0 g, 8.90 mmol) in EtOH (30 mL) was treated with bis(pinacolato)diboron (3.39 g, 13.36 mmol) and KOAc (2.62 g, 26.72 mmol). The reaction mixture was degassed by bubbling argon for 5 min, then X-Phos (0.170 g, 0.35 mmol) and X-Phos-Pd-G2 (0.140 g, 0.17 mmol) were added and the vessel was sealed with a Teflon screw cap. The reaction mixture was stirred at 80° C. for 16 h. Progress of the reaction was monitored by TLC (mobile phase: 30% EtOAc in pet ether. Rf: 0.45. detection: UV). The reaction mixture was cooled to room temperature, filtered through a pad of Celite and washed with EtOAc (150 mL). The filtrate was concentrated under reduced pressure to afford tert-butyl ((6-(4-fluorophenyl)-4-(4,4,5,5-tetramethyl-1,3,2-dioxaborolan-2-yl)pyridin-3-yl)methyl)carbamate (Int-69) as a brown gum (5.0 g, LC/MS: 52%). (LC/MS; m/z 347.4 [M+H]$^+$).

Example 119: Synthesis of N-((6-(4-fluorophenyl)-1'-methyl-2'-oxo-1',2'-dihydro-[4,4'-bipyridin]-3-yl)methyl)acrylamide (Cpd. No. 276)

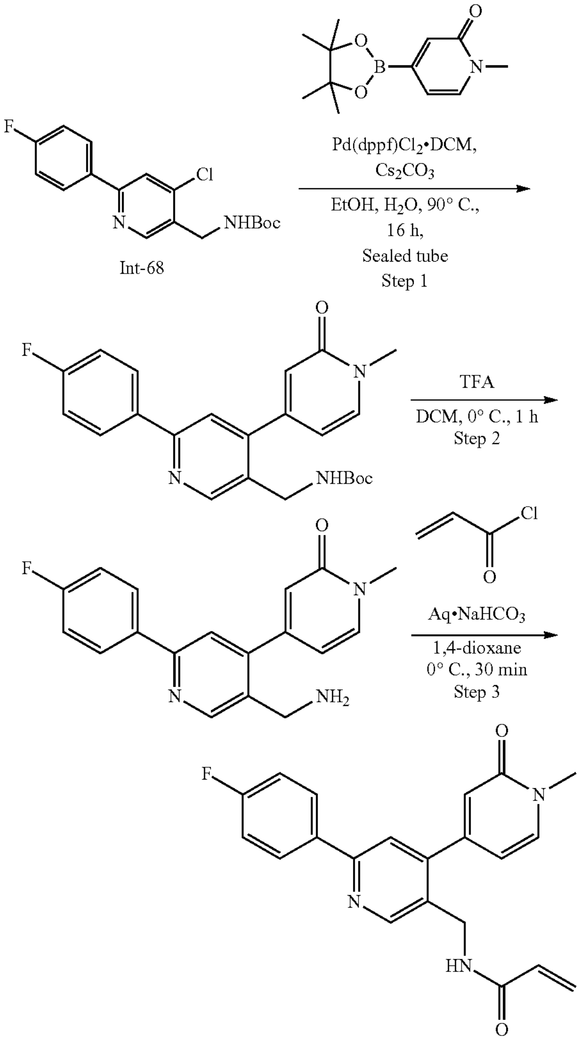

Cpd. No. 276

Step 1: In a glass screw-cap pressure vessel, a solution of Int-68 (150 mg, 0.44 mmol) in EtOH (4 mL) and $H_2O$ (0.4 mL) was treated with 1-methyl-6-(4,4,5,5-tetramethyl-1,3,2-dioxaborolan-2-yl)pyridin-2(1H)-one (209 mg, 0.89 mmol) and $Cs_2CO_3$ (362 mg, 1.11 mmol). The reaction mixture was degassed by bubbling argon for 10 min, then $PdCl_2$(dppf)·DCM (36 mg, 0.04 mmol) was added and the vessel was sealed with a Teflon screw-cap. The reaction mixture was heated to 90° C. and stirred for 16 h. The reaction was monitored by TLC (mobile phase: 10% MeOH in DCM: Rf: 0.28. detection: UV). The reaction mixture was cooled to room temperature, diluted with aqueous $NH_4Cl$ (30 mL) and extracted with EtOAc (2×30 mL). The combined organic layer was dried over anhydrous $Na_2SO_4$ and concentrated under reduced pressure to afford a brown gum (200 mg, LC/MS: 76%), which was purified by gravity column chromatography (silica gel) with an eluent of 4% MeOH in DCM. The desired product fractions were collected and concentrated under reduced pressure to afford tert-butyl ((6-(4-fluorophenyl)-1'-methyl-2'-oxo-1',2'-dihydro-[4,4'-bipyridin]-3-yl)methyl)carbamate as a brown solid (150 mg). (LC/MS; m/z 410.3 [M+H]$^+$).

Step 2: A solution of tert-butyl ((6-(4-fluorophenyl)-1'-methyl-2'-oxo-1',2'-dihydro-[4,4'-bipyridin]-3-yl)methyl) carbamate (250 mg, 0.21 mmol) in DCM (1.5 mL) was treated with TFA (0.5 mL). The reaction mixture was stirred at 0° C. for 1 h and monitored by TLC (mobile phase: 10% MeOH in DCM. Rf: 0.22. detection: UV). The reaction mixture was concentrated under reduced pressure, and the residue was triturated with pentane (2×10 mL) and diethyl ether (10 mL) and dried under high vacuum to afford 5'-(aminomethyl)-2'-(4-fluorophenyl)-1-methyl-[4,4'-bipyridin]-2(1H)-one as a brown solid (200 mg, LC/MS: 85%). (LC/MS; m/z 310.4 [M+H]$^+$).

Step 3: A solution of 5'-(aminomethyl)-2'-(4-fluorophenyl)-1-methyl-[4,4'-bipyridin]-2(1H)-one (140 mg, 0.45 mmol) in 1,4-dioxane (3.0 mL) and $H_2O$ (0.3 mL) was cooled to 0° C. and treated with $NaHCO_3$ (152 mg, 1.81 mmol) and acryloyl chloride (0.04 mL, 0.54 mmol) under nitrogen atmosphere. The reaction mixture was stirred at 0° C. for 30 min. The reaction was monitored by TLC (Mobile phase: 10% MeOH in DCM. Rf: 0.5. Detection: UV). The reaction mixture was diluted with EtOAC (30 mL), washed with brine (2×30 mL), dried over anhydrous $Na_2SO_4$ and concentrated under reduced pressure to afford a brown gum (160 mg, LC/MS: 84%). The crude product was purified by preparative HPLC method H2 and the fractions were concentrated under reduced pressure to afford N-((6-(4-fluorophenyl)-1'-methyl-2'-oxo-1',2'-dihydro-[4,4'-bipyridin]-3-yl)methyl)acrylamide (Cpd. No. 276) as a white solid (87 mg, LC/MS: 99.8%). (LC/MS; m/z 364.4 [M+H]$^+$).

The following compounds were prepared in a manner similar (use of appropriate reagents and purification methods known to the person skilled in the art) to Cpd. No. 276: Cpd. No. 277, Cpd. No. 280, Cpd. No. 282, Cpd. No. 285, Cpd. No. 293.

Synthesis of 3-bromo-4-(4-methoxybenzyl)-5-(trifluoromethyl)-4H-1,2,4-triazole (Int-C) and 5-bromo-1-(4-methoxybenzyl)-2-((4-methoxybenzyl)oxy)-1H-pyrrolo[2,3-c]pyridine (Int-D)

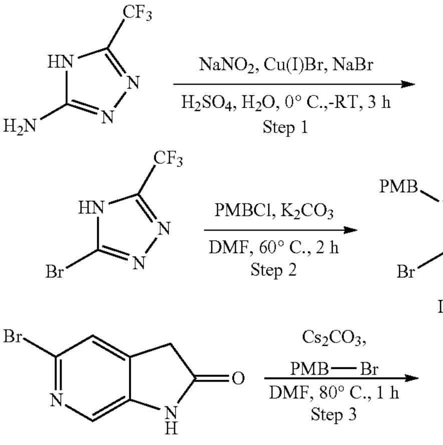

-continued

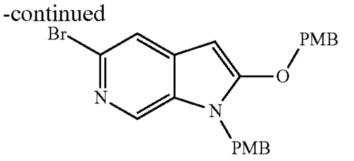

Int-D

Step 1: A solution of 5-(trifluoromethyl)-4H-1,2,4-triazol-3-amine (4.0 g, 26.3 mmol) in $H_2SO_4$ (2.8 mL) and $H_2O$ (58 mL) was treated with a solution of $NaNO_2$ (2.72 g, 39.45 mmol) in $H_2O$ (24 mL) at 0° C. and stirred for 30 min. Cu(I)Br (1.12 g, 7.89 mmol) and a solution of NaBr (5.41 g, 52.60 mmol) in $H_2O$ (58 mL) were added to the reaction mixture at 0° C. and the mixture was then stirred at room temperature for 3 h, monitored by TLC (mobile phase: 10% MeOH in DCM. Rf: 0.07. detection: UV). The reaction mixture was cooled to 0° C., quenched with addition of $NaHCO_3$powder (5 g) and concentrated under reduced pressure to afford a green solid (15 g), which was diluted with MeOH (100 mL) and stirred for 20 min. The resulting solids were filtered through a pad of Celite and washed with MeOH (60 mL). The filtrate was concentrated under reduced pressure to afford a light green solid (10 g, LC/MS: 12%), which was diluted with 10% MeOH in DCM (100 mL), stirred for 20 min, filtered through a pad of Celite and rinsed with 10% MeOH in DCM (60 mL). The filtrate was concentrated under reduced pressure to afford a light green gum (4.0 g, LC/MS: 25%), which was purified by gravity column (normal phase) using silica gel and an eluent of 10% MeOH in DCM to afford 3-bromo-5-(trifluoromethyl)-4H-1,2,4-triazole as a pale brown solid (2.0 g). (LC/MS; m/z 216.0 $[M+H]^+$).

Step 2: A solution of 3-bromo-5-(trifluoromethyl)-4H-1,2,4-triazole 2 (2.0 g, 9.26 mmol) in DMF (30 mL) was treated with $K_2CO_3$ (5.11 g, 37.0 mmol) and 4-methoxybenzyl chloride (1.88 mL, 13.89 mmol) at room temperature. The reaction mixture was heated and stirred at 60° C. for 2 h. Progress of the reaction was monitored by TLC (mobile phase: 70% EtOAc in pet ether. Rf: 0.39. detection: UV). The reaction mixture was cooled to room temperature, quenched with cold water (200 mL) and extracted EtOAc (2×60 mL). The combined organic layer was washed with water (60 mL), brine (60 mL), dried over $Na_2SO_4$ and concentrated under reduced pressure to afford a brown gum (2.5 g, LC/MS: 55%). The crude product was purified by flash column chromatography (40 g silica column) using an eluent of 20% EtOAc in pet ether to afford 3-bromo-4-(4-methoxybenzyl)-5-(trifluoromethyl)-4H-1,2,4-triazole (Int-C) as a pale yellow liquid (1.8 g, yield 55%). (LC/MS; m/z 336.2 $[M+H]^+$).

Step 3: A solution of 5-bromo-1,3-dihydro-2H-pyrrolo[2,3-c]pyridin-2-one (500 mg, 2.35 mmol) in DMF (10 mL) was cooled to 0° C., treated with $Cs_2CO_3$ (1.5 g, 4.694 mmol) and followed by addition of 1-(bromomethyl)-4-methoxybenzene (519 mg, 2.58 mmol) under nitrogen atmosphere. The reaction mixture was stirred at 80° C. for 1 h. The reaction was monitored by TLC (mobile phase: 50% EtOAc in pet ether. Rf: 0.54. detection: UV). The reaction mixture was poured into ice water (50 mL), extracted with EtOAc (3×20 mL), washed with cold water (3×10 mL), brine (15 mL), dried over anhydrous $Na_2SO_4$ and concentrated under reduced pressure to afford 5-bromo-1-(4-methoxybenzyl)-2-((4-methoxybenzyl)oxy)-1H-pyrrolo[2,3-c]pyridine (Int-D) as a brown gum (750 mg, LC/MS: 72%). (LC/MS; m/z 453.3 $[M+H]^+$).

Example 120: Synthesis of N-((4-cyano-6'-(4-fluorophenyl)-[2,4'-bipyridin]-3'-yl)methyl)acrylamide (Cpd. No. 278)

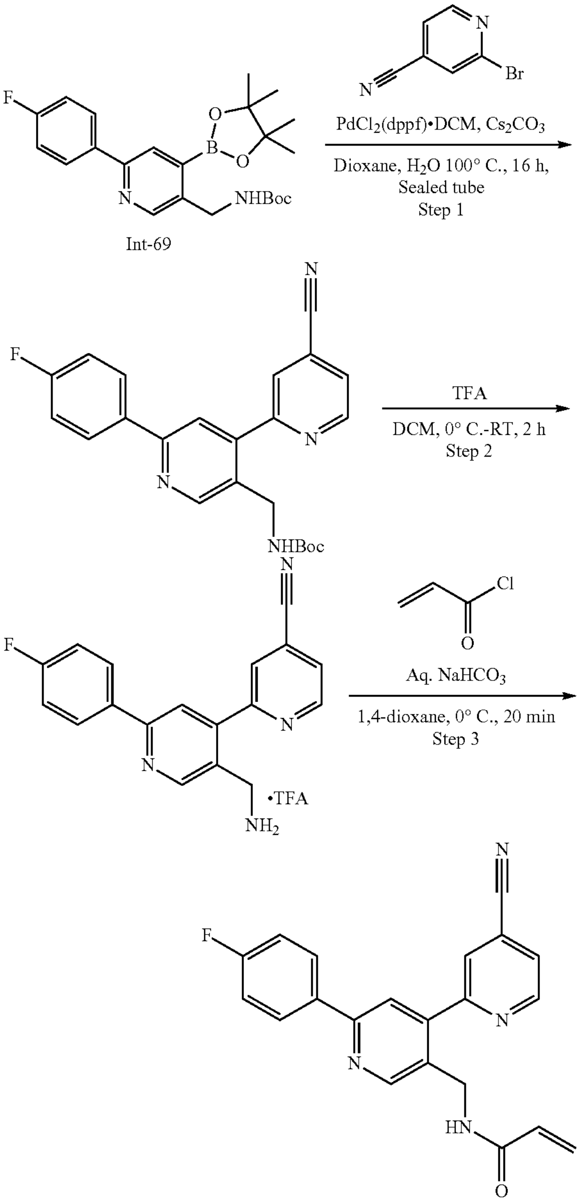

Int-69

Cpd. No. 278

Step 1: In a glass screw-cap pressure vessel, a solution of Int-69 (1.5 g, 3.50 mmol) in 1,4-dioxane (60 mL) and $H_2O$ (6.0 mL) were treated with 2-bromoisonicotinonitrile (1.28 g, 7.00 mmol) and $Cs_2CO_3$ (3.41 g, 10.50 mmol). The reaction mixture was degassed by bubbling argon for 10 min, then $Pd(dppf)Cl_2{\cdot}DCM$ (0.143 g, 0.17 mmol) was added and the vessel was sealed with a Teflon screw-cap. The reaction mixture was stirred at 100° C. for 16 h. The reaction was monitored by TLC (mobile phase: 20% EtOAc in pet ether. Rf: 0.19. detection: UV). The reaction mixture was cooled to room temperature, diluted with water (150 mL) and extracted with EtOAc (2×80 mL). The combined organic layer was washed with water (80 mL), brine (50 mL), dried over $Na_2SO_4$ and concentrated under reduced pressure to afford a brown gum (1.0 g, LC/MS: 22%). The crude product was purified by flash column chromatography (48 g silica gel column) eluted with 40% EtOAc in pet ether to afford tert-butyl ((4-cyano-6'-(4-fluorophenyl)-[2,4'-bipyridin]-3'-yl)methyl)carbamate as a pale yellow solid (350 mg, LC/MS: 94%). (LC/MS; m/z 405.4 $[M+H]^+$).

Step 2: A solution of tert-butyl ((4-cyano-6'-(4-fluorophenyl)-[2,4'-bipyridin]-3'-yl)methyl)carbamate (280 mg, 0.69 mmol) in DCM (6 mL) was treated with TFA (1.4 mL) at 0° C. The reaction mixture was stirred at room temperature for 2 h. The reaction was monitored by TLC (mobile phase: 10% MeOH in DCM. Rf: 0.15. detection: UV). The reaction mixture was concentrated under reduced pressure to afford 5'-(aminomethyl)-2'-(4-fluorophenyl)-[2,4'-bipyridine]-4-carbonitrile TFA salt as a brown gum (200 mg; LC/MS: 98%). (LC/MS; m/z 305.4 $[M+H]^+$).

Step 3: A solution of 5'-(aminomethyl)-2'-(4-fluorophenyl)-[2,4'-bipyridine]-4-carbonitrile TFA salt (200 mg, 0.49 mmol) in 1,4-dioxane (5.5 mL) was cooled to 0° C., treated with a solution of $NaHCO_3$ (251 mg, 2.99 mmol) in $H_2O$ (1.0 mL) and a solution of acryloyl chloride (0.048 mL, 0.59 mmol) in 1,4-dioxane (0.5 mL) under nitrogen atmosphere. The reaction mixture was stirred at 0° C. for 20 min. The reaction was monitored by TLC (mobile phase: 10% MeOH in DCM. Rf: 0.49. detection: UV). The reaction mixture was diluted with $H_2O$ (50 mL) and extracted with EtOAc (2×30 mL). The combined organic layer was washed with brine (20 mL), dried over anhydrous $Na_2SO_4$ and concentrated under reduced pressure to afford a brown gum (135 mg, LC/MS: 90%). The crude product was purified by preparative HPLC method H2 and the fractions were concentrated under reduced pressure to afford N-((4-cyano-6'-(4-fluorophenyl)-[2,4'-bipyridin]-3'-yl)methyl)acrylamide (Cpd. No. 278) as a white solid (53 mg, LC/MS: 98%). (LC/MS; m/z 359.4 $[M+H]^+$).

The following compounds were prepared in a manner similar (use of appropriate reagents and purification methods known to the person skilled in the art) to Cpd. No. 278: Cpd. No. 283, Cpd. No. 284, Cpd. No. 286, Cpd. No. 287, Cpd. No. 288, Cpd. No. 289, Cpd. No. 290, Cpd. No. 291, Cpd. No. 294, Cpd. No. 296, Cpd. No. 297, Cpd. No. 298, Cpd. No. 301, Cpd. No. 302 (using Pd-118 in step 1), Cpd. No. 303, Cpd. No. 304, Cpd. No. 306, Cpd. No. 312, Cpd. No. 313, Cpd. No. 315, Cpd. No. 318, Cpd. No. 320, Cpd. No. 312, Cpd. No. 322, Cpd. No. 323, Cpd. No. 324, Cpd. No. 326 (using Int-C in step 1), Cpd. No. 327 (using Int-D in step 1), Cpd. No. 332, Cpd. No. 333, Cpd. No. 336, Cpd. No. 339, Cpd. No. 340 (employing propionyl chloride in step 3), Cpd. No. 341 (employing MsCl in step 3).

Example 121: Synthesis of 2-((3-(1-(3-cyano-5-isopropoxybenzyl)-1H-pyrazol-3-yl)-[1,1'-biphenyl]-4-yl)amino)-N-methylethane-1-sulfonamide (Cpd. No. 305)

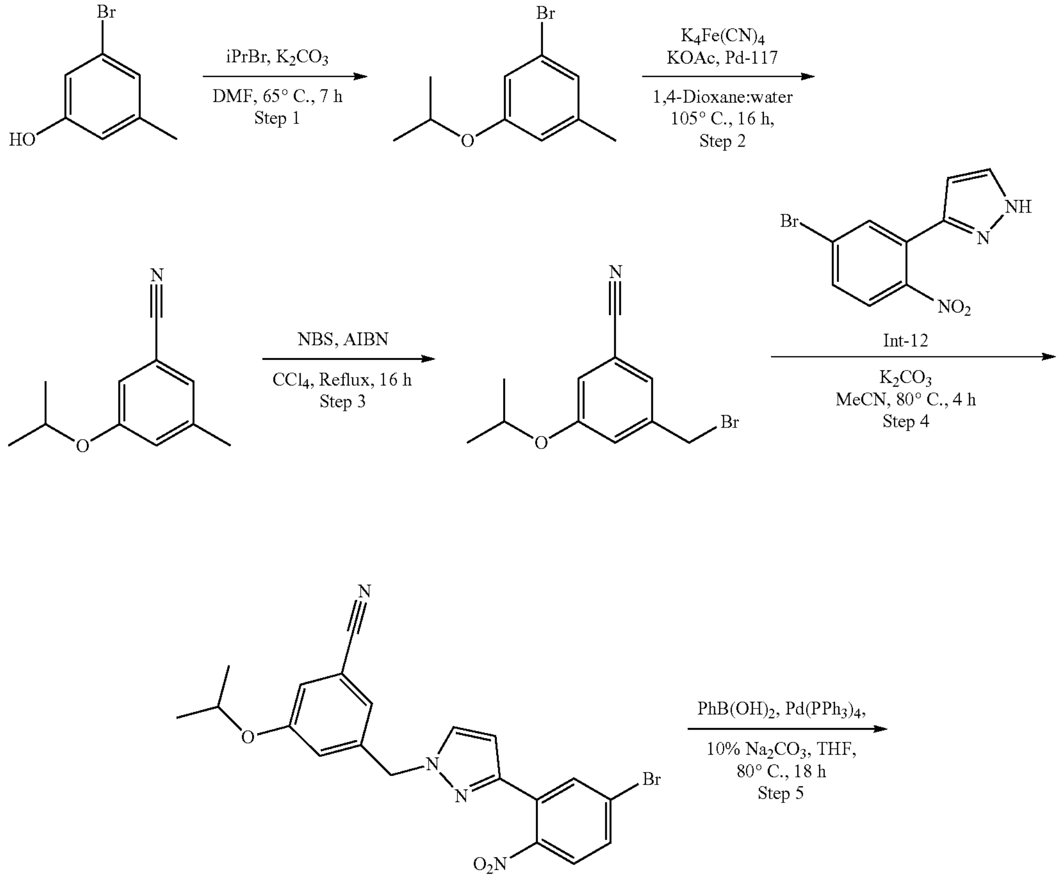

-continued

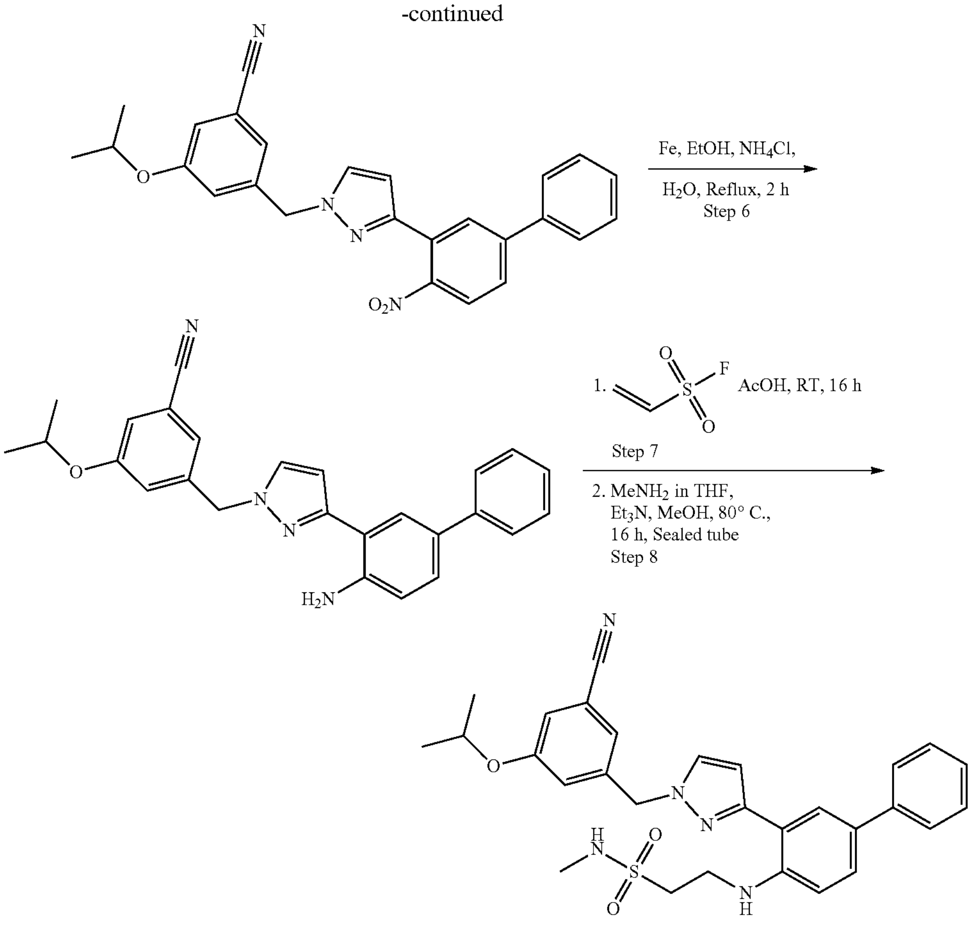

Cpd. No. 305

Step 1: A solution of 3-bromo-5-methylphenol (15 g, 80.20 mmol) in DMF (150 mL) was treated with 2-bromopropane (39.459 g, 320.80 mmol) and $K_2CO_3$ (33.251 g, 240.60 mmol) at room temperature. The resulting mixture was stirred at 65° C. for 7 h, monitored by TLC (mobile phase: 100% Pet ether, Rf: 0.92, detection: UV). The reaction mixture was cooled to room temperature, poured on ice cold water (300 mL) and extracted with EtOAc (2×90 mL). The combined organic layer was washed with brine (100 mL), dried over anhydrous $Na_2SO_4$ and evaporated under reduced pressure to afford a liquid (20 g), which was purified by flash column chromatography (silica gel) with 100% pet ether as eluent. The pure fractions were collected and concentrated under reduced pressure to afford 1-bromo-3-isopropoxy-5-methylbenzene as a colorless liquid.

(15 g). $^1H$ NMR (400 MHz, $CDCl_3$) δ ppm: 6.88 (s, 1H), 6.83 (s, 1H), 6.62 (s, 1H), 4.52-4.46 (m, 1H), 2.27 (s, 3H), 1.30 (s, 6H).

Step 2: 1-bromo-3-isopropoxy-5-methylbenzene (3.0 g, 13.10 mmol) was dissolved in 1:1 water:1,4-Dioxane (48 mL) that had been degassed by 3 freeze-pump cycles and the mixture was treated with $K_4Fe(CN)_6 \cdot 3H_2O$ (27.65 g, 65.45 mmol), KOAc (6.424 g, 65.45 mmol) and Pd-117 (936.091 mg, 1.31 mmol) under argon atmosphere in a sealed tube. The reaction mixture was degassed by bubbling argon for 10 min and sealed with a Teflon screw-cap. The reaction mixture was stirred at 105° C. for 16 h, monitored by TLC (mobile phase: 100% Pet ether, Rf: 0.14, detection: UV). The reaction mixture was cooled to room temperature and filtered, and the filtrate was washed with EtOAc (2×25 mL) and water (30 mL). The aqueous layer was extracted with EtOAc (30 mL) and the combined organic phase was dried over $Na_2SO_4$ and concentrated to afford a dark brown liquid (4 g), which was purified by flash column chromatography (silica gel) with a gradient of 0 to 2% EtOAc/pet ether as eluent. The pure fractions were combined and concentrated under reduced pressure to afford 3-isopropoxy-5-methylbenzonitrile as a colorless liquid (1.63 g). $^1H$ NMR (400 MHz, $CDCl_3$) δ ppm: 7.02 (s, 1H), 6.93 (s, 1H), 6.91 (s, 1H), 4.55-4.49 (m, 1H), 2.36 (s, 3H), 1.33 (s, 6H).

Step 3: A solution of 3-isopropoxy-5-methylbenzonitrile (5.0 g, 28.53 mmol) in $CCl_4$ (75 mL) was treated with AIBN (cat.) and NBS (7.62 g, 42.80 mmol) at room temperature and the resulting reaction mixture was heated to reflux for 16 h, monitored by TLC (mobile phase: 1% EtOAc in Pet ether; Rf: 0.32; detection: UV). The reaction mixture was cooled to room temperature, diluted with water (50 mL) and extracted with DCM (2×40 mL). The combined organic phase was dried over $Na_2SO_4$ and concentrated under reduced pressure to afford the crude product (6 g), which was purified by flash column chromatography (silica gel) with 1% EtOAc in pet ether as an eluent to afford 3-(bromomethyl)-5-isopropoxybenzonitrile as pale-yellow liquid (3.7 g). $^1H$ NMR (400 MHz, $CDCl_3$) δ ppm: 7.23 (s, 1H), 7.11 (s, 1H), 7.04 (s, 1H), 4.59-4.53 (m, 1H), 4.40 (s, 2H), 1.36 (s, 6H).

Step 4: A solution of Int-12 (2.5 g, 9.365 mmol) in ACN (38 mL) was treated with 3-(bromomethyl)-5-isopropoxybenzonitrile (3.69 g, 14.56 mmol) and $K_2CO_3$ (3.88 g, 28.01 mmol) at room temperature. The reaction mixture was heated to reflux for 4 h, monitored by TLC (mobile phase: 13% EtOAc in pet ether; Rf: 0.52; detection: UV). The solvent was evaporated under reduced pressure and the residue was diluted with water (40 mL) and extracted with EtOAc (2×35 mL). The combined organic phase was dried over $Na_2SO_4$ and concentrated under reduced pressure to afford crude product (5.5 g, LC/MS: 54%), which was purified by flash column chromatography using silica gel and 5-7% EtOAc in pet ether as an eluent. The pure fractions were collected and concentrated under reduced pressure to afford 3-((3-(5-bromo-2-nitrophenyl)-1H-pyrazol-1-yl)methyl)-5-isopropoxybenzonitrile as a pale-yellow solid (2.4 g, LC/MS: 84%). (LC/MS; m/z 441.2 $[M+H]^+$).

Step 5: A solution of 3-((3-(5-bromo-2-nitrophenyl)-1H-pyrazol-1-yl)methyl)-5-isopropoxybenzonitrile (500 mg, 1.13 mmol) in THF (6 mL) was treated with phenylboronic acid (166 mg, 1.36 mmol) and 10% aqueous $Na_2CO_3$ (2.5 mL). The reaction mixture was degassed by bubbling argon for 10 min, $Pd(PPh_3)_4$ (26 mg, 0.023 mmol) was added and the vessel was sealed with a Teflon screw-cap. The reaction mixture was heated and stirred at 80° C. for 18 h, monitored by TLC (mobile phase: 15% EtOAc in pet ether, Rf: 0.46, detection: UV). The reaction mixture was diluted with $H_2O$ (10 mL) and extracted with EtOAc (2×10 mL). The combined organic layer was dried over anhydrous $Na_2SO_4$ and concentrated under reduced pressure to afford crude product (600 mg, LC/MS: 80%), which was purified by silica gel with an eluent of 8% EtOAc in pet ether to afford 3-isopropoxy-5-((3-(4-nitro-[1,1'-biphenyl]-3-yl)-1H-pyrazol-1-yl)methyl)benzonitrile as a pale yellow gum (450 mg, LC/MS: 88%). (LC/MS; m/z 439.3 $[M+H]^+$).

Step 6: A solution of 3-isopropoxy-5-((3-(4-nitro-[1,1'-biphenyl]-3-yl)-1H-pyrazol-1-yl)methyl)benzonitrile (350 mg, 0.78 mmol) in EtOH (5 mL) was treated with iron powder (223 mg, 3.4 mmol) and saturated aqueous $NH_4Cl$ (1.0 mL) at room temperature. The reaction mixture was stirred at 80° C. for 2 h and monitored by TLC (mobile phase: 20% EtOAc in Pet ether; Rf: 0.46, detection: UV). The reaction mixture was cooled to room temperature, filtered through a pad of Celite and washed with EtOAc (30 mL). The filtrate was washed with $H_2O$ (30 mL) and the aqueous phase was extracted with EtOAc (30 mL). The combined organic fraction was dried over anhydrous $Na_2SO_4$ and concentrated under reduced pressure to afford the crude product (450 mg, LC/MS: 92%), which was purified by column chromatography using silica gel and a gradient of 15-20% EtOAc in pet ether as eluent to afford 3-((3-(4-amino-[1,1'-biphenyl]-3-yl)-1H-pyrazol-1-yl)methyl)-5-isopropoxybenzonitrile as a brown gum (280 mg, LC/MS: 96%). (LC/MS; m/z 409.5 $[M+H]^+$).

Step 7: A solution of 3-((3-(4-amino-[1,1'-biphenyl]-3-yl)-1H-pyrazol-1-yl)methyl)-5-isopropoxybenzonitrile (280 mg, 0.69 mmol) in AcOH (3 mL) was treated with ethenesulfonyl fluoride (91 mg, 0.84 mmol) at room temperature. The reaction mixture was stirred at room temperature for 16 h, monitored by TLC (mobile phase: 25% EtOAc in pet ether, Rf: 0.5, detection: UV). The solvent was evaporated and the residue was diluted with cold water (15 mL) and extracted with EtOAc (2×20 mL). The combined organic layer was dried over anhydrous $Na_2SO_4$ and concentrated under reduced pressure to afford crude product (350 mg, LC/MS: 75%), which was purified by flash column chromatography using silica gel and a gradient of 10-15% EtOAc in pet ether as an eluent. The pure fractions were collected and concentrated under reduced pressure to afford 2-((3-(1-(3-cyano-5-isopropoxybenzyl)-1H-pyrazol-3-yl)-[1,1'-biphenyl]-4-yl) amino)ethane-1-sulfonyl fluoride as a brown sticky solid (200 mg, LC/MS: 95%). (LC/MS; m/z 519.2 $[M+H]^+$).

Step 8: A solution of 2-((3-(1-(3-cyano-5-isopropoxybenzyl)-1H-pyrazol-3-yl)-[1,1'-biphenyl]-4-yl)amino)ethane-1-sulfonyl fluoride (150 mg, 0.29 mmol) in MeOH (3 mL) was treated with $MeNH_2$ (3.0 mL, 2.0 M solution in THF) in a sealed tube at room temperature. The reaction mixture was heated at 80° C. for 16 h, monitored by TLC (mobile phase: 30% EtOAc in pet ether, Rf: 0.12, detection: UV). The reaction mixture was cooled to room temperature and volatiles were evaporated to afford the crude product (200 mg, LC/MS: 32%). The crude product was purified by silica gel column with 20% EtOAc in pet ether as eluent to afford a sticky brown solid (45 mg, LC/MS: 90%), which was purified further by preparative HPLC method H9. The pure fractions were concentrated under reduced pressure to afford 2-((3-(1-(3-cyano-5-isopropoxybenzyl)-1H-pyrazol-3-yl)-[1,1'-biphenyl]-4-yl)amino)-N-methylethane-1-sulfonamide (Cpd. No. 305) as an off-white solid (28 mg, LC/MS: 99%). (LC/MS; m/z 530.4 $[M+H]^+$).

The following compounds were prepared in a manner similar (use of appropriate reagents and purification methods known to the person skilled in the art) to Cpd. No. 305: Cpd. No. 316, Cpd. No. 317.

Example 122: Synthesis of 3-isopropoxy-5-((3-(4-((2-(N-methylsulfamoyl)ethyl)amino)-[1,1'-biphenyl]-3-yl)-1H-pyrazol-1-yl)methyl)benzamide (Cpd. No. 309)

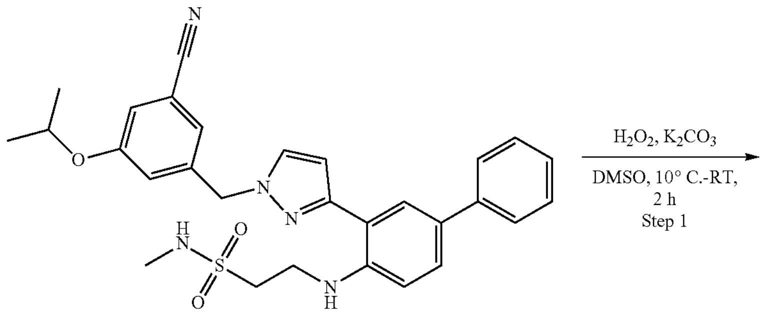

Cpd. No. 305

-continued

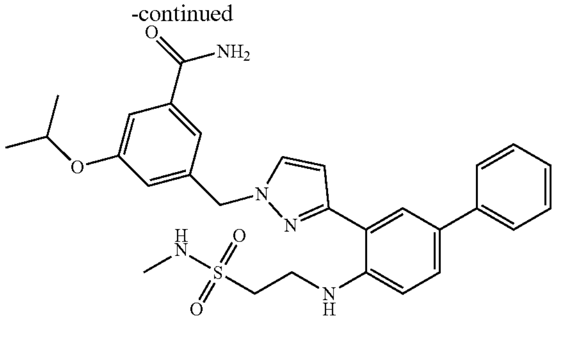

Cpd. No. 309

Step 1: A solution of Cpd. No. 305 (270 mg, 0.493 mmol) in DMSO (5 mL) was treated with $K_2CO_3$ (68 mg, 0.493 mmol) at room temperature. The reaction mixture was cooled to 10° C. and $H_2O_2$ (2.0 mL, 30% solution) was added. The temperature was raised to room temperature and the reaction mixture was stirred for 2 h, monitored by TLC (mobile phase: 5% MeOH in DCM. Rf: 0.2. detection: UV). The reaction mixture was diluted with cold water (10 mL) and stirred for 15 min, and the resulting solid was collected by filtration, washed with cold water (15 mL). The solid was dissolved in DCM (30 mL), was washed with water (20 mL) and brine (5 mL), dried over $Na_2SO_4$ and concentrated to afford a white solid (270 mg, LC/MS: 84%). The crude product was purified by preparative HPLC method H8. The pure fractions were concentrated under reduced pressure to afford 3-isopropoxy-5-((3-(4-((2-(N-methylsulfamoyl)ethyl)amino)-[1,1'-biphenyl]-3-yl)-1H-pyrazol-1-yl)methyl)benzamide (Cpd. No. 309) as a white solid (140 mg, LC/MS: 99.8%). (LC/MS; m/z 548.3 $[M+H]^+$).

The following compounds were prepared in a manner similar (use of appropriate reagents and purification methods known to the person skilled in the art) to Cpd. No. 309: Cpd. No. 310 (using Cpd. No. 316 in step 1), Cpd. No. 311 (using Cpd. No. 317 in step 1).

Synthesis of methyl 5-(1-(tert-butoxycarbonyl)pyrrolidin-3-yl)-2-(4-fluorophenyl) isonicotinate (Int-F)

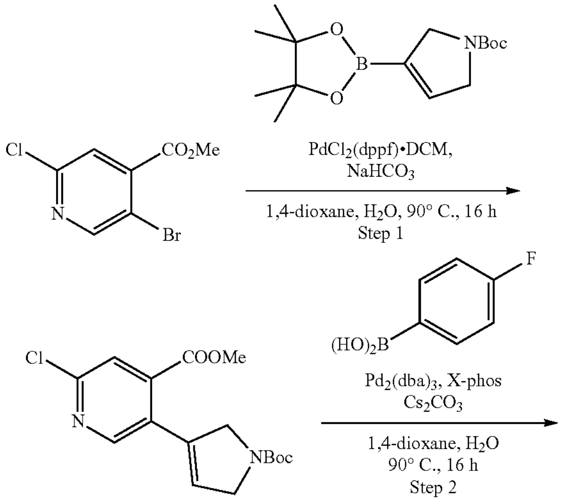

-continued

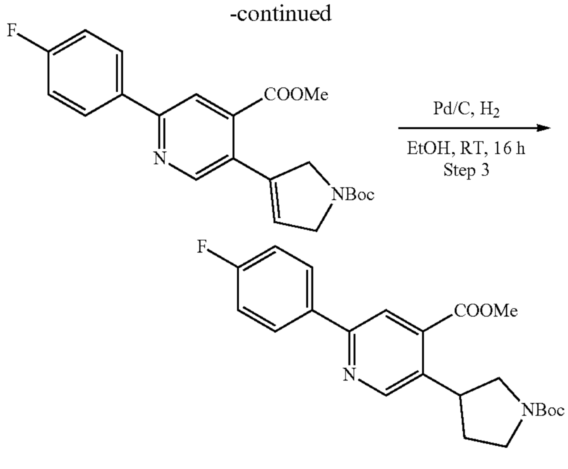

Int-F

Step 1: A solution of methyl 5-bromo-2-chloroisonicotinate (4.0 g, 15.96 mmol) in 1,4-dioxane (25 mL) was treated with tert-butyl 3-(4,4,5,5-tetramethyl-1,3,2-dioxaborolan-2-yl)-2,5-dihydro-1H-pyrrole-1-carboxylate (5.65 g, 19.16 mmol) and $NaHCO_3$ (2.71 g, 31.93 mmol) in $H_2O$ (5.0 mL) and degassed with argon for 5 min. Then, $PdCl_2$ (dppf)·DCM (0.261 g, 0.319 mmol) was added and the reaction mixture was stirred at 90° C. for 16 h in a sealed tube. Progress of the reaction was monitored by TLC (mobile phase: 20% EtOAc in pet-ether, Rf: 0.49, detection: UV). The reaction mixture was cooled to room temperature, diluted with EtOAc (30 mL), filtered through a Celite pad and washed with EtOAc (25 mL). The filtrate was concentrated under reduced pressure to obtain a brown gum (5.50 g). The crude product was purified by normal phase chromatography using an 80 g column (silica) and 12% EtOAc in pet ether as an eluent to afford methyl 5-(1-(tert-butoxycarbonyl)-2,5-dihydro-1H-pyrrol-3-yl)-2-chloroisonicotinate as a brown gum (3.60 g, LC/MS: 90%). (LC/MS; m/z 339.2 $[M+H]^+$).

Step 2: A solution of methyl 5-(1-(tert-butoxycarbonyl)-2,5-dihydro-1H-pyrrol-3-yl)-2-chloroisonicotinate (3.50 g, 10.33 mmol) in 1,4-dioxane (15 mL) was treated with (4-fluorophenyl)boronic acid (1.73 g, 12.39 mmol) and $Cs_2CO_3$ (6.73 g, 20.66 mmol) in $H_2O$ (5.0 mL) was degassed with argon for 5 min, then $Pd_2(dba)_3$ (9.46 mg, 0.010 mmol) and X-phos (9.83 mg, 0.21 mmol) were added and the reaction mixture was stirred at 90° C. for 16 h in a sealed tube. Progress of the reaction was monitored by TLC (mobile phase: 30% EtOAc in pet-ether, Rf: 0.25, detection:

UV). The reaction mixture was filtered through a Celite pad, washed with EtOAc (50 mL) and the filtrate was concentrated under reduced pressure to get the crude compound of methyl 5-(1-(tert-butoxycarbonyl)-2,5-dihydro-1H-pyrrol-3-yl)-2-(4-fluorophenyl) isonicotinate as a brown gum (4.20 g, LC/MS: 49%). The crude product was purified by normal phase chromatography using 40 g column (silica) and an eluent of 20% EtOAc in pet ether to afford methyl 5-(1-(tert-butoxycarbonyl)-2,5-dihydro-1H-pyrrol-3-yl)-2-(4-fluorophenyl) isonicotinate as a brown gum (1.80 g, LC/MS: 90%). (LC/MS; m/z 399.3 $[M+H]^+$).

Step 3: A solution of methyl 5-(1-(tert-butoxycarbonyl)-2,5-dihydro-1H-pyrrol-3-yl)-2-(4-fluorophenyl) isonicotinate (2.25 g, 5.64 mmol) in EtOH (15 mL) was treated with 10% Pd/C (500 mg) and stirred at room temperature for 16 h under $H_2$ atmosphere (balloon pressure). The progress of the reaction was monitored by TLC (mobile phase: 30% EtOAc in Pet-ether; Rf: 0.39, detection: UV). The reaction mixture was filtered through a Celite pad, washed with EtOH (20 mL) and the filtrate was concentrated under reduced pressure to afford methyl 5-(1-(tert-butoxycarbonyl)pyrrolidin-3-yl)-2-(4-fluorophenyl)isonicotinate (Int-F) as brown gum (1.80 g, LC/MS: 71%). (LC/MS; m/z 401.3 $[M+H]^+$).

Example 123: Synthesis N-((6-(4-fluorophenyl)-4-(5-(2-methoxyethyl)-1,3,4-oxadiazol-2-yl)pyridin-3-yl)methyl)acrylamide (Cpd. No. 314)

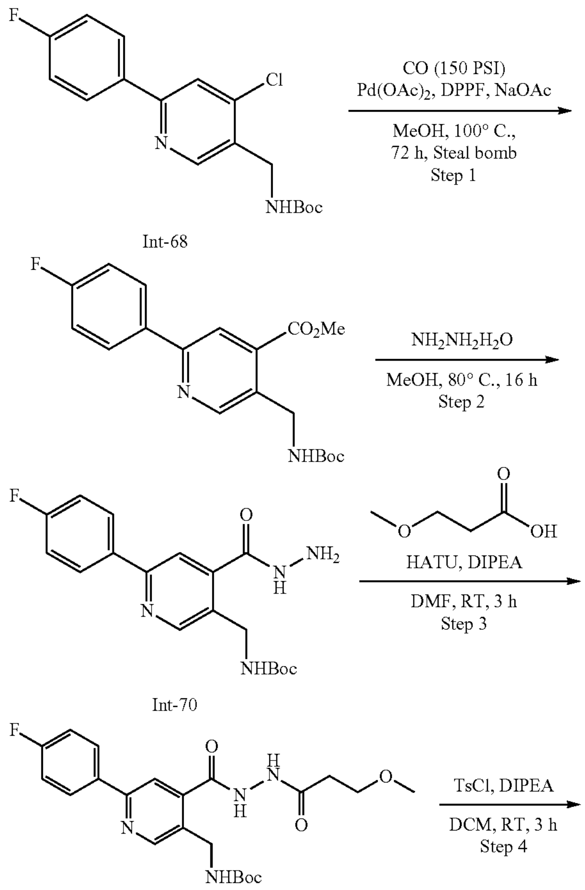

Int-68
Int-70

-continued

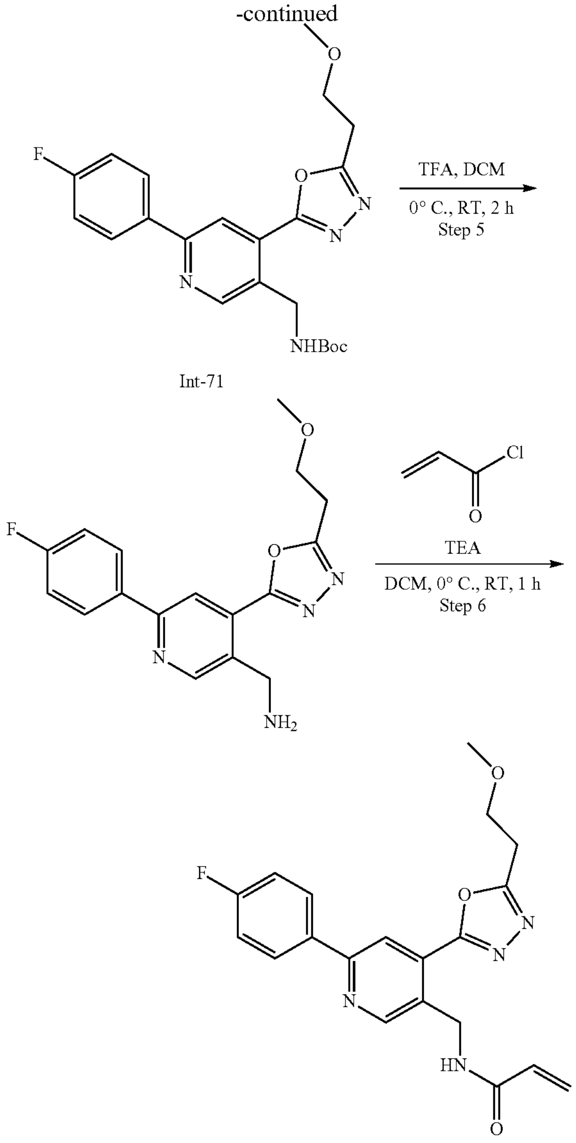

Int-71
Cpd. No. 314

Step 1: In a stainless steel pressure bomb, a solution of Int-68 (6 g, 17.81 mmol) in MeOH (200 ml) was treated with NaOAc (4.38 g, 53.44 mmol), DPPF (988 mg, 1.78 mmol) and $Pd(OAc)_2$ (400 mg, 1.78 mmol) at room temperature and the vessel was sealed. The vessel was pressurized with carbon monoxide (CO) to 150 psi and stirred at 100° C. for 72 h. The vessel was allowed to cool to room temperature, carefully opened and the contents transferred to a round bottom flask and concentrated. Reaction progress was monitored by TLC (mobile phase: 30% EtOAc in Pet ether. Rf: 0.35. detection: UV). The reaction mixture was filtered through a pad of Celite and washed with MeOH (50 mL). The filtrate was concentrated under reduced pressure, the residue was diluted with EtOAc (250 mL), washed with brine (2×250 mL), dried over anhydrous $Na_2SO_4$ and concentrated under reduced pressure to afford a black gum (5 g, LC/MS: 37%). The crude product was purified by normal phase column chromatography using a 48 g column (silica) and an eluent of 14% EtOAc in pet ether to afford methyl 5-(((tert-butoxycarbonyl)amino)methyl)-2-(4-fluorophenyl) isonicotinate as an off-white solid (800 mg, LC/MS: 93%). (LC/MS; m/z 361.3 $[M+H]^+$).

Step 2: A solution of 5-(((tert-butoxycarbonyl)amino)methyl)-2-(4-fluorophenyl)isonicotinate (800 mg, 2.22 mmol) in MeOH (20 mL) was treated with hydrazine hydrate (1.08 ml, 22.19 mmol) at room temperature. The reaction mixture was stirred at 80° C. for 16 h. The reaction progress was monitored by TLC (mobile phase: 10% MeOH in DCM. Rf: 0.3. detection: UV). The reaction mixture was concentrated under reduced pressure to afford tert-butyl ((6-(4-fluorophenyl)-4-(hydrazinecarbonyl)pyridin-3-yl)methyl)carbamate (Int-70) as a white solid (750 mg, LC/MS: 95%). (LC/MS; m/z 361.4 [M+H]$^+$).

Step 3: A solution of Int-70 (720 mg, 0.11 mmol) in DMF (10 mL) was treated with 3-methoxypropanoic acid (229 mg, 2.19 mmol), HATU (911 mg, 2.39 mmol) and DIPEA (1.41 ml, 7.99 mmol) at room temperature. The reaction mixture was stirred at room temperature for 3 h. Progress of the reaction was monitored by TLC (mobile phase: 10% MeOH in DCM. Rf: 0.5. detection: UV). The reaction mixture was diluted with water (50 mL) and extracted with EtOAc (2×100 mL). The EtOAc layer was washed with brine (2×75 mL), dried over anhydrous $Na_2SO_4$ and concentrated under reduced pressure. The residue was washed with diethyl ether (10 mL) and dried under high vacuum to afford tert-butyl ((6-(4-fluorophenyl)-4-(2-(3-methoxypropanoyl)hydrazine-1-carbonyl)pyridin-3-yl)methyl)carbamate as a yellow solid (680 mg, LC/MS: 86%). (LC/MS; m/z 447.4 [M+H]$^+$).

Step 4: A solution of tert-butyl ((6-(4-fluorophenyl)-4-(2-(3-methoxypropanoyl)hydrazine-1-carbonyl)pyridin-3-yl)methyl)carbamate (680 mg, 1.52 mmol) in DCM (15 ml) was treated with DIPEA (0.79 ml, 4.56 mmol) and para-toluene sulfonyl chloride (319 mg, 1.67 mmol) at 0° C. The reaction mixture was stirred at room temperature for 3 h. Progress of the reaction was monitored by TLC (mobile phase: 50% EtOAc in Pet ether. Rf: 0.5. detection: UV). The reaction mixture was diluted with DCM (100 mL), washed with brine (2×70 mL), dried over anhydrous $Na_2SO_4$and concentrated under reduced pressure to afford a brown solid (700 mg, LC/MS: 90%). The crude product was purified by normal phase column chromatography using a 24 g column (silica) and an eluent of 25% EtOAc in pet ether to afford tert-butyl ((6-(4-fluorophenyl)-4-(5-(2-methoxyethyl)-1,3,4-oxadiazol-2-yl)pyridin-3-yl)methyl)carbamate (Int-71) as a white solid (370 mg, LC/MS: 99.5%). (LC/MS; m/z 429.0 [M+H]$^+$).

Step 5: A solution of Int-71 (120 mg, 0.28 mmol) in DCM (5 mL) was treated with TFA (319 mg, 2.80 mmol) at 0° C. The reaction mixture was stirred at room temperature for 2 h. Progress of the reaction was monitored by TLC (mobile phase: 10% MeOH in DCM. Rf: 0.04. detection: UV). The reaction mixture was concentrated under reduced pressure, the residue was diluted with EtOAc (50 mL), washed with saturated $NaHCO_3$ (30 mL), brine (2×30 mL), dried over anhydrous $Na_2SO_4$and concentrated under reduced pressure to afford (6-(4-fluorophenyl)-4-(5-(2-methoxyethyl)-1,3,4-oxadiazol-2-yl)pyridin-3-yl)methanamine as a yellow solid (80 mg, LC/MS: 88%). (LC/MS; m/z 329.4 [M+H]$^+$).

Step 6: A solution of (6-(4-fluorophenyl)-4-(5-(2-methoxyethyl)-1,3,4-oxadiazol-2-yl)pyridin-3-yl)methanamine (75 mg, 0.22 mmol) in DCM (7 mL) was cooled to 0° C., treated with TEA (92 mg, 0.91 mmol) and a solution of acryloyl chloride (21 mg, 0.22 mmol) in DCM (1 mL) under nitrogen atmosphere. The reaction mixture was stirred at room temperature for 1 h. Progress of the reaction was monitored by TLC (mobile phase: 10% MeOH in DCM. Rf: 0.5. detection: UV). The reaction mixture was diluted with DCM (60 mL), washed with brine (2×60 mL), dried over anhydrous $Na_2SO_4$, and concentrated under reduced pressure to afford a yellow solid (80 mg, LC/MS: 72%). The crude product was purified by preparative HPLC method H2 to afford N-((6-(4-fluorophenyl)-4-(5-(2-methoxyethyl)-1,3,4-oxadiazol-2-yl)pyridin-3-yl)methyl)acrylamide (Cpd. No. 314) as a white solid (26 mg, LC/MS: 99.6%). (LC/MS; m/z 383.4 [M+H]$^+$).

Cpd. No. 417 was prepared in a manner similar (use of appropriate reagents and purification methods known to the person skilled in the art) to Cpd. No. 314 by employing intermediate Int-F in step 2.

Example 124: Synthesis of N-((6-(4-fluorophenyl)-4-(5-(2-hydroxyethyl)-1,3,4-oxadiazol-2-yl)pyridin-3-yl)methyl)acrylamide (Cpd. No. 325)

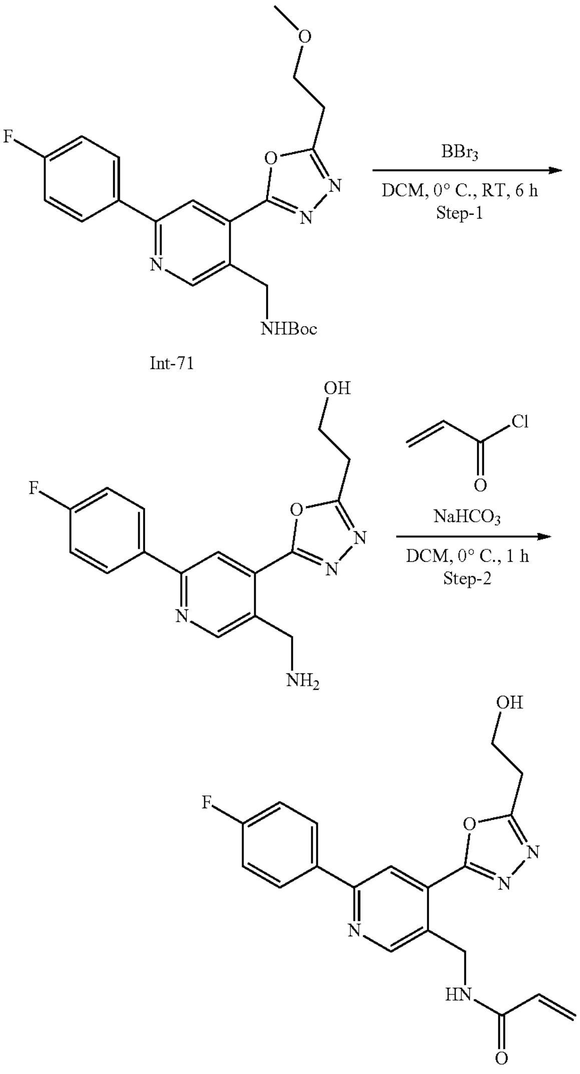

Int-71

Cpd. No. 325

Step 1: A solution of Int-71 (300 mg, 0.7 mmol) in DCM (30 mL) was treated with 1M $BBr_3$ in DCM (0.7 ml, 0.7 mmol) at 0° C. The reaction mixture was stirred at room temperature for 6 h. Progress of the reaction was monitored by TLC (mobile phase: 10% MeOH in DCM. Rf: 0.03. detection: UV). The reaction mixture was cooled to 0° C., quenched with MeOH (10 mL), stirred for 10 min, diluted with saturated $NaHCO_3$ (25 mL) and extracted with EtOAc (2×100 mL). The organic layer was washed with brine (50 mL), dried over anhydrous $Na_2SO_4$, and concentrated under reduced pressure to afford 2-(5-(5-(aminomethyl)-2-(4-fluorophenyl)pyridin-4-yl)-1,3,4-oxadiazol-2-yl)ethan-1-ol as a brown solid (230 mg, LC/MS: 48%). (LC/MS; m/z 315.1 $[M+H]^+$).

Step 2: A solution of 2-(5-(5-(aminomethyl)-2-(4-fluorophenyl) pyridin-4-yl)-1,3,4-oxadiazol-2-yl)ethan-1-ol (200 mg, 0.63 mmol) in DCM (18 mL) was treated with $NaHCO_3$ (63 mg, 0.74 mmol) and a solution of acryloyl chloride (58 mg, 0.63 mmol) in DCM (2 mL) at 0° C. The reaction mixture was stirred at room temperature for 1 h. Progress of the reaction was monitored by TLC (mobile phase: 10% MeOH in DCM. Rf: 0.3. detection: UV). The reaction mixture was diluted with DCM (100 mL) and washed with brine (2×50 mL). The organic layer was dried over anhydrous $Na_2SO_4$, and concentrated under reduced pressure to afford a red solid (310 mg, LC/MS: 41%). The crude product was purified by preparative HPLC method H1 to afford N-((6-(4-fluorophenyl)-4-(5-(2-hydroxyethyl)-1,3,4-oxadiazol-2-yl)pyridin-3-yl)methyl)acrylamide (Cpd. No. 325) as a pale purple solid (8.5 mg, LC/MS: 97%). (LC/MS; m/z 369.4 $[M+H]^+$).

Example 125: Synthesis of N-((5-(4-fluorophenyl)-3-(oxazol-2-yl)pyridin-2-yl)methyl)acrylamide (Cpd. No. 328)

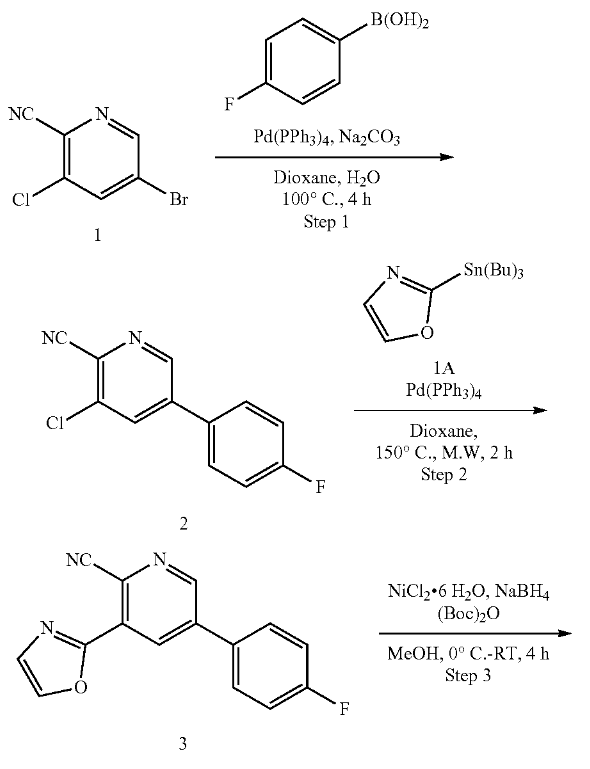

-continued

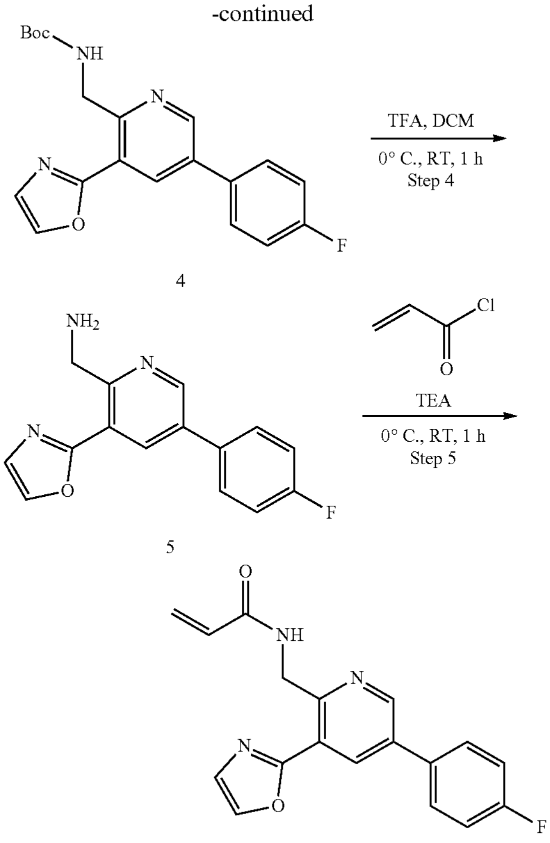

Cpd. No. 328

Step 1: A solution of 5-bromo-3-chloropicolinonitrile (2 g, 9.19 mmol) in 1,4-dioxane (60 mL) and $H_2O$ (20 mL) was treated with (4-fluorophenyl)boronic acid (1.41 g, 10.11 mmol) and $Na_2CO_3$ (2.92 g, 27.59 mmol) and was degassed with argon for 20 min, then $Pd(PPh_3)_4$ (1.06 g, 0.92 mmol) was added at room temperature. The reaction mixture was stirred at 100° C. for 4 h and progress of the reaction was monitored by TLC (mobile phase: 20% EtOAc in Pet ether. Rf: 0.37. detection: UV). The reaction mixture was filtered through a pad of Celite and the pad was washed with EtOAc (100 mL). The filtrate was washed with brine (100 ml) and dried over $Na_2SO_4$ and concentrated under reduced pressure. The residue was triturated with diethyl ether (50 mL) and dried under high vacuum to afford 3-chloro-5-(4-fluorophenyl)picolinonitrile as a white solid (2 g, LC/MS: 86%). (LC/MS; m/z 233.3 $[M+H]^+$).

Step 2: A solution of 3-chloro-5-(4-fluorophenyl)picolinonitrile (1 g, 4.29 mmol) in 1,4 dioxane (20 mL) was treated with 2-(tributylstannyl)oxazole (2.3 g, 6.44 mmol) at room temperature. The reaction mixture was degassed with argon for 20 min followed by addition of $Pd(PPh_3)_4$ (0.24 g, 0.21 mmol) at room temperature. The reaction mixture was stirred at 150° C. for 2 h under microwave irradiation and progress of the reaction was monitored by TLC (mobile phase: 20% EtOAc in Pet ether. Rf: 0.2. detection: UV). The reaction mixture was filtered through a pad of Celite and the pad was washed with EtOAc (100 mL). The filtrate was washed with brine (70 mL), dried over $Na_2SO_4$ and concentrated under reduced pressure to afford a yellow gum (1 g, LC/MS: 26%). The crude product was purified by normal phase flash chromatography using a 40 g column (silica) and an eluent of 10% EtOAc in pet ether to afford 5-(4-fluorophenyl)-3-(oxazol-2-yl)picolinonitrile as a white solid (250 mg; LC/MS: 87%). (LC/MS; m/z 266.2 $[M+H]^+$).

Step 3: A solution of 5-(4-fluorophenyl)-3-(oxazol-2-yl) picolinonitrile (250 mg, 0.94 mmol) in MeOH (5 mL) was treated with $NiCl_2 \cdot 6H_2O$ (22 mg, 0.09 mmol) and $(Boc)_2O$ (0.43 ml, 1.88 mmol). $NaBH_4$ (174 mg, 4.71 mmol) was added slowly portion wise at 0° C. The reaction mixture was stirred at room temperature for 4 h and progress of the reaction was monitored by TLC (mobile phase: 40% EtOAc in Pet ether. Rf: 0.31. TLC. detection: UV). The reaction mixture was filtered through a pad of Celite and the pad was washed with EtOAc (100 mL). The filtrate was washed with brine (100 mL), dried over $Na_2SO_4$ and concentrated under reduced pressure to a brown gum (170 mg, LC/MS: 68%), which was purified by gravity column chromatography using silica gel and an eluent of 5% EtOAc in pet ether to afford tert-butyl ((5-(4-fluorophenyl)-3-(oxazol-2-yl)pyridin-2-yl)methyl)carbamate as an off white solid (140 mg; LC/MS: 79%). (LC/MS; m/z 370.2 $[M+H]^+$).

Step 4: A solution of tert-butyl ((5-(4-fluorophenyl)-3-(oxazol-2-yl)pyridin-2-yl)methyl)carbamate (140 mg, 0.16 mmol) in DCM (5 mL) was treated with TFA (0.29 mL, 3.79 mmol) at 0° C. The reaction mixture was stirred at room temperature for 1 h and progress of the reaction was monitored by TLC (mobile phase: 10% MeOH in DCM. Rf: 0.1. detection: UV). The reaction mixture was concentrated under reduced pressure and the residue was diluted with EtOAc (100 mL) and washed with saturated $NaHCO_3$ (50 mL), washed with brine (50 mL), dried over $Na_2SO_4$ and concentrated under reduced pressure to afford (5-(4-fluorophenyl)-3-(oxazol-2-yl)pyridin-2-yl)methanamine as a yellow gum (100 mg, LC/MS: 89%). (LC/MS; m/z 270.2 $[M+H]^+$).

Step 5: A solution of (5-(4-fluorophenyl)-3-(oxazol-2-yl) pyridin-2-yl)methanamine (120 mg, 0.44 mmol) in DCM (9 mL) was treated with TEA (0.24 ml, 1.78 mmol) and a solution of acryloyl chloride (40 mg, 0.44 mmol) in DCM (1 mL) at 0° C. The reaction mixture was stirred at room temperature for 1 h and progress of the reaction was monitored by TLC (mobile phase: 10% MeOH in DCM. Rf: 0.5. detection: UV). The reaction mixture was diluted with DCM (50 mL), washed with brine (2×60 mL), dried over $Na_2SO_4$ and concentrated under reduced pressure to a yellow gum (119 mg, LC/MS: 79%). The crude product was purified by preparative HPLC method H2. The obtained fractions were concentrated under reduced pressure to afford N-((5-(4-fluorophenyl)-3-(oxazol-2-yl)pyridin-2-yl)methyl)acrylamide (Cpd. No. 328) as a white solid (46.1 mg, LC/MS: 99.9%). (LC/MS; m/z 324.3 $[M+H]^+$).

The following compounds were prepared in a manner similar (use of appropriate reagents and purification methods known to the person skilled in the art) to Cpd. No. 328: Cpd. No. 330 (using 2,6-dichloronicotinonitrile in step 1).

Example 126: Synthesis of N-((6-(4-fluorophenyl)-4-(5-((N-methylcyanamido)methyl)-1,3,4-oxadiazol-2-yl)pyridin-3-yl)methyl)acrylamide (Cpd. No. 329)

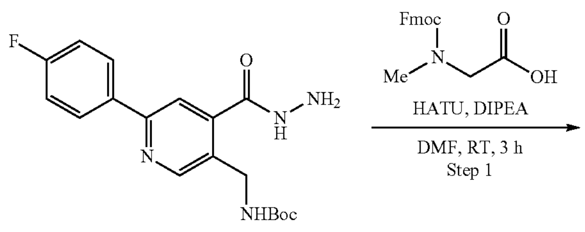

Int-70

-continued

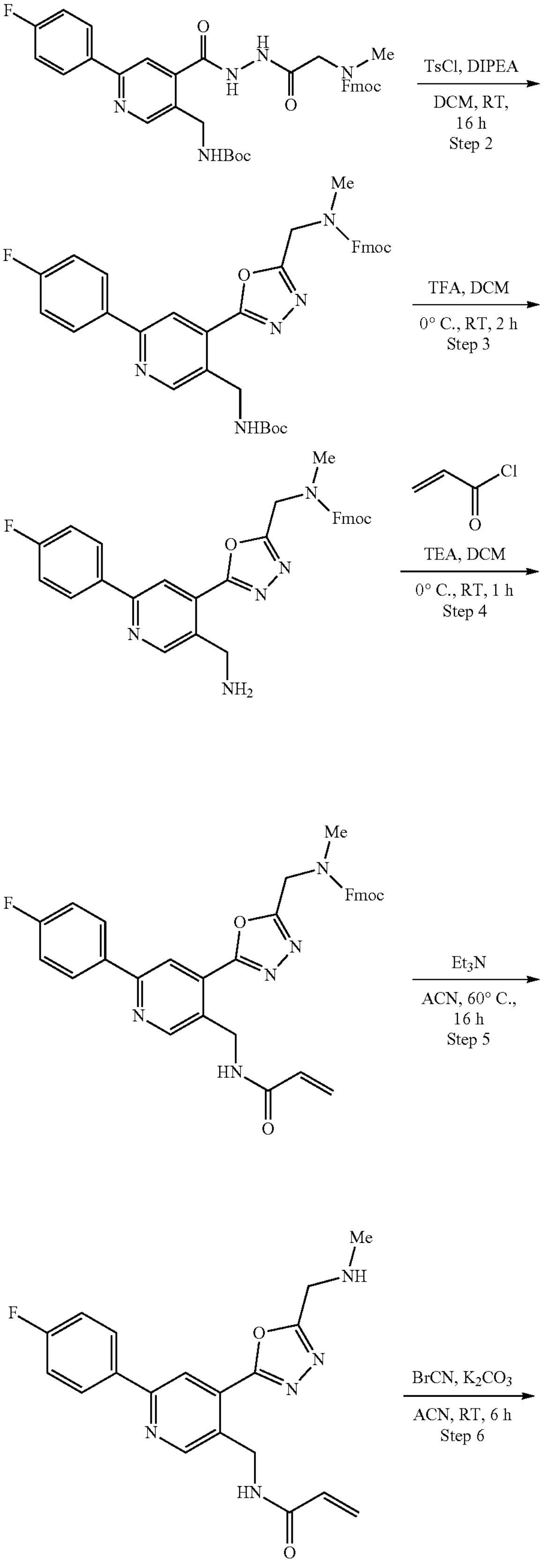

-continued

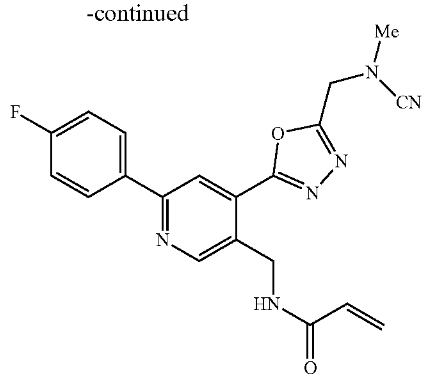

Cpd. No. 329

Step 1: A solution of Int-70 (600 mg, 1.66 mmol) in DMF (10 mL) was treated with N-(((9H-fluoren-9-yl)methoxy) carbonyl)-N-methylglycine (570 mg, 1.83 mmol), HATU (759 mg, 1.99 mmol) and DIPEA (1.16 mL, 6.65 mmol) at room temperature. The reaction mixture was stirred at room temperature for 3 h and progress of the reaction was monitored by TLC (mobile phase: 10% MeOH in DCM. Rf: 0.5. detection: UV). The reaction mixture was diluted with water (100 mL) and extracted with EtOAc (100 mL). The organic layer was washed with brine (80 mL), dried over $Na_2SO_4$ and concentrated under reduced pressure to afford crude (9H-fluoren-9-yl)methyl-(2-(2-(5-(((tert-butoxycarbonyl) amino)methyl)-2-(4-fluorophenyl)isonicotinoyl)hydrazineyl)-2-oxoethyl)(methyl)carbamate as a yellow solid (1 g; LC/MS: 47%). (LC/MS; m/z 654.5 $[M+H]^+$).

Step 2: A solution of (9H-fluoren-9-yl)methyl-(2-(2-(5-(((tert-butoxycarbonyl)amino)methyl)-2-(4-fluorophenyl) isonicotinoyl)hydrazineyl)-2-oxoethyl)(methyl)carbamate (900 mg, 1.37 mmol) in DCM (25 mL) was added DIPEA (0.7 mL, 4.13 mmol) and 4-toluenesulfonyl chloride (289 mg, 1.51 mmol) at 0° C. The reaction was stirred at room temperature for 16 h and progress of the reaction was monitored by TLC (mobile phase: 50% EtOAc in pet ether. Rf: 0.2. detection: UV). The reaction mixture was diluted with DCM (300 mL) and washed with brine (2×200 mL). The organic layer was dried over $Na_2SO_4$ and concentrated under reduced pressure to afford a brown solid (700 mg, LC/MS: 58%). The crude product was purified by flash column chromatography using a 24 g column (silica) and 40% EtOAc in Pet ether as a eluent to afford (9H-fluoren-9-yl)methyl-((5-(5-(((tert-butoxycarbonyl)amino)methyl)-2-(4-fluorophenyl)pyridin-4-yl)-1,3,4-oxadiazol-2-yl) methyl)(methyl)carbamate as an off-white solid (380 mg, LC/MS: 69%). (LC/MS; m/z 636.3 $[M+H]^+$).

Step 3: A solution of (9H-fluoren-9-yl)methyl-((5-(5-(((tert-butoxycarbonyl)amino)methyl)-2-(4-fluorophenyl) pyridin-4-yl)-1,3,4-oxadiazol-2-yl)methyl)(methyl)carbamate (240 mg, 0.37 mmol) in DCM (4 mL) was treated with TFA (0.3 mL, 3.77 mmol) at 0° C. The reaction was stirred at room temperature for 2 h and progress of the reaction was monitored by TLC (mobile phase: 20% MeOH in DCM. Rf: 0.2. detection: UV). The reaction mixture was concentrated under reduced pressure and the residue was diluted with EtOAc (50 mL) and washed with saturated $NaHCO_3$ (30 mL) and brine (2×20 mL), dried over $Na_2SO_4$ and concentrated under reduced pressure to afford (9H-fluoren-9-yl) methyl-((5-(5-(aminomethyl)-2-(4-fluorophenyl)pyridin-4-yl)-1,3,4-oxadiazol-2-yl)methyl)(methyl)carbamate as a brown gum (170 mg, LC/MS: 53%). (LC/MS; m/z 536.4 $[M+H]^+$).

Step 4: A solution of (9H-fluoren-9-yl)methyl-((5-(5-(aminomethyl)-2-(4-fluorophenyl)pyridin-4-yl)-1,3,4-oxadiazol-2-yl)methyl)(methyl)carbamate (170 mg, 0.31 mmol) in DCM (3 mL) was treated with $Et_3N$ (0.17 mL, 1.27 mmol) and acryloyl chloride (29 mg, 0.31 mmol) at 0° C. The reaction mixture was stirred at room temperature for 1 h and progress of the reaction was monitored by TLC (mobile phase: 50% EtOAc in pet ether. Rf: 0.3. detection: UV). The reaction mixture was concentrated under reduced pressure and the residue was diluted with water (50 mL) and extracted with EtOAc (50 mL). The organic layer was washed with brine (50 mL), dried over $Na_2SO_4$ and concentrated under reduced pressure to afford (9H-fluoren-9-yl)methyl-((5-(5-(acrylamidomethyl)-2-(4-fluorophenyl) pyridin-4-yl)-1,3,4-oxadiazol-2-yl)methyl)(methyl) carbamate as a brown gum (140 mg, LC/MS purity: 54%). (LC/MS; m/z 590.3 $[M+H]^+$).

Step 5: A solution of (9H-fluoren-9-yl)methyl-((5-(5-(acrylamidomethyl)-2-(4-fluorophenyl)pyridin-4-yl)-1,3,4-oxadiazol-2-yl)methyl)(methyl)carbamate (140 mg, 0.23 mmol) in ACN (5 mL) was treated with $Et_3N$ (0.09 mL, 0.71 mmol) at room temperature.

The reaction mixture was stirred at 60° C. for 16 h and progress of the reaction was monitored by TLC (mobile phase: 70% EtOAc in pet ether. Rf: 0.2. detection: UV). The reaction mixture was concentrated under reduced pressure and the residue was diluted with water (50 mL) and extracted with EtOAc (50 mL). The organic layer was washed with brine (50 mL), dried over $Na_2SO_4$ and concentrated under reduced pressure to afford a brown gum (120 mg, LC/MS: 25%), which was purified by normal phase column chromatography using a 12 g column (silica) and an eluent of 60% EtOAc in Pet ether to afford N-((6-(4-fluorophenyl)-4-(5-((methylamino)methyl)-1,3,4-oxadiazol-2-yl)pyridin-3-yl) methyl) acrylamide as an off-white solid (70 mg; LC/MS: 64%). (LC/MS; m/z 368.4 $[M+H]^+$).

Step 6: A solution of N-((6-(4-fluorophenyl)-4-(5-((methylamino)methyl)-1,3,4-oxadiazol-2-yl)pyridin-3-yl)methyl) acrylamide (100 mg, 0.014 mmol) in ACN (15 ml) was treated with $K_2CO_3$ (45 mg, 0.32 mmol) and BrCN (58 mg, 0.54 mmol) at 0° C. The reaction mixture was stirred at room temperature for 6 h and progress of the reaction was monitored by TLC (mobile phase: 70% EtOAC in Pet ether. Rf: 0.4. detection: UV). The reaction mixture was diluted with EtOAc (100 mL) and washed with brine (2×30 mL). The organic layer was dried over $Na_2SO_4$ and concentrated under reduced pressure. The residue was triturated with diethyl ether (5 mL) and dried under high vacuum to afford a brown solid (50 mg, LC/MS: 53%). The crude product was purified by preparative HPLC method H14 and the fractions were concentrated under reduced pressure to afford N-((6-(4-fluorophenyl)-4-(5-((N-methylcyanamido)methyl)-1,3,4-oxadiazol-2-yl)pyridin-3-yl)methyl) acrylamide (Cpd. No. 329) as an off-white solid (6.5 mg, LC/MS: 99%). (LC/MS; m/z 393.4 $[M+H]^+$).

Example 127: Synthesis of N-((2-(4-fluorophenyl)-4-(oxazol-2-yl)pyrimidin-5-yl)methyl)acrylamide (Cpd. No. 331)

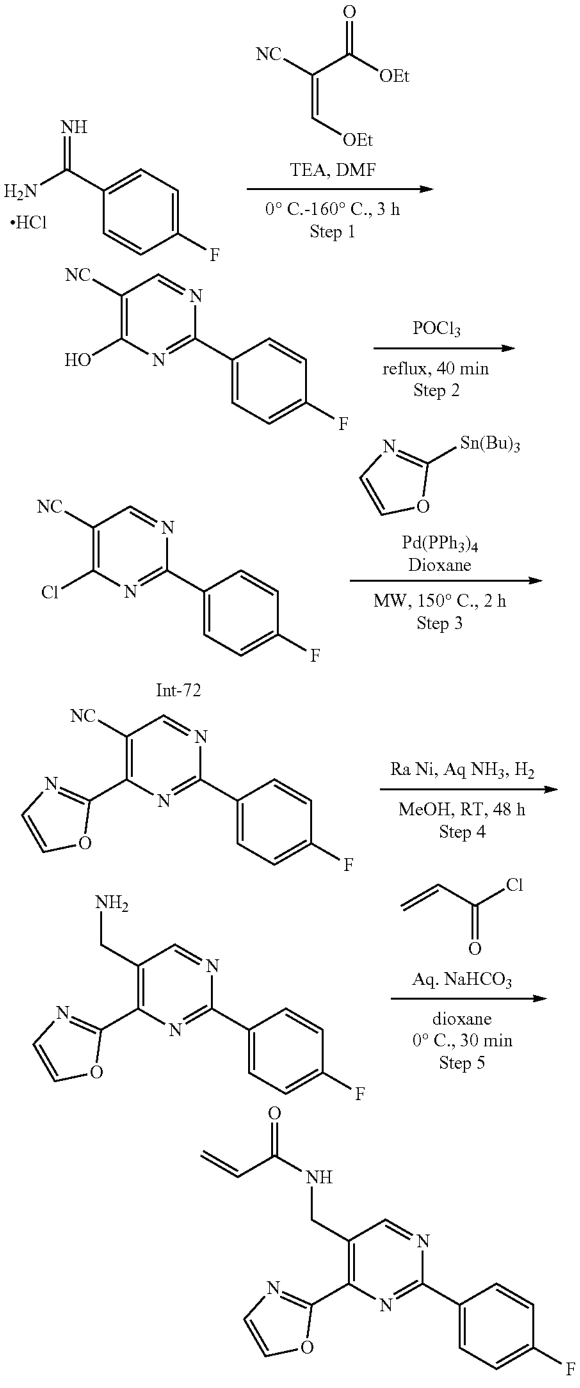

Cpd. No. 331

Step 1: A solution of 4-fluorobenzimidamide HCl salt (50 g, 28.63 mmol in DMF (40 mL) was treated with $Et_3N$ (3.91 mL, 28.63 mmol) and a solution of ethyl (Z)-2-cyano-3-ethoxyacrylate (4.84 g, 28.63 mmol) in DMF (10 mL) at 0° C. The reaction mixture was stirred at 160° C. for 3 h. The reaction was monitored by TLC (mobile phase: 70% EtOAc in Pet ether. Rf: 0.23. detection: UV). The reaction mixture was cooled to room temperature, then poured into cold water (100 mL) stirred for 10 min. The resulting precipitate was filtered and the wet cake was dissolved in EtOAc (100 mL), washed with cold water (2×30 mL) and brine (50 mL), dried over $Na_2SO_4$ and concentrated under reduced pressure to afford a yellow gummy solid (3.0 g, LC/MS: 46%). The crude product was triturated with diethyl ether (3×20 mL) and dried under vacuum to afford 2-(4-fluorophenyl)-4-hydroxypyrimidine-5-carbonitrile as a yellow solid (1.2 g, LC/MS: 95%). (LC/MS; m/z 216.3 $[M+H]^+$).

Step 2: 2-(4-fluorophenyl)-4-hydroxypyrimidine-5-carbonitrile (1.2 g, 5.57 mmol) was suspended in $POCl_3$ (15 mL) at room temperature. The reaction mixture was stirred at reflux for 40 min. The reaction was monitored by TLC (mobile phase: 20% EtOAc in Pet ether. Rf: 0.71. detection: UV). The reaction mixture was concentrated under reduced pressure and the residue was diluted with EtOAc (100 mL) and washed with water (50 mL), saturated $NaHCO_3$ (2×30 mL) and brine (20 mL), and then dried over $Na_2SO_4$ and concentrated under reduced pressure to afford 4-chloro-2-(4-fluorophenyl)pyrimidine-5-carbonitrile (Int-72) as a yellow solid (1.0 g, LC/MS: 97%). (LC/MS; m/z 234.2 $[M+H]^+$).

Step 3: A solution of Int-72 (1.0 g, 4.28 mmol) in 1,4-dioxane (20 mL) was treated with 2-(tributylstannyl) oxazole (2.30 g, 6.42 mmol) at room temperature. The reaction mixture was degassed by bubbling argon for 5 min, then $Pd(PPh_3)_4$ (247 mg, 0.21 mmol) was added at room temperature. The reaction mixture was stirred under microwave irradiation at 150° C. for 2 h. The reaction was monitored by TLC (mobile phase: 20% EtOAc in pet ether. Rf: 0.36. detection: UV). The reaction mixture was diluted with water (100 mL) and extracted with EtOAc (3×25 mL), and the combined organic layer was washed with brine (20 mL), dried over $Na_2SO_4$ and concentrated under reduced pressure to afford a yellow gummy solid (1.1 g, LC/MS: 36%). The crude product was purified by column chromatography using silica gel eluted with a gradient of 10-20% EtOAc in pet ether. The pure fractions were collected and concentrated under reduced pressure to afford 2-(4-fluorophenyl)-4-(oxazol-2-yl)pyrimidine-5-carbonitrile as a yellow solid (400 mg, LC/MS: 88%). (LC/MS; m/z 267.3 $[M+H]^+$).

Step 4: A solution of 2-(4-fluorophenyl)-4-(oxazol-2-yl) pyrimidine-5-carbonitrile (400 mg, 1.50 mmol) in methanol (40 mL) was treated with aqueous $NH_3$ (25 drops) at room temperature. The reaction mixture was stirred in a steel bomb under hydrogen atmosphere (50 psi) at room temperature for 48 h. The reaction was monitored by TLC (mobile phase: 10% MeOH in DCM. Rf: 0.12. detection: UV). The reaction mixture was filtered through a celite pad, washed with methanol (100 mL) and the filtrate was concentrated under reduced pressure to afford (2-(4-fluorophenyl)-4-(oxazol-2-yl)pyrimidin-5-yl)methanamine as a brown gummy solid (160 mg, LC/MS: 68%). (LC/MS; m/z 271.2 $[M+H]^+$).

Step 5: A solution of (2-(4-fluorophenyl)-4-(oxazol-2-yl) pyrimidin-5-yl)methanamine (160 mg, 0.59 mmol) in 1,4-dioxane (3 mL) and water (1 mL) was treated with $NaHCO_3$ (149.18 mg, 1.77 mmol) and a solution of acryloyl chloride (48.222 mg, 0.533 mmol) in 1,4-dioxane (1 mL) under nitrogen atmosphere at 0° C. The reaction mixture was stirred at 0° C. for 30 min and progress was monitored by TLC (mobile phase: 10% MeOH in DCM. Rf: 0.40. detection: UV). The reaction mixture was diluted with water (50 mL) and extracted EtOAc (2×50 mL). The organic layer was washed with water (50 mL) and brine (30 mL), dried over $Na_2SO_4$ and concentrated under reduced pressure to afford a brown semi-solid (80 mg, LC/MS: 37%). The crude product was purified by preparative HPLC method H8. The pure fractions were concentrated under reduced pressure to afford N-((2-(4-fluorophenyl)-4-(oxazol-2-yl)pyrimidin-5-yl)methyl)acrylamide (Cpd. No. 331) as a white solid (11.4 mg, LC/MS: 99%). (LC/MS; m/z 325.3 $[M+H]^+$).

Example 128: Synthesis of N-((4-(1-(difluoromethyl)-1H-1,2,4-triazol-5-yl)-6-(4-fluorophenyl)pyridin-3-yl)methyl)acrylamide (Cpd. No. 334)

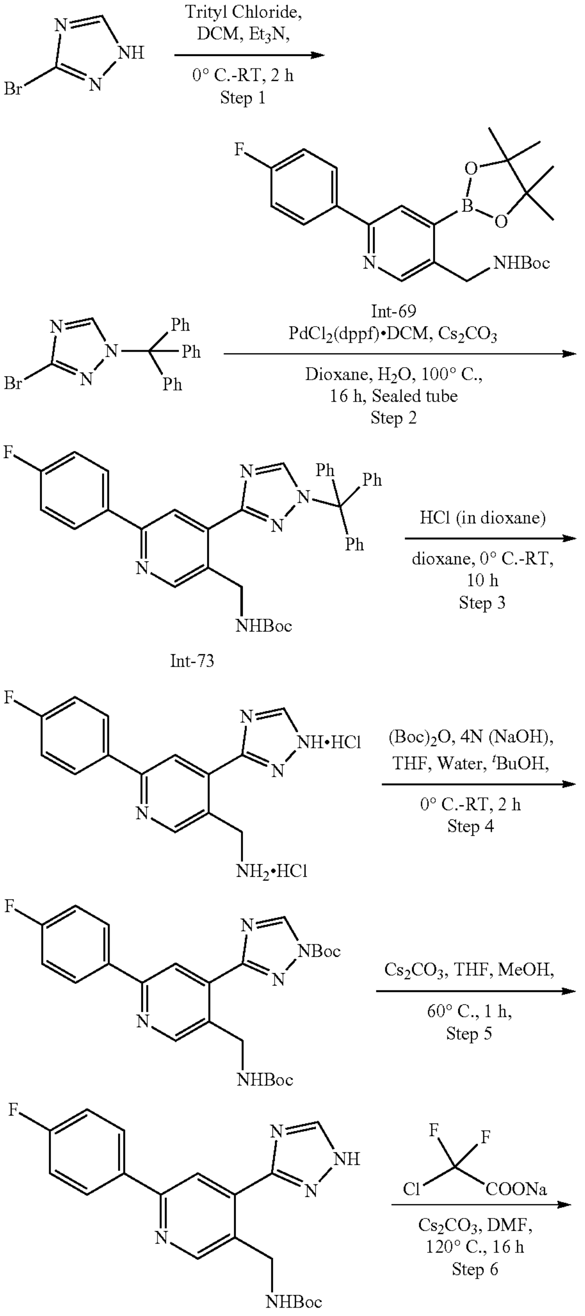

-continued

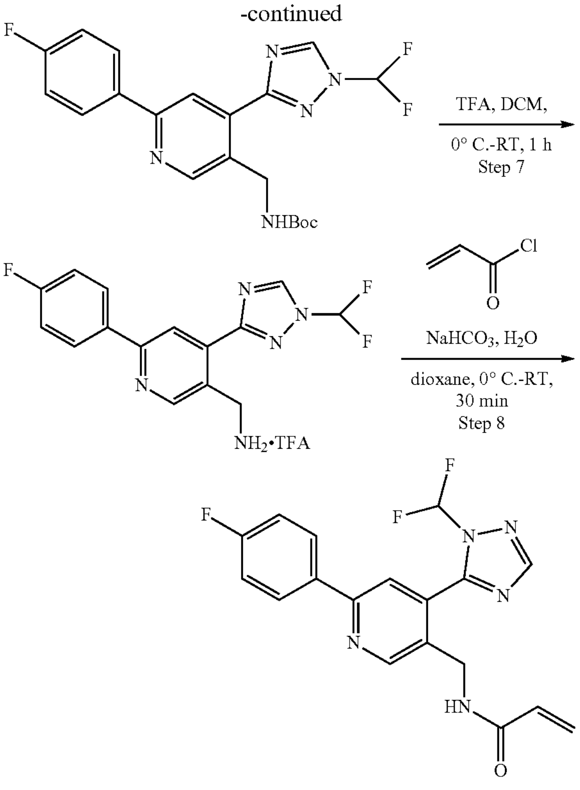

Cpd. No. 334

Step 1: A solution of 3-bromo-1H-1,2,4-triazole (3.5 g, 23.65 mmol) in DCM (35 mL) was treated with trityl chloride (6.6 g, 23.66 mmol) at room temperature. The reaction mixture was cooled to 0° C. and treated slowly with $Et_3N$ (2.84 g, 26.00 mmol). The reaction mixture was stirred at room temperature for 2 h and monitored by TLC (mobile phase, 5% EtOAc in pet ether, Rf: 0.22, detection: UV). The reaction mixture was diluted with water (90 mL) and extracted with DCM (180 mL). The aqueous phase was again extracted with DCM (100 mL) and the combined organic phase was dried over $Na_2SO_4$ and concentrated under reduced pressure to afford a white solid (10 g), which was triturated with 5% EtOAc in hexane (90 mL) and dried under reduced pressure to afford 3-bromo-1-trityl-1H-1,2,4-triazole as a white solid (8.5 g, $^1H$ NMR: 90%). $^1H$ NMR (400 MHz, $CDCl_3$) δ ppm: 7.85 (s, 1H), 7.30-7.40 (m, 9H), 7.10-7.20 (m, 6H).

Step 2: In a glass screw-cap pressure vessel, a solution of Int-69 (1.5 g, 3.50 mmol) in 1,4-dioxane (15 mL) and water (3 mL) was treated with 3-bromo-1-trityl-1H-1,2,4-triazole (2.05 g, 5.253 mmol) and $Cs_2CO_3$ (3.42 g, 10.51 mmol). The reaction mixture was degassed by bubbling argon for 10 min, then $[PdCl_2(dppf)]CH_2Cl_2$ (286 mg, 0.35 mmol) was added at room temperature. The reaction mixture was stirred at 100° C. for 16 h. The reaction progress was monitored by TLC (mobile phase: 30% EtOAc in hexane, Rf: 0.5, detection: UV). The reaction mixture was filtered through a pad of Celite and washed with EtOAc (25 mL). The filtrate was diluted with $H_2O$ (25 mL), separated into two layers and the aqueous layer was extracted with EtOAc (22 mL). The combined organic layer was dried over anhydrous $Na_2SO_4$ and concentrated under reduced pressure to afford a brown liquid (1.8 g, LC/MS: 32%), which was purified by reverse phase column chromatography with a gradient of 80-100%

ACN in water as an eluent. The pure fractions were evaporated under reduced pressure to afford tert-butyl (6-(4-fluorophenyl)-4-(1-trityl-1H-1,2,4-triazol-3-yl)pyridin-3-yl)methylcarbamate (Int-73) as a light brown solid (400 mg, LC/MS: 85%). (LC/MS; m/z 612.5 $[M+H]^+$).

Step 3: A solution of Int-73 (400 mg, 0.65 mmol) in 1,4-dioxane (10 mL) was treated with HCl (6.0 mL, 4.0 M HCl in dioxane) at 0° C. The temperature was raised to room temperature and stirred for 10 h, monitored by TLC (mobile phase: 10% MeOH in DCM, Rf: 0.05, detection: UV). The reaction mixture was evaporated under reduced pressure to afford a light brown semi-solid (460 mg, LC/MS: 51%). The crude product was triturated with n-pentane (2×20 mL) and dried under vacuum to afford (6-(4-fluorophenyl)-4-(1H-1,2,4-triazol-3-yl)pyridin-3-yl)methanamine dihydrochloride as a brown solid (270 mg, LC/MS: 96%). (LC/MS; m/z 270.3 $[M+H]^+$).

Step 4: A solution of (6-(4-fluorophenyl)-4-(1H-1,2,4-triazol-3-yl)pyridin-3-yl)methanamine dihydrochloride (270 mg, 1.00 mmol) in water (3 mL), THF (3 mL) and t-BuOH (0.5 mL) was treated with $(Boc)_2O$ (875 mg, 4.01 mmol) followed by 4N NaOH (2.0 mL) at 0° C. The reaction mixture was stirred at room temperature for 2 h, monitored by TLC (mobile phase: 30% EtOAc in hexane, Rf: 0.72, detection: UV). The reaction mixture was evaporated under reduced pressure, diluted with $H_2O$ (12 mL) and extracted with EtOAc (2×20 mL). The combined organic layer was dried over anhydrous $Na_2SO_4$ and concentrated under reduced pressure to afford tert-butyl 3-(5-((tert-butoxycarbonyl)amino)methyl)-2-(4-fluorophenyl)pyridin-4-yl)-1H-1,2,4-triazole-1-carboxylate as a brown solid (300 mg, LC/MS: 88%). (LC/MS; m/z 470.4 $[M+H]^+$).

Step 5: A solution of tert-butyl 3-(5-(((tert-butoxycarbonyl)amino)methyl)-2-(4-fluorophenyl)pyridin-4-yl)-1H-1,2,4-triazole-1-carboxylate (370 mg, 0.788 mmol) in THF (4 mL) and MeOH (7 mL) was treated with $Cs_2CO_3$ (384 mg, 1.18 mmol) at room temperature. The temperature was raised to 60° C. and stirred for 1 h, monitored by TLC, (mobile phase: 30% EtOAc in hexane, Rf: 0.1, detection: UV). The reaction mixture was concentrated under reduced pressure, diluted with $H_2O$ (20 mL) and extracted with EtOAc (2×25 mL). The combined organic phase was dried over $Na_2SO_4$ and concentrated under reduced pressure to obtain a brown solid (340 mg). The crude product was triturated with n-pentane (2×8 mL) and dried under vacuum to afford tert-butyl (6-(4-fluorophenyl)-4-(1H-1,2,4-triazol-3-yl)pyridin-3-yl)methylcarbamate as a brown solid (250 mg, LC/MS: 92%). (LC/MS; m/z 370.4 $[M+H]^+$).

Step 6: A stirred solution of tert-butyl (6-(4-fluorophenyl)-4-(1H-1,2,4-triazol-3-yl)pyridin-3-yl)methylcarbamate (300 mg, 0.81 mmol) in DMF (4.5 mL) was treated with $Cs_2CO_3$ (1.06 g, 3.25 mmol) and sodium 2-chloro-2,2-difluoroacetate (495 mg, 3.25 mmol) at room temperature. The reaction mixture was stirred at 120° C. for 16 h, monitored by TLC (mobile phase: 30% EtOAc in hexane, Rf: 0.42, detection: UV). The reaction mixture was diluted with ice cold water (15 mL) and extracted with cold EtOAc (2×15 mL). The combined organic layer was washed with cold water (10 mL), dried over anhydrous $Na_2SO_4$ and concentrated under reduced pressure to afford the crude product (310 mg, LC/MS: 63%). The crude product was purified by normal phase column chromatography (silica) with 25% EtOAc in pet ether as an eluent. Pure fractions were collected and concentrated under reduced pressure to afford tert-butyl (4-(1-(difluoromethyl)-1H-1,2,4-triazol-3-yl)-6-(4-fluorophenyl)pyridin-3-yl)methylcarbamate as a pale yellow solid (110 mg, LC/MS: 85%). (LC/MS; m/z 420.4 $[M+H]^+$).

Step 7: A stirred solution of tert-butyl (4-(1-(difluoromethyl)-1H-1,2,4-triazol-3-yl)-6-(4-fluorophenyl)pyridin-3-yl)methylcarbamate (110 mg, 0.262 mmol) in DCM (3 mL) was treated with TFA (0.7 mL) at 0° C. The reaction mixture was stirred at room temperature for 1 h, monitored by TLC (mobile phase: 10% MeOH in DCM, Rf: 0.1, detection: UV). The resulting reaction mixture was concentrated under reduced pressure and the residue was triturated with n-pentane (3×10 mL) and dried under reduced pressure to afford (4-(1-(difluoromethyl)-1H-1,2,4-triazol-3-yl)-6-(4-fluorophenyl)pyridin-3-yl)methanamine TFA salt as a light brown gum (150 mg, LC/MS: 96%). (LC/MS; m/z 320.2 $[M+H]^+$).

Step 8: A stirred solution of (4-(1-(difluoromethyl)-1H-1,2,4-triazol-3-yl)-6-(4-fluorophenyl)pyridin-3-yl)methanamine. TFA (150 mg, 0.36 mmol) in 1,4-Dioxane (3.0 mL) and water (0.5 mL) was treated with $NaHCO_3$ (121 mg, 1.44 mmol) and acryloyl chloride (39 mg, 0.43 mmol) at 0° C. The reaction mixture was stirred at room temperature for 20 min, and progress was monitored by TLC (mobile phase: 5% MeOH in DCM, Rf: 0.44, detection: UV). The reaction mixture treated again with $NaHCO_3$ (61 mg, 0.72 mmol) and acryloyl chloride (7 mg, 0.07 mmol) at 0° C. and stirred for 10 min at room temperature and progress was monitored by TLC (mobile phase: 5% MeOH in DCM, Rf: 0.44, detection: UV). The reaction mixture was evaporated and the residue was diluted with $H_2O$ (5 mL) and extracted with EtOAc (2×10 mL). The combined organic layer was dried over anhydrous $Na_2SO_4$ and concentrated under reduced pressure to afford the crude product (100 mg, LC/MS: 68%). The crude product was purified by preparative HPLC method H9. The pure fractions were concentrated under reduced pressure to afford N-((4-(1-(difluoromethyl)-1H-1,2,4-triazol-5-yl)-6-(4-fluorophenyl)pyridin-3-yl)methyl)acrylamide (Cpd. No. 334) as a white fluffy solid (6.0 mg). (LC/MS; m/z 374.2 $[M+H]^+$).

Example 129: Synthesis of N-((6-(4-fluorophenyl)-4-(1H-1,2,4-triazol-3-yl)pyridin-3-yl)methyl)acrylamide (Cpd. No. 335)

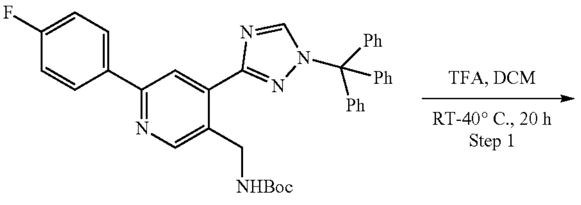

Int-73

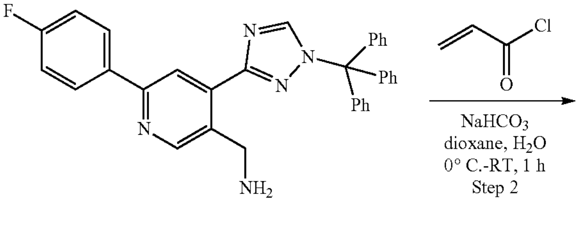

-continued

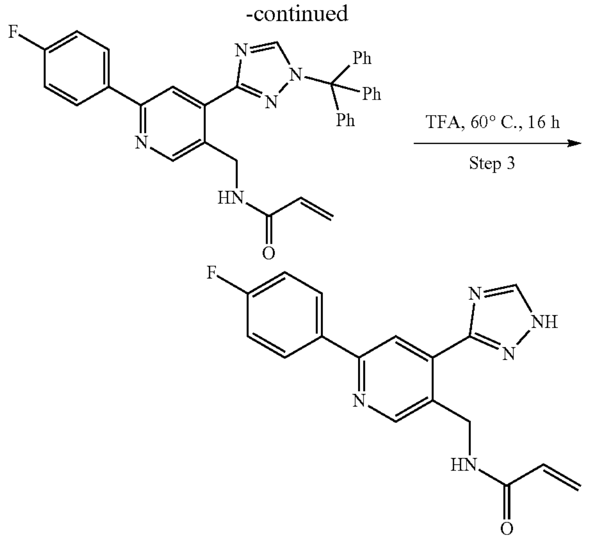

Cpd. No. 335

Step 1: A solution of Int-73 (550 mg, 0.899 mmol) in DCM (11 mL) was treated with TFA (1.8 ml) at room temperature and stirred at 40° C. for 20 h, monitored by TLC (mobile phase: 10% MeOH in DCM, detection: UV). The reaction mixture was concentrated under reduced pressure, diluted with water (25 mL) and extracted with DCM (2×20 mL). The combined organic layer was dried over $Na_2SO_4$ and concentrated under reduced pressure to afford (6-(4-fluorophenyl)-4-(1-trityl-1H-1,2,4-triazol-3-yl)pyridin-3-yl)methanamine as a pale yellow gum (430 mg, LC/MS: 98%). (LC/MS; m/z 512.0 $[M+H]^+$).

Step 2: A stirred solution of (6-(4-fluorophenyl)-4-(1-trityl-1H-1,2,4-triazol-3-yl)pyridin-3-yl)methanamine. TFA salt (410 mg, 0.8 mmol) in 1,4-dioxane (4 mL) and water (0.5 mL) was treated with $NaHCO_3$ (337 mg, 4.00 mmol) and acryloyl chloride (87 mL, 0.96 mmol) at 0° C. under nitrogen atmosphere. The reaction mixture was stirred at room temperature for 1 h, monitored by TLC (mobile phase: 5% MeOH in DCM, Rf: 0.76, detection: UV). The reaction mixture was concentrated under reduced pressure, diluted with water (10 mL) and extracted with EtOAc (2×15 mL). The combined organic layer was dried over $Na_2SO_4$ and concentrated under reduced pressure to give a gummy solid (450 mg, LC/MS: 76%), which was triturated with n-pentane (2×20 mL) and dried under reduced pressure to afford N-((6-(4-fluorophenyl)-4-(1-trityl-1H-1,2,4-triazol-3-yl)pyridin-3-yl)methyl)acrylamide as a brown solid (250 mg, LC/MS: 77%). (LC/MS; m/z 566.4 $[M+H]^+$).

Step 3: A stirred solution of N-((6-(4-fluorophenyl)-4-(1-trityl-1H-1,2,4-triazol-3-yl)pyridin-3-yl)methyl)acrylamide (250 mg, 0.43 mmol) in TFA (4 mL) was heated to 60° C. for 16 h, monitored by TLC (mobile phase: 5% MeOH/DCM, Rf: 0.12, detection: UV active). The reaction mixture was concentrated under reduced pressure, diluted with EtOAc (10 mL) and neutralized with saturated $NaHCO_3$ (1 mL). The volatiles were evaporated, 10% MeOH in DCM (10 mL) was added and the mixture was filtered and washed with 10% MeOH in DCM (10 mL). The filtrate was concentrated under reduced pressure to afford a pale yellow sticky solid (270 mg, LC/MS: 15%). The crude product was purified by preparative HPLC method H13. Pure fractions were concentrated under reduced pressure to afford N-((6-(4-fluorophenyl)-4-(1H-1,2,4-triazol-3-yl)pyridin-3-yl)methyl)acrylamide (Cpd. No. 335) as a fluffy white solid (5.5 mg, LC/MS: 99%). (LC/MS; m/z 324.3 $[M+H]^+$).

Example 130: Synthesis of N-((5-(4-fluorophenyl)-3-(1-methyl-1H-1,2,3-triazol-4-yl)pyridin-2-yl)methyl)acrylamide (Cpd. No. 337)

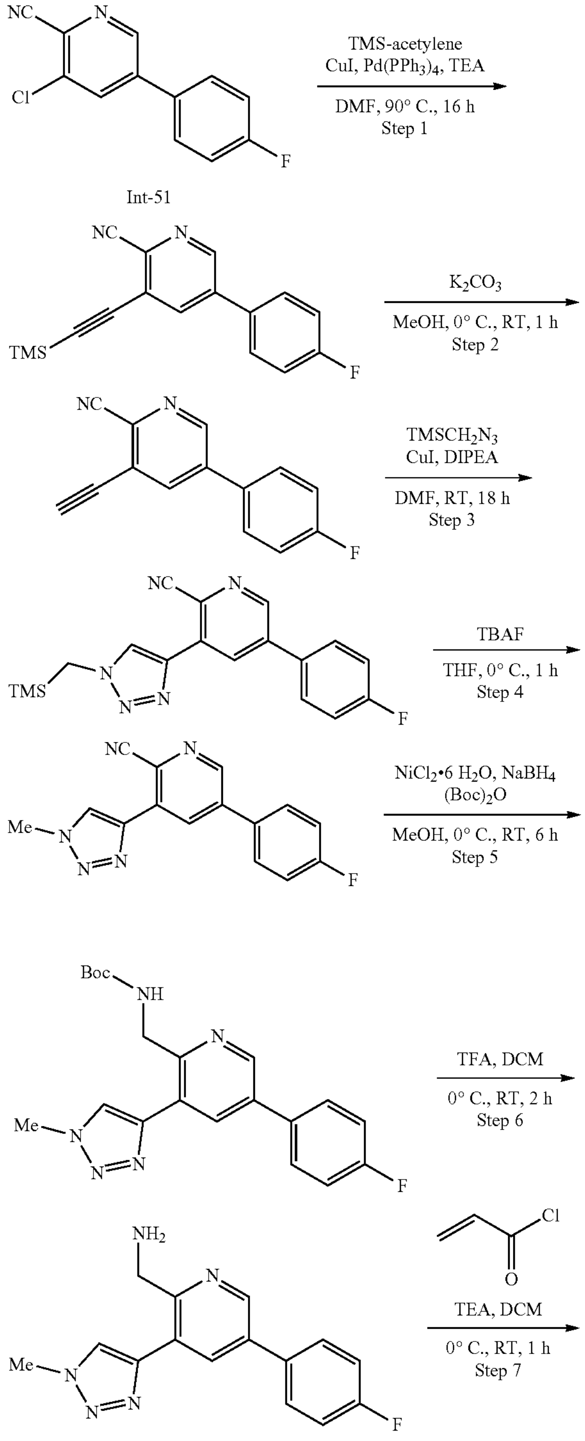

-continued

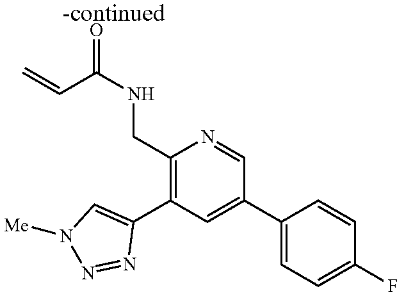

Cpd. No. 337

Step 1: A solution of Int-51 (5 g, 21.49 mmol) in DMF (50 mL), was treated with $Et_3N$ (12 mL, 85.96 mmol), TMS-acetylene (30.6 mL, 214.92 mmol) and CuI (408 mg, 2.14 mmol) and was degassed with argon for 20 min followed by the addition of $Pd(PPh_3)_4$ (869 mg, 0.75 mmol) at room temperature. The reaction mixture was stirred at 90° C. for 16 h. Progress of the reaction monitored by TLC (mobile phase: 20% EtOAc in Pet ether. Rf: 0.45. detection: UV). The reaction mixture was filtered through a pad of Celite and the pad was washed with EtOAc (200 mL). The filtrate was washed with brine (2×100 mL), dried over anhydrous $Na_2SO_4$ and concentrated under reduced pressure to afford a black gum (7 g, LC/MS: 8%). The crude product was purified by gravity column chromatography using silica gel and 5% EtOAc in pet ether as an eluent to afford as a 5-(4-fluorophenyl)-3-((trimethylsilyl)ethynyl)picolinonitrile as an off-white solid (800 mg, LC/MS: 72%). (LC/MS; m/z 295.5 $[M+H]^+$).

Step 2: A solution of 5-(4-fluorophenyl)-3-((trimethylsilyl)ethynyl)picolinonitrile (800 mg, 2.72 mmol) in MeOH (16 mL) was treated with $K_2CO_3$ (375 mg, 2.72 mmol) at 0° C. The reaction mixture was stirred at room temperature for 1 h, progress of the reaction was monitored by TLC (mobile phase: 20% EtOAc in Pet ether. Rf: 0.35. detection: UV). The reaction mixture was diluted with water (100 mL) and extracted with EtOAc (2×150 mL). The combined organic layer was washed with brine solution (2×50 mL), dried over $Na_2SO_4$ and concentrated under reduced pressure and the residue was triturated with diethyl ether (15 mL) and dried under high vacuum to afford 3-ethynyl-5-(4-fluorophenyl) picolinonitrile as an off-white solid (400 mg, LC/MS: 95%). (LC/MS; m/z 223.2 $[M+H]^+$).

Step 3: A solution of 3-ethynyl-5-(4-fluorophenyl)picolinonitrile (400 mg, 1.80 mmol) in DMF (8 mL) was treated with (azidomethyl)trimethylsilane (298 mg, 2.30 mmol), CuI (21 mg, 0.10 mmol), and DIPEA (28 mg, 0.21 mmol) at room temperature and stirred for 18 h, progress of the reaction was monitored by TLC (mobile phase: 20% EtOAc in Pet ether. Rf: 0.45. detection: UV). The reaction mixture was filtered through a pad of Celite and the pad was washed with EtOAc (50 mL). The filtrate was washed with brine (2×20 mL), dried over $Na_2SO_4$ and concentrated under reduced pressure and the residue was triturated with diethyl ether (10 mL) and dried under high vacuum to afford 5-(4-fluorophenyl)-3-(1-((trimethylsilyl)methyl)-1H-1,2,3-triazol-4-yl)picolinonitrile as a yellow solid (250 mg, LC/MS: 70%). (LC/MS; m/z 352.2 $[M+H]^+$).

Step 4: A solution of 5-(4-fluorophenyl)-3-(1-((trimethylsilyl)methyl)-1H-1,2,3-triazol-4-yl)picolinonitrile (250 mg, 0.71 mmol) in THF (2.5 mL) was treated with TBAF (1 M in THF) (0.85 mL, 0.85 mmol) at 0° C. The reaction mixture was stirred at room temperature for 1 h, progress of the reaction was monitored by TLC (mobile phase: 20% EtOAc in Pet ether. Rf: 0.30. detection: UV). The reaction mixture was diluted with EtOAc (50 mL), washed with brine (2×30 mL), dried over $Na_2SO_4$ and concentrated under reduced pressure to afford 5-(4-fluorophenyl)-3-(1-methyl-1H-1,2,3-triazol-4-yl)picolinonitrile as a yellow solid (180 mg, LC/MS: 75%). (LC/MS; m/z 280.2 $[M+H]^+$).

Step 5: A solution of 5-(4-fluorophenyl)-3-(1-methyl-1H-1,2,3-triazol-4-yl)picolinonitrile (250 mg, 0.89 mmol) in MeOH (5 mL) was treated with $NiCl_2 \cdot 6H_2O$ (127 mg, 0.53 mmol) and $(Boc)_2O$ (0.24 mL, 1.07 mmol) at 0° C. $NaBH_4$ (232 mg, 6.26 mmol) was added portion wise at 0° C. and the mixture was stirred at room temperature for 6 h. Progress of the reaction was monitored by TLC (mobile phase: 20% EtOAc in Pet ether. Rf: 0.46. detection: UV). The reaction mixture was filtered through a pad of Celite and washed with EtOAc (70 mL). The filtrate was washed with brine solution (2×50 mL), dried over $Na_2SO_4$ and concentrated under reduced pressure to afford a brown gum (290 mg, LC/MS: 62%), which was purified by gravity column chromatography using silica gel and an eluent of 5% EtOAc in pet ether to afford tert-butyl ((5-(4-fluorophenyl)-3-(1-methyl-1H-1,2,3-triazol-4-yl)pyridin-2-yl)methyl)carbamate as an off-white solid (160 mg, LC/MS: 90%). (LC/MS; m/z 384.6 $[M+H]^+$).

Step 6: A solution of tert-butyl ((5-(4-fluorophenyl)-3-(1-methyl-1H-1,2,3-triazol-4-yl)pyridin-2-yl)methyl)carbamate (160 mg, 0.41 mmol) in DCM (3 mL) was treated with TFA (0.3 mL, 4.17 mmol) at 0° C. The reaction mixture was stirred at room temperature for 2 h and progress of the reaction was monitored by TLC (mobile phase: 10% MeOH in DCM. Rf: 0.2. detection: UV). The reaction mixture was concentrated under reduced pressure to afford (5-(4-fluorophenyl)-3-(1-methyl-1H-1,2,3-triazol-4-yl)pyridin-2-yl) methanamine (TFA salt) as a yellow gum (130 mg, LC/MS: 92%). (LC/MS; m/z 284.2 $[M+H]^+$).

Step 7: A solution of (5-(4-fluorophenyl)-3-(1-methyl-1H-1,2,3-triazol-4-yl)pyridin-2-yl)methanamine TFA salt (125 mg, 0.31 mmol) in DCM (8 mL) was treated with TEA (0.22 ml, 1.57 mmol) and a solution of acryloyl chloride (29 mg, 0.31 mmol) in DCM (2 mL) at 0° C. The reaction mixture was stirred at room temperature for 1 h and progress of the reaction was monitored by TLC (mobile phase: 10% MeOH in DCM. Rf: 0.5. detection: UV). The reaction mixture was diluted with DCM (50 mL) and washed with brine (2×50 mL), dried over $Na_2SO_4$ and concentrated under reduced pressure to afford a yellow gum (147 mg, LC/MS: 55%). The crude product was purified by preparative HPLC method H2 and the collected fractions were concentrated under reduced pressure to afford N-((5-(4-fluorophenyl)-3-(1-methyl-1H-1,2,3-triazol-4-yl)pyridin-2-yl)methyl)acrylamide (Cpd. No. 337) as a white solid (45.3 mg, LC/MS: 99.6%). (LC/MS; m/z 338.3 $[M+H]^+$).

The following compounds were prepared in a manner similar (use of appropriate reagents and purification methods known to the person skilled in the art) to Cpd. No. 337: Cpd. No. 338 (using Int-44 in step 1).

Example 131: Synthesis of N-((6-(4-fluorophenyl)-4-(pyrrolidin-1-yl)pyridin-3-yl)methyl)acrylamide (Cpd. No. 350)

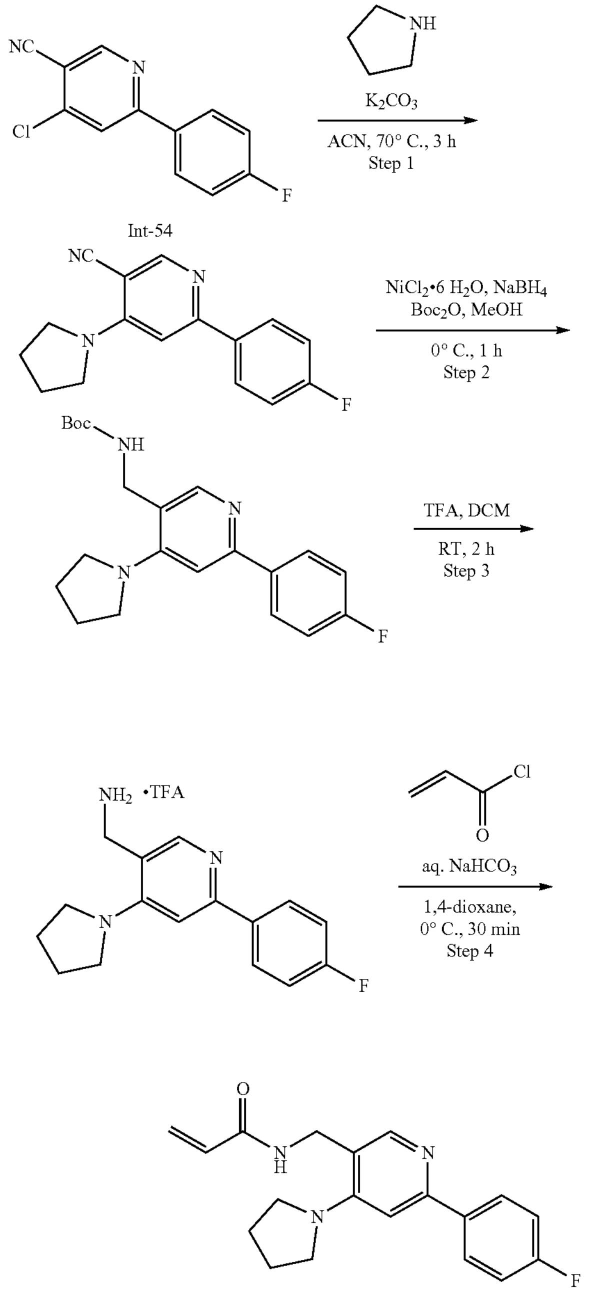

Cpd. No. 350

Step 1: A solution of Int-54 (1.5 g, 6.45 mmol) in ACN (20 mL) was treated with $K_2CO_3$ (2.22 g, 16.12 mmol) and pyrrolidine (3.0 mL, 36.11 mmol). The reaction mixture was stirred at 70° C. for 3 h. Progress of the reaction was monitored by TLC (mobile phase: 30% EtOAc in pet ether. Rf: 0.15. detection: UV). The reaction mixture was diluted with water (50 mL) and extracted with EtOAc (3×50 mL). The combined organic layer was washed with brine (50 mL), dried over anhydrous $Na_2SO_4$ and concentrated under reduced pressure to afford a brown gum (1.9 g, LC/MS: 67%). The crude product was purified by normal phase column chromatography on a 40 g column (silica) using an eluent of 80% EtOAc in Pet ether to afford 6-(4-fluorophenyl)-4-(pyrrolidin-1-yl)nicotinonitrile as a yellow solid (1.2 g, LC/MS: 97%). (LC/MS; m/z 268.3 $[M+H]^+$).

Step 2: A solution of 6-(4-fluorophenyl)-4-(pyrrolidin-1-yl) nicotinonitrile (1.1 g, 4.11 mmol) in MeOH (20 mL) was treated with nickel(II)chloride hexahydrate (489 mg, 2.06 mmol) and $(Boc)_2O$ (1.9 mL, 8.23 mmol) and then $NaBH_4$ (3.9 g, 102.88 mmol) was added portion wise at 0° C. The reaction mixture was stirred at 0° C. for 1 h. Progress of the reaction was monitored by TLC (mobile phase: 30% EtOAc in pet ether. Rf: 0.39. detection: UV). The reaction mixture was poured into ice water (100 mL) and extracted with ethyl acetate (3×50 mL). The combined organic layer was washed with brine (25 mL), dried over anhydrous $Na_2SO_4$ and concentrated under reduced pressure to afford a pale-yellow gum (1.2 g, LC/MS: 70%). The crude product was purified by normal phase column chromatography using a 40 g column (silica) and an eluent of 50% EtOAc in Pet ether to afford tert-butyl ((6-(4-fluorophenyl)-4-(pyrrolidin-1-yl) pyridin-3-yl)methyl)carbamate as an off-white solid (800 mg, LC/MS: 98%). (LC/MS; m/z 372.4 $[M+H]^+$).

Step 3: A solution of tert-butyl ((6-(4-fluorophenyl)-4-(pyrrolidin-1-yl)pyridin-3-yl)methyl)carbamate (600 mg, 1.62 mmol) in DCM (5 mL) was treated with TFA (3 mL) at 0° C. The reaction was stirred at room temperature for 2 h. Progress of the reaction was monitored by TLC (mobile phase: 70% EtOAc in pet ether. Rf: 0.1. detection: UV). The reaction mixture was concentrated under reduced pressure to afford crude product (500 mg, LC/MS: 88%). The crude product was washed with diethyl ether (3 mL) and concentrated under reduced pressure to afford (6-(4-fluorophenyl)-4-(pyrrolidin-1-yl)pyridin-3-yl)methanamine TFA salt as an off-white solid (400 mg, LC/MS: 93%). (LC/MS; m/z 272.4 $[M+H]^+$).

Step 4: A solution of (6-(4-fluorophenyl)-4-(pyrrolidin-1-yl)pyridin-3-yl)methanamine TFA salt (200 mg, 0.54 mmol) in 1,4-dioxane (5.0 mL) and water (0.5 mL) was treated with $NaHCO_3$ (228 mg, 2.716 mmol) and acryloyl chloride (63.9 mg, 0.70 mmol) at 0° C. The reaction was stirred at 0° C. for 30 min. Progress of the reaction was monitored by TLC (mobile phase: 30% EtOAc. Rf: 0.39. detection: UV). The reaction mixture was diluted with water (50 mL) and extracted with EtOAc (3×25 mL). The combined organic layer was washed with brine (50 mL), dried over $Na_2SO_4$ and concentrated under reduced pressure to afford a pale-yellow solid (110 mg, LC/MS: 90%). The crude product was purified by preparative HPLC method H2 and the collected fractions were concentrated under reduced pressure to afford N-((6-(4-fluorophenyl)-4-(pyrrolidin-1-yl)pyridin-3-yl) methyl) acrylamide (Cpd. No. 350) as a white solid (27.3 mg; LC/MS: 95%). (LC/MS; m/z 326.3 $[M+H]^+$).

The following compounds were prepared in a manner similar (use of appropriate reagents and purification methods known to the person skilled in the art) to Cpd. No. 350: Cpd. No. 342 (using propionyl chloride in step 4), Cpd. No. 343 (using Int-44 in step 1), Cpd. No. 344 (using Int-44 in step 1 and MsCl in step 4), Cpd. No. 351 (using MsCl in step 4), Cpd. No. 352 (using Int-44 in step 1 and propionyl chloride in step 4).

Example 132: Synthesis of 6-((3-(5-(acrylamidomethyl)-2-(4-fluorophenyl)pyridin-4-yl)-1H-pyrazol-1-yl)methyl)picolinic acid (Cpd. No. 353)

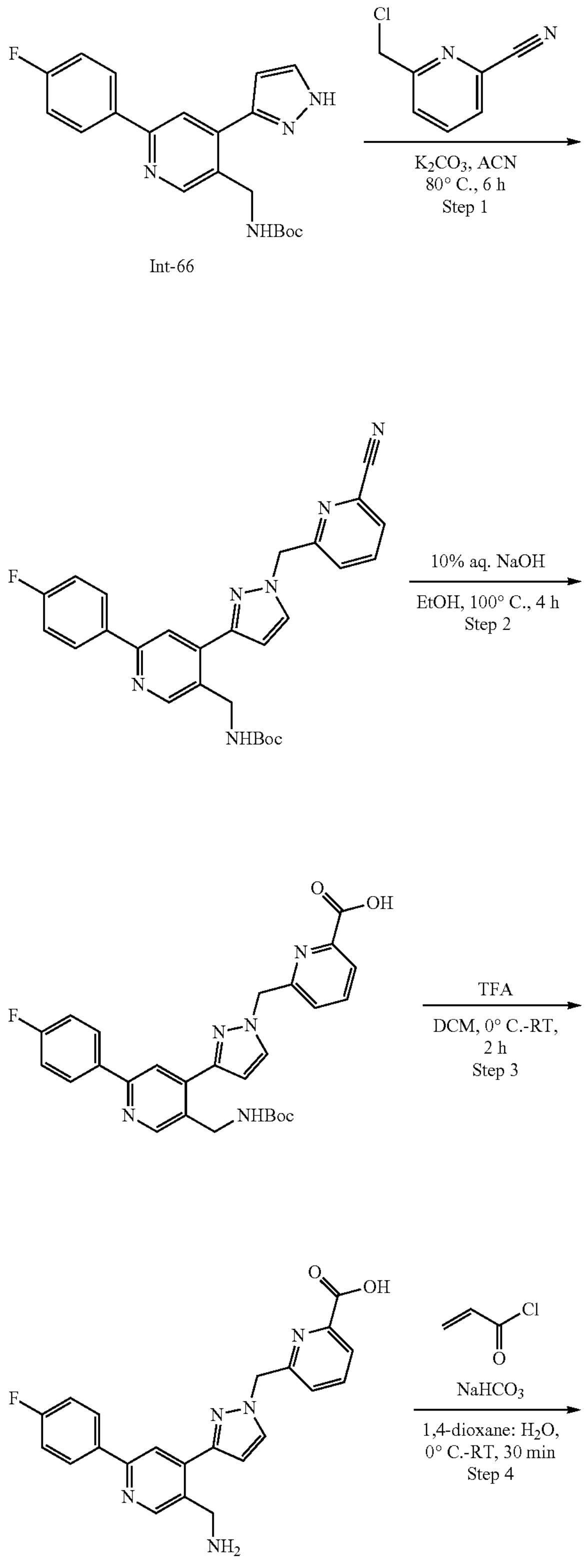

Int-66

-continued

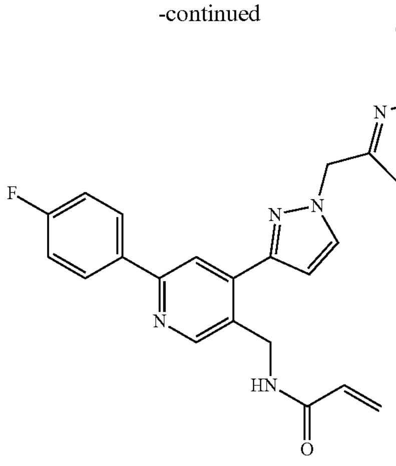

Cpd. No. 353

Step 1: A solution of Int-66 (2 g, 5.42 mmol) in ACN (20 mL) was treated with $K_2CO_3$ (2.24 g, 16.28 mmol) and 6-(chloromethyl)picolinonitrile (0.99 g, 6.51 mmol) at room temperature. The reaction mixture was stirred at 80° C. for 6 h and progress of the reaction was monitored by TLC (mobile phase: 40% EtOAc in pet ether. Rf: 0.3. detection: UV). The reaction mixture was concentrated under reduced pressure and the residue was diluted with water (50 mL) and extracted with EtOAc (100 mL). The organic layer was washed with brine (50 mL), dried over $Na_2SO_4$ and concentrated under reduced pressure to afford a pale yellow gum (2.3 g, LC/MS: 60%). The crude product was purified by normal phase column chromatography (24 g silica gel column) using 30% EtOAc in pet ether as an eluent to afford tert-butyl ((4-(1-((6-cyanopyridin-2-yl)methyl)-1H-pyrazol-3-yl)-6-(4-fluorophenyl)pyridin-3-yl)methyl)carbamate as an off white solid (1.6 g, LC/MS: 96%). (LC/MS; m/z 485.4 $[M+H]^+$).

Step 2: A solution of tert-butyl ((4-(1-((6-cyanopyridin-2-yl)methyl)-1H-pyrazol-3-yl)-6-(4-fluorophenyl)pyridin-3-yl)methyl)carbamate (500 mg, 1.03 mmol) in EtOH (20 mL) was treated with 10% aq. NaOH (2 mL, 5.16 mmol) at room temperature. The reaction mixture was stirred at 100° C. for 4 h. Progress of the reaction was monitored by TLC (mobile phase: 10% MeOH in DCM. Rf: 0.2. detection: UV). The reaction mixture was concentrated under reduced pressure and the residue was diluted with water (30 mL) and acidified with 1 N HCl and extracted with EtOAc (70 mL). The organic layer was washed with brine (20 mL), dried over $Na_2SO_4$ and concentrated under reduced pressure to afford 6-((3-(5-(((tert-butoxycarbonyl)amino)methyl)-2-(4-fluorophenyl)pyridin-4-yl)-1H-pyrazol-1-yl)methyl)picolinic acid as pale yellow solid (320 mg; LC/MS: 83%). (LC/MS; m/z 504.7 $[M+H]^+$).

Step 3: A solution of 6-((3-(5-(((tert-butoxycarbonyl)amino)methyl)-2-(4-fluorophenyl)pyridin-4-yl)-1H-pyrazol-1-yl)methyl)picolinic acid (300 mg, 0.59 mmol) in DCM (3 mL) was treated with TFA (0.4 mL, 5.95 mmol) at 0° C. The reaction mixture was stirred at room temperature for 2 h and progress of the reaction was monitored by TLC (mobile phase: 20% MeOH in DCM. Rf: 0.2. detection: UV). The reaction mixture was concentrated under reduced pressure and the residue was diluted with EtOAC (40 mL) and washed with saturated $NaHCO_3$ (30 mL) and brine (2×30 mL). The organic layer was dried over $Na_2SO_4$ and concentrated under reduced pressure to afford 6-((3-(5-

(aminomethyl)-2-(4-fluorophenyl)pyridin-4-yl)-1H-pyrazol-1-yl)methyl)picolinic acid as a brown gum (270 mg, LC/MS: 93%). (LC/MS; m/z 404.4 [M+H]$^+$).

Step 4: A solution of 6-((3-(5-(aminomethyl)-2-(4-fluorophenyl)pyridin-4-yl)-1H-pyrazol-1-yl)methyl)picolinic acid 2 (270 mg, 0.66 mmol) in 1,4-dioxane (5 mL) and water (0.5 mL) was treated with $NaHCO_3$ (224 mg, 2.67 mmol) and acryloyl chloride (60 mg, 0.66 mmol) at 0° C. The reaction mixture was stirred at room temperature for 30 minutes and progress of the reaction was monitored by TLC (mobile phase: 10% MeOH in DCM. Rf: 0.3. detection: UV). The reaction mixture was concentrated under reduced pressure and the residue was diluted with water (30 mL) and extracted with ethyl acetate (40 mL). The organic layer was washed with brine (30 mL), dried over $Na_2SO_4$ and concentrated under reduced pressure to afford a pale yellow gum (245 mg, LC/MS: 81%). The crude product was purified by preparative HPLC method H17 and the collected fractions were concentrated under reduced pressure to afford 6-((3-(5-(acrylamidomethyl)-2-(4-fluorophenyl)pyridin-4-yl)-1H-pyrazol-1-yl)methyl)picolinic acid (Cpd. No. 353) as a white solid (45 mg, LC/MS: 99%). (LC/MS; m/z 458.4 [M+H]$^+$).

Example 133: Synthesis of N-((2-(4-fluorophenyl)-4-(1-methyl-1H-1,2,3-triazol-4-yl)pyrimidin-5-yl)methyl)acrylamide (Cpd. No. 355)

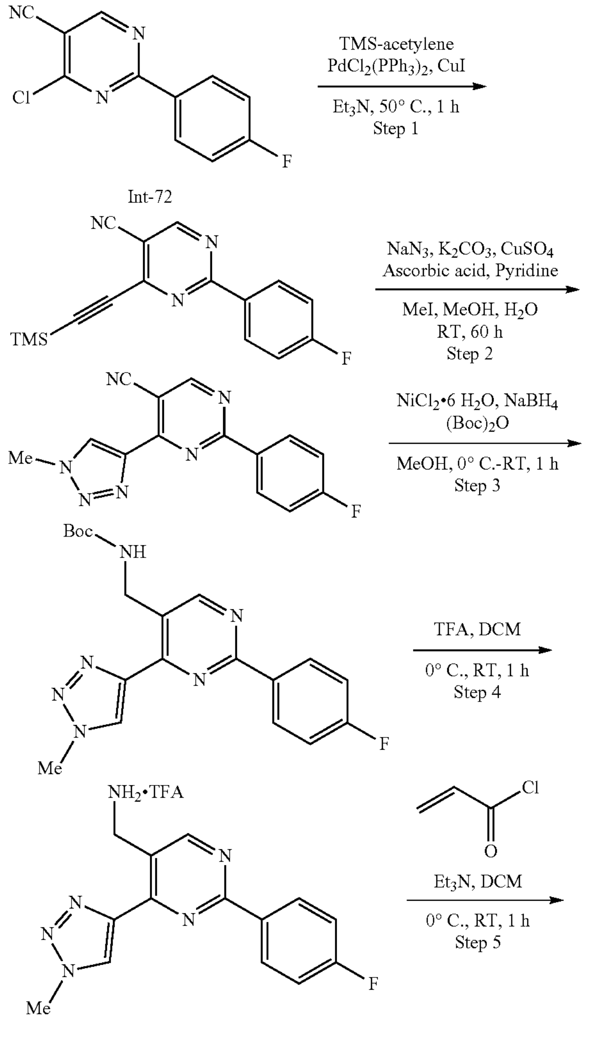

-continued

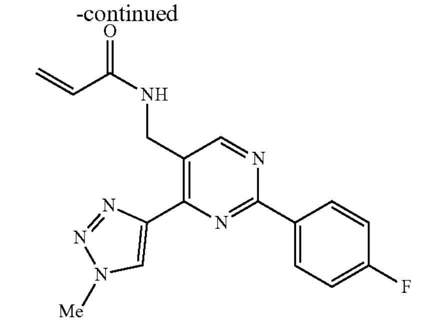

Cpd. No. 355

Step 1: A solution of Int-72 (750 mg, 3.21 mmol) in TEA (9 mL) was treated with TMS-acetylene (0.5 mL, 3.53 mmol) and CuI (18 mg, 0.09 mmol) at room temperature. The reaction mixture was degassed with argon for 10 min followed by addition of $Pd(PPh_3)_2Cl_2$ (45 mg, 0.064 mmol) at room temperature. The reaction mixture was stirred at 50° C. for 1 h and progress of the reaction was monitored by TLC (mobile phase: 10% EtOAc in Pet ether. Rf: 0.45. detection: UV). The reaction mixture was filtered through a pad of celite and washed with DCM (50 mL). The filtrate was washed with brine (2×25 mL) and concentrated under reduced pressure to afford 2-(4-fluorophenyl)-4-((trimethylsilyl)ethynyl)pyrimidine-5-carbonitrile as a brown solid (625 mg, LC/MS: 76%). (LC/MS; m/z 296.5 [M+H]$^+$).

Step 2: Sodium azide (198 mg, 3.04 mmol), ascorbic acid (143 mg, 0.81 mmol), potassium carbonate (505 mg, 3.65 mmol), and copper(II) sulphate (65 mg, 0.40 mmol) were combined and then water (16 mL) and methanol (16 mL) were added. The mixture was stirred at room temperature for 10 min, then 2-(4-fluorophenyl)-4-((trimethylsilyl)ethynyl)pyrimidine-5-carbonitrile (600 mg, 2.03 mmol), MeI (0.37 mL, 6.09 mmol) and pyridine (0.81 mL, 10.15 mmol) were added, and the mixture was stirred at room temperature for 60 h. The reaction progress was monitored TLC (mobile phase: 30% EtOAc in pet ether. Rf: 0.15. detection: UV). The reaction mixture was evaporated to approximately half volume and extracted with DCM (150 mL). The organic layer was washed with brine (2×50 mL) and dried over $Na_2SO_4$ and concentrated under reduced pressure to afford a red gum (650 mg, LC/MS: 13%). The crude product was purified by normal phase column chromatography using silica gel (20 g) and 25% EtOAc in Pet ether as an eluent to afford 2-(4-fluorophenyl)-4-(1-methyl-1H-1,2,3-triazol-4-yl)pyrimidine-5-carbonitrile as a brown solid (38 mg; LC/MS: 75%). (LC/MS; m/z 281.3 [M+H]$^+$).

Step 3: A solution of 2-(4-fluorophenyl)-4-(1-methyl-1H-1,2,3-triazol-4-yl)pyrimidine-5-carbonitrile (37 mg, 0.13 mmol) in methanol (2 mL) was treated with $NiCl_2 \cdot 6H_2O$ (19 mg, 0.079 mmol) and $(Boc)_2O$ (35 mg, 0.15 mmol) at 0° C. $NaBH_4$ (34 mg, 0.92 mmol) was added portion wise at 0° C. and then the reaction mixture was stirred at room temperature for 1 h. Progress of the reaction was monitored by TLC (mobile phase: 30% EtOAc in pet ether. Rf: 0.23. detection: UV). The reaction mixture was filtered through a Celite pad and washed with ethyl acetate (50 mL). The filtrate was washed with brine (2×10 mL), dried over $Na_2SO_4$ and concentrated under reduced pressure to afford a brown gum (40 mg, LC/MS: 52%). The crude product was purified by gravity column chromatography using silica gel (3 g) and 20% ethyl acetate in pet ether as an eluent to afford tert-butyl ((2-(4-fluorophenyl)-4-(1-methyl-1H-1,2,3-triazol-4-yl)pyrimidin-5-yl)methyl)carbamate as a yellow gum (26 mg, LC/MS: 74%). (LC/MS; m/z 385.4 $[M+H]^+$).

Step 4: A solution of tert-butyl ((2-(4-fluorophenyl)-4-(1-methyl-1H-1,2,3-triazol-4-yl)pyrimidin-5-yl)methyl)carbamate (25 mg, 0.065 mmol) in DCM (0.5 mL) was treated with TFA (0.05 mL, 0.65 mmol) at 0° C. The reaction mixture was stirred at room temperature for 1 h and progress of the reaction was monitored by TLC (mobile phase: 10% MeOH in DCM. Rf: 0.2. detection: UV). The reaction mixture was concentrated under reduced pressure to afford (2-(4-fluorophenyl)-4-(1-methyl-1H-1,2,3-triazol-4-yl)pyrimidin-5-yl)methanamine (TFA salt) as a yellow gum (21 mg, LC/MS: 72%). (LC/MS; m/z 285.3 $[M+H]^+$).

Step 7: A solution of (2-(4-fluorophenyl)-4-(1-methyl-1H-1,2,3-triazol-4-yl)pyrimidin-5-yl)methanamine TFA salt (20 mg, 0.05 mmol) in DCM (4 mL) was treated with TEA (21 mg, 0.20 mmol) and a solution of acryloyl chloride (5 mg, 0.05 mmol) in DCM (1 mL) at 0° C. The reaction mixture was stirred at room temperature for 1 h and progress of the reaction was monitored by TLC (mobile phase: 10% MeOH in DCM. Rf: 0.45. detection: UV). The reaction mixture was diluted with DCM (50 mL) and washed with brine (2×20 mL), dried over $Na_2SO_4$ and concentrated under reduced pressure to afford a yellow solid (21 mg, LC/MS: 53%). The crude product was purified by preparative HPLC method H8 and the collected fractions were concentrated under reduced pressure to afford N-((2-(4-fluorophenyl)-4-(1-methyl-1H-1,2,3-triazol-4-yl)pyrimidin-5-yl)methyl) acrylamide (Cpd. No. 355) as a white solid (6.8 mg, LC/MS: 99.6%). (LC/MS; m/z 339.4 $[M+H]^+$).

Example 134: Synthesis of N-((4-(1-(cyanomethyl)-1H-imidazol-2-yl)-6-(4-fluorophenyl)pyridin-3-yl)methyl)acrylamide (Cpd. No. 356)

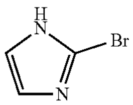

1

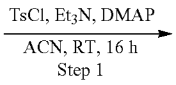

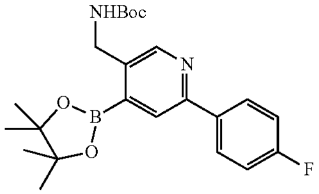

Int-69

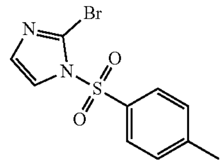

2

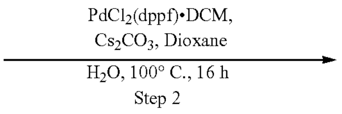

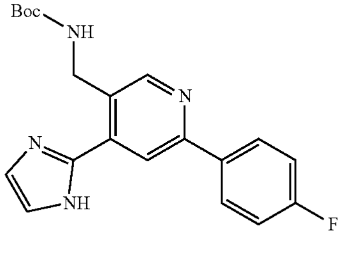

Int-74

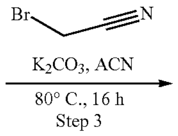

-continued

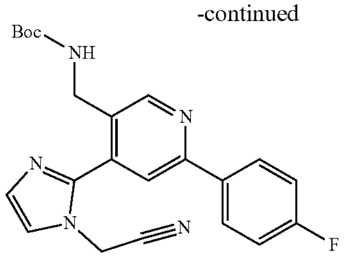

4

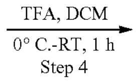

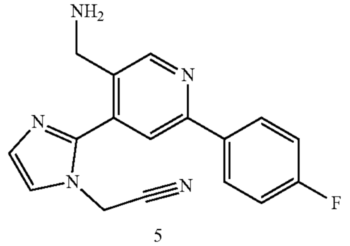

5

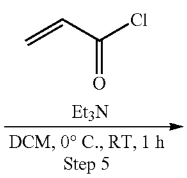

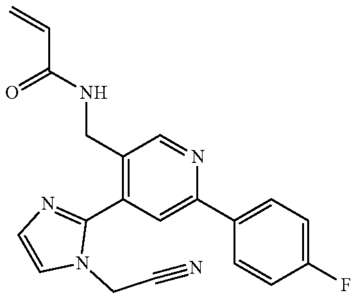

Cpd. No. 356

Step 1: A solution of 2-bromo-1H-imidazole (8 g, 54.43 mmol) in ACN (100 mL) was treated with $Et_3N$ (9 mL, 65.31 mmol), DMAP (664 mg, 5.44 mmol) and p-toluenesolfonyl chloride (11.41 g, 0.21 mmol) at room temperature. The reaction mixture was stirred at room temperature for 16 h and progress of the reaction was monitored by TLC (mobile phase: 30% EtOAc in pet ether. Rf: 0.3. detection: UV). The reaction mixture was concentrated under reduced pressure and the residue was diluted with water (100 mL) and extracted with EtOAc (120 mL). The organic layer was washed with brine (80 mL), dried over $Na_2SO_4$and concentrated under reduced pressure to afford a pale-yellow gum (17.2 g, LC/MS: 43%). The crude product was purified by normal phase column chromatography using a 60 g column (silica) and 20% EtOAc in pet ether as an eluent to afford 2-bromo-1-tosyl-1H-imidazole as an off white solid (10 g, LC/MS: 97%). (LC/MS; m/z 301.1 $[M+H]^+$).

Step 2: A solution of 2-bromo-1-tosyl-1H-imidazole (1 g, 3.32 mmol), Int-69 (2.13 g, 4.98 mmol), $Cs_2CO_3$ (3.22 g, 9.96 mmol) in 1,4-dioxane (30 mL) and $H_2O$ (3 mL) was degassed for 10 min with nitrogen and then treated with $PdCl_2$(dppf)·DCM (270 mg, 0.33 mmol) at room temperature. The reaction mixture was stirred at 100° C. for 16 h and progress of the reaction was monitored by TLC (mobile phase: 50% EtOAc in pet ether. Rf: 0.2. detection: UV). The reaction mixture was filtered through a pad of Celite and washed with EtOAc (50 mL). The filtrate was washed with brine (50 mL) and dried over anhydrous $Na_2SO_4$ and concentrated under reduced pressure to afford a brown gum (1.8 g, LC/MS: 33%). The crude product was purified by normal phase column chromatography using 24 g column (silica) and 40% EtOAc in Pet ether as an eluent to afford tert-butyl ((6-(4-fluorophenyl)-4-(1H-imidazol-2-yl)pyridin-3-yl)methyl)carbamate (Int-74) as a pale yellow gum (400 mg, LC/MS: 91%). (LC/MS; m/z 369.3 $[M+H]^+$).

Step 3: A solution of tert-butyl ((6-(4-fluorophenyl)-4-(1H-imidazol-2-yl)pyridin-3-yl)methyl)carbamate (350 mg, 0.95 mmol) in MeCN (5 mL) was treated with $K_2CO_3$ (393 mg, 2.85 mmol) and 2-bromoacetonitrile (125 mg, 1.04 mmol) at room temperature. The reaction mixture was stirred at 80° C. for 16 h and progress of the reaction was monitored by TLC (mobile phase: 70% EtOAc in pet ether. Rf: 0.3. detection: UV). The reaction mixture was concentrated under reduced pressure and the residue was diluted with water (30 mL) and extracted with EtOAc (30 mL). The organic layer was washed with brine (30 mL), dried over $Na_2SO_4$ and concentrated under reduced pressure to afford a brown gum (370 mg; LC/MS: 33%). The crude product was purified by normal phase column chromatography using a 12 g column (silica) and 50% EtOAc in Pet ether as eluent to afford tert-butyl ((4-(1-(cyanomethyl)-1H-imidazol-2-yl)-6-(4-fluorophenyl)pyridin-3-yl)methyl)carbamate as a pale yellow gum (250 mg; LC/MS: 55%). (LC/MS; m/z 408.3 $[M+H]^+$).

Step 4: A solution of tert-butyl ((4-(1-(cyanomethyl)-1H-imidazol-2-yl)-6-(4-fluorophenyl)pyridin-3-yl)methyl)carbamate (250 mg, 0.61 mmol) in DCM (3 mL) was treated with TFA (0.5 mL, 6.13 mmol) at 0° C. The reaction mixture was stirred at room temperature for 1 h and progress of the reaction was monitored by TLC (mobile phase: 20% MeOH in DCM. Rf: 0.2. detection: UV). The reaction mixture was concentrated under reduced pressure and the residue was diluted with EtOAc (30 mL) and washed with saturated $NaHCO_3$ (30 mL) and brine (2×20 mL). The organic layer was dried over $Na_2SO_4$ and concentrated under reduced pressure to afford 2-(2-(5-(aminomethyl)-2-(4-fluorophenyl)pyridin-4-yl)-1H-imidazol-1-yl)acetonitrile as a brown gum (170 mg; LC/MS: 54%). (LC/MS; m/z 308.2 $[M+H]^+$).

Step 5: A solution of 2-(2-(5-(aminomethyl)-2-(4-fluorophenyl)pyridin-4-yl)-1H-imidazol-1-yl)acetonitrile (170 mg, 0.55 mmol) in DCM (2 mL) was treated with $Et_3N$ (279 mg, 2.76 mmol) and acryloyl chloride (55 mg, 0.60 mmol) at 0° C. The reaction was stirred at room temperature for 1 h and progress of the reaction was monitored by TLC (mobile phase: 70% EtOAc in pet ether. Rf: 0.3. detection: UV). The reaction mixture was concentrated under reduced pressure and the residue was diluted with water (30 mL) and extracted with EtOAc (30 mL). The organic layer was washed with brine (30 mL), dried over $Na_2SO_4$ and concentrated under reduced pressure to afford a pale-yellow gum (100 mg, LC/MS: 56%). The crude product was purified by preparative HPLC method H17 and the collected fractions were concentrated under reduced pressure to afford N-((4-(1-(cyanomethyl)-1H-imidazol-2-yl)-6-(4-fluorophenyl)pyridin-3-yl)methyl)acrylamide as an off white solid (Cpd. No. 356) (41 mg, LC/MS: 99%). (LC/MS; m/z 362.3 $[M+H]^+$).

Synthesis of 6-methyl-4-(((methylsulfonyl)oxy)methyl)picolinate (Int-E)

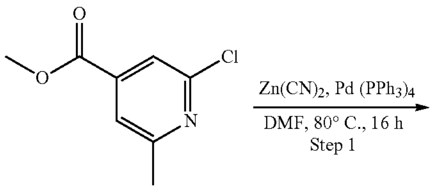

-continued

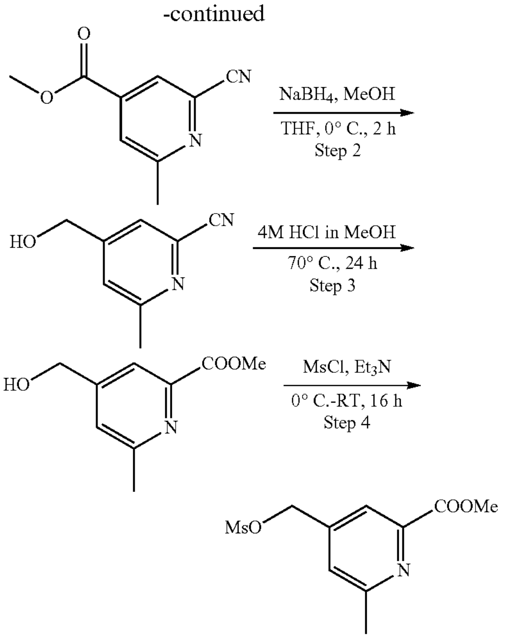

Int-E

Step 1: A solution of methyl 2-chloro-6-methylisonicotinate (6 g, 32.32 mmol) in DMF (80 mL) was treated with $Zn(CN)_2$ (4.53 g, 38.79 mmol) at room temperature. The reaction mixture was degassed with argon for 20 min followed by addition of $Pd(PPh_3)_4$ (3.73 g, 3.23 mmol) at room temperature. The reaction mixture was stirred at 80° C. for 16 h and progress of the reaction was monitored by TLC (mobile phase: 30% EtOAc in pet ether. Rf: 0.35. detection: UV). The reaction mixture was cooled and filtered through a pad of Celite and washed with EtOAc (500 mL). The filtrate was washed with brine (100 mL), dried over sodium sulphate and concentrated under reduced pressure to afford a brown gum (6 g, LC/MS: 30%). The crude product was purified by normal phase column chromatography using a 48 g column (silica) and 10% EtOAc in pet ether as eluent to afford methyl 2-cyano-6-methylisonicotinate as a white solid (2.5 g, LC/MS: 99%). (LC/MS; m/z 177.0 $[M+H]^+$).

Step 2: A solution of methyl 2-cyano-6-methylisonicotinate (1.9 g, 10.78 mmol) in THF (15 mL) and MeOH (36 mL) was treated with $NaBH_4$ (1.19 g, 32.35 mmol) at 0° C. The reaction mixture was stirred at 0° C. for 2 h and progress of the reaction was monitored by TLC (mobile phase: 30% EtOAc in pet ether. Rf: 0.22. detection: UV). The reaction mixture was concentrated under reduced pressure and the residue was diluted with EtOAc (200 mL). The organic layer was washed with 1N HCl (50 mL), brine (2×120 mL), dried over sodium sulphate and concentrated under reduced pressure to afford 4-(hydroxymethyl)-6-methylpicolinonitrile as a white solid (1.6 g, LC/MS: 87%). (LC/MS; m/z 149.1 $[M+H]^+$).

Step 3: A solution of 4-(hydroxymethyl)-6-methylpicolinonitrile (1.6 g, 10.81 mmol) in 4M HCl in MeOH (10 mL) was stirred at 70° C. for 24 h and progress of the reaction was monitored by TLC (mobile phase: 30% EtOAc in pet ether. Rf: 0.14. detection: UV). The reaction mixture was concentrated under reduced pressure and the residue was diluted with EtOAc (500 mL) and washed with saturated $NaHCO_3$ (100 mL), brine (100 mL), dried over sodium sulphate and concentrated under reduced pressure to afford methyl 4-(hydroxymethyl)-6-methylpicolinate as a yellow solid (950 mg; LC/MS: 91%). (LC/MS; m/z 182.1 [M+H]$^+$).

Step 4: A solution of methyl 4-(hydroxymethyl)-6-methylpicolinate (900 mg, 4.96 mmol) in THF (15 mL) was treated with TEA (2.07 mL, 14.90 mmol) and MsCl (0.91 mL, 11.92 mmol) at 0° C. The reaction mixture was stirred at room temperature for 16 h and progress of the reaction was monitored by TLC (mobile phase: 30% EtOAc in pet ether. Rf: 0.3. detection: UV). The reaction mixture was concentrated under reduced pressure and the residue was diluted with EtOAc (200 mL) and washed with saturated $NaHCO_3$ (100 mL), brine (100 mL), dried over sodium sulphate and concentrated under reduced pressure to afford a yellow gum (1.9 g, LC/MS: 73%). The crude product was purified by column chromatography using silica gel (12 g) and 20% EtOAc in pet ether as eluent to afford methyl 6-methyl-4-(((methylsulfonyl)oxy)methyl)picolinate (Int-E) as a white solid (1.1 g, LC/MS: 96%). (LC/MS; m/z 260.2 [M+H]$^+$).

Example 135: Synthesis of 3-((3-(5-(acrylamidomethyl)-2-(4-fluorophenyl)pyridin-4-yl)-1H-pyrazol-1-yl)methyl)-N-methylbenzamide (Cpd. No. 360)

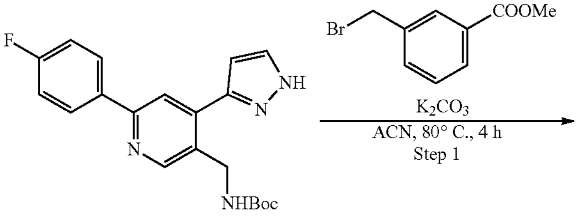

Int-66

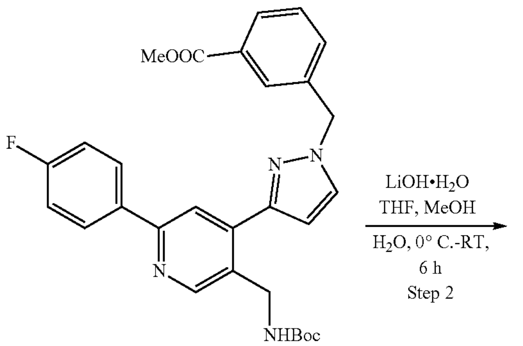

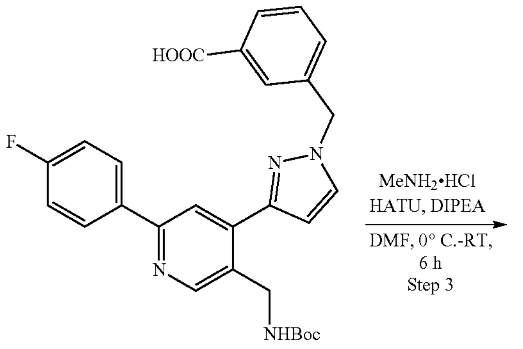

2

-continued

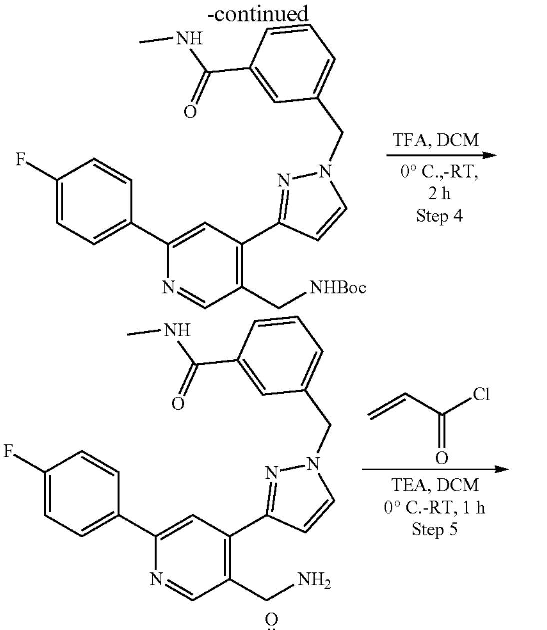

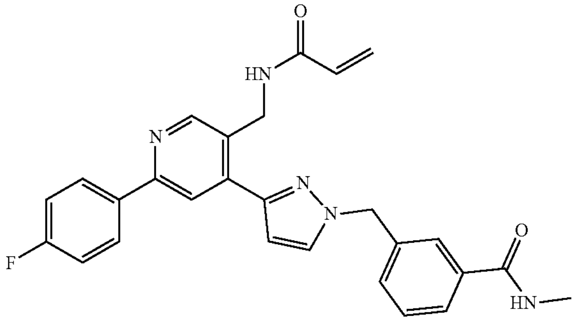

Cpd. No. 360

Step 1: A solution of Int-66 (400 mg, 1.08 mmol) in ACN (10 mL) was treated with $K_2CO_3$ (450 mg, 3.25 mmol) and methyl 3-(bromomethyl)benzoate (323 mg, 1.41 mmol) at room temperature. The reaction mixture was stirred at 80° C. for 4 h and progress of the reaction was monitored by TLC (mobile phase: 30% EtOAc in pet ether. Rf: 0.36. detection: UV). The reaction mixture was diluted with water (50 mL) and extracted with EtOAc (2×70 mL). The combined organic layer was washed with brine solution (50 mL), dried over anhydrous $Na_2SO_4$ and concentrated under reduced pressure. The residue was triturated with diethyl ether (10 mL) and dried under high vacuum to afford methyl 3-((3-(5-(((tert-butoxycarbonyl)amino)methyl)-2-(4-fluorophenyl)pyridin-4-yl)-1H-pyrazol-1-yl)methyl)benzoate as a yellow solid (400 mg; LC/MS: 71%). (LC/MS; m/z 516.8 [M+H]$^+$).

Step 2: A solution of methyl 3-((3-(5-(((tert-butoxycarbonyl)amino)methyl)-2-(4-fluorophenyl)pyridin-4-yl)-1H-pyrazol-1-yl)methyl)benzoate (300 mg, 0.58 mmol) in THF (9 mL), MeOH (1 mL) and water (1 mL) was treated with lithium hydroxide monohydrate (146 mg, 3.48 mmol) at 0° C. The reaction mixture was stirred at room temperature for 6 h and progress of the reaction was monitored by TLC (mobile phase: EtOAc. Rf: 0.19. detection: UV). The reaction mixture was concentrated under reduced pressure and the residue was diluted with water (10 mL) and pH adjusted to 3 by addition of 1 N HCl. The resulting precipitate was filtered and then dried under high vacuum to afford 3-((3-(5-(((tert-butoxycarbonyl)amino)methyl)-2-(4-fluorophenyl)pyridin-4-yl)-1H-pyrazol-1-yl)methyl)benzoic acid as an off-white solid (250 mg; LC/MS: 92%). (LC/MS; m/z 503.3 [M+H]$^+$).

Step 3: A solution of 3-((3-(5-(((tert-butoxycarbonyl)amino)methyl)-2-(4-fluorophenyl)pyridin-4-yl)-1H-pyrazol-1-yl)methyl)benzoic acid (240 mg, 0.47 mmol) in DMF (15 mL) was treated with HATU (336 mg, 0.88 mmol), methylamine hydrochloride (322 mg, 4.77 mmol) and DIPEA (1.13 mL, 6.49 mmol) at 0° C. The reaction mixture was stirred at room temperature for 6 h and progress of the reaction was monitored by TLC (mobile phase: 70% EtOAc in Pet ether. Rf: 0.2. detection: UV). The reaction mixture was diluted with water (50 mL) and extracted with EtOAc (2×100 mL). The combined organic layer was washed with brine (50 mL), dried over anhydrous sodium sulphate and concentrated under reduced pressure to afford tert-butyl ((6-(4-fluorophenyl)-4-(1-(3-(methylcarbamoyl)benzyl)-1H-pyrazol-3-yl)pyridin-3-yl)methyl)carbamate as a yellow gum (245 mg; LC/MS: 82%). (LC/MS; m/z 516.4 [M+H]$^+$).

Step 4: A solution of tert-butyl ((6-(4-fluorophenyl)-4-(1-(3-(methylcarbamoyl)benzyl)-1H-pyrazol-3-yl)pyridin-3-yl)methyl)carbamate (200 mg, 0.38 mmol) in DCM (4 mL) was treated with TFA (0.29 mL, 3.87 mmol) at 0° C. The reaction mixture was stirred at room temperature for 2 h and progress of the reaction was monitored by TLC (mobile phase: 10% MeOH in DCM. Rf: 0.1. detection: UV). The reaction mixture was concentrated under reduced pressure and the residue was diluted with water (25 mL) and basified by addition of saturated $NaHCO_3$ and extracted with EtOAc (2×50 mL). The organic layer was dried over sodium sulphate and concentrated under reduced pressure to afford crude 3-((3-(5-(aminomethyl)-2-(4-fluorophenyl)pyridin-4-yl)-1H-pyrazol-1-yl)methyl)-N-methylbenzamide as a yellow gum (150 mg, LC/MS: 84%). (LC/MS; m/z 416.2 [M+H]$^+$).

Step 5: A solution of 3-((3-(5-(aminomethyl)-2-(4-fluorophenyl)pyridin-4-yl)-1H-pyrazol-1-yl)methyl)-N-methylbenzamide (80 mg, 0.19 mmol) in DCM (8 mL) was treated with $Et_3N$ (0.1 mL, 0.77 mmol) and a solution of acryloyl chloride (18 mg, 0.19 mmol) in DCM (2 mL) at 0° C. The reaction mixture was stirred at room temperature for 1 h and progress of the reaction was monitored by TLC (mobile phase: 10% MeOH in DCM. Rf: 0.55. detection: UV). The reaction mixture was diluted with DCM (100 mL) and washed with brine solution (2×50 mL), dried over sodium sulphate and concentrated under reduced pressure to afford a yellow solid (120 mg, LC/MS: 78%). The crude product was purified by preparative HPLC method H18 and the collected fractions were concentrated under reduced pressure to afford 3-((3-(5-(acrylamidomethyl)-2-(4-fluorophenyl)pyridin-4-yl)-1H-pyrazol-1-yl)methyl)-N-methylbenzamide (Cpd. No. 360) as a white solid (31 mg, LC/MS: 99.5%). (LC/MS; m/z 470.4 [M+H]$^+$).

The following compounds were prepared in a manner similar (use of appropriate reagents and purification methods known to the person skilled in the art) to Cpd. No. 360: Cpd. No. 361 (using acetic anhydride and acetic acid at 120° C. in step 5), Cpd. No. 362, Cpd. No. 364 (using acetyl chloride in Step 5), Cpd. No. 368 (using Int-E in step 1), Cpd. No. 372 (using Int-E in step 1 and acetyl chloride in step 5), Cpd. No. 388 (omitting step 5), Cpd. No. 397 (using 4-chlorobutanoyl chloride and then KOtBu in step 5).

Example 136: Synthesis of N-((6-(4-fluorophenyl)-4-(1-(2-hydroxyethyl)-1H-imidazol-2-yl)pyridin-3-yl)methyl)acrylamide (Cpd. No. 366)

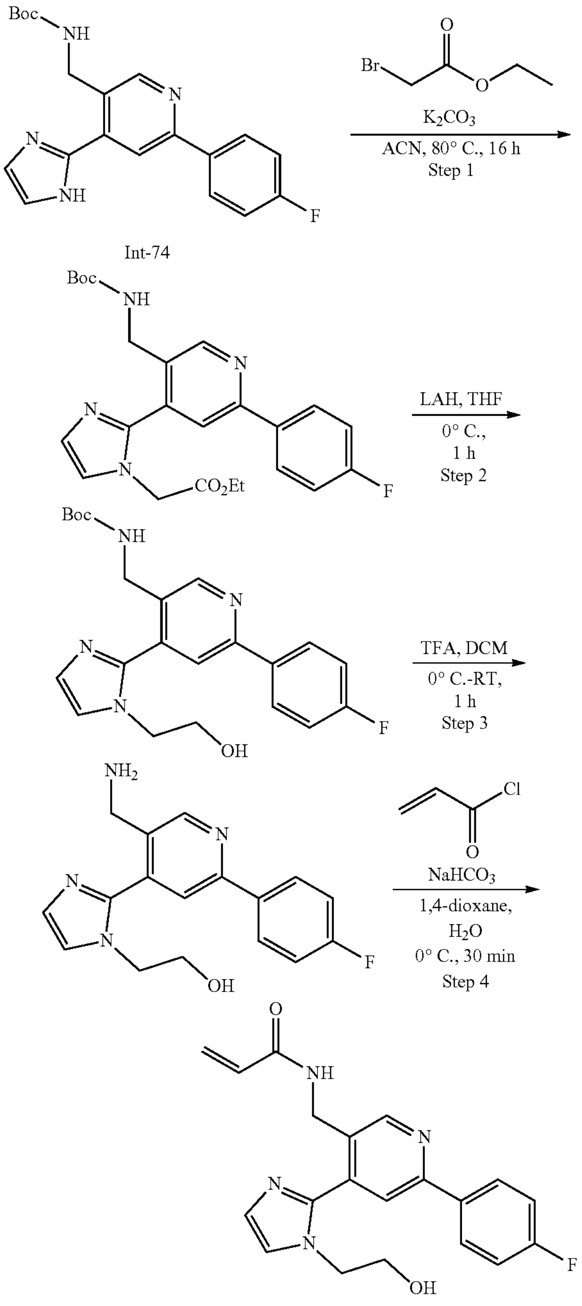

Cpd. No. 366

Step 1: A solution of Int-74 (280 mg, 0.76 mmol) in MeCN (3 mL) was treated with $K_2CO_3$ (315 mg, 2.28 mmol) and ethyl 2-bromoacetate (381 mg, 2.28 mmol) at room temperature. The reaction mixture was stirred at 80° C. for 16 h and progress of the reaction was monitored by TLC (mobile phase: 70% EtOAc in pet ether. Rf: 0.3. detection: UV). The reaction mixture was concentrated under reduced pressure and the residue was diluted with water (20 mL) and extracted with EtOAc (2×20 mL). The combined organic layer was washed with brine (20 mL), dried over sodium sulphate and concentrated under reduced pressure to afford a brown gum (300 mg, LC/MS: 44%). The crude product was purified by normal phase column chromatography using silica gel (10 g) and 40% EtOAc in Pet ether as eluent to afford ethyl 2-(2-(5-(((tert-butoxycarbonyl)amino)methyl)-2-(4-fluorophenyl)pyridin-4-yl)-1H-imidazol-1-yl)acetate as a brown liquid (140 mg, LC/MS: 96%). (LC/MS; m/z 455.3 [M+H]$^+$).

Step 2: A solution of ethyl 2-(2-(5-(((tert-butoxycarbonyl)amino)methyl)-2-(4-fluorophenyl)pyridin-4-yl)-1H-imidazol-1-yl)acetate (100 mg, 0.22 mmol) in THF (2 mL) was treated with LAH (2 M in THF) (0.12 mL, 0.24 mmol) at 0° C. The reaction mixture was stirred at 0° C. for 1 h and progress was monitored by TLC (mobile phase: 70% EtOAc in pet ether. Rf: 0.15. detection: UV). The reaction was quenched with aqueous ammonium chloride (30 mL) and extracted with EtOAc (100 mL). The organic layer was washed with brine (100 mL), dried over sodium sulphate and concentrated under reduced pressure to afford tert-butyl ((6-(4-fluorophenyl)-4-(1-(2-hydroxyethyl)-1H-imidazol-2-yl)pyridin-3-yl)methyl)carbamate as a yellow gum (85 mg, LC/MS: 87%). (LC/MS; m/z 413.3 [M+H]$^+$).

Step 3: A solution of tert-butyl ((6-(4-fluorophenyl)-4-(1-(2-hydroxyethyl)-1H-imidazol-2-yl)pyridin-3-yl)methyl) carbamate (100 mg, 0.24 mmol) in DCM (4 mL) was treated with TFA (0.37 mL, 4.84 mmol) at 0° C. The reaction mixture was stirred at room temperature for 1 h and progress of the reaction was monitored by TLC (mobile phase: 10% MeOH in DCM. Rf: 0.1. detection: UV). The reaction mixture was concentrated under reduced pressure and the residue was diluted with water (30 mL), basified by addition of saturated $NaHCO_3$ and extracted with EtOAc (2×50 mL). The combined organic layer was dried over sodium sulphate and concentrated under reduced pressure to afford 2-(2-(5-(aminomethyl)-2-(4-fluorophenyl)pyridin-4-yl)-1H-imidazol-1-yl)ethan-1-ol as a yellow gum (74 mg, LC/MS: 85%). (LC/MS; m/z 313.2 [M+H]$^+$).

Step 4: A solution of 2-(2-(5-(aminomethyl)-2-(4-fluorophenyl)pyridin-4-yl)-1H-imidazol-1-yl)ethan-1-ol (74 mg, 0.23 mmol) in 1,4-dioxane (9 mL) and water (0.5 mL) was treated with $NaHCO_3$ (80 mg, 0.94 mmol) and a solution of acryloyl chloride (22 mg, 0.23 mmol) in 1,4-dioxane (1 mL) at 0° C. The reaction mixture was stirred at 0° C. for 30 min and progress of the reaction was monitored by TLC (mobile phase: 10% MeOH in DCM. Rf: 0.3. detection: UV). The reaction mixture was diluted with EtOAc (50 mL) and washed with brine solution (2×30 mL), dried over sodium sulphate and concentrated under reduced pressure to afford a yellow gum (71 mg, LC/MS: 38%). The crude product was purified by preparative HPLC method H2 and the collected fractions were concentrated under reduced pressure to afford N-((6-(4-fluorophenyl)-4-(1-(2-hydroxyethyl)-1H-imidazol-2-yl)pyridin-3-yl)methyl)acrylamide (Cpd. No. 366) as a white solid (9.2 mg, LC/MS: 92%). (LC/MS; m/z 367.4 [M+H]$^+$).

Example 137: Synthesis of 1-(4-(6-(4-fluorophenyl)-4-(1-methyl-1H-pyrazol-3-yl)pyridin-3-yl)piperazin-1-yl)prop-2-en-1-one (Cpd. No. 375)

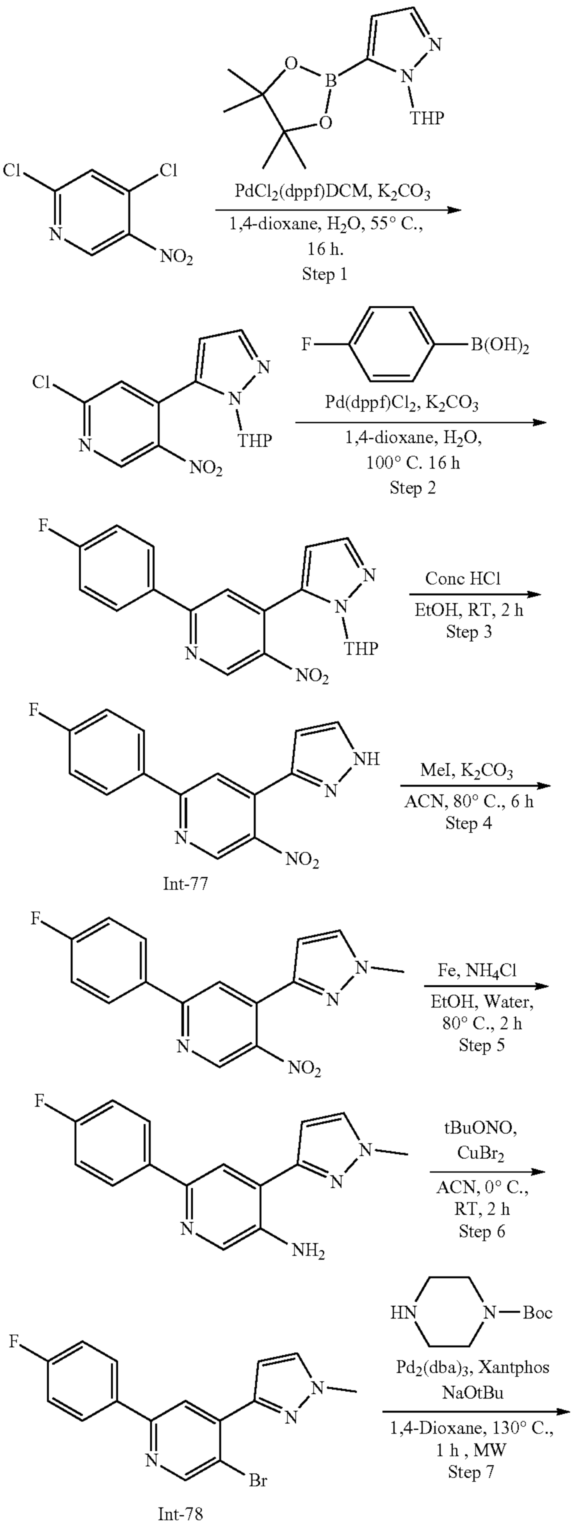

-continued

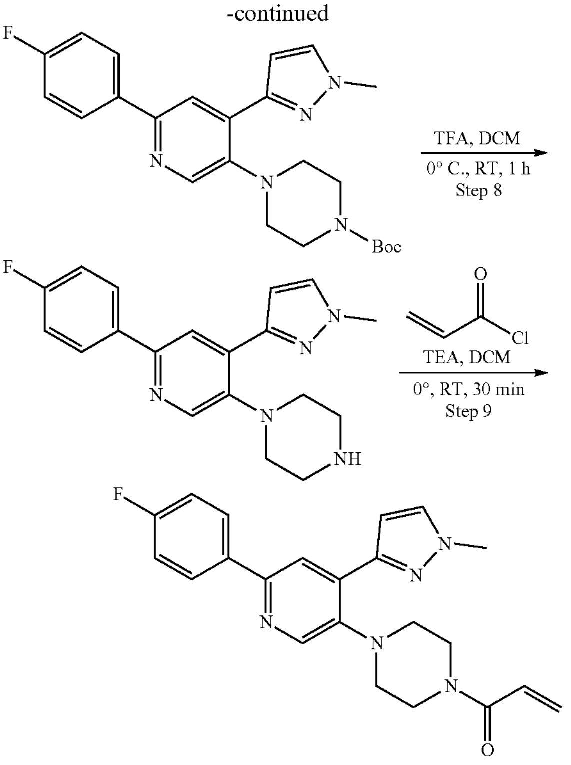

Cpd. No. 375

Step 1: A solution of 2,4-dichloro-5-nitropyridine (25 g, 129.54 mmol) in 1,4-dioxane (500 mL) and $H_2O$ (32.5 mL) was treated with 1-(tetrahydro-2H-pyran-2-yl)-5-(4,4,5,5-tetramethyl-1,3,2-dioxaborolan-2-yl)-1H-pyrazole (36 g, 129.54 mmol) and $K_2CO$ (35.8 g, 259.08 mmol) and was degassed with argon for 20 min followed by addition of $PdCl_2$(dppf)·DCM (5.28 g, 6.47 mmol) at room temperature. The reaction mixture was stirred at 60° C. for 16 h and progress of the reaction was monitored by TLC (mobile phase: 20% EtOAC in pet ether. Rf: 0.2. detection: UV). The reaction mixture was filtered through Celite and washed with EtOAc (1000 mL). The filtrate was washed with brine (200 mL), dried over sodium sulphate and concentrated under reduced pressure to afford crude a brown gum (25 g, LC/MS: 26%). The crude product was purified by normal phase column chromatography using silica gel (250 g) and 15% EtOAC in pet ether as eluent to afford 2-chloro-5-nitro-4-(1-(tetrahydro-2H-pyran-2-yl)-1H-pyrazol-5-yl)pyridine as a yellow liquid (8.5, LC/MS: 90%). (LC/MS; m/z 225.2 $[M+H-THP]^+$).

Step 2: A solution of 2-chloro-5-nitro-4-(1-(tetrahydro-2H-pyran-2-yl)-1H-pyrazol-5-yl)pyridine (8.5 g, 27.53 mmol) in 1,4-dioxane (85 mL) and $H_2O$ (8.5 mL) was treated with (4-fluorophenyl)boronic acid (4.6 g, 33.03 mmol) and $K_2CO_3$ (7.2 g, 52.31 mmol) and was degassed with argon for 20 min followed by addition of $PdCl_2$(dppf) (604 mg, 0.82 mmol) at room temperature. The reaction mixture was stirred at 100° C. for 16 h and progress of the reaction was monitored by TLC (mobile phase: 20% EtOAc in Pet ether. Rf: 0.3. detection: UV). The reaction mixture was filtered through a celite bed and washed with EtOAc (200 mL). The filtrate was washed with brine (200 mL), dried over sodium sulphate and concentrated under reduced pressure to afford a yellow gum (9.5 g; LC/MS: 82%). The crude product was purified by gravity column chromatography using silica gel (60 g) and 10% of EtOAc in pet ether as an eluent to afford 2-(4-fluorophenyl)-5-nitro-4-(1-(tetrahydro-2H-pyran-2-yl)-1H-pyrazol-5-yl)pyridine as a white solid (6.5 g, LC/MS: 89%). (LC/MS; m/z 369.1 $[M+H]^+$).

Step 3: A solution of 2-(4-fluorophenyl)-5-nitro-4-(1-(tetrahydro-2H-pyran-2-yl)-1H-pyrazol-5-yl)pyridine (6 g, 16.28 mmol) in EtOH (138 mL) was treated with concentrated HCl (13.8 mL) at room temperature. The reaction mixture was stirred at room temperature for 2 h and progress of the reaction was monitored by TLC (mobile phase: 20% EtOAC in pet ether. Rf: 0.2. detection: UV). The pH was adjusted to 8 by addition of 1 N NaOH and the mixture was extracted with ethyl acetate (200 mL). The organic layer was washed with brine (200 mL), dried over sodium sulphate and concentrated under reduced pressure to afford 2-(4-fluorophenyl)-5-nitro-4-(1H-pyrazol-3-yl)pyridine (Int-77) as an off-white solid (5.1 g; LC/MS: 97%). (LC/MS; m/z 285.5 $[M+H]^+$).

Step 4: A solution of Int-77 (4 g, 14.07 mmol) in ACN (60 mL) was treated with MeI (2.39 g, 16.88 mmol) and $K_2CO_3$ (5.82 g, 42.21 mmol) at room temperature. The reaction mixture was stirred at 80° C. for 6 h and progress of the reaction was monitored by TLC (mobile phase: 20% EtOAC in pet ether. Rf: 0.3. detection: UV). The reaction mixture was diluted with water (100 mL) and extracted with EtOAc (100 mL). The organic layer was washed with brine (80 mL), dried over sodium sulphate, and concentrated under reduced pressure to afford a yellow solid (3.5 g, LC/MS: 86%). The crude product was purified by normal phase column chromatography using a 40 g column (silica) and 20% EtOAc in Pet ether as an eluent to afford 2-(4-fluorophenyl)-4-(1-methyl-1H-pyrazol-3-yl)-5-nitropyridine as an off-white solid (3 g, LC/MS: 86%). (LC/MS; m/z 298.9 $[M+H]^+$).

Step 5: A solution of 2-(4-fluorophenyl)-4-(1-methyl-1H-pyrazol-3-yl)-5-nitropyridine (3 g, 10.05 mmol) in EtOH (30 mL) and $H_2O$ (3 mL) was treated with iron powder (1.69 g, 30.17 mmol) and $NH_4Cl$ (1.0 g, 20.11 mmol) at room temperature. The reaction mixture was stirred at 80° C. for 2 h and progress of the reaction was monitored by TLC (mobile phase: 40% EtOAc in Pet ether. Rf: 0.3. detection: UV). The reaction mixture was concentrated under reduced pressure and the residue was diluted with water (100 mL) and extracted with EtOAc (100 mL). The organic layer was washed with brine (100 mL), dried over sodium sulphate and concentrated under reduced pressure to afford 6-(4-fluorophenyl)-4-(1-methyl-1H-pyrazol-3-yl)pyridin-3-amine as a brown gum (2.4 g; LC/MS: 86%). (LC/MS; m/z 269.3 $[M+H]^+$).

Step 6: A solution of 6-(4-fluorophenyl)-4-(1-methyl-1H-pyrazol-3-yl)pyridin-3-amine (2.5 g, 9.31 mmol) in ACN (25 mL) was treated with tBuONO (4.8 g, 46.59 mmol) and $CuBr_2$ (1.03 g, 4.65 mmol) at 0° C. The reaction mixture was stirred at room temperature for 2 h. Progress of the reaction was monitored by TLC (mobile phase: 40% EtOAC in pet ether. Rf: 0.6. detection: UV). The reaction mixture was diluted with water (70 mL) and extracted with EtOAc (70 mL). The organic layer was washed with brine (60 mL), dried over sodium sulphate and concentrated under reduced pressure to afford a brown gum (2.3 g, LC/MS: 58%). The crude product was purified by normal phase column chromatography using a 40 g column (silica) and 20% EtOAc in Pet ether as an eluent to afford 5-bromo-2-(4-fluorophenyl)-4-(1-methyl-1H-pyrazol-3-yl)pyridine (Int-78) as pale yellow solid (1.5 g, LC/MS: 84%). (LC/MS; m/z 332.2) $[M+H]^+$).

Step 7: A solution of Int-78 (300 mg, 0.90 mmol) in 1,4-dioxane (5 mL) was treated with tert-butyl piperazine-1-carboxylate (168 mg, 0.90 mmol), Xantphos (52 mg, 0.09 mmol) and NaOtBu (260 mg, 2.70 mmol) and was degassed with argon for 20 min followed by addition of $Pd_2(dba)_3$ (41 mg, 0.04 mmol) at room temperature. The reaction mixture was stirred at 130° C. for 1 h under microwave irradiation. Progress of the reaction was monitored by TLC (mobile phase: 40% EtOAC in pet ether. Rf: 0.3. detection: UV active). The reaction mixture was filtered through Celite and washed with EtOAc (50 mL). The filtrate was washed with brine (40 mL), dried over sodium sulphate and concentrated under reduced pressure to afford as a brown gum (480 mg; LC/MS: 35%). The crude product was purified by normal phase column chromatography using 24 g column (silica) and 30% EtOAc in Pet ether as an eluent to afford tert-butyl 4-(6-(4-fluorophenyl)-4-(1-methyl-1H-pyrazol-3-yl)pyridin-3-yl)piperazine-1-carboxylate as yellow gum (200 mg; LC/MS: 53%). (LC/MS; m/z 438.1 $[M+H]^+$).

Step 8: A solution of tert-butyl 4-(6-(4-fluorophenyl)-4-(1-methyl-1H-pyrazol-3-yl)pyridin-3-yl)piperazine-1-carboxylate (190 mg, 0.43 mmol) in DCM (2 mL) was treated with TFA (0.3 mL, 4.34 mmol) at 0° C. The reaction mixture was stirred at room temperature for 1 h and progress of the reaction was monitored by TLC (mobile phase: 10% MeOH in DCM. Rf: 0.1. detection: UV). The reaction mixture was concentrated under reduced pressure and the residue was diluted with EtOAC (80 mL) and washed with saturated $NaHCO_3$ (50 mL) and brine (70 mL). The organic layer was dried over sodium sulphate and concentrated under reduced pressure to afford 1-(6-(4-fluorophenyl)-4-(1-methyl-1H-pyrazol-3-yl)pyridin-3-yl)piperazine as brown gum (160 mg, LC/MS: 54%). (LC/MS; m/z 338.3 $[M+H]^+$).

Step 9: A solution of 1-(6-(4-fluorophenyl)-4-(1-methyl-1H-pyrazol-3-yl)pyridin-3-yl)piperazine (155 mg, 0.46 mmol) in DCM (2 mL) was treated with $Et_3N$ (0.3 mL, 2.30 mmol) and acryloyl chloride (45 mg, 0.50 mmol) at 0° C. The reaction mixture was stirred at room temperature for 30 minutes. Progress of the reaction was monitored by TLC. (mobile phase: 10% MeOH in DCM. Rf: 0.3. detection: UV). The reaction mixture was diluted with DCM (50 mL) and washed with brine (30 mL), dried over sodium sulphate, and concentrated under reduced pressure to afford a brown gum (195 mg, LC/MS: 46%). The crude product was purified by preparative HPLC method H17 and the collected fractions were concentrated under reduced pressure to afford 1-(4-(6-(4-fluorophenyl)-4-(1-methyl-1H-pyrazol-3-yl)pyridin-3-yl)piperazin-1-yl)prop-2-en-1-one (Cpd. No. 375) as a white solid (47 mg, LC/MS: 99%). (LC/MS; m/z 392.3 $[M+H]^+$).

The following compounds were prepared in a manner similar (use of appropriate reagents and purification methods known to the person skilled in the art) to Cpd. No. 375: Cpd. No. 376 (using acetyl chloride in step 9), Cpd. No. 377 (using MsCl in step 9).

Example 138: Synthesis of 3-((3-(5-(1-acryloylpyrrolidin-3-yl)-2-(4-fluorophenyl)pyridin-4-yl)-1H-pyrazol-1-yl)methyl)-N-methylbenzamide (Cpd. No. 374)

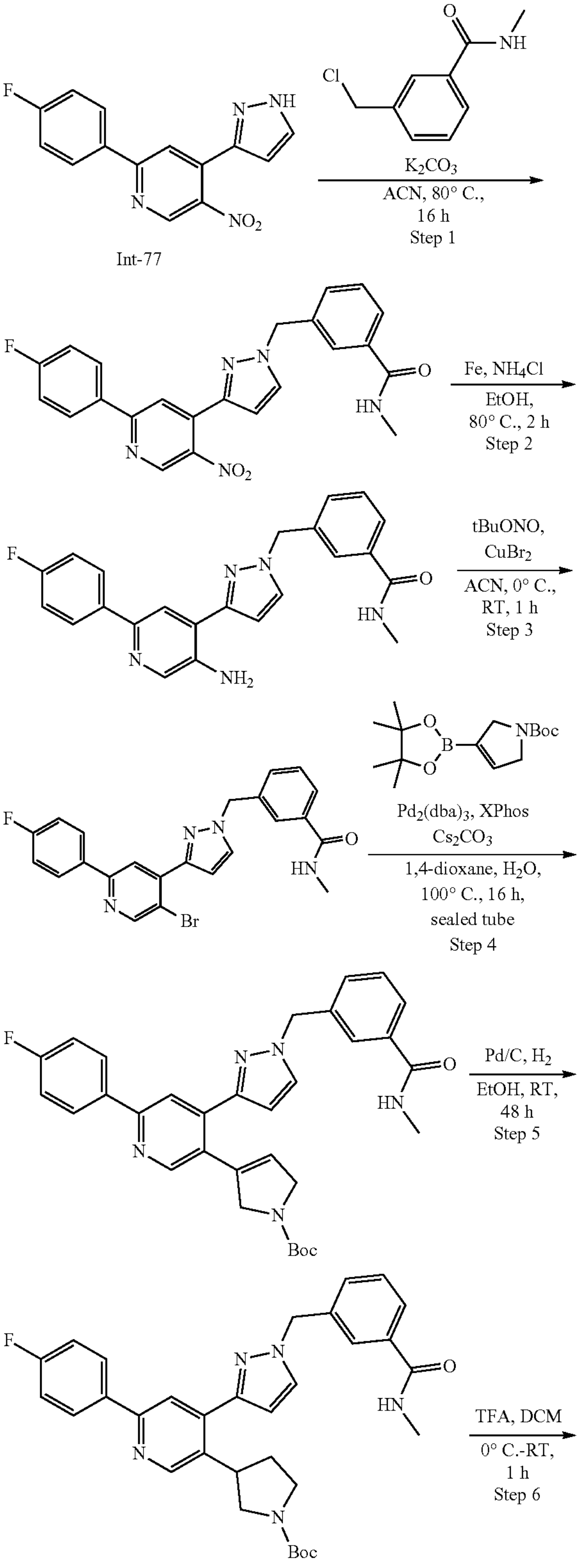

-continued

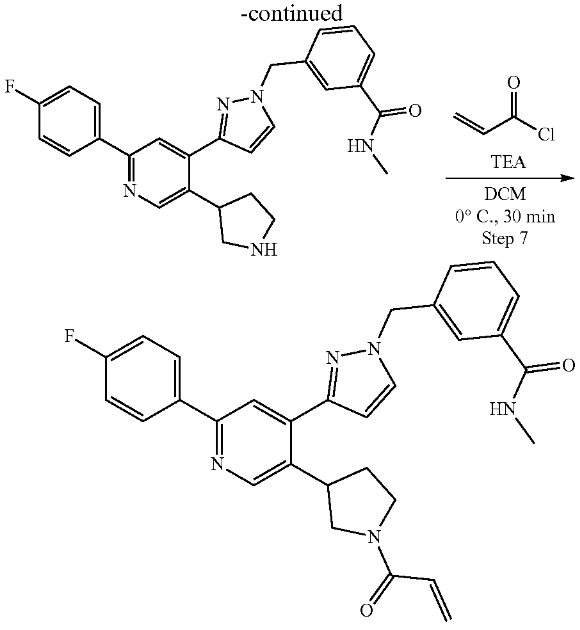

Cpd. No. 374

Step 1: A solution of Int-77 (1 g, 3.52 mmol) in ACN (15 mL) was treated with 3-(chloromethyl)-N-methylbenzamide (0.647 mg, 3.52 mmol) and $K_2CO_3$ (1.45 g, 10.56 mmol) at room temperature. The reaction mixture was stirred for 16 h at 80° C. and progress of the reaction was monitored by TLC (mobile phase: 70% EtOAC in pet ether. Rf: 0.3. detection: UV). The reaction mixture was diluted with water (50 mL) and extracted with EtOAc (2×70 mL). The organic layer was washed with brine (50 mL), dried over sodium sulphate and concentrated under reduced pressure to afford 3-((3-(2-(4-fluorophenyl)-5-nitropyridin-4-yl)-1H-pyrazol-1-yl) methyl)-N-methylbenzamide as an off-white solid (450 mg; LC/MS: 99%). (LC/MS; m/z 432.2 $[M+H]^+$).

Step 2: A solution of 3-((3-(2-(4-fluorophenyl)-5-nitropyridin-4-yl)-1H-pyrazol-1-yl)methyl)-N-methylbenzamide (450 mg, 1.04 mmol) in EtOH (10 mL) and $H_2O$ (1 mL) was treated with iron powder (175 mg, 3.13 mmol) and $NH_4Cl$ (112 mg, 2.08 mmol) at room temperature. The reaction mixture was stirred at 80° C. for 2 h and progress of the reaction monitored by TLC (mobile phase: 80% EtOAc in Pet ether. Rf: 0.2. detection: UV). The reaction mixture was filtered through a celite bed and washed with EtOAc (50 mL). The filtrate was washed with brine (50 mL), dried over sodium sulphate and concentrated under reduced pressure to afford 3-((3-(5-amino-2-(4-fluorophenyl)pyridin-4-yl)-1H-pyrazol-1-yl)methyl)-N-methylbenzamide as a pale yellow solid (380 mg, LC/MS: 94%). (LC/MS; m/z 402.1 $[M+H]^+$).

Step 3: A solution of 3-((3-(5-amino-2-(4-fluorophenyl) pyridin-4-yl)-1H-pyrazol-1-yl)methyl)-N-methylbenzamide (250 mg, 0.62 mmol) in ACN (3 mL) was treated with tBuONO (321 mg, 3.11 mmol) and $CuBr_2$ (69 mg, 0.31 mmol) at 0° C. The reaction mixture was stirred at room temperature for 1 h and progress of the reaction was monitored by TLC (mobile phase: 80% EtOAC in pet ether. Rf: 0.4. detection: UV). The reaction mixture was diluted with water (50 mL) and extracted with EtOAc (70 mL). The organic layer was washed with brine (50 mL), dried over sodium sulphate, and concentrated under reduced pressure to afford a brown gum (350 mg, LC/MS: 50%). The crude product was purified by normal phase column chromatography using a 12 g column (silica) and 60% EtOAc in Pet ether as an eluent to afford 3-((3-(5-bromo-2-(4-fluorophenyl)pyridin-4-yl)-1H-pyrazol-1-yl)methyl)-N-methylbenzamide as a pale yellow solid (150 mg, LC/MS: 74%). (LC/MS; m/z 465.0 $[M+H]^+$).

Step 4: A solution of 3-((3-(5-bromo-2-(4-fluorophenyl) pyridin-4-yl)-1H-pyrazol-1-yl)methyl)-N-methylbenzamide (150 mg, 0.32 mmol) in 1,4 dioxane (2 mL) and $H_2O$ (0.2 mL) was treated with tert-butyl 3-(4,4,5,5-tetramethyl-1,3,2-dioxaborolan-2-yl)-2,5-dihydro-1H-pyrrole-1-carboxylate (114 mg, 0.38 mmol), X-Phos (7 mg, 0.01 mmol) and $Cs_2CO_3$ (314 mg, 0.96 mmol) and degassed with argon for 20 min followed by addition of $Pd_2(dba)_3$ (9 mg, 0.01 mmol) at room temperature. The reaction mixture was stirred at 100° C. for 16 h in a sealed tube and progress of the reaction was monitored by TLC (mobile phase: 80% EtOAC in pet ether. Rf: 0.3. detection: UV). The reaction mixture was filtered through a Celite bed and washed with EtOAc (40 mL). The filtrate was washed with brine (30 mL), dried over anhydrous sodium sulphate and concentrated under reduced pressure to afford a brown gum (170 mg, LC/MS: 50%). The crude product was purified by normal phase column chromatography using a 12 g column (silica) and 60% EtOAc in Pet ether as an eluent to afford tert-butyl 3-(6-(4-fluorophenyl)-4-(1-(3-(methylcarbamoyl)benzyl)-1H-pyrazol-3-yl) pyridin-3-yl)-2,5-dihydro-1H-pyrrole-1-carboxylate as yellow gum (140 mg; LC/MS: 55%). (LC/MS; m/z 555.5 $[M+H]^+$).

Step 5: A solution of tert-butyl 3-(6-(4-fluorophenyl)-4-(1-(3-(methylcarbamoyl)benzyl)-1H-pyrazol-3-yl)pyridin-3-yl)-2,5-dihydro-1H-pyrrole-1-carboxylate (140 mg, 0.25 mmol) in EtOH (3 mL) was treated 10% Pd/C (140 mg) at room temperature. The reaction mixture was stirred at room temperature for 48 h under hydrogen balloon. Progress of the reaction was monitored by TLC (mobile phase: 80% EtOAC in pet ether. Rf: 0.26. detection: UV). The reaction mixture was passed through a Celite bed and washed with EtOAc (50 mL). The filtrate was concentrated under reduced pressure to afford tert-butyl 3-(6-(4-fluorophenyl)-4-(1-(3-(methylcarbamoyl)benzyl)-1H-pyrazol-3-yl)pyridin-3-yl) pyrrolidine-1-carboxylate as a pale yellow gum (140 mg; LC/MS: 66%). (LC/MS; m/z 556.4 $[M+H]^+$).

Step 6: A solution of tert-butyl 3-(6-(4-fluorophenyl)-4-(1-(3-(methylcarbamoyl)benzyl)-1H-pyrazol-3-yl)pyridin-3-yl)pyrrolidine-1-carboxylate (140 mg, 0.25 mmol) in DCM (2 mL) was treated with TFA (0.2 mL, 2.52 mmol) at 0° C. The reaction was stirred at room temperature for 1 h and progress of the reaction was monitored by TLC (mobile phase: 10% MeOH in DCM. Rf: 0.2. detection: UV). The reaction mixture was concentrated under reduced pressure and the residue was diluted with EtOAC (70 mL) and washed with saturated $NaHCO_3$ (30 mL) and brine (30 mL). The organic layer was dried over sodium sulphate and concentrated under reduced pressure to afford 3-((3-(2-(4-fluorophenyl)-5-(pyrrolidin-3-yl)pyridin-4-yl)-1H-pyrazol-1-yl)methyl)-N-methylbenzamide as a brown gum (125 mg; LC/MS: 65%). (LC/MS; m/z 456.3 $[M+H]^+$).

Step 7: A solution of 3-((3-(2-(4-fluorophenyl)-5-(pyrrolidin-3-yl)pyridin-4-yl)-1H-pyrazol-1-yl)methyl)-N-methylbenzamide (125 mg, 0.27 mmol) in DCM (2 mL) was treated with $Et_3N$ (0.19 mL, 1.37 mmol) and acryloyl chloride (27 mg, 0.30 mmol) at 0° C. The reaction mixture was stirred at for 30 minutes at 0° C. Progress of the reaction was monitored by TLC (mobile phase: 80% EtOAc in pet ether. Rf: 0.3. detection: UV). The reaction mixture was diluted with DCM (30 mL), washed with brine (30 mL), dried over sodium sulphate and concentrated under reduced pressure to afford a pale yellow gum (102 mg, LC/MS: 57%). The crude product was purified by preparative HPLC method H18 and the collected fractions were concentrated under reduced pressure to afford 3-((3-(5-(1-acryloylpyrrolidin-3-yl)-2-(4-fluorophenyl)pyridin-4-yl)-1H-pyrazol-1-yl)methyl)-N-methylbenzamide (Cpd. No. 374) as an off-white solid (17.4 mg, LC/MS: 99%). (LC/MS; m/z 510.3 $[M+H]^+$).

The following compounds were prepared in a manner similar (use of appropriate reagents and purification methods known to the person skilled in the art) to Cpd. No. 374: Cpd. No. 383 (using acetyl chloride in step 7), Cpd. No. 384 (using MsCl in step 7).

Example 139: Synthesis of 1-(6-(4-fluorophenyl)-4-(1-methyl-1H-pyrazol-3-yl)pyridin-3-yl)piperidine-4-carbonitrile (Cpd. No. 399) and 1-(6-(4-fluorophenyl)-4-(1-methyl-1H-pyrazol-3-yl)pyridin-3-yl)piperidine-4-carboxylic acid (Cpd. No. 385)

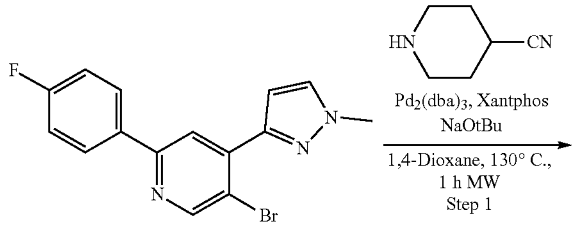

Int-78

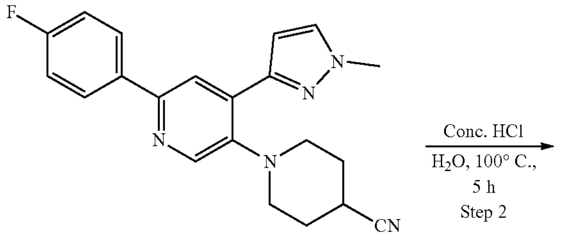

Cpd. No. 399

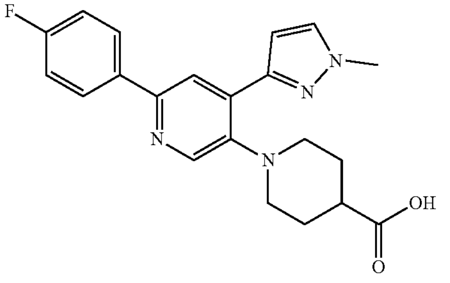

Cpd. No. 385

Step 1: A solution of Int-78 (400 mg, 1.20 mmol) in 1,4-dioxane (5 mL) was treated with piperidine-4-carbonitrile (132 mg, 1.20 mmol), Xantphos (69 mg, 0.12 mmol) and NaOtBu (347 mg, 3.61 mmol) and was degassed with argon for 20 min followed by addition of $Pd_2(dba)_3$ (55 mg, 0.06 mmol) at room temperature. The reaction mixture was stirred at 130° C. for 1 h under microwave irradiation. Progress of the reaction was monitored by TLC (mobile phase: 40% EtOAC in pet ether. Rf: 0.3. detection: UV). The reaction mixture was filtered through Celite and washed with EtOAc (50 mL). The filtrate was washed with brine (40 mL) and dried over anhydrous $Na_2SO_4$ and concentrated under reduced pressure to afford a brown gum (380 mg, LC/MS: 56%). The crude product (157 mg) was purified by preparative HPLC method H9 and the collected fraction was concentrated under reduced pressure to afford 1-(6-(4-fluorophenyl)-4-(1-methyl-1H-pyrazol-3-yl)pyridin-3-yl)piperidine-4-carbonitrile (Cpd. No. 399) as an off-white solid (26 mg, LC/MS: 97%). (LC/MS; m/z 362.3 $[M+H]^+$).

Step 2: A solution of Cpd. No. 399 (160 mg, 0.44 mmol) in $H_2O$ (0.3 mL) was treated with concentrated HCl (1.1 mL) at room temperature. The reaction mixture was stirred at 100° C. for 5 h. Progress of the reaction was monitored by TLC (mobile phase: 10% MeOH in DCM. Rf: 0.2. detection: UV). The reaction mixture was concentrated under reduced pressure to afford a pale-yellow gum (190 mg, LC/MS: 86%). The crude compound was purified by preparative HPLC method H17 and the collected fractions were concentrated under reduced pressure to afford 1-(6-(4-fluorophenyl)-4-(1-methyl-1H-pyrazol-3-yl)pyridin-3-yl)piperidine-4-carboxylic acid (Cpd. No. 385) as an off-white solid (54 mg, LC/MS: 99.6%). (LC/MS; m/z 381.2 $[M+H]^+$).

Example 140: Synthesis of 3-chloro-5-((3-(2-(4-fluorophenyl)pyridin-4-yl)-1H-pyrazol-1-yl)methyl)-N-methylbenzamide (Cpd. No. 393)

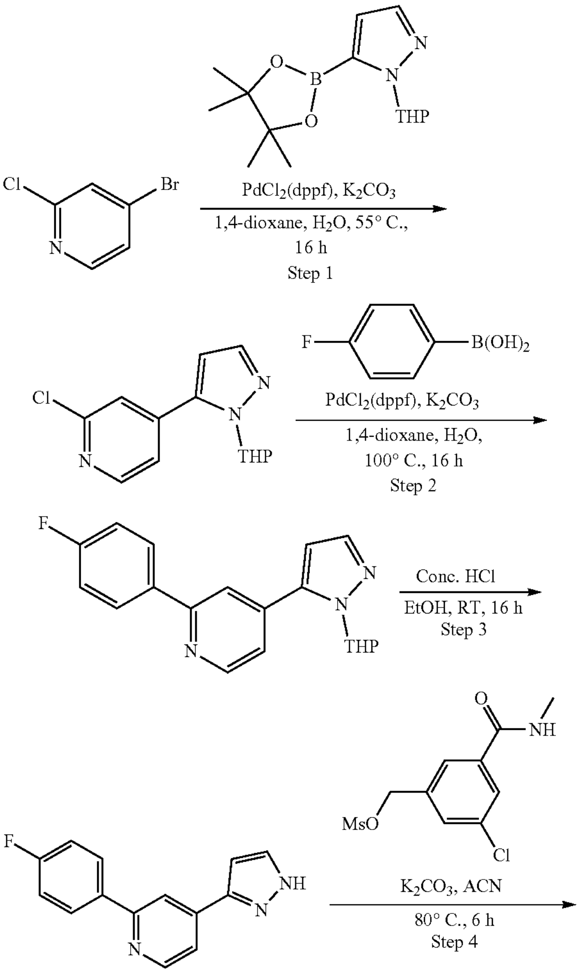

-continued

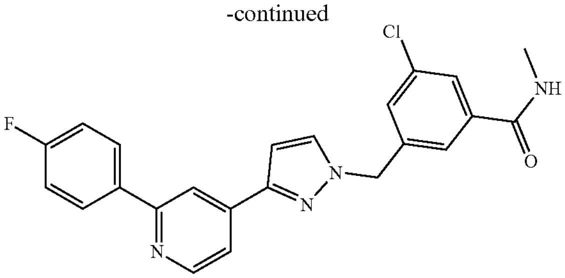

Cpd. No. 393

Step 1: A mixture of 4-bromo-2-chloropyridine (3 g, 15.58 mmol), 1-(tetrahydro-2H-pyran-2-yl)-5-(4,4,5,5-tetramethyl-1,3,2-dioxaborolan-2-yl)-1H-pyrazole (4.77 g, 17.14 mmol) and $K_2CO_3$ (6.45, 46.76 mmol) in 1,4-dioxane (60 mL) and $H_2O$ (9 mL) was degassed with argon for 20 min followed by addition of $PdCl_2$(dppf) (578 mg, 0.77 mmol) at room temperature. The reaction mixture was stirred at 55° C. for 16 h under argon. Progress of the reaction was monitored by TLC (mobile phase: 30% EtOAc in pet ether. Rf: 0.35. detection: UV). The reaction mixture was filtered through a Celite bed and washed with EtOAc (150 mL). The filtrate was washed with brine (2×100 mL) and dried over anhydrous $Na_2SO_4$ and concentrated under reduced pressure to afford the crude product (3.5 g, LC/MS: 29%). The crude product was purified by normal phase column chromatography using a 24 g column and 20% EtOAc in Pet ether as an eluent to afford 2-chloro-4-(1-(tetrahydro-2H-pyran-2-yl)-1H-pyrazol-5-yl)pyridine as an off-white solid (2.1 g, LC/MS: 62%). (LC/MS; m/z 264.1 $[M+H]^+$).

Step 2: A mixture of 2-chloro-4-(1-(tetrahydro-2H-pyran-2-yl)-1H-pyrazol-5-yl)pyridine (2.1 g, 7.96 mmol), (4-fluorophenyl)boronic acid (1.33 g, 9.55 mmol) and $K_2CO_3$ (3.29 g, 23.88 mmol) in 1,4-dioxane (26 mL) and $H_2O$ (4 mL) was degassed with argon for 20 min followed by addition of $PdCl_2$(dppf) (295 mg, 0.39 mmol) at room temperature. The reaction mixture was stirred at 100° C. for 16 h under argon. Progress of the reaction was monitored by TLC (mobile phase: 30% EtOAc in pet ether. Rf: 0.3. detection: UV). The reaction mixture was filtered through a Celite bed and washed with EtOAc (100 mL). The filtrate was washed with brine (100 ml) and dried over anhydrous $Na_2SO_4$ and concentrated under reduced pressure to afford a yellow gum (2.5 g, LC/MS: 67%). The crude product was purified by normal phase column chromatography using a 24 g column (silica) and 20% EtOAc in Pet ether as an eluent to afford 2-(4-fluorophenyl)-4-(1-(tetrahydro-2H-pyran-2-yl)-1H-pyrazol-5-yl)pyridine as an off-white solid (1.5 g, LC/MS: 56%). (LC/MS; m/z 324.3 $[M+H]^+$).

Step 3: A solution of 2-(4-fluorophenyl)-4-(1-(tetrahydro-2H-pyran-2-yl)-1H-pyrazol-5-yl)pyridine 3 (1.5 g, 4.63 mmol) in EtOH (35 mL) was treated with concentrated HCl (3.3 mL) at room temperature. The reaction mixture was stirred at room temperature for 16 h and progress of the reaction was monitored by TLC (mobile phase: 50% EtOAc in pet ether. Rf: 0.2. detection: UV). The reaction mixture was diluted with DEE (50 mL) and the resulting solid was collected by filtration and dried under high vacuum to afford 2-(4-fluorophenyl)-4-(1H-pyrazol-3-yl)pyridine as a white solid (750 mg, LC/MS: 93%). (LC/MS; m/z 240.1 $[M+H]^+$).

Step 4: A solution of 2-(4-fluorophenyl)-4-(1H-pyrazol-3-yl)pyridine (400 mg, 1.67 mmol) in ACN (20 mL) was treated with Int-F (557 mg, 2.00 mmol) and $K_2CO_3$ (692 mg, 5.01 mmol) at room temperature. The reaction mixture was stirred at 80° C. for 6 h and reaction progress was monitored by TLC (mobile phase: 60% EtOAc in pet ether. Rf: 0.2. detection: UV). The reaction mixture was concentrated under reduced pressure and the residue was diluted with water (100 mL) and extracted with ethyl acetate (2×100 mL). The combined organic layer was washed with brine (50 mL), dried over anhydrous $Na_2SO_4$ and concentrated under reduced pressure to afford a brown solid (470 mg, LC/MS: 79%). The crude product was purified by preparative HPLC method H18 and the collected fractions were concentrated under reduced pressure to afford 3-chloro-5-((3-(2-(4-fluorophenyl)pyridin-4-yl)-1H-pyrazol-1-yl)methyl)-N-methylbenzamide (Cpd. No. 393) as a white solid (200 mg, LC/MS: 99.4%). (LC/MS; m/z 421.3 $[M+H]^+$).

The following compound was prepared in a manner similar (use of appropriate reagents and purification methods known to the person skilled in the art) to Cpd. No. 393: Cpd. No. 418.

Synthesis of tert-butyl 3-(6-chloro-4-(1-methyl-1H-pyrazol-3-yl)pyridin-3-yl)-2,5-dihydro-1H-pyrrole-1-carboxylate (Int-79) and tert-butyl 3-(6-chloro-4-(1-methyl-1H-pyrazol-3-yl)pyridin-3-yl)pyrrolidine-1-carboxylate (Int-80)

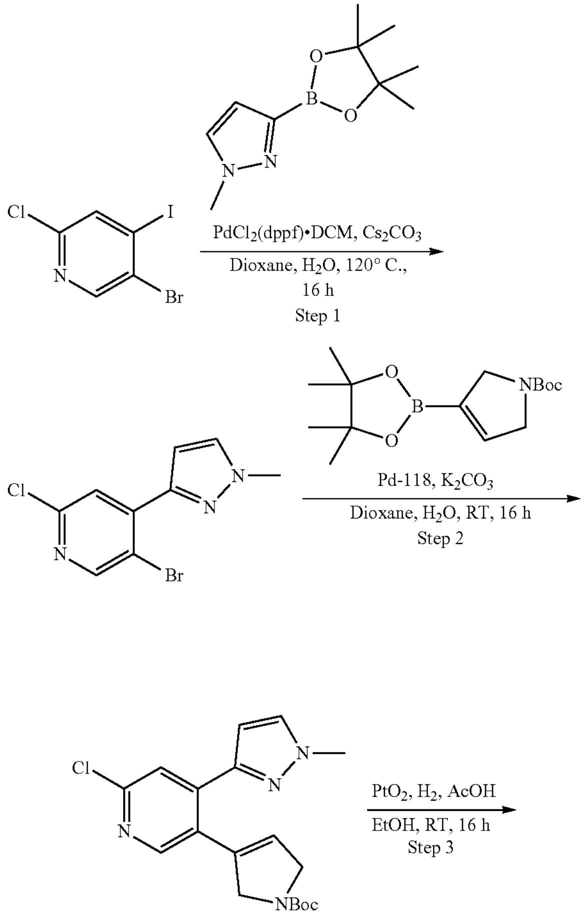

Int-79

-continued

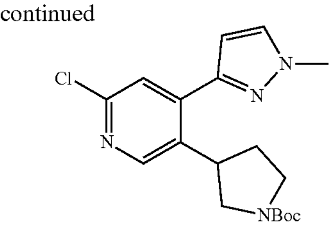

Int-80

Step 1: A solution of 5-bromo-2-chloro-4-iodopyridine (12.0 g, 37.69 mmol) in 1,4-dioxane (25 mL) was treated with 1-methyl-3-(4,4,5,5-tetramethyl-1,3,2-dioxaborolan-2-yl)-1H-pyrazole (14.11 g, 67.85 mmol) and $Cs_2CO_3$ (36.84 g, 113.08 mmol) in $H_2O$ (7.0 mL) was degassed with argon for 5 min and then $PdCl_2$(dppf)·DCM (0.615 g, 0.75 mmol) was added. The mixture was stirred at 120° C. for 16 h in a sealed tube. Progress of the reaction was monitored by TLC. (mobile phase: 20% EtOAc in pet-ether, Rf: 0.40, detection: UV). The reaction mixture was cooled to room temperature and diluted with EtOAc (30 mL), filtered through a Celite pad, washed with EtOAc (25 mL) and the filtrate was concentrated under reduced pressure to obtain a pale yellow solid (14 g). The crude product was purified by normal phase chromatography using an 80 g column (silica) and a 8% EtOAc in pet ether as an eluent to afford 5-bromo-2-chloro-4-(1-methyl-1H-pyrazol-3-yl) pyridine as an off-white solid (5.70 g, LC/MS: 94%). (LC/MS; m/z 274.0 $[M+H]^+$).

Step 2: A stirred solution of 5-bromo-2-chloro-4-(1-methyl-1H-pyrazol-3-yl)pyridine (4.0 g, 14.67 mmol) in 1,4-dioxane (20 mL) was treated with tert-butyl 3-(4,4,5,5-tetramethyl-1,3,2-dioxaborolan-2-yl)-2,5-dihydro-1H-pyrrole-1-carboxylate (6.499 g, 22.01 mmol) and a solution of $K_2CO_3$ (6.08 g, 44.03 mmol) in $H_2O$ (5 mL). The mixture was degassed with argon for 5 min, followed by the addition of Pd-118 (0.191 g, 0.29 mmol). The reaction mixture was stirred at room temperature for 16 h. Progress of the reaction was monitored by TLC (mobile phase: 30% EtOAc in pet-ether, Rf: 0.31, detection: UV). The reaction mixture was filtered through a Celite pad, washed with EtOAc (50 mL) and the filtrate was concentrated under reduced pressure to obtain a brown gum (5.0 g, LC/MS: 74%). The crude product was purified by normal phase chromatography (silica) using a 40 g column and 15% EtOAc in pet ether as eluent to afford tert-butyl 3-(6-chloro-4-(1-methyl-1H-pyrazol-3-yl)pyridin-3-yl)-2,5-dihydro-1H-pyrrole-1-carboxylate (Int-79) as a brown gum (3.50 g, LC/MS: 85%). (LC/MS; m/z 361.2 $[M+H]^+$).

Step 3: A solution of Int-79 (3.0 g, 8.31 mmol) in EtOH (30 mL) was treated with $PtO_2$ (150 mg) and AcOH (0.499 mg, 0.008) and stirred at room temperature for 16 h under $H_2$ atmosphere (balloon pressure). The progress of the reaction was monitored by TLC (mobile phase: 50% EtOAc in Pet-ether; Rf: 0.24, detection: UV). The reaction mixture was filtered through a Celite pad, washed with EtOH (20 mL) and the filtrate was concentrated under reduced pressure to obtain a black gum (3.20 g). The crude product was purified by normal phase chromatography using a 40 g column (silica) and 30% EtOAc in pet ether as an eluent to afford tert-butyl 3-(6-chloro-4-(1-methyl-1H-pyrazol-3-yl) pyridin-3-yl)pyrrolidine-1-carboxylate (Int-80) as a brown gum (2.10 g, LC/MS: 84%). (LC/MS; m/z 363.4 $[M+H]^+$).

Example 141: Synthesis of 1-(3-(4-(1-methyl-1H-pyrazol-3-yl)-6-(3,3,4,4-tetrafluoro-pyrrolidin-1-yl) pyridin-3-yl)pyrrolidin-1-yl)prop-2-en-1-one (Cpd. No. 406)

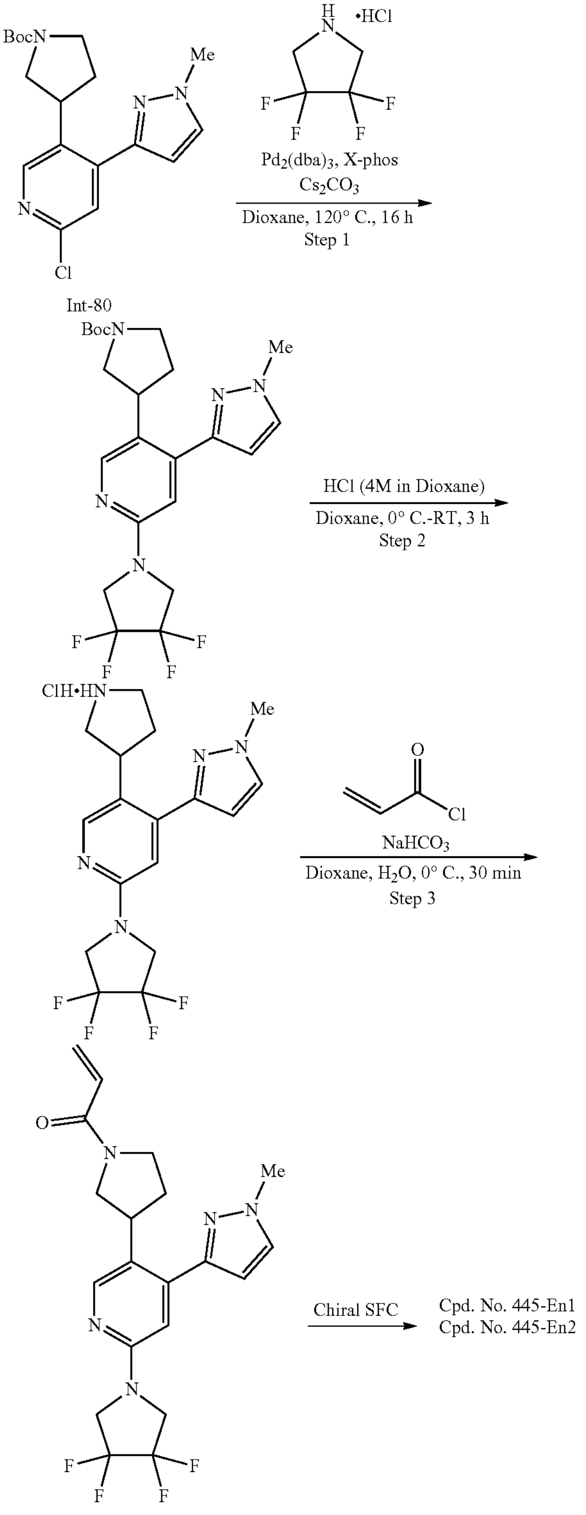

Cpd. No. 406

Step 1: A solution of Int-80 (300 mg, 0.82 mmol) in 1,4-dioxane (20 mL) was treated with 3,3,4,4-tetrafluoropyrrolidine hydrochloride (444.22 mg, 2.48 mmol) and $Cs_2CO_3$ (1.34 g, 4.13 mmol) and was degassed with argon for 10 min, then $Pd_2(dba)_3$ (7.57 mg, 0.008 mmol) and X-phos (7.87 mg, 0.017 mmol) were added. The reaction mixture was stirred at 120° C. for 16 h in a sealed tube and progress of the reaction was monitored by TLC (mobile phase: 50% EtOAc in pet-ether, Rf: 0.16, detection: UV). The reaction mixture was filtered through a Celite pad, washed with EtOAc (50 mL) and the filtrate was concentrated under reduced pressure to obtain the crude product (350 mg). The crude product was purified by normal phase chromatography using a 24 g column (silica) and an eluent of 30% EtOAc in pet ether to afford tert-butyl 3-(4-(1-methyl-1H-pyrazol-3-yl)-6-(3,3,4,4-tetrafluoropyrrolidin-1-yl)pyridin-3-yl)pyrrolidine-1-carboxylate (210 mg, LC/MS: 90%). (LC/MS; m/z 470.4 $[M+H]^+$).

Step 2: A solution of tert-butyl 3-(4-(1-methyl-1H-pyrazol-3-yl)-6-(3,3,4,4-tetrafluoropyrrolidin-1-yl)pyridin-3-yl) pyrrolidine-1-carboxylate (200 mg, 0.42 mmol) in 1,4-dioxane (15 mL) was treated with HCl (4 M in dioxane) (5.0 mL) at 0° C. The reaction mixture was stirred at room temperature for 3 h. Progress of the reaction was monitored by TLC. (mobile phase: 5% MeOH in DCM, Rf: 0.04, detection: UV). The reaction mixture was concentrated under reduced pressure to afford 4-(1-methyl-1H-pyrazol-3-yl)-5-(pyrrolidin-3-yl)-2-(3,3,4,4-tetrafluoropyrrolidin-1-yl) pyridine hydrochloride as a brown gum (180 mg, LC/MS: 93%). (LC/MS; m/z 370.3 $[M+H]^+$).

Step 3: A solution of 4-(1-methyl-1H-pyrazol-3-yl)-5-(pyrrolidin-3-yl)-2-(3,3,4,4-tetrafluoropyrrolidin-1-yl)pyridine hydrochloride (170 mg, 0.41 mmol) in 1,4-dioxane (12 mL) and water (5 mL) was cooled to 0° C., and treated with $NaHCO_3$ (177.82 mg, 2.09 mmol) followed by a solution of acryloyl chloride (45.49 mg, 0.50 mmol) in 1,4-dioxane (3.0 mL). The reaction mixture was stirred at 0° C. for 30 min and progress of the reaction was monitored by TLC (mobile phase: 70% EtOAc in Pet-ether, RF: 0.34. detection: UV). The reaction mixture was diluted with $H_2O$ (20 mL) and extracted with EtOAc (2×15 mL). The combined organic layer was washed with brine (20 mL), dried over anhydrous $Na_2SO_4$ and concentrated under reduced pressure to obtain the crude procut (160 mg, LC/MS: 59%). The crude product was purified by preparative HPLC method H17 and the collected fraction was lyophilized to afford 1-(3-(4-(1-methyl-1H-pyrazol-3-yl)-6-(3,3,4,4-tetrafluoropyrrolidin-1-yl)pyridin-3-yl)pyrrolidin-1-yl)prop-2-en-1-one (Cpd. No. 406) as an off-white sticky solid (14 mg, LC/MS: 99%). (LC/MS; m/z 424.3 $[M+H]^+$). Chiral SFC purification: 178 mg of Cpd. No. 406 was purified by preparative SFC method K8 to afford Cpd. No. 445-En1 (73 mg) and Cpd. No. 445-En2 (67 mg), both as an off-white solid. The chiral purity of both enantiomers was assessed by analytical SFC method S9: Cpd. No. 445-En1 (99.8% ee); Cpd. No. 445-En2 (99.4% ee).

The following compounds were prepared in a manner similar (use of appropriate reagents and purification methods known to the person skilled in the art) to Cpd. No. 406: Cpd. No. 398, Cpd. No. 407, Cpd. No. 408, Cpd. No. 421, Cpd. No. 422, Cpd. No. 423, Cpd. No. 424, Cpd. No. 427, Cpd. No. 431, Cpd. No. 432, Cpd. No. 433, Cpd. No. 451.

The following single enantiomers were isolated in a manner similar (use of appropriate purification methods known to the person skilled in the art) to Cpd. No. 445-En1 and Cpd. No. 445-En2: Cpd. No. 462-En1 (99.7% ee), Cpd. No. 462-En2 (97% ee), Cpd. No. 462-En3 (99.9% ee), Cpd. No. 462-En4 (99.6% ee), Cpd. No. 463-En1 (99.9% ee), Cpd. No. 463-En2 (98.6% ee), Cpd. No. 463-En3 (99.9% ee), Cpd. No. 463-En4 (99.9% ee).

Example 142: Synthesis of 1-(3-(6-(3,3-dimethylpyrrolidin-1-yl)-4-(1-methyl-1H-pyrazol-3-yl)pyridin-3-yl)pyrrolidin-1-yl)prop-2-en-1-one (Cpd. No. 430)

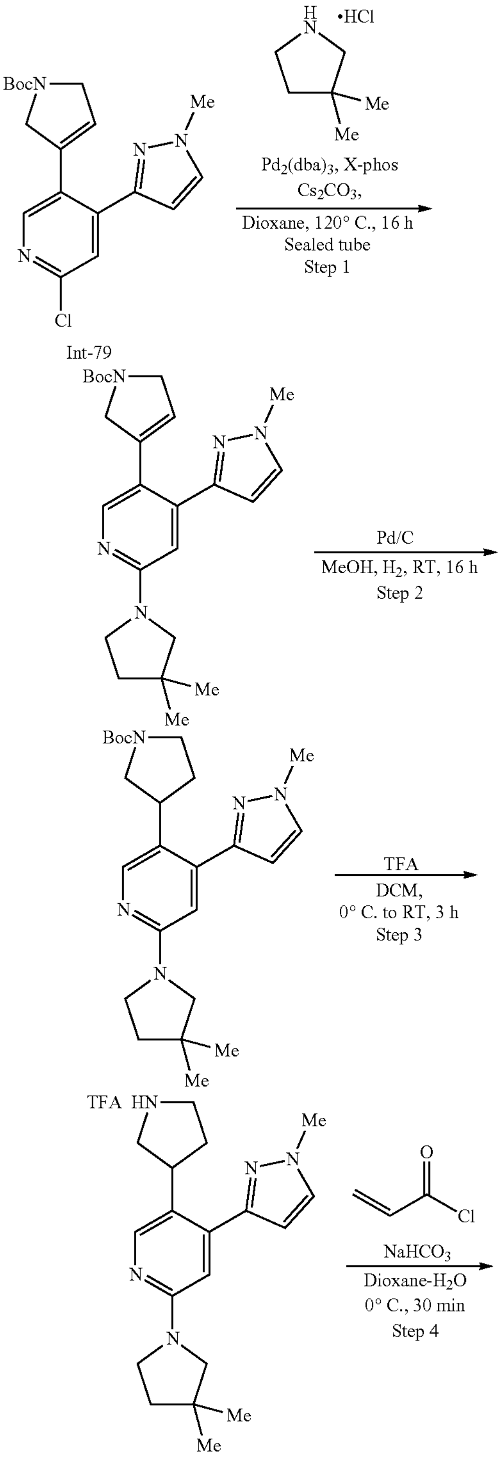

-continued

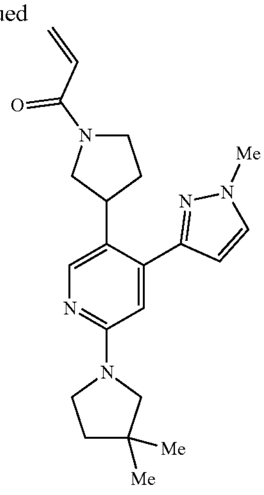

Cpd. No. 430

Step 1: A solution of Int-79 (400 mg, 1.109 mmol) in 1,4-dioxane (6 mL) was treated with 3,3-dimethylpyrrolidine HCl salt (300.630 mg, 2.217 mmol) and $Cs_2CO_3$ (1805.887 mg, 5.543 mmol). The reaction mixture was degassed with argon for 10 min followed by addition of $Pd_2(dba)_3$ (50.754 mg, 0.055 mmol) and X-phos (52.843 mg, 0.111 mmol). The reaction mixture was stirred at 120° C. for 16 h in a sealed tube and the progress of the reaction was monitored by TLC (mobile phase: 50% EtOAc in pet ether, Rf: 0.19, detection: UV). The reaction mixture was filtered through a pad of Celite and washed with EtOAc (50 mL). The filtrate was washed with $H_2O$ (50 mL). The organic layer was dried over anhydrous $Na_2SO_4$ and concentrated under reduced pressure to afford a pale brown semi solid (600 mg, LC/MS: 35%). The crude compound was purified by column chromatography by using silica gel and a gradient of 20-30% EtOAc in pet ether as eluent. The pure fractions were collected and concentrated under reduced pressure to afford tert-butyl 3-(6-(3,3-dimethylpyrrolidin-1-yl)-4-(1-methyl-1H-pyrazol-3-yl)pyridin-3-yl)-2,5-dihydro-1H-pyrrole-1-carboxylate as a pale brown semi solid (130 mg, LC/MS: 88% of desired). (LC/MS; m/z 424.4 $[M+H]^+$).

Step 2: A solution of tert-butyl 3-(6-(3,3-dimethylpyrrolidin-1-yl)-4-(1-methyl-1H-pyrazol-3-yl)pyridin-3-yl)-2,5-dihydro-1H-pyrrole-1-carboxylate (130 mg, 0.307 mmol) in MeOH (5 mL) was treated with 10% Pd/C (50% moist) (60 mg) at room temperature. The reaction mixture was stirred at room temperature for 16 h under $H_2$ (balloon). The reaction was monitored by TLC (mobile phase: 50% EtOAc in pet ether, Rf: 0.53. detection: UV). The reaction mixture was filtered through a pad of Celite and washed with MeOH (50 mL). The filtrate was concentrated under reduced pressure to afford tert-butyl 3-(6-(3,3-dimethylpyrrolidin-1-yl)-4-(1-methyl-1H-pyrazol-3-yl)pyridin-3-yl)pyrrolidine-1-carboxylate as a pale brown semi solid (130 mg, LC/MS 86%). (LC/MS; m/z 426.6 $[M+H]^+$).

Step 3: A solution of tert-butyl 3-(6-(3,3-dimethylpyrrolidin-1-yl)-4-(1-methyl-1H-pyrazol-3-yl)pyridin-3-yl)pyrrolidine-1-carboxylate (130 mg, 0.305 mmol) in DCM (5 mL) was treated with TFA (1 mL) at 0° C. The reaction mixture was stirred at room temperature for 3 h and monitored by TLC (mobile phase: 10% MeOH in DCM, Rf: 0.15, detection: UV). The reaction mixture was concentrated under reduced pressure and washed with n-pentane (10 mL) to afford 2-(3,3-dimethylpyrrolidin-1-yl)-4-(1-methyl-1H-pyrazol-3-yl)-5-(pyrrolidin-3-yl)pyridine TFA salt as a pale brown semi solid (100 mg, LC/MS: 82%). (LC/MS; m/z 326.5 $[M+H]^+$).

Step-4: A solution of 2-(3,3-dimethylpyrrolidin-1-yl)-4-(1-methyl-1H-pyrazol-3-yl)-5-(pyrrolidin-3-yl)pyridine TFA salt (100 mg, 0.307 mmol) in 1,4-dioxane (4 mL) and water (1 mL) was cooled to 0° C., treated with $NaHCO_3$ (129.052 mg, 1.536 mmol) and a solution of acryloyl chloride (30.590 mg, 0.338 mmol) in 1,4-dioxane (1 mL) under nitrogen atmosphere. The reaction mixture was stirred at 0° C. for 30 min and monitored by TLC (mobile phase: 10% MeOH in DCM, Rf: 0.45. detection: UV). The reaction mixture was diluted with $H_2O$ (20 mL) and extracted with EtOAc (2×20 mL). The organic layer was washed with brine (10 mL), dried over anhydrous $Na_2SO_4$ and concentrated under reduced pressure to afford a pale brown semi solid (100 mg, LC/MS: 73%). The crude product was purified by preparative HPLC method H1 and the pure fractions were concentrated under reduced pressure to afford 1-(3-(6-(3,3-dimethylpyrrolidin-1-yl)-4-(1-methyl-1H-pyrazol-3-yl)pyridin-3-yl)pyrrolidin-1-yl)prop-2-en-1-one (Cpd. No. 430) as an off-white solid (23 mg, LC/MS: 99%). (LC/MS; m/z 380.4 $[M+H]^+$).

The following compounds were prepared in a manner similar (use of appropriate reagents and purification methods known to the person skilled in the art) to Cpd. No. 430: Cpd. No. 438, Cpd. No. 439, Cpd. No. 441, Cpd. No. 442, Cpd. No. 446, Cpd. No. 447.

The racemic compound Cpd. No. 439 (85 mg) was purified by Chiral SFC method $K_6$ to afford Cpd. No. 439-En1 (22 mg) and Cpd. No. 439-En2 (24 mg), both as an off-white solid. The chiral purity of both enantiomers was assessed by analytical SFC method S7: Cpd. No. 439-En1 (99.9% ee); Cpd. No. 439-En2 (99.4% ee).

The following single enantiomers were isolated in a manner similar (use of appropriate purification methods known to the person skilled in the art) to Cpd. No. 439-En1 and Cpd. No. 439-En2: Cpd. No. 458-En1 (99.3% ee), Cpd. No. 458-En2 (99.3% ee).

Example 143: Synthesis of 2-((((6-(4-fluorophenyl)-4-(1-methyl-1H-pyrazol-3-yl)pyridin-3-yl)methyl)amino)methyl)acrylic acid (Cpd. No. 412)

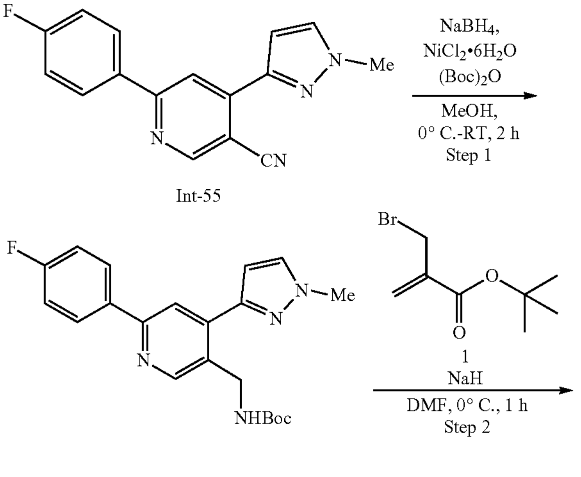

-continued

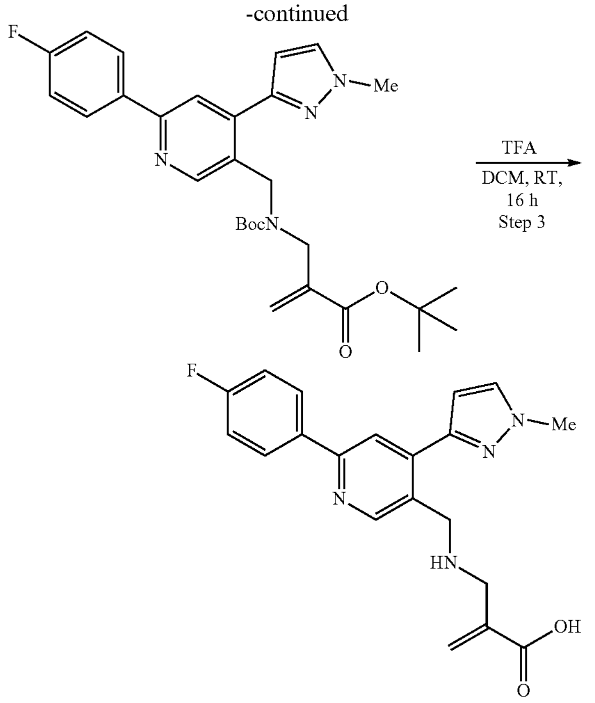

Cpd. No. 412

Step 1: A solution of Int-55 (2 g, 7.18 mmol) in MeOH (40 mL) was treated with $NiCl_2 \cdot 6H_2O$ (1.02 g, 4.31 mmol), $(Boc)_2O$ (1.88 g, 8.62 mmol) and $NaBH_4$ (1.91 g, 50.30 mmol) at 0° C. The reaction mixture was stirred at room temperature for 2 h. Progress of the reaction was monitored by TLC (mobile phase: 30% EtOAc in Pet ether. Rf: 0.28. Detection: UV). The reaction mixture was filtered through a Celite pad and washed with EtOAc (100 mL). The filtrate was washed with brine (3x30 mL), dried over anhydrous $Na_2SO_4$ and concentrated under reduced pressure to afford a yellow solid (1.75 g, LC/MS: 78%). The crude product was purified by normal phase column chromatography using a 24 g column (silica) and 20% EtOAc in Pet ether as an eluent to afford tert-butyl ((6-(4-fluorophenyl)-4-(1-methyl-1H-pyrazol-3-yl)pyridin-3-yl)methyl)carbamate as an off-white solid (1.4 g, LC/MS: 93%). (LC/MS; m/z 383.2 $[M+H]^+$).

Step 2: A solution of tert-butyl ((6-(4-fluorophenyl)-4-(1-methyl-1H-pyrazol-3-yl)pyridin-3-yl)methyl)carbamate (50 mg, 0.13 mmol) in DMF (0.5 mL) was treated with NaH (16 mg, 0.65 mmol, 60%) and tert-butyl 2-(bromomethyl)acrylate (43 mg, 0.19 mmol) at 0° C. The reaction mixture was stirred at 0° C. for 1 h and progress of the reaction was monitored by TLC (mobile phase: 30% EtOAc in Pet ether. Rf: 0.4. detection: UV). The reaction mixture was quenched with ice cold water (10 mL) and extracted with EtOAc (2x20 mL). The organic layer was washed with cold water (2x10 mL) and brine (10 mL), dried over anhydrous $Na_2SO_4$ and concentrated under reduced pressure to afford tert-butyl 2-(((tert-butoxycarbonyl)((6-(4-fluorophenyl)-4-(1-methyl-1H-pyrazol-3-yl)pyridin-3-yl)methyl)amino)methyl)acrylate as a yellow gum (60 mg, LC/MS: 71%). (LC/MS; m/z 523.5 $[M+H]^+$).

Step 3: A solution of tert-butyl 2-(((tert-butoxycarbonyl)((6-(4-fluorophenyl)-4-(1-methyl-1H-pyrazol-3-yl)pyridin-3-yl)methyl)amino)methyl)acrylate (200 mg, 0.38 mmol) in DCM (1 mL) was treated with TFA (0.29 mL) at 0° C. The reaction mixture was stirred at room temperature for 16 h and progress of the reaction was monitored by TLC (mobile phase: 10% MeOH in DCM. Rf: 0.05. detection: UV). The reaction mixture was concentrated under reduced pressure and the residue was diluted with water (10 mL) and the pH was adjusted to 8 by addition of saturated $NaHCO_3$. Then the pH adjusted to 2 by addition of 0.1 M formic acid in water. The aqueous layer was extracted with EtOAc (2x200 mL) and the combined organic layer was dried over anhydrous $Na_2SO_4$ and concentrated under reduced pressure to afford a yellow gum (184 mg, LC/MS: 57%). The crude product was purified by preparative HPLC method H19 and the collected fractions were concentrated under reduced pressure to afford an off-white solid (24 mg, LC/MS: 79%). This solid was further purified by preparative HPLC method H13 and the collected fractions were concentrated under reduced pressure to afford 2-((((6-(4-fluorophenyl)-4-(1-methyl-1H-pyrazol-3-yl)pyridin-3-yl)methyl)amino)methyl)acrylic acid (Cpd. No. 412) as a white solid (11.6 mg, LC/MS: 98%). (LC/MS; m/z 367.3 $[M+H]^+$).

Example 144: Synthesis of 1-(3-(6-methyl-4-(1-methyl-1H-pyrazol-3-yl)pyridin-3-yl) pyrrolidin-1-yl)prop-2-en-1-one (Cpd. No. 413)

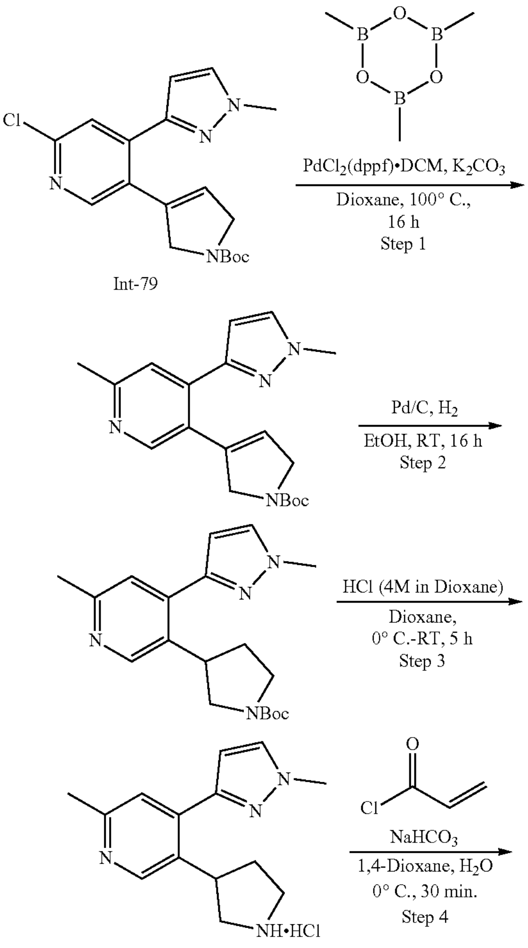

-continued

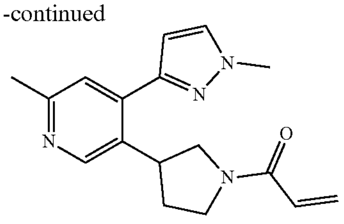

Cpd. No. 413

Step 1: A solution of Int-79 (550 mg, 1.52 mmol) in 1,4-dioxane (15 mL) was treated with 2,4,6-trimethyl-1,3,5,2,4,6-trioxatriborinane (0.460 ml, 1.82 mmol, (50% in THF)) and $K_2CO_3$ (737.31 mg, 5.33 mmol) and degassed with argon for 5 min. $PdCl_2$(dppf)·DCM (24.87 mg, 0.03 mmol) was then added and the reaction mixture was stirred at 100° C. for 16 h in sealed tube. Progress of the reaction was monitored by TLC (mobile phase: 30% EtOAc in pet-ether, Rf: 0.09, detection: UV). The reaction mixture was cooled to room temperature and diluted with EtOAc (15 mL), filtered through a Celite pad, washed with EtOAc (10 mL) and the filtrate was concentrated under reduced pressure to afford a brown gum (650 mg, LC/MS: 48%). The crude product was purified by normal phase chromatography using a 24 g column (silica) and 15% EtOAc in pet ether as an eluent to afford tert-butyl 3-(6-methyl-4-(1-methyl-1H-pyrazol-3-yl)pyridin-3-yl)-2,5-dihydro-1H-pyrrole-1-carboxylate as a brown gum (400 mg, LC/MS: 90%). (LC/MS; m/z 341.3 $[M+H]^+$).

Step 2: A solution of tert-butyl 3-(6-methyl-4-(1-methyl-1H-pyrazol-3-yl) pyridin-3-yl)-2,5-dihydro-1H-pyrrole-1-carboxylate (400 mg, 1.17 mmol) in EtOH (10 mL) was treated with Pd/C (10% wet) (100 mg) and stirred at room temperature for 16 h under $H_2$ atmosphere (balloon pressure). The progress of the reaction was monitored by TLC (mobile phase: 40% EtOAc in Pet-ether; Rf: 0.24, detection: UV). The reaction mixture was filtered through a Celite pad, washed with EtOH (20 mL), and the filtrate was concentrated under reduced pressure to afford tert-butyl 3-(6-methyl-4-(1-methyl-1H-pyrazol-3-yl)pyridin-3-yl)pyrrolidine-1-carboxylate as a colorless gum (380 mg, LC/MS: 95%). (LC/MS; m/z 343.3 $[M+H]^+$).

Step 3: A solution of tert-butyl 3-(6-methyl-4-(1-methyl-1H-pyrazol-3-yl)pyridin-3-yl)pyrrolidine-1-carboxylate (380 mg, 1.10 mmol) in 1,4-dioxane (15 mL) was treated with HCl (4 M in dioxane) (10 mL) at 0° C. The reaction mixture was stirred at room temperature for 5 h. Progress of the reaction was monitored by TLC (mobile phase: 5% MeOH on DCM, Rf: 0.04, detection: UV). The reaction mixture was concentrated under reduced pressure to afford 2-methyl-4-(1-methyl-1H-pyrazol-3-yl)-5-(pyrrolidin-3-yl) pyridine hydrochloride as a brown gummy solid (380 mg, LC/MS: 87%). (LC/MS; m/z 243.2 $[M+H]^+$).

Step 4: A solution of 2-methyl-4-(1-methyl-1H-pyrazol-3-yl)-5-(pyrrolidin-3-yl)pyridine hydrochloride (250 mg, LC/MS: 87%) in 1,4-dioxane (8.0 mL) and $H_2O$ (3.0 mL) was cooled to 0° C. and treated with $NaHCO_3$ (376.68 mg, 4.48 mmol) and a solution of acryloyl chloride (0.10 mL, 1.076 mmol) in 1,4-dioxane (2.0 mL). The reaction mixture was stirred at 0° C. for 30 min and progress of the reaction was monitored by TLC (mobile phase: 70% EtOAc in Pet-ether, RF: 0.34. detection: UV). The reaction mixture was diluted with $H_2O$ (20 mL) and extracted with EtOAc (2×15 mL). The combined organic layer was washed with brine (20 mL), dried over anhydrous $Na_2SO_4$ and concentrated under reduced pressure to obtain the crude product (200 mg, LC/MS: 91%). The crude product was purified by preparative HPLC method H18 and the collected fraction was lyophilized to afford 1-(3-(6-methyl-4-(1-methyl-1H-pyrazol-3-yl)pyridin-3-yl)pyrrolidin-1-yl) prop-2-en-1-one (Cpd. No. 413) as an off-white solid (37 mg, LC/MS: 95%). (LC/MS; m/z 297.2 $[M+H]^+$).

The following compounds were prepared in a manner similar (use of appropriate reagents and purification methods known to the person skilled in the art) to Cpd. No. 413: Cpd. No. 450, Cpd. No. 453 (using $Pd_2(dba)_3$ and XPhos in step 1), Cpd. No. 454 (using $Pd_2(dba)_3$ and XPhos in step 1).

The racemic compound Cpd. No. 450 (119 mg) was purified by Chiral SFC method K7 to afford Cpd. No. 459-En1 (41 mg) and Cpd. No. 459-En2 (34 mg), both as an off white solid. The chiral purity of both enantiomers was assessed by analytical SFC method S8: Cpd. No. 459-En1 (99.8% ee); Cpd. No. 459-En2 (98.9% ee).

The following single enantiomers were isolated in a manner similar (use of appropriate purification methods known to the person skilled in the art) to Cpd. No. 459-En1 and Cpd. No. 459-En-2: Cpd. No. 473-En1 (99.9% ee), Cpd. No. 473-En2 (99.3% ee).

Synthesis of 3-chloro-6-(4-fluorophenyl)-4-(1-methyl-1H-pyrazol-3-yl)pyridazine (Int-82)

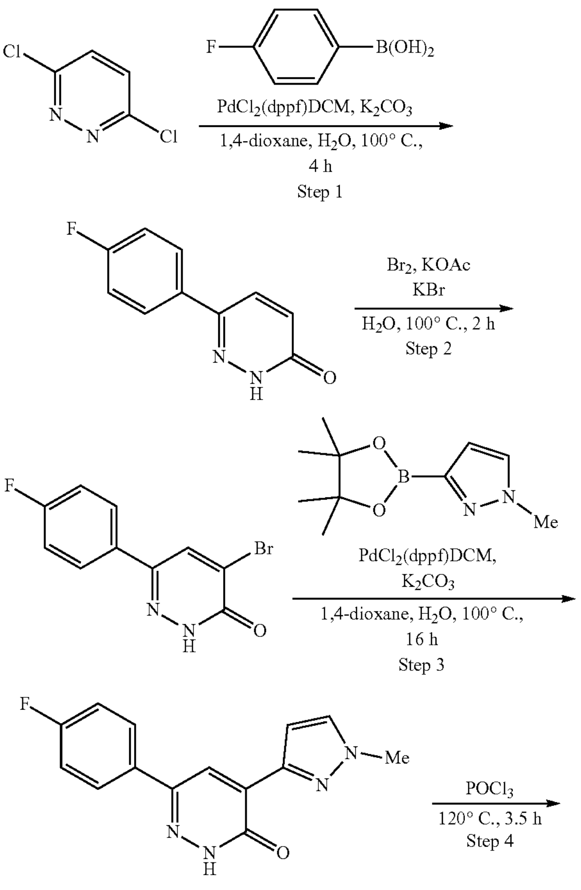

-continued

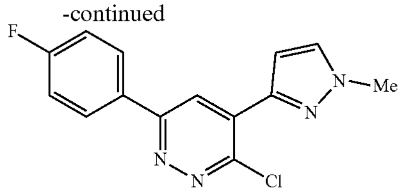

Int-82

Step 1: A solution of 3,6-dichloropyridazine (10 g, 67.12 mmol) in 1,4 dioxane (100 mL) and $H_2O$ (10 mL) was treated with (4-fluorophenyl)boronic acid (9.3 g, 67.12 mmol) and $K_2CO_3$ (27.7 g, 201.36 mmol) at room temperature. The mixture was degassed with argon for 20 min followed by addition of $PdCl_2$(dppf)·DCM (2.7 g, 3.35 mmol) at room temperature. The reaction mixture was stirred at 100° C. for 4 h. The reaction progress was monitored by TLC (mobile phase: 50% EtOAc in pet ether. Rf: 0.32. detection: UV). The reaction mixture was filtered through a pad of Celite and washed with EtOAc (800 mL). The filtrate was washed with brine (200 mL), dried over anhydrous $Na_2SO_4$ and concentrated under reduced pressure to afford a yellow gum (10 g, LC/MS: 32%). The crude product was purified by gravity column chromatography using silica gel and 40% EtOAc in pet-ether as eluent to afford 6-(4-fluorophenyl) pyridazin-3(2H)-one as a white solid (4 g, LC/MS: 82%). (LC/MS; m/z 191.1 $[M+H]^+$).

Step 2: A solution of 6-(4-fluorophenyl)pyridazin-3(2H)-one (4 g, 21.03 mmol) in $H_2O$ (100 mL) were treated with KOAc (3.09 mg, 31.55 mmol), KBr (7.5 g, 63.09 mmol) and $Br_2$ (3.2 mL, 63.09 mmol) at room temperature. The reaction mixture was stirred at 100° C. for 2 h and progress was monitored by TLC (mobile phase: 50% EtOAc in pet ether. Rf: 0.68. detection: UV). The reaction mixture was filtered and the collected solid was washed with $H_2O$ (200 mL) and dried under reduced pressure to afford 4-bromo-6-(4-fluorophenyl)pyridazin-3(2H)-one as a pale brown solid (2.0 g, LC/MS: 82%). (LC/MS; m/z 269.0 $[M+H]^+$).

Step 3: A solution of 4-bromo-6-(4-fluorophenyl) pyridazin-3(2H)-one (2 g, 7.43 mmol) in 1,4-dioxane (34 mL) and water (6 mL) was treated with 1-methyl-3-(4,4,5,5-tetramethyl-1,3,2-dioxaborolan-2-yl)-1H-pyrazole (1.54 g, 7.43 mmol) and $K_2CO_3$ (3.07 g, 22.29 mmol) at room temperature. The reaction mixture was degassed with argon for 20 minutes, followed by addition of $PdCl_2$(dppf)·DCM (304 mg, 0.37 mmol) at room temperature. The reaction mixture was stirred at 100° C. for 16 h and progress was monitored by TLC (mobile phase: 30% EtOAc in Pet ether. Rf: 0.2. detection: UV). The reaction mixture was filtered through a pad of Celite and washed with EtOAc (100 mL). The filtrate was washed with brine (100 mL), dried over anhydrous $Na_2SO_4$ and concentrated under reduced pressure to afford a pale yellow solid (2.1 g, LC/MS: 63%). The crude product was purified by normal phase column chromatography (24 g silica) using 20% EtOAc in pet ether as an eluent to afford 6-(4-fluorophenyl)-4-(1-methyl-1H-pyrazol-3-yl) pyridazin-3(2H)-one as an off-white solid (1.1 g, LC/MS: 91%). (LC/MS; m/z 271.1 $[M+H]^+$).

Step 4: $POCl_3$ (2.352 mL, 25.160 mmol) was added dropwise to 6-(4-fluorophenyl)-4-(1-methyl-1H-pyrazol-3-yl)pyridazin-3(2H)-one (1.0 g, 3.70 mmol) over a period of 10 min at room temperature. The reaction mixture was then stirred at 120° C. for 3.5 h and reaction progress was monitored by TLC (mobile phase: 50% EtOAc in pet ether. Rf: 0.35. detection: UV). The mixture was cooled to 0° C. and water (50 mL) was added. The resulting mixture was stirred at 0-5° C. for 30 min. The resulting solid was collected by filtration, washed with water and dried under high vacuum at 45° C. to afford a pale yellow solid (1.5 g, LCMS: 14%). The crude product was purified by reverse phase column chromatography (80 g RP-$C_{18}$ column) using a gradient of 30-45% MeCN in water as eluent. The collected fraction was concentrated under reduced pressure and the remaining aqueous mixture was extracted with EtOAc (3×50 mL). The combined organic extract was dried over anhydrous $Na_2SO_4$ and concentrated under reduced pressure to afford t3-chloro-6-(4-fluorophenyl)-4-(1-methyl-1H-pyrazol-3-yl)pyridazine (Int-82) as an off white solid (900 mg, LC/MS: 89%). (LC/MS; m/z 289.5 $[M+H]^+$).

The following intermediates were prepared in a manner similar (use of appropriate reagents and purification methods known to the person skilled in the art) to Int-82:

| Intermediate | Structure | Comments |
|---|---|---|
| Int-83 | 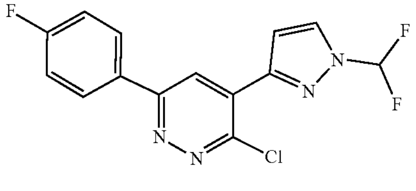 [SMILES: Fc1ccc(-c2cc(-c3ccn(C(F)F)n3)c(Cl)nn2)cc1] | Using 1-(difluoromethyl)-3-(4,4,5,5-tetramethyl-1,3,2-dioxaborolan-2-yl)-1H-pyrazole in step 3 and $SOCl_2$ in step 4 |
| Int-84 | 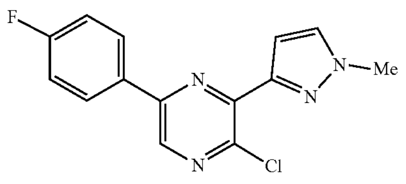 [SMILES: Cn1ccc(-c2nc(-c3ccc(F)cc3)cnc2Cl)n1] | Using 5-bromopyrazin-2(1H)-one in step 1 and NBS in step 2 |

Example 145: Synthesis of 1-(3-(5-(4-fluorophenyl)-3-(1-methyl-1H-pyrazol-3-yl)pyridin-2-yl)pyrrolidin-1-yl)prop-2-en-1-one (Cpd. No. 414)

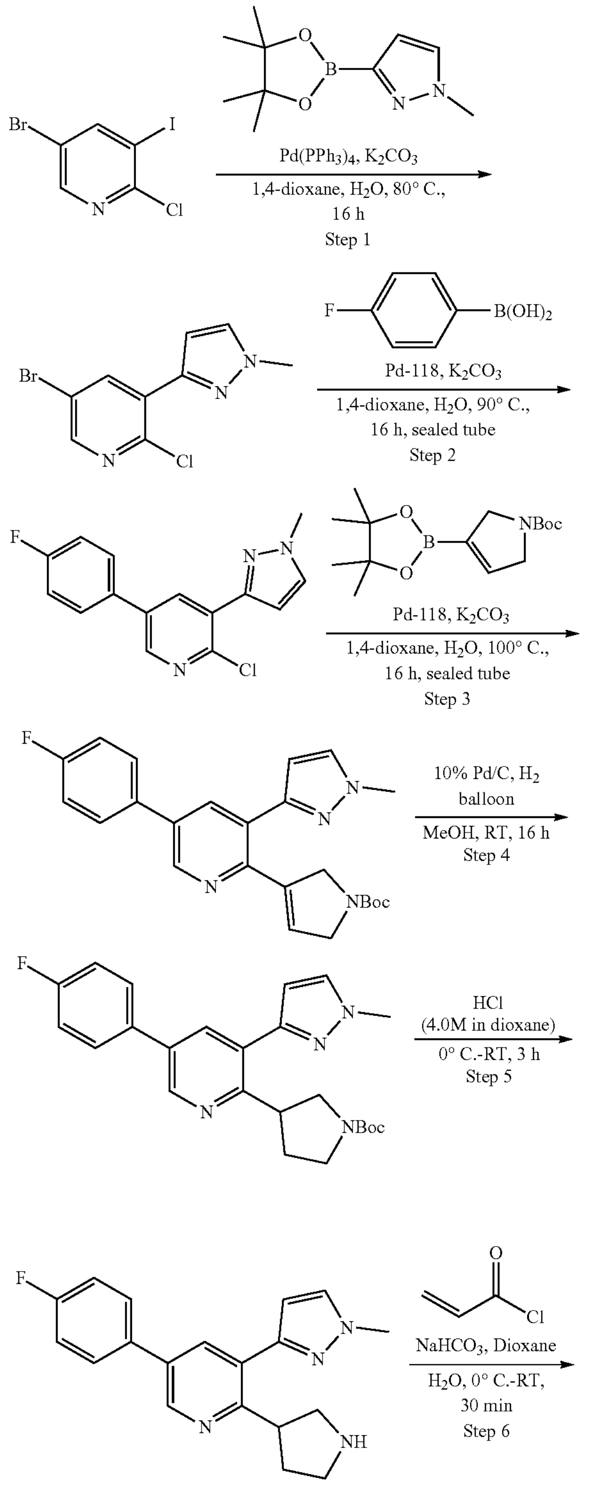

-continued

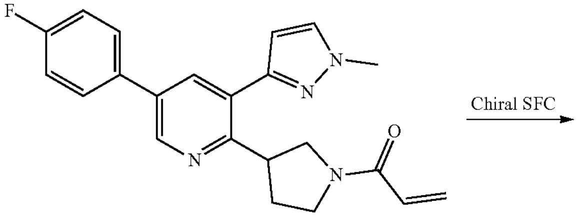

Cpd. No. 414

Cpd. No. 420-En1
Cpd. No. 420-En2

Step 1: In a glass screw-cap pressure vessel, a solution of 5-bromo-2-chloro-3-iodopyridine (5.0 g, 15.7 mmol) in 1,4-dioxane (50 ml) and water (8 mL) was treated with 1-methyl-3-(4,4,5,5-tetramethyl-1,3,2-dioxaborolan-2-yl)-1H-pyrazole (3.26 g, 15.7 mmol) and $K_2CO_3$ (5.41 g, 39.26 mmol) at room temperature. The reaction mixture was degassed by bubbling argon for 5 min, then tetrakis(triphenylphosphine) palladium (977.15 mg, 0.78 mmol) was added and the vessel was sealed with a Teflon screw-cap. The reaction mixture was stirred at 80° C. for 16 h. The progress of the reaction was monitored by TLC (mobile phase: 10% EtOAc in hexane, Rf: 0.45, detection: UV). On completion, the reaction mixture was allowed to cool to 26° C., diluted with water (50 mL) and extracted with EtOAc (2×60 mL). The combined organic layer was dried over $Na_2SO_4$ and concentrated under reduced pressure to afford crude compound as a brown gum (4.0 g, LC/MS: 43%). The crude product was purified by flash chromatography using an 80 g column (silica) and 7-8% EtOAc in pet. ether as eluent. The pure fractions were combined and concentrated under reduced pressure to afford 5-bromo-2-chloro-3-(1-methyl-1H-pyrazol-3-yl)pyridine as an off-white solid (1.9 g, LC/MS: 98%). (LC/MS; m/z 274.0 $[M+H]^+$).

Step 2: In a glass screw-cap pressure vessel, a solution of 5-bromo-2-chloro-3-(1-methyl-1H-pyrazol-3-yl)pyridine (1.9 g, 6.97 mmol) in 1,4-dioxane (20 ml) and water (4.0 mL) was treated with (4-fluorophenyl)boronic acid (1.07 g, 7.66 mmol) and $K_2CO_3$ (2.88 g, 20.9 mmol) at room temperature. The reaction mixture was degassed by bubbling argon for 10 min, then Pd-118 (227 mg, 0.35 mmol) was added and the vessel was sealed with a Teflon screw-cap. The reaction mixture was stirred at 90° C. for 16 h and progress of the reaction was monitored by TLC (mobile phase: 20% EtOAc in hexane, Rf: 0.40, TLC detection: UV). On completion, the reaction mixture was allowed to cool to 26° C., quenched with water (40 mL) and extracted with EtOAc (2×50 mL). The combined organic layers were dried over $Na_2SO_4$ and filtered. The filtrate was concentrated under reduced pressure to afford the a pale yellow oil (1.6 g, LC/MS: 80%). The crude product was purified by normal phase flash chromatography using a 40 g column (silica) eluted with 15-20% EtOAc in pet ether. The pure fractions were combined and concentrated under reduced pressure to afford 2-chloro-5-(4-fluorophenyl)-3-(1-methyl-1H-pyrazol-3-yl)pyridine) as a pale yellow solid (1.2 g, LC/MS: 92%). (LC/MS; m/z 288.2 $[M+H]^+$).

Step 3: In a glass screw-cap pressure vessel, a solution of 2-chloro-5-(4-fluorophenyl)-3-(1-methyl-1H-pyrazol-3-yl) pyridine (1.1 g, 3.82 mmol) in 1,2-dioxane (17.0 ml) and $H_2O$ (6 mL) was treated with tert-butyl 3-(4,4,5,5-tetramethyl-1,3,2-dioxaborolan-2-yl)-2,5-dihydro-1H-pyrrole-1-carboxylate (1.24 g, 4.20 mmol) and $K_2CO_3$ (1.58 g, 11.5 mmol) at room temperature. The reaction mixture was degassed by bubbling argon for 5 min, then Pd-118 (124 mg, 0.19 mmol) was added and the vessel was sealed with a Teflon screw-cap. The reaction mixture was stirred at 100° C. for 16 h. The progress of the reaction was monitored by TLC (mobile phase: 30% EtOAc in hexane, Rf=0.21, detection: UV). On completion, the reaction mixture was allowed to cool to 26° C., quenched with water (50 mL) and extracted with EtOAc (2×60 mL). The combined organic layers were dried over $Na_2SO_4$ and concentrated under reduced pressure to afford a brown oil (1.6 g, LC/MS: 74%). The crude product was purified by flash chromatography using a 40 g silica column eluted with 23-25% EtOAc in pet. ether. The pure fractions were concentrated under reduced pressure to afford tert-butyl 3-(5-(4-fluorophenyl)-3-(1-methyl-1H-pyrazol-3-yl)pyridin-2-yl)-2,5-dihydro-1H-pyrrole-1-carboxylate as a brown solid (1.2 g, LC/MS: 95%). (LC/MS; m/z 321.3 [M-Boc]*).

Step 4: To a stirred solution of tert-butyl 3-(5-(4-fluorophenyl)-3-(1-methyl-1H-pyrazol-3-yl)pyridin-2-yl)-2,5-dihydro-1H-pyrrole-1-carboxylate (1.2 g, 2.85 mmol) in MeOH (20 mL) was added 10% Pd/C (350 mg, 50% moisture) at room temperature. The resulting reaction mixture was stirred for 16 h under $H_2$ atmosphere. The progress of the reaction was monitored by TLC (mobile phase: 50% EtOAc in Hexane, Rf=0.61, detection: UV). On completion, the reaction mixture was filtered on a Celite bed and washed with MeOH (2×30 mL). The filtrate was concentrated under reduced pressure to afford the crude product which was triturated with n-pentane (2×25 mL) and dried to afford tert-butyl 3-(5-(4-fluorophenyl)-3-(1-methyl-1H-pyrazol-3-yl)pyridin-2-yl)pyrrolidine-1-carboxylate as pale yellow solid (1.1 g, LC/MS: 95%). (LC/MS; m/z 367.3 $[M-tBu]^+$).

Step 5: To a stirred solution of tert-butyl 3-(5-(4-fluorophenyl)-3-(1-methyl-1H-pyrazol-3-yl)pyridin-2-yl)pyrrolidine-1-carboxylate (1.0 g, 2.367 mmol) in DCM (25 mL) was added HCl (8 mL, 4.0 M in dioxane) at 0° C. The resulting reaction mixture was allowed to warm to 26° C. and stirred for 3 h under nitrogen atmosphere. The progress of the reaction was monitored by TLC (mobile phase: 5% MeOH/DCM, Rf=0.21, detection: UV). The reaction mixture was concentrated under reduced pressure and the residue was triturated with n-pentane (2×30 mL) and dried under vacuum to afford 5-(4-fluorophenyl)-3-(1-methyl-1H-pyrazol-3-yl)-2-(pyrrolidin-3-yl)pyridine hydrochloride as a pale yellow solid (700 mg, LC/MS: 98%). (LC/MS; m/z 323.0 $[M+H]^+$).

Step 6: A stirred solution of 5-(4-fluorophenyl)-3-(1-methyl-1H-pyrazol-3-yl)-2-(pyrrolidin-3-yl)pyridine hydrochloride (300 mg, 0.83 mmol) in 1,4-dioxane (5 mL) and water (3.0 mL) was treated with $NaHCO_3$ (351.12 mg, 3.16 mmol) and a solution of acryloyl chloride (83.23 mg, 0.92 mmol) in 1,4-dioxane (1.0 mL) at 0° C. The reaction mixture was stirred at 0° C. for 30 min at room temperature. Progress of the reaction was monitored by TLC (mobile phase: 10% MeOH in DCM, Rf: 0.52, detection: UV). The reaction mixture was diluted with water (30 mL) and extracted in EtOAc (2×40 mL). The combined organic phase was dried over $Na_2SO_4$ and concentrated under reduced pressure to get obtain a pale yellow solid (300 mg, LC/MS: 91%). The crude product was purified by preparative HPLC method H13. The pure fractions were concentrated under reduced pressure to afford 1-(3-(5-(4-fluorophenyl)-3-(1-methyl-1H-pyrazol-3-yl)pyridin-2-yl)pyrrolidin-1-yl)prop-2-en-1-one (Cpd. No. 414) as a white solid (49 mg, LC/MS: 99%). (LC/MS; m/z 377.2 $[M+H]^+$). Chiral HPLC purification: 250 mg of Cpd. No. 414 was purified by preparative chiral HPLC method K4 to afford Cpd. No. 420-En1 (32 mg) and Cpd. No. 420-En2 (42 mg), both as an off-white solid. The chiral purity of both enantiomers was assessed by chiral analytical HPLC method S3: Cpd. No. 420-En1 (99.8% ee); Cpd. No. 420-En2 (97.0% ee).

The following compounds were prepared in a manner similar (use of appropriate reagents and purification methods known to the person skilled in the art) to Cpd. No. 414: Cpd. No. 394, Cpd. No. 469 (employing Int-81 in step 3), Cpd. No. 392 (employing Int-82 in step 3), Cpd. No. 464 (employing Int-84 in step 3), Cpd. No. 465 (employing Int-83 in step 3), Cpd. No. 467 (employing Int-82 and tert-butyl-4-(4,4,5,5-tetramethyl-1,3,2-dioxaborolan-2-yl)-3,6-dihydropyridine-1(2H)-carboxylate in step 3).

The following single enantiomers were isolated in a manner similar (use of appropriate purification methods known to the person skilled in the art) to Cpd. No. 420-En1 and Cpd. No. 420-En2: Cpd. No. 396-En1 (99.9% ee), Cpd. No. 396-En2 (98.6% ee), Cpd. No. 470-En1 (99.9% ee), Cpd. No. 470-En2 (99.6% ee).

Example 146: Synthesis of 1-(3-(2-(1-methyl-1H-pyrazol-3-yl)-6-(3,3,3-trifluoropropoxy)pyridin-3-yl)pyrrolidin-1-yl)prop-2-en-1-one (Cpd. No. 434)

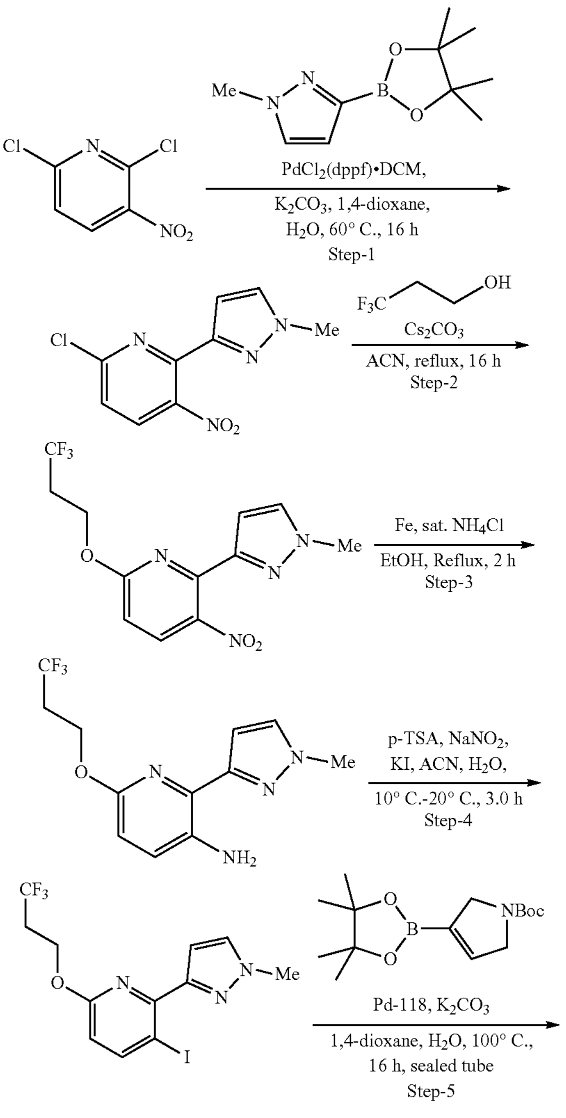

-continued

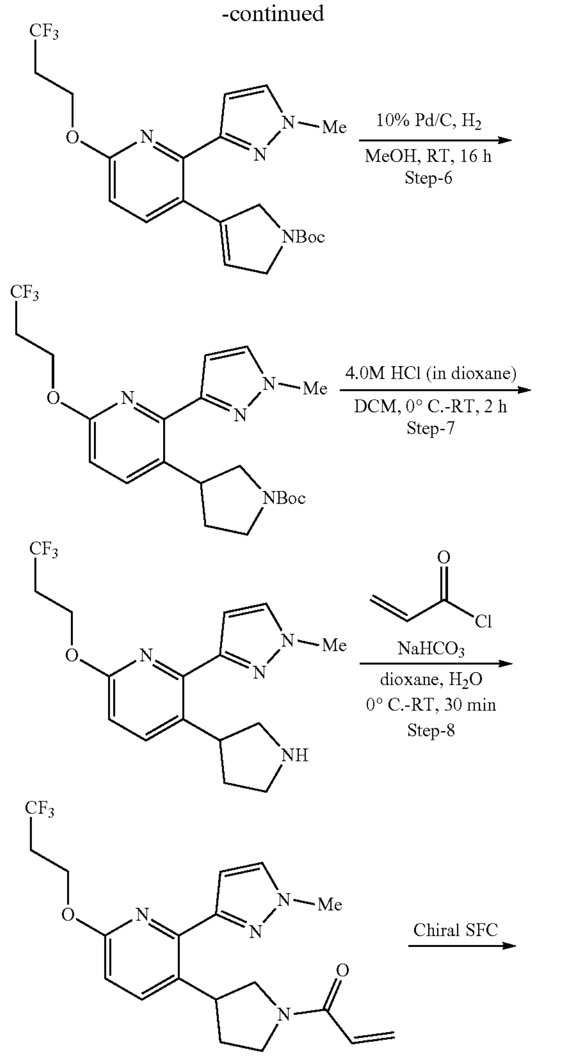

Cpd. No. 434

Cpd. No. 452-En1
Cpd. No. 452-En2

Step 1: In a glass screw-cap pressure vessel, a solution of 2,6-dichloro-3-nitropyridine (4.5 g, 23.31 mmol) in 1,4-dioxane (50 ml) and water (10 mL) was treated with 1-methyl-3-(4,4,5,5-tetramethyl-1,3,2-dioxaborolan-2-yl)-1H-pyrazole (5.33 g, 25.65 mmol) and $K_2CO_3$ (9.66 g, 69.95 mmol) at room temperature. The reaction mixture was degassed by bubbling argon for 5 min, then $PdCl_2$(dppf)·DCM (952 mg, 1.166 mmol) was added and the vessel was sealed with a Teflon screw-cap. The reaction mixture was heated and stirred at 60° C. for 16 h and monitored by TLC (mobile phase: 20% EtOAc in hexane, Rf: 0.42, detection: UV). The reaction mixture was cooled to room temperature, diluted with water (40 mL) and extracted with EtOAc (2×100 mL). The combined organic layer was dried over $Na_2SO_4$ and concentrated under reduced pressure to afford a pale brown semi-solid (5.5 g, LC/MS: 34%). The crude product purified by flash chromatography using a silica column (80 g) and a gradient of 8-10% EtOAc in pet. ether as eluent. The pure fractions were combined and concentrated under reduced pressure to afford 6-chloro-2-(1-methyl-1H-pyrazol-3-yl)-3-nitropyridine as a pale yellow solid (1.4 g, LC/MS: 89%). (LC/MS; m/z 239.1 $[M+H]^+$).

Step 2: A stirred solution of 6-chloro-2-(1-methyl-1H-pyrazol-3-yl)-3-nitropyridine (1.5 g, 6.28 mmol) in dry ACN (30 mL) was treated with 3,3,3-trifluoropropan-1-ol (860.43 mg, 7.54 mmol) followed by $Cs_2CO_3$ (8.2 g, 25.14 mmol) at room temperature. The resulting reaction mixture was refluxed for 16 h under nitrogen atmosphere. The progress of the reaction was monitored by TLC (mobile phase: 30% EtOAc in pet ether, Rf=0.44, detection: UV). On completion, the reaction mixture was cooled to room temperature and concentrated under reduced pressure. The reaction mixture was diluted with water (40 mL) and extracted with EtOAc (2×60 mL) and the combined organic layer was dried over $Na_2SO_4$ and filtered. The filtrate was concentrated under reduced pressure to afford a pale brown gummy oil (1.4 g, LC/MS: 45%). The crude product was purified by flash chromatography using a silica column (40 g) and 20% EtOAc in pet. ether as eluent. The pure fractions were combined and concentrated under reduced pressure to afford 2-(1-methyl-1H-pyrazol-3-yl)-3-nitro-6-(3,3,3-trifluoropropoxy)pyridine as a pale yellow solid. (760 mg, LC/MS: 94%). (LC/MS; m/z 317.2 $[M+H]^+$).

Step 3: A stirred solution of 2-(1-methyl-1H-pyrazol-3-yl)-3-nitro-6-(3,3,3-trifluoropropoxy)pyridine (1.65 g, 5.218 mmol) in EtOH (20 mL) was treated with iron powder (1.457 g, 26.08 mmol) and saturated solution of $NH_4Cl$ (3.5 mL) at room temperature. The reaction mixture was heated and stirred at reflux for 2 h. The progress of the reaction was monitored by TLC (mobile phase: 20% EtOAc in Pet ether; Rf: 0.05, detection: UV). The reaction mixture was cooled to room temperature, filtered and washed with EtOAc (2×20 mL). The filtrate was evaporated under reduced pressure and the residue was diluted with $H_2O$ (25 mL) and extracted with EtOAc (2×10 mL). Combined organic layers were dried over $Na_2SO_4$ and concentrated under reduced pressure to afford a brown solid (1.5 g, LC/MS: 96%). The crude product was triturated with n-pentane (2×20 mL), collected by filtration, rinsed with n-pentane, and dried under high vacuum to afford the 2-(1-methyl-1H-pyrazol-3-yl)-6-(3,3,3-trifluoropropoxy)pyridin-3-amine as an brown solid (1.4 g, LC/MS: 96%). (LC/MS; m/z 287.2 $[M+H]^+$).

Step 4: A solution of p-TSA (2.19 g, 11.52 mmol) in ACN (110 mL) was treated with 2-(1-methyl-1H-pyrazol-3-yl)-6-(3,3,3-trifluoropropoxy)pyridin-3-amine (1.1 g, 3.84 mmol) at 10° C.-15°, then a solution of $NaNO_2$ (530.3 mg, 7.68 mmol) and KI (3.19 g, 19.21 mmol) in water (10 mL) was added gradually at same temperature. The reaction mixture was stirred at 10° C. for 10 min and then the temperature was raised to 20° C. and stirred for 3 h. Progress of the reaction was monitored by TLC (mobile phase: 20% EtOAc in hexane. Rf: 0.67. detection: UV). The mixture was concentrated under reduced pressure, diluted with water (40 mL) and extracted with EtOAc (2×60 mL). The combined organic layer was washed with brine (50 mL), dried over $Na_2SO_4$ and concentrated under reduced pressure to afford a brown semi-solid (1.1 g, LC/MS: 62%). The crude product by flash chromatography using a silica column (24 g) and eluted with 20% EtOAc in pet. ether. The pure fractions were combined and concentrated under reduced pressure to afford 3-iodo-2-(1-methyl-1H-pyrazol-3-yl)-6-(3,3,3-trifluoropropoxy)pyridine as a brown liquid (900 mg, LC/MS: 86%). (LC/MS; m/z 398.1 $[M+H]^+$).

Step 5: In a glass screw-cap pressure vessel, a solution of 3-iodo-2-(1-methyl-1H-pyrazol-3-yl)-6-(3,3,3-trifluoropropoxy)pyridine (1.05 g, 2.644 mmol) in 1,4-dioxane (12 mL) and water (2.5 mL) was treated with tert-butyl 3-(4,4,5,5-tetramethyl-1,3,2-dioxaborolan-2-yl)-2,5-dihydro-1H-pyrrole-1-carboxylate (858.48 mg, 2.9 mmol) and $K_2CO_3$ (1.09 g, 7.93 mmol) at room temperature. The reaction mixture was degassed by bubbling argon for 10 min, then Pd-118 (51.635 mg, 0.079 mmol) was added and the vessel was sealed with a Teflon screw-cap. The reaction mixture was stirred at 100° C. for 16 h and progress of the reaction was monitored by TLC (mobile phase: 20% EtOAc in hexane, Rf: 0.32, detection: UV). The reaction mixture was allowed to cool to 26° C., quenched with water (25 mL) and extracted with EtOAc (2×35 mL). The combined organic layer was dried over $Na_2SO_4$ and filtered. The filtrate was concentrated under reduced pressure to afford a brown oil (1.3 g, LC/MS: 72%). The crude product was purified by flash chromatography using a silica column (40 g) eluted with 35% EtOAc in pet. ether. The pure fractions were combined and concentrated under reduced pressure to afford tert-butyl 3-(2-(1-methyl-1H-pyrazol-3-yl)-6-(3,3,3-trifluoropropoxy)pyridin-3-yl)-2,5-dihydro-1H-pyrrole-1-carboxylate as a pale brown solid (970 mg, LC/MS: 98%). (LC/MS; m/z 439.4 $[M+H]^+$).

Step 6: To a stirred solution of tert-butyl 3-(2-(1-methyl-1H-pyrazol-3-yl)-6-(3,3,3-trifluoropropoxy)pyridin-3-yl)-2,5-dihydro-1H-pyrrole-1-carboxylate (870 mg, 1.984 mmol) in MeOH (30 mL) was added 10% Pd/C (400 mg) at room temperature. The reaction mixture was stirred for 16 h at room temperature under $H_2$ atmosphere. The progress of the reaction was monitored by TLC (mobile phase: 30% EtOAc in hexane, Rf=0.53, detection: UV). The reaction mixture was filtered on a Celite bed and washed with MeOH (2×80 mL). The filtrate was concentrated under reduced pressure to afford tert-butyl 3-(2-(1-methyl-1H-pyrazol-3-yl)-6-(3,3,3-trifluoropropoxy)pyridin-3-yl)pyrrolidine-1-carboxylate as an off-white oil (850 mg, LC/MS purity: 98%). (LC/MS; m/z 385.3 $[M+H]^+$).

Step 7: To a stirred solution of tert-butyl 3-(2-(1-methyl-1H-pyrazol-3-yl)-6-(3,3,3-trifluoropropoxy)pyridin-3-yl) pyrrolidine-1-carboxylate (850 mg, 1.93 mmol) in DCM (20 mL) was added HCl (10 mL, 4.0 M in 1,4-dioxane) at 0° C. The resulting reaction mixture was allowed to warm to 26° C. and stirred for 3 h under nitrogen atmosphere. The progress of the reaction was monitored by TLC (mobile phase: 10% MeOH/DCM, Rf=0.05, detection: UV). The mixture was concentrated under reduced pressure to afford 2-(1-methyl-1H-pyrazol-3-yl)-3-(pyrrolidin-3-yl)-6-(3,3,3-trifluoropropoxy)pyridine hydrochloride as an off white gum (750 mg, LC/MS: 95%). (LC/MS; m/z 341.3 $[M+H]^+$).

Step 8: A stirred solution of 2-(1-methyl-1H-pyrazol-3-yl)-3-(pyrrolidin-3-yl)-6-(3,3,3-trifluoropropoxy)pyridine hydrochloride (400 mg, 1.062 mmol) in 1,4-dioxane (8 mL) and water (3 mL) was treated with $NaHCO_3$ (732.46 mg, 5.308 mmol) and a solution of acryloyl chloride (105.68 mg, 1.168 mmol) in 1,4-dioxane (2 mL) at 0° C. The reaction mixture was stirred for 30 min at room temperature and monitored by TLC (mobile phase: 10% MeOH in DCM, Rf: 0.28, detection: UV). The reaction mixture was diluted with water (20 mL) and extracted with EtOAc (2×25 mL). The combined organic phase was dried over $Na_2SO_4$ and concentrated under reduced pressure to obtain a pale brown sticky solid (300 mg, LC/MS: 86%). The crude product was purified by preparative HPLC method H8. The pure fractions were combined and lyophilized to afford 1-(3-(2-(1-methyl-1H-pyrazol-3-yl)-6-(3,3,3-trifluoropropoxy)pyridin-3-yl)pyrrolidin-1-yl)prop-2-en-1-one (Cpd. No. 434) as a colorless gum (78 mg, LC/MS: 99%). (LC/MS; m/z 395.0) $[M+H]^+$). Chiral SFC purification: 72 mg of Cpd. No. 434 was purified by preparative SFC method K5 to afford Cpd. No. 452-En1 (23 mg) and Cpd. No. 452-En2 (26 mg), both as an off-white gum. The chiral purity of both enantiomers was assessed by analytical SFC method S6: Cpd. No. 452-En1 (99.9% ee); Cpd. No. 452-En2 (98% ee).

Example 147: Synthesis of 1-(3-fluoro-3-(6-(4-fluorophenyl)-4-(1-methyl-1H-pyrazol-3-yl)pyridin-3-yl)pyrrolidin-1-yl)prop-2-en-1-one (Cpd. No. 449)

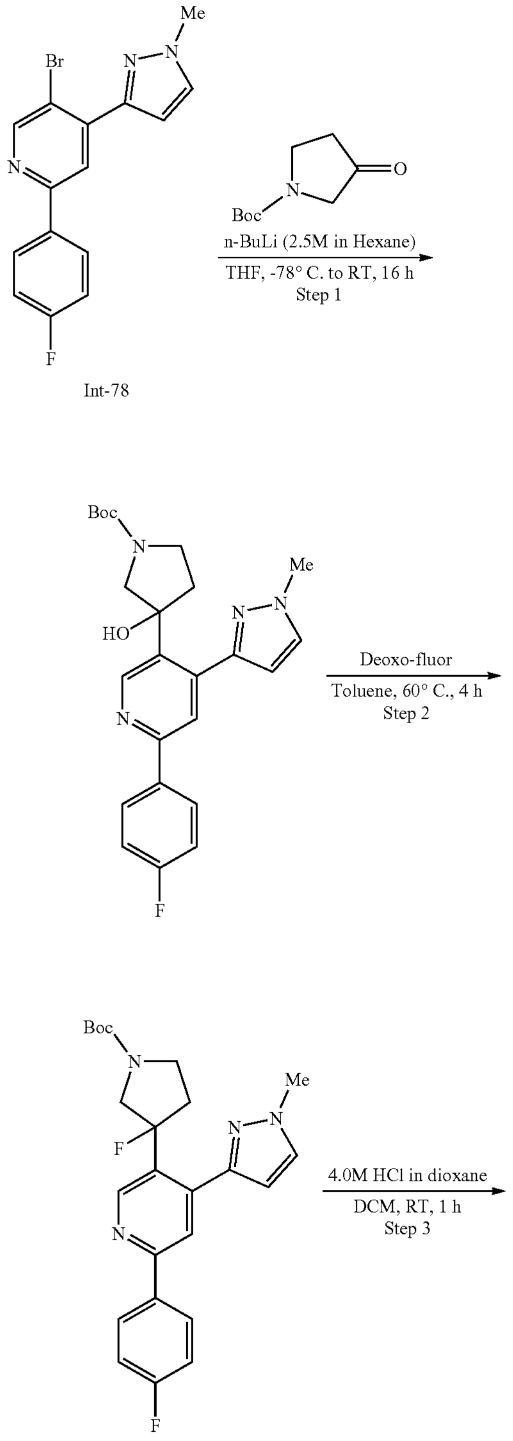

-continued

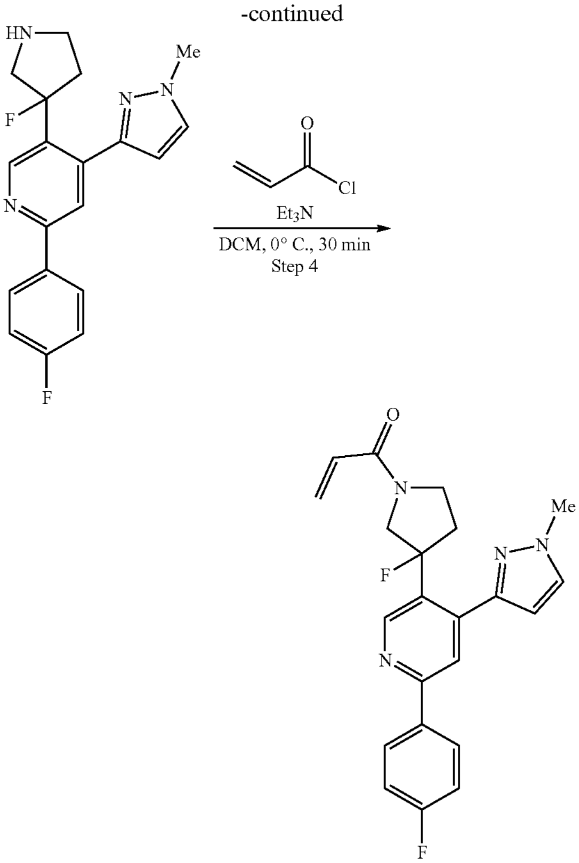

Cpd. No. 449

Step 1: A solution of Int-78 (1.2 g, 3.61 mmol) and tert-butyl 3-oxopyrrolidine-1-carboxylate (1.33 g, 7.22 mmol) in THF (12 mL) was treated with n-BuLi (2.5 M in hexane, 1.73 mL, 4.33 mmol) at −78° C. The reaction mixture was stirred at room temperature for 16 h and progress of the reaction was monitored by TLC (mobile phase: 40% EtOAc in pet ether. Rf: 0.27. detection: UV). The reaction mixture was diluted with aqueous $NH_4Cl$ (50 mL) and extracted with EtOAc (2×50 mL). The combined organic layer was washed with brine (50 mL), dried over sodium sulphate and concentrated under reduced pressure to afford a red gum (2.0 g, LC/MS: 18%). The crude product was purified by gravity column chromatography using silica gel and 20% EtOAc in pet ether as an eluent to afford tert-butyl 3-(6-(4-fluorophenyl)-4-(1-methyl-1H-pyrazol-3-yl)pyridin-3-yl)-3-hydroxypyrrolidine-1-carboxylate as an off-white solid (550 mg, LC/MS: 88%). (LC/MS; m/z 439.4 $[M+H]^+$).

Step 2: A solution of Deoxo-Fluor (50% in toluene) (2.1 mL) in toluene (1 mL) was treated with a solution of tert-butyl 3-(6-(4-fluorophenyl)-4-(1-methyl-1H-pyrazol-3-yl)pyridin-3-yl)-3-hydroxypyrrolidine-1-carboxylate (500 mg, 1.14 mmol) in toluene (0.4 mL) at room temperature under nitrogen atmosphere. The reaction mixture was stirred at 60° C. for 4 h. Progress of the reaction was monitored by TLC (mobile phase: 40% EtOAc in pet ether. Rf: 0.35. detection: UV). The reaction mixture was diluted with EtOAc (100 mL) and washed with brine (2×50 mL) and the organic layer was dried over sodium sulphate and concentrated under reduced pressure to afford a black gum (700 mg, LC/MS: 11%). The crude product was purified by gravity column chromatography by using silica gel and 20% EtOAc in pet ether as an eluent to afford tert-butyl 3-fluoro-3-(6-(4-fluorophenyl)-4-(1-methyl-1H-pyrazol-3-yl)pyridin-3-yl)pyrrolidine-1-carboxylate as a black gum (550 mg, LC/MS: 63%). (LC/MS; m/z 441.4 $[M+H]^+$).

Step 3: A solution of tert-butyl 3-fluoro-3-(6-(4-fluorophenyl)-4-(1-methyl-1H-pyrazol-3-yl)pyridin-3-yl)pyrrolidine-1-carboxylate (100 mg, 0.22 mmol) in DCM (1 mL) was treated with 4 M HCl in 1,4-dioxane (1 mL) at 0° C. The reaction mixture was stirred at room temperature for 1 h. Progress of the reaction was monitored by TLC (mobile phase: 10% MeOH in DCM. Rf: 0.2. detection: UV). The reaction mixture was concentrated under reduced pressure and the residue was diluted with EtOAc (30 mL) and washed with saturated $NaHCO_3$ (2×10 mL) and brine (2×10 mL). The organic layer was dried over sodium sulphate and concentrated under reduced pressure to afford 2-(4-fluorophenyl)-5-(3-fluoropyrrolidin-3-yl)-4-(1-methyl-1H-pyrazol-3-yl)pyridine as a black gum (60 mg, LC/MS: 81%). (LC/MS; m/z 341.2 $[M+H]^+$).

Step 4: A solution of 2-(4-fluorophenyl)-5-(3-fluoropyrrolidin-3-yl)-4-(1-methyl-1H-pyrazol-3-yl)pyridine (60 mg, 0.17 mmol) in DCM (4 mL) was treated with TEA (0.1 mL, 0.70 mmol) and a solution of acryloyl chloride (16 mg, 0.17 mmol) in DCM (1 mL) at 0° C. The reaction mixture was stirred at 0° C. for 30 min and progress of the reaction was monitored by TLC (mobile phase: 10% MeOH in DCM. Rf: 0.55. detection: UV). The reaction mixture was diluted with DCM (50 mL) and washed with brine (2×40 mL), the organic layer was dried over anhydrous $Na_2SO_4$ and then concentrated under reduced pressure to afford a brown gum (82 mg, LC/MS: 67%). The crude product was purified by preparative HPLC method H17 and the collected fraction was concentrated under reduced pressure to afford 1-(3-fluoro-3-(6-(4-fluorophenyl)-4-(1-methyl-1H-pyrazol-3-yl)pyridin-3-yl)pyrrolidin-1-yl)prop-2-en-1-one (Cpd. No. 449) as a brown solid (10 mg, LC/MS: 98%). (LC/MS; m/z 395.1 $[M+H]^+$).

Example 148: Synthesis of 1-(3-(6-(3,3-difluorocyclopentyl)-4-(1-methyl-1H-pyrazol-3-yl)pyridin-3-yl)pyrrolidin-1-yl)prop-2-en-1-one (Cpd. No. 456)

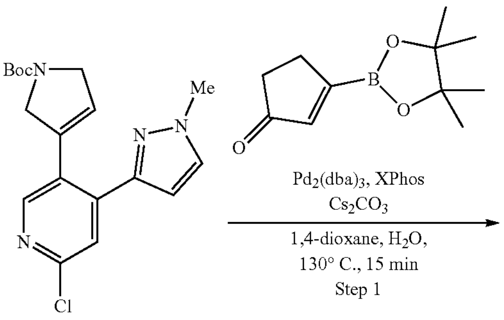

Int-79

-continued

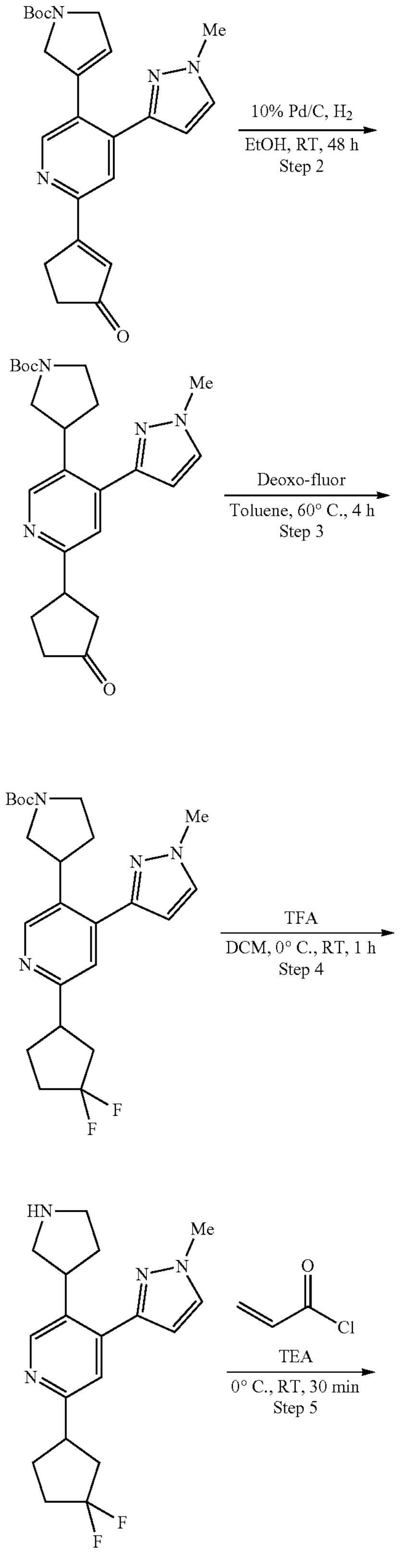

-continued

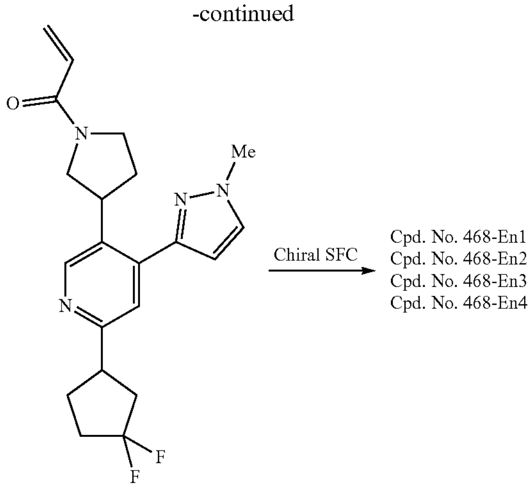

Cpd. No. 456

Step 1: A solution of Int-79 (1.5 g, 4.15 mmol) in 1,4-dioxane (5 mL) and $H_2O$ (0.5 mL) were treated with 3-(4,4,5,5-tetramethyl-1,3,2-dioxaborolan-2-yl)cyclopent-2-en-1-one (1.03 g, 4.98 mmol) and $Cs_2CO_3$ (2.70 g, 8.31 mmol) at room temperature. The reaction mixture was degassed with argon for 10 min followed by addition of XPhos (119 mg, 0.24 mmol) and $Pd_2(dba)_3$ (114 mg, 0.12 mmol) at room temperature. The reaction mixture was stirred at 130° C. for 15 min under microwave irradiation. Progress of the reaction was monitored by TLC (mobile phase: 50% EtOAc in pet ether. Rf: 0.18. detection: UV). The reaction mixture was filtered through a pad of Celite and washed with EtOAc (200 mL). The filtrate was washed with brine (100 mL), dried over anhydrous $Na_2SO_4$ and concentrated under reduced pressure to afford a brown gum (1.6 g, LC/MS: 65%). The crude product was purified by normal phase column chromatography using an 80 g column (silica) and 30% EtOAc in Pet ether as an eluent to afford tert-butyl 3-(4-(1-methyl-1H-pyrazol-3-yl)-6-(3-oxocyclopent-1-en-1-yl)pyridin-3-yl)-2,5-dihydro-1H-pyrrole-1-carboxylate as a brown gum (900 mg, LC/MS: 82%). (LC/MS; m/z 407.4 $[M+H]^+$).

Step 2: A solution of tert-butyl 3-(4-(1-methyl-1H-pyrazol-3-yl)-6-(3-oxocyclopent-1-en-1-yl)pyridin-3-yl)-2,5-dihydro-1H-pyrrole-1-carboxylate (900 mg, 2.21 mmol) in EtOH (10 mL) was treated with Pd/C (1.8 g) under $H_2$ balloon pressure at room temperature for 48 h. Progress of the reaction monitored by TLC (mobile phase: 50% EtOAc in pet ether. Rf: 0.18, detection: UV). The reaction mixture was filtered through a pad of Celite and washed with EtOH (50 mL). The filtrate was concentrated under reduced pressure to afford tert-butyl 3-(4-(1-methyl-1H-pyrazol-3-yl)-6-(3-oxocyclopentyl)pyridin-3-yl)pyrrolidine-1-carboxylate as a pale yellow gum (950 mg, LC/MS: 69%). (LC/MS; m/z 411.4 $[M+H]^+$).

Step 3: A solution of tert-butyl 3-(4-(1-methyl-1H-pyrazol-3-yl)-6-(3-oxocyclopentyl)pyridin-3-yl)pyrrolidine-1-carboxylate (400 mg, 0.97 mmol) in toluene (1.14 mL) was treated with Deoxo-fluor (50% in toluene) (1.68 mL) at room temperature. The reaction mixture was stirred at 60° C. for 4 h. The progress of the reaction was monitored by TLC (mobile phase: 50% EtOAc in pet-ether. Rf: 0.29. detection: UV). The reaction mixture was quenched with water (20 mL) and extracted with EtOAc (2×50 mL). The combined organic layer was washed with brine (50 mL), dried over anhydrous $Na_2SO_4$ and concentrated under reduced pressure to afford a pale yellow gum (390 mg, LC/MS: 34%). The crude product was purified by normal phase column chromatography (silica) using 30% EtOAc in Pet ether as an eluent to afford tert-butyl 3-(6-(3,3-difluorocyclopentyl)-4-(1-methyl-1H-pyrazol-3-yl)pyridin-3-yl)pyrrolidine-1-carboxylate as a yellow gum (220 mg, LC/MS: 74%). (LC/MS; m/z 433.4 $[M+H]^+$).

Step 4: A solution of tert-butyl 3-(6-(3,3-difluorocyclopentyl)-4-(1-methyl-1H-pyrazol-3-yl)pyridin-3-yl)pyrrolidine-1-carboxylate 3 (220 mg, 0.50 mmol) in DCM (2 mL) was treated with TFA (0.58 mL, 7.63 mmol) at 0° C. The reaction mixture was stirred at room temperature for 1 h, progress of the reaction was monitored by TLC (mobile phase: 10% MeOH in DCM. Rf: 0.13. detection: UV). The reaction mixture was concentrated under reduced pressure to afford 2-(3,3-difluorocyclopentyl)-4-(1-methyl-1H-pyrazol-3-yl)-5-(pyrrolidin-3-yl)pyridine TFA salt as a brown gum (180 mg, LC/MS: 61%). (LC/MS; m/z 333.3 $[M+H]^+$).

Step 5: A solution of 2-(3,3-difluorocyclopentyl)-4-(1-methyl-1H-pyrazol-3-yl)-5-(pyrrolidin-3-yl)pyridine TFA salt (180 mg, 0.54 mmol) in DCM (2.5 mL) was treated with $Et_3N$ (0.30 mL, 2.16 mmol) and acryloyl chloride (54 mg, 0.59 mmol) at 0° C. The reaction mixture was stirred at room temperature for 30 min and progress of the reaction monitored by TLC (mobile phase: 80% EtOAc in Pet ether. Rf: 0.27. detection: UV). The reaction mixture was diluted with water (20 mL) and extracted with EtOAc (2×30 mL). The combined organic layer was washed with brine (30 mL), dried over anhydrous $Na_2SO_4$ and concentrated under reduced pressure to afford a brown gum (201 mg, LC/MS: 64%). The crude product was purified by preparative HPLC method H9 and the collected fractions were concentrated under reduced pressure to afford 1-(3-(6-(3,3-difluorocyclopentyl)-4-(1-methyl-1H-pyrazol-3-yl)pyridin-3-yl)pyrrolidin-1-yl)prop-2-en-1-one (Cpd. No. 456) as a pale yellow gummy solid (66 mg, LC/MS: 99%). (LC/MS; m/z 387.3 $[M+H]^+$). Chiral SFC purification: 68 mg of Cpd. No. 456 was purified by preparative SFC method K9 to afford Cpd. No. 468-En1 (9 mg), Cpd. No. 468-En2 (9 mg), Cpd. No. 468-En3 (7 mg) and Cpd. No. 468-En4 (8 mg), each as an off-white solid. The chiral purity of the first and second eluting compounds was assessed by analytical SFC method S10: Cpd. No. 468-En1 (99.8% ee), Cpd. No. 468-En2 (99.1% ee). The chiral purity of the third and fourth eluting compounds was assessed by analytical SFC method S11: Cpd. No. 468-En3 (99.5% ee) and Cpd. No. 468-En4 (98.5% ee).

Example 149: Synthesis of 1-(3-(6-(4-fluorophenyl)-2-(1-methyl-1H-pyrazol-3-yl)pyridin-3-yl)-3-hydroxypyrrolidin-1-yl)prop-2-en-1-one (Cpd. No. 461)

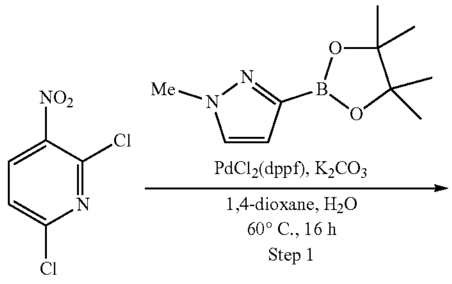

-continued

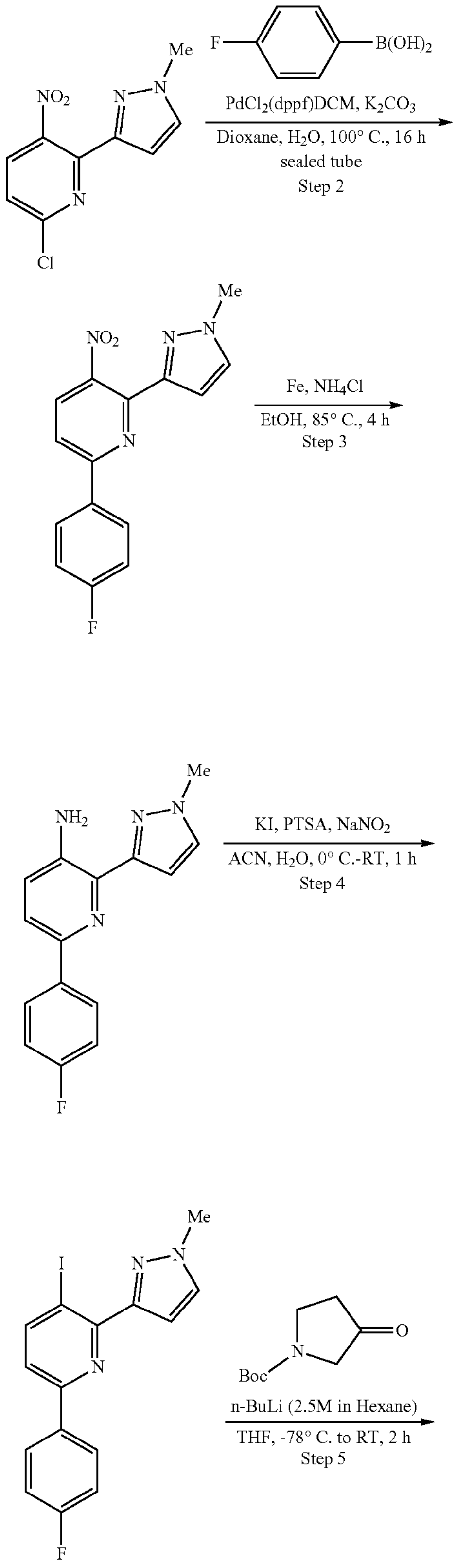

Int-81

-continued

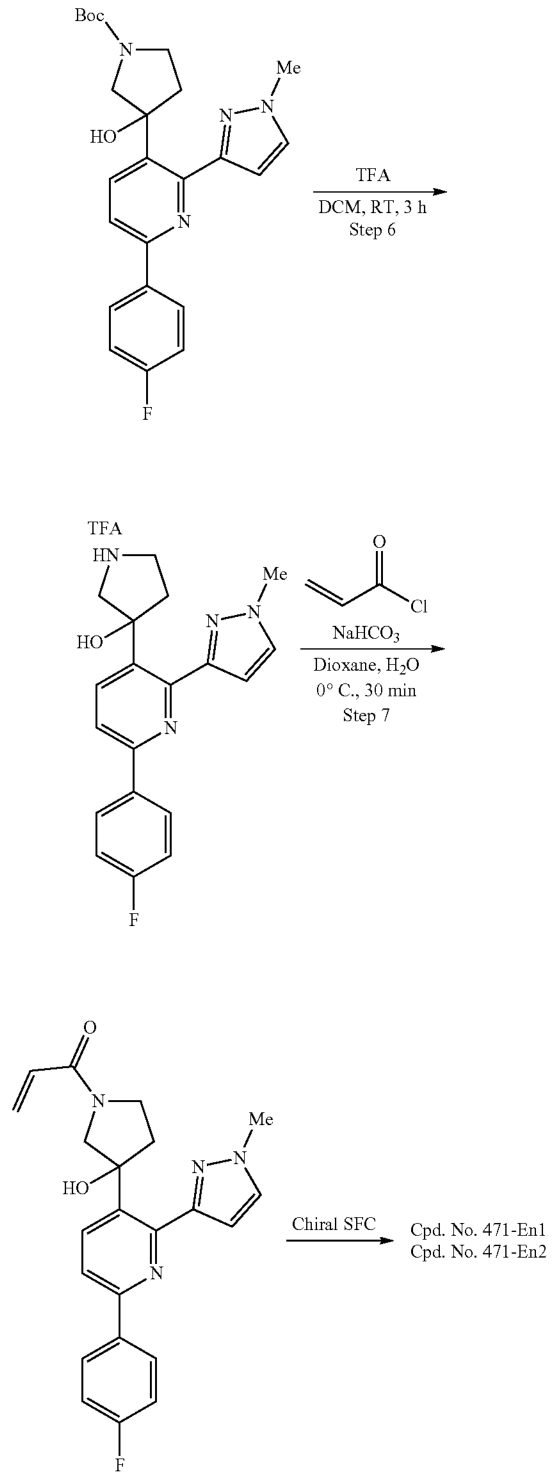

Cpd. No. 461

Steps 1-4: These steps were executed in a manner similar (use of appropriate reagents and purification methods known to the person skilled in the art) to step 1, 2, 5 and 6 towards Int-78. Employing 2,6-dichloro-3-nitropyridine (5 g, 25.9 mmol) and 1-methyl-3-(4,4,5,5-tetramethyl-1,3,2-dioxaborolan-2-yl)-1H-pyrazole (8.086 g, 38.863 mmol) in step 1 yielded 6-(4-fluorophenyl)-3-iodo-2-(1-methyl-1H-pyrazol-3-yl)pyridine (Int-81) as a pale brown semi-solid (1.3 g, LC/MS: 97%). (LC/MS; m/z 380.3 $[M+H]^+$).

Step 5: A solution of Int-81 (1 g, 2.637 mmol) in THF (10 mL) was treated with tert-butyl 3-oxopyrrolidine-1-carboxylate (0.977 g, 5.275 mmol) at room temperature. The reaction mixture was cooled to −78° C. and n-BuLi (2.5M in hexane, 1.05 mL, 2.637 mmol) was added. The reaction mixture was stirred at room temperature for 16 h and progress of the reaction monitored by TLC (mobile phase: 50% EtOAc in Pet ether. Rf: 0.22, detection: UV). The reaction mixture was quenched with aqueous $NH_4Cl$ (100 mL) and extracted with EtOAc (3×100 mL). The combined organic layer was washed with brine (50 mL), dried over $Na_2SO_4$ and concentrated under reduced pressure to afford the crude product (1.2 g, LC/MS: 16%). The crude product was purified by normal phase column chromatography (24 g silica column) using 30% EtOAc in Pet ether as eluent to afford tert-butyl 3-(6-(4-fluorophenyl)-2-(1-methyl-1H-pyrazol-3-yl)pyridin-3-yl)-3-hydroxypyrrolidine-1-carboxylate as a pale yellow semi solid (380 mg, LC/MS: 81%). (LC/MS; m/z 439.3 $[M+H]^+$).

Step 6: A solution of tert-butyl 3-(6-(4-fluorophenyl)-2-(1-methyl-1H-pyrazol-3-yl)pyridin-3-yl)-3-hydroxypyrrolidine-1-carboxylate (360 mg, 0.821 mmol) in DCM (10 mL) was treated with TFA (3 mL) at 0° C. The reaction mixture was stirred at room temperature for 3 h, monitored by TLC (mobile phase: 10% MeOH in DCM, Rf: 0.12, detection: UV). The reaction mixture was concentrated under reduced pressure and washed with n-pentane (50 mL) to afford 3-(6-(4-fluorophenyl)-2-(1-methyl-1H-pyrazol-3-yl)pyridin-3-yl)pyrrolidin-3-ol TFA salt as a pale brown semi solid (360 mg, LC/MS: 95%). (LC/MS; m/z 339.4 $[M+H]^+$).

Step 7: A solution of 3-(6-(4-fluorophenyl)-2-(1-methyl-1H-pyrazol-3-yl)pyridin-3-yl)pyrrolidin-3-ol TFA salt (360 mg, 1.064 mmol) in 1,4-dioxane (5 mL) and water (2 mL) was cooled to 0° C. and treated with $NaHCO_3$ (446 mg, 5.319 mmol) and a solution of acryloyl chloride (105 mg, 1.170 mmol) in 1,4-dioxane (1 mL). The reaction mixture was stirred at 0° C. for 1 h and progress of the reaction was monitored by TLC (mobile phase: 10% MeOH in DCM, Rf: 0.40. detection: UV). The reaction mixture was diluted with $H_2O$ (30 mL) and extracted with EtOAc (2×100 mL). The combined organic layer was washed with brine (30 mL), dried over anhydrous $Na_2SO_4$ and concentrated under reduced pressure to afford a pale brown semi solid (240 mg, LC/MS: 94%). The crude product was purified by preparative HPLC method H13 and the pure fraction was concentrated reduced pressure to afford 1-(3-(6-(4-fluorophenyl)-2-(1-methyl-1H-pyrazol-3-yl)pyridin-3-yl)-3-hydroxypyrrolidin-1-yl)prop-2-en-1-one (Cpd. No. 461) as an off white solid (63.5 mg, LC/MS: 99%). (LC/MS; m/z 393.2 $[M+H]^+$). Chiral SFC purification: 57.4 mg of Cpd. No. 461 was purified by preparative SFC method K10 to afford Cpd. No. 471-En1 (12 mg) and Cpd. No. 471-En2 (20 mg), each as an off-white solid. The chiral purity of each enantiomer was assessed by analytical SFC method S17: Cpd. No. 471-En1 (99.9% ee) and Cpd. No. 471-En2 (99.9% ee).

The following compounds were prepared in a manner similar (use of appropriate reagents and purification methods known to the person skilled in the art) to Cpd. No. 461 by employing Int-78 in step 5: Cpd. No. 405, Cpd. No. 409, Cpd. No. 425.

Example 150: Synthesis of 1-(3-(6-(4-fluorophenyl)-4-(1-methyl-1H-pyrazol-3-yl)pyridazin-3-yl)-3-hydroxypyrrolidin-1-yl)prop-2-en-1-one (Cpd. No. 472)

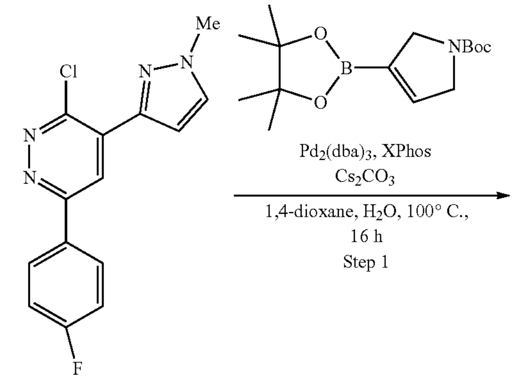

Int-82

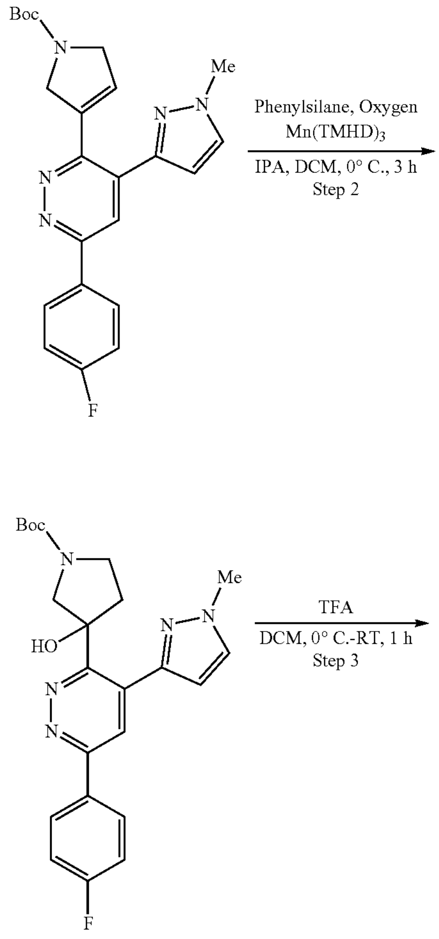

-continued

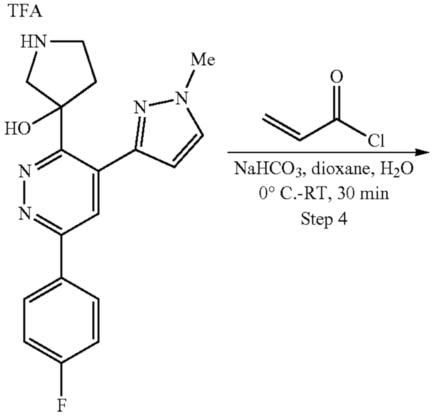

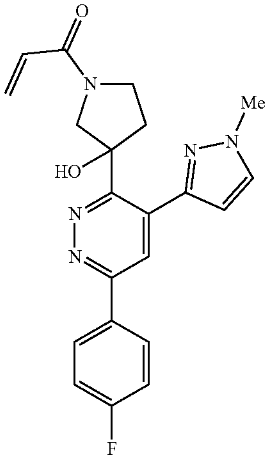

Cpd. No. 472

Step 1: A solution of Int-82 (900 mg, 3.11 mmol) in dioxane (10 mL) and $H_2O$ (3 mL) were treated with tert-butyl 3-(4,4,5,5-tetramethyl-1,3,2-dioxaborolan-2-yl)-2,5-dihydro-1H-pyrrole-1-carboxylate (920 mg, 3.11 mmol) and $Cs_2CO_3$ (2026.255 mg, 6.23 mmol) at room temperature. The reaction was degassed with argon for 20 min followed by addition of $Pd_2(dba)_3$ (57 mg, 0.062 mmol) and X-Phos (59.450 mg, 0.125 mmol) at room temperature. The reaction mixture was stirred at 100° C. for 16 h. The reaction progress was monitored by TLC (mobile phase: 50% EtOAc in pet ether. Rf: 0.38. detection: UV). The reaction mixture was filtered through a pad of Celite and washed with EtOAc (30 mL). The filtrate was washed with brine (10 mL), dried over anhydrous $Na_2SO_4$ and concentrated under reduced pressure to afford a pale yellow liquid (1.2 g, LC/MS: 54%). The crude product was purified by reverse phase column chromatography (80 g RP-C18 column) using a gradient of 40-55% MeCN in water as eluent. The collected fraction was concentrated under reduced pressure and the resulting aqueous mixture was extracted with EtOAc (3×50 mL) and the combined organic layer was washed with brine (2×50 mL), dried over $Na_2SO_4$ and concentrated under reduced pressure to afford tert-butyl 3-(6-(4-fluorophenyl)-4-(1-methyl-1H-pyrazol-3-yl)pyridazin-3-yl)-2,5-dihydro-1H-pyrrole-1-carboxylate as an off-white solid (600 mg, LC/MS: 89%). (LC/MS; m/z 422.3 $[M+H]^+$).

Step 2: A solution of tert-butyl 3-(6-(4-fluorophenyl)-4-(1-methyl-1H-pyrazol-3-yl)pyridazin-3-yl)-2,5-dihydro-1H-pyrrole-1-carboxylate (80 mg, 0.190 mmol) in IPA (1.5 mL) and DCM (0.2 mL) was treated with $Mn(TMHD)_3$ (3 mg, 0.005 mmol) and phenylsilane (41.080 mg, 0.380 mmol) at 0° C. under 02 atmosphere (balloon). The reaction mixture was stirred at 0° C. for 3 h and monitored by TLC (mobile phase: 50% EtOAc in pet ether, Rf: 0.30, detection: UV). The reaction mixture was quenched with addition of saturated aqueous $Na_2S203$ (5 mL) and extracted with EtOAc (2×20 mL). The combined organic layer was washed with brine (10 mL), dried over anhydrous $Na_2SO_4$ and evaporated to afford a brown gummy solid (100 mg, LC/MS: 24%). The crude product was purified by column chromatography using silica gel and a gradient of 20-30% EtOAc in pet ether as eluent. The pure fraction was concentrated under reduced pressure to afford tert-butyl 3-(6-(4-fluorophenyl)-4-(1-methyl-1H-pyrazol-3-yl)pyridazin-3-yl)-3-hydroxy-pyrrolidine-1-carboxylate as a pale brown semi solid (40 mg, LC/MS: 73%). (LC/MS; m/z 440.2 $[M+H]^+$).

Step 3: A solution of tert-butyl 3-(6-(4-fluorophenyl)-4-(1-methyl-1H-pyrazol-3-yl)pyridazin-3-yl)-3-hydroxypyrrolidine-1-carboxylate (80 mg, 0.182 mmol) in DCM (3 mL) was treated with TFA (0.3 mL) at 0° C. The reaction mixture was stirred at room temperature for 3 h, monitored by TLC (mobile phase: 10% MeOH in DCM, Rf: 0.12, detection: UV). The reaction mixture was concentrated under reduced pressure and washed with n-pentane (50 mL) to afford 3-(6-(4-fluorophenyl)-4-(1-methyl-1H-pyrazol-3-yl)pyridazin-3-yl)pyrrolidin-3-ol TFA salt as a pale brown semi solid (80 mg, LC/MS: 78%). (LC/MS; m/z 340.3 $[M+H]^+$).

Step 4: A stirred solution of 3-(6-(4-fluorophenyl)-4-(1-methyl-1H-pyrazol-3-yl)pyridazin-3-yl)pyrrolidin-3-ol TFA salt (2) (80 mg, 0.236 mmol) in 1,4-dioxane (3 mL) and water (1 mL) was cooled to 0° C. and treated with $NaHCO_3$ (99.006 mg, 1.179 mmol) and a solution of acryloyl chloride (23.468 mg, 0.259 mmol) in 1,4-dioxane (1 mL). The reaction mixture was stirred at 0° C. for 30 min and monitored by TLC (mobile phase: 10% MeOH in DCM, Rf: 0.40. detection: UV). The reaction mixture was diluted with H O (30 mL) and extracted with EtOAc (3×30 mL). The combined organic layer was washed with brine (20 mL), dried over anhydrous $Na_2SO_4$ and concentrated under reduced pressure to afford a pale brown semi solid (73 mg, LC/MS: 70%). The crude product was purified by preparative HPLC method H18 and the collected fraction was concentrated under reduced pressure to afford 1-(3-(6-(4-fluorophenyl)-4-(1-methyl-1H-pyrazol-3-yl)pyridazin-3-yl)-3-hydroxypyrrolidin-1-yl)prop-2-en-1-one (Cpd. No. 472) as an off white solid (6.97 mg, LC/MS: 99%). (LC/MS; m/z 394.3 $[M+H]^+$).

Example 151: Synthesis of 2'-(1-(3-chloro-5-(methylcarbamoyl)benzyl)-1H-pyrazol-3-yl)-4'-methoxy-[1,1'-biphenyl]-4-carboxylic acid (Cpd. No. 378) and 2'-(1-(3-chloro-5-(methylcarbamoyl)benzyl)-1H-pyrazol-5-yl)-4'-methoxy-[1,1'-biphenyl]-4-carboxylic acid (Cpd. No. 379)

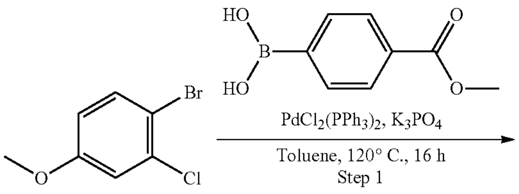

-continued

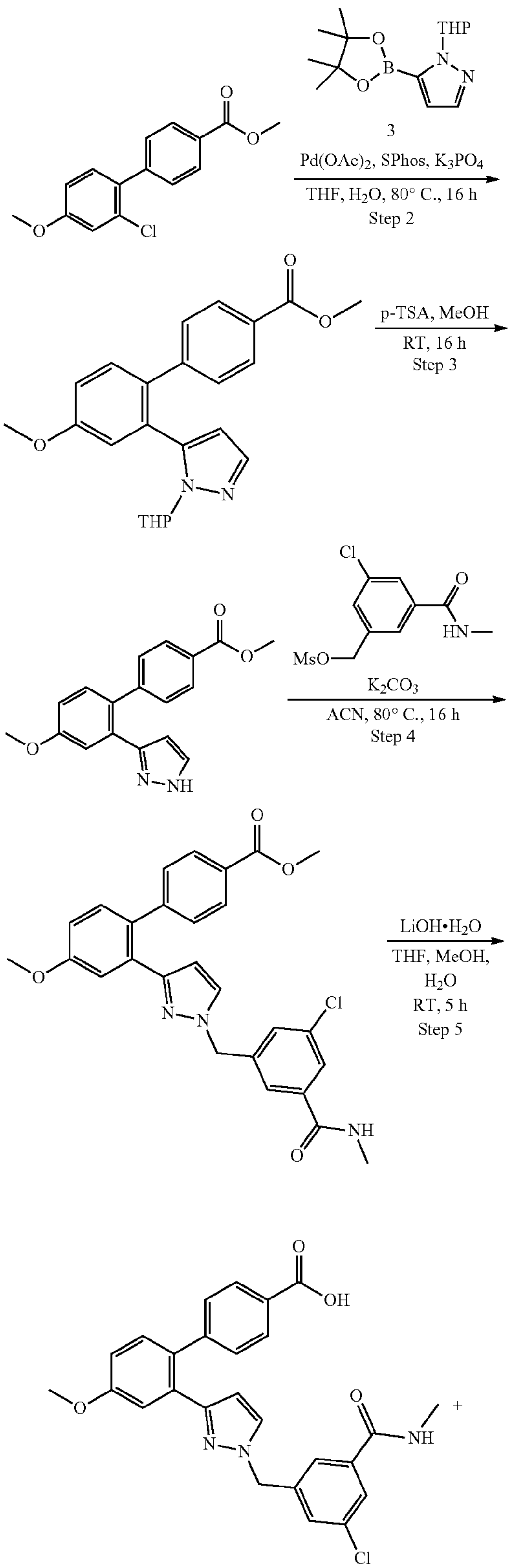

Cpd. No. 378

-continued

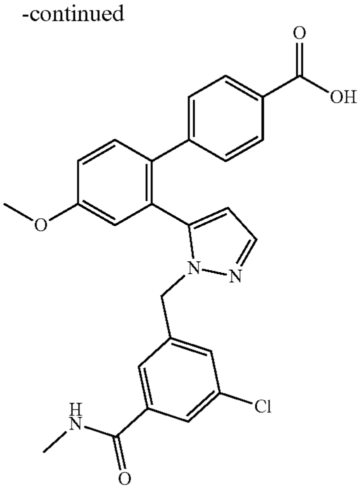

Cpd. No. 379

Step 1: A solution of (4-(methoxycarbonyl)phenyl)boronic acid (5 g, 27.78 mmol) in toluene (50 mL) were treated with 1-bromo-2-chloro-4-methoxybenzene (8 g, 36.11 mmol) and $K_3PO_4$ (17.67 g, 83.34 mmol) at room temperature. The reaction mixture was degassed with argon for 20 min followed by addition of $PdCl_2(PPh_3)_2$ (1.36 g, 1.94 mmol) at room temperature. The reaction mixture was stirred at 120° C. for 16 h and progress of the reaction monitored by TLC (mobile phase: 10% EtOAc in Pet ether. Rf: 0.40. detection: UV). The reaction mixture was filtered through a pad of Celite and washed with EtOAc (500 mL). The filtrate was washed with brine (100 mL), dried over anhydrous $Na_2SO_4$ and concentrated under reduced pressure to afford a yellow gum (5 g, LC/MS: 63%). The crude was purified by gravity column chromatography by using silica gel and 5% EtOAc in pet-ether as eluent to afford methyl 2'-chloro-4'-methoxy-[1,1'-biphenyl]-4-carboxylate as a white solid (3.2 g, LC/MS: 96%). (LC/MS; m/z 277.2 $[M+H]^+$).

Step 2: A solution of methyl 2'-chloro-4'-methoxy-[1,1'-biphenyl]-4-carboxylate (3.2 g, 11.56 mmol) in THF (30 mL) and $H_2O$ (10 mL) was treated with 1-(tetrahydro-2H-pyran-2-yl)-5-(4,4,5,5-tetramethyl-1,3,2-dioxaborolan-2-yl)-1H-pyrazole (3.5 g, 12.72 mmol) and $K_3PO_4$ (7.3 g, 34.69 mmol) at room temperature. The reaction mixture was degassed with argon for 20 min followed by addition of $Pd(OAc)_2$ (100 mg, 0.80 mmol) and SPhos (200 mg, 1.61 mmol) at room temperature. The reaction mixture was stirred at 80° C. for 16 h and progress of the reaction was monitored by TLC (mobile phase: 20% EtOAc in Pet ether. Rf: 0.12. detection: UV). The reaction mixture was filtered through a pad of Celite and washed with EtOAc (100 mL). The filtrate was washed with brine (50 mL), dried over anhydrous $Na_2SO_4$ and concentrated under reduced pressure to afford a yellow gum (4 g, LC/MS: 40%). The crude product was purified by gravity column chromatography using silica gel and 9% EtOAc in pet-ether as an eluent to afford methyl 4'-methoxy-2'-(1-(tetrahydro-2H-pyran-2-yl)-1H-pyrazol-5-yl)-[1,1'-biphenyl]-4-carboxylate as a white solid (2.2 g, 47%, LC/MS: 88%). (LC/MS; m/z 309.2 [M-THP]*).

Step 3: A solution of methyl 4'-methoxy-2'-(1-(tetrahydro-2H-pyran-2-yl)-1H-pyrazol-5-yl)-[1,1'-biphenyl]-4-carboxylate 4 (2.2 g, 5.60 mmol) in MeOH (50 mL) was treated with p-TSA (850 mg, 4.48 mmol) at room temperature. The reaction mixture was stirred at room temperature for 16 h and progress of the reaction was monitored by TLC (mobile phase: 40% EtOAc in pet ether. Rf: 0.2. detection: UV). The reaction mixture was concentrated under reduced pressure and the residue was diluted with water (100 mL) and extracted with EtOAc (100 mL). The organic layer was washed with brine (50 mL), dried over anhydrous $Na_2SO_4$ and concentrated under reduced pressure to afford methyl 4'-methoxy-2'-(1H-pyrazol-3-yl)-[1,1'-biphenyl]-4-carboxylate as a white solid (1.8 g, LC/MS: 90%). (LC/MS; m/z 309.3 $[M+H]^+$).

Step 4: A solution of Int-F (500 mg, 1.80 mmol) in ACN (10 mL) was treated with $K_2CO_3$ (993 mg, 7.20 mmol) and methyl 4'-methoxy-2'-(1H-pyrazol-3-yl)-[1,1'-biphenyl]-4-carboxylate (333 mg, 1.08 mmol) at room temperature. The reaction mixture was stirred at 80° C. for 16 h and progress of the reaction was monitored by TLC (mobile phase: 70% EtOAc in pet ether. Rf: 0.28. detection: UV). The reaction mixture was diluted with water (100 mL) and extracted with EtOAc (500 mL). The organic layer was washed with brine (150 mL), dried over anhydrous $Na_2SO_4$ and concentrated under reduced pressure to afford a yellow gum (600 mg, LC/MS: 26% and 27% of regiomers). The crude was purified by gravity column chromatography using silica gel and a 40% EtOAc in pet ether as an eluent to afford methyl 2'-(1-(3-chloro-5-(methylcarbamoyl)benzyl)-1H-pyrazol-3-yl)-4'-methoxy-[1,1'-biphenyl]-4-carboxylate as a white solid (400 mg, LC/MS: 47% & 46% of regiomers). (LC/MS; m/z 490.4 $[M+H]^+$).

Step 5: A solution of methyl 2'-(1-(3-chloro-5-(methylcarbamoyl)benzyl)-1H-pyrazol-3-yl)-4'-methoxy-[1,1'-biphenyl]-4-carboxylate (400 mg, 0.81 mmol) in THF (8 mL), MeOH (1 mL) and water (1 mL) was treated with $LiOH{\cdot}H_2O$ (206 mg, 4.89 mmol) at 0° C. The reaction mixture was stirred at room temperature for 5 h and progress of the reaction was monitored by TLC (mobile phase: 10% MeOH in DCM. Rf: 0.20. detection: UV). The reaction mixture was concentrated under reduced pressure and the residue was diluted with water (10 mL) and the pH was adjusted to 5 by addition of 1N HCl. The aqueous layer was extracted with EtOAc (2×50 mL) and the combined organic layer was dried over anhydrous $Na_2SO_4$ and concentrated under reduced pressure to afford a yellow gum (280 mg, LC/MS: 53% & 40% of regioisomers). The crude product was purified by preparative HPLC method H17 and the collected fractions were concentrated under reduced pressure to afford 2'-(1-(3-chloro-5-(methylcarbamoyl)benzyl)-1H-pyrazol-5-yl)-4'-methoxy-[1,1'-biphenyl]-4-carboxylic acid (Cpd. No. 379) as a white solid (28 mg, LC/MS: 99%) and 2'-(1-(3-chloro-5-(methylcarbamoyl)benzyl)-1H-pyrazol-3-yl)-4'-methoxy-[1,1'-biphenyl]-4-carboxylic acid (Cpd. No. 378) as a white solid (23 mg, LC/MS: 98%). (LC/MS; m/z 476.2 $[M+H]^+$).

Example 152: Synthesis of 3-((3-(5-(1-acryloylpyrrolidin-3-yl)-2-(4-fluorophenyl)pyridin-4-yl)-1H-pyrazol-1-yl)methyl)-5-chloro-N-methylbenzamide (Cpd. No. 386)

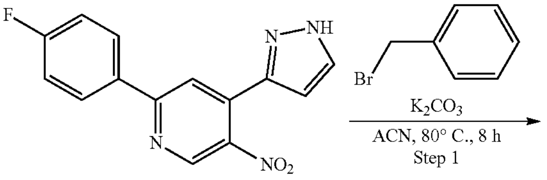

Int-77

-continued

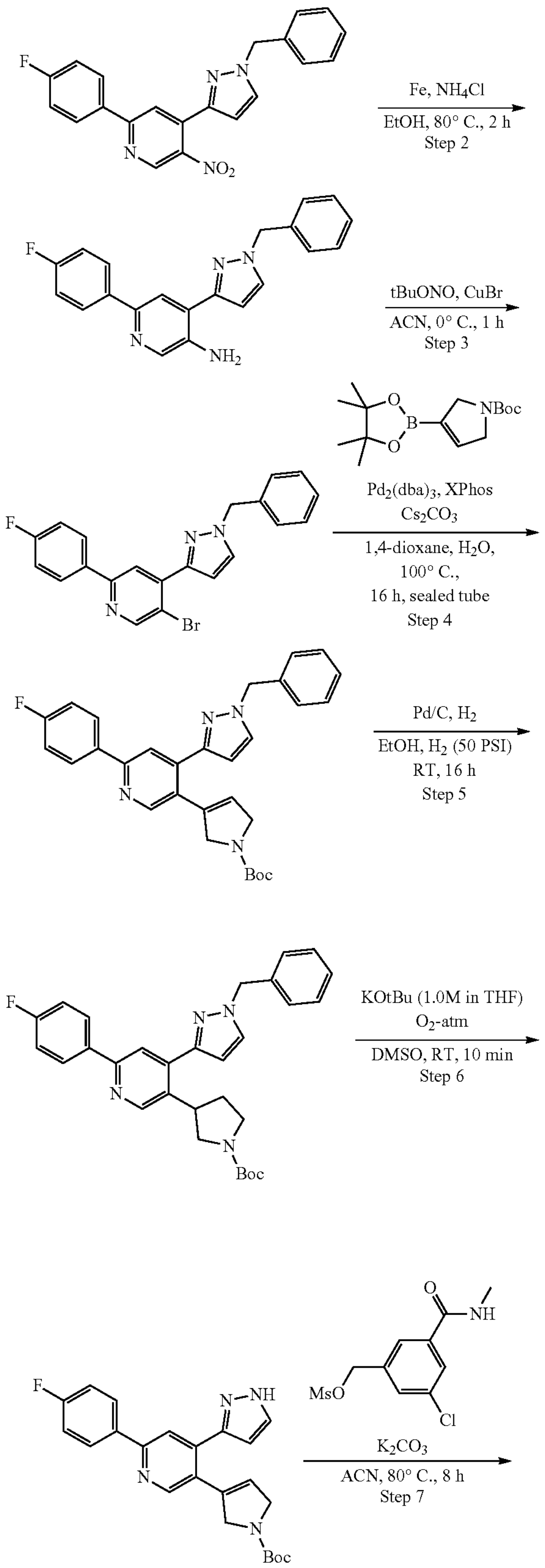

-continued

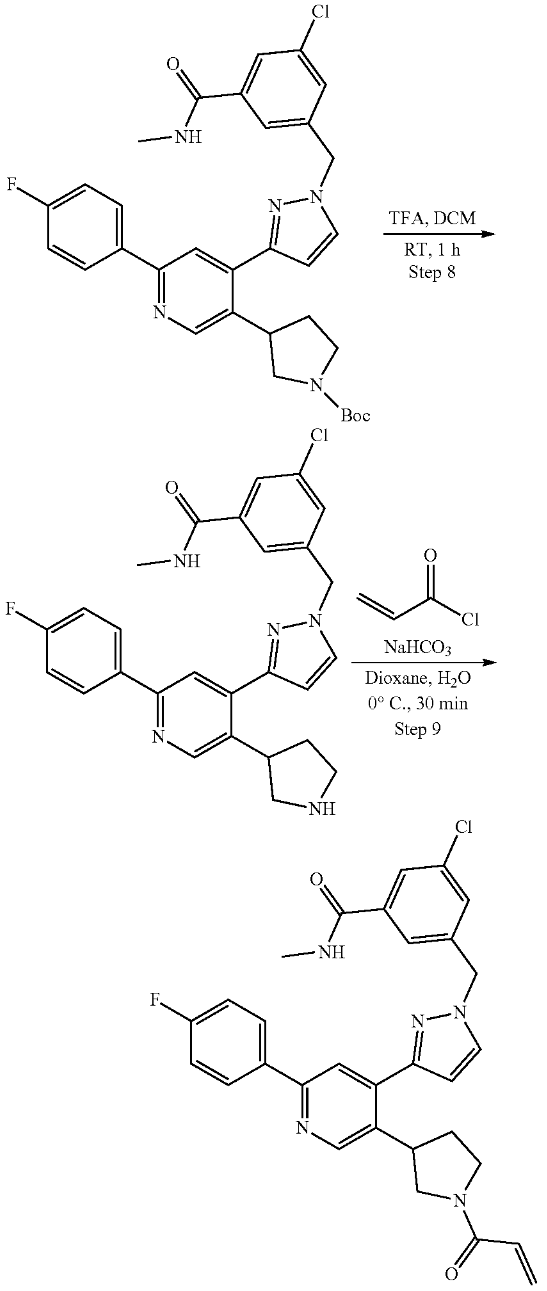

Cpd. No. 386

Step 1: A solution of 2-(4-fluorophenyl)-5-nitro-4-(1H-pyrazol-3-yl) pyridine (4 g, 14.08 mmol) in ACN (100 mL) was treated with (bromomethyl)benzene (2.40 g, 14.08 mmol) and $K_2CO_3$ (5.83 g, 42.24 mmol) at room temperature. The reaction mixture was stirred at 80° C. for 8 h. The reaction was monitored by TLC (mobile phase: 30% EtOAc in pet ether. Rf: 038. detection: UV). The reaction mixture was quenched with water (200 mL) and extracted with EtOAc (200 mL). The organic layer was washed with brine (200 mL), dried over anhydrous $Na_2SO_4$ and concentrated under reduced pressure to afford a pale-yellow gum (6.0 g, LC/MS: 58%). The crude product was purified by gravity column chromatography using silica gel and a gradient of 15-20% EtOAc in pet-ether as an eluent. The pure fraction was concentrated under reduced pressure to afford 4-(1-benzyl-1H-pyrazol-3-yl)-2-(4-fluorophenyl)-5-nitropyridine as a yellow solid (4.6 g, LC/MS: 75%). (LC/MS; m/z 375.2 $[M+H]^+$).

Step 2: A solution of 4-(1-benzyl-1H-pyrazol-3-yl)-2-(4-fluorophenyl)-5-nitropyridine (4.6 g, 12.29 mmol) in EtOH (50 mL) was treated with iron powder (4.12 g, 73.77 mmol) and $NH_4Cl$ (6.57 g, 122.95 mmol) at room temperature. The reaction mixture was stirred at 80° C. for 2 h. The reaction progress was monitored by TLC (mobile phase: 30% EtOAc in pet ether. Rf: 0.2. detection: UV). The reaction mixture was filtered through a pad of Celite and washed with EtOAc (200 mL). The filtrate was washed with brine (100 mL), dried over anhydrous $Na_2SO_4$ and concentrated under reduced pressure to afford 4-(1-benzyl-1H-pyrazol-3-yl)-6-(4-fluorophenyl)pyridin-3-amine as a pale yellow solid (4.0 g, LC/MS: 81%). (LC/MS; m/z 345.5 $[M+H]^+$).

Step 3: A stirred solution of 4-(1-benzyl-1H-pyrazol-3-yl)-6-(4-fluorophenyl)pyridin-3-amine (4 g, 11.61 mmol) in ACN (60 mL) was treated with tert-butyl nitrite (8.3 mL, 69.68 mmol) followed by Cu(I)Br (0.83 g, 5.80 mmol) at 0° C. The reaction mixture was stirred at 0° C. for 1 h. The reaction progress was monitored by TLC (mobile phase: 40% EtOAc in hexane. Rf: 0.4. detection: UV). The reaction mixture was quenched with $H_2O$ (200 mL) and extracted with EtOAc (2×100 mL). The organic layer was washed with water (100 mL), brine (100 mL), dried over $Na_2SO_4$ and concentrated under reduced pressure to afford a pale yellow semi solid (4.0 g, LC/MS: 13%). The crude product was purified by column chromatography using silica gel a gradient of 8-10% EtOAc in pet ether as eluent. The pure fractions were collected and concentrated under reduced pressure to afford 4-(1-benzyl-1H-pyrazol-3-yl)-5-bromo-2-(4-fluorophenyl)pyridine (2.0 g, LC/MS: 76%). (LC/MS; m/z 410.2 $[M+H]^+$).

Step 4: In a glass screw-cap pressure vessel, a solution of 4-(1-benzyl-1H-pyrazol-3-yl)-5-bromo-2-(4-fluorophenyl) pyridine (1 g, 2.44 mmol) in 1,4 dioxane (10 mL) and $H_2O$ (2 mL) was treated with tert-butyl 3-(4,4,5,5-tetramethyl-1,3,2-dioxaborolan-2-yl)-2,5-dihydro-1H-pyrrole-1-carboxylate (0.87 g, 2.93 mmol) and XPhos (0.06 g, 0.12 mmol) $Cs_2CO_3$ (2.39 g, 7.34 mmol) was degassed with argon for 20 min followed by addition of $Pd_2(dba)_3$ (0.06 g, 0.06 mmol) at room temperature. The reaction mixture was stirred at 100° C. for 16 h. The reaction progress was monitored by TLC (mobile phase: 20% EtOAc in pet ether. Rf: 0.3. detection: UV). The reaction mixture was filtered through a pad of Celite and washed with EtOAc (100 mL) and the filtrate was dried over anhydrous $Na_2SO_4$ and concentered under reduced pressure to afford a pale yellow gum (900 mg, LC/MS: 62%). The crude product was purified by reverse phase column chromatography (80 g RP-$C_{18}$ column) with a gradient of 50-65% ACN in water as eluent. The pure fraction was concentrated under reduced pressure and the remaining aqueous mixture was extracted with EtOAc (3×100 mL). The combined organic layer was dried over $Na_2SO_4$ and concentrated under reduced pressure to afford the tert-butyl 3-(4-(1-benzyl-1H-pyrazol-3-yl)-6-(4-fluorophenyl) pyridin-3-yl)-2,5-dihydro-1H-pyrrole-1-carboxylate as a green liquid (700 mg, LC/MS: 85%). (LC/MS; m/z 497.6 $[M+H]^+$).

Step 5: A stirred solution of tert-butyl 3-(4-(1-benzyl-1H-pyrazol-3-yl)-6-(4-fluorophenyl)pyridin-3-yl)-2,5-dihydro-1H-pyrrole-1-carboxylate (600 mg, 1.20 mmol) in EtOH (10 mL) was treated with Pd/C (300 mg, 50% moist) in a pressure vessel. The vessel was sealed with hydrogen pressure (50 psi) and stirred at room temperature for 16 h. The reaction progress was monitored by TLC (mobile phase: 40% EtOAc in pet ether. Rf: 0.4. detection: UV). The reaction mixture was diluted with EtOH (100 mL), filtered through a pad of Celite and the filtrate was concentrated under reduced pressure to afford tert-butyl 3-(4-(1-benzyl-1H-pyrazol-3-yl)-6-(4-fluorophenyl) pyridin-3-yl) pyrrolidine-1-carboxylate as a pale yellow liquid (550 mg, LC/MS: 84%). (LC/MS; m/z 499.9 $[M+H]^+$).

Step 6: A stirred solution of tert-butyl 3-(4-(1-benzyl-1H-pyrazol-3-yl)-6-(4-fluorophenyl)pyridin-3-yl)pyrrolidine-1-carboxylate (500 mg, 1.00 mmol) in DMSO (0.712 mL, 10.02 mmol) was treated with KOtBu (1.0M THF, 7.02 mL, 7.02 mmol) at 10° C. The reaction mixture was stirred under an oxygen atmosphere (balloon) for 10 min and monitored by TLC (mobile phase: 50% EtOAc in pet ether. Rf: 0.26. detection: UV). The reaction was quenched with saturated $NH_4Cl$ (100 mL), diluted with water (100 mL) and extracted with EtOAc (3×100 mL). The combined organic layer was dried over $Na_2SO_4$ and concentrated under reduced pressure to afford a pale-yellow liquid (350 mg, LC/MS: 59%). The crude product was purified by gravity column chromatography using silica gel and a gradient of 25-30% EtOAc in pet-ether as an eluent. The pure fraction was concentrated under reduced pressure to afford tert-butyl 3-(6-(4-fluorophenyl)-4-(1H-pyrazol-3-yl) pyridin-3-yl)pyrrolidine-1-carboxylate as a yellow solid (300 mg, LC/MS: 73%). (LC/MS; m/z 409.6 $[M+H]^+$).

Step 7: A solution of tert-butyl 3-(6-(4-fluorophenyl)-4-(1H-pyrazol-3-yl)pyridin-3-yl)pyrrolidine-1-carboxylate (250 mg, 0.61 mmol) in ACN (5 mL) was treated with $K_2CO_3$ (422.30 mg, 3.06 mmol) and Int-F (203.97 mg, 3.06 mmol) at room temperature. The reaction mixture was stirred at 80° C. for 8 h and monitored by TLC (mobile phase: 70% EtOAc in pet ether. Rf: 0.28. detection: UV). The reaction mixture was quenched with water (100 mL) and extracted with EtOAc (3×100 mL). The combined organic layer was washed with brine (50 mL), dried over $Na_2SO_4$ and concentrated under reduced pressure to afford tert-butyl 3-(4-(1-(3-chloro-5-(methylcarbamoyl)benzyl)-1H-pyrazol-3-yl)-6-(4-fluorophenyl)pyridin-3-yl)pyrrolidine-1-carboxylate as a yellow gum (300 mg, LC/MS: 42%). (LC/MS; m/z 590.4 $[M+H]^+$).

Step 8: A stirred solution of tert-butyl 3-(4-(1-(3-chloro-5-(methylcarbamoyl) benzyl)-1H-pyrazol-3-yl)-6-(4-fluorophenyl)pyridin-3-yl)pyrrolidine-1-carboxylate (300 mg, 0.50 mmol) in DCM (5 mL) was treated with TFA (0.5 mL) at 0° C. and stirred at room temperature for 1 h. The reaction progress was monitored by TLC (mobile phase: 10% MeOH in DCM. Rf: 0.06. detection: UV). The reaction mixture was concentrated under reduced pressure, triturated with n-pentane (2×50 mL) and dried to afford 3-chloro-5-((3-(2-(4-fluorophenyl)-5-(pyrrolidin-3-yl)pyridin-4-yl)-1H-pyrazol-1-yl)methyl)-N-methylbenzamide TFA salt as a light liquid (200 mg, LC/MS: 68%). (LC/MS; m/z 490.3 $[M+H]^+$).

Step 9: A stirred solution of 3-chloro-5-((3-(2-(4-fluorophenyl)-5-(pyrrolidin-3-yl)pyridin-4-yl)-1H-pyrazol-1-yl) methyl)-N-methylbenzamide TFA salt (150 mg, 0.30 mmol) in water (1 mL) and 1,4-dioxane (3 mL) was treated with $NaHCO_3$ (77.14 mg, 0.91 mmol) followed by a solution of acryloyl chloride (24.93 mg, 0.27 mmol) in 1,4-dioxane (1 mL) at 0° C. The reaction mixture was stirred at 0° C. for 30 min and monitored by TLC (mobile phase: 10% MeOH in DCM. Rf: 0.53. detection: UV). The reaction mixture was quenched with water (50 mL) and extracted with EtOAc (2×100 mL). The combined organic layer was dried over $Na_2SO_4$ and concentrated under reduced pressure to afford a pale yellow gum (120 mg, LC/MS: 64%). The crude product was purified by preparative HPLC method H14. The pure fraction was concentrated under reduced pressure and lyophilized to afford 3-((3-(5-(1-acryloylpyrrolidin-3-yl)-2-(4-fluorophenyl) pyridin-4-yl)-1H-pyrazol-1-yl)methyl)-5-chloro-N-methylbenzamide (Cpd. No. 386) as an off-white solid (7.4 mg, LC/MS: 99.6%). (LC/MS; m/z 544.3 [M+H]+).

The following compound was prepared in a manner similar (use of appropriate reagents and purification methods known to the person skilled in the art) to Cpd. No. 386: Cpd. No. 387 (using MsCl and TEA in step 9), Cpd. No. 389 (using acetyl chloride and TEA in step 9).

Example 153: Synthesis of 1-(3-(5'-(4-fluorophenyl)-1-methyl-1H,2'H-[3,3'-bipyrazol]-2'-yl)pyrrolidin-1-yl)prop-2-en-1-one (Cpd. No. 416)

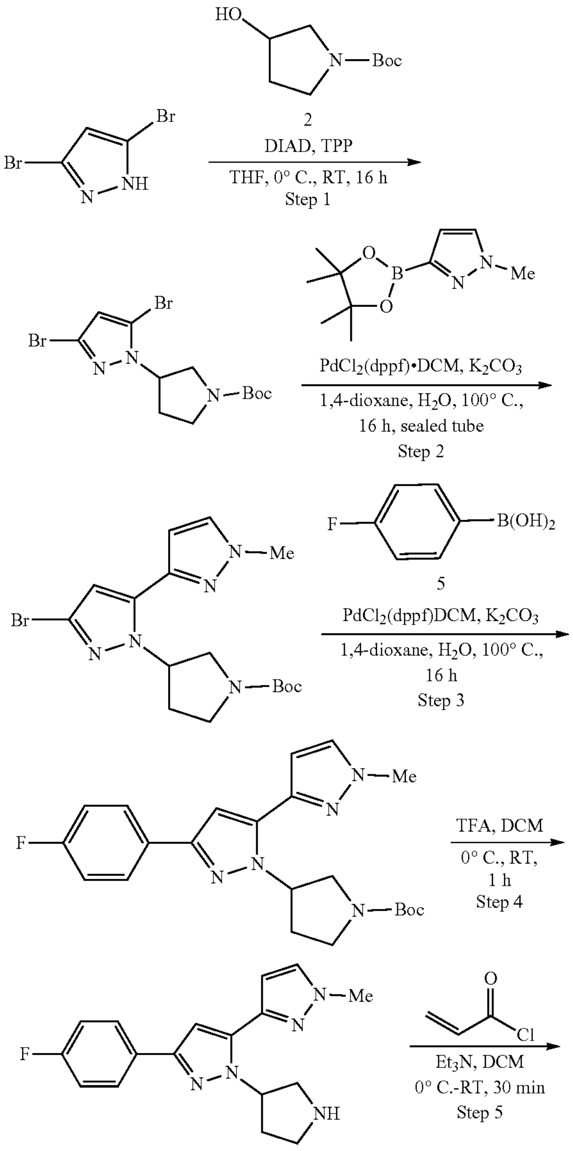

-continued

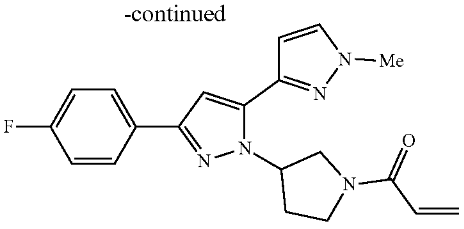

Cpd. No. 416

Step 1: A solution of 3,5-dibromo-1H-pyrazole (2.0 g, 8.85 mmol) in THF (20 mL) was treated with tert-butyl 3-hydroxypyrrolidine-1-carboxylate (1.99 g, 10.626 mmol) and triphenylphosphine (3.48 g, 13.282 mmol) at 0° C. The reaction mixture was stirred at 0° C. for 10 min and diisopropyl azodicarboxylate (2.6 mL, 13.282 mmol) was added to the reaction mixture at 0° C. The reaction mixture was stirred at room temperature for 16 h and progress of the reaction was monitored by TLC (mobile phase: 30% EtOAc in Pet Ether. Rf: 0.44. detection: KMnO4). The reaction mixture was diluted with water (100 mL) and extracted with EtOAc (3×100 mL). The combined organic layer was washed with brine (50 mL), dried over anhydrous $Na_2SO_4$ and concentrated under reduced pressure to afford a brown gum (4 g, LC/MS: 29%). The crude product was purified by normal phase column chromatography using an 80 g column (silica) and 20% EtOAc in Pet ether as eluent to afford tert-butyl 3-(3,5-dibromo-1H-pyrazol-1-yl)pyrrolidine-1-carboxylate as a brown gum (3 g, LC/MS: 99%). (LC/MS; m/z 394.1 [M+H]+).

Step 2: A solution of tert-butyl 3-(3,5-dibromo-1H-pyrazol-1-yl)pyrrolidine-1-carboxylate (2.0 g, 5.06 mmol) in dioxane (60 mL) and $H_2O$ (20 mL) was treated with 1-methyl-3-(4,4,5,5-tetramethyl-1,3,2-dioxaborolan-2-yl)-1H-pyrazole (1.36 g, 6.58 mmol) and potassium carbonate (2.09 g, 15.18 mmol) at room temperature. The reaction mixture was degassed with nitrogen for 10 min, followed by addition of $PdCl_2$(dppf)·DCM (413 mg, 0.50 mmol) and stirred at 100° C. for 16 h in a sealed tube. The reaction progress was monitored by TLC (mobile phase: 30% EtOAc in Pet Ether. Rf: 0.36. detection: UV). The reaction mixture was filtered through a pad of Celite and washed with EtOAc (50 mL). The filtrate was washed with water (50 mL) and extracted with EtOAc (3×25 mL). The combined organic layer was washed with brine (25 mL), dried over anhydrous $Na_2SO_4$ and concentrated under reduced pressure to afford the crude product (4 g, LC/MS: 37%). The crude product was purified by normal phase column chromatography using a 40 g column (silica) and an eluent of 15% EtOAc in Pet ether to afford tert-butyl 3-(5'-bromo-1-methyl-1H,2'H-[3,3'-bipyrazol]-2'-yl)pyrrolidine-1-carboxylate as an off-white solid (1.2 g, LC/MS: 71%). (LC/MS; m/z 396.3 [M+H]+).

Step 3: A solution of tert-butyl 3-(5'-bromo-1-methyl-1H,2'H-[3,3'-bipyrazol]-2'-yl)pyrrolidine-1-carboxylate (1.1 g, 2.78 mmol) in 1,4-dioxane (11 mL) and water (1.1 mL) was treated with (4-fluorophenyl)boronic acid (500 mg, 3.62 mmol) and $K_2CO_3$ (1.1 g, 8.35 mmol) at room temperature. The reaction mixture was degassed with argon for 10 minutes followed by addition of $PdCl_2$(dppf)·DCM (220 mg, 0.27 mmol) at room temperature. The reaction mixture was stirred at 100° C. for 16 h and progress of the reaction was monitored by TLC (mobile phase: 30% EtOAc in pet ether. Rf: 0.32. detection: UV). The reaction mixture was filtered through a pad of Celite and washed with EtOAc (80 mL). The filtrate was washed with brine (50 mL), dried over anhydrous $Na_2SO_4$ and concentrated under reduced pressure to afford a brown gum (1.2 g, LC/MS: 55%). The crude product was purified by gravity column chromatography using silica gel and 15% EtOAc in pet ether as an eluent to afford tert-butyl 3-(5'-(4-fluorophenyl)-1-methyl-1H,2'H-[3,3'-bipyrazol]-2'-yl)pyrrolidine-1-carboxylate as a white solid (800 mg, LC/MS: 94%). (LC/MS; m/z 412.4 [M+H]$^+$).

Step 4: A solution of tert-butyl 3-(5'-(4-fluorophenyl)-1-methyl-1H,2'H-[3,3'-bipyrazol]-2'-yl)pyrrolidine-1-carboxylate (800 mg, 1.94 mmol) in DCM (10 mL) was treated with TFA (1.488 mL, 19.44 mmol) at 0° C. The reaction mixture was stirred at room temperature for 1 and progress of the reaction was monitored by TLC (mobile phase: 10% MeOH in DCM. Rf: 0.1. detection: UV). The reaction mixture was concentrated under reduced pressure and the residue was diluted with EtOAC (50 mL), washed with saturated $NaHCO_3$ (2×20 mL) and brine (10 mL), dried over anhydrous $Na_2SO_4$ and concentrated under reduced pressure to afford 5'-(4-fluorophenyl)-1-methyl-2'-(pyrrolidin-3-yl)-1H,2'H-3,3'-bipyrazole as a yellow gum (550 mg, LC/MS: 97%). (LC/MS; m/z 312.2 [M+H]$^+$).

Step 5: A solution of 5'-(4-fluorophenyl)-1-methyl-2'-(pyrrolidin-3-yl)-1H,2'H-3,3'-bipyrazole (550 mg, 1.76 mmol) in DCM (9 mL) was treated with $Et_3N$ (1.22 mL, 8.83 mmol) and a solution of acryloyl chloride (159 mg, 1.76 mmol) in DCM (1 mL) at 0° C.

The reaction mixture was stirred at room temperature for 30 min and progress of the reaction was monitored by TLC (mobile phase: 10% MeOH in DCM. Rf: 0.5. detection: UV). The reaction mixture was diluted with DCM (80 mL), washed with brine (20 mL), dried over anhydrous $Na_2SO_4$ and concentrated under reduced pressure to afford a yellow gum (470 mg, LC/MS: 75%). The crude product was purified by preparative HPLC method H8 and the collected fraction was concentrated under reduced pressure to afford 1-(3-(5'-(4-fluorophenyl)-1-methyl-1H,2'H-[3,3'-bipyrazol]-2'-yl)pyrrolidin-1-yl)prop-2-en-1-one (Cpd. No. 416) as a white solid (136 mg, LC/MS: 99%). (LC/MS; m/z 366.3 [M+H]$^+$). Chiral SFC purification: 120 mg of Cpd. No. 416 was purified by preparative SFC method $K_{11}$ to afford Cpd. No. 401-En1 (28 mg) and Cpd. No. 401-En2 (19 mg), both as a white solid. The chiral purity of both enantiomers was assessed by analytical SFC method S19: Cpd. No. 401-En1 (98.6% ee); Cpd. No. 401-En2 (93% ee).

Example 154: Synthesis of 1-(3-(1'-(4-fluorophenyl)-1-methyl-1H,1'H-[3,4'-bipyrazol]-3'-yl)pyrrolidin-1-yl)prop-2-en-1-one (Cpd. No. 403) and 1-(3-(1'-(4-fluorophenyl)-2-methyl-1'H,2H-[3,4'-bipyrazol]-3'-yl)pyrrolidin-1-yl)prop-2-en-1-one (Cpd. No. 404)

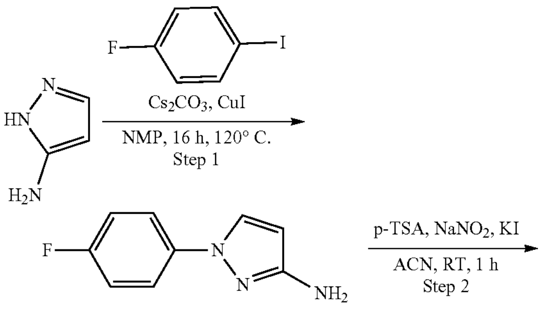

-continued

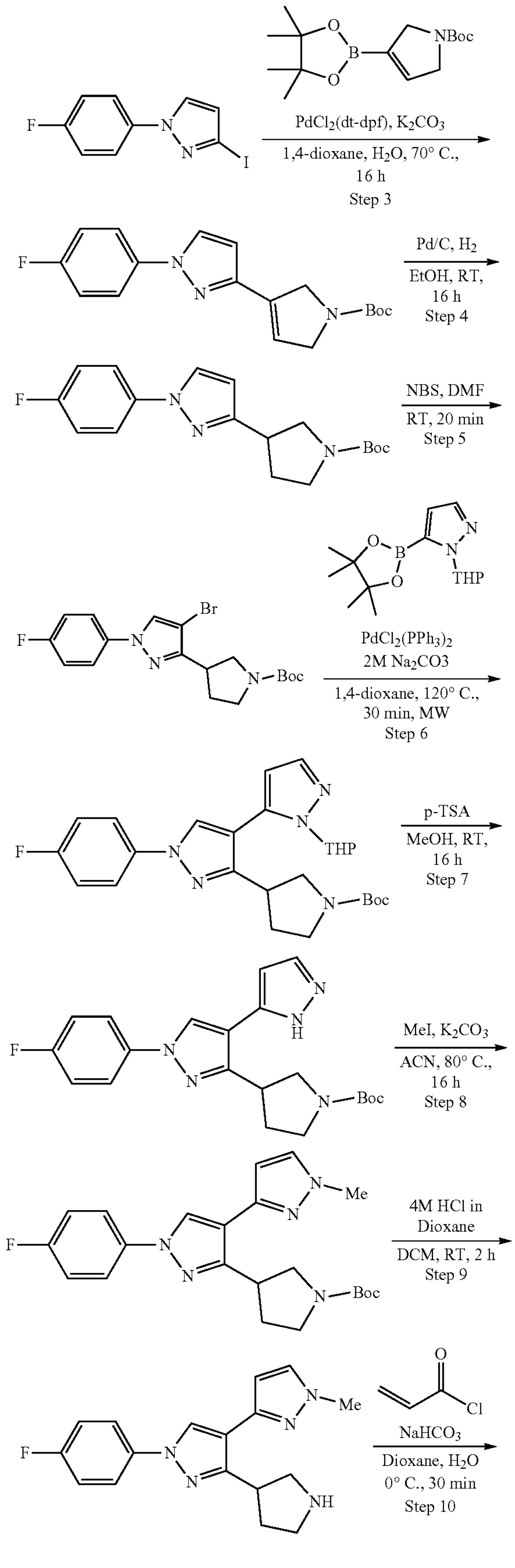

-continued

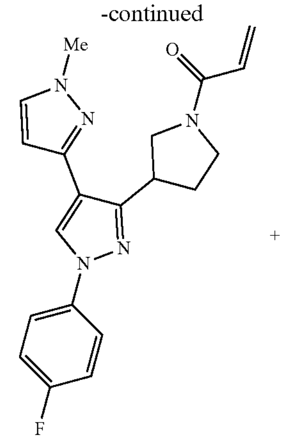

Cpd. No. 403

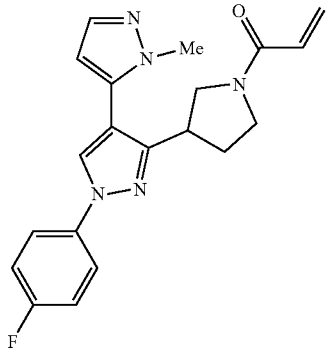

Cpd. No. 404

Step 1: A solution of 1H-pyrazol-5-amine (10 g, 120.34 mmol) in NMP (150 mL) was treated with 1-fluoro-4-iodobenzene (40.07 g, 180.51 mmol), $Cs_2CO_3$ (39.21 g, 120.34 mmol) and CuI (2.29 g, 12.03 mmol) and degassed with argon for 20 min at room temperature. The reaction mixture was stirred at 120° C. for 16 h, monitored by TLC (mobile phase: 50% EtOAC/pet ether, compound Rf: 0.30, detection: UV). The reaction mixture was filtered through pad of Celite and washed with EtOAc (500 mL). The filtrate was washed with brine (200 mL), dried over $Na_2SO_4$ and concentrated under reduced pressure to afford 1-(4-fluorophenyl)-1H-pyrazol-3-amine as a yellow gum (7.0 g, LCMS: 54%). (LC/MS; m/z 179.2 $[M+H]^+$).

Step 2: A solution of 1-(4-fluorophenyl)-1H-pyrazol-3-amine (7 g, 39.50 mmol) in ACN (70 mL) was treated with p-TSA (26.30 g, 118.52 mmol) and $NaNO_2$ (5.45 g, 79.01 mmol) and KI (24.59 g, 148.15 mmol) at room temperature. The reaction mixture was stirred at room temperature for 1 h, monitored by TLC (mobile phase: 50% EtOAc in pet ether, RF: 0.30, detection: UV). The reaction mixture was filtered through pad of Celite and washed with EtOAc (300 mL). The filtrate was washed with brine (100 mL), dried over anhydrous $Na_2SO_4$ and concentrated under reduced pressure to afford a yellow gum (12 g, LCMS: 26%). The crude product was purified by reverse phase column chromatography (50 g RP-$C_{18}$) with a gradient of 30-45% MeCN in water as eluent. The pure fraction was concentrated to afford the 1-(4-fluorophenyl)-3-iodo-1H-pyrazole as a pale yellow solid (7.0 g, LC/MS: 70%). (LC/MS; m/z 289.0 $[M+H]^+$).

Step 3: A solution of 1-(4-fluorophenyl)-3-iodo-1H-pyrazole (5 g, 17.35 mmol) in 1,4-dioxane (50 mL) and $H_2O$ (5 mL) was treated with tert-butyl 3-(4,4,5,5-tetramethyl-1,3,2-dioxaborolan-2-yl)-2,5-dihydro-1H-pyrrole-1-carboxylate (5.63 g, 19.09 mmol) and $K_2CO_3$ (7.18 g, 52.07 mmol) and degassed with argon for 20 min followed by addition of $PdCl_2$(dtbpf) (0.56 g, 0.86 mmol) at room temperature. The reaction mixture was stirred at 70° C. for 16 h and monitored by TLC (mobile phase: 50% EtOAc in pet ether, Rf: 0.48, detection: UV). The reaction mixture was filtered through a pad of celite and washed with EtOAc (300 mL). The filtrate was washed with brine (100 mL), dried over anhydrous $Na_2SO_4$ and concentrated under reduced pressure to afford tert-butyl 3-(1-(4-fluorophenyl)-1H-pyrazol-3-yl)-2,5-dihydro-1H-pyrrole-1-carboxylate as a pale yellow solid (3.0 g, LC/MS: 75%). (LC/MS; m/z 274.2 $[M+H]^+$).

Step 4: A solution of tert-butyl 3-(1-(4-fluorophenyl)-1H-pyrazol-3-yl)-2,5-dihydro-1H-pyrrole-1-carboxylate (3.0 g, 9.10 mmol) in EtOH (30 mL) was treated with palladium on activated carbon (4 g, 10% Pd, unreduced, dry) at room temperature. The reaction mixture was stirred under an $H_2$ atmosphere at room temperature for 16 h and monitored by TLC (mobile phase: 50% EtOAc in pet ether, Rf: 0.54, detection: UV). The reaction mixture was filtered through a pad of celite and washed with EtOH (100 mL) and concentrated under reduced pressure to afford tert-butyl 3-(1-(4-fluorophenyl)-1H-pyrazol-3-yl)pyrrolidine-1-carboxylate as a pale yellow solid (2.5 g, LC/MS: 98%). (LC/MS; m/z 337.3 $[M+H]^+$).

Step 5: A stirred solution of tert-butyl 3-(1-(4-fluorophenyl)-1H-pyrazol-3-yl)pyrrolidine-1-carboxylate (2.5 g, 7.54 mmol) in DMF (20 mL) was treated with NBS (1.34 g, 7.54 mmol) at room temperature. The reaction mixture was stirred under argon at room temperature for 20 min and monitored by TLC (mobile phase: 50% EtOAc in pet ether, Rf: 0.5, detection: UV). The reaction was quenched with cold water (100 mL) and extracted with EtOAc (3×100). The combined organic layer was dried over $Na_2SO_4$ and concentrated under reduced pressure to afford tert-butyl 3-(4-bromo-1-(4-fluorophenyl)-1H-pyrazol-3-yl)pyrrolidine-1-carboxylate as a pale yellow solid (2.8 g, LC/MS: 97%). (LC/MS; m/z 410.3 $[M+H]^+$).

Step 6: A solution of tert-butyl 3-(4-bromo-1-(4-fluorophenyl)-1H-pyrazol-3-yl)pyrrolidine-1-carboxylate (2.8 g, 6.82 mmol) in 1,4-dioxane (15 mL) was treated with (1-(tetrahydro-2H-pyran-2-yl)-5-(4,4,5,5-tetramethyl-1,3,2-dioxaborolan-2-yl)-1H-pyrazole (2.46 g, 8.87 mmol) and 2M $Na_2CO_3$ (6.8 mL, 13.64 mmol) and degassed with argon for 20 min followed by addition of $PdCl_2(PPh_3)_2$ (0.18 g, 0.23 mmol) at room temperature. The reaction mixture was stirred under microwave irradiation at 120° C. for 30 min and monitored by TLC (mobile phase: 50% EtOAc in pet ether, Rf: 0.48, detection: UV). The reaction mixture was filtered through pad of Celite and washed with EtOAc (200 mL). The filtrate was washed with brine (100 mL), dried over anhydrous $Na_2SO_4$ and concentrated under reduced pressure afford a pale yellow liquid (3.5 g, LC/MS: 10%). The crude product was purified by reverse phase column chromatography with a gradient of 50-65% MeCN in water as eluent. The pure fraction was concentrated under reduced pressure to afford tert-butyl 3-(1'-(4-fluorophenyl)-2-(tetrahydro-2H-pyran-2-yl)-1'H,2H-[3,4'-bipyrazol]-3'-yl)pyrrolidine-1-carboxylate as a pale yellow solid (1.4 g, LC/MS: 90%). (LC/MS; m/z 398.4 [M-THP]*).

Step 7: A solution of tert-butyl 3-(1'-(4-fluorophenyl)-2-(tetrahydro-2H-pyran-2-yl)-1'H,2H-[3,4'-bipyrazol]-3'-yl)pyrrolidine-1-carboxylate (1.4 g, 2.90 mmol) in MeOH (20 mL) was treated with p-TSA (0.25 g, 1.45 mmol) at room temperature. The reaction mixture was stirred at room temperature for 16 h. The progress of the reaction was monitored by TLC (mobile phase: 50% EtOAc in Pet ether. Rf: 0.48. detection: UV). The reaction mixture was quenched with water (100 mL) and extracted with DCM (200 mL). The organic layer was washed with brine (100 mL), dried over anhydrous $Na_2SO_4$ and concentrated under reduced pressure to afford tert-butyl 3-(1'-(4-fluorophenyl)-1'H,2H-[3,4'-bipyrazol]-3'-yl)pyrrolidine-1-carboxylate as a pale yellow solid (900 mg, LC/MS: 80%). (LC/MS; m/z 398.4 $[M+H]^+$).

Step 8: A solution of tert-butyl 3-(1'-(4-fluorophenyl)-1'H, 2H-[3,4'-bipyrazol]-3'-yl)pyrrolidine-1-carboxylate (680 mg, 1.71 mmol) in DMF (10 mL) was treated with KOtBu (209 mg, 1.86 mmol) at room temperature. The reaction mixture was cooled to 0° C. and treated with iodomethane (0.12 mL, 1.86 mmol). The reaction mixture was then stirred at room temperature for 16 h. The progress of the reaction was monitored by TLC (mobile phase: 50% EtOAc in Pet ether. Rf: 0.29. detection: UV). The reaction mixture was quenched with cold water (100 mL) and extracted with EtOAc (2×200 mL). The combined organic layer was washed with brine (100 ml), dried over $Na_2SO_4$ and concentrated under reduced pressure to afford a pale yellow liquid (800 mg, LC/MS: 56% & 20% of regioisomers). The crude product was purified by reverse phase column chromatography (80 g $C_{18}$ column) using a gradient of 30-45% MeCN in water as eluent. The pure fractions were combined and concentrated and the remaining aqueous mixture was extracted with EtOAc (3×200 mL). The combined organic extract was washed with water (100 mL), dried over $Na_2SO_4$ and concentrated under reduced pressure to afford a mixture of tert-butyl 3-(1'-(4-fluorophenyl)-1-methyl-1H,1'H-[3,4'-bipyrazol]-3'-yl)pyrrolidine-1-carboxylate and its regioisomer as a pale yellow solid (500 mg, LC/MS: 64% & 30% of regioiosmers). (LC/MS; m/z 412.4 $[M+H]^+$).

Step 9: A stirred solution of tert-butyl 3-(1'-(4-fluorophenyl)-1-methyl-1H,1'H-[3,4'-bipyrazol]-3'-yl)pyrrolidine-1-carboxylate (500 mg, 1.21 mmol, 1.0 eq) in DCM (10 mL) was treated with 4N HCl in 1,4-dioxane (4 mL) at 0° C. and stirred room temperature for 2 h. The reaction was monitored by TLC (mobile phase: 10% MeOH in DCM. Rf: 0.06. detection: UV). The reaction mixture was concentrated under reduced pressure and the residue was triturated with diethyl ether (2×50 mL) and the resulting solid was dried to afford 1'-(4-fluorophenyl)-1-methyl-3'-(pyrrolidin-3-yl)-1H, 1'H-3,4'-bipyrazole HCl salt and its regioisomer as a pale brown semi solid (425 mg, LC/MS: 51% & 16% of regiomers). (LC/MS; m/z 312.3 $[M+H]^+$).

Step 10: A stirred solution of 1'-(4-fluorophenyl)-1-methyl-3'-(pyrrolidin-3-yl)-1H,1'H-3,4'-bipyrazole HCl salt (425 mg, 1.36 mmol) in 1,4-dioxane (3 mL) and water (1 mL) was treated with $NaHCO_3$ (344 mg, 4.09 mmol) followed by a solution of acryloyl chloride (111 mg, 1.22 mmol) in dioxane (2 mL) at 0° C. The reaction mixture was stirred at 0° C. for 30 min and progress of the reaction was monitored by TLC (mobile phase: 10% MeOH/DCM. RF: 0.4 & 0.37. detection: UV). The reaction mixture was diluted with $H_2O$ (50 mL) and extracted with EtOAc (2×100 mL). The combined organic layer was dried over $Na_2SO_4$ and concentrated under reduced pressure to afford a pale yellow gum (440 mg, LC/MS: 47% & 23% of regioisomers). The crude product was purified by reverse phase preparative HPLC method H18 and the pure fraction was concentrated and lyophilized to afford 1-(3-(1'-(4-fluorophenyl)-1-methyl-1H,1'H-[3,4'-bipyrazol]-3'-yl)pyrrolidin-1-yl)prop-2-en-1-one (Cpd. No. 403) as an off-white solid (32 mg, LC/MS: 99%) and 1-(3-(1'-(4-fluorophenyl)-2-methyl-1'H, 2H-[3,4'-bipyrazol]-3'-yl)pyrrolidin-1-yl)prop-2-en-1-one (Cpd. No. 404) as an off-white solid (29 mg, LC/MS: 98%). (LC/MS; m/z 366.3 $[M+H]^+$).

Example 155: Synthesis of N-((4'-fluoro-2-methoxy-5-(1-methyl-1H-pyrazol-3-yl)-[1,1'-biphenyl]-4-yl)methyl)acrylamide (Cpd. No. 410)

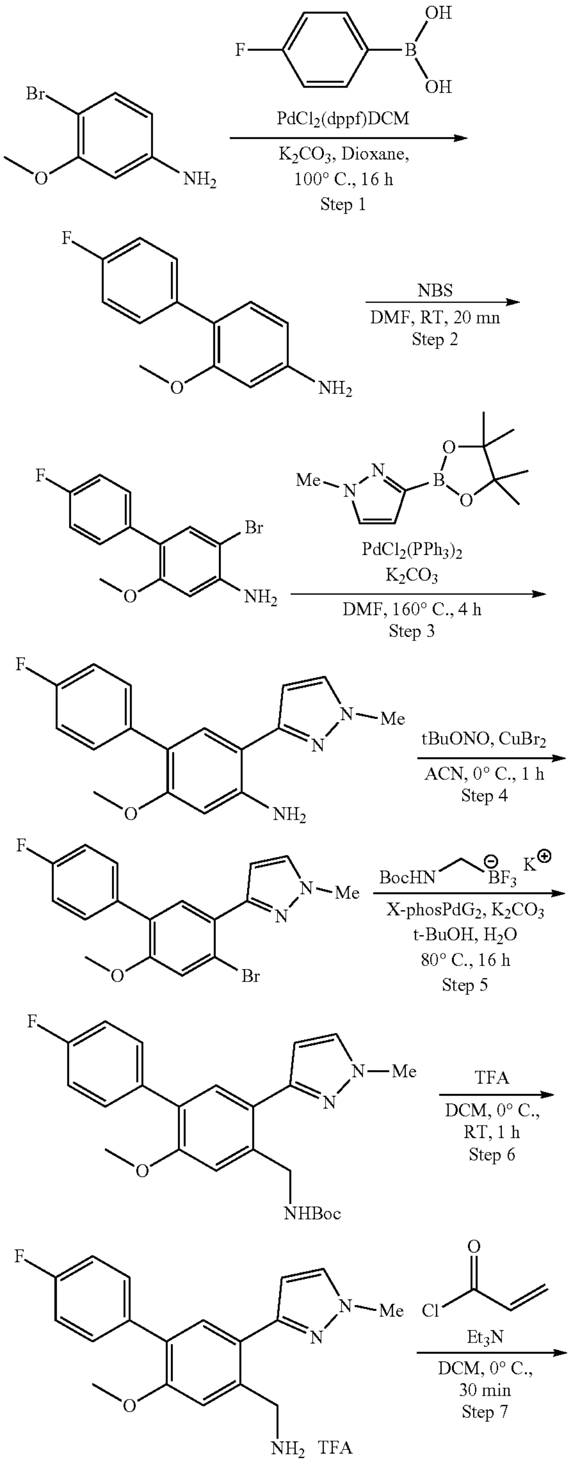

-continued

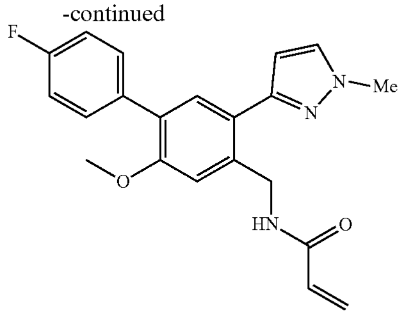

Cpd. No. 410

Step 1: In a glass screw-cap pressure vessel, a solution of 4-bromo-3-methoxyaniline (1 g, 4.94 mmol) in 1,4-dioxane (8 mL) and $H_2O$ (2 mL) was treated with (4-fluorophenyl) boronic acid (0.69 g, 4.94 mmol) and $K_2CO_3$ (2.05 g, 14.84 mmol) was degassed with argon for 20 min followed by addition of $PdCl_2$(dppf)·DCM (0.20 g, 0.24 mmol) at room temperature. The reaction mixture was stirred at 100° C. for 16 h and monitored by TLC (mobile phase: 50% EtOAc in pet ether. Rf: 0.30. detection: UV). The reaction mixture was filtered through a pad of Celite and washed with EtOAc (100 mL). The organic layer was washed with brine (100 mL), dried over anhydrous $Na_2SO_4$ and concentrated under reduced pressure to afford a pale-yellow gum (1.5 g, LC/MS: 57%). The crude product was purified by reverse phase column chromatography using an 80 g RP-C18 column and a gradient of 40-55% MeCN in water as eluent. The collected fraction was concentrated under reduced pressure and the resulting aqueous mixture was extracted with EtOAc (3×100 mL). The combined organic extract was dried over $Na_2SO_4$ and concentrated under reduced pressure to afford 4'-fluoro-2-methoxy-[1,1'-biphenyl]-4-amine as a pale yellow solid (1.3 g, LC/MS: 82%). (LC/MS; m/z 218.0 $[M+H]^+$).

Step 2: A solution of 4'-fluoro-2-methoxy-[1,1'-biphenyl]-4-amine (1.2 g, 5.52 mmol) in DMF (12 mL) was treated with NBS (0.28 g, 4.97 mmol) at room temperature. The reaction mixture was stirred under argon at room temperature for 20 min and monitored by TLC (mobile phase: 50% EtOAc in pet ether. Rf: 0.5. detection: UV). The reaction was quenched with cold water (100 mL) and extracted with EtOAc (3×100 mL). The combined organic layer was dried over $Na_2SO_4$ and concentrated to afford a pale-yellow solid (2.0 g, LC/MS: 72%). The crude product was purified by reverse phase chromatography using an 80 g RP-C18 column and a gradient of 45-55% MeCN in water as eluent. The collected fraction was concentrated under reduced pressure and the resulting aqueous mixture was extracted with EtOAc (3×100 mL). The combined organic extract was washed with water (100 mL), dried over $Na_2SO_4$ and concentrated under reduced pressure to afford 5-bromo-4'-fluoro-2-methoxy-[1,1'-biphenyl]-4-amine as a pale green solid (1.5 g, LC/MS: 83%). (LC/MS; m/z 296.0 $[M+H]^+$).

Step 3: A solution of 5-bromo-4'-fluoro-2-methoxy-[1,1'-biphenyl]-4-amine (1 g, 3.37 mmol) in DMF (5 mL) and $H_2O$ (1 mL) was treated with 1-methyl-3-(4,4,5,5-tetramethyl-1,3,2-dioxaborolan-2-yl)-1H-pyrazole (1.05 g, 5.06 mmol) and $K_2CO_3$ (1.86 g, 13.50 mmol) was degassed with argon for 20 min followed by addition of $PdCl_2(PPh_3)_2$ (0.13 g, 0.16 mmol) at room temperature. The reaction mixture was stirred at 160° C. for 4 h. The reaction was monitored by TLC (mobile phase: 50% EtOAc in Pet ether. Rf: 0.13. detection: UV). The reaction mixture was filtered through a pad of Celite and washed with EtOAc (100 mL). The organic layer was washed with cold water (100 mL), dried over anhydrous $Na_2SO_4$ and concentrated under reduced pressure to afford a pale-yellow solid compound (1.5 g, LC/MS: 67%). The crude product was purified by reverse phase chromatography using an 80 g RP-C18 column and a gradient of 30-45% MeCN in water as eluent. The collected fraction was concentrated under reduced pressure and the resulting aqueous mixture was extracted with EtOAc (3×100 mL). The combined organic extract was washed with water (100 mL), dried over $Na_2SO_4$ and concentrated under reduced pressure to afford 4'-fluoro-2-methoxy-5-(1-methyl-1H-pyrazol-3-yl)-[1,1'-biphenyl]-4-amine as an off-white solid (1.0 g, LC/MS: 94%). (LC/MS; m/z 298.1 $[M+H]^+$).

Step 4: A stirred solution of 4'-fluoro-2-methoxy-5-(1-methyl-1H-pyrazol-3-yl)-[1,1'-biphenyl]-4-amine (1.0 g, 3.36 mmol) in ACN (10 mL) was treated with tert-butyl nitrite (2.08 g, 20.17 mmol) followed by $CuBr_2$ (0.37 g, 1.68 mmol) at 0° C. The reaction mixture was stirred at room temperature for 1 h. The reaction progress was monitored by TLC (mobile phase: 40% EtOAc in pet ether. Rf: 0.4. detection: UV). The reaction mixture was quenched with $H_2O$ (100 mL) and extracted with EtOAc (2×100 mL). The combined organic layer was washed with brine (30 mL), dried over anhydrous $Na_2SO_4$ and concentrated under reduced pressure to afford a pale-yellow semi solid (2.5 g, LC/MS: 20%). The crude product was purified by reverse phase chromatography using an 80 g RP-C18 column and a gradient of 60-75% MeCN in water as eluent. The collected fraction was concentrated under reduced pressure and the resulting aqueous solution was extracted with EtOAc (3×100 mL), the organic layer was washed with water (2×100 mL), dried over $Na_2SO_4$ and concentrated under reduced pressure to afford 3-(4-bromo-4'-fluoro-6-methoxy-[1,1'-biphenyl]-3-yl)-1-methyl-1H-pyrazole as a pale-yellow solid (1.5 g, LC/MS: 62%). (LC/MS; m/z 363.1 $[M+H]^+$).

Step 5: A solution of 3-(4-bromo-4'-fluoro-6-methoxy-[1,1'-biphenyl]-3-yl)-1-methyl-1H-pyrazole (5) (500 mg, 1.38 mmol) in t-BuOH (10 mL) and $H_2O$ (3 mL) was treated with potassium [[(tert-butoxycarbonyl)amino]methyl]trifluoroborate (492 mg, 2.07 mmol) and $K_2CO_3$ (382 mg, 2.76 mmol) and the mixture was degassed with argon for 20 min followed by addition of X-phosPdG2 (54 mg, 0.06 mmol) at room temperature. The reaction mixture was stirred at 80° C. for 16 h and monitored by TLC (mobile phase: 30% EtOAc in pet ether. Rf: 0.39. detection: UV). The reaction mixture was filtered through a pad of Celite and washed with EtOAc (100 mL). The organic layer was washed with brine (50 mL), dried over anhydrous $Na_2SO_4$ and concentrated under reduced pressure to afford a pale-yellow liquid (800 mg, LC/MS: 64%). The crude product was purified by reverse phase column chromatography using an 80 g RP-C18 column and a gradient of 30-45% MeCN in water as eluent. The collected fraction was concentrated under reduced pressure and the resulting aqueous solution was extracted with EtOAc (3×100 mL). The combined organic extract was washed with water (100 mL), dried over $Na_2SO_4$ and concentrated under reduced pressure to afford tert-butyl ((4'-fluoro-2-methoxy-5-(1-methyl-1H-pyrazol-3-yl)-[1,1'-biphenyl]-4-yl)methyl)carbamate as an off-white solid (600 mg, LC/MS: 90%). (LC/MS; m/z 412.5 $[M+H]^+$).

Step-6: A stirred solution of tert-butyl ((4'-fluoro-2-methoxy-5-(1-methyl-1H-pyrazol-3-yl)-[1,1'-biphenyl]-4-yl)methyl)carbamate (600 mg, 1.45 mmol) in DCM (10 mL) was treated with TFA (2 mL) at 0° C. and stirred room temperature for 1 h. The reaction was monitored by TLC (mobile phase: 10% MeOH in DCM. Rf: 0.06. detection: UV). The reaction mixture was concentrated and the residue was triturated with diethyl ether (2×50 mL) and dried to afford 4'-fluoro-2-methoxy-5-(1-methyl-1H-pyrazol-3-yl)-[1,1'-biphenyl]-4-yl)methanamine TFA salt as a light green liquid (400 mg, LC/MS: 84%). (LC/MS; m/z 312.3 $[M+H]^+$).

Step 7: A solution of (4'-fluoro-2-methoxy-5-(1-methyl-1H-pyrazol-3-yl)-[1,1'-biphenyl]-4-yl)methanamine TFA salt (400 mg, 1.28 mmol) in 1,4-dioxane (3 mL) and water (1 mL) was treated with $NaHCO_3$ (323 mg, 3.85 mmol) followed by a solution of acryloyl chloride (116 mg, 1.28 mmol) in 1,4-dioxane (2 mL) at 0° C. The reaction mixture was stirred at 0° C. for 30 min and monitored by TLC (mobile phase: 10% MeOH in DCM. Rf: 0.53. detection: UV). The reaction mixture was diluted with water (50 mL) and extracted with EtOAc (2×50 mL). The combined organic layer was washed with brine (30 mL), dried over $Na_2SO_4$ and concentrated under reduced pressure to afford a pale-yellow gum (500 mg, LC/MS: 64%), which was purified by preparative HPLC method H17. The pure fraction was concentrated under reduced pressure to afford N-((4'-fluoro-2-methoxy-5-(1-methyl-1H-pyrazol-3-yl)-[1,1'-biphenyl]-4-yl)methyl)acrylamide (Cpd. No. 410) as an off white sticky solid (200 mg, LC/MS: 99.9%). (LC/MS; m/z 366.1 $[M+H]^+$).

Example 156: Synthesis of 1-(3-(2-(4-fluorophenyl)-4-(1-methyl-1H-pyrazol-3-yl)pyrimidin-5-yl) pyrrolidin-1-yl)prop-2-en-1-one (Cpd. No. 436)

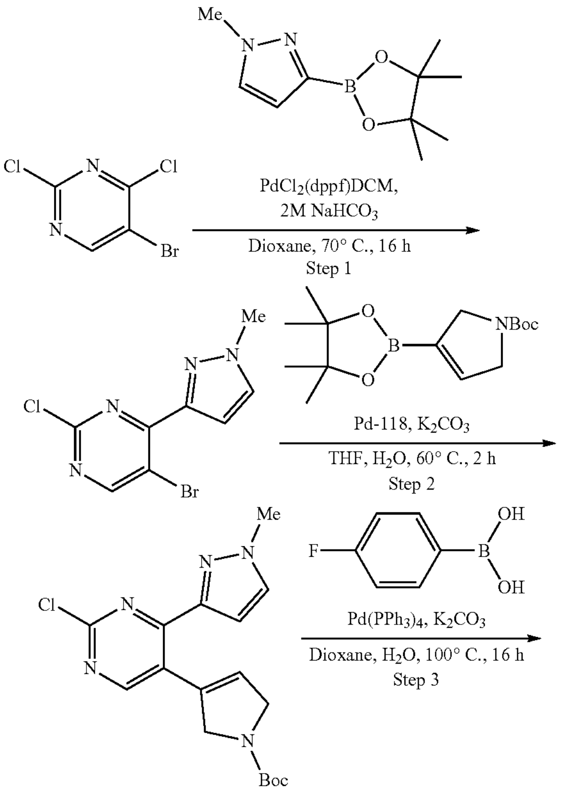

-continued

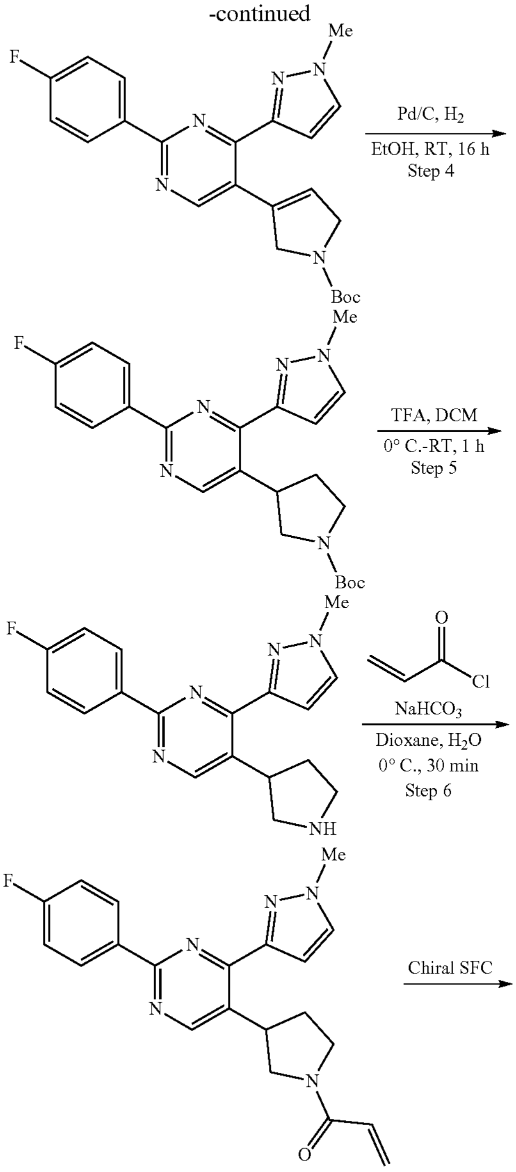

Cpd. No. 436

Cpd. No. 448-En1
Cpd. No. 448-En2

Step 1: A solution of 2,4-dichloro-5-nitropyrimidine (5.0 g, 21.94 mmol) in 1,4-dioxane (50 mL) was treated with 1-methyl-3-(4,4,5,5-tetramethyl-1,3,2-dioxaborolan-2-yl)-1H-pyrazole (4.56 g, 21.94 mmol) and 2.0 M $Na_2CO_3$ (22.5 mL) and degassed with argon for 5 min followed by addition of Pd[dppf]$C_{12}$ (0.32 g, 0.44 mmol). The reaction mixture was stirred at 70° C. for 16 h and monitored by TLC (mobile phase: 30% EtOAC/pet ether, compound Rf: 0.40, detection: UV). The reaction mixture was filtered through a pad of Celite and washed with EtOAc (300 mL). The filtrate was washed with brine (100 mL), dried over $Na_2SO_4$ and concentrated under reduced pressure to afford a yellow liquid (6.5 g, LC/MS: 20%). The crude product was purified by normal phase column chromatography on silica gel with a gradient of 10-15% EtOAc in pet. ether as eluent. Pure fractions were combined and concentrated under reduced pressure to afford 5-bromo-2-chloro-4-(1-methyl-1H-pyrazol-3-yl)pyrimidine as a pale yellow solid (2.3 g, LC/MS: 89%). (LC/MS; m/z 275.2 $[M+H]^+$).

Step 2: A solution of 5-bromo-2-chloro-4-(1-methyl-1H-pyrazol-3-yl)pyrimidine (2.3 g, 8.45 mmol) in THF (25 mL) and water (3 mL) was treated with tert-butyl 3-(4,4,5,5-tetramethyl-1,3,2-dioxaborolan-2-yl)-2,5-dihydro-1H-pyrrole-1-carboxylate (2.49 g, 8.45 mmol) and $K_2CO_3$ (5.83 g, 42.28 mmol) and degassed with argon for 5 min followed by addition of Pd(dt-bpf)$Cl_2$ (0.27 g, 0.42 mmol). The reaction mixture was stirred at 60° C. for 2 h and monitored by TLC (mobile phase: 30% EtOAc in pet ether, RF: 0.40, TLC detection: UV). The reaction mixture was filtered through a pad of Celite and washed with EtOAc (300 mL). The organic layer was dried over anhydrous $Na_2SO_4$ and concentrated under reduced pressure to afford a pale yellow solid (3.5 g, LC/MS: 56%). The crude product was purified by normal phase flash column chromatography on silica gel eluted with 15-20% EtOAc in pet. ether. The pure fractions were combined and concentrated under reduced pressure to afford tert-butyl 3-(2-chloro-4-(1-methyl-1H-pyrazol-3-yl)pyrimidin-5-yl)-2,5-dihydro-1H-pyrrole-1-carboxylate as a yellow solid (2.0 g, LC/MS: 83%). (LC/MS; m/z 362.3 $[M+H]^+$).

Step 3: A solution of tert-butyl 3-(2-chloro-4-(1-methyl-1H-pyrazol-3-yl)pyrimidin-5-yl)-2,5-dihydro-1H-pyrrole-1-carboxylate 3 (2.0 g, 5.52 mmol) in 1,4-dioxane (20 mL) and water (4 mL) was treated with (4-fluorophenyl)boronic acid (0.77 g, 5.52 mmol) and $K_2CO_3$ (2.29 g, 16.58 mmol) and degassed with argon for 5 min followed by addition of $Pd(PPh_3)_4$ (0.64 g, 0.55 mmol). The reaction mixture was stirred at 100° C. for 16 h and monitored by TLC (mobile phase: 30% EtOAc in pet ether, Rf: 0.24, detection: UV). The reaction mixture was filtered through a pad of Celite and extracted with EtOAc (300 mL) The organic layer was washed brine (100 mL), dried over anhydrous $Na_2SO_4$ and concentrated under reduced pressure to afford a pale yellow solid (2.2 g, LC/MS: 39%). The crude product was purified on normal phase flash column chromatography on silica gel and eluted with 20-25% EtOAc in pet. ether. The pure fractions were combined and concentrated under reduced pressure to afford tert-butyl 3-(2-(4-fluorophenyl)-4-(1-methyl-1H-pyrazol-3-yl)pyrimidin-5-yl)-2,5-dihydro-1H-pyrrole-1-carboxylate as a pale green solid (0.8 g, LC/MS: 95%). (LC/MS; m/z 422.4 $[M+H]^+$).

Step 4: A solution of tert-butyl 3-(2-(4-fluorophenyl)-4-(1-methyl-1H-pyrazol-3-yl)pyrimidin-5-yl)-2,5-dihydro-1H-pyrrole-1-carboxylate (800 mg, 1.89 mmol) in EtOH (10 mL) in a steel bomb was treated with Pd/C (400 mg) at 26° C. under nitrogen atmosphere. The reaction vessel was sealed and stirred under $H_2$ (50 psi) at room temperature for 16 h. The reaction progress was monitored by TLC (mobile phase: 40% EtOAc in pet ether, Rf: 0.4, detection: UV). The reaction mixture was diluted with EtOH (100 mL), filtered throughout a pad of Celite and concentrated under reduced pressure to afford tert-butyl 3-(2-(4-fluorophenyl)-4-(1-methyl-1H-pyrazol-3-yl)pyrimidin-5-yl)-2,5-dihydro-1H-pyrrole-1-carboxylate as a pale yellow solid (600 mg, LC/MS: 82%). (LC/MS; m/z 424.4 $[M+H]^+$).

Step 5: A stirred solution of tert-butyl 3-(2-(4-fluorophenyl)-4-(1-methyl-1H-pyrazol-3-yl)pyrimidin-5-yl)pyrrolidine-1-carboxylate (600 mg, 1.41 mmol, 1.0 eq) in DCM (10 mL) was treated with 1,4-dioxane in 4N HCl (4 mL) at 0° C. and stirred at room temperature for 1 h. The reaction progress was monitored by TLC (mobile phase: 10% MeOH in DCM. Rf: 0.06. detection: UV). The reaction mixture was concentrated under reduced pressure and the residue was triturated with diethyl ether (2×50 mL) and dried to afford 2-(4-fluorophenyl)-4-(1-methyl-1H-pyrazol-3-yl)-5-(pyrrolidin-3-yl)pyrimidine HCl salt as a pale yellow solid (500 mg, LC/MS: 91%). (LC/MS; m/z 324.3 $[M+H]^+$).

Step 6: A stirred solution of 2-(4-fluorophenyl)-4-(1-methyl-1H-pyrazol-3-yl)-5-(pyrrolidin-3-yl)pyrimidine HCl salt (300 mg, 0.92 mmol) in DCM (4 mL) was treated with TEA (0.39 mL, 2.78 mmol) followed by a solution of acryloyl chloride (75 mg, 0.83 mmol) in DCM (2 mL) at 0° C. The reaction mixture was stirred at 0° C. for 30 min. Progress of the reaction was monitored by TLC mobile phase: 10% MeOH/DCM. RF: 0.4. detection: UV). The reaction mixture was quenched with $H_2O$ (50 mL) and extracted with DCM (3×50 mL). The combined organic layer was dried over anhydrous $Na_2SO_4$ and concentrated under reduced pressure to afford a pale yellow gum (210 mg, LC/MS: 77%). The crude product was purified by preparative HPLC method H13 and the collected fraction was concentrated and lyophilized to afford 1-(3-(2-(4-fluorophenyl)-4-(1-methyl-1H-pyrazol-3-yl)pyrimidin-5-yl)pyrrolidin-1-yl)prop-2-en-1-one (Cpd. No. 436) as an off-white solid (77 mg, LC/MS: 99.8%). (LC/MS; m/z 424.4 $[M+H]^+$). Chiral SFC purification: 77 mg of Cpd. No. 436 was purified by preparative SFC method K2 to afford Cpd. No. 448-En1 (24 mg) and Cpd. No. 448-En2 (24 mg), both as an off-white solid. The chiral purity of both enantiomers was assessed by analytical SFC method S20: Cpd. No. 448-En1 (99.9% ee); Cpd. No. 448-En2 (99.6% ee).

Example 157: Synthesis of 1-((cis)-4-(6-(4-fluorophenyl)-4-(1-methyl-1H-pyrazol-3-yl)pyridin-3-yl)-2-methylpyrrolidin-1-yl)prop-2-en-1-one (Cpd. No. 437)

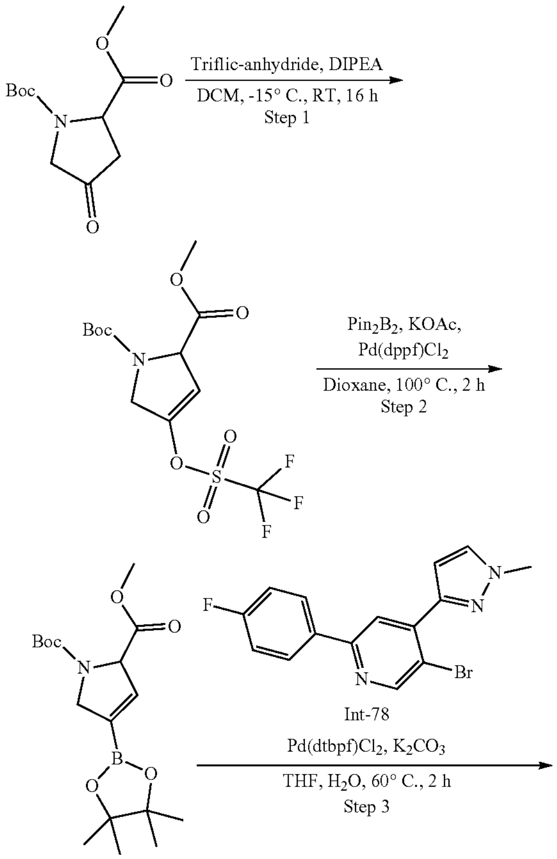

-continued
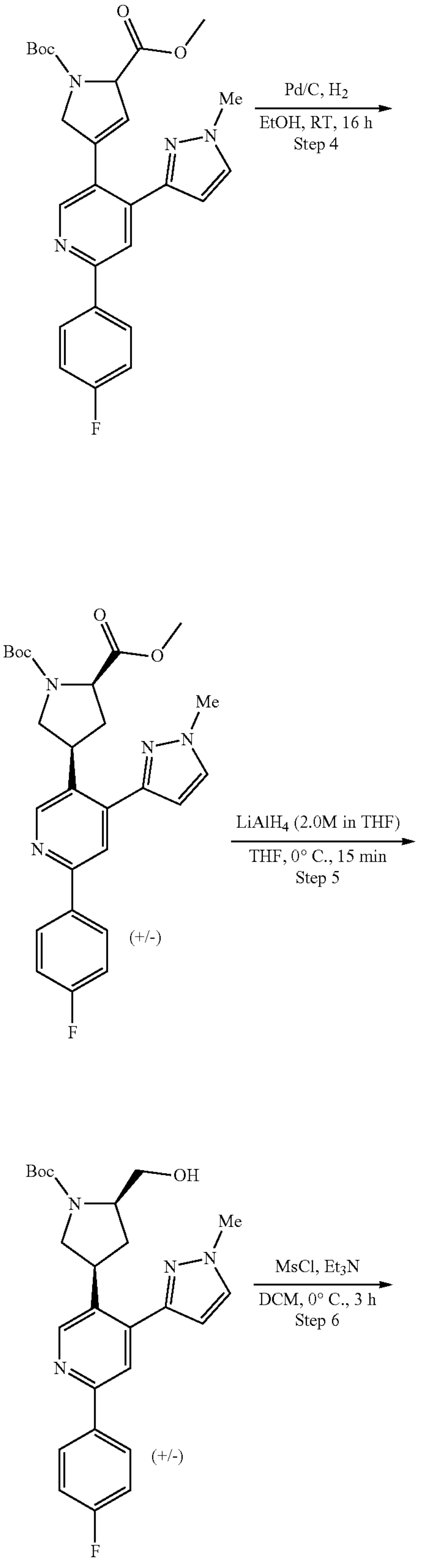
-continued
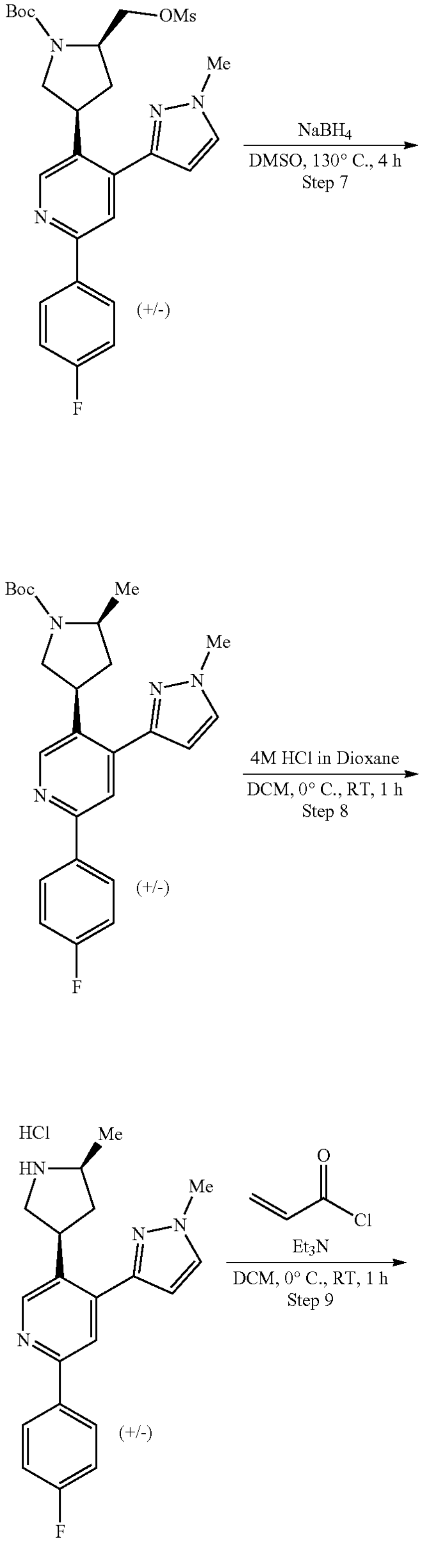

-continued

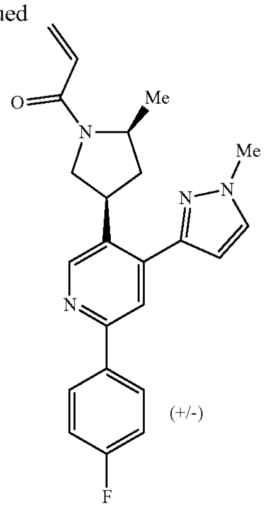

Cpd. No. 437

Step 1: A solution of 1-(tert-butyl) 2-methyl-4-oxopyrrolidine-1,2-dicarboxylate (6.0 g, 24.66 mmol) in DCM (100 mL) was treated with DIPEA (21.9 mL, 125.79 mmol) and trifluoromethanesulfonic anhydride (7.87 mL, 46.86 mmol) at −15° C. The reaction mixture was stirred at room temperature for 16 h and progress of the reaction was monitored by TLC (mobile phase: 50% EtOAC in pet ether. Rf: 0.50. detection: UV). The reaction mixture was quenched with water (200 mL) and extracted with DCM (300 mL). The organic layer was dried over anhydrous $Na_2SO_4$ and concentrated under reduced pressure to afford a yellow liquid (7.0 g). The crude product was purified by normal phase flash column chromatography using silica gel with 25% EtOAc in pet ether as eluent. The pure fractions were combined and concentrated under reduced pressure to afford 1-(tert-butyl) 2-methyl-4-(((trifluoromethyl)sulfonyl)oxy)-2,5-dihydro-1H-pyrrole-1,2-dicarboxylate as a pale yellow solid (3.0 g, LC/MS: 75%). (LC/MS; m/z 376.4 $[M+H]^+$).

Step 2: A mixture of 1-(tert-butyl) 2-methyl-4-(((trifluoromethyl)sulfonyl)oxy)-2,5-dihydro-1H-pyrrole-1,2-dicarboxylate (2.0 g, 5.32 mmol), $Pin_2B_2$ (2.03 g, 7.99 mmol) and KOAc (1.67 g, 17.05 mmol) in 1,4-dioxane (20 mL) was degassed with argon for 5 min followed by addition of $PdCl_2$(dppf) (0.23 g, 0.32 mmol) at room temperature. The reaction mixture was stirred at 100° C. for 2 h under argon and monitored by TLC (mobile phase: 20% EtOAc in pet ether, RF: 0.17, detection: UV). The reaction mixture was quenched with $H_2O$ (100 mL) and extracted with EtOAc (2×100 mL). The organic layer was dried over anhydrous $Na_2SO_4$ and concentrated under reduced pressure to afford 1-(tert-butyl) 2-methyl-4-(4,4,5,5-tetramethyl-1,3,2-dioxaborolan-2-yl)-2,5-dihydro-1H-pyrrole-1,2-dicarboxylate as a pale green liquid (2.6 g), which was used immediately in the next step.

Step 3: A solution of 1-(tert-butyl) 2-methyl-4-(4,4,5,5-tetramethyl-1,3,2-dioxaborolan-2-yl)-2,5-dihydro-1H-pyrrole-1,2-dicarboxylate (2.0 g, 5.66 mmol) in THF (20 mL) and water (5 mL) was treated with Int-78 (1.88 g, 5.66 mmol) and $K_2CO_3$ (3.90 g, 28.31 mmol) and degassed with argon for 5 min followed by addition of Pd(dt-bpf)$Cl_2$ (0.18 g, 0.28 mmol). The reaction mixture was stirred at 60° C. for 2 h and monitored by TLC (mobile phase: 30% EtOAc in pet ether, Rf: 0.4, detection: UV). The reaction mixture was filtered through a pad of Celite and washed with EtOAc (200 mL). The filtrate was washed with $H_2O$ (50 mL), brine (100 mL), dried over anhydrous $Na_2SO_4$ and concentrated under reduced pressure to afford a pale-yellow solid (3.5 g, LC/MS: 80%). The crude product was purified by flash column chromatography on silica gel using a gradient of 15-20% EtOAc in pet ether as eluent. The pure fraction was concentrated under reduced pressure to afford 1-(tert-butyl) 2-methyl-4-(6-(4-fluorophenyl)-4-(1-methyl-1H-pyrazol-3-yl)pyridin-3-yl)-2,5-dihydro-1H-pyrrole-1,2-dicarboxylate as an off-white solid (2.6 g, LC/MS: 89%). (LC/MS; m/z 479.5 $[M+H]^+$).

Step 4: A stirred suspension of 10% Pd/C (1.25 g) in EtOH (30 mL) was treated with 1-(tert-butyl) 2-methyl-4-(6-(4-fluorophenyl)-4-(1-methyl-1H-pyrazol-3-yl)pyridin-3-yl)-2,5-dihydro-1H-pyrrole-1,2-dicarboxylate (2.6 g, 5.433 mmol) and stirred at room temperature for 16 h under $H_2$ atmosphere. Progress of the reaction was monitored by TLC (mobile phase: 30% EtOAc in pet ether, Rf: 0.53, detection: UV). The reaction mixture was filtered through a pad of Celite and washed with EtOH (200 mL). The filtrate was concentered under reduced pressure to afford 1-(tert-butyl) 2-methyl-4-(6-(4-fluorophenyl)-4-(1-methyl-1H-pyrazol-3-yl)pyridin-3-yl)pyrrolidine-1,2-dicarboxylate as a pale yellow liquid (2.1 g, LC/MS: 92%). (LC/MS; m/z 481.5 $[M+H]^+$).

Step 5: To a stirred the solution of $LiAlH_4$ (2.0 M in THF) (4.1 mL, 8.32 mmol) in dry THF (20 mL) was slowly added 1-(tert-butyl) 2-methyl-4-(6-(4-fluorophenyl)-4-(1-methyl-1H-pyrazol-3-yl)pyridin-3-yl)pyrrolidine-1,2-dicarboxylate (2.0 g, 4.16 mmol) at 0° C. The reaction mixture was stirred at 0° C. for 15 min and the reaction was monitored by TLC (mobile phase: 50% EtOAc in Pet ether. Rf: 0.46. detection: UV active). The reaction mixture was quenched with saturated $Na_2SO_4$ (100 mL) and extracted with EtOAc (3×100 mL). The organic layer was washed with water (100 mL), dried over anhydrous $Na_2SO_4$ and concentrated under reduced pressure to afford tert-butyl 4-(6-(4-fluorophenyl)-4-(1-methyl-1H-pyrazol-3-yl)pyridin-3-yl)-2-(hydroxymethyl)pyrrolidine-1-carboxylate as a pale yellow liquid (1.7 g, LC/MS: 91%). (LC/MS; m/z 453.5 $[M+H]^+$).

Step 6: A stirred solution of tert-butyl 4-(6-(4-fluorophenyl)-4-(1-methyl-1H-pyrazol-3-yl)pyridin-3-yl)-2-(hydroxymethyl)pyrrolidine-1-carboxylate (1.3 g, 2.87 mmol) in DCM (15 mL) was treated with $Et_3N$ (1.20 mL, 8.61 mmol) followed by a solution of mesyl chloride (0.65 g, 2.87 mmol) in DCM (5 mL) at 0° C. The reaction mixture was stirred at room temperature for 2 h and monitored by TLC (mobile phase: 10% MeOH in DCM, Rf: 0.4, detection: UV). The reaction mixture was quenched with $H_2O$ (100 mL) and extracted with DCM (3×100 mL). The combined organic layer was dried over anhydrous $Na_2SO_4$ and concentrated under reduced pressure to afford crude product as a pale-yellow gum (1.7 g, LC/MS purity: 89%). The crude product was purified by flash column chromatography on silica gel with a gradient of 3-5% MeOH in DCM as eluent. The pure fraction was concentrated under reduced pressure to afford tert-butyl 4-(6-(4-fluorophenyl)-4-(1-methyl-1H-pyrazol-3-yl)pyridin-3-yl)-2-(((methylsulfonyl)oxy)methyl) pyrrolidine-1-carboxylate as a pale-yellow gum (1.3 g, LC/MS: 84%). (LC/MS; m/z 531.4 $[M+H]^+$).

Step 7: To a stirred solution of tert-butyl 4-(6-(4-fluorophenyl)-4-(1-methyl-1H-pyrazol-3-yl)pyridin-3-yl)-2-(((methylsulfonyl)oxy)methyl)pyrrolidine-1-carboxylate (1.3 g, 2.82 mmol) in DMSO (10 mL) was slowly added $NaBH_4$ (0.53 g, 14.13 mmol) at room temperature. The reaction mixture was stirred at 130° C. for 4 h and monitored by TLC (mobile phase: 50% EtOAc in Pet ether. Rf: 0.5.

detection: UV). The reaction mixture was quenched with 1N HCl (pH=1-2), diluted with water (100 mL) and extracted with EtOAc (3×200 mL). The combined organic extract was dried over anhydrous $Na_2SO_4$ and concentrated under reduced pressure to afford tert-butyl 4-(6-(4-fluorophenyl)-4-(1-methyl-1H-pyrazol-3-yl)pyridin-3-yl)-2-methylpyrrolidine-1-carboxylate as a pale-yellow gum (860 mg, LC/MS: 86%). (LC/MS; m/z 437.4 $[M+H]^+$).

Step 8: A stirred solution of tert-butyl 4-(6-(4-fluorophenyl)-4-(1-methyl-1H-pyrazol-3-yl)pyridin-3-yl)-2-methylpyrrolidine-1-carboxylate (860 mg, 1.970 mmol) in DCM (10 mL) was treated with 4N HCl in 1,4-dioxane (5 mL) at 0° C. The reaction mixture was stirred at room temperature for 1 h and the monitored by TLC (mobile phase: 10% MeOH in DCM. Rf: 0.06. detection: UV). The reaction mixture was concentrated under reduced pressure and the residue was triturated with diethyl ether (2×50 mL) and dried to afford 2-(4-fluorophenyl)-4-(1-methyl-1H-pyrazol-3-yl)-5-(5-methylpyrrolidin-3-yl)pyridine HCl salt as a pale yellow solid (720 mg, LC/MS: 86%). (LC/MS; m/z 337.3 $[M+H]^+$).

Step 9: A stirred solution of 2-(4-fluorophenyl)-4-(1-methyl-1H-pyrazol-3-yl)-5-(5-methylpyrrolidin-3-yl)pyridine HCl salt (710 mg, 2.11 mmol) in DCM (15 mL) was treated with $Et_3N$ (1.18 mL, 8.44 mmol) followed by a solution of acryloyl chloride (0.171 mL, 2.11 mmol) in DCM (5 mL) at 0° C. The reaction mixture was stirred at room temperature for 1 h and progress of the reaction was monitored by TLC (mobile phase: 10% MeOH/DCM. RF: 0.4. detection: UV). The reaction mixture was quenched with $H_2O$ (100 mL) and extracted with DCM (3×100 mL). The combined organic extract was dried over anhydrous $Na_2SO_4$ and concentrated under reduced pressure to afford crude a pale yellow gum (650 mg, LC/MS purity: 63%). The crude product was purified by preparative HPLC method H13 and the pure fraction was concentrated and lyophilized to afford 1-(4-(6-(4-fluorophenyl)-4-(1-methyl-1H-pyrazol-3-yl)pyridin-3-yl)-2-methylpyrrolidin-1-yl)prop-2-en-1-one (Cpd. No. 437) as a pale brown solid (143 mg, LC/MS: 95%, single diastereomer (cis)). (LC/MS; m/z 391.3 $[M+H]^+$). Chiral SFC purification: 130 mg of Cpd. No. 437 was purified by preparative SFC method K12 to afford Cpd. No. 455-En1 (25 mg) and Cpd. No. 455-En2 (53 mg), both as a white solid. The chiral purity of both enantiomers was assessed by analytical SFC method S21: Cpd. No. 455-En1 (99.9% ee); Cpd. No. 455-En2 (94% ee).

Example 158: Synthesis of 1-((trans)-3-(6-(4-fluorophenyl)-4-(1-methyl-1H-pyrazol-3-yl)pyridin-3-yl)-4-hydroxypyrrolidin-1-yl)prop-2-en-1-one (Cpd. No. 460)

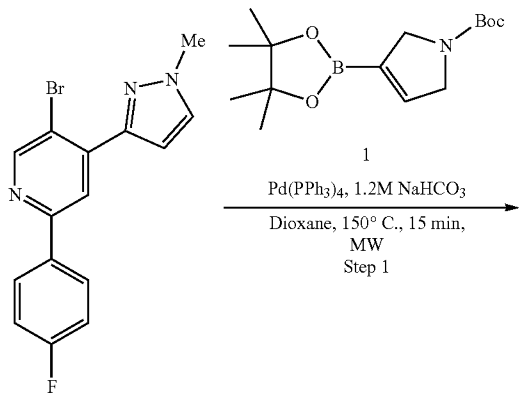

Int-78

-continued

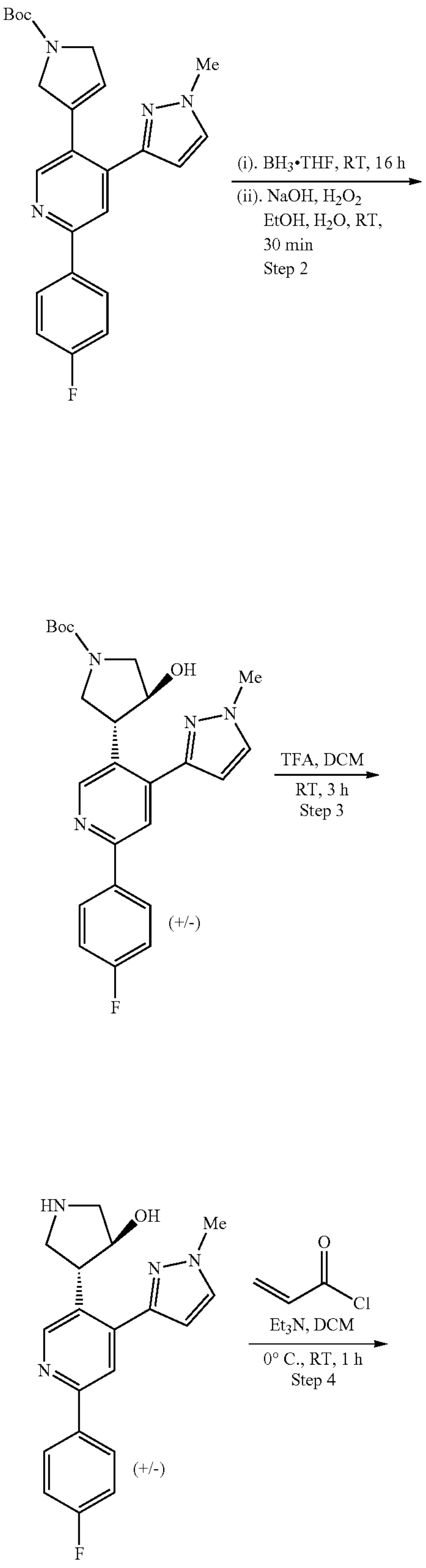

-continued

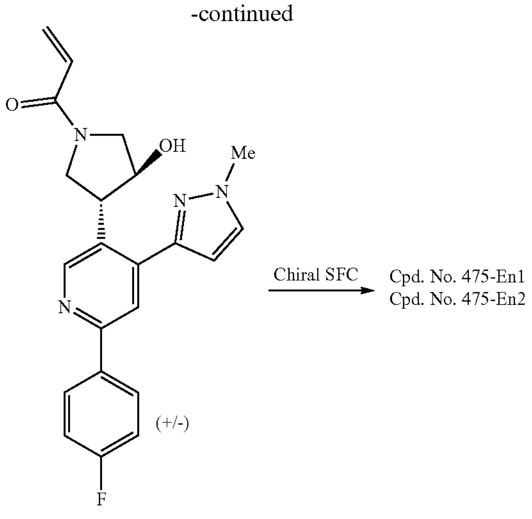

Cpd. No. 460

Step 1: A solution of Int-78 (500 mg, 1.50 mmol) in 1,4-dioxane (8 mL) was treated with tert-butyl 3-(4,4,5,5-tetramethyl-1,3,2-dioxaborolan-2-yl)-2,5-dihydro-1H-pyrrole-1-carboxylate (578 mg, 1.95 mmol) and 1.2 M $NaHCO_3$ (8 mL) at room temperature. The reaction mixture was degassed with argon for 10 min followed by addition of $Pd(PPh_3)_4$ (174 g, 0.15 mmol) at room temperature. The reaction mixture was stirred at 150° C. for 15 min under microwave irradiation and progress of the reaction was monitored by TLC (mobile phase: 20% EtOAc in pet ether. Rf: 0.18. detection: UV). The reaction mixture was filtered through a pad of Celite and washed with EtOAc (50 mL). The filtrate was washed with brine (3×30 mL), dried over anhydrous $Na_2SO_4$ and concentrated under reduced pressure to afford a brown gum (520 mg, LC/MS: 47%). The crude product was purified by flash column chromatography using a 40 g column and 10% EtOAc in pet ether as an eluent to afford tert-butyl 3-(6-(4-fluorophenyl)-4-(1-methyl-1H-pyrazol-3-yl)pyridin-3-yl)-2,5-dihydro-1H-pyrrole-1-carboxylate as a brown solid (250 mg, LC/MS: 90%). (LC/MS; m/z 421.4 $[M+H]^+$).

Step 2: A stirred solution of tert-butyl 3-(6-(4-fluorophenyl)-4-(1-methyl-1H-pyrazol-3-yl)pyridin-3-yl)-2,5-dihydro-1H-pyrrole-1-carboxylate (100 mg, 0.23 mmol) in THF (1 mL) was treated with 1M $BH_3$·THF (0.72 mL, 0.72 mmol) at room temperature. The reaction mixture was stirred at room temperature for 16 h, then 6M NaOH (1 mL) was added followed by $H_2O_2$ (1 mL) and EtOH (0.6 mL) at room temperature. The reaction mixture was further stirred for 30 min and progress of the reaction was monitored by TLC (mobile phase: 50% EtOAc in pet-ether. Rf:0.13. detection: UV). The reaction mixture was diluted with water (40 mL) and extracted with EtOAc (2×10 mL). The combined organic layer was dried over sodium sulphate and concentrated under reduced pressure to afford an off-white solid (90 mg, LC/MS: 17%). The crude product was purified by flash column chromatography (silica) using 30% EtOAc in pet ether as an eluent to afford tert-butyl 3-(6-(4-fluorophenyl)-4-(1-methyl-1H-pyrazol-3-yl)pyridin-3-yl)-4-hydroxypyrrolidine-1-carboxylate as a white solid (20 mg, LC/MS: 90%). (LC/MS; m/z 439.6 $[M+H]^+$).

Step 3: A solution of tert-butyl 3-(6-(4-fluorophenyl)-4-(1-methyl-1H-pyrazol-3-yl)pyridin-3-yl)-4-hydroxypyrrolidine-1-carboxylate (20 mg, 0.04 mmol) in DCM (0.5 mL) was treated with TFA (0.05 mL, 0.68 mmol) at 0° C. The reaction mixture was stirred at room temperature for 30 min and progress of the reaction was monitored by TLC (mobile phase: 10% MeOH in DCM. Rf: 0.12. Detection: UV). The reaction mixture was concentrated under reduced pressure to afford 4-(6-(4-fluorophenyl)-4-(1-methyl-1H-pyrazol-3-yl)pyridin-3-yl)pyrrolidin-3-ol TFA salt as a brown gum (18 mg, LC/MS: 84%). (LC/MS; m/z 339.4 $[M+H]^+$).

Step 4: A solution of 4-(6-(4-fluorophenyl)-4-(1-methyl-1H-pyrazol-3-yl)pyridin-3-yl)pyrrolidin-3-ol TFA salt (18 mg, 0.05 mmol) in DCM (1 mL) was treated with triethylamine (0.03 mL, 0.21 mmol) and acryloyl chloride (6 mg, 0.05 mmol) at 0° C. The reaction mixture was stirred at room temperature for 1 h and progress of the reaction was monitored by TLC (mobile phase: 80% EtOAc in pet ether. Rf: 0.3. detection: UV). The reaction mixture was diluted with water (5 mL) and extracted with EtOAc (25 mL). The organic layer was washed with brine (15 mL), dried over sodium sulfate and concentrated under reduced pressure to afford a brown gum (17 mg, LC/MS: 75%). The crude product was purified by preparative HPLC method H20 and the collected fraction was concentrated under reduced pressure and dried to afford 1-((trans)-3-(6-(4-fluorophenyl)-4-(1-methyl-1H-pyrazol-3-yl)pyridin-3-yl)-4-hydroxypyrrolidin-1-yl)prop-2-en-1-one as an off-white semi solid (Cpd. No. 460) (4.5 mg, LC/MS: 99%). (LC/MS; m/z 393.3 $[M+H]^+$). Chiral SFC purification: 130 mg of Cpd. No. 460 was purified by preparative SFC method K13 to afford Cpd. No. 475-En1 (23 mg) and Cpd. No. 475-En2 (42 mg), both as an off white solid. The chiral purity of both enantiomers was assessed by analytical SFC method S22: Cpd. No. 475-En1 (99.6% ee); Cpd. No. 475-En2 (99.2% ee).

Example 159: Synthesis of 1-(3-(6-(4-fluorophenyl)-4-(1-methyl-1H-pyrazol-3-yl)pyridin-3-yl)azetidin-1-yl)prop-2-en-1-one (Cpd. No. 474)

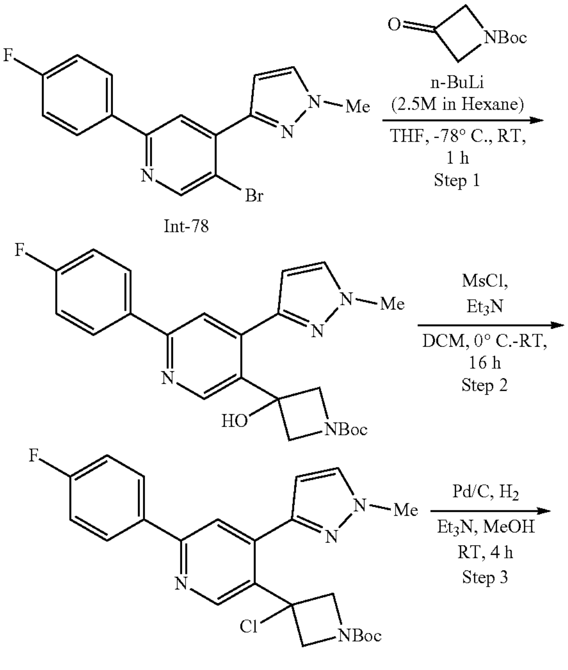

-continued

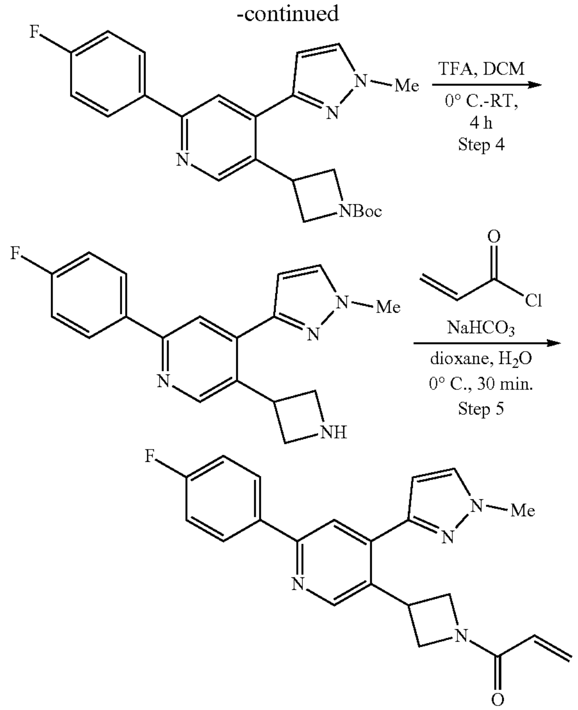

Cpd. No. 474

Step 1: A solution of Int-78 (4.0 g, 12.048 mmol) in THF (40 mL) was treated with tert-butyl 3-oxoazetidine-1-carboxylate (4.125 g, 24.096 mmol) followed by n-BuLi (1.6 M in hexane) (9.03 mL, 14.458 mmol) at −78° C. The reaction mixture was stirred at room temperature for 1 h under nitrogen atmosphere. Progress of the reaction was monitored by TLC (mobile phase: 50% EtOAc in pet ether. Rf: 0.21. detection: UV). The reaction mixture was quenched with saturated $NH_4Cl$ (50 mL) and extracted with EtOAc (2×100 mL). The combined organic layer was washed with brine (50 mL), dried over anhydrous $Na_2SO_4$ and concentrated under reduced pressure to afford a pale-yellow oil (4.5 g, LC/MS: 25%). The crude product was purified by column chromatography using silica gel and and a gradient of 25-35% EtOAc in pet ether as eluent. The pure fraction was concentrated under reduced pressure to afford tert-butyl 3-(6-(4-fluorophenyl)-4-(1-methyl-1H-pyrazol-3-yl)pyridin-3-yl)-3-hydroxyazetidine-1-carboxylate as an off-white solid (2 g, LC/MS: 94%). (LC/MS; m/z 425.3 $[M+H]^+$).

Step 2: A solution of tert-butyl 3-(6-(4-fluorophenyl)-4-(1-methyl-1H-pyrazol-3-yl)pyridin-3-yl)-3-hydroxyazetidine-1-carboxylate (500 mg, 1.178 mmol) in DCM (10 mL) was treated with $Et_3N$ (0.109 mL, 1.414 mmol) and methanesulfonyl chloride (0.109 mL, 1.414 mmol) at 0° C. The reaction mixture was stirred at room temperature for 16 h and monitored by TLC (mobile phase: 50% EtOAc in pet ether, Rf: 0.54, detection: UV). The reaction mixture was concentrated under reduced pressure and purified by normal phase chromatography column (silica) using 30% EtOAc in pet ether as eluent. The pure fraction was concentrated under reduced pressure to afford tert-butyl 3-chloro-3-(6-(4-fluorophenyl)-4-(1-methyl-1H-pyrazol-3-yl)pyridin-3-yl)azetidine-1-carboxylate as an off-white solid (400 mg, LC/MS: 86%). (LC/MS; m/z 443.3 $[M+H]^+$).

Step 3: A solution of tert-butyl 3-chloro-3-(6-(4-fluorophenyl)-4-(1-methyl-1H-pyrazol-3-yl)pyridin-3-yl)azetidine-1-carboxylate (400 mg, 0.903 mmol) in MeOH (6 mL) and $Et_3N$ (1.5 mL) was treated with 10% Pd/C (50% moist) (200 mg) at room temperature and stirred for 4 h under $H_2$ atmosphere (balloon). The reaction progress was monitored by TLC (mobile phase: 50% EtOAc in pet ether, Rf: 0.40. detection: UV). The reaction mixture was filtered through a pad of Celite and washed with MeOH (100 mL). The filtrate was concentrated under reduced pressure to afford tert-butyl 3-(6-(4-fluorophenyl)-4-(1-methyl-1H-pyrazol-3-yl)pyridin-3-yl)azetidine-1-carboxylate as a pale brown semi solid (400 mg, LC/MS: 68%). (LC/MS; m/z 409.3 $[M+H]^+$).

Step 4: A solution of tert-butyl 3-(6-(4-fluorophenyl)-4-(1-methyl-1H-pyrazol-3-yl)pyridin-3-yl)azetidine-1-carboxylate (400 mg, 0.979 mmol) in DCM (5 mL) was treated with TFA (2 mL) at 0° C. The reaction mixture was stirred at room temperature for 4 h and monitored by TLC (mobile phase: 10% MeOH in DCM, Rf: 0.11, detection: UV). The reaction mixture was concentrated under reduced pressure and the residue was triturated with n-pentane (50 mL) and dried to afford 5-(azetidin-3-yl)-2-(4-fluorophenyl)-4-(1-methyl-1H-pyrazol-3-yl)pyridine TFA salt as a pale brown semi solid (410 mg, LC/MS: 69%). (LC/MS; m/z 309.2 $[M+H]^+$).

Step 5: A solution of 5-(azetidin-3-yl)-2-(4-fluorophenyl)-4-(1-methyl-1H-pyrazol-3-yl)pyridine TFA salt (410 mg, 0.971 mmol) in 1,4-dioxane (6 mL) and water (2 mL) was cooled to 0° C. and treated with a solution of $NaHCO_3$ (407.709 mg, 4.854 mmol) and a solution of acryloyl chloride (96.643 mg, 1.068 mmol) in 1,4-dioxane (2 mL) at 0° C. The reaction mixture was stirred at 0° C. for 30 min and monitored by TLC (mobile phase: 10% MeOH in DCM, Rf: 0.38. detection: UV). The reaction mixture was diluted with $H_2O$ (20 mL) and extracted with EtOAc (2×50 mL). The combined organic layer was washed with brine (30 mL), dried over anhydrous $Na_2SO_4$ and concentrated under reduced pressure to afford a pale brown semi solid (320 mg, LC/MS: 11%). The crude product was purified by preparative HPLC method H9. The pure fraction was concentrated under reduced pressure to afford 1-(3-(6-(4-fluorophenyl)-4-(1-methyl-i H-pyrazol-3-yl)pyridin-3-yl)azetidin-1-yl)prop-2-en-1-one (Cpd. No. 474) as an off white solid (4 mg, LC/MS: 95%). (LC/MS; m/z 363.2 $[M+H]^+$).

TABLE 2

Analytical data for synthesized compounds of the disclosure

| Cpd. No. | $[M + H]^+$ (m/z) : | LC/MS or UPLC Method | RT (min.) | $^1$H NMR (δ ppm) |
|---|---|---|---|---|
| 001 | 356.2 | U1 | 1.83 | (DMSO-$d_6$) δ ppm: 9.12 (1H, d), 9.07 (1H, d), 8.47 (1H, s), 8.13 (1H, s), 7.92 (1H, d), 7.89 (1H, d), 7.70 (1H, d), 7.52-7.58 (1H, m), 7.33-7.39 (2H, m), 7.26-7.32 (3H, m), 6.94 (1H, d), 5.42 (2H, s) |

TABLE 2-continued

| Analytical data for synthesized compounds of the disclosure | | | | |
|---|---|---|---|---|
| Cpd. No. | $[M + H]^+$ (m/z) : | LC/MS or UPLC Method | RT (min.) | $^1$H NMR (δ ppm) |
| 002 | 355.2 | U1 | 2.66 | (DMSO-$d_6$) δ ppm: 9.07 (1H, s), 9.03 (1H, s), 8.51 (1H, s), 8.29 (1H, s), 8.15 (1H, s), 7.93 (1H, d), 7.89 (1H, d), 7.66-7.75 (2H, m), 7.51-7.59 (1H, m), 7.33-7.40 (2H, m), 7.25-7.32 (3H, m), 6.92 (1H, d), 5.42 (2H, s) |
| 003 | 327.2 | U1 | 2.78 | (DMSO-$d_6$) δ ppm: 8.06 (1H, d), 7.98 (1H, s), 7.94 (1H, d), 7.91 (1H, d), 7.80 (1H, d), 7.44-7.56 (2H, m), 7.32-7.40 (2H, m), 7.24-7.32 (3H, m), 7.19 (1H, t), 6.86 (1H, d), 5.43 (2H, s), 5.40 (2H, s) |
| 004 | 381.2 | U1 | 3.20 | (DMSO-$d_6$) δ ppm: 10.50 (1H, s), 8.85 (1H, d), 8.65 (1H, d), 8.39 (1H, t), 8.06 (1H, s), 7.92 (1H, d), 7.86 (1H, d), 7.59-7.64 (1H, m), 7.51-7.57 (1H, m), 7.33-7.40 (2H, m), 7.25-7.32 (3H, m), 6.89 (1H, d), 6.43-6.52 (1H, m), 6.28-6.37 (1H, m), 5.77-5.89 (1H, m), 5.42 (2H, s) |
| 005 | 337.2 | U1 | 3.70 | (DMSO-$d_6$) δ ppm: 9.25 (1H, d), 9.03 (1H, s), 8.73 (1H, s), 8.17 (1H, s), 7.89-7.95 (2H, m), 7.74 (1H, d), 7.55 (1H, t), 7.33-7.39 (2H, m), 7.26-7.32 (3H, m), 6.95 (1H, d), 5.41 (2H, s) |
| 006 | 383.2 | U1 | 3.19 | (DMSO-$d_6$) δ ppm: 10.20 (1H, s), 8.78 (1H, d), 8.59 (1H, d), 8.29-8.35 (1H, m), 8.04 (1H, s), 7.92 (1H, d), 7.85 (1H, d), 7.56-7.63 (1H, m), 7.49-7.56 (1H, m), 7.32-7.40 (2H, m), 7.24-7.34 (3H, m), 6.88 (1H, d), 5.41 (2H, s), 2.39 (2H, q), 1.11 (3H, t) |
| 007 | 369.2 | U1 | 2.86 | (DMSO-$d_6$) δ ppm: 10.27 (1H, s), 8.76 (1H, d), 8.60 (1H, d), 8.30 (1H, s), 8.04 (1H, s), 7.92 (1H, d), 7.85 (1H, d), 7.49-7.62 (2H, m), 7.33-7.42 (2H, m), 7.22-7.33 (3H, m), 6.88 (1H, d), 5.41 (2H, s), 2.11 (3H, s) |
| 008 | 380.2 | U1 | 3.75 | (DMSO-$d_6$) δ ppm: 9.49 (1H, s), 7.88 (1H, d), 7.72-7.81 (2H, m), 7.55 (1H, d), 7.21-7.47 (10H, m), 6.73 (1H, d), 6.25-6.37 (1H, m), 6.08-6.20 (1H, m), 5.62 (1H, dd), 5.37 (2H, s) |
| 009 | 381.2 | U1 | 3.81 | (DMSO-$d_6$) δ ppm: 10.84 (1H, s), 8.54 (1H, s), 8.42 (1H, d), 8.11 (1H, s), 7.85-7.98 (2H, m), 7.62-7.67 (1H, m), 7.53-7.60 (1H, m), 7.49 (1H, dd), 7.33-7.40 (2H, m), 7.25-7.32 (3H, m), 6.88 (1H, d), 6.65 (1H, dd), 6.34 (1H, dd), 5.81 (1H, dd), 5.42 (2H, s) |
| 010 | 381.2 | U1 | 3.82 | (DMSO-$d_6$) δ ppm: 10.86 (1H, s), 8.72 (1H, d), 8.30 (1H, d), 8.17 (1H, dd), 8.08 (1H, s), 7.91 (1H, d), 7.82 (1H, d), 7.63 (1H, d), 7.46-7.54 (1H, m), 7.33-7.40 (2H, m), 7.25-7.32 (3H, m), 6.91 (1H, d), 6.65 (1H, dd), 6.34 (1H, dd), 5.78-5.84 (1H, m), 5.41 (2H, s) |
| 011 | 449.2 | U1 | 3.92 | (DMSO-$d_6$) δ ppm: 10.49 (1H, s), 8.84 (1H, d), 8.65 (1H, d), 8.40 (1H, t), 8.07 (1H, s), 7.98 (1H, d), 7.87 (1H, d), 7.74 (2H, d), 7.59-7.64 (1H, m), 7.51-7.58 (1H, m), 7.46 (2H, d), 6.93 (1H, d), 6.41-6.54 (1H, m), 6.27-6.37 (1H, m), 5.84 (1H, dd), 5.54 (2H, s) |
| 012 | 449.2 | U1 | 3.87 | (DMSO-$d_6$) δ ppm: 10.49 (1H, s), 8.84 (1H, d), 8.64 (1H, d), 8.36-8.47 (1H, m), 8.06 (1H, s), 8.00 (1H, d), 7.87 (1H, d), 7.64-7.71 (2H, m), 7.58-7.64 (2H, m), 7.50-7.58 (2H, m), 6.92 (1H, d), 6.41-6.55 (1H, m), 6.26-6.38 (1H, m), 5.84 (1H, dd), 5.54 (2H, s) |
| 013 | 305.2 | U1 | 2.19 | (DMSO-$d_6$) δ ppm: 10.50 (1H, s), 8.85 (1H, d), 8.65 (1H, d), 8.42 (1H, t), 8.07 (1H, s), 7.85 (1H, d), 7.77 (1H, d), 7.58-7.64 (1H, m), 7.49-7.59 (1H, m), 6.82 (1H, d), 6.43-6.56 (1H, m), 6.27-6.39 (1H, m), 5.85 (1H, dd), 3.91 (3H, s) |
| 014 | 312.2 | U2 | 1.14 | ($CDCl_3$) δ ppm: 8.53-8.64 (m, 2H), 8.01-8.08 (m, 1H), 7.75-7.82 (m, 1H), 7.66 (d, 2H), 7.51-7.61 (m, 2H), 7.40-7.51 (m, 4H), 7.27-7.40 (m, 2H), 6.55-6.75 (m, 1H), 5.30-5.47 (m, 2H) |
| 015 | 312.2 | U1 | 3.53 | ($CDCl_3$) δ ppm: 8.50 (d, 1H), 8.31-8.39 (m, 1H), 7.60-7.70 (m, 2H), 7.32-7.57 (m, 8H), 7.29 (br s, 1H), 7.18-7.24 (m, 1H), 6.41 (s, 1H), 5.41 (s, 2H) |
| 016 | 313.2 | U2 | 0.73 | ($CDCl_3$) δ ppm: 9.17-9.29 (m, 1H), 8.94-9.09 (m, 2H), 8.01-8.13 (m, 1H), 7.85-7.93 (m, 1H), 7.46-7.60 (m, 2H), 7.26-7.45 (m, 7H), 6.46-6.76 (m, 1H), 5.18-5.54 (m, 1H) |

TABLE 2-continued

| Analytical data for synthesized compounds of the disclosure | | | | |
|---|---|---|---|---|
| Cpd. No. | $[M + H]^+$ (m/z) : | LC/MS or UPLC Method | RT (min.) | $^1H$ NMR (δ ppm) |
| 017 | 313.2 | U1 | 2.81 | ($CDCl_3$) δ ppm: 9.15-9.27 (m, 1H), 8.80 (s, 2H), 7.66 (d, 1H), 7.51-7.64 (m, 2H), 7.44 (d, 2H), 7.26-7.36 (m, 4H), 7.06 (d, 2H), 6.36-6.48 (m, 1H), 5.39 (s, 2H) |
| 018 | 329.2 | U2 | 2.33 | (DMSO-$d_6$) δ ppm: 8.04 (1H, s), 7.95 (1H, d), 7.80 (1H, d), 7.70 (2H, d), 7.58 (1H, d), 7.45-7.53 (3H, m), 7.33-7.44 (2H, m), 7.04-7.18 (3H, m), 6.89 (1H, d), 5.43 (2H, s) |
| 019 | 341.3 | L2 | 3.34 | (DMSO-$d_6$) δ ppm: 8.03-8.04 (t, 1H), 7.90-7.91 (d, 1H), 7.78-7.80 (m, 1H), 7.69-7.71 (m, 2H), 7.58-7.59 (m, 1H), 7.46-7.50 (m, 3H), 7.36-7.40 (m, 1H), 7.24-7.28 (m, 1H), 6.82-6.87 (m, 4H), 5.36 (s, 2H), 3.72 (s, 3H) |
| 020 | 336.3 | L2 | 3.22 | (DMSO-$d_6$) δ ppm: 8.03-8.04 (t, 1H), 7.96-7.97 (d, 1H), 7.77-7.80 (m, 2H), 7.75 (s, 1H), 7.69-7.71 (m, 2H), 7.56-7.61 (m, 3H), 7.46-7.50 (m, 3H), 7.36-7.40 (m, 1H), 6.90-6.91 (d, 1H), 5.48 (s, 2H) |
| 021 | 312.3 | L2 | 2.94 | (DMSO-$d_6$) δ ppm: 8.54-8.56 (m, 1H), 8.03-8.04 (m, 1H), 7.94-7.95 (d, 1H), 7.70-7.80 (m, 2H), 7.68-7.69 (m, 2H), 7.56-7.57 (m, 1H), 7.46-7.50 (m, 3H), 7.38-7.40 (m, 1H), 7.31-7.33 (m, 1H), 7.09-7.11 (d, 1H), 6.89-6.90 (d, 1H), 5.50 (s, 2H). |
| 022 | 312.1 | L2 | 2.02 | (DMSO-$d_6$) δ ppm: 8.52-8.54 (d, 2H), 8.04 (s, 1H), 8.97-8.98 (m, 1H), 7.79-7.81 (d, 1H), 7.69-7.71 (d, 2H), 7.57-7.59 (m, 1H), 7.46-7.51 (m, 3H), 7.36-7.40 (m, 1H), 7.16-7.18 (d, 2H), 6.92-6.93 (d, 1H), 5.48 (s, 2H) |
| 023 | 326.1 | L2 | 1.99 | (DMSO-$d_6$) δ ppm: 8.36-8.39 (m, 2H), 8.02-8.03 (s, 1H), 7.78-7.79 (m, 1H), 7.70-7.77 (m, 2H), 7.67-7.68 (m, 1H), 7.58-7.59 (m, 2H), 7.46-7.51 (m, 3H), 7.37-7.41 (m, 1H), 7.27-7.31 (m, 1H), 6.75-6.76 (d, 1H), 4.41-4.45 (t, 2H), 3.17-3.20 (t, 2H) |
| 024 | 342.3 | L2 | 2.64 | (DMSO-$d_6$) δ ppm: 8.04-8.05 (t, 1H), 7.92-7.93 (d, 1H), 7.79-7.81 (m, 1H), 7.69-7.72 (m, 2H), 7.63-7.66 9m, 1H), 7.57-7.60 (m, 1H), 7.46-7.51 (m, 3H), 7.36-7.40 (m, 1H), 6.91-6.92 (d, 1H), 6.03-6.04 (m, 2H), 5.26 (s, 1H), 3.36 (s, 3H) |
| 025 | 407.1 | L2 | 2.36 | (DMSO-$d_6$) δ ppm: 8.04 (s, 1H), 7.77-7.81 (m, 2H), 7.69-7.72 (m, 2H), 7.56-7.58 (d, 1H), 7.46-7.51 (m, 3H), 7.37-7.40 (t, 1H), 6.79-6.80 (d, 1H), 4.26-4.30 (t, 2H), 3.54-3.56 (t, 4H), 2.73-2.76 (t, 2H), 2.41-2.43 (t, 4H) |
| 026 | 319.1 | L2 | 2.63 | (DMSO-$d_6$) δ ppm: 8.03 (s, 1H), 7.77-7.79 (m, 2H), 7.69-7.71 (m, 2H), 7.56-7.58 (m, 1H), 7.46-7.51 (m, 3H), 7.37-7.40 (m, 1H), 6.80-6.81 (d, 1H), 4.04-4.06 (d, 2H), 3.81-3.85 (m, 2H), 3.22-3.32 (q, 2H), 2.07-2.13 (m, 1H), 1.41-1.44 (m, 2H), 1.21-1.31 (m, 2H) |
| 027 | 337.2 | L2 | 3.07 | ($CDCl_3$) δ ppm: 8.65 (s, 1H), 8.02-8.03 (t, 1H), 7.75-7.78 (m, 1H), 7.63-7.66 (m, 4H), 7.54-7.56 (m, 1H), 7.49-7.51 (m, 1H), 7.43-7.47 (m, 3H), 7.34-7.38 (m, 1H), 6.69-6.70 (d, 1H). 5.46 (s, 2H) |
| 028 | 355.2 | L2 | 2.78 | (DMSO-$d_6$) δ ppm: 8.59 (s, 1H), 8.09 (s, 1H), 7.98-8.04 (m, 3H), 7.81-7.84 (m, 1H), 7.80-7.84 (m, 1H), 7.77-7.79 (m, 2H), 7.69-7.71 (s, 1H), 7.56-7.62 (m, 1H), 7.46-7.50 (m, 3H), 7.38-7.40 (m, 1H), 6.90-6.91 (s, 1H), 5.55 (s, 2H) |
| 029 | 341.3 | L3 | 3.67 | ($CDCl_3$) δ ppm: 8.54 (s, 1H), 8.03-8.04 (m, 1H), 7.76-7.79 (m, 1H), 7.64-7.66 (m, 2H), 7.52-7.58 (m, 2H), 7.42-7.48 (m, 4H), 7.35-7.37 (m, 1H), 7.26-7.28 (m, 1H), 6.63-6.64 (d, 1H), 5.38 (s, 2H), 3.98 (s, 2H) |
| 030 | 318.3 | L5 | 3.88 | (DMSO-$d_6$) δ ppm: 8.02-8.05 (m, 1H), 7.65-7.80 (m, 2H), 7.68-7.72 (m, 2H), 7.55-7.59 (m, 1H), 7.45-7.52 (m, 3H), 7.36-7.41 (m 1H), 3.99-4.01 (d, 2H), 2.87-2.90 (m, 2H), 2.31-2.41 (m, 2H), 2.88-2.93 (m, 1H), 1.40-1.43 (m, 2H), 1.08-1.12 (m, 2H) |

TABLE 2-continued

Analytical data for synthesized compounds of the disclosure

| Cpd. No. | $[M + H]^+$ (m/z) : | LC/MS or UPLC Method | RT (min.) | $^1H$ NMR (δ ppm) |
|---|---|---|---|---|
| 031 | 360.3 | L2 | 2.87 | ($CDCl_3$) δ ppm: 8.01-8.04 (m, 1H), 7.75-7.78 (m, 1H), 7.64-7.66 (m, 2H), 7.51-7.54 (m, 1H), 7.43-7.48 (m, 3H), 7.26-7.38 (m 2H), 6.58-6.59 (d, 1H), 4.63-4.67 (m, 1H), 3.98-4.07 (m, 2H), 3.80-3.83 (m, 1H), 2.99-3.06 (m, 1H), 2.49-2.56 (m, 1H), 2.22-2.26 (m, 1H), 2.08 (s, 3H), 1.66-1.69 (m, 2H), 1.18-1.25 (m, 2H) |
| 032 | 332.3 | L2 | 2.31 | ($CDCl_3$) δ ppm: 8.01-8.02 (m, 1H), 7.76-7.78 (m, 1H), 7.64-7.66 (m, 2H), 7.50-7.52 (m, 1H), 7.43-7.47 (m, 3H), 7.26-7.39 (m, 2H), 6.56-6.57 (d, 1H), 4.02-4.04 (d, 2H), 2.84-2.87 (m, 2H), 2.27 (s, 3H), 1.89-2.00 (m, 3H), 1.61-1.64 (m, 2H), 1.35-1.42 (m, 2H) |
| 033 | 338.3 | L6 | 5.05 | (DMSO-$d_6$) δ ppm: 8.53-8.54 (d, 1H), 8.03-8.04 (t, 1H), 7.96-7.91 (d, 1H), 7.77-7.79 (d, 1H), 7.71-7.69 (m, 3H), 7.67 (m, 1H), 7.57-7.56 (m, 4H), 7.50-7.48 (m, 1H), 6.88-6.87 (d, 1H), 6.83-6.80 (dd, 1H), 6.23-6.18 (d, 1H), 5.46-5.47 (dd, 1H), 5.44 (s, 2H) |
| 034 | 327.2 | L2 | 2.34 | (DMSO-$d_6$) δ ppm: 8.02 (s, 1H), 7.95-7.96 (d, 1H), 7.81-7.82 (d, 1H), 7.76-7.78 (d, 1H), 7.69-7.71 (d, 2H), 7.55-7.57 (d, 1H), 7.45-7.50 (m, 3H), 7.36-7.40 (m, 2H), 6.81-6.82 (d, 1H), 6.39-6.41 (d, 1H), 5.95 (s, 2H), 5.16 (s, 2H) |
| 035 | 338.2 | L2 | 2.84 | (DMSO-$d_6$) δ ppm: 8.49-8.50 (d, 1H), 8.04-8.05 (t, 1H), 7.97-7.98 (d, 1H), 7.79-7.81 (d, 1H), 7.69-7.71 (m, 2H), 7.57 (s, 1H), 7.46-7.50 (m, 3H), 7.38-7.42 (m, 1H), 7.33 (s, 1H), 7.03-7.05 (m, 1H), 6.92-6.93 (d, 1H), 6.75-6.92 (m, 1H), 6.17-6.22 (dd, 1H), 5.48-5.44 (m, 3H) |
| 036 | 341.3 | L2 | 2.33 | (DMSO-$d_6$) δ ppm: 8.04-8.05 (m, 1H), 7.90-7.92 (m, 2H), 7.78-7.81 (m, 1H), 7.69-7.71 (m, 2H), 7.56-7.59 (m, 1H), 7.48-7.50 (m, 3H), 7.38-7.46 (m, 1H), 6.89-6.90 (d, 1H), 6.48-6.50 (q, 1H), 6.30-6.32 (dd, 1H), 6.18 (s, 1H), 5.28 (s, 2H), 2.70-2.71 (d, 3H) |
| 037 | 381.3 | L2 | 2.92 | (DMSO-$d_6$) δ ppm: 10.79 (s, 1H), 8.34-8.35 (s, 1H), 8.16-8.18 (d, 1H), 8.03 (s, 1H), 7.94-7.93 (d, 1H), 7.79-7.76 (m, 2H), 7.71-7.69 (m, 2H), 7.58-7.56 (m, 1H), 7.50-7.46 (m, 3H), 7.40-7.36 (m, 1H), 6.87-6.876 (d, 1H), 6.62-6.55 (m, 1H), 6.31-6.27 (dd, 1H), 5.78-5.75 (dd, 1H), 5.39 (s, 2H) |
| 038 | 381.3 | L2 | 2.29 | (DMSO-$d_6$) δ ppm: 8.03-8.04 (s, 1H), 7.92-7.94 (m, 2H), 7.78-7.80 (d, 1H), 7.69-7.71 (d, 2H), 7.57-7.62 (m, 2H), 7.47-7.50 (m, 3H), 7.37-7.41 (m, 1H), 6.87-6.88 (d, 1H), 6.73-6.75 (d, 1H), 5.24 (s, 2H), 4.28-4.32 (t, 2H), 2.45-2.46 (t, 2H) |
| 039 | 383.3 | L2 | 2.89 | (DMSO-do) δ ppm: 10.46 (s, 1H), 8.30-8.29 (d, 1H), 8.02-8.07 (m, 2H), 7.91-7.92 (m, 1H), 7.69-7.79 (m, 4H), 7.56 (m, 1H), 7.46-7.50 (m, 3H), 7.38-7.40 (m, 1H), 6.86 (d, 1H), 5.37 (s, 2H), 2.36-2.38 (q, 2H), 1.02-1.06 (t, 3H) |
| 040 | 356.2 | L2 | 2.69 | (DMSO-$d_6$) δ ppm: 12.8-14.20 (br s, 1H), 8.98 (s, 1H), 8.74 (s, 1H), 8.13 (s, 1H), 8.00-8.03 (m, 2H), 7.78-7.79 (d, 1H), 7.69-7.70 (d, 2H), 7.57-7.59 (d, 1H), 7.46-7.50 (m, 3H), 7.36-7.40 (m, 1H), 6.89-6.90 (d, 1H), 5.54 (s, 2H) |
| 041 | 355.3 | L6 | 2.57 | (DMSO-$d_6$) δ ppm: 8.96-8.97 (d, 1H), 8.68-8.69 (d, 1H), 8.18 (s, 1H), 8.11-8.13 (t, 1H), 8.02-8.03 (t, 1H), 7.98-7.99 (d, 1H), 7.77-7.79 (m, 1H), 7.69-7.71 (m, 2H), 7.56-7.61 (m, 2H), 7.46-7.50 (m, 3H), 7.36-7.40 (m, 1H), 6.90 (d, 1H), 5.51 (s, 2H) |
| 042 | 356.3 | L2 | 2.50 | (DMSO-$d_6$) δ ppm: 8.50-8.51 (d, 1H), 8.12 (s, 1H), 8.03-8.04 (t, 1H), 7.931-7.936 (d, 1H), 7.77-7.79 (m, 1H), 7.69-7.72 (d, 2H), 7.58-7.60 (m, 2H), 7.46-7.56 (t, 3H), 7.36-7.40 (m, 1H), 6.85-8.88 (d, 1H), 5.76 (s, 2H) |
| 043 | 355.3 | L2 | 2.54 | (DMSO-$d_6$) δ ppm: 8.59-8.60 (d, 1H), 8.33 (s, 1H), 8.29 (s, 1H), 8.01-8.02 (t, 1H), 7.90-7.91 (d, 1H), 7.86 (s, 1H), 7.76-7.79 (m, 1H), 7.69-7.71 (m, 2H), 7.56-7.59 (m, 1H), 7.45-7.50 (m, 4H), 7.36-7.40 (m, 1H), 6.88-6.89 (d, 1H), 5.62 (s, 2H) |

TABLE 2-continued

| Cpd. No. | $[M + H]^+$ (m/z) : | LC/MS or UPLC Method | RT (min.) | $^1H$ NMR (δ ppm) |
|---|---|---|---|---|
| Analytical data for synthesized compounds of the disclosure | | | | |
| 044 | 327.3 | L2 | 2.76 | ($DMSO-d_6$) δ ppm: 8.53-8.54 (m, 1H), 8.19 (s, 1H), 7.90-7.91 (d, 1H), 7.74-7.79 (m, 1H), 7.50 (s, 1H), 7.29-7.32 (m, 1H), 7.21-7.24 (m, 4H), 7.00-7.08 (m, 4H), 6.83-6.80 (t, 1H), 6.68-6.69 (d, 1H), 5.46 (s, 2H) |
| 045 | 327.2 | L2 | 2.49 | ($DMSO-d_6$) δ ppm: 8.54-8.53 (m, 1H), 8.49-8.51 (m, 1H), 8.21 (s, 1H), 7.91-7.92 (d, 1H), 7.65-7.68 (m, 1H), 7.50 (s, 1H), 7.36-7.39 (m, 1H), 7.21-7.25 (m, 4H), 7.06-7.08 (d, 2H), 7.00-7.03 (m, 1H), 6.80-6.84 (m, 1H), 6.66-6.67 (d, 1H), 5.41 (s, 2H) |
| 046 | 341.3 | L2 | 2.30 | ($DMSO-d_6$) δ ppm: 8.38-8.40 (m, 1H), 8.34-8.35 (d, 1H), 8.21 (s, 1H), 7.62-7.63 (d, 1H), 7.52-7.56 (m, 2H), 7.20-7.29 (m, 5H), 7.07-7.09 (m, 2H), 6.99-7.02 (m, 1H), 6.81-6.84 (t, 1H), 6.54-6.55 (d, 1H), 4.41-4.38 (t, 2H), 3.17-3.14 (t, 2H) |
| 047 | 314.2 | U1 | 3.78 | ($DMSO-d_6$) δ ppm: 8.74 (1H, d), 8.60 (1H, dd), 8.28 (1H, s), 8.05 (1H, d), 7.80-7.90 (2H, m), 7.73 (2H, d), 7.62-7.70 (1H, m), 7.48-7.55 (2H, m), 7.39-7.48 (2H, m), 6.11 (2H, s) |
| 048 | 289.2 | U1 | 3.00 | ($DMSO-d_6$) δ ppm: 10.34 (1H, s), 8.54 (1H, d), 8.47 (1H, dd), 7.93 (1H, s), 7.71-7.82 (1H, m), 7.54-7.63 (3H, m), 7.47 (2H, t), 7.31-7.43 (4H, m), 3.73 (2H, s) |
| 049 | 437.4 | L2 | 2.73 | ($DMSO-d_6$) δ ppm: 8.61-8.62 (d, 1H), 8.51-8.53 (dd, 1H), 8.03 (s, 1H), 7.98-7.99 (d, 1H), 7.87-7.88 (d, 1H), 7.74-7.76 (m, 1H), 7.64-7.66 (m, 2H), 7.48-7.50 (m, 1H), 7.37-7.42 (m, 3H), 7.26-7.28 (d, 1H), 6.953-6.959 (d, 1H), 6.86-6.88 (d, 1H), 5.44 (s, 2H), 4.21-4.26 (m, 2H), 3.80-3.85 (m, 2H). |
| 050 | 448.4 | L3 | 4.18 | ($DMSO-d_6$) δ ppm: 8.63-8.64 (d, 1H), 8.51-8.53 (dd, 1H), 7.97-7.98 (d, 1H), 7.89 (t, 1H), 7.852-7.857 (d, 1H), 7.77-7.8 (m, 1H), 7.64-7.66 (dd, 1H), 7.38-7.42 (m, 3H), 7.23-7.27 (t, 1H), 7.09-7.11 (d, 1H), 6.922-6.928 (d, 1H), 6.78-6.8 (d, 1H), 5.45-5.53 (s, 2H), 3.29-3.62 (m, 4H), 2.58-2.59 (d, 3H). |
| 051 | 445.3 | L2 | 2.40 | ($DMSO-d_6$) δ ppm: 8.52-8.54 (m, 2H), 7.96-7.97 (d, 1H), 7.82-7.83 (d, 1H), 7.56-7.66 (m, 4H), 7.27-7.47 (m, 5H), 7.05-7.06 (d, 1H), 5.47 (s, 2H), 3.17-3.31 (m, 8H). |
| 052 | 448.3 | L2 | 2.34 | ($DMSO-d_6$) δ ppm: 8.50-8.55 (m, 2H), 7.92-7.93 (m, 1H, 7.63-7.68 (m, 3H), 7.40-7.47 (m, 2H), 7.36-7.39 (m, 2H), 7.27-7.28 (t, 1H), 7.03-7.06 (m, 2H), 6.76-6.80 (m, 2H), 5.87-5.89 (t, 1H), 5.44 (s, 2H), 3.49-3.54 (q, 2H), 3.25-3.28 (t, 2H), 2.58 (s, 3H) |
| 053 | 462.3 | L2 | 2.68 | ($DMSO-d_6$) δ ppm: 8.63-8.64 (d, 1H), 8.51-8.53 (dd, 1H), 7.98-7.99 (d, 1H), 7.91-7.92 (d, 1H), 7.860-7.866 (d, 1H), 7.76-7.79 (m, 1H), 7.64-7.66 (m, 2H), 7.48-7.51 (m, 1H), 7.37-7.42 (m, 3H), 7.23-7.27 (m, 1H), 6.93-6.94 (d, 1H), 6.80-6.82 (d, 1H), 5.45 (s, 2H), 3.62-3.66 (t, 2H), 3.36-3.33 (t, 2H), 2.77 (s, 6H). |
| 054 | 434.2 | L2 | 2.34 | ($DMSO-d_6$) δ ppm: 8.63-8.64 (d, 1H), 8.51-8.53 (dd, 1H), 7.97-7.976 (d, 1H), 7.78-7.88 (m, 3H), 7.64-7.66 (t, 2H), 7.48-7.50 (q, 1H), 7.38-7.42 (m, 3H), 7.23-7.27 (t, 1H), 7.003 (s, 2H), 6.91-6.92 (d, 1H), 6.79-6.81 (dd, 1H), 5.45 (s, 2H), 3.63-3.68 (q, 2H), 3.27-3.31 (t, 2H). |
| 055 | 445.3 | L2 | 2.33 | ($DMSO-d_6$) δ ppm: 8.54-8.55 (d, 1H), 8.50-8.52 (dd, 1H), 7.94 (d, 1H), 7.67-7.72 (m, 3H), 7.45-7.52 (m, 3H), 7.36-7.40 (m, 3H), 7.17-7.18 (t, 1H), 6.90-6.91 (d, 1H), 5.45 (s, 2H), 3.87-3.90 (m, 4H), 3.17-3.19 (m, 4H) |
| 056 | 369.1 | L5 | 4.26 | ($DMSO-d_6$) δ ppm: 7.88-7.91 (t, 1H), 7.840-7.847 (d, 1H), 7.77-7.78 (d, 1H), 7.64-7.66 (m, 2H), 7.48-7.50 (dd, 1H), 7.38-7.42 (m, 2H), 7.23-7.27 (m, 1H), 7.07-7.08 (m, 1H), 6.851-6.857 (d, 1H), 6.78-6.81 (d, 1H), 3.92 (s, 3H), 3.62-3.67 (q, 2H), 3.31-3.36 (m, 2H), 2.59-2.60 (d, 3H). |

TABLE 2-continued

Analytical data for synthesized compounds of the disclosure

| Cpd. No. | [M + H]$^+$ (m/z) : | LC/MS or UPLC Method | RT (min.) | $^1$H NMR (δ ppm) |
|---|---|---|---|---|
| 057 | 358.2 | L5 | 3.25 | (DMSO-$d_6$) δ ppm: 7.80-7.81 (d, 1H), 7.74-7.73 (d, 1H), 7.66-7.64 (dd, 2H), 7.50-7.48 (dd, 1H), 7.42 (t, 2H), 7.26 (t, 1H), 6.83-6.82 (d, 1H), 6.77-6.75 (d, 1H), 3.91 (s, 3H), 3.50-3.47 (t, 2H), 2.78-2.74 (t, 2H) |
| 058 | 357.2 | L2 | 2.61 | (DMSO-$d_6$) δ ppm: 7.87-7.90 (t, 1H), 7.84-7.85 (d, 1H), 7.77-7.78 (d, 1H), 7.643-7.645 (d, 1H), 7.66-7.67 (d, 1H), 7.47-7.49 (dd, 1H), 7.39-7.42 (m, 2H), 7.23-7.27 (m, 1H), 6.98 (s, 2H), 6.81-6.86 (m, 2H), 3.91 (s, 2H), 3.67-3.72 (q, 2H), 3.33-3.37 (t, 2H). |
| 059 | 499.3 | L3 | 2.57 | (DMSO-$d_6$) δ ppm: 8.65 (s, 1H), 8.52 (s, 1H), 7.96-7.97 (d, 1H), 7.77-7.83 (m, 3H), 7.62-7.64 (d, 1H), 7.37-7.47 (m, 4H), 7.21-7.25 (t, 1H), 6.92-6.91 (d, 1H), 6.76-6.78 (d, 1H), 5.42 (s, 2H), 3.33-3.4 (m, 2H), 2.49-2.5 (m, 2H). |
| 060 | 412.3 | L3 | 2.41 | (DMSO-$d_6$) δ ppm: 8.632-8.636 (d, 1H), 8.51-8.53 (dd, 1H), 7.96-7.97 (d, 1H), 7.88 (d, 1H), 7.830-7.836 (d, 1H), 7.77-7.79 (m, 2H), 7.62-7.64 (d, 2H), 7.45-7.47 (dd, 1H), 7.37-7.42 (t, 3H), 7.23-7.25 (t, 1H), 6.91-6.92 (d, 1H), 6.78-6.8 (d, 1H), 5.44 (s, 2H), 3.41-3.45 (q, 2H), 2.56-2.57 (d, 3H), 2.41-2.44 (t, 2H). |
| 061 | 399.3 | L2 | 2.22 | (DMSO-$d_6$) δ ppm: 8.50-8.55 (m, 2H), 7.90-7.91 (d, 1H), 7.61-7.69 (m, 2H), 7.34-7.46 (m, 4H), 7.20 (s, 1H), 7.00 (s, 1H), 6.72-6.75 (m, 2H), 5.44 (s, 2H), 3.21-3.24 (m, 2H), 2.28 (t, 2H) |
| 062 | 412.4 | L2 | 3.27 | (DMSO-$d_6$) δ ppm: 8.50-8.55 (m, 2H), 7.91-7.92 (d, 1H), 7.81-7.83 (m, 1H), 7.62-7.69 (m, 3H), 7.33-7.47 (m, 4H), 7.21-7.22 (m, 1H), 7.02-7.03 (m, 1H), 6.75 (d, 2H), 5.74-5.77 (t, 1H), 5.44 (s, 2H), 3.32 (m, 2H), 2.50-2.67 (m, 3H), 2.36-2.49 (m, 2H) |
| 063 | 322.4 | L2 | 2.32 | (DMSO-$d_6$) δ ppm: 7.85-7.96 (d, 1H), 7.78-7.79 (d, 1H), 7.666-7.669 (d, 1H), 7.646-7.648 (d, 1H), 7.49-7.50 (dd, 1H), 7.39-7.43 (q, 2H), 7.24-7.27 (t, 1H), 6.86-6.88 (t, 2H), 3.91 (s, 3H), 3.47-3.50 (t, 2H), 2.59-2.63 (t, 2H). |
| 064 | 335.4 | L1 | 2.17 | (DMSO-$d_6$) δ ppm: 7.91-7.92 (d, 1H), 7.821-7.827 (d, 1H), 7.770-7.776 (d, 1H), 7.707-7.734 (t, 1H), 7.63-7.65 (dd, 2H), 7.44-7.47 (dd, 1H), 7.38-7.42 (q, 2H), 7.221-7.264 (m, 1H), 6.84-6.85 (d, 1H), 6.78-6.81 (dd, 1H), 3.91 (s, 3H), 3.42-3.47 (q, 2H), 2.59-2.60 (d, 3H), 2.43-2.46 (q, 2H). |
| 065 | 401.3 | L3 | 5.01 | (DMSO-$d_6$) δ ppm: 8.62 (d, 1H), 8.52 (dd, 1H), 8.00 (d, 1H), 7.8-7.848 (m, 2H), 7.76 (dd, 1H), 7.65 (dd, 2H), 7.46 (dd, 1H), 7.41-7.38 (m, 3H), 7.24 (t, 1H), 6.93 (d, 1H), 6.78 (d, 1H), 5.44 (s, 2H), 3.41 (q, 2H), 2.73 (t, 2H), 2.08 (s, 3H). |
| 066 | 432.3 | L2 | 3.66 | (DMSO-$d_6$) δ ppm: 8.62-8.63 (m, 1H), 8.52-8.53 (m, 1H), 7.99 (d, 1H), 7.83-7.85 (m, 2H), 7.77 (m, 1H), 7.59-7.65 (m, 3H), 7.48-7.50 (m, 1H), 7.38-7.42 (m, 3H), 7.23-7.27 (t, 1H), 6.93 (d, 1H), 6.84-6.87 (d, 1H), 5.45 (s, 2H), 3.68-3.70 (m, 2H), 3.31-3.37 (m, 2H), 2.91 (s, 3H). |
| 067 | 462.4 | L1 | 1.92 | (DMSO-$d_6$) δ ppm: 8.56 (d, 1H), 8.49-8.50 (dd, 1H), 7.93 (d, 1H), 7.86-7.87 (d, 1H), 7.56-7.67 (m, 4H), 7.43-7.46 (q, 2H), 7.31-7.45 (m, 2H), 7.23-7.25 (m, 1H), 6.90 (d, 1H), 5.46 (s, 2H), 3.24-3.32 (m, 2H), 3.12-3.20 (m, 2H), 2.63 (s, 3H), 2.42 (s, 3H). |
| 068 | 459.3 | L2 | 2.65 | (DMSO-$d_6$) δ ppm: 8.59-8.60 (d, 1H), 8.52-8.54 (dd, 1H), 8.02-8.03 (d, 1H), 7.863-7.869 (d, 1H), 7.73-7.16 (m, 2H), 7.63-7.65 (m, 2H), 7.38-7.47 (m, 4H), 7.23-7.27 (t, 1H), 6.962-6.968 (d, 1H), 6.86-6.88 (d, 1H), 5.46 (s, 2H), 3.86-3.88 (t, 1H), 3.28-3.35 (m, 2H), 3.06-3.09 (m, 2H), 2.22-2.25 (m, 2H), 1.82-1.90 (m, 2H). |
| 069 | 457.3 | L2 | 2.37 | (DMSO-$d_6$) δ ppm: 8.50-8.54 (m, 2H), 7.92 (d, 1H), 7.62-7.68 (m, 3H), 7.35-7.47 (m, 4H), 7.22-7.23 (t, 1H), 7.09-7.10 (t, 1H), 6.79-6.80 (t, 1H), 6.75-6.76 (d, 1H), 5.87-5.90 (d, 1H), 5.43 (s, 2H), 3.81-3.85 (m, 1H), 3.14-3.25 (m, 4H), 2.19-2.33 (m, 2H), 1.96-2.07 (m, 2H) |

TABLE 2-continued

| Cpd. No. | [M + H]+ (m/z) : | LC/MS or UPLC Method | RT (min.) | 1H NMR (δ ppm) |
|---|---|---|---|---|
| Analytical data for synthesized compounds of the disclosure | | | | |
| 070 | 411.3 | L2 | 2.89 | (DMSO-$d_6$) δ ppm: 8.63-8.64 (d, 1H), 8.52-8.53 (dd, 1H), 8.023-8.029 (d, 1H), 7.84-7.88 (m, 2H), 7.75-7.78 (d, 1H), 7.62-7.64 (d, 2H), 7.37-7.44 (m, 4H), 7.22-7.25 (m, 1H), 6.93-6.94 (d, 1H), 6.81-6.83 (d, 1H), 5.43 (s, 2H), 3.64-3.83 (m, 1H), 3.58-3.63 (m, 1H), 3.47-3.50 (m, 1H), 3.22-3.31 (m, 1H), 1.88-1.92 (m, 1H), 1.64-1.65 (m, 1H), 1.46-1.52 (m, 1H). |
| 071 | 411.4 | L2 | 2.52 | (DMSO-$d_6$) δ ppm: 8.50-8.54 (m, 2H), 7.91-7.92 (d, 1H), 7.61-7.67 (m, 3H), 7.38-7.46 (m, 4H), 7.34-7.37 (t, 1H), 7.18-7.19 (t, 1H), 6.74-6.79 (m, 2H), 5.64-5.70 (d, 1H), 5.44 (s, 2H), 3.88-3.92 (m, 1H), 3.71-3.76 (m, 1H), 3.48-3.50 (m, 1H), 3.34-3.43 (m, 1H), 3.08-3.12 (m, 1H), 1.98-2.01 (m, 1H), 1.70-1.71 (m, 1H), 1.59-1.62 (m, 1H), 1.45-1.48 (m, 1H) |
| 072 | 424.3 | L2 | 2.43 | (DMSO-$d_6$) δ ppm: 8.62-8.63 (d, 1H), 8.52-8.53 (dd, 1H), 8.01-8.02 (d, 1H), 7.82-7.86 (m, 2H), 7.75-7.77 (m, 1H), 7.62-7.65 (d, 2H), 7.55 (s, 1H), 7.38-7.46 (m, 4H), 7.24-7.26 (d, 1H), 6.94-6.95 (d, 1H), 6.84-6.86 (d, 1H), 5.43 (s, 2H), 3.93-3.97 (t, 1H), 3.18-3.23 (m, 1H), 2.54-2.56 (dd, 1H), 2.02-2.14 (m, 2H), 1.63 (m, 1H). |
| 073 | 424.4 | L2 | 2.17 | ($CDCl_3$) δ ppm: 8.50-8.55 (m, 2H), 7.91-7.92 (d, 1H), 7.62-7.68 (M, 3H), 7.62-7.66 (m, 1H), 7.40-7.54 (m, 2H), 7.35-7.39 (m, 2H), 7.21-7.22 (t, 1H), 7.07-7.10 (m, 1H), 6.79-6.80 (t, 1H), 6.75-6.76 (d, 1H), 5.80-5.82 (d, 1H), 5.43 (s, 2H), 3.85-3.90 (m, 1H), 3.20-3.23 (m, 2H), 2.53-2.57 (m, 1H), 2.00-2.14 (m, 2H), 1.61-1.63 (m, 1H) |
| 074 | 398.3 | L2 | 2.35 | (DMSO-$d_6$) δ ppm: 8.66-8.67 (d, 1H), 8.50-8.52 (dd, 1H), 8.12-8.13 (t, 1H), 7.94-7.98 (m, 2H), 7.85-7.89 (m, 2H), 7.63-7.65 (d, 2H), 7.45-7.48 (dd, 1H), 7.36-7.41 (m, 3H), 7.22-7.26 (t, 1H), 6.93-6.94 (d, 1H), 6.56-6.58 (d, 1H), 5.44 (s, 2H), 3.84-3.85 (d, 2H), 2.66-2.67 (d, 3H). |
| 075 | 424.3 | L2 | 2.40 | (DMSO-$d_6$) δ ppm: 8.60-8.61 (d, 1H), 8.52 (dd, 1H), 8.51 (t, 1H), 7.96 (d, 1H), 7.84-7.85 (d, 1H), 7.75 (t, 1H), 7.73 (dt, 1H), 7.63-7.75 (d, 1H), 7.48 (dd, 1H), 7.38-7.46 (m, 3H), 7.24-7.37 (m, 1H), 6.92-6.93 (d, 1H), 6.83-6.85 (d, 1H), 6.19-6.22 (q, 1H), 6.12 (dd, 1H), 5.55-5.59 (dd, 1H), 5.45 (s, 2H), 3.42-3.45 (q, 2H), 3.32-3.35 (q, 2H). |
| 076 | 445.3 | L2 | 2.33 | (DMSO-$d_6$) δ ppm: 8.50-8.55 (m, 2H), 7.86-7.92 (m, 2H), 7.65-7.68 (m, 1H), 7.59-7.61 (d, 2H), 7.38-7.47 (m, 4H), 7.26-7.37 (m, 1H), 7.01-7.02 (m, 1H), 6.71-6.74 (m, 2H), 6.12 (t, 1H), 5.44 (s, 2H), 3.70-3.72 (d, 2H), 2.60-2.67 (d, 3H) |
| 077 | 426.3 | L2 | 2.40 | (DMSO-$d_6$) δ ppm: 8.61 (d, 1H), 8.51-8.53 (dd, 1H), 7.97 (d, 1H), 7.93-7.94 (t, 1H), 7.84 (d, 1H), 7.73-7.75 (m, 2H), 7.63-7.65 (m, 2H), 7.47-7.48 (d, 1H), 7.40-7.45 (m, 3H), 7.22-7.39 (m, 1H), 6.93 (d 1H), 6.81-6.83 (d, 1H), 5.48 (s, 2H), 3.32-3.35 (q, 2H), 3.27-3.29 (q, 2H), 2.03-2.09 (q, 2H), 0.94-0.98 (t, 3H). |
| 078 | 385.3 | L2 | 2.20 | (DMSO-$d_6$) δ ppm: 8.54-8.55 (m, 1H), 8.50-8.51 (m, 1H), 7.91-7.92 (d, 1H), 7.61-7.68 (m, 3H), 7.33-7.47 (m, 4H), 7.25 (m, 1H), 7.02 (m, 1H), 6.74-6.75 (t, 2H), 5.44 (s, 2H), 3.86 (m, 2H) |
| 079 | 476.5 | L2 | 2.59 | (DMSO-$d_6$) δ ppm: 11.238 (s, 1H), 8.686-8.690 (d, 1H), 8.554-8.570 (m, 1H), 8.447-8.468 (d, 1H), 8.12-8.13 (d, 1H), 8.021-8.026 (d, 1H), 7.84-7.87 (m, 1H), 7.724-7.745 (m, 2H), 7.60-7.63 (m, 1H), 7.447-7.485 (m, 3H), 7.338-7.375 (m, 1H), 7.086-7.152 (m, 2H), 5.539 (s, 2H), 3.349-3.386 (m, 2H), 2.712-2.749 (t, 2H), 2.492-2.510 (d, 3H). |
| 080 | 381.3 | L2 | 2.71 | (DMSO-$d_6$) δ ppm: 8.54-8.64 (m, 3H), 8.14-8.15 (d, 1H), 8.05-8.058 (d, 1H), 7.73-7.76 (d, 3H), 7.62-7.65 (dd, 1H), 7.36-7.49 (m, 4H), 7.120-7.126 (d, 1H), 6.12-6.19 (m, 2H), 5.73-5.76 (dd, 1H), 5.56 (s, 2H). |
| 081 | 394.3 | L2 | 2.63 | DMSO-$d_6$) δ ppm: 11.498 (s, 1H), 8.660-8.664 (d, 1H), 8.531-8.547 (d, 1H), 8.389-8.411 (d, 1H), 8.104-8.110 (d, 1H), 8.036-8.042 (d, 1H), 7.775- |

TABLE 2-continued

Analytical data for synthesized compounds of the disclosure

| Cpd. No. | [M + H]+ (m/z) : | LC/MS or UPLC Method | RT (min.) | $^1$H NMR (δ ppm) |
|---|---|---|---|---|
| | | | | 7.80 (m, 1H), 7.733-7.754 (m, 2H), 7.634-7.661 (m, 1H), 7.366-7.491 (m, 4H), 7.086-7.092 (d, 1H), 5.55 (s, 2H), 4.03 (s, 2H). |
| 082 | 462.2 | L2 | 2.50 | (DMSO-$d_6$) δ ppm: 11.60 (s, 1H), 8.661-8.666 (d, 1H), 8.480-8.541 (m, 2H), 8.078-8.084 (d, 1H), 8.027-8.032 (d, 1H), 7.806-7.835 (m, 1H),7.732-7.753 (m, 2H), 7.628-7.655 (m, 1H), 7.345-7.649 (m, 5H), 7.078-7.084 (d, 1H), 5.547 (s, 2H), 4.203 (s, 2H), 2.651 (s, 3H). |
| 083 | 381.3 | L2 | 2.34 | (DMSO-$d_6$) δ ppm: 10.31 (s, 1H), 8.51-8.57 (m, 2H), 7.98-8.01 (m, 3H), 7.68-7.73 (m, 4H), 7.52-7.67 (t, 2H), 7.42-750 (m, 2H), 6.84-6.85 (d, 1H), 6.43-6.45 (q, 1H), 6.30-6.31 (dd, 1H), 5.76-5.79 (dd, 1H), 5.46 (s, 2H) |
| 084 | 380.3 | L2 | 2.65 | (DMSO-$d_6$) δ ppm: 8.644-8.648 (d, 1H), 8.51-8.53 (dd, 1H), 8.00-8.006 (d, 1H), 7.93-7.96 (t, 1H), 7.78-7.87 (m, 1H), 7.64-7.66 (dd, 2H), 7.46-7.49 (d, 1H), 7.37-7.42 (m, 3H), 7.23-7.27 (m, 1H), 6.95-6.96 (d, 1H), 6.85-6.87 (d, 1H), 5.45 (s, 2H), 3.53-3.57 (m, 2H), 2.82-2.85 (t, 2H). |
| 085 | 366.2 | L2 | 2.58 | (DMSO-$d_6$) δ ppm: 8.62-8.624 (m, 1H), 8.531-8.535 (m, 1H), 8.00-8.02 (m, 2H), 7.913-7.919 (m, 1H), 7.74-7.77 (m, 1H), 7.673-7.69 (m, 2H), 7.55-7.58 (m, 1H), 7.38-7.44 (m, 3H), 7.28-7.30 (t, 1H), 6.95-6.99 (m, 2H), 5.48 (s, 2H), 4.52-4.54 (d, 2H). |
| 086 | 466.3 | L2 | 2.27 | (DMSO-$d_6$) δ ppm: 8.634-8.638 (d, 1H), 8.516-8.532 (m, 1H), 7.974-7.980 (m, 1H), 7.899 (t, 1H), 7.827-7.833 (m, 1H), 7.779-7.799 (m, 1H), 7.663-7.698 (m, 2H), 7.458-7.485 (m, 2H), 7.199-7.412 (m, 2H), 7.10 (s, 1H), 6.931-6.937 (d, 1H), 6.772-6.794 (d, 1H), 5.45 (s, 2H), 3.607-3.622 (q, 2H), 3.294 (s, 2H), 2.585 (s, 3H). |
| 087 | 516.6 | L4 | 4.73 | (DMSO-$d_6$) δ ppm: 8.63-8.64 (d, 1H), 8.518-8.534 (m, 1H), 8.052 (t, 1H), 7.990-7.996 (d, 1H), 7.954-7.960 (m, 1H), 7.886-7.906 (m, 2H), 7.779-7.809 (m, 1H), 7.718-7.739 (m, 2H), 7.585-7.612 (m, 1H), 7.381-7.414 (m, 1H), 7.102-7.114 (q, 1H), 6.968-6.975 (m, 1H), 6.817-6.838 (d, 1H), 5.463 (s, 2H), 3.616-3.663 (q, 2H), 3.318-3.343 (s, 2H), 2.58-2.59 (s, 3H). |
| 088 | 466.3 | L2 | 2.61 | (DMSO-$d_6$) δ ppm: 8.63-8.64 (d, 1H), 8.51-8.53 (q, 1H), 7.98-8.00 (m, 2H), 7.901-7.907 (d, 1H), 7.78-7.802 (dd, 1H), 7.49-7.56 (m, 3H), 7.37-7.43 (m, 2H), 7.06-7.10 (q, 2H), 6.98-6.99 (d, 1H), 6.78-6.80 (d, 1H), 5.45 (s, 2H), 3.60-3.65 (q, 2H), 3.30-3.33 (t, 2H), 2.58-2.59 (d, 3H). |
| 089 | 516.3 | L2 | 2.80 | (DMSO-$d_6$) δ ppm: 8.632-8.637 (d, 1H), 8.51-8.53 (q, 1H), 7.96-7.98 (t, 2H), 7.920-7.926 (m, 2H), 7.80-7.83 (m, 1H), 7.58-7.67 (m, 3H), 7.40-7.43 (m, 1H), 6.97-6.98 (d, 1H), 6.83-6.85 (d, 1H), 5.46 (s, 2H), 3.62-3.67 (q, 2H), 3.31-3.34 (t, 2H), 2.59(s, 3H). |
| 090 | 478.3 | L2 | 2.54 | ($CDCl_3$) δ ppm: 8.60 (s, 2H), 7.70-7.72 (m, 2H), 7.52 (d, 1H), 7.46-7.48 (dd, 1H), 7.31-7.35 (m, 3H), 7.14-7.17 (m, 1H), 7.09-7.10 (t, 1H), 6.78-6.85 (m, 2H), 6.64 (d, 1H), 5.42-5.44 (m, 1H), 5.37 (s, 2H), 3.83-3.87 (m, 5H), 3.32-3.34 (t, 2H), 2.41-2.42 (d, 3H). |
| 091 | 482.2 | L2 | 1.75 | (DMSO-$d_6$) δ ppm: 8.63 (d, 1H), 8.51-8.53 (dd, 1H), 7.97 (d, 1H), 7.88 (d, 1H), 7.81-7.83 (dt, 1H), 7.00-7.71 (t, 1H), 7.63-7.64 (m, 1H), 7.53-7.56 (dd, 1H), 7.40-7.46 (m, 2H), 7.29-7.32 (ddd, 1H), 6.97-6.98 (d, 1H), 6.81-6.83 (d, 1H), 5.46 (s, 2H), 3.62-3.69 (t, 2H), 3.30-3.34 (t, 2H), 2.59 (s, 3H). |
| 092 | 484.3 | L2 | 2.62 | (DMSO-$d_6$) δ ppm: 8.633-8.637 (d, 1H), 8.51-8.53 (dd, 1H), 8.007-8.03 (t, 1H), 7.970-7.976 (d, 1H), 7.78-7.80 (m, 2H), 7.37-7.43 (m, 3H), 7.27-7.32 (m, 1H), 7.10-7.15 (m, 2H), 6.861-6.867 (d, 1H), 6.78-6.80 (dd, 1H), 5.45 (s, 2H), 3.60-3.65 (q, 2H), 3.30-3.32 (t, 2H), 2.58 (s, 3H). |
| 093 | 484.3 | L3 | 4.40 | ($CDCl_3$) δ ppm: 8.58-8.61 (m, 2H), 7.69-7.72 (m, 1H), 7.63 (d, 1H), 7.54 (d, 1H), 7.31-7.40 (m, 4H), 7.23-7.25 (m, 1H), 7.17-7.21 (m, 1H), 6.77-6.79 |

TABLE 2-continued

| Cpd. No. | [M + H]+ (m/z) : | LC/MS or UPLC Method | RT (min.) | $^1$H NMR (δ ppm) |
|---|---|---|---|---|
| Analytical data for synthesized compounds of the disclosure | | | | |
| | | | | (d, 1H), 6.64-6.65 (d, 1H), 5.37-5.40 (s, 3H), 3.82-3.86 (m, 2H), 3.30-3.33 (t, 2H), 2.45 (s, 3H). |
| 094 | 449.3 | L2 | 1.69 | (DMSO-$d_6$) δ ppm: 8.90 (d, 1H), 8.63 (d, 1H), 8.51-8.53 (dd, 1H), 8.44-8.46 (dd, 1H), 8.04-8.07 (m, 2H), 8.02 (d, 1H), 7.98 (d, 1H), 7.78-7.80 (m, 1H), 7.56-7.58 (dd, 1H), 7.38-7.55 (m, 3H), 6.99 (d, 1H), 6.81-6.83 (d, 1H), 5.46 (s, 2H), 3.62-3.64 (t, 2H), 3.31-3.33 (t, 2H), 2.58 (s, 3H). |
| 095 | 454.3 | L3 | 4.62 | (DMSO-$d_6$) δ ppm: 8.60 (d, 1H), 8.51 (dd, 1H), 7.93 (d, 1H), 7.75 (dt, 1H), 7.53 (t, 1H), 7.40-7.36 (m, 2H), 7.04 (d, 1H), 7.00 (dd, 1H), 6.75 (d, 1H), 6.61 (d, 1H), 5.42 (s, 2H), 3.54-3.50 (m, 2H), 3.26-3.23 (m, 2H), 2.56 (d, 3H), 2.43-2.37 (m, 1H), 1.78-1.67 (m, 5H), 1.40-1.29 (m, 5H). |
| 096 | 452.1 | L5 | 3.35 | (DMSO-$d_6$) δ ppm: 8.63-8.64 (d, 1H), 8.51-8.53 (dd, 1H), 8.00 (d, 1H), 7.92 (d, 1H), 7.80-7.81 (m, 2H), 7.65 (d, 1H), 7.57-7.60 (d, 1H), 7.40-7.41 (q, 1H), 7.10 (q, 1H), 6.81 (d, 1H), 6.71-6.73 (dd, 1H), 6.60-6.61 (d, 1H), 5.45 (s, 2H), 3.84 (s, 3H), 3.56-3.61 (t, 2H), 3.30-3.31 (t, 2H), 2.59 (s, 3H). |
| 097 | 498.2 | L2 | 2.57 | (DMSO-$d_6$) δ ppm: 8.63-8.64 (d, 1H), 8.51-8.53 (dd, 1H), 7.98-8.0 (m, 2H), 7.91-7.92 (d, 1H), 7.77-7.81 (m, 3H), 7.55-7.59 (m, 3H), 7.38-7.41 (m, 1H), 6.90-7.18 (m, 3H), 6.8-6.82 (d, 1H), 5.46 (s, 2H), 3.6-3.65 (q, 2H), 3.3-3.33 (m, 2H), 2.58 (s, 3H). |
| 098 | 532.3 | L2 | 2.79 | (DMSO-$d_6$) δ ppm: 8.63-8.64 (d, 1H), 8.51-8.53 (dd, 1H), 7.95-7.97 (m, 2H), 7.87 (d, 1H), 7.75-7.80 (m, 3H), 7.50-7.52 (dd, 1H), 7.36-7.41 (m, 3H), 7.08-7.11 (m, 1H), 6.94 (d, 1H), 6.79-6.81 (dd, 1H), 5.45 (s, 2H), 3.60-3.63 (t, 2H), 3.31-3.33 (t, 2H), 2.58 (s, 3H). |
| 099 | 514.2 | L2 | 2.56 | (DMSO-$d_6$) δ ppm: 8.63-8.64 (d, 1H), 8.52-8.53 (dd, 1H), 7.98 (d, 1H), 7.90-7.93 (t, 1H), 7.84-7.85 (d, 1H), 7.80-7.90 (dt, 1H), 7.69-7.71 (d, 2H), 7.47-7.50 (dd, 1H), 7.10-7.43 (m, 5H), 7.05-7.08 (d, 1H), 6.93-6.94 (d, 1H), 5.46 (s, 2H), 3.59-3.64 (q, 2H), 3.30-3.33 (t, 2H), 2.58-2.59 (d, 3H). |
| 100 | 574.2 | L2 | 2.88 | (DMSO-$d_6$) δ ppm: 8.64 (d, 1H), 8.52-8.53 (dd, 1H), 8.07-8.10 (t, 1H), 7.99 (d, 1H), 7.96 (d, 1H), 7.88 (s, 4H), 7.78-7.81 (dt, 1H), 7.58-7.61 (dd, 1H), 7.38-7.41 (m, 1H), 7.10-7.13 (q, 1H), 6.97 (d, 1H), 6.82-6.84 (d, 1H), 5.46 (s, 2H), 3.62-3.67 (q, 2H), 3.12-3.34 (t, 2H), 2.58-2.59 (d, 3H). |
| 101 | 484.2 | L4 | 4.34 | (DMSO-$d_6$) δ ppm: 8.63-8.64 (d, 1H), 8.51-8.53 (dd, 1H), 8.10 (t, 1H), 7.982-7.988 (d, 1H), 7.96-7.95 (d, 1H), 7.77-7.80 (m, 1H), 7.58-7.61 (dd, 1H), 7.38-7.46 (m, 3H), 7.05-7.11 (m, 3H), 6.77-6.79 (d, 1H), 5.46 (s, 2H), 3.60-3.65 (q, 2H), 3.32 (t, 2H), 2.58-2.59 (d, 3H). |
| 102 | 447.2 | L2 | 3.10 | (DMSO-$d_6$) δ ppm: 7.92 (d, 1H), 7.91 (brs, 1H), 7.85 (d, 1H), 7.65 (d, 2H), 7.51 (dd, 1H), 7.49-7.23 (m, 8H), 7.08 (d, 1H), 6.90 (d, 1H), 6.79 (d, 1H), 5.40 (s, 2H), 3.61 (q, 2H), 3.30 (t, 2H), 2.58 (d, 3H). |
| 103 | 533.3 | L2 | 3.37 | (DMSO-$d_6$) δ ppm: 8.05-8.08 (t, 1H), 7.96-7.97 (t, 2H), 7.89-7.91 (d, 2H), 7.72-7.74 (d, 2H), 7.59-7.61 (dd, 1H), 7.38-7.44 (m, 1H), 7.07-7.20 (m, 4H), 6.97-6.98 (d, 1H), 6.82-6.84 (d, 1H), 5.43 (s, 2H), 3.64-3.67 (m, 2H), 3.31-3.34 (m, 2H), 2.57-2.81 (d, 3H). |
| 104 | 472.3 | L2 | 3.03 | (DMSO-$d_6$) δ ppm: 7.740-7.746 (d, 1H), 7.478-7.643 (m, 8H), 7.399-7.438 (t, 2H), 7.26-7.31 (m, 2H), 6.80-6.82 (d, 1H), 6.67-6.68 (d, 1H), 5.38 (s, 2H), 5.23-5.24 (m, 1H), 3.84-3.89 (q, 2H), 3.33-3.36 (t, 2H), 2.39-2.41 (d, 3H). |
| 105 | 483.3 | L2 | 3.14 | (DMSO-$d_6$) δ ppm: 8.10-8.13 (t, 1H), 7.95 (d, 1H), 7.89 (d, 2H), 7.80 (d, 1H), 7.72-7.74 (d, 2H), 7.58-7.61 (dd, 1H), 7.06-7.09 (m, 1H), 6.89 (d, 1H), 6.82-6.84 (d, 1H), 4.32-4.35 (t, 2H), 3.75-3.78 (t, 2H), 3.64-3.69 (m, 2H), 3.33-3.37 (m, 2H), 3.29 (s, 3H), 2.59 (d, 3H). |
| 106 | 482.2 | L2 | 2.75 | (DMSO-$d_6$) δ ppm: 8.639-8.635 (d, 1H), 8.53-8.51 (dd, 1H), 7.98-7.95(m, 2H), 7.87-7.86 (d, |

TABLE 2-continued

| Analytical data for synthesized compounds of the disclosure | | | | |
|---|---|---|---|---|
| Cpd. No. | $[M + H]^+$ (m/z) : | LC/MS or UPLC Method | RT (min.) | $^1$H NMR (δ ppm) |
| | | | | 1H), 7.80-7.77 (m, 1H), 7.70-7.68 (d, 2H), 7.52-7.49 (dd, 1H), 7.44-7.37 (m, 3H), 7.10-7.09 (q, 1H), 6.95-6.94 (d, 1H), 6.80-6.78 (d, 1H), 5.45 (s, 2H), 3.64-3.59 (q, 2H), 3.31 (s, 2H), 2.59-2.57 (d, 3H). |
| 107 | 469.2 | L5 | 3.48 | (DMSO-$d_6$) δ ppm: 8.62-8.61 (d, 1H), 8.52-8.51 (dd, 1H), 7.93-7.92 (d, 1H), 7.91-7.90 (m, 1H), 7.81-7.80 (d, 1H), 7.69-7.66 (m, 2H), 7.54-7.45 (m, 4H), 6.86-6.85 (d, 1H), 6.83 (s, 1H), 5.45 (s, 2H), 3.54-3.51 (t, 2H), 2.92-2.88 (t, 2H) |
| 108 | 442.1 | L5 | 3.53 | (DMSO-$d_6$) δ ppm: 8.63-8.62 (d, 1H), 8.52-8.51 (dd, 1H), 8.014 (s, 1H), 7.97-7.96 (d, 1H), 7.79-7.72 (m, 4H), 7.40-7.33 (m, 2H), 7.07 (s, 1H), 6.89-6.88 (d, 1H), 6.70-6.68 (d, 1H), 5.44 (s, 2H), 3.83 (s, 3H), 3.58-3.56 (q, 2H), 3.31-3.26 (m, 2H), 2.57 (s, 1H). |
| 109 | 439.3 | L5 | 2.78 | (DMSO-$d_6$) δ ppm: 8.62 (br s, 1H), 8.52-8.51 (dd, 1H), 7.98 (s, 1H), 7.92-7.93 (d, 1H), 7.91-7.89 (m, 1H), 7.79 (s, 1H), 7.70-7.69 (d, 1H), 7.49-7.46 (dd, 1H), 7.38-7.36 (dd, 1H), 6.85-6.84 (d, 1H), 6.74-6.72 (d, 1H), 5.43 (s, 2H), 3.85 (s, 3H), 3.49-3.45 (t, 2H), 2.86-2.83 (t, 2H) |
| 110 | 467.30 | L3 | 4.56 | (DMSO-$d_6$) δ ppm: 8.61-8.62 (s, 1H), 8.51-8.53 (d, 1H), 7.98-7.99 (d, 1H), 7.95 (t, 1H), 7.77-7.80 (m, 2H), 7.56-7.59 (m, 2H), 7.39-7.46 (m, 2H), 6.97-7.00 (d, 2H), 6.93-6.94 (d, 1H), 6.83-6.93 (d, 1H), 5.44 (s, 2H), 4.16-4.20 (q, 2H), 3.84-3.81 (m, 2H) |
| 111 | 478.3 | L2 | 2.49 | DMSO-$d_6$) δ ppm: 8.632-8.637 (s, 1H), 8.51-8.53 (m, 1H), 7.970-7.975 (d, 1H), 7.77-7.82 (m, 3H), 7.55-7.58 (d, 2H), 7.38-7.44 (m, 2H), 7.07-7.10 (m, 1H), 6.95-6.98 (d, 2H), 6.900-6.906 (d, 1H), 6.78-6.80 (d, 1H), 5.45 (s, 2H), 3.77 (s, 3H), 3.57-3.61 (m, 2H), 3.28-3.31 (m, 2H), 2.57-2.58 (s, 3H). |
| 112 | 469.3 | L2 | 2.87 | (DMSO-$d_6$) δ ppm: 8.08-8.11 (t, 1H), 7.95 (d, 1H), 7.89-7.91 (d, 2H), 7.80 (d, 1H), 7.72-7.74 (d, 2H), 7.58-7.60 (dd, 1H), 7.06-7.09 (m, 1H), 6.89 (d, 1H), 6.82-6.84 (d, 1H), 4.89-4.92 (t, 1H), 4.21-4.24 (t, 1H), 3.79-3.83 (m, 2H), 3.64-3.69 (m, 2H), 3.33-3.37 (m, 2H), 2.59 (d, 3H). |
| 113 | 490.3 | L2 | 2.69 | (DMSO-$d_6$) δ ppm: 7.80-7.98 (m, 6H), 7.64-7.66 (d, 2H), 7.38-7.51 (m, 6H), 7.23-7.27 (t, 1H), 7.06 (br s, 1H), 6.918-6.924 (d, 1H), 6.78-6.80 (d, 1H), 5.45 (s, 2H), 3.59-3.63 (m, 2H), 3.30-3.33 (m, 2H), 2.57 (s, 3H). |
| 114 | 449.3 | L2 | 1.70 | (DMSO-$d_6$) δ ppm: 8.65 (s, 1H), 8.57-8.58 (d, 1H), 8.52-8.53 (d, 1H), 8.29-8.30 (d, 1H), 8.04-8.07 (t, 1H), 7.99-8.00 (d, 1H), 7.91-7.95 (m, 2H), 7.76-7.80 (m, 2H), 7.38-7.41 (q, 1H), 7.19-7.22 (q, 1H), 7.11-7.12 (d, 1H), 6.88-6.90 (d, 1H), 6.79-6.81 (d, 1H), 5.46 (s, 2H), 3.61-3.66 (q, 2H), 3.31-3.35 (t, 2H), 2.59-2.67 (d, 3H). |
| 115 | 462.3 | L2 | 2.58 | (DMSO-$d_6$) δ ppm: 8.605-8.609 (d, 1H), 8.50-8.51 (dd, 1H), 7.92-7.93 (d, 1H), 7.73-7.75 (m, 1H), 7.588 (t, 1H), 7.450-7.455 (d, 1H), 7.35-7.39 (m, 1H), 7.20-7.27 (m, 4H), 7.14-7.16 (t, 1H), 7.041 (s, 1H), 6.98-7.0 (dd, 1H), 6.62-6.69 (d, 1H), 6.6-6.62 (d, 1H), 5.42 (s, 2H) 3.83 (s, 2H), 3.5-3.54 (m, 2H), 3.23-3.26 (t, 2H), 2.55 (s, 3H). |
| 116 | 463.1 | L3 | 3.55 | (DMSO-$d_6$) δ ppm: 8.62 (d, 1H), 8.52 (dd, 1H), 7.94 (d, 1H), 7.78 (d, 1H), 7.61 (s, 1H), 7.41-7.37 (m, 2H), 7.32 (d, 1H), 7.12-7.05 (m, 3H), 6.99 (dd, 1H), 6.81 (dd, 2H), 6.68 (d, 1H), 6.64-6.61 (m, 2H), 5.43 (s, 2H), 3.54 (q, 2H), 3.28 (t, 2H), 2.58 (d, 3H). |
| 117 | 389.2 | L2 | 2.78 | (DMSO-$d_6$) δ ppm: 7.901 (t, 1H), 7.77-7.81 (d, 2H), 7.66-7.70 (t, 2H), 7.45-7.47 (d, 1H), 7.20-7.24 (t, 2H), 7.07-7.08 (d, 1H), 6.86 (s, 1H), 6.78-6.80 (d, 1H), 3.91 (s, 3H), 3.63-3.65 (d, 2H), 3.32 (s, 2H), 2.59-2.60 (d, 3H). |
| 118 | 439.2 | L2 | 3.01 | (DMSO-$d_6$) δ ppm: 8.04-8.07 (t, 1H), 7.94 (d, 1H), 7.89-7.91 (d, 2H), 7.79 (d, 1H), 7.14-7.72 (d, 2H), 7.57-7.60 (m, 1H), 7.09 (m, 1H), 6.89-6.90 (d, |

TABLE 2-continued

| Analytical data for synthesized compounds of the disclosure | | | | |
|---|---|---|---|---|
| Cpd. No. | [M + H]$^+$ (m/z) : | LC/MS or UPLC Method | RT (min.) | $^1$H NMR (δ ppm) |
| | | | | 1H), 6.82-6.84 (d, 1H), 3.92 (s, 3H), 3.64-3.69 (m, 2H), 3.33-3.37 (m, 2H), 2.60 (d, 3H). |
| 119 | 389.2 | L2 | 2.78 | (DMSO-$d_6$) δ ppm: 8.00 (t, 1H), 7.88 (d, 1H), 7.78 (d, 1H), 7.49-7.55 (m, 3H), 7.40-7.46 (m, 1H), 7.03-7.08 (m, 2H), 6.91-6.92 (d, 1H), 6.78-6.80 (d, 1H), 3.92 (s, 3H), 3.63-3.68 (m, 2H), 3.31-3.36 (m, 2H), 2.59 (s, 3H). |
| 120 | 438.9 | L1 | 2.57 | (DMSO-$d_6$) δ ppm: 7.97-8.03 (m, 2H), 7.92-7.94 (m, 2H), 7.78-7.79 (d, 1H), 7.56-7.65 (m, 3H), 7.08-7.09 (q, 1H), 6.933-6.939 (d, 1H), 6.81-6.83 (d, 1H), 3.92 (s, 3H), 3.64-3.69 (q, 2H), 3.31-3.37 (m, 2H), 2.60-2.61 (d, 3H). |
| 121 | 405.2 | L2 | 2.95 | (DMSO-$d_6$) δ ppm: 7.94-7.97 (t, 1H), 7.85-7.86 (d, 1H), 7.77-7.78 (d, 1H), 7.67-7.71 (m, 2H), 7.48-7.51 (m, 1H), 7.42-7.48 (d, 2H), 7.06-7.09 (d, 1H), 6.87-6.88 (d, 1H), 6.78-6.80 (d, 1H), 3.92 (s, 3H), 3.62-3.65 (q, 2H), 3.31-3.35 (m, 2H), 2.59-2.60 (d, 3H). |
| 122 | 405.2 | L2 | 2.97 | (DMSO-$d_6$) δ ppm: 7.99-8.00 (t, 1H), 7.88 (d, 1H), 7.78 (d, 1H), 7.71-7.72 (m, 1H), 7.62-7.65 (m, 1H), 7.51-7.54 (dd, 1H), 7.40-7.44 (t, 1H), 7.28-7.31 (m, 1H), 7.09 (m, 1H), 6.92-6.93 (d, 1H), 6.78-6.81 (d, 1H), 3.92 (s, 3H), 3.63-3.68 (m, 2H), 3.31-3.36 (m, 2H), 2.59 (d, 3H). |
| 123 | 407.2 | L2 | 2.81 | (DMSO-$d_6$) δ ppm: 8.007-8.036 (t, 1H), 7.771-7.777 (d, 2H), 7.39-7.44 (m, 2H), 7.278-7.33 (m, 1H), 7.079-7.169 (m, 2H), 6.79-6.81 (dd, 2H), 3.92 (s, 3H), 3.63-3.68 (q, 2H), 3.31-3.36 (q, 2H), 2.59-2.60 (d, 3H). |
| 124 | 407.2 | L2 | 2.89 | (DMSO-$d_6$) δ ppm: 7.98-8.01 (t, 1H), 7.86 (d, 1H), 7.73-7.78 (m, 2H), 7.50-7.52 (m, 2H), 7.40-7.47 (m, 1H), 7.06-7.10 (m, 1H), 6.93 (d, 1H), 6.77-6.79 (d, 1H), 3.92 (s, 3H), 3.62-3.67 (m, 2H), 3.31-3.39 (m, 2H), 2.59-2.60 (d, 3H). |
| 125 | 407.2 | L2 | 2.84 | (DMSO-$d_6$) δ ppm: 8.00-8.03 (t, 1H), 7.76-7.78 (m, 2H), 7.32-7.41 (m, 3H), 7.22-7.30 (m, 1H), 7.06-7.10 (q, 1H), 6.81-6.83 (d, 1H), 6.76-6.77 (d, 1H), 3.92 (s, 3H), 3.64-3.69 (q, 2H), 3.32-3.37 (t, 2H), 2.60-2.61 (d, 3H). |
| 126 | 407.2 | L2 | 2.90 | (DMSO-$d_6$) δ ppm: 8.09-8.12 (t, 1H), 7.93-7.94 (d, 1H), 7.784-7.789 (d, 1H), 7.57-7.60 (m, 1H), 7.42-7.47 (m, 2H), 6.98-7.10 (m, 3H), 6.78-6.80 (d, 1H), 3.92 (s, 3H), 3.64-3.68 (q, 2H), 3.31-3.36 (m, 2H), 2.59-2.60 (d, 3H). |
| 127 | 457.2 | L2 | 3.04 | (DMSO-$d_6$) δ ppm: 8.16-8.19 (t, 1H), 8.00 (d, 1H), 7.85-7.88 (d, 1H), 7.77-7.79 (d, 1H), 7.74-7.75 (m, 2H), 7.64-7.66 (dd, 1H), 7.07-7.11 (m, 1H), 6.96-6.97 (d, 1H), 6.81-6.83 (d, 1H), 3.92 (s, 3H), 3.65-3.70 (m, 2H), 3.31-3.37 (m, 2H), 2.59-2.61 (d, 3H). |
| 128 | 457.2 | L2 | 3.05 | (DMSO-$d_6$) δ ppm: 8.12-8.15 (t, 1H), 7.984-7.989 (d, 1H), 7.89-7.92 (d, 1H), 7.85 (s, 1H), 7.791-7.797 (d, 1H), 7.63-7.66 (m, 1H), 7.48-7.50 (d, 1H), 7.08-7.11 (q, 1H), 7.002-7.008 (m, 1H), 6.80-6.82 (d, 1H), 3.92 (s, 3H), 3.64-3.69 (q, 2H), 3.31-3.37 (m, 2H), 2.59-2.61 (d, 3H). |
| 129 | 455.2 | L2 | 3.08 | (DMSO-$d_6$) δ ppm: 8.01-8.04 (t, 1H), 7.89-7.90 (d, 1H), 7.78-7.79 (d, 1H), 7.71-7.73 (d, 1H), 7.63 (bs, 1H), 7.51-7.56 (m, 2H), 7.22-7.24 (d, 1H), 7.07-7.11 (q, 1H), 6.92-6.93 (d, 1H), 6.79-6.82 (d, 1H), 3.92 (s, 3H), 3.64-3.68 (q, 2H), 3.32-3.36 (t, 2H), 2.60-2.61 (d, 3H). |
| 130 | 476.3 | L8 | 5.00 | (DMSO-$d_6$) δ ppm: 8.48-8.49 (d, 1H), 8.32-8.35 (m, 4H), 7.74-8.03 (m, 4H), 7.55-7.56 (d, 1H), 7.09-7.13 (q, 1H), 3.78-3.83 (q, 2H), 3.40-3.44 (t, 2H), 2.59-2.61 (d, 3H). |
| 131 | 426.3 | L2 | 2.50 | (DMSO-$d_6$) δ ppm: 8.46-8.47 (d, 1H), 8.28 (s, 1H), 8.13-8.19 (m, 3H), 7.73-8.03 (m, 1H), 7.59-7.62 (t, 1H), 7.51-7.52 (d, 1H), 7.24-7.28 (t, 2H), 7.10 (s, 1H), 3.75-3.80 (q, 2H), 3.40-3.42 (t, 2H), 2.59 (s, 3H). |

TABLE 2-continued

| Cpd. No. | $[M + H]^+$ (m/z) : | LC/MS or UPLC Method | RT (min.) | $^1H$ NMR (δ ppm) |
|---|---|---|---|---|
| Analytical data for synthesized compounds of the disclosure | | | | |
| 132 | 426.1 | L3 | 6.23 | (DMSO-$d_6$) δ ppm: 8.38-8.39 (d, 1H), 8.12-8.15 (m, 2H), 7.73-7.89 (m, 3H), 7.24-7.30 (m, 4H), 7.08-7.12 (dd, 1H), 3.69-3.74 (t, 2H), 3.36-3.39 (t, 2H), 2.60 (d, 3H). |
| 133 | 440.3 | L3 | 5.57 | (DMSO-$d_6$) δ ppm: 8.38-8.39 (d, 1H), 8.12-8.16 (m, 2H), 7.73-8.02 (m, 3H), 7.24-7.33 (m, 4H), 3.73-3.78 (m, 2H), 3.39-3.43 (t, 2H), 2.79 (s, 6H). |
| 134 | 476.3 | L3 | 5.75 | (DMSO-$d_6$) δ ppm: 8.41-8.42 (d, 1H), 8.31-8.33 (d, 2H), 7.74-8.03 (m, 5H), 7.32-7.34 (m, 2H), 7.09-7.13 (t, 1H), 3.71-3.76 (m, 2H), 3.37-3.40 (t, 2H), 2.59-2.60 (d, 3H). |
| 135 | 318.3 | L2 | 2.69 | (DMSO-$d_6$) δ ppm: 7.68-7.70 (t, 2H), 7.610-7.618 (dd, 2H), 7.49-7.59 (dd, 2H), 7.42-7.49 (m, 2H), 7.35-7.40 (m, 2H), 6.65-6.66 (d, 1H), 6.30-6.37 (q, 1H), 6.10-6.15 (dd, 1H), 5.61-5.64 (dd, 1H), 4.61-4.63 (d, 2H), 3.93 (s, 3H). |
| 136 | 395.1 | L6 | 1.73 | / |
| 137 | 318.2 | L2 | 2.55 | (DMSO-$d_6$) δ ppm: 8.66-8.69 (t, 1H), 7.91 (s, 1H), 7.70-7.75 (m, 4H), 7.47-7.51 (m, 1H), 6.80 (d, 1H), 6.30-6.35 (q, 1H), 6.12-6.17 (dd, 1H), 5.62-5.65 (dd, 1H), 4.45-4.47 (d, 2H), 3.90 (s, 3H) |
| 138 | 320.3 | L3 | 4.01 | (DMSO-$d_6$) δ ppm: 8.33-8.36 (t, 3H), 7.89-7.90 (t, 1H), 7.50-7.54 (d, 1H), 7.67-7.69 (m, 3H), 7.47-7.51 (m, 2H), 7.41-7.44 (m, 1H), 7.34-7.40 (m, 1H), 6.77-6.78 (d, 1H), 4.35-4.38 (d, 2H), 3.90 (s, 3H), 2.14-2.20 (q, 2H), 1.03-1.06 (t, 3H) |
| 139 | 395.3 | L2 | 2.27 | (DMSO-$d_6$) δ ppm: 8.66 (t, 1H), 8.55 (d, 1H), 8.50-8.52 (dd, 1H), 7.96 (d, 1H), 7.90-7.91 (t, 1H), 7.67-7.71 (m, 4H), 7.47-7.51 (m, 3H), 7.37-7.41 (m, 2H), 6.90 (d, 1H), 6.26-6.33 (q, 1H), 6.11-6.12 (dd, 1H), 5.61-5.64 (dd, 1H), 5.46 (s, 2H), 4.46 (s, 2H) |
| 140 | 386.2 | L2 | 2.89 | (DMSO-$d_6$) δ ppm: 8.52-8.55 (t, 1H), 7.92-7.94 (d, 2H), 7.87-7.88 (d, 1H), 7.81-7.83 (m, 3H), 7.67-7.70 (dd, 1H), 7.44-7.46 (d, 1H), 6.69 (d, 1H), 6.31-6.38 (m, 1H), 6.10-6.15 (dd, 1H), 5.61-5.65 (dd, 1H), 4.63-4.65 (d, 2H), 3.93 (s, 3H). |
| 141 | 386.3 | L2 | 2.87 | (DMSO-$d_6$) δ ppm: 8.52-8.55 (t, 1H), 8.01-8.03 (m, 1H), 7.99 (s, 1H), 7.86-7.87 (d, 1H), 7.80-7.81(d, 1H), 7.68-7.75 (m, 3H), 7.44-7.46 (d, 1H), 6.71-6.72 (d, 1H), 6.31-6.38 (m, 1H), 6.11-6.16 (dd, 1H), 5.62-5.65 (dd, 1H), 4.64-4.65 (d, 2H), 3.94-3.96 (s, 3H). |
| 142 | 336.2 | L2 | 2.68 | (DMSO-$d_6$) δ ppm: 8.51 (t, 1H), 7.83-7.84 (d, 1H), 7.80-7.81 (d, 1H), 7.63-7.66 (dd, 1H), 7.50-7.57 (m, 3H), 7.41-7.43 (d, 1H), 7.20-7.22 (m, 1H), 6.70-6.71 (d, 1H), 6.31-6.38 (m, 1H), 6.10-6.15 (dd, 1H), 5.61-5.64 (dd, 1H), 4.63-4.64 (d, 2H), 3.93 (s, 3H). |
| 143 | 336.2 | L2 | 2.67 | (DMSO-$d_6$) δ ppm: 7.78-7.80 (dd, 2H), 7.71-7.75 (m, 2H), 7.57-7.59 (dd, 1H), 7.39-7.41 (d, 1H), 7.27-7.31 (m, 2H), 6.66-6.67 (d, 1H), 6.30-6.33 (m, 1H), 6.10-6.15 (dd, 1H), 5.61-5.64 (dd, 1H), 4.61-4.62 (d, 2H), 3.93 (s, 3H). |
| 144 | 354.2 | L2 | 2.72 | (DMSO-$d_6$) δ ppm: 8.49-8.52 (t, 1H), 7.79-7.85 (m, 3H), 7.61-7.63 (m, 1H), 7.50-7.56 (m, 2H), 6.70 (d, 1H), 6.30-6.37 (m, 1H), 6.10-6.15 (dd, 1H), 5.61-5.64 (dd, 1H), 4.62-4.64 (d, 2H), 3.93 (s, 3H). |
| 145 | 354.2 | L7 | 2.69 | (DMSO-$d_6$) δ ppm: 8.52 (t, 1H), 7.78 (d, 1H), 7.65 (m, 1H), 7.60-7.63 (m, 1H), 7.36-7.47 (m, 3H), 7.17-7.22 (m, 1H), 6.60-6.61 (d, 1H), 6.30-6.37 (m, 1H), 6.10-6.15 (dd, 1H), 5.61-5.64 (d, 1H), 4.61-4.63 (d, 2H), 3.92 (s, 3H). |
| 146 | 404.3 | L3 | 4.98 | (DMSO-$d_6$) δ ppm: 7.77-7.84 (m, 4H), 7.68-7.70 (d, 1H), 7.54-7.55 (d, 1H), 7.45-7.47 (d, 1H), 6.62-6.63 (d, 1H), 6.31-6.38 (dd, 1H), 6.11-6.15 (dd, 1H), 5.62-5.65 (dd, 1H), 4.64-4.65 (d, 2H), 3.92 (s, 3H). |

TABLE 2-continued

Analytical data for synthesized compounds of the disclosure

| Cpd. No. | $[M + H]^+$ (m/z) : | LC/MS or UPLC Method | RT (min.) | $^1H$ NMR (δ ppm) |
|---|---|---|---|---|
| 147 | 387.2 | L2 | 2.66 | (DMSO-de) δ ppm: 9.13-9.14 (d, 1H), 8.54-8.57 (t, 1H), 8.40-8.43 (dd, 1H), 7.96-7.99 (dd, 2H), 7.82 (d, 1H), 7.75-7.78 (dd, 1H), 7.48-7.50 (d, 1H), 6.74 (d, 1H), 6.32-6.38 (m, 1H), 6.11-6.16 (dd, 1H), 5.62-5.65 (dd, 1H), 4.66-4.68 (d, 2H), 3.94 (s, 3H). |
| 148 | 387.3 | L2 | 2.52 | ($DMSO-d_6$) δ ppm: 9.13-9.14 (d, 1H), 8.54-8.57 (t, 1H), 8.40-8.43 (dd, 1H), 7.96-8.00 (m, 2H), 7.82 (d, 1H), 7.75-7.78 (dd, 1H), 7.48-7.53 (d, 1H), 6.73-6.74 (d, 1H), 6.32-6.38 (dd, 1H), 6.11-6.16 (dd, 1H), 5.62-5.65 (dd, 1H), 4.67-4.68 (d, 2H), 3.94 (s, 3H). |
| 149 | 380.2 | L2 | 2.80 | (DMSO-de) δ ppm: 8.47 (t, 1H), 7.82-7.82 (d, 1H), 7.79-7.80 (d, 1H), 7.72-7.76 (m, 2H), 7.57-7.59 (dd, 1H), 7.39-7.41 (d, 1H), 7.27-7.31 (m, 2H), 6.68-6.69 (d, 1H), 6.29-6.36 (m, 1H), 6.10-6.14 (dd, 1H), 5.61-5.64 (dd, 1H), 4.61-4.63 (d, 2H), 4.33-4.35 (t, 2H), 3.73-3.76 (t, 2H), 3.25 (s, 3H). |
| 150 | 364.2 | L2 | 3.02 | ($DMSO-d_6$) δ ppm: 8.45-8.47 (t, 1H), 7.86-7.87 (d, 1H), 7.78-7.79 (d, 1H), 7.72-7.76 (m, 2H), 7.56-7.59 (dd, 1H), 7.39-7.41 (d, 1H), 7.27-7.31 (m, 2H), 6.67-6.68 (d, 1H), 6.29-6.36 (m, 1H), 6.10-6.14 (dd, 1H), 5.61-5.64 (dd, 1H), 4.54-4.63 (m, 3H), 1.46-1.48 (d, 6H). |
| 151 | 366.3 | L3 | 4.08 | ($DMSO-d_6$) δ ppm: 8.47-8.50 (t, 1H), 7.72-7.80 (m, 4H), 7.56-7.59 (dd, 1H), 7.40-7.42 (d, 1H), 7.27-7.31 (m, 2H), 6.67-6.68 (d, 1H), 6.29-6.36 (m, 1H), 6.09-6.14 (dd, 1H), 6.09-6.14 ( dd, 1H), 5.60-5.63 (dd, 1H), 4.94-4.96 (t, 1H), 4.62-4.63 (d, 2H), 4.21-4.24 (t, 2H), 3.78-3.82 (m, 2H). |
| 152 | 378.3 | L2 | 3.10 | ($DMSO-d_6$) δ ppm: 8.45-8.48 (t, 1H), 7.81-7.82 (d, 1H), 7.78-7.79 (d, 1H), 7.72-7.75 (m, 2H), 7.57-7.59 (dd, 1H), 7.38-7.40 (d, 1H), 7.27-7.31 (t, 2H), 6.67-6.68 (d, 1H), 6.29-6.36 (m, 1H), 6.09-6.14 (dd, 1H), 5.61-5.64 (dd, 1H), 4.61-4.62 (d, 2H), 3.98-4.00 (d, 2H), 2.07-2.20 (m, 1H), 0.87-0.88 (d, 6H). |
| 153 | 376.3 | L2 | 3.00 | ($DMSO-d_6$) δ ppm: 8.46-8.49 (t, 1H), 7.87-7.88 (d, 1H), 7.796-7.801 (d, 1H), 7.72-7.77 (2H), 7.57-7.59 (dd, 1H), 7.39-7.41 (d, 1H), 7.26-7.32 (t, 2H), 6.69-6.70 (d, 1H), 6.30-6.37 (m, 1H), 6.10-6.15 (dd, 1H), 5.61-5.64 (dd, 1H), 4.63-4.64 (d, 2H), 4.05-4.07 (d, 2H), 1.26-1.33 (m, 1H), 0.53-0.57 (m, 2H), 0.39-0.41 (m, 2H). |
| 154 | 378.8 | L2 | 2.70 | ($DMSO-d_6$) δ ppm: 8.51-8.52 (t, 1H), 7.99-8.00 (d, 1H), 7.82-7.83 (d, 1H), 7.74-7.78 (m, 2H), 7.60-7.63 (dd, 1H), 7.42-7.44 (d, 1H), 7.27-7.32 (t, 2H), 6.77-6.78 (d, 1H), 6.29-6.36 (m, 1H), 6.10-6.15 (dd, 1H), 5.60-5.65 (m, 2H), 4.95-4.97 (m, 4H), 4.65-4.67 (d, 2H). |
| 155 | 434.3 | L3 | 5.24 | ($DMSO-d_6$) δ ppm: 8.44-8.45 (t, 1H), 7.892-7.897 (d, 1H), 7.72-7.80 (m, 3H), 7.58-7.61 (dd, 1H), 7.39-7.41 (d, 1H), 7.27-7.32 (m, 2H), 6.72-6.73 (d, 1H), 6.29-6.36 (m, 1H), 6.1-6.15 ( dd, 1H), 5.60-5.63 (dd, 1H), 4.61-4.62 (d, 1H), 4.50-4.54 (m, 4H). |
| 156 | 430.3 | L2 | 2.99 | ($DMSO-d_6$) δ ppm: 8.49 (t, 1H), 7.95-7.89 (m, 2H), 7.82 (t, 1H), 7.70-7.67 (m, 3H), 7.47-7.45 (m, 1H), 6.71-6.70 (m, 1H), 6.36-6.30 (m, 1H), 6.15-6.10 (m, 1H), 5.64-5.61 (m, 1H), 4.65-4.64 (m, 1H), 4.36-4.34 (m, 2H), 3.76-3.74 (m, 2H), 3.25 (s, 3H). |
| 157 | 352.2 | L2 | 2.88 | ($DMSO-d_6$) δ ppm: 8.49-8.52 (t, 1H), 7.79-7.81 (m, 2H), 7.71-7.75 (d, 2H), 7.60-7.62 (dd, 1H), 7.50-7.53 (d, 2H), 7.41-7.42 (d, 1H), 6.67-6.68 (d, 1H), 6.30-6.37 (m, 1H), 6.10-6.15 (dd, 1H), 5.638-5.644 (dd, 1H), 4.61-4.63 (d, 2H), 3.93 (s, 3H). |
| 158 | 378.2 | L3 | 6.18 | ($DMSO-d_6$) δ ppm: 8.49 (t, 1H), 7.89 (d, 1H), 7.80 (d, 1H), 7.72 (t, 2H), 7.61 (dd, 1H), 7.53-7.50 (m, 2H), 7.41 (d, 1H), 6.68 (d, 1H), 6.33 (q, 1H), 6.13 (dd, 1H), 5.63 (dd, 1H), 4.61 (d, 2H), 3.84-3.78 (m, 1H), 1.13-1.09 (m, 2H), 1.02-0.99 (m, 2H). |

TABLE 2-continued

Analytical data for synthesized compounds of the disclosure

| Cpd. No. | $[M + H]^+$ (m/z) : | LC/MS or UPLC Method | RT (min.) | $^1H$ NMR (δ ppm) |
|---|---|---|---|---|
| 159 | 392.3 | L3 | 4.36 | (DMSO-$d_6$) δ ppm: 8.43-8.46 (t, 1H), 7.86-7.87 (d, 1H), 7.72-7.78 (m, 3H), 7.57-7.59 (dd, 1H), 7.39-7.41 (d, 1H), 7.27-7.31 (m, 2H), 6.70-6.71(d, 1H), 6.30-6.37 (m, 1H), 6.10-6.15 (dd, 1H), 5.61-5.64 (dd, 1H), 4.65-4.69 (dd, 2H), 4.61-4.62 (d, 2H), 4.45-4.50 (dd, 4H), 3.41-3.50 (m, 1H). |
| 160 | 404.2 | L2 | 2.94 | (DMSO-$d_6$) δ ppm: 8.47-8.48 (t, 1H), 7.97-7.98 (d, 1H), 7.80 (d, 1H), 7.73-7.77 (q, 2H), 7.61-7.64 (dd, 1H), 7.41-7.43 (d, 1H), 7.27-7.32 (t, 2H), 6.84-6.85 (d, 1H), 6.28-6.35 (q, 1H), 6.10-6.15 (dd, 1H), 5.61-5.64 (dd, 1H), 5.20-5.25 (q, 2H), 4.59-4.61 (d, 2H). |
| 161 | 322.2 | L2 | 2.56 | (DMSO-$d_6$) δ ppm: 12.79 (s, 1H), 8.20 (s, 1H), 7.69-7.72 (m, 4H), 7.55 (s, 1H), 7.43-7.45 (d, 1H), 7.21-7.26 (t, 2H), 6.61 (s, 1H), 6.26-6.33 (m, 1H), 6.08-6.12 (dd, 1H), 5.56-5.59 (dd, 1H), 4.58 (s, 2H). |
| 162 | 336.2 | L2 | 2.58 | (DMSO-$d_6$) δ ppm: 8.58-8.61 (t, 1H), 8.03 (s, 1H), 7.72-7.77 (m, 3H), 7.60-7.61 (d, 1H), 7.52-7.55 (dd, 1H), 7.38-7.40 (d, 1H), 7.26-7.32 (m, 2H), 6.30-6.34 (m, 1H), 6.12-6.17 (dd, 1H), 5.62-5.65 (dd, 1H), 4.44-4.46 (d, 2H), 3.90 (s, 3H). |
| 163 | 336.2 | L2 | 2.59 | (DMSO-$d_6$) δ ppm: 8.54 (t, 1H), 7.74-7.77 (m, 3H), 7.56-7.57 (d, 1H), 7.48-7.52 (m, 2H), 7.26-7.30 (t, 2H), 6.37-6.38 (d, 1H), 6.24-6.31 (m, 1H), 6.07-6.12 (dd, 1H), 5.59-5.63 (dd, 1H), 4.16-4.18 (d, 2H), 3.67 (s, 3H). |
| 164 | 333.2 | L2 | 2.24 | (DMSO-$d_6$) δ ppm: 8.56-8.68 (m, 3H), 7.91-7.93 (m, 1H), 7.76-7.79 (m, 2H), 7.70-7.73 (m, 1H), 7.49-7.53 (m, 3H), 7.27-7.31 (t, 2H), 6.22-6.29 (m, 1H), 6.06-6.07 (m, 1H), 5.58-5.62 (dd, 1H), 4.29-4.30 (d, 2H). |
| 165 | 333.2 | L2 | 2.43 | (DMSO-$d_6$) δ ppm: 8.69-8.71 (m, 1H), 8.48 (t, 1H), 7.91-7.93 (m, 1H), 7.67-7.79 (m, 5H), 7.46-7.48 (d, 1H), 7.41-7.43 (m, 1H), 7.27-7.32 (t, 2H), 6.25-6.29 (m, 1H), 6.06-6.11 (dd, 1H), 5.58-5.61 (dd, 1H), 4.48-4.49 (d, 2H). |
| 166 | 362.4 | L2 | 2.91 | (DMSO-$d_6$) δ ppm: 8.45-8.55 (t, 1H), 7.88-7.89 (d, 1H), 7.77-7.78 (d, 1H), 7.72-7.76 (m, 2H), 7.57-7.60 (dd, 1H), 7.39-7.41 (d, 1H), 7.27-7.32 (m, 2H), 6.67-6.68 (d, 1H), 6.30-6.36 (m, 1H), 6.10-6.15 (dd, 1H), 5.61-5.64 (d, 1H), 4.60-4.61 (d, 2H), 3.78-3.84 (m, 1H), 1.09-1.13 (m, 2H), 1.01-1.02 (m, 2H). |
| 167 | 412.3 | L3 | 5.42 | (DMSO-$d_6$) δ ppm: 8.52 (t, 1H), 7.94 (d, 2H), 7.90 (d, 1H), 7.87 (d, 1H), 7.82 (d, 2H), 7.69 (dd, 1H), 7.45 (d, 1H), 6.70 (d, 1H), 6.33 (q, 1H), 6.13 (dd, 1H), 5.63 (dd, 1H), 4.63 (d, 2H), 3.84-3.79 (m, 1H), 1.14-1.12 (m, 2H), 1.02-1.00 (m, 2H). |
| 168 | 412.3 | L2 | 2.93 | (DMSO-$d_6$) δ ppm: 8.59-8.62 (t, 1H), 8.12 (s, 1H), 7.93-7.95 (d, 2H), 7.80-7.82 (d, 2H), 7.75-7.76 (d, 1H), 7.71-7.72 (d, 1H), 7.62-7.64 (dd, 1H), 7.43-7.45 (d, 1H), 6.29-6.36 (dd, 1H), 6.12-6.17 (dd, 1H), 5.62-5.65 (dd, 1H), 4.46-4.48 (d, 2H), 3.74-3.80 (m, 1H), 1.06-1.13 (m, 4H). |
| 169 | 362.3 | L2 | 2.74 | (DMSO-$d_6$) δ ppm: 7.88 (t, 1H), 7.87 (s, 1H), 7.82-7.83 (d, 1H), 7.71-7.76 (m, 3H), 7.45 (s, 1H), 7.29-7.35 (m, 2H), 6.78-6.79 (d, 1H), 6.28-6.34 (q, 1H), 6.12-6.16 (dd, 1H), 5.62-5.65 (dd, 1H), 4.45-4.46 (d, 2H), 3.73-3.79 (m, 1H), 1.03-1.11 (m, 4H) |
| 170 | 372.2 | L2 | 2.88 | (DMSO-$d_6$) δ ppm: 8.52-8.55 (t, 1H), 8.37-8.38 (d, 1H), 7.75-8.05 (t, 1H), 7.83-7.84 (d, 1H), 7.76-7.79 (m, 3H), 7.67-7.70 (dd, 1H), 7.45-7.47 (d, 1H), 7.28-7.33 (m, 2H), 7.03-7.04 (d, 1H), 6.29-6.36 (m, 1H), 6.10-6.15 (dd, 1H), 5.62-5.65 (dd, 1H), 4.61-4.62 (d, 2H). |
| 171 | 372.2 | L2 | 2.72 | (DMSO-$d_6$) δ ppm: 8.52-8.55 (t, 1H), 7.90-7.91 (d, 1H), 7.80-7.83 (dd, 1H), 7.72-7.76 (m, 2H), 7.41-7.70 (t, 1H), 7.51-7.56 (m, 3H), 7.28-7.32 (m, 2H), 6.667-6.671 (d, 1H), 6.23-6.30 (m, 1H), 6.07-6.12 (dd, 1H), 5.60-5.63 (dd, 1H), 4.16-4.17 (d, 2H). |

TABLE 2-continued

Analytical data for synthesized compounds of the disclosure

| Cpd. No. | [M + H]+ (m/z) : | LC/MS or UPLC Method | RT (min.) | $^1$H NMR (δ ppm) |
|---|---|---|---|---|
| 172 | 422.3 | L3 | 5.31 | (DMSO-$d_6$) δ ppm: 8.56 (t, 1H), 8.39 (d, 1H), 8.05-7.76 (m, 7H), 7.51-7.49 (m, 1H), 7.06-7.05 (m, 1H), 6.36-6.29 (m, 1H), 6.15-6.10 (m, 1H), 5.65-5.62 (m, 1H), 4.64-4.63 (m, 2H). |
| 173 | 422.3 | L2 | 2.97 | (DMSO-$d_6$) δ ppm: 8.64-8.67 (t, 1H), 8.60 (s, 1H), 8.16 (s, 1H), 7.78-8.02 (m, 6H), 7.71-7.74 (dd, 1H), 7.48-7.50 (d, 1H), 6.28-6.35 (m, 1H), 6.11-6.16 (dd, 1H), 5.62-5.65 (dd, 1H), 4.46-4.47 (d, 2H). |
| 174 | 372.3 | L2 | 2.78 | (DMSO-$d_6$) δ ppm: 8.68-8.70 (t, 1H), 8.32-8.33 (d, 1H), 7.73-8.02 (m, 5H), 7.57 (s, 1H), 7.31-7.35 (t, 2H), 7.161-7.168 (d, 1H), 6.27-6.34 (dd, 1H), 6.12-6.19 (dd, 1H), 5.62-5.65 (dd, 1H), 4.47-4.49 (d, 2H) |
| 175 | 376.3 | L2 | 3.00 | (DMSO-$d_6$) δ ppm: 8.48-8.51 (t, 1H), 7.90-7.91 (d, 1H), 7.73-7.78 (m, 3H), 7.57-7.60 (dd, 1H), 7.39-7.41 (d, 1H), 7.27-7.32 (m, 2H), 6.66-6.67 (d, 1H), 6.29-6.36 (q, 1H), 6.10-6.15 (dd, 1H), 5.61-5.64 (dd, 1H), 4.61-4.63 (d, 2H), 1.63 (s, 3H), 1.24-1.27 (m, 2H), 0.92-0.95 (m, 2H). |
| 176 | 350.3 | L2 | 2.83 | (DMSO-$d_6$) δ ppm: 8.48-8.51 (t, 1H), 7.70-7.74 (m, 3H), 7.55-7.57 (dd, 1H), 7.37-7.39 (dd, 1H), 7.25-7.31 (m, 2H), 6.47 (s, 1H), 6.30-6.37 (m, 1H), 6.10-6.15 (dd, 1H), 5.61-5.64 ( dd, 1H), 4.61-4.62 (d, 2H), 3.80 (s, 3H), 2.31 ( s, 3H). |
| 177 | 404.3 | L2 | 3.16 | (DMSO-$d_6$) δ ppm: 9.03-9.06 (t, 1H), 7.93-7.95 (d, 2H), 7.88-7.89 (d, 1H), 7.81-7.83 (m, 3H), 7.67-7.70 (dd, 1H), 7.42-7.44 (d, 1H), 6.75-6.75 (d, 1H), 5.50-5.63 (dd, 1H), 5.28-5.33 (dd, 1H), 4.63-4.65 (d, 2H), 3.94 (s, 3H). |
| 178 | 392.3 | L3 | 5.19 | (DMSO-$d_6$) δ ppm: 8.42-8.45 (t, 1H), 7.757-7.763 (d, 1H), 7.40-7.41 (d, 1H), 7.24-7.26 (m, 1H), 7.16-7.18 (m, 1H), 6.50-6.51 (d, 1H), 6.28-6.35 (m, 1H), 6.08-6.13 (m, 1H), 5.58-5.61 (dd, 1H), 4.50-4.52 (d, 2H), 3.90 (s, 3H), 2.50-2.59 (m, 1H), 2.34-2.38 (m, 1H), 1.87-1.98 (dd, 4H), 1.50-1.60 (q, 2H), 1.37-1.46 (q, 2H). |
| 179 | 392.3 | L3 | 5.02 | (DMSO-$d_6$) δ ppm: 8.42-8.45 (t, 1H), 7.76-7.76 (d, 1H), 7.408-7.413 (d, 1H), 7.26-7.28 (m, 1H), 7.19-7.21 (m, 1H), 6.50-6.51 (d, 1H), 6.28-6.35 (m, 1H), 6.08-6.13 (m, 1H), 5.59-5.62 (dd, 1H), 4.51-4.52 (d, 2H), 3.90 (s, 3H), 2.77-2.79 (m, 1H), 2.49-2.54 (m, 1H), 1.75-1.85 (m, 8H). |
| 180 | 360.3 | L2 | 2.71 | (DMSO-$d_6$) δ ppm: 8.40-8.43 (t, 1H), 7.76 (d, 1H), 7.41 (d, 1H), 7.25-7.27 (dd, 1H), 7.18-7.20 (dd, 1H), 6.52-6.53 (d, 1H), 6.28-6.34 (q, 1H), 6.01-6.08 (dd, 1H), 5.58-5.62 (dd, 1H), 4.51-4.53 (d, 2H), 3.90 (s, 3H), 2.69-2.73 (m, 1H), 1.86-2.11 (m, 6H), 1.65-1.73 (m, 2H). |
| 181 | 393.3 | L2 | 2.61 | (DMSO-$d_6$) δ ppm: 7.42-7.45 (m, 3H), 7.06-7.06 (d, 1H), 6.86-6.89 (dd, 1H), 6.43-6.44 (d, 1H), 6.22-6.26 (dd, 1H), 6.05-6.12 (m, 1H), 5.56-5.59 (dd, 1H), 4.44-4.46 (d, 2H), 3.97 (s, 3H), 3.76-3.79 (d, 2H), 2.68-2.75 (m, 2H), 2.14-2.18 (m, 1H), 1.95-1.98 (d, 2H), 1.74-1.80 (m, 2H). |
| 182 | 361.3 | L2 | 2.50 | (DMSO-$d_6$) δ ppm: 8.31-8.34 (t, 1H), 7.74-7.50 (d, 1H), 7.18-7.20 (d, 1H), 7.116-7.122 (d, 1H), 6.27-6.34 (m, 1H), 6.07-6.12 (dd, 1H), 5.57-5.60 (dd, 1H), 4.45-4.46 (d, 2H), 3.90 (s, 3H), 3.32-3.34 (d, 4H), 2.00-2.10 (m, 4H). |
| 183 | 339.3 | L3 | 3.36 | (DMSO-$d_6$) δ ppm: 8.46-8.48 (t, 1H), 7.62-7.68 (m, 3H), 7.39-7.42 (dd, 1H), 7.26-7.32 (m, 3H), 6.25-6.32 (q, 1H), 6.10-6.15 (dd, 1H), 5.59-5.62 (dd, 1H), 4.41-4.43 (d, 2H), 3.56-3.60 (m, 1H), 2.72-2.76 (m, 2H), 2.56-2.60 (m, 2H), 2.23-2.30 (m, 4H), 1.79-1.81 (m, 1H). |
| 184 | 337.2 | L2 | 2.50 | (DMSO-$d_6$) δ ppm: 8.56-8.59 (t, 1H), 8.51 (s, 1H), 7.89 (d, 1H), 7.73-7.77 (m, 2H), 7.63-7.66 (dd, 1H), 7.43-7.45 (d, 1H), 7.29-7.33 (m, 2H), 6.30-6.37 (q, 1H), 6.11-6.16 (d, 1H), 5.62-5.65 (dd, 1H), 4.60-4.62 (d, 2H), 4.13 (s, 3H). |
| 185 | 373.3 | L2 | 2.75 | (DMSO-$d_6$) δ ppm: 9.17 (s, 1H), 8.57-8.60 (t, 1H), 8.21-8.50 (t, 1H), 7.95 (s, 1H), 7.77-7.80 (t, 2H), 7.71-7.73 (dd, 1H), 7.48-7.50 (d, 1H), 7.29-7.33 |

TABLE 2-continued

Analytical data for synthesized compounds of the disclosure

| Cpd. No. | $[M + H]^+$ (m/z) : | LC/MS or UPLC Method | RT (min.) | $^1H$ NMR (δ ppm) |
|---|---|---|---|---|
| | | | | (t, 2H), 6.28-6.35 (m, 1H), 6.09-6.14 (dd, 1H), 5.61-5.64 (dd, 1H), 4.62-4.63 (d, 2H). |
| 186 | 373.3 | L3 | 4.84 | (DMSO-$d_6$) δ ppm: 8.71 (s, 1H), 8.56-8.59 (t, 1H), 8.08-8.37 (t, 1H), 7.96-7.97 (s, 1H), 7.75-7.82 (m, 3H), 7.49-7.51 (d, 1H), 7.30-7.34 (t, 2H), 6.27-6.34 (m, 1H), 6.09-6.14 (dd, 1H), 5.61-5.64 (dd, 1H), 4.61-4.62 (d, 2H). |
| 187 | 337.3 | L2 | 2.68 | (DMSO-$d_6$) δ ppm: 8.52-8.55 (t, 1H), 8.20 (s, 1H), 7.86-7.87 (d, 1H), 7.75-7.78 (m, 2H), 7.65-7.68 (m, 1H), 7.44-7.46 (dd, 1H), 7.28-7.33 (t, 2H), 6.29-6.36 (m, 1H), 6.10-6.15 (dd, 1H), 5.61-5.64 (dd, 1H), 4.59-4.61 (d, 1H), 4.24 (s, 3H). |
| 188 | 338.2 | L2 | 2.67 | (DMSO-$d_6$) δ ppm: 8.54-8.57 (t, 1H), 8.16-8.17 (d, 1H), 7.74-7.82 (m, 3H), 7.52-7.54 (dd, 1H), 7.30-7.34 (m, 2H), 6.29-6.36 (m, 1H), 6.10-6.14 (dd, 1H), 5.61-5.64 (dd, 1H), 4.74-4.75 (d, 2H), 4.47 (s, 3H). |
| 189 | 338.2 | L2 | 2.48 | (DMSO-$d_6$) δ ppm: 8.52-8.55 (t, 1H), 7.87-7.92 (m, 2H), 7.77-7.81 (m, 2H), 7.59-7.61 (dd, 1H), 7.29-7.34 (m, 2H), 6.17-6.23 (dd, 1H), 6.03-6.07 (dd, 1H), 5.57-5.60 (dd, 1H), 4.25-4.27 (dd, 2H), 4.00 (s, 3H). |
| 190 | 374.3 | L2 | 2.88 | (DMSO-$d_6$) δ ppm: 8.54-8.82 (m, 2H), 8.22-8.23 (d, 1H), 7.88-7.90 (dd, 1H), 7.77-7.80 (m, 2H), 7.57-7.59 (d, 1H), 7.31-7.35 (t, 2H), 6.26-6.34 (m, 1H), 6.09-6.13 (dd, 1H), 5.61-5.64 (dd, 1H), 4.74-4.75 (d, 2H). |
| 191 | 323.2 | L2 | 2.45 | (DMSO-$d_6$) δ ppm: 8.64 (s, 1H), 8.59-8.57 (t, 1H), 8.01-8.00 (d, 1H), 7.88-7.86 (dd, 1H), 7.83-7.80 (m, 2H), 7.76-7.75 (d, 1H), 7.58-7.56 (dd, 1H), 7.34-7.29 (m, 2H), 6.30-6.23 (dd, 1H), 6.12-6.07 (dd, 1H), 5.64-5.61 (dd, 1H), 4.25-4.24 (d, 2H). |
| 192 | 404.2 | L2 | 2.99 | (DMSO-$d_6$) δ ppm: 7.97-7.99 (d, 2H), 7.75-7.86 (m, 4H), 7.61-7.64 (dd, 1H), 6.64-6.65 (s, 1H), 6.24-6.30 (m, 1H), 6.09-6.14 (m, 1H), 5.59-5.62 (dd, 1H), 5.56-5.59 (dd, 1H), 4.612 (s, 2H), 3.93 (s, 3H). |
| 193 | 337.2 | L2 | 2.67 | (DMSO-$d_6$) δ ppm: 8.54-8.57 (t, 1H), 8.19-8.22 (q, 2H), 7.82-7.88 (m, 2H), 7.73-7.75 (d, 1H), 7.30-7.35 (t, 2H), 6.99-7.00 (d, 1H), 6.33-6.40 (m, 1H), 6.11-6.16 (dd, 1H), 5.63-5.66 (dd, 1H), 4.81-4.83 (d, 2H), 3.97 (s, 3H). |
| 194 | 319.4 | L2 | 2.58 | (DMSO-$d_6$) δ ppm: 8.54-8.57 (t, 1H), 8.14-8.16 (m, 2H), 7.74-7.89 (m, 3H), 7.49-7.53 (m, 2H), 7.41-7.46 (m, 1H), 6.99-7.00 (d, 1H), 6.33-6.40 (m, 1H), 6.11-6.16 (dd, 1H), 5.63-5.66 (dd, 1H), 4.82-4.83 (d, 2H), 3.976 (s, 3H). |
| 195 | 377.3 | L2 | 3.01 | (DMSO-$d_6$) δ ppm: 8.07-8.04 (m, 2H), 7.94 (d, 1H), 7.84-7.80 (m, 1H), 7.59-7.57 (m, 2H), 7.17-7.12 (m, 3H), 6.26-6.21 (m, 1H), 6.10-6.03 (m, 1H), 5.60-5.57 (dd, 1H), 4.72 (dd, 2H), 4.09 (d, 2H), 1.56-1.32 (m, 1H), 0.74-0.71 (m, 2H), 0.46-0.44 (m, 2H). |
| 196 | 363.2 | L2 | 2.90 | (DMSO-$d_6$) δ ppm: 8.04-8.07 (q, 2H), 7.89-7.95 (q, 2H), 7.57-7.59 (t, 2H), 7.12-7.16 (t, 2H), 7.06-7.07 (d, 1H), 6.22-6.27 (dd, 1H), 6.05-6.12 (q, 1H), 5.59-5.62 (dd, 1H), 4.67-4.69 (d, 2H), 3.69-3.72 (m, 1H), 1.12-1.20 (m, 4H). |
| 197 | 363.2 | L2 | 2.54 | (DMSO-$d_6$) δ ppm: 8.65-8.68 (t, 1H), 8.15-8.18 (q, 2H), 8.05-8.03 (d, 1H), 7.88-7.90 (d, 1H), 7.50 (d, 1H), 7.30-7.34 (t, 2H), 6.58 (d, 1H), 6.25-6.31 (q, 1H), 6.09-6.13 (dd, 1H), 5.62-5.65 (dd, 1H), 4.34-4.35 (d, 2H), 3.77-3.83 (m, 1H), 0.95-0.98 (m, 2H), 0.88-0.77 (m, 2H). |
| 198 | 373.3 | L2 | 2.88 | (DMSO-$d_6$) δ ppm: 8.59-8.62 (t, 1H), 8.39-8.40 (d, 1H), 8.21-8.25 (m, 2H), 7.80-8.09 (m, 3H), 7.32-7.36 (m, 2H), 7.261-7.267 (d, 1H), 6.31-6.38 (dd, 1H), 6.12-6.16 (dd, 1H), 5.64-5.67 ( dd, 1H), 4.80-4.81 (d, 2H). |
| 199 | 375.2 | L2 | 2.70 | (DMSO-$d_6$) δ ppm: 8.58-8.86 (m, 2H), 8.19-8.23 (m, 3H), 7.97-7.99 (d, 1H), 7.35-7.39 (m, 2H), 6.24-6.31 (m, 1H), 6.08-6.13 (dd, 1H), 5.62-5.65 (dd, 1H), 4.73-4.74 (d, 2H). |

TABLE 2-continued

Analytical data for synthesized compounds of the disclosure

| Cpd. No. | [M + H]+ (m/z) : | LC/MS or UPLC Method | RT (min.) | $^1$H NMR (δ ppm) |
|---|---|---|---|---|
| 200 | 325.2 | L2 | 2.37 | (DMSO-$d_6$) δ ppm: 8.69 (t, 1H), 8.33-8.37 (m, 2H), 8.09-8.11 (d, 1H), 7.89-7.91 (d, 1H), 7.34-7.39 (t, 2H), 6.31-6.35 (q, 1H), 6.11-6.15 (dd, 1H), 5.63-5.66 (dd, 1H), 4.83-4.85 (d, 2H). |
| 201 | 337.2 | L2 | 2.40 | (DMSO-$d_6$) δ ppm: 8.79-8.80 (d, 1H), 8.50 (t, 1H), 8.18-8.19 (d, 1H), 7.83-7.87 (m, 3H), 7.33-7.37 (m, 2H), 6.80-6.81 (d, 1H), 6.38-6.44 (m, 1H), 6.07-6.11 (dd, 1H), 5.57-5.61 (dd, 1H), 4.78-4.79 (d, 2H), 3.95 (s, 3H). |
| 202 | 363.2 | L3 | 4.17 | (DMSO-$d_6$) δ ppm: 8.79-8.80 (d, 1H), 8.46-8.49 (t, 1H), 8.18-8.19 (d, 1H), 7.94-7.95 (d, 1H), 7.83-7.86 (m, 2H), 7.32-7.37 (m, 2H), 6.81-6.82 (d, 1H), 6.37-6.44 (m, 1H), 6.06-6.11 (dd, 1H), 5.57-5.60 (dd, 1H), 4.77-4.78 (d, 2H), 3.81-3.86 (m, 1H), 1.12-1.16 (m, 2H), 1.02-1.07 (m, 2H). |
| 203 | 373.3 | L4 | 1.86 | (DMSO-$d_6$) δ ppm: 8.88-8.89 (d, 1H), 8.53-8.56 (t, 1H), 8.42-8.43 (d, 1H), 8.25-8.26 (d, 1H), 7.77-8.07 (m, 3H), 7.33-7.38 (m, 2H), 7.15-7.16 (d, 1H), 6.35-6.42 (m, 1H), 6.05-6.10 (dd, 1H), 5.57-5.60 (dd, 1H), 4.76-4.77 (d, 2H). |
| 204 | 375.2 | L2 | 2.67 | (DMSO-$d_6$) δ ppm: 9.08-9.09 (d, 1H), 8.58-8.63 (m, 3H), 7.88-7.91 (m, 2H), 7.36-7.40 (t, 2H), 6.30-6.37 (q, 1H), 6.04-6.09 (dd, 1H), 5.57-5.60 (dd, 1H), 4.87-4.89 (d, 2H). |
| 205 | 337.2 | L2 | 2.21 | (DMSO-$d_6$) δ ppm: 8.58 (s, 1H), 8.50-8.53 (t, 1H), 8.17-8.21 (m, 2H), 8.12 (s, 2H), 7.88-7.89 (d, 1H), 7.30-7.34 (m, 2H), 6.96-6.97 (d, 1H), 6.29-6.34 (m, 1H), 6.10-6.15 (dd, 1H), 5.61-5.64 (dd, 1H), 4.71-4.72 (d, 2H), 3.97 (s, 3H). |
| 206 | 363.2 | L2 | 2.52 | (DMSO-$d_6$) δ ppm: 8.57 (s, 1H), 8.51-8.48 (t, 1H), 8.21-8.18 (m, 2H), 8.12 (s, 1H), 7.99-7.98 (d, 1H), 7.34-7.30 (m, 2H), 6.98-6.97 (d, 1H), 6.35-6.28 (q, 1H), 6.15-6.10 (dd, 1H), 5.65-5.61 (dd, 1H), 4.72-4.70 (d, 2H), 3.89-3.84 (m, 1H), 1.10-1.06 (m, 2H), 1.24-1.13 (m, 2H). |
| 207 | 373.2 | L2 | 2.60 | (DMSO-$d_6$) δ ppm: 8.65 (s, 1H), 8.57-8.54 (m, 1H), 8.47-8.46 (m, 1H), 8.24-8.21 (m, 2H), 8.18 (s, 1H), 8.10-7.80 (m, 1H), 7.35-7.31 (m, 2H), 7.29-7.28 (m, 1H), 6.34-6.27 (m, 1H), 6.15-6.10 (m, 1H), 5.65-5.62 (m, 1H), 4.71-4.69 (m, 2H). |
| 208 | 430.3 | L2 | 2.22 | (DMSO-$d_6$) δ ppm: 8.64 (s, 1H), 8.40-8.41 (d, 2H), 8.17-8.20 (m, 2H), 8.13 (s, 1H), 7.74-8.03 (m, 1H), 7.32-7.36 (t, 2H), 7.22-7.23 (d, 1H), 6.59-6.66 (m, 1H) 6.10-6.14 (d, 1H), 4.69 (s, 2H), 3.01-3.02 (d, 2H), 2.14 (s, 6H). |
| 209 | 423.2 | L2 | 2.89 | (DMSO-$d_6$) δ ppm: 8.71 (s, 1H), 8.58-8.61 (m, 1H), 8.48-8.49 (d, 1H), 8.39-8.41 (d, 2H), 8.29 (s, 1H), 7.81-8.11 (m, 3H), 7.30-7.31 (d, 1H), 6.28-6.32 (m, 1H), 6.10-6.15 (dd, 1H), 5.62-5.66 (dd, 1H), 4.72-4.74 (d, 2H). |
| 210 | 389.3 | L2 | 2.78 | ($CDCl_3$) δ ppm: 8.66 (s, 1H), 8.55-8.57 (t, 1H), 8.46-8.47 (d, 1H), 8.19-8.22 (m, 3H), 7.80-8.10 (m, 1H), 7.56-7.58 (dd, 2H), 7.28-7.29 (d, 1H), 6.27-6.34 (m, 1H), 6.10-6.15 (dd, 1H), 5.62-5.65 (dd, 1H), 4.70-4.71 (d, 2H). |
| 211 | 373.3 | L2 | 2.63 | (DMSO-$d_6$) δ ppm: 8.67 (s, 1H), 8.55-8.58 (t, 1H), 8.47-8.48 (d, 1H), 8.23 (s, 1H), 7.80-8.10 (m, 3H), 7.53-7.58 (q, 1H), 7.27-7.32 (m, 2H), 6.27-6.32 (m, 1H), 6.10-6.15 (dd, 1H), 5.62-5.65 (dd, 1H), 4.71-4.73 (d, 2H). |
| 212 | 375.3 | L2 | 2.62 | (DMSO-$d_6$) δ ppm: 8.65 (s, 1H), 8.46-8.47 (d, 1H), 8.21-8.26 (t, 2H), 7.80-8.10 (m, 3H), 7.52-7.58 (q, 1H), 7.26-7.31 (m, 2H), 4.61-4.62 (d, 2H), 2.15-2.26 (q, 2H), 1.00-1.04 (t, 3H). |
| 213 | 389.1 | L3 | 4.29 | (DMSO-$d_6$) δ ppm: 8.67 (s, 1H), 8.56-8.59 (t, 1H), 8.47-8.48 (d, 1H), 8.23-8.24 (m, 2H), 8.14-8.17 (dd, 1H), 7.98-8.10 (s, 1H), 7.81 (s, 1H), 7.50-7.56 (m, 2H), 7.32-7.33 (d, 1H), 6.28-6.34 (m, 1H), 6.10-6.15 (d, 1H), 5.62-5.65 (d, 1H), 4.71-4.73 (d, 1H). |
| 214 | 391.2 | L2 | 2.77 | (DMSO-$d_6$) δ ppm: 8.66 (s, 1H), 8.46-8.47 (s, 1H), 8.14-8.27 (dd, 3H), 7.95-8.10 (s, 1H), 7.50-7.56 (m, 2H), 7.31-7.32 (d, 1H), 4.61-4.62 (d, 2H), 2.15-2.20 (m, 2H), 1.00-1.04 (t, 3H). |

TABLE 2-continued

| Cpd. No. | [M + H]+ (m/z) : | LC/MS or UPLC Method | RT (min.) | $^1$H NMR (δ ppm) |
|---|---|---|---|---|
| Analytical data for synthesized compounds of the disclosure | | | | |
| 215 | 423.2 | L2 | 2.86 | (DMSO-$d_6$) δ ppm: 8.70 (s, 1H), 8.59 (t, 1H), 8.48-8.51 (dd, 3H), 8.32 (s, 1H), 7.82-8.11 (dd, 2H), 7.76 (t, 1H), 7.33-7.34 (d, 1H), 6.32-6.35 (m, 1H), 6.10-6.15 (d, 1H), 5.63-5.66 (d, 1H), 4.72-4.73 (d, 2H). |
| 216 | 425.3 | L2 | 2.85 | (DMSO-$d_6$) δ ppm: 8.69 (s, 1H), 8.47-8.51 (m, 3H), 8.25-8.30 (m, 2H), 7.96-8.10 (s, 2H), 7.74-7.83 (m, 1H), 7.32-7.33 (d, 1H), 4.62-4.63 (d, 2H), 2.15-2.21 (m, 2H), 1.01-1.05 (t, 3H). |
| 217 | 405.3 | L2 | 2.72 | (DMSO-$d_6$) δ ppm: 8.69 (s, 1H), 8.57-8.60 (m, 1H), 8.47-8.49 (m, 1H), 8.25-8.32 (m, 3H), 7.81-8.10 (m, 1H), 7.69-7.72 (m, 2H), 6.97-7.29 (m, 2H), 6.28-6.34 (m, 1H), 6.10-6.15 (dd, 1H), 5.62-5.65 (dd, 1H), 4.71-4.72 (d, 2H). |
| 218 | 373.3 | L2 | 2.68 | (DMSO-$d_6$) δ ppm: 8.79-8.83 (t, 1H), 8.42 (d, 1H), 8.24-8.29 (m, 3H), 7.78-8.08 (m, 1H), 7.73-7.74 (d, 1H), 7.33-7.39 (m, 3H), 6.35-6.38 (q, 1H), 6.14-6.19 (dd, 1H), 5.65-5.68 (dd, 1H), 4.57-4.58 (d, 2H) |
| 219 | 380.1 | L2 | 1.98 | (DMSO-$d_6$) δ ppm: 8.71 (s, 1H), 8.44-8.45 (m, 1H), 8.35-8.37 (m, 2H), 8.29 (s, 1H), 7.77-8.06 (m, 3H), 7.28 (d, 1H), 6.28-6.35 (m, 1H), 6.12-6.16 (m, 1H), 5.66-5.69 (m, 1H), 4.73 (s, 2H). |
| 220 | 380.3 | L2 | 2.66 | ($CDCl_3$) δ ppm: 8.63 (s, 1H), 8.61 (s, 1H), 8.52 (d, 1H), 8.45 (d, 1H), 8.31 (s, 1H), 7.72-7.93 (m, 3H), 7.31-7.32 (d, 1H), 6.28-6.35 (m, 1H), 6.12-6.16 (d, 1H), 5.66-5.69 (d, 1H), 4.74 (s, 2H). |
| 221 | 398.2 | L2 | 2.36 | (DMSO-$d_6$) δ ppm: 8.39-8.40 (d, 1H), 8.29 (t, 1H), 8.15 (s, 1H), 7.90 (t, 1H), 7.14 (s, 1H), 7.07-7.08 (d, 1H), 6.22-6.26 (dd, 1H), 6.06-6.10 (dd, 1H), 5.57-5.60 (d, 1H), 4.47-4.49 (d, 2H), 3.73 (t, 4H), 1.93-2.01 (m, 4H). |
| 222 | 398.2 | L2 | 2.81 | (DMSO-$d_6$) δ ppm: 8.61 (t, 1H), 8.36 (s, 1H), 8.31-8.32 (d, 1H), 7.88 (t, 1H), 7.58 (s, 1H), 7.03-7.04 (d, 1H), 6.27-6.34 (dd, 1H), 6.13-6.18 (dd, 1H), 5.64-5.67 (dd, 1H), 4.44-4.45 (dd, 2H), 3.15 (t, 4H), 2.12-2.19 (m, 4H). |
| 223 | 397.3 | L2 | 2.37 | (DMSO-$d_6$) δ ppm: 8.48-8.50 (m, 2H), 8.41-8.42 (d, 1H), 7.72-8.06 (m, 1H), 7.56 (s, 1H), 7.07-7.08 (d, 1H), 6.24-6.31 (dd, 1H), 6.08-6.13 (dd, 1H), 5.60-5.63 (dd, 1H), 4.60-4.61 (d, 2H), 2.90-2.96 (t, 1H), 1.93-2.12 (m, 8H). |
| 224 | 373.3 | L2 | 2.49 | (DMSO-$d_6$) δ ppm: 8.79 (s, 1H), 8.67-8.69 (t, 1H), 8.60 (s, 1H), 8.32 (s, 1H), 8.21-8.24 (m, 2H), 7.76-8.06 (m, 2H), 7.30-7.35 (t, 2H), 6.25-6.32 (m, 1H), 6.11-6.16 (dd, 1H), 5.62-5.65 (dd, 1H), 4.52-4.54 (d, 2H). |
| 225 | 373.3 | L2 | 2.65 | (DMSO-$d_6$) δ ppm: 8.74-8.76 (t, 1H), 8.36-8.37 (d, 1H), 8.09-8.10 (d, 1H), 7.77-7.92 (m, 3H), 7.58-7.59 (d, 1H), 7.37-7.41 (t, 2H), 7.14-7.15 (d, 1H), 6.34-6.41 (m, 1H), 6.13-6.18 (dd, 1H), 5.64-5.67 (dd, 1H), 4.57-4.58 (d, 2H) |
| 226 | 375.3 | L2 | 2.61 | (DMSO-$d_6$) δ ppm: 8.36-8.42 (m, 2H), 7.77-8.08 (m, 4H), 7.56-7.57 (m, 1H), 7.37-7.41 (t, 2H), 7.14-7.15 (d, 1H), 4.47-4.48 (d, 2H), 2.20-2.26 (m, 2H), 1.04-1.08 (t, 3H) |
| 227 | 373.3 | L2 | 2.69 | (DMSO-$d_6$) δ ppm: 8.94 (s, 1H), 8.68-8.71 (t, 1H), 8.47 (s, 1H), 7.74-8.06 (m, 4H), 7.476-7.479 (d, 1H), 7.38-7.42 (m, 2H), 6.35-6.42 (dd, 1H), 6.13-6.18 (dd, 1H), 5.64-5.67 (dd, 1H), 4.53-4.55 (d, 2H) |
| 228 | 397.3 | L2 | 2.90 | (DMSO-$d_6$) δ ppm: 8.68-8.71 (t, 1H), 8.32-8.33 (d, 1H), 7.74-8.04 (m, 2H), 7.19-7.20 (d, 1H), 7.062-7.069 (d, 1H), 6.32-6.39 (m, 1H), 6.12-6.17 (dd, 1H), 5.64-5.67 (dd, 1H), 4.48-4.49 (d, 2H), 2.08-2.86 (t, 1H), 1.90-2.13 (m, 6H), 1.65-1.72 (m, 2H) |
| 229 | 374.3 | L2 | 2.49 | (DMSO-$d_6$) δ ppm: 9.43 (s, 1H), 8.68 (s, 1H), 8.59-8.61 (t, 1H), 8.23-8.55 (m, 2H), 8.20-8.22 (m, 2H), 7.33-7.37 (m, 2H), 6.26-6.32 (m, 1H), 6.09-6.14 (dd, 1H), 5.60-5.64 (dd, 1H), 4.74-4.75 (d, 2H). |
| 230 | 374.3 | L2 | 2.63 | (DMSO-$d_6$) δ ppm: 8.90 (s, 1H), 8.70 (s, 1H), 8.57-8.60 (t, 1H), 8.13-8.41 (m, 4H), 7.33-7.38 |

TABLE 2-continued

| Cpd. No. | [M + H]+ (m/z) : | LC/MS or UPLC Method | RT (min.) | $^1$H NMR (δ ppm) |
|---|---|---|---|---|
| | | | | (m, 2H), 6.24-6.26 (m, 1H), 6.08-6.13 (dd, 1H), 5.61-5.64 (dd, 1H), 4.69-4.71 (d, 2H). |
| 231 | 377.3 | L2 | 2.51 | (DMSO-$d_6$) δ ppm: 8.51-8.56 (m, 2H), 8.16-8.20 (m, 2H), 8.08 (s, 1H), 7.29-7.33 (m, 2H), 6.72 (s, 1H), 6.30-6.36 (m, 1H), 6.10-6.15 (dd, 1H), 5.61-5.64 (dd, 1H), 4.70-4.71 (d, 2H), 4.17-4.20 (t, 2H), 2.82-2.85 (m, 2H), 2.01-2.04 (m, 2H), 1.82-1.85 (m, 2H). |
| 232 | 379.3 | L2 | 2.50 | (DMSO-$d_6$) δ ppm: 8.55 (s, 1H), 8.16-8.24 (m, 3H), 8.07 (s, 1H), 7.29-7.33 (m, 2H), 6.71 (s, 1H), 4.59-4.61 (d, 2H), 4.16-4.19 (t, 2H), 2.81-2.85 (t, 2H), 2.15-2.20 (m, 2H), 1.99-2.04 (m, 2H), 1.82-1.86 (m, 2H), 1.03-1.05 (m, 3H). |
| 233 | 353.3 | L3 | 3.36 | (DMSO-$d_6$) δ ppm: 7.80-7.84 (m, 3H), 7.30-7.35 (m, 2H), 6.81 (s, 1H), 6.64-6.65 (m, 1H), 6.26-6.28 (m, 1H), 6.07-6.12 (m, 1H), 4.43 (s, 1H), 3.91 (s, 3H). |
| 234 | 353.2 | L2 | 2.05 | / |
| 235 | 353.3 | L3 | 3.00 | (DMSO-$d_6$) δ ppm: 7.72-7.73 (m, 2H), 7.49-7.53 (m, 2H), 7.32-7.37 (m, 2H), 6.52-6.53 (d, 1H), 6.30-6.40 (m, 2H), 6.12-6.17 (m, 1H), 5.66-5.69 (m, 1H), 4.49-4.50 (d, 2H), 3.86 (s, 3H). |
| 236 | 355.3 | L2 | 2.32 | (DMSO-$d_6$) δ ppm: 8.24-8.27 (t, 1H), 7.71-7.72 (d, 2H), 7.49-7.52 (m, 2H), 7.32-7.37 (m, 2H), 6.50-6.51 (d, 1H), 6.32 (s, 1H), 4.38-4.39 (d, 2H), 3.85 (s, 3H), 2.19-2.25 (m, 2H), 1.03-1.06 (t, 3H). |
| 237 | 377.1 | L4 | 1.71 | (DMSO-$d_6$) δ ppm: 7.72-7.73 (d, 2H), 7.50-7.54 (d, 2H), 7.33-7.37 (m, 2H), 6.65 (s, 1H), 6.52-6.53 (d, 1H), 4.33 (s, 2H), 3.86 (s, 3H), 2.95 (s, 3H). |
| 238 | 392.2 | L13 | 2.15 | (DMSO-$d_6$) δ ppm: 7.72-7.73 (d, 1H), 7.69 (s, 1H), 7.50-7.54 (m, 2H), 7.33-7.41 (m, 3H), 6.84-6.88 (m, 1H), 6.69 (s, 1H), 6.49-6.50 (d, 1H), 4.16-4.18 (d, 2H), 3.85 (s, 3H), 2.49 (s, 3H). |
| 239 | 323.2 | L2 | 2.44 | (DMSO-$d_6$) δ ppm: 8.67 (s, 1H), 8.52-8.55 (m, 2H), 8.21-8.26 (m, 2H), 8.06 (s, 1H), 7.89-7.90 (d, 1H), 7.31-7.37 (m, 2H), 6.65-6.66 (m, 1H), 6.25-6.32 (m, 1H), 6.08-6.13 (dd, 1H), 5.61-5.64 (dd, 1H), 4.61-4.62 (d, 2H). |
| 240 | 337.2 | L2 | 2.55 | (DMSO-$d_6$) δ ppm: 8.63 (s, 1H), 8.52-8.54 (t, 1H), 8.41-8.42 (d, 1H), 8.20-8.24 (m, 2H), 8.01 (s, 1H), 7.31-7.36 (m, 2H), 6.44-6.45 (d, 1H), 6.26-6.33 (m, 1H), 6.09-6.13 (dd, 1H), 5.61-5.64 (dd, 1H), 4.63-4.64 (d, 2H), 2.31 (s, 3H). |
| 241 | 336.3 | L2 | 2.73 | (DMSO-$d_6$) δ ppm: 8.53-8.54 (t, 1H), 8.09 (s, 1H), 7.76-7.79 (m, 2H), 7.68-7.70 (dd, 1H), 7.60-7.61 (s, 1H), 7.44-7.46 (d, 1H), 7.28-7.32 (t, 2H), 6.26-6.33 (m, 2H), 6.09-6.14 (dd, 1H), 5.61-5.64 (dd, 1H), 4.37-4.39 (d, 2H), 2.28 (s, 3H). |
| 242 | 338.3 | L2 | 2.74 | (DMSO-$d_6$) δ ppm: 8.16-8.19 (t, 1H), 8.07-8.08 (s, 1H), 7.76-7.79 (t, 2H), 7.67-7.69 (dd, 1H), 7.59 (s, 1H), 7.44-7.46 (d, 1H), 7.27-7.32 (t, 2H), 6.31-6.32 (s, 1H), 4.27-4.28 (d, 2H), 2.49-2.50 (s, 3H), 2.12-2.27 (q, 2H), 1.00-1.01 (t, 3H). |
| 243 | 337.3 | L2 | 2.60 | ($CDCl_3$) δ ppm: 8.64 (s, 1H), 8.55-8.57 (t, 1H), 8.35 (s, 1H), 8.21-8.25 (m, 2H), 8.01 (s, 1H), 7.72 (s, 1H), 7.31-7.35 (m,3H), 6.27-6.33 (m, 1H), 6.08-6.13 (d, 1H), 5.61-5.64 (d, 1H), 4.62-4.64 (d, 2H), 2.14-2.29 (s, 3H), 1.60 (s, 1H). |
| 244 | 338.2 | L2 | 2.61 | (DMSO-$d_6$) δ ppm: 8.71 (s, 1H), 8.49-8.53 (t, 1H), 8.26 (s, 1H), 8.16-8.20 (m, 2H), 8.08 (s, 1H), 7.32-7.36 (m, 2H), 6.26-6.32 (m, 1H), 6.08-6.13 (dd, 1H), 5.60-5.64 (dd, 1H), 4.76-4.77 (d, 2H), 2.42 (s, 3H). |
| 245 | 340.3 | L2 | 2.63 | (DMSO-$d_6$) δ ppm: 8.69 (s, 1H), 8.16-8.24 (m, 4H), 8.07 (s, 1H), 7.32-7.36 (m, 2H), 4.65-4.66 (d, 2H), 2.49-2.51 (m, 3H), 2.12-2.18 (m, 2H), 0.98-1.02 (t, 3H). |
| 246 | 391.2 | L2 | 2.83 | (DMSO-$d_6$) δ ppm: 8.69-8.72 (m, 2H), 8.57-8.59 (m, 1H), 8.23-8.27 (m, 2H), 8.14 (s, 1H), 7.33-7.37 (m, 2H), 7.141-7.147 (d, 1H), 6.20-6.27 (m, 1H), 6.06-6.11 (m, 1H), 5.60-5.63 (m, 1H), 4.53-4.54 (d, 2H). |
| 247 | 363.3 | L3 | 4.49 | (DMSO-$d_6$) δ ppm: 8.61 (s, 1H), 8.50-8.52 (t, 1H), 8.40-8.41 (d, 1H), 8.20-8.24 (m, 2H), 8.00 (s, 1H), |

Analytical data for synthesized compounds of the disclosure

TABLE 2-continued

Analytical data for synthesized compounds of the disclosure

| Cpd. No. | $[M + H]^+$ (m/z) : | LC/MS or UPLC Method | RT (min.) | $^1$H NMR (δ ppm) |
|---|---|---|---|---|
| | | | | 7.31-7.35 (t, 2H), 6.38-6.39 (d, 1H), 6.26-6.33 (m, 1H), 6.09-6.14 (dd, 1H), 5.62-5.65 (dd, 1H), 4.62-4.63 (d, 2H), 1.99-2.03 (m, 1H), 0.92-0.97 (m, 2H), 0.77-0.79 (m, 2H). |
| 248 | 391.2 | L2 | 2.82 | (DMSO-$d_6$) δ ppm: 9.17 (s, 1H), 8.72 (s, 1H), 8.52-8.55 (t, 1H), 8.33 (s, 1H), 8.24-8.27 (m, 2H), 8.16 (s, 1H), 7.33-7.37 (t, 2H), 6.21-6.25 (m, 1H), 6.06-6.11 (m, 1H), 5.59-5.63 (m, 1H), 4.58-4.59 (d, 2H). |
| 249 | 339.2 | L2 | 2.52 | (DMSO-$d_6$) δ ppm: 8.85 (s, 1H), 8.55-8.58 (t, 1H), 8.35 (s, 1H), 8.21-8.25 (m, 2H), 7.34-7.38 (t, 2H), 6.18-6.25 (m, 1H), 6.05-6.10 (m, 1H), 5.59-5.62 (m, 1H), 4.64-4.65 (d, 2H), 2.64 (s, 3H). |
| 250 | 339.2 | L2 | 2.32 | (DMSO-$d_6$) δ ppm: 8.88 (s, 1H), 8.56-8.59 (t, 1H), 8.29 (s, 1H), 8.20-8.23 (m, 2H), 7.34-7.38 (m, 2H), 6.10-6.17 (m, 1H), 6.00-6.05 (m, 1H), 5.57-5.60 (m, 1H), 4.20-4.22 (d, 2H), 2.51 (s, 3H). |
| 251 | 341.4 | L4 | 1.83 | (DMSO-$d_6$) δ ppm: 8.83 (s, 1H), 8.33 (s, 1H), 8.21-8.25 (m, 3H), 7.33-7.38 (t, 2H), 4.53-4.54 (d, 2H), 2.64 (s, 3H), 2.06-2.12 (m, 2H), 0.94-0.98 (t, 3H). |
| 252 | 341.2 | L2 | 2.31 | (DMSO-$d_6$) δ ppm: 8.86 (s, 1H), 8.28 (s, 1H), 8.20-8.25 (m, 3H), 7.34-7.38 (t, 2H), 4.11-4.12 (d, 2H), 2.51 (s, 3H), 1.99-2.07 (m, 2H), 0.90-0.94 (t, 3H). |
| 253 | 338.2 | L3 | 4.37 | (DMSO-$d_6$) δ ppm: 8.74 (s, 1H), 8.50-8.58 (m, 3H), 7.92-7.93 (d, 1H), 7.34-7.38 (m, 2H), 7.22 (d, 1H), 6.32-6.35 (q, 1H), 6.12-6.16 (dd, 1H), 5.63-5.66 (dd, 1H), 4.84-4.85 (d, 2H) , 4.02 (s, 3H). |
| 254 | 374.2 | L2 | 2.85 | (DMSO-$d_6$) δ ppm: 8.83 (s, 1H), 8.60-8.63 (t, 1H), 8.50-8.56 (m, 3H), 7.85-8.14 (m, 1H), 7.45-7.46 (d, 1H), 7.35-7.40 (t, 2H), 6.29-6.36 (m, 1H), 6.11-6.16 (dd, 1H), 5.64-5.67 (dd, 1H), 4.83-4.84 (d, 2H). |
| 255 | 374.2 | L2 | 2.72 | (DMSO-$d_6$) δ ppm: 8.83-8.86 (t, 1H), 8.40-8.41 (d, 1H), 8.32-8.35 (m, 2H), 7.83-8.12 (m, 2H), 7.41-7.45 (m, 2H), 7.273-7.279 (d, 1H), 6.35-6.42 (dd, 1H), 6.14-6.19 (dd, 1H), 5.67-5.70 (dd, 1H), 4.56-4.57 (d, 2H) |
| 256 | 362.3 | L2 | 2.92 | (DMSO-$d_6$) δ ppm: 8.31 (s, 1H), 7.81-7.85 (m, 2H), 7.70-7.74 (m, 3H), 7.51-7.53 (dd, 1H), 7.26-7.31 (m, 2H), 6.74-6.75 (d, 1H), 6.18-6.24 (m, 1H), 5.99-6.03 (dd, 1H), 5.53-5.56 (dd, 1H), 4.00 (s, 3H), 1.02-1.05 (t, 2H), 0.82-0.85 (t, 2H). |
| 257 | 344.2 | L3 | 4.47 | (DMSO-$d_6$) δ ppm: 8.30-8.40 (dd, 1H), 7.65-7.75 (m, 4H), 7.43-7.52 (m, 3H), 7.35-7.37 (m, 1H), 7.12-7.14 (dd, 1H), 6.57-6.58 (d, 0.57H), 6.36-6.37 (d, 0.43H), 6.09-6.18 (m, 2H), 5.58-5.63 (m, 1H), 3.90 (s, 1.7H), 3.66 (s, 1.3H), 3.08-3.32 (m, 1H), 2.39-2.43 (m, 0.43H), 1.66-1.75 (m, 0.57H), 1.17-1.27 (m, 2H) (43:57 mixture of diastereoisomers). |
| 258 | 376.3 | L2 | 2.80 | (DMSO-$d_6$) δ ppm: 7.70-7.79 (m, 3H), 7.59-7.64 (m, 2H), 7.49-7.56 (dd, 1H), 7.26-7.30 (t, 2H), 6.53-6.62 (m, 2H), 6.12-6.17 (tt, 1H), 5.63-5.69 (m, 1H), 3.54-4.00 (m, 7H), 3.31-3.39 (m, 1H), 2.03-2.30 (m, 2H). |
| 259 | 378.2 | L5 | 4.29 | (DMSO-$d_6$) δ ppm: 7.78-7.79 (dd, 1H), 7.70-7.74 (m, 2H), 7.59-7.64 (m, 2H), 7.47-7.55 (dd, 1H), 7.26-7.30 (m, 2H), 6.51-6.55 (dd, 1H), 3.58-3.91 (m, 6H), 3.38-3.43 (m, 1H), 3.23-3.27 (m, 1H), 2.07-2.28 (m, 4H), 0.96-1.01 (m, 3H). |
| 260 | 436.3 | L3 | 4.90 | (DMSO-$d_6$) δ ppm: 8.37-8.38 (d, 1H), 7.65-8.03 (m, 6H), 7.27-7.32 (t, 2H), 6.92-6.93 (d, 1H), 3.84-3.90 (m, 1H), 3.60-3.65 (m, 1H), 3.45-3.50 (m, 1H), 3.17-3.27 (m, 2H), 2.92 (s, 3H), 2.09-2.24 (m, 2H). |
| 261 | 412.3 | L2 | 3.00 | (DMSO-$d_6$) δ ppm: 8.36-8.37 (m, 1H), 7.27-8.02 (m, 8H), 6.89-6.91 (dd, 1H), 6.57-6.60 (m, 1H), 6.12-6.17 (m, 1H), 5.63-5.69 (m, 1H), 3.76-4.00 (m, 3H), 3.39-3.68 (m, 2H), 2.04-2.32 (m, 2H). |

TABLE 2-continued

Analytical data for synthesized compounds of the disclosure

| Cpd. No. | $[M + H]^+$ (m/z) : | LC/MS or UPLC Method | RT (min.) | $^1H$ NMR (δ ppm) |
|---|---|---|---|---|
| 261-En1 | 412.3 | S1 | 1.65 | (DMSO-$d_6$) δ ppm: 8.36-8.37 (m, 1H), 7.27-8.02 (m, 8H), 6.89-6.91 (m, 1H), 6.54-6.60 (m, 1H), 6.11-6.17 (m, 1H), 5.63-5.69 (m, 1H), 3.27-4.00 (m, 5H), 2.01-2.28 (m, 2H). |
| 261-En2 | 412.3 | S1 | 2.13 | (DMSO-$d_6$) δ ppm: 8.36-8.37 (m, 1H), 7.55-8.02 (m, 8H), 6.89-6.91 (m, 1H), 6.54-6.60 (m, 1H), 6.12-6.17 (m, 1H), 5.66-5.69 (m, 1H), 3.54-3.87 (m, 5H), 2.14-2.25 (m, 2H). |
| 262 | 413.3 | L2 | 2.76 | (DMSO-$d_6$) δ ppm: 8.76-8.82 (d, 1H), 8.45-8.46 (d, 1H), 8.19-8.23 (m, 2H), 7.78-8.07 (m, 2H), 7.30-7.34 (t, 2H), 7.12-7.15 (m, 1H), 6.55-6.63 (m, 1H), 6.13-6.19 (m, 1H), 5.64-5.71 (m, 1H), 3.59-4.04 (m, 5H), 2.15-2.49 (m, 2H). |
| 262-En1 | 413.3 | S2 | 2.92 | (DMSO-$d_6$) δ ppm: 8.76-8.82 (d, 1H), 8.45-8.46 (d, 1H), 8.19-8.23 (m, 2H), 7.78-8.08 (m, 2H), 7.31-7.35 (m, 2H), 7.13-7.15 (m, 1H), 6.55-6.62 (m, 1H), 6.13-6.18 (m, 1H), 5.64-5.71 (m, 1H), 3.40-4.05 (m, 5H), 2.15-2.49 (m, 2H). |
| 262-En2 | 413.3 | S2 | 4.86 | (DMSO-$d_6$) δ ppm: 8.76-8.82 (d, 1H), 8.45-8.46 (d, 1H), 8.19-8.23 (m, 2H), 7.78-8.08 (m, 2H), 7.31-7.35 (m, 2H), 7.13-7.15 (m, 1H), 6.55-6.62 (m, 1H), 6.13-6.18 (m, 1H), 5.64-5.71 (m, 1H), 3.40-4.05 (m, 5H), 2.15-2.49 (m, 2H). |
| 263 | 452.3 | L2 | 2.88 | (DMSO-$d_6$) δ ppm: 8.83 (s, 1H), 8.46-8.47 (d, 1H), 8.20-8.24 (m, 2H), 7.76-8.06 (m, 2H), 7.31-7.35 (m, 2H), 7.13-7.14 (d, 1H), 7.06 (br.s, 1H), 4.03-4.07 (m, 1H), 3.61-3.65 (m, 1H), 3.43-3.48 (m, 1H), 3.22-3.29 (m, 2H), 2.58 (s, 3H), 2.29-2.34 (m, 1H), 2.18-2.23 (m, 1H). |
| 264 | 413.3 | L2 | 3.05 | (DMSO-$d_6$) δ ppm: 8.36-8.37 (d, 1H), 8.29-8.31 (m, 2H), 7.77-7.98 (m, 3H), 7.32-7.37 (m, 2H), 7.22-7.23 (d, 1H), 6.61-6.70 (m, 1H), 6.14-6.20 (m, 1H), 5.66-5.72 (m, 1H), 3.41-4.18 (m, 5H), 2.32-2.45 (m, 1H), 2.10-2.20 (m, 1H) |
| 265 | 413.3 | L2 | 3.08 | (DMSO-$d_6$) δ ppm: 8.33-8.34 (dd, 1H), 7.89-8.06 (m, 4H), 7.68-7.71 (dd, 1H), 7.34-7.38 (m, 2H), 7.07-7.11 (dd, 1H), 6.60-6.66 (m, 1H), 6.12-6.17 (m, 1H), 5.63-5.69 (m, 1H), 3.42-4.06 (m, 5H), 2.17-2.39 (m, 2H) |
| 266 | 362.4 | L1 | 2.30 | (DMSO-$d_6$) δ ppm: 8.61 (s, 1H), 8.50-8.53 (t, 1H), 8.19-8.22 (q, 2H), 8.14 (s, 1H), 8.05-8.06 (d, 1H), 7.31-7.35 (t, 2H), 7.110-7.116 (d, 1H), 6.28-6.35 (dd, 1H), 6.10-6.15 (dd, 1H), 5.62-5.65 (m, 3H), 4.69-4.71 (d, 2H). |
| 267 | 376.3 | L1 | 2.16 | (DMSO-$d_6$) δ ppm: 8.59 (s, 1H), 8.41-8.43 (t, 1H), 8.19-8.23 (m, 2H), 8.15 (s, 1H), 8.001-8.007 (d, 1H), 7.30-7.35 (t, 2H), 7.05-7.06 (d, 1H), 6.29-6.36 (dd, 1H), 6.10-6.15 (dd, 1H), 5.60-5.64 (dd, 1H), 4.72-4.74 (d, 2H), 4.51-4.54 (t, 2H), 3.14-3.17 (t, 2H). |
| 268 | 432.3 | L1 | 2.35 | (DMSO-$d_6$) δ ppm: 8.55-8.57 (m, 2H), 8.40-8.43 (t, 1H), 8.17-8.21 (m, 2H), 8.13 (s, 1H), 8.060-8.066 (s, 1H), 7.70-7.73 (m, 1H), 7.30-7.34 (t, 3H), 7.06-7.066 (s, 1H), 6.23-6.30 (dd, 1H), 6.07-6.12 (dd, 1H), 5.64-5.67 (dd, 1H), 5.57 (s, 1H), 4.65-4.66 (d, 2H). |
| 269 | 457.3 | L2 | 2.09 | (DMSO-$d_6$) δ ppm: 13.1 (br. s, 1H), 8.57 (s, 1H), 8.39-8.42 (t, 1H), 8.17-8.21 (q, 2H), 8.13 (s, 1H), 8.07-8.08 (d, 1H), 7.91 (s, 1H), 7.86-7.87 (dd, 1H), 7.53-7.55 (d, 1H), 7.45-7.49 (t, 1H), 7.29-7.34 (t, 2H), 7.052-7.058 (d, 1H), 6.21-6.26 (dd, 1H), 6.07-6.12 (dd, 1H), 5.58-5.61 (dd, 1H), 5.50 (s, 2H), 4.66-4.68 (d, 2H), 3.84 (s, 3H), 1.38 (s, 9H). |
| 270 | 438.4 | L2 | 2.59 | (DMSO-$d_6$) δ ppm: 8.58 (s, 1H), 8.39-8.42 (t, 1H), 8.17-8.21 (m, 2H), 8.13 (s, 1H), 8.07-8.08 (d, 1H), 7.78-7.80 (dd, 2H), 7.63-7.65 (dd, 1H), 7.56-7.60 (dd, 1H), 7.29-7.34 (t, 2H), 7.06-7.07 (d, 1H), 6.23-6.29 (dd, 1H), 6.08-6.12 (dd, 1H), 5.59-5.62 (dd, 1H), 5.54 (s, 2H), 4.66-4.68 (d, 2H). |

TABLE 2-continued

Analytical data for synthesized compounds of the disclosure

| Cpd. No. | [M + H]+ (m/z) : | LC/MS or UPLC Method | RT (min.) | $^1$H NMR (δ ppm) |
|---|---|---|---|---|
| 271 | 457.3 | L2 | 2.29 | (DMSO-$d_6$) δ ppm: 8.57 (s, 1H), 8.38-8.41 (t, 1H), 8.18-8.21 (m, 2H), 8.13 (s, 1H), 8.05-8.06 (d, 1H), 7.88-7.90 (dd, 2H), 7.29-7.36 (m, 4H), 7.05-7.06 (d, 1H), 6.21-6.27 (dd, 1H), 6.07-6.12 (dd, 1H), 5.58-5.61 (dd, 1H), 5.54 (s, 2H), 4.67-4.69 (dd, 2H). |
| 272 | 432.4 | L2 | 2.25 | (DMSO-$d_6$) δ ppm: 8.54-8.57 (m, 2H), 8.41-8.47 (m, 2H), 8.17-8.21 (m, 2H), 8.09-8.12 (m, 3H), 7.67-7.71 (m, 1H), 7.30-7.34 (m, 2H), 7.06-7.07 (m, 1H), 6.24-6.30 (m, 1H), 6.08-6.13 (dd, 1H), 5.57-5.62 (m, 3H), 4.66-4.68 (m, 2H). |
| 273 | 380.4 | L2 | 1.97 | (DMSO-$d_6$) δ ppm: 8.58 (s, 1H), 8.40-8.43 (t, 1H), 8.18-8.22 (m, 2H), 8.13 (s, 1H), 7.903-7.909 (s, 1H), 7.64 (s, 1H), 7.38 (s, 1H), 7.30-7.34 (t, 2H), 7.01-7.02 (d, 1H), 6.25-6.32 (m, 1H), 6.06-6.11 (dd, 1H), 5.57-5.60 (dd, 1H), 4.93 (s, 2H), 4.69-4.71 (d, 2H). |
| 274 | 456.3 | L2 | 2.22 | (DMSO-$d_6$) δ ppm: 8.57 (s, 1H), 8.38-8.41 (t, 1H), 8.17-8.21 (m, 2H), 8.13 (s, 1H), 8.05-8.06 (d, 1H), 7.98 (s, 1H), 7.88 (s, 1H), 7.79-7.82 (dd, 1H), 7.46-7.52 (m, 3H), 7.31-7.07 (m, 2H), 7.05-7.06 (d, 1H), 6.21-6.28 (dd, 1H), 6.07-6.12 (dd, 1H), 5.59-5.62 (dd, 1H), 5.51 (s, 2H), 4.67-4.68 (d, 2H). |
| 275 | 444.4 | L2 | 2.12 | (DMSO-$d_6$) δ ppm: 8.58 (s, 1H), 8.43-8.44 (t, 1H), 8.18-8.22 (m, 2H), 8.14 (s, 1H), 8.04-8.05 (d, 1H), 7.64-7.65 (d, 1H), 7.30-7.34 (t, 2H), 7.081-7.086 (d, 1H), 6.24-6.28 (dd, 1H), 6.06-6.13 (m, 3H), 5.60-5.63 (dd, 1H), 5.34 (s, 2H), 4.68-4.69 (d, 2H), 3.37 (s, 3H). |
| 276 | 364.4 | L2 | 2.08 | (DMSO-$d_6$) ppm: 8.65 (s, 1H), 8.57-8.60 (t, 1H), 8.17-8.20 (m, 2H), 7.80-7.82 (m, 2H), 7.28-7.33 (m, 2H), 6.50-6.51 (d, 1H), 6.35-6.37 (dd, 1H), 6.20-6.26 (m, 1H) 6.06-6.11 (dd, 1H), 5.59-5.62 (dd, 1H) 4.37-4.38 (d, 2H), 3.48 (s, 3H). |
| 277 | 349.4 | L2 | 1.86 | (DMSO-$d_6$) δ ppm 8.62 (s, 1H), 8.57-8.59 (t, 1H), 8.17-8.21 (m, 2H), 8.00-8.01 (d, 1H), 7.78 (s, 1H), 7.28-7.32 (m, 2H), 6.60-6.61 (dd, 1H), 6.48 (s, 1H), 6.22-6.29 (dd, 1H), 6.07-6.12 (m, 3H), 5.60-5.63 (dd, 1 H), 4.35-4.36 (d, 2H). |
| 278 | 359.4 | L2 | 2.49 | (DMSO-$d_6$) δ ppm: 8.97-8.98 (d, 1H), 8.70 (s, 1H), 8.42-8.44 (t, 1H), 8.39-8.40 (m, 1H), 8.22-8.26 (m, 2H), 8.10 (s, 1H), 7.96-7.98 (m, 1H), 7.31-7.36 (m, 2H), 6.15-6.22 (m, 1H), 6.01-6.06 (dd, 1H), 5.55-5.59 (dd, 1H), 4.57-4.59 (d, 2H). |
| 279 | 394.4 | L2 | 1.99 | (DMSO-$d_6$) δ ppm: 8.59 (s, 1H), 8.44-8.47 (t, 1H), 8.18-8.22 (m, 2H), 8.12 (s, 1H), 7.86-7.87 (d, 1H), 7.44 (s, 1H), 7.30-7.34 (t, 2H), 6.97-6.98 (d, 1H), 6.94 (s, 1H), 6.32-6.39 (dd, 1H), 6.10-6.14 (dd, 1H), 5.60-5.63 (dd, 1H), 4.70-4.71 (d, 2H), 4.42-4.45 (t, 2H), 2.68-2.72 (t, 2H). |
| 280 | 364.4 | L2 | 2.63 | (DMSO-$d_6$) δ ppm: 8.65 (s, 1H), 8.17-8.20 (dd, 2H), 7.99 (s, 1H), 7.91-7.87 (q, 1H), 7.43-7.41 (d, 1H), 7.31-7.35 (t, 2H), 6.93-6.91 (d, 1H), 6.26-6.19 (m, 1H), 6.05-6.10 (m, 1H), 5.60-5.63 (dd, 1H), 4.66 (s, 2H), 3.90 (s, 3H). |
| 281 | 439.3 | L2 | 2.36 | (DMSO-$d_6$) δ ppm: 9.010-9.017 (d, 1H), 8.57 (s, 1H), 8.401-8.408 (t, 1H), 8.29-8.31 (dd, 1H), 8.18-8.21 (q, 2H), 8.13 (s, 1H), 8.09-8.10 (d, 1H), 7.30-7.34 (m, 3H), 7.091-7.097 (d, 1H), 6.22-6.29 (dd, 1H), 6.07-6.12 (dd, 1H), 5.71 (s, 2H), 5.59-5.62 (dd, 1H), 4.64-4.66 (dd, 1H). |
| 282 | 350.0 | U3 | 1.77 | (DMSO-$d_6$) ppm: 12.0 (br. s, 1H), 8.64 (s, 1H), 8.56-8.59 (t, 1H), 8.17-8.21 (q, 2H), 7.80 (s, 1H), 7.47-7.49 (d, 1H), 7.28-7.33 (t, 2H), 6.40-6.41 (d, 1H), 6.22-6.40 (m, 2H), 6.06-6.11 (dd, 1H), 5.59-5.62 (dd, 1H), 4.39 (s, 2H). |
| 283 | 377.4 | L1 | 2.05 | (DMSO-$d_6$) δ ppm: 9.18-9.19 (d, 1H), 8.69 (s, 1H), 8.47-8.49 (t, 1H), 8.38-8.40 (dd, 1H), 8.20-8.27 (m, 3H), 8.04 (s, 1H), 7.95-7.97 (dd, 1H), 7.69 (s, 1H), 7.30-7.35 (m, 2H), 6.19-6.23 (m, 1H), 6.03-6.08 (dd, 1H), 5.56-5.59 (dd, 1H), 4.56-4.57 (d, 2H). |

TABLE 2-continued

Analytical data for synthesized compounds of the disclosure

| Cpd. No. | [M + H]+ (m/z) : | LC/MS or UPLC Method | RT (min.) | $^1$H NMR (δ ppm) |
|---|---|---|---|---|
| 284 | 359.4 | U4 | 2.45 | (DMSO-$d_6$) δ ppm: 9.17-9.18 (d, 1H), 8.71 (s, 1H), 8.52-8.71 (dd, 1H), 8.41-8.44 (t, 1H), 8.20-8.24 (m, 2H), 8.05-8.09 (m, 2H), 7.31-7.36 (m, 2H), 6.13-6.20 (m, 1H), 6.00-6.05 (dd, 1H), 5.51-5.58 (dd, 1H), 4.55-4.56 (d, 2H). |
| 285 | 352.4 | L2 | 2.50 | (DMSO-$d_6$) δ ppm: 8.67 (s, 1H), 8.47-8.50 (t, 1H), 8.15-8.23 (m, 3H), 8.02 (s, 1H), 7.78-7.80 (dd, 1H), 7.29-7.34 (m, 3H), 6.16-6.23 (dd, 1H), 6.02-6.07 (dd, 1H), 5.56-5.59 (dd, 1H), 4.56-4.58 (d, 2H). |
| 286 | 352.4 | L2 | 2.48 | (DMSO-$d_6$) δ ppm: 8.75-8.79 (m, 1H), 8.68 (s, 1H), 8.44-8.47 (t, 1H), 8.21-8.25 (m, 2H), 8.04 (s, 1H), 7.85-7.88 (dd, 1H), 7.43-7.47 (m, 1H), 7.30-7.35 (m, 2H), 6.19-6.25 (m, 1H), 6.03-6.08 (dd, 1H), 5.57-5.60 (dd, 1H), 4.56-4.58 (d, 2H). |
| 287 | 402.4 | L2 | 2.79 | (DMSO-$d_6$) δ ppm: 8.69 (s, 1H), 8.44-8.47 (t, 1H), 8.28-8.32 (m, 1H), 8.17-8.24 (m, 3H), 8.07 (s, 1H), 8.00-8.02 (m, 1H), 7.31-7.35 (m, 2H), 6.14-6.21 (m, 1H), 6.01-6.06 (dd, 1H), 5.56-5.59 (dd, 1H), 4.54-4.56 (d, 2H). |
| 288 | 402.2 | L3 | 5.81 | (DMSO-$d_6$) δ ppm: 9.12 (s, 1H), 8.72 (s, 1H), 8.40-8.43 (m, 2H), 8.20-8.24 (q, 2H), 8.07-8.09 (d, 2H), 7.31-7.35 (t, 2H), 6.13-6.20 (m, 1H), 6.00-6.05 (dd, 1H), 5.54-5.57 (dd, 1H), 4.55-4.57 (d, 1H). |
| 289 | 364.4 | L2 | 2.09 | (DMSO-$d_6$) δ ppm: 8.65 (s, 1H), 8.53-8.55 (d, 1H), 8.17-8.20 (q, 2H), 7.96 (s, 1H), 7.31-7.36 (m, 3H), 7.07-7.09 (dd, 1H), 6.21-6.28 (m, 1H), 6.07-6.11 (dd, 1H), 5.62-6.65 (dd, 1H), 4.53 (s, 2H), 3.92 (s, 3H). |
| 290 | 364.3 | L2 | 1.99 | (DMSO-$d_6$) δ ppm: 8.54 (s, 1H), 8.41-8.44 (t, 1H), 8.13-8.16 (m, 2H), 7.84-7.86 (dd 1H), 7.74 (s, 1H), 7.56-7.58 (dd, 1H), 7.27-7.32 (t, 2H), 6.35-6.39 (t, 1H), 6.17-6.21 (m, 1H), 6.07-6.08 (dd, 1H), 5.56-5.59 (dd, 1H), 4.30-4.31 (d, 2H), 3.52 (s, 3H). |
| 291 | 373.4 | L2 | 2.05 | (DMSO-$d_6$) δ ppm: 8.67-8.68 (t, 1H), 8.59-8.62 (m, 3H), 8.36 (s, 1H), 8.18-8.24 (m, 2H), 7.69-7.72 (d, 1H), 7.32-7.37 (t, 3H), 6.97-7.01 (t, 1H), 6.30-6.37 (m, 1H), 6.11-6.16 (dd, 1H), 5.62-5.65 (d, 1H), 4.82-4.83 (m, 2H). |
| 292 | 429.3 | L5 | 3.65 | (DMSO-$d_6$) δ ppm: 8.59 (s, 1H), 8.40-8.43 (t, 1H), 8.17-8.21 (m, 2H), 8.12 (s, 1H), 7.89-8.03 (m, 5H), 7.30-7.35 (t, 2H), 7.053-7.059 (d, 1H), 6.93-6.95 (d, 1H), 6.25-6.32 (m, 1H), 6.10-6.14 (dd, 1H), 5.61-5.64 (dd, 1H), 5.36 (s, 2H), 4.68-4.69 (d, 2H). |
| 293 | 419.4 | L2 | 2.45 | (DMSO-$d_6$) δ ppm: 8.61 (s, 1H), 8.49-8.52 (t, 1H), 8.17-8.20 (m, 2H), 7.94 (s, 1H), 7.72-7.76 (m, 1H), 7.29-7.33 (m, 2H), 7.09-7.11 (d, 1H), 6.92-6.94 (d, 1H), 6.22-6.29 (m, 1H), 6.06-6.11 (dd, 1H), 5.58-5.62 (dd, 1H), 4.56-4.57(d, 2H), 3.69-3.71 (m, 4H), 3.48-3.50 (m, 4H). |
| 294 | 324.3 | L2 | 2.35 | (DMSO-$d_6$) δ ppm: 8.72 (s, 1H), 8.58-8.61 (t, 1H), 8.430-8.432 (d, 1H), 8.36 (s, 1H), 8.18-8.21 (m, 2H), 7.604-7.606 (d, 1H), 7.32-7.37 (m, 2H), 6.28-6.35 (m, 1H), 6.10-6.15 (dd, 1H), 5.61-5.65 (dd, 1H), 4.86-4.87 (d, 2H). |
| 295 | 429.4 | L2 | 1.94 | (DMSO-$d_6$) δ ppm: 8.59 (s, 1H), 8.42-8.45 (t, 1H), 8.18-8.22 (m, 2H), 8.14 (s, 1H), 8.02-8.03 (d, 1H), 7.84-7.85 (dd, 1H), 7.30-7.34 (dd, 2H), 7.072-7.078 (d, 1H), 6.34-6.36 (dd, 1H), 6.23-6.30 (dd, 1H), 6.20 (s, 1H), 6.121-6.127 (d, 1H), 6.08 (s, 2H), 5.60-5.63 (dd, 1H), 5.35 (s, 2H), 4.69-4.71 (d, 2H). |
| 296 | 377.4 | L2 | 2.04 | (DMSO-$d_6$) δ ppm: 8.87-8.88 (dd, 1H), 8.68 (s, 1H), 8.46-8.49 (t, 1H), 8.33 (s, 1H), 8.21-8.25 (m, 2H), 8.18 (s, 1H), 8.08 (s, 1H), 7.84-7.86 (dd, 2H), 7.31-7.35 (t, 2H), 6.19-6.26 (dd, 1H), 6.03-6.05 (dd, 1H), 5.57-5.60 (dd, 1H), 4.58-4.59 (dd, 2H). |

TABLE 2-continued

Analytical data for synthesized compounds of the disclosure

| Cpd. No. | $[M + H]^+$ (m/z) : | LC/MS or UPLC Method | RT (min.) | $^1$H NMR (δ ppm) |
|---|---|---|---|---|
| 297 | 352.4 | L2 | 2.49 | (DMSO-$d_6$) δ ppm: 8.74 (s, 1H), 8.66 (s, 1H), 8.43-8.46 (t, 1H), 8.19-8.23 (q, 2H), 8.0 (s, 1H), 7.93-7.95 (dd, 2H), 7.30-7.34 (t, 2H), 6.18-6.25 (dd, 1H), 6.03-6.08 (dd, 1H), 5.56-5.60 (dd, 1H), 4.54-4.55 (dd, 2H). |
| 298 | 391.2 | U8 | 2.11 | (DMSO-$d_6$) δ ppm: 8.68 (s, 1H) 8.42 (br. s, 1H), 8.17-8.21 (q, 2H), 8.07 (s, 1H), 7.33-7.38 (t, 2H), 7.21 (s, 1H), 6.24-6.30 (m, 1H), 6.11-6.16 (dd, 1H) 5.66-5.69 (dd, 1H) 4.55 (s, 2H). |
| 299 | 439.4 | L2 | 2.25 | (DMSO-$d_6$) δ ppm: 8.98-8.99 (d, 1H), 8.863-8.868 (d, 1H), 8.58 (s, 1H), 8.39-8.42 (t, 1H), 8.28-8.29 (t, 1H), 8.17-8.21 (q, 2H), 8.12 (s, 1H), 8.09-8.10 (d, 1H), 7.29-7.34 (t, 2H), 7.07-7.08 (d, 1H), 6.24-6.30 (dd, 1H), 6.08-6.13 (dd, 1H), 5.61-5.62 (d, 1H), 5.59 (s, 2H), 4.66-4.67 (d, 2H). |
| 300 | 444.4 | L2 | 2.08 | (DMSO-$d_6$) δ ppm: 8.58 (s, 1H), 8.41-8.44 (t, 1H), 8.17-8.21 (q, 2H), 8.12 (s, 1H), 7.98-7.986 (d, 1H), 7.85-7.86 (d, 1H), 7.45-7.48 (dd, 1H), 7.30-7.34 (t, 2H), 7.023-7.029 (d, 1H), 6.36-6.38 (dd, 1H), 6.25-6.32 (dd, 1H), 6.09-6.14 (dd, 1H), 5.60-5.63 (dd, 1H), 5.17 (s, 2H), 4.68-4.70 (d, 2H), 3.41 (s, 3H). |
| 301 | 364.4 | L2 | 2.30 | (DMSO-$d_6$) δ ppm: 8.63 (s, 1H), 8.46-8.49 (m, 2H), 8.18-8.22 (q, 2H), 7.98 (s, 1H), 7.83-7.86 (d, 1H), 7.56-7.59 (dd, 1H), 7.29-7.34 (t, 2H), 6.23-6.29 (dd, 1H), 6.06-6.10 (dd, 1H), 5.58-5.61 (dd, 1H), 4.56-4.57 (dd, 2H), 3.91 (s, 3H). |
| 302 | 350.5 | L2 | 1.92 | (DMSO-$d_6$) δ ppm: 11.98 (s, 1H), 8.45-8.54 (m, 3H), 8.13-8.17 (q, 2H), 7.75 (s, 1H), 7.59-7.61 (dd, 1H), 7.52-7.53 (dd, 1H), 7.27-7.32 (t, 2H), 6.33-6.36 (t, 1H), 6.18-6.25 (m, 1H), 6.04-6.09 (dd, 1H), 5.57-5.60 (dd, 1H), 4.32-4.34 (d, 2H). |
| 303 | 374.4 | L2 | 2.06 | (DMSO-$d_6$) δ ppm: 13.87 (br. s, 1H), 9.20 (s, 1H), 8.653 (s, 1H), 8.46-8.50 (t, 1H), 8.34 (s, 1H), 8.21-8.24 (m, 3H), 8.06 (s, 1H), 7.30-7.34 (t, 2H), 6.21-6.28 (m, 1H), 6.03-6.08 (dd, 1H), 5.56-5.59 (dd, 1H), 4.60-4.61 (d, 2H). |
| 304 | 390.4 | L2 | 2.95 | (DMSO-$d_6$) δ ppm: 8.78 (s, 1H), 8.60-8.63 (s, 1H), 8.53 (t, 1H), 8.19-8.28 (m, 5H), 7.56-7.66 (m, 2H), 7.34-7.38 (t, 2H), 6.25-7.32 (m, 1H), 6.07-6.12 (dd, 1H), 5.59-5.62 (dd, 1H), 4.84-4.85 (d, 2H). |
| 305 | 530.4 | L2 | 3.28 | (DMSO-$d_6$) δ ppm: 8.52 (s, 1H), 7.98 (d, 1H), 7.94-7.91 (m, 1H), 7.86 (d, 1H), 7.66-7.64 (m, 2H), 7.52-7.49 (dd, 1H), 7.49-7.38 (m, 2H), 7.36-7.34 (m, 2H), 7.27-7.23 (m, 1H), 7.20 (m, 1H), 7.09 (m, 1H), 6.94 (d, 1H), 6.80 (d, 1H), 5.41 (s, 2H), 4.70-4.67 (m, 1H), 3.66-3.61 (m, 2H), 3.32-3.30 (m, 2H), 2.57 (d, 3H), 1.25-1.24 (d, 6H). |
| 306 | 373.4 | L2 | 2.33 | (DMSO-$d_6$) δ ppm : 13.40 (br. s, 1H) 8.72-8.76 (m, 2H), 8.44 (s, 1H), 8.23-8.27 (q, 2H), 7.73 (br. s, 2H), 7.37-7.41 (t, 2H), 7.30-7.32 (m, 2H), 6.30-6.37 (m, 1H), 6.10-6.14 (dd, 1H), 5.61-5.64 (dd, 1H), 4.97-4.99 (d, 2H). |
| 307 | 471.4 | L2 | 2.27 | (DMSO-$d_6$) δ ppm: 10.53 (s, 1H), 8.57 (s, 1H), 8.38-8.41 (t, 1H), 8.34-8.35 (d, 1H), 8.17-8.21 (m, 2H), 8.11 (s, 1H), 8.04-8.06 (m, 2H), 7.75-7.78 (dd, 1H), 7.29-7.34 (t, 2H), 7.03-7.04 (d, 1H), 6.23-6.30 (dd, 1H), 6.08-6.13 (dd, 1H), 5.60-5.62 (dd, 1H), 5.44 (s, 2H), 4.67-4.68 (d, 2H), 2.07 (s, 3H). |
| 308 | 471.4 | L2 | 2.12 | (DMSO-$d_6$) δ ppm: 10.5 (s, 1H), 8.58 (s, 1H), 8.39-8.42 (t, 1H), 8.20-8.24 (m, 3H), 8.16 (s, 1H), 8.064-8.069 (d, 1H), 8.01 (s, 1H), 7.30-7.34 (m, 2H), 7.05-7.06 (d, 1H), 6.89-6.91 (dd, 1H), 6.22-6.29 (m, 1H), 6.07-6.12 (dd, 1H), 5.59-5.62 (dd, 1H), 5.53 (s, 2H), 4.66-4.67 (d, 2H), 2.06 (s, 3H). |
| 309 | 548.3 | U4 | 3.40 | (DMSO-$d_6$) δ ppm: 7.96-7.94 (m, 3H), 7.86 (d, 1H), 7.66-7.64 (dd, 2H), 7.51-7.48 (dd, 1H), 7.44-7.33 (m, 5H), 7.27-7.23 (m, 1H), 7.06 (m, 1H), 7.01 (m, 1H), 6.92 (d, 1H), 6.80 (m, 1H), 5.40 (s, 2H), 4.67-4.64 (m, 1H), 3.65-3.60 (m, 2H), 3.31 (s, 2H), 2.58-2.49 (d, 3H), 1.26-1.25 (d, 6H). |

TABLE 2-continued

Analytical data for synthesized compounds of the disclosure

| Cpd. No. | $[M + H]^+$ (m/z) : | LC/MS or UPLC Method | RT (min.) | $^1$H NMR (δ ppm) |
|---|---|---|---|---|
| 310 | 582.4 | L3 | 5.58 | (DMSO-$d_6$) δ ppm: 8.02-7.99 (m, 1H), 7.94 (d, 2H), 7.87 (d, 1H), 7.71-7.68 (m, 2H), 7.52-7.49 (dd, 1H), 7.45-7.42 (m, 3H), 7.36-7.34 (m,2H), 7.06 (m, 1H), 7.00 (m, 1H), 6.94 (d, 1H), 6.79 (d, 1H), 5.40 (s, 2H), 4.66-4.63 (m, 1H), 3.65-3.60 (m, 2H), 3.34-3.31 (m, 2H), 2.58-2.56 (d, 3H), 1.26-1.25 (d, 6H). |
| 311 | 616.3 | U4 | 3.62 | (DMSO-$d_6$) δ ppm: 8.08-8.11 (t, 1H), 7.95-7.96 (m, 3H), 7.89-7.91 (d, 2H), 7.71-7.73 (d, 2H), 7.58-7.61 (dd, 1 H),7.44 (s, 1H), 7.34-7.36 (d, 2H), 7.06-7.09 (q, 1H), 7.01 (s, 1H), 6.96-6.97 (d, 1H), 6.82-6.84 (d, 1H), 5.40 (s, 2H), 4.62-4.67 (m, 1H), 3.62-3.67 (m, 2H), 3.32 (s, 2H), 2.57-2.58 (d, 3H), 1.25-1.26 (d, 6H). |
| 312 | 359.4 | L2 | 2.53 | (DMSO-$d_6$) δ ppm: 8.70 (s, 1 H), 8.43-8.44 (t, 1H), 8.20-8.26 (m, 3H), 8.12-8.15 (m, 2H), 8.04 (s, 1H), 7.31-7.35 (t, 2H), 6.11-6.18 (dd, 1H), 5.99-6.04 (dd, 1H), 5.54-5.57 (dd, 1H), 4.53-4.55 (d, 2H). |
| 313 | 364.4 | L2 | 2.18 | (DMSO-$d_6$) δ ppm: 8.73 (s, 1H), 8.56-8.59 (t, 1H), 8.19-8.22 (q, 2H), 8.01 (s, 1H), 7.45-7.49 (q, 1H), 7.29-7.34 (t, 2H), 6.46-6.49 (d, 1H), 6.15-6.21 (m, 2H), 6.02-6.07 (dd, 1H), 5.58-5.61 (dd, 1H), 4.32-4.38 (dd, 1H), 4.16-4.21 (dd, 1H) 3.15 (s, 3H). |
| 314 | 383.4 | L2 | 2.41 | (DMSO-$d_6$) δ ppm: 8.79 (s, 1H), 8.61-8.63 (t, 1H), 8.34 (s, 1H), 8.19-8.23 (q, 2H), 7.34-7.38 (t, 2H), 6.26-6.33 (dd, 1H), 6.10-6.15 (dd, 1H), 5.62-5.65 (dd, 1H), 4.80-4.81 (d, 2H), 3.80-3.83 (t, 2H), 3.27 (s, 3H), 3.24-3.25 (t, 2H). |
| 315 | 366.4 | L2 | 2.02 | (DMSO-$d_6$) δ ppm: 14.03 (br. s, 1H), 8.67 (br. s, 1H), 8.61 (s, 1H), 8.17-8.20 (m, 2H), 8.08 (s, 1H), 7.88 (br. s, 1H), 7.50 (br. s, 1H), 7.31-7.36 (m, 3H), 6.28-6.35 (m, 1H), 6.11-6.16 (dd, 1H), 5.62-5.66 (dd, 1H), 4.66-4.67 (d, 2H). |
| 316 | 564.4 | L3 | 6.34 | (DMSO-$d_6$) δ ppm: 8.00-7.97 (m, 2H), 7.88 (d, 1H), 7.71-7.68 (m, 2H), 7.53-7.50 (dd, 1H), 7.45-7.42 (m, 2H), 7.36-7.33 (m, 2H), 7.19 (m, 1H), 7.10-7.06 (m, 1H), 6.96 (d, 1H), 6.80 (d, 1H), 5.41 (s, 2H), 4.72-4.66 (m, 1H), 3.66-3.61 (m, 2H), 3.33-3.31 (m, 2H), 2.56 (d, 3H), 1.25-1.24 (d, 6H). |
| 317 | 598.4 | L3 | 6.35 | (DMSO-$d_6$) δ ppm: 8.07-8.09 (t, 1H), 7.96-7.99 (m, 2H), 7.89-7.91 (d, 2H), 7.72-7.74 (d, 2H), 7.59-7.62 (dd, 1 H), 7.34-7.36 (dd, 2H), 7.20 (s, 1H), 7.07-7.11 (dd, 1H), 6.98-6.94 (d, 1H), 6.82-6.84 (d, 1H), 5.42 (s, 2H), 4.66-4.72 (m, 1H), 3.63-3.68 (m, 2H), 3.31 (s, 2H), 2.56-2.58 (d, 3H), 1.24-1.25 (d, 6H). |
| 318 | 349.3 | L2 | 1.95 | (DMSO-$d_6$) δ ppm: 8.61 (s, 1H), 8.40-8.42 (t, 1H), 8.16-8.19 (q, 2H), 7.91 (s, 1H), 7.52-7.56 (t, 1H), 7.28-7.33 (t, 2H), 6.88-6.90 (d, 1H), 6.52-6.54 (d, 1H), 6.31-6.38 (m, 1H), 6.09-6.17 (m, 3H), 5.60-5.63 (dd, 1H), 4.52-4.54 (d, 2H). |
| 319 | 377.3 | L2 | 2.17 | (DMSO-$d_6$) δ ppm: 8.72 (s, 1H), 8.61-8.63 (t, 1H), 8.10-8.25 (m, 6H), 8.01-8.03 (dd, 1H), 7.75 (s, 1H), 7.30-7.35 (t, 2H), 6.19-6.26 (m, 1H), 6.03-6.08 (dd, 1H), 5.56-5.59 (dd, 1H), 4.56-4.57 (dd, 2H). |
| 320 | 350.4 | L2 | 2.11 | (DMSO-$d_6$) δ ppm: 11.8-11.98 (s, 1H), 8.63-8.66 (m, 2H), 8.18-8.21 (m, 2H), 7.92 (s, 1H), 7.57-7.61 (dd, 1H), 7.30-7.34 (m, 2H), 6.47-6.56 (m, 2H), 6.22-6.29 (dd, 1H), 6.07-6.12 (dd, 1H), 5.60-5.63 (dd, 1H), 4.44-4.45 (d, 2H). |
| 321 | 353.3 | L2 | 1.91 | (DMSO-$d_6$) δ ppm: 13.25 (br. s, 1H), 8.57 (s, 2H), 8.18-8.22 (m, 2H), 8.10 (s, 1H), 7.29-7.34 (t, 2H), 6.86 (br. s, 1H), 6.29-6.36 (m, 1H), 6.11-6.15 (dd, 1H), 5.62-5.65 (dd, 1H), 5.45 (br. s, 1H), 4.73 (br. s, 2H), 4.57 (s, 2H). |
| 322 | 391.2 | U4 | 2.50 | (DMSO-$d_6$) δ ppm: 8.84-8.85 (t, 1H), 8.65-8.66 (d, 2H), 8.63 (s, 1H), 8.33 (s, 1H), 8.18-8.22 (m, 2H), 7.77-7.81 (m, 1H), 7.42-7.47 (t, 1H), 7.32-7.36 (t, 2H), 6.29-6.36 (dd, 1H), 6.11-6.15 (dd, 1H), 5.61-5.65 (dd, 1H), 4.80-4.82 (d, 2H). |

TABLE 2-continued

Analytical data for synthesized compounds of the disclosure

| Cpd. No. | $[M + H]^+$ (m/z) : | LC/MS or UPLC Method | RT (min.) | $^1$H NMR (δ ppm) |
|---|---|---|---|---|
| 323 | 420.4 | L2 | 2.95 | (DMSO-$d_6$) δ ppm: 8.75 (s, 1H), 8.59-8.62 (t, 1H), 8.20-8.24 (m, 3H), 8.07-8.09 (d, 1H), 7.821-7.827 (d, 1H), 7.34-7.38 (t, 2H), 7.21-7.24 (dd, 1H), 6.27-6.34 (dd, 1H), 6.08-6.13 (dd, 1H), 5.60-5.63 (dd, 1H), 4.84-4.85 (d, 2H), 3.89 (s, 3H). |
| 324 | 338.4 | L2 | 2.15 | (DMSO-$d_6$) δ ppm: 8.72 (s, 1H), 8.65 (s, 1H), 8.55-8.50 (m, 1H), 8.39 (s, 1H), 8.15-8.12 (m, 2H), 7.35-7.31 (m, 2H), 6.36-6.29 (m, 1H), 6.14-6.09 (dd, 1H), 5.64-5.61 (dd, 1H), 4.85 (d, 2H), 4.01 (s, 3H). |
| 325 | 369.4 | U5 | 2.08 | (DMSO-$d_6$) δ ppm: 8.78 (s, 1H), 8.61-8.64 (t, 1H), 8.34 (s, 1H), 8.19-8.23 (q, 2H), 7.32-7.38 (t, 2H), 6.27-6.33 (dd, 1H), 6.10-6.15 (dd, 1H), 5.62-5.65 (dd, 1H), 5.04 (br. s, 1H), 4.80-4.82 (d, 2H), 3.87-3.90 (t, 2H), 3.12-3.15 (t, 2H). |
| 326 | 392.3 | L2 | 2.68 | (DMSO-$d_6$) δ ppm: 15.66 (br. s, 1H), 8.73 (s, 1H), 8.60-8.63 (t, 1H), 8.34 (s, 1H), 8.19-8.22 (m, 2H), 7.36-7.41 (m, 2H), 6.22-6.29 (dd, 1H), 6.07-6.12 (dd, 1H), 5.61-5.64 (dd, 1H), 4.77-4.78 (d, 2H). |
| 327 | 389.4 | L2 | 2.01 | (DMSO-$d_6$) δ ppm: 8.84 (s, 1H), 8.35 (s, 1H), 7.99-8.03 (q, 2H), 7.82 (s, 1H), 7.71 (s, 1H), 7.60 (s, 1H), 7.26-7.28 (s, 1H), 7.14-7.18 (t, 2H), 6.26-6.31 (dd, 1H), 6.08-6.15 (m, 1H), 5.63-5.65 (dd, 1H), 4.53-4.55 (d, 2H), 3.69 (s, 2H). |
| 328 | 324.3 | L2 | 2.46 | (DMSO-$d_6$) δ ppm: 8.972-8.978 (d, 1H), 8.55-8.57 (t, 1H), 8.51-8.52 (d, 1H), 8.387-8.389 (d, 1H), 7.86-7.90 (m, 2H), 7.557-7.559 (d, 1H), 7.38-7.39 (d, 1H), 7.35-7.37 (t, 2H), 6.37-6.44 (dd, 1H), 6.07-6.12 (dd, 1H), 5.58-5.61 (dd, 1H), 4.97-4.99 (dd, 2H). |
| 329 | 393.4 | U5 | 2.07 | (DMSO-$d_6$) δ ppm: 8.81 (s, 1H), 8.65-8.68 (t, 1H), 8.33 (s, 1H), 8.17-8.21 (m, 2H), 7.35-7.39 (m, 2H), 6.26-6.33 (dd, 1H), 6.10-6.14 (dd, 1H), 5.62-5.65 (dd, 1H), 4.81-4.83 (d, 2H), 4.77 (s, 2H), 3.00 (s, 3H). |
| 330 | 324.2 | U5 | 2.01 | (DMSO-$d_6$) δ ppm: 8.64-8.67 (t, 1H), 8.38 (s, 1H), 8.20-8.23 (m, 2H), 8.09-8.11 (dd, 1H), 7.87-7.89 (dd, 1H), 7.55-7.56 (d, 1H), 7.34-7.39 (m, 2H), 6.31-6.38 (m, 1H), 6.11-6.16 (dd, 1H), 5.63-5.67 (dd, 1H), 4.87-4.88 (d, 2H). |
| 331 | 325.3 | U5 | 1.96 | (DMSO-$d_6$) δ ppm: 8.94 (s, 1H), 8.63-8.66 (t, 1H), 8.48-8.51 (m, 3H), 7.680-7.681 (d, 1H), 7.37-7.42 (m, 2H), 6.29-6.35 (m, 1H), 6.10-6.15 (dd, 1H), 5.63-5.66 (dd, 1H), 4.89-4.90 (d, 2H). |
| 332 | 349.3 | U5 | 1.91 | (DMSO-$d_6$) δ ppm: 8.887-8.889 (d, 2H), 8.70 (s, 1H), 8.44-8.47 (t, 1H), 8.34 (s, 1H), 8.14-8.18 (m, 2H), 7.31-7.35 (m, 2H), 6.21-6.28 (m, 1H), 6.04-6.09 (dd, 1H), 5.57-5.60 (dd, 1H), 4.77-4.78 (d, 2H), 2.38 (s, 3H). |
| 333 | 403.3 | U5 | 2.11 | (DMSO-$d_6$) δ ppm: 9.491-9.493 (d, 2H), 8.77 (s, 1H), 8.41-8.44 (t, 1H), 8.36 (s, 1H), 8.15-8.19 (m, 2H), 7.32-7.37 (m, 2H), 6.13-6.20 (dd, 1H), 6.00-6.05 (dd, 1H), 5.54-5.58 (dd, 1H), 4.77-4.78 (d, 2H). |
| 334 | 374.2 | U6 | 4.16 | (DMSO-$d_6$) δ ppm: 8.79 (s, 1H), 8.57-8.55 (m, 1H), 8.49 (s, 1H), 8.21-8.16 (m, 2H), 8.04 (s, 1H), 7.98-7.70 (m, 1H), 7.38-7.32 (m, 2H), 6.19-6.13 (m, 1H), 6.06-6.01 (m, 1H), 5.58 (dd, 1H), 4.36 (d, 2H), |
| 335 | 324.2 | U5 | 1.76 | (DMSO-$d_6$) δ ppm: 8.64 (m, 3H), 8.47-8.43 (m, 2H), 8.17-8.13 (m, 2H), 7.36-7.31 (m, 2H), 6.36-6.28 (dd, 1H), 6.13-6.09 (d, 1H), 5.63-5.60 (d, 1H), 4.85 (m, 2H). |
| 336 | 338.3 | U5 | 1.74 | (DMSO-$d_6$) δ ppm: 8.78 (s, 1H), 8.59-8.62 (m, 2H), 8.23 (s, 1H), 8.17-8.20 (m, 2H), 7.31-7.36 (t, 2H), 6.28-6.35 (m, 1H), 6.10-6.15 (dd, 1H), 5.61-5.65 (dd, 1H), 4.71-4.72 (d, 2H), 4.17 (s, 3H). |
| 337 | 338.3 | U5 | 1.82 | (DMSO-$d_6$) δ ppm: 8.854-8.859 (d, 1H), 8.63 (s, 1H), 8.56-8.58 (t, 2H), 8.29-8.30 (d, 1H), 7.83-7.87 (m, 2H), 7.34-7.38 (t, 2H), 6.36-6.43 (dd, 1H), 6.07-6.11 (dd, 1H), 5.58-5.61 (dd, 1H), 4.75-4.77 (d, 2H), 4.16 (s, 3H). |
| 338 | 338.3 | U5 | 1.95 | (DMSO-$d_6$) δ ppm: 8.77 (s, 1H), 8.59-8.62 (t, 1H), 8.21-8.25 (q, 2H), 7.92-7.94 (d, 1H), 7.79-7.82 |

TABLE 2-continued

| Cpd. No. | $[M + H]^+$ (m/z) : | LC/MS or UPLC Method | RT (min.) | $^1$H NMR (δ ppm) |
|---|---|---|---|---|
| Analytical data for synthesized compounds of the disclosure | | | | |
| | | | | (d, 1H), 7.31-7.35 (t, 2H), 6.32-6.39 (dd, 1H), 6.01-6.15 (dd, 1H), 5.62-5.65 (dd, 1H), 4.88-4.89 (d, 2H), 4.17 (s, 3H). |
| 339 | 377.4 | U5 | 2.07 | (DMSO-$d_6$) δ ppm: 8.63 (s, 1H), 8.45-8.48 (t, 1H), 8.16-8.19 (m, 2H), 7.75 (s, 1H), 7.36-7.75 (m, 2H), 7.27-7.32 (m, 3H), 7.18-7.20 (d, 1H), 6.20-6.27 (m, 1H), 6.04-6.09 (dd, 1H), 5.58-5.61 (dd, 1H), 4.58 (s, 1H), 4.03-4.17 (m, 2H), 3.46 (s, 2H), 2.51-2.67 (m, 1H), 2.32-2.51 (m, 1H). |
| 340 | 379.4 | L3 | 5.11 | (DMSO-$d_6$) δ ppm: 8.60 (s, 1H), 8.12-8.19 (m, 3H), 7.73 (s, 1H), 7.36-7.42 (q, 2H), 7.26-7.33 (m, 3H), 7.17-7.19 (d, 1H), 4.56-4.59 (t, 1H), 3.95-4.06 (m, 2H), 3.43-3.48 (q, 2H), 2.57-2.64 (m, 1H), 2.44-2.51 (m, 1H), 2.06-2.12 (q, 2H), 0.95-0.99 (t, 3H). |
| 341 | 401.4 | U8 | 2.12 | (DMSO-$d_6$) δ ppm: 8.79 (s, 1H), 8.17-8.21 (m, 2H), 7.76 (s, 1H), 7.81-7.49 (m, 3H), 7.28-7.34 (m, 3H), 7.19-7.21 (d, 1H), 3.88-4.00 (m, 2H), 3.44-3.51 (m, 2H), 2.75 (s, 3H), 2.57-2.62 (m, 1H), 2.44-2.51 (m, 1H). |
| 342 | 328.4 | U5 | 1.61 | (DMSO-$d_6$) δ ppm: 8.11 (s, 1H), 8.04-8.08 (m, 3H), 7.23-7.27 (t, 2H), 6.97 (s, 1H), 4.34-4.35 (d, 2H), 3.46-3.49 (m, 4H), 2.09-2.15 (q, 2H), 1.89-1.93 (m, 4H), 0.99-1.02 (t, 3H). |
| 343 | 326.4 | U5 | 2.05 | (DMSO-$d_6$) δ ppm: 8.46-8.49 (t, 1H), 8.07-8.11 (m, 2H), 7.46-7.48 (dd, 1H), 7.24-7.28 (m, 3H), 6.28-6.35 (m, 1H), 6.10-6.15 (dd, 1H), 5.61-5.64 (dd, 1H), 4.40-4.41 (d, 2H), 3.55-3.58 (m, 4H), 1.88-1.91 (m, 4H). |
| 344 | 350.3 | U5 | 2.17 | (DMSO-$d_6$) δ ppm: 8.09-8.13 (m, 2H), 7.63-7.65 (dd, 1H), 7.35-7.37 (t, 1H), 7.24-7.31 (m, 3H), 4.21-4.23 (d, 2H), 3.57-3.60 (m, 4H), 2.93 (s, 3H), 1.88-1.91 (m, 4H). |
| 347 | 457.3 | U8 | 1.86 | (DMSO-$d_6$) δ ppm: 8.58 (s, 1H), 8.40-8.43 (t, 1H), 8.17-8.21 (m, 3H), 8.14 (s, 1H), 8.01 (s, 1H), 7.94-7.99 (m, 2H), 7.72 (s, 1H), 7.29-7.34 (m, 3H), 7.08-7.09 (d, 1H), 6.22-6.29 (m, 1H), 6.07-6.12 (dd, 1H), 5.64 (s, 2H), 5.59-5.62 (dd, 1H), 4.66-4.67 (d, 2H). |
| 348 | 430.3 | U8 | 1.87 | (DMSO-$d_6$) δ ppm: 11.53 (s, 1H), 8.58 (s, 1H), 8.43-8.46 (t, 1H), 8.18-8.22 (m, 2H), 8.14 (s, 1H), 8.051-8.056 (d, 1H), 7.30-7.34 (m, 3H), 7.080-7.086 (d, 1H), 6.24-6.31 (dd, 1H), 6.08-6.13 (dd, 1H), 6.01-6.02 (d, 2H), 5.60-5.62 (dd, 1H), 5.33 (s, 2H), 4.68-4.69 (dd, 2H). |
| 349 | 432.4 | U8 | 1.88 | (DMSO-$d_6$) δ ppm: 11.53 (s, 1H), 8.56 (s, 1H), 8.18-8.22 (m, 2H), 8.10-8.13 (m, 2H), 8.051-8.057 (d, 1H), 7.30-7.34 (m, 3H), 7.073-7.079 (d, 1H), 5.99-6.02 (dd, 2H), 5.33 (s, 2H), 4.57-4.58 (d, 2H), 2.11-2.17 (q, 2H), 0.98-1.02 (t, 3H). |
| 350 | 326.3 | U5 | 1.40 | (DMSO-$d_6$) δ ppm: 8.38-8.40 (t, 1H), 8.13 (s, 1H), 8.04-8.08 (m, 2H), 7.23-7.28 (m, 2H), 6.98 (s, 1H), 6.25-6.32 (m, 1H), 6.09-6.14 (dd, 1H), 5.58-5.61 (dd, 1H), 4.45-4.68 (d, 2H), 3.48-3.51 (m, 4H), 1.89-1.93 (m, 4H). |
| 351 | 350.5 | U7 | 2.53 | (DMSO-$d_6$) δ ppm: 8.18 (s, 1H), 8.06-8.09 (m, 2H), 7.24-7.28 (m, 3H), 6.97 (s, 1H), 4.27 (s, 2H), 3.54-3.57 (m, 4H), 2.93 (s, 3H), 1.93 (m, 4H). |
| 352 | 328.3 | U8 | 2.01 | (DMSO-$d_6$) δ ppm: 8.14-8.17 (t, 1H), 8.07-8.11 (m, 2H), 7.45-7.47 (dd, 1H), 7.23-7.28 (m, 3H), 4.29-4.31 (d, 2H), 3.53-3.56 (m, 4H), 2.13-2.19 (q, 2H), 1.87-1.90 (m, 4H), 1.01-1.04 (t, 3H). |
| 353 | 458.4 | U8 | 1.98 | (DMSO-$d_6$) δ ppm: 8.58 (s, 1H), 8.42-8.45 (t, 1H), 8.18-8.22 (m, 2H), 8.14 (s, 2H), 7.81-7.85 (m, 2H), 7.29-7.33 (t, 2H), 7.07-7.11 (m, 2H), 6.23-6.30 (m, 1H), 6.07-6.11 (dd, 1H), 5.58-5.68 (m, 3H) 4.68-4.69 (d, 2H). |
| 354 | 439.3 | U8 | 2.20 | (DMSO-$d_6$) δ ppm: 8.58 (s, 1H), 8.39-8.42 (t, 1H), 8.18-8.21 (m, 2H), 8.14 (s, 1H), 8.10-8.11 (d, 1H), 8.04-8.08 (t, 1H), 7.99-8.00 (d, 1H), 7.47-7.49 (dd, 1H), 7.30-7.34 (t, 2H), 7.094-7.099 (d, 1H), 6.22-6.29 (m, 1H), 6.07-6.12 (dd, 1H), 5.67 (s, 2H), 5.59-5.62 (dd, 1H), 4.64-4.66 (d, 2H). |

TABLE 2-continued

| Analytical data for synthesized compounds of the disclosure | | | | |
|---|---|---|---|---|
| Cpd. No. | [M + H]+ (m/z) : | LC/MS or UPLC Method | RT (min.) | $^1$H NMR (δ ppm) |
| 355 | 339.4 | L4 | 1.73 | (DMSO-$d_6$) δ ppm: 9.08 (s, 1H), 8.82 (s, 1H), 8.66-8.69 (t, 1H), 8.51-8.55 (m, 3H), 7.34-7.39 (m, 2H), 6.30-6.37 (m, 1H), 6.10-6.14 (dd, 1H), 5.61-5.64 (dd, 1H), 4.91-4.92 (d, 2H), 4.20 (s, 3H). |
| 356 | 362.3 | U7 | 2.58 | (DMSO-$d_6$) δ ppm: 8.71 (s, 1H), 8.51-8.54 (t, 1H), 8.18-8.21 (m, 2H), 7.97 (s, 1H), 7.57-7.58 (d, 1H), 7.32-7.36 (m, 2H), 7.220-7.223 (d, 1H), 6.21-6.28 (m, 1H), 6.06-6.11 (dd, 1H), 5.59-5.62 (m, 1H), 5.34 (s, 2H), 4.38-4.40 (d, 2H). |
| 357 | 475.4 | U8 | 2.36 | (DMSO-$d_6$) δ ppm: 11.6 (br.s, 1H), 8.44-7.47 (t, 1H), 7.97 (d, 1H), 7.80 (d, 1H), 7.72-7.76 (m, 2H), 7.58-7.61 (dd, 1H), 7.39-7.41 (d, 1H), 7.27-7.33 (m, 3H), 6.78-6.79 (d, 1H), 6.27-6.33 (q, 1H), 6.09-6.13 (dd, 1H), 5.99-6.01 (d, 2H), 5.60-5.63 (dd, 1H), 5.29 (s, 2H), 4.59-4.60 (d, 2H). |
| 358 | 431.3 | U8 | 2.12 | (DMSO-$d_6$) δ ppm: 11.6 (br. s, 1H), 8.09-8.12 (t, 1H), 7.96-7.97 (s, 1H), 7.74-7.79 (m, 1H), 7.72-7.74 (t, 2H), 7.57-7.60 (dd, 1H), 7.39-7.41 (s, 1H), 7.27-7.33 (m, 3H), 6.77-6.78 (s, 1H), 5.98-6.00 (dd, 2H), 5.28 (s, 2H), 4.48-4.50 (d, 2H), 2.12-2.18 (t, 2H), 1.00-1.03 (t, 3H). |
| 359 | 454.3 | U8 | 1.94 | (DMSO-$d_6$) δ ppm: 11.52 (s, 1H), 8.74 (s, 1H), 8.21- 8.24 (m, 2H), 8.14 (s, 1H), 8.062-8.068 (d, 1H), 7.31-7.39 (m, 4H), 7.11-7.12 (d, 1H), 6.02-6.03 (d, 2H), 5.33 (s, 2H), 4.51-4.53 (d, 2H), 2.89 (s, 3H). |
| 360 | 470.4 | L3 | 3.60 | (DMSO-$d_6$) δ ppm: 8.57 (s, 1H), 8.39-8.45 (m, 2H), 8.17-8.21 (m, 2H), 8.13 (s, 1H), 8.05-8.06 (d, 1H), 7.83 (s, 1H), 7.74-7.76 (t, 1H), 7.42-7.45 (m, 2H), 7.29-7.34 (t, 2H), 7.05-7.056 (d, 1H), 6.12-6.28 (m, 1H), 6.07-6.12 (dd, 1H), 5.59-5.62 (dd, 1H), 5.51 (s, 2H), 4.67-4.68 (d, 2H), 2.76-2.77 (d, 3H). |
| 361 | 458.4 | U8 | 1.97 | (DMSO-$d_6$) δ ppm: 8.57 (s, 1H), 8.44-8.45 (t, 1H), 8.17-8.21 (m, 2H), 8.11-8.15 (m, 2H), 8.051-8.057 (d, 1H), 7.83 (s, 1H), 7.74-7.76 (t, 1H), 7.44-7.45 (dd, 2H), 7.29-7.34 (t, 2H), 7.03-7.04 (d, 1H), 5.51 (s, 2H), 4.56-4.57 (d, 2H), 2.76-2.77 (d, 3H), 1.84 (s, 3H). |
| 362 | 504.3 | U8 | 2.14 | (DMSO-$d_6$) δ ppm: 8.57 (s, 2H), 8.40-8.43 (t, 1H), 8.18-8.21 (m, 2H), 8.13 (s, 1H), 8.08-8.09 (d, 1H), 7.78-7.81 (dd, 2H), 7.55 (s, 1H), 7.29-7.34 (t, 2H), 7.063-7.069 (d, 1H), 6.22-6.29 (m, 1H), 6.07-6.12 (dd, 1H), 5.59-5.62 (dd, 1H), 5.35 (s, 2H), 4.66-4.67 (d, 2H), 2.75-2.76 (d, 3H). |
| 363 | 453.2 | U5 | 2.17 | (DMSO-$d_6$) δ ppm: 7.98 (s, 1H), 7.78-7.80 (m, 1H), 7.54-7.77 (m, 2H), 7.64 (t, 2H), 7.27-7.33 (m, 3H), 6.81 (s, 1H), 5.99-6.01 (d, 2H), 5.28 (s, 2H), 4.40 (s, 2H), 2.84 (s, 3H). |
| 364 | 492.3 | U8 | 2.12 | (DMSO-$d_6$) δ ppm: 8.57 (s, 2H), 8.11-8.21 (m, 4H), 8.082-8.087 (d, 1H), 7.81 (s, 1H), 7.78 (s, 1H), 7.55 (s, 1H), 7.29-7.34 (t, 2H), 7.051-7.056 (d, 1H), 5.53 (s, 2H), 4.55-4.57 (d, 2H), 2.75-2.76 (d, 3H), 1.85 (s, 3H). |
| 365 | 471.4 | U8 | 1.98 | (DMSO-$d_6$) δ ppm: 8.76 (m, 1H), 8.58-8.60 (m, 2H), 8.39-8.42 (t, 1H), 8.18-8.22 (m, 2H), 8.12-8.15 (dd, 2H), 7.89 (s, 1H), 7.39-7.40 (m, 1H), 7.30-7.34 (m, 2H), 7.103-7.103 (d, 1H), 6.22-6.28 (dd, 1H), 6.06-6.11 (dd, 1H), 5.65 (s, 2H), 5.58-5.61 (dd, 1H), 4.66-4.68 (dd, 2H), 2.79 - 2.80 (d, 3H). |
| 366 | 367.4 | U7 | 2.24 | (DMSO-$d_6$) δ ppm: 8.66 (s, 1H), 8.48-8.51 (t, 1H), 8.17-8.23 (m, 2H), 8.10 (s, 1H), 7.480-7.483 (d, 1H), 7.28-7.34 (m, 2H), 7.133-7.135 (d, 1H), 6.21-6.28 (m, 1H), 6.06-6.11 (dd, 1H), 5.59-5.62 (dd, 1H), 5.12 (s, 1H), 4.39-4.40 (d, 2H), 3.98-4.02 (t, 2H), 3.64-3.67 (t, 2H). |
| 367 | 459.4 | U8 | 1.96 | (DMSO-$d_6$) δ ppm: 8.76-8.77 (m, 1H), 8.59-8.61 (m, 1H), 8.58 (s, 1H), 8.18-8.22 (m, 2H), 8.12-8.17 (m, 3H), 7.884-7.886 (d, 1H), 7.39-7.41 (dd, 1H), 7.29-7.34 (m, 2H), 7.091-7.097 (d, 1H), 5.65 (s, 2H), 4.55-4.56 (d, 2H), 2.79-2.80 (d, 3H), 1.84 (s, 3H). |

TABLE 2-continued

Analytical data for synthesized compounds of the disclosure

| Cpd. No. | $[M + H]^+$ (m/z) : | LC/MS or UPLC Method | RT (min.) | $^1H$ NMR (δ ppm) |
|---|---|---|---|---|
| 368 | 485.4 | U8 | 2.13 | (DMSO-$d_6$) δ ppm: 8.58-8.59 (m, 2H), 8.40-8.43 (t, 1H), 8.18-8.22 (m, 2H), 8.14 (s, 1H), 8.10-8.11 (d, 1H), 7.69 (s, 1H), 7.28-7.34 (m, 3H), 7.094-7.099 (d, 1H), 6.21-6.28 (dd, 1H), 6.06-6.11 (dd, 1H), 5.58-5.61 (m, 3H), 4.66-4.68 (d, 2H), 2.79-2.80 (d, 3H), 2.52 (s, 3H). |
| 369 | 488.2 | U8 | 2.08 | (DMSO-$d_6$) δ ppm: 8.62 (s, 1H), 8.43-8.47 (m, 2H), 8.04-8.05 (d, 1H), 7.95-8.01 (m, 2H), 7.82 (s, 1H), 7.73-7.76 (m, 1H), 7.36-7.44 (m, 3H), 7.21-7.26 (m, 1H), 6.882-6.888 (d, 1H), 6.22-6.29 (dd, 1H), 6.08-6.13 (dd, 1H), 5.60-5.63 (dd, 1H), 5.51 (s, 2H), 4.67-4.68 (d, 2H), 2.75-2.77 (d, 3H). |
| 370 | 476.5 | L3 | 3.59 | (DMSO-$d_6$) δ ppm: 8.62 (s, 1H), 8.44-8.45 (t, 1H), 8.18-8.21 (t, 1H), 8.04-8.05 (d, 1H), 7.95-7.99 (m, 2H), 7.81 (s, 1H), 7.74-7.76 (m, 1H), 7.36-7.45 (m, 3H), 7.23-7.24 (d, 1H), 6.872-6.878 (d, 1H), 5.51 (s, 2H), 4.56-4.57 (d, 2H), 2.66-2.77 (m, 3H), 1.85 (s, 3H). |
| 371 | 520.4 | U8 | 2.29 | (DMSO-$d_6$) δ ppm: 8.60 (s, 1H), 8.47-8.52 (m, 1H), 8.02-8.03 (d, 1H), 7.88 (s, 1H), 7.79 (s, 1H), 7.73-7.75 (m, 2H), 7.62-7.64 (d, 1H), 7.54-7.57 (dd, 1H), 7.45-7.46 (m, 2H), 6.900-6.906 (d, 1H), 6.21-6.28 (m, 1H), 6.10-6.14 (dd, 1H), 5.63-5.66 (dd, 1H), 5.50 (s, 2H), 4.69-4.70 (d, 2H), 2.77-2.78 (d, 3H). |
| 372 | 473.3 | L3 | 3.37 | (DMSO-$d_6$) δ ppm: 8.58-8.59 (m, 2H), 8. 19-8.22 (m, 3H), 8.12-8.18 (m, 1H), 8.101-8. 107 (d, 1H), 7.68 (s, 1H), 7.29-7.34 (m, 3H), 7.081-7.087 (d, 1H), 5.59 (s, 2H), 4.55-4.57 (d, 2H), 2.79-2.80 (d, 3H), 2.52 (s, 3H), 1.84 (s, 3H). |
| 373 | 508.4 | L3 | 3.98 | (DMSO-$d_6$) δ ppm: 8.60 (s, 1H), 8.43-8.44 (d, 1H), 8.19-8.22 (t, 1H), 8.03-8.04 (d, 1H), 7.88 (s, 1H), 7.81 (s, 1H), 7.73-7.75 (m, 2H), 7.62-7.64 (d, 1H), 7.53-7.56 (dd, 1H), 7.43-7.44 (d, 2H), 6.89-6.90 (d, 1H), 5.50 (s, 2H), 4.58-4.60 (d, 2H), 2.75-2.76 (d, 3H), 1.86 (s, 3H). |
| 374 | 510.3 | U8 | 2.08 | (DMSO-$d_6$) δ ppm: 8.67-8.73 (d, 1H), 8.43 (s, 2H), 8.16-8.20 (m, 2H), 8.05-8.06 (m, 1H), 7.98-7.99 (d, 1H), 7.80-7.82 (d, 1H), 7.72-7.74 (d, 1H), 7.37-7.44 (m, 2H), 5.45 (s, 2H), 7.29-7.33 (t, 2H), 6.87-6.90 (dd, 1H), 6.48-6.64 (m, 1H), 6.11-6.19 (m, 1H), 5.61-5.71 (m, 1H), 5.47 (s, 2H), 3.92-4.11 (m, 1H), 3.75-3.82 (m, 2H), 3.57-3.64 (m, 2H), 2.75-2.77 (dd, 3H), 2.10-2.19 (m, 2H). |
| 375 | 392.3 | U8 | 2.01 | (DMSO-$d_6$) δ ppm: 8.44 (s, 1H), 8.12 (s, 1H), 8.04-8.08 (m, 2H), 7.83-7.84 (d, 1H), 7.27-7.31 (t, 2H), 7.143-7.148 (d, 1H), 6.80-6.87 (d, 1H), 6.12-6.16 (dd, 1H), 5.69-5.72 (dd, 1H), 3.95 (s, 3H), 3.71 (br. s, 4H), 2.95-2.98 (m, 4H). |
| 376 | 380.3 | U8 | 1.95 | (DMSO-$d_6$) δ ppm: 8.43 (s, 1H), 8.12 (s, 1H), 8.04-8.08 (m, 2H), 7.832-7.838 (d, 1H), 7.27-7.31 (t, 2H), 7.12-7.13 (d, 1H), 3.95 (s, 3H), 3.58-3.59 (m, 4H), 2.90-2.98 (m, 4H), 2.03 (s, 3H). |
| 377 | 416.3 | U7 | 3.57 | (DMSO-$d_6$) δ ppm: 8.49 (s, 1H), 8.14 (s, 1H), 8.05-8.08 (m, 2H), 7.833-7.838 (d, 1H), 7.27-7.32 (t, 2H), 7.112-7.118 (d, 1H), 3.96 (s, 3H), 3.26-3.28 (m, 4H), 3.06-3.08 (m, 4H), 2.96 (s, 3H). |
| 378 | 476.2 | U8 | 2.26 | (DMSO-$d_6$) δ ppm: 12.97 (br. s, 1H), 8.57-8.58 (m, 1H), 7.78-7.83 (m, 3H), 7.68 (d, 1H), 7.63 (s, 1H), 7.27-7.30 (m, 2H), 7.17-7.24 (m, 2H), 7.18 (d, 1H), 7.00-7.03 (m, 1H), 5.60 (d, 1H), 5.38 (s, 2H), 3.82 (s, 3H), 2.77 (d, 3H). |
| 379 | 476.2 | U8 | 2.25 | (DMSO-$d_6$) δ ppm: 12.87 (s, 1H), 8.46-8.47 (m, 1H), 7.73-7.76 (m, 2H), 7.67-7.68 (m, 1H), 7.51 (d, 1H), 7.44 (d, 1H), 7.33 (s, 1H), 7.12-7.16 (m, 3H), 6.86 (d, 1H), 6.78 (s, 1H), 6.30 (d, 1H), 4.88 (s, 2H), 3.77 (s, 3H), 2.74 (d, 3H). |
| 380 | 427.3 | U8 | 2.35 | (DMSO-$d_6$) δ ppm: 8.72 (s, 1H), 8.450-8.457 (d, 1H), 8.17-8.21 (m, 2H), 7.78-8.08 (m, 2H), 7.28-7.33 (t, 2H), 7.112-7.119 (d, 1H), 6.81-6.88 (m, 1H), 6.09-6.14 (dd, 1H), 5.66-5.69 (d, 1H), 4.60-4.63 (m, 1H), 4.18-4.22 (m, 1H), 3.48-3.54 (m, 1H), 3.03-3.09 (m, 1H), 2.59-2.66 (m, 1H), 1.87-1.90 (m, 2H), 1.68-1.74 (m, 2H). |

TABLE 2-continued

| Analytical data for synthesized compounds of the disclosure | | | | |
|---|---|---|---|---|
| Cpd. No. | $[M + H]^+$ (m/z) : | LC/MS or UPLC Method | RT (min.) | $^1$H NMR (δ ppm) |
| 381 | 415.2 | U8 | 2.26 | (DMSO-$d_6$) δ ppm: 8.72 (s, 1H), 8.44 (d, 1H), 8.17-8.21 (m, 2H), 8.01 (s, 1H), 7.92 (t, 1H), 7.29-7.34 (m, 2H), 7.10 (d, 1H), 4.55 (d, 1H), 3.93 (d, 1H), 3.44-3.50 (m, 1H), 3.01-3.07 (m, 1H), 2.47 (s, 1H), 2.03 (s, 3H), 1.76-1.86 (m, 3H), 1.60-1.68 (m, 1H). |
| 382 | 451.3 | U9 | 1.78 | (DMSO-$d_6$) δ ppm: 8.78 (s, 1H), 8.45-8.46 (d, 1H), 8.18-8.22 (m, 2H), 7.78-8.07 (m, 2H), 7.30-7.34 (m, 2H), 7.102-7.109 (d, 1H), 3.68-3.71 (d, 2H), 3.31 (m, 1H), 2.90 (s, 3H), 2.71-2.77 (m, 2H), 1.86-1.94 (m, 4H). |
| 383-En1/2 | 498.3 | L5 | 3.73 | (DMSO-$d_6$) δ ppm: 8.61-8.67 (d, 1H), 8.10-8.14 (m, 2H), 7.95-7.96 (d, 1H), 7.90 (s, 1H), 7.79 (s, 1H), 7.72-7.73 (d, 1H), 7.39-7.46 (m, 2H), 7.23-7.29 (m, 2H), 6.77-6.78 (d, 1H), 5.45 (s, 2H), 3.97-4.10 (m, 1H), 3.67-3.76 (m, 1H), 3.54-3.63 (m, 1H), 3.35-3.48 (m, 2H), 2.79 (s, 3H), 2.34-2.12 (m, 2H), 1.97-2.08 (d, 3H). |
| 384-En1/2 | 534.3 | U10 | 3.62 | (DMSO-$d_6$) δ ppm: 8.77 (s, 1H), 8.43-8.44 (d, 1H), 8.17-8.21 (m, 2H), 8.05-8.06 (d, 1H), 7.99 (s, 1H), 7.81 (s, 1H), 7.74-7.77 (m, 1H), 7.44-7.45 (dd, 2H), 7.29-7.33 (t, 2H), 6.92-6.30 (d, 1H), 5.48 (s, 2H), 4.10-4.16 (m, 1H), 3.61-3.66 (m, 1H), 3.44-3.49 (m, 1H), 3.22-3.31 (m, 2H), 2.89 (s, 3H), 2.76-2.77 (d, 3H), 2.02-2.27 (m, 2H). |
| 385 | 381.2 | U8 | 1.61 | (DMSO-$d_6$) δ ppm: 12.32 (s, 1H), 8.43 (s, 1H), 8.11 (s, H), 8.03-8.06 (m, 2H), 7.83-7.84 (d, 1H), 7.26-7.31 (t, 2H), 7.04-7.05 (d, 1H), 3.95 (s, 3H), 3.15-3.17 (m, 2H), 2.66-2.77 (m, 2H), 2.32-2.38 (m, 1H), 1.88-1.90 (m, 2H), 1.66-1.76 (m, 2H). |
| 386-En1/2 | 544.3 | U8 | 1.88 | (DMSO-$d_6$) δ ppm: 8.70 (d, 1H), 8.55 (t, 1H), 8.17-8.20 (m, 2H), 8.09 (t, 1H), 7.99 (d, 1H), 7.74-7.80 (m, 2H), 7.50-7.52 (m, 1H), 7.29-7.33 (m, 2H), 6.90 (dd, 1H), 6.46-6.58 (m, 1H), 6.12-6.17 (m, 1H), 5.67-5.70 (m, 1H), 5.49 (s, 2H), 4.02-4.14 (m, 1H), 3.90-3.94 (m, 1H), 3.74-3.79 (m, 1H), 3.60-3.67 (m, 1H), 3.42-3.51 (m, 1H), 2.74-2.76 (m, 3H), 2.08-2.24 (m, 2H). |
| 387-En1/2 | 568.4 | U8 | 1.91 | (DMSO-$d_6$) δ ppm: 8.78 (s, 1H), 8.56-8.57 (m, 1H), 8.17-8.21 (m, 2H), 8.08 (d, 1H), 8.00 (s, 1H), 7.82 (s, 1H), 7.75 (s, 1H), 7.53 (s, 1H), 7.29-7.33 (m, 2H), 6.94 (d, 1H), 5.50 (s, 2H), 4.12-4.16 (m, 1H), 3.59-3.62 (m, 2H), 3.28-3.30 (m, 2H), 2.89 (s, 3H), 2.76 (d, 3H), 2.25 (m, 1H), 2.08-2.16 (m, 1H). |
| 388 | 450.2 | U9 | 1.60 | (DMSO-$d_6$) δ ppm: 8.780-8.789 (m, 1H), 8.69 (s, 1H), 8.30 (s, 1H), 8.21-8.24 (m, 2H), 8.15 (s, 1H), 8.09 (d, 1H), 7.81-7.82 (m, 2H), 7.57 (s, 1H), 7.31-7.34 (m, 2H), 7.14 (d, 1H), 5.53 (s, 2H), 4.04 (s, 2H), 2.78 (d, 3H). |
| 389-En1/2 | 532.3 | L5 | 3.88 | (DMSO-$d_6$) δ ppm: 8.69 (d, 1H), 8.54-8.55 (m, 1H), 8.17-8.20 (m, 2H), 8.08-8.09 (q, 1H), 7.97 (d, 1H), 7.81-7.82 (m, 1H), 7.97 (d, 1H), 7.52 (t, 1H), 7.29-7.33 (m, 2H), 6.89 (dd, 1H), 5.49 (d, 2H), 3.91-4.01 (m, 1H), 3.65-3.71 (m, 2H), 3.17 (s, 2H), 2.76 (s, 3H), 1.98-2.20 (m, 2H), 1.89 (d, 3H). |
| 390 | 351.3 | U9 | 1.77 | (DMSO-$d_6$) δ ppm: 8.55 (s, 1H), 8.48-8.51 (t, 1H), 8.17-8.21 (m, 2H), 8.15 (s, 1H), 7.910-7.915 (d, 1H), 7.32-7.36 (t, 2H), 7.03-7.04 (d, 1H), 5.73 (s, 1H), 5.39 (s, 1H), 4.67-4.68 (d, 2H), 3.98 (s, 3H), 1.90 (s, 3H). |
| 391 | 355.2 | U9 | 1.81 | (DMSO-$d_6$) δ ppm: 9.00-9.03 (t, 1H), 8.56 (s, 1H), 8.19-8.22 (m, 2H), 8.12 (s, 1H), 7.903-7.908 (d, 1H), 7.30-7.34 (m, 2H), 7.032-7.037 (d, 1H), 5.62-5.63 (dd, 1H), 5.28-5.31 (dd, 1H), 4.70-4.72 (d, 2H), 3.97 (s, 3H). |
| 392-En1/2 | 378.3 | U9 | 1.76 | (DMSO-$d_6$) δ ppm: 8.27-8.31 (m, 3H), 7.93 (d, 1H), 7.38-7.42 (m, 2H), 7.06 (dd, 1H), 6.58-6.66 (m, 1H), 6.12-6.17 (m, 1H), 5.66-5.69 (m, 1H), 4.50-4.62 (m, 1H), 4.00-4.07 (m, 1H), 3.98 (s, 3H), 3.85-3.90 (m, 1H), 3.50-3.78 (m, 2H), 2.44-2.24 (m, 2H). |
| 393 | 421.3 | U9 | 1.82 | (DMSO-$d_6$) δ ppm: 8.63-8.65 (d, 1H), 8.58-8.59 (t, 1H), 8.25 (s, 1H), 8.18-8.22 (m, 2H), 8.05-8.06 |

TABLE 2-continued

Analytical data for synthesized compounds of the disclosure

| Cpd. No. | $[M + H]^+$ (m/z) : | LC/MS or UPLC Method | RT (min.) | $^1$H NMR (δ ppm) |
|---|---|---|---|---|
| | | | | (d, 1H), 7.81 (s, 1H), 7.71-7.73 (m, 2H), 7.50 (s, 1H), 7.31-7.35 (t, 2H), 7.143-7.149 (d, 1H), 5.51 (s, 2H), 2.75-2.76 (d, 3H). |
| 394-En1/2 | 391.3 | L4 | 1.58 | (DMSO-$d_6$) δ ppm: 8.75 (s, 1H), 8.16-8.19 (m, 2H), 7.95-7.96 (m, 1H), 7.85-7.87 (m, 1H), 7.29-7.33 (m, 2H), 6.73-6.88 (m, 2H), 6.08-6.13 (m, 1H), 5.64-5.69 (m, 1H), 4.53- 4.56 (m, 1H), 4.10-4.20 (m, 1H), 3.89-3.92 (m, 3H), 3.48-3.51 (m, 1H), 3.15-3.21 (m, 1H), 2.64-3.0 (m, 1H), 1.79-2.06 (m, 3H), 1.38-1.41 (m, 1H). |
| 395-En1/2 | 377.3 | L4 | 1.75 | (DMSO-$d_6$) δ ppm: 8.18-8.21 (m, 2H), 7.87-7.96 (m, 2H), 7.30-7.33 (t, 2H), 6.88-6.89 (m, 1H), 6.57-6.66 (m, 1H), 6.13-6.18 (m, 1H), 5.66-5.70 (m, 1H), 4.41-4.53 (m, 1H), 3.86-4.08 (m, 4H), 3.54-3.67 (m, 2H), 3.36-3.43 (m, 1H), 2.21-2.33 (m, 1H), 2.06-2.16 (m, 1H). |
| 396-En1 | 378.3 | S18 | 5.21 | (DMSO-$d_6$) δ ppm: 8.27-8.31 (m, 3H), 7.94 (d, 1H), 7.38-7.42 (m, 2H), 7.07 (dd, 1H), 6.95-6.66 (m, 1H), 6.12-6.17 (m, 1H), 5.64-5.69 (m, 1H), 4.51-4.62 (m, 1H), 4.00-4.08 (m, 1H), 3.98 (s, 3H), 3.85-3.90 (m, 1H), 3.50-3.78 (m, 2H), 2.40-2.44 (m, 1H), 2.24-2.39 (m, 1H). |
| 396-En2 | 378.3 | S18 | 7.49 | (DMSO-$d_6$) δ ppm: 8.27-8.31 (m, 3H), 7.94 (d, 1H), 7.38-7.42 (m, 2H), 7.07 (dd, 1H), 6.95-6.66 (m, 1H), 6.12-6.17 (m, 1H), 5.64-5.69 (m, 1H), 4.51-4.62 (m, 1H), 4.00-4.08 (m, 1H), 3.98 (s, 3H), 3.85-3.90 (m, 1H), 3.50-3.78 (m, 2H), 2.40-2.44 (m, 1H), 2.24-2.39 (m, 1H). |
| 397 | 518.3 | L4 | 1.82 | (DMSO-$d_6$) δ ppm: 8.56-8.58 (t, 1H), 8.47 (s, 1H), 8.19-8.22 (m, 2H), 8.11 (s, 1H), 8.07-8.08 (d, 1H), 7.77-7.81 (d, 2H), 7.55 (s, 1H), 7.29-7.34 (t, 2H), 7.03-7.04 (d, 1H), 5.51 (s, 2H), 4.78, (s, 2H), 3.11-3.15 (t, 2H), 2.75-2.76 (d, 3H), 2.24-2.28 (t, 2H), 1.85-1.89 (t, 2H). |
| 398-En1/2 | 388.3 | U9 | 1.33 | (DMSO-$d_6$) δ ppm: 8.14-8.15 (d, 1H), 7.80 (s, 1H), 6.53-6.61 (m, 3H), 6.11-6.15 (d, 1H), 5.63-5.68 (t, 1H), 3.72-3.94 (m, 8H), 3.46-3.64 (m, 3H), 3.23-3.31 (m, 1H), 2.36-2.49 (m, 2H), 1.99-2.19 (m, 2H). |
| 399 | 362.3 | U8 | 1.79 | (DMSO-$d_6$) δ ppm: 8.44 (s, 1H), 8.10 (s, 1H), 8.03-8.07 (m, 2H), 7.83 (d, 1H), 7.27-7.31 (m, 2H), 7.06 (d, 1H), 3.95 (s, 3H), 3.00-3.09 (m, 3H), 2.86-2.90 (m, 2H), 1.99-2.03 (m, 2H), 1.83-1.90 (m, 2H). |
| 400 | 415.2 | L4 | 1.73 | (DMSO-$d_6$) δ ppm: 9.0 (t, 1H), 8.59 (s, 1H), 8.19-8.23 (m, 2H), 8.15 (s, 1H), 7.92 (d, 1H), 7.30-7.35 (m, 2H), 7.09 (d, 1H), 6.77 (d, 1H), 6.18 (d, 1H), 4.65 (d, 2H), 4.00 (s, 3H). |
| 401-En1 | 366.3 | S19 | 4.01 | (DMSO-$d_6$) δ ppm: 7.80-7.85 (m, 3H), 7.21-7.25 (m, 2H), 7.04 (s, 1H), 6.55-6.70 (m, 2H), 6.12-6.18 (m, 1H), 5.65-5.85 (m, 2H), 3.53-4.10 (m, 7H), 2.32-2.50 (m, 2H). |
| 401-En2 | 366.3 | S19 | 4.88 | (DMSO-$d_6$) δ ppm: 7.80-7.85 (m, 3H), 7.21-7.25 (m, 2H), 7.04 (s, 1H), 6.55-6.70 (m, 2H), 6.12-6.18 (m, 1H), 5.65-5.85 (m, 2H), 3.53-4.10 (m, 7H), 2.32-2.50 (m, 2H). |
| 402 | 374.2 | L4 | 1.94 | (DMSO-$d_6$) δ ppm: 10.83 (s, 1H), 10.31 (s, 1H), 8.57 (s, 1H), 8.25 (s, 1H), 8.18-8.21 (m, 2H), 7.69 (d, 1H), 7.64 (d, 1H), 7.34-7.38 (m, 2H), 6.94 (s, 1H), 6.90 (d, 1H), 5.76 (d, 1H), 3.87 (s, 3H). |
| 403-En1/2 | 366.3 | L4 | 1.85 | (DMSO-$d_6$) δ ppm: 8.74 (d, 1H), 7.84-7.88 (m, 2H), 7.72 (d, 1H), 7.31-7.36 (m, 2H), 6.56-6.70 (m, 1H), 6.49-6.50 (m, 1H), 6.14 (dd, 1H), 5.63-5.68 (m, 1H), 3.97-4.06 (m, 1H), 3.77-3.97 (m, 5H), 3.64-3.70 (m, 1H), 3.43-3.59 (m, 1H), 2.07-2.39 (m, 2H). |
| 404-En1/2 | 366.3 | L4 | 1.78 | (DMSO-$d_6$) δ ppm: 8.73 (d, 1H), 8.80-8.91 (m, 2H), 7.50 (s, 1H), 7.30-7.39 (m, 2H), 6.54-6.62 (m, 1H), 6.43 (dd, 1H), 6.14 (dd, 1H), 5.62-5.67 (m, 1H), 3.70-3.96 (m, 5H), 3.52-3.66 (m, 2H), 3.32-3.51 (m, 1H), 1.98-2.32 (m, 2H). |
| 405-En1/2 | 393.3 | L4 | 1.58 | (DMSO-$d_6$) δ ppm: 8.81 (d, 1H), 8.19-8.22 (m, 2H), 7.94-7.99 (m, 2H), 7.31-7.35 (m, 2H), 6.92 (dd, 1H), 6.36-6.63 (m, 1H), 6.10 (dd, 1H), 5.64- |

TABLE 2-continued

Analytical data for synthesized compounds of the disclosure

| Cpd. No. | [M + H]+ (m/z) : | LC/MS or UPLC Method | RT (min.) | $^1$H NMR (δ ppm) |
|---|---|---|---|---|
| | | | | 5.67 (m, 1H), 3.93 (d, 3H), 3.67-3.79 (m, 3H), 3.53 (m, 1H), 3.40-3.43 (m, 1H), 2.159-2.435 (m, 2H). |
| 406-En1/2 | 424.3 | L4 | 1.64 | (DMSO-$d_6$) δ ppm: 8.19-8.24 (d, 1H), 7.82 (s, 1H), 6.71 (s, 1H), 6.63-6.66 (d, 1H), 6.52-6.60 (m, 1H), 6.11-6.16 (d, 1H), 5.62-5.68 (t, 1H), 4.13-4.18 (t, 4H), 3.51-3.96 (m, 7H), 3.25-3.27 (m, 1H), 2.11-2.32 (m, 2H). |
| 407-En1/2 | 388.3 | L4 | 1.34 | (DMSO-$d_6$) δ ppm: 8.13-8.18 (d, 1H), 7.80 (s, 1H), 6.52-6.63 (m, 3H), 6.10-6.65 (dd, 1H), 5.62-5.68 (t, 1H), 5.47-5.49 (m, 2H), 3.79-3.89 (m, 6H), 3.56-3.65 (m, 6H), 2.02-2.18 (m, 2H). |
| 408-En1/2 | 388.3 | U9 | 1.23 | (DMSO-$d_6$) δ ppm: 8.13-8.18 (d, 1H), 7.80-7.81 (d, 1H), 6.53-6.62 (m, 3H), 6.11-6.15 (m, 1H), 5.65-5.68 (m, 1H), 5.41-5.52 (m, 2H), 3.90 (s, 4H), 3.67-3.86 (m, 6H), 3.51-3.62 (m, 1H), 3.23-3.49 (m, 1H), 2.11-2.12 (m, 2H). |
| 409 | 379.2 | U12 | 9.53 | (DMSO-$d_6$) δ ppm: 8.77 (s, 1H), 8.19-8.22 (m, 2H), 8.07 (s, 1H), 7.92 (d, 1H), 7.31-7.36 (m, 2H), 6.97 (d, 1H), 6.66 (s, 1H), 6.26 (dd, 1H), 6.05 (dd, 1H), 5.63 (dd, 1H), 4.54 (d, 1H), 4.31 (d, 1H), 4.16 (d, 1H), 3.97-4.00 (m, 4H). |
| 410 | 366.1 | U9 | 1.94 | (DMSO-$d_6$) δ ppm: 8.50 (t, 1H), 7.73 (d, 1H), 7.51-7.54 (m, 2H), 7.45 (s, 1H), 7.23 (t, 2H), 7.08 (s, 1H), 6.52 (d, 1H), 6.31-6.38 (m, 1H), 6.13 (dd, 1H), 5.62 (dd, 1H), 4.60 (d, 2H), 3.89 (s, 3H), 3.76 (s, 3H). |
| 411 | 349.3 | U8 | 1.61 | (DMSO-$d_6$) δ ppm: 8.33 (s, 1H), 8.18-8.21 (m, 2H), 8.12 (s, 1H), 7.882-7.888 (d, 1H), 7.29-7.34 (m, 3H), 6.98-6.99 (d, 1H), 6.17-6.20 (m, 1H), 4.98 (s, 2H), 4.02 (s, 2H), 3.96 (s, 3H). |
| 412 | 367.3 | U9 | 1.45 | (DMSO-$d_6$) δ ppm: 8.67 (s, 1H), 8.20-8.24 (m, 2H), 8.14 (s, 1H), 7.87-7.88 (d, 1H), 7.30-7.35 (t, 2H), 7.05-7.06 (d, 1H), 5.95-5.96 (d, 1H), 5.52 (s, 1H), 4.08 (s, 2H), 3.97 (s, 3H), 3.49 (s, 2H). |
| 413-En1/2 | 297.2 | U9 | 1.16 | (DMSO-$d_6$) δ ppm: 8.51 (s, 1H), 7.82-7.83 (s, 1H), 7.35 (s, 1H), 6.54-6.64 (m, 2H), 6.11-6.17 (dd, 1H), 5.63-5.69 (t, 1H), 3.96-4.10 (m, 2H), 3.90-3.91 (m, 3H), 3.74-3.82 (m, 1H), 3.55-3.67 (m, 1H), 3.32-3.40 (m, 1H), 2.49-2.50 (s, 3H), 2.05-2.28 (m, 2H). |
| 414-En1/2 | 377.2 | U9 | 1.83 | (DMSO-$d_6$): δ 8.28-8.21 (m, 1H), 8.08-8.06 (m, 1H), 784-7.82 (m, 3H), 7.35-7.31 (m, 2H), 7.72-7.70 (dd, 1H), 6.64-6.57 (m, 1H), 6.15-6.11 (dd, 1H), 5.67-5.63 (m, 1H), 4.31-4.18 (m, 1H), 3.99-3.78 (m, 5H), 3.68-3.38 (m, 2H), 2.31-2.16 (m, 2H). |
| 415-En1/2 | 377.2 | U9 | 1.49 | (DMSO-$d_6$) δ ppm: 8.71 (s, 1H), 8.16-8.19 (m, 2H), 7.98 (s, 1H), 7.87 (d, 1H), 7.29-7.33 (m, 2H), 6.82 (dd, 1H), 6.56-6.66 (m, 1H), 6.13-6.18 (m, 1H), 5.64-5.71 (m, 1H), 3.79-4.17 (m, 5H), 3.32-3.71 (m, 3H), 2.10-2.35 (m, 2H). |
| 416-En1/2 | 366.3 | U9 | 1.91 | (DMSO-$d_6$) δ ppm: 7.80-7.85 (m, 3H), 7.21-7.26 (m, 2H), 7.03 (s, 1H), 6.55-6.70 (m, 2H), 6.12-6.18 (m, 1H), 5.69-5.86 (m, 2H), 3.54-4.10 (m, 7H), 2.33-2.50 (m, 2H). |
| 417-En1/2 | 423.3 | U9 | 1.79 | (DMSO-$d_6$) δ ppm: 8.90-8.96 (d, 1H), 8.30-8.32 (m, 1H), 8.19-8.22 (t, 2H), 7.34-7.38 (t, 2H), 6.59-6.68 (m, 1H), 6.14-6.20 (dd, 1H), 5.69-5.72 (m, 1H), 4.07-4.20 (m, 1H), 3.92-3.97 (m, 1H), 3.66-3.85 (m, 4H), 3.42-3.53 (m, 1H), 3.27-3.33 (m, 3H), 3.24-3.26 (m, 2H), 2.30-2.35 (m, 2H). |
| 418 | 435.3 | U8 | 1.85 | (DMSO-$d_6$) δ ppm: 8.57-8.58 (d, 1H), 8.53 (s, 1H), 8.13-8.18 (m, 2H), 8.08 (s, 1H), 8.052-8.058 (d, 1H), 7.81-7.82 (t, 1H), 7.775-7.779 (d, 1H), 7.52-7.53 (t, 1H), 7.27-7.33 (t, 2H), 6.95-6.96 (d, 1H), 5.51 (s, 2H), 2.75-2.77 (d, 3H), 2.49 (s, 3H). |
| 419 | 508.3 | U8 | 1.65 | (DMSO-$d_6$) δ ppm: 8.55-8.58 (m, 2H), 8.18-8.22 (q, 2H), 8.11 (s, 1H), 8.080-8.086 (d, 1H), 7.78-7.82 (s, 2H), 7.54 (s, 1H), 7.40-7.42 (m, 1H), 7.29-7.34 (t, 2H), 7.082-7.087 (d, 1H), 5.53 (s, 2H), 4.49-4.51 (d, 2H), 3.53 (s, 3H), 2.75-2.76 (d, 3H). |

TABLE 2-continued

| Cpd. No. | [M + H]+ (m/z) : | LC/MS or UPLC Method | RT (min.) | $^1$H NMR (δ ppm) |
|---|---|---|---|---|
| Analytical data for synthesized compounds of the disclosure | | | | |
| 420-En1 | 377.3 | S3 | 11.86 | (DMSO-$d_6$): 8.82-8.21 (m, 1H), 8.08-8.06 (m, 1H), 7.85-7.81 (m, 3H), 7.33 (t, 2H), 6.72-6.70 (m, 1H), 6.65-6.56 (m, 1H), 6.16-6.11 (dd, 1H), 5.68-5.62 (m, 1H), 4.29-4.16 (m, 1H), 4.00-3.77 (m, 5H), 3.70-3.45 (m, 2H), 2.36-2.27 (m, 1H), 2.24-212 (m, 1H). |
| 420-En2 | 377.2 | S3 | 18.02 | (DMSO-$d_6$): 8.82-8.21 (m, 1H), 8.08-8.06 (m, 1H), 7.85-7.81 (m, 3H), 7.33 (t, 2H), 6.72-6.70 (m, 1H), 6.65-6.56 (m, 1H), 6.16-6.11 (dd, 1H), 5.68-5.62 (m, 1H), 4.29-4.16 (m, 1H), 4.00-3.77 (m, 5H), 3.70-3.45 (m, 2H), 2.36-2.27 (m, 1H), 2.24-212 (m, 1H). |
| 421-En1/2 | 366.3 | U9 | 1.34 | (DMSO-$d_6$) δ ppm: 8.06-8.12 (s, 1H), 7.78 (s, 1H), 6.52-6.62 (m, 2H), 6.41 (s, 1H), 6.10-6.15 (m, 1H), 5.62-5.68 (t, 1H), 3.79-3.82 (m, 4H), 3.69-3.75 (m, 2H), 3.60-3.62 (m, 1H), 3.56-3.59 (m, 1H), 3.32-3.55 (m, 2H), 3.16-3.23 (m, 1H), 2.89-2.94 (t, 1H), 2.30-2.35 (m, 1H), 2.16-2.19 (m, 3H), 1.53-1.58 (m, 1H), 1.23 (s, 2H), 1.06-1.08 (d, 3H). |
| 422-En1/2 | 420.3 | U9 | 1.37 | (DMSO-$d_6$) δ ppm: 8.11-8.17 (d, 1H), 7.79-7.80 (d, 1H), 6.52-6.63 (m, 3H), 6.10-6.15 (m, 1H), 5.62-5.68 (m, 1H), 3.68-3.94 (m, 7H), 3.36-3.63 (m, 5H), 3.22-3.27 (m, 1H), 1.98-2.32 (m, 4H). |
| 423-En1/2 | 364.3 | U8 | 1.23 | (DMSO-$d_6$) δ ppm: 7.85-7.94 (m, 2H), 6.74-6.94 (m, 2H), 6.52-6.63 (m, 1H), 6.11-6.16 (d, 1H), 5.64-5.69 (t, 1H), 3.91-3.98 (m, 5H), 3.70-3.76 (m, 3H), 3.56-3.62 (m, 1H), 3.40-3.52 (m, 2H), 3.27-3.32 (m, 1H), 1.93-2.23 (m, 2H), 1.75-1.76 (m, 2H), 1.22-1.25 (m, 4H). |
| 424-En1/2 | 354.3 | U9 | 1.30 | (DMSO-$d_6$) δ ppm: 8.10 (d, 1H), 7.78 (d, 1H), 6.52-6.62 (m, 3H), 6.12 (dd, 1H), 5.62-5.68 (m, 1H), 3.71-3.89 (m, 6H), 3.52-3.60 (m, 1H), 3.44-3.48 (t, 2H), 3.20-3.25 (m, 1H), 2.98 (s, 3H), 1.95-2.14 (m, 2H), 1.50-1.56 (m, 2H), 0.85 (t, 3H). |
| 425 | 407.3 | U9 | 1.70 | (DMSO-$d_6$) δ ppm: 8.92 (d, 1H), 8.16- 8.20 (m, 2H), 7.88 (d, 1H), 7.84 (s, 1H), 7.29-7.33 (m, 2H), 6.74-6.81 (m, 2H), 6.26 (s, 1H), 6.09 (dd, 1H), 5.64 (dd, 1H), 4.25 (d, 1H), 3.86-3.88 (m, 4H), 3.45 (t, 1H), 3.04 (t, 1H), 2.00-2.08 (m, 2H), 1.68-1.71 (m, 2H). |
| 426-En1 | 377.3 | S5 | 6.91 | (DMSO-$d_6$) δ ppm: 8.18-8.21 (m, 2H), 7.80-7.96 (m, 2H), 7.80 (s, 1H), 7.30-7.33 (t, 2H), 6.87-6.89 (m, 1H), 6.57-6.66 (m, 1H), 6.13-6.18 (m, 1H), 5.64-5.70 (m, 1H), 4.40-4.51 (m, 1H), 3.85-4.08 (m, 4H), 3.54-3.67 (m, 2H), 3.36-3.43 (m, 1H), 2.21-2.33 (m, 1H), 2.06-2.16 (m, 1H). |
| 426-En2 | 377.3 | S5 | 9.30 | (DMSO-$d_6$) δ ppm: 8.17-8.21 (m, 2H), 7.88-7.96 (m, 2H), 7.80 (s, 1H), 7.30-7.33 (t, 2H), 6.87-6.89 (m, 1H), 6.57-6.66 (m, 1H), 6.13-6.18 (m, 1H), 5.64-5.70 (m, 1H), 4.40-4.51 (m, 1H), 3.85-4.08 (m, 4H), 3.54-3.67 (m, 2H), 3.35-3.43 (m, 1H), 2.06-2.49 (m, 2H). |
| 427-En1/2 | 378.3 | U9 | 1.37 | (DMSO-$d_6$) δ ppm: 8.07-8.12 (s, 1H), 7.77-7.78 (s, 1H), 6.52-6.62 (m, 2H), 6.42 (s, 1H), 6.10-6.15 (d, 1H), 5.62-5.67 (t, 1H), 3.89 (m, 6H), 3.46-3.56 (m, 4H), 3.23-3.26 (m, 2H), 1.94-2.17 (m, 2H), 1.86-1.90 (t, 2H), 0.60-0.62 (d, 4H), |
| 428 | 391.3 | U9 | 1.71 | (DMSO-$d_6$) δ ppm: 8.65 (s, 1H), 8.13-8.17 (m, 2H), 7.95 (s, 1H), 7.87 (d, 1H), 7.28-7.33 (m, 2H), 6.86 (dd, 1H), 6.80 (d, 1H), 6.11 (dd, 1H), 5.68 (dd, 1H), 4.60-4.63 (m, 1H), 4.18-4.22 (m, 1H), 3.95 (s, 3H), 3.62-3.68 (m, 1H), 3.07-3.16 (m, 1H), 2.66-2.67 (m, 1H), 1.87-1.90 (m, 2H), 1.66-1.76 (m, 2H). |
| 429-En1/2 | 365.3 | U10 | 5.02 | (DMSO-$d_6$) δ ppm: 8.17-8.21 (m, 2H), 7.87-7.96 (m, 2H), 7.79-7.80 (t, 1H), 7.29-7.33 (m, 2H), 6.86-6.88 (m, 1H), 4.37-4.50 (m, 1H), 3.75-3.94 (m, 4H), 3.44-3.64 (m, 2H), 3.25-3.34 (m, 1H), 2.10-2.13 (m, 1H), 2.01-2.03 (m, 1H), 1.96-1.98 (d, 3H). |
| 430-En1/2 | 380.4 | U10 | 4.08 | (DMSO-$d_6$) δ ppm: 8.06-8.11 (d, 1H), 7.782-7.788 (d, 1H), 6.52-6.62 (m, 2H), 6.40 (s, 1H), |

TABLE 2-continued

Analytical data for synthesized compounds of the disclosure

| Cpd. No. | [M + H]+ (m/z) : | LC/MS or UPLC Method | RT (min.) | $^1$H NMR (δ ppm) |
|---|---|---|---|---|
| | | | | 6.10-6.15 (m, 1H), 5.62-5.68 (m, 1H), 3.71-3.91 (m, 6H), 3.52-3.60 (m, 1H), 3.44-3.47 (t, 2H), 3.16-3.28 (m, 3H), 1.94-2.20 (m, 2H), 1.72-1.76 (t, 2H), 1.09 (s, 6H). |
| 431-En1/2 | 414.3 | U9 | 1.37 | (DMSO-$d_6$) δ ppm: 7.86-7.94 (m, 2H), 6.92-6.96 (m, 1H), 6.81 (br. s, 1H), 6.54-6.62 (m, 1H), 6.12-6.17 (d, 1H), 5.64-5.70 (t, 1H), 3.93-3.99 (m, 5H), 3.51-3.77 (m, 7H), 2.07-2.27 (m, 4H), 1.69-1.73 (m, 2H). |
| 432-En1/2 | 378.3 | U9 | 1.35 | (DMSO-$d_6$) δ ppm: 8.12-8.17 (t, 2H), 7.94-7.98 (s, 1H), 6.53-6.62 (m, 3H), 6.11-6.15 (d, 1H), 5.63-5.68 (t, 1H), 3.89-3.92 (m, 4H), 3.73-3.75 (m, 1H), 3.64-3.67 (m, 2H), 3.48-3.61 (m, 2H), 3.24-3.31 (m, 1H), 3.15-3.19 (m, 2H), 3.00 (m, 2H), 2.09-2.36 (m, 4H), 1.69-1.70 (m, 2H). |
| 433-En1/2 | 392.3 | U9 | 1.40 | (DMSO-$d_6$) δ ppm: 8.08-8.13 (d, 1H), 7.78 (s, 1H), 6.52-6.61 (m, 2H), 6.48 (s, 1H), 6.10-6.15 (d, 1H), 5.62-5.67 (t, 1H), 3.89-3.91 (m, 4H), 3.71-3.74 (m, 2H), 3.53-3.57 (m, 3H), 3.21-3.29 (m, 1H), 3.15-3.18 (m, 2H), 2.72-2.73 (m, 2H), 1.81-2.08 (m, 2H), 1.78-1.80 (m, 2H), 1.67-1.68 (m, 1H), 1.55-1.57 (m, 1H), 1.44-1.47 (m, 2H). |
| 434-En1/2 | 395.1 | U9 | 1.96 | (DMSO-$d_6$): δ 7.84-7.76 (m, 2H), 6.77-6.74 (m, 2H), 6.65-6.54 (m, 1H), 6.17-6.11 (m, 1H), 5.6-5.62 (m, 1H), 4.54-4.36 (m, 3H), 4.02-3.61 (m, 6H), 3.58-3.36 (m, 1H), 2.85-2.74 (m, 2H), 2.15-2.12 (m, 1H), 2.10-1.98 (m, 1H). |
| 435-En1/2 | 417.2 | U10 | 4.92 | (DMSO-$d_6$) δ ppm: 8.67 (d, 1H), 8.11-8.15 (m, 2H), 7.98 (d, 1H), 7.86 (dd, 1H), 7.31-7.36 (m, 2H), 6.70-6.93 (m, 2H), 6.14-6.23 (m, 1H), 5.70 (dd, 1H), 4.33-4.65 (m, 3H), 3.89-3.97 (d, 3H), 3.41-3.47 (m, 1H), 2.50-2.33 (m, 1H), 1.57-2.04 (m, 7H). |
| 436-En1/2 | 378.1 | U9 | 1.99 | (DMSO-$d_6$) δ ppm: 8.92 (d, 1H), 8.48-8.52 (m, 2H), 7.90 (d, 1H), 7.34-7.38 (m, 2H), 7.16 (t, 1H), 6.57-6.68 (m, 1H), 6.14-6.19 (m, 1H), 5.65-5.72 (m, 1H), 4.50-4.63 (m, 1H), 3.84-4.93 (m, 4H), 3.64-3.83 (m, 1H), 2.14-2.43 (m, 2H). |
| 437-En1/2 | 391.3 | U10 | 5.02 | (DMSO-$d_6$) δ ppm: 8.83 (s, 1H), 8.16-8.22 (m, 2H), 7.94-7.98 (m, 1H), 7.86 (d, 1H), 7.29-7.34 (m, 2H), 6.77-6.82 (m, 1H), 6.55-6.67 (m, 1H), 6.10-6.18 (m, 1H), 5.62-5.71 (m, 1H), 3.89-4.23 (m, 6H), 3.39-3.66 (m, 1H), 2.46-2.67 (m, 1H), 1.81-1.89 (m, 1H), 1.31-1.34 (m, 3H). |
| 438-En1/2 | 408.2 | U9 | 1.41 | (DMSO-$d_6$) δ ppm: 8.14-8.20 (d, 1H), 7.802-7.807 (d, 1H), 6.53-6.62 (m, 3H), 6.11-6.15 (d, 1H), 5.63-5.69 (m, 1H), 3.81-3.92 (m, 7H), 3.73-3.79 (m, 2H), 3.17-3.32 (m, 1H), 3.00 (s, 3H), 2.50-2.57 (m, 2H), 1.98-2.20 (m, 2H). |
| 439-En1/2 | 395.1 | U9 | 1.83 | (DMSO-$d_6$) δ ppm: 8.18-8.25 (d, 1H), 7.822-7.827 (d, 1H), 6.69-6.90 (d, 1H), 6.66-6.68 (m, 1H), 6.53-6.64 (m, 1H), 6.11-6.16 (m, 1H), 5.63-5.69 (m, 1H), 4.48-4.51 (m, 2H), 3.95-4.06 (m, 2H), 3.90 (s, 3H), 3.76-3.81 (m, 1H), 3.52-3.62 (m, 1H), 3.29-3.37 (m, 1H), 2.74-2.83 (s, 2H), 2.03-2.49 (m, 2H). |
| 439-En1 | 395.3 | S7 | 1.35 | (DMSO-$d_6$) δ ppm: 8.21 (d, 1H), 7.82 (d, 1H), 6.90 (d, 1H), 6.66-6.68 (m, 1H), 6.53-6.64 (m, 1H), 6.11-6.16 (m, 1H), 5.63-5.69 (m, 1H), 4.48-4.51 (m, 2H), 3.95-4.06 (m, 2H), 3.90 (s, 3H), 3.76-3.81 (m, 1H), 3.52-3.62 (m, 1H), 3.29-3.37 (m, 1H), 2.74-2.83 (m, 2H), 2.03-2.49 (m, 2H). |
| 439-En2 | 395.3 | S7 | 2.21 | (DMSO-$d_6$) δ ppm: 8.21 (d, 1H), 7.82 (d, 1H), 6.90 (d, 1H), 6.66-6.68 (m, 1H), 6.53-6.64 (m, 1H), 6.11-6.16 (m, 1H), 5.63-5.69 (m, 1H), 4.48-4.51 (m, 2H), 3.95-4.06 (m, 2H), 3.90 (s, 3H), 3.76-3.81 (m, 1H), 3.52-3.62 (m, 1H), 3.29-3.37 (m, 1H), 2.74-2.83 (m, 2H), 2.03-2.49 (m, 2H). |
| 440-En1/2 | 353.4 | U9 | 1.42 | (DMSO-$d_6$) δ ppm: 8.56 (d, 1H), 7.82 (d, 1H), 7.28 (s, 1H), 6.54-6.64 (m, 2H), 6.11-6.17 (m, 1H), 5.63-5.69 (m, 1H), 3.57-4.04 (m, 7H), 3.33-3.38 (m, 1H), 2.83-2.89 (m, 1H), 2.15-2.20 (m, 2H), 1.47-1.69 (m, 2H), 1.11-1.23 (m, 5H), 0.83 (t, 3H). |

TABLE 2-continued

| Cpd. No. | [M + H]+ (m/z) : | LC/MS or UPLC Method | RT (min.) | $^1$H NMR (δ ppm) |
|---|---|---|---|---|
| Analytical data for synthesized compounds of the disclosure | | | | |
| 441-En1/2 | 378.4 | U9 | 1.38 | (DMSO-$d_6$) δ ppm: 8.10 (d, 1H), 7.79 (d, 1H), 6.52-6.62 (m, 2H), 6.37 (s, 1H), 6.10-6.15 (m, 1H), 5.62-5.68 (m, 1H), 3.69-3.94 (m, 10H), 3.42-3.63 (m, 1H), 3.21-3.39 (m, 1H), 1.97-2.18 (m, 6H), 1.77-1.84 (m, 2H). |
| 442-En1/2 | 446.2 | U9 | 1.50 | (DMSO-$d_6$) δ ppm: 8.07-8.13 (d, 1H), 7.79-7.80 (d, 1H), 6.52-6.62 (m, 2H), 6.41 (s, 1H), 6.10-6.15 (m, 1H), 5.62-5.68 (m, 1H), 3.81-3.98 (m, 8H), 3.70-3.75 (m, 1H), 3.46-3.60 (m, 2H), 3.21-3.26 (m, 1H), 3.03-3.16 (m, 1H), 2.49-2.50 (m, 2H), 2.27-2.32 (m, 2H), 1.94-2.19 (m, 2H). |
| 443-En1/2 | 365.2 | U9 (at 50° C.) | 1.64 | (DMSO-$d_6$) δ ppm: 8.71 (d, 1H), 8.15-8.19 (m, 2H), 7.97 (d, 1H), 7.87 (t, 1H), 7.29-7.33 (m, 2H), 6.81 (dd, 1H), 4.06-4.19 (m, 1H), 3.94-3.95 (d, 3H), 3.35-3.90 (m, 3H), 3.26-3.31 (m, 1H), 2.17-2.33 (m, 2H), 1.97 (d, 3H). |
| 444-En1 | 377.1 | S4 | 15.61 | (DMSO-$d_6$) δ ppm: 8.71 (s, 1H), 8.16-8.19 (m, 2H), 7.98 (s, 1H), 7.87 (d, 1H), 7.29-7.33 (m, 2H), 6.82 (dd, 1H), 6.56-6.66 (m, 1H), 6.13-6.18 (m, 1H), 5.67-5.71 (m, 1H), 4.02-4.19 (m, 1H), 3.94 (s, 3H), 3.81-3.88 (m, 1H), 3.61-3.69 (m, 1H), 3.32-3 46 (m, 1H), 2.14-2.33 (m, 2H). |
| 444-En2 | 377.1 | S4 | 22.45 | (DMSO-$d_6$) δ ppm: 8.71 (s, 1H), 8.16-8.19 (m, 2H), 7.98 (s, 1H), 7.87 (d, 1H), 7.29-7.33 (m, 2H), 6.82 (dd, 1H), 6.56-6.66 (m, 1H), 6.13-6.18 (m, 1H), 5.67-5.71 (m, 1H), 4.02-4.19 (m, 1H), 3.94 (s, 3H), 3.81-3.88 (m, 1H), 3.61-3.69 (m, 1H), 3.32-3 46 (m, 1H), 2.14-2.33 (m, 2H). |
| 445-En1 | 424.2 | S9 | 3.81 | (DMSO-$d_6$) δ ppm: 8.19-8.24 (d, 1H), 7.82 (s, 1H), 6.71 (s, 1H), 6.63-6.66 (m, 1H), 6.52-6.60 (m, 1H), 6.11-6.16 (d, 1H), 5.62-5.68 (m, 1H), 4.12-4.19 (m, 4H), 3.49-3.98 (m, 7H), 3.25-3.37 (m, 1H), 1.97-2.24 (m, 2H). |
| 445-En2 | 424.1 | S9 | 5.64 | (DMSO-$d_6$) δ ppm: 8.19-8.24 (d, 1H), 7.82 (s, 1H), 6.71 (s, 1H), 6.63-6.66 (m, 1H), 6.52-6.60 (m, 1H), 6.11-6.16 (d, 1H), 5.62-5.68 (m, 1H), 4.12-4.18 (m, 4H), 3.51-3.98 (m, 7H), 3.25-3.37 (m, 1H), 1.97-2.22 (m, 2H). |
| 446-En1/2 | 414.4 | U9 | 1.38 | (DMSO-$d_6$) δ ppm: 8.12 (d, 1H), 7.80 (d, 1H), 6.52-6.62 (m, 2H), 6.43 (s, 1H), 6.10-6.15 (m, 1H), 5.62-5.68 (m, 1H), 4.03 (s, 4H), 3.89-3.94 (m, 4H), 3.70-3.85 (m, 2H), 3.53-3.61 (m, 1H), 3.22-3.27 (m, 1H), 2.81-2.88 (t, 4H), 1.95-2.10 (m, 2H). |
| 447-En1/2 | 364.2 | U9 | 1.29 | (DMSO-$d_6$) δ ppm: 8.10 (d, 1H), 7.79 (d, 1H), 6.52-6.62 (m, 3H), 6.10-6.15 (m, 1H), 5.62-5.68 (m, 1H), 4.71 (d, 1H), 3.49-3.95 (m, 7H), 3.31-3.47 (m, 3H), 2.90-2.92 (m, 1H), 2.04-2.20 (m, 2H), 1.91-2.01 (m, 2H), 1.26-1.32 (m, 2H). |
| 448-En1 | 378.1 | S20 | 5.81 | (DMSO-$d_6$) δ ppm: 8.92 (d, 1H), 8.48-8.52 (m, 2H), 7.90 (d, 1H), 7.34-7.38 (m, 2H), 7.16 (t, 1H), 6.57-6.68 (m, 1H), 6.14-6.19 (m, 1H), 5.65-5.72 (m, 1H), 4.50-4.63 (m, 1H), 3.84-4.93 (m, 4H), 3.64-3.83 (m, 1H), 2.14-2.43 (m, 2H). |
| 448-En2 | 378.1 | S20 | 11.39 | (DMSO-$d_6$) δ ppm: 8.92 (d, 1H), 8.48-8.52 (m, 2H), 7.90 (d, 1H), 7.34-7.38 (m, 2H), 7.16 (t, 1H), 6.57-6.68 (m, 1H), 6.14-6.19 (m, 1H), 5.65-5.72 (m, 1H), 4.50-4.63 (m, 1H), 3.84-4.93 (m, 4H), 3.64-3.83 (m, 1H), 2.14-2.43 (m, 2H). |
| 449-En1/2 | 395.1 | U9 | 1.90 | (DMSO-$d_6$) δ ppm: 8.90-8.92 (m, 1H), 8.20-8.23 (m, 2H), 7.96 (d, 1H), 7.85-7.86 (m, 1H), 7.32-7.35 (m, 2H), 6.40-6.68 (m, 2H), 6.14-6.18 (m, 1H), 5.70-5.72 (m, 1H), 4.14-4.23 (m, 1H), 3.89-3.95 (m, 1H), 3.88 (d, 1H), 3.68-3.82 (m, 1H), 3.44-3.50 (m, 1H), 3.44-3.50 (m, 1H), 2.632-2.639 (m, 1H). |
| 450-En1/2 | 401.4 | U9 | 1.47 | (DMSO-$d_6$) δ ppm: 8.58 (d, 1H), 7.85 (d, 1H), 7.42 (s, 1H), 6.70 (s, 1H), 6.54-6.64 (m, 1H), 6.12-6.17 (m, 1H), 5.65-5.69 (m, 1H), 3.98-4.02 (m, 2H), 3.92 (d, 3H), 3.79-3.84 (m, 1H), 3.58-3.65 (m, 2H), 2.90 (s, 1H), 1.90-2.20 (m, 8H), 1.80-1.85 (m, 2H). |
| 451-En1/2 | 400.3 | U9 | 1.34 | (DMSO-$d_6$) δ ppm: 8.13 (d, 1H), 7.80 (d, 1H), 6.52-6.62 (m, 2H), 6.46 (s, 1H), 6.10-6.15 (m, |

TABLE 2-continued

Analytical data for synthesized compounds of the disclosure

| Cpd. No. | [M + H]+ (m/z) : | LC/MS or UPLC Method | RT (min.) | $^1$H NMR (δ ppm) |
|---|---|---|---|---|
| | | | | 1H), 5.62-5.68 (m, 1H), 3.89-3.91 (m, 4H), 3.75-3.80 (m, 2H), 3.65-3.72 (m, 3H), 3.51-3.62 (m, 2H), 3.21-3.28 (m, 1H), 2.64-2.67 (d, 2H), 1.98-2.20 (m, 2H). |
| 452-En1 | 395.3 | S6 | 3.33 | (DMSO-$d_6$) δ ppm: 7.82-7.84 (d, 1H), 7.74-7.78 (m, 1H), 6.74-6.78 (m, 2H), 6.54-6.65 (m, 1H), 6.11-6.17 (dd, 1H), 5.62-5.69 (m, 1H), 4.36-4.54 (m, 3H), 3.30-3.94 (m, 7H), 2.64-2.65 (m, 2H), 1.92-2.2 (m, 2H). |
| 452-En2 | 395.2 | S6 | 4.05 | (DMSO-$d_6$) δ ppm: 7.82-7.84 (d, 1H), 7.76-7.78 (m, 1H), 6.74-6.78 (m, 2H), 6.54-6.65 (m, 1H), 6.11-6.17 (dd, 1H), 5.62-5.69 (m, 1H), 4.36-4.54 (m, 3H), 3.30-3.94 (m, 7H), 2.64-2.65 (m, 2H), 1.98-2.2 (m, 2H). |
| 453-En1/2 | 363.2 | U9 | 1.38 | (DMSO-$d_6$) δ ppm: 8.52 (d, 1H), 7.82 (d, 1H), 7.26 (s, 1H), 6.53-6.64 (m, 2H), 6.11-6.17 (m, 1H), 5.63-5.69 (m, 1H), 3.90-4.00 (m, 5H), 3.77-3.82 (m, 1H), 3.58-3.63 (m, 3H), 3.34-3.39 (m, 1H), 2.04-2.32 (m, 6H), 1.31-1.33 (m, 2H), 0.42-0.47 (m, 1H), 0.19-0.20 (m, 1H). |
| 454-En1/2 | 433.2 | U9 | 2.06 | (DMSO-$d_6$) δ ppm: 8.65 (d, 1H), 8.13 (d, 1H), 7.99-8.00 (m, 1H), 7.89 (d, 2H), 7.75 (d, 1H), 6.83-6.85 (m, 1H), 6.55-6.66 (m, 1H), 6.12-6.18 (m, 1H), 5.64-5.70 (m, 1H), 4.10-4.22 (m, 1H), 3.81-4.08 (m, 4H), 3.58-3.80 (m, 2H), 3.34-3.45 (m, 1H), 2.12-2.36 (m, 2H). |
| 455-En1 | 393.3 | S21 | 2.33 | (DMSO-$d_6$) δ ppm: 8.83 (s, 1H), 8.18 (dd, 2H), 7.94-7.96 (m, 1H), 7.86 (d, 1H), 7.31 (dd, 2H), 6.76-6.82 (m, 1H), 6.55-6.67 (m, 1H), 6.10-6.18 (m, 1H), 5.62-5.68 (m, 1H), 4.05-4.25 (m, 2H), 3.91-4.01 (m, 4H), 3.61-3.66 (m, 1H), 3.31-3.42 (m, 1H), 2.49-2.67 (m, 1H), 1.81-1.91 (m, 1H), 1.23-1.34 (m, 3H). |
| 455-En2 | 393.3 | S21 | 4.68 | (DMSO-$d_6$) δ ppm: 8.83 (s, 1H), 8.18 (dd, 2H), 7.94-7.96 (m, 1H), 7.86 (d, 1H), 7.31 (dd, 2H), 6.76-6.82 (m, 1H), 6.55-6.67 (m, 1H), 6.10-6.18 (m, 1H), 5.62-5.68 (m, 1H), 4.05-4.25 (m, 2H), 3.91-4.01 (m, 4H), 3.61-3.66 (m, 1H), 3.31-3.42 (m, 1H), 2.49-2.67 (m, 1H), 1.81-1.91 (m, 1H), 1.23-1.34 (m, 3H). |
| 456-En1/2 | 387.3 | U9 | 1.52 | (DMSO-$d_6$) δ ppm: 8.56-8.62 (d, 1H), 7.83-7.84 (d, 1H), 7.41 (s, 1H), 6.54-6.66 (m, 2H), 6.12-6.17 (m, 1H), 5.64-5.70 (m, 1H), 3.97-4.09 (m, 1H), 3.91 (s, 3H), 3.79-3.82 (m, 1H), 3.46-3.65 (m, 3H), 3.31-3.40 (m, 1H), 2.43-2.50 (m, 2H), 2.10-2.32 (m, 5H), 1.95-1.98 (m, 1H). |
| 457-En1/2 | 413.4 | U9 | 2.16 | (DMSO-$d_6$) δ ppm: 8.38 (d, 1H), 8.20-8.24 (m, 2H), 7.77-8.06 (m, 3H), 7.31-7.35 (m, 2H), 7.14-7.16 (m, 1H), 6.55-6.67 (m, 1H), 6.13-6.19 (m, 1H), 5.64-5.71 (m, 1H), 4.24-4.36 (m, 1H), 4.03-4.07 (m, 1H), 3.78-3.88 (m, 2H), 3.37-3.46 (m, 1H), 2.15-2.35 (m, 1H), 2.05-2.13 (m, 1H). |
| 458-En1 | 378.4 | S16 | 5.03 | (DMSO-$d_6$) δ ppm: 8.10 (d, 1H), 7.79 (d, 1H), 6.52-6.62 (m, 2H), 6.37 (s, 1H), 6.10-6.15 (m, 1H), 5.62-5.68 (m, 1H), 3.69-3.91 (m, 8H), 3.44-3.62 (m, 3H), 3.20-3.31 (m, 1H), 1.94-2.18 (m, 6H), 1.79-1.84 (m, 2H). |
| 458-En2 | 378.4 | S16 | 2.46 | (DMSO-$d_6$) δ ppm: 8.10 (d, 1H), 7.79 (d, 1H), 6.52-6.62 (m, 2H), 6.37 (s, 1H), 6.10-6.15 (m, 1H), 5.62-5.68 (m, 1H), 3.69-3.91 (m, 8H), 3.44-3.62 (m, 3H), 3.20-3.31 (m, 1H), 1.94-2.18 (m, 6H), 1.79-1.84 (m, 2H). |
| 459-En1 | 401.4 | S8 | 2.75 | (DMSO-$d_6$) δ ppm: 8.58 (d, 1H), 7.85 (d, 1H), 7.42 (s, 1H), 6.70 (s, 1H), 6.54-6.64 (m, 1H), 6.12-6.17 (m, 1H), 5.65-5.69 (m, 1H), 3.98-4.02 (m, 2H), 3.92 (d, 3H), 3.79-3.84 (m, 1H), 3.58-3.65 (m, 2H), 2.90 (s, 1H), 1.90-2.20 (m, 8H), 1.80-1.85 (m, 2H). |
| 459-En2 | 401.4 | S8 | 4.01 | (DMSO-$d_6$) δ ppm: 8.58 (d, 1H), 7.85 (d, 1H), 7.42 (s, 1H), 6.70 (s, 1H), 6.54-6.64 (m, 1H), 6.12-6.17 (m, 1H), 5.65-5.69 (m, 1H), 3.98-4.02 (m, 2H), 3.92 (d, 3H), 3.79-3.84 (m, 1H), 3.58-3.65 (m, 2H), 2.90 (s, 1H), 1.90-2.20 (m, 8H), 1.80-1.85 (m, 2H). |

TABLE 2-continued

| Cpd. No. | $[M + H]^+$ (m/z) : | LC/MS or UPLC Method | RT (min.) | $^1$H NMR (δ ppm) |
|---|---|---|---|---|
| Analytical data for synthesized compounds of the disclosure | | | | |
| 460-En1/2 | 393.3 | U8 | 1.59 | (DMSO-$d_6$) δ ppm: 8.63 (d, 1H), 8.15-8.19 (m, 2H), 8.01 (d, 1H), 7.88 (d, 1H), 7.29-7.33 (m, 2H), 6.85 (dd, 1H), 6.58-6.66 (m, 1H), 6.17 (dd, 1H), 5.66-5.69 (m, 1H), 5.48 (s, 1H), 4.49-4.57 (m, 1H), 3.90-4.15 (m, 6H), 3.72-3.81 (m, 1H), 3.26-3.54 (m, 1H). |
| 461-En1/2 | 393.2 | U11 | 1.83 | (DMSO-$d_6$) δ ppm: 8.20-8.24 (m, 2H), 8.00-8.05 (m, 1H), 7.92-7.96 (m, 2H), 7.31-7.36 (t, 2H), 6.79-6.91 (m, 2H), 6.38-6.65 (m, 1H), 6.09-6.14 (m, 1H), 5.62-5.69 (m, 1H), 3.93-3.95 (d, 3H), 3.34-3.82 (m, 4H), 2.16-2.46 (m, 2H). |
| 462-En1 | 420.2 | S12 | 9.54 | (DMSO-$d_6$) δ ppm: 8.14 (d, 1H), 7.80 (d, 1H), 6.52-6.63 (m, 3H), 6.10-6.15 (m, 1H), 5.62-5.68 (m, 1H), 3.70-3.94 (m, 5H), 3.36-3.67 (m, 7H), 3.22-3.27 (m, 1H), 1.98-2.32 (m, 4H). |
| 462-En2 | 420.2 | S12 | 12.02 | (DMSO-$d_6$) δ ppm: 8.14 (d, 1H), 7.80 (d, 1H), 6.52-6.63 (m, 3H), 6.10-6.15 (m, 1H), 5.62-5.68 (m, 1H), 3.70-3.94 (m, 5H), 3.36-3.67 (m, 7H), 3.22-3.27 (m, 1H), 1.98-2.32 (m, 4H). |
| 462-En3 | 420.2 | S13 | 2.75 | (DMSO-$d_6$) δ ppm: 8.11-8.17 (d, 1H), 7.79-7.80 (d, 1H), 6.52-6.63 (m, 3H), 6.10-6.15 (m, 1H), 5.62-5.68 (m, 1H), 3.70-3.94 (m, 5H), 3.36-3.67 (m, 7H), 3.22-3.27 (m, 1H), 1.98-2.32 (m, 4H). |
| 462-En4 | 420.2 | S13 | 3.14 | (DMSO-$d_6$) δ ppm: 8.11-8.17 (d, 1H), 7.79-7.80 (d, 1H), 6.52-6.63 (m, 3H), 6.10-6.15 (m, 1H), 5.62-5.68 (m, 1H), 3.70-3.94 (m, 5H), 3.36-3.67 (m, 7H), 3.22-3.27 (m, 1H), 1.98-2.32 (m, 4H). |
| 463-En1 | 414.2 | S14 | 10.21 | (DMSO-$d_6$) δ ppm: 8.13 (d, 1H), 7.80 (d, 1H), 6.55-6.63 (m, 2H), 6.51 (d, 1H), 6.10-6.15 (m, 1H), 5.62-5.68 (m, 1H), 3.81-3.94 (m, 4H), 3.70-3.76 (m, 1H), 3.45-3.64 (m, 6H), 3.21-3.32 (m, 1H), 1.96-2.22 (m, 4H), 1.58-1.70 (m, 2H). |
| 463-En2 | 414.2 | S14 | 13.05 | (DMSO-$d_6$) δ ppm: 8.13 (d, 1H), 7.80 (d, 1H), 6.55-6.63 (m, 2H), 6.51 (d, 1H), 6.10-6.15 (m, 1H), 5.62-5.68 (m, 1H), 3.81-3.94 (m, 4H), 3.70-3.76 (m, 1H), 3.45-3.64 (m, 6H), 3.21-3.32 (m, 1H), 1.96-2.22 (m, 4H), 1.58-1.70 (m, 2H). |
| 463-En3 | 414.3 | S15 | 2.89 | (DMSO-$d_6$) δ ppm: 8.13 (d, 1H), 7.80 (d, 1H), 6.55-6.63 (m, 2H), 6.52 (d, 1H), 6.10-6.15 (m, 1H), 5.62-5.68 (m, 1H), 3.81-3.87 (m, 4H), 3.70-3.76 (m, 1H), 3.45-3.64 (m, 6H), 3.22-3.32 (m, 1H), 1.96-2.22 (m, 4H), 1.58-1.70 (m, 2H). |
| 463-En4 | 414.2 | S15 | 4.29 | (DMSO-$d_6$) δ ppm: 8.13 (d, 1H), 7.80 (d, 1H), 6.55-6.63 (m, 2H), 6.52 (d, 1H), 6.10-6.15 (m, 1H), 5.62-5.68 (m, 1H), 3.81-3.87 (m, 4H), 3.70-3.76 (m, 1H), 3.45-3.64 (m, 6H), 3.22-3.32 (m, 1H), 1.96-2.22 (m, 4H), 1.58-1.70 (m, 2H). |
| 464-En1/2 | 378.3 | US | 2.00 | (DMSO-$d_6$) δ ppm: 9.13 (d, 1H), 8.25-8.28 (m, 2H), 7.88 (d, 1H), 7.36-7.40 (m, 2H), 7.02-7.03 (m, 1H), 6.56-6.66 (m, 1H), 6.14 (dd, 1H), 5.63-5.69 (m, 1H), 4.63-4.78 (m, 1H), 3.79-4.07 (m, 5H), 3.45-3.70 (m, 2H), 2.07-2.30 (m, 2H). |
| 465-En1/2 | 414.1 | U11 | 1.86 | (DMSO-$d_6$) δ ppm: 8.5 (dd, 1H), 8.3 (d, 1H), 8.31-8.34 (m, 2H), 7.98(t, 1H), 7.39-7.44 (m, 2H), 7.34-7.36 (dd, 1H), 6.57-6.67 (m, 1H), 6.12-6.17 (m, 1H), 5.64-5.69 (m, 1H), 4.37-4.49 (m, 1H), 4.06 (d, 1H), 3.46-3.87 (m, 3H), 2.21-2.50 (m, 2H). |
| 466-En1 | 378.1 | S20 | 5.81 | (DMSO-$d_6$) δ ppm: 8.92 (d, 1H), 8.48-8.52 (m, 2H), 7.90 (d, 1H), 7.34-7.38 (m, 2H), 7.16 (t, 1H), 6.57-6.68 (m, 1H), 6.14-6.19 (m, 1H), 5.65-5.72 (m, 1H), 4.50-4.63 (m, 1H), 3.84-4.93 (m, 4H), 3.64-3.83 (m, 1H), 2.14-2.43 (m, 2H). |
| 466-En2 | 378.1 | S20 | 11.39 | (DMSO-$d_6$) δ ppm: 8.92 (d, 1H), 8.48-8.52 (m, 2H), 7.90 (d, 1H), 7.34-7.38 (m, 2H), 7.16 (t, 1H), 6.57-6.68 (m, 1H), 6.14-6.19 (m, 1H), 5.65-5.72 (m, 1H), 4.50-4.63 (m, 1H), 3.84-4.93 (m, 4H), 3.64-3.83 (m, 1H), 2.14-2.43 (m, 2H). |
| 467 | 392.2 | U11 | 1.71 | (DMSO-$d_6$) δ ppm: 8.24-8.30 (m, 2H), 8.21 (s, 1H), 7.93 (d, 1H), 7.36-7.42 (m, 2H), 7.01 (d, 1H), 6.87 (dd, 1H), 6.13 (dd, 1H), 5.68 (dd, 1H), 4.58-4.62 (m, 1H), 4.20-4.24 (m, 1H), 3.98-4.07 (m, 4H), 3.16-3.23 (m, 1H), 2.73-2.79 (m, 1H), 1.81-1.95 (m, 4H). |

TABLE 2-continued

Analytical data for synthesized compounds of the disclosure

| Cpd. No. | $[M + H]^+$ (m/z) : | LC/MS or UPLC Method | RT (min.) | $^1$H NMR (δ ppm) |
|---|---|---|---|---|
| 468-En1 | 387.2 | S10 | 3.95 | (DMSO-$d_6$) δ ppm: 8.59 (d, 1H), 7.83 (d, 1H), 7.41 (s, 1H), 6.54-6.66 (m, 2H), 6.12-6.17 (m, 1H), 5.63-5.69 (m, 1H), 3.79-4.11 (m, 1H), 3.77 (s, 3H), 3.63-3.76 (m, 1H), 3.55-3.60 (m, 3H), 3.35-3.40 (m, 1H), 2.50-2.51 (d, 2H), 1.91-2.40 (m, 6H). |
| 468-En2 | 387.2 | S10 | 5.48 | (DMSO-$d_6$) δ ppm: 8.59 (d, 1H), 7.83 (d, 1H), 7.41 (s, 1H), 6.54-6.66 (m, 2H), 6.12-6.17 (m, 1H), 5.63-5.69 (m, 1H), 3.79-4.11 (m, 1H), 3.77 (s, 3H), 3.63-3.76 (m, 1H), 3.55-3.60 (m, 3H), 3.35-3.40 (m, 1H), 2.50-2.51 (d, 2H), 1.91-2.40 (m, 6H). |
| 468-En3 | 387.2 | S11 | 9.76 | (DMSO-$d_6$) δ ppm: 8.59 (d, 1H), 7.83 (d, 1H), 7.41 (s, 1H), 6.54-6.66 (m, 2H), 6.12-6.17 (m, 1H), 5.63-5.69 (m, 1H), 3.79-4.11 (m, 1H), 3.77 (s, 3H), 3.63-3.76 (m, 1H), 3.55-3.60 (m, 3H), 3.35-3.40 (m, 1H), 2.50-2.51 (d, 2H), 1.91-2.40 (m, 6H). |
| 468-En4 | 387.2 | S11 | 12.16 | (DMSO-$d_6$) δ ppm: 8.59 (d, 1H), 7.83 (d, 1H), 7.41 (s, 1H), 6.54-6.66 (m, 2H), 6.12-6.17 (m, 1H), 5.63-5.69 (m, 1H), 3.79-4.11 (m, 1H), 3.77 (s, 3H), 3.63-3.76 (m, 1H), 3.55-3.60 (m, 3H), 3.35-3.40 (m, 1H), 2.50-2.51 (d, 2H), 1.91-2.40 (m, 6H). |
| 469 | 391.3 | U9 | 1.97 | (DMSO-$d_6$) δ ppm: 8.16-8.19 (m, 2H), 7.79-7.87 (m, 3H), 7.28-7.33 (m, 2H), 6.82-6.89 (m, 2H), 6.11 (dd, 1H), 5.68 (dd, 1H), 4.62 (d, 1H), 4.20 (d, 1H), 3.95-4.00 (m, 4H), 3.10-3.17 (m, 1H), 2.66-2.71 (m, 1H), 1.88 (s, 2H), 1.56-1.61 (m, 2H). |
| 470-En1 | 378.3 | S4 | 13.60 | (DMSO-$d_6$) δ ppm: 9.12 (d, 1H), 8.25-8.28 (m, 2H), 7.87 (d, 1H), 7.36-7.40 (m, 2H), 7.01-7.02 (m, 1H), 6.56-6.66 (m, 1H), 6.12-6.16 (dd, 1H), 5.63- 5.69 (m, 1H), 4.63-4.78 (m, 1H), 3.80-4.07 (m, 5H), 3.45-3.71 (m, 2H), 2.13-2.38 (m, 2H). |
| 470-En2 | 378.3 | S4 | 22.15 | DMSO-$d_6$) δ ppm: 9.12 (d, 1H), 8.25-8.28 (m, 2H), 7.87 (d, 1H), 7.36-7.40 (m, 2H), 7.01-7.02 (m, 1H), 6.56-6.66 (m, 1H), 6.12-6.16 (dd, 1H), 5.63-5.69 (m, 1H), 4.63-4.78 (m, 1H), 3.80-4.07 (m, 5H), 3.45-3.71 (m, 2H), 2.13-2.38 (m, 2H). |
| 471-En1 | 393.3 | S17 | 5.87 | (DMSO-$d_6$) δ ppm: 8.19-8.23 (m, 2H), 8.00-8.05 (m, 1H), 7.91-7.96 (m, 2H), 7.31-7.35 (m, 2H), 6.78-6.90 (m, 2H), 6.37-6.64 (m, 1H), 6.08-6.14 (m, 1H), 5.61-5.68 (m, 1H), 3.93-3.94 (d, 3H), 3.34-3.82 (m, 4H), 2.07-2.46 (m, 2H). |
| 471-En2 | 393.3 | S17 | 8.59 | (DMSO-$d_6$) δ ppm: 8.19-8.23 (m, 2H), 8.00-8.05 (m, 1H), 7.91-7.96 (m, 2H), 7.31-7.35 (m, 2H), 6.78-6.90 (m, 2H), 6.37-6.64 (m, 1H), 6.08-6.14 (m, 1H), 5.61-5.68 (m, 1H), 3.93-3.94 (d, 3H), 3.34-3.82 (m, 4H), 2.07-2.46 (m, 2H). |
| 472-En1/2 | 394.3 | U11 | 1.66 | (DMSO-$d_6$) δ ppm: 8.30-8.34 (m, 3H), 8.00-8.02 (m, 1H), 7.40-7.44 (m, 2H), 7.15-7.17 (m, 1H), 6.84-6.85 (m, 1H), 6.49-6.64 (m, 1H), 6.09-6.15 (m, 1H), 5.65-5.67 (m, 1H), 3.73-4.30 (m, 6H), 3.50-3.55 (m, 1H), 2.24-2.67 (m, 2H). |
| 473-En1 | 433.3 | S21 | 1.93 | (DMSO-$d_6$) δ ppm: 8.66 (d, 1H), 8.13 (d, 1H), 7.99-8.00 (m, 1H), 7.89 (d, 1H), 7.76 (d, 1H), 6.85 (d, 1H), 6.55-6.66 (m, 1H), 6.13-6.18 (m, 1H), 5.64-5.71 (m, 1H), 4.10-4.20 (m, 1H), 4.01-4.05 (m, 1H), 3.94 (s, 3H), 3.79-3.87 (m, 1H), 3.60-3.69 (m, 1H), 3.38-3.45 (m, 1H), 2.09-2.32 (m, 2H). |
| 473-En2 | 433.3 | S21 | 3.13 | (DMSO-$d_6$) δ ppm: 8.66 (d, 1H), 8.13 (d, 1H), 7.99-8.00 (m, 1H), 7.89 (d, 1H), 7.76 (d, 1H), 6.85 (d, 1H), 6.55-6.66 (m, 1H), 6.13-6.18 (m, 1H), 5.64-5.71 (m, 1H), 4.10-4.20 (m, 1H), 4.01-4.05 (m, 1H), 3.94 (s, 3H), 3.79-3.87 (m, 1H), 3.60-3.69 (m, 1H), 3.38-3.45 (m, 1H), 2.09-2.32 (m, 2H). |
| 474 | 363.2 | U12 | 8.08 | (DMSO-$d_6$) δ ppm: 8.81 (s, 1H), 8.19-8.23 (m, 2H), 8.05 (s, 1H), 7.87 (d, 1H), 7.30-7.34 (m, 2H), 6.89 (d, 1H), 6.34 (dd, 1H), 6.10 (dd, 1H), 5.66 (dd, 1H), 4.53-4.64 (m, 2H), 4.29-4.33 (m, 2H), 3.96-4.02 (m, 1H), 3.90 (s, 3H). |

TABLE 2-continued

| Analytical data for synthesized compounds of the disclosure | | | | |
|---|---|---|---|---|
| Cpd. No. | $[M + H]^+$ (m/z) : | LC/MS or UPLC Method | RT (min.) | $^1$H NMR (δ ppm) |
| 475-En1 | 393.3 | S22 | 6.24 | (DMSO-$d_6$) δ ppm: 8.64 (d, 1H), 8.15-8.19 (m, 2H), 8.01 (d, 1H), 7.88 (d, 1H), 7.29-7.33 (m, 2H), 6.84-6.87 (m, 1H), 6.58-6.66 (m, 1H), 6.15-6.20 (m, 1H), 5.68-5.72 (m, 1H), 5.44 (br. s, 1H), 4.48-4.58 (m, 1H), 4.10-4.15 (m, 1H), 3.90-4.03 (m, 5H), 3.72-3.81 (m, 1H), 3.42-3.54 (m, 1H), 3.22-3.39 (m, 1H). |
| 475--En2 | 393.3 | S22 | 8.39 | (DMSO-$d_6$) δ ppm: 8.64 (d, 1H), 8.15-8.19 (m, 2H), 8.01 (d, 1H), 7.88 (d, 1H), 7.29-7.33 (m, 2H), 6.84-6.87 (m, 1H), 6.58-6.66 (m, 1H), 6.15-6.20 (m, 1H), 5.68-5.72 (m, 1H), 4.48-4.58 (m, 1H), 4.10-4.15 (m, 1H), 3.90-4.03 (m, 5H), 3.72-3.81 (m, 1H), 3.42-3.54 (m, 1H), 3.22-3.39 (m, 1 H). |

Part B: Experimental Biology Procedures

Example 117: Activity of Compounds of the Invention in a Reporter Gene Assay for Measuring the Inhibition of YAP/TAZ-TEAD Transcription Hek293T cells are cultured in DMEM supplemented with 10% fetal bovine serum, Sodium pyruvate, Sodium bicarbonate, L-glutamine. The cells are harvested and transiently transfected with TEAD-responsive element luciferase reporter. Transfected cells are plated in 384-wells plate containing pre-diluted compounds. After 24 hours incubation at 37° C./5% CO2, assay plates were cooled down to RT and levelled to an equal volume per well, prior to the addition of 25 uL luciferase substrate SteadyLite (Perkin Elmer)/well. The plate was shaken for 10 min at 600 rpm, centrifuged for 1 min at 500 rpm and measured with an Envision reader (PerkinElmer). The amount of relative light units produced by the TEAD reporter is used to calculated percent of inhibition.

The percent of reporter inhibition was calculated in the presence of a positive control inhibitor (100% inhibition) versus a condition with the presence of the vehicle basal activity of the reporter (0% inhibition). The ability of a test compound to inhibit this activity was determined as:

Percentage inhibition=[1−((RLU determined in the presence of vehicle−RLU determined for sample with test compound present) divided by (RLU determined in the presence of vehicle−RLU determined for sample with positive control inhibitor))]*100

The activities of the example compounds tested are depicted in the table below. The activity ranges A, B and C refer to $EC_{50}$ values in the reporter gene assay assay as described as follows: "A": $EC_{50}$<1 μM; "B": 1 μM s $EC_{50}$≤20 μM and "C": $EC_{50}$>20 μM, NT=not tested.

TABLE 3

| Cpd. No. | $EC_{50}$ |
|---|---|
| 001 | C |
| 002 | A |
| 003 | B |
| 004 | A |
| 005 | B |

TABLE 3-continued

Activities of compounds of the disclosure in the gene reporter assay for measuring YAP/TAZ-TEAD transcription activity

| Cpd. No. | $EC_{50}$ |
|---|---|
| 006 | B |
| 007 | A |
| 008 | B |
| 009 | A |
| 010 | B |
| 011 | B |
| 012 | B |
| 013 | B |
| 014 | B |
| 015 | C |
| 016 | B |
| 017 | B |
| 018 | B |
| 019 | B |
| 020 | B |
| 021 | B |
| 022 | B |
| 023 | B |
| 024 | B |
| 025 | B |
| 026 | C |
| 027 | B |
| 028 | B |
| 029 | B |
| 030 | B |
| 031 | B |
| 032 | B |
| 033 | B |
| 034 | C |
| 035 | B |
| 036 | B |
| 037 | B |
| 038 | C |
| 039 | B |
| 040 | C |
| 041 | B |
| 042 | C |
| 043 | B |
| 044 | B |
| 045 | B |
| 046 | B |
| 047 | B |
| 048 | B |
| 049 | B |
| 050 | A |
| 051 | C |
| 052 | B |
| 053 | A |
| 054 | A |
| 055 | B |

TABLE 3-continued

Activities of compounds of the disclosure in the gene reporter assay for measuring YAP/TAZ-TEAD transcription activity

| Cpd. No. | $EC_{50}$ |
|---|---|
| 056 | A |
| 057 | C |
| 058 | A |
| 059 | A |
| 060 | A |
| 061 | C |
| 062 | B |
| 063 | A |
| 064 | A |
| 065 | B |
| 066 | A |
| 067 | B |
| 068 | B |
| 069 | B |
| 070 | A |
| 071 | B |
| 072 | B |
| 073 | B |
| 074 | B |
| 075 | B |
| 076 | B |
| 077 | A |
| 078 | C |
| 079 | B |
| 080 | B |
| 081 | B |
| 082 | B |
| 083 | A |
| 084 | B |
| 085 | A |
| 086 | A |
| 087 | A |
| 088 | A |
| 089 | A |
| 090 | A |
| 091 | A |
| 092 | A |
| 093 | A |
| 094 | B |
| 095 | A |
| 096 | B |
| 097 | A |
| 098 | A |
| 099 | A |
| 100 | A |
| 101 | A |
| 102 | A |
| 103 | A |
| 104 | A |
| 105 | A |
| 106 | A |
| 107 | C |
| 108 | B |
| 109 | C |
| 110 | B |
| 111 | A |
| 112 | A |
| 113 | A |
| 114 | B |
| 115 | A |
| 116 | A |
| 117 | A |
| 118 | A |
| 119 | A |
| 120 | A |
| 121 | A |
| 122 | A |
| 123 | A |
| 124 | A |
| 125 | A |
| 126 | A |
| 127 | A |
| 128 | A |
| 129 | B |
| 130 | A |

TABLE 3-continued

Activities of compounds of the disclosure in the gene reporter assay for measuring YAP/TAZ-TEAD transcription activity

| Cpd. No. | $EC_{50}$ |
|---|---|
| 131 | A |
| 132 | A |
| 133 | A |
| 134 | A |
| 135 | A |
| 136 | A |
| 137 | A |
| 138 | B |
| 139 | A |
| 140 | A |
| 141 | A |
| 142 | A |
| 143 | A |
| 144 | A |
| 145 | A |
| 146 | A |
| 147 | A |
| 148 | A |
| 149 | A |
| 150 | A |
| 151 | A |
| 152 | A |
| 153 | A |
| 154 | A |
| 155 | B |
| 156 | A |
| 157 | A |
| 158 | A |
| 159 | A |
| 160 | A |
| 161 | A |
| 162 | A |
| 163 | C |
| 164 | A |
| 165 | A |
| 166 | A |
| 167 | A |
| 168 | A |
| 169 | A |
| 170 | A |
| 171 | B |
| 172 | A |
| 173 | A |
| 174 | A |
| 175 | A |
| 176 | A |
| 177 | A |
| 178 | A |
| 179 | A |
| 180 | A |
| 181 | A |
| 182 | A |
| 183 | B |
| 184 | A |
| 185 | A |
| 186 | A |
| 187 | A |
| 188 | A |
| 189 | B |
| 190 | A |
| 191 | A |
| 192 | A |
| 193 | A |
| 194 | A |
| 195 | A |
| 196 | A |
| 197 | B |
| 198 | A |
| 199 | A |
| 200 | C |
| 201 | A |
| 202 | A |
| 203 | A |
| 204 | A |
| 205 | A |

TABLE 3-continued

Activities of compounds of the disclosure in the gene reporter assay for measuring YAP/TAZ-TEAD transcription activity

| Cpd. No. | $EC_{50}$ |
|---|---|
| 206 | A |
| 207 | A |
| 208 | C |
| 209 | A |
| 210 | A |
| 211 | A |
| 212 | B |
| 213 | A |
| 214 | C |
| 215 | A |
| 216 | C |
| 217 | A |
| 218 | A |
| 219 | A |
| 220 | A |
| 221 | A |
| 222 | B |
| 223 | A |
| 224 | B |
| 225 | A |
| 226 | A |
| 227 | A |
| 228 | A |
| 229 | A |
| 230 | A |
| 231 | A |
| 232 | A |
| 233 | C |
| 234 | A |
| 235 | C |
| 236 | B |
| 237 | C |
| 238 | C |
| 239 | A |
| 240 | A |
| 241 | A |
| 242 | C |
| 243 | A |
| 244 | A |
| 245 | A |
| 246 | C |
| 247 | A |
| 248 | A |
| 249 | A |
| 250 | C |
| 251 | C |
| 252 | C |
| 253 | A |
| 254 | A |
| 255 | A |
| 256 | A |
| 257 | A |
| 258 | A |
| 259 | B |
| 260 | C |
| 261 | A |
| 261-En1 | A |
| 261-En2 | A |
| 262 | A |
| 262-En1 | A |
| 262-En2 | A |
| 263 | C |
| 264 | A |
| 265 | A |

Example 118: Activity of Compounds of the Invention in Mesothelioma Cell Line Proliferation Assays Mesothelioma cell lines, NCI-H226 and NCI-H2052 (all sourced from the ATCC cell culture collection) are plated in 96-well plates (Corning® 96 Well White Polystyrene Microplate clear flat bottom, white polystyrene (TC-Treated)), at 1500 cells/well in full medium (RPMI 1640 ATCC modification with L-glutamine, HEPES, Phenol Red, Sodium Pyruvate, High glucose, Low sodium bicarbonate and 10% fetal bovine serum). Cells are incubated overnight at 37° C. in an incubator with 5% $CO_2$. Then compounds, dissolved in DMSO, are added in dose-response. Cells are incubated with compound dilutions for another 6 days at 37° C. in an incubator with 5% $CO_2$. Cell viability is quantitated using the ATPlite kit (Perkin-Elmer) and the luminescence is read-out using an Envision instrument (Perkin-Elmer). The amount of relative light units produced using the ATPlite kit is used to calculated percent of inhibition.

The activities of example compounds tested are depicted in the table below. The activity ranges A, B and C refer to $EC_{50}$ values in the mesothelioma cell line proliferation assay as described as follows: "A": $EC_{50}$<1 μM; "B": 1 μM s $EC_{50}$≤10 μM and "C": $EC_{50}$>10 μM. NT: not tested.

TABLE 4

Activities of a selection of compounds in the mesothelioma cell line proliferation assay

| | $EC_{50}$ | | |
|---|---|---|---|
| Cpd. No. | H226 | H2052 | H2452 |
| 004 | B | NT | NT |
| 052 | C | C | NT |
| 054 | A | NT | NT |
| 075 | A | NT | NT |
| 083 | A | B | NT |
| 086 | B | NT | C |
| 087 | B | NT | C |
| 088 | C | NT | NT |
| 093 | A | NT | C |
| 102 | C | NT | C |
| 117 | C | NT | C |
| 118 | B | NT | C |
| 119 | C | NT | C |
| 121 | B | NT | NT |
| 124 | B | NT | C |
| 131 | B | C | NT |
| 132 | C | C | NT |
| 135 | A | NT | NT |
| 137 | A | C | NT |
| 140 | A | A | NT |
| 141 | A | A | NT |
| 142 | A | A | NT |
| 143 | A | A | NT |
| 144 | A | A | NT |
| 145 | A | A | NT |
| 149 | A | A | NT |
| 153 | A | A | NT |
| 157 | A | A | NT |
| 161 | A | A | NT |
| 162 | A | A | NT |
| 165 | A | A | NT |
| 166 | A | A | NT |
| 167 | B | A | NT |
| 169 | A | B | NT |
| 170 | A | A | NT |
| 172 | A | A | NT |
| 174 | A | B | NT |
| 176 | A | A | NT |
| 177 | A | A | NT |
| 179 | A | A | NT |
| 180 | A | A | NT |
| 182 | A | A | NT |
| 184 | A | A | NT |
| 185 | A | B | NT |
| 187 | A | B | NT |
| 188 | A | A | NT |
| 190 | A | B | NT |
| 193 | A | A | NT |
| 194 | A | A | NT |
| 198 | A | A | NT |

TABLE 4-continued

| Activities of a selection of compounds in the mesothelioma cell line proliferation assay | | | |
|---|---|---|---|
| | $EC_{50}$ | | |
| Cpd. No. | H226 | H2052 | H2452 |
| 201 | A | A | NT |
| 202 | A | A | NT |
| 203 | A | A | NT |
| 205 | A | A | NT |
| 206 | A | A | NT |
| 207 | A | A | NT |
| 211 | A | B | NT |
| 213 | A | B | NT |
| 215 | A | B | NT |
| 221 | A | B | NT |
| 223 | A | B | NT |
| 225 | A | B | NT |
| 227 | A | C | NT |
| 228 | A | C | NT |
| 231 | A | C | NT |
| 240 | A | A | NT |
| 241 | A | B | NT |
| 243 | A | B | NT |
| 244 | A | A | NT |
| 249 | A | B | NT |
| 253 | A | A | NT |
| 254 | A | A | NT |
| 255 | A | B | NT |
| 258 | A | A | NT |
| 261 | A | B | NT |
| 261-En1 | A | B | NT |
| 261-En2 | A | C | NT |
| 262 | A | B | NT |
| 262-En1 | A | B | NT |
| 262-En2 | A | C | NT |

The invention claimed is:

1. A compound selected from 1-(3-(6-(4-fluorophenyl)-4-(1-methyl-1H-pyrazol-3-yl) pyridazin-3-yl) pyrrolidin-1-yl) prop-2-en-1-one and pharmaceutically acceptable salts thereof.

2. The compound of claim 1, wherein the compound is (R)-1-(3-(6-(4-fluorophenyl)-4-(1-methyl-1H-pyrazol-3-yl) pyridazin-3-yl) pyrrolidin-1-yl) prop-2-en-1-one or a pharmaceutically acceptable salt thereof.

3. The compound of claim 1, wherein the compound is (S)-1-(3-(6-(4-fluorophenyl)-4-(1-methyl-1H-pyrazol-3-yl) pyridazin-3-yl) pyrrolidin-1-yl) prop-2-en-1-one or a pharmaceutically acceptable salt thereof.

4. A pharmaceutical composition comprising a compound of claim 1 and a pharmaceutically acceptable carrier.

5. A method of treating a YAP/TAZ-TEAD activation mediated disorder in a patient in need thereof comprising administering to the patient an effective amount of a compound of claim 1.

6. The method of claim 5, further comprising administering to the patient one or more additional active agents selected from the group consisting of EGFR inhibitors, MEK inhibitors, AXL inhibitors, B-RAF inhibitors, RAS inhibitors, and any combination of any of the foregoing.

7. A pharmaceutical composition comprising a compound of claim 2 and a pharmaceutically acceptable carrier.

8. A method of treating a YAP/TAZ-TEAD activation mediated disorder in a patient in need thereof comprising administering to the patient an effective amount of a compound of claim 2.

9. The method of claim 8, further comprising administering to the patient one or more additional active agents selected from the group consisting of EGFR inhibitors, MEK inhibitors, AXL inhibitors, B-RAF inhibitors, RAS inhibitors, and any combination of any of the foregoing.

10. A pharmaceutical composition comprising a compound of claim 3 and a pharmaceutically acceptable carrier.

11. A method of treating a YAP/TAZ-TEAD activation mediated disorder in a patient in need thereof comprising administering to the patient an effective amount of a compound of claim 3.

12. The method of claim 11, further comprising administering to the patient one or more additional active agents selected from the group consisting of EGFR inhibitors, MEK inhibitors, AXL inhibitors, B-RAF inhibitors, RAS inhibitors, and any combination of any of the foregoing.

* * * * *